US011555012B2

(12) United States Patent
Leit de Moradei et al.

(10) Patent No.: US 11,555,012 B2
(45) Date of Patent: Jan. 17, 2023

(54) ACLY INHIBITORS AND USES THEREOF

(71) Applicant: Nimbus Artemis, Inc., Cambridge, MA (US)

(72) Inventors: Silvana Marcel Leit de Moradei, Burlington, MA (US); Eric Therrien, Bronx, NY (US)

(73) Assignee: Nimbus Artemis, Inc., Boston, MA (US)

( * ) Notice: Subject to any disclaimer, the term of this patent is extended or adjusted under 35 U.S.C. 154(b) by 237 days.

(21) Appl. No.: 16/677,768

(22) Filed: Nov. 8, 2019

(65) Prior Publication Data

US 2020/0148634 A1 May 14, 2020

Related U.S. Application Data

(60) Provisional application No. 62/758,410, filed on Nov. 9, 2018.

(51) Int. Cl.

| | | |
|---|---|---|
| *C07C 311/29* | (2006.01) | |
| *C07C 311/21* | (2006.01) | |
| *C07D 491/113* | (2006.01) | |
| *C07D 295/135* | (2006.01) | |
| *C07D 333/20* | (2006.01) | |
| *C07D 257/04* | (2006.01) | |
| *C07D 295/10* | (2006.01) | |
| *C07D 205/04* | (2006.01) | |
| *C07D 277/34* | (2006.01) | |
| *C07D 209/80* | (2006.01) | |
| *C07D 231/38* | (2006.01) | |
| *C07D 263/32* | (2006.01) | |
| *C07D 401/12* | (2006.01) | |
| *C07D 413/06* | (2006.01) | |
| *C07D 401/04* | (2006.01) | |
| *C07D 409/12* | (2006.01) | |
| *C07D 213/04* | (2006.01) | |

(52) U.S. Cl.
CPC .......... *C07C 311/21* (2013.01); *C07C 311/29* (2013.01); *C07D 205/04* (2013.01); *C07D 209/80* (2013.01); *C07D 213/04* (2013.01); *C07D 231/38* (2013.01); *C07D 257/04* (2013.01); *C07D 263/32* (2013.01); *C07D 277/34* (2013.01); *C07D 295/10* (2013.01); *C07D 295/135* (2013.01); *C07D 333/20* (2013.01); *C07D 401/04* (2013.01); *C07D 401/12* (2013.01); *C07D 409/12* (2013.01); *C07D 413/06* (2013.01); *C07D 491/113* (2013.01)

(58) Field of Classification Search
CPC .................................................. C07C 311/29
See application file for complete search history.

(56) References Cited

U.S. PATENT DOCUMENTS

| | | | | |
|---|---|---|---|---|
| 3,806,542 | A * | 4/1974 | Werner ................. | C07D 307/52 549/426 |
| 6,284,923 | B1 * | 9/2001 | Medina ................. | C07C 311/21 564/86 |
| 6,962,929 | B2 * | 11/2005 | Flygare ................. | C07C 311/21 514/312 |
| 8,524,778 | B2 * | 9/2013 | Greig ...................... | A61P 19/00 564/92 |

FOREIGN PATENT DOCUMENTS

WO    WO-2007/008541 A2 *    1/2007

OTHER PUBLICATIONS

Chemical Abstracts Registry No. 1057942-46-7, indexed in the Registry file on STN CAS Online Oct. 7, 2008. (Year: 2008).*
Li et al., Bioorganic & Medicinal Chemistry Letters (2007), 17(11), 3208-3211. (Year: 2007).*
Abu-Elheiga et al., "Acetyl-CoA carboxylase 2 mutant mice are protected against obesity and diabetes induced by high-fat/high-carbohydrate diets," Proc. Natl. Acad Sci. USA, 2003, vol. 100, No. 18, pp. 10207-10212.
Abu-Elheiga et al., "Mutant mice lacking acetyl-CoA carboxylase 1 are embryonically lethal," Proc. Natl. Acad. Sci. USA, 2005, vol. 102, No. 34, pp. 12011-12016.
Ballantyne et al., "ETC-1002 Lowers LDL-C and beneficially modulates other cardio-metabolic risk factors in hypercholesterolemic subjects with either normal or eleveated triglycerides," J. Am. Coll. Cardiol, 2012, vol. 59, No. 13, Supplement, E1625.
Barañano et al., "The ketogenic diet: uses in epilepsy and other neurologic illnesses," Curr. Treat. Opin. Neurol., 2008, vol. 10, No. 6, pp. 410-419.
Beckers et al. "Chemical Inhibition of Acetyl-CoA Carboxylase Induces Growth Arrest and Cytotoxicity Selectivity in Cancer Cells," Cancer Res., 2007, vol. 67, No. 17, pp. 8180-8187.
Berge et al., "Pharmaceutical salts", J. Pharmaceutical Sciences, 1977, vol. 66, No. 1 (pp. 1-19).
Berkhout et al., "The effect of (−)-hydroxycitrate on the activity of the low-density-lipoprotein receptor and 3-hydroxy-3-methylglutaryl-CoA reductase levels in the human hepatoma cell line Hep G2," Biochem J, 1990, vol. 272, No. 1, pp. 181-186.
Brunet et al., "BRCA1 and Acetyl-CoA Carboxylase: The Metabolic Syndrome of Breast Cancer," Molecular Carcinogenesis, 2008, vol. 47, No. 2, pp. 157-163.
Brusselmans et al. "RNA Interference-Mediated Silencing of the Acetyl-CoA-Carboxylase-alpha Gene Induces Growth Inhibition and Apoptosis of Prostate Cancer Cells" Cancer Res., 2005, vol. 65, No. 15, pp. 6719-6725.
Cairns et al., "Regulation of Cancer Cell Metabolism," Nat Rev Cancer, 2011, vol. 11, No. 2, pp. 85-95.
Chajès et al., "Acetyl-CoA Carboxylase alpha Is Essential to Breast Cancer Cell Survival," Cancer Res., 2006, vol. 66, No. 10, 5287-5294.

(Continued)

*Primary Examiner* — Laura L Stockton

(74) *Attorney, Agent, or Firm* — Andrea L. C. Reid; Joseph W. Arico; Dechert LLP

(57) ABSTRACT

The present invention provides compounds useful as inhibitors of ATP citrate lyase (ACLY), compositions thereof, and methods of using the same.

8 Claims, No Drawings

(56) References Cited

OTHER PUBLICATIONS

Cheng et al., "Synthesis and structure-activity relationship of small-molecule malonyl coenzyme A decarboxylase inhibitors," J Med. Chem., 2006, vol. 49, No. 5, pp. 1517-1525.
Chiaradonna et al., "From Cancer Metabolism to New Biomarkers and Drug Targets," Biotechnology Advances, 2012, vol. 30, No. 1, pp. 30-51.
Costantini et al., "Hypometabolism as a therapeutic target in Alzheimer's disease," BMC Neurosci., 2008, vol. 9, Suppl. 2, S16, 9 pages.
Ference et al., "Genetic target validation for ATP-Citrate Lyase inhibition," J. Am. Col. Cardio, 2017, vol. 69, Suppl. 11, 1655.
Furler et al., "The ACC inhibitor CP-640186 acutely increases muscle fatty acid clearance independently of glucose clearance and cellular energy demand," 2006, Diabetes, 55: A333.
Harwood et al., "Isozyme-nonselective N-Substituted Bipiperidylcarboxamide Acetyl-CoA Carboxylase Inhibitors Reduce Tissue Malonyl-CoA Concentrations, Inhibit Fatty Acid Synthesis, and Increase Fatty Acid Oxidation in Cultured Cells and in Experimental Animals," J. Biol. Chem., 2003, vol. 278, pp. 37099-37111.
Harwood Jr., "Treating the metabolic syndrome: Acetyl-CoA carboxylase inhibition," Expert Opin Ther Targets, 2005, vol. 9, pp. 267-281.
Hatzivassiliou et al., "ATP citrate lyase inhibition can suppress tumor cell growth," Cancer Cell, 2005, vol. 8, No. 4, pp. 311-321.
Henderson et al., "Ketone bodies as a therapeutic for Alzheimer's disease," Neurotherapeutics, 2008, vol. 5, No. 3, pp. 470-480.
Infantino et al., "ATP-citrate lyase is essential for macrophage inflammatory response," Biochemical and Biophysical Research Communications, 2009, vol. 440, No. 1, pp. 105-111.
International Search Report and Written Opinion for Application No. PCT/US2019/060378, dated Mar. 3, 2020 (10 pages).
Kolwicz Jr. et al. "Cardiac-specific deletion of acetyl CoA carboxylase 2 prevents metabolic remodeling during pressure-overload hypertrophy," Circ. Res , 2012, vol. 111, No. 6, pp. 728-738.
Lawitz et al., "Acetyl-CoA carboxylase (ACC) inhibitor GS-0976 leads to suppression of hepatic de novo lipogenesis and significant improvements in MRI-PDFF, MRE, and markers of fibrosis after 12 weeks of therapy in patients with NASH," J Hepatol, 2017, vol. 66, No. 1, p. S34.
Makowski et al. "Role of LKB1 in Lung Cancer Development" British Journal of Cancer (2008) 99, 683-688.
Migita et al., "ATP Citrate Lyase: Activation and Therapeutic Implications in Non-Small Cell Lung Cancer," Cancer Research, 2008, vol. 68, No. 20, pp. 8547-8554.
Olsen et al., "Fatty acid synthesis is a therapeutic target in human liposarcoma," International J. of Oncology, 2010, vol. 36, No. 5, pp. 1309-1314.
Pearce et al., "The role of ATP citrate-lyase in the metabolic regulation of plasma lipids. Hypolipidaemic effects of SB-204990, a lactone prodrug of the potent ATP citrate-lyase inhibitor SB-201076," Biochem J, 1998, vol. 34, No. 1, pp. 113-119.
Petti et al., "AMPK activators inhibit the proliferation of human melanomas bearing the activated MAPK pathway," Melanoma Research, 2012, vol. 22, No. 5, pp. 341-350.
Pietrocolo et al., "Acetyl coenzyme A: a central metabolite and second messenger," Cell Metabolism, 2015, vol. 21, No. 6, pp. 805-821.
Pubchem, Substance Record for SID 329827770. Available Date: Mar. 3, 2017. [retrieved on Dec. 10, 2019], Retrieved from the Internet: <https://pubchem.ncbi.nlm.nih.gov/substance/329827770>.
Saha et al., "Reversal of insulin resistance in rat muscle by the acety/-CoA carboxylase inhibitor CP-640186," 2006, Diabetes, 55: A288.
Savage et al., "Reversal of diet-induced hepatic steatosis and hepatic insulin resistance by antisense oligonucleotide inhibitors of acetyl-CoA carboxylases 1 and 2," J. Clin. Invest., 2006, vol. 116, No. 3, pp. 817-824.
Steide et al., "Acetyl-coenzyme A carboxylase inhibition reduces de novo lipogenesis in overweight male subjects: A randomized, double-blind, crossover study," Hepatology, 2017, vol. 66, No. 2, pp. 324-334.
Svensson et al. "Lipid Synthesis Is a Metabolic Liability of Non-Small Cell Lung Cancer," Cold Spring Harbor Symp Quant Biol, 2017, vol. 81, pp. 93-103.
Tong et al., "Acetyl-coenzyme A carboxylases: Versatile targets for drug discovery," J. Cellular Biochem., 2006, vol. 99, No. 6, pp. 1476.
Tong et al., "Acetyl-coenzyme A carboxylase: crucial metabolic enzyme and attractive target for drug discovery," Cell and Molecular Life Sciences, 2005, vol. 62, No. 16, pp. 1784-1803.
Varis et al., "Targets of Gene Amplification and Overexpression at 17q in Gastric Cancer," Cancer Research, 2002, vol. 62, pp. 2625-2629.
Wang et al., "Deficiency in hepatic ATP-citrate lyase affects VLDL-triglyceride mobilization and liver fatty acid composition in mice," J Lipid Research, 2010, vol. 51, No. 9, pp. 2516-2526.
Wang et al., "Abrogation of hepatic ATP-citrate lyase protects against fatty liver and ameliorates hyperglycemia in leptin receptor-deficient mice," Hepatology, 2009, vol. 49, No. 4, pp. 1166-1175.
Wang et al., "Acetyl-CoA Carboxylase-alpha Inhibitor TOFA Induces Human Cancer Cell Apoptosis," Biochem Biophys Res Commun., 2009, vol. 385, No. 3, pp. 302-306.
Yancy et al., "Metastatic progression and gene expression between breast cancer cell lines from African American and Caucasian women," J Carcinog, 2007, vol. 6, No. 8, 12 pages.
Zhang et al., "Cullin3-KLHL25 ubiquitin ligase targets ACLY for degradation to inhibit lipid synthesis and tumor progression," Genes and Development, 2016, vol. 30, pp. 1956-1970.
Zhao et al., "ATP-citrate lyase controls a glucose-to-acetate metabolic switch," Cell Reports, 2016, vol. 17, No. 4, pp. 1037-1052.

* cited by examiner

ACLY INHIBITORS AND USES THEREOF

RELATED APPLICATIONS

This application claims the benefit of U.S. Provisional patent application 62/758,410, filed on Nov. 9, 2018, the content of which is incorporated herein in its entirety.

BACKGROUND OF THE INVENTION

ATP citrate lyase (ACLY) is a homotetrameric enzyme that catalyzes the ATP dependent cleavage of citrate into acetyl coenzyme A (acetyl-CoA) and oxaloacetate (OAA). Acetyl-CoA is an important cellular metabolite and second messenger, thus ACLY enzymatic activity is positioned at the nexus of intermediary metabolism. The acetyl-CoA forming reaction is initiated upon phosphorylation of ACLY at histidine 760, which then catalyzes the formation of citryl phosphate followed by the formation of a citryl-CoA intermediate after a CoA attack. Finally, the citryl-CoA intermediate is cleaved, and acetyl-CoA and OAA are released. ACLY derived acetyl-CoA serves as the carbon source for the production of cholesterol in the mevalonate pathway and fatty acids (FA) in the de novo lipogenesis (DNL) pathway, and is also required for protein acetylation, thus linking cellular metabolism with the epigenome and gene regulation. Acetyl-CoA production therefore functions as a key metabolic checkpoint used by cells to coordinate cellular metabolism in response to nutrients and plays a key role in sterol and lipid production in a number of tissues. Thus, direct inhibition of ACLY activity may have important therapeutic implications for treating a wide range of diseases including hypercholesteremia and cardiovascular disease (CVD), obesity, diabetes, insulin resistance, fatty liver disease, metabolic syndrome and cancer.

SUMMARY OF THE INVENTION

It has now been found that compounds of this invention, and pharmaceutically acceptable compositions thereof, are effective as inhibitors of ATP citrate lyase (ACLY). Such compounds have the general formula I":

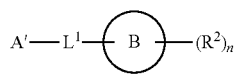

or a pharmaceutically acceptable salt thereof, wherein each variable is as defined and described herein.

Compounds of the present invention, and pharmaceutically acceptable compositions thereof, are useful for treating a variety of diseases, disorders or conditions, associated with regulation of the production of sterols or lipids. Such diseases, disorders, or conditions include those described herein.

Compounds provided by this invention are also useful for the study of ACLY enzymes in biological and pathological phenomena; the study of intracellular signal transduction pathways occurring in lipogenic tissues; and the comparative evaluation of new ACLY inhibitors or other regulators of fatty acid levels in vitro or in vivo.

DETAILED DESCRIPTION OF CERTAIN EMBODIMENTS

1. General Description of Compounds of the Invention

In certain embodiments, the present invention provides inhibitors of ACLY. In some embodiments, the present invention provides a compound of formula I":

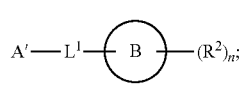

A' is optionally substituted $C_{1-6}$ aliphatic; or A' is Ring A, wherein Ring A is phenyl; naphthalenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur, or a 9-11 membered saturated or partially unsaturated bicyclic ring having 0-3 heteroatoms independently selected from nitrogen, oxygen, and sulfur; each of which is substituted by m instances of $R^1$ and q instances of $R^{1'}$;

each $R^1$ is independently hydrogen, halogen, —OR, —CN, —$NO_2$, —$N(R)_2$, —C(O)OR, —OC(O)R, —C(O)R, —OC(O)N(R)_2$, —SR, —S(O)R, —$S(O)_2R$, —N(R)$S(O)_2R$, —C(O)N(R)_2$, —C(O)N(OR)(R), or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur;

or two instances of $R^1$ are optionally taken together to form an oxo; or two $R^{1'}$ groups are taken together with their intervening atoms to form an optionally substituted 4-7 membered saturated, partially unsaturated, or heteroaryl ring having 0-3 heteroatoms, in addition to the nitrogen, independently selected from nitrogen, oxygen, and sulfur;

each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, a 5-6 membered heteroaryl ring having 1-4 heteroatoms independently selected from nitrogen, oxygen, and sulfur, and a bicyclic 9-11 membered saturated or partially unsaturated bicyclic heterocyclic ring having 1-4 heteroatoms independently selected from nitrogen, oxygen, and sulfur; or:

two R groups on the same nitrogen are taken together with their intervening atoms to form an optionally substituted 4-7 membered saturated, partially unsaturated, or heteroaryl ring having 0-3 heteroatoms, in addition to the nitrogen, independently selected from nitrogen, oxygen, and sulfur;

each $R^{1'}$ is independently hydrogen, halogen, —OR, —CN, —NO$_2$, —N(R)$_2$, —C(O)OR, —OC(O)R, —C(O)R, —OC(O)N(R)$_2$, —SR, —S(O)R, —S(O)$_2$R, —N(R)S(O)$_2$R, —S(O)$_2$N(R)$_2$, —C(O)N(R)$_2$, —C(O)N(OR)(R), or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur; or two instances of $R^{1'}$ are optionally taken together to form an oxo; or two $R^{1'}$ groups are taken together with their intervening atoms to form an optionally substituted 4-7 membered saturated, partially unsaturated, or heteroaryl ring having 0-3 heteroatoms, in addition to the nitrogen, independently selected from nitrogen, oxygen, and sulfur;

Ring B is phenyl; naphthalenyl; a 5-6 membered monocyclic heteroaryl ring having 1-4 heteroatoms independently selected from nitrogen, oxygen, and sulfur; an 8-10 membered bicyclic aryl or heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 8-10 membered saturated or partially unsaturated bicyclic heterocyclic ring having 1-4 heteroatoms independently selected from nitrogen, oxygen, and sulfur;

each $R^2$ is independently hydrogen, halogen, —OR, —CN, —NO$_2$, —N(R)$_2$, —C(O)OR, —SR, —S(O)R, —S(O)$_2$R, —C(O)N(R)$_2$, —N(R)C(O)R, —C(O)N(R)S(O)$_2$R, —C(O)N(OR)(R), or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, an 8-10 membered bicyclic aryl or heteroaryl with 1-4 heteroatoms independently selected from nitrogen, oxygen or sulfur, and a 5-6 membered heteroaryl ring having 1-4 heteroatoms independently selected from nitrogen, oxygen, and sulfur;

or two instances of $R^2$ are optionally taken together to form an oxo;

$L^1$ is a covalent bond or a C$_{1-6}$ bivalent saturated or unsaturated, straight or branched hydrocarbon chain wherein one or two methylene units of the chain are optionally and independently replaced by —C(R)$_2$—, —CH(R)—, —N(R)—, —N(R)C(O)—, —C(O)N(R)—, —N(C(O)R)C(O)—, —C(O)N(C(O)R)—, —N(R)C(O)N(R)—, —N(R)S(O)$_2$—, —S(O)$_2$N(R)—, —O—, —C(O)—, —OC(O)—, —C(O)O—, —S—, —S(O)—, or —S(O)$_2$—, wherein two R groups on the same carbon are optionally taken together to form a bivalent C$_{2-4}$ alkylene chain;

wherein each hydrogen bound to carbon can be optionally and independently replaced by deuterium;

each instance of m, n, and q, is independently 0, 1, 2, 3, or 4; and wherein the compound is other than a compound in Table 2.

2. Compounds and Definitions

Compounds of this invention include those described generally above, and are further illustrated by the classes, subclasses, and species disclosed herein. As used herein, the following definitions shall apply unless otherwise indicated.

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic C$_3$-C$_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a C$_{1-4}$ straight or branched alkyl group. Exemplary lower alkyl groups are methyl, ethyl, propyl, isopropyl, butyl, isobutyl, and tert-butyl.

The term "lower haloalkyl" refers to a C$_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent C$_{1-8}$ (or C$_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

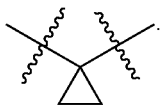 [SMILES: *C1(*)CC1]

As used herein, the term "cyclobutylenyl" refers to a bivalent cyclobutyl group of the following structure:

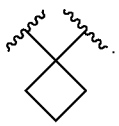

As used herein, the term "oxetanyl" refers to a bivalent oxetanyl group of the following structure:

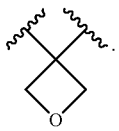

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted"

group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^○$; $-(CH_2)_{0-4}R^○$; $-O(CH_2)_{0-4}R^○$, $-O-(CH_2)_{0-4}C(O)OR^○$; $-(CH_2)_{0-4}CH(OR^○)_2$; $-(CH_2)_{0-4}SR^○$; $-(CH_2)_{0-4}Ph$, which may be substituted with $R^○$; $-(CH_2)_{0-4}O(CH_2)_{0-1}Ph$ which may be substituted with $R^○$; $-CH=CHPh$, which may be substituted with $R^○$; $-(CH_2)_{0-4}O(CH_2)_{0-1}$-pyridyl which may be substituted with $R^○$; $-NO_2$; $-CN$; $-N_3$; $-(CH_2)_{0-4}N(R^○)_2$; $-(CH_2)_{0-4}N(R^○)C(O)R^○$; $-N(R^○)C(S)R^○$; $-(CH_2)_{0-4}N(R^○)C(O)NR^○_2$; $-N(R^○)C(S)NR^○_2$; $-(CH_2)_{0-4}N(R)C(O)OR^○$; $-N(R^○)N(R^○)C(O)R^○$; $-N(R^○)N(R^○)C(O)NR^○_2$; $-N(R^○)N(R^○)C(O)OR^○$; $-(CH_2)_{0-4}C(O)R^○$; $-C(S)R^○$; $-(CH_2)_{0-4}C(O)OR^○$; $-(CH_2)_{0-4}C(O)SR^○$; $-(CH_2)_{0-4}C(O)OSiR^○_3$; $-(CH_2)_{0-4}OC(O)R^○$; $-OC(O)(CH_2)_{0-4}SR-$, $SC(S)SR^○$; $-(CH_2)_{0-4}SC(O)R$; $-(CH_2)_{0-4}C(O)NR^○_2$; $-C(S)NR^○_2$; $-C(S)SR^○$; $-SC(S)SR^○$, $-(CH_2)_{0-4}OC(O)NR^○_2$; $-C(O)N(OR^○)R^○$; $-C(O)C(O)R^○$; $-C(O)CH_2C(O)R$; $-C(NOR^○)R^○$; $-(CH_2)_{0-4}SSR^○$; $-(CH_2)_{0-4}S(O)_2R^○$; $-(CH_2)_{0-4}S(O)_2OR^○$; $-(CH_2)_{0-4}OS(O)_2R^○$; $-S(O)_2NR^○_2$; $-(CH_2)_{0-4}S(O)R^○$; $-N(R^○)S(O)_2NR^○_2$; $-N(R^○)S(O)_2R^○$; $-N(OR)R^○$; $-C(NH)NR^○_2$; $-P(O)_2R^○$; $-P(O)R^○_2$; $-OP(O)R^○_2$; $-OP(O)(OR^○)_2$; $SiR^○_3$; $-(C_{1-4}$ straight or branched alkylene)$O-N(R^○)_2$; or $-(C_{1-4}$ straight or branched alkylene)$C(O)O-N(R^○)_2$, wherein each $R^○$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^○$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^○$ (or the ring formed by taking two independent occurrences of $R^○$ together with their intervening atoms), are independently halogen, $-(CH_2)_{0-2}R^●$, $-(haloR^●)$, $-(CH_2)_{0-2}OH$, $-(CH_2)_{0-2}OR^●$, $-(CH_2)_{0-2}CH(OR^●)_2$; $-O(haloR^●)$, $-CN$, $-N_3$, $-(CH_2)_{0-2}C(O)R^●$, $-(CH_2)_{0-2}C(O)OH$, $-(CH_2)_{0-2}C(O)OR^●$, $-(CH_2)_{0-2}SR^●$, $-(CH_2)_{0-2}SH$, $-(CH_2)_{0-2}NH_2$, $-(CH_2)_{0-2}NHR^●$, $-(CH_2)_{0-2}NR^●_2$, $-NO_2$, $-SiR^●_3$, $-OSiR^●_3$, $-C(O)SR^●$, $-(C_{1-4}$ straight or branched alkylene)$C(O)OR^●$, or $-SSR^●$ wherein each $R^●$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^○$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^●$, $-(haloR^●)$, $-OH$, $-OR^●$, $-O(haloR^●)$, $-CN$, $-C(O)OH$, $-C(O)OR^●$, $-NH_2$, $-NHR^●$, $-NR^●_2$, or $-NO_2$, wherein each $R^●$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^†$, $-NR^†_2$, $-C(O)R^†$, $-C(O)OR^†$, $-C(O)C(O)R^†$, $-C(O)CH_2C(O)R^†$, $-S(O)_2R^†$, $-S(O)_2NR^†_2$, $-C(S)NR^†_2$, $-C(NH)NR^†_2$, or $-N(R^●)S(O)_2R^●$; wherein each $R^†$ is independently hydrogen, $C_{1-4}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^●$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, $-R^●$, $-(haloR^●)$, $-OH$, $-OR^*$, $-O(haloR^●)$, $-CN$, $-C(O)OH$, $-C(O)OR^●$, $-NH_2$, $-NHR^●$, $-NR^●_2$, or $-NO_2$, wherein each $R^●$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+$ $(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

3. Description of Exemplary Embodiments

In certain embodiments, the present invention provides inhibitors of ACLY. In some embodiments, the present invention provides a compound of formula I":

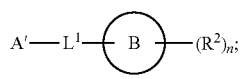

A' is optionally substituted $C_{1-6}$ aliphatic; or A' is Ring A, wherein Ring A is phenyl; naphthalenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur, or a 9-11 membered saturated or partially unsaturated bicyclic ring having 0-3 heteroatoms independently selected from nitrogen, oxygen, and sulfur; each of which is substituted by m instances of $R^1$ and q instances of $R^{1'}$;

each $R^1$ is independently hydrogen, halogen, —OR, —CN, —NO$_2$, —N(R)$_2$, —C(O)OR, —OC(O)R, —C(O)R, —OC(O)N(R)$_2$, —SR, —S(O)R, —S(O)$_2$R, —N(R)S(O)$_2$R, —C(O)N(R)$_2$, —C(O)N(OR)(R), or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur;

or two instances of $R^1$ are optionally taken together to form an oxo; or two $R^{1'}$ groups are taken together with their intervening atoms to form an optionally substituted 4-7 membered saturated, partially unsaturated, or heteroaryl ring having 0-3 heteroatoms, in addition to the nitrogen, independently selected from nitrogen, oxygen, and sulfur;

each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, a 5-6 membered heteroaryl ring having 1-4 heteroatoms independently selected from nitrogen, oxygen, and sulfur, and a bicyclic 9-11 membered saturated or partially unsaturated bicyclic heterocyclic ring having 1-4 heteroatoms independently selected from nitrogen, oxygen, and sulfur; or:

two R groups on the same nitrogen are taken together with their intervening atoms to form an optionally substituted 4-7 membered saturated, partially unsaturated, or heteroaryl ring having 0-3 heteroatoms, in addition to the nitrogen, independently selected from nitrogen, oxygen, and sulfur;

each $R^{1'}$ is independently hydrogen, halogen, —OR, —CN, —NO$_2$, —N(R)$_2$, —C(O)OR, —OC(O)R, —C(O)R, —OC(O)N(R)$_2$, —SR, —S(O)R, —S(O)$_2$R, —N(R)S(O)$_2$R, —S(O)$_2$N(R)$_2$, —C(O)N(R)$_2$, —C(O)N(OR)(R), or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur;

or two instances of $R^{1'}$ are optionally taken together to form an oxo; or two $R^{1'}$ groups are taken together with their intervening atoms to form an optionally substituted 4-7 membered saturated, partially unsaturated, or heteroaryl ring having 0-3 heteroatoms, in addition to the nitrogen, independently selected from nitrogen, oxygen, and sulfur;

Ring B is phenyl; naphthalenyl; a 5-6 membered monocyclic heteroaryl ring having 1-4 heteroatoms independently selected from nitrogen, oxygen, and sulfur; an 8-10 membered bicyclic aryl or heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 8-10 membered saturated or partially unsaturated bicyclic heterocyclic ring having 1-4 heteroatoms independently selected from nitrogen, oxygen, and sulfur;

each $R^2$ is independently hydrogen, halogen, —OR, —CN, —NO$_2$, —N(R)$_2$, —C(O)OR, —SR, —S(O)R, —S(O)$_2$R, —C(O)N(R)$_2$, —N(R)C(O)R, —C(O)N(R)S(O)$_2$R, —C(O)N(OR)(R), or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, an 8-10 membered bicyclic aryl or heteroaryl with 1-4 heteroatoms independently selected from nitrogen, oxygen or sulfur, and a 5-6 membered heteroaryl ring having 1-4 heteroatoms independently selected from nitrogen, oxygen, and sulfur;

or two instances of $R^2$ are optionally taken together to form an oxo;

$L^1$ is a covalent bond or a C$_{1-6}$ bivalent saturated or unsaturated, straight or branched hydrocarbon chain wherein one or two methylene units of the chain are optionally and independently replaced by —C(R)$_2$—, —CH(R)—, —N(R)—, —N(R)C(O)—, —C(O)N(R)—, —N(C(O)R)C(O)—, —C(O)N(C(O)R)—, —N(R)C(O)N(R)—, —N(R)S(O)$_2$—, —S(O)$_2$N(R)—, —O—, —C(O)—, —OC(O)—, —C(O)O—, —S—, —S(O)—, or —S(O)$_2$—, wherein two R groups on the same carbon are optionally taken together to form a bivalent C$_{2-4}$ alkylene chain;

wherein each hydrogen bound to carbon can be optionally and independently replaced by deuterium;

each instance of m, n, and q, is independently 0, 1, 2, 3, or 4; and wherein the compound is other than a compound in Table 2.

In certain embodiments, the present invention provides inhibitors of ACLY. In some embodiments, such compounds include those of formula I:

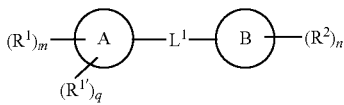

I or a pharmaceutically acceptable salt thereof, wherein:

Ring A is phenyl; naphthalenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur, or a 9-11 membered saturated or partially unsaturated bicyclic ring having 0-3 heteroatoms independently selected from nitrogen, oxygen, and sulfur;

each $R^1$ is independently hydrogen, halogen, —OR, —CN, —NO$_2$, —N(R)$_2$, —C(O)OR, —OC(O)R, —C(O)R, —OC(O)N(R)$_2$, —SR, —S(O)R, —S(O)$_2$R, —N(R)S(O)$_2$R, —C(O)N(R)$_2$, —C(O)N(OR)(R), or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur;

or two instances of $R^1$ are optionally taken together to form an oxo; or two $R^1$ groups are taken together with their intervening atoms to form an optionally substituted 4-7 membered saturated, partially unsaturated, or heteroaryl ring having 0-3 heteroatoms, in addition to the nitrogen, independently selected from nitrogen, oxygen, and sulfur;

each R is independently hydrogen, or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, a 5-6 membered heteroaryl ring having 1-4 heteroatoms independently selected from nitrogen, oxygen, and sulfur, and a bicyclic 9-11 membered saturated or partially unsaturated bicyclic heterocyclic ring having 1-4 heteroatoms independently selected from nitrogen, oxygen, and sulfur; or:

two R groups on the same nitrogen are taken together with their intervening atoms to form an optionally substituted 4-7 membered saturated, partially unsaturated, or heteroaryl ring having 0-3 heteroatoms, in addition to the nitrogen, independently selected from nitrogen, oxygen, and sulfur;

each $R^{1'}$ is independently hydrogen, halogen, —OR, —CN, —NO$_2$, —N(R)$_2$, —C(O)OR, —OC(O)R, —C(O)R, —OC(O)N(R)$_2$, —SR, —S(O)R, —S(O)$_2$R, —N(R)S(O)$_2$R, —C(O)N(R)$_2$, —C(O)N(OR)(R), or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur;

or two instances of $R^1$ are optionally taken together to form an oxo; or two $R^{1'}$ groups are taken together with their intervening atoms to form an optionally substituted 4-7 membered saturated, partially unsaturated, or heteroaryl ring having 0-3 heteroatoms, in addition to the nitrogen, independently selected from nitrogen, oxygen, and sulfur;

Ring B is phenyl; naphthalenyl; a 5-6 membered monocyclic heteroaryl ring having 1-4 heteroatoms independently selected from nitrogen, oxygen, and sulfur; an 8-10 membered bicyclic aryl or heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 8-10 membered saturated or partially unsaturated bicyclic heterocyclic ring having 1-4 heteroatoms independently selected from nitrogen, oxygen, and sulfur;

each $R^2$ is independently hydrogen, halogen, —OR, —CN, —NO$_2$, —N(R)$_2$, —C(O)OR, —SR, —S(O)R, —S(O)$_2$R, —C(O)N(R)$_2$, —N(R)C(O)R, —C(O)N(R)S(O)$_2$R, —C(O)N(OR)(R), or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, an 8-10 membered bicyclic aryl or heteroaryl with 1-4 heteroatoms independently selected from nitrogen, oxygen or sulfur, and a 5-6 membered heteroaryl ring having 1-4 heteroatoms independently selected from nitrogen, oxygen, and sulfur;

or two instances of $R^2$ are optionally taken together to form an oxo;

$L^1$ is a covalent bond or a $C_{1-6}$ bivalent saturated or unsaturated, straight or branched hydrocarbon chain wherein one or two methylene units of the chain are optionally and independently replaced by —C(R)$_2$—, —CH(R)—, —N(R)—, —N(S(O)$_2$R)—, —N(R)C(O)—, —C(O)N(R)—, —N(C(O)R)C(O)—, —C(O)N(C(O)R)—, —N(R)C(O)N(R)—, —N(R)S(O)$_2$—, —S(O)$_2$N(R)—, —O—, —C(O)—, —OC(O)—, —C(O)O—, —S—, —S(O)—, or —S(O)$_2$—, wherein two R groups on the same carbon are optionally taken together to form a bivalent $C_{2-4}$ alkylene chain;

wherein each hydrogen bound to carbon can be optionally and independently replaced by deuterium;

each instance of m, n, and q, is independently 0, 1, 2, 3, or 4; and wherein the compound is other than a compound in Table 2.

In certain embodiments, A' is optionally substituted $C_{1-6}$ aliphatic or A' is Ring A.

In certain embodiments, A' is optionally substituted $C_{1-6}$ aliphatic.

In certain embodiments, A' is selected from -Me,

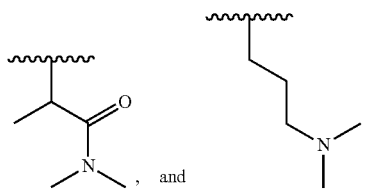

, and

In certain embodiments, A' is Ring A. As defined generally above, Ring A is phenyl; naphthalenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur, or a 9-11 membered saturated or partially unsaturated bicyclic ring having 0-3 heteroatoms independently selected from nitrogen, oxygen, and sulfur.

In some embodiments, Ring A is phenyl; naphthalenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur, or a 9-11 membered saturated or partially unsaturated bicyclic ring having 0-3 heteroatoms independently selected from nitrogen, oxygen, and sulfur.

In certain embodiments, Ring A is selected from:

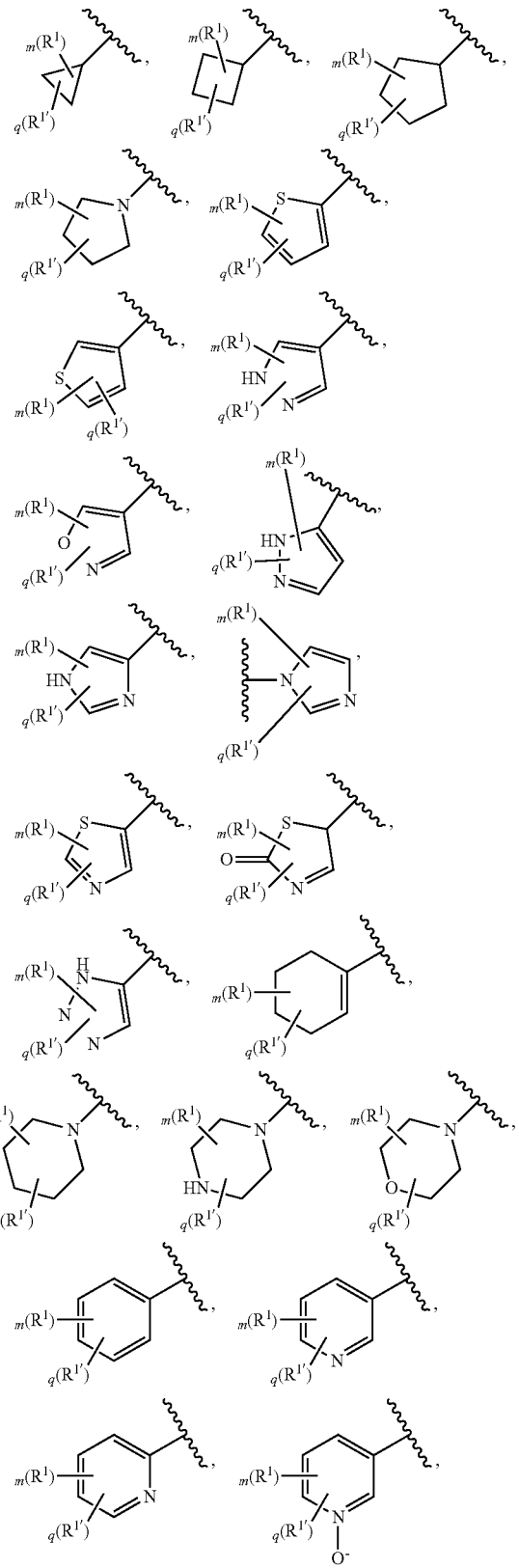

-continued
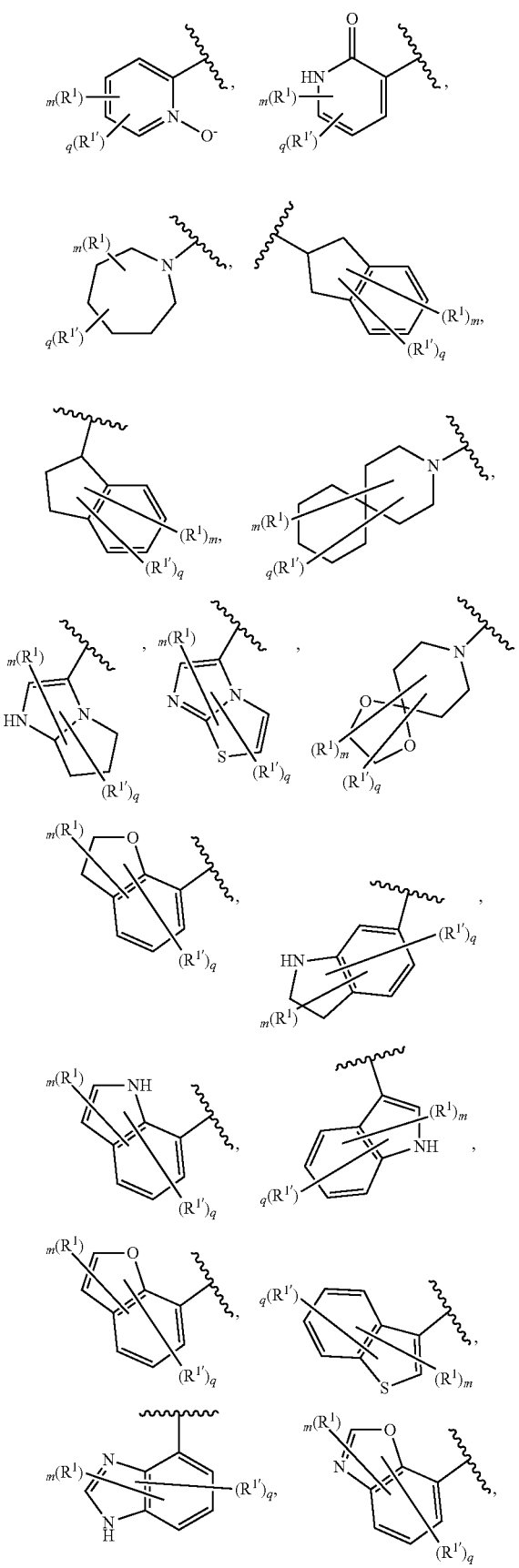
-continued
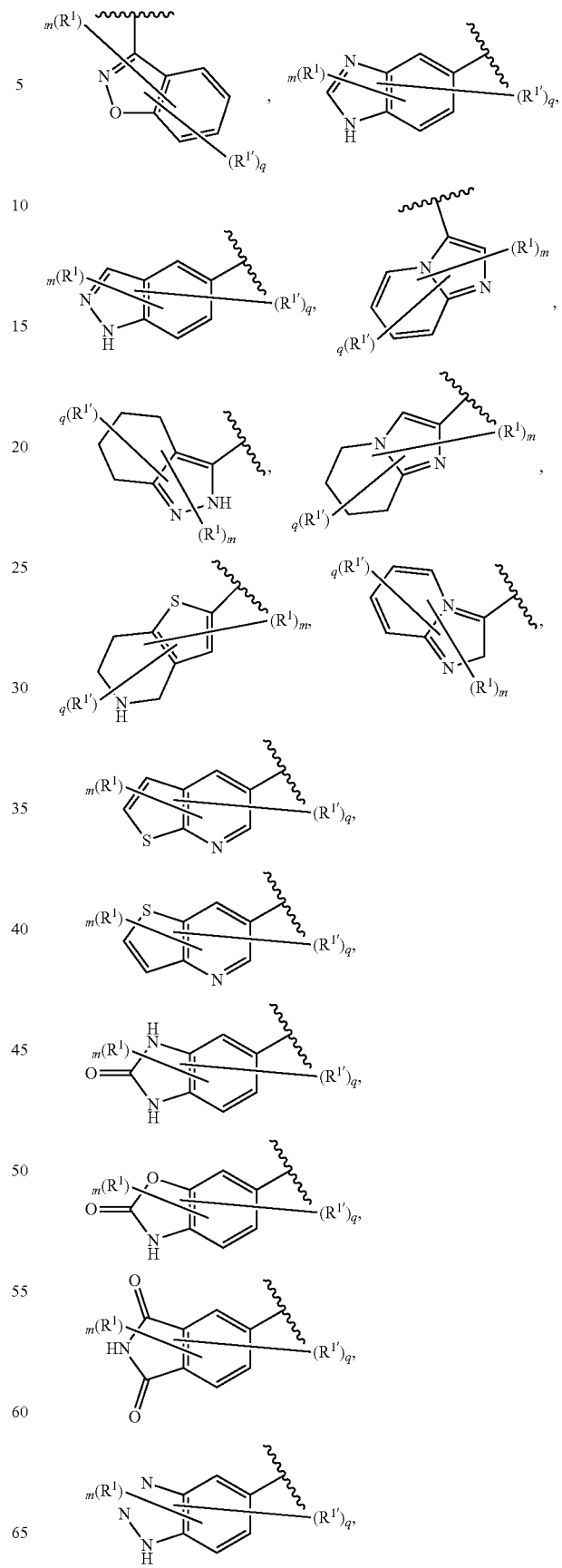

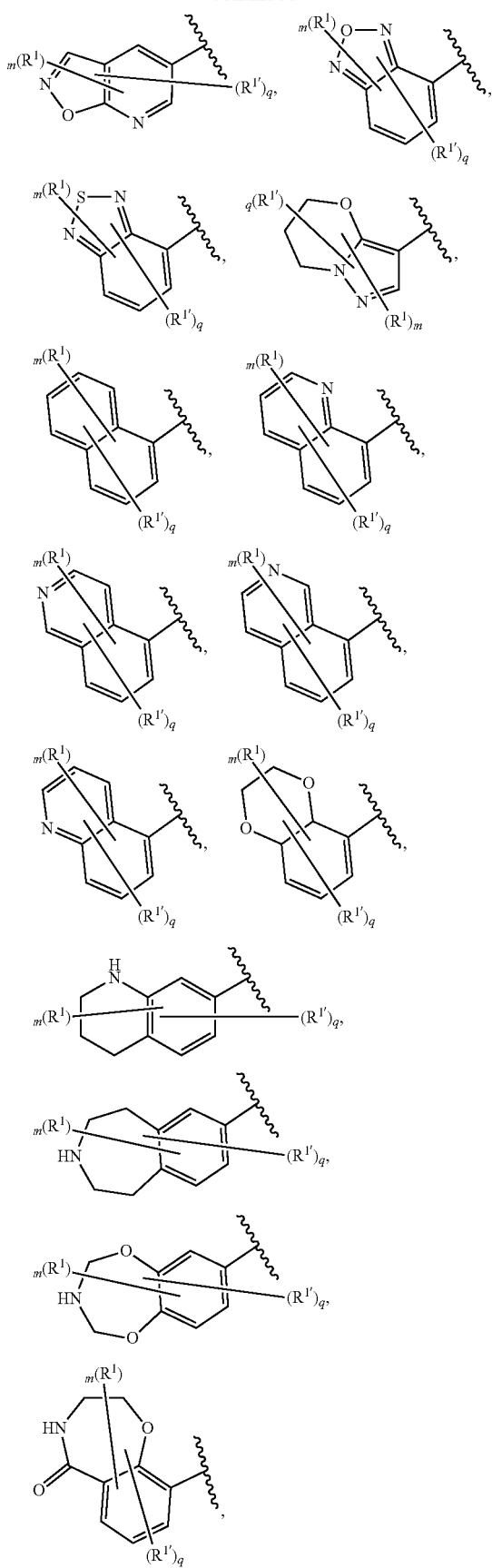

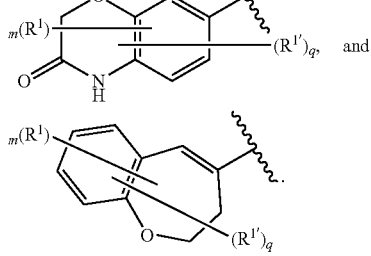

In some embodiments, Ring A is selected from those depicted in Table 1, below.

As defined generally above, each $R^1$ is independently hydrogen, halogen, —OR, —CN, —NO$_2$, —N(R)$_2$, —C(O)OR, —OC(O)R, —C(O)R, —OC(O)N(R)$_2$, —SR, —S(O)R, —S(O)$_2$R, —N(R)S(O)$_2$R, —C(O)N(R)$_2$, —C(O)N(OR)(R), or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or two instances of $R^1$ are optionally taken together to form an oxo.

In some embodiments, each $R^1$ is independently hydrogen, halogen, —OR, —CN, —NO$_2$, —N(R)$_2$, —C(O)OR, —OC(O)R, —C(O)R, —OC(O)N(R)$_2$, —SR, —S(O)R, —S(O)$_2$R, —N(R)S(O)$_2$R, —C(O)N(R)$_2$, or —C(O)N(OR)(R). In some embodiments, $R^1$ is an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, two instances of $R^1$ are optionally taken together to form an oxo.

In some embodiments, each $R^1$ is independently hydrogen, —F, —Cl, —Br, -Me, -Et, -t-Bu, —CF$_3$, —NH$_2$, —N(Me)$_2$, —NO$_2$, —OH, —OMe, —OEt, —OBn, —CN, —C(O)Me, —C(O)Et, —C(O)NH$_2$, —C(O)OH, —C(O)OMe, —C(O)OEt, —S(O)$_2$Me,

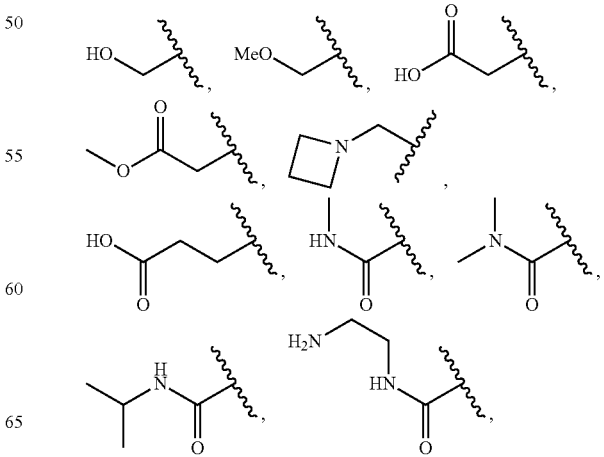

-continued
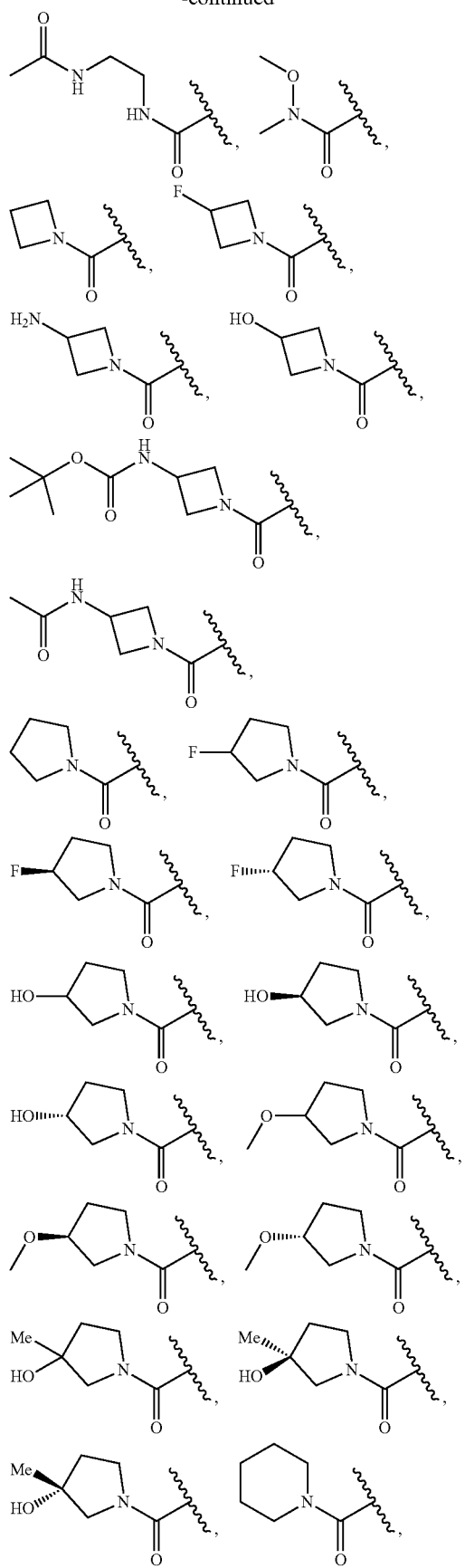
-continued
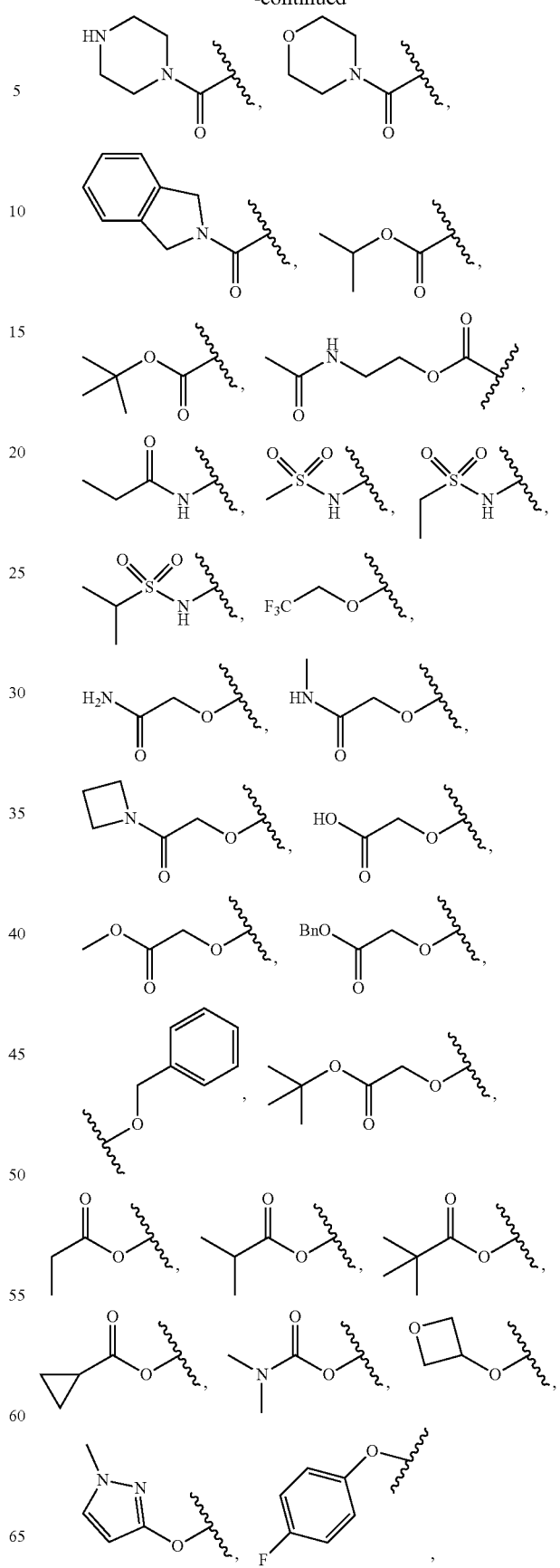

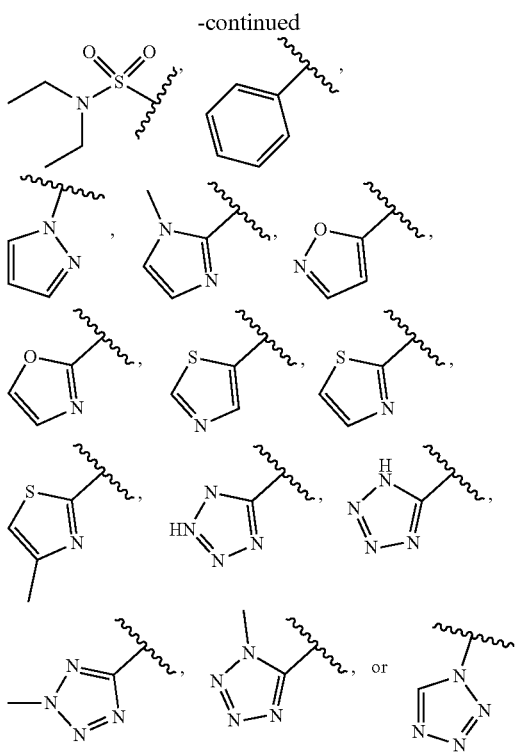

In some embodiments, $R^1$ is selected from those depicted in Table 1, below.

As defined generally above, each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, a 5-6 membered heteroaryl ring having 1-4 heteroatoms independently selected from nitrogen, oxygen, and sulfur, and a bicyclic 9-11 membered saturated or partially unsaturated bicyclic heterocyclic ring having 1-4 heteroatoms independently selected from nitrogen, oxygen, and sulfur, or two R groups on the same nitrogen are taken together with their intervening atoms to form an optionally substituted 4-7 membered saturated, partially unsaturated, or heteroaryl ring having 0-3 heteroatoms, in addition to the nitrogen, independently selected from nitrogen, oxygen, and sulfur.

In some embodiments, R is hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, a 5-6 membered heteroaryl ring having 1-4 heteroatoms independently selected from nitrogen, oxygen, and sulfur, and a bicyclic 9-11 membered saturated or partially unsaturated bicyclic heterocyclic ring having 1-4 heteroatoms independently selected from nitrogen, oxygen, and sulfur.

In some embodiments, two R groups on the same nitrogen are taken together with their intervening atoms to form an optionally substituted 4-7 membered saturated, partially unsaturated, or heteroaryl ring having 0-3 heteroatoms, in addition to the nitrogen, independently selected from nitrogen, oxygen, and sulfur.

In some embodiments, R is selected from those depicted in Table 1, below.

As depicted generally above, each $R^{1'}$ is independently hydrogen, halogen, —OR, —CN, —NO$_2$, —N(R)$_2$, —C(O) OR, —OC(O)R, —C(O)R, —OC(O)N(R)$_2$, —SR, —S(O) R, —S(O)$_2$R, —N(R)S(O)$_2$R, —S(O)$_2$N(R)$_2$, —C(O) N(R)$_2$, —C(O)N(OR)(R), or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or two instances of $R^{1'}$ are optionally taken together to form an oxo.

In some embodiments, $R^{1'}$ is hydrogen, halogen, —OR, —CN, —NO$_2$, —N(R)$_2$, —C(O)OR, —OC(O)R, —C(O)R, —OC(O)N(R)$_2$, —SR, —S(O)R, —S(O)$_2$R, —N(R)S(O)$_2$ R, —S(O)$_2$N(R)$_2$, —C(O)N(R)$_2$, or —C(O)N(OR)(R). In some embodiments, $R^{1'}$ is an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, two instances of $R^{1'}$ are optionally taken together to form an oxo.

In some embodiments, each $R^{1'}$ is independently hydrogen, —F, —Cl, —Br, -Me, -Et, -t-Bu, —CF$_3$, —NH$_2$, —NO$_2$, —OH, —OMe, —OEt, —OBn, —CN, —C(O)Me, —C(O)Et, —C(O)NH$_2$, —C(O)OH, —C(O)OMe, —C(O) OEt, —S(O)$_2$Me,

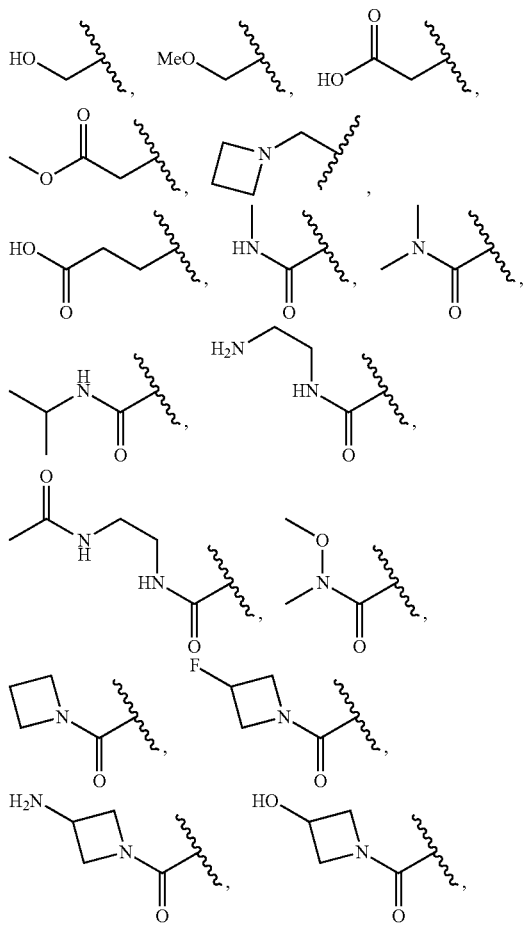

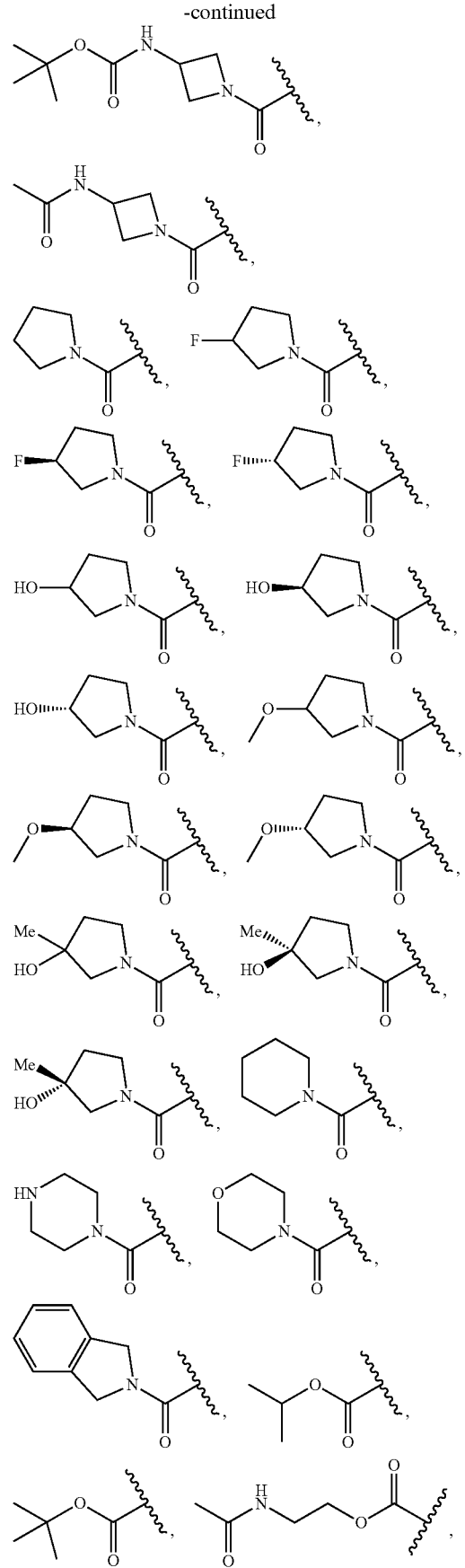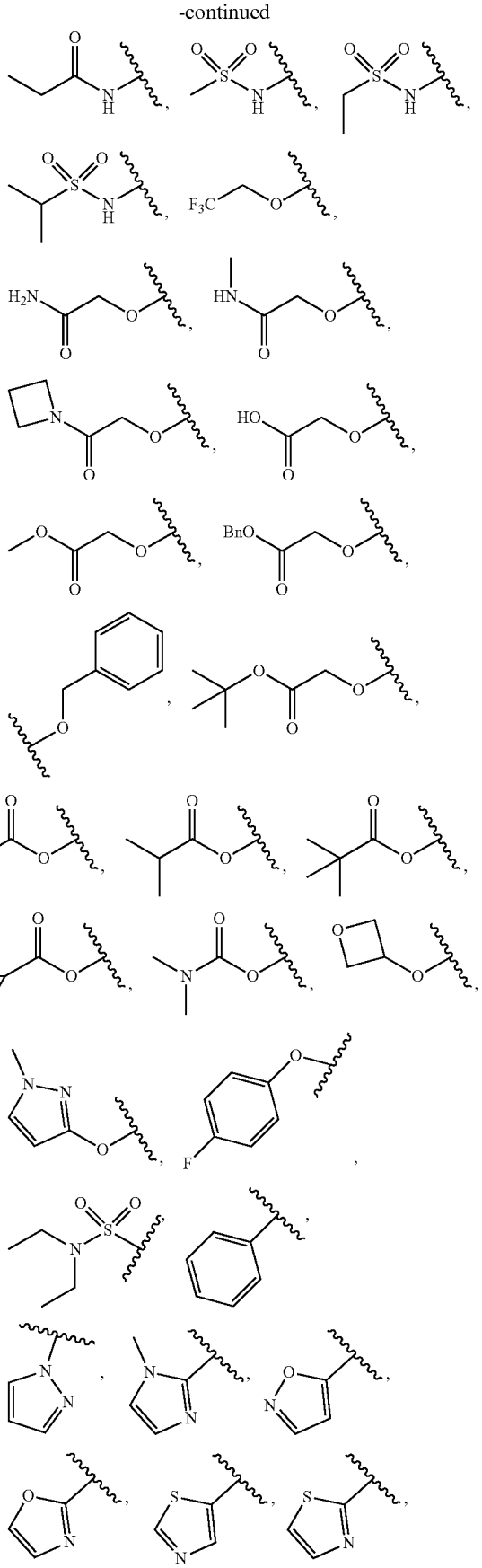

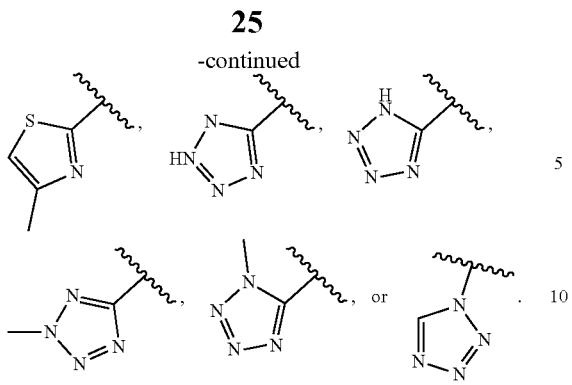

In some embodiments, $R^{1'}$ is selected from those depicted in Table 1, below.

As defined generally above, Ring B is phenyl; naphthalenyl; a 5-6 membered monocyclic heteroaryl ring having 1-4 heteroatoms independently selected from nitrogen, oxygen, and sulfur; an 8-10 membered bicyclic aryl or heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 8-10 membered saturated or partially unsaturated bicyclic heterocyclic ring having 1-4 heteroatoms independently selected from nitrogen, oxygen, and sulfur.

In some embodiments, Ring B is phenyl; naphthalenyl; a 5-6 membered monocyclic heteroaryl ring having 1-4 heteroatoms independently selected from nitrogen, oxygen, and sulfur; an 8-10 membered bicyclic aryl or heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 8-10 membered saturated or partially unsaturated bicyclic heterocyclic ring having 1-4 heteroatoms independently selected from nitrogen, oxygen, and sulfur.

In certain embodiments, Ring B is selected from

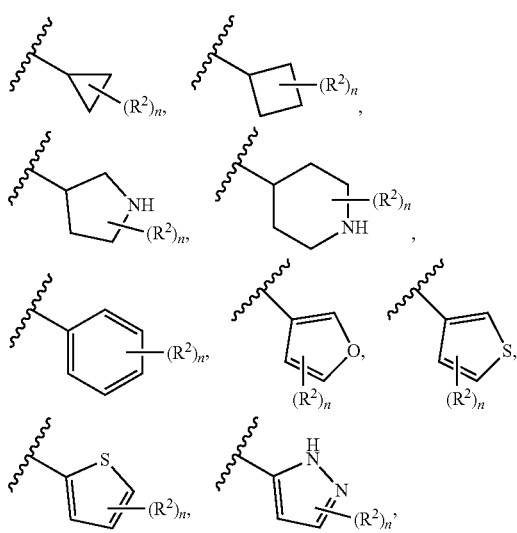

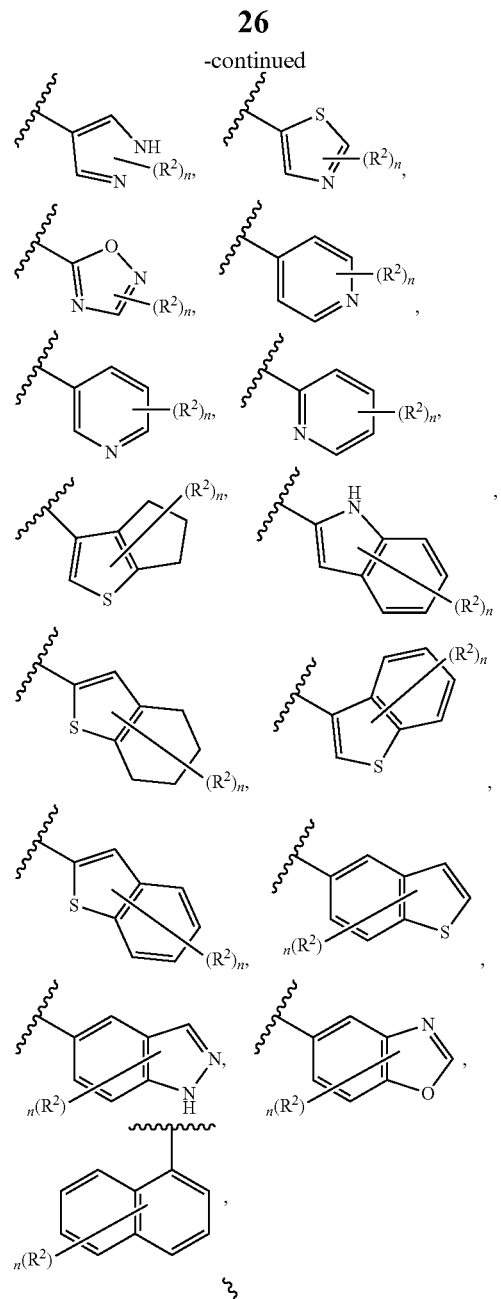

In some embodiments, Ring B is selected from those depicted in Table 1, below.

As defined generally above, each $R^2$ is independently hydrogen, halogen, —OR, —CN, —$NO_2$, —$N(R)_2$, —C(O)OR, —SR, —S(O)R, —S(O)$_2$R, —C(O)N(R)$_2$, —N(R)C(O)R, —C(O)N(R)S(O)$_2$R, —C(O)N(OR)(R), or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, an 8-10 membered bicyclic aryl or heteroaryl with 1-4 heteroatoms independently selected from nitrogen, oxygen or sulfur, and a 5-6 membered heteroaryl ring having 1-4 heteroatoms independently selected from nitrogen, oxygen, and sulfur, or two instances of $R^2$ are optionally taken together to form an oxo.

In some embodiments, each $R^2$ is independently hydrogen, halogen, —OR, —CN, —NO$_2$, —N(R)$_2$, —C(O)OR, —SR, —S(O)R, —S(O)$_2$R, —C(O)N(R)$_2$, —N(R)C(O)R, —C(O)N(R)S(O)$_2$R, or —C(O)N(OR)(R).

In some embodiments, each $R^2$ is independently an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, an 8-10 membered bicyclic aryl or heteroaryl with 1-4 heteroatoms independently selected from nitrogen, oxygen or sulfur, and a 5-6 membered heteroaryl ring having 1-4 heteroatoms independently selected from nitrogen, oxygen, and sulfur.

In some embodiments, two instances of $R^2$ are optionally taken together to form an oxo.

In certain embodiments, each $R^2$ is independently selected from hydrogen, —F, —Cl, —Br, -Me, -i-Pr, —CF$_3$, —NH$_2$, —OH, —OMe, —OCF$_3$, —C(O)NH$_2$, —C(O)OH, —C(O)OMe,

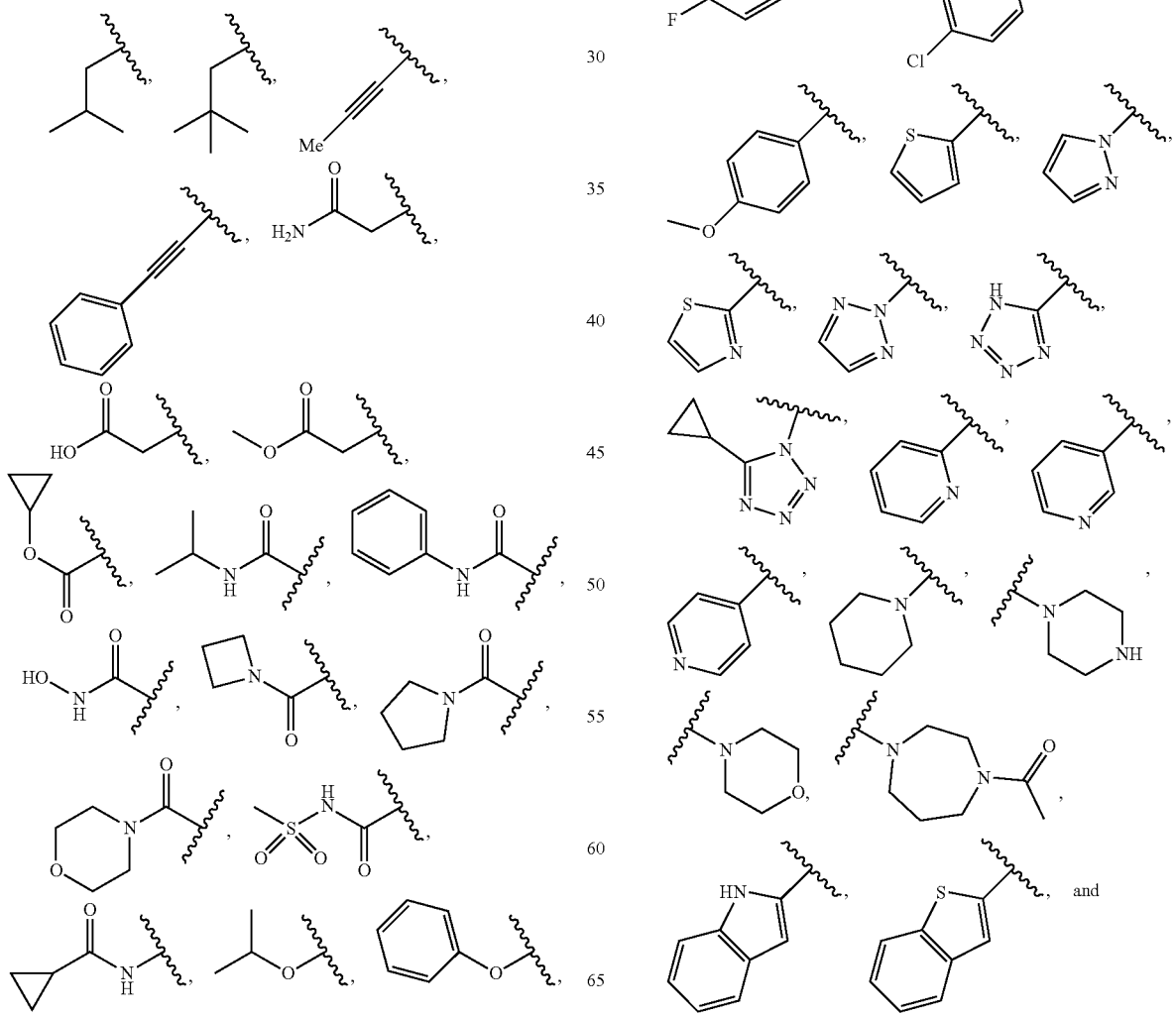

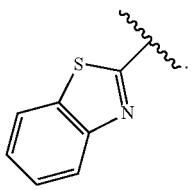

In some embodiments, R² is selected from those depicted in Table 1, below.

As defined generally above, L¹ is a covalent bond or a C₁₋₆ bivalent saturated or unsaturated, straight or branched hydrocarbon chain wherein one or two methylene units of the chain are optionally and independently replaced by —C(R)₂—, —CH(R)—, —N(R)—, —N(R)C(O)—, —C(O)N(R)—, —N(C(O)R)C(O)—, —C(O)N(C(O)R)—, —N(R)C(O)N(R)—, —N(R)S(O)₂—, —S(O)₂N(R)—, —O—, —C(O)—, —OC(O)—, —C(O)O—, —S—, —S(O)—, or —S(O)₂—, wherein two R groups on the same carbon are optionally taken together to form a bivalent C₂₋₄ alkylene chain.

In some embodiments, L¹ is a covalent bond. In some embodiments, L¹ is a C₁₋₆ bivalent saturated or unsaturated, straight or branched hydrocarbon chain wherein one or two methylene units of the chain are optionally and independently replaced by —C(R)₂—, —CH(R)—, —N(R)—, —N(S(O)₂R)—, —N(R)C(O)—, —C(O)N(R)—, —N(C(O)R)C(O)—, —C(O)N(C(O)R)—, —N(R)C(O)N(R)—, —N(R)S(O)₂—, —S(O)₂N(R)—, —O—, —C(O)—, —OC(O)—, —C(O)O—, —S—, —S(O)—, or —S(O)₂—, wherein two R groups on the same carbon are optionally taken together to form a bivalent C₂₋₄ alkylene chain.

In some embodiments, L¹ is selected from —SCH₂—, —S(O)₂CH₂—, —S(O)₂N(R)—, —S(O)₂N(R)—CH₂—, —S(O)₂N(R)—CH₂CH₂—, —S(O)₂N(R)—CH(Me)-, —S(O)₂N(R)—CH₂C(Me)(Me)-, —CH₂—S(O)₂N(R)—, —CH₂—N(S(O)₂Me)-, —CH₂CH₂—S(O)₂N(R)—, —CH₂CH₂CH₂—S(O)₂N(R)—, —N(R)S(O)₂—, —CH₂S—, —CH₂S(O)₂—, —CH₂—N(R)S(O)₂—, —CH₂CH₂—N(R)S(O)₂—, —CH(Me)-N(R)S(O)₂—, —C(Me)(Me)CH₂—N(R) S(O)₂—, —N(R)CH₂—, —N(R)S(O)₂CH₂—, —N(R)S(O)₂CH₂CH₂—, —N(R)S(O)₂CH₂CH₂CH₂—, —N(R)CH₂—, —N(R)C(O)—, —N(R)C(O)—CH₂—, —CH₂—N(R)C(O)—, —C(O)N(R)—, —N(R)S(O)₂N(Me)-, and

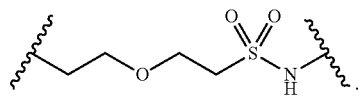 [SMILES: *CCOCCS(=O)(=O)N*]

In certain embodiments of L¹, each R is independently -Me, -Et, —SO₂Me,

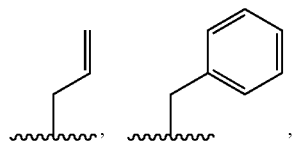

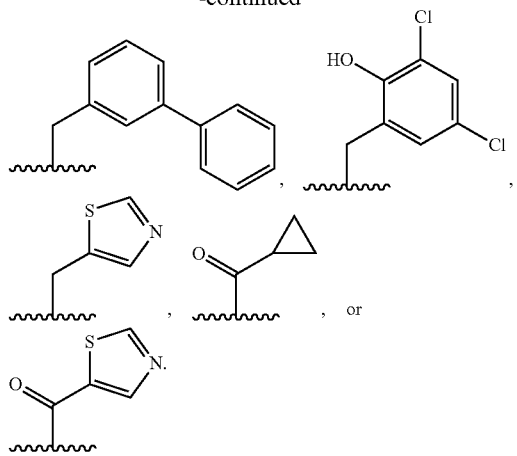

In some embodiments, L¹ is selected from —SCH₂—, —S(O)₂CH₂—, —S(O)₂NH—, —S(O)₂NH—CH₂—, —S(O)₂NH—CH₂CH₂—, —S(O)₂NH—CH(Me)-, —S(O)₂ NH—CH₂C(Me)(Me)-, —CH₂—S(O)₂NH—, —CH₂CH₂—S(O)₂NH—, —CH₂CH₂CH₂—S(O)₂NH—, —NHS(O)₂—, —CH₂S—, —CH₂S(O)₂—, —CH₂—NHS(O)₂—, —CH₂CH₂—NHS(O)₂—, —CH(Me)-NHS(O)₂—, —C(Me)(Me)CH₂—NHS(O)₂—, —NHCH₂—, —NHS(O)₂ CH₂—, —NHS(O)₂CH₂CH₂—, —NHS(O)₂ CH₂CH₂CH₂—, —NH—CH₂—, —NHC(O)—, —NHC(O)—CH₂—, —CH₂—NHC(O)—, —C(O)NH—, —NHS(O)₂N(Me)-, and

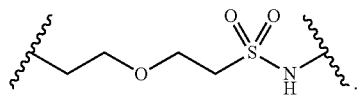 [SMILES: *CCOCCS(=O)(=O)N*]

In some embodiments, L¹ is selected from those depicted in Table 1, below.

As defined generally above, each hydrogen bound to carbon can be optionally and independently replaced by deuterium.

In some embodiments, a hydrogen bound to carbon is optionally and independently replaced by deuterium.

In some embodiments, a hydrogen bound to carbon that is replaced by deuterium is selected from those depicted in Table 1, below.

As defined generally above each instance of m, n, and q, is independently 0, 1, 2, 3, or 4.

In some embodiments, m is 0. In some embodiments, m is 1. In some embodiments, m is 2. In some embodiments, m is 3. In some embodiments, m is 4.

In some embodiments, m is selected from those depicted in Table 1, below.

In some embodiments, n is 0. In some embodiments, n is 1. In some embodiments, n is 2. In some embodiments, n is 3. In some embodiments, n is 4.

In some embodiments, n is selected from those depicted in Table 1, below.

In some embodiments, q is 0. In some embodiments, q is 1. In some embodiments, q is 2. In some embodiments, q is 3. In some embodiments, q is 4.

In some embodiments, q is selected from those depicted in Table 1, below.

As defined generally above, a compound of formula I is other than a compound in Table 2, below.

In certain embodiments, the present invention provides a compound of formula I, wherein Ring A is phenyl, $L^1$ is —S(O)$_2$NH—, and m is 2, 3, or 4 to form a compound of formula I-a:

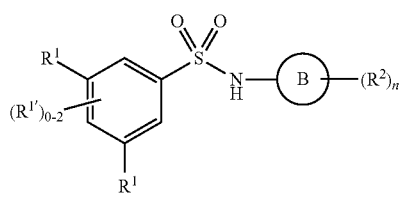

I-a or a pharmaceutically acceptable salt thereof, wherein at least one $R^1$ group is other than chloro and each of Ring B, $R^{1'}$, $R^2$ and n is as described in embodiments for formula I, supra, or described in embodiments herein, both singly and in combination.

In certain embodiments, the invention provides for a compound of formula I-a, wherein when both $R^1$ groups are Cl, and $R^{1'}$ is ortho OH (relative to sulfonamide), then ring B is not

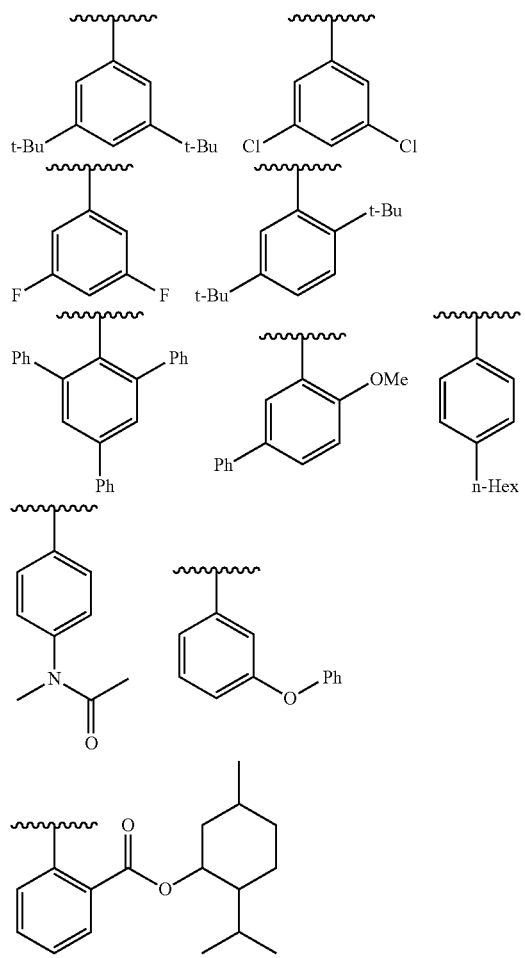

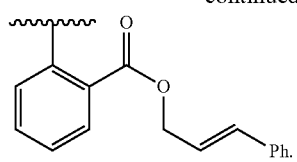

In certain embodiments, the present invention provides a compound of formula I, wherein Ring A is pyridone, $L^1$ is —S(O)$_2$NH—, and m is 3 or 4 to form a compound of formula I-b:

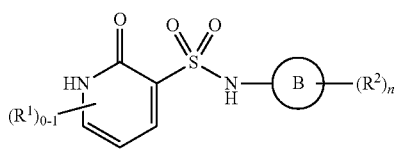

I-b or a pharmaceutically acceptable salt thereof, wherein at least one $R^1$ group meta to the —S(O)$_2$NH— linker is other than chloro and Ring B, $R^2$ and n are as defined above.

In certain embodiments, the present invention provides a compound of formula II:

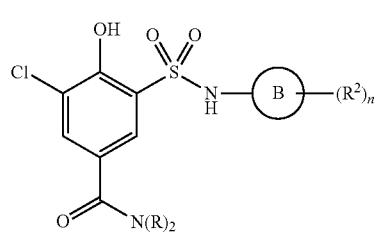

II or a pharmaceutically acceptable salt thereof, wherein each of Ring B, R, $R^2$ and n is as described in embodiments for formula I, supra, or described in embodiments herein, both singly and in combination.

In certain embodiments, the present invention provides a compound of formula II, wherein Ring B is phenyl, thereby providing a compound of formula II-a:

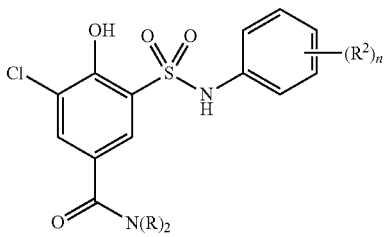

II-a or a pharmaceutically acceptable salt thereof, wherein each of R, $R^2$ and n is as described in embodiments for formula I, supra, or described in embodiments herein, both singly and in combination.

Exemplary compounds of formula I are set forth in Table 1, below:

TABLE 1

Exemplary Compounds of Formula I

| | |
|---|---|
| (structure) | I-1 |
| (structure) | I-2 |
| (structure) | I-3 |
| (structure) | I-4 |
| (structure) | I-5 |
| (structure) | I-6 |

TABLE 1-continued
Exemplary Compounds of Formula I
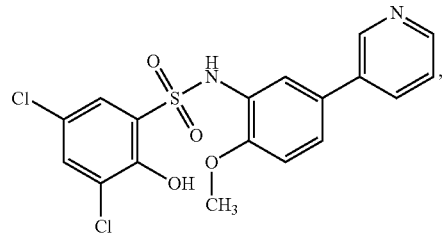 [SMILES: COc1ccc(-c2cccnc2)cc1NS(=O)(=O)c1cc(Cl)cc(Cl)c1O]
I-7
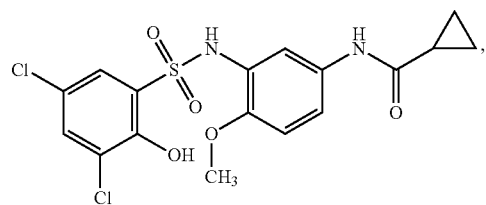 [SMILES: COc1ccc(NC(=O)C2CC2)cc1NS(=O)(=O)c1cc(Cl)cc(Cl)c1O]
I-8
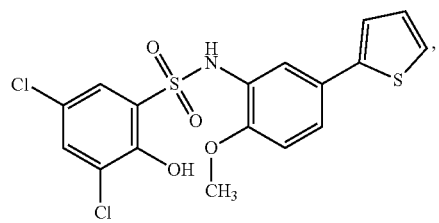 [SMILES: COc1ccc(-c2cccs2)cc1NS(=O)(=O)c1cc(Cl)cc(Cl)c1O]
I-9
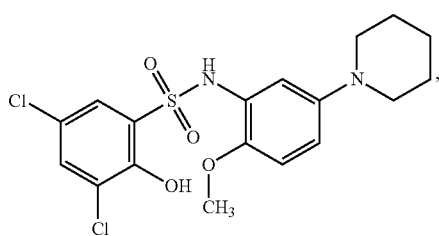 [SMILES: COc1ccc(N2CCCCC2)cc1NS(=O)(=O)c1cc(Cl)cc(Cl)c1O]
I-10
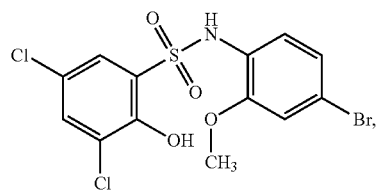 [SMILES: COc1cc(Br)ccc1NS(=O)(=O)c1cc(Cl)cc(Cl)c1O]
I-11
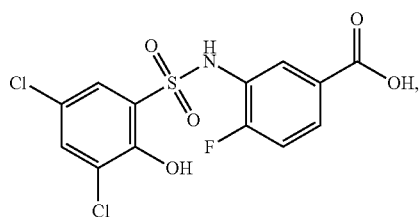 [SMILES: O=C(O)c1ccc(F)c(NS(=O)(=O)c2cc(Cl)cc(Cl)c2O)c1]
I-12
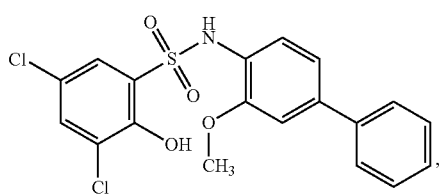 [SMILES: COc1cc(-c2ccccc2)ccc1NS(=O)(=O)c1cc(Cl)cc(Cl)c1O]
I-13

TABLE 1-continued
Exemplary Compounds of Formula I
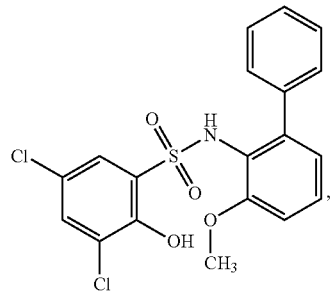 [SMILES: COc1cccc(-c2ccccc2)c1NS(=O)(=O)c1cc(Cl)cc(Cl)c1O]
I-14
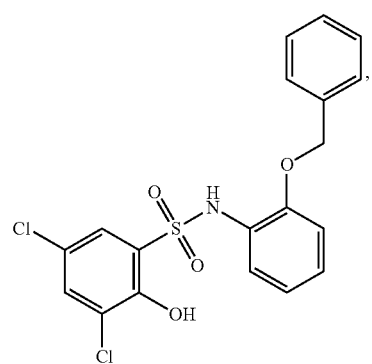 [SMILES: O=S(=O)(Nc1ccccc1OCc1ccccc1)c1cc(Cl)cc(Cl)c1O]
I-15
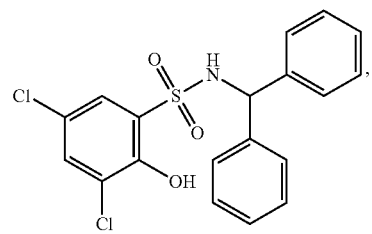 [SMILES: O=S(=O)(NC(c1ccccc1)c1ccccc1)c1cc(Cl)cc(Cl)c1O]
I-16
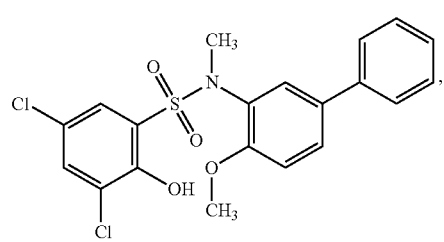 [SMILES: COc1ccc(-c2ccccc2)cc1N(C)S(=O)(=O)c1cc(Cl)cc(Cl)c1O]
I-17
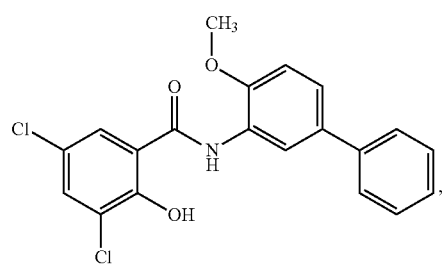 [SMILES: COc1ccc(-c2ccccc2)cc1NC(=O)c1cc(Cl)cc(Cl)c1O]
I-18

TABLE 1-continued
Exemplary Compounds of Formula I
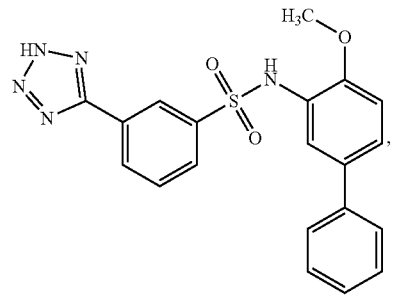 [SMILES: COc1ccc(-c2ccccc2)cc1NS(=O)(=O)c1cccc(-c2nn[nH]n2)c1]
I-19
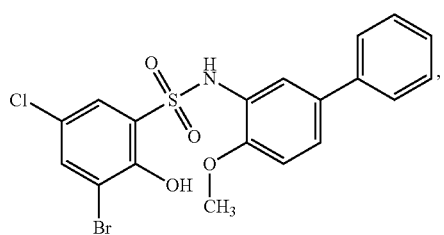 [SMILES: COc1ccc(-c2ccccc2)cc1NS(=O)(=O)c1cc(Cl)cc(Br)c1O]
I-20
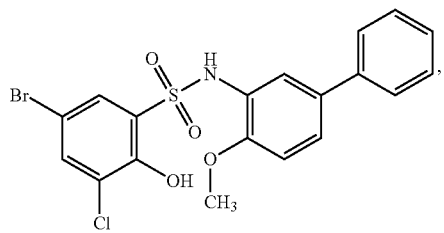
I-21
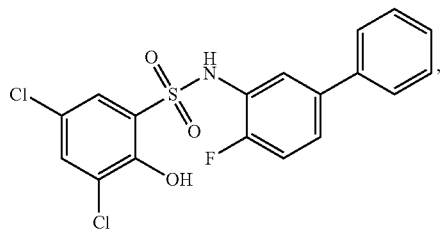 [SMILES: O=S(=O)(Nc1cc(-c2ccccc2)ccc1F)c1cc(Cl)cc(Cl)c1O]
I-22
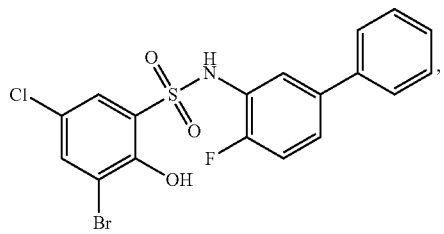 [SMILES: O=S(=O)(Nc1cc(-c2ccccc2)ccc1F)c1cc(Cl)cc(Br)c1O]
I-23
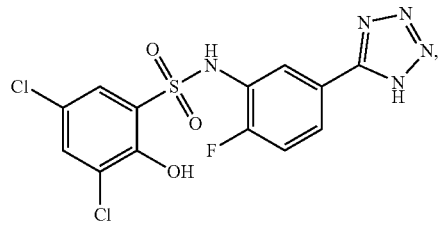 [SMILES: O=S(=O)(Nc1cc(-c2nnn[nH]2)ccc1F)c1cc(Cl)cc(Cl)c1O]
I-24

TABLE 1-continued
Exemplary Compounds of Formula I
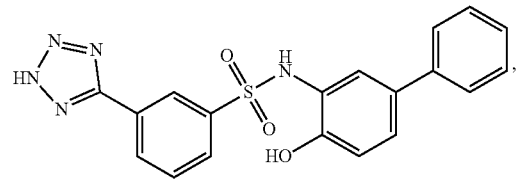 [SMILES: O=S(=O)(Nc1cc(-c2ccccc2)ccc1O)c1cccc(-c2nn[nH]n2)c1]
I-25
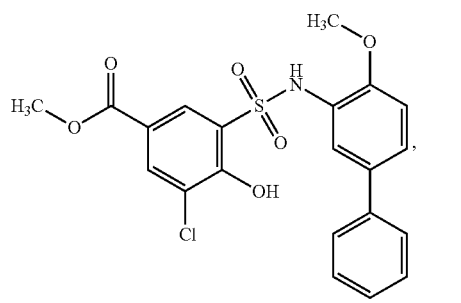 [SMILES: COC(=O)c1cc(Cl)c(O)c(S(=O)(=O)Nc2cc(-c3ccccc3)ccc2OC)c1]
I-26
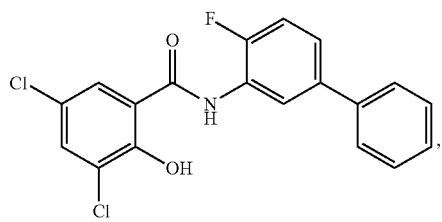 [SMILES: O=C(Nc1cc(-c2ccccc2)ccc1F)c1cc(Cl)cc(Cl)c1O]
I-27
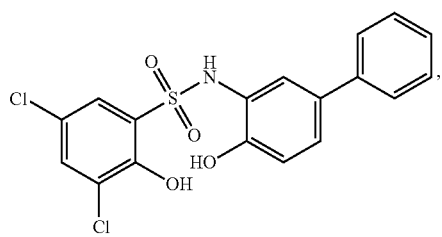 [SMILES: O=S(=O)(Nc1cc(-c2ccccc2)ccc1O)c1cc(Cl)cc(Cl)c1O]
I-28
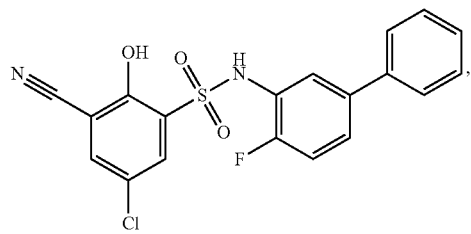 [SMILES: N#Cc1cc(Cl)cc(S(=O)(=O)Nc2cc(-c3ccccc3)ccc2F)c1O]
I-29
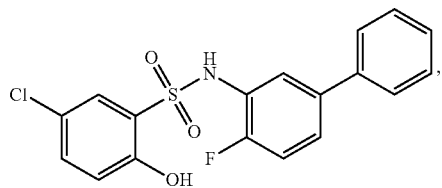 [SMILES: O=S(=O)(Nc1cc(-c2ccccc2)ccc1F)c1cc(Cl)ccc1O]
I-30

TABLE 1-continued
Exemplary Compounds of Formula I
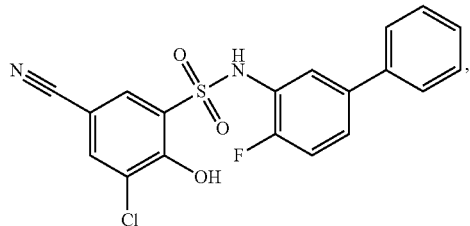 [SMILES: N#Cc1cc(Cl)c(O)c(S(=O)(=O)Nc2cc(-c3ccccc3)ccc2F)c1] I-31
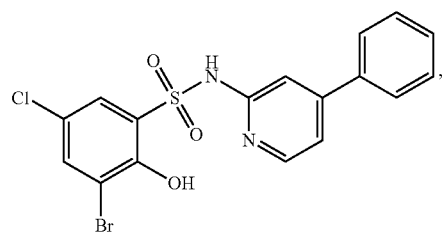 [SMILES: O=S(=O)(Nc1cc(-c2ccccc2)ccn1)c1cc(Cl)cc(Br)c1O] I-32
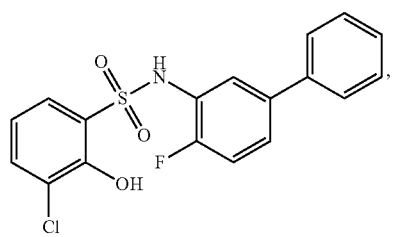 [SMILES: O=S(=O)(Nc1cc(-c2ccccc2)ccc1F)c1cccc(Cl)c1O] I-33
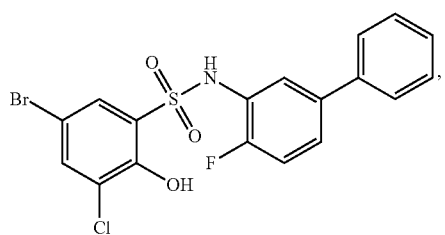 [SMILES: O=S(=O)(Nc1cc(-c2ccccc2)ccc1F)c1cc(Br)cc(Cl)c1O] I-34
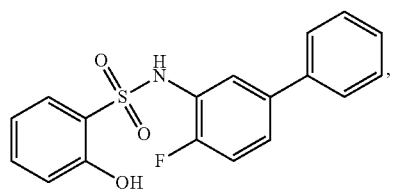 [SMILES: O=S(=O)(Nc1cc(-c2ccccc2)ccc1F)c1ccccc1O] I-35
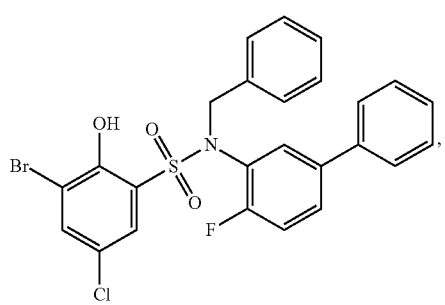 [SMILES: O=S(=O)(c1cc(Cl)cc(Br)c1O)N(Cc1ccccc1)c1cc(-c2ccccc2)ccc1F] I-36

TABLE 1-continued
Exemplary Compounds of Formula I
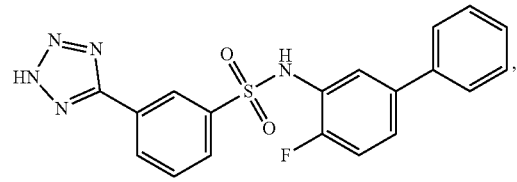 [SMILES: O=S(=O)(Nc1cc(-c2ccccc2)ccc1F)c1cccc(-c2nn[nH]n2)c1]
I-37
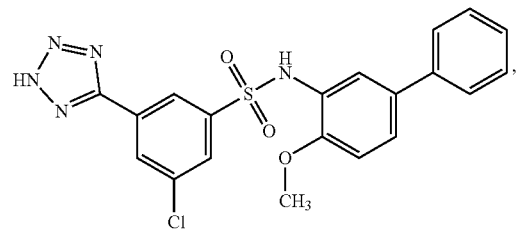 [SMILES: COc1ccc(-c2ccccc2)cc1NS(=O)(=O)c1cc(Cl)cc(-c2nn[nH]n2)c1]
I-38
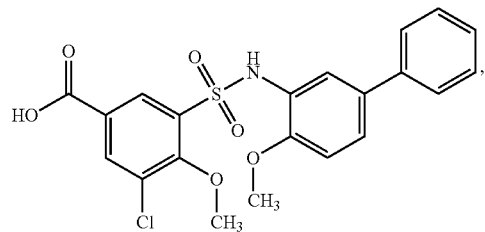 [SMILES: COc1ccc(-c2ccccc2)cc1NS(=O)(=O)c1cc(C(=O)O)cc(Cl)c1OC]
I-39
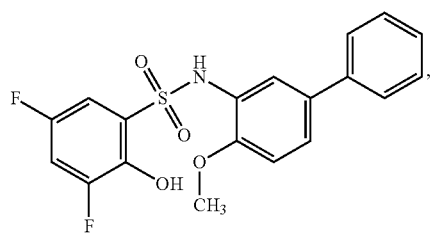 [SMILES: COc1ccc(-c2ccccc2)cc1NS(=O)(=O)c1cc(F)cc(F)c1O]
I-40
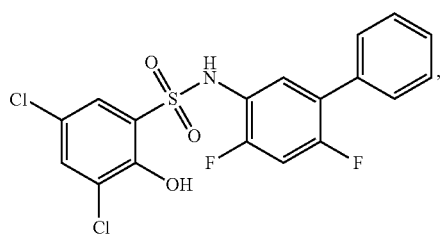 [SMILES: O=S(=O)(Nc1cc(-c2ccccc2)c(F)cc1F)c1cc(Cl)cc(Cl)c1O]
I-41
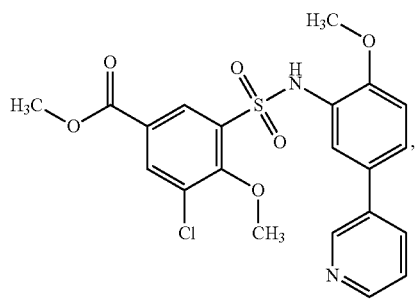 [SMILES: COC(=O)c1cc(Cl)c(OC)c(S(=O)(=O)Nc2cc(-c3cccnc3)ccc2OC)c1]
I-42

TABLE 1-continued
Exemplary Compounds of Formula I
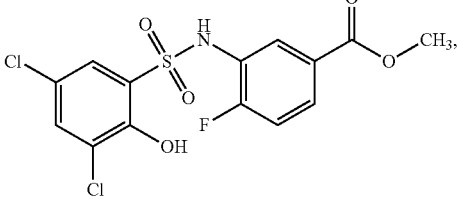 I-43
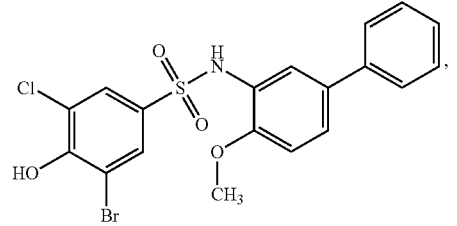 [SMILES: COc1ccc(-c2ccccc2)cc1NS(=O)(=O)c1cc(Cl)c(O)c(Br)c1] I-44
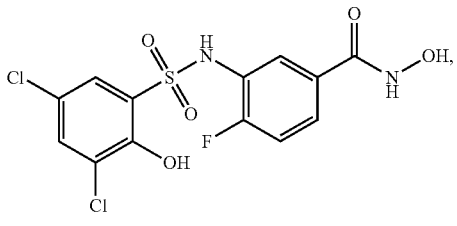 [SMILES: O=C(NO)c1ccc(F)c(NS(=O)(=O)c2cc(Cl)cc(Cl)c2O)c1] I-45
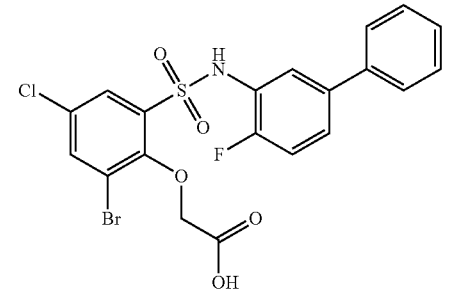 [SMILES: O=C(O)COc1c(Br)cc(Cl)cc1S(=O)(=O)Nc1cc(-c2ccccc2)ccc1F] I-46
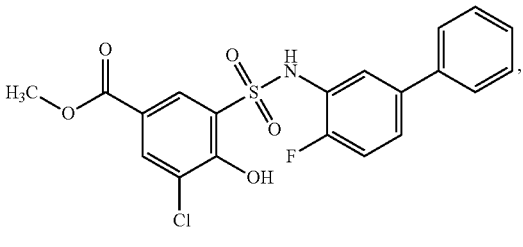 [SMILES: COC(=O)c1cc(Cl)c(O)c(S(=O)(=O)Nc2cc(-c3ccccc3)ccc2F)c1] I-47
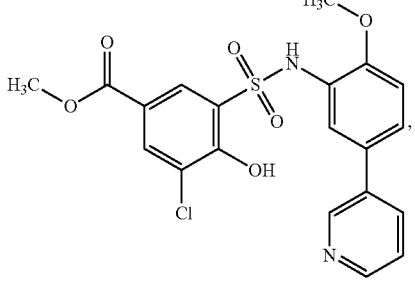 I-48

TABLE 1-continued
Exemplary Compounds of Formula I
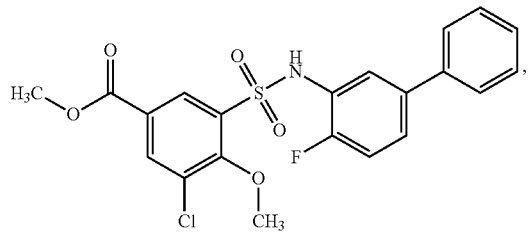 [SMILES: COC(=O)c1cc(Cl)c(OC)c(S(=O)(=O)Nc2cc(-c3ccccc3)ccc2F)c1]
I-49
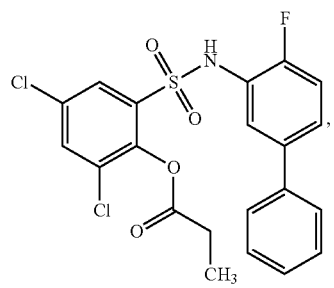 [SMILES: CCC(=O)Oc1c(Cl)cc(Cl)cc1S(=O)(=O)Nc1cc(-c2ccccc2)ccc1F]
I-50
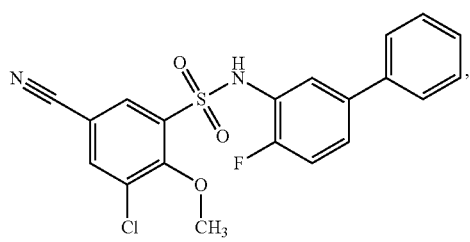 [SMILES: COc1c(Cl)cc(C#N)cc1S(=O)(=O)Nc1cc(-c2ccccc2)ccc1F]
I-51
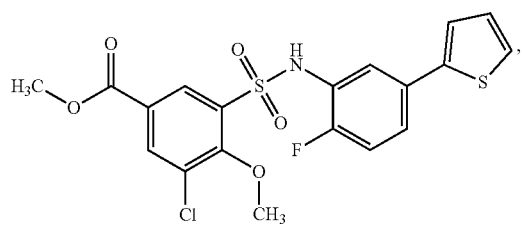 [SMILES: COC(=O)c1cc(Cl)c(OC)c(S(=O)(=O)Nc2cc(-c3cccs3)ccc2F)c1]
I-52
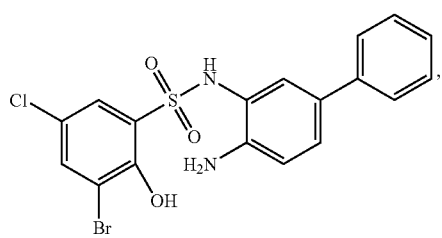 [SMILES: Nc1ccc(-c2ccccc2)cc1NS(=O)(=O)c1cc(Cl)cc(Br)c1O]
I-53
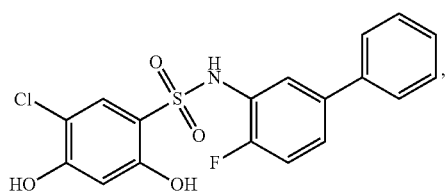 [SMILES: O=S(=O)(Nc1cc(-c2ccccc2)ccc1F)c1cc(Cl)c(O)cc1O]
I-54

TABLE 1-continued
Exemplary Compounds of Formula I
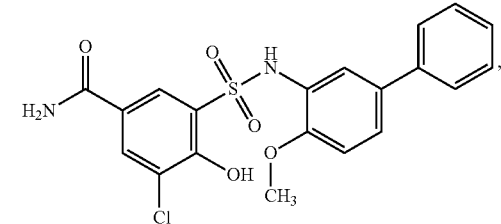 [SMILES: COc1ccc(-c2ccccc2)cc1NS(=O)(=O)c1cc(C(N)=O)cc(Cl)c1O]
I-55
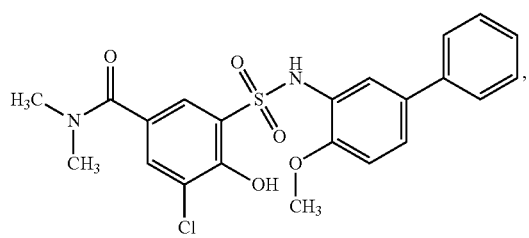 [SMILES: COc1ccc(-c2ccccc2)cc1NS(=O)(=O)c1cc(C(=O)N(C)C)cc(Cl)c1O]
I-56
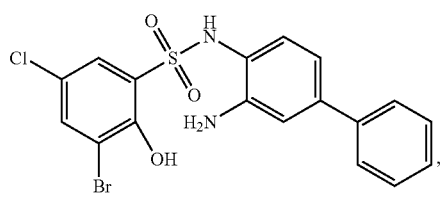 [SMILES: Nc1cc(-c2ccccc2)ccc1NS(=O)(=O)c1cc(Cl)cc(Br)c1O]
I-57
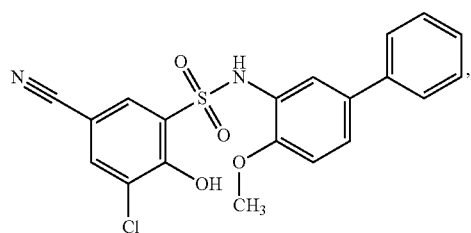 [SMILES: COc1ccc(-c2ccccc2)cc1NS(=O)(=O)c1cc(C#N)cc(Cl)c1O]
I-58
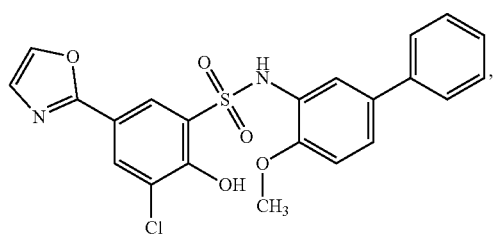 [SMILES: COc1ccc(-c2ccccc2)cc1NS(=O)(=O)c1cc(-c2ncco2)cc(Cl)c1O]
I-59
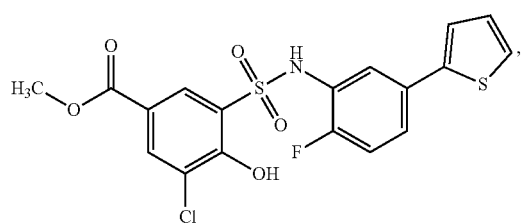 [SMILES: COC(=O)c1cc(Cl)c(O)c(S(=O)(=O)Nc2cc(-c3cccs3)ccc2F)c1]
I-60

TABLE 1-continued
Exemplary Compounds of Formula I
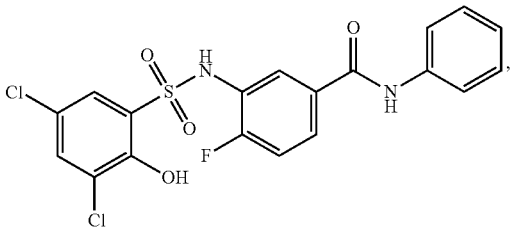 [SMILES: O=C(Nc1ccccc1)c1ccc(F)c(NS(=O)(=O)c2cc(Cl)cc(Cl)c2O)c1]
I-61
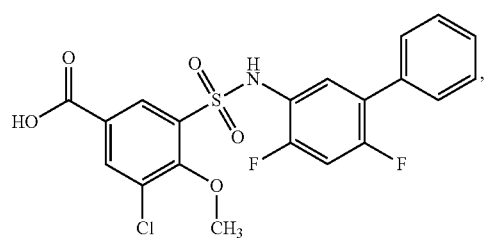 [SMILES: COc1c(Cl)cc(C(=O)O)cc1S(=O)(=O)Nc1cc(-c2ccccc2)c(F)cc1F]
I-62
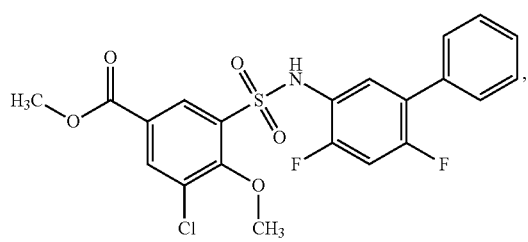 [SMILES: COC(=O)c1cc(Cl)c(OC)c(S(=O)(=O)Nc2cc(-c3ccccc3)c(F)cc2F)c1]
I-63
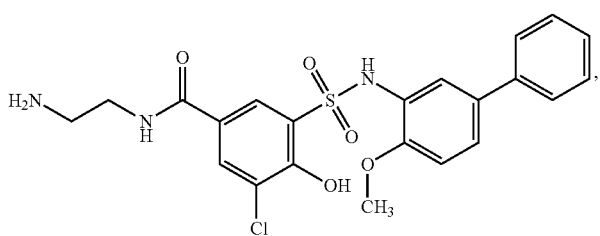 [SMILES: COc1ccc(-c2ccccc2)cc1NS(=O)(=O)c1cc(C(=O)NCCN)cc(Cl)c1O]
I-64
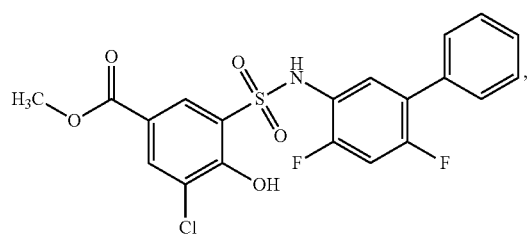 [SMILES: COC(=O)c1cc(Cl)c(O)c(S(=O)(=O)Nc2cc(-c3ccccc3)c(F)cc2F)c1]
I-65
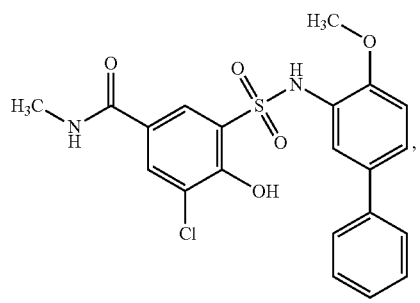 [SMILES: CNC(=O)c1cc(Cl)c(O)c(S(=O)(=O)Nc2cc(-c3ccccc3)ccc2OC)c1]
I-66

TABLE 1-continued
Exemplary Compounds of Formula I
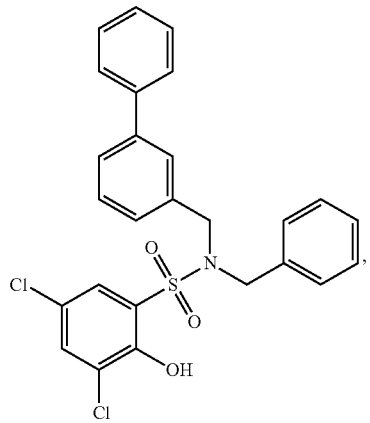 [SMILES: O=S(=O)(c1cc(Cl)cc(Cl)c1O)N(Cc1ccccc1)Cc1cccc(-c2ccccc2)c1]
I-67
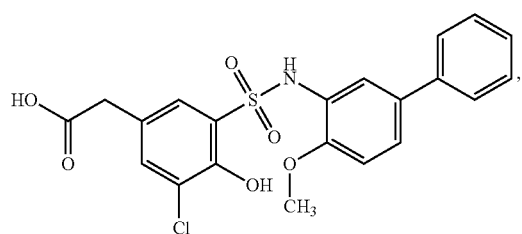 [SMILES: COc1ccc(-c2ccccc2)cc1NS(=O)(=O)c1cc(CC(=O)O)cc(Cl)c1O]
I-68
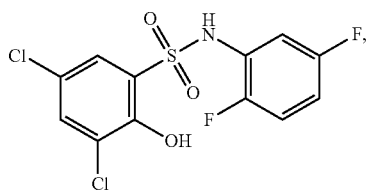 [SMILES: O=S(=O)(Nc1cc(F)ccc1F)c1cc(Cl)cc(Cl)c1O]
I-69
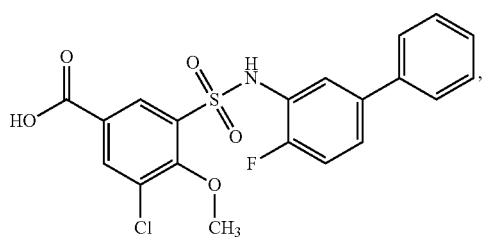 [SMILES: COc1c(Cl)cc(C(=O)O)cc1S(=O)(=O)Nc1cc(-c2ccccc2)ccc1F]
I-70
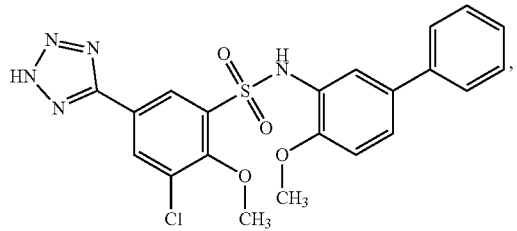 [SMILES: COc1ccc(-c2ccccc2)cc1NS(=O)(=O)c1cc(-c2nn[nH]n2)cc(Cl)c1OC]
I-71
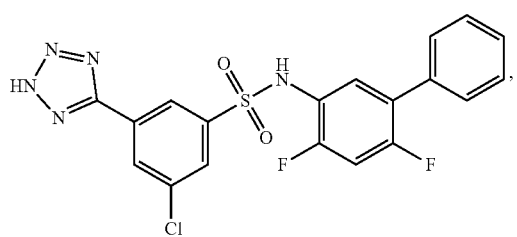 [SMILES: O=S(=O)(Nc1cc(-c2ccccc2)c(F)cc1F)c1cc(Cl)cc(-c2nn[nH]n2)c1]
I-72

TABLE 1-continued
Exemplary Compounds of Formula I
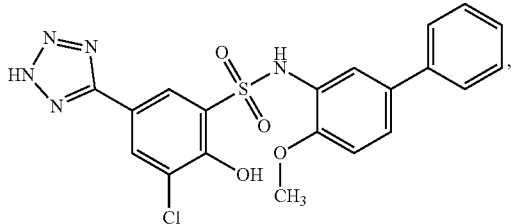 [SMILES: COc1ccc(-c2ccccc2)cc1NS(=O)(=O)c1cc(-c2nn[nH]n2)cc(Cl)c1O] I-73
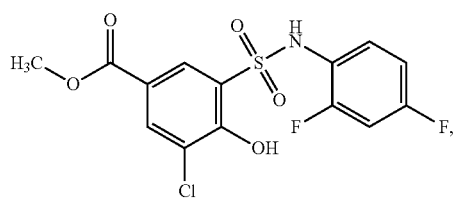 [SMILES: COC(=O)c1cc(Cl)c(O)c(S(=O)(=O)Nc2ccc(F)cc2F)c1] I-74
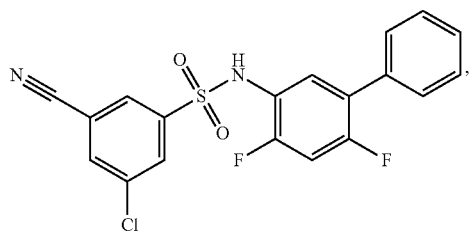 [SMILES: N#Cc1cc(Cl)cc(S(=O)(=O)Nc2cc(-c3ccccc3)c(F)cc2F)c1] I-75
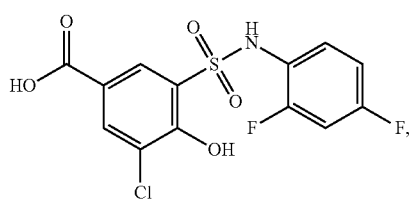 [SMILES: O=C(O)c1cc(Cl)c(O)c(S(=O)(=O)Nc2ccc(F)cc2F)c1] I-76
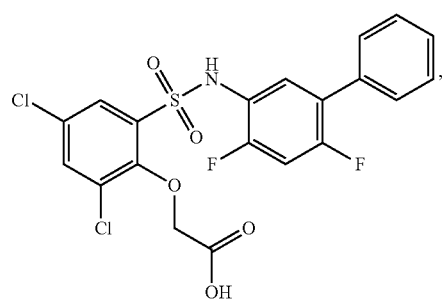 [SMILES: O=C(O)COc1c(Cl)cc(Cl)cc1S(=O)(=O)Nc1cc(-c2ccccc2)c(F)cc1F] I-77
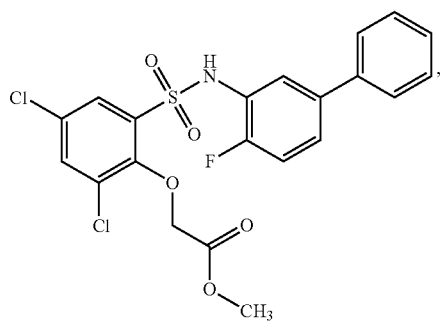 [SMILES: COC(=O)COc1c(Cl)cc(Cl)cc1S(=O)(=O)Nc1cc(-c2ccccc2)ccc1F] I-78

TABLE 1-continued
Exemplary Compounds of Formula I
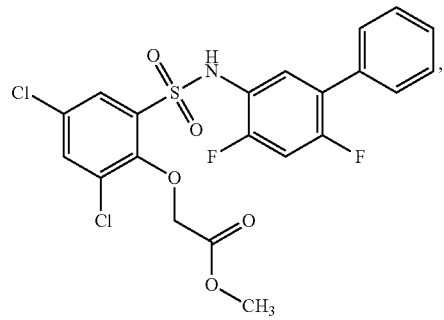 [SMILES: COC(=O)COc1c(Cl)cc(Cl)cc1S(=O)(=O)Nc1cc(-c2ccccc2)c(F)cc1F]
I-79
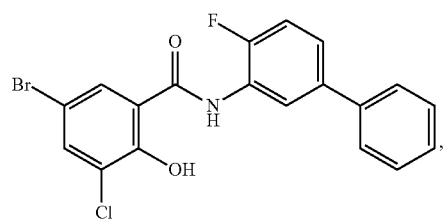 [SMILES: O=C(Nc1cc(-c2ccccc2)ccc1F)c1cc(Br)cc(Cl)c1O]
I-80
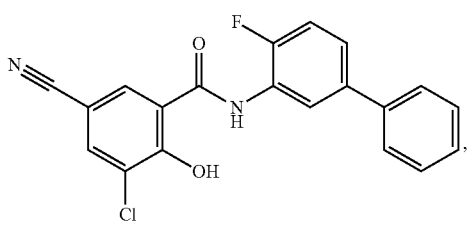 [SMILES: N#Cc1cc(Cl)c(O)c(C(=O)Nc2cc(-c3ccccc3)ccc2F)c1]
I-81
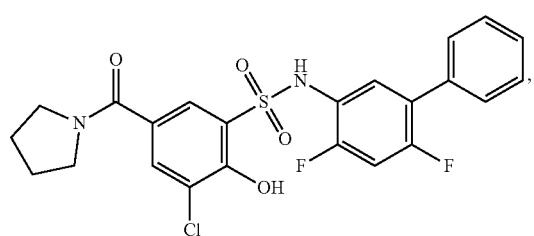 [SMILES: O=C(c1cc(Cl)c(O)c(S(=O)(=O)Nc2cc(-c3ccccc3)c(F)cc2F)c1)N1CCCC1]
I-82
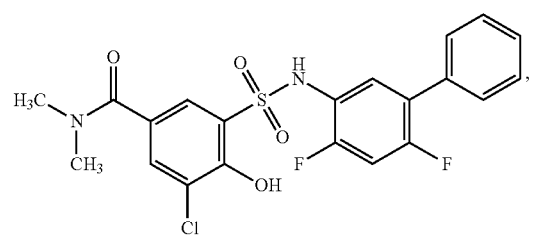 [SMILES: CN(C)C(=O)c1cc(Cl)c(O)c(S(=O)(=O)Nc2cc(-c3ccccc3)c(F)cc2F)c1]
I-83
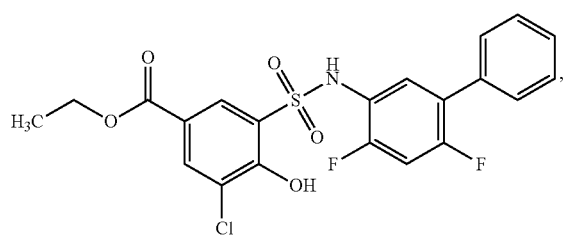 [SMILES: CCOC(=O)c1cc(Cl)c(O)c(S(=O)(=O)Nc2cc(-c3ccccc3)c(F)cc2F)c1]
I-84

TABLE 1-continued
Exemplary Compounds of Formula I
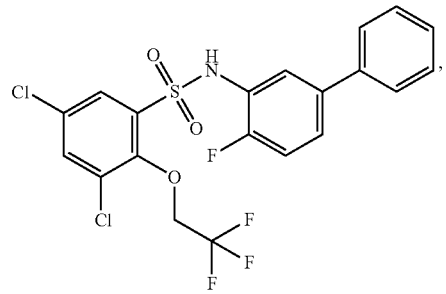 [SMILES: O=S(=O)(Nc1cc(-c2ccccc2)ccc1F)c1cc(Cl)cc(Cl)c1OCC(F)(F)F]
I-85
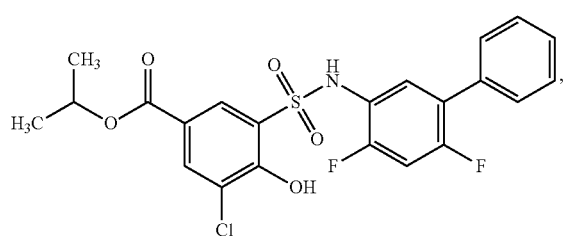 [SMILES: CC(C)OC(=O)c1cc(Cl)c(O)c(S(=O)(=O)Nc2cc(-c3ccccc3)c(F)cc2F)c1]
I-86
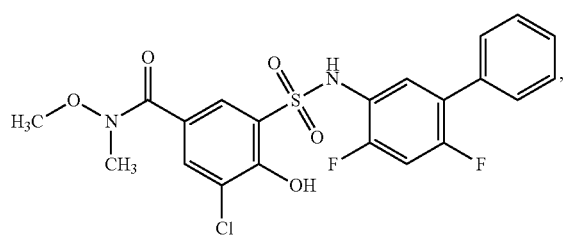 [SMILES: CON(C)C(=O)c1cc(Cl)c(O)c(S(=O)(=O)Nc2cc(-c3ccccc3)c(F)cc2F)c1]
I-87
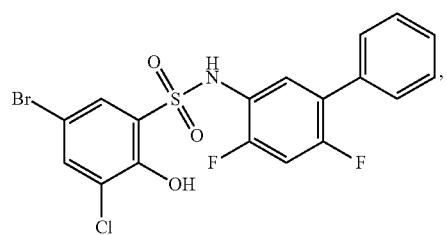 [SMILES: O=S(=O)(Nc1cc(-c2ccccc2)c(F)cc1F)c1cc(Br)cc(Cl)c1O]
I-88
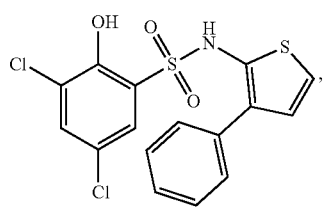 [SMILES: O=S(=O)(Nc1sccc1-c1ccccc1)c1cc(Cl)cc(Cl)c1O]
I-89
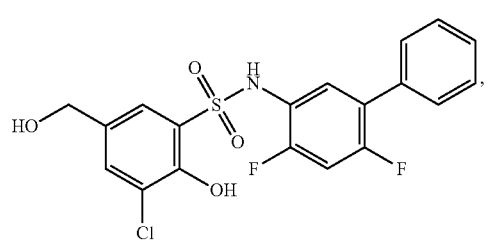 [SMILES: O=S(=O)(Nc1cc(-c2ccccc2)c(F)cc1F)c1cc(CO)cc(Cl)c1O]
I-90

TABLE 1-continued
Exemplary Compounds of Formula I
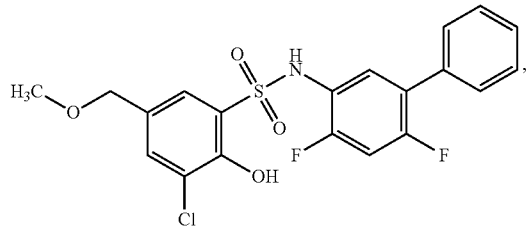 [SMILES: COCc1cc(Cl)c(O)c(S(=O)(=O)Nc2cc(-c3ccccc3)c(F)cc2F)c1]
I-91
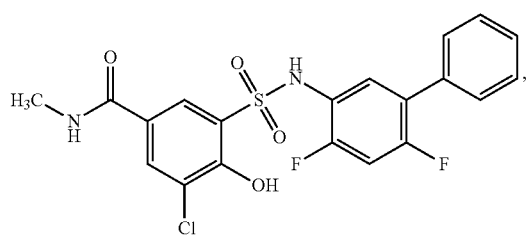
I-92
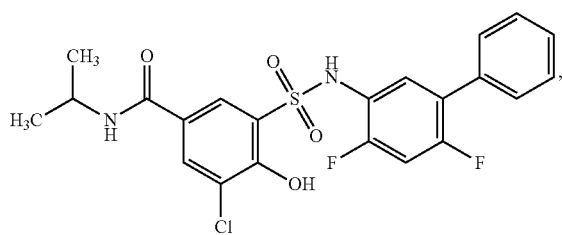 [SMILES: CC(C)NC(=O)c1cc(Cl)c(O)c(S(=O)(=O)Nc2cc(-c3ccccc3)c(F)cc2F)c1]
I-93
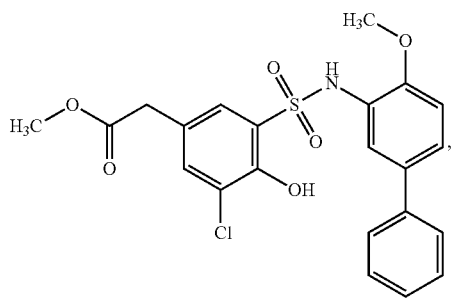 [SMILES: COC(=O)Cc1cc(Cl)c(O)c(S(=O)(=O)Nc2cc(-c3ccccc3)ccc2OC)c1]
I-94
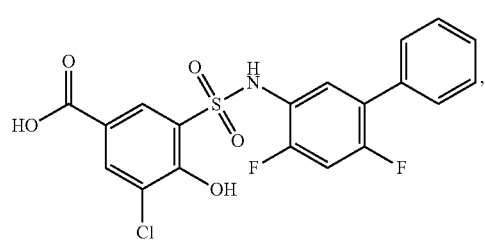 [SMILES: O=C(O)c1cc(Cl)c(O)c(S(=O)(=O)Nc2cc(-c3ccccc3)c(F)cc2F)c1]
I-95
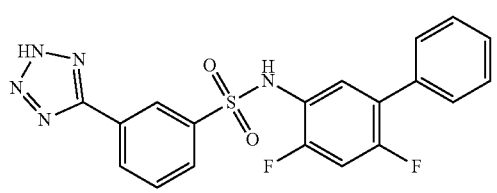 [SMILES: O=S(=O)(Nc1cc(-c2ccccc2)c(F)cc1F)c1cccc(-c2nn[nH]n2)c1]
I-96

TABLE 1-continued
Exemplary Compounds of Formula I
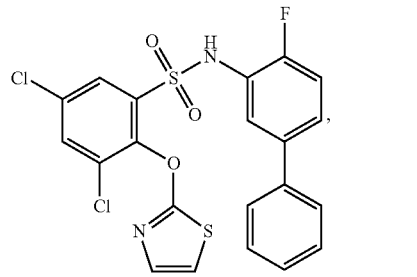 [SMILES: O=S(=O)(Nc1cc(-c2ccccc2)ccc1F)c1cc(Cl)cc(Cl)c1Oc1nccs1]
I-97
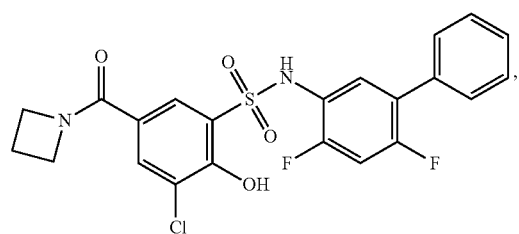 [SMILES: O=C(c1cc(Cl)c(O)c(S(=O)(=O)Nc2cc(-c3ccccc3)c(F)cc2F)c1)N1CCC1]
I-98
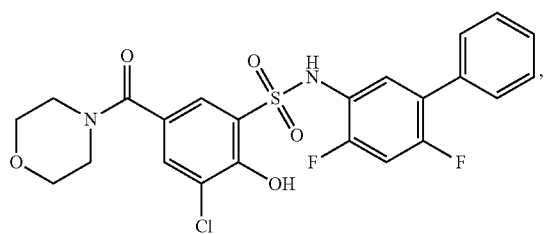 [SMILES: O=C(c1cc(Cl)c(O)c(S(=O)(=O)Nc2cc(-c3ccccc3)c(F)cc2F)c1)N1CCOCC1]
I-99
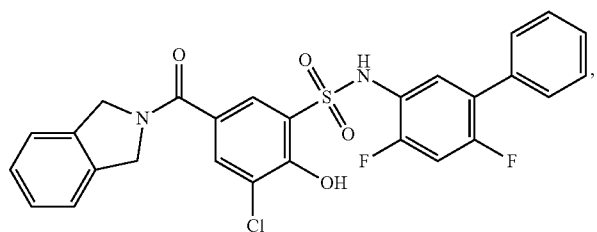 [SMILES: O=C(c1cc(Cl)c(O)c(S(=O)(=O)Nc2cc(-c3ccccc3)c(F)cc2F)c1)N1Cc2ccccc2C1]
I-100
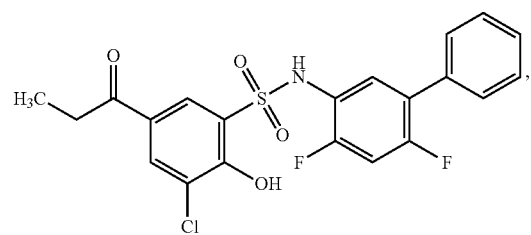 [SMILES: CCC(=O)c1cc(Cl)c(O)c(S(=O)(=O)Nc2cc(-c3ccccc3)c(F)cc2F)c1]
I-101
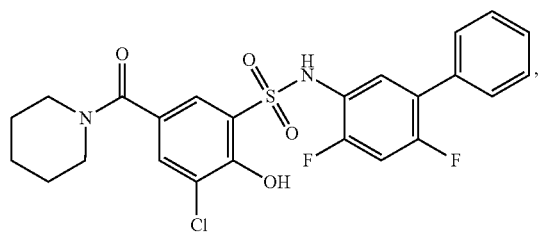 [SMILES: O=C(c1cc(Cl)c(O)c(S(=O)(=O)Nc2cc(-c3ccccc3)c(F)cc2F)c1)N1CCCCC1]
I-102

TABLE 1-continued
Exemplary Compounds of Formula I
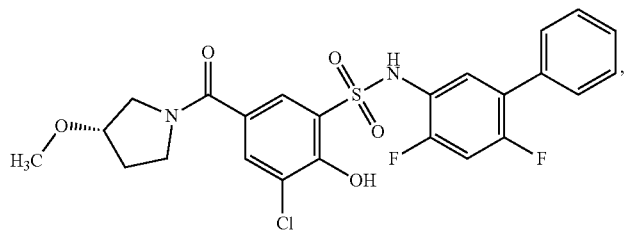 [SMILES: CO[C@H]1CCN(C(=O)c2cc(Cl)c(O)c(S(=O)(=O)Nc3cc(-c4ccccc4)c(F)cc3F)c2)C1] I-103
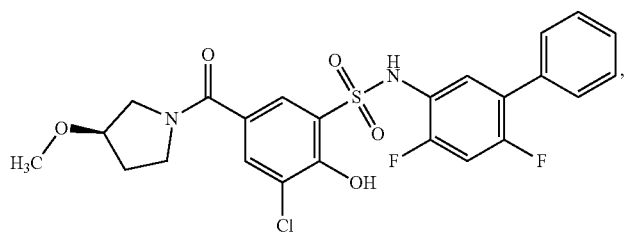 [SMILES: CO[C@@H]1CCN(C(=O)c2cc(Cl)c(O)c(S(=O)(=O)Nc3cc(-c4ccccc4)c(F)cc3F)c2)C1] I-104
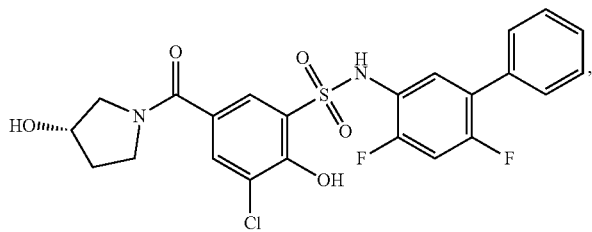 [SMILES: O=C(c1cc(Cl)c(O)c(S(=O)(=O)Nc2cc(-c3ccccc3)c(F)cc2F)c1)N1CC[C@H](O)C1] I-105
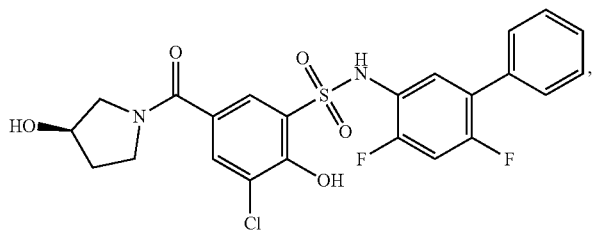 [SMILES: O=C(c1cc(Cl)c(O)c(S(=O)(=O)Nc2cc(-c3ccccc3)c(F)cc2F)c1)N1CC[C@@H](O)C1] I-106
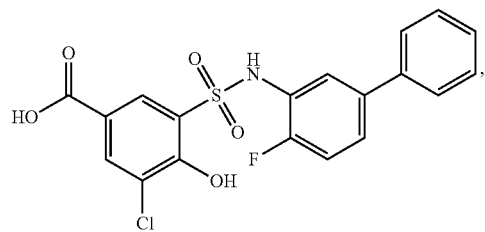 [SMILES: O=C(O)c1cc(Cl)c(O)c(S(=O)(=O)Nc2cc(-c3ccccc3)ccc2F)c1] I-107
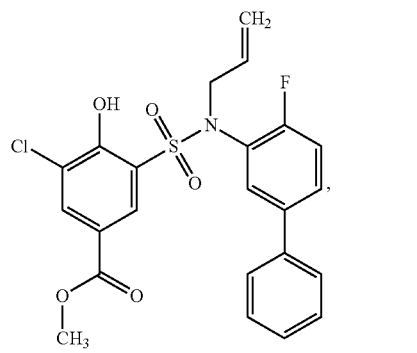 [SMILES: C=CCN(c1cc(-c2ccccc2)ccc1F)S(=O)(=O)c1cc(C(=O)OC)cc(Cl)c1O] I-108

TABLE 1-continued
Exemplary Compounds of Formula I
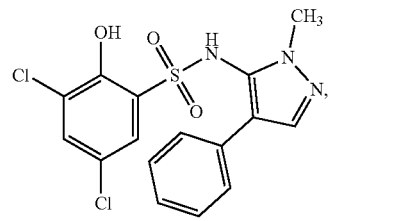 [SMILES: Cn1ncc(-c2ccccc2)c1NS(=O)(=O)c1cc(Cl)cc(Cl)c1O]
I-109
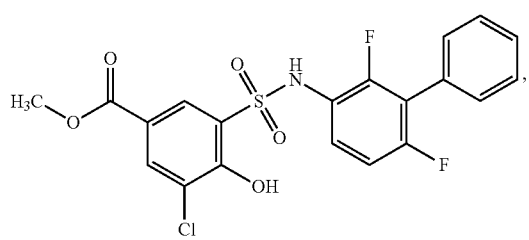 [SMILES: COC(=O)c1cc(Cl)c(O)c(S(=O)(=O)Nc2ccc(F)c(-c3ccccc3)c2F)c1]
I-110
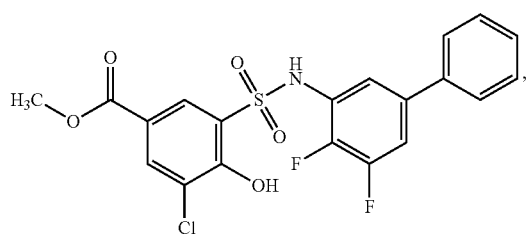
I-111
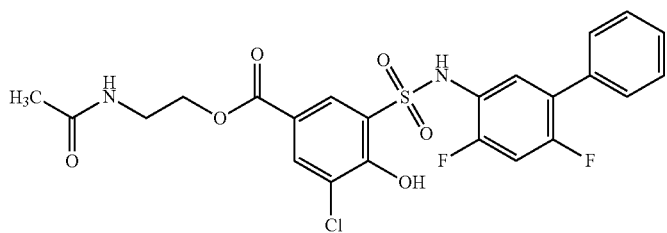 [SMILES: CC(=O)NCCOC(=O)c1cc(Cl)c(O)c(S(=O)(=O)Nc2cc(-c3ccccc3)c(F)cc2F)c1]
I-112
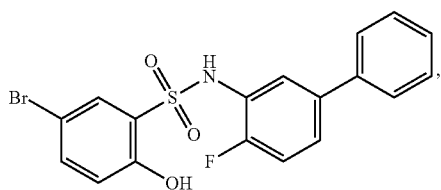 [SMILES: O=S(=O)(Nc1cc(-c2ccccc2)ccc1F)c1cc(Br)ccc1O]
I-113
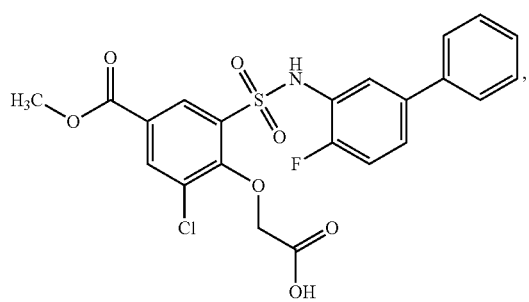 [SMILES: COC(=O)c1cc(Cl)c(OCC(=O)O)c(S(=O)(=O)Nc2cc(-c3ccccc3)ccc2F)c1]
I-114

TABLE 1-continued
Exemplary Compounds of Formula I
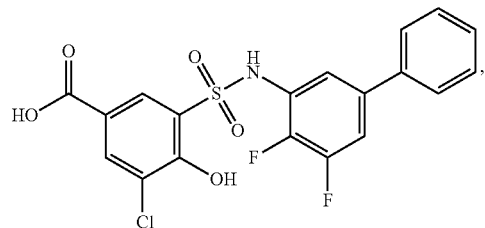 [SMILES: O=C(O)c1cc(Cl)c(O)c(S(=O)(=O)Nc2cc(-c3ccccc3)cc(F)c2F)c1]
I-115
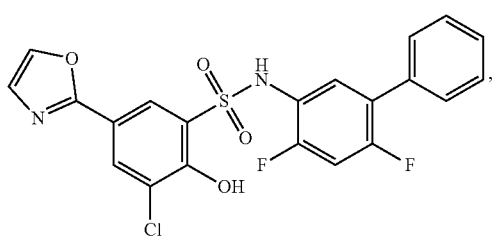 [SMILES: O=S(=O)(Nc1cc(-c2ccccc2)c(F)cc1F)c1cc(-c2ncco2)cc(Cl)c1O]
I-116
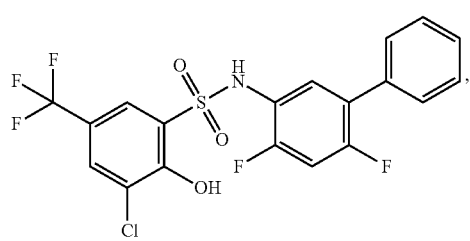 [SMILES: O=S(=O)(Nc1cc(-c2ccccc2)c(F)cc1F)c1cc(C(F)(F)F)cc(Cl)c1O]
I-117
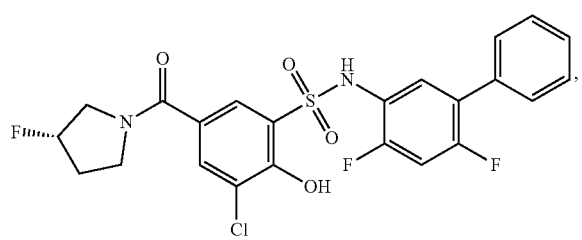 [SMILES: O=C(c1cc(Cl)c(O)c(S(=O)(=O)Nc2cc(-c3ccccc3)c(F)cc2F)c1)N1CC[C@H](F)C1]
I-118
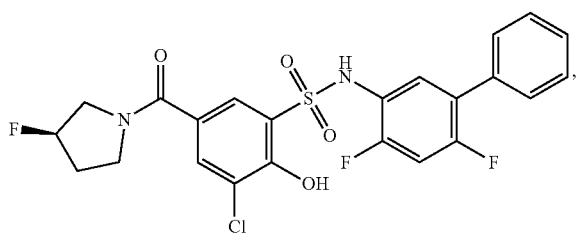 [SMILES: O=C(c1cc(Cl)c(O)c(S(=O)(=O)Nc2cc(-c3ccccc3)c(F)cc2F)c1)N1CC[C@@H](F)C1]
I-119
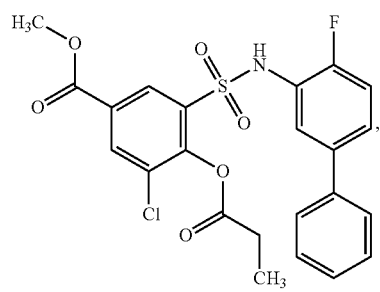 [SMILES: CCC(=O)Oc1c(Cl)cc(C(=O)OC)cc1S(=O)(=O)Nc1cc(-c2ccccc2)ccc1F]
I-120

TABLE 1-continued
Exemplary Compounds of Formula I
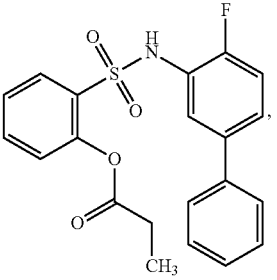 [SMILES: CCC(=O)Oc1ccccc1S(=O)(=O)Nc1cc(-c2ccccc2)ccc1F]
I-121
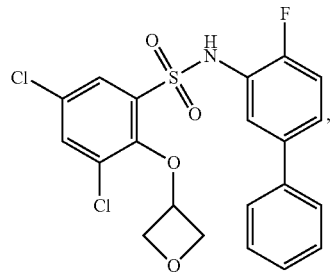 [SMILES: O=S(=O)(Nc1cc(-c2ccccc2)ccc1F)c1cc(Cl)cc(Cl)c1OC1COC1]
I-122
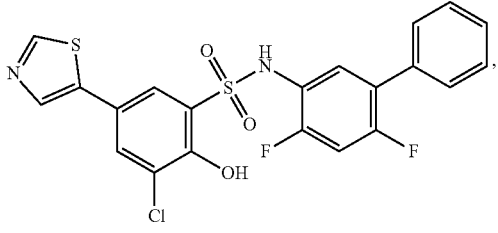 [SMILES: O=S(=O)(Nc1cc(-c2ccccc2)c(F)cc1F)c1cc(-c2cncs2)cc(Cl)c1O]
I-123
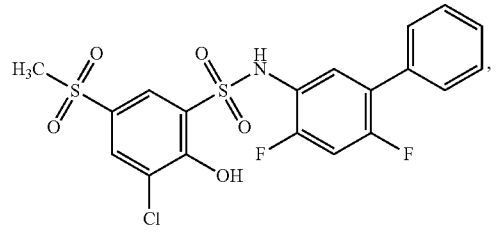 [SMILES: CS(=O)(=O)c1cc(Cl)c(O)c(S(=O)(=O)Nc2cc(-c3ccccc3)c(F)cc2F)c1]
I-124
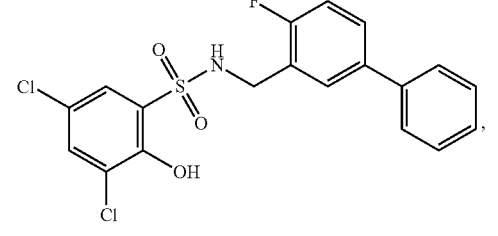
I-125
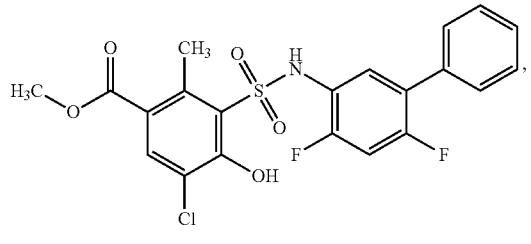 [SMILES: COC(=O)c1cc(Cl)c(O)c(S(=O)(=O)Nc2cc(-c3ccccc3)c(F)cc2F)c1C]
I-126

TABLE 1-continued
Exemplary Compounds of Formula I
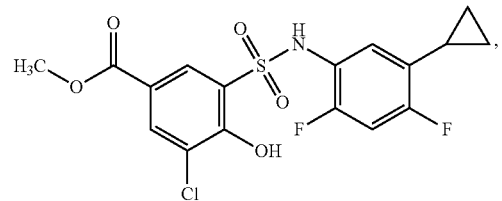 [SMILES: COC(=O)c1cc(Cl)c(O)c(S(=O)(=O)Nc2cc(C3CC3)c(F)cc2F)c1] I-127
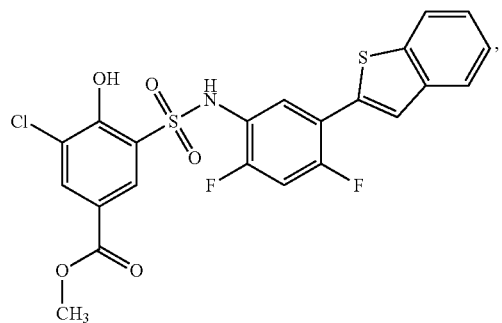 [SMILES: COC(=O)c1cc(Cl)c(O)c(S(=O)(=O)Nc2cc(-c3cc4ccccc4s3)c(F)cc2F)c1] I-128
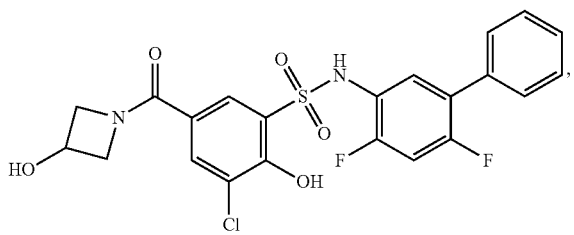 [SMILES: O=C(c1cc(Cl)c(O)c(S(=O)(=O)Nc2cc(-c3ccccc3)c(F)cc2F)c1)N1CC(O)C1] I-129
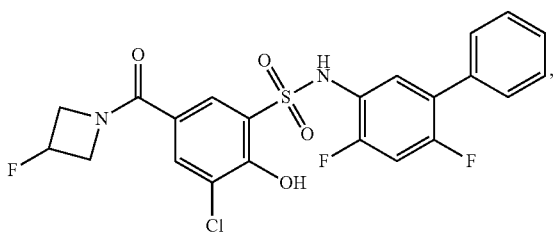 [SMILES: O=C(c1cc(Cl)c(O)c(S(=O)(=O)Nc2cc(-c3ccccc3)c(F)cc2F)c1)N1CC(F)C1] I-130
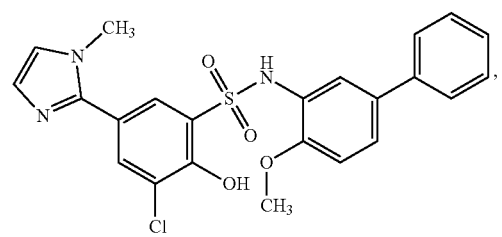 [SMILES: COc1ccc(-c2ccccc2)cc1NS(=O)(=O)c1cc(-c2nccn2C)cc(Cl)c1O] I-131
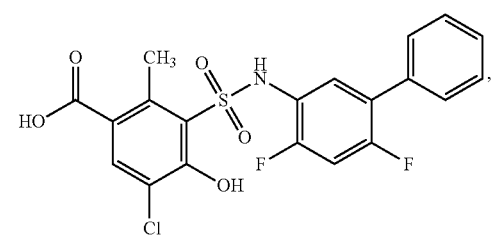 [SMILES: Cc1c(C(=O)O)cc(Cl)c(O)c1S(=O)(=O)Nc1cc(-c2ccccc2)c(F)cc1F] I-132

TABLE 1-continued
Exemplary Compounds of Formula I
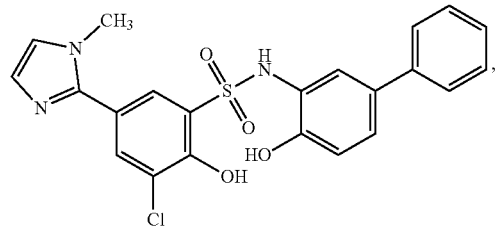 [SMILES: Cn1ccnc1-c1cc(Cl)c(O)c(S(=O)(=O)Nc2cc(-c3ccccc3)ccc2O)c1] I-133
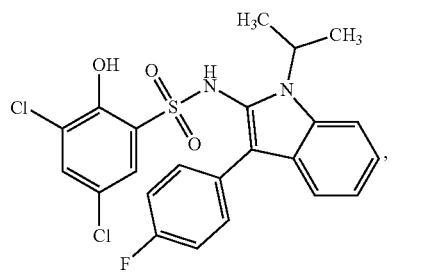 [SMILES: CC(C)n1c(NS(=O)(=O)c2cc(Cl)cc(Cl)c2O)c(-c2ccc(F)cc2)c2ccccc21] I-134
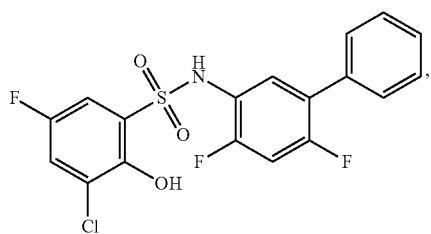 [SMILES: O=S(=O)(Nc1cc(-c2ccccc2)c(F)cc1F)c1cc(F)cc(Cl)c1O] I-135
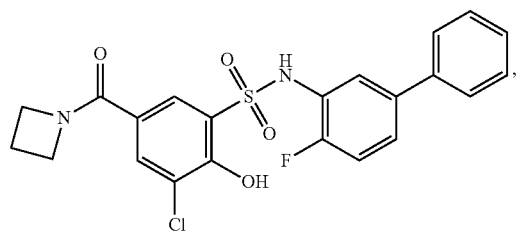 [SMILES: O=C(c1cc(Cl)c(O)c(S(=O)(=O)Nc2cc(-c3ccccc3)ccc2F)c1)N1CCC1] I-136
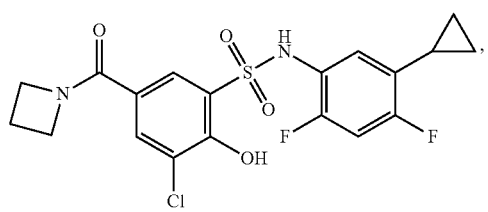 [SMILES: O=C(c1cc(Cl)c(O)c(S(=O)(=O)Nc2cc(C3CC3)c(F)cc2F)c1)N1CCC1] I-137
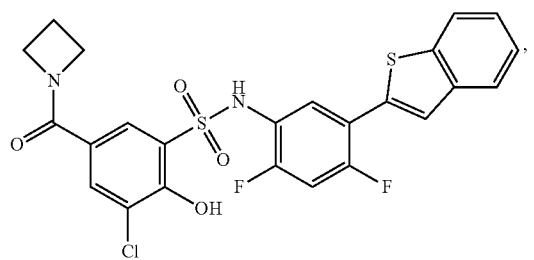 [SMILES: O=C(c1cc(Cl)c(O)c(S(=O)(=O)Nc2cc(-c3cc4ccccc4s3)c(F)cc2F)c1)N1CCC1] I-138

TABLE 1-continued

Exemplary Compounds of Formula I

I-139

I-140

I-141

I-142

I-143

I-144

TABLE 1-continued
Exemplary Compounds of Formula I
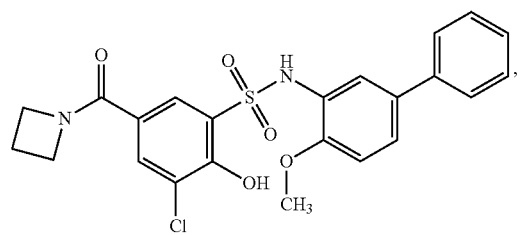 [SMILES: COc1ccc(-c2ccccc2)cc1NS(=O)(=O)c1cc(C(=O)N2CCC2)cc(Cl)c1O] I-145
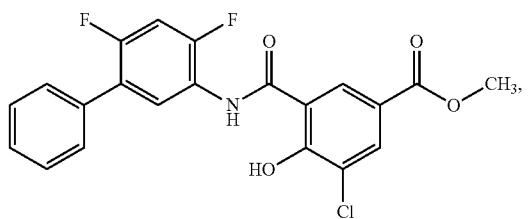 [SMILES: COC(=O)c1cc(Cl)c(O)c(C(=O)Nc2cc(-c3ccccc3)c(F)cc2F)c1] I-146
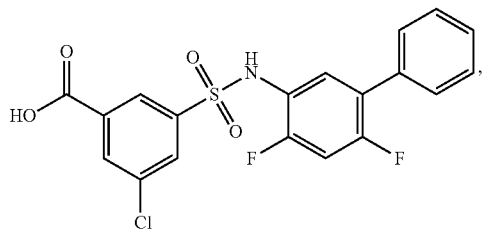 [SMILES: O=C(O)c1cc(Cl)cc(S(=O)(=O)Nc2cc(-c3ccccc3)c(F)cc2F)c1] I-147
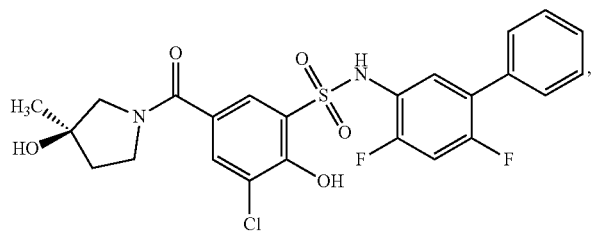 [SMILES: C[C@@]1(O)CCN(C(=O)c2cc(Cl)c(O)c(S(=O)(=O)Nc3cc(-c4ccccc4)c(F)cc3F)c2)C1] I-148
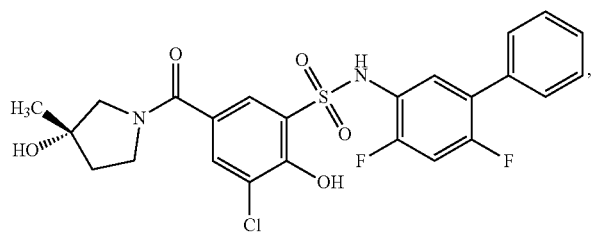 [SMILES: C[C@]1(O)CCN(C(=O)c2cc(Cl)c(O)c(S(=O)(=O)Nc3cc(-c4ccccc4)c(F)cc3F)c2)C1] I-149
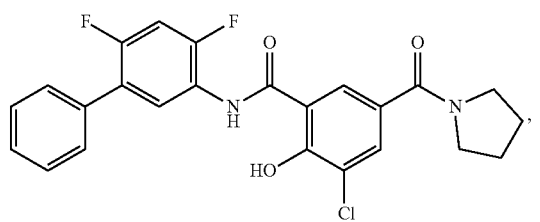 [SMILES: O=C(Nc1cc(-c2ccccc2)c(F)cc1F)c1cc(C(=O)N2CCCC2)cc(Cl)c1O] I-150

TABLE 1-continued
Exemplary Compounds of Formula I
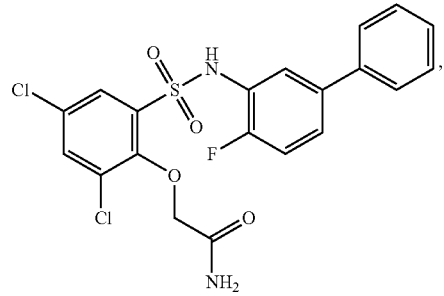 [SMILES: NC(=O)COc1c(Cl)cc(Cl)cc1S(=O)(=O)Nc1cc(-c2ccccc2)ccc1F]
I-151
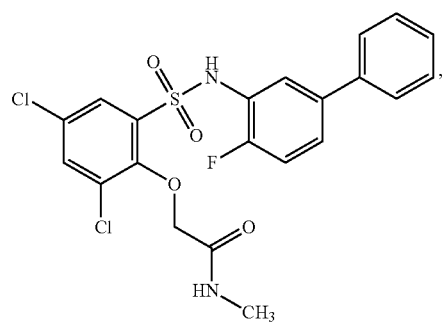 [SMILES: CNC(=O)COc1c(Cl)cc(Cl)cc1S(=O)(=O)Nc1cc(-c2ccccc2)ccc1F]
I-152
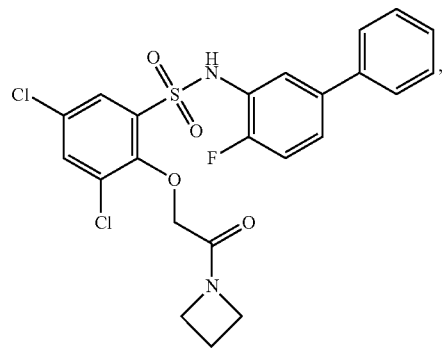 [SMILES: O=C(COc1c(Cl)cc(Cl)cc1S(=O)(=O)Nc1cc(-c2ccccc2)ccc1F)N1CCC1]
I-153
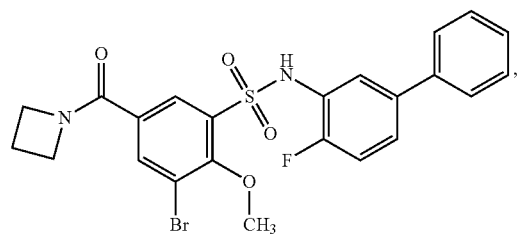 [SMILES: COc1c(Br)cc(C(=O)N2CCC2)cc1S(=O)(=O)Nc1cc(-c2ccccc2)ccc1F]
I-154
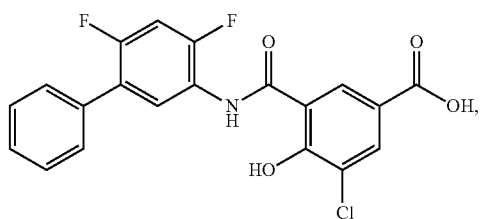 [SMILES: O=C(O)c1cc(Cl)c(O)c(C(=O)Nc2cc(-c3ccccc3)c(F)cc2F)c1]
I-155

TABLE 1-continued
Exemplary Compounds of Formula I
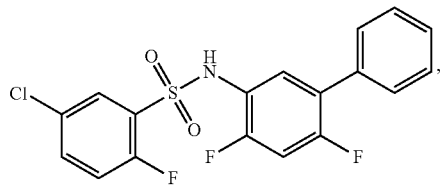 [SMILES: O=S(=O)(Nc1cc(-c2ccccc2)c(F)cc1F)c1cc(Cl)ccc1F]
I-156
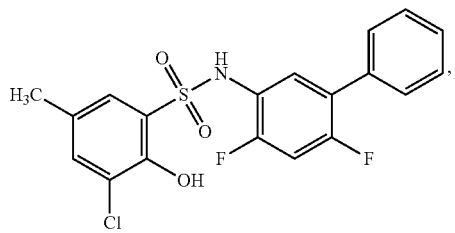 [SMILES: Cc1cc(Cl)c(O)c(S(=O)(=O)Nc2cc(-c3ccccc3)c(F)cc2F)c1]
I-157
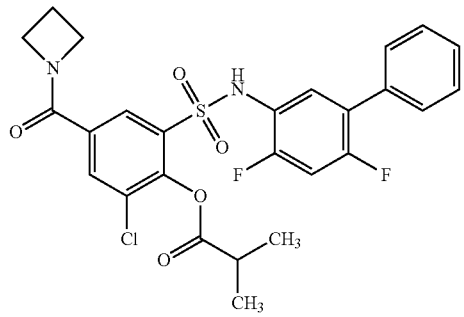 [SMILES: CC(C)C(=O)Oc1c(Cl)cc(C(=O)N2CCC2)cc1S(=O)(=O)Nc1cc(-c2ccccc2)c(F)cc1F]
I-158
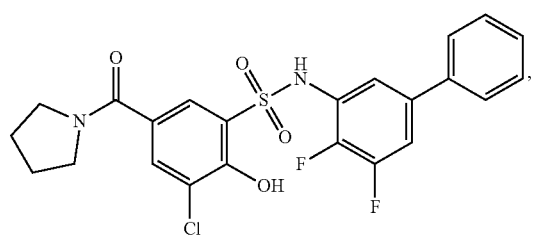 [SMILES: O=C(c1cc(Cl)c(O)c(S(=O)(=O)Nc2cc(-c3ccccc3)cc(F)c2F)c1)N1CCCC1]
I-159
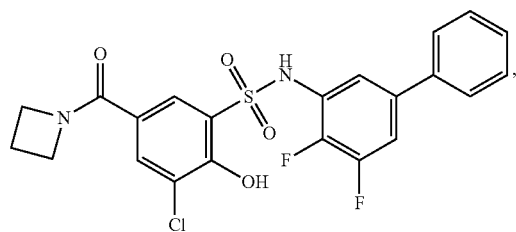 [SMILES: O=C(c1cc(Cl)c(O)c(S(=O)(=O)Nc2cc(-c3ccccc3)cc(F)c2F)c1)N1CCC1]
I-160
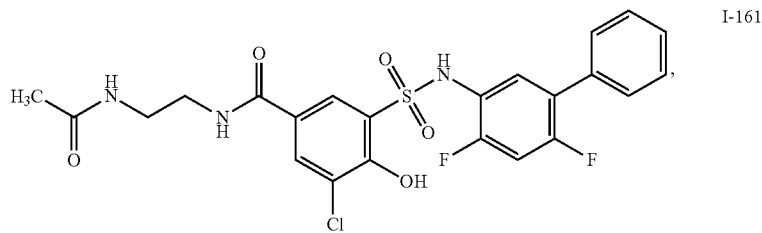
I-161

US 11,555,012 B2
87                                   88
TABLE 1-continued
Exemplary Compounds of Formula I
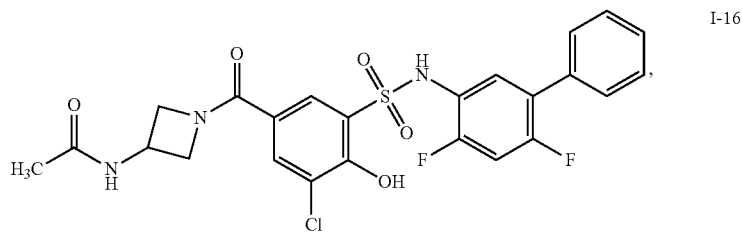 I-162
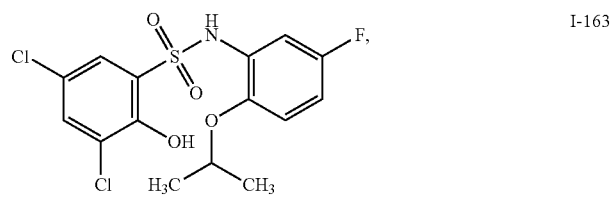 I-163
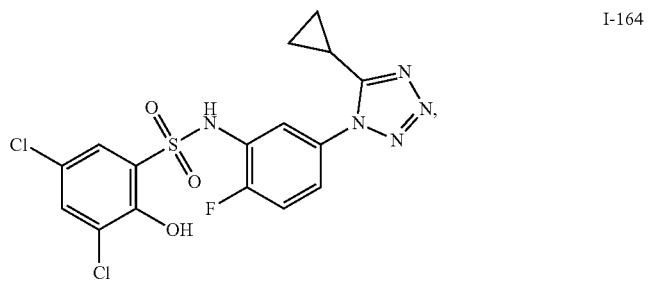 I-164
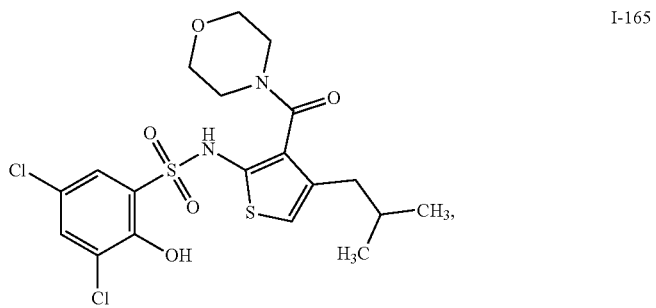 I-165
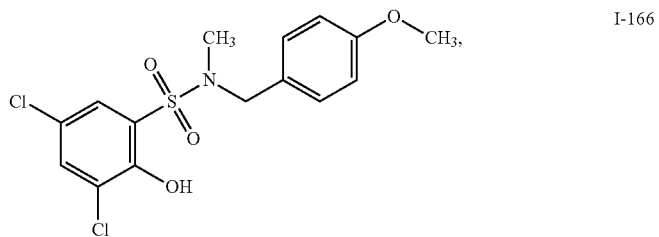 I-166
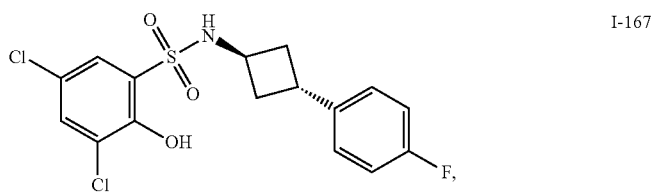 I-167

TABLE 1-continued
Exemplary Compounds of Formula I
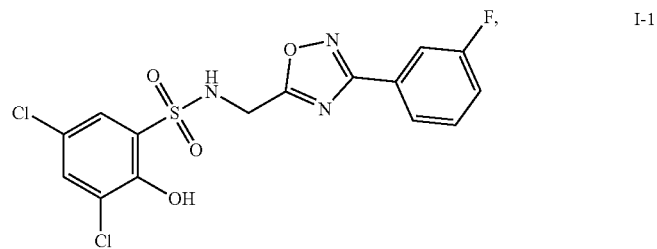 I-168
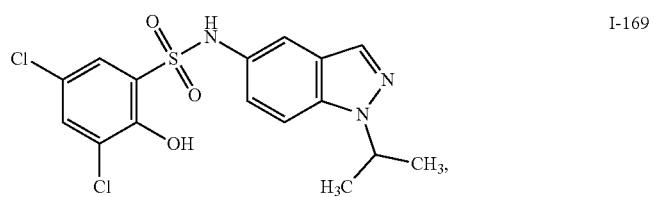 I-169
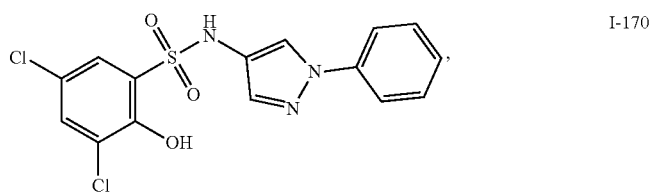 I-170
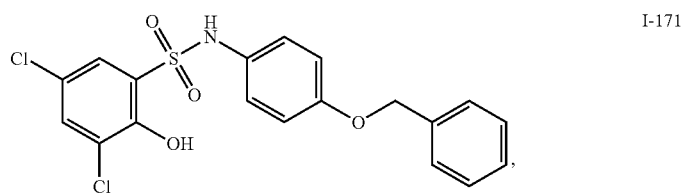 I-171
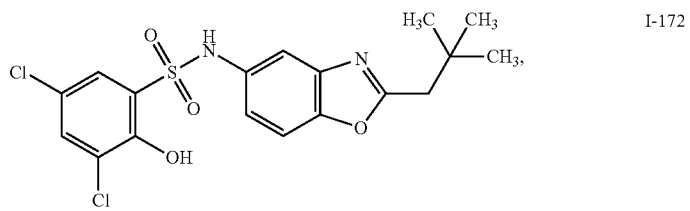 I-172
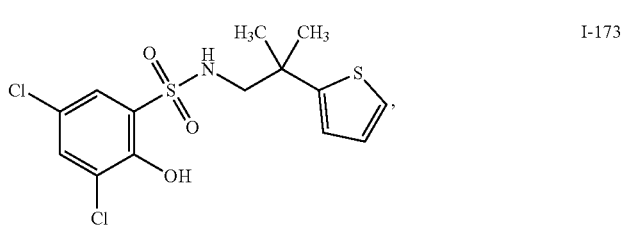 I-173
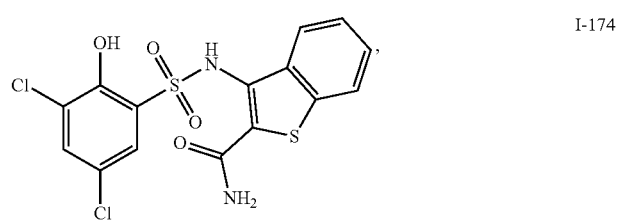 I-174

TABLE 1-continued
Exemplary Compounds of Formula I
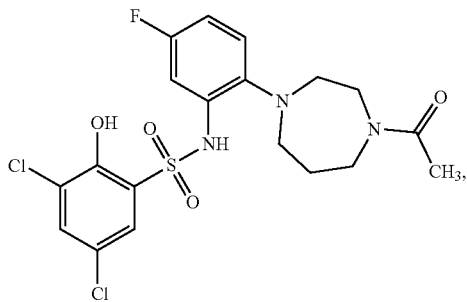 [SMILES: CC(=O)N1CCCN(c2ccc(F)cc2NS(=O)(=O)c2cc(Cl)cc(Cl)c2O)CC1] I-175
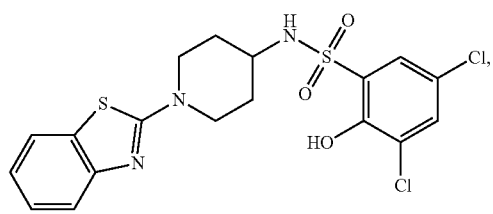 [SMILES: O=S(=O)(NC1CCN(c2nc3ccccc3s2)CC1)c1cc(Cl)cc(Cl)c1O] I-176
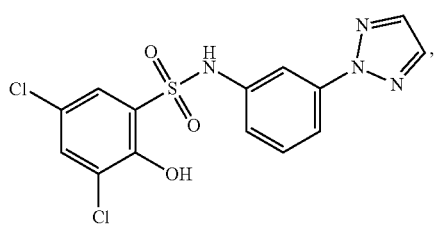 [SMILES: O=S(=O)(Nc1cccc(-n2nccn2)c1)c1cc(Cl)cc(Cl)c1O] I-177
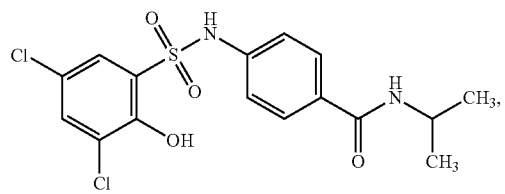 [SMILES: CC(C)NC(=O)c1ccc(NS(=O)(=O)c2cc(Cl)cc(Cl)c2O)cc1] I-178
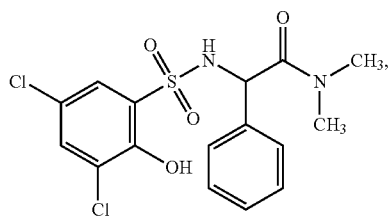 [SMILES: CN(C)C(=O)C(NS(=O)(=O)c1cc(Cl)cc(Cl)c1O)c1ccccc1] I-179
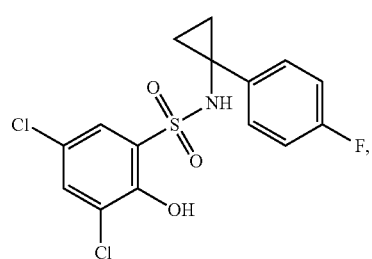 [SMILES: O=S(=O)(NC1(c2ccc(F)cc2)CC1)c1cc(Cl)cc(Cl)c1O] I-180

TABLE 1-continued
Exemplary Compounds of Formula I
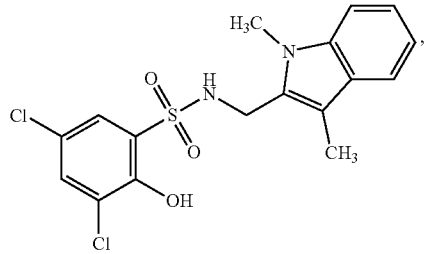 [SMILES: Cc1c(CNS(=O)(=O)c2cc(Cl)cc(Cl)c2O)n(C)c2ccccc12]
I-181
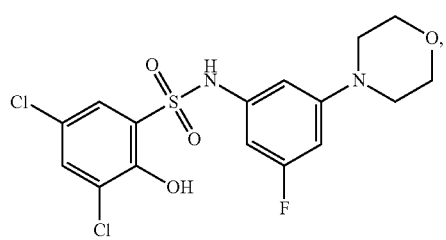 [SMILES: O=S(=O)(Nc1cc(F)cc(N2CCOCC2)c1)c1cc(Cl)cc(Cl)c1O]
I-182
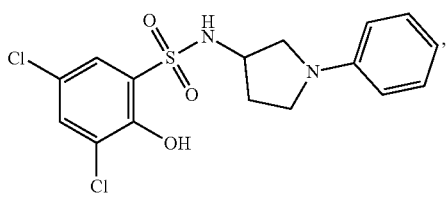 [SMILES: O=S(=O)(NC1CCN(c2ccccc2)C1)c1cc(Cl)cc(Cl)c1O]
I-183
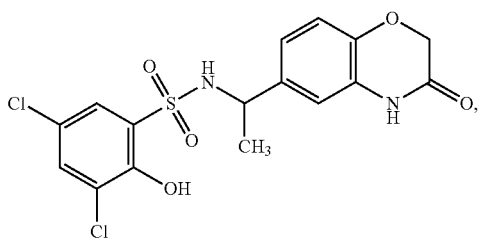 [SMILES: CC(NS(=O)(=O)c1cc(Cl)cc(Cl)c1O)c1ccc2c(c1)NC(=O)CO2]
I-184
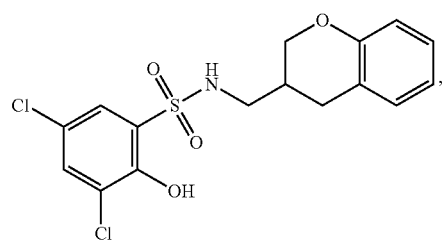 [SMILES: O=S(=O)(NCC1COc2ccccc2C1)c1cc(Cl)cc(Cl)c1O]
I-185
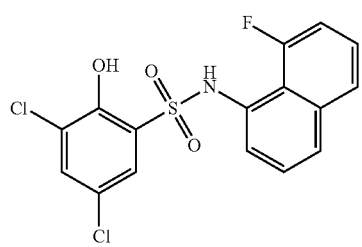 [SMILES: O=S(=O)(Nc1cccc2cccc(F)c12)c1cc(Cl)cc(Cl)c1O]
I-186

US 11,555,012 B2
TABLE 1-continued
Exemplary Compounds of Formula I
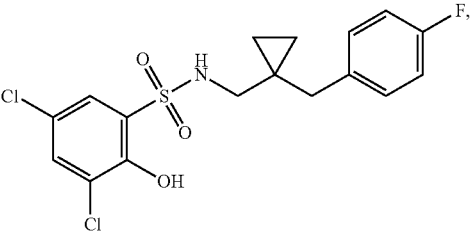 [SMILES: O=S(=O)(NCC1(Cc2ccc(F)cc2)CC1)c1cc(Cl)cc(Cl)c1O] I-187
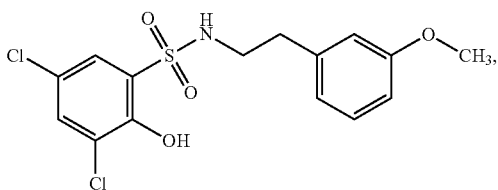 [SMILES: COc1cccc(CCNS(=O)(=O)c2cc(Cl)cc(Cl)c2O)c1] I-188
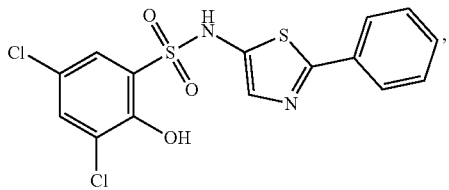 [SMILES: O=S(=O)(Nc1cnc(-c2ccccc2)s1)c1cc(Cl)cc(Cl)c1O] I-189
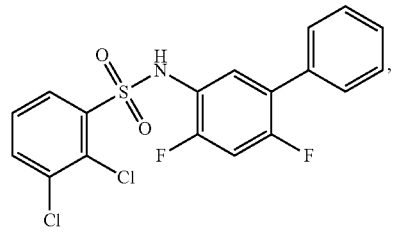 [SMILES: O=S(=O)(Nc1cc(-c2ccccc2)c(F)cc1F)c1cccc(Cl)c1Cl] I-190
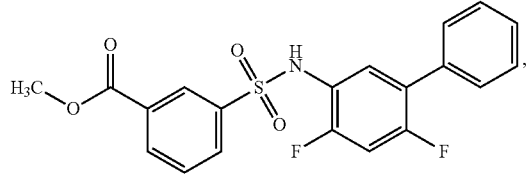 [SMILES: COC(=O)c1cccc(S(=O)(=O)Nc2cc(-c3ccccc3)c(F)cc2F)c1] I-191
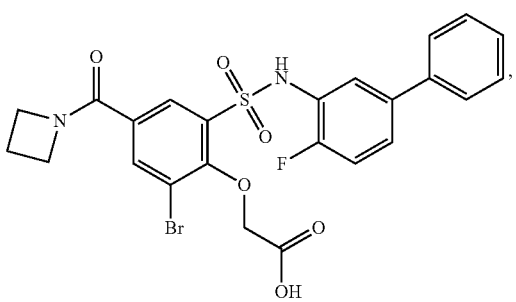 [SMILES: O=C(O)COc1c(Br)cc(C(=O)N2CCC2)cc1S(=O)(=O)Nc1cc(-c2ccccc2)ccc1F] I-192
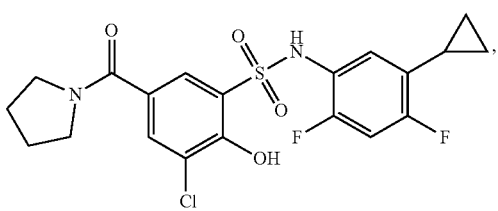 [SMILES: O=C(c1cc(Cl)c(O)c(S(=O)(=O)Nc2cc(C3CC3)c(F)cc2F)c1)N1CCCC1] I-193

TABLE 1-continued
Exemplary Compounds of Formula I
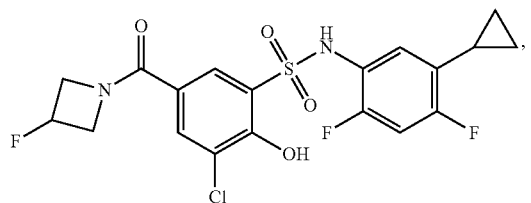 [SMILES: O=C(c1cc(Cl)c(O)c(S(=O)(=O)Nc2cc(C3CC3)c(F)cc2F)c1)N1CC(F)C1] I-194
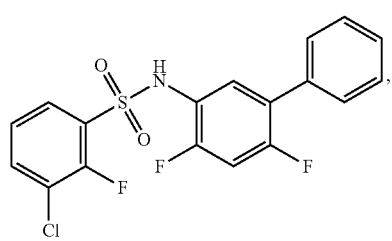 I-195
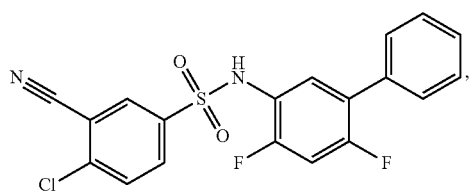 [SMILES: N#Cc1cc(S(=O)(=O)Nc2cc(-c3ccccc3)c(F)cc2F)ccc1Cl] I-196
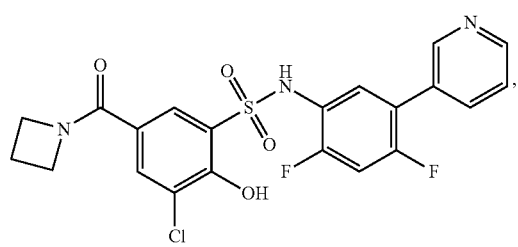 [SMILES: O=C(c1cc(Cl)c(O)c(S(=O)(=O)Nc2cc(-c3cccnc3)c(F)cc2F)c1)N1CCC1] I-197
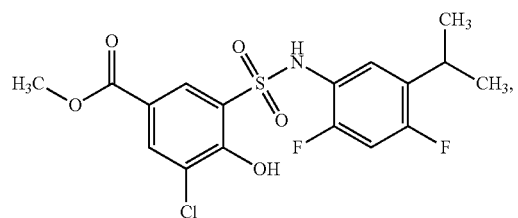 [SMILES: COC(=O)c1cc(Cl)c(O)c(S(=O)(=O)Nc2cc(C(C)C)c(F)cc2F)c1] I-198
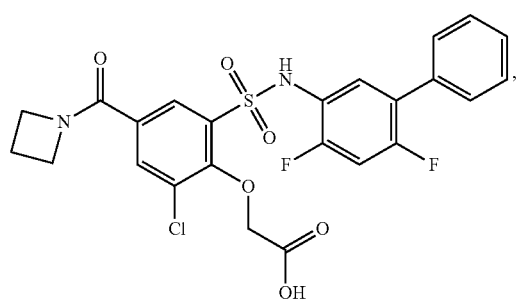 [SMILES: O=C(O)COc1c(Cl)cc(C(=O)N2CCC2)cc1S(=O)(=O)Nc1cc(-c2ccccc2)c(F)cc1F] I-199

TABLE 1-continued
Exemplary Compounds of Formula I
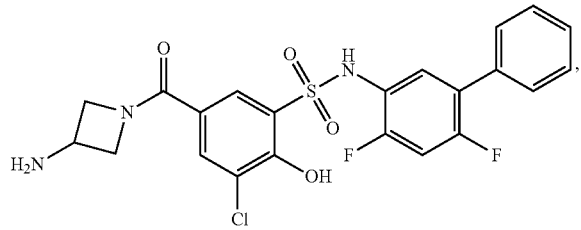 [SMILES: NC1CN(C(=O)c2cc(Cl)c(O)c(S(=O)(=O)Nc3cc(-c4ccccc4)c(F)cc3F)c2)C1]
I-200
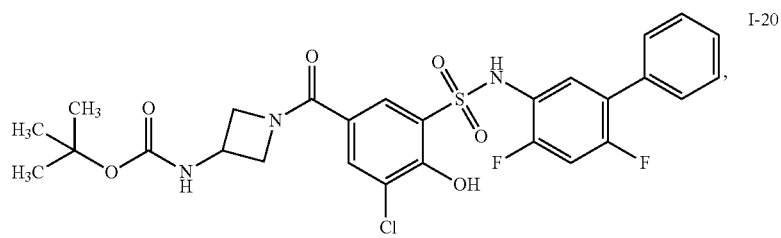
I-201
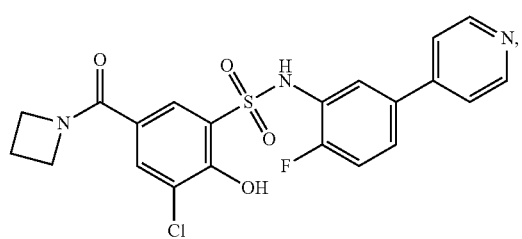 [SMILES: O=C(c1cc(Cl)c(O)c(S(=O)(=O)Nc2cc(-c3ccncc3)ccc2F)c1)N1CCC1]
I-202
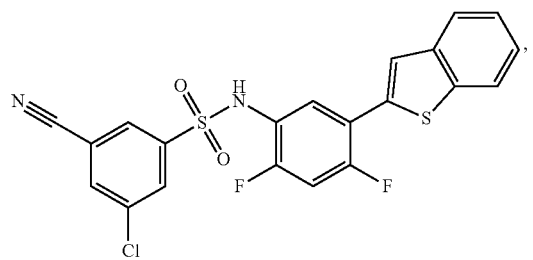 [SMILES: N#Cc1cc(Cl)cc(S(=O)(=O)Nc2cc(-c3cc4ccccc4s3)c(F)cc2F)c1]
I-203
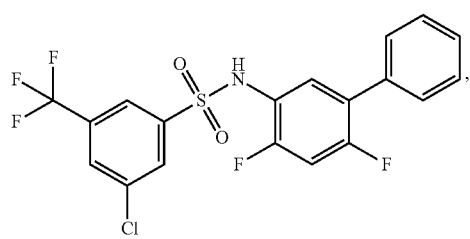 [SMILES: O=S(=O)(Nc1cc(-c2ccccc2)c(F)cc1F)c1cc(Cl)cc(C(F)(F)F)c1]
I-204
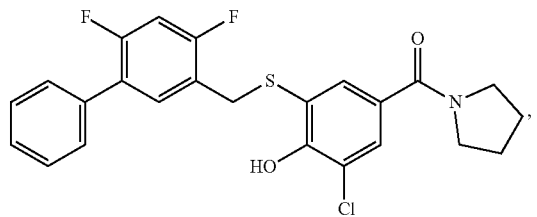 [SMILES: O=C(c1cc(Cl)c(O)c(SCc2cc(-c3ccccc3)c(F)cc2F)c1)N1CCCC1]
I-205

TABLE 1-continued
Exemplary Compounds of Formula I
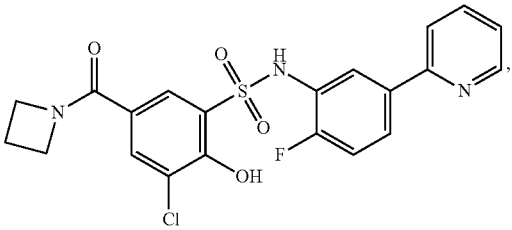 [SMILES: O=C(c1cc(Cl)c(O)c(S(=O)(=O)Nc2cc(-c3ccccn3)ccc2F)c1)N1CCC1]
I-206
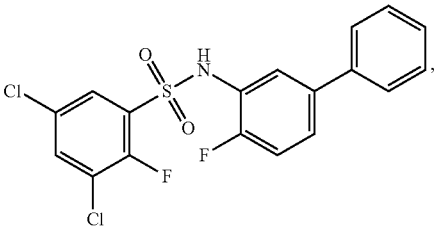 [SMILES: O=S(=O)(Nc1cc(-c2ccccc2)ccc1F)c1cc(Cl)cc(Cl)c1F]
I-207
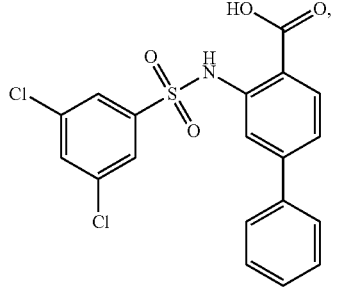
I-208
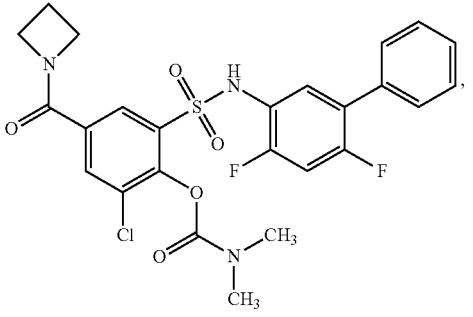 [SMILES: CN(C)C(=O)Oc1c(Cl)cc(C(=O)N2CCC2)cc1S(=O)(=O)Nc1cc(-c2ccccc2)c(F)cc1F]
I-209
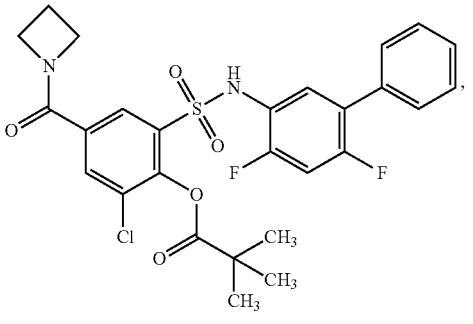 [SMILES: CC(C)(C)C(=O)Oc1c(Cl)cc(C(=O)N2CCC2)cc1S(=O)(=O)Nc1cc(-c2ccccc2)c(F)cc1F]
I-210

TABLE 1-continued
Exemplary Compounds of Formula I
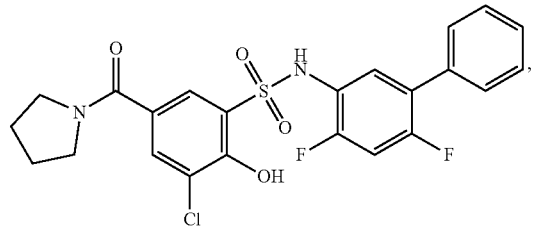 [SMILES: O=C(c1cc(Cl)c(O)c(S(=O)(=O)Nc2cc(-c3ccccc3)c(F)cc2F)c1)N1CCCC1] I-211
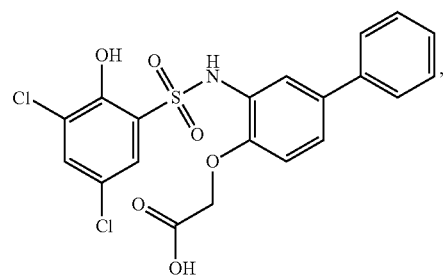 [SMILES: O=C(O)COc1ccc(-c2ccccc2)cc1NS(=O)(=O)c1cc(Cl)cc(Cl)c1O] I-212
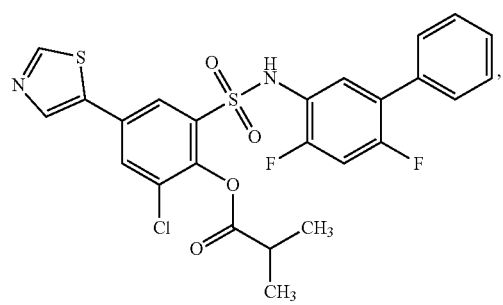 [SMILES: CC(C)C(=O)Oc1c(Cl)cc(-c2cncs2)cc1S(=O)(=O)Nc1cc(-c2ccccc2)c(F)cc1F] I-213
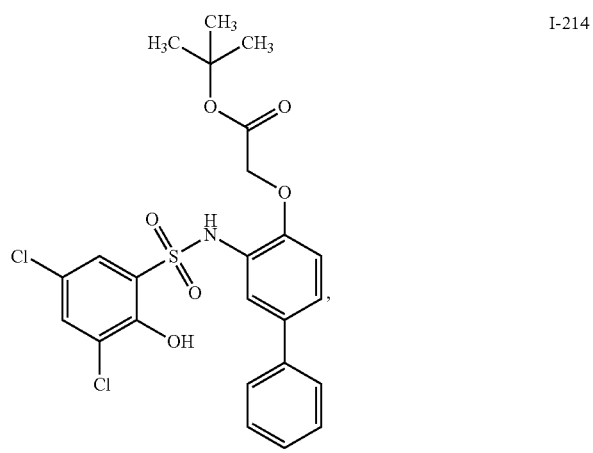 I-214
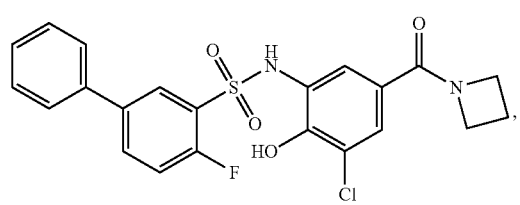 [SMILES: O=C(c1cc(Cl)c(O)c(NS(=O)(=O)c2cc(-c3ccccc3)ccc2F)c1)N1CCC1] I-215

TABLE 1-continued
Exemplary Compounds of Formula I
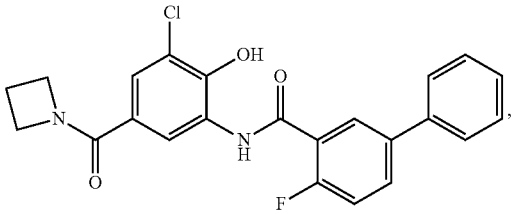 [SMILES: O=C(Nc1cc(C(=O)N2CCC2)cc(Cl)c1O)c1cc(-c2ccccc2)ccc1F]
I-216
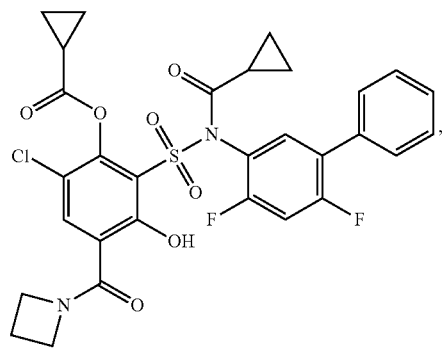 [SMILES: O=C(Oc1c(Cl)cc(C(=O)N2CCC2)c(O)c1S(=O)(=O)N(C(=O)C1CC1)c1cc(-c2ccccc2)c(F)cc1F)C1CC1]
I-217
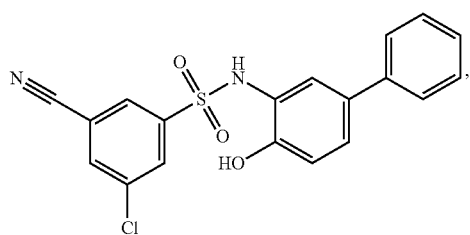 [SMILES: N#Cc1cc(Cl)cc(S(=O)(=O)Nc2cc(-c3ccccc3)ccc2O)c1]
I-218
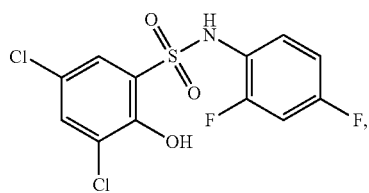 [SMILES: O=S(=O)(Nc1ccc(F)cc1F)c1cc(Cl)cc(Cl)c1O]
I-219
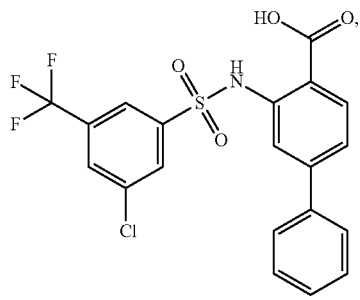 [SMILES: O=C(O)c1ccc(-c2ccccc2)cc1NS(=O)(=O)c1cc(Cl)cc(C(F)(F)F)c1]
I-220
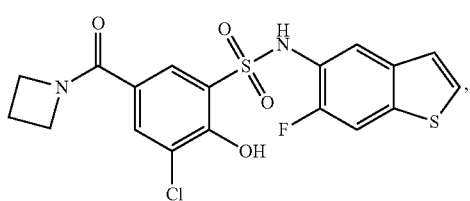 [SMILES: O=C(c1cc(Cl)c(O)c(S(=O)(=O)Nc2cc3ccsc3cc2F)c1)N1CCC1]
I-221

TABLE 1-continued
Exemplary Compounds of Formula I
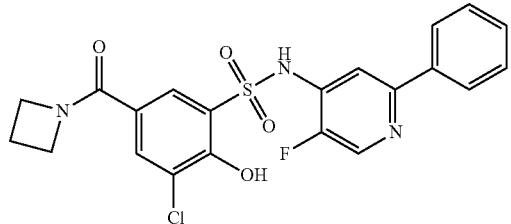 [SMILES: O=C(c1cc(Cl)c(O)c(S(=O)(=O)Nc2cc(-c3ccccc3)ncc2F)c1)N1CCC1] I-222
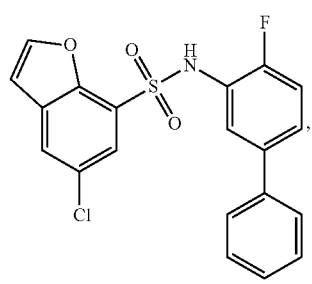 [SMILES: O=S(=O)(Nc1cc(-c2ccccc2)ccc1F)c1cc(Cl)cc2ccoc12] I-223
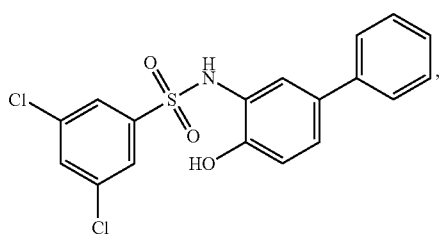 [SMILES: O=S(=O)(Nc1cc(-c2ccccc2)ccc1O)c1cc(Cl)cc(Cl)c1] I-224
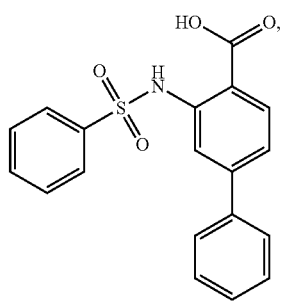 [SMILES: O=C(O)c1ccc(-c2ccccc2)cc1NS(=O)(=O)c1ccccc1] I-225
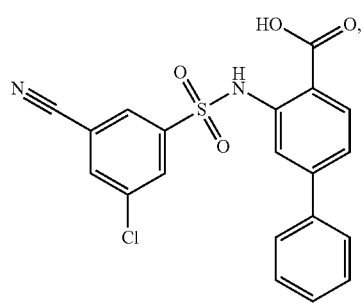 I-226

TABLE 1-continued
Exemplary Compounds of Formula I
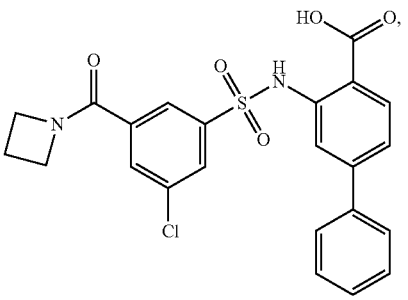 [SMILES: O=C(O)c1ccc(-c2ccccc2)cc1NS(=O)(=O)c1cc(Cl)cc(C(=O)N2CCC2)c1] I-227
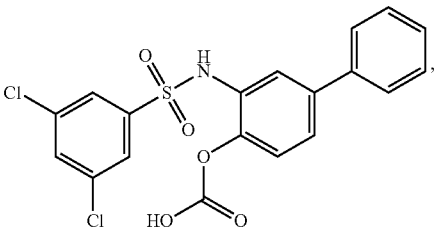 [SMILES: O=C(O)Oc1ccc(-c2ccccc2)cc1NS(=O)(=O)c1cc(Cl)cc(Cl)c1] I-228
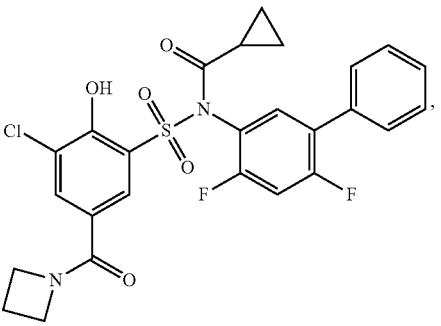 [SMILES: O=C(c1cc(Cl)c(O)c(S(=O)(=O)N(C(=O)C2CC2)c2cc(-c3ccccc3)c(F)cc2F)c1)N1CCC1] I-229
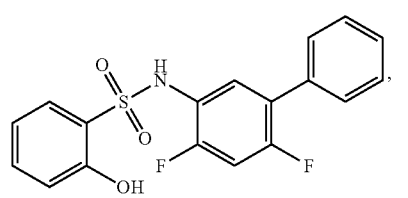 [SMILES: O=S(=O)(Nc1cc(-c2ccccc2)c(F)cc1F)c1ccccc1O] I-230
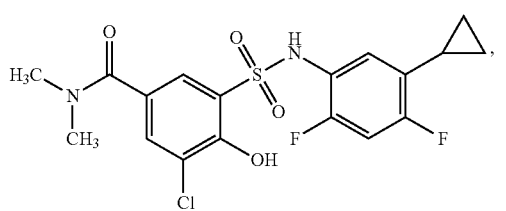 [SMILES: CN(C)C(=O)c1cc(Cl)c(O)c(S(=O)(=O)Nc2cc(C3CC3)c(F)cc2F)c1] I-231
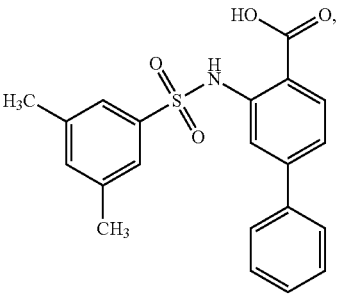 [SMILES: Cc1cc(C)cc(S(=O)(=O)Nc2cc(-c3ccccc3)ccc2C(=O)O)c1] I-232

TABLE 1-continued
Exemplary Compounds of Formula I
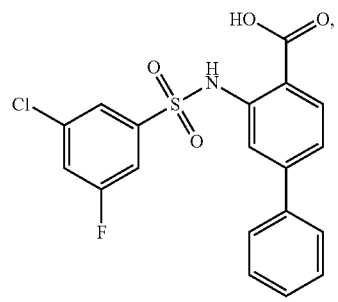 [SMILES: O=C(O)c1ccc(-c2ccccc2)cc1NS(=O)(=O)c1cc(F)cc(Cl)c1]
I-233
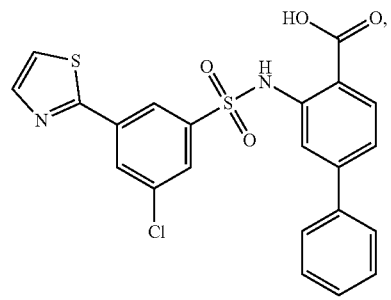 [SMILES: O=C(O)c1ccc(-c2ccccc2)cc1NS(=O)(=O)c1cc(Cl)cc(-c2nccs2)c1]
I-234
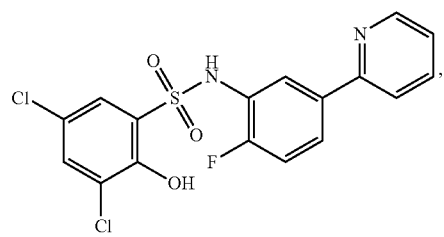 [SMILES: O=S(=O)(Nc1cc(-c2ccccn2)ccc1F)c1cc(Cl)cc(Cl)c1O]
I-235
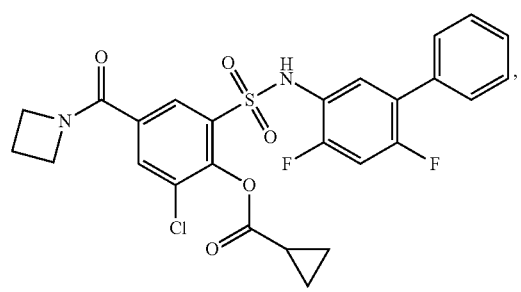 [SMILES: O=C(Oc1c(Cl)cc(C(=O)N2CCC2)cc1S(=O)(=O)Nc1cc(-c2ccccc2)c(F)cc1F)C1CC1]
I-236
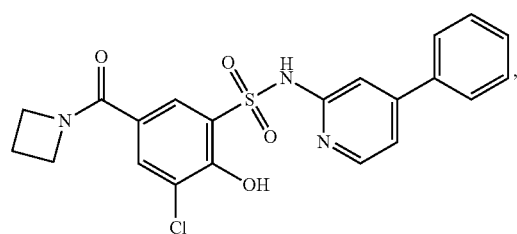 [SMILES: O=C(c1cc(Cl)c(O)c(S(=O)(=O)Nc2cc(-c3ccccc3)ccn2)c1)N1CCC1]
I-237

TABLE 1-continued
Exemplary Compounds of Formula I
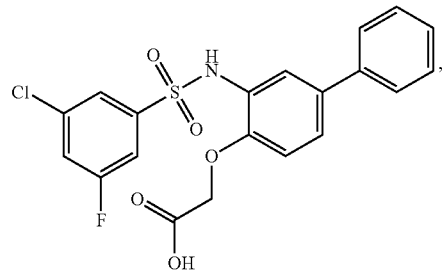 [SMILES: O=C(O)COc1ccc(-c2ccccc2)cc1NS(=O)(=O)c1cc(F)cc(Cl)c1]
I-238
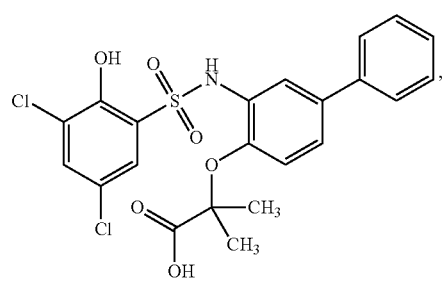 [SMILES: CC(C)(Oc1ccc(-c2ccccc2)cc1NS(=O)(=O)c1cc(Cl)cc(Cl)c1O)C(=O)O]
I-239
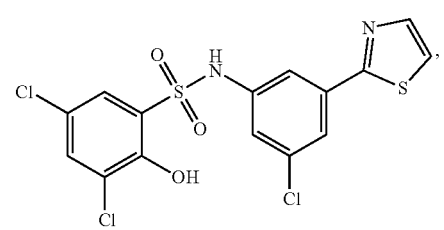 [SMILES: O=S(=O)(Nc1cc(Cl)cc(-c2nccs2)c1)c1cc(Cl)cc(Cl)c1O]
I-240
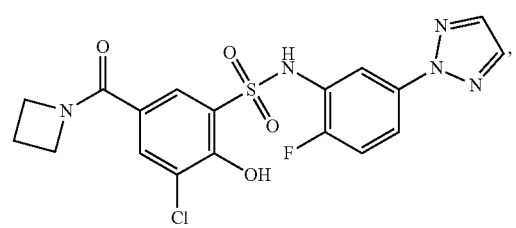 [SMILES: O=C(c1cc(Cl)c(O)c(S(=O)(=O)Nc2cc(-n3nccn3)ccc2F)c1)N1CCC1]
I-241
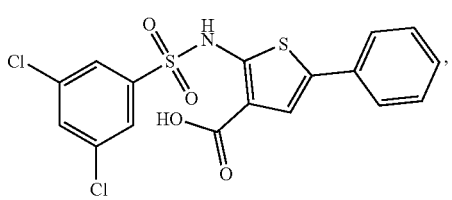 [SMILES: O=C(O)c1cc(-c2ccccc2)sc1NS(=O)(=O)c1cc(Cl)cc(Cl)c1]
I-242
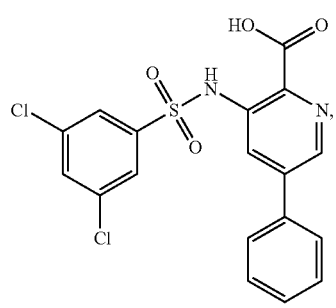 [SMILES: O=C(O)c1ncc(-c2ccccc2)cc1NS(=O)(=O)c1cc(Cl)cc(Cl)c1]
I-243

TABLE 1-continued
Exemplary Compounds of Formula I
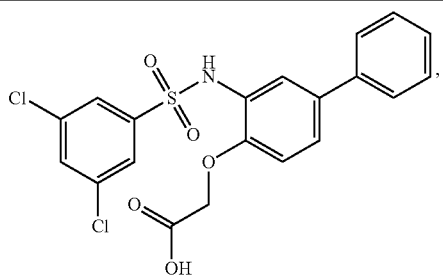 I-244
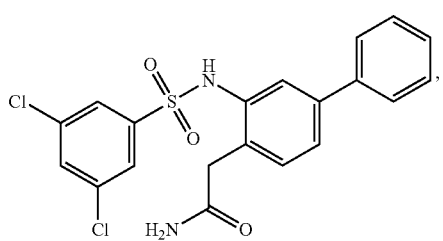 [SMILES: NC(=O)Cc1ccc(-c2ccccc2)cc1NS(=O)(=O)c1cc(Cl)cc(Cl)c1] I-245
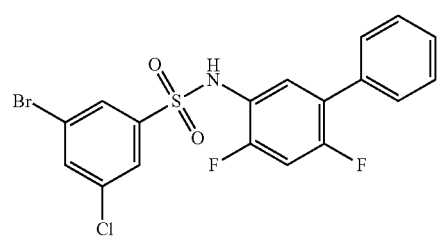 [SMILES: O=S(=O)(Nc1cc(-c2ccccc2)c(F)cc1F)c1cc(Cl)cc(Br)c1] I-246
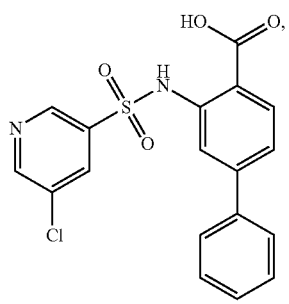 [SMILES: O=C(O)c1ccc(-c2ccccc2)cc1NS(=O)(=O)c1cncc(Cl)c1] I-247
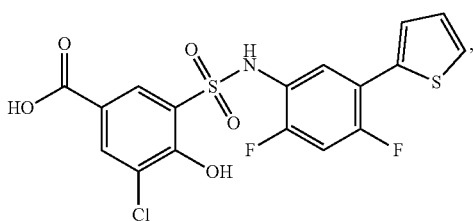 [SMILES: O=C(O)c1cc(Cl)c(O)c(S(=O)(=O)Nc2cc(-c3cccs3)c(F)cc2F)c1] I-248
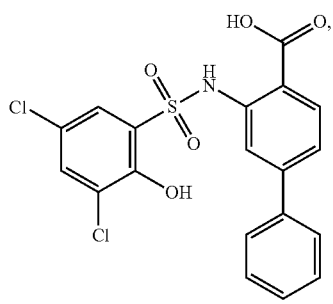 [SMILES: O=C(O)c1ccc(-c2ccccc2)cc1NS(=O)(=O)c1cc(Cl)cc(Cl)c1O] I-249

TABLE 1-continued
Exemplary Compounds of Formula I
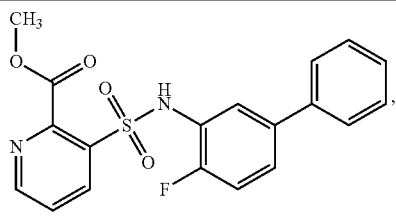
I-250
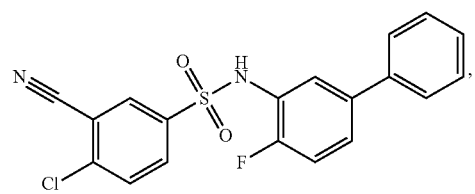 [SMILES: N#Cc1cc(S(=O)(=O)Nc2cc(-c3ccccc3)ccc2F)ccc1Cl]
I-251
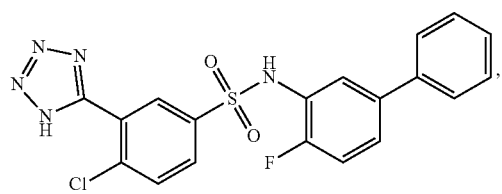 [SMILES: O=S(=O)(Nc1cc(-c2ccccc2)ccc1F)c1ccc(Cl)c(-c2nnn[nH]2)c1]
I-252
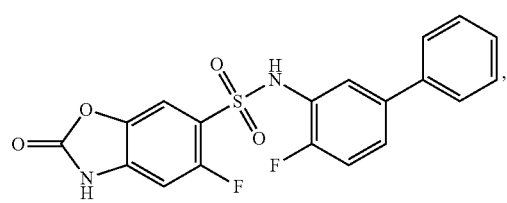 [SMILES: O=c1[nH]c2cc(F)c(S(=O)(=O)Nc3cc(-c4ccccc4)ccc3F)cc2o1]
I-253
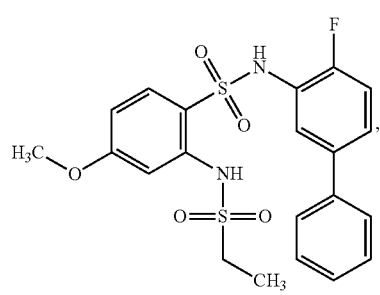 [SMILES: CCS(=O)(=O)Nc1cc(OC)ccc1S(=O)(=O)Nc1cc(-c2ccccc2)ccc1F]
I-254
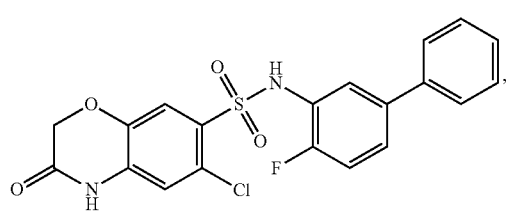 [SMILES: O=C1COc2cc(S(=O)(=O)Nc3cc(-c4ccccc4)ccc3F)c(Cl)cc2N1]
I-255
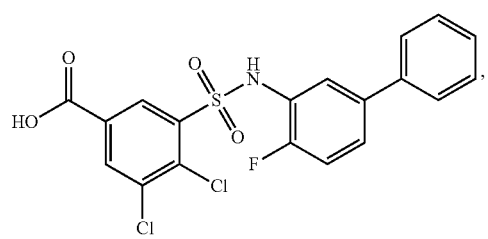 [SMILES: O=C(O)c1cc(Cl)c(Cl)c(S(=O)(=O)Nc2cc(-c3ccccc3)ccc2F)c1]
I-256

TABLE 1-continued
Exemplary Compounds of Formula I
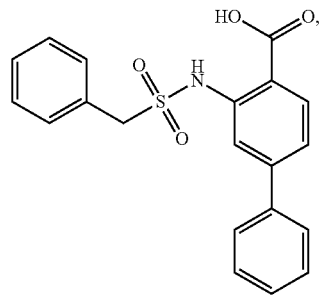 [SMILES: O=C(O)c1ccc(-c2ccccc2)cc1NS(=O)(=O)Cc1ccccc1]
I-257
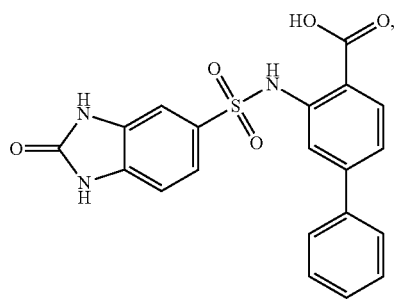 [SMILES: O=C(O)c1ccc(-c2ccccc2)cc1NS(=O)(=O)c1ccc2[nH]c(=O)[nH]c2c1]
I-258
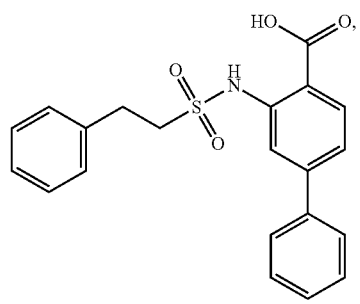 [SMILES: O=C(O)c1ccc(-c2ccccc2)cc1NS(=O)(=O)CCc1ccccc1]
I-259
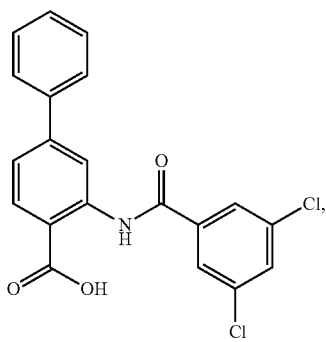 [SMILES: O=C(Nc1cc(-c2ccccc2)ccc1C(=O)O)c1cc(Cl)cc(Cl)c1]
I-260
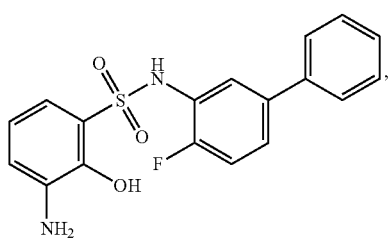 [SMILES: Nc1cccc(S(=O)(=O)Nc2cc(-c3ccccc3)ccc2F)c1O]
I-261

TABLE 1-continued
Exemplary Compounds of Formula I
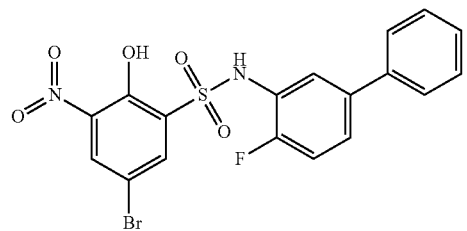 [SMILES: O=[N+]([O-])c1cc(Br)cc(S(=O)(=O)Nc2cc(-c3ccccc3)ccc2F)c1O]
I-262
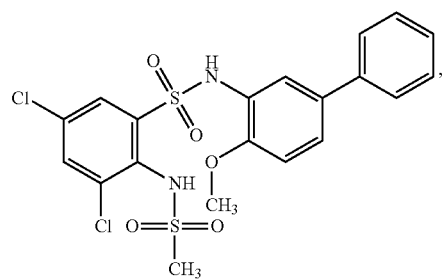 [SMILES: COc1ccc(-c2ccccc2)cc1NS(=O)(=O)c1cc(Cl)cc(Cl)c1NS(C)(=O)=O]
I-263
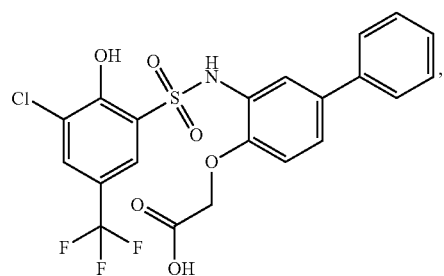 [SMILES: O=C(O)COc1ccc(-c2ccccc2)cc1NS(=O)(=O)c1cc(C(F)(F)F)cc(Cl)c1O]
I-264
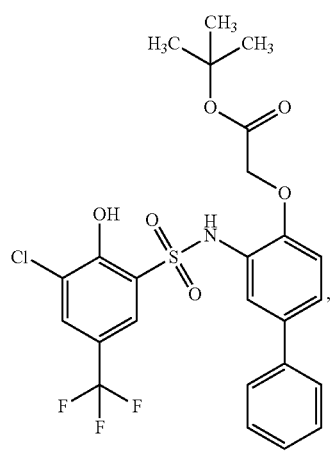 [SMILES: CC(C)(C)OC(=O)COc1ccc(-c2ccccc2)cc1NS(=O)(=O)c1cc(C(F)(F)F)cc(Cl)c1O]
I-265

TABLE 1-continued
Exemplary Compounds of Formula I
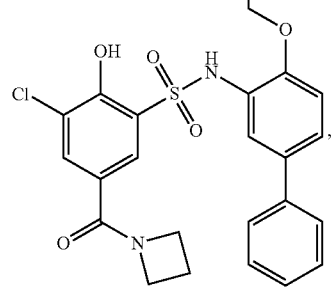
I-266
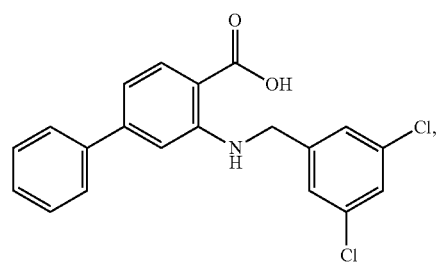 [SMILES: O=C(O)c1ccc(-c2ccccc2)cc1NCc1cc(Cl)cc(Cl)c1]
I-267
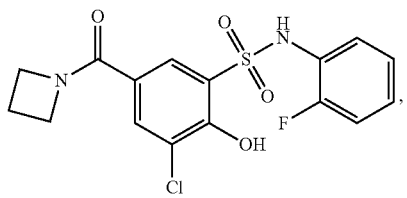 [SMILES: O=C(c1cc(Cl)c(O)c(S(=O)(=O)Nc2ccccc2F)c1)N1CCC1]
I-268
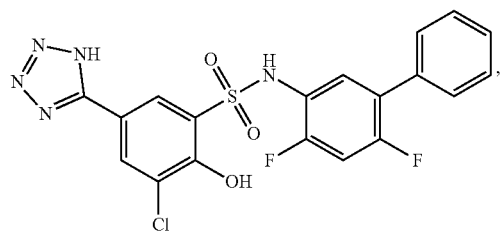 [SMILES: O=S(=O)(Nc1cc(-c2ccccc2)c(F)cc1F)c1cc(-c2nnn[nH]2)cc(Cl)c1O]
I-269
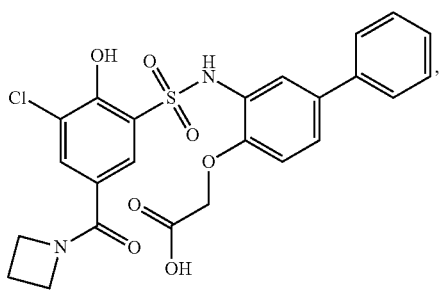 [SMILES: O=C(O)COc1ccc(-c2ccccc2)cc1NS(=O)(=O)c1cc(C(=O)N2CCC2)cc(Cl)c1O]
I-270

TABLE 1-continued
Exemplary Compounds of Formula I
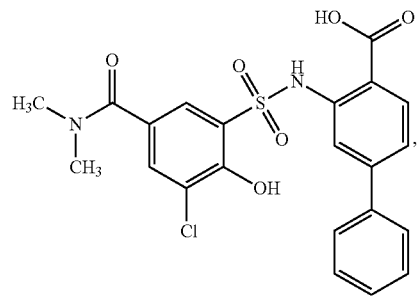 [SMILES: CN(C)C(=O)c1cc(Cl)c(O)c(S(=O)(=O)Nc2cc(-c3ccccc3)ccc2C(=O)O)c1]
I-271
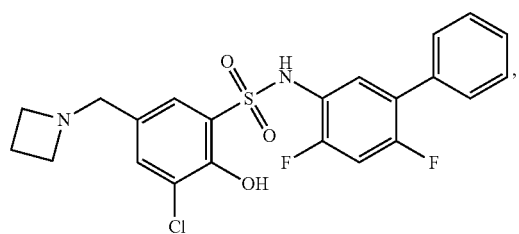 [SMILES: O=S(=O)(Nc1cc(-c2ccccc2)c(F)cc1F)c1cc(CN2CCC2)cc(Cl)c1O]
I-272
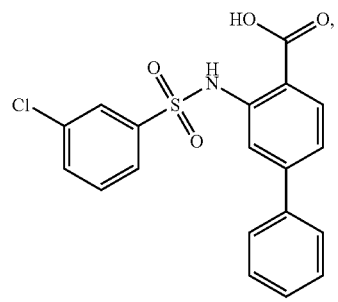 [SMILES: O=C(O)c1ccc(-c2ccccc2)cc1NS(=O)(=O)c1cccc(Cl)c1]
I-273
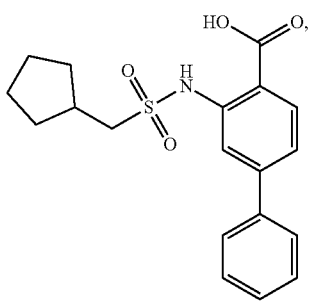 [SMILES: O=C(O)c1ccc(-c2ccccc2)cc1NS(=O)(=O)CC1CCCC1]
I-274
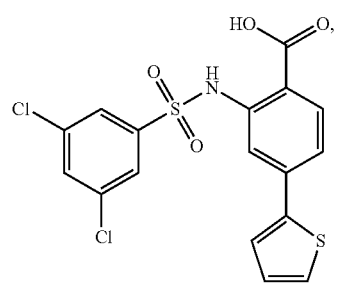 [SMILES: O=C(O)c1ccc(-c2cccs2)cc1NS(=O)(=O)c1cc(Cl)cc(Cl)c1]
I-275

TABLE 1-continued
Exemplary Compounds of Formula I
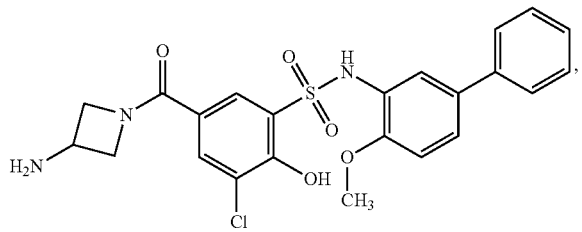 [SMILES: COc1ccc(-c2ccccc2)cc1NS(=O)(=O)c1cc(C(=O)N2CC(N)C2)cc(Cl)c1O]
I-276
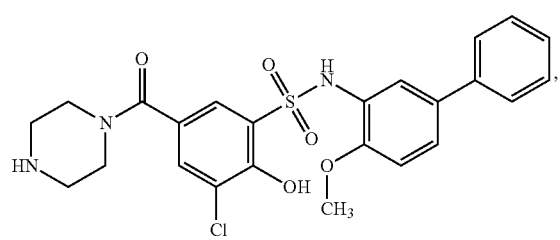 [SMILES: COc1ccc(-c2ccccc2)cc1NS(=O)(=O)c1cc(C(=O)N2CCNCC2)cc(Cl)c1O]
I-277
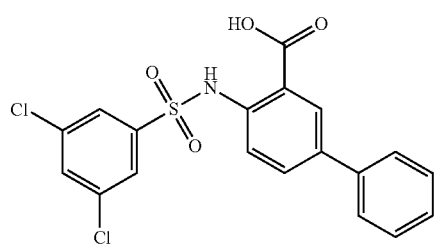 [SMILES: O=C(O)c1cc(-c2ccccc2)ccc1NS(=O)(=O)c1cc(Cl)cc(Cl)c1]
I-278
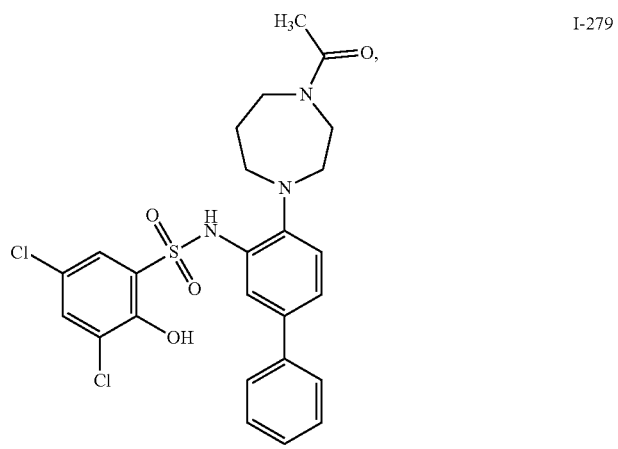
I-279
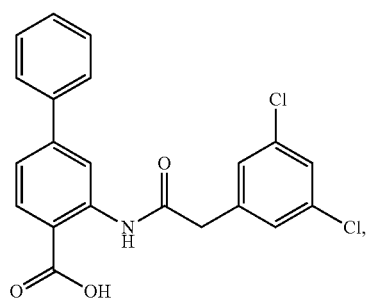 [SMILES: O=C(Cc1cc(Cl)cc(Cl)c1)Nc1cc(-c2ccccc2)ccc1C(=O)O]
I-280

TABLE 1-continued
Exemplary Compounds of Formula I
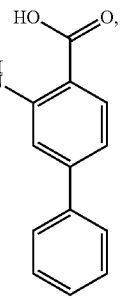
I-281
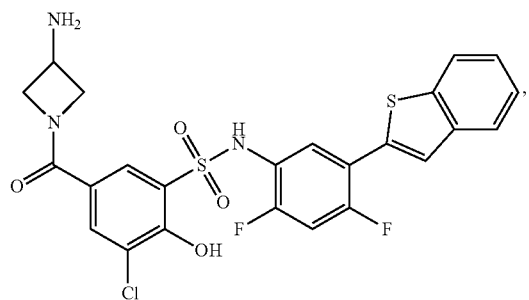 [SMILES: NC1CN(C(=O)c2cc(Cl)c(O)c(S(=O)(=O)Nc3cc(-c4cc5ccccc5s4)c(F)cc3F)c2)C1]
I-282
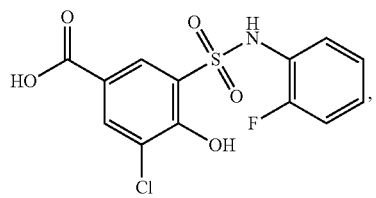 [SMILES: O=C(O)c1cc(Cl)c(O)c(S(=O)(=O)Nc2ccccc2F)c1]
I-283
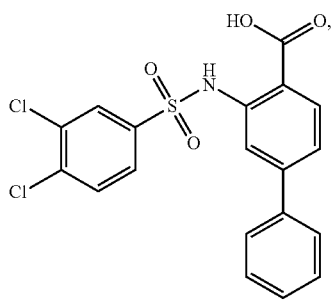 [SMILES: O=C(O)c1ccc(-c2ccccc2)cc1NS(=O)(=O)c1ccc(Cl)c(Cl)c1]
I-284
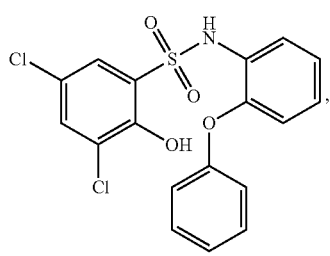 [SMILES: O=S(=O)(Nc1ccccc1Oc1ccccc1)c1cc(Cl)cc(Cl)c1O]
I-285

TABLE 1-continued
Exemplary Compounds of Formula I
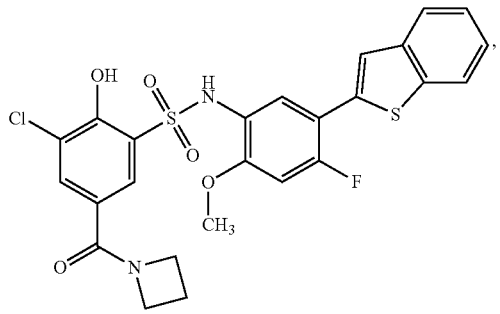 [SMILES: COc1cc(F)c(-c2cc3ccccc3s2)cc1NS(=O)(=O)c1cc(C(=O)N2CCC2)cc(Cl)c1O]
I-286
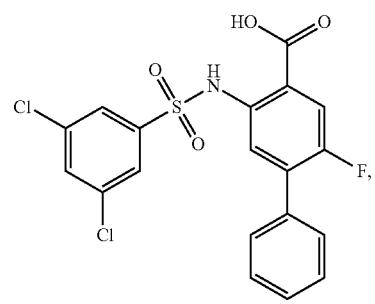 [SMILES: O=C(O)c1cc(F)c(-c2ccccc2)cc1NS(=O)(=O)c1cc(Cl)cc(Cl)c1]
I-287
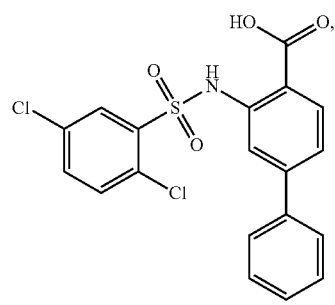 [SMILES: O=C(O)c1ccc(-c2ccccc2)cc1NS(=O)(=O)c1cc(Cl)ccc1Cl]
I-288
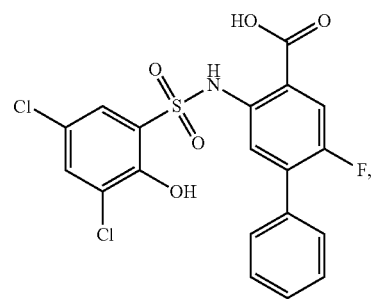 [SMILES: O=C(O)c1cc(F)c(-c2ccccc2)cc1NS(=O)(=O)c1cc(Cl)cc(Cl)c1O]
I-289
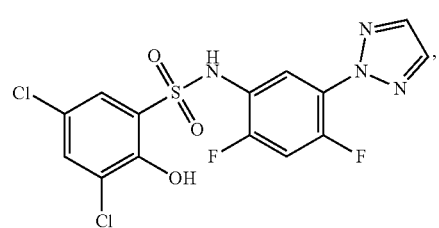 [SMILES: O=S(=O)(Nc1cc(-n2nccn2)c(F)cc1F)c1cc(Cl)cc(Cl)c1O]
I-290

TABLE 1-continued
Exemplary Compounds of Formula I
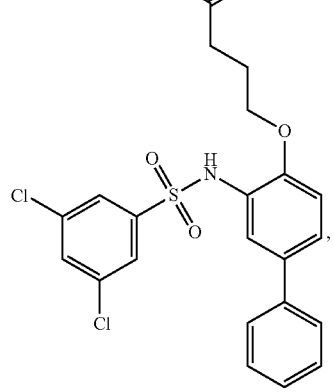
I-291
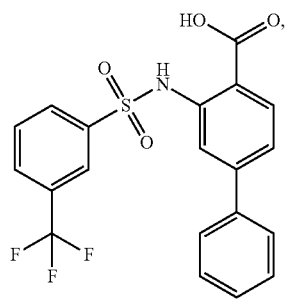 [SMILES: O=C(O)c1ccc(-c2ccccc2)cc1NS(=O)(=O)c1cccc(C(F)(F)F)c1]
I-292
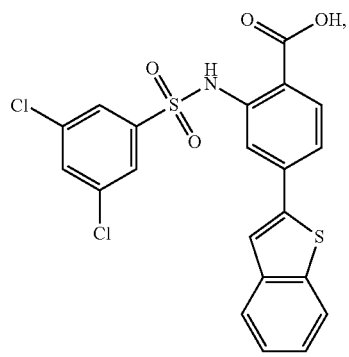 [SMILES: O=C(O)c1ccc(-c2cc3ccccc3s2)cc1NS(=O)(=O)c1cc(Cl)cc(Cl)c1]
I-293
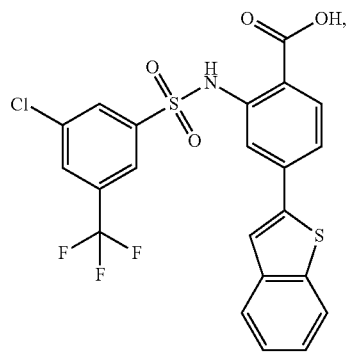 [SMILES: O=C(O)c1ccc(-c2cc3ccccc3s2)cc1NS(=O)(=O)c1cc(Cl)cc(C(F)(F)F)c1]
I-294

TABLE 1-continued
Exemplary Compounds of Formula I
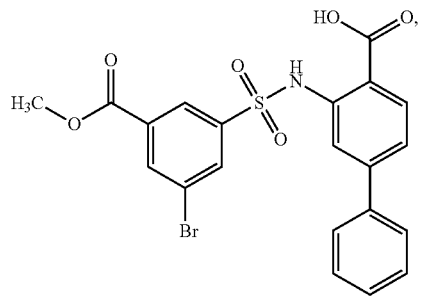 [SMILES: COC(=O)c1cc(Br)cc(S(=O)(=O)Nc2cc(-c3ccccc3)ccc2C(=O)O)c1]
I-295
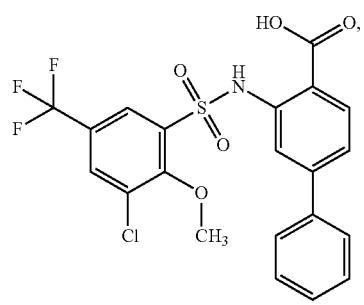 [SMILES: COc1c(Cl)cc(C(F)(F)F)cc1S(=O)(=O)Nc1cc(-c2ccccc2)ccc1C(=O)O]
I-296
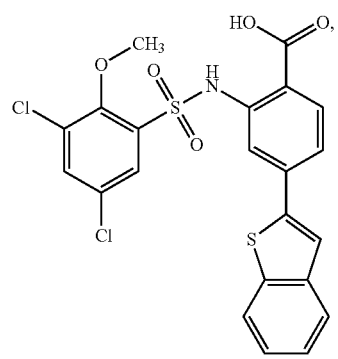 [SMILES: COc1c(Cl)cc(Cl)cc1S(=O)(=O)Nc1cc(-c2cc3ccccc3s2)ccc1C(=O)O]
I-297
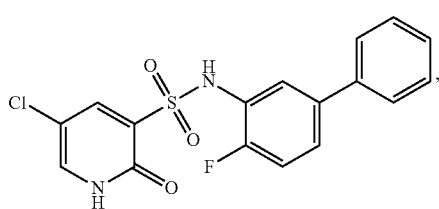 [SMILES: O=c1[nH]cc(Cl)cc1S(=O)(=O)Nc1cc(-c2ccccc2)ccc1F]
I-298
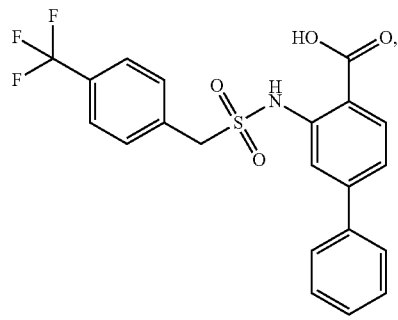 [SMILES: O=C(O)c1ccc(-c2ccccc2)cc1NS(=O)(=O)Cc1ccc(C(F)(F)F)cc1]
I-299

TABLE 1-continued
Exemplary Compounds of Formula I
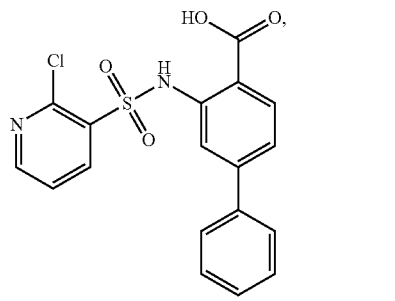 [SMILES: O=C(O)c1ccc(-c2ccccc2)cc1NS(=O)(=O)c1cccnc1Cl]
I-300
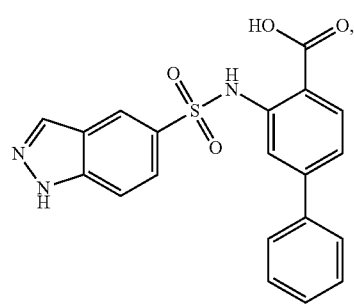 [SMILES: O=C(O)c1ccc(-c2ccccc2)cc1NS(=O)(=O)c1ccc2[nH]ncc2c1]
I-301
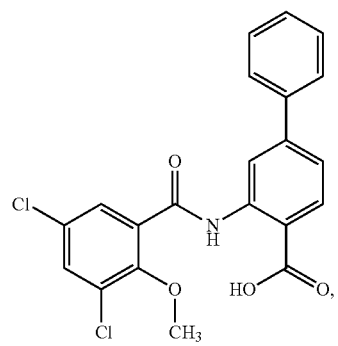 [SMILES: COc1c(Cl)cc(Cl)cc1C(=O)Nc1cc(-c2ccccc2)ccc1C(=O)O]
I-302
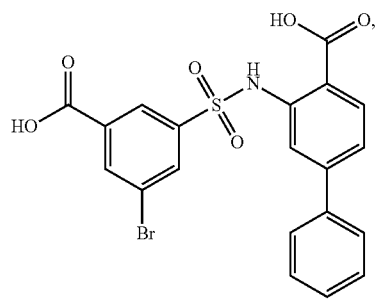 [SMILES: O=C(O)c1cc(Br)cc(S(=O)(=O)Nc2cc(-c3ccccc3)ccc2C(=O)O)c1]
I-303
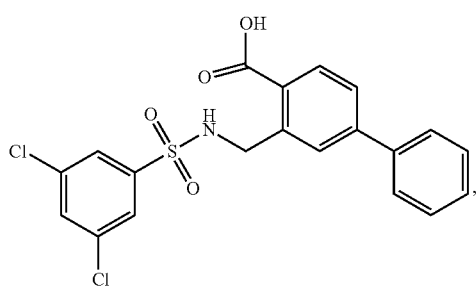 [SMILES: O=C(O)c1ccc(-c2ccccc2)cc1CNS(=O)(=O)c1cc(Cl)cc(Cl)c1]
I-304

TABLE 1-continued
Exemplary Compounds of Formula I
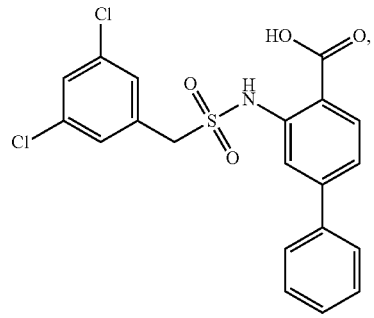 [SMILES: O=C(O)c1ccc(-c2ccccc2)cc1NS(=O)(=O)Cc1cc(Cl)cc(Cl)c1]
I-305
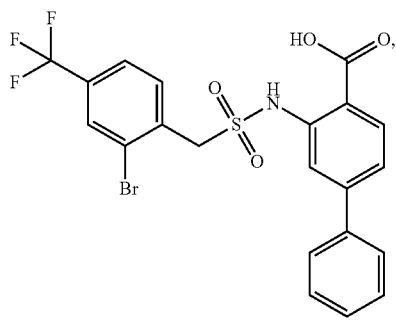 [SMILES: O=C(O)c1ccc(-c2ccccc2)cc1NS(=O)(=O)Cc1ccc(C(F)(F)F)cc1Br]
I-306
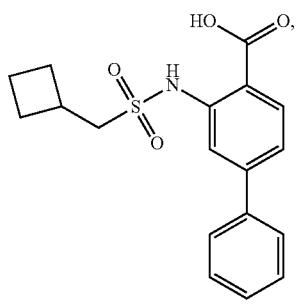 [SMILES: O=C(O)c1ccc(-c2ccccc2)cc1NS(=O)(=O)CC1CCC1]
I-307
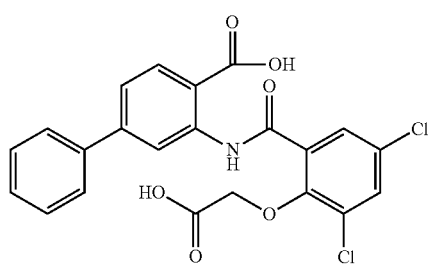 [SMILES: O=C(O)COc1c(Cl)cc(Cl)cc1C(=O)Nc1cc(-c2ccccc2)ccc1C(=O)O]
I-308
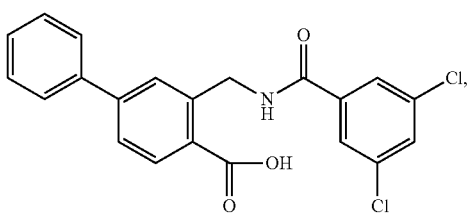 [SMILES: O=C(NCc1cc(-c2ccccc2)ccc1C(=O)O)c1cc(Cl)cc(Cl)c1]
I-309

TABLE 1-continued
Exemplary Compounds of Formula I
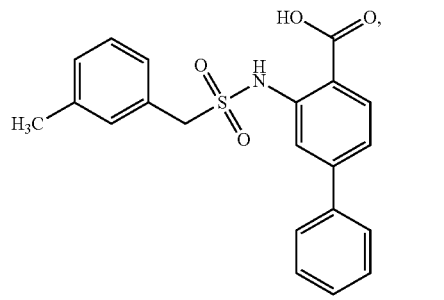 [SMILES: Cc1cccc(CS(=O)(=O)Nc2cc(-c3ccccc3)ccc2C(=O)O)c1]
I-310
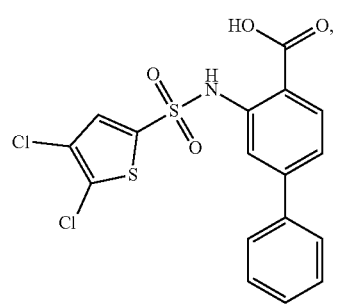 [SMILES: O=C(O)c1ccc(-c2ccccc2)cc1NS(=O)(=O)c1cc(Cl)c(Cl)s1]
I-311
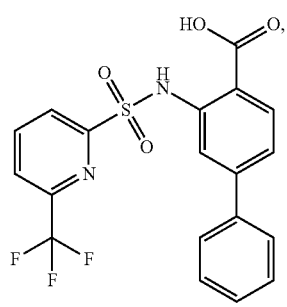 [SMILES: O=C(O)c1ccc(-c2ccccc2)cc1NS(=O)(=O)c1cccc(C(F)(F)F)n1]
I-312
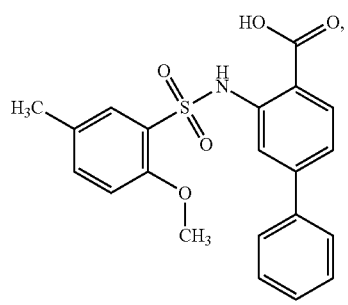 [SMILES: COc1ccc(C)cc1S(=O)(=O)Nc1cc(-c2ccccc2)ccc1C(=O)O]
I-313
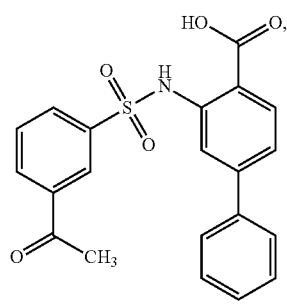
I-314

TABLE 1-continued
Exemplary Compounds of Formula I
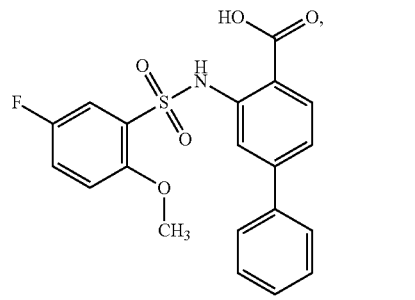 [SMILES: COc1ccc(F)cc1S(=O)(=O)Nc1cc(-c2ccccc2)ccc1C(=O)O] I-315
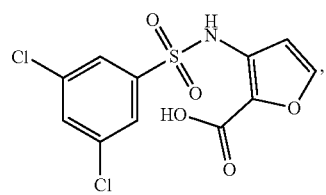 [SMILES: O=C(O)c1occc1NS(=O)(=O)c1cc(Cl)cc(Cl)c1] I-316
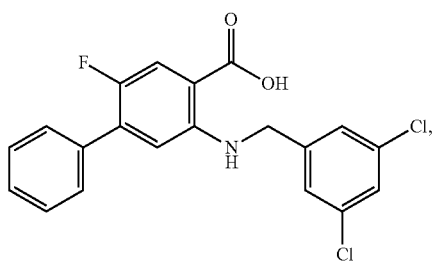 [SMILES: O=C(O)c1cc(F)c(-c2ccccc2)cc1NCc1cc(Cl)cc(Cl)c1] I-317
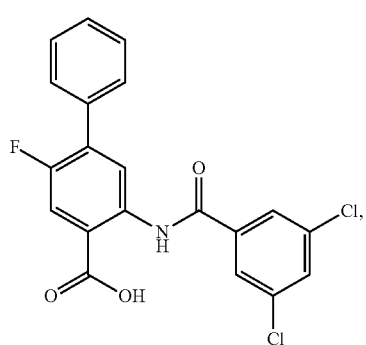 [SMILES: O=C(Nc1cc(-c2ccccc2)c(F)cc1C(=O)O)c1cc(Cl)cc(Cl)c1] I-318
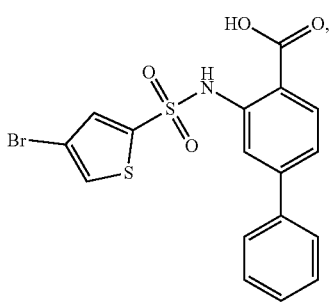 I-319

TABLE 1-continued
Exemplary Compounds of Formula I
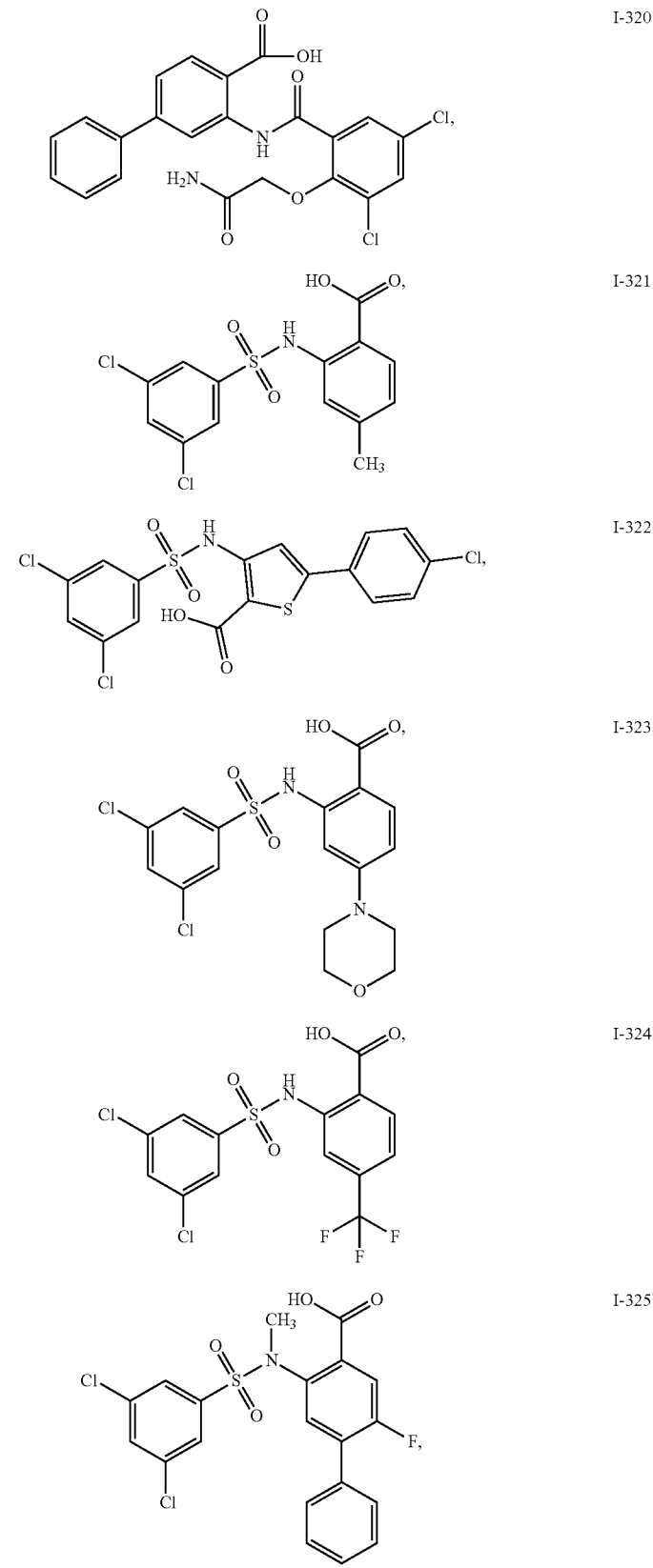
I-320
I-321
I-322
I-323
I-324
I-325

TABLE 1-continued
Exemplary Compounds of Formula I
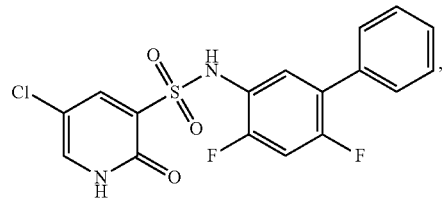 [SMILES: O=c1[nH]cc(Cl)cc1S(=O)(=O)Nc1cc(-c2ccccc2)c(F)cc1F]
I-326
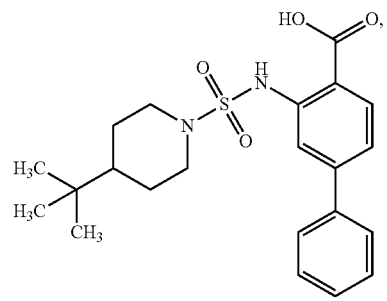 [SMILES: CC(C)(C)C1CCN(S(=O)(=O)Nc2cc(-c3ccccc3)ccc2C(=O)O)CC1]
I-327
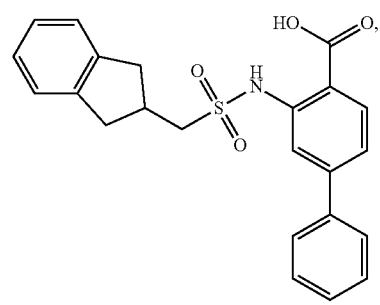 [SMILES: O=C(O)c1ccc(-c2ccccc2)cc1NS(=O)(=O)CC1Cc2ccccc2C1]
I-328
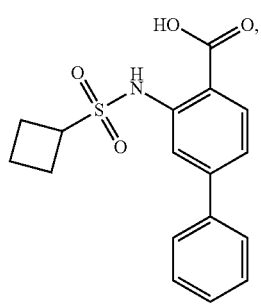 [SMILES: O=C(O)c1ccc(-c2ccccc2)cc1NS(=O)(=O)C1CCC1]
I-329
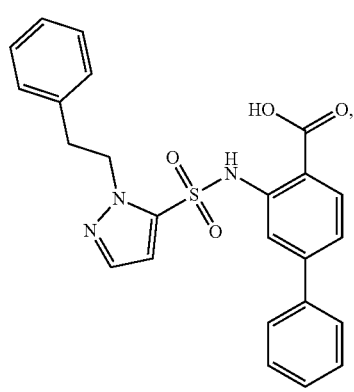 [SMILES: O=C(O)c1ccc(-c2ccccc2)cc1NS(=O)(=O)c1ccnn1CCc1ccccc1]
I-330

TABLE 1-continued
Exemplary Compounds of Formula I
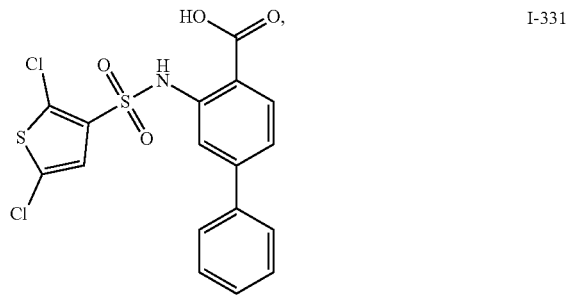
I-331
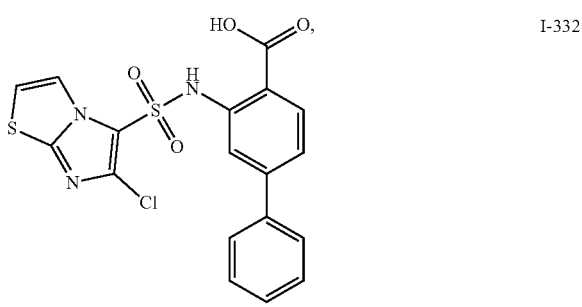
I-332
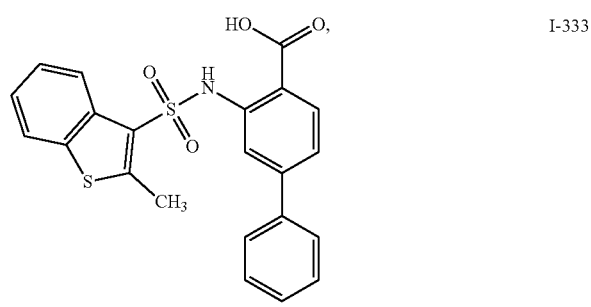
I-333
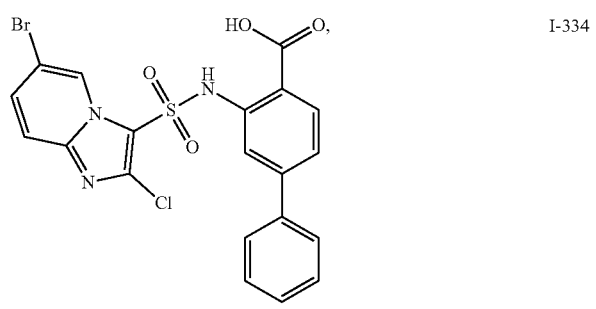
I-334
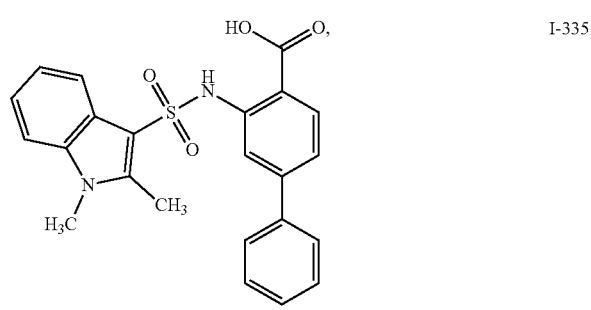
I-335

TABLE 1-continued
Exemplary Compounds of Formula I
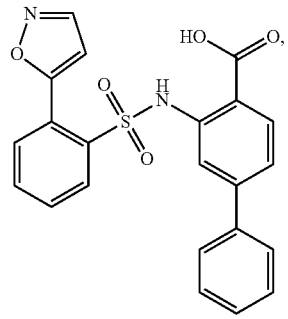 [SMILES: O=C(O)c1ccc(-c2ccccc2)cc1NS(=O)(=O)c1ccccc1-c1ccno1]
I-336
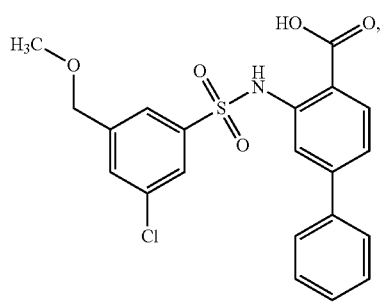 [SMILES: COCc1cc(Cl)cc(S(=O)(=O)Nc2cc(-c3ccccc3)ccc2C(=O)O)c1]
I-337
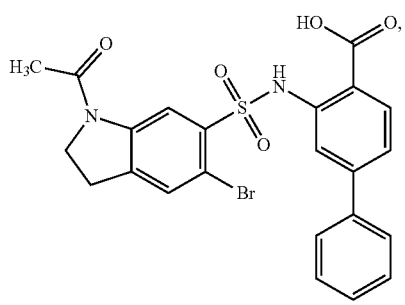 [SMILES: CC(=O)N1CCc2cc(Br)c(S(=O)(=O)Nc3cc(-c4ccccc4)ccc3C(=O)O)cc21]
I-338
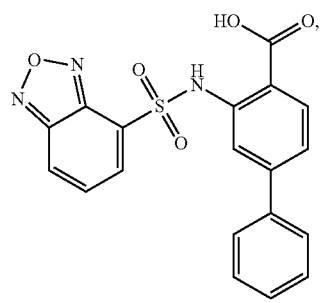 [SMILES: O=C(O)c1ccc(-c2ccccc2)cc1NS(=O)(=O)c1cccc2nonc12]
I-339
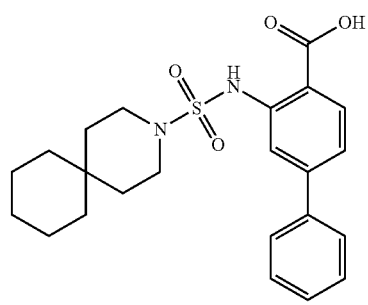 [SMILES: O=C(O)c1ccc(-c2ccccc2)cc1NS(=O)(=O)N1CCC2(CCCCC2)CC1]
I-340

154
TABLE 1-continued
Exemplary Compounds of Formula I
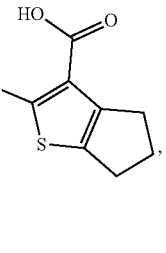
I-341
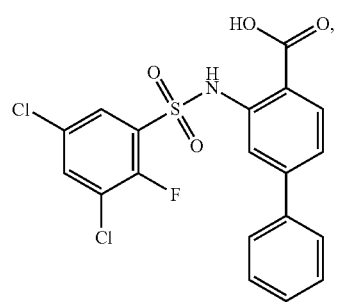 [SMILES: O=C(O)c1ccc(-c2ccccc2)cc1NS(=O)(=O)c1cc(Cl)cc(Cl)c1F]
I-342
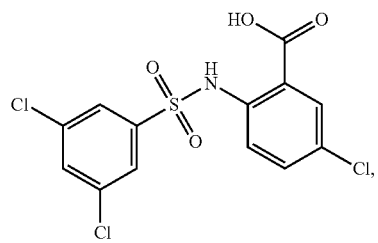 [SMILES: O=C(O)c1cc(Cl)ccc1NS(=O)(=O)c1cc(Cl)cc(Cl)c1]
I-343
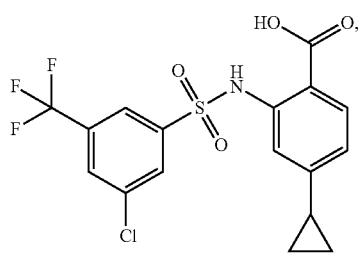 [SMILES: O=C(O)c1ccc(C2CC2)cc1NS(=O)(=O)c1cc(Cl)cc(C(F)(F)F)c1]
I-344
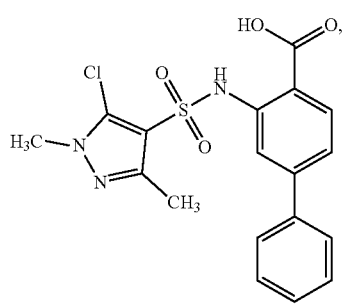 [SMILES: Cc1nn(C)c(Cl)c1S(=O)(=O)Nc1cc(-c2ccccc2)ccc1C(=O)O]
I-345

TABLE 1-continued
Exemplary Compounds of Formula I
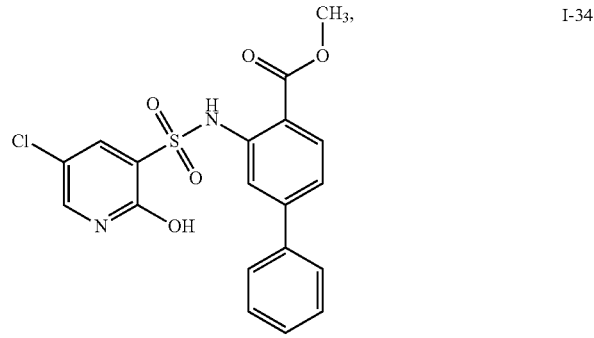
I-346
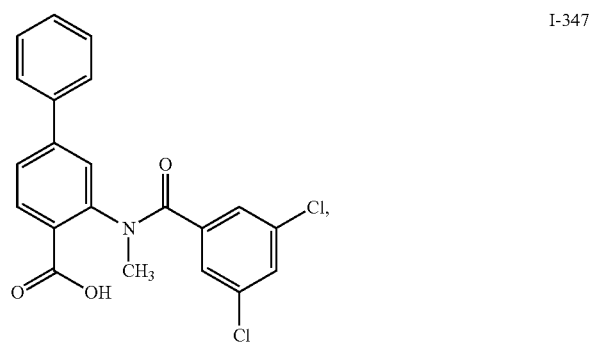
I-347
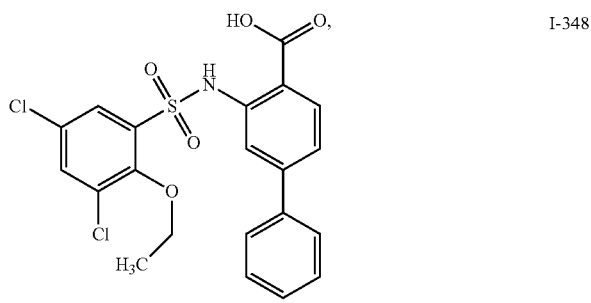
I-348
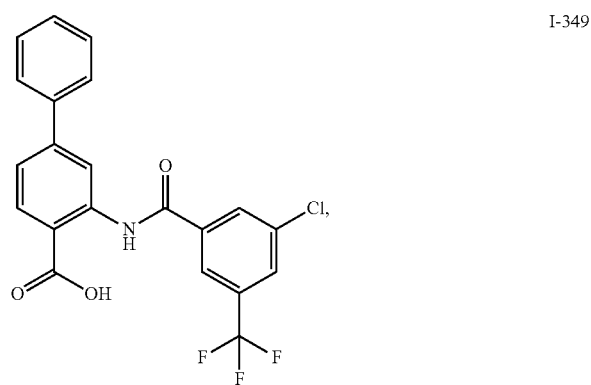
I-349

TABLE 1-continued
Exemplary Compounds of Formula I
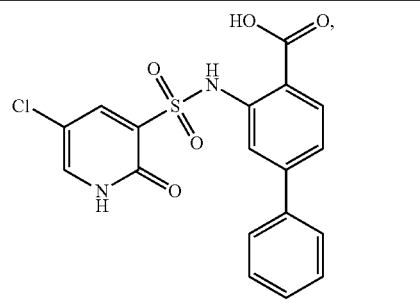
I-350
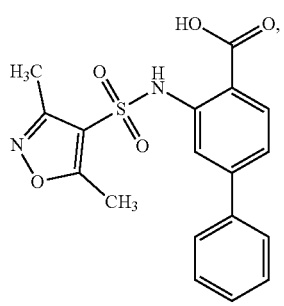 [SMILES: Cc1noc(C)c1S(=O)(=O)Nc1cc(-c2ccccc2)ccc1C(=O)O]
I-351
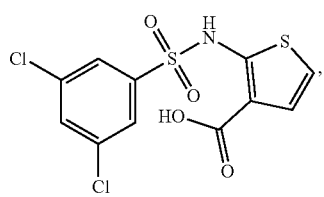 [SMILES: O=C(O)c1ccsc1NS(=O)(=O)c1cc(Cl)cc(Cl)c1]
I-352
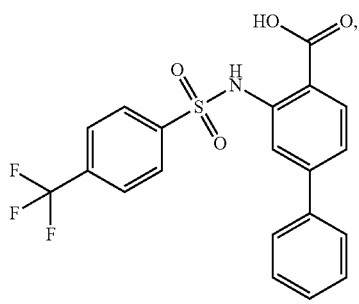 [SMILES: O=C(O)c1ccc(-c2ccccc2)cc1NS(=O)(=O)c1ccc(C(F)(F)F)cc1]
I-353
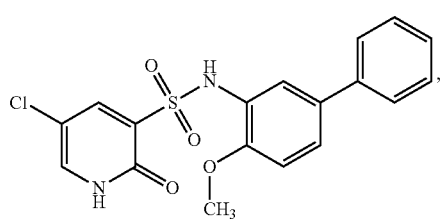 [SMILES: COc1ccc(-c2ccccc2)cc1NS(=O)(=O)c1cc(Cl)c[nH]c1=O]
I-354
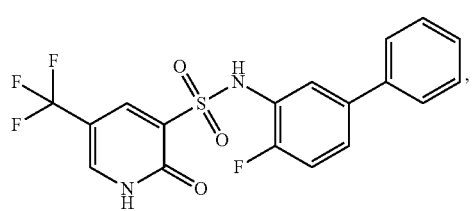 [SMILES: O=c1[nH]cc(C(F)(F)F)cc1S(=O)(=O)Nc1cc(-c2ccccc2)ccc1F]
I-355

TABLE 1-continued
Exemplary Compounds of Formula I
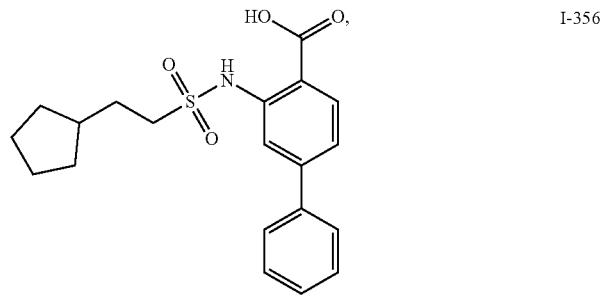
I-356
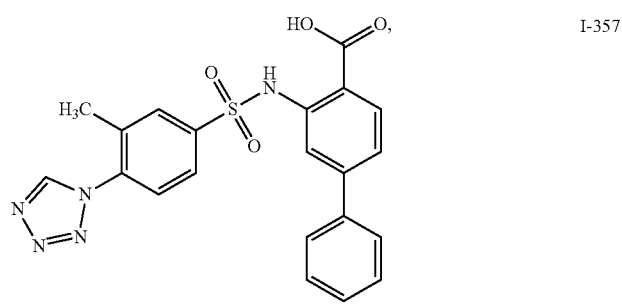
I-357
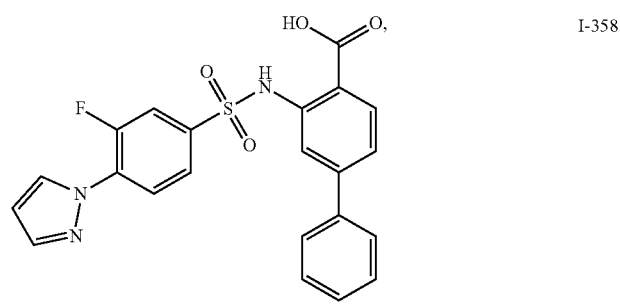
I-358
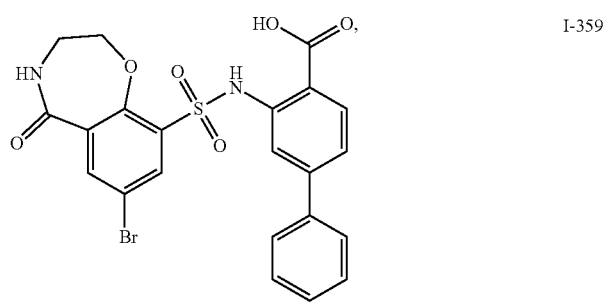
I-359
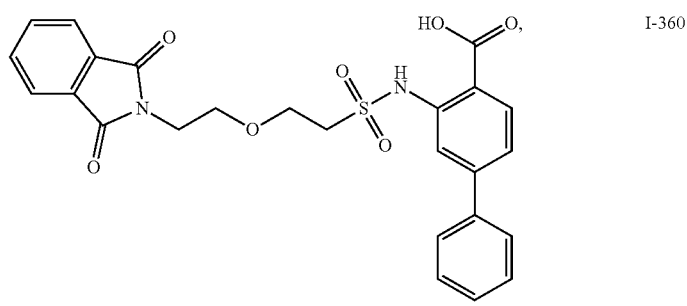
I-360

TABLE 1-continued
Exemplary Compounds of Formula I
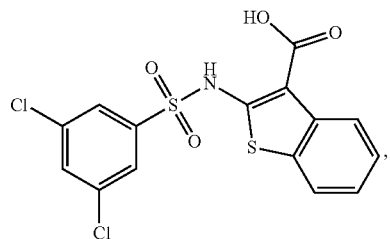 [SMILES: O=C(O)c1c(NS(=O)(=O)c2cc(Cl)cc(Cl)c2)sc2ccccc12]
I-361
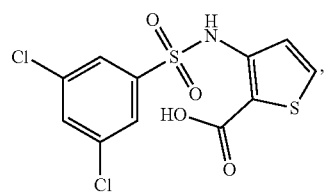 [SMILES: O=C(O)c1sccc1NS(=O)(=O)c1cc(Cl)cc(Cl)c1]
I-362
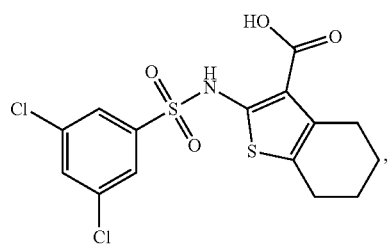 [SMILES: O=C(O)c1c(NS(=O)(=O)c2cc(Cl)cc(Cl)c2)sc2c1CCCC2]
I-363
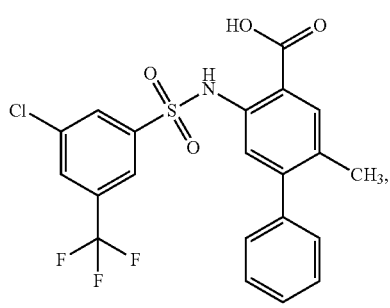 [SMILES: Cc1cc(C(=O)O)c(NS(=O)(=O)c2cc(Cl)cc(C(F)(F)F)c2)cc1-c1ccccc1]
I-364
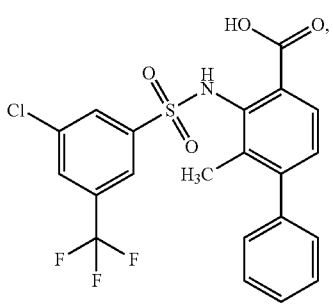 [SMILES: Cc1c(-c2ccccc2)ccc(C(=O)O)c1NS(=O)(=O)c1cc(Cl)cc(C(F)(F)F)c1]
I-365
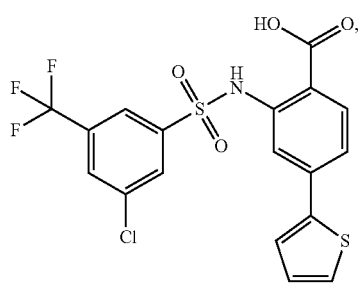 [SMILES: O=C(O)c1ccc(-c2cccs2)cc1NS(=O)(=O)c1cc(Cl)cc(C(F)(F)F)c1]
I-366

TABLE 1-continued
Exemplary Compounds of Formula I
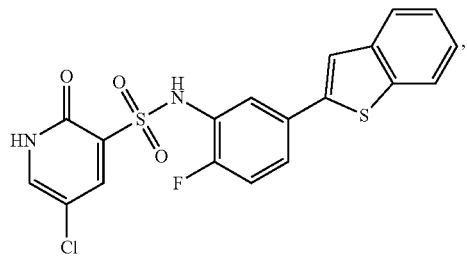 [SMILES: O=c1[nH]cc(Cl)cc1S(=O)(=O)Nc1cc(-c2cc3ccccc3s2)ccc1F] I-367
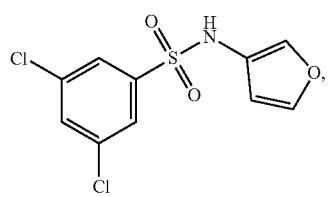 [SMILES: O=S(=O)(Nc1ccoc1)c1cc(Cl)cc(Cl)c1] I-368
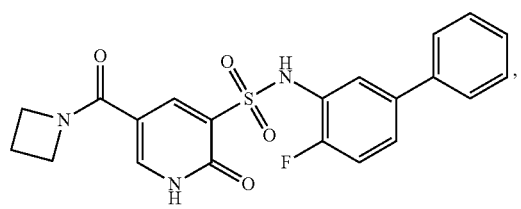 [SMILES: O=C(c1c[nH]c(=O)c(S(=O)(=O)Nc2cc(-c3ccccc3)ccc2F)c1)N1CCC1] I-369
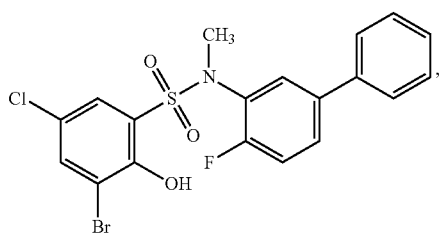 [SMILES: CN(c1cc(-c2ccccc2)ccc1F)S(=O)(=O)c1cc(Cl)cc(Br)c1O] I-370
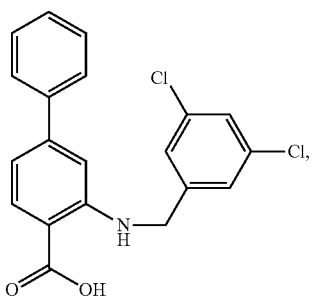 [SMILES: O=C(O)c1ccc(-c2ccccc2)cc1NCc1cc(Cl)cc(Cl)c1] I-371
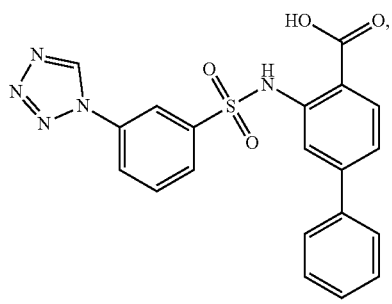 [SMILES: O=C(O)c1ccc(-c2ccccc2)cc1NS(=O)(=O)c1cccc(-n2cnnn2)c1] I-372

TABLE 1-continued
Exemplary Compounds of Formula I
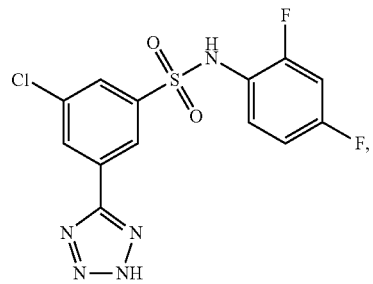 [SMILES: O=S(=O)(Nc1ccc(F)cc1F)c1cc(Cl)cc(-c2nn[nH]n2)c1]
I-373
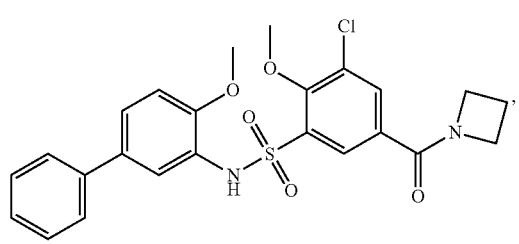 [SMILES: COc1ccc(-c2ccccc2)cc1NS(=O)(=O)c1cc(C(=O)N2CCC2)cc(Cl)c1OC]
I-374
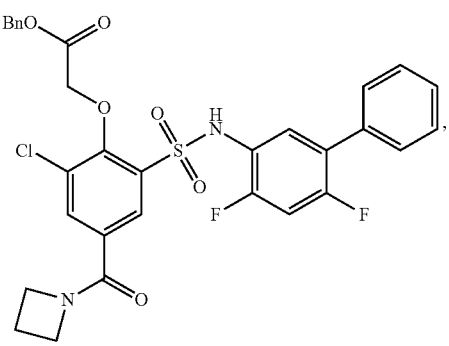 [SMILES: O=C(COc1c(Cl)cc(C(=O)N2CCC2)cc1S(=O)(=O)Nc1cc(-c2ccccc2)c(F)cc1F)OCc1ccccc1]
I-375
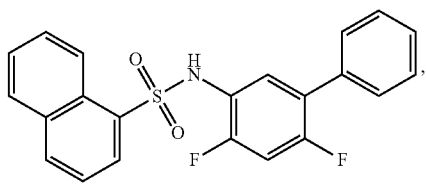 [SMILES: O=S(=O)(Nc1cc(-c2ccccc2)c(F)cc1F)c1cccc2ccccc12]
I-376
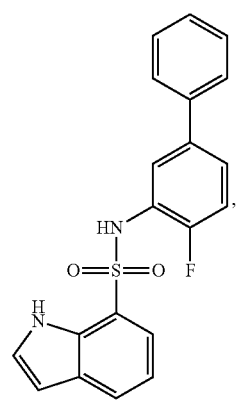 [SMILES: O=S(=O)(Nc1cc(-c2ccccc2)ccc1F)c1cccc2cc[nH]c12]
I-377

TABLE 1-continued
Exemplary Compounds of Formula I
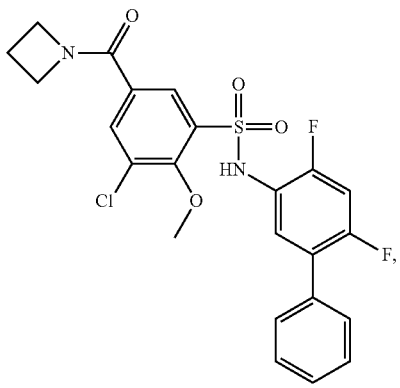 [SMILES: COc1c(Cl)cc(C(=O)N2CCC2)cc1S(=O)(=O)Nc1cc(-c2ccccc2)c(F)cc1F]
I-378
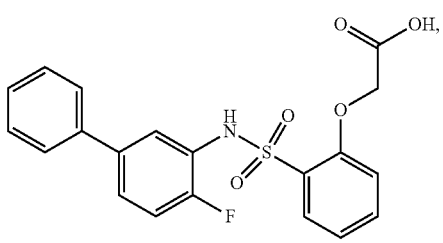 [SMILES: O=C(O)COc1ccccc1S(=O)(=O)Nc1cc(-c2ccccc2)ccc1F]
I-379
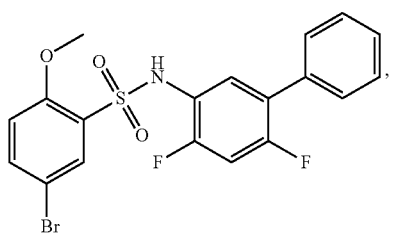 [SMILES: COc1ccc(Br)cc1S(=O)(=O)Nc1cc(-c2ccccc2)c(F)cc1F]
I-380
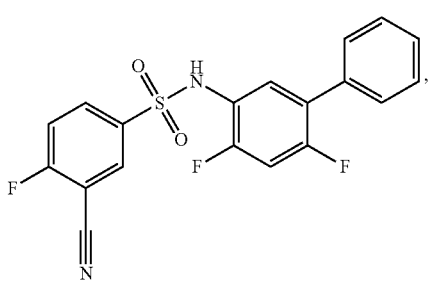 [SMILES: N#Cc1cc(S(=O)(=O)Nc2cc(-c3ccccc3)c(F)cc2F)ccc1F]
I-381
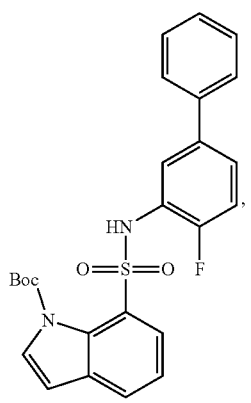 [SMILES: CC(C)(C)OC(=O)n1ccc2cccc(S(=O)(=O)Nc3cc(-c4ccccc4)ccc3F)c21]
I-382

TABLE 1-continued
Exemplary Compounds of Formula I
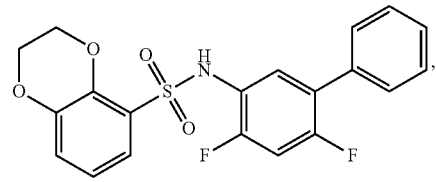 [SMILES: O=S(=O)(Nc1cc(-c2ccccc2)c(F)cc1F)c1cccc2c1OCCO2] I-383
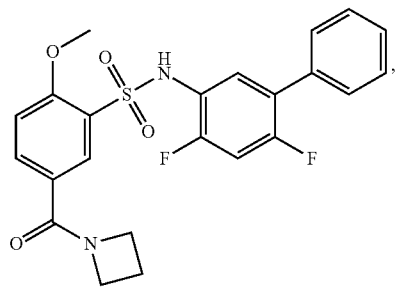 [SMILES: COc1ccc(C(=O)N2CCC2)cc1S(=O)(=O)Nc1cc(-c2ccccc2)c(F)cc1F] I-384
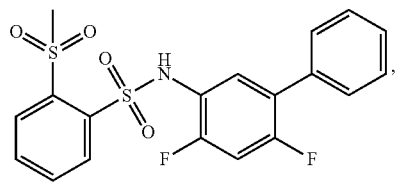 [SMILES: CS(=O)(=O)c1ccccc1S(=O)(=O)Nc1cc(-c2ccccc2)c(F)cc1F] I-385
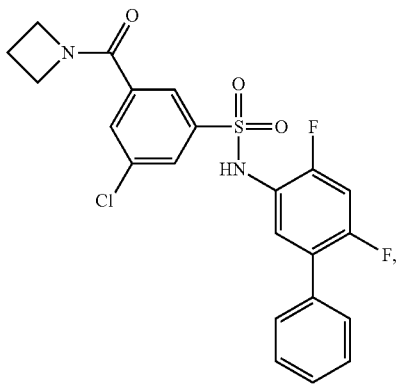 [SMILES: O=C(c1cc(Cl)cc(S(=O)(=O)Nc2cc(-c3ccccc3)c(F)cc2F)c1)N1CCC1] I-386
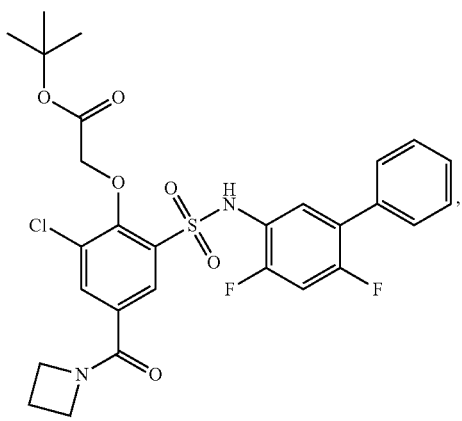 [SMILES: CC(C)(C)OC(=O)COc1c(Cl)cc(C(=O)N2CCC2)cc1S(=O)(=O)Nc1cc(-c2ccccc2)c(F)cc1F] I-387

TABLE 1-continued
Exemplary Compounds of Formula I
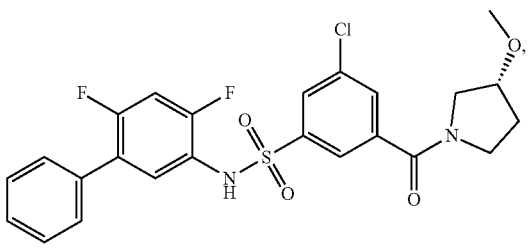 [SMILES: CO[C@@H]1CCN(C(=O)c2cc(Cl)cc(S(=O)(=O)Nc3cc(-c4ccccc4)c(F)cc3F)c2)C1]
I-388
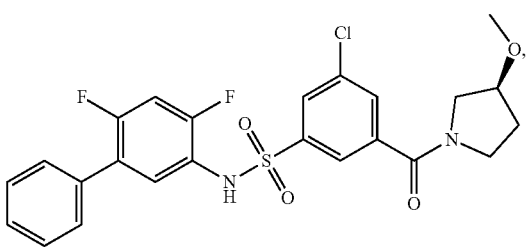 [SMILES: CO[C@H]1CCN(C(=O)c2cc(Cl)cc(S(=O)(=O)Nc3cc(-c4ccccc4)c(F)cc3F)c2)C1]
I-389
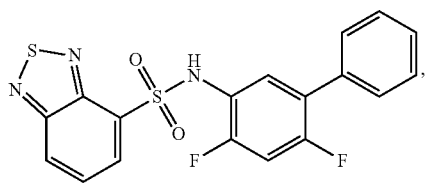 [SMILES: O=S(=O)(Nc1cc(-c2ccccc2)c(F)cc1F)c1cccc2nsnc12]
I-390
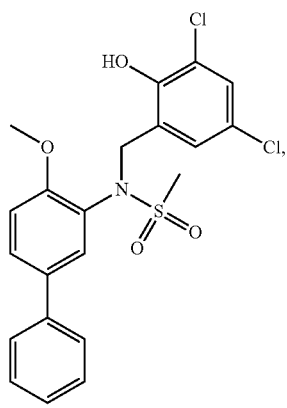 [SMILES: COc1ccc(-c2ccccc2)cc1N(Cc1cc(Cl)cc(Cl)c1O)S(C)(=O)=O]
I-391
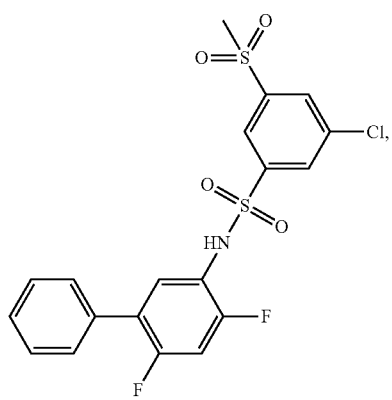 [SMILES: CS(=O)(=O)c1cc(Cl)cc(S(=O)(=O)Nc2cc(-c3ccccc3)c(F)cc2F)c1]
I-392

TABLE 1-continued
Exemplary Compounds of Formula I
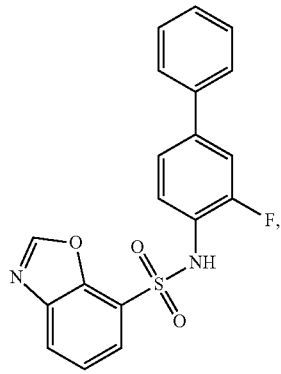 [SMILES: O=S(=O)(Nc1ccc(-c2ccccc2)cc1F)c1cccc2ncoc12]
I-393
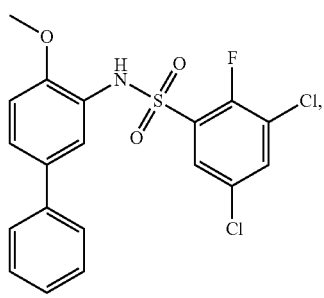 [SMILES: COc1ccc(-c2ccccc2)cc1NS(=O)(=O)c1cc(Cl)cc(Cl)c1F]
I-394
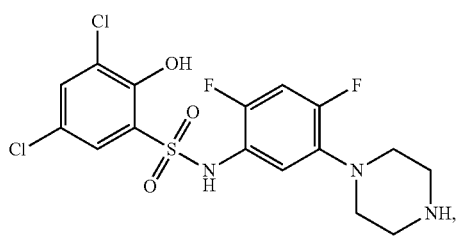 [SMILES: O=S(=O)(Nc1cc(N2CCNCC2)c(F)cc1F)c1cc(Cl)cc(Cl)c1O]
I-395
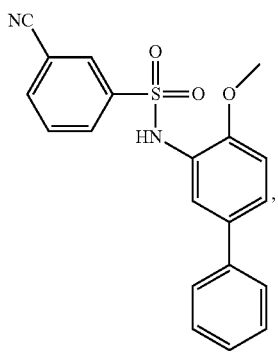 [SMILES: COc1ccc(-c2ccccc2)cc1NS(=O)(=O)c1cccc(C#N)c1]
I-396
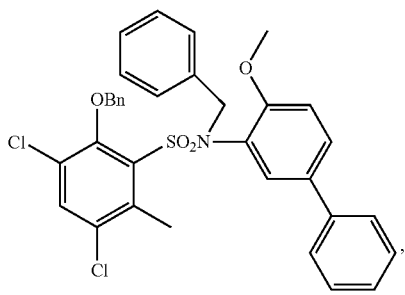
I-397

TABLE 1-continued
Exemplary Compounds of Formula I
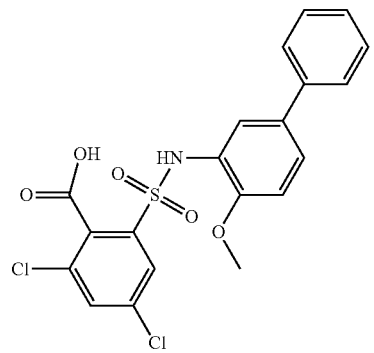 [SMILES: COc1ccc(-c2ccccc2)cc1NS(=O)(=O)c1cc(Cl)cc(Cl)c1C(=O)O]
I-398
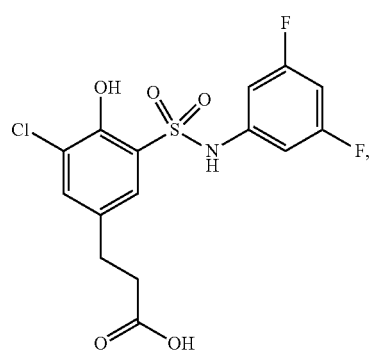 [SMILES: O=C(O)CCc1cc(Cl)c(O)c(S(=O)(=O)Nc2cc(F)cc(F)c2)c1]
I-399
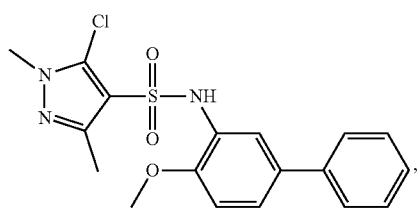 [SMILES: COc1ccc(-c2ccccc2)cc1NS(=O)(=O)c1c(C)nn(C)c1Cl]
I-400
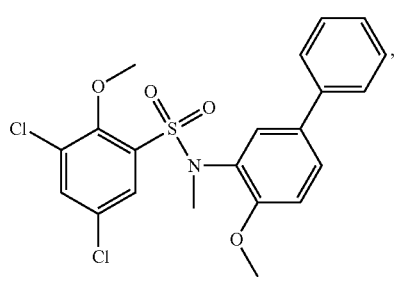 [SMILES: COc1ccc(-c2ccccc2)cc1N(C)S(=O)(=O)c1cc(Cl)cc(Cl)c1OC]
I-401
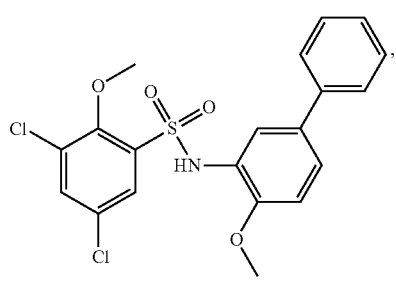 [SMILES: COc1ccc(-c2ccccc2)cc1NS(=O)(=O)c1cc(Cl)cc(Cl)c1OC]
I-402

TABLE 1-continued
Exemplary Compounds of Formula I
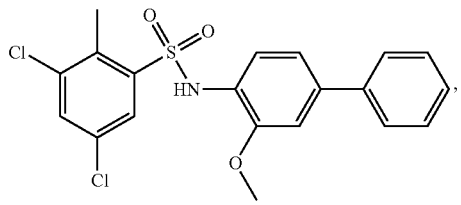 [SMILES: COc1cc(-c2ccccc2)ccc1NS(=O)(=O)c1cc(Cl)cc(Cl)c1C]
I-403
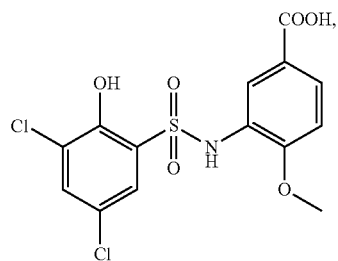 [SMILES: COc1ccc(C(=O)O)cc1NS(=O)(=O)c1cc(Cl)cc(Cl)c1O]
I-404
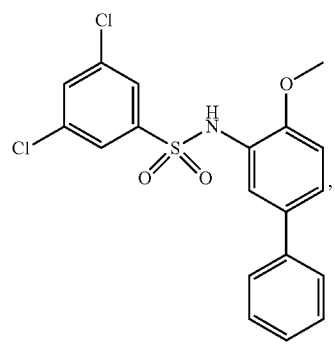 [SMILES: COc1ccc(-c2ccccc2)cc1NS(=O)(=O)c1cc(Cl)cc(Cl)c1]
I-405
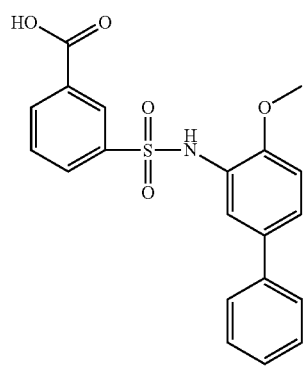 [SMILES: COc1ccc(-c2ccccc2)cc1NS(=O)(=O)c1cccc(C(=O)O)c1]
I-406
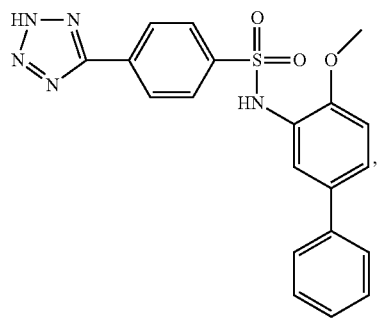 [SMILES: COc1ccc(-c2ccccc2)cc1NS(=O)(=O)c1ccc(-c2nn[nH]n2)cc1]
I-407

TABLE 1-continued
Exemplary Compounds of Formula I
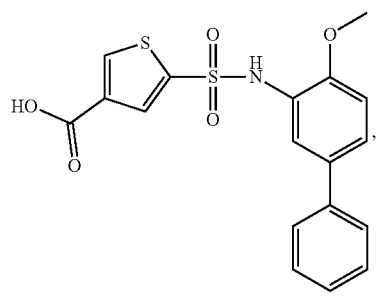 [SMILES: COc1ccc(-c2ccccc2)cc1NS(=O)(=O)c1cc(C(=O)O)cs1]
I-408
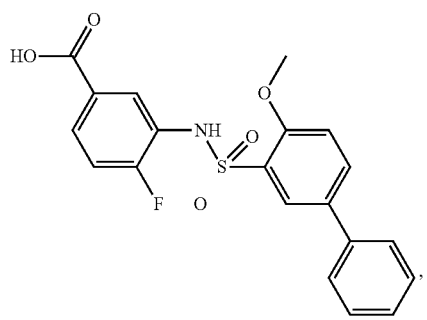
I-409
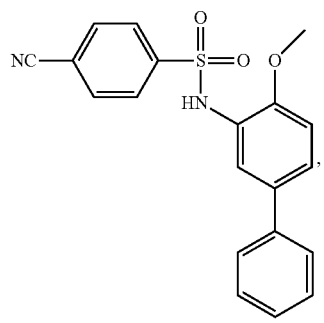 [SMILES: COc1ccc(-c2ccccc2)cc1NS(=O)(=O)c1ccc(C#N)cc1]
I-410
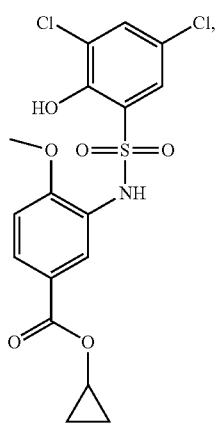 [SMILES: COc1ccc(C(=O)OC2CC2)cc1NS(=O)(=O)c1cc(Cl)cc(Cl)c1O]
I-411
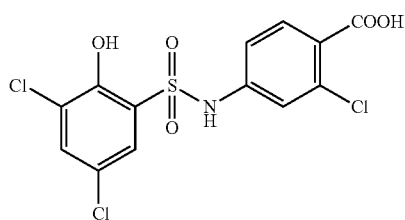 [SMILES: O=C(O)c1ccc(NS(=O)(=O)c2cc(Cl)cc(Cl)c2O)cc1Cl]
I-412

TABLE 1-continued
Exemplary Compounds of Formula I
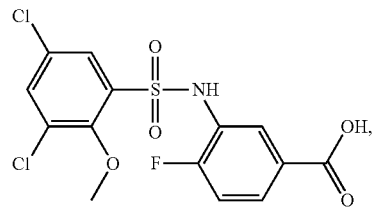 [SMILES: COc1c(Cl)cc(Cl)cc1S(=O)(=O)Nc1cc(C(=O)O)ccc1F]
I-413
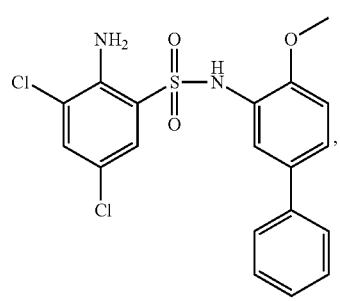 [SMILES: COc1ccc(-c2ccccc2)cc1NS(=O)(=O)c1cc(Cl)cc(Cl)c1N]
I-414
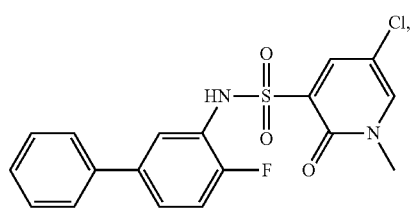 [SMILES: Cn1cc(Cl)cc(S(=O)(=O)Nc2cc(-c3ccccc3)ccc2F)c1=O]
I-415
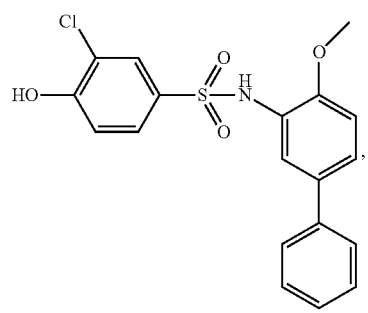 [SMILES: COc1ccc(-c2ccccc2)cc1NS(=O)(=O)c1ccc(O)c(Cl)c1]
I-416
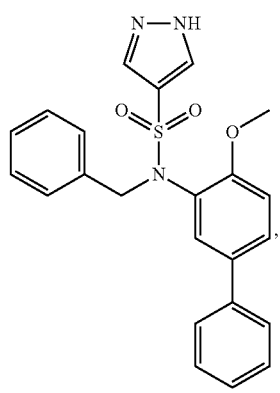 [SMILES: COc1ccc(-c2ccccc2)cc1N(Cc1ccccc1)S(=O)(=O)c1cn[nH]c1]
I-417

TABLE 1-continued
Exemplary Compounds of Formula I
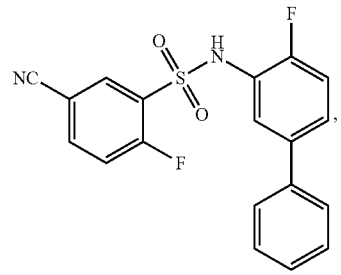 [SMILES: N#Cc1ccc(F)c(S(=O)(=O)Nc2cc(-c3ccccc3)ccc2F)c1]
I-418
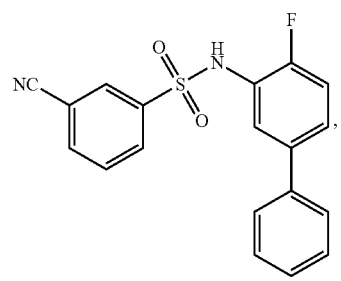 [SMILES: N#Cc1cccc(S(=O)(=O)Nc2cc(-c3ccccc3)ccc2F)c1]
I-419
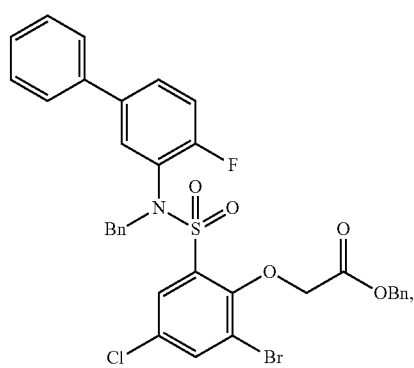 [SMILES: O=C(COc1c(Br)cc(Cl)cc1S(=O)(=O)N(Cc1ccccc1)c1cc(-c2ccccc2)ccc1F)OCc1ccccc1]
I-420
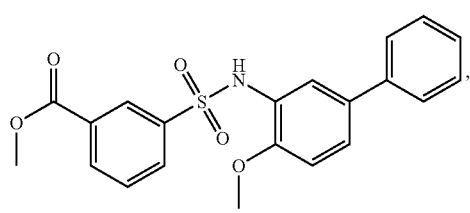 [SMILES: COC(=O)c1cccc(S(=O)(=O)Nc2cc(-c3ccccc3)ccc2OC)c1]
I-421
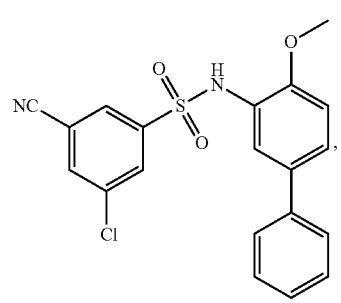 [SMILES: COc1ccc(-c2ccccc2)cc1NS(=O)(=O)c1cc(Cl)cc(C#N)c1]
I-422

TABLE 1-continued
Exemplary Compounds of Formula I
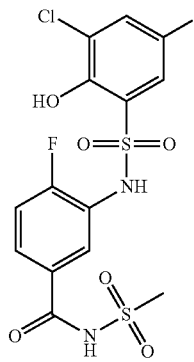
I-423
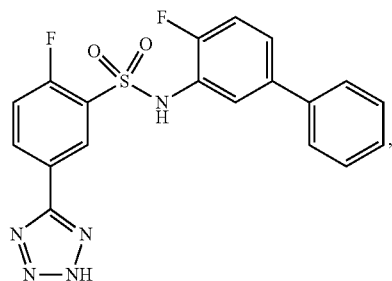 [SMILES: O=S(=O)(Nc1cc(-c2ccccc2)ccc1F)c1cc(-c2nn[nH]n2)ccc1F]
I-424
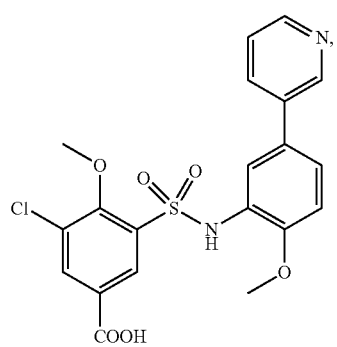 [SMILES: COc1ccc(-c2cccnc2)cc1NS(=O)(=O)c1cc(C(=O)O)cc(Cl)c1OC]
I-425
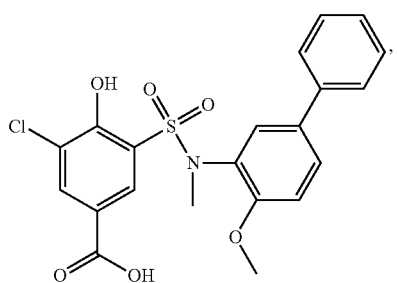 [SMILES: COc1ccc(-c2ccccc2)cc1N(C)S(=O)(=O)c1cc(C(=O)O)cc(Cl)c1O]
I-426

TABLE 1-continued
Exemplary Compounds of Formula I
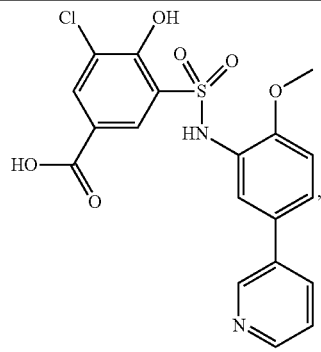
I-427
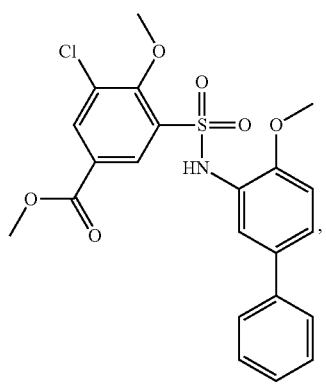 [SMILES: COC(=O)c1cc(Cl)c(OC)c(S(=O)(=O)Nc2cc(-c3ccccc3)ccc2OC)c1]
I-428
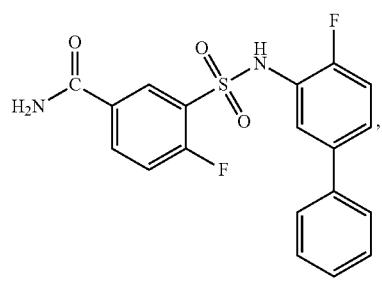 [SMILES: NC(=O)c1ccc(F)c(S(=O)(=O)Nc2cc(-c3ccccc3)ccc2F)c1]
I-429
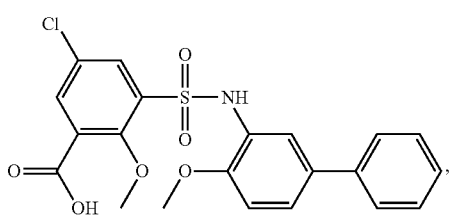 [SMILES: COc1ccc(-c2ccccc2)cc1NS(=O)(=O)c1cc(Cl)cc(C(=O)O)c1OC]
I-430
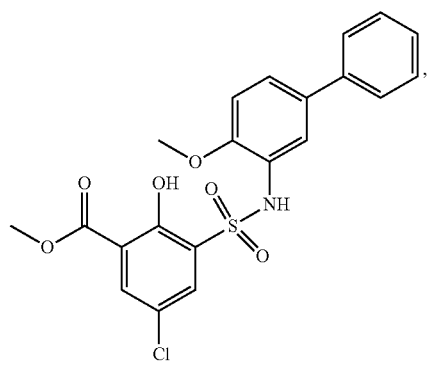 [SMILES: COC(=O)c1cc(Cl)cc(S(=O)(=O)Nc2cc(-c3ccccc3)ccc2OC)c1O]
I-431

TABLE 1-continued
Exemplary Compounds of Formula I
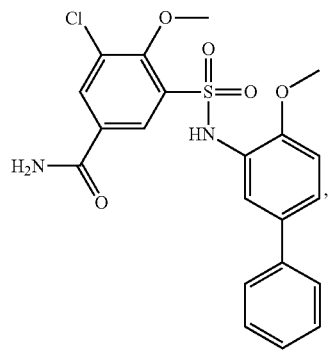 [SMILES: COc1ccc(-c2ccccc2)cc1NS(=O)(=O)c1cc(C(N)=O)cc(Cl)c1OC]
I-432
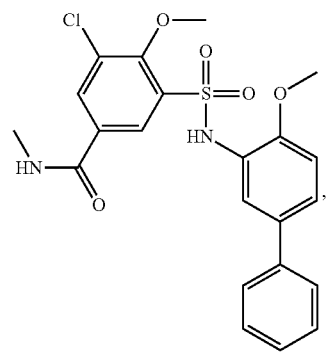 [SMILES: CNC(=O)c1cc(Cl)c(OC)c(S(=O)(=O)Nc2cc(-c3ccccc3)ccc2OC)c1]
I-433
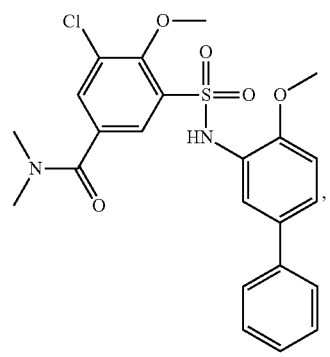 [SMILES: COc1ccc(-c2ccccc2)cc1NS(=O)(=O)c1cc(C(=O)N(C)C)cc(Cl)c1OC]
I-434
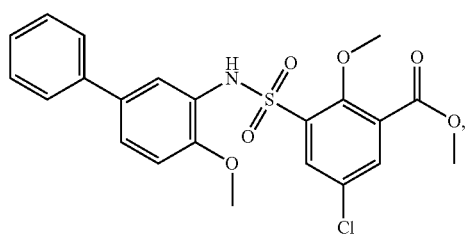 [SMILES: COC(=O)c1cc(Cl)cc(S(=O)(=O)Nc2cc(-c3ccccc3)ccc2OC)c1OC]
I-435

TABLE 1-continued
Exemplary Compounds of Formula I
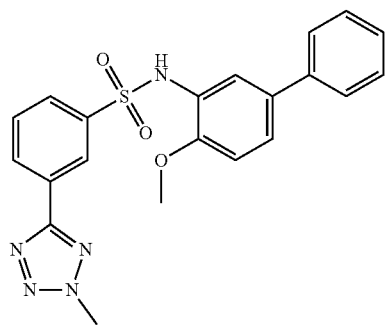 [SMILES: COc1ccc(-c2ccccc2)cc1NS(=O)(=O)c1cccc(-c2nnn(C)n2)c1]
I-436
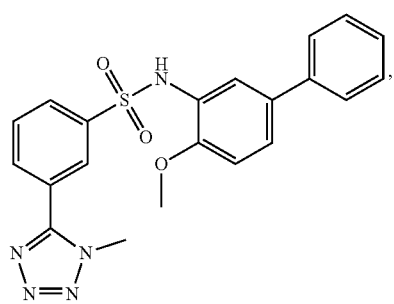 [SMILES: COc1ccc(-c2ccccc2)cc1NS(=O)(=O)c1cccc(-c2nnnn2C)c1]
I-437
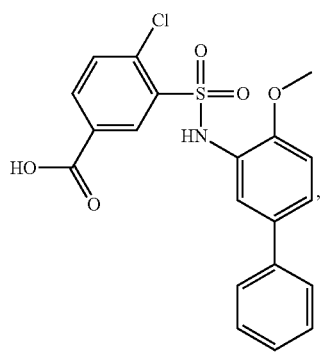 [SMILES: COc1ccc(-c2ccccc2)cc1NS(=O)(=O)c1cc(C(=O)O)ccc1Cl]
I-438
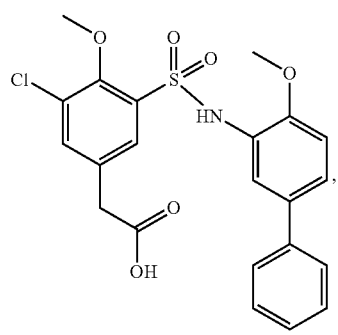 [SMILES: COc1ccc(-c2ccccc2)cc1NS(=O)(=O)c1cc(CC(=O)O)cc(Cl)c1OC]
I-439

TABLE 1-continued
Exemplary Compounds of Formula I
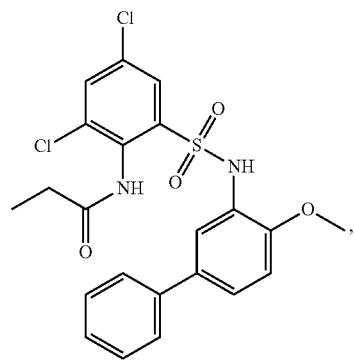 [SMILES: CCC(=O)Nc1c(Cl)cc(Cl)cc1S(=O)(=O)Nc1cc(-c2ccccc2)ccc1OC]
I-440
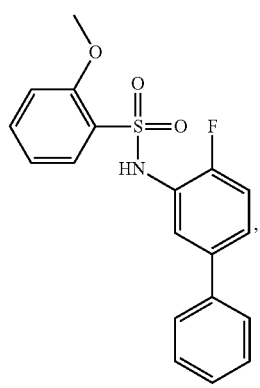 [SMILES: COc1ccccc1S(=O)(=O)Nc1cc(-c2ccccc2)ccc1F]
I-441
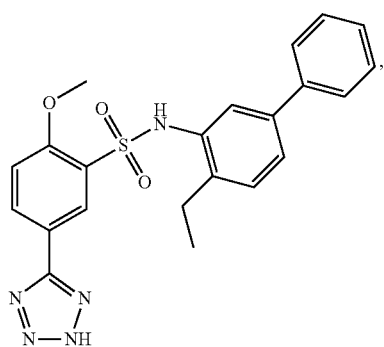 [SMILES: CCc1ccc(-c2ccccc2)cc1NS(=O)(=O)c1cc(-c2nn[nH]n2)ccc1OC]
I-442
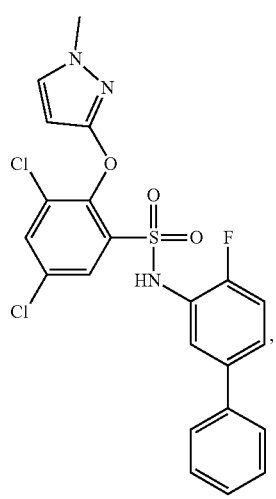 [SMILES: Cn1ccc(Oc2c(Cl)cc(Cl)cc2S(=O)(=O)Nc2cc(-c3ccccc3)ccc2F)n1]
I-443

TABLE 1-continued
Exemplary Compounds of Formula I
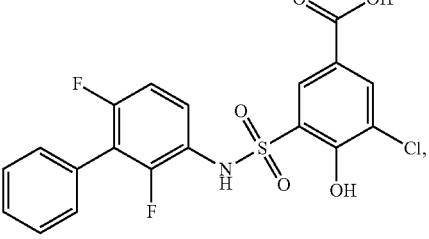 I-444
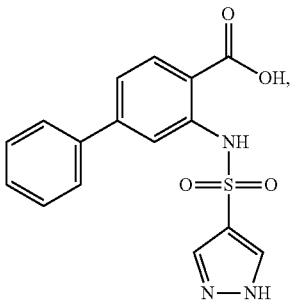 [SMILES: O=C(O)c1ccc(-c2ccccc2)cc1NS(=O)(=O)c1cn[nH]c1] I-445
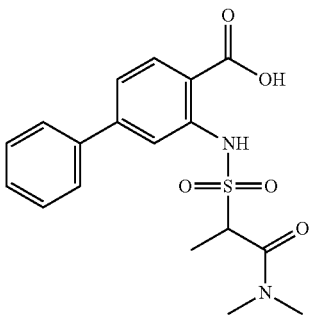 [SMILES: CC(C(=O)N(C)C)S(=O)(=O)Nc1cc(-c2ccccc2)ccc1C(=O)O] I-446
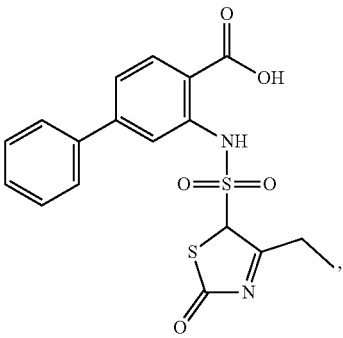 [SMILES: CCC1=NC(=O)SC1S(=O)(=O)Nc1cc(-c2ccccc2)ccc1C(=O)O] I-447
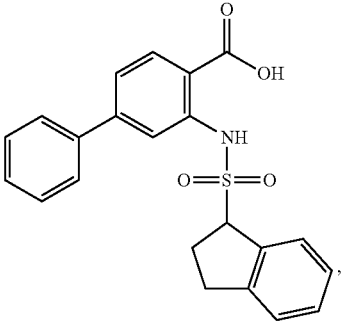 [SMILES: O=C(O)c1ccc(-c2ccccc2)cc1NS(=O)(=O)C1CCc2ccccc21] I-448

TABLE 1-continued
Exemplary Compounds of Formula I
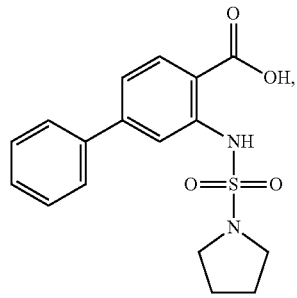 [SMILES: O=C(O)c1ccc(-c2ccccc2)cc1NS(=O)(=O)N1CCCC1]
I-449
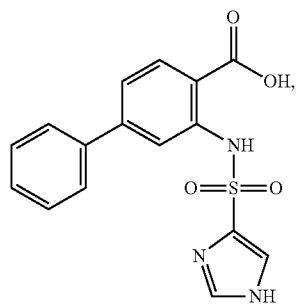 [SMILES: O=C(O)c1ccc(-c2ccccc2)cc1NS(=O)(=O)c1c[nH]cn1]
I-450
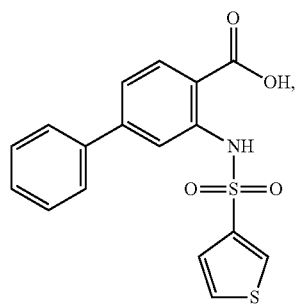 [SMILES: O=C(O)c1ccc(-c2ccccc2)cc1NS(=O)(=O)c1ccsc1]
I-451
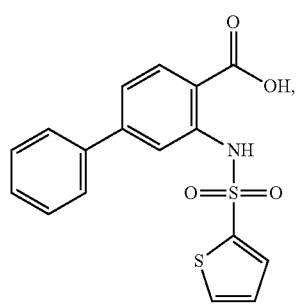 [SMILES: O=C(O)c1ccc(-c2ccccc2)cc1NS(=O)(=O)c1cccs1]
I-452
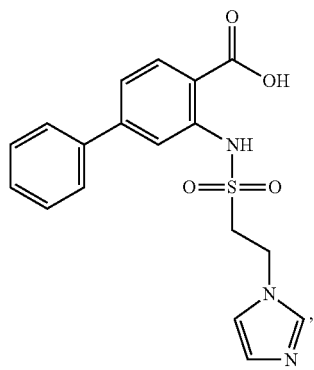 [SMILES: O=C(O)c1ccc(-c2ccccc2)cc1NS(=O)(=O)CCn1ccnc1]
I-453

TABLE 1-continued
Exemplary Compounds of Formula I
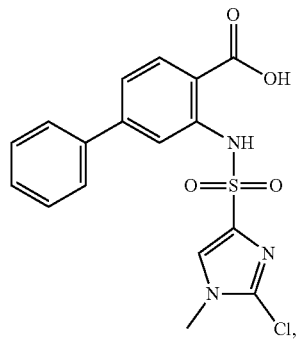 [SMILES: Cn1cc(S(=O)(=O)Nc2cc(-c3ccccc3)ccc2C(=O)O)nc1Cl]
I-454
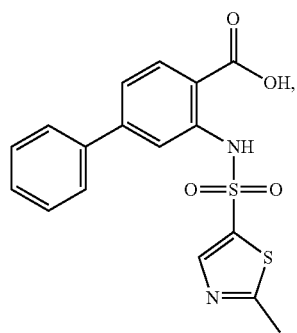 [SMILES: Cc1ncc(S(=O)(=O)Nc2cc(-c3ccccc3)ccc2C(=O)O)s1]
I-455
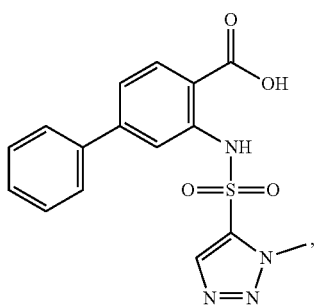 [SMILES: Cn1nncc1S(=O)(=O)Nc1cc(-c2ccccc2)ccc1C(=O)O]
I-456
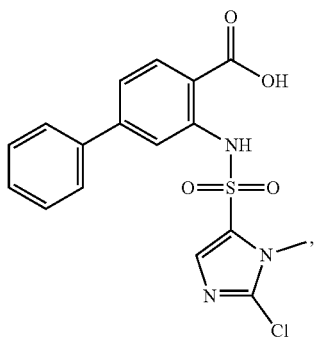 [SMILES: Cn1c(S(=O)(=O)Nc2cc(-c3ccccc3)ccc2C(=O)O)cnc1Cl]
I-457

TABLE 1-continued
Exemplary Compounds of Formula I
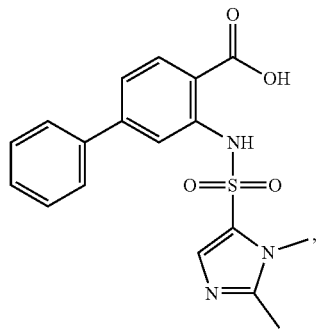 [SMILES: Cc1ncc(S(=O)(=O)Nc2cc(-c3ccccc3)ccc2C(=O)O)n1C]
I-458
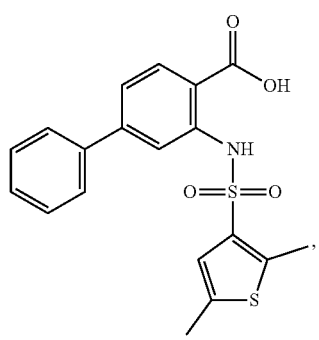 [SMILES: Cc1cc(S(=O)(=O)Nc2cc(-c3ccccc3)ccc2C(=O)O)c(C)s1]
I-459
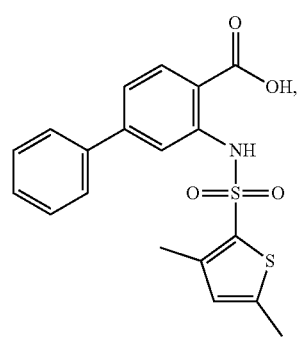 [SMILES: Cc1cc(C)c(S(=O)(=O)Nc2cc(-c3ccccc3)ccc2C(=O)O)s1]
I-460
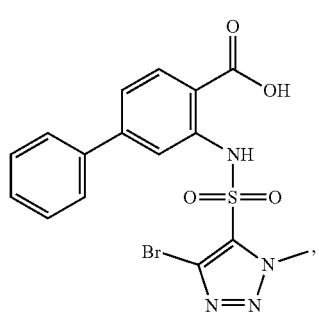 [SMILES: Cn1nnc(Br)c1S(=O)(=O)Nc1cc(-c2ccccc2)ccc1C(=O)O]
I-461

TABLE 1-continued
Exemplary Compounds of Formula I
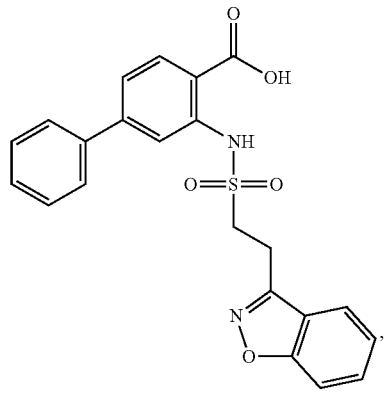 [SMILES: O=C(O)c1ccc(-c2ccccc2)cc1NS(=O)(=O)CCc1noc2ccccc12]
I-462
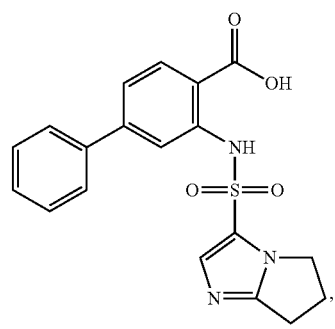 [SMILES: O=C(O)c1ccc(-c2ccccc2)cc1NS(=O)(=O)c1cnc2n1CCC2]
I-463
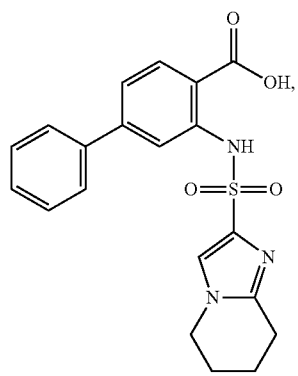 [SMILES: O=C(O)c1ccc(-c2ccccc2)cc1NS(=O)(=O)c1cn2c(n1)CCCC2]
I-464
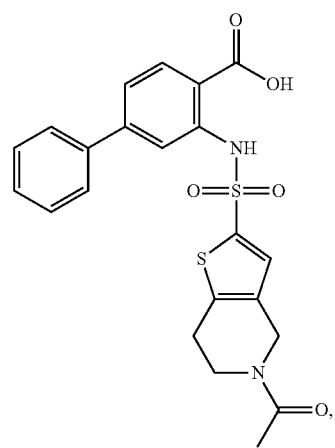 [SMILES: CC(=O)N1CCc2sc(S(=O)(=O)Nc3cc(-c4ccccc4)ccc3C(=O)O)cc2C1]
I-465

TABLE 1-continued
Exemplary Compounds of Formula I
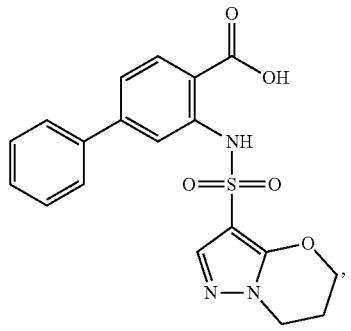 [SMILES: O=C(O)c1ccc(-c2ccccc2)cc1NS(=O)(=O)c1cnn2c1OCCC2]
I-466
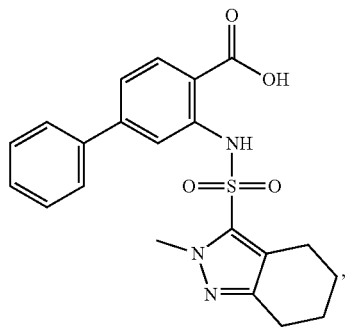 [SMILES: Cn1nc2c(c1S(=O)(=O)Nc1cc(-c3ccccc3)ccc1C(=O)O)CCCC2]
I-467
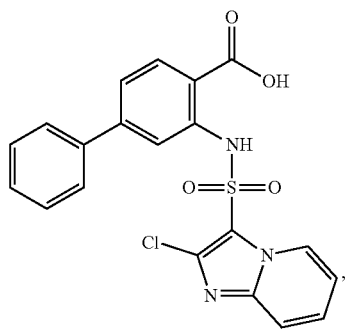 [SMILES: O=C(O)c1ccc(-c2ccccc2)cc1NS(=O)(=O)c1c(Cl)nc2ccccn12]
I-468
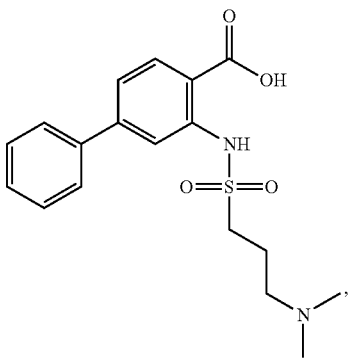 [SMILES: CN(C)CCCS(=O)(=O)Nc1cc(-c2ccccc2)ccc1C(=O)O]
I-469

TABLE 1-continued
Exemplary Compounds of Formula I
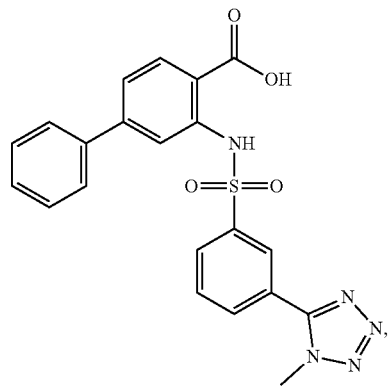 [SMILES: Cn1nnnc1-c1cccc(S(=O)(=O)Nc2cc(-c3ccccc3)ccc2C(=O)O)c1]
I-470
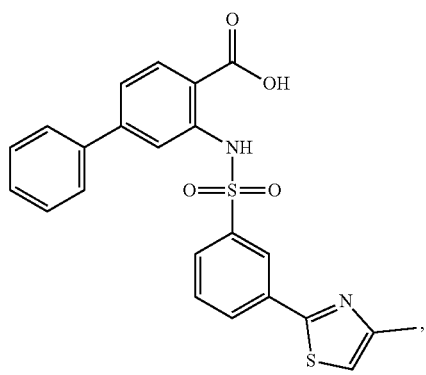 [SMILES: Cc1csc(-c2cccc(S(=O)(=O)Nc3cc(-c4ccccc4)ccc3C(=O)O)c2)n1]
I-471
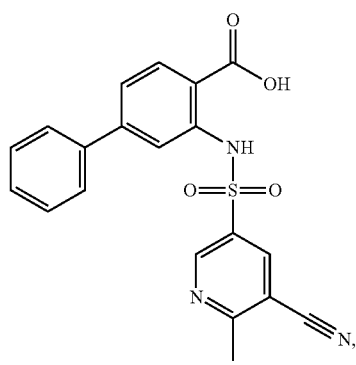 [SMILES: Cc1ncc(S(=O)(=O)Nc2cc(-c3ccccc3)ccc2C(=O)O)cc1C#N]
I-472
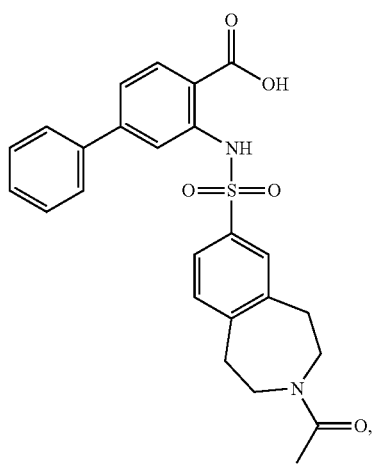 [SMILES: CC(=O)N1CCc2ccc(S(=O)(=O)Nc3cc(-c4ccccc4)ccc3C(=O)O)cc2CC1]
I-473

TABLE 1-continued
Exemplary Compounds of Formula I
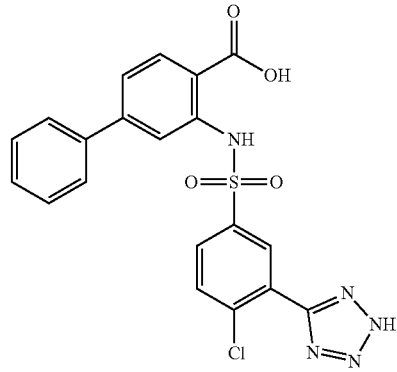 [SMILES: O=C(O)c1ccc(-c2ccccc2)cc1NS(=O)(=O)c1ccc(Cl)c(-c2nn[nH]n2)c1]
I-474
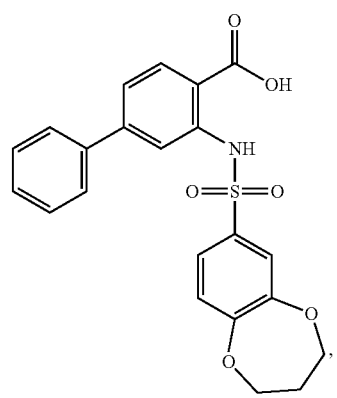 [SMILES: O=C(O)c1ccc(-c2ccccc2)cc1NS(=O)(=O)c1ccc2c(c1)OCCCO2]
I-475
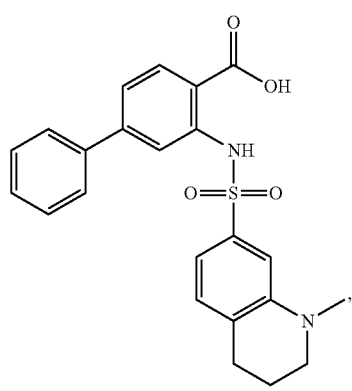 [SMILES: CN1CCCc2ccc(S(=O)(=O)Nc3cc(-c4ccccc4)ccc3C(=O)O)cc21]
I-476
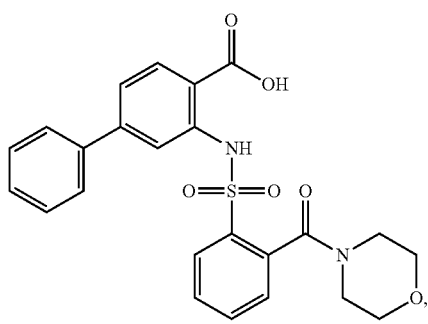 [SMILES: O=C(O)c1ccc(-c2ccccc2)cc1NS(=O)(=O)c1ccccc1C(=O)N1CCOCC1]
I-477

TABLE 1-continued
Exemplary Compounds of Formula I
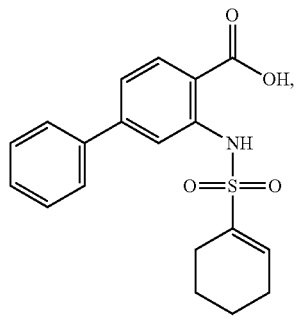 [SMILES: O=C(O)c1ccc(-c2ccccc2)cc1NS(=O)(=O)C1=CCCCC1]
I-478
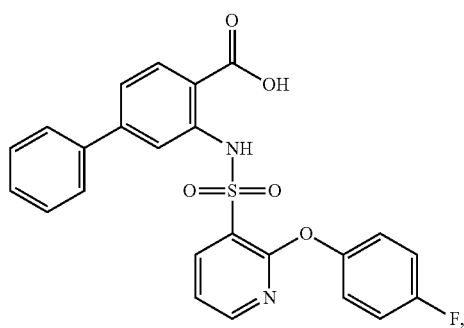 [SMILES: O=C(O)c1ccc(-c2ccccc2)cc1NS(=O)(=O)c1cccnc1Oc1ccc(F)cc1]
I-479
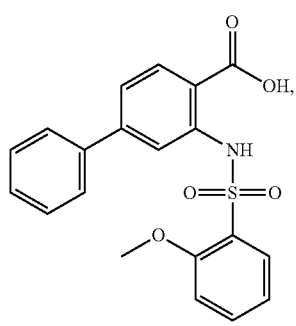 [SMILES: COc1ccccc1S(=O)(=O)Nc1cc(-c2ccccc2)ccc1C(=O)O]
I-480
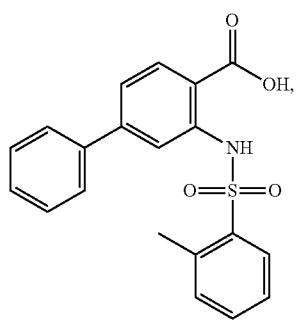 [SMILES: Cc1ccccc1S(=O)(=O)Nc1cc(-c2ccccc2)ccc1C(=O)O]
I-481

TABLE 1-continued
Exemplary Compounds of Formula I
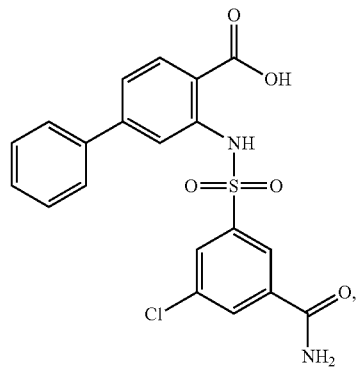 [SMILES: NC(=O)c1cc(Cl)cc(S(=O)(=O)Nc2cc(-c3ccccc3)ccc2C(=O)O)c1]
I-482
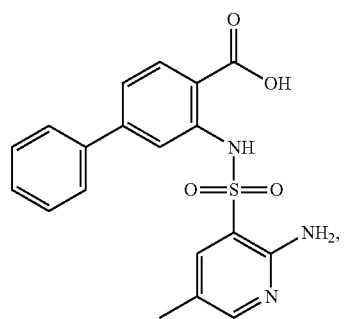 [SMILES: Cc1cnc(N)c(S(=O)(=O)Nc2cc(-c3ccccc3)ccc2C(=O)O)c1]
I-483
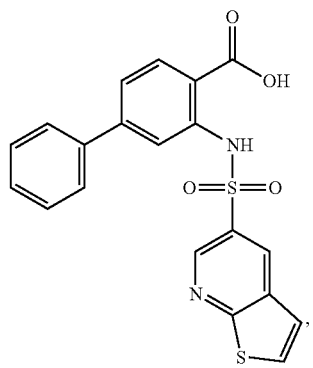 [SMILES: O=C(O)c1ccc(-c2ccccc2)cc1NS(=O)(=O)c1cnc2sccc2c1]
I-484
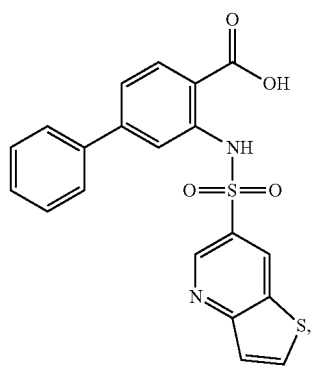 [SMILES: O=C(O)c1ccc(-c2ccccc2)cc1NS(=O)(=O)c1cnc2ccsc2c1]
I-485

TABLE 1-continued
Exemplary Compounds of Formula I
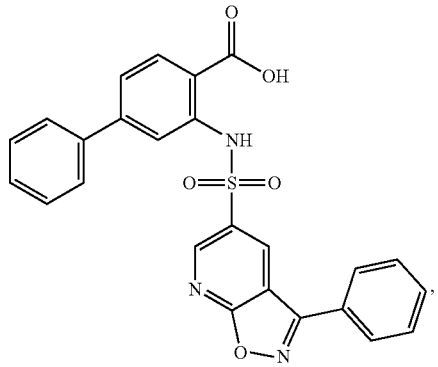 [SMILES: O=C(O)c1ccc(-c2ccccc2)cc1NS(=O)(=O)c1cnc2onc(-c3ccccc3)c2c1]
I-486
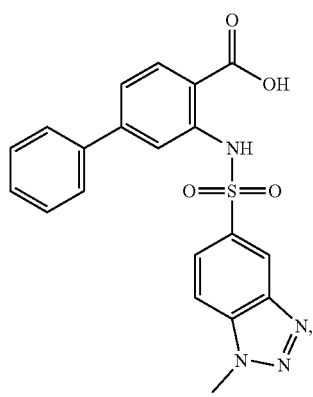 [SMILES: Cn1nnc2cc(S(=O)(=O)Nc3cc(-c4ccccc4)ccc3C(=O)O)ccc21]
I-487
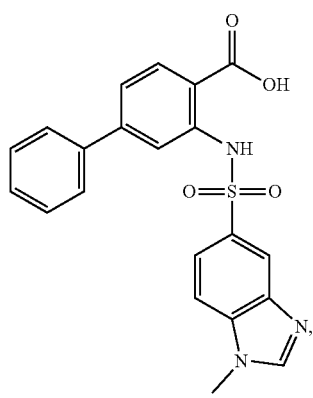 [SMILES: Cn1cnc2cc(S(=O)(=O)Nc3cc(-c4ccccc4)ccc3C(=O)O)ccc21]
I-488
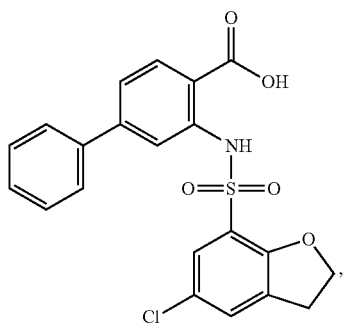 [SMILES: O=C(O)c1ccc(-c2ccccc2)cc1NS(=O)(=O)c1cc(Cl)cc2c1OCC2]
I-489

TABLE 1-continued
Exemplary Compounds of Formula I
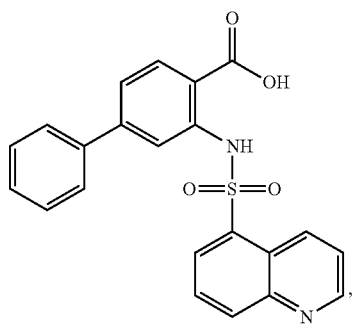 [SMILES: O=C(O)c1ccc(-c2ccccc2)cc1NS(=O)(=O)c1cccc2ncccc12]
I-490
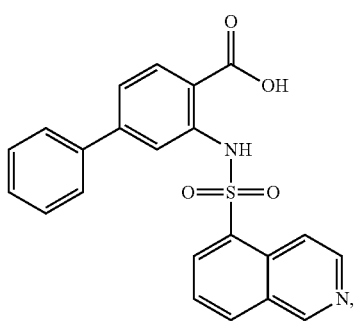 [SMILES: O=C(O)c1ccc(-c2ccccc2)cc1NS(=O)(=O)c1cccc2cnccc12]
I-491
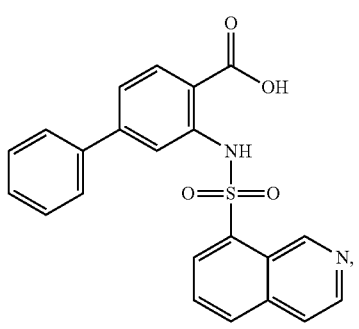 [SMILES: O=C(O)c1ccc(-c2ccccc2)cc1NS(=O)(=O)c1cccc2ccncc12]
I-492
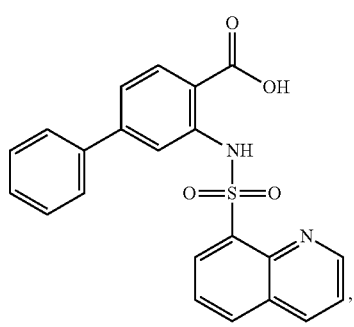 [SMILES: O=C(O)c1ccc(-c2ccccc2)cc1NS(=O)(=O)c1cccc2cccnc12]
I-493

TABLE 1-continued
Exemplary Compounds of Formula I
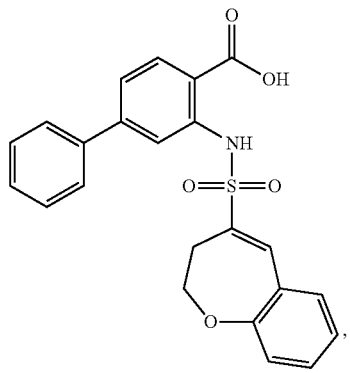 [SMILES: O=C(O)c1ccc(-c2ccccc2)cc1NS(=O)(=O)C1=Cc2ccccc2OCC1]
I-494
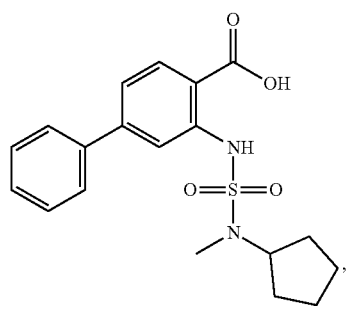 [SMILES: CN(C1CCCC1)S(=O)(=O)Nc1cc(-c2ccccc2)ccc1C(=O)O]
I-495
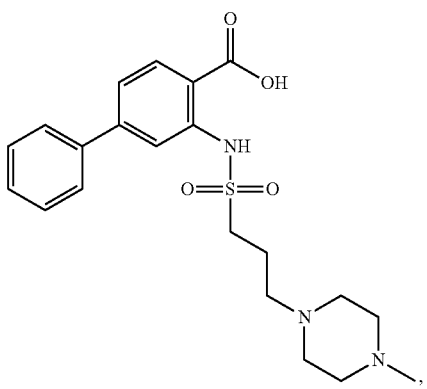 [SMILES: CN1CCN(CCCS(=O)(=O)Nc2cc(-c3ccccc3)ccc2C(=O)O)CC1]
I-496
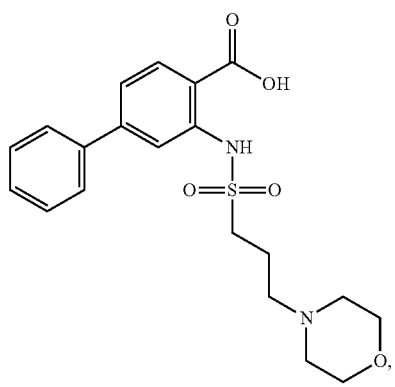 [SMILES: O=C(O)c1ccc(-c2ccccc2)cc1NS(=O)(=O)CCCN1CCOCC1]
I-497

TABLE 1-continued
Exemplary Compounds of Formula I
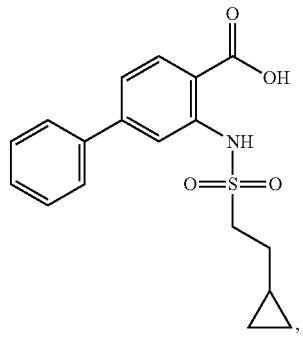 [SMILES: O=C(O)c1ccc(-c2ccccc2)cc1NS(=O)(=O)CCC1CC1]
I-498
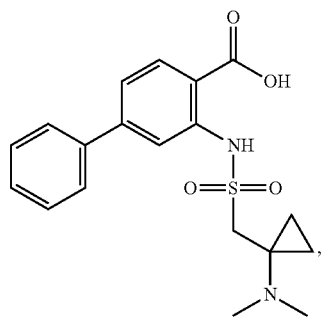 [SMILES: CN(C)C1(CS(=O)(=O)Nc2cc(-c3ccccc3)ccc2C(=O)O)CC1]
I-499
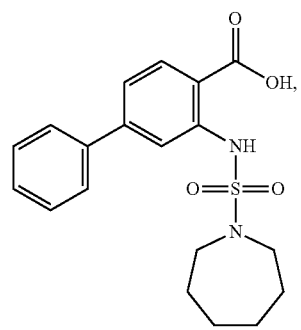 [SMILES: O=C(O)c1ccc(-c2ccccc2)cc1NS(=O)(=O)N1CCCCCC1]
I-500
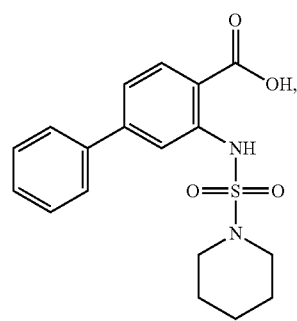 [SMILES: O=C(O)c1ccc(-c2ccccc2)cc1NS(=O)(=O)N1CCCCC1]
I-501

TABLE 1-continued
Exemplary Compounds of Formula I
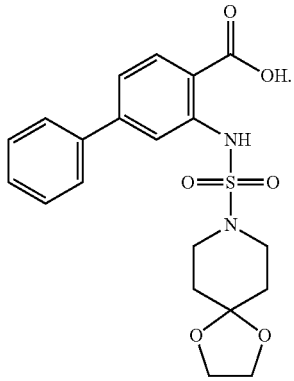 [SMILES: O=C(O)c1ccc(-c2ccccc2)cc1NS(=O)(=O)N1CCC2(CC1)OCCO2]
I-502
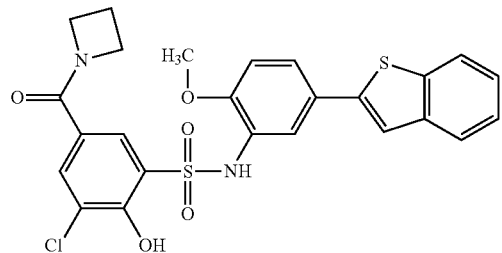 [SMILES: COc1ccc(-c2cc3ccccc3s2)cc1NS(=O)(=O)c1cc(C(=O)N2CCC2)cc(Cl)c1O]
I-503
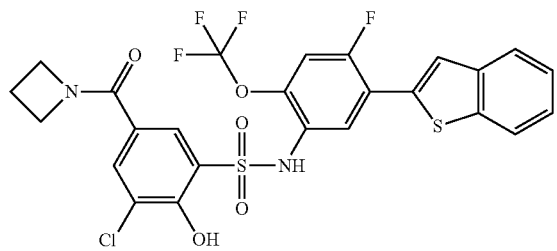 [SMILES: O=C(c1cc(Cl)c(O)c(S(=O)(=O)Nc2cc(-c3cc4ccccc4s3)c(F)cc2OC(F)(F)F)c1)N1CCC1]
I-504
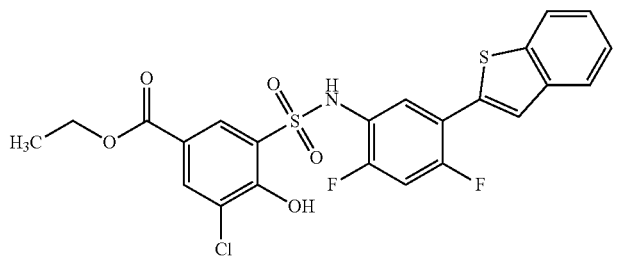 [SMILES: CCOC(=O)c1cc(Cl)c(O)c(S(=O)(=O)Nc2cc(-c3cc4ccccc4s3)c(F)cc2F)c1]
I-505
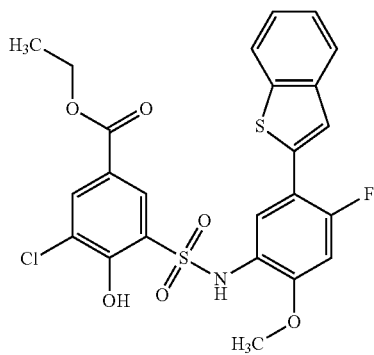 [SMILES: CCOC(=O)c1cc(Cl)c(O)c(S(=O)(=O)Nc2cc(-c3cc4ccccc4s3)c(F)cc2OC)c1]
I-506

TABLE 1-continued
Exemplary Compounds of Formula I
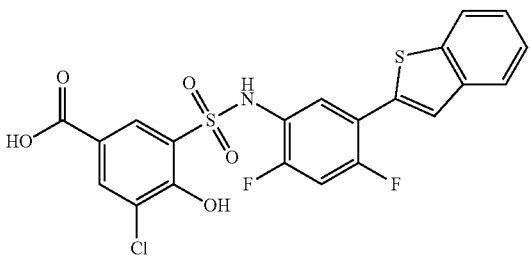 [SMILES: O=C(O)c1cc(Cl)c(O)c(S(=O)(=O)Nc2cc(-c3cc4ccccc4s3)c(F)cc2F)c1]
I-507
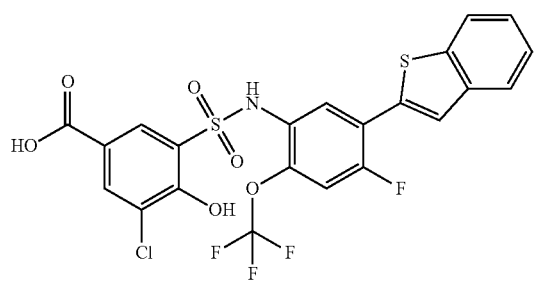 [SMILES: O=C(O)c1cc(Cl)c(O)c(S(=O)(=O)Nc2cc(-c3cc4ccccc4s3)c(F)cc2OC(F)(F)F)c1]
I-508
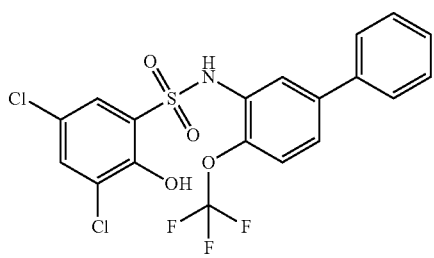 [SMILES: O=S(=O)(Nc1cc(-c2ccccc2)ccc1OC(F)(F)F)c1cc(Cl)cc(Cl)c1O]
I-509
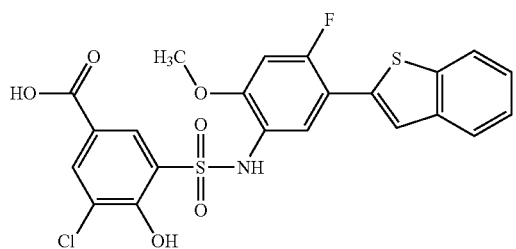 [SMILES: COc1cc(F)c(-c2cc3ccccc3s2)cc1NS(=O)(=O)c1cc(C(=O)O)cc(Cl)c1O]
I-510
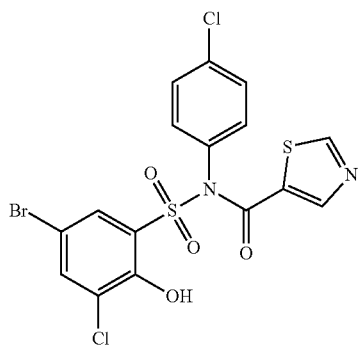 [SMILES: O=C(c1cncs1)N(c1ccc(Cl)cc1)S(=O)(=O)c1cc(Br)cc(Cl)c1O]
I-511

TABLE 1-continued
Exemplary Compounds of Formula I
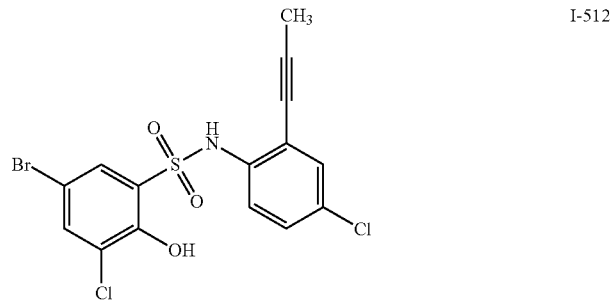
I-512
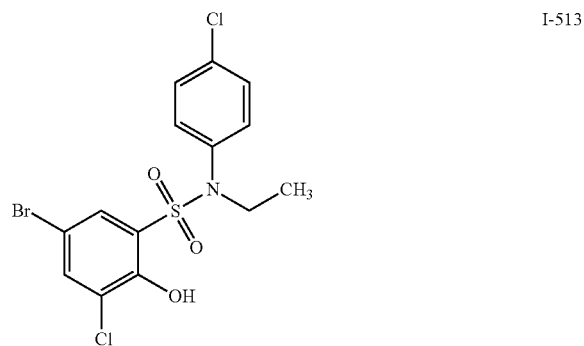
I-513
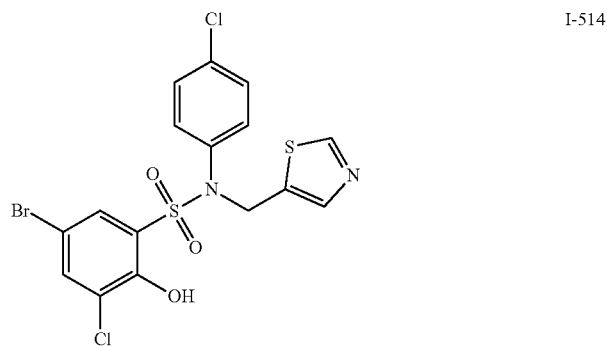
I-514
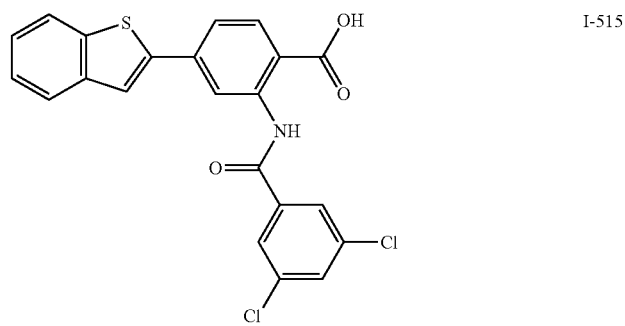
I-515

TABLE 1-continued
Exemplary Compounds of Formula I
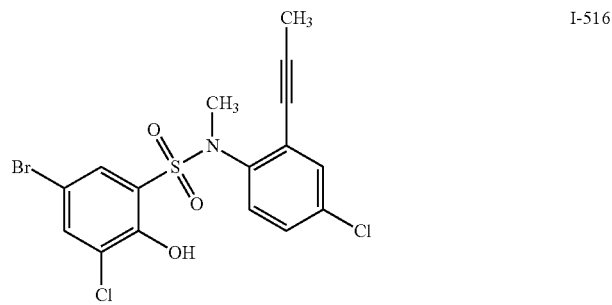
I-516
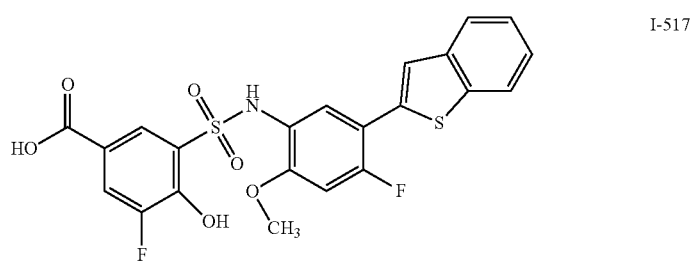
I-517
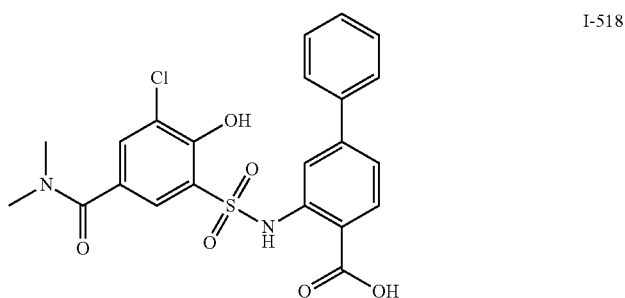
I-518
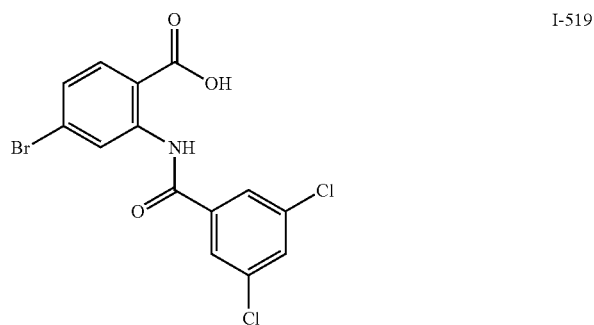
I-519
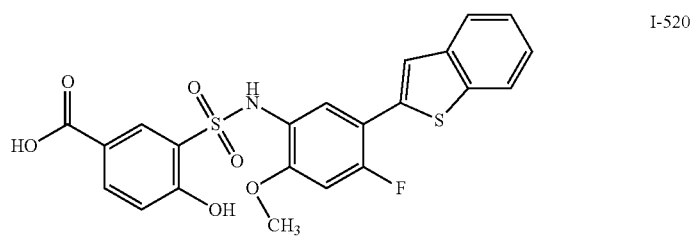
I-520

TABLE 1-continued
Exemplary Compounds of Formula I
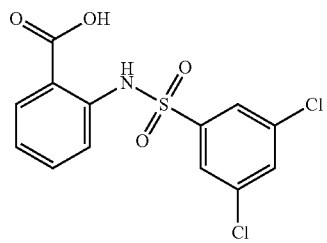 [SMILES: O=C(O)c1ccccc1NS(=O)(=O)c1cc(Cl)cc(Cl)c1]
I-522
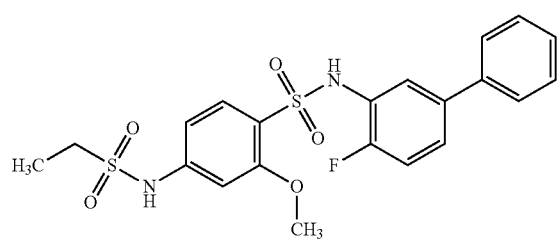 [SMILES: CCS(=O)(=O)Nc1ccc(S(=O)(=O)Nc2cc(-c3ccccc3)ccc2F)c(OC)c1]
I-523
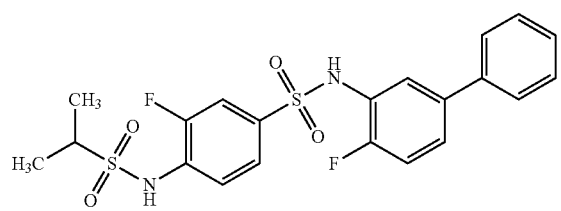 [SMILES: CC(C)S(=O)(=O)Nc1ccc(S(=O)(=O)Nc2cc(-c3ccccc3)ccc2F)cc1F]
I-524
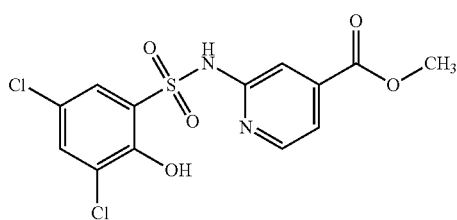 [SMILES: COC(=O)c1ccnc(NS(=O)(=O)c2cc(Cl)cc(Cl)c2O)c1]
I-525
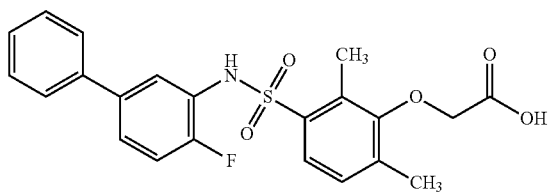 [SMILES: Cc1ccc(S(=O)(=O)Nc2cc(-c3ccccc3)ccc2F)c(C)c1OCC(=O)O]
I-526
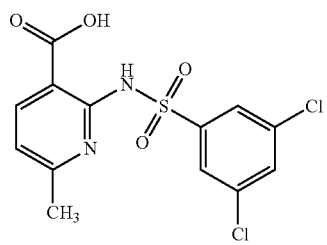 [SMILES: Cc1ccc(C(=O)O)c(NS(=O)(=O)c2cc(Cl)cc(Cl)c2)n1]
I-527

TABLE 1-continued
Exemplary Compounds of Formula I
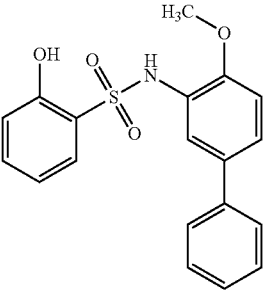 [SMILES: COc1ccc(-c2ccccc2)cc1NS(=O)(=O)c1ccccc1O]
I-528
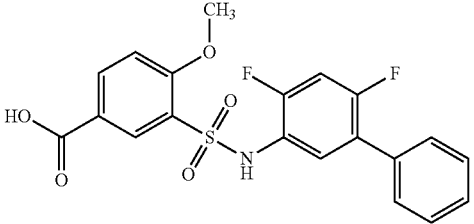 [SMILES: COc1ccc(C(=O)O)cc1S(=O)(=O)Nc1cc(-c2ccccc2)c(F)cc1F]
I-529
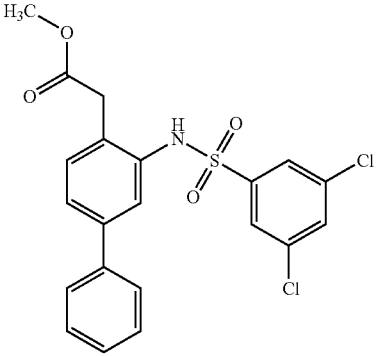 [SMILES: COC(=O)Cc1ccc(-c2ccccc2)cc1NS(=O)(=O)c1cc(Cl)cc(Cl)c1]
I-530
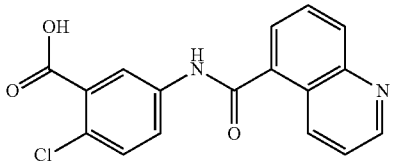 [SMILES: O=C(O)c1cc(NC(=O)c2cccc3ncccc23)ccc1Cl]
I-531
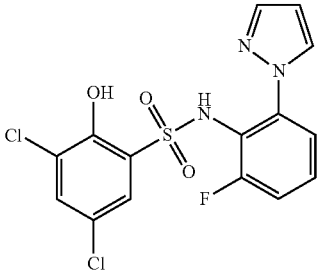 [SMILES: O=S(=O)(Nc1c(F)cccc1-n1cccn1)c1cc(Cl)cc(Cl)c1O]
I-532
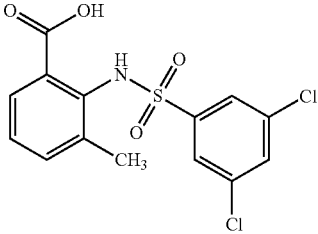 [SMILES: Cc1cccc(C(=O)O)c1NS(=O)(=O)c1cc(Cl)cc(Cl)c1]
I-533

TABLE 1-continued
Exemplary Compounds of Formula I
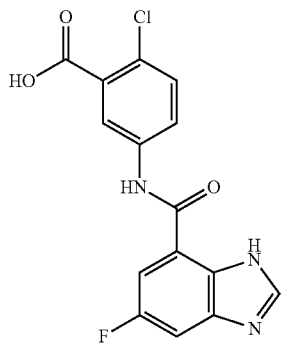 [SMILES: O=C(O)c1cc(NC(=O)c2cc(F)cc3nc[nH]c23)ccc1Cl]
I-535
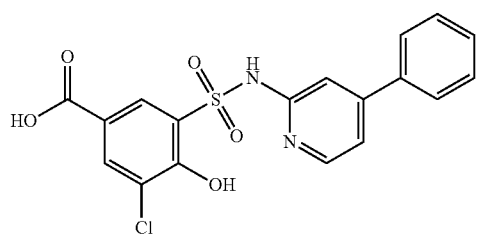 [SMILES: O=C(O)c1cc(Cl)c(O)c(S(=O)(=O)Nc2cc(-c3ccccc3)ccn2)c1]
I-536
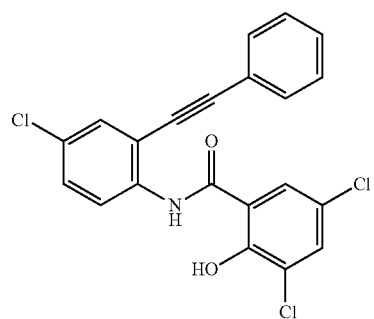 [SMILES: O=C(Nc1ccc(Cl)cc1C#Cc1ccccc1)c1cc(Cl)cc(Cl)c1O]
I-537
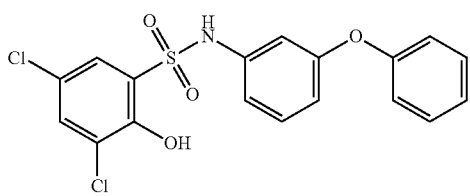 [SMILES: O=S(=O)(Nc1cccc(Oc2ccccc2)c1)c1cc(Cl)cc(Cl)c1O]
I-538
or pharmaceutically acceptable salts thereof.
In certain embodiments, the present invention provides any compound selected from those depicted in Table 1, above, or a pharmaceutically acceptable salt thereof.
TABLE 2
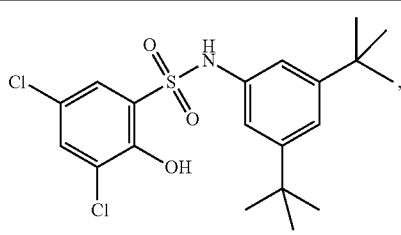
TABLE 2-continued
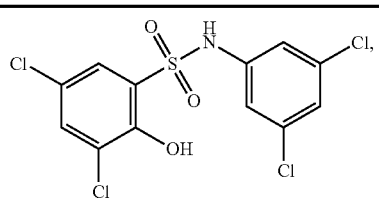
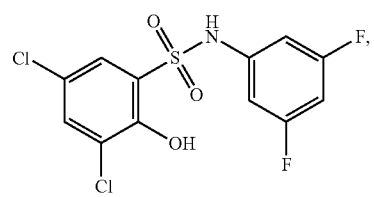 [SMILES: O=S(=O)(Nc1cc(F)cc(F)c1)c1cc(Cl)cc(Cl)c1O]

TABLE 2-continued

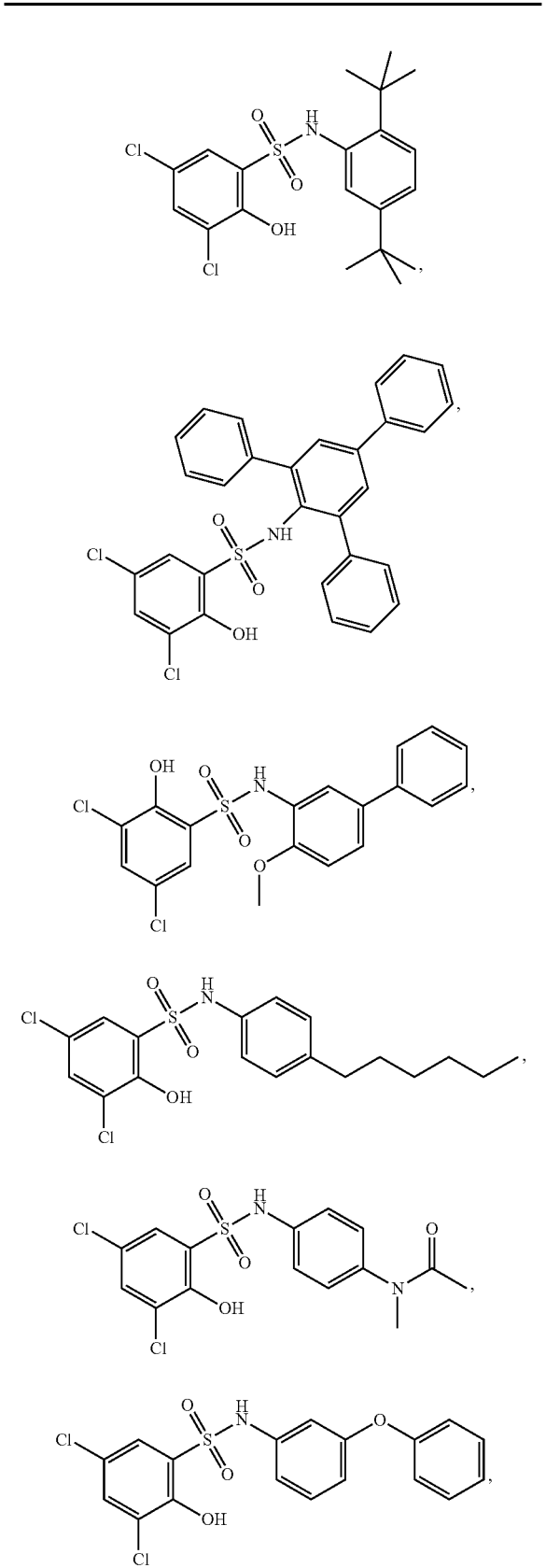

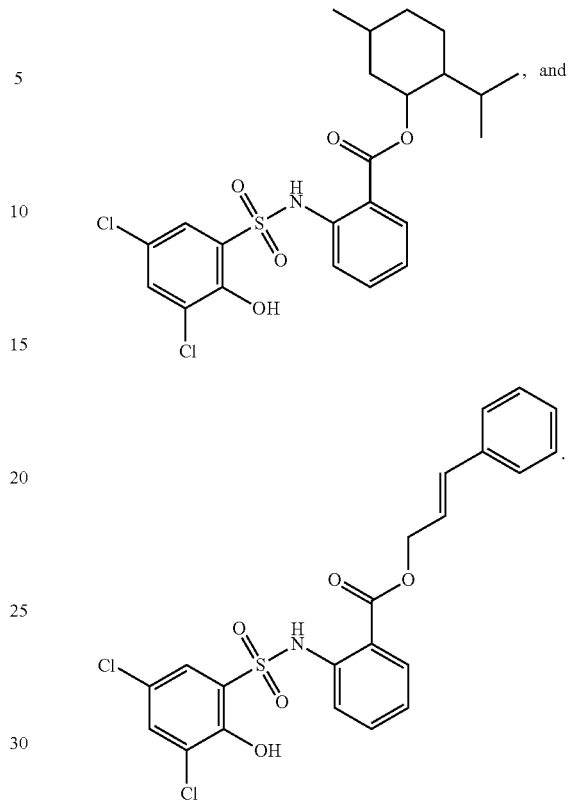

In certain embodiments, the present invention provides a compound other than one selected from those depicted in Table 2, above, or a pharmaceutically acceptable salt thereof.

4. Uses, Formulation and Administration and Pharmaceutically Acceptable Compositions According to another embodiment, the invention provides a composition comprising a compound of this invention or a pharmaceutically acceptable salt, ester, or salt of ester thereof and a pharmaceutically acceptable carrier, adjuvant, or vehicle. The amount of compound in compositions of this invention is such that is effective to measurably inhibit ACLY, in a biological sample or in a patient. In certain embodiments, the amount of compound in compositions of this invention is such that is effective to measurably inhibit ACLY, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of ACLY.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

In mammals ACLY is most abundantly expressed in the liver and white adipose tissue. It also exhibits low levels of expression in brain, heart, small intestine and muscles as well as pancreatic beta cells [Wang, Q., et al. 2010. J Lipid Research 285, 2516-2526]. While its cellular localization is mostly cytosolic, ACLY has also been detected in nuclei of different mammalian cells and may be involved in the compartmentalized production of acetyl-CoA. Within cells, ACLY functions as a critical link between glucose metabolism and FA and cholesterol synthesis. In the cytoplasm, glucose-derived citrate is transformed into acetyl-CoA by ACLY. Acetyl-CoA functions as the essential substrate for the cholesterol and FA synthesis pathways [Pietrocolo, F., et al. 2015. Cell Metabolism 805-821]. In the fatty acid synthesis pathway, acetyl-CoA is carboxylated into malonyl-CoA by acetyl-CoA carboxylase (ACC). Next, fatty-acid-synthase (FASN) performs condensation of acetyl-CoA and malonyl-CoA to produce the long-chain fatty acid palmitate, and the subsequent synthesis of endogenously derived FA's occurs in the pathway. Alternatively, ACLY derived acetyl-CoA is shunted into the mevalonate pathway and functions as a precursor for the synthesis of cholesterol as well as a number of intermediates required for posttranslational modification of a variety of proteins. Additionally, acetyl-CoA can also be used for acetylation of histone and non-histone proteins, and thus regulates global chromatin architecture and gene transcription in metabolic cells and tissues.

Given its critical role in promoting FA and cholesterol biosynthesis, ACLY inhibition has been considered an attractive target for lipid lowering. Reduced intracellular cholesterol synthesis triggers a feedback response involving sterol response element binding protein 2 (SREBP2) mediated upregulation of the low-density lipoprotein receptor (LDL), such that cells require more cholesterol scavenging from circulating LDL particles, thus reducing LDL-C and the potential of atherosclerotic cardiovascular disease (ASCVD). ACLY inhibition is predicted to not only reduce intracellular cholesterol synthesis but to also promote the effects of LDL mediated LDL-C clearance, and this is supported by in vitro studies of ACLY in human livers [Berkhout, T A., et al. 1990. Biochem J 272, 181-186]. Interestingly, single nucleotide polymorphisms (SNPs) in the ACLY gene region have been shown to correlate with lowered LDL-C levels and also associated with a shift in plasma biomarkers such as apolipoprotein B (ApoB), high density lipoprotein C (HDL-C), C reactive protein (CRP) and triglycerides, analogous to LDL-C lowering polymorphisms in hydroxy-3-methylglutaryl-CoA reductase (HMGR) and the effects of statins [Ference, B A. 2017. J. Am. Col. Cardio 69 (Suppl 11) 1655]. Furthermore, lower LDL-C levels mediated by ACLY SNPs was found to be causally associated with a reduction in ASCVD risk [Ference, B A. 2017. J. Am. Col. Cardio 69 (Suppl 11) 1655]. Thus, ACLY inhibitors might be useful as LDL-C lowering drugs that reduce the risk of ASCVD. In fact, recent clinical evidence suggests that pharmacological inhibition of ACLY by bempedoic acid (BA) can promote dose dependent LDL-C lowering and proportional reductions in several plasma biomarkers associated with ASCVD risk [Ballantyne, C. M., et al. 2012. J. Am. Coll. Cardiol 59, E1625-E1625]. Additionally, the robust cholesterol lowering effects and decreases in plasma triglycerides that have been reported suggest that pharmacologic ACLY inhibitors may also have utility as anti-obesity drugs [Pearce, N.J., et al. 1998. Biochem J 34, 113-119].

ACLY blockade leads to a dramatic reduction in de novo FA production. Thus, shutdown of FA synthesis resulting from ACLY inhibition may have therapeutic benefits for a number of other lipid related metabolic diseases and disease outcomes associated with metabolic syndrome. In the liver, accumulation of lipids leads to liver steatosis and the onset of fatty liver disease (non-alcoholic fatty liver disease, NAFLD). Progression of NAFLD into the more severe form of non-alcoholic steatohepatitis (NASH) due to excessive lipid accumulation, inflammation, tissue scarring and fibrosis, is a precursor for the development of cirrhosis and hepatocellular carcinoma (HCC), the most common type of liver cancer. ACLY inhibitors are expected to have a dramatic impact on FA metabolism in the liver through DNL inhibition and fatty acid oxidation induction and should therefore inhibit FA accumulation and the development and progression of fatty liver diseases to terminal liver disease states. The therapeutic utility of inhibiting DNL in NASH patients has been recently been described where hepatic ACC inhibition was reported to rapidly reduce DNL, hepatic steatosis and reduce markers of liver fibrosis within 12 weeks [Steide. K., et al. 2017. Hepatology 66, 324-344, Lawitz. E., et al. 2017. J Hepatol 66, S34]. ACLY is positioned one step upstream of ACC in the DNL pathway and controls its activity due to the dependence of ACC on acetyl-CoA production from ACLY. Thus, ACLY inhibitors should be efficacious at inhibiting DNL in humans. In preclinical studies, liver specific knockdown of ACLY using RNA interference (RNAi) led to reductions in hepatic acetyl-CoA and malonyl-CoA levels as well as lowered expression of lipogenesis, steatosis and gluconeogenesis genes which, importantly, promoted improvements in insulin sensitivity and glucose tolerance in animals [Wang, Q., et al. 2009. Hepatology 49, 1166-1175]. Furthermore, ACLY inhibition or gene silencing by siRNA was shown to reduce a variety of inflammatory mediators in macrophage cells [Infantino. V., et al. 2009. BBRC 440, 105-111], suggesting that ACLY inhibitors may also possess anti-inflammatory properties that could directly lower hepatic inflammation to improve tissue scarring and fibrosis. Thus, the potential for pharmacologic ACLY suppression to reduce DNL, inflammation, fibrosis and to restore insulin sensitivity could have profound therapeutic impacts in fatty liver, dyslipidemia and metabolic disease states.

ACLY inhibitors may also possess therapeutic utility in oncology. Interestingly, upregulation of ACLY expression has been documented in many human cancers including hepatocellular carcinoma, non-small cell lung cancer, breast cancer, colorectal cancer, and prostate cancer [Yancy, H. F., et al. 2007. J Carcinog 6, 8, Varis, A., et al. 2002. Cancer Research 62, 2625-9]. Furthermore, ACLY has also been proposed as a prognostic biomarker in some cancer patients [Migita, T., et al. 2009. Cancer Research 66, 8547-54]. The pro cancer role of ACLY may be related to enhanced DNL associated with its activity and thus the growth and survival advantage that DNL confers over normal cells [Svensson, R U., et al. 2017. Cold Spring Harbor Symp Quant Biol, 81, 93-103]. Thus, direct ACLY inhibition may be effective as an anti-cancer strategy and several lines of evidence suggest this. Inhibition of ACLY by either RNAi or pharmacological inhibitors results in cell cycle arrest and induction of apoptosis in vitro and in vivo [Hatzivassiliou, G., et al. 2005. Cancer Cell 8, 311-321]. Genetic knockout of ACLY in LN229 human glioblastoma cells led to profound defects in FA synthesis, histone acetylation and cellular proliferation [Zhao, S., et al. 2016. Cell Reports 17, 1037-1052]. Furthermore, ACLY knockdown in H1299 and H358 lung cancer cells led to a dramatic reduction in xenograft tumor growth in vivo [Zhang, C., et al. 2016. Genes and Development 30, 1956-1970].

ACLY derived acetyl-CoA is a critical precursor for malonyl-CoA production, which serves as the rate limiting metabolite for FA synthesis. Malonyl-CoA not only serves as the substrate for FA synthesis but also is required to suppress fatty acid oxidation in mitochondria. Hence, ACLY inhibition is expected to reduce cytosolic acetyl-CoA and Malonyl-CoA production, which will simultaneously reduce de novo lipid synthesis and promote the oxidation of existing fat. This dual effect on lipid metabolism raises the possibility that ACLY inhibitors will be substantially more effective in reducing excess fat than other mechanisms, and coupled to the effect of cholesterol synthesis inhibition, ACLY inhibitors are expected to be far superior than current therapies. Furthermore, ACLY inhibitors will impact insulin sensitivity, plasma and tissue triglycerides, and fasting plasma glucose as a consequence of whole-body and tissue-specific fat mass reduction, without the need for poly-pharmacy.

As ACLY inhibition is expected to reduce cytosolic acetyl-CoA, it is expected to have an impact on the enzyme immediately downstream of ACLY, Acetyl-CoA carboxylase. Acetyl-CoA carboxylase (ACC) catalyzes the ATP-dependent carboxylation of acetyl-CoA to form malonyl-CoA. This reaction, which proceeds in two half-reactions, a biotin carboxylase (BC) reaction and a carboxyltransferase (CT) reaction, is the first committed step in fatty acid (FA) biosynthesis and is the rate-limiting reaction for the pathway. In addition to its role as a substrate in FA biosynthesis, malonyl-CoA, the product of the ACC-catalyzed reaction, also plays an important regulatory role in controlling mitochondrial FA uptake through allosteric inhibition of carmitine palmitoyltransferase I (CPT-I), the enzyme catalyzing the first committed step in mitochondrial FA oxidation. Malonyl-CoA, therefore, is a key metabolic signal for the control of FA production and utilization in response to dietary changes and altered nutritional requirements in animals, for example during exercise, and therefore plays a key role in controlling the switch between carbohydrate and fat utilization in liver and skeletal muscle [Harwood, 2005].

In mammals, ACC exists as two tissue-specific isozymes, ACC1 which is present in lipogenic tissues (liver, adipose) and ACC2, which is present in oxidative tissues (liver, heart, skeletal muscle). ACC1 and ACC2 are encoded by separate genes, display distinct cellular distributions, and share 75% overall amino acid sequence identity, except for an extension at the N-terminus of ACC2 that direct ACC2 to the mitochondrial membrane. ACC1, which lacks this targeting sequence, is localized to the cytoplasm. In the heart and skeletal muscle, which have a limited capacity to synthesize fatty acids, the malonyl-CoA formed by ACC2 functions to regulate FA oxidation. In the liver, the malonyl-CoA formed in the cytoplasm through the actions of ACC1 is utilized for FA synthesis and elongation leading to triglyceride formation and VLDL production, whereas the malonyl-CoA formed at the mitochondrial surface by ACC2 acts to regulate FA oxidation [Tong and Harwood, J. Cellular Biochem. 99: 1476, 2006]. This compartmentalization of malonyl-CoA results from a combination of synthesis proximity [Abu-Elheiga et al., PNAS (USA) 102: 12011, 2005] and the rapid action of malonyl-CoA decarboxylase [Cheng et al., J. Med. Chem. 49:1517, 2006].

Simultaneous suppression of the enzymatic activities of ACC1 and ACC2 via ACLY offers the ability to inhibit de novo FA production in lipogenic tissues (e.g. liver & adipose) while at the same time stimulating FA oxidation in oxidative tissues (e.g. liver & skeletal muscle) and therefore offers an attractive modality for favorably affecting, in a concerted manner, a multitude of cardiovascular risk factors associated with obesity, diabetes, insulin resistance, and the metabolic syndrome.

Several lines of evidence strongly support the concept of inhibition of ACC activity as an important therapeutic target for treating obesity, diabetes, insulin resistance, and the metabolic syndrome.

Abu-Elheiga et al. [Proc. Natl. Acad. Sci. USA 100: 10207-10212, 2003] demonstrated that ACC2 knock-out mice exhibit reduced skeletal and cardiac muscle malonyl-CoA, increased muscle FA oxidation, reduced hepatic fat, reduced total body fat, elevated skeletal muscle uncoupling protein-3 (UCP3) which is indicative of increased energy expenditure, reduced body weight, reduced plasma free FAs, reduced plasma glucose, and reduced tissue glycogen, and are protected from diet-induced diabetes and obesity.

Savage et al. [J. Clin. Invest. 116: 817, 2006], using ACC1 and ACC2 antisense oligonucleotides, demonstrated stimulation of FA oxidation in isolated rat hepatocytes and in rats fed high-fat diets, and lowering of hepatic triglycerides, improvements in insulin sensitivity, reductions in hepatic glucose production, and increases in UCP1 mRNA in high fat-fed rats. These effects were greater when both ACC1 and ACC2 expression were suppressed than when either ACC1 or ACC2 expression alone was suppressed.

Harwood et al. [J. Biol. Chem. 278: 37099, 2003] demonstrated that the isozyme-nonselective ACC inhibitor, CP-640186, which equally inhibits ACC1 and ACC2 ($IC_{50}$=~60 nM) isolated from rat, mouse, monkey and human without inhibiting either pyruvate carboxylase or propionyl-CoA carboxylase, reduced FA synthesis, triglyceride synthesis and secretion in Hep-G2 cells without affecting cholesterol synthesis, and reduced apoB secretion without affecting apoA1 secretion. CP-640186 also stimulated FA oxidation in C2C12 cells and in rat muscle slices and increased CPT-I activity in Hep-G2 cells. In experimental animals, CP-640186 acutely reduced malonyl-CoA concentration in both lipogenic and oxidative tissues in both the fed and fasted state, reduced liver and adipose tissue FA synthesis, and increased whole body FA oxidation. In sucrose-fed rats treated with CP-640186 for three weeks, CP-640186 time- and dose-dependently reduced liver, muscle and adipose triglycerides, reduced body weight due to selective fat reduction without reducing lean body mass, reduced leptin levels, reduced the hyperinsulinemia produced by the high sucrose diet without changing plasma glucose levels, and improved insulin sensitivity.

Saha et al. [Diabetes 55: A288, 2006] demonstrated stimulation of insulin sensitivity in insulin-resistant rat muscle tissue by CP-640186 within 30 min of compound administration, and studies by Furler et al. [Diabetes 55: A333, 2006] used dual tracer analysis to show that acute (46 min) treatment of rats with CP-640186 stimulated FA clearance without decreasing glucose clearance.

ACC is the rate-limiting enzyme in fatty acid synthesis and its product, malonyl CoA, serves as an important regulator of fatty acid oxidation. Hence, the suppression of ACC activity via ACLY may both reduce de novo lipid synthesis and promote the oxidation of existing fat. This dual effect on lipid metabolism raises the possibility that ACC suppression via ACLY inhibition will be substantially more effective in reducing excess fat than other mechanisms. Furthermore, ACLY inhibitors will impact insulin sensitivity, plasma and tissue triglycerides, and fasting plasma glucose as a consequence of whole-body and tissue-specific fat mass reduction without the need for poly-pharmacy.

ACLY inhibitors need only access the liver and muscle in the peripheral compartment. Avoiding the CNS will address many of side effects associated with the late-stage obesity programs targeting CNS receptors. ACLY inhibitors are also expected to have superior safety profiles to existing metabolic disease agents. For example, it is unlikely that an ACLY inhibitor will precipitate life-threatening hypoglycemia as is often seen with insulin mimetics, insulin secretagogues, and insulin degradation inhibitors. Also, since ACLY inhibitors will reduce whole-body fat mass, they will be superior to the glitazones that increase whole-body fat mass as part of their mechanism of action.

A peripherally acting agent that causes significant weight loss and improves other metabolic endpoints fits well within the US FDA's requirements for approval of a new obesity agent. However, if an approval for obesity continues to be challenging in 5-7 years, ACLY inhibitors could be approved for familial combined hyperlipidemia and non-alcoholic steatohepatitis (NASH). There are currently no marketed ACLY inhibitors, so an ACLY inhibitor would represent first-in-class therapy for treating obesity and metabolic syndrome.

The activity of a compound utilized in this invention as an inhibitor of ACLY or treatment for obesity, metabolic syndrome, NAFLD, NASH, dyslipidemia, cancer or hypercholesteremia may be assayed in vitro or in vivo. An in vivo assessment of the efficacy of the compounds of the invention may be made using an animal model of aforementioned indications, e.g., a rodent or primate model. Cell-based assays may be performed using a relevant cell line isolated from a tissue that expresses ACLY. Additionally, biochemical, biophysical, molecular and mechanism-based assays, e.g., transcription assays using a purified protein, western blot, northern blot, RT-PCR, luminescence or fluorescence-based enzyme assays etc., may be performed. In vitro assays include assays that determine cell proliferation, protein expression, cytotoxicity, enzyme inhibitory activity, and/or the subsequent functional consequences of treatment of cells with compounds of the invention. Additional in vitro assays may include stable isotope labeling of carbons and radiolabel quantitation in inhibitor treated cells. Additionally, metabolic flux and metabolomics may be used. Alternate in vitro assays quantitate the ability of the inhibitor to bind to protein or nucleic acid molecules within the cell. Inhibitor binding may be measured by radiolabeling the inhibitor prior to binding, isolating the inhibitor/target molecule complex and determining the amount of radiolabel bound. Alternatively, inhibitor binding may be determined by additional biophysical techniques e.g. surface plasma resonance (SPR). Detailed conditions for assaying a compound utilized in this invention as an inhibitor of ACLY are set forth in the Examples below. The aforementioned assays are exemplary and not intended to limit the scope of the invention. The skilled practitioner can appreciate that modifications can be made to conventional assays to develop equivalent assays that obtain the same result.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The compounds and compositions, according to the method of the present invention, may be administered using any amount and any route of administration effective for treating or lessening the severity of a metabolic disorder or condition, cancer, an autoimmune disorder, a neurodegenerative or neurological disorder, schizophrenia, a bone-related disorder, liver disease, or a cardiac disorder.

In some embodiments, the compounds and compositions, according to the method of the present invention, may be administered using any amount and any route of administration effective for treating or lessening the severity of a disease associated with ACLY.

In some embodiments, the compounds and compositions, according to the method of the present invention, may be administered using any amount and any route of administration effective for treating or lessening the severity of a disease associated with ACC (Tong et al. "Acetyl-coenzyme A carboxylase: crucial metabolic enzyme and attractive target for drug discovery" Cell and Molecular Life Sciences (2005) 62, 1784-1803).

In some embodiments, the compounds and compositions, according to the method of the present invention, may be administered using any amount and any route of administration effective for treating or lessening the severity of a metabolic disorder, disease, or condition. In some embodiments, the metabolic disorder is obesity, metabolic syndrome, diabetes or diabetes-related disorders including Type 1 diabetes (insulin-dependent diabetes mellitus, IDDM) and Type 2 diabetes (non-insulin-dependent diabetes mellitus, NIDDM), impaired glucose tolerance, insulin resistance, hyperglycemia, diabetic complications, including, but not limited to atherosclerosis, coronary heart disease, stroke, peripheral vascular disease, nephropathy, hypertension, neuropathy and nephropathy; obesity comorbidities including but not limited to metabolic syndrome, dyslipidemia, Type III dyslipidemia, hypertension, insulin resistance, diabetes (including Type 1 and Type 2 diabetes), coronary artery disease, and heart failure. In some embodiments, the metabolic disorder, disease or condition is non-alcoholic fatty liver disease or hepatic insulin resistance.

In some embodiments, the present invention provides a method of treating a metabolic disorder, disease, or condition described herein, comprising administering a compound of the invention in conjunction with one or more pharmaceutical agents. Suitable pharmaceutical agents that may be used in combination with the compounds of the present invention include anti-obesity agents (including appetite suppressants), anti-diabetic agents, anti-hyperglycemic agents, lipid lowering agents, and anti-hypertensive agents.

Suitable lipid lowering agents that can be used in conjunction with compounds of the present invention include but are not limited to, bile acid sequestrants, HMG-CoA reductase inhibitors, HMG-CoA synthase inhibitors, cholesterol absorption inhibitors, acyl coenzyme A-cholesterol acyl transferase (ACAT) inhibitors, CETP inhibitors, squalene synthetase inhibitors, PPAR-alpha agonists, FXR receptor modulators, LXR receptor modulators, lipoprotein synthesis inhibitors, renin-angiotensin system inhibitors, PPAR-delta partial agonists, bile acid reabsorption inhibitors, PPAR-gamma agonists, triglyceride synthesis inhibitors, microsomal triglyceride transport inhibitors, transcription modulators, squalene epoxidase inhibitors, low density lipoprotein receptor inducers, platelet aggregation inhibitors, 5-LO or FLAP inhibitors, niacin, and niacin-bound chromium.

Suitable anti-hypertensive agents that can be used in conjunction with compounds of the present invention include but are not limited to diuretics, beta-adrenergic blockers, calcium channel blockers, angiotensin converting enzyme (ACE) inhibitors, neutral endopeptidase inhibitors, endothelin antagonists, vasodilators, angiotensin II receptor antagonists, alpha/beta adrenergic blockers, alpha 1 blockers, alpha 2 agonists, aldosterone inhibitors, mineralocorticoid receptor inhibitors, renin inhibitors, and angiopoietin 2 binding agents.

Suitable anti-diabetic agents that can be used in conjunction with compounds of the present invention include but are not limited to other acetyl-CoA carboxylase (ACC) inhibitors, DGAT-1 inhibitors, AZD7687, LCQ908, DGAT-2 inhibitors, monoacylglycerol O-acyltransferase inhibitors, PDE-10 inhibitors, AMPK activators, sulfonylureas (e.g. acetohexamide, chlorpropamide, diabinese, glibenclamide, glipizide, glyburide, blimipiride, gliclazide, glipentide, gliquidone, glisolamide, tolazamide, tolbutamide), meglitinides, alpha-amylase inhibitors (e.g. tendamistat, treastatin, AL-3688), alpha-glucoside hydrolase inhibitors (e.g. acarbose), alpha-glucosidase inhibitors (e.g. adiposine, camiglibose, emiglitate, miglitol, voglibose, pradimicin-Q, sarbostatin), PPAR-gamma agonists (e.g. balaglitazone, ciglitazone, darglitazone, englitazone, isaglitazone, pioglitazone, rosiglitazone, troglitazone), PPAR-alpha/gamma agonists (e.g. CLX-0940, GW-1536, GW-1929, GW-2433, KRP-297, L-796449, LR-90, MK-0767, SB-219994), biguanides (e.g. metformin, buformin), GLP-1 modulators (exendin-3, exendin-4), liraglutide, albiglutide, exenatide (Byetta), taspoglutide, lixisenatide, dulaglutide, semaglutide, N,N-9924, TTP-054, PTP-1B inhibitors (trodusquemine, hyrtiosal extract), SIRT-1 inhibitors (e.g. resveratrol, GSK2245840, GSK184072), DPP-IV inhibitors (e.g. sitagliptin, vildagliptin, alogliptin, dutogliptin, linagliptin, saxagliptin), insulin secretagogues, fatty acid oxidation inhibitors, A2 antagonists, JNK inhibitors, glucokinase activators (e.g. TTP-399, TTP-355, TTP-547, AZD1656, ARRY403, MK-0599, TAK-329, AZD5658, GKM-001), insulin, insulin mimetics, glycogen phosphorylase inhibitors (e.g. GSK1362885), VPAC2 receptor agonists, SGLT2 inhibitors (dapagliflozin, canagliflozin, BI-10733, tofogliflozin, ASP-1941, THR1474, TS-071, ISIS388626, LX4211), glucagon receptor modulators, GPR119 modulators (e.g. MBX-2982, GSK1292263, APD597, PSN821), FGF21 derivatives, TGR5 (GPBAR1) receptor agonists (e.g. INT777), GPR40 agonists (e.g. TAK-875), GPR120 agonists, nicotinic acid receptor (HM74A) activators, SGLT1 inhibitors (e.g. GSK1614235), carnitine palmitoyl transferase enzyme inhibitors, fructose 1,6-diphosphatase inhibitors, aldose reductase inhibitors, mineralocorticoid receptor inhibitors, TORC2 inhibitors, CCR2 inhibitors, CCR5 inhibitors, PKC (e.g. PKC-alpha, PKC-beta, PKC-gamma) inhibitors, fatty acid synthetase inhibitors, serine palmitoyl transferase inhibitors, GPR81 modulators, GPR39 modulators, GPR43 modulators, GPR41 modulators, GPR105 modulators, Kv1.3 inhibitors, retinol binding protein 4 inhibitors, glucocorticoid receptor modulators, somatostatin receptor (e.g. SSTR1, SSTR2, SSTR3, SSTR5) inhibitors, PDHK2 inhibitors, PDHK4 inhibitors, MAP4K4 inhibitors, IL1-beta modulators, and RXR-alpha modulators.

Suitable anti-obesity agents include but are not limited to, 11-beta-hydroxysteroid dehydrogenase 1 inhibitors, stearoyl-CoA desaturase (SCD-1) inhibitors, MCR-4 agonists, CCK-A agonists, monoamine reuptake inhibitors (e.g. sibutramine), sympathomimetic agents, beta-3-adrenergic receptor agonists, dopamine receptor agonists (e.g. bromocriptine), melanocyte-stimulating hormone and analogs thereof, 5-HT$_{2C}$ agonists (e.g. lorcaserin/Belviq), melanin concentrating hormone antagonists, leptin, leptin analogs, leptin agonists, galanin antagonists, lipase inhibitors (e.g. tetrahydrolipstatin/Orlistat), anorectic agents (e.g. bombesin agonists), NPY antagonists (e.g. velneperit), PYY$_{3-36}$ (and analogs thereof), BRS3 modulators, opioid receptor mixed antagonists, thyromimetic agents, dehydroepiandrosterone, glucocorticoid agonists or antagonists, orexin antagonists, GLP-1 agonists, ciliary neurotrophic factors (e.g. Axokine), human agouti-related protein (AGRP) inhibitors, H3 antagonists or inverse agonists, neuromedin U agonists, MTP/ApoB inhibitors (e.g. gut-selective MTP inhibitors such as dirlotapide, JTT130, Usistapide, SLX4090), MetAp2 inhibitors (e.g. ZGN-433), agents with mixed modulatory activity at two or more of glucagon, GIP, and GLP1 receptors (e.g. MAR-701, ZP2929), norepinephrine reuptake inhibitors, opioid antagonists (e.g. naltrexone), CB1 receptor antagonists or inverse agonists, ghrelin agonists or antagonists, oxyntomodulin and analogs thereof, monoamine uptake inhibitors (e.g. tesofensine), and combination agents (e.g. buproprion plus zonisamide (Empatic), pramlintide plus metreleptin, buproprion plus naltrexone (Contrave), phentermine plus topiramate (Qsymia).

In some embodiments, the anti-obesity agents used in combination with compounds of the invention are selected from gut-selective MTP inhibitors (e.g. dirlotapide, mitratapide, implitapide, R56918), CCK-A agonists, 5-HT$_{2C}$ agonists (e.g. lorcaserin/Belviq), MCR4 agonists, lipase inhibitors (e.g. Cetilistat), PYY$_{3-36}$ (including analogs and PEGylated analogs thereof), opioid antagonists (e.g. naltrexone), oleoyl estrone, obinepitide, pramlintide, tesofensine, leptin, bromocriptine, orlistat, AOD-9604, and sibutramine.

In some embodiments, the compounds and compositions, according to the method of the present invention, may be administered using any amount and any route of administration effective for treating or lessening the severity of a LKB1 or Kras associated disease. In some embodiments, the LKB1 or Kras associated disease is selected from hepatocellular carcinoma, LKB1 mutant cancers, LKB1 loss of heterozygosity (LOH) driven cancers, Kras mutant cancers, Peutz-Jeghers syndrome (PJS), Cowden's disease (CD), and tubeous sclerosis (TS) (Makowski et a. "Role of LKB1 in Lung Cancer Development" British Journal of Cancer (2008) 99, 683-688). In some embodiments, the LKB1 or Kras associated disease is a Kras positive/LKB1 deficient lung tumor.

In some embodiments, the compounds and compositions, according to the method of the present invention, may be administered using any amount and any route of administration effective for treating or lessening the severity of a cancer, or inhibiting the growth of or inducing apoptosis in cancer cells (Wang et al. "Acetyl-CoA Carboxylase-alpha Inhibitor TOFA Induces Human Cancer Cell Apoptosis" Biochem Biophys Res Commun. (2009) 385(3), 302-306; Chajes et al. "Acetyl-CoA Carboxylase alpha Is Essential to Breast Cancer Cell Survival" Cancer Res. (2006) 66, 5287-

5294; Beckers et al. "Chemical Inhibition of Acetyl-CoA Carboxylase Induces Growth Arrest and Cytotoxicity Selectivity in Cancer Cells" Cancer Res. (2007) 8180-8187; Brusselmans et al. "RNA Interference-Mediated Silencing of the Acetyl-CoA-Carboxylase-alpha Gene Induces Growth Inhibition and Apoptosis of Prostate Cancer Cells" Cancer Res. (2005) 65, 6719-6725; Brunet et al. "BRCA1 and Acetyl-CoA Carboxylase: The Metabolic Syndrom of Breast Cancer" Molecular Carcinogenesis (2008) 47, 157-163; Cairns et al. "Regulation of Cancer Cell Metabolism" (2011) 11, 85-95; Chiaradonna et al. "From Cancer Metabolism to New Biomarkers and Drug Targets" Biotechnology Advances (2012) 30, 30-51).

In some embodiments, the compounds and compositions, according to the method of the present invention, may be administered using any amount and any route of administration effective for treating or lessening the severity of a melanoma. In some embodiments, the melanoma is one bearing an activated MAPK pathway (Petti et al. "AMPK activators inhibit the proliferation of human melanomas bearing the activated MAPK pathway" Melanoma Research (2012) 22, 341-350).

Compounds of the present invention find special utility in triple negative breast cancer, as the tumor suppressor protein BRCA1 binds and stabilizes the inactive form of ACC, thus upregulating de novo lipid synthesis, resulting in cancer cell proliferation Brunet et al. "BRCA1 and acetyl-CoA carboxylase: the metabolic syndrome of breast cancer" Mol. Carcinog. (2008) 47(2), 157-163.

In some embodiments, the compounds and compositions, according to the method of the present invention, may be administered using any amount and any route of administration effective for treating or lessening the severity of a liposarcoma. Liposarcomas have been shown to depend on de novo long-chain fatty acid synthesis for growth, and inhibition of ACC by soraphen A inhibited lipogenesis as well as tumor cell growth (Olsen et al. "Fatty acid synthesis is a therapeutic target in human liposarcoma" International J. of Oncology (2010) 36, 1309-1314).

In some embodiments, the compounds and compositions, according to the method of the present invention, may be administered using any amount and any route of administration effective for treating or lessening the severity of a liver disease. In some embodiments, the liver disease is selected from hepatitis C, hepatocellular carcinoma, familial combined hyperlipidemia and non-alcoholic steatohepatitis (NASH), liver cancer, cholangiocarcinoma, angiosarcoma, hemangiosarcoma, and progressive familial intrahepatic cholestasis.

In some embodiments, the compounds and compositions, according to the method of the present invention, may be administered using any amount and any route of administration effective for treating or lessening the severity of a neurological disease (Henderson et al. Neurotherapeutics (2008) 5, 470-480; Costantini et al. Neurosci. (2008) 9 Suppl. 2: S16; Baranano et al. Curr. Treat. Opin. Neurol. (2008) 10, 410-419).

In some embodiments, the compounds and compositions, according to the method of the present invention, may be administered using any amount and any route of administration effective for treating or lessening the severity of a cardiac disorder. In some embodiments, the cardiac disorder is cardiac hypertrophy. In some embodiments the cardiac disorder is treated or its severity lessened by the cardioprotective mechanism resulting from increased fatty acid oxidation by indirect ACC inhibition via ACLY (Kolwicz et al. "Cardiac-specific deletion of acetyl CoA carboxylase 2 (ACC2) prevents metabolic remodeling during pressure-overload hypertrophy" Circ. Res. (2012); DOI: 10.1161/CIRCRESAHA.112.268128).

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting ACLY in a biological sample comprising the step of contacting said biological sample with a compound of this invention, or a composition comprising said compound.

In certain embodiments, the invention relates to a method of modulating fatty acid levels in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of enzymes in a biological sample is useful for a variety of purposes that are known to one of skill in the art. Examples of such purposes include, but are not limited to biological assays, gene expression studies, and biological target identification.

Another embodiment of the present invention relates to a method of inhibiting ACLY in a patient comprising the step of administering to said patient a compound of the present invention, or a composition comprising said compound.

According to another embodiment, the invention relates to a method of inhibiting fatty acid production, inhibiting sterol production, or both, in a patient comprising the step of administering to said patient a compound of the present invention, or a composition comprising said compound. According to certain embodiments, the invention relates to a method of inhibiting fatty acid production, inhibiting sterol production, or both in a patient, leading to decreasing obesity or alleviating symptoms of metabolic syndrome, comprising the step of administering to said patient a compound of the present invention, or a composition comprising said compound. In other embodiments, the present invention provides a method for treating a disorder mediated by ACLY, in a patient in need thereof, comprising the step of administering to said patient a compound according to the present invention or pharmaceutically acceptable composition thereof. Such disorders are described in detail herein.

In some embodiments the compounds and compositions of the present invention may be used in a method of treating obesity or another metabolic disorder. In certain embodiments the compounds and compositions of the present invention may be used to treat obesity or other metabolic disorder in a mammal. In certain embodiments the mammal is a human patient. In certain embodiments the compounds and compositions of the present invention may be used to treat obesity or other metabolic disorder in a human patient.

In some embodiments the present invention provides a method of treating obesity or another metabolic disorder, comprising administering a compound or composition of the present invention to a patient with obesity or another metabolic disorder. In certain embodiments the method of treating obesity or another metabolic disorder comprises administering compounds and compositions of the present invention to a mammal. In certain embodiments the mammal is a human. In some embodiments the metabolic disorder is dyslipidemia, Type III dyslipidemia, or hyperlipidemia. In some embodiments, the obesity is a symptom of Prader-Willi syndrome, Bardet-Biedl syndrome, Cohen syndrome or MOMO syndrome. In some embodiments, the obesity is a side effect of the administration of another medication, including but not limited to insulin, sulfonylureas, thiazolidinediones, antipsychotics, antidepressants, steroids, anticonvulsants (including phenytoin and valproate), pizotifen, or hormonal contraceptives.

In certain embodiments, the present invention provides a method of treating cancer or another proliferative disorder, comprising administering a compound or composition of the present invention to a patient with cancer or another proliferative disorder. In certain embodiments, the method of treating cancer or another proliferative disorder comprises administering compounds and compositions of the present invention to a mammal. In certain embodiments, the mammal is a human.

As used herein, the terms "inhibition of cancer" and "inhibition of cancer cell proliferation" refer to the inhibition of the growth, division, maturation or viability of cancer cells, and/or causing the death of cancer cells, individually or in aggregate with other cancer cells, by cytotoxicity, nutrient depletion, or the induction of apoptosis.

Examples of tissues containing cancerous cells whose proliferation is inhibited by the compounds and compositions described herein and against which the methods described herein are useful include but are not limited to breast, prostate, brain, blood, bone marrow, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous glands, muscle, heart, and stomach.

In some embodiments, the cancer treated by compounds or compositions of the invention is a melanoma, liposarcoma, lung cancer, breast cancer, prostate cancer, leukemia, kidney cancer, esophageal cancer, brain cancer, lymphoma or colon cancer. In certain embodiments, the cancer is a primary effusion lymphoma (PEL). In certain preferred embodiments the cancer to be treated by compounds or compositions of the invention is one bearing an activated MAPK pathway. In some embodiments the cancer bearing an activated MAPK pathway is a melanoma. In certain preferred embodiments the cancer treated by compounds or compositions of the invention is one associated with BRCA1 mutation. In an especially preferred embodiment, the cancer treated by compounds or compositions of the invention is a triple negative breast cancer.

In certain embodiments, the disease which can be treated by compounds of the invention are neurological disorders. In some embodiments, the neurological disorder is Alzheimer's Disease, Parkinson's Disease, epilepsy, ischemia, Age Associated Memory Impairment, Mild Cognitive Impairment, Friedreich's Ataxia, GLUT1-deficient epilepsy, Leprechaunism, Rabson-Mendenhall Syndrome, Coronary Arterial Bypass Graft dementia, anaesthesia-induced memory loss, amyotrophic lateral sclerosis, gliomaor Huntington's Disease.

Combinations

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated".

In certain embodiments, a provided compound, or composition thereof, is administered in combination with another inhibitor of ACLY or antiobesity agent. In some embodiments, a provided compound, or composition thereof, is administered in combination with one or more other therapeutic agents. Such therapeutic agents include, but are not limited to agents such as orlistat (Xenical), CNS stimulants, Qsymia, or Belviq.

In certain embodiments, a provided compound, or a composition thereof, is administered in combination with another anti-cancer, cytotoxin, or chemotherapeutic agent, to a patient in need thereof.

In certain embodiments, the anti-cancer or chemotherapeutic agents used in combination with compounds or compositions of the invention include, but are not limited to metformin, phenformin, buformin, imatinib, nilotinib, gefitinib, sunitinib, carfilzomib, salinosporamide A, retinoic acid, cisplatin, carboplatin, oxaliplatin, mechlorethamine, cyclophosphamide, chlorambucil, ifosfamide, azathioprine, mercaptopurine, doxifluridine, fluorouracil, gemcitabine, methotrexate, tioguanine, vincristine, vinblastine, vinorelbine, vindesine, podophyllotoxin, etoposide, teniposide, tafluposide, paclitaxel, docetaxel, irinotecan, topotecan, amsacrine, actinomycin, doxorubicin, daunorubicin, valrubicin, idarubicin, epirubicin, plicamycin, mitomycin, mitoxantrone, melphalan, busulfan, capecitabine, pemetrexed, epothilones, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Citrovorum Factor, Cladribine, Cortisone, Cosmegen®, CPT-11, Cytadren®, Cytosar-U®, Cytoxan®, Dacarbazine, Dacogen, Dactinomycin, Darbepoetin Alfa, Dasatinib, Daunomycin, Daunorubicin Hydrochloride, Daunorubicin Liposomal, DaunoXome®, Decadron, Decitabine, Delta-Cortef®, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab, ozogamicin, Gemzar Gleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab, Tiuxetan, Idamycin®, Idarubicin Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase®, Lanacort®, Lapatinib, L-asparaginase, LCR, Lenalidomide, Letrozole, Leucovorin, Leukeran, Leukine™, Leuprolide, Leucrocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, Octreotide, Octreotide acetate, Ofatumumab, Oncospar®, Oncovin®, Ontak®, Onxal™, Oprelvekin, Orapred®, Orasone®, Oxaliplatin, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a), Romiplostim, Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, Xeloda®, Zanosar®, Zevalin™, Zinecard®, Zoladex®, Zoledronic acid, Zolinza, Zometa®, or combinations of any of the above.

In certain embodiments, compounds of the present invention may be administered together with a biguanide selected from metformin, phenformin, or buformin, to a patient in need thereof. In certain embodiments, the patient administered a combination of a compound of the invention and a biguanide is suffering from a cancer, obesity, a liver disease, diabetes or two or more of the above.

In certain embodiments, a combination of 2 or more therapeutic agents may be administered together with compounds of the invention. In certain embodiments, a combination of 3 or more therapeutic agents may be administered with compounds of the invention.

Other examples of agents the inhibitors of this invention may also be combined with include, without limitation: vitamins and nutritional supplements, cancer vaccines, treatments for neutropenia (e.g. G-CSF, filgrastim, lenograstim), treatments for thrombocytopenia (e.g. blood transfusion, erythropoietin), PI3 kinase (PI3K) inhibitors, MEK inhibitors, mTOR inhibitors, CPT1 inhibitors, AMPK activators, PCSK9 inhibitors, SREBP site 1 protease inhibitors, HMG CoA-reductase inhibitors, antiemetics (e.g. 5-$HT_3$ receptor antagonists, dopamine antagonists, NK1 receptor antagonists, histamine receptor antagonists, cannabinoids, benzodiazepines, or anticholinergics), treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anticonvulsants, ion channel blockers, riluzole, and anti-Parkinsonian agents; agents for treating cardiovascular disease such as beta-blockers, ACE inhibitors, diuretics, nitrates, calcium channel blockers, and statins, fibrates, cholesterol absorption inhibitors, bile acid sequestrants, and niacin; agents for treating liver disease such as corticosteroids, cholestyramine, interferons, and anti-viral agents; agents for treating blood disorders such as corticosteroids, anti-leukemic agents, and growth factors; agents for treating immunodeficiency disorders such as gamma globulin; and anti-diabetic agents such as biguanides (metformin, phenformin, buformin), thiazolidinediones (rosiglitazone, pioglitazone, troglitazone), sulfonylureas (tolbutamide, acetohexamide, tolazamide, chlorpropamide, glipizide, glyburide, glimepiride, gliclazide), meglitinides (repaglinide, nateglinide), alpha-glucosidase inhibitors (miglitol, acarbose), incretin mimetics (exenatide, liraglutide, taspoglutide), gastric inhibitory peptide analogs, DPP-4 inhibitors (vildagliptin, sitagliptin, saxagliptin, linagliptin, alogliptin), amylin analogs (pramlintide), and insulin and insulin analogs.

In certain embodiments, compounds of the present invention, or a pharmaceutically acceptable composition thereof, are administered in combination with antisense agents, a monoclonal or polyclonal antibody or an siRNA therapeutic.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another, normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, an additional therapeutic agent, and a pharmaceutically acceptable carrier, adjuvant, or vehicle.

The amount of both, an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of formula I can be present in different crystal modifications whose biological activity may differ. They are likewise subject matter of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Reaction Schemes

Chlorosulfonation I.

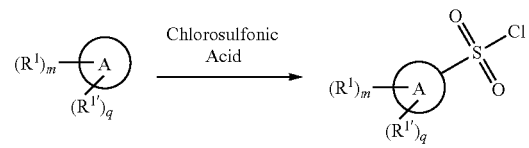

A 3-necked round-bottom flask purged and maintained with an inert atmosphere of nitrogen is charged with aryl compound A (1 eq.) and chlorosulfonic acid. The resulting solution is stirred overnight at between about 65° C. to 115° C. Upon completion the reaction is quenched by the addition of water/ice. The resulting solution is then extracted with ethyl acetate and the combined organic layers are concentrated under vacuum to the target sulfonylchloride.

Chlorosulfonation II.

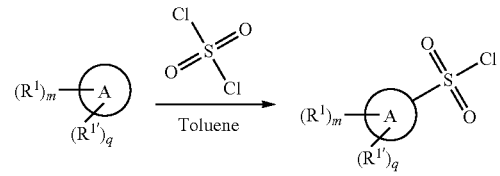

A 3-necked round-bottom flask purged and maintained with an inert atmosphere of nitrogen is charged with aryl compound A (1 eq.), sulfuroyl dichloride (6 eq.), and toluene. The resulting solution is stirred at about 65° C. Upon completion the reaction is quenched by the addition of water/ice. Product sulfonylchloride is collected by filtration or extraction with ethyl acetate.

Sulfonamide Linker Formation.

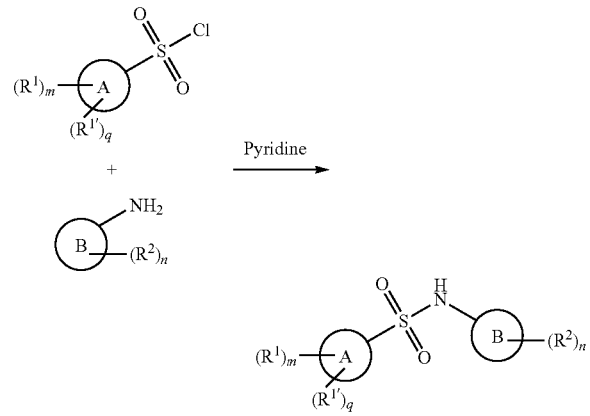

A round-bottom flask is charged with sulfonyl chloride A (1 eq.), amine B (1.2 eq.), pyridine, and DCM. The reaction solution is stirred at room temperature. Upon completion the reaction is quenched by the addition of water and the pH is adjusted with 1M HCl. The resulting solution is extracted with ethyl acetate and the combined organic layers are concentrated under vacuum. The product sulfonamide is then further purified by column chromatography.

Amide Linker Formation.

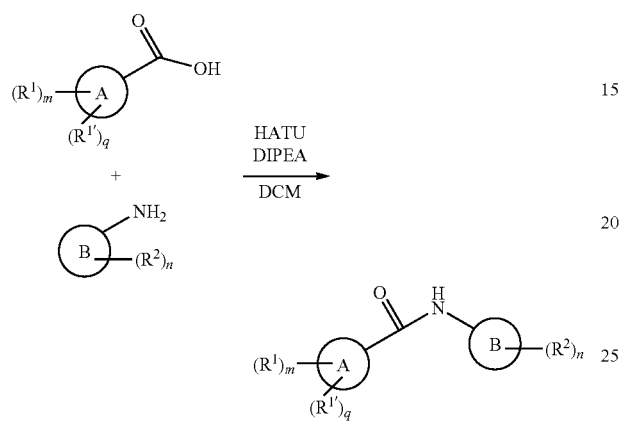

A round-bottom flask is charged with carboxylic acid A (1 eq.), amine B (1.2 eq.), DIPEA (2 eq.), and DCM. The reaction solution is stirred at 40° C. overnight. Upon completion the reaction is diluted with water and extracted with ethyl acetate and the combined organic layers are concentrated under vacuum. The product amide is then further purified by column chromatography.

In certain embodiments, compounds of the present invention are generally prepared according to Scheme I set forth below:

Example 1. Synthesis of Methyl 3-chloro-5-(N-(4,6-difluoro-[1,1'-biphenyl]-3-yl) sulfamoyl)-4-methoxybenzoate, I-63

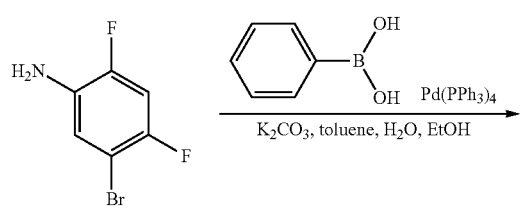

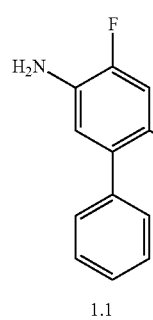

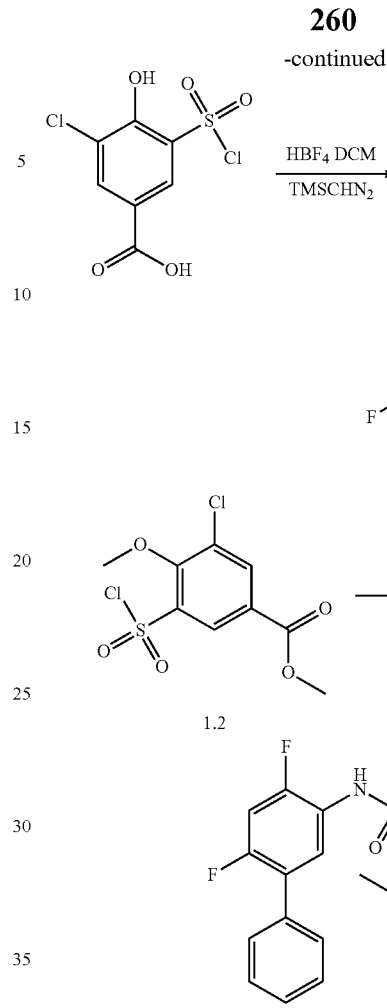

Synthesis of Compound 1.1

To a stirred mixture of 5-bromo-2,4-difluoroaniline (15 g, 72.11 mmol, 1 equiv) and phenylboronic acid (10.6 g, 86.54 mmol, 1.2 equiv) in toluene (50 mL), $H_2O$ (50 mL), EtOH (50 mL) were added $Pd(PPh_3)_4$ (8.3 g, 7.21 mmol, 0.1 equiv), $K_2CO_3$ (49.8 g, 360.33 mmol, 4.997 equiv). The reaction was stirred for 12 h at 80° C. under nitrogen atmosphere. The resulting mixture was filtered, the filter cake was washed with EtOAc (2×500 mL). The filtrate was concentrated under reduced pressure. The residue was purified by silica gel column chromatography, eluted with PE/EtOAc (10:1) to afford 1.1 (12 g, 81.09%) as a brown oil.

Synthesis of Compound 1.2

To a stirred mixture of 3-chloro-5-(chlorosulfonyl)-4-hydroxybenzoic acid (1.5 g, 5.53 mmol, 1 equiv) and $HBF_4$ (1.0 g, 11.07 mmol, 2 equiv) in DCM (15 mL) was added $TMSCHN_2$ (2.5 g, 22.13 mmol, 4 equiv) at 0° C. under nitrogen atmosphere. After 12, the reaction solution was quenched with water (100 mL) at room temperature, and then extracted with $CH_2Cl_2$ (2×100 mL). The combined organic layers were concentrated under vacuum. The residue was purified by Prep-TLC ($CH_2Cl2/MeOH$=20:1) to afford 1.2 (464 mg, 28.03%) as a brown solid.

Synthesis of I-63

Into a 25 mL round bottom flask, were added 1.2 (464 mg, 1.55 mmol, 1 equiv), 1.1 (382.0 mg, 1.86 mmol, 1.2 equiv) and pyridine (4.6 mL) at room temperature. The resulting mixture was stirred for 12 h at 50° C. under nitrogen atmosphere. The reaction was quenched with 1M HCl. The resulting solution was extracted with EtOAc (2×100 mL), and the combined organic layers were concentrated under vacuum. The residue was purified by Prep-TLC (CH$_2$Cl$_2$/MeOH=20:1) to afford I-63 (246 mg, 33.90%) as a white solid. (ES, m/z): [M–H]$^-$ 466.0, $^1$H-NMR (300 MHz, DMSO, ppm): δ10.45 (s, 1H), δ8.26 (d, J=2.4 Hz, 1H), δ8.17 (d, J=2.1 Hz, 1H), δ7.51-7.40 (m, 6H), δ7.38-7.31 (m, 1H), δ3.98 (s, 3H), δ3.86 (s, 3H).

Example 2. Synthesis of Methyl 3-chloro-5-[(2,4-difluoro-5-phenylphenyl) sulfamoyl]-4-hydroxybenzoate, I-65

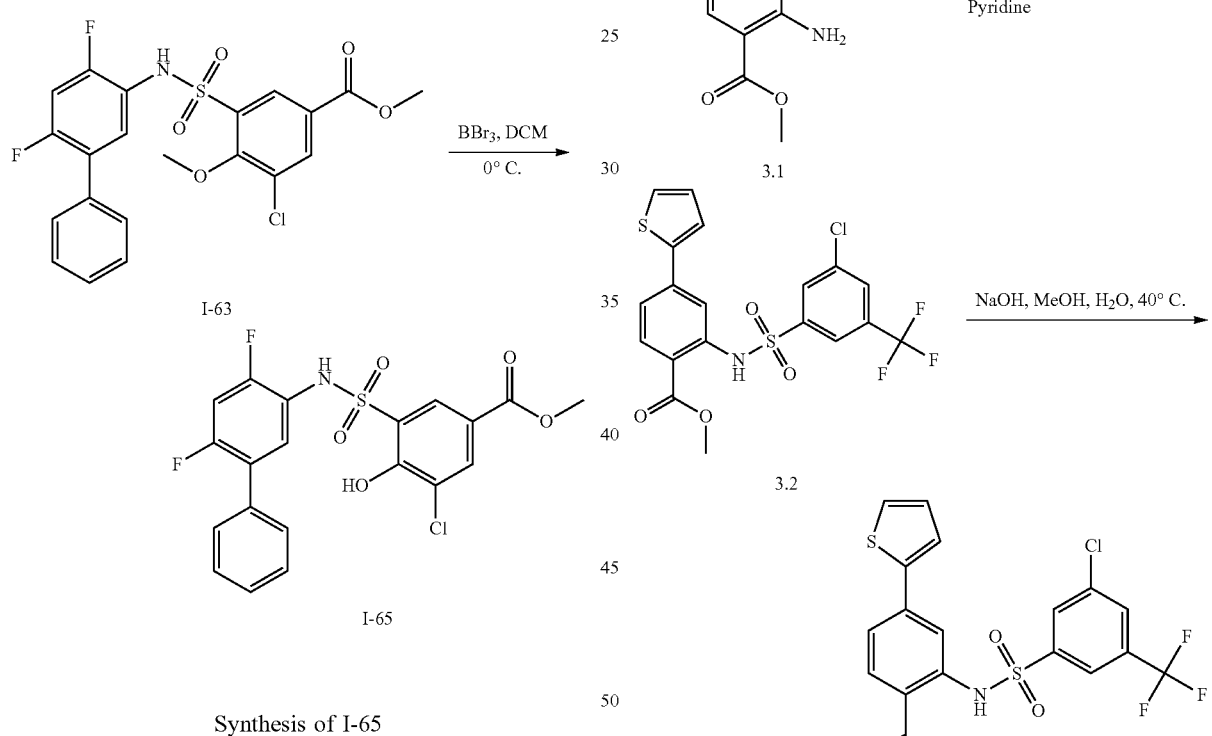

Synthesis of I-65

Into a 25 mL round bottom flask, were added methyl I-63 (134 mg, 0.29 mmol, 1 equiv) and BBr$_3$ (215.3 mg, 0.86 mmol, 3 equiv) and DCM (10 mL). The resulting mixture was stirred for 12 h at 0° C. under nitrogen atmosphere. The reaction solution was quenched by sat. NaHCO$_3$ (aq.) at 0° C. The resulting solution was extracted with EtOAc (2×100 mL), and the combined organic layers were concentrated under vacuum. The residue was purified by Prep-TLC (CH$_2$Cl$_2$/MeOH=20:1) to afford I-65 (60.5 mg, 46.54%) as a white solid. (ES, m/z): [M–H]$^-$ 452.2, $^1$H-NMR (300 MHz, DMSO-d$_6$, ppm): δ7.87 (d, J=2.4 Hz, 1H), δ7.79 (d, J=2.4 Hz, 1H), δ7.46-7.38 (m, 3H), δ7.36-7.31 (m, 3H), δ7.28-7.25 (m, 1H), δ7.08 (s, 1H), δ6.91 (s, 1H), δ3.69 (s, 3H).

Example 3. Synthesis of 2-((3-chloro-5-(trifluoromethyl)phenyl)sulfonamido)-4-(thiophen-2-yl)benzoic Acid, I-366

Synthesis of Compound 3.1

Into a 100-mL round-bottom flask, was placed methyl 2-amino-4-bromobenzoate (500 mg, 2.173 mmol, 1 equiv), dioxane (5 mL), H$_2$O (5 mL), (thiophen-2-yl)boronic acid (417.12 mg, 3.260 mmol, 1.5 equiv), K$_2$CO$_3$ (901.10 mg, 6.520 mmol, 3 equiv), Pd(dppf)Cl$_2$ (159.02 mg, 0.217 mmol, 0.1 equiv). The resulting solution was stirred for 12 h at 85° C. The resulting mixture was concentrated under vacuum. The residue was applied onto a silica gel column with ethyl acetate/petroleum ether (10:1). This resulted in 300 mg (59%) of 3.1 as a light yellow solid. (ES, m/z): [M+H]+ 234.1

Synthesis of Compound 3.2

Into a 100-mL round-bottom flask, was placed 3.1 (150 mg, 0.643 mmol, 1 equiv), 3-chloro-5-(trifluoromethyl)benzene-1-sulfonyl chloride (179.42 mg, 0.643 mmol, 1.00 equiv), Py (6 mL). The resulting solution was stirred for 12 h at 25° C. The resulting mixture was concentrated under vacuum. The residue was applied onto Prep-TLC with ethyl acetate/petroleum ether (2:1). This resulted in 90 mg (29%) of 3.2 as a white solid. (ES, m/z): [M−H]− 474.2

Synthesis of I-366

Into a 100-mL round-bottom flask, was placed 3.2 (80 mg, 0.168 mmol, 1 equiv), H$_2$O (3 mL), MeOH (3 mL), NaOH (67.24 mg, 1.681 mmol, 10.00 equiv). The resulting solution was stirred for 12 h at 25° C. The reaction was then quenched by the addition of 10 mL of diluted hydrochloric acid. The resulting solution was extracted with 3×15 mL of ethyl acetate and the organic layers combined. The crude product was purified by Flash-Prep-HPLC with the following conditions (IntelFlash-1): Column, C18; mobile phase, ACN:H$_2$O=15% increasing to ACN:H$_2$O=60% within 15 min. This resulted in 6.3 mg (8%) of I-366 as a white solid. (ES, m/z): [M−H]− 459.9, $^1$H-NMR (400 MHz, DMSO-d$_6$, ppm): δ8.11 (d, J=14.4 Hz, 2H), 8.00 (s, 1H), 7.87 (d, J=8.4 Hz, 1H), 7.65 (d, J=4 Hz, 1H), 7.53-7.49 (m, 2H), 7.30-7.09 (m, 3H), 6.96 (s, 1H).

The compounds of Table 1 were synthesized in a manner analogous to the procedures set out in Examples 1-3.

Example 4. Synthesis of 2-[3-chloro-4-methoxy-5-[(2-methoxy-5-phenylphenyl)sulfamoyl]phenyl]acetic Acid, I-439

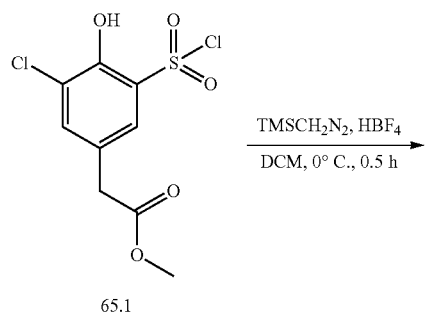

65.1

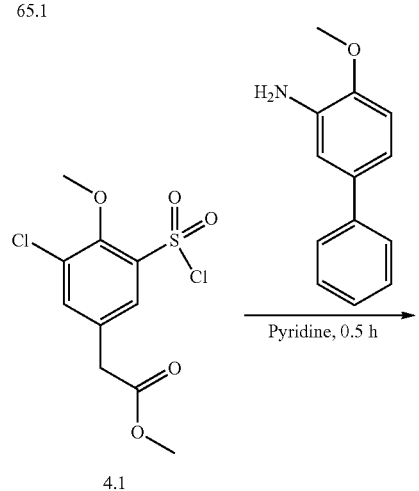

4.1

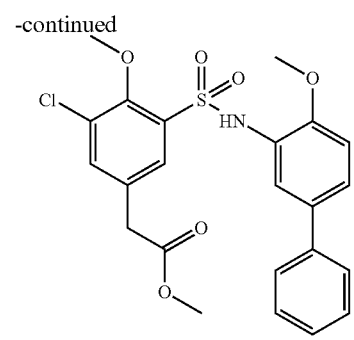

4.2

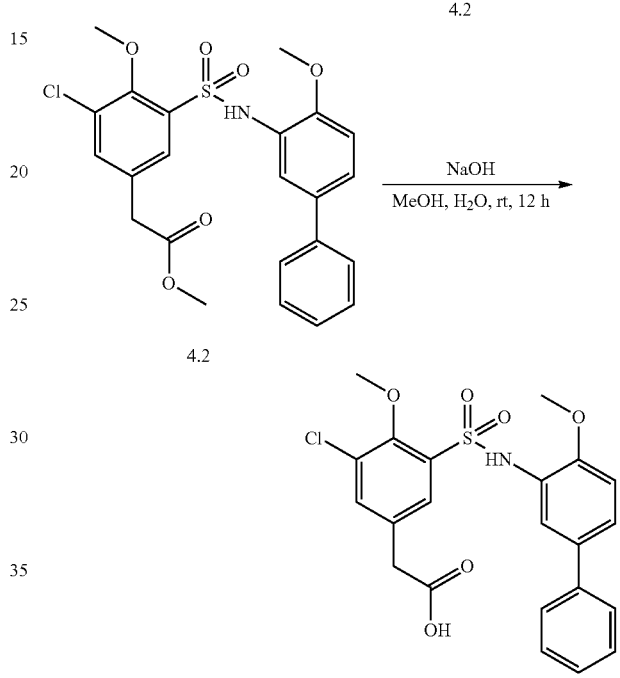

I-439

Synthesis of Compound 4.1

Into a 100-mL round-bottom flask purged and maintained with an inert atmosphere of nitrogen, was placed 65.1 (500 mg, 1.67 mmol, 1 equiv), HBF$_4$ (293.6 mg, 3.34 mmol, 2 equiv), DCM (10 mL), TMSCH$_2$N$_2$ (3.345 mL, 2M, 6.689 mmol, 4 equiv). The resulting solution was stirred for 0.5 h at 0° C. in a water/ice bath. The resulting solution was diluted was 5 mL of water and extracted with 3×10 mL of dichloromethane. The organic extracts was washed with 10 mL of brine, dried over anhydrous sodium sulfate and concentrated under vacuum. The residue was applied onto a silica gel column with ethyl acetate/petroleum ether (1:3). This resulted in 150 mg (28.66%) of 4.1 as a white solid. (ES, m/z): [M−H]− 310.9.

Synthesis of Compound 4.2

Into a 100-mL round-bottom flask purged and maintained with an inert atmosphere of nitrogen, was placed 4.1 (150 mg, 0.48 mmol, 1 equiv), 2-methoxy-5-phenylaniline (114.5 mg, 0.57 mmol, 1.2 equiv), Pyridine (5 mL). The resulting solution was stirred for 0.5 h at room temperature. The reaction mixture was concentrated, and the residue was applied onto a silica gel column with ethyl acetate/petroleum ether (1:1). This resulted in 100 mg (43.86%) of 4.2 as a white solid. (ES, m/z): [M−H]⁻ 474.0.

Synthesis of I-439

Into a 100-mL round-bottom flask purged and maintained with an inert atmosphere of nitrogen, was placed 4.2 (100 mg, 0.21 mmol, 1 equiv), NaOH (16.8 mg, 0.42 mmol, 1.999 equiv), MeOH (4 mL), H$_2$O (1 mL). The resulting solution was stirred for 2 h at room temperature. The pH value of the solution was adjusted to 7 with 1M HCl. The resulting solution was extracted with 3×10 mL of ethyl acetate. The combined organic layers were dried over anhydrous sodium sulfate and concentrated under vacuum. This resulted in 66.3 mg (68.31%) of I-439 as a white solid. (ES, m/z): [M+H]⁺ 462.2, ¹H-NMR (400 MHz, DMSO-d$_6$, ppm): δ3.57 (s, 3H), δ3.65 (s, 2H), δ3.92 (s, 3H), δ6.68 (d, J=2.4 Hz, 1H), δ7.00 (d, J=2.4 Hz, 1H), δ7.30-7.33 (m, 1H), δ7.41-7.45 (m, 4H), δ7.49-7.51 (m, 2H), δ7.61 (d, J=2.4 Hz, 1H), δ9.40 (s, 1H), δ12.41 (s, 1H).

Example 5. Synthesis of N-[2,4-dichloro-6-[(2-methoxy-5-phenylphenyl) sulfamoyl]phenyl]propanamide, I-440

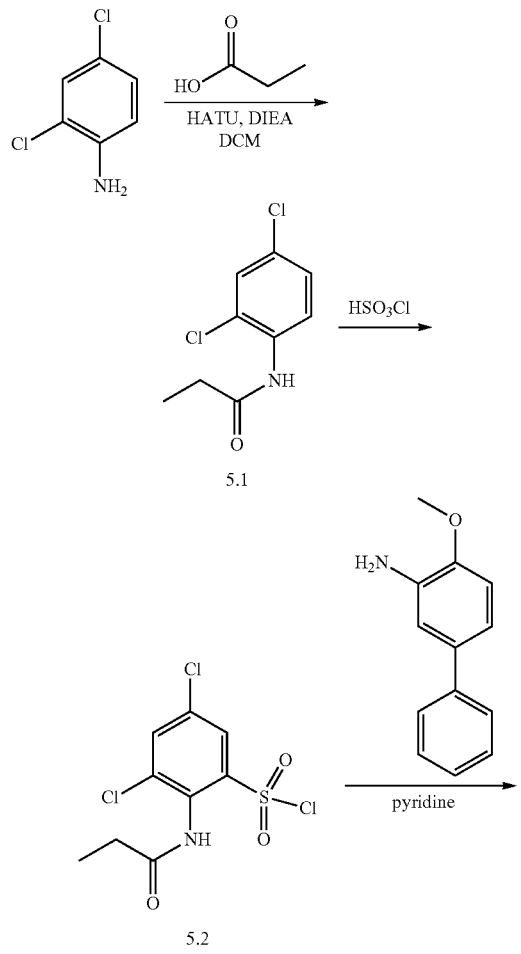

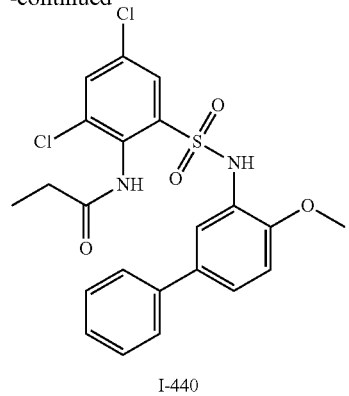

Synthesis of Compound 5.1

Into a 25-mL 3-necked round-bottom flask purged and maintained with an inert atmosphere of nitrogen, was placed 2,4-dichloroaniline (1 g, 6.17 mmol, 1 equiv), DCM (15 mL), propionic acid (0.5 g, 6.75 mmol, 1 equiv), DIEA (1.6 g, 12.34 mmol, 2 equiv), HATU (2.8 g, 7.40 mmol, 1.2 equiv). The resulting solution was stirred for 12 h at room temperature. The reaction mixture was then quenched by the addition of 20 mL of water and extracted with ethyl acetate (3×20 mL). The combined organic layers were concentrated under vacuum. The residue was applied onto a silica gel column with dichloromethane/methanol (80:1). This resulted in 1.05 g (78.01%) of 5.1 as a white solid.

Synthesis of Compound 5.2

Into a 25-mL 3-necked round-bottom flask purged and maintained with an inert atmosphere of nitrogen, was placed 353.1 (1.03 g, 4.72 mmol, 1 equiv), sulfonoperoxoyl chloride (10 mL). The resulting solution was stirred for 12 h at room temperature. The reaction was then quenched by the addition of 40 mL of water/ice. The resulting solution was extracted with ethyl acetate (3×20 mL) and the combined organic layers were concentrated under vacuum. This resulted in 1.25 g (crude) of 5.2 as a grey solid.

Synthesis of I-440

Into a 50-mL 3-necked round-bottom flask purged and maintained with an inert atmosphere of nitrogen, was placed 5.2 (1.25 g, 3.95 mmol, 1 equiv, crude), pyridine (15 mL), 2-methoxy-5-phenylaniline (0.9 g, 4.74 mmol, 1.2 equiv). The resulting solution was stirred for 4 h at room temperature and then concentrated under vacuum. The residue was applied onto a silica gel column with dichloromethane/methanol (60:1). The crude product was purified by Prep-HPLC with the following conditions: Column, XBridge Prep OBD C18 Column 30*150 mm 5 um; Mobile Phase A: water (10 mmol/L NH$_4$HCO$_3$), Mobile Phase B: ACN; Flow rate: 60 mL/min; Gradient: 55% B to 55% B in 10 min; Detector UV 254/220 nm, Rt: 8.47 min. This resulted in 28.4 mg (66.08%) of I-440 as a white solid. (ES, m/z): [M−H]⁻ 477.0, ¹H-NMR (300 MHz, DMSO-d$_6$, ppm): δ1.05 (t, J=7.5 Hz, 3H), δ2.36-2.44 (m, 2H), δ3.59 (s, 3H), δ7.03 (d, J=8.4 Hz, 1H), δ7.29-7.34 (m, 1H), δ7.34-7.46 (m, 4H), δ7.50-7.53 (m, 2H), δ7.92 (s, 1H), δ8.37 (s, 1H), δ9.68 (s, 1H), δ9.84 (s, 1H).

Example 6. Synthesis of 2-methoxy-N-(2-methoxy-5-phenylphenyl)-5-(2H-1,2,3,4-tetrazol-5-yl)benzene-1-sulfonamide, I-442

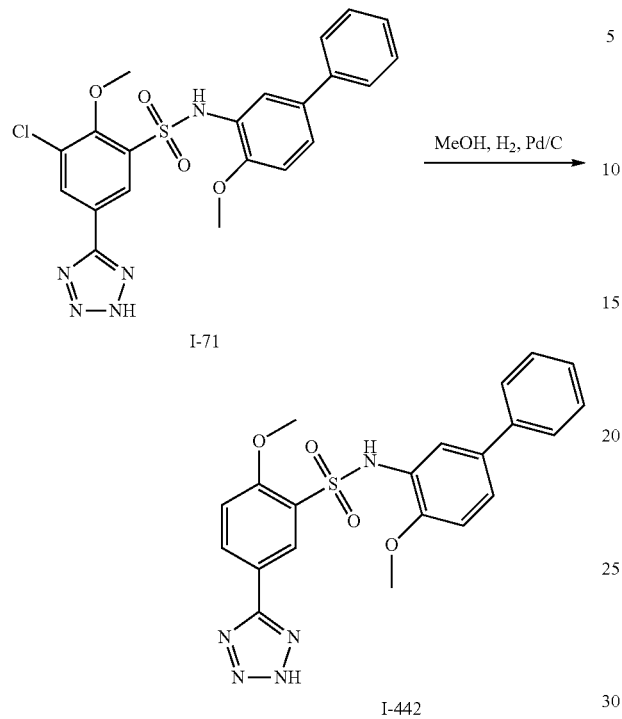

Synthesis of I-442

Into a 25-mL round-bottom flask, was placed I-71 (28.9 mg, 0.06 mmol, 1 equiv), MeOH (10 mL), Pd/C (10 mg). The flask was evacuated and flushed three times with nitrogen, followed by flushing with hydrogen. The mixture was stirred 2 days at room temperature under an atmosphere of hydrogen (balloon). The solids were filtered out. The resulting mixture was concentrated under vacuum. The crude product was purified by Flash-Prep-HPLC with the following conditions (IntelFlash-1): Column, C18; mobile phase, ACN/H$_2$O=15% increasing to ACN/H$_2$O=60% within 15 min; Detector, UV 254 nm. This resulted in 5.4 mg (20%) of I-442 as a white solid. (ES, m/z): [M−H]$^-$ 436.1, $^1$H-NMR (300 MHz, DMSO-d$_6$, ppm): δ3.66 (s, 3H), δ3.97 (s, 3H), δ6.99-7.02 (d, J=8.4 Hz, 1H), δ7.29-7.40 (m, 5H), δ7.43-7.47 (m, 3H), δ7.51-7.52 (d, J=2.1 Hz, 1H), δ 8.20-8.24 (m, 1H), δ8.38-8.39 (d, J=2.4 Hz, 1H), δ9.07 (s, 1H).

Example 7. Synthesis of 3,5-dichloro-N-(4-fluoro-[1,1'-biphenyl]-3-yl)-2-((1-methyl-1H-pyrazol-3-yl)oxy)benzenesulfonamide, I-443

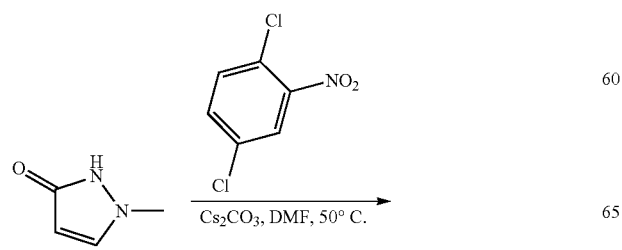

-continued

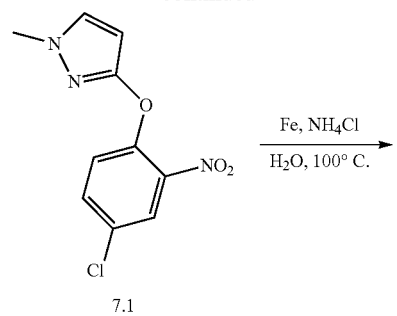

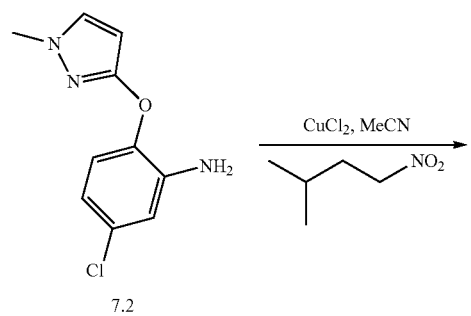

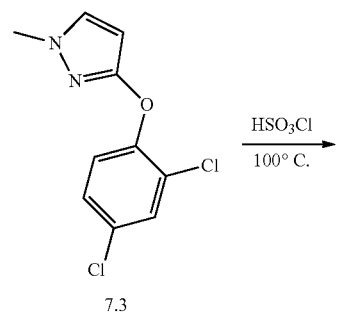

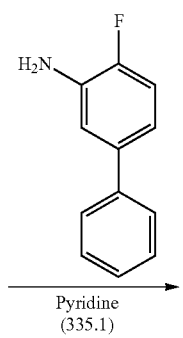

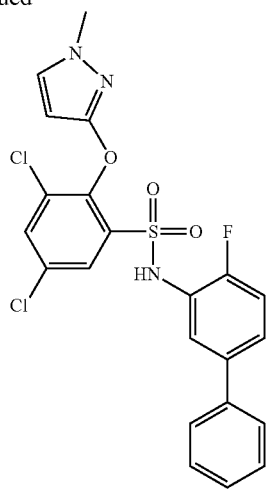

I-443

Synthesis of Compound 7.1

To a stirred mixture of 1-methyl-2,3-dihydro-1H-pyrazol-3-one (5 g, 50.97 mmol, 1 equiv) and 1,4-dichloro-2-nitrobenzene (10.76 g, 56.06 mmol, 1.1 equiv) in DMF (50 mL) were added $Cs_2CO_3$ (33.21 g, 101.93 mmol, 2 equiv) at 50° C. under nitrogen atmosphere. The resulting solution was stirred for 12 h. The resulting mixture was diluted with 50 mL of water. The resulting mixture was extracted with EtOAc (2×30 mL) and the combined organic layers were concentrated under reduced pressure. The residue was purified by silica gel column chromatography, eluted with PE/EtOAc (10:1) to afford 7.1 (13.2 g, 78.90%) as a yellow oil.

Synthesis of Compound 7.2

To a stirred solution of 7.1 (13 g, 51.25 mmol, 1 equiv) in water (100 mL) were added $NH_4Cl$ (13.71 mg, 256.27 mmol, 5 equiv) and Fe (8.59 mg, 153.76 mmol, 3 equiv) at 100° C. under nitrogen atmosphere. The resulting solution was stirred for 12 h. The resulting mixture was extracted with EtOAc (2×100 mL). The combined organic layers were concentrated under reduced pressure. The residue was purified by silica gel column chromatography, eluted with PE/EtOAc (10:1) to afford 7.2 (10.8 g, 94.21%) as a yellow oil.

Synthesis of Compound 7.3

To a stirred mixture of 7.2 (5 g, 22.36 mmol, 1 equiv) and 3-methyl-1-nitrobutane (3.143 g, 26.83 mmol, 1.2 equiv) in MeCN (50 mL) were added $CuCl_2$ (3.607 g, 26.83 mmol, 1.20 equiv) at room temperature under nitrogen atmosphere. The resulting solution was stirred for 12 h. The reaction was quenched by the addition of 50 mL of sat. $NaHCO_3$ (aq.). The resulting mixture was extracted with EtOAc (2×30 mL). The combined organic layers were concentrated under reduced pressure. The residue was purified by silica gel column chromatography, eluted with PE/EtOAc (10:1) to afford 7.3 (3.85 g, 70.85%) as a yellow oil.

Synthesis of Compound 7.4

Into a 250 mL 3-necked round-bottom flask were added 355.3 (1 g, 4.11 mmol, 1 equiv) and $HSO_3Cl$ (5.8 g, 49.36 mmol, 12 equiv) at 0° C. The temperature was up to 100° C. The resulting solution was stirred for 2 h. The reaction was quenched by the addition of water/ice (20 mL). The resulting mixture was extracted with EtOAc (2×15 mL). The combined organic layers were concentrated under reduced pressure. This resulted in 1.035 g (73.66%) of 7.4 as a brown solid.

Synthesis of I-443

To a stirred solution of 335.1 (394.6 mg, 2.11 mmol, 1.2 equiv) in pyridine (10 mL) were added 7.4 (600 mg, 1.76 mmol, 1 equiv) at room temperature under nitrogen atmosphere. The resulting mixture was stirred for 0.5 h. The resulting mixture was concentrated under reduced pressure. The residue was purified by Prep-TLC (hexane/EtOAc=2:1) to afford I-443 (184 mg, 21.28%) as a white solid (ES, m/z): $[M+H]^+$ 491.9, $^1$H-NMR (300 MHz, $CDCl_3$, ppm): δ3.57 (s, 3H), δ7.06-7.08 (m, 2H), δ7.11-7.17 (m, 1H), δ7.19-7.23 (m, 1H), δ7.26-7.33 (m, 1H), δ7.36-7.45 (m, 4H), δ7.50-7.53 (m, 2H), δ7.65 (s, 1H), δ7.85-7.88 (m, 1H).

Example 8. Synthesis of 3,5-dichloro-2-hydroxy-N-(4-methoxy-[1,1'-biphenyl]-3-yl)-6-methylbenzene-sulfonamide, I-1

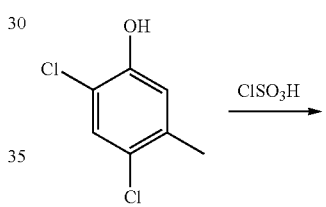

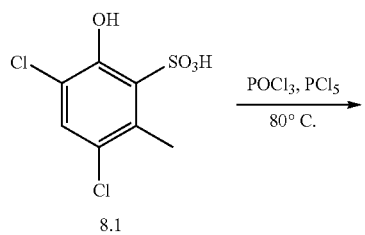

8.1

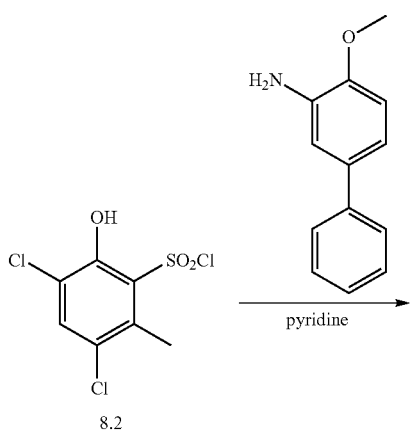

8.2

-continued

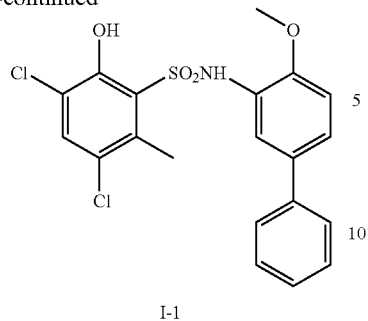

I-1

Synthesis of Compound 8.1

Into a 25-mL 3-necked round-bottom flask purged and maintained with an inert atmosphere of nitrogen, was placed 2,4-dichloro-5-methylphenol (500 mg, 2.82 mmol, 1.00 equiv), O-(chlorosulfonyl)oxidanol (5 mL). The resulting solution was stirred overnight at room temperature. The reaction was then quenched by the addition of 20 mL of water/ice. The solids were collected by filtration. This resulted in 600 mg (83%) of 8.1 as a white solid.

Synthesis of Compound 8.2

Into a 8-mL sealed tube purged and maintained with an inert atmosphere of nitrogen, was placed 8.1 (200 mg, 0.78 mmol, 1.00 equiv), $POCl_3$ (2 mL), $PCl_5$ (321.9 mg, 1.55 mmol, 2.00 equiv). The resulting solution was stirred for 4 h at 80° C. The resulting mixture was concentrated under vacuum. This resulted in 180 mg (84%) of 8.2 as a white solid.

Synthesis of I-1

Into a 8-mL sealed tube purged and maintained with an inert atmosphere of nitrogen, was placed 8.2 (180 mg, 0.65 mmol, 1.00 equiv), pyridine (2 mL), 2-methoxy-5-phenylaniline (143.80 mg, 0.72 mmol, 1.10 equiv). The resulting solution was stirred for 5 h at room temperature. The reaction was then quenched by the addition of 5 mL of water. The resulting solution was extracted with of ethyl acetate and the organic layers combined and concentrated under vacuum. The residue was applied onto a silica gel column with ethyl acetate/petroleum ether (1:5). This resulted in 59.1 mg (21%) of I-1 as a white solid. (ES, m/z): [M−H]⁻ 436.0, ¹H-NMR (400 MHz, $CDCl_3$, ppm): δ2.71 (s, 3H), δ3.83 (s, 3H), δ6.89-6.91 (d, J=8.4 Hz, 1H), δ7.34-7.36 (m, 3H), δ7.42-7.46 (m, 5H), δ7.58 (s, 1H), δ10.42 (br s, 1H).

Example 9. Synthesis of 3-chloro-4-hydroxy-5-(N-(4-methoxy-[1,1'-biphenyl]-3-yl)sulfamoyl)benzoic Acid, I-2

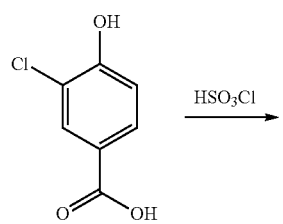

-continued

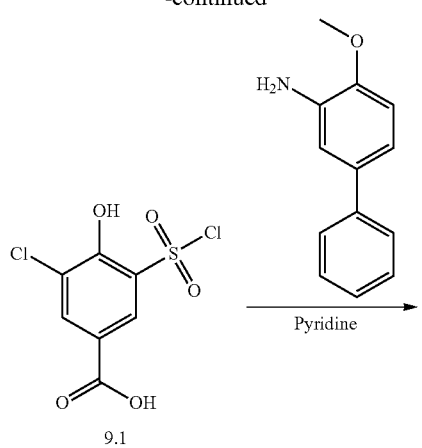

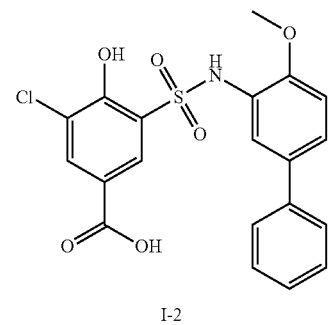

I-2

Synthesis of Compound 9.1

Into a 25-mL round-bottom flask purged and maintained with an inert atmosphere of nitrogen, was placed 3-chloro-4-hydroxybenzoic acid (1000 mg, 5.80 mmol, 1 equiv), sulfurochloridic acid (4051.5 mg, 34.77 mmol, 6.00 equiv). The resulting solution was stirred for 2 hr at 65° C. in an oil bath. The reaction was then quenched by the addition of 10 mL of water/ice. The solids were collected by filtration. This resulted in 1000 mg (64%) of 9.1 as a white solid. (ES, m/z): [M−H]⁻ 268.9

Synthesis of I-2

Into a 25-mL round-bottom flask purged and maintained with an inert atmosphere of nitrogen, was placed 9.1 (500 mg, 1.84 mmol, 1 equiv), 4-methoxy-[1,1-biphenyl]-3-amine (441.1 mg, 2.21 mmol, 1.2 equiv), pyridine (5 mL). The resulting solution was stirred for 2 hr at room temperature. The reaction was then quenched by the addition of 20 mL of HCl (1 N). The resulting solution was extracted with 3×20 ml of ethyl acetate. The resulting mixture was washed with 1×20 ml of brine. The resulting mixture was concentrated. The residue was applied onto a silica gel column with ethyl acetate/petroleum ether (1:1). This resulted in 31.5 mg (4%) of I-2 as a light yellow solid. (ES, m/z): [M+H]⁺ 434.1, ¹H NMR δ 8.22 (s, 2H), 8.04 (s, 1H), 7.61-7.59 (d, J=5.2 Hz, 2H), 7.46-7.39 (m, 3H), 7.31-7.27 (m, 1H), 7.15-7.13 (d, J=8.8 Hz, 1H), 3.96 (s, 3H).

Example 10. Synthesis of 5-chloro-2-hydroxy-3-(N-(4-methoxy-[1,1'-biphenyl]-3-yl) sulfamoyl)benzoic Acid, I-3

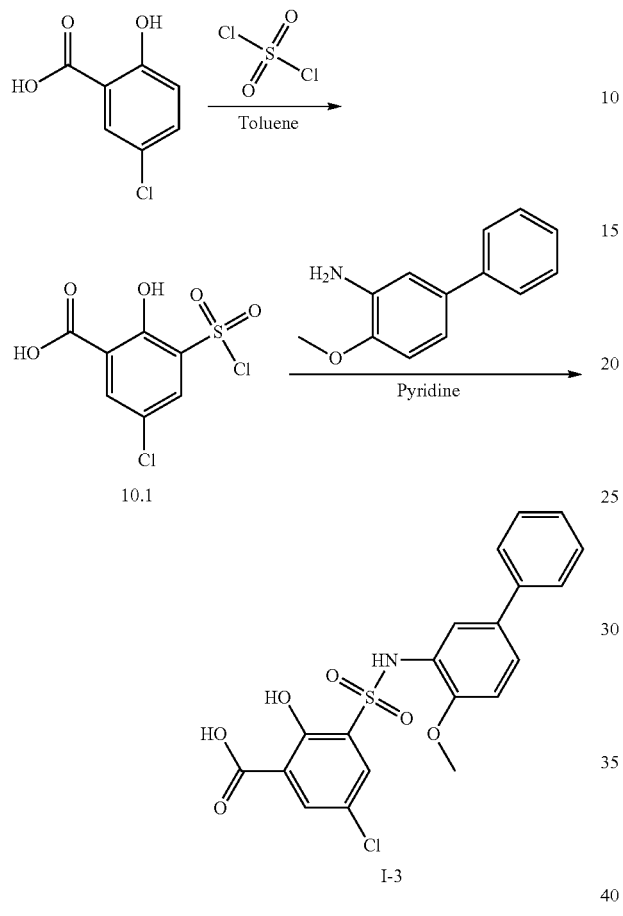

Synthesis of Compound 10.1

Into a 100-mL 3-necked round-bottom flask purged and maintained with an inert atmosphere of nitrogen, was placed 5-chloro-2-hydroxybenzoic acid (1 g, 5.79 mmol, 1.00 equiv), sulfuroyl dichloride (4.1 g, 30.38 mmol, 6.00 equiv), toluene (10 mL). The resulting solution was stirred for 2 h at 65° C. in an oil bath. The reaction was then quenched by the addition of 20 mL of water/ice. The solids were collected by filtration. This resulted in 1 g (64%) of 10.1 as a white solid. (ES, m/z): [M−H]⁻ 268.9

Synthesis of I-3

Into a 50-mL round-bottom flask purged and maintained with an inert atmosphere of nitrogen, was placed 10.1 (200 mg, 0.74 mmol, 1.00 equiv), 2-methoxy-5-phenylaniline (176 mg, 0.88 mmol, 1.20 equiv), pyridine (2 mL). The resulting solution was stirred for 2 h at room temperature. The reaction was then quenched by the addition of 2 mL of 1M HCl (aq.). The resulting solution was extracted with 3×5 mL of ethyl acetate. The organic layers were combined, washed with 5 mL of saturated brine, dried and concentrated under vacuum. The residue was applied onto a silica gel column with ethyl acetate/petroleum ether (1:1). This resulted in 13.7 mg (4%) of I-3 as a white solid. (ES, m/z): [M+H]⁺ 433.9, ¹H-NMR (400 MHz, CD₃OD, ppm): δ8.76-8.75 (d, J=2 Hz, 1H), δ8.18-8.17 (d, J=2.8 Hz, 1H), δ7.84-7.83 (d, J=2.8 Hz, 1H), δ7.63-7.61 (m, 2H), δ7.44-7.38 (m, 3H), δ7.31-7.28 (m, 1H), δ7.15-7.13 (m, 1H), δ4.00 (s, 3H).

Example 11. Synthesis of N-(5-bromo-2-methoxyphenyl)-3,5-dichloro-2-Hydroxybenzenesulfonamide, I-4

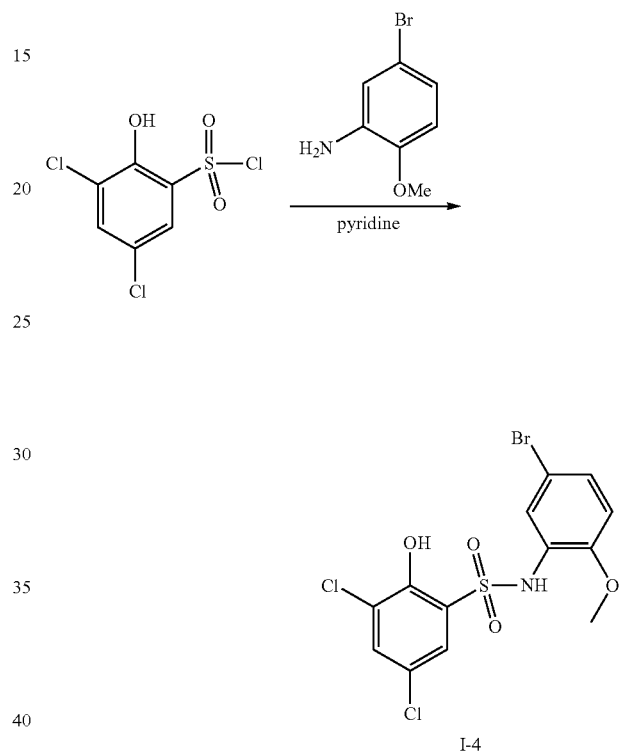

Synthesis of I-4

Into a 100-mL 3-necked round-bottom flask purged and maintained with an inert atmosphere of nitrogen, was placed 3,5-dichloro-2-hydroxybenzene-1-sulfonyl chloride (1 g, 3.82 mmol, 1.00 equiv), 5-bromo-2-methoxyaniline (920 mg, 4.55 mmol, 1.20 equiv), pyridine (13 mL). The resulting solution was stirred for 2 h at 25° C. The reaction was then quenched by the addition of 100 mL of 1 M hydrochloric acid (aq.). The resulting solution was extracted with 3×100 mL of ethyl acetate and the organic layers combined and concentrated under vacuum. The residue was applied onto a silica gel column with dichloromethane/methanol (20:1). The crude product was purified by Flash-Prep-HPLC with the following conditions (IntelFlash-1): Column, C18; mobile phase, H₂O:ACN=15% increasing to H₂O:ACN=60% within 15 min; Detector, UV 254 nm. This resulted in 77.7 mg (5%) of I-4 as a white solid. (ES, m/z): [M−H]⁻ 425.9, ¹H-NMR (300 MHz, DMSO-d₆, ppm): δ3.59 (s, 3H), δ6.92-6.95 (d, J=8.7 Hz, 1H), δ7.28-7.31 (m, 1H), δ7.36-7.37 (d, J=2.4 Hz, 1H), δ7.49-7.50 (d, J=2.7 Hz, 1H), δ7.80-7.81 (d, J=2.7 Hz, 1H), δ10.33 (br s, 2H).

Example 12. Synthesis of 3,5-dichloro-N-(4,4'-dimethoxy-[1,1'-biphenyl]-3-yl)-2-hydroxybenzenesulfonamide, I-5

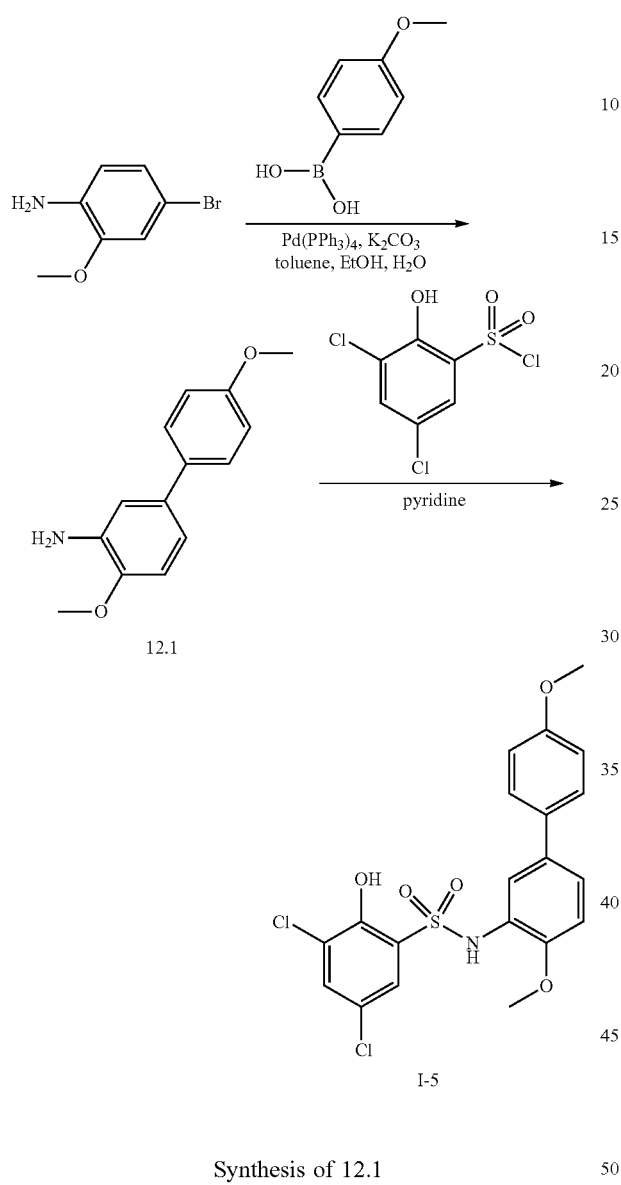

Synthesis of 12.1

Into a 50-mL 3-necked round-bottom flask purged and maintained with an inert atmosphere of nitrogen, was placed 4-bromo-2-methoxyaniline (1 g, 4.95 mmol, 1 equiv), toluene (5 mL), EtOH (5 mL), H$_2$O (5 mL), K$_2$CO$_3$ (2.1 g, 15.1 mmol, 3 equiv), (4-methoxyphenyl)boronic acid (1.1 g, 7.24 mmol, 1.5 equiv), Pd(PPh$_3$)$_4$ (0.6 g, 0.495 mmol, 0.1 equiv). The reaction solution was stirred for 12 h at 80° C., and concentrated under vacuum. The residue was applied onto a silica gel column with ethyl acetate/petroleum ether (1:20). This resulted in 500 mg (44.06%) of 12.1 as a yellow solid.

Synthesis of Compound I-5

Into a 8-mL vial purged and maintained with an inert atmosphere of nitrogen, a stirred solution of 12.1 (300 mg, 1.31 mmol, 1 equiv) in pyridine (5 mL) was placed 3,5-dichloro-2-hydroxybenzene-1-sulfonyl chloride (308 mg, 1.18 mmol, 0.9 equiv) at room temperature. After 2 h, the resulting mixture was concentrated under vacuum. The residue was applied onto a silica gel column with dichloromethane/methanol (30:1). This resulted in 68.4 mg (11.51%) of I-5 as a white solid. (ES, m/z): [M+H]$^+$ 453.9, $^1$H-NMR (300 MHz, DMSO-d$_6$, ppm): δ3.62 (s, 3H), δ3.79 (s, 3H), δ6.98-7.02 (m, 3H), δ7.37-7.42 (m, 4H), δ7.53-7.54 (d, J=2.4 Hz, 1H), δ7.83-7.84 (d, J=2.4 Hz, 1H), δ9.41 (br s, 1H), δ10.95 (br s, 1H).

Example 13. Synthesis of 3,5-dichloro-N-(4'-fluoro-4-methoxy-[1,1'-biphenyl]-3-yl)-2-hydroxybenzenesulfonamide, I-6

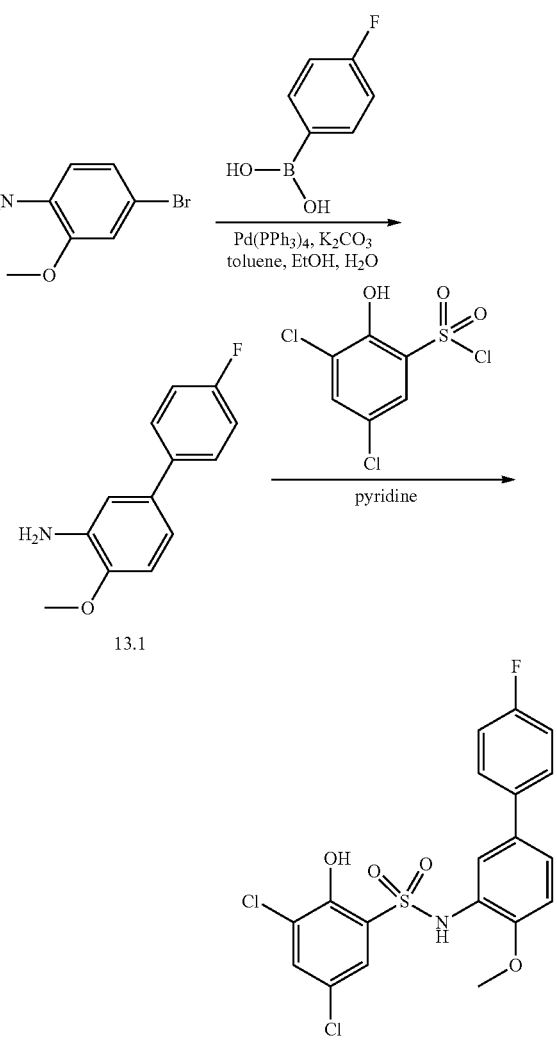

Synthesis of 13.1

Into a 100-mL 3-necked round-bottom flask purged and maintained with an inert atmosphere of nitrogen, was placed 2-bromo-5-methoxyaniline (1 g, 4.95 mmol, 1.00 equiv), toluene (5 mL), EtOH (5 mL), water (5 mL), (4-fluorophenyl)boronic acid (836 mg, 5.97 mmol, 1.20 equiv), potassium carbonate (3.43 g, 24.82 mmol, 5.00 equiv), Pd(PPh$_3$)$_4$ (1.14 g, 0.99 mmol, 0.20 equiv). The reaction solution was stirred for 12 h at 80° C. and concentrated under vacuum. The residue was applied onto a silica gel column with ethyl acetate/petroleum ether (10:1). This resulted in 510 mg (47%) of 13.1 as a white solid.

Synthesis of I-6

Into a 25-mL round-bottom flask purged and maintained with an inert atmosphere of $N_2$, was placed 13.1 (510 mg, 2.35 mmol, 1 equiv), 3,5-dichloro-2-hydroxybenzene-1-sulfonyl chloride (552.5 mg, 2.11 mmol, 0.9 equiv), pyridine (10 mL) at room temperature. After stirring for 2 h, the resulting mixture was concentrated under vacuum. The residue was applied onto a silica gel column with dichloromethane/methanol (20:1). This resulted in 145.6 mg (14.02%) of I-6 as a white solid. (ES, m/z): [M−H]⁻ 439.9, ¹H-NMR (300 MHz, DMSO-$d_6$, ppm): δ3.69 (s, 3H), δ7.01-7.04 (d, J=5.4 Hz, 1H), δ7.23-7.34 (m, 3H), δ7.39-7.40 (d, J=2.7 Hz, 1H), δ7.51-7.57 (m, 4H).

Example 14. Synthesis of 3,5-dichloro-2-hydroxy-N-(2-methoxy-5-(pyridin-3-yl) phenyl)benzene-sulfonamide, I-7

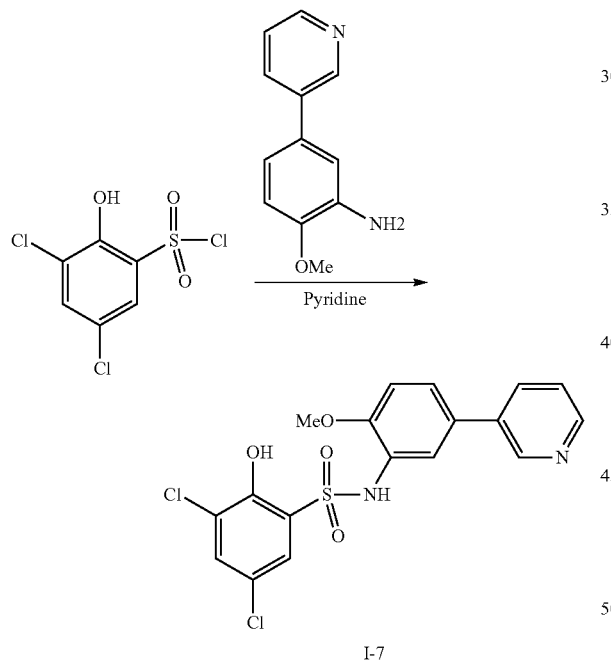

I-7

Synthesis of Compound I-12

Into a 100-mL 3-necked round-bottom flask purged and maintained with an inert atmosphere of nitrogen, was placed 3,5-dichloro-2-hydroxybenzene-1-sulfonyl chloride (300 mg, 1.15 mmol, 1.00 equiv), 2-methoxy-5-(pyridin-3-yl) aniline (277 mg, 1.38 mmol, 1.20 equiv), pyridine (5 mL). The resulting solution was stirred for 2 h at 25° C. The resulting mixture was concentrated under vacuum. The residue was applied onto Prep-TLC with dichloromethane/methanol (20:1). The crude product was purified by Flash-Prep-HPLC with the following conditions (IntelFlash-1): Column, C18; mobile phase, $H_2O$:ACN=10% increasing to $H_2O$:ACN=60% within 15 min; Detector, UV 254 nm. This resulted in 88.5 mg (18%) of I-12 as a white solid. (ES, m/z): [M−H]⁻ 423.0, ¹H-NMR (300 MHz, DMSO-$d_6$, ppm): δ3.68 (s, 3H), δ7.02-7.10 (m, 1H), δ7.44-7.48 (m, 3H), δ7.57-7.58 (d, J=2.1 Hz, 1H), δ7.66-7.67 (d, J=2.7 Hz, 1H), δ7.91-7.94 (m, 1H), δ8.53-8.54 (d, J=3.9 Hz, 1H), δ8.75-8.76 (d, J=1.5 Hz, 1H).

Example 15. Synthesis of N-(3-((3,5-dichloro-2-hydroxyphenyl)sulfonamido)-4-methoxyphenyl) cyclopropanecarboxamide, I-8

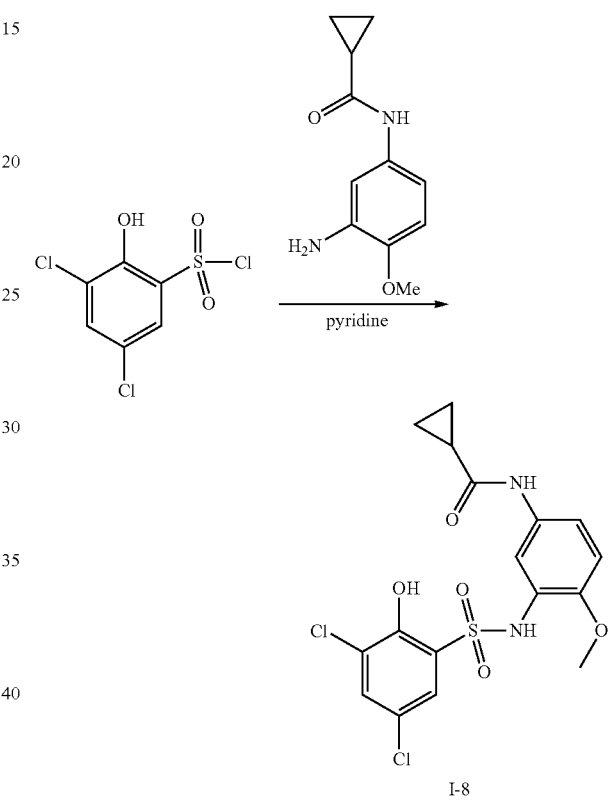

I-8

Synthesis of I-8

Into a 100-mL 3-necked round-bottom flask purged and maintained with an inert atmosphere of nitrogen, was placed 3,5-dichloro-2-hydroxybenzene-1-sulfonyl chloride (421 mg, 1.61 mmol, 1.00 equiv), N-(2-amino-4-methoxyphenyl) cyclopropanecarboxamide (400 mg, 1.94 mmol, 1.20 equiv), pyridine (10 mL). The resulting solution was stirred for 20 min at 25° C. The reaction was then quenched by the addition of 100 mL of 1 M hydrochloric acid (aq.). The resulting solution was extracted with 3×200 mL of ethyl acetate and the organic layers combined and concentrated under vacuum. The residue was applied onto a silica gel column with dichloromethane/methanol (20:1). The crude product was purified by Flash-Prep-HPLC with the following conditions (IntelFlash-1): Column, C18; mobile phase, $H_2O$:ACN=10% increasing to $H_2O$:ACN=60% within 15 min; Detector, UV 254 nm. This resulted in 84.5 mg (12%) of I-8 as a white solid. (ES, m/z): [M+H]⁺ 431.1, ¹H-NMR (300 MHz, DMSO-$d_6$, ppm): δ0.72-0.78 (m, 4H), δ1.68-1.77 (m, 1H), δ3.59 (s, 3H), δ6.85-6.88 (d, J=12 Hz, 1H), δ7.35-7.39 (m, 1H), δ7.43-7.44 (d, J=2.7 Hz, 1H), δ7.56-7.57 (d, J=2.7 Hz, 1H), δ7.66-7.67 (d, J=2.1 Hz, 1H), δ10.06 (s, 1H).

Example 16. Synthesis of 3,5-dichloro-2-hydroxy-N-(2-methoxy-5-(thiophen-2-yl) phenyl)benzenesulfonamide, I-9

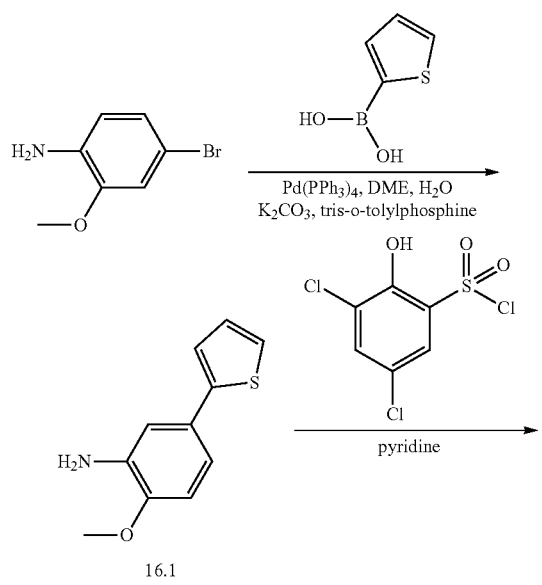

16.1

I-9

Synthesis of Compound 16.1

Into a 50-mL vial purged and maintained with an inert atmosphere of nitrogen, was placed 4-bromo-2-methoxybenamine (1 g, 4.95 mmol, 1 equiv), thiophen-2-ylboronic acid (0.95 g, 7.42 mmol, 1.5 equiv), DME (2 mL), H₂O (1 mL), K₂CO₃ (2.05 g, 14.85 mmol, 3 equiv), Pd(PPh₃)₄ (0.6 g, 0.495 mmol, 0.1 equiv), tris-o-tolylphosphine (1.5 g, 4.95 mmol, 1 equiv). The reaction solution was stirred for 2 h at room temperature and concentrated under vacuum. The residue was applied onto a silica gel column with dichloromethane/methanol (20:1). This resulted in 600 mg (59.11%) of 16.1 as a yellow solid.

Synthesis of Compound I-9

Into a 8-mL vial purged and maintained with an inert atmosphere of nitrogen, was placed 16.1 (100 mg, 0.49 mmol, 1 equiv), 3,5-dichloro-2-hydroxybenzene-1-sulfonyl chloride (114.7 mg, 0.44 mmol, 0.9 equiv), pyridine (2 mL). The resulting solution was stirred for 2 h at room temperature. The reaction was then quenched by the addition of 5 mL of 1M HCl. The resulting solution was extracted with 3×5 mL of ethyl acetate and the combined organic layers were concentrated under vacuum. The residue was applied onto a silica gel column with dichloromethane/methanol (20:1). This resulted in 17.3 mg (8.25%) of I-9 as a white solid. (ES, m/z): [M–H]⁻ 427.9, ¹H-NMR (400 MHz, CDCl₃, ppm): δ3.80 (s, 3H), δ6.80-6.82 (d, J=8.4 Hz, 1H), δ7.09-7.10 (d, J=3.9 Hz, 1H), δ7.24-7.25 (d, J=3.2 Hz, 2H), δ7.39-7.44 (m, 1H), δ7.51-7.54 (d, J=11.6 Hz, 2H), δ7.70 (s, 1H).

Example 17. Synthesis of 3,5-dichloro-2-hydroxy-N-(2-methoxy-5-(piperidin-1-yl) phenyl)benzenesulfonamide, I-10

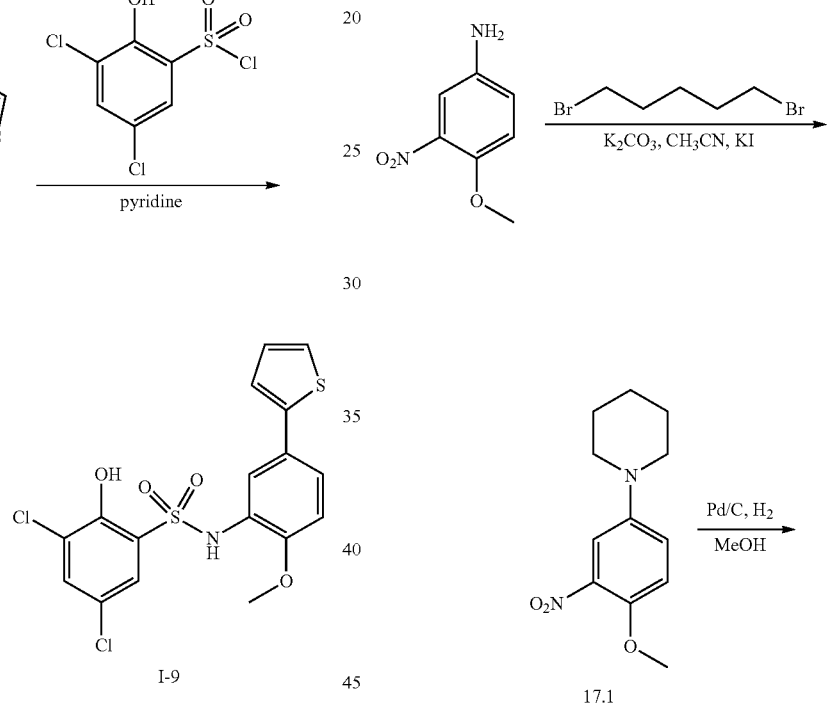

17.1

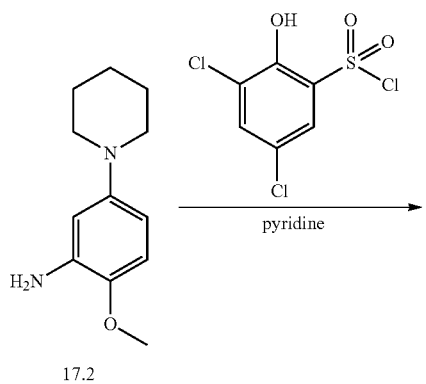

17.2

-continued

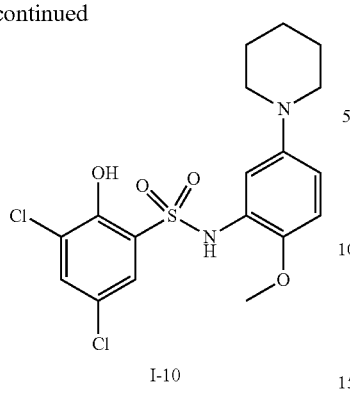

I-10

Synthesis of Compound 17.1

Into a 25-mL 3-necked round-bottom flask purged and maintained with an inert atmosphere of nitrogen, was placed 4-methoxy-3-nitroaniline (1 g, 5.95 mmol, 1 equiv), $CH_3CN$ (15 mL), KI (2.0 g, 12.05 mmol, 2 equiv), 1,5-dibromopentane (1.4 g, 6.14 mmol, 1 equiv), $K_2CO_3$ (1.6 g, 11.59 mmol, 2 equiv). The resulting solution was stirred for 10 h at 80° C. The resulting mixture was concentrated under vacuum. The residue was applied onto a silica gel column with dichloromethane/methanol (50:1). This resulted in 800 mg (56.94%) of 17.1 as a white solid.

Synthesis of Compound 17.2

Into a 25-mL round-bottom flask, was placed 17.1 (400 mg, 1.69 mmol, 1 equiv), MeOH (5 mL). This was followed by the addition of Pd/C (80 mg). To the above $H_2$ (g) was introduced in. The resulting solution was stirred for 12 h at room temperature. The solids were filtered out. The residue was concentrated under vacuum, and purified by a silica gel column with dichloromethane/methanol (80:1). This resulted in 320 mg (91.63%) of 17.2 as a white solid.

Synthesis of I-10

Into a 8-mL vial purged and maintained with an inert atmosphere of nitrogen, was placed 17.2 (320 mg, 1.55 mmol, 1 equiv), 3,5-dichloro-2-hydroxybenzene-1-sulfonyl chloride (365.1 mg, 1.40 mmol, 0.9 equiv), pyridine (5 mL). After stirring for 4 h at room temperature, the resulting mixture was concentrated under vacuum. The residue was applied onto a silica gel column with dichloromethane/methanol (50:1). The crude product was purified by Flash-Prep-HPLC with the following conditions (IntelFlash-1): Column, C18; mobile phase, $CH_3CN/H_2O$ ($NH_4HCO_3$)=1:10 increasing to $CH_3CN/H_2O$ ($NH_4HCO_3$)=19:3 within 40; Detector, UV 254 nm. This resulted in 78.4 mg (11.72%) of I-10 as a white solid. (ES, m/z): [M–H]⁻ 429.1, ¹H-NMR (300 MHz, $CDCl_3$, ppm): δ1.52-1.59 (m, 2H), δ1.67-1.75 (m, 4H), δ3.01-3.04 (t, J=5.4 Hz, 4H), δ3.61 (s, 3H), δ6.66-6.73 (m, 2H), δ7.04-7.05 (d, J=2.4 Hz, 1H), δ7.43-7.46 (m, 2H).

Example 18. Synthesis of N-(4-bromo-2-methoxyphenyl)-3,5-dichloro-2-hydroxybenzenesulfonamide, I-11

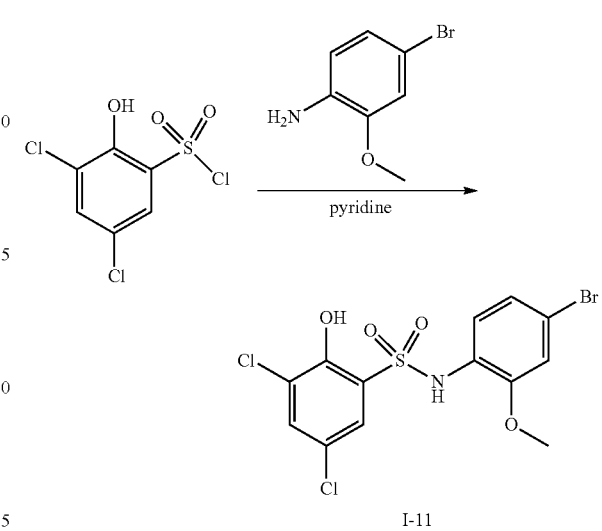

I-11

Synthesis of Compound I-11

Into a 25-mL round-bottom flask purged and maintained with an inert atmosphere of nitrogen, was placed 3,5-dichloro-2-hydroxybenzene-1-sulfonyl chloride (500 mg, 1.91 mmol, 1 equiv), 4-bromo-2-methoxyaniline (463.6 mg, 2.29 mmol, 1.2 equiv), pyridine (5 mL). The resulting solution was stirred for 2 h at room temperature. The resulting mixture was concentrated under vacuum. Then, added 10 mL of water to the mixture, and extracted with 3×10 mL of ethyl acetate. The combined organic layers was evaporated to dryness, and applied onto a silica gel column with dichloromethane/methanol (50:1). The crude product was purified by Flash-Prep-HPLC with the following conditions (IntelFlash-1): Column, C 18; mobile phase, $CH_3CN/H_2O$ ($NH_4HCO_3$)=1:10 increasing to $CH_3CN/H_2O$ ($NH_4HCO_3$)=19:3 within 40; Detector, UV 254 nm. This resulted in 315.8 mg (38.65%) of I-11 as a white solid. (ES, m/z): [M+H]⁺ 426.0, ¹H-NMR (300 MHz, $CDCl_3$, ppm): δ3.69 (s, 3H), δ6.92-6.93 (d, J=1.8 Hz, 1H), δ7.08-7.11 (m, 1H), δ7.32-7.35 (d, J=8.4 Hz, 1H), δ7.44-7.45 (d, J=2.4 Hz, 1H), δ7.49-7.50 (d, J=2.4 Hz, 1H).

Example 19. Synthesis of 3-((3,5-dichloro-2-hydroxyphenyl)sulfonamido)-4-fluorobenzoic Acid, I-12

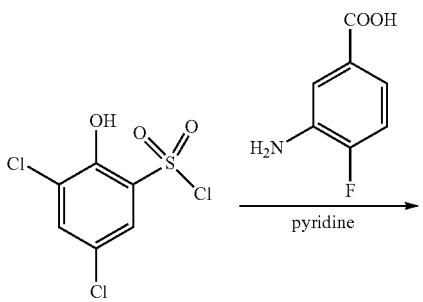

283

-continued

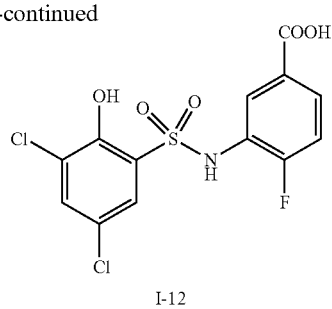

I-12

Synthesis of I-12

Into a 25-mL round-bottom flask purged and maintained with an inert atmosphere of nitrogen, was placed 3,5-dichloro-2-hydroxybenzene-1-sulfonyl chloride (300 mg, 1.15 mmol, 1 equiv), 3-amino-4-fluorobenzoic acid (213.6 mg, 1.38 mmol, 1.2 equiv), pyridine (5 mL). The resulting solution was stirred for 4 h at room temperature. The resulting mixture was concentrated under vacuum. The residue was absorbed onto silica and purified by column chromatography with dichloromethane/methanol (60:1). The crude product was purified by Flash-Prep-HPLC with the following conditions (IntelFlash-1): Column, C 18; mobile phase, $CH_3CN/H_2O$ ($NH_4HCO_3$)=1:10 increasing to $CH_3CN/H_2O$ ($NH_4HCO_3$)=19:3 within 40 min; Detector, UV 254 nm. This gave the title compound of I-12 (213.6 mg, 48.98%) as a white solid. (ES, m/z): [M−H]⁻ 378.0, $^1$H-NMR (300 MHz, DMSO-$d_6$, ppm): δ7.30-7.36 (m, 1H), δ7.54-7.55 (d, J=2.7 Hz, 1H), δ7.75-7.80 (m, 1H), δ7.82-7.87 (m, 2H), δ10.80 (br s, 2H), δ13.01 (br s, 1H).

Example 20. Synthesis of 3,5-dichloro-2-hydroxy-N-(3-methoxy-[1,1'-biphenyl]-4-yl)benzenesulfonamide, I-13

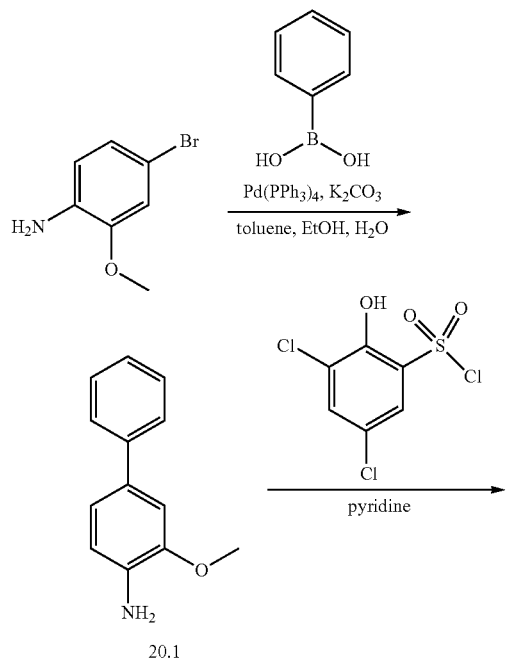

284

-continued

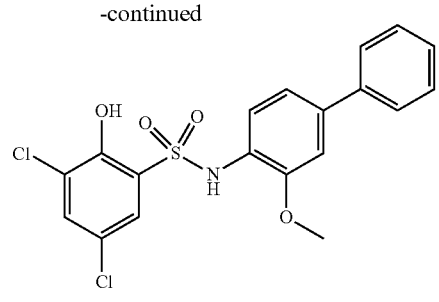

I-13

Synthesis of Compound 20.1

Into a 50-mL 3-necked round-bottom flask purged and maintained with an inert atmosphere of nitrogen, was placed 4-bromo-2-methoxyaniline (1 g, 4.95 mmol, 1 equiv), toluene (10 mL), EtOH (10 mL), $H_2O$ (10 mL), $K_2CO_3$ (2.1 g, 14.85 mmol, 3 equiv), phenylboronic acid (0.7 g, 5.74 mmol, 1.2 equiv), Pd(PPh$_3$)$_4$ (0.6 g, 0.52 mmol, 0.1 equiv). The resulting solution was stirred for 12 h at 80° C. The resulting mixture was concentrated under vacuum. The residue was applied onto a silica gel column with ethyl acetate/petroleum ether (1:20). This resulted in 550 mg (55.77%) of 20.1 as a yellow solid.

Synthesis of I-13

Into a 25-mL 3-necked round-bottom flask purged and maintained with an inert atmosphere of nitrogen, was placed 20.1 (550 mg, 2.76 mmol, 1 equiv), 3,5-dichloro-2-hydroxy-benzene-1-sulfonyl chloride (649.7 mg, 2.48 mmol, 0.9 equiv), pyridine (10 mL). The reaction solution was stirred for 2 h at room temperature. The resulting mixture was concentrated under vacuum, then, applied onto a silica gel column with dichloromethane/methanol (20:1). The crude product was purified by Flash-Prep-HPLC with the following conditions (IntelFlash-1): Column, C 18; mobile phase, $CH_3CN/H_2O$ ($NH_4HCO_3$)=1:9 increasing to $CH_3CN/H_2O$ ($NH_4HCO_3$)=17:3 within 40 min; Detector, UV 254 nm. This resulted in 446.9 mg (38.16%) of I-13 as a white solid. (ES, m/z): [M−H]⁻ 422.1, $^1$H-NMR (400 MHz, CDCl$_3$, ppm): δ3.74 (s, 3H), δ6.97-6.99 (m, 1H), δ7.16-7.18 (m, 1H), δ7.33-7.37 (m, 1H), δ7.41-7.48 (m, 4H), δ7.50-7.53 (m, 3H).

Example 21 Synthesis of N-(2-(benzyloxy)phenyl)-3,5-dichloro-2-hydroxybenzenesulfonamide, I-15

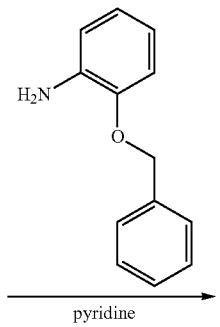

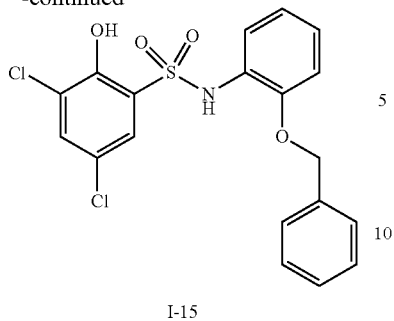

I-15

Synthesis of I-15

Into a 25-mL round-bottom flask purged and maintained with an inert atmosphere of nitrogen, was placed 3,5-dichloro-2-hydroxybenzene-1-sulfonyl chloride (500 mg, 1.91 mmol, 1 equiv), 2-(benzyloxy)aniline (457.1 mg, 2.29 mmol, 1.2 equiv), pyridine (5 mL). The resulting solution was stirred for 2 h at room temperature. The resulting mixture was concentrated under vacuum. The residue was applied onto a silica gel column with dichloromethane/methanol (30:1). The crude product was purified by Flash-Prep-HPLC with the following conditions (IntelFlash-1): Column, C18; mobile phase, $CH_3CN/H_2O$ ($NH_4HCO_3$)=1:9 increasing to $CH_3CN/H_2O$ ($NH_4HCO_3$)=19:3 within 40 min; Detector, UV 254 nm. This resulted in 436.4 mg (53.79%) of I-15 as a white solid. (ES, m/z): [M−H]⁻ 422.1, $^1$H-NMR (400 MHz, CDCl$_3$, ppm): δ4.94 (s, 2H), δ6.88-6.90 (d, J=8 Hz, 1H), δ6.98-7.02 (m, 1H), δ7.14-7.19 (m, 1H), δ7.26-7.28 (m, 2H), δ7.40-7.48 (m, 5H), δ7.54-7.56 (m, 1H).

Example 22. Synthesis of 3,5-dichloro-2-hydroxy-N-(4-methoxy-[1,1'-biphenyl]-3-yl)-N-methylbenzenesulfonamide, I-17

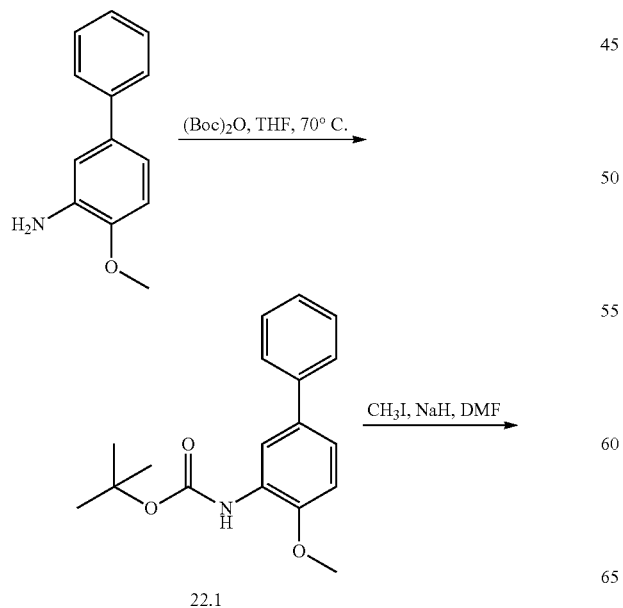

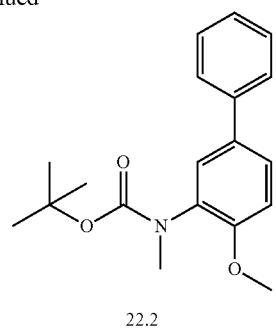

Synthesis of Compound 22.1

Into a 25-mL 3-necked round-bottom flask purged and maintained with an inert atmosphere of nitrogen, was placed 2-methoxy-5-phenylaniline (1 g, 5.02 mmol, 1 equiv), (Boc)$_2$O (1.1 g, 5.02 mmol, 1 equiv), THF (10 mL). The resulting solution was stirred for 12 h at 70° C. The resulting mixture was concentrated under vacuum. The residue was applied onto a silica gel column with ethyl acetate/petroleum ether (1:20). This resulted in 1 g (66.56%) of 22.1 as a white solid.

Synthesis of Compound 22.2

Into a 50-mL 3-necked round-bottom flask purged and maintained with an inert atmosphere of nitrogen, was placed 22.1 (980 mg, 3.27 mmol, 1 equiv), DMF (50 mL). This was followed by the addition of NaH (78.6 mg, 1.97 mmol, 1 equiv). The above mixture was stirred for 1 h at room temperature. Subsequently, $CH_3I$ (464.7 mg, 3.27 mmol, 1 equiv) was added. The resulting solution was stirred for 1 h at room temperature. The reaction was quenched by the addition of 20 mL of sat.$NH_4Cl$ (aq.), then, extracted with ethyl acetate (3×20 mL) and the combined organic layers were concentrated under vacuum. The residue was applied onto a silica gel column with ethyl acetate/petroleum ether (1:40). This resulted in 940 mg (91.63%) of 22.2 as a white solid.

Synthesis of Compound 22.3

Into a 25-mL 3-necked round-bottom flask purged and maintained with an inert atmosphere of nitrogen, was placed 22.2 (940 mg, 3 mmol, 1 equiv), DCM (10 mL), TFA (5 mL). The resulting solution was stirred for 2 h at room temperature. The mixture was concentrated under vacuum. This resulted in 800 mg (85.93%) of 22.3 as a white solid.

Synthesis of I-17

Into a 25-mL 3-necked round-bottom flask purged and maintained with an inert atmosphere of nitrogen, was placed 22.3 (400 mg, 1.29 mmol, 1 equiv), pyridine (5 mL), 3,5-dichloro-2-hydroxybenzene-1-sulfonyl chloride (304.4 mg, 1.16 mmol, 0.9 equiv). The resulting solution was stirred for 2 h at room temperature. The resulting mixture was concentrated under vacuum. The residue was applied onto a silica gel column with dichloromethane/methanol (40:1). The crude product was purified by Flash-Prep-HPLC with the following conditions (IntelFlash-1): Column, C 18; mobile phase, $CH_3CN/H_2O$ ($NH_4HCO_3$)=1:10 increasing to $CH_3CN/H_2O$ ($NH_4HCO_3$)=19:3 within 40 min; Detector, UV 254 nm. This resulted in 157.5 mg (27.78%) of I-17 as a white solid. (ES, m/z): $[M+H]^+$ 438.2, $^1$H-NMR (400 MHz, $CDCl_3$, ppm): δ3.28 (s, 3H), δ3.60 (s, 3H), δ6.93-6.95 (m, 1H), δ7.32-7.35 (m, 1H), δ7.41-7.45 (m, 2H), δ7.53-7.59 (m, 6H), δ8.95 (s, 1H).

Example 23. Synthesis of N-(4-methoxy-[1,1'-biphenyl]-3-yl)-3-(2H-tetrazol-5-yl)benzenesulfonamide, I-19

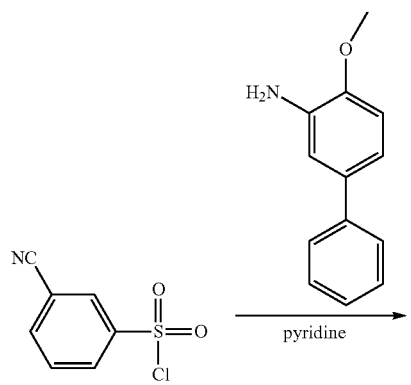

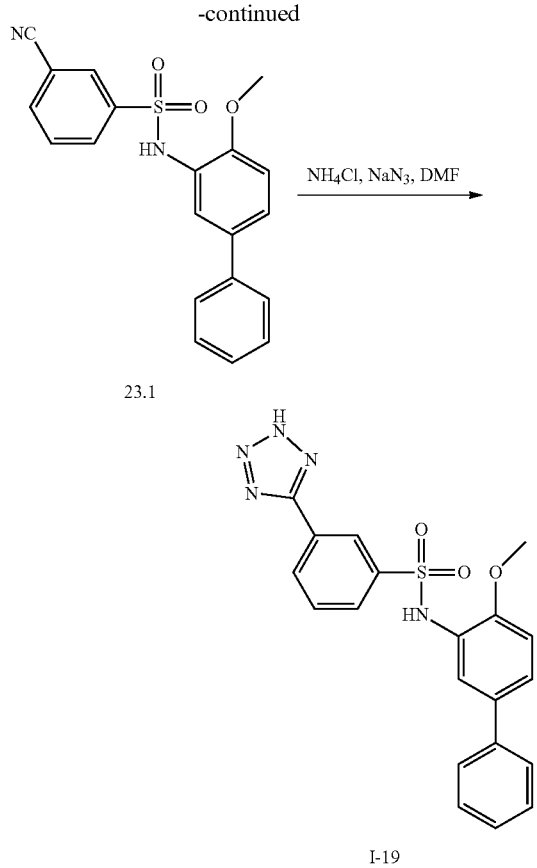

Synthesis of Compound 23.1

Into a 100-mL 3-necked round-bottom flask purged and maintained with an inert atmosphere of nitrogen, was placed 3-cyanobenzene-1-sulfonyl chloride (500 mg, 2.48 mmol, 1.00 equiv), 2-methoxy-5-phenylaniline (594 mg, 2.98 mmol, 1.20 equiv), pyridine (13 mL). The resulting solution was stirred for 2 h at 25° C. The reaction was then quenched by the addition of 60 mL of 1M hydrochloric acid (aq.). The resulting solution was extracted with 3×80 mL of ethyl acetate and the organic layers combined and concentrated under vacuum. The residue was applied onto a silica gel column with dichloromethane/methanol (100:1). This resulted in 800 mg (89%) of 23.1 as a red solid.

Synthesis of I-19

Into a 100-mL 3-necked round-bottom flask, was placed 23.1 (300 mg, 0.82 mmol, 1.00 equiv), $NH_4Cl$ (176 mg, 3.29 mmol, 4.00 equiv), DMF (15 mL), NaN3 (162 mg, 2.49 mmol, 3.00 equiv). The resulting solution was stirred for 12 h at 130° C. The solids were filtered out. The crude product was purified by Prep-HPLC with Column: XBridge Prep OBD C 18 Column 30*150 mm 5 um; Mobile Phase A: water (10 mmol/L $NH_4HCO_3$+0.1%$NH_3.H_2O$), Mobile Phase B: ACN; Flow rate: 60 mL/min; Gradient: 20% B to 45% B in 8 min; 254/220 nm; Rt: 6.88 min. This resulted in 64.6 mg (19%) of I-19 as a white solid. (ES, m/z): $[M-H]^-$ 406.1, $^1$H-NMR (300 MHz, DMSO-$d_6$, ppm): δ3.53 (s, 3H), δ6.97-7.00 (d, J=8.7 Hz, 1H), δ7.28-7.33 (m, 1H), δ7.38-7.43 (m, 3H), δ7.48-7.49 (d, J=2.4 Hz, 2H), δ7.52-7.60 (m, 3H), δ8.16-8.18 (m, 1H), δ8.48 (s, 1H).

289
Example 24. Synthesis of 3-bromo-5-chloro-2-hydroxy-N-(2-methoxy-5-phenylphenyl)benzene-1-sulfonamide, I-20

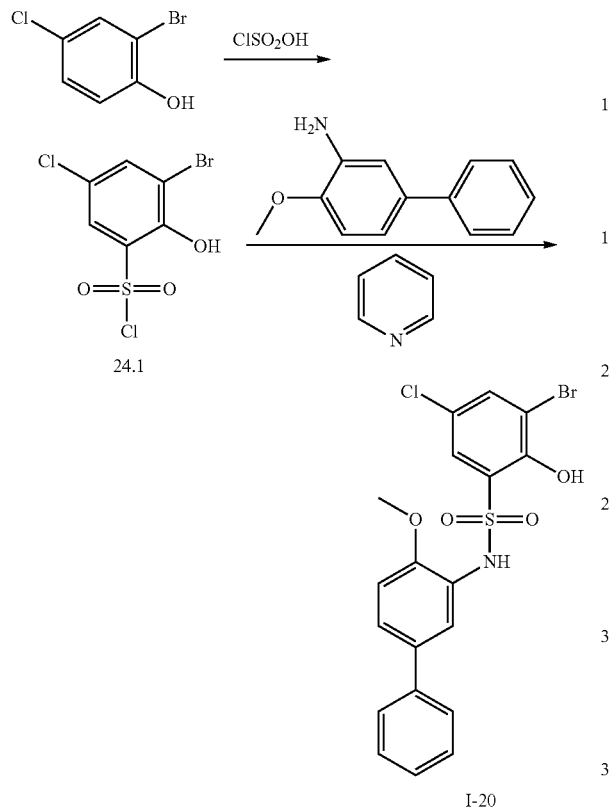

Synthesis of Compound 24.1

To a stirred solution of 2-bromo-4-chlorophenol (1 g, 4.82 mmol, 1 equiv) was added O-(chlorosulfonyl)oxidanol (10 mL) dropwise at 0° C. under nitrogen atmosphere. The resulting mixture was stirred overnight at 25° C. The reaction was quenched by the addition of water/ice (100 mL) at 0° C. The precipitated solids were collected by filtration and washed with water (2×10 mL). The resulting solid was dried in an oven under reduced pressure to afford 24.1 (1.3 g, 88.14%) as a white solid.

Synthesis of I-20

To a stirred solution of 24.1 (303 mg, 0.99 mmol, 1 equiv) in pyridine (10 mL) was added 2-methoxy-5-phenylaniline (197.3 mg, 0.99 mmol, 1 equiv) in portions at 25° C. under air atmosphere. The resulting mixture was stirred overnight at 25° C. The resulting mixture was diluted with 10 mL of water. The resulting mixture was extracted with EA (3×10 mL). The combined organic layers were washed with EA (2×10 mL). After filtration, the filtrate was concentrated under reduced pressure. The residue was purified by Prep-TLC (CH$_2$Cl$_2$/MeOH=20:1) to afford I-20 (157.7 mg, 33.97%) as a white solid. (ES, m/z): [M+H]$^+$ 467.9, $^1$H-NMR (400 MHz, DMSO-d$_6$, ppm): δ10.61 (br s, 1H), δ9.45 (br s, 1H), δ7.96-7.95 (d, J=2.4 Hz, 1H), δ7.57-7.42 (m, 7H), δ7.34-7.31 (m, 1H), δ7.06-7.04 (d, J=8.4 Hz, 1H), δ3.63 (s, 3H).

290
Example 25. Synthesis of 3-bromo-5-chloro-N-(4-fluoro-[1,1'-biphenyl]-3-yl)-2-hydroxybenzenesulfonamide, I-23

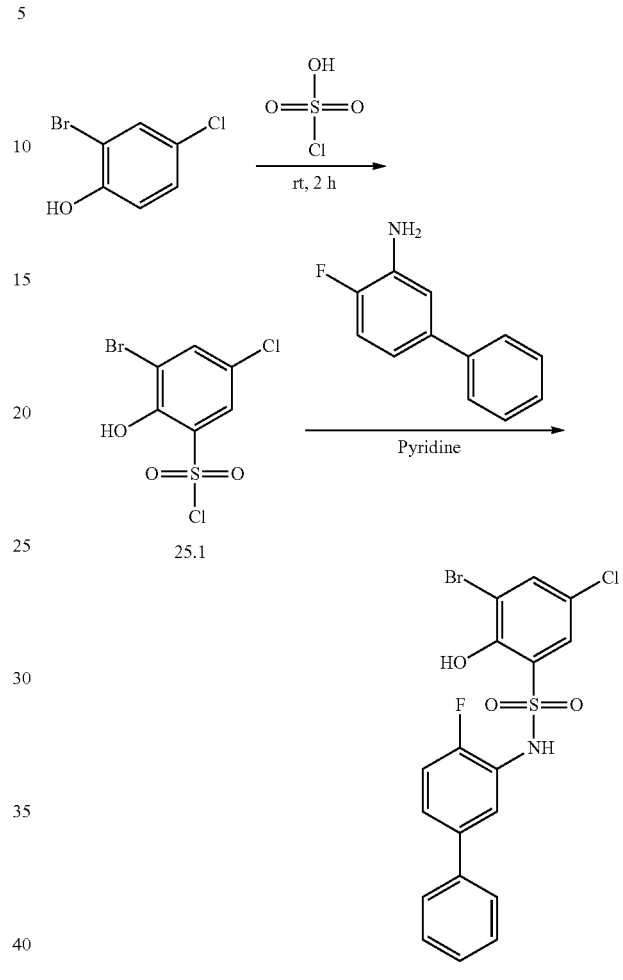

Synthesis of Compound 25.1

Into a 100-mL round-bottom flask purged and maintained with an inert atmosphere of nitrogen, was placed 2-bromo-4-chlorophenol (1 g, 4.82 mmol, 1.00 equiv), O-(chlorosulfonyl)oxidanol (3.4 g, 29.18 mmol, 6.00 equiv). The resulting solution was stirred for 2 h at room temperature. The reaction was then quenched by the addition of 10 mL of water/ice, and extracted with 3×10 mL of ethyl acetate. The organic layers were combined, washed with 10 mL of brine, dried and concentrated under vacuum. This resulted in 1 g (68%) of 25.1 as a white solid.

Synthesis of I-23

Into a 25-mL round-bottom flask purged and maintained with an inert atmosphere of nitrogen, was placed 25.1 (200 mg, 0.65 mmol, 1.00 equiv), 2-fluoro-5-phenylaniline (150 mg, 1.90 mmol, 1.20 equiv), pyridine (10 mL). The resulting solution was stirred for 12 h at room temperature. The reaction was then quenched by the addition of 10 mL of 1 M hydrogen chloride, followed by extracted with 3×10 mL of ethyl acetate. The organic layers were combined, washed with 10 mL of brine, dried and concentrated under vacuum. The crude product was purified by Flash-Prep-HPLC with the following conditions (IntelFlash-1): Column, C 18; mobile phase, $CH_3CN/H_2O=30:70$ increasing to $CH_3CN/H_2O=70:30$ within 25 min; Detector, UV 254 nm. This resulted in 140.3 mg (47%) of I-23 as a white solid. (ES, m/z): $[M+H]^+$456.0, $^1$H-NMR (400 MHz, DMSO-$d_6$, ppm): δ7.69-7.41 (m, 7H), δ7.37-7.33 (m, 1H), δ7.20-7.12 (m, 2H).

Example 26. Synthesis of 3,5-dichloro-N-[2-fluoro-5-(2H-1,2,3,4-tetrazol-5-yl) phenyl]-2-hydroxybenzene-1-sulfonamide, I-24

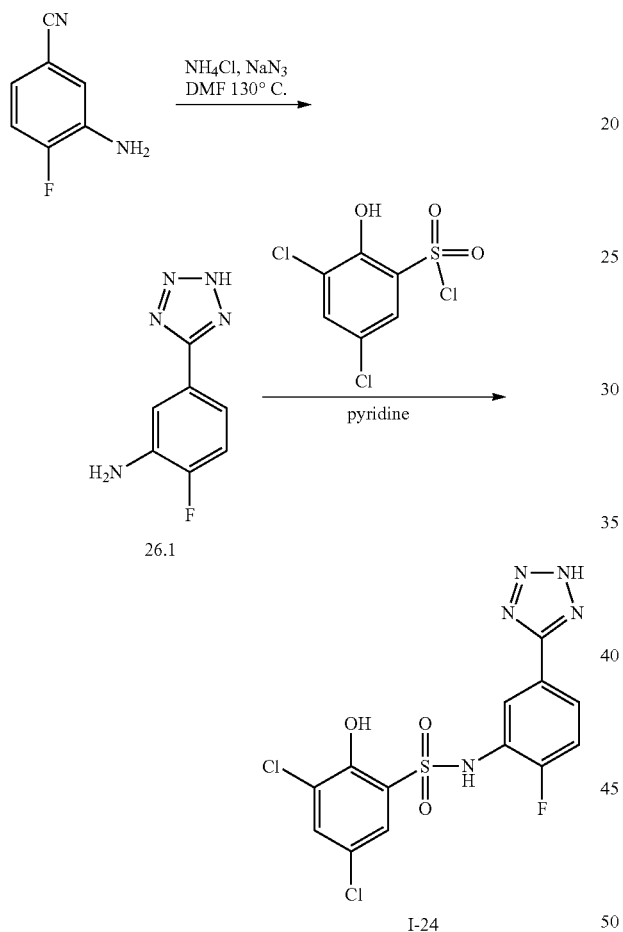

Synthesis of Compound 26.1

Into a 100-mL 3-necked round-bottom flask, was placed 3-amino-4-fluorobenzonitrile (2 g, 14.69 mmol, 1 equiv), DMF (20 mL), $NH_4Cl$ (3.1 g, 58.77 mmol, 4 equiv), $NaN_3$ (2.9 g, 44.08 mmol, 3 equiv). The resulting solution was stirred for 12 h at 130° C. The resulting mixture was concentrated under vacuum. The residue was applied onto a silica gel column with dichloromethane/methanol (100:1). This resulted in 1.5 g (56.99%) of 26.1 as an off-white solid.

Synthesis of I-24

Into a 100-mL 3-necked round-bottom flask, was placed 26.1 (1.4 g, 9.49 mmol, 1.2 equiv), 3,5-dichloro-2-hydroxybenzene-1-sulfonyl chloride (1.7 g, 11.39 mmol, 1 equiv), pyridine (20 mL). The resulting solution was stirred for 2 h at 25° C. The resulting mixture was concentrated under vacuum. The crude product was purified by Prep-HPLC with the following conditions:Column, XBridge Prep OBD C18 Column 30×150 mm 5 um; Mobile Phase A:water (10 mmol/L $NH_4HCO_3$+0.1% $NH_3.H_2O$), Mobile Phase B: ACN; Flow rate: 60 mL/min; Gradient: 5% B to 30% B in 8 min; 254/220 nm; Rt: 6.47 min. This resulted in 114.4 mg (4.35%) of I-24 as a light yellow solid. (ES, m/z): $[M+H]^+$ 403.9, $^1$H-NMR (300 MHz, DMSO-$d_6$, ppm): δ7.12-7.25 (m, 2H), δ7.39 (m, 1H), δ7.46-7.52 (m, 2H), δ7.96-8.05 (m, 1H).

Example 27. Synthesis of N-(2-hydroxy-5-phenylphenyl)-3-(2H-1,2,3,4-tetrazol-5-yl) benzene-1-sulfonamide, I-25

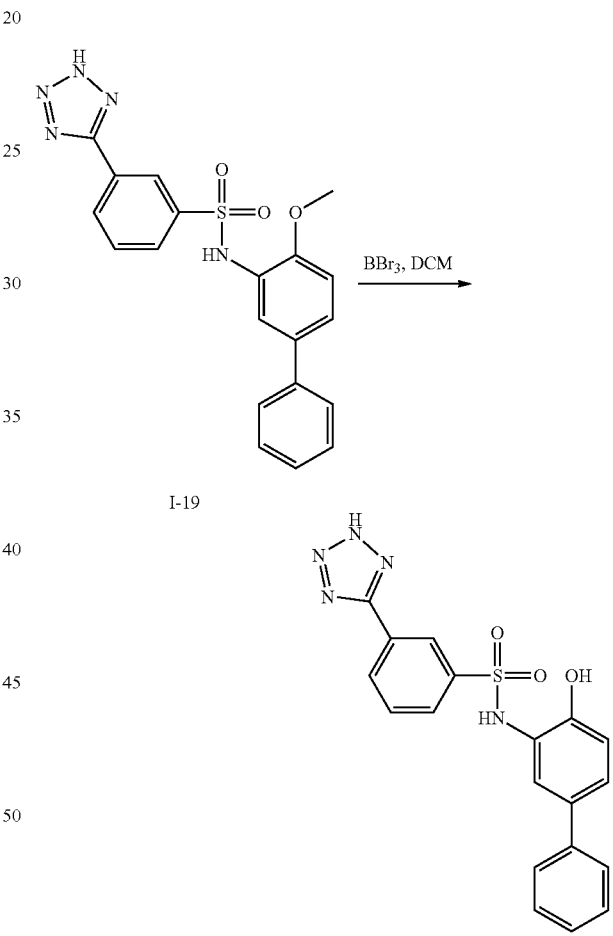

Synthesis of I-25

Into a 8-mL vial purged and maintained with an inert atmosphere of nitrogen, was placed I-19 (60 mg, 0.15 mmol, 1 equiv), DCM (2 mL), $BBr_3$ (73.8 mg, 0.29 mmol, 2 equiv). The resulting solution was stirred for 12 h at room temperature. The reaction was quenched by the addition of 5 mL of sat.$NaHCO_3$ (aq.) and the resulting solution was extracted with ethyl acetate (3×10 mL). The combined organic layers were concentrated under vacuum. The residue was purified by Prep-HPLC with the following conditions (2 #-AnalyseHPLC-SHIMADZU(HPLC-10)): Column: XBridge Prep OBD C18 Column 19*250 mm, 5 um; Mobile Phase A:water (0.05% NH3.H$_2$O), Mobile Phase B: ACN; Flow rate: 20 mL/min; Gradient: 22% B to 35% B in 7 min; Detector UV 254/220 nm; Rt: 6.32 min. This resulted in 21.4 mg (36.94%) of I-25 as a white solid. (ES, m/z): [M−H]⁻ 392.1, $^1$H-NMR (400 MHz, CD$_3$OD, ppm): δ6.74-6.76 (d, J=7.6 Hz, 1H), δ7.20-7.27 (m, 2H), δ7.34-7.38 (m, 2H), δ7.45-7.47 (m, 2H), δ7.50-7.58 (m, 2H), δ7.76-7.78 (d, J=8.0 Hz, 1H), δ8.23-8.27 (m, 1H), δ8.60 (s, 1H).

Example 28. Synthesis of 3,5-dichloro-2-hydroxy-N-(2-hydroxy-5-phenylphenyl) benzene-1-sulfonamide, I-28

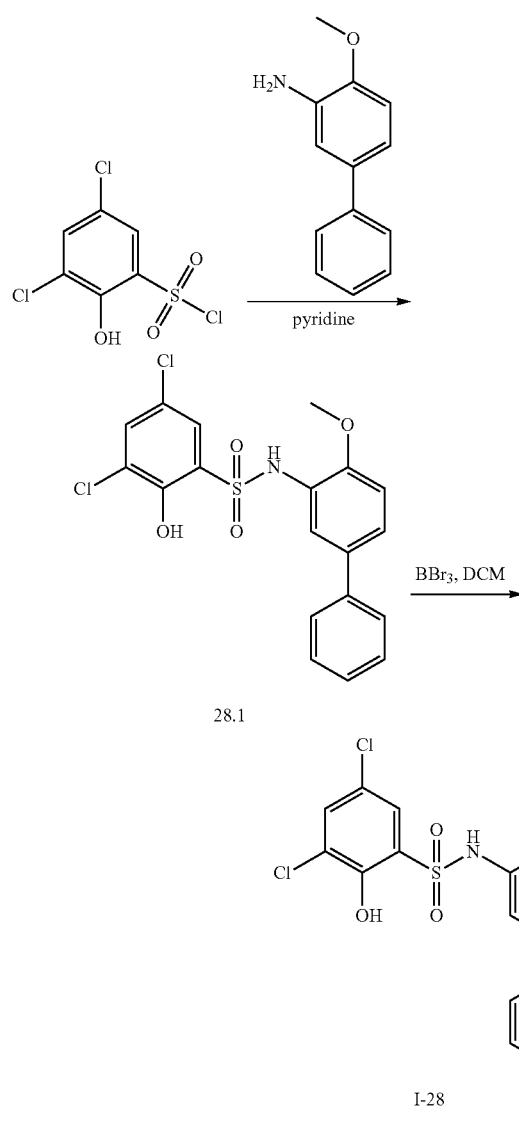

Synthesis of Compound 28.1

Into a 100-mL 3-necked round-bottom flask, was placed 3,5-dichloro-2-hydroxybenzene-1-sulfonyl chloride (300 mg, 1.15 mmol, 1 equiv), 2-methoxy-5-phenylaniline (284 mg, 1.43 mmol, 1.242 equiv), pyridine (7 mL). The resulting solution was stirred for 2 h at 25° C. The reaction was then quenched by the addition of 20 mL of 1M hydrochloric acid. The resulting solution was extracted with ethyl acetate (3×20 mL) and the combined organic layers were concentrated under vacuum. The residue was applied onto Prep-TLC with dichloromethane/methanol (20:1). This resulted in 400 mg (82.18%) of 28.1 as a red oil.

Synthesis of I-28

Into a 25-mL round-bottom flask purged and maintained with an inert atmosphere of nitrogen, was placed 28.1 (250 mg, 0.59 mmol, 1 equiv), DCM (5 mL), BBr$_3$ (442.8 mg, 1.77 mmol, 3 equiv), followed by stirring for 12 h at room temperature. The reaction was then quenched by the addition of 10 mL of sat.NaHCO$_3$ (aq.). The resulting solution was extracted with ethyl acetate (3×10 mL) and the combined organic layers were concentrated under vacuum. The crude product was purified by Flash-Prep-HPLC with the following conditions (IntelFlash-1): Column, C 18; mobile phase, CH$_3$CN/H$_2$O (NH$_4$HCO$_3$)=1:10 increasing to CH$_3$CN/H$_2$O (NH$_4$HCO$_3$)=17:3 within 40; Detector, UV 254 nm. This resulted in 110.2 mg (45.59%) of I-28 as a white solid. (ES, m/z): [M−H]⁻ 407.9, $^1$H-NMR (400 MHz, DMSO-d$_6$, ppm): δ6.86-6.88 (d, J=8.4 Hz, 1H), δ7.28-7.32 (m, 2H), δ7.40-7.48 (m, 5H), δ7.59-7.60 (d, J=2.8 Hz, 1H), δ7.84-7.85 (d, 1H), δ9.14 (s, 1H), δ10.30 (br s, 2H).

Example 29. Synthesis of 5-chloro-3-cyano-N-(2-fluoro-5-phenylphenyl)-2-hydroxybenzene-1-sulfonamide, I-29

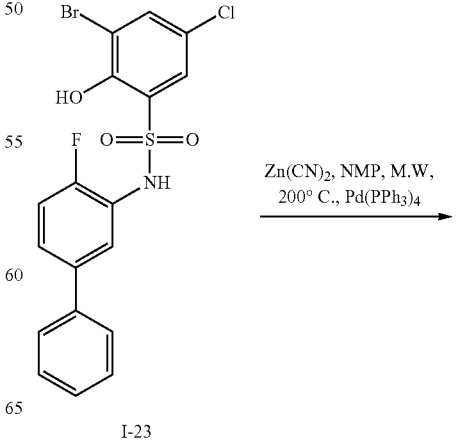

295
-continued

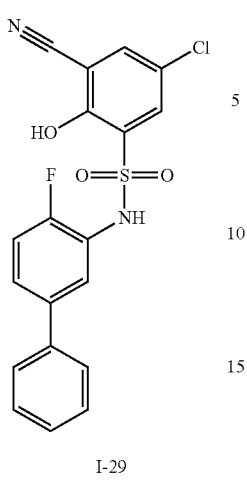

I-29

Synthesis of I-29

To a stirred solution of I-23 (100 mg, 0.22 mmol, 1 equiv) and Zn(CN)$_2$ (51.4 mg, 0.44 mmol, 2 equiv) in NMP (1 mL) were added Pd(PPh$_3$)$_4$ (50.6 mg, 0.04 mmol, 0.2 equiv). The final reaction mixture was irradiated with microwave radiation for 1 hr at 200° C. The reaction was quenched by the addition of water (10 mL) at room temperature. The aqueous layer was extracted with EtOAc (2×30 mL). The resulting mixture was concentrated under reduced pressure. The residue was purified by Prep-TLC with DCM/MeOH (25:1) to afford I-29 (39 mg, 44.22%) as a light yellow solid. (ES, m/z): [M–H]$^-$ 400.9, $^1$H-NMR (300 MHz, DMSO-d$_6$, ppm): δ6.92-7.38 (m, 3H), δ7.40-7.58 (m, 7H).

Example 30. Synthesis of 5-chloro-N-(2-fluoro-5-phenylphenyl)-2-hydroxybenzene-1-sulfonamide, I-30

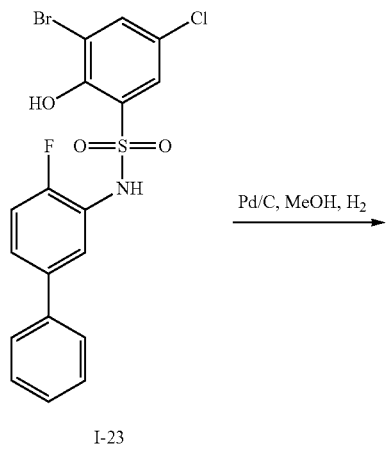

I-23

296
-continued

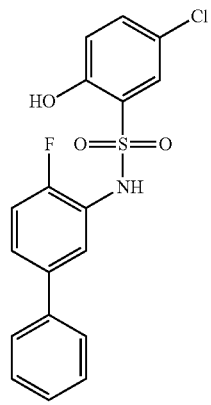

I-30

Synthesis of I-30

To a stirred solution of I-23 (60 mg, 0.13 mmol, 1 equiv) in MeOH (40 mL) was added Pd/C (12 mg) under nitrogen atmosphere. To the above H$_2$ (g) was introduced in. The resulting mixture was stirred for 1 h at room temperature. The precipitated solids were filtrated out, and washed with MeOH (2×30 mL). The resulting mixture was concentrated under reduced pressure. The residue was purified by Prep-TLC (CH$_2$Cl$_2$/MeOH=25:1) to afford I-30 (38.1 mg, 76.76%) as a white solid. (ES, m/z): [M–H]$^-$ 375.9, $^1$H-NMR (400 MHz, DMSO-d$_6$, ppm): δ7.01-7.04 (d, J=8.8 Hz, 1H), δ7.23-7.27 (m, 1H), δ7.35-7.56 (m, 8H), δ10.70-10.86 (br s, 1H).

Example 31. Synthesis of 3-chloro-5-cyano-N-(4-fluoro-[1,1'-biphenyl]-3-yl)-2-hydroxybenzenesulfonamide, I-31

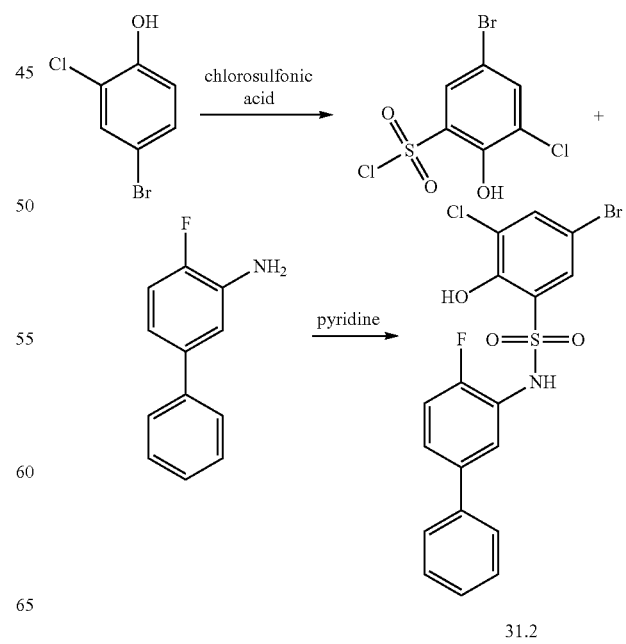

31.2

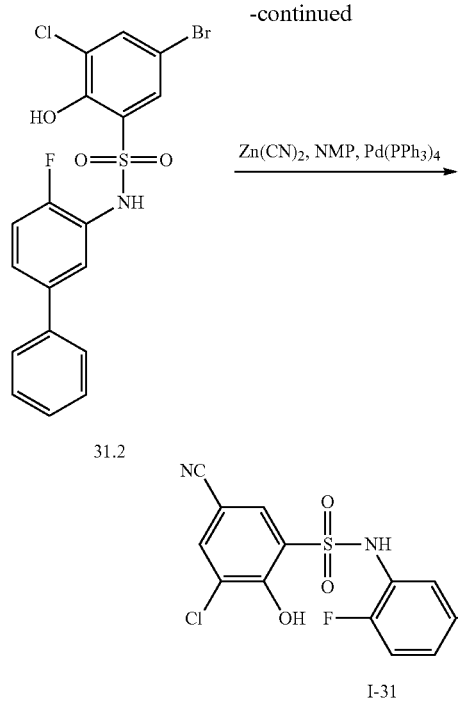

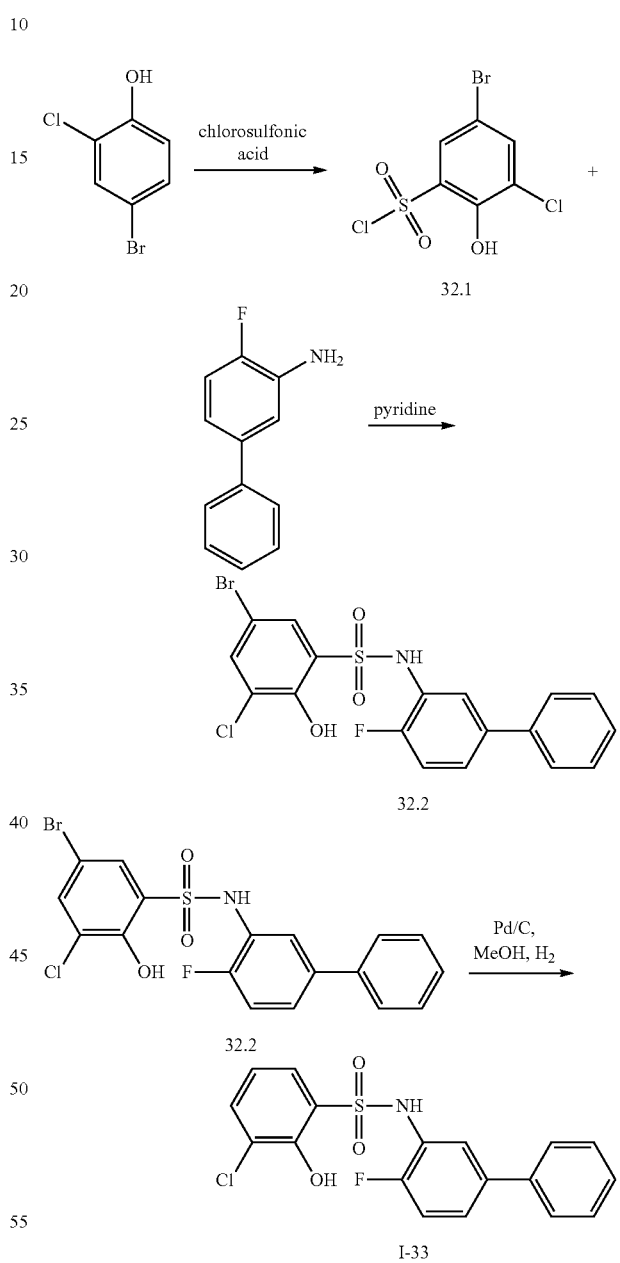

Synthesis of Compound 31.1

Into a 100-mL 3-necked round-bottom flask, was placed 4-bromo-2-chlorophenol (5 g, 24.10 mmol, 1 equiv), O-(chlorosulfonyl)oxidanol (15 mL). The resulting solution was stirred for 2 h at room temperature. The reaction was then quenched by the addition of water/ice (40 mL). The resulting solution was extracted with ethyl acetate (2×40 mL) and the combined organic layers were concentrated under vacuum. This resulted in 6.9 g (93.57%) of 31.1 as a brown solid.

Synthesis of Compound 31.2

Into a 50-mL round-bottom flask, was placed 31.1 (300 mg, 0.98 mmol, 1 equiv), 2-fluoro-5-phenylaniline (221 mg, 1.18 mmol, 1.204 equiv), pyridine (5 mL). The resulting solution was stirred for 6 h at room temperature. The resulting mixture was concentrated. The resulting mixture was washed with 1M HCl (aq.). The resulting solution was extracted with ethyl acetate (2×10 mL) and the combined organic layers were concentrated under vacuum. The residue was applied onto Prep-TLC with dichloromethane/methanol (10:1). This resulted in 225 mg (50.24%) of 31.2 as a brown solid.

Synthesis of I-31

Into a 10-mL purged and maintained with an inert atmosphere of nitrogen, was placed 31.2 (190 mg, 0.42 mmol, 1.00 equiv), NMP (1.5 mL), Pd(PPh$_3$)$_4$ (96 mg, 0.08 mmol, 0.20 equiv), Zn(CN)$_2$ (96 mg, 0.82 mmol, 2.00 equiv). The resulting solution was stirred for 1 h at 200° C. The resulting mixture was washed with H$_2$O. The resulting solution was extracted with 2×5 mL of ethyl acetate and the organic layers combined and concentrated under vacuum. The residue was applied onto Prep-TLC with dichloromethane/methanol (20:1). This resulted in 68.6 mg (41%) of I-31 as a white solid.

(ES, m/z): [M–H]$^-$ 401.0, $^1$H-NMR (300 MHz, CD$_3$OD, ppm): δ7.79-7.78 (d, J=2.4 Hz, 1H), δ7.61-7.57 (m, 2H), δ7.48-7.40 (m, 4H), δ7.36-7.25 (m, 2H), δ7.08-7.01 (m, 1H).

Example 32. Synthesis of 3-chloro-N-(4-fluoro-[1,1'-biphenyl]-3-yl)-2-hydroxybenzenesulfonamide, I-33

Synthesis of Compound 32.1

Into a 100-mL 3-necked round-bottom flask, was placed 4-bromo-2-chlorophenol (5 g, 24.10 mmol, 1 equiv), O-(chlorosulfonyl)oxidanol (15 mL). The resulting solution was stirred for 2 h at room temperature. The reaction was then quenched by the addition of 20 mL of water/ice. The resulting solution was extracted with ethyl acetate (3×15 mL) and the combined organic layers were concentrated under vacuum. This resulted in 6.9 g (93.57%) of 32.1 as a brown solid.

Synthesis of Compound 32.2

Into a 50-mL round-bottom flask, was placed 32.1 (200 mg, 0.658 mmol, 1 equiv), 2-fluoro-5-phenylaniline (148 mg, 0.789 mmol, 1.204 equiv), pyridine (5 mL). The resulting solution was stirred for 6 h at room temperature. The resulting mixture was washed with 1M HCl (aq.). The resulting solution was extracted with ethyl acetate (3×10 mL) and the combined organic layers were concentrated under vacuum. The residue was applied onto Prep-TLC with dichloromethane/methanol (10:1). This resulted in 180 mg (50.24%) of 32.2 as a brown solid.

Synthesis of I-33

Into a 50-mL round-bottom flask was placed 32.2 (60 mg, 0.13 mmol, 1 equiv), methanol (2 mL), Pd/C (12 mg). To the above $H_2$ was introduced in. The resulting solution was stirred for 1 h at room temperature. The solids were filtered out. The filtrated was concentrated under vacuum. The crude product was purified by Flash-Prep-HPLC with the following conditions (IntelFlash-1): Column, C 18; mobile phase, ACN/$H_2$O (0.1% $NH_4HCO_3$)=0 increasing to ACN/$H_2$O (0.1% $NH_4HCO_3$)=1/1 within 25 mins; Detector, UV 254 nm. This resulted in 11.9 mg (23.97%) of I-33 as a white solid. (ES, m/z): [M−H]⁻ 375.9, ¹H-NMR (300 MHz, DMSO-$d_6$, ppm): δ7.58-7.38 (m, 8H), δ7.37-7.18 (m, 3H), δ6.88-6.82 (t, J=7.8 Hz, 1H).

Example 33. Synthesis of 5-bromo-3-chloro-N-(2-fluoro-5-phenylphenyl)-2-hydroxybenzene-1-sulfonamide, I-34

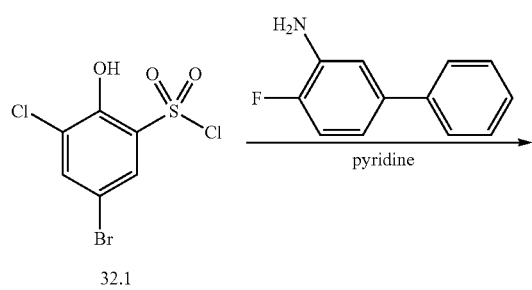

Synthesis of I-34

Into a 50-mL round-bottom flask, was placed 32.1 (200 mg, 0.65 mmol, 1 equiv), 2-fluoro-5-phenylaniline (148 mg, 0.79 mmol, 1.209 equiv), pyridine (5 mL). The resulting solution was stirred for 6 h at room temperature. The reaction was then quenched by the addition of water/ice (5 mL). The resulting solution was extracted with of ethyl acetate (3×10 mL) and the organic layers were combined and concentrated under vacuum. The crude product was purified by Flash-Prep-HPLC with the following conditions (IntelFlash-1): Column, C 18; mobile phase, ACN/$H_2$O (0.1% $NH_4HCO_3$)=0 increasing to ACN/$H_2$O (0.1% $NH_4HCO_3$)=1/1 within 30; Detector, UV 254 nm. This resulted in 180 mg (60.29%) of I-34 as a light yellow solid. (ES, m/z): [M+H]⁺455.8, ¹H-NMR (300 MHz, DMSO-$d_6$, ppm): δ7.61 (s, 1H), δ7.57-7.42 (m, 6H), δ7.38-7.32 (m, 1H), δ7.27-7.19 (m, 2H).

Example 34. Synthesis of N-(2-fluoro-5-phenylphenyl)-2-hydroxybenzene-1-sulfonamide, I-35

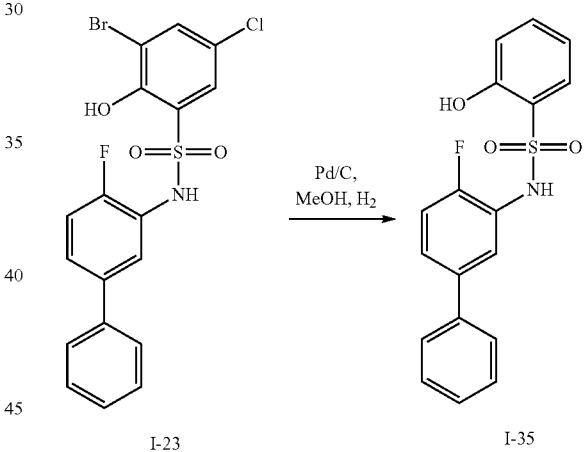

Synthesis of I-35

To a stirred solution of I-23 (60 mg, 0.13 mmol, 1 equiv) in MeOH (40 mL) were added Pd/C (12 mg) under nitrogen atmosphere. To the above $H_2$ (g) was introduced in. The resulting mixture was stirred overnight at room temperature. The solids were filtered out and washed with MeOH (2×30 mL). The resulting mixture was concentrated under reduced pressure. The residue was purified by Prep-TLC ($CH_2Cl_2$/MeOH=25:1) to afford I-35 (10.6 mg, 23.50%) as a white solid. (ES, m/z): [M−H]⁻ 342.0, ¹H-NMR (400 MHz, DMSO-$d_6$, ppm): 56.85-6.89 (m, 1H), δ6.96-7.02 (m, 1H), δ7.21-7.27 (m, 1H), δ7.34-7.39 (m, 2H), δ7.40-7.59 (m, 6H), δ7.60-7.68 (m, 1H), δ9.80 (br s, 1H).

Example 35. Synthesis of N-benzyl-3-bromo-5-chloro-N-(4-fluoro-[1,1'-biphenyl]-3-yl)-2-hydroxy-benzenesulfonamide, I-36

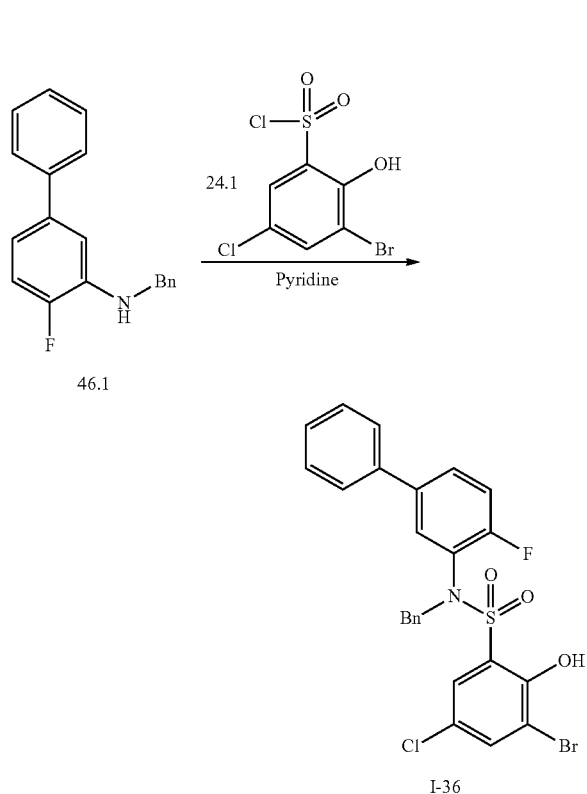

Synthesis of I-36

Into a 100-mL round-bottom flask purged and maintained with an inert atmosphere of nitrogen, was placed 46.1 (1 g, 3.61 mmol, 1.00 equiv), 24.1 (736 mg, 2.41 mmol, 1.20 equiv), pyridine (10 mL). The resulting solution was stirred for 0.5 h at room temperature. The resulting mixture was concentrated under vacuum. The residue was applied onto a silica gel column with ethyl acetate/petroleum ether (1:5). This resulted in 11.2 mg (1%) of I-36 as a white solid. (ES, m/z): [M+H]+ 546.1, 1H-NMR (DMSO-$d_6$, 400 MHz, ppm): δ11.03 (s, 1H), 8.01 (s, 1H), 7.59-7.22 (m, 14H), 4.99 (s, 2H).

Example 36. Synthesis of N-(2-fluoro-5-phenylphenyl)-3-(2H-1,2,3,4-tetrazol-5-yl) benzene-1-sulfonamide, I-37

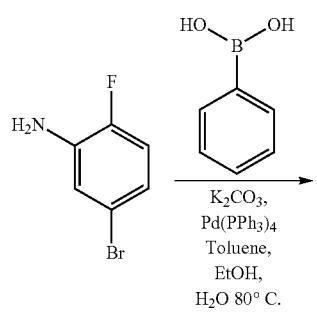

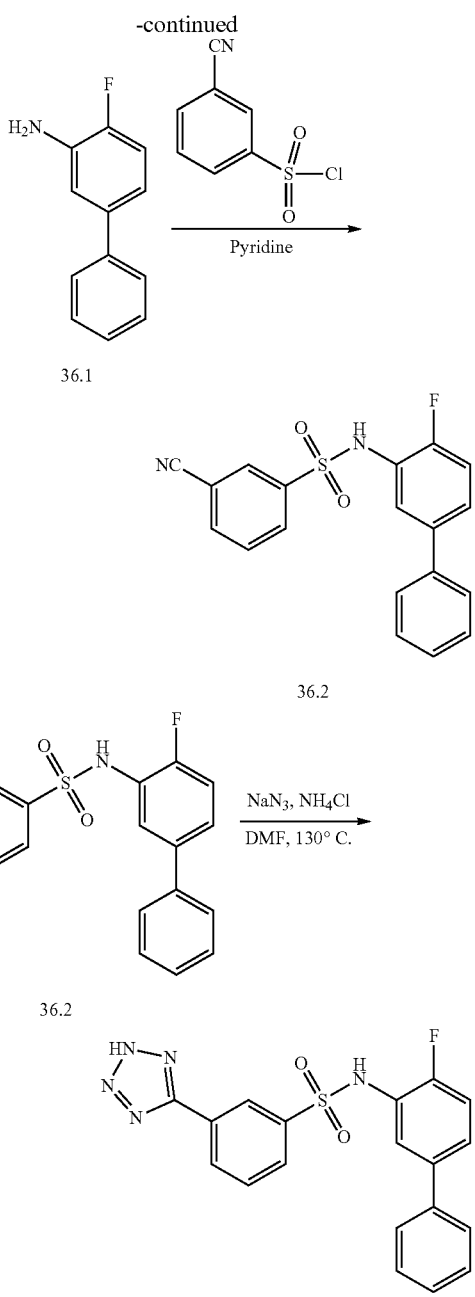

Synthesis of Compound 36.1

Into a 500-mL 3-necked round-bottom flask purged and maintained with an inert atmosphere of nitrogen, was placed 5-bromo-2-fluoroaniline (15 g, 78.94 mmol, 1 equiv), phenylboronic acid (11.6 g, 94.73 mmol, 1.2 equiv), $K_2CO_3$ (54.6 g, 394.71 mmol, 5 equiv), toluene (60 mL), EtOH (60 mL), $H_2O$ (60 mL), Pd(PPh$_3$)$_4$ (9.1 g, 7.89 mmol, 0.1 equiv). The resulting solution was stirred overnight at 80° C. in an oil bath. The resulting mixture was concentrated under vacuum. The residue was applied onto a silica gel column with ethyl acetate/petroleum ether (1/20). This resulted in 14.2 g (93.20%) of 36.1 as an off-white solid.

Synthesis of 36.2

Into a 50-mL round-bottom flask, was placed 36.1 (557 mg, 1.2 equiv.), 3-cyanobenzene-1-sulfonyl chloride (500 mg, 1 equiv), pyridine (10 mL). The resulting solution was stirred overnight at 25° C. The pH value of the solution was adjusted to 7-8 with 1 M HCl (aq.). The resulting solution was washed with $H_2O$ (20 mL). The resulting solution was extracted with 3×15 mL of ethyl acetate, and the combined organic layers were concentrated under vacuum. The residue was applied onto a silica gel column with ethyl acetate/petroleum ether (1/10). This resulted in 630 mg (70.65%) of 36.2 as a light yellow solid. (ES, m/z): [M−H]⁻ 351.0, ¹H-NMR (300 MHz, DMSO-$d_6$, ppm): δ10.56 (s, 1H), δ8.19-8.15 (m, 2H), δ8.07-8.04 (m, 1H), δ7.84-7.79 (m, 1H), δ7.56-7.25 (m, 8H).

Synthesis of I-37

Into a 100-mL round-bottom flask, was placed 36.2 (300 mg, 0.85 mmol, 1 equiv), $NH_4Cl$ (182.2 mg, 3.41 mmol, 4 equiv), DMF (15 mL), $NaN_3$ (166.0 mg, 2.55 mmol, 3 equiv). The resulting solution was stirred overnight at 130° C. in an oil bath. The solids were collected by filtration and concentrated under vacuum. The crude product was purified by Flash-Prep-HPLC with the following conditions (Intel-Flash-1): Column, C18; mobile phase, MeCN/$H_2O$=10% increasing to MeCN/$H_2O$=60% within 15 mins; Detector, UV 220 nm. This resulted in 100 mg (58.8%) of I-37 as a white solid. (ES, m/z): [M−H]⁻ 394.0, ¹H-NMR (400 MHz, DMSO-$d_6$, ppm): δ10.39 (s, 1H), δ8.48-8.47 (d, J=1.6 Hz, 1H), δ8.25-8.23 (m, 1H), δ7.72-7.69 (m, 1H), δ7.67-7.63 (m, 1H), δ7.49-7.39 (m, 6H), δ7.37-7.33 (m, 1H), δ7.27-7.22 (m, 1H), δ7.09-6.96 (m, 1H).

Example 37. Synthesis of 5-bromo-3-chloro-2-hydroxy-N-(2-methoxy-5-phenylphenyl)benzene-1-sulfonamide, I-21

Synthesis of Compound 37.1

Into a 50-mL round-bottom flask, was placed 4-bromo-2-chlorophenol (1 g, 4.82 mmol, 1.00 equiv), chlorosulfonic acid (10 mL). The resulting solution was stirred for 2 h at room temperature. The reaction was then quenched by the addition of water (10 mL). The resulting solution was extracted with (3×10 mL) of ethyl acetate and the organic layers combined and concentrated under vacuum. This resulted in 1.1 g (crude) of 37.1 as a brown solid.

Synthesis of I-21

Into a 50-mL round-bottom flask, was placed 2-methoxy-6-phenylaniline (468 mg, 2.35 mmol, 1.20 equiv), pyridine (10 mL), 37.1 (600 mg, 1.96 mmol, 1.00 equiv). The resulting solution was stirred for 4 h at room temperature. The resulting mixture was washed with 1 M hydrogen chloride (aq.). The resulting solution was extracted with (3×10 mL) of ethyl acetate and the organic layers combined and concentrated under vacuum. The residue was applied onto Prep-TLC with ethyl acetate/petroleum ether (1:5). This resulted in 158.3 mg (17%) of I-21 as a light yellow solid. (ES, m/z): [M+H]⁺ 467.9, ¹H-NMR (300 MHz, DMSO-$d_6$, ppm): δ7.89-7.88 (d, J=2.1 Hz, 1H), δ7.64-7.63 (d, J=2.4 Hz, 1H), δ7.54-7.42 (m, 6H), δ7.36-7.31 (m, 1H), δ7.07-7.04 (d, J=8.4 Hz, 1H), δ3.66 (s, 3H), δ2.08 (s, 2H).

Example 38. Synthesis of 3-chloro-N-(2-methoxy-5-phenylphenyl)-5-(2H-1,2,3,4-tetrazol-5-yl)benzene-1-sulfonamide, I-38

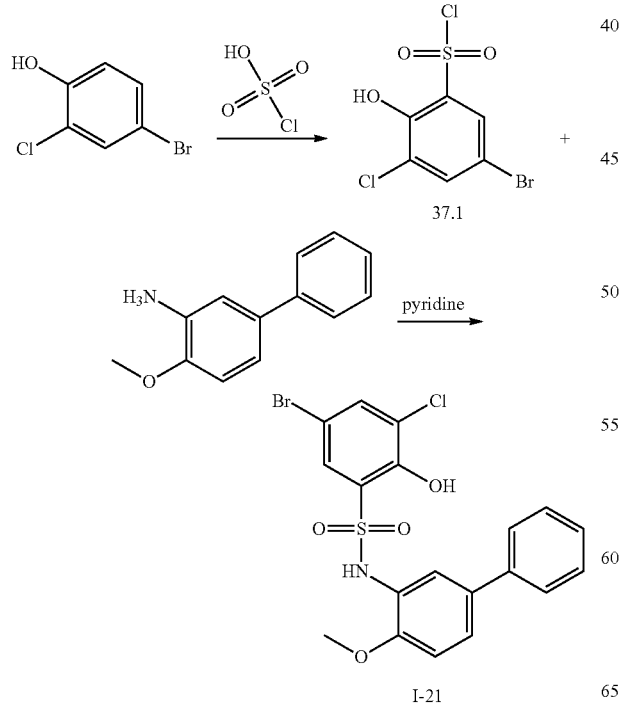

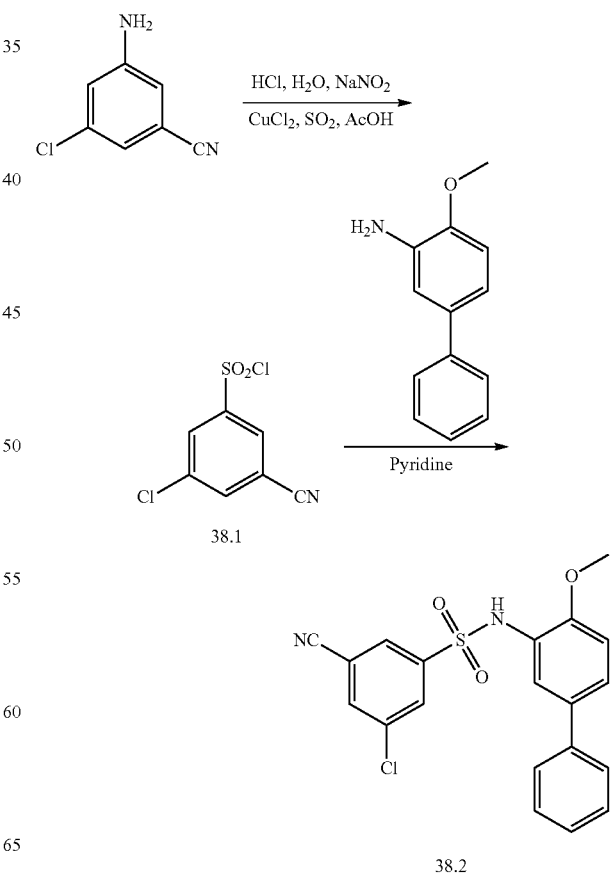

305

-continued

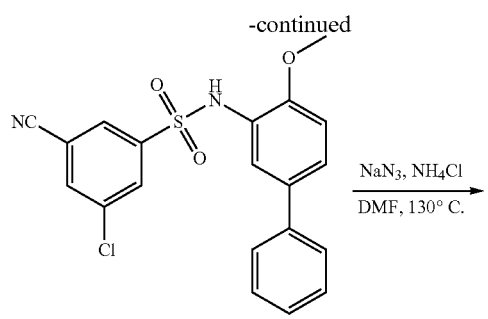

38.2

NaN₃, NH₄Cl
―――――――→
DMF, 130° C.

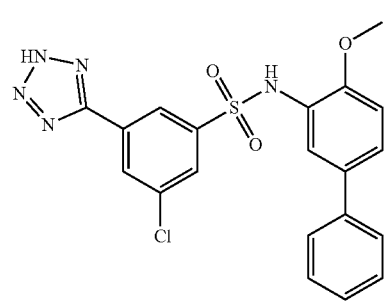

I-38

Synthesis of Compound 38.1

A solution of NaNO₂ (940 mg, 13.65 mmol, 1 equiv) in water (3 mL) was added to a suspension of 3-amino-5-chlorobenzonitrile (2.0 g, 13.16 mmol, 1 equiv) in 6 M HCl (12.5 mL) and water (12.5 mL) at 0° C. over 5 mins. After the completion of addition, the resulting solution was stirred for a further 30 mins. Meanwhile, AcOH (15.5 mL) was saturated with SO₂, then CuCl₂ (130 mg, 1.10 mmol, 0.08 equiv) was added and SO₂ bubbled through for a further 5 mins. The AcOH mixture was cooled to 5° C., then the above diazonium solution added over 5 mins. The resulting mixture was stirred for a further 1 h at 0° C. then 1 h at room temperature. The solution was diluted with water (20 mL) and extracted with CH₂Cl₂ (3×20 mL). The combined organic extracts were washed twice with water, dried (Na₂SO₄) and concentrated under vacuum. This gave the title compound of 38.1 (3.0 g, 97%) as a white solid. (ES, m/z): [M−H]⁻ 233.9

Synthesis of 38.2

Into a 50-mL 3-necked round-bottom flask, was placed 2-methoxy-5-phenylaniline (2.18 g, 10.94 mmol, 1 equiv), pyridine (10 mL), 38.1 (3.1 g, 13.13 mmol, 1.2 equiv). The resulting solution was stirred overnight at 25° C. The pH value of the solution was adjusted to 7-8 with 1M HCl (aq.). The resulting solution was extracted with ethyl acetate (3×20 mL). The combined organic layers were washed with H₂O and concentrated under vacuum. The residue was applied onto a silica gel column with ethyl acetate/petroleum ether (1:10) and purified by crystallization with ethyl acetate/petroleum ether (1:30). This resulted in 3.1 g (71.04%) of 38.2 as a grey solid. (ES, m/z): [M−H]⁻ 396.9, ¹H-NMR (400 MHz, DMSO-d₆, ppm): δ10.17 (s, 1H), δ8.38-8.37 (d, J=1.6 Hz, 1H), δ8.11-8.10 (d, J=1.6 Hz, 1H), δ8.06-8.05 (d, J=1.6 Hz, 1H), δ7.59-7.43 (m, 6H), δ7.36-7.32 (m, 1H), δ7.06-7.04 (d, J=8.4 Hz, 1H), δ3.53 (s, 3H).

306

Synthesis of I-38

Into a 50-mL round-bottom flask, was placed 38.2 (200 mg, 0.50 mmol, 1 equiv), NH₄Cl (107.3 mg, 2.01 mmol, 4 equiv), DMF (10 mL), NaN₃ (97.8 mg, 1.50 mmol, 3 equiv). The resulting solution was stirred overnight at 130° C. The solids were filtered out. The resulting mixture was concentrated under vacuum. The crude product was purified by Flash-Prep-HPLC with the following conditions (IntelFlash-1): Column, C18; mobile phase, MeCN/H₂O=10% increasing to MeCN/H₂O=70% within 16 mins; Detector, UV 220 nm. This resulted in 146.8 mg (66.25%) of I-38 as an orange solid. (ES, m/z): [M−H]⁻ 440.0, ¹H-NMR (400 MHz, CD₃OD, ppm): δ8.39-8.38 (t, J=1.2 Hz, 1H), δ8.25-8.24 (t, J=1.6 Hz, 1H), δ7.83-7.82 (t, J=2.0 Hz, 1H), δ7.69-7.68 (d, J=2.0 Hz, 1H), δ7.55-7.52 (m, 2H), δ7.42-7.37 (m, 3H), δ7.32-7.27 (m, 1H), δ6.91-6.88 (d, J=7.2 Hz, 1H), δ3.54 (s, 3H).

Example 39. Synthesis of 3-chloro-4-methoxy-5-(N-(4-methoxy-[1,1'-biphenyl]-3-yl)sulfamoyl)benzoic Acid, I-39

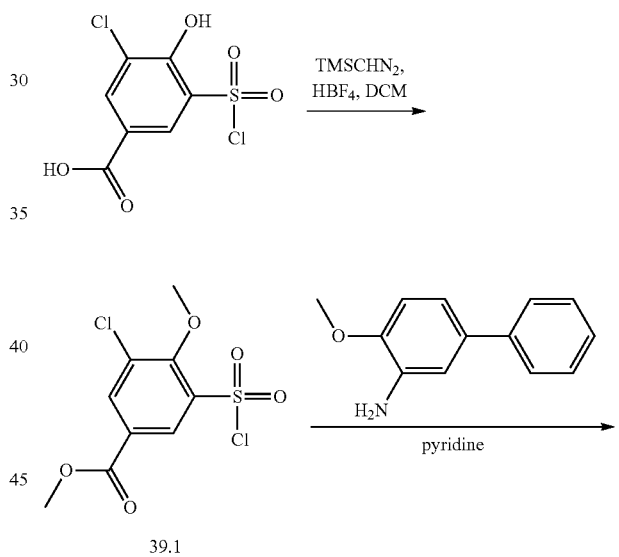

39.1

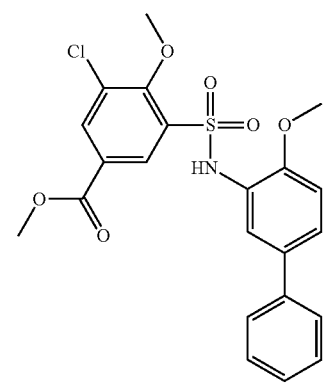

39.2

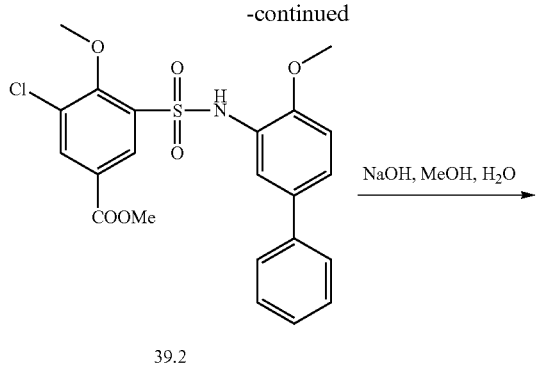

39.2

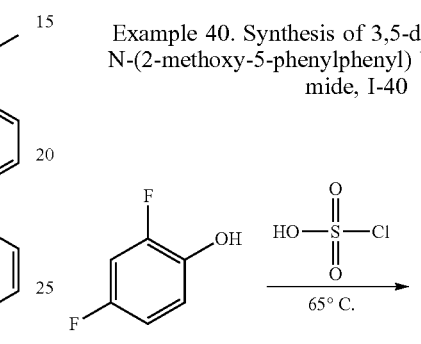

I-39

Synthesis of Compound 39.1

Into a 50-mL 3-necked round-bottom flask was placed 3-chloro-5-(chlorosulfonyl)-4-hydroxybenzoic acid (200 mg, 0.74 mmol, 1 equiv), DCM (5 mL), HBF$_4$ (244 mg, 1.11 mmol, 1.5 equiv), TMSCHN$_2$ (1.48 mL, 2 M, 4 equiv). The resulting solution was stirred for 2 h at 0° C. The reaction was then quenched by the addition of water (5 mL). The resulting solution was extracted with dichloromethane (3×5 mL) and the combined organic layers were concentrated under vacuum. This resulted in 170 mg (77.03%) of 39.1 as a light yellow solid.

Synthesis of 39.2

Into a 25-mL round-bottom flask, was placed methyl 39.1 (170 mg, 0.57 mmol, 1 equiv), 2-methoxy-5-phenylaniline (135.9 mg, 0.68 mmol, 1.2 equiv), pyridine (3 mL). The resulting solution was stirred for 4 h at room temperature. The resulting mixture was washed with 1 M HCl (aq.). The resulting solution was extracted with ethyl acetate (3×5 mL) and the combined organic layers were concentrated under vacuum. The crude product was purified by Flash-Prep-HPLC with the following conditions (IntelFlash-1): Column, C 18; mobile phase, ACN/H$_2$O (0.1% NH$_4$HCO$_3$)=0 increasing to ACN/H$_2$O (0.1% NH$_4$HCO$_3$)=1/1 within 25; Detector, UV 254 nm. This resulted in 13.4 mg (5.10%) of 39.2 as a white solid. (ES, m/z): [M−H]$^-$ 460.0, $^1$H-NMR (400 MHz, DMSO-d$_6$, ppm): δ9.77 (s, 1H), δ8.24-8.23 (d, J=2.4 Hz, 1H), δ8.16-8.15 (d, J=2.4 Hz, 1H), δ7.55-7.52 (m, 2H), δ7.49-7.42 (m, 4H), δ7.35-7.31 (m, 1H), δ7.03-7.00 (m, 1H), δ4.01 (s, 3H), δ3.85 (s, 3H), δ3.53 (s, 3H).

Synthesis of I-39

Into a 8-mL vial, 39.2 (240 mg, 0.52 mmol, 1 equiv) in MeOH (5 mL) and H$_2$O (1 mL) was added NaOH (41.6 mg, 1.04 mmol, 2 equiv), followed by stirring at room temperature for 12 h. The reaction was then quenched by the addition of 5 mL of 1 M HCl. The resulting solution was extracted with ethyl acetate (3×10 mL) and the combined organic layers were concentrated under vacuum. The residue was purified using a silica gel column (elution solvent: dichloromethane/methanol=20:1) to afford I-39 (131.4 mg, 56.46%) as a white solid. (ES, m/z): [M−H]$^-$ 446.2, $^1$H-NMR (300 MHz, CDCl$_3$, ppm): δ3.71 (s, 3H), δ4.18 (s, 3H), δ6.77-6.80 (d, J=8.4 Hz, 1H), δ7.25-7.27 (m, 1H), δ7.28-7.31 (m, 1H), δ7.36-7.41 (t, J=7.8 Hz, 2H), δ7.48-7.51 (m, 2H), δ7.56 (s, 1H), δ7.75-7.76 (d, J=2.1 Hz, 1H), δ8.24 (s, 1H), δ8.42 (s, 1H).

Example 40. Synthesis of 3,5-difluoro-2-hydroxy-N-(2-methoxy-5-phenylphenyl) benzene-1-sulfonamide, I-40

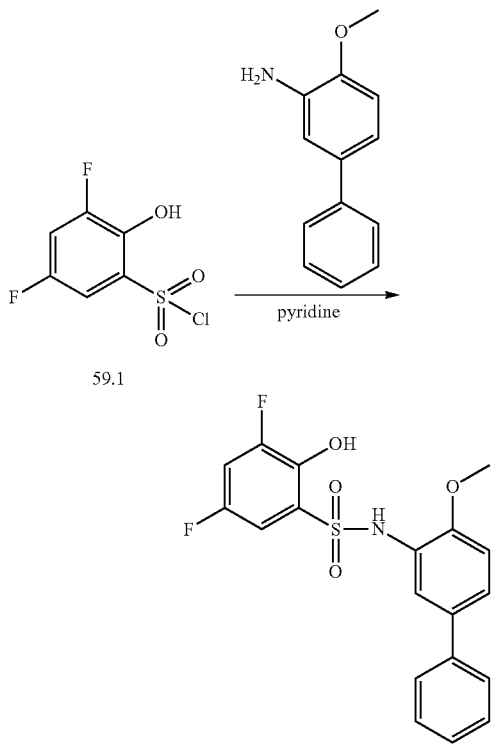

I-40

Synthesis of Compound 59.1

Into a 50-mL 3-necked round-bottom flask, was placed O-(chlorosulfonyl)oxidanol (5 mL), 2,4-difluorophenol (2 g, 15.37 mmol, 1 equiv) at 0° C. The resulting solution was stirred for 5 min at 0° C. The resulting solution was stirred for 3 h at 25° C. The reaction was then quenched by the addition of 15 mL of water/ice. The resulting solution was extracted with 3×30 mL of ethyl acetate and the organic layers combined and concentrated under vacuum. This resulted in 1.38 g (39.27%) of 59.1 as a yellow solid.

Synthesis of I-40

Into a 50-mL round-bottom flask, was placed 59.1 (560 mg, 2.45 mmol, 1 equiv), 2-methoxy-5-phenylaniline (590.6 mg, 2.96 mmol, 1.21 equiv), pyridine (6 mL). The resulting solution was stirred for 2 h at 25° C. The reaction was then quenched by the addition of 15 mL of diluted hydrochloric acid (aq.). The resulting solution was extracted with 3×30 mL of ethyl acetate and the combined organic layers were concentrated under vacuum. The residue was applied onto Prep-TLC with dichloromethane/methanol (20:1). The crude product was purified by Flash-Prep-HPLC with the following conditions (IntelFlash-1): Column, C18; mobile phase, $H_2O$:ACN=15% increasing to $H_2O$:ACN=60% within 15; Detector, UV 254/220 nm. This resulted in 115.3 mg (12.03%) of I-40 as a white solid. (ES, m/z): [M−H]⁻ 390.0, $^1$H-NMR (400 MHz, DMSO-$d_6$, ppm): δ3.67 (s, 3H), δ7.03-7.05 (d, J=8.8 Hz, 1H), δ7.23-7.25 (d, J=8.0 Hz, 1H), δ7.31-7.34 (m, 1H), δ7.38-7.50 (m, 3H), δ7.51-7.57 (m, 4H).

Example 41. Synthesis of 3,5-dichloro-N-(2,4-difluoro-5-phenylphenyl)-2-hydroxybenzene-1-sulfonamide, I-41

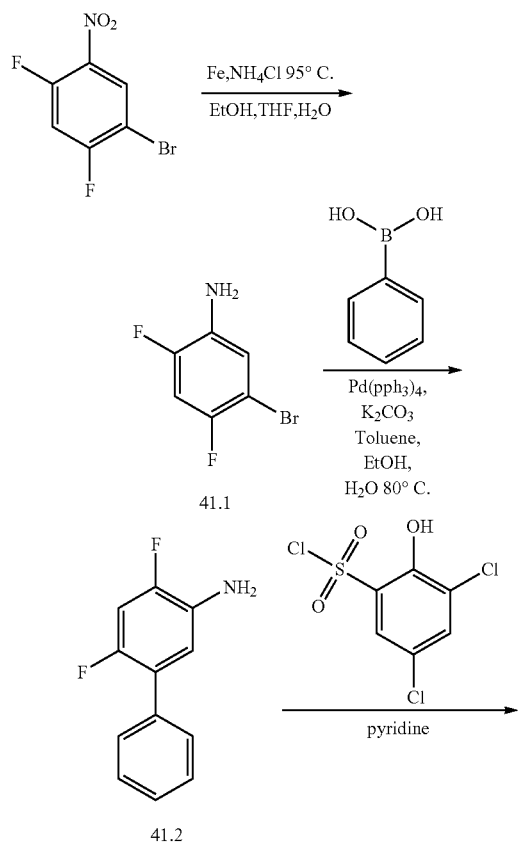

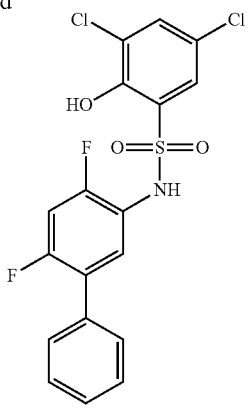

I-41

Synthesis of Compound 41.1

Into a 500-mL 3-necked round-bottom flask, was placed 1-bromo-2,4-difluoro-5-nitrobenzene (5.04 g, 21.18 mmol, 1 equiv), $H_2O$ (25 mL), THF (50 mL), EtOH (100 mL), $NH_4Cl$ (25 mL), Fe (5.0 g, 88.95 mmol, 4.2 equiv). The resulting solution was stirred for 1.5 h at 95° C. The resulting solution was extracted with 3×100 mL of ethyl acetate and the organic layers combined and concentrated under vacuum. The residue was applied onto a silica gel column with ethyl acetate/petroleum ether (10:1). This resulted in 2.6 g (59.02%) of 41.1 as a black solid.

Synthesis of Compound 41.2

Into a 100-mL 3-necked round-bottom flask, was placed toluene (7 mL), ethanol (7 mL), water (7 mL), 41.1 (2 g, 9.62 mmol, 1 equiv), phenylboronic acid (1.4 g, 11.54 mmol, 1.2 equiv), potassium methaneperoxoate (6.7 g, 48.08 mmol, 5 equiv), Pd(PPh₃)₄ (2.2 g, 1.92 mmol, 0.2 equiv). The resulting solution was stirred overnight at 80° C. The resulting mixture was concentrated under vacuum. The residue was applied onto a silica gel column with ethyl acetate/petroleum ether (20:1). This resulted in 900 mg (45.61%) of 41.2 as a yellow solid.

Synthesis of I-41

Into a 50-mL round-bottom flask, was placed 41.2 (300 mg, 1.46 mmol, 1.2 equiv), 3,5-dichloro-2-hydroxybenzene-1-sulfonyl chloride (317 mg, 0.877 mmol, 1 equiv), pyridine (5 mL). The resulting solution was stirred for 2 h at 25° C. The reaction was then quenched by the addition of 15 mL of diluted hydrochloric acid (aq.). The resulting solution was extracted with 3×25 mL of ethyl acetate and the organic layers combined and concentrated under vacuum. The residue was applied onto Prep-TLC with dichloromethane/methanol (20:1). This resulted in 226.9 mg (43.51%) of I-41 as a light yellow solid. (ES, m/z): [M−H]⁻ 427.9, $^1$H-NMR (400 MHz, DMSO-$d_6$, ppm): δ7.31-7.49 (m, 8H), δ7.63-7.66 (s, 1H).

Example 42. Synthesis of Methyl 3-chloro-4-methoxy-5-(N-(2-methoxy-5-(pyridine-3-yl)phenyl)sulfamoyl)benzoate, I-42

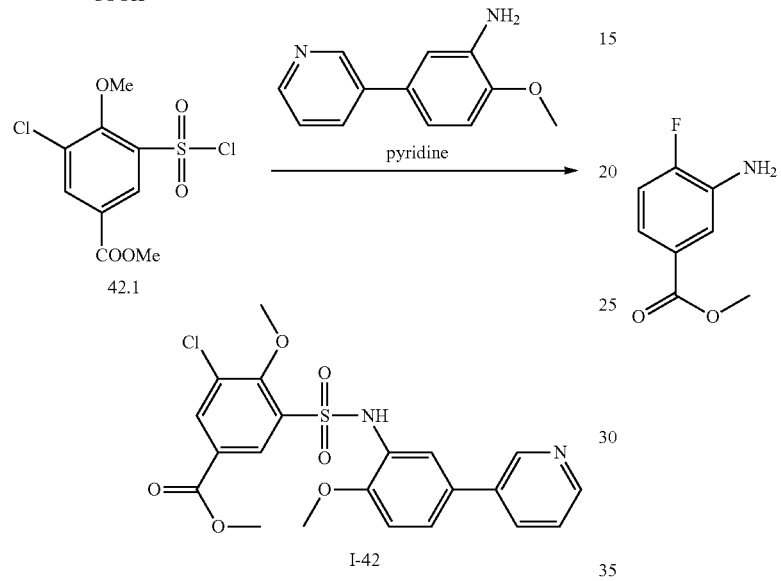

Synthesis of Compound 42.1

Into a 50-mL 3-necked round-bottom flask purged and maintained with an inert atmosphere of nitrogen, was placed 3-chloro-5-(chlorosulfonyl)-4-hydroxybenzoic acid (800 mg, 2.95 mmol, 1 equiv), DCM (3 mL), HBF$_4$ (1036.6 mg, 11.80 mmol, 4 equiv), TMSCHN$_2$ (505.6 mg, 4.43 mmol, 1.5 equiv). The resulting solution was stirred for 2 h at 0° C. The reaction was then quenched by the addition of water (10 mL). The resulting solution was extracted with dichloromethane (3×10 mL) and concentrated under vacuum. This resulted in 660 mg (74.76%) of 42.1 as a white solid.

Synthesis of I-42

Into a 50-mL round-bottom flask was placed 42.1 (660 mg, 2.21 mmol, 1 equiv), 2-methoxy-5-(pyridin-3-yl)aniline (530.2 mg, 2.65 mmol, 1.2 equiv), pyridine (10 mL). The resulting solution was stirred for 6 h at room temperature. The resulting mixture was concentrated. The crude product was purified by Flash-Prep-HPLC with the following conditions (IntelFlash-1): Column, C 18; mobile phase, ACN/H$_2$O (0.1% NH$_4$HCO$_3$)=0 increasing to ACN/H$_2$O (0.1%°NH$_4$HCO$_3$)=6/4 within 30; Detector, UV 254 nm. This resulted in 470 mg (46.02%) of I-42 as a yellow solid. (ES, m/z): [M+H]$^+$ 463.2, $^1$H-NMR (400 MHz, DMSO-d$_6$, ppm): δ9.85 (s, 1H), δ8.78-8.77 (d, J=2.0 Hz, 1H), δ8.54-8.53 (m, 1H), δ8.23-8.22 (d, J=2.0 Hz, 1H), δ8.16-8.15 (d, J=2.4 Hz, 1H), δ7.97-7.94 (m, 1H), δ7.56-7.54 (m, 2H), δ7.48-7.44 (m, 1H), δ7.06-7.04 (t, J=2.4 Hz, 1H), δ4.00 (s, 3H), δ3.85 (s, 3H), δ3.53 (s, 3H).

Example 43. Synthesis of Methyl 3-((3,5-dichloro-2-hydroxyphenyl) sulfonamido)-4-fluorobenzoate, I-43

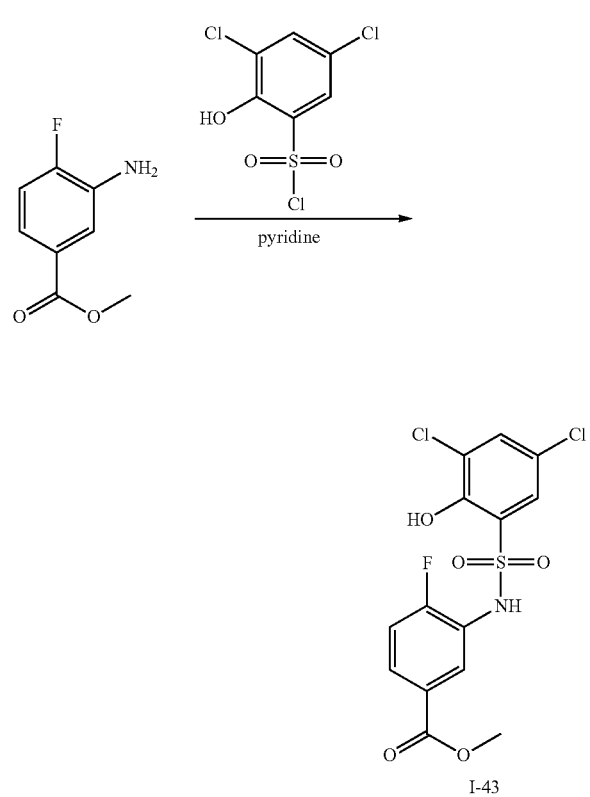

Synthesis of I-43

To a stirred solution of 3,5-dichloro-2-hydroxybenzene-1-sulfonyl chloride (2 g, 7.65 mmol, 1 equiv) and methyl 3-amino-4-fluorobenzoate (1.6 g, 9.46 mmol, 1.2 equiv) in pyridine (20 mL) at room temperature under nitrogen atmosphere. The resulting mixture was stirred for 1 h at room temperature. The reaction was quenched by the addition of water/ice (10 mL) at room temperature. The aqueous layer was extracted with EtOAc (2×30 mL). The combined organic layers were washed with 2×20 mL of 1 M HCl and concentrated under reduced pressure. The crude product was purified by Prep-TLC (CH$_2$Cl$_2$/MeOH=50:1). This resulted in 1-43 (900 mg, 29.85%) as a white solid. (ES, m/z): [M−H]$^-$ 391.9, $^1$H-NMR (400 MHz, DMSO-d$_6$, ppm): δ3.82 (s, 3H), δ7.11 (br s, 2H), δ7.21-7.25 (m, 1H), δ7.44-7.50 (m, 2H), δ7.57-7.58 (d, J=2.8 Hz, 1H), δ7.95-7.97 (m, 1H).

313

Example 44. Synthesis of 3-bromo-5-chloro-4-hydroxy-N-(2-methoxy-5-phenylphenyl)benzene-1-sulfonamide, I-44

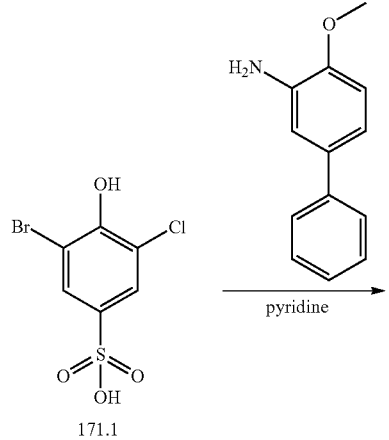

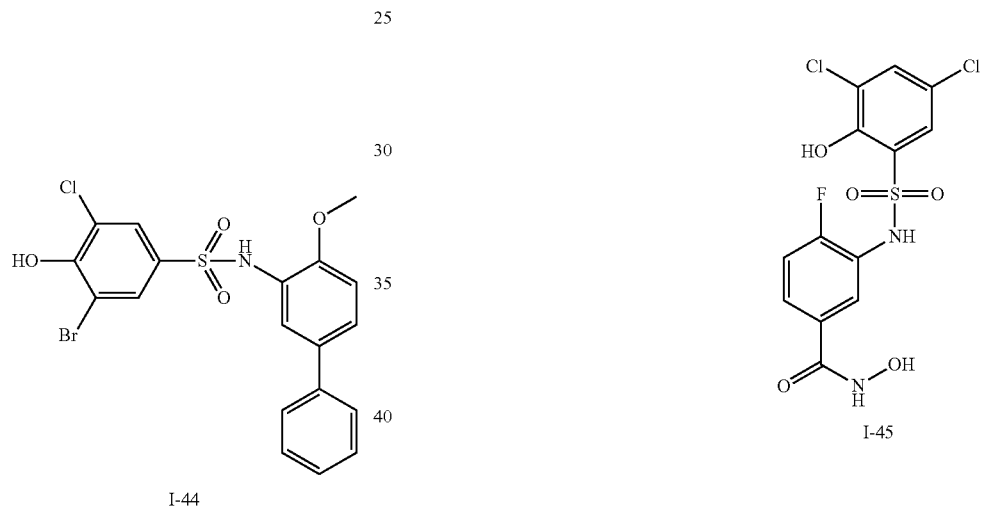

Synthesis of I-44

Into a 50-mL round-bottom flask, was placed 3-bromo-5-chloro-4-hydroxybenzene-1-sulfonic acid (555 mg, 1.93 mmol, 1 equiv), 2-methoxy-5-phenylaniline (461.5 mg, 2.32 mmol, 1.2 equiv), pyridine (10 mL). The resulting solution was stirred for 2 h at 25° C. The reaction was then quenched by the addition of 20 mL of 1M hydrochloric acid (aq.). The resulting solution was extracted with 3×30 mL of ethyl acetate and the organic layers combined and concentrated under vacuum. The residue was purified by Prep-TLC with dichloromethane/methanol (20:1). This resulted in 62.0 mg (6.85%) of I-44 as a white solid. (ES, m/z): [M+H]$^+$ 467.9, $^1$H-NMR (400 MHz, DMSO-d$_6$, ppm): δ3.63 (s, 3H), δ7.03-7.06 (d, J=9.2 Hz, 1H), δ7.32-7.35 (m, 1H), δ7.45-7.47 (m, 4H), δ7.53-7.55 (d, J=6.4 Hz, 2H), δ7.64-7.65 (s, 1H), δ7.76-7.77 (s, 1H), δ9.61 (s, 1H).

314

Example 45. Synthesis of 3-[(3,5-dichloro-2-hydroxybenzene)sulfonamido]-4-fluoro-N-hydroxybenzamide, I-45

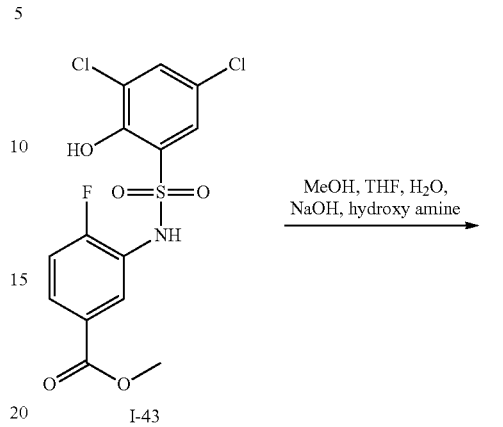

Synthesis of I-45

Into a 50-mL round-bottom flask, was placed I-43 (150 mg, 0.38 mmol, 1 equiv), MeOH (15 mL), THF (2 mL), hydroxylamine (50% aqua) (0.8 mL), a solution of NaOH (152.3 mg, 3.81 mmol, 10 equiv) in H$_2$O (0.6 mL). The resulting solution was stirred for 3 h at room temperature. The pH value of the solution was adjusted to 8-9 with 1M HCl (aq.). The resulting mixture was concentrated. The crude product (200 mg) was purified by Prep-HPLC with the following conditions (2 #-AnalyseHPLC-SHIMADZU (HPLC-10)): Column, XBridge Prep C18 OBD Column, 19*150 mm 5 um; mobile phase, water (10 mmol/L, NH$_4$HCO$_3$) and ACN (14% Phase B up to 20% in 17 min); Detector, UV 254/220 nm. Rt: 13.53 min. This resulted in 31.3 mg (20.8%) of I-45 as a light grey solid. (ES, m/z): [M−H]$^−$ 393.1, $^1$H-NMR (300 MHz, DMSO-d$_6$, ppm): δ7.11-7.20 (m, 3H), δ7.31-7.39 (m, 1H), δ7.50-7.51 (d, J=2.7 Hz, 1H), δ7.73-7.76 (m, 1H), δ11.14 (s, 1H).

Example 46. Synthesis of 2-(2-bromo-4-chloro-6-(N-(4-fluoro-[1,1'-biphenyl]-3-yl)sulfamoyl)phenoxy)acetic Acid, I-46

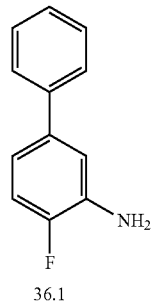

36.1

NaH, BnBr, THF →

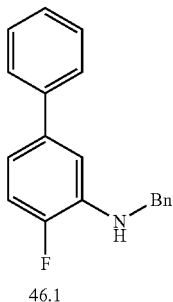

46.1

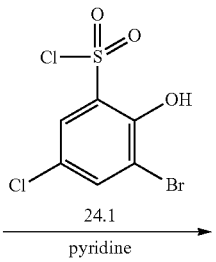

24.1 pyridine →

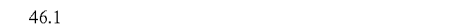

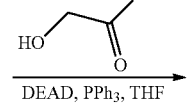

46.2

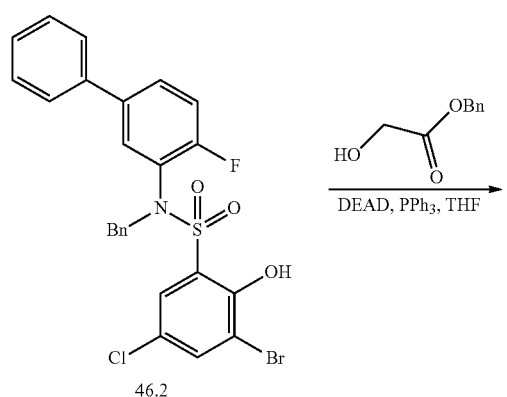

DEAD, PPh₃, THF →

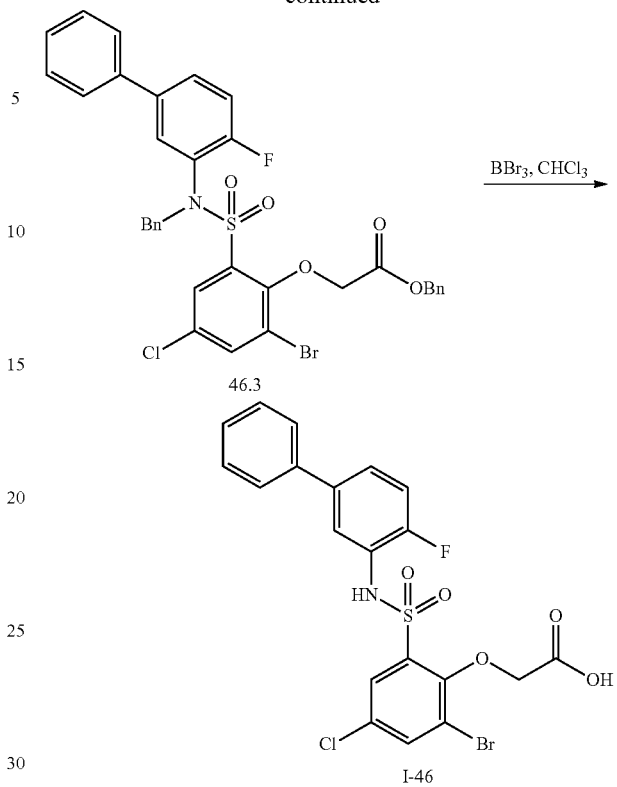

Synthesis of Compound 46.1

Into a 250-mL 3-necked round-bottom flask purged and maintained with an inert atmosphere of nitrogen, was placed 36.1 (4.0 g, 21.37 mmol, 1 equiv) in THF (10 mL), then to the solution was added NaH (1.0 g, 25 mmol, 1.12 equiv) at 0° C. The resulting mixture was stirred at 0° C. for 0.5 h, then to the mixture was added BnBr (5.5 g, 32.05 mmol, 1.5 equiv). The resulting solution was stirred for 12 h at 50° C. The reaction was then quenched by the addition of 50 mL of sat.NH₄Cl (aq.). The resulting solution was extracted with 3×50 mL of ethyl acetate. The combined organic layers were washed with 50 mL of brine, dried and concentrated under vacuum. The residue was applied onto a silica gel column with ethyl acetate/petroleum ether (1:5). This resulted in 4.0 g (70%) of 46.1 as yellow oil. (ES, m/z): [M+H]⁺ 278.1.

Synthesis of Compound 46.2

Into a 100-mL 3-necked round-bottom flask purged and maintained with an inert atmosphere of nitrogen, was placed 46.1 (1.0 g, 3.61 mmol, 1.00 equiv), 24.1 (0.7 g, 2.41 mmol, 1.20 equiv), and pyridine (10 mL). The resulting solution was stirred for 0.5 h at room temperature. The resulting mixture was concentrated under vacuum. The residue was applied onto a silica gel column with ethyl acetate/petroleum ether (1:5). This resulted in 0.7 g (36%) of 46.2 as a white solid. (ES, m/z): [M−H]⁻ 543.9.

Synthesis of Compound 46.3

Into a 100-mL round-bottom flask purged and maintained with an inert atmosphere of nitrogen, was placed 46.2 (400 mg, 0.73 mmol, 1.00 equiv), DEAD (260 mg, 1.49 mmol, 2.00 equiv), PPh$_3$ (380 mg, 1.45 mmol, 2.00 equiv), tetrahydrofuran (10 mL), benzyl 2-hydroxyacetate (180 mg, 1.08 mmol, 1.50 equiv). The resulting solution was stirred for 12 h at room temperature. The resulting solution was extracted with 3×10 mL of ethyl acetate. The organic layers were combined, washed with 10 mL of brine, dried and concentrated under vacuum. The residue was applied onto a silica gel column with ethyl acetate/petroleum ether (1:5). This resulted in 230 mg (45%) of 46.3 as a white solid. (ES, m/z): [M−H]$^-$ 692.0

Synthesis of I-46

Into a 100-mL round-bottom flask purged and maintained with an inert atmosphere of nitrogen, was placed 46.3 (100 mg, 0.14 mmol, 1 equiv), BBr$_3$ (36.0 mg, 0.14 mmol, 1 equiv), CHCl$_3$ (10 mL). The resulting solution was stirred for 2 h at room temperature. The reaction was then quenched by the addition of 10 mL of water/ice. The resulting solution was extracted with 3×10 mL of dichloromethane. The combined organic layers were washed with 10 mL of brine, dried and concentrated under vacuum. The residue was applied onto a silica gel column with ethyl acetate/petroleum ether (1:0). This resulted in 12 mg (16%) of I-46 as a white solid (ES, m/z): [M+H$_2$O]$^+$533.1, $^1$H-NMR (400 MHz, DMSO-d$_6$, ppm): δ8.00 (s, 1H), δ7.71-7.70 (d, J=2.8 Hz, 1H), δ7.45-7.41 (m, 4H), δ7.38-7.29 (m, 3H), δ7.18-7.12 (m, 2H), δ4.52 (s, 2H).

Example 47. Synthesis of Methyl 3-chloro-5-(N-(4-fluoro-[1,1'-biphenyl]-3-yl)sulfamoyl)-4-hydroxybenzoate, I-47

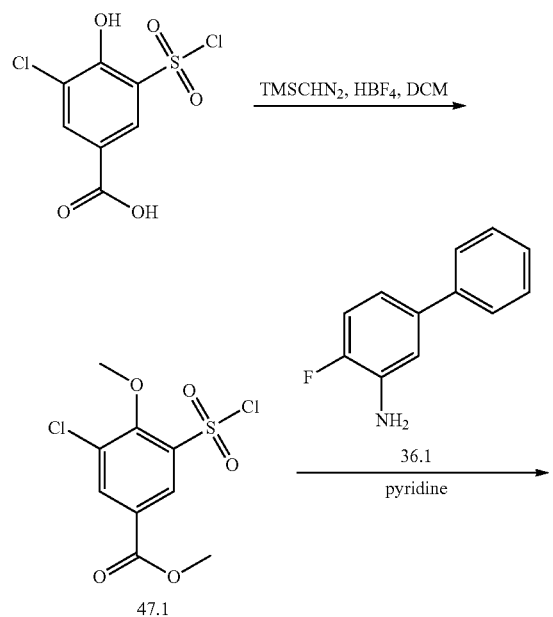

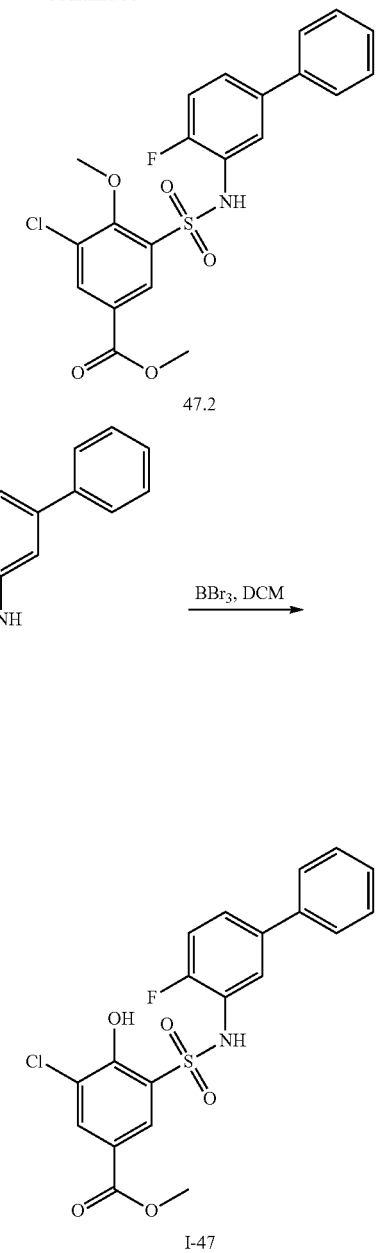

Synthesis of Compound 47.1

Into a 100-mL round-bottom flask purged and maintained with an inert atmosphere of argon, was placed 3-chloro-5-(chlorosulfonyl)-4-hydroxybenzoic acid (1000 mg, 3.69 mmol, 1 equiv), TMSCHN$_2$ (1685.5 mg, 14.76 mmol, 4 equiv), HBF$_4$ (647.9 mg, 7.38 mmol, 2 equiv), DCM (20 mL). The resulting solution was stirred for 0.5 h at 0° C. in a water/ice bath. The resulting solution was extracted with 3×20 mL of dichloromethane. The combined organic layers were washed with 20 mL of brine, dried and concentrated under vacuum. The residue was applied onto a silica gel column with ethyl acetate/petroleum ether (1:1). This resulted in 800 mg (73%) of 47.1 as a white solid. (ES, m/z): [M−H]$^-$ 296.9.

Synthesis of Compound 47.2

Into a 100-mL round-bottom flask purged and maintained with an inert atmosphere of nitrogen, was placed 47.1 (500 mg, 1.67 mmol, 1 equiv), 36.1 (375.5 mg, 2.01 mmol, 1.2 equiv), pyridine (10 mL). The resulting solution was stirred for 0.5 h at room temperature. The resulting mixture was concentrated. The residue was applied onto a silica gel column with ethyl acetate/petroleum ether (1:5). This resulted in 161 mg (20%) of 47.2 as a white solid. (ES, m/z): [M−H]⁻ 448.0.

Synthesis of I-47

Into a 100-mL round-bottom flask purged and maintained with an inert atmosphere of nitrogen, was placed 47.2 (120 mg, 0.27 mmol, 1 equiv), BBr$_3$ (200.5 mg, 0.80 mmol, 3 equiv), DCM (10 mL). The resulting solution was stirred for 12 h at room temperature. The reaction was then quenched by the addition of 10 mL of water/ice. The resulting solution was extracted with 3×10 mL of dichloromethane. The combined organic layers were washed with 10 mL of brine, dried and concentrated under vacuum. The residue was applied onto a silica gel column with ethyl acetate/petroleum ether (1:2). This resulted in 92.7 mg (80%) of I-47 as a white solid. (ES, m/z): [M−H]⁻ 434.0, ¹H-NMR (400 MHz, DMSO-d$_6$, ppm): δ8.01-8.00 (d, J=2.0 Hz, 1H), δ7.89-7.88 (d, J=1.6 Hz, 1H), δ7.53-7.33 (m, 6H), δ7.27-7.21 (m, 1H), δ7.08 (s, 1H), δ6.95 (s, 2H), δ3.73 (s, 3H).

Example 48. Synthesis of Methyl 3-chloro-4-hydroxy-5-(N-(2-methoxy-5-(pyridin-3-yl)phenyl)sulfamoyl)benzoate, I-48

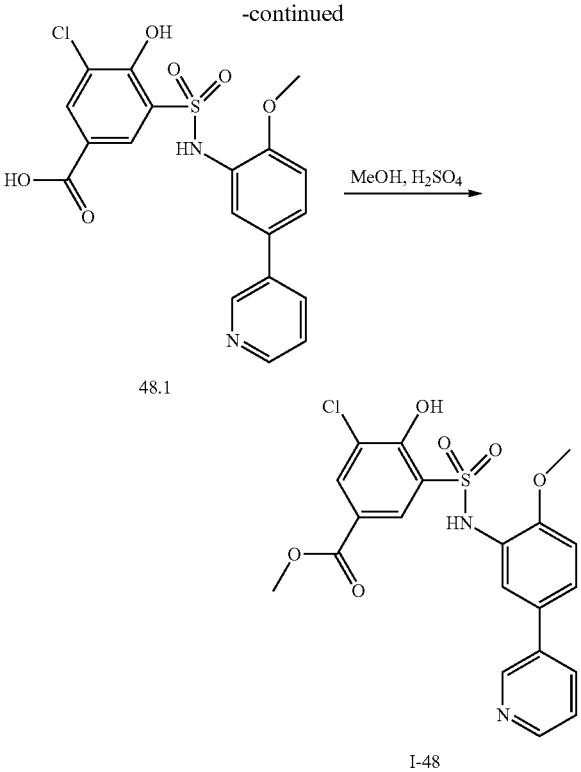

Synthesis of 48.1

Into a 8-mL vial purged and maintained with an inert atmosphere of nitrogen, was placed 3-chloro-5-(chlorosulfonyl)-4-hydroxybenzoic acid (200 mg, 0.74 mmol, 1 equiv), 2-methoxy-5-(pyridin-3-yl)aniline (177.3 mg, 0.89 mmol, 1.2 equiv), pyridine (5 mL). The reaction solution was stirred for 5 h at room temperature. The resulting mixture was concentrated under vacuum. The crude product was purified by Prep-HPLC with the following conditions (2 #-AnalyseHPLC-SHIMADZU(HPLC-10)): Column: XBridge Prep OBD C18 Column 30×150 mm 5 um; Mobile Phase A: water (0.05% NH$_3$.H$_2$O), Mobile Phase B: ACN; Flow rate: 60 mL/min; Gradient: 5% B to 5% B in 7 min; Detector UV 254/220 nm; Rt: 8.88 min. This resulted in 82 mg (25.56%) of 48.1 as a white solid. (ES, m/z): [M+H]⁺ 434.9, ¹H-NMR (400 MHz, DMSO-d$_6$, ppm): δ3.78 (s, 3H), δ6.98-7.23 (m, 2H), δ7.33-7.35 (m, 1H), δ7.42-7.45 (m, 1H), δ7.62-7.63 (d, J=2.0 Hz, 1H), δ7.71 (s, 1H), δ7.84-7.87 (m, 1H), δ7.98-7.99 (d, J=2.4 Hz, 1H), δ8.51-8.53 (m, 1H), δ8.70 (s, 1H), δ11.95 (br s, 1H).

Synthesis of I-48

Into a 10-mL round-bottom flask purged and maintained with an inert atmosphere of argon, was placed 48.1 (50 mg, 0.11 mmol, 1 equiv), MeOH (2 mL), H$_2$SO$_4$ (22.6 mg, 0.23 mmol, 2 equiv). The resulting solution was stirred for 12 h at room temperature. The resulting solution was extracted with 3×10 mL of ethyl acetate. The combined organic layers were washed with 10 mL of brine, dried and concentrated under vacuum. The residue was applied onto a silica gel column with ethyl acetate/petroleum ether (1:5). This resulted in 25.5 mg (49%) of I-48 as a white solid. (ES, m/z): [M+H]⁺ 449.2, ¹H-NMR (400 MHz, DMSO-d$_6$, ppm): δ9.05

(br s, 1H), δ8.73 (s, 1H), δ8.54 (s, 1H), δ8.04-8.03 (d, J=2.0 Hz, 1H), δ7.92-7.85 (m, 2H), δ7.61 (s, 1H), δ7.48-7.39 (m, 2H), δ7.08-7.06 (d, J=8.8 Hz, 1H), δ3.74 (s, 3H), 3.72 (s, 3H).

Example 49. Synthesis of Methyl 3-chloro-5-(N-(4-fluoro-[1,1'-biphenyl]-3-yl)sulfamoyl)-4-methoxybenzoate, I-49

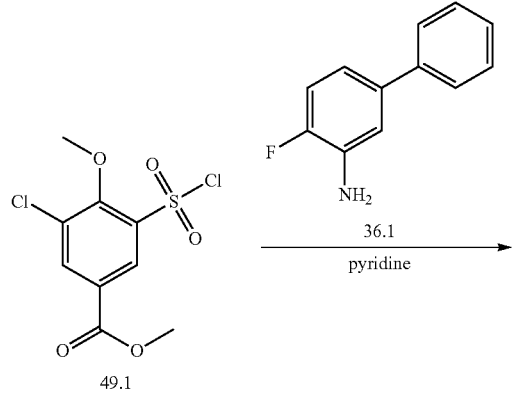

Synthesis of I-49

Into a 100-mL round-bottom flask purged and maintained with an inert atmosphere of nitrogen, was placed 49.1 (500 mg, 1.67 mmol, 1 equiv), 36.1 (375.5 mg, 2.01 mmol, 1.2 equiv), and pyridine (10 mL). The resulting solution was stirred for 0.5 h at room temperature. The resulting mixture was concentrated under vacuum. The residue was applied onto a silica gel column with ethyl acetate/petroleum ether (1:5). This resulted in 30.7 mg (4%) of I-49 as a white solid. (ES, m/z): [M−H]⁻ 448.0, ¹H-NMR (400 MHz, DMSO-d₆, ppm): δ10.50 (s, 1H), δ8.26-8.25 (d, J=2.4 Hz, 1H), δ8.21-8.20 (d, J=2.0 Hz, 1H), δ7.53-7.46 (m, 6H), δ7.40-7.36 (m, 1H), δ7.31-7.26 (m, 1H), δ4.00 (s, 3H), δ3.86 (s, 3H).

Example 50. Synthesis of 2,4-dichloro-6-(N-(4-fluoro-[1,1'-biphenyl]-3-yl)sulfamoyl)phenyl propionate, I-50

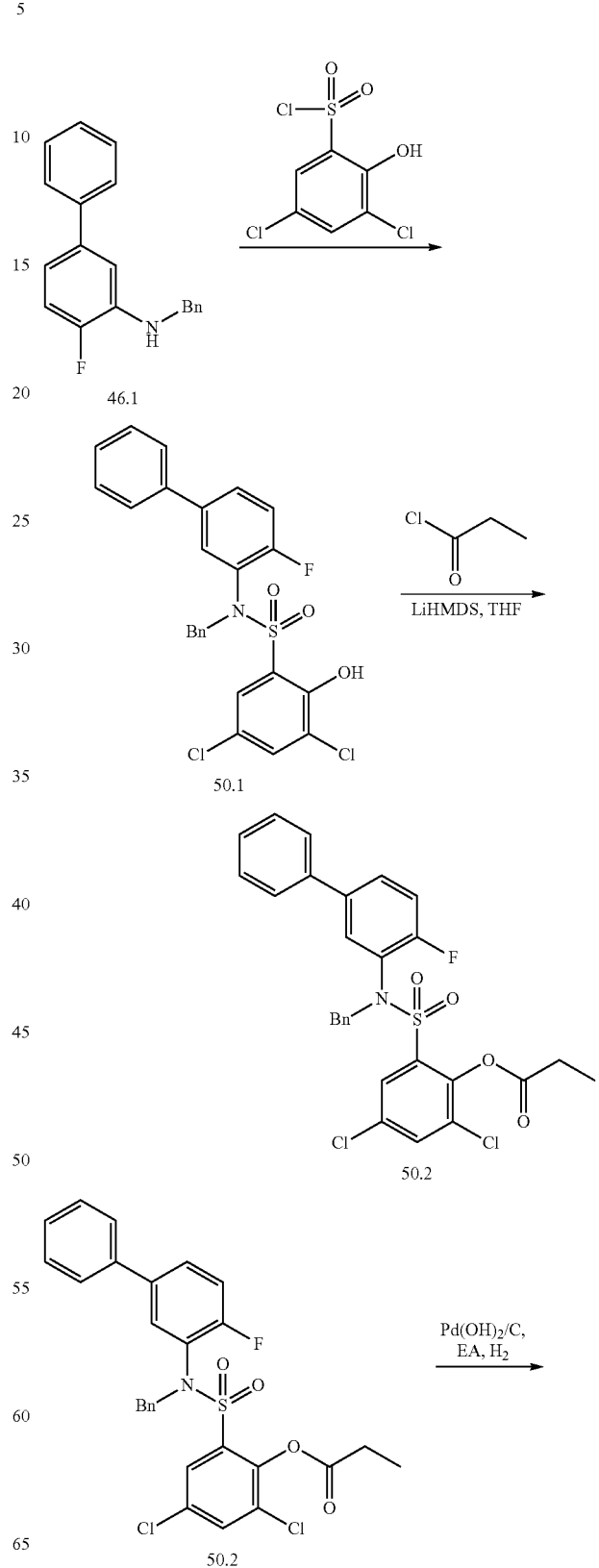

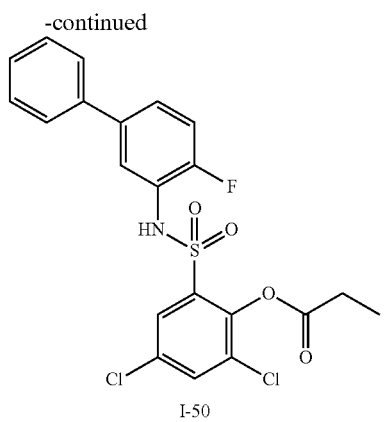

I-50

Synthesis of Compound 50.1

Into a 100-mL 3-necked round-bottom flask purged and maintained with an inert atmosphere of nitrogen, was placed 46.1 (2 g, 7.21 mmol, 1 equiv), 3,5-dichloro-2-hydroxybenzene-1-sulfonyl chloride (2.3 g, 8.66 mmol, 1.2 equiv), pyridine (20 mL). The resulting solution was stirred for 0.5 h at room temperature. The resulting mixture was concentrated. The residue was applied onto a silica gel column with ethyl acetate/petroleum ether (1:2). This resulted in 1.1 g (34%) of 50.1 as a white solid. (ES, m/z): [M−H]⁻ 500.1.

Synthesis of Compound 50.2

Into a 100-mL round-bottom flask purged and maintained with an inert atmosphere of nitrogen, was placed 50.1 (400 mg, 0.80 mmol, 1 equiv) in THF (10 mL), then to the solution was added dropwised LiHMDS (0.88 mL, 1 M in THF, 0.88 mmol, 1.1 equiv) at −78° C. After the addition, the solution was stirred at −78° C. for 0.5 h, and the solution was added propanoyl chloride (88.4 mg, 0.96 mmol, 1.2 equiv). The resulting solution was stirred for 12 h at room temperature. The resulting solution was diluted with 10 mL of water. The resulting solution was extracted with 3×10 mL of ethyl acetate. The combined organic layers were washed with 10 mL of brine, dried and concentrated under vacuum. The residue was applied onto a silica gel column with ethyl acetate/petroleum ether (1:1). This resulted in 180 mg (40%) of 50.2 as a white solid. (ES, m/z): [M−H]⁻ 556.0.

Synthesis of I-50

Into a 100-mL round-bottom flask purged and maintained with an inert atmosphere of nitrogen, was placed 50.2 (180 mg, 0.32 mmol, 1 equiv), Pd(OH)₂/C (50 mg), EA (20 mL). The resulting solution was stirred for 12 h at room temperature. The solids were filtered out. The resulting mixture was concentrated. The residue was applied onto a silica gel column with ethyl acetate/petroleum ether (1:1). This resulted in 31.9 mg (21%) of I-50 as a white solid. (ES, m/z): [M−H]⁻ 466.0, ¹H-NMR (400 MHz, DMSO-d₆, ppm): δ10.68 (s, 1H), δ8.18-8.17 (d, J=2.4 Hz, 1H), δ7.83-7.82 (d, J=2.4 Hz, 1H), δ7.58-7.55 (m, 3H), δ7.49-7.41 (m, 3H), δ7.39-7.32 (m, 2H), δ2.42-2.41 (m, 2H), δ1.02-0.98 (t, J=7.6 Hz, 3H). tit Example 51. Synthesis of 3-chloro-5-cyano-N-(4-fluoro-[1,1'-biphenyl]-3-yl)-2-methoxybenzenesulfonamide, I-51

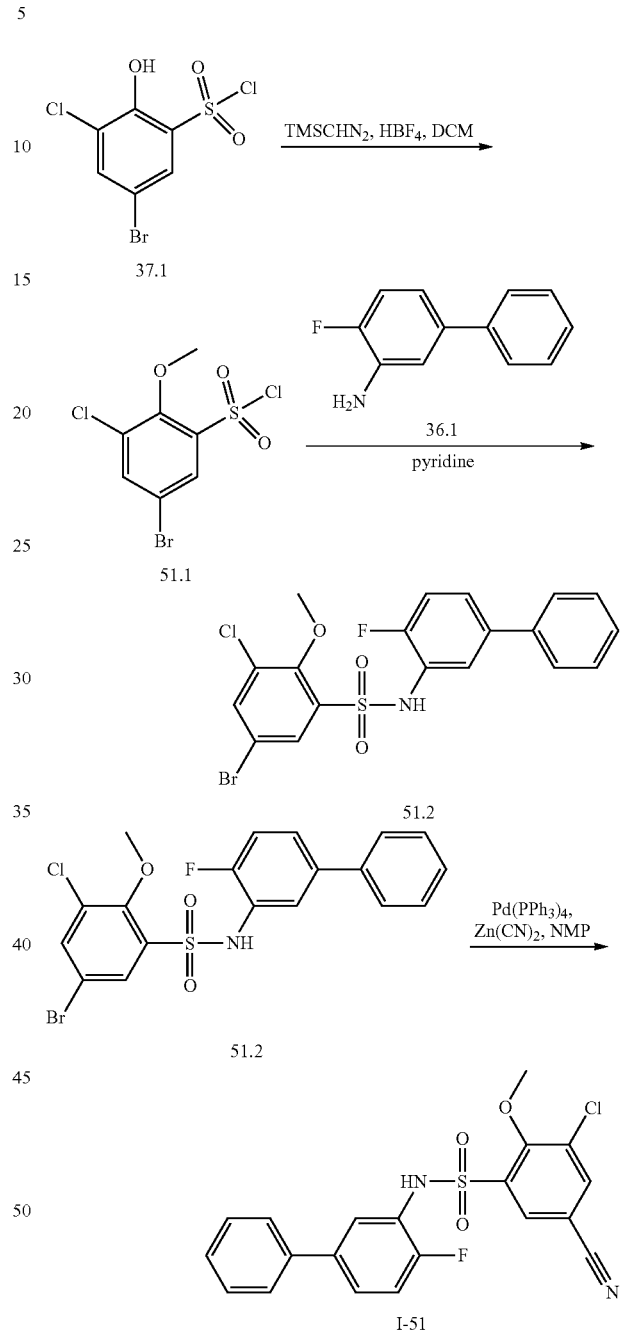

Synthesis of Compound 51.1

Into a 50-mL 3-necked round-bottom flask, was placed 37.1 (500 mg, 1.63 mmol, 1 equiv), DCM (5 mL), HBF₄ (493 mg, 2.45 mmol, 1.5 equiv), TMSCHN₂ (3.27 mL, 2 M, 4 equiv). The resulting solution was stirred for 2 h at 0° C. The reaction was then quenched by the addition of water (5 mL). The resulting solution was extracted with dichloromethane (3×10 mL). The organic layers were combined and concentrated under vacuum. This resulted in 510 mg (97.5%) of 51.1 as a grey solid. (ES, m/z): [M−H]⁻ 316.8.

Synthesis of Compound 51.2

Into a 50-mL round-bottom flask, was placed 51.1 (510 mg, 1.59 mmol, 1 equiv), 36.1 (358.1 mg, 1.91 mmol, 1.2 equiv), pyridine (5 mL). The resulting solution was stirred for 6 h at room temperature. The resulting mixture was washed with 1M HCl (aq.). The resulting solution was extracted with ethyl acetate (3×10 mL). The organic layers were combined and concentrated under vacuum. The residue was applied onto Prep-TLC with dichloromethane/methanol (10:1). This resulted in 300 mg (40.0%) of 51.2 as a brown solid. (ES, m/z): [M−H]⁻ 467.9.

Synthesis of I-51

Into a 10-mL macrowave tube purged and maintained with an inert atmosphere of nitrogen, was placed 51.2 (160 mg, 0.34 mmol, 1 equiv), NMP (2 mL), Zn(CN)$_2$ (47.9 mg, 0.41 mmol, 1.2 equiv), Pd(PPh$_3$)$_4$ (39.3 mg, 0.03 mmol, 0.1 equiv). The resulting solution was stirred for 1 h at 120° C. The resulting mixture was washed with H$_2$O (5 mL). The resulting solution was extracted with ethyl acetate (3×5 mL). The organic layers were combined and concentrated under vacuum. The crude product was purified by Flash-Prep-HPLC with the following conditions (IntelFlash-1): Column, C 18; mobile phase, ACN/H$_2$O (0.1% NH$_4$HCO$_3$)=0 increasing to ACN/H$_2$O (0.1% NH$_4$HCO$_3$)=1/1 within 25; Detector, UV 254 nm. This resulted in 40.5 mg (29.6%) of I-51 as a white solid. (ES, m/z): [M−H]⁻ 415.0, ¹H-NMR (300 MHz, DMSO-d$_6$, ppm): δ10.55 (s, 1H), δ8.47-8.46 (d, J=2.1 Hz, 1H), δ8.14-8.13 (d, J=1.8 Hz, 1H), δ7.56-7.44 (m, 6H), δ7.41-7.36 (m, 1H), δ7.32-7.26 (m, 1H), δ4.00 (s, 3H).

Example 52. Synthesis of Methyl 3-chloro-5-(N-(2-fluoro-5-(thiophen-2-yl)phenyl) sulfamoyl)-4-methoxybenzoate, I-52

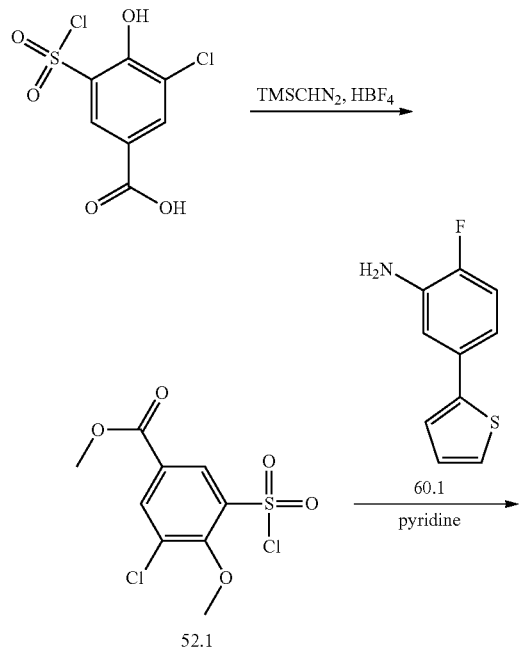

-continued

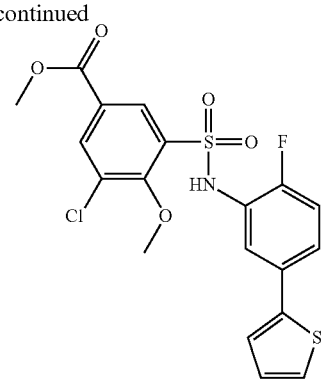

I-52

Synthesis of 52.1

Into a 100-mL 3-necked round-bottom flask, was placed 3-chloro-5-(chlorosulfonyl)-4-hydroxybenzoic acid (1 g, 3.69 mmol, 1 equiv), DCM (20 mL), HBF4 (1.6 g, 18.22 mmol, 4.939 equiv), TMSCHN$_2$ (7.38 mL, 2 M, 4 equiv) at 0° C. The resulting solution was stirred for 0.5 h at 0° C. The reaction was then quenched by the addition of 25 mL of water/ice. The resulting solution was extracted with 3×35 mL of ethyl acetate and the organic layers combined and concentrated under vacuum. This resulted in 1 g (90.6%) of 52.1 as a white solid. (ES, m/z): [M−H]⁻ 296.9.

Synthesis of I-52

Into a 50-mL round-bottom flask, was placed 52.1 (375.2 mg, 1.94 mmol, 1.2 equiv), 60.1 (1.0 equiv), and pyridine (6 mL). The resulting solution was stirred for 2 h at 25° C. The resulting mixture was concentrated under vacuum. The residue was applied Prep-TLC with dichloromethane/methanol (20:1). The crude product was purified by Flash-Prep-HPLC with the following conditions (IntelFlash-1): Column, C18; mobile phase, H$_2$O:ACN=15% increasing to H$_2$O:ACN=60% within 18; Detector, 254 nm. This resulted in 12.8 mg (1.74%) of I-52 as an off-white solid. (ES, m/z): [M−H]⁻ 454.0, ¹H-NMR (300 MHz, CDCl$_3$, ppm): δ3.89-3.92 (s, 3H), δ4.19 (s, 3H), δ6.94-6.97 (t, J=1.2 Hz, 1H), δ7.00-7.08 (m, 1H), δ7.22-7.31 (m, 4H), δ7.75-7.78 (m, 1H), δ8.24-8.25 (d, J=2.1 Hz, 1H), δ8.38-8.39 (d, J=2.1 Hz, 1H).

Example 53. Synthesis of N-(2-amino-5-phenylphenyl)-3-bromo-5-chloro-2-hydroxybenzene-1-sulfonamide, I-53

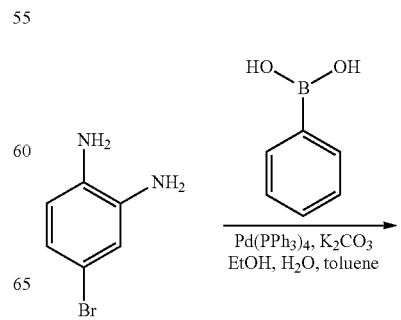

Synthesis of Compound 53.1

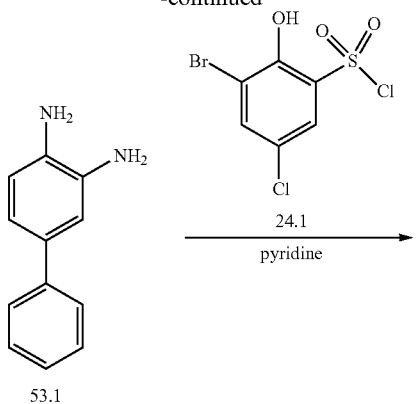

Into a 100-mL 3-necked round-bottom flask, was placed toluene (7 mL), water (7 mL), ethanol (7 mL), 4-bromobenzene-1,2-diamine (2 g, 10.69 mmol, 1 equiv), phenylboronic acid (1.6 g, 12.83 mmol, 1.2 equiv), potassium potassium methaneperoxoate (7.4 g, 53.47 mmol, 5 equiv), Pd(PPh$_3$)$_4$ (2.5 g, 2.14 mmol, 0.2 equiv). The resulting solution was stirred for 12 h at 80° C. The resulting mixture was concentrated under vacuum. The residue was applied onto a silica gel column with ethyl acetate/petroleum ether (20:1). This resulted in 800 mg (40.61%) of 53.1 as a light yellow solid.

Synthesis of I-53

Into a 50-mL 3-necked round-bottom flask, was placed 24.1 (660 mg, 2.16 mmol, 1 equiv), 53.1 (397.4 mg, 2.16 mmol, 1 equiv), pyridine (8 mL). The resulting solution was stirred for 2 h at 25° C. The resulting mixture was concentrated under vacuum. The crude product was purified by Prep-HPLC with the following conditions (2 #-AnalyseHPLC-SHIMADZU(HPLC-10)): Column: X Bridge Prep Phenyl OBD Column 19×150 mm 5 um 13 nm; Mobile Phase A: water (0.05% TFA), Mobile Phase B: ACN; Flow rate: 25 mL/min; Gradient: 42% B to 42% B in 12 min; 254/220 nm; Rt: 8.28, 10.13 min. This resulted in 43.3 mg (4.42%) of I-53 as a grey solid. (ES, m/z): [M+H]$^+$ 454.9, $^1$H-NMR (300 MHz, DMSO-d$_6$, ppm): δ6.75-6.78 (d, J=8.4 Hz, 1H), δ7.07-7.08 (d, J=2.1 Hz, 1H), δ7.22-7.40 (m, 6H), δ7.55-7.56 (d, J=2.7 Hz, 1H), δ8.00-8.01 (d, J=2.4 Hz, 1H).

Example 54. Synthesis of 5-chloro-N-(2-fluoro-5-phenylphenyl)-2,4-dihydroxybenzene-1-sulfonamide, I-54

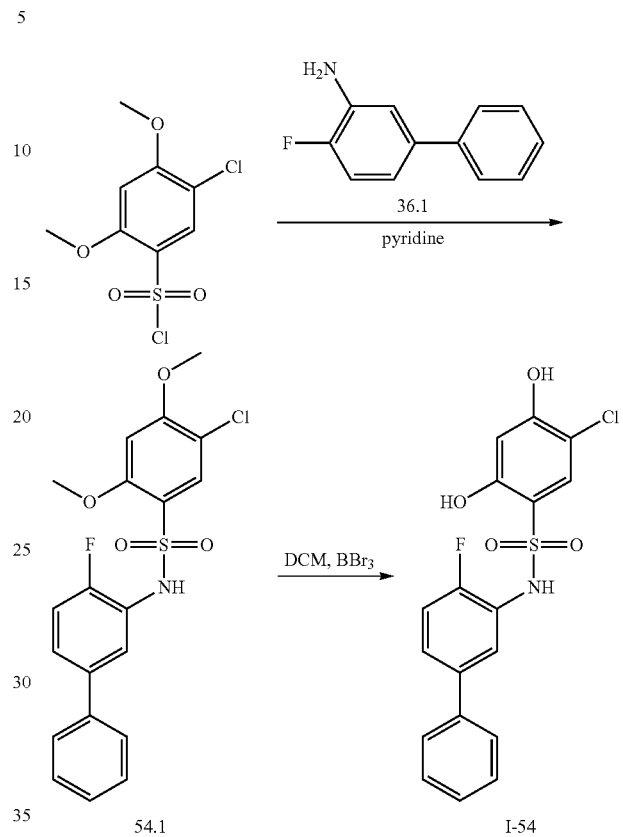

Synthesis of Compound 54.1

Into a 50-mL round-bottom flask, was placed 5-chloro-2,4-dimethoxybenzene-1-sulfonyl chloride (500 mg, 1.84 mmol, 1 equiv), 36.1 (414.3 mg, 2.21 mmol, 1.200 equiv), pyridine (5 mL). The resulting solution was stirred for 6 h at room temperature. The resulting mixture was washed with 1M HCl (aq.). The resulting solution was extracted with ethyl acetate (3×10 mL). The organic layers was combined and concentrated under vacuum. The residue was applied onto Prep-TLC with ethyl acetate/petroleum ether (1:2). This resulted in 330 mg (42.42%) of 54.1 as a brown solid. (ES, m/z): [M−H]$^-$ 420.0.

Synthesis of I-54

Into a 50-mL round-bottom flask was placed 54.1 (280 mg, 0.66 mmol, 1 equiv), DCM (4 mL), BBr$_3$ (665.1 mg, 2.65 mmol, 4.00 equiv). The resulting solution was stirred for 6 h at room temperature. The reaction was then quenched by the addition of water (5 mL). The resulting solution was extracted with ethyl acetate (3×5 mL). The combined organic layers were concentrated under vacuum. The crude product was purified by Flash-Prep-HPLC with the following conditions (IntelFlash-1): Column, C 18; mobile phase, ACN/H$_2$O (0.1% NH$_4$HCO$_3$)=0 increasing to ACN/H$_2$O (0.1% NH$_4$HCO$_3$)=1/1 within 25 mins; Detector, UV 254 nm. This resulted in 46.8 mg (17.9%) of I-54 as a white solid. (ES, m/z): [M−H]⁻ 391.9, ¹H-NMR (300 MHz, DMSO-d₆, ppm): δ7.47-7.34 (m, 8H), δ7.26-7.20 (m, 1H), δ6.61 (s, 1H).

Example 55. Synthesis of 3-chloro-4-hydroxy-5-[(2-methoxy-5-phenylphenyl) sulfamoyl]benzamide, I-55

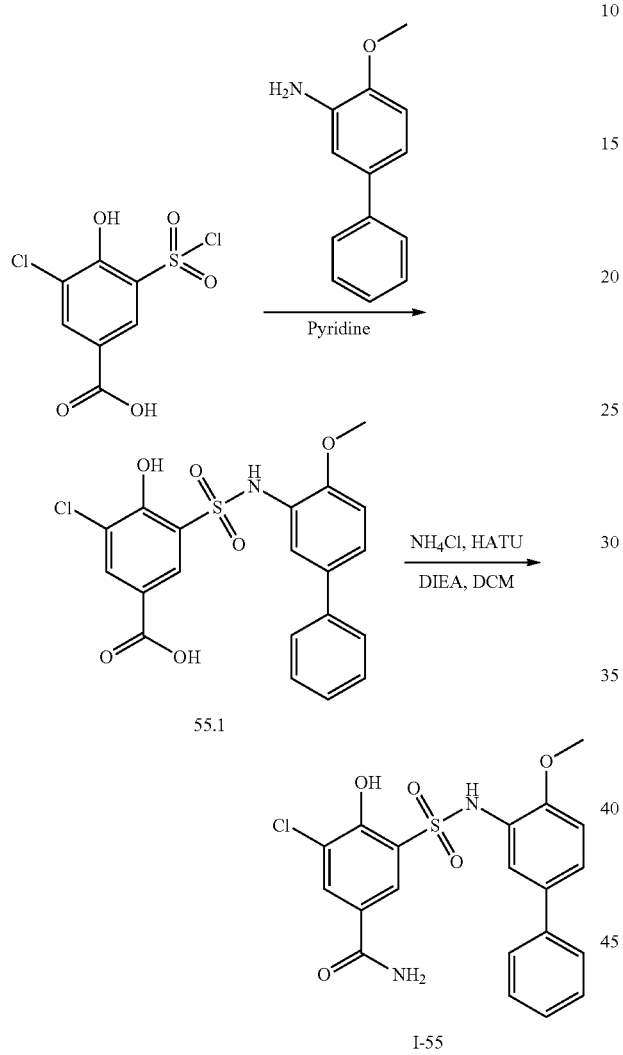

Synthesis of Compound 55.1

Into a 50-mL round-bottom flask, was placed 3-chloro-5-(chlorosulfonyl)-4-hydroxybenzoic acid (2 g, 7.38 mmol, 1 equiv), 2-methoxy-5-phenylaniline (1.7 g, 8.54 mmol, 1.2 equiv), pyridine (20 mL). The resulting solution was stirred for 12 h at 25° C. The pH value of the solution was adjusted to 4 with 1M HCl. The resulting solution was extracted with 3×20 mL of ethyl acetate and the combined organic layers were concentrated under vacuum. This resulted in 994 mg (31.06%) of 55.1 as a white solid.

Synthesis of I-55

Into a 10-mL sealed tube purged and maintained with an inert atmosphere of nitrogen, was placed 55.1 (200 mg, 0.46 mmol, 1 equiv), NH₄Cl (246.6 mg, 4.61 mmol, 10 equiv), HATU (350.6 mg, 0.92 mmol, 2 equiv), DIEA (178.7 mg, 1.38 mmol, 3 equiv), DCM (3 mL). The resulting solution was stirred for 12 h at 25° C. The resulting mixture was concentrated under vacuum. The residue was applied onto a silica gel column with dichloromethane/methanol (10:1). The crude product (19.2 mg) was purified by Flash-Prep-HPLC with the following conditions (IntelFlash-1): Column, C 18; mobile phase, MeCN:H₂O=10% increasing to MeCN:H₂O=60% within 15; Detector, 254 nm. This resulted in 11.4 mg (5.71%) of I-55 as a yellow solid. (ES, m/z): [M−H]⁻ 431.0, ¹H-NMR (400 MHz, DMSO-d₆, ppm): δ8.15-8.14 (d, J=2.0 Hz, 1H), δ8.10 (s, 1H), δ7.96 (s, 1H), δ7.51-7.43 (m, 3H), δ7.41-7.23 (m, 5H), δ7.03-7.01 (d, J=8.8 Hz, 1H), δ3.66 (s, 3H).

Example 56. Synthesis of 3-chloro-4-hydroxy-5-[(2-methoxy-5-phenylphenyl) sulfamoyl]-N,N-dimethylbenzamide, I-56

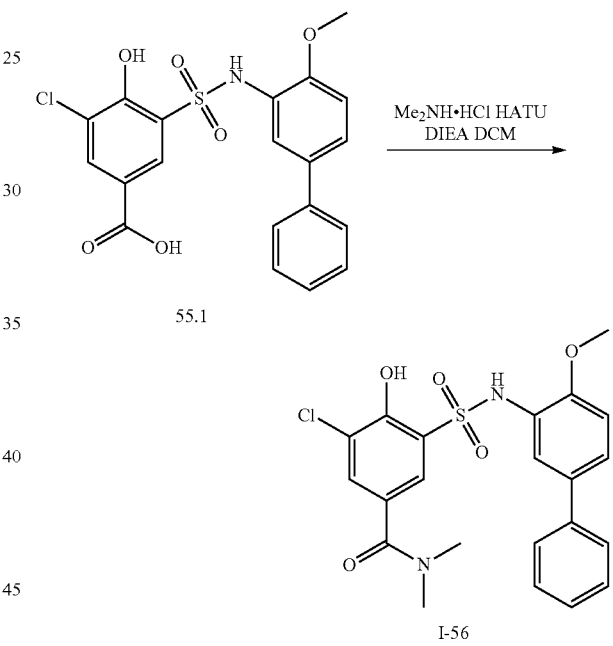

Synthesis of I-56

Into a 10-mL sealed tube purged and maintained with an inert atmosphere of nitrogen, was placed 55.1 (200 mg, 0.46 mmol, 1 equiv), (CH₃)₂NHHCl (373.4 mg, 4.61 mmol, 10 equiv), HATU (351 mg, 0.92 mmol, 2.003 equiv), DIEA (178.7 mg, 1.38 mmol, 2.999 equiv), DCM (3 mL). The resulting solution was stirred for 12 h at 25° C. The resulting mixture was concentrated under vacuum. The residue was applied onto a silica gel column with dichloromethane/methanol (15:1). The crude product (88.7 mg) was purified by Flash-Prep-HPLC with the following conditions (IntelFlash-1): Column, C18; mobile phase, MeCN:H₂O=10% increasing to MeCN:H₂O=60% within 15 min; Detector, 254 nm. This resulted in 29.1 mg (13.70%) of I-56 as a white solid. (ES, m/z): [M+H]⁺ 461.2, 1H-NMR (400 MHz, CDCl₃, ppm): δ8.79 (s, 1H), δ7.72-7.71 (d, J=2.0 Hz, 1H), δ7.66-7.65 (d, J=2.0 Hz, 1H), δ7.52-7.50 (t, J=1.6 Hz, 3H), δ7.45-7.41 (m, 2H), δ7.36-7.32 (m, 2H), δ7.20 (s, 1H), δ6.83-6.81 (d, J=8.4 Hz, 1H), δ3.69 (s, 3H), δ2.98-2.74 (m, 6H).

Example 57. Synthesis of N-(2-amino-4-phenylphenyl)-3-bromo-5-chloro-2-hydroxybenzene-1-sulfonamide, I-57

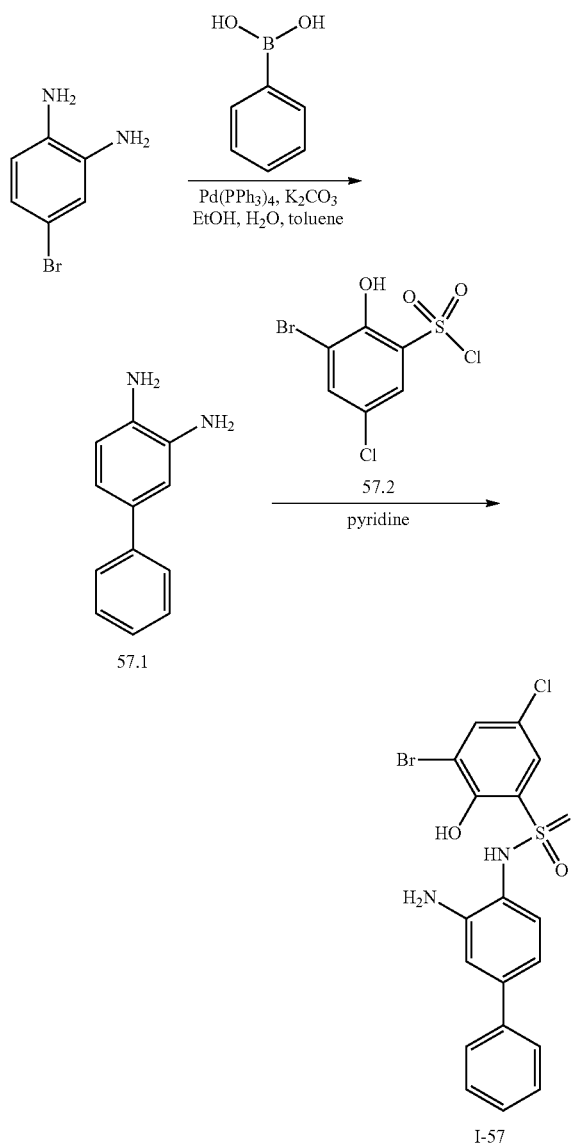

Synthesis of Compound 57.1

Into a 100-mL 3-necked round-bottom flask purged and maintained with an inert atmosphere of nitrogen, was placed toluene (7 mL), water (7 mL), ethanol (7 mL), 4-bromobenzene-1,2-diamine (2 g, 10.69 mmol, 1 equiv), phenylboronic acid (1.6 g, 12.83 mmol, 1.2 equiv), $K_2CO_3$ (7.4 g, 53.47 mmol, 5 equiv), $Pd(PPh_3)_4$ (2.5 g, 2.14 mmol, 0.2 equiv). The resulting solution was stirred for 12 h at 80° C. The resulting mixture was concentrated under vacuum. The residue was applied onto a silica gel column with ethyl acetate/petroleum ether (20:1). This resulted in 800 mg (40.61%) of 57.1 as a light yellow solid.

Synthesis of I-57

Into a 50-mL 3-necked round-bottom flask, was placed 57.2 (660 mg, 2.16 mmol, 1 equiv), 4-phenylbenzene-1,2-diamine (397.4 mg, 2.16 mmol, 1 equiv), and pyridine (8 mL). The resulting solution was stirred for 2 h at 25° C. The resulting mixture was concentrated under vacuum. The crude product was purified by Prep-HPLC with the following conditions (2 #-AnalyseHPLC-SHIMADZU (HPLC-10)): Column, X Bridge Prep Phenyl OBD Column, 19*150 mm 5 um 13 nm; mobile phase, water (0.05% TFA) and ACN (hold 42% Phase B in 12 min); Detector, UV 254/220 nm, Rt: 9.89 min. This resulted in 43.9 mg (4.49%) of I-57 as a red solid. (ES, m/z): $^1$H-NMR (400 MHz, DMSO-$d_6$, ppm): δ6.80-6.83 (m, 1H), δ6.90-6.92 (d, J=8.0 Hz, 1H), δ6.98-6.99 (d, J=1.6 Hz, 1H), δ7.30-7.34 (t, J=6.4 Hz, 1H), δ7.39-7.43 (t, J=8.7 Hz, 2H), δ7.51-7.54 (m, 3H), δ7.96-7.97 (d, J=2.4 Hz, 1H).

Example 58. Synthesis of 3-chloro-5-cyano-2-hydroxy-N-(2-methoxy-5-phenylphenyl)benzene-1-sulfonamide, I-58

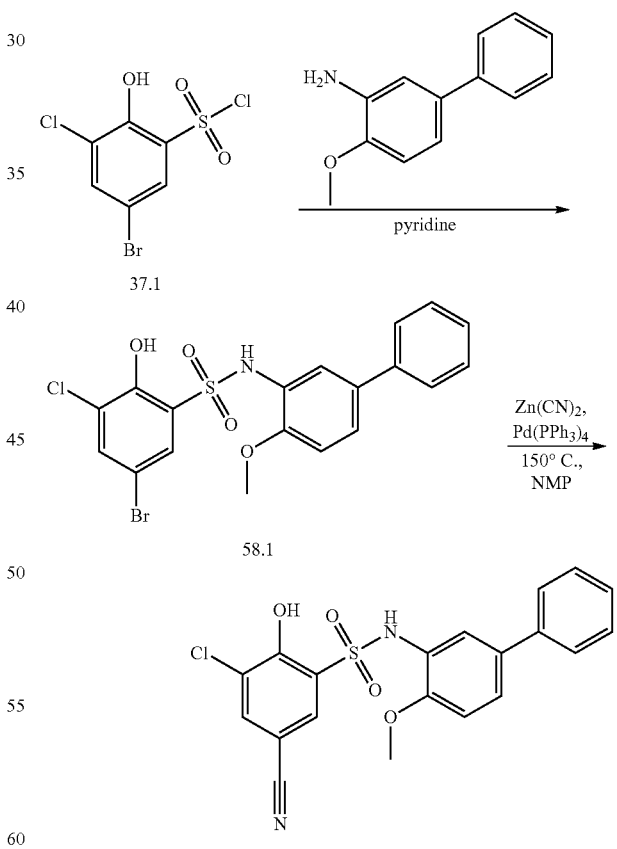

Synthesis of Compound 58.1

Into a 100-mL round-bottom flask, was placed 37.1 (1 g, 3.27 mmol, 1 equiv), 2-methoxy-5-phenylaniline (0.8 g, 3.92 mmol, 1.2 equiv), pyridine (10 mL). The resulting solution was stirred for 12 h at 25° C. The reaction was then quenched by the addition of 20 mL of 1M hydrochloric acid. The resulting solution was extracted with 3×60 mL of ethyl acetate and the organic layers combined and concentrated under vacuum. The crude product was purified by Flash-Prep-HPLC with the following conditions (IntelFlash-1): Column, C18; mobile phase, H₂O:ACN=15% increasing to H₂O:ACN=60% within 40 min; Detector, UV 254 nm. This resulted in 800 mg (52.22%) of 58.1 as a white solid.

Synthesis of I-58

Into a 8-mL sealed tube purged and maintained with an inert atmosphere of nitrogen, was placed 58.1 (400 mg, 0.85 mmol, 1 equiv), NMP (7 mL), Zn(CN)$_2$ (200.4 mg, 1.71 mmol, 2 equiv), Pd(PPh$_3$)$_4$ (197.2 mg, 0.17 mmol, 0.2 equiv). The final reaction mixture was irradiated with microwave radiation for 1 h at 150° C. The reaction was then quenched by the addition of 15 mL of water. The resulting solution was extracted with 3×20 mL of ethyl acetate and the organic layers combined and concentrated under vacuum. The crude product was purified by Flash-Prep-HPLC with the following conditions (IntelFlash-1): Column, C18; mobile phase, H₂O:ACN=15% increasing to H₂O:ACN=60% within 15; Detector, UV 254 nm. This resulted in 46.7 mg (13.19%) of I-58 as a white solid. (ES, m/z): [M−H]⁻ 413.0, ¹H-NMR (400 MHz, DMSO-d$_6$, ppm): δ3.76 (s, 3H), δ6.96 (s, 1H), δ7.02-7.04 (d, J=8.4 Hz, 1H), δ7.09 (s, 1H), δ7.21 (s, 1H), δ7.27-7.49 (m, 5H), δ7.57-7.59 (m, 1H), δ7.63-7.64 (d, J=2.4 Hz, 1H), δ8.80 (br s, 1H).

Example 59. Synthesis of 3-chloro-2-hydroxy-N-(2-methoxy-5-phenylphenyl)-5-(1,3-oxazol-2-yl)benzene-1-sulfonamide, I-59

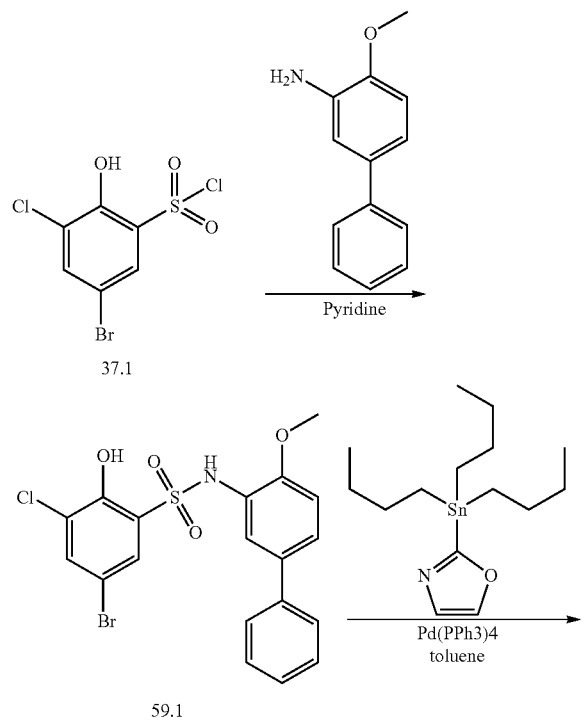

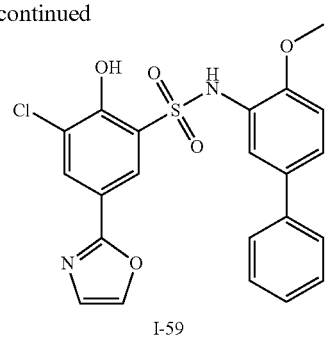

I-59

Synthesis of Compound 59.1

Into a 100-mL 3-necked round-bottom flask purged and maintained with an inert atmosphere of nitrogen, was placed 37.1 (3.97 g, 12.98 mmol, 1.00 equiv), 2-methoxy-5-phenylaniline (3.1 g, 15.56 mmol, 1.20 equiv), pyridine (50 mL). The resulting solution was stirred for 4 h at room temperature. The resulting mixture was concentrated under vacuum. The pH value of the solution was adjusted to 4 with 1M hydrogen chloride. The resulting solution was extracted with ethyl acetate (3×30 mL) and the combined organic layers were concentrated under vacuum. The residue was applied onto a silica gel column with ethyl acetate/hexane (1:20). This resulted in 5.1 g (84%) of 59.1 as a white solid. (ES, m/z): [M−H]⁻ 465.8.

Synthesis of I-59

Into a 10-mL sealed tube purged and maintained with an inert atmosphere of nitrogen, was placed 59.1 (183.6 mg, 0.39 mmol, 1 equiv), 2-(tributylstannyl)-1,3-oxazole (210.4 mg, 0.59 mmol, 1.5 equiv), Pd(PPh$_3$)$_4$ (90.5 mg, 0.08 mmol, 0.2 equiv), toluene (2 mL). The final reaction mixture was irradiated with microwave radiation for 24 h at 150° C. The resulting mixture was concentrated under vacuum. The residue was applied onto a silica gel column with dichloromethane/methanol (20:1). The crude product (12 mg) was purified by Flash-Prep-HPLC with the following conditions (IntelFlash-1): Column, C18; mobile phase, MeCN:H₂O=10% increasing to MeCN:H₂O=60% within 15; Detector, 254 nm. This resulted in 2.5 mg (1.40%) of I-59 as a white solid. (ES, m/z): [M+H]⁺ 457.2, ¹H-NMR (400 MHz, CDCl$_3$, ppm): δ8.22-8.19 (t, J=2.0 Hz, 2H), δ7.72-7.71 (d, J=2.0 Hz, 1H), δ7.67-7.66 (d, J=7.6 Hz, 1H), δ7.52-7.50 (d, J=7.6 Hz, 2H), δ7.44-7.40 (m, 2H), δ7.35-7.31 (m, 2H), δ7.26-7.20 (m, 1H), δ6.81-6.79 (d, J=8.4 Hz, 1H), δ3.67 (s, 3H).

Example 60. Synthesis of Methyl 3-chloro-5-[[2-fluoro-5-(thiophen-2-yl)phenyl] sulfamoyl]-4-hydroxybenzoate, I-60

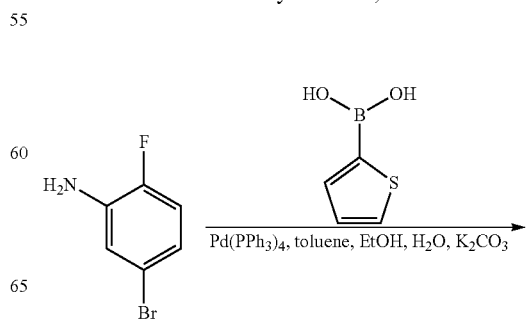

-continued

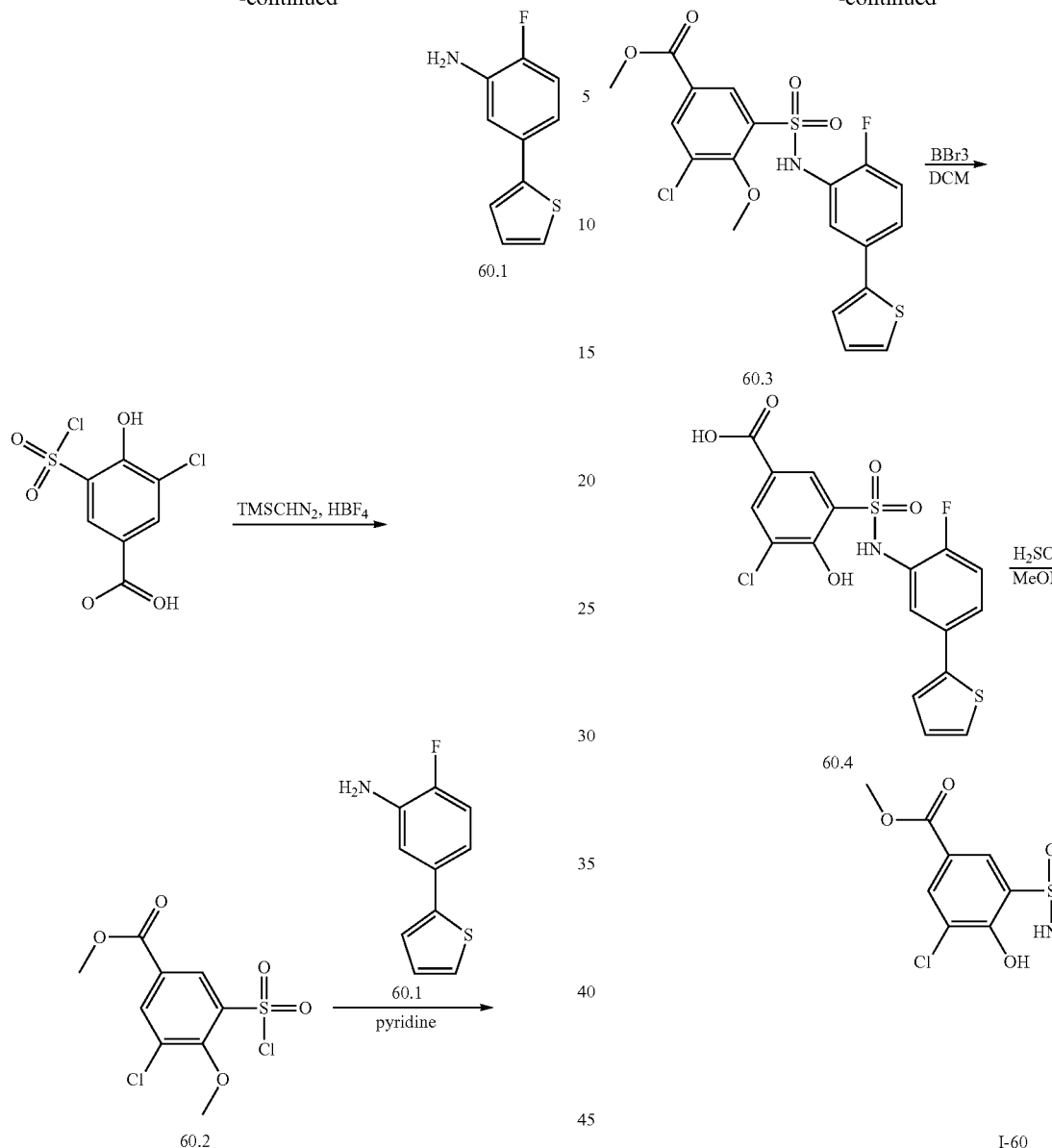

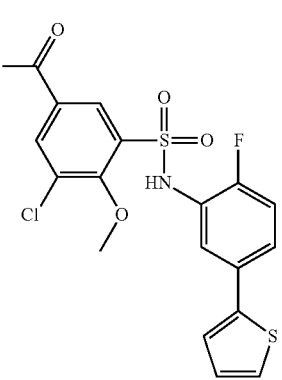

Synthesis of Compound 60.1

Into a 250-mL 3-necked round-bottom flask purged and maintained with an inert atmosphere of nitrogen, was placed 5-bromo-2-fluoroaniline (6.2 g, 32.63 mmol, 1 equiv), (thiophen-2-yl)boronic acid (5.0 g, 39.16 mmol, 1.2 equiv), toluene (20 mL), EtOH (20 mL), $H_2O$ (20 mL), $K_2CO_3$ (13.5 g, 97.89 mmol, 3 equiv), $Pd(PPh_3)_4$ (3.8 g, 3.26 mmol, 0.1 equiv). The reaction solution was stirred for 12 h at 80° C. The resulting mixture was concentrated under vacuum. The residue was applied onto a silica gel column with ethyl acetate/petroleum ether (20:1) to afford the title compound of 60.1 (1.2 g, 19.0%) as a yellow solid. (ES, m/z): [M−H]⁻ 192.0.

Synthesis of Compound 60.2

Into a 100-mL 3-necked round-bottom flask, was placed 3-chloro-5-(chlorosulfonyl)-4-hydroxybenzoic acid (1 g, 3.69 mmol, 1 equiv), DCM (20 mL), HBF$_4$ (1.6 g, 18.22 mmol, 4.939 equiv), TMSCHN$_2$ (7.38 mL, 2M in hexane, 4 equiv) at 0° C. After stirred for 0.5 h at 0° C., the reaction was quenched by the addition of 25 mL of water/ice. Then, the mixture was extracted with 3×35 mL of ethyl acetate. The layers were separated, and the organic phase was combined and concentrated to dryness in vacuo. This resulted in 1 g (90.6%) of 60.2 as a solid. (ES, m/z): [M−H]$^-$ 296.9.

Synthesis of Compound 60.3

Into a 50-mL round-bottom flask, was placed 60.2 (900 mg, 3.01 mmol, 1 equiv), 60.1 (697.7 mg, 3.61 mmol, 1.2 equiv), pyridine (10 mL). The reaction mixture was stirred for 2 h at 25° C. Then, the resulting mixture was concentrated under vacuum to yield the crude product which was purified by Prep-TLC with dichloromethane/methanol (20:1). This resulted in title compound of 60.3 (150 mg, 10.9%) as a white solid. (ES, m/z): [M−H]$^-$ 454.0.

Synthesis of Compound 60.4

Into a 25-mL round-bottom flask, was placed 60.3 (154 mg, 0.34 mmol, 1 equiv), DCM (4 mL), BBr$_3$ (677.0 mg, 2.70 mmol, 8 equiv) at −10° C. The reaction solution was stirred for 12 h at 25° C. The mixture was then quenched by the addition of 10 mL of water/ice, then, extracted with 3×15 mL of ethyl acetate. The layers were separated, and the organic phase was concentrated to dryness under vacuum. This resulted in 53 mg (36%) of 60.4 as a brown solid. (ES, m/z): [M−H]$^-$ 425.9.

Synthesis of I-60

Into a 25-mL round-bottom flask, was placed 60.4 (53 mg, 0.12 mmol, 1 equiv), MeOH (5 mL), conc.H$_2$SO$_4$ (24.3 mg, 0.25 mmol, 2 equiv). The resulting solution was stirred for 4 h at 65° C. The reaction was then quenched by the addition of 10 mL of water/ice. The resulting solution was extracted with 3×15 mL of ethyl acetate and the organic layers combined and concentrated under vacuum. The residue was applied onto Prep-TLC with dichloromethane/methanol (20:1). The crude product was purified by Flash-Prep-HPLC with the following conditions (IntelFlash-1): Column, C18; mobile phase, H$_2$O:ACN=15% increasing to H$_2$O: ACN=60% within 14 min; Detector, UV 254 nm. This resulted in 16.8 mg (30.7%) of I-60 as a white solid. (ES, m/z): [M−H]$^-$ 440.1, $^1$H-NMR (400 MHz, DMSO-d$_6$, ppm): δ3.68 (s, 3H), δ7.01-7.11 (m, 3H), δ7.14-7.23 (m, 1H), δ7.29-7.30 (d, J=3.9 Hz, 1H), δ7.33-7.37 (m, 1H), δ7.51-7.53 (d, J=5.2 Hz, 2H), δ7.73-7.74 (d, J=2.4 Hz, 1H), δ7.90-7.91 (d, J=2.0 Hz, 1H).

Example 61. Synthesis of 3-((3,5-dichloro-2-hydroxyphenyl)sulfonamido)-4-fluoro-N-phenylbenzamide, I-61

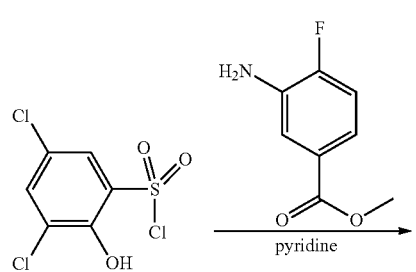

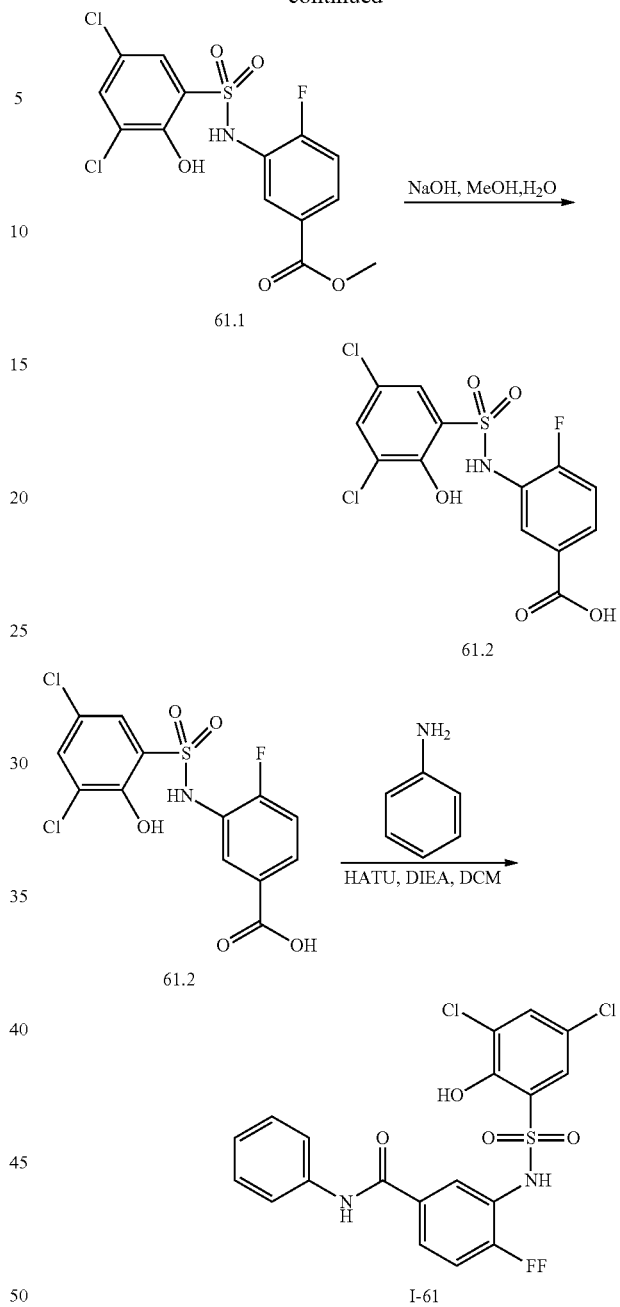

Synthesis of Compound 61.1

Into a 50-mL round-bottom flask, was placed 3,5-dichloro-2-hydroxybenzene-1-sulfonyl chloride (500 mg, 1.91 mmol, 1 equiv), methyl 3-amino-4-fluorobenzoate (388.1 mg, 2.29 mmol, 1.2 equiv), pyridine (5 mL). The resulting solution was stirred for 6 h at room temperature. The resulting mixture was washed with 1 M HCl. The resulting solution was extracted with ethyl acetate (2×10 mL). The organic layers were combined and concentrated under vacuum. The residue was applied onto a TLC with dichloromethane/methanol (20:1). This resulted in 510 mg (67.7%) of 61.1 as a brown solid. (ES, m/z): [M−H]$^-$ 391.9.

Synthesis of Compound 61.2

Into a 50-mL round-bottom flask, was placed 61.1 (500 mg, 1.27 mmol, 1 equiv), MeOH (5 mL), H₂O (0.5 mL), NaOH (202.9 mg, 5.07 mmol, 4 equiv). The resulting solution was stirred for 4 h at 65° C. The pH value of the solution was adjusted to 7 with CH₃COOH. The resulting mixture was concentrated under vacuum. The residue was purified by Flash-Prep-HPLC with the following conditions (IntelFlash-1): Column, C 18; mobile phase, ACN/H₂O (0.1% NH₄HCO₃)=0 increasing to ACN/H₂O (0.1% NH₄HCO₃)=1/1 within 25; Detector, UV 254 nm. This resulted in 310 mg (64.3%) of 61.2 as a yellow solid. (ES, m/z): [M−H]⁻ 377.9.

Synthesis of I-61

Into a 50-mL round-bottom flask, was placed 61.2 (310 mg, 0.82 mmol, 1 equiv), DCM (5 mL), aniline (113.9 mg, 1.22 mmol, 1.5 equiv), HATU (620.1 mg, 1.63 mmol, 2 equiv), DIEA (316.2 mg, 2.45 mmol, 3 equiv). The resulting solution was stirred for 6 h at room temperature. The resulting solution was concentrated under vacuum. The crude product was purified by Flash-Prep-HPLC with the following conditions (IntelFlash-1): Column, C 18; mobile phase, ACN/H₂O (0.1% NH₄HCO₃)=0 increasing to ACN/H₂O (0.1% NH₄HCO₃)=1/1 within 25; Detector, UV 254 nm. This resulted in 153.4 mg (41.3%) of I-61 as a white solid. (ES, m/z): [M+H]⁺ 455.2, ¹H-NMR (300 MHz, DMSO-d₆, ppm): δ10.25 (s, 1H), δ7.91-7.88 (m, 1H), δ7.76-7.70 (m, 4H), δ7.49-7.48 (d, J=2.7 Hz, 1H), δ7.40-7.26 (m, 4H), δ7.13-6.92 (m, 2H).

Example 62. Synthesis of 3-chloro-5-[(2,4-difluoro-5-phenylphenyl)sulfamoyl]-4-methoxybenzoic Acid, I-62

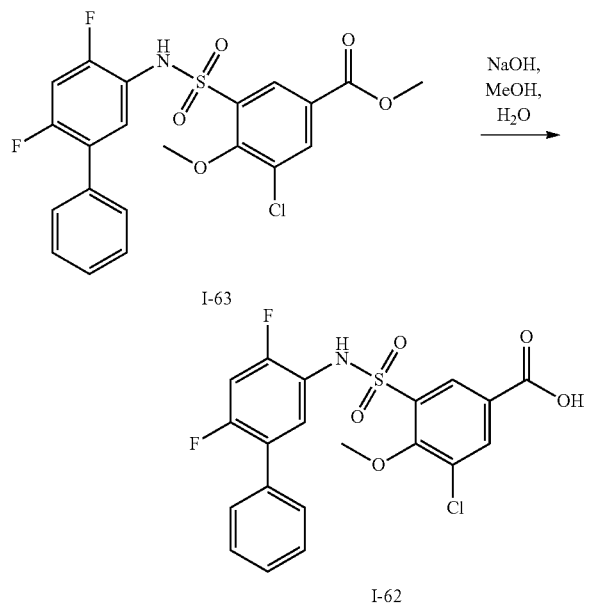

Synthesis of I-62

To a stirred mixture of methyl I-63 (80 mg, 0.17 mmol, 1 equiv) and water (0.5 mL) in MeOH (0.5 mL) was added MeOH (0.5 mL) at room temperature under air atmosphere. The final reaction mixture was irradiated with microwave radiation for 2 h at room temperature. The reaction was quenched with 1M HCl at room temperature, followed by extracted with EtOAc (2×50 mL). The combined organic layers were concentrated under vacuum. The residue was purified by Flash-Prep-HPLC with the following conditions (IntelFlash-1): Column, C 18; mobile phase, CH₃CN:H₂O=0:100 to CH₃CN:H₂O=60:40 in 30 min; Detector, UV 254/220 nm. This resulted in 45.9 mg (59.2%) of I-62 as a white solid. (ES, m/z): [M−H]⁻ 452.0, ¹H-NMR (300 MHz, DMSO-d₆, ppm): δ8.21-8.22 (d, J=2.1 Hz, 1H), δ8.17-8.16 (d, J=2.1 Hz, 1H), δ7.48-7.29 (m, 8H), δ3.96 (s, 3H).

Example 63. Synthesis of N-(2-aminoethyl)-3-chloro-4-hydroxy-5-[(2-methoxy-5-phenylphenyl)sulfamoyl]benzamide, I-64

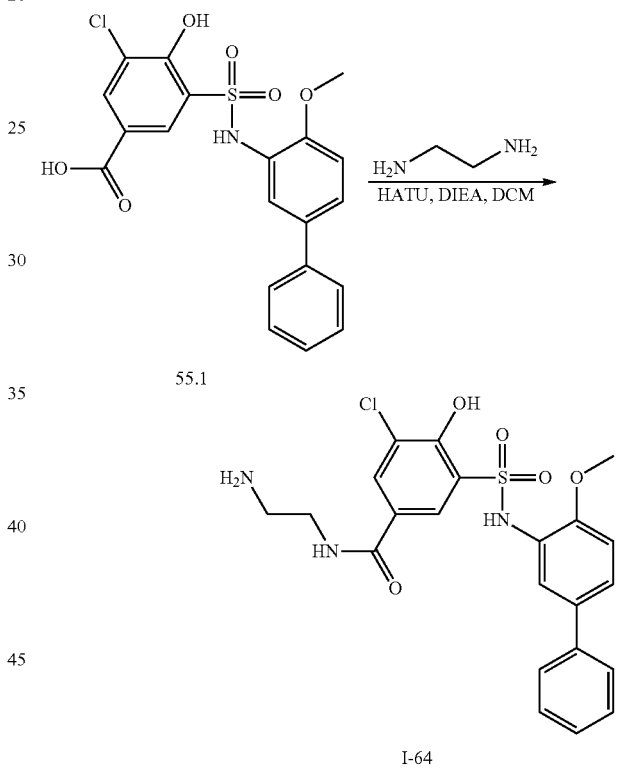

Synthesis of I-64

Into a 8-mL vial purged and maintained with an inert atmosphere of nitrogen, was placed 55.1 (250 mg, 0.58 mmol, 1 equiv), DCM (5 mL), DIEA (148.9 mg, 1.15 mmol, 2 equiv), ethane-1,2-diamine (69.3 mg, 1.15 mmol, 2 equiv), HATU (262.9 mg, 0.69 mmol, 1.2 equiv), followed by stirring for 12 h at room temperature. The reaction was then quenched by the addition of 10 mL of water. The resulting solution was extracted with ethyl acetate (3×20 mL) and the combined organic layers were concentrated under vacuum. The residue was applied onto a silica gel column with dichloromethane/methanol (20:1). The crude product was purified by Flash-Prep-HPLC with the following conditions (IntelFlash-1): Column, C 18; mobile phase, CH₃CN/H₂O (NH₄HCO₃)=1:10 increasing to CH₃CN/H₂O (NH₄HCO₃)

=17:3 within 40; Detector, UV 254 nm. This resulted in 15 mg (5.47%) of I-64 as a white solid. (ES, m/z): [M+H]+ 476.2, 1H-NMR (400 MHz, DMSO-$d_6$ and $D_2O$, ppm): 2.85-2.95 (m, 2H), 3.42-3.50 (m, 2H), 3.75 (s, 3H), 7.02 (d, 1H, J: 5.9 Hz), 7.22-7.24 (m, 1H), 7.25-7.31 (m, 1H), 7.40-7.44 (m, 2H), 7.45-7.49 (m, 2H), 7.65 (broad s, 1H), 7.77 (broad s, 1H), 7.95 (broad s, 1H), 8.11-8.13 (m, 1H).

Example 64. Synthesis of 3-chloro-4-hydroxy-5-[(2-methoxy-5-phenylphenyl) sulfamoyl]-N-methyl-benzamide, I-66

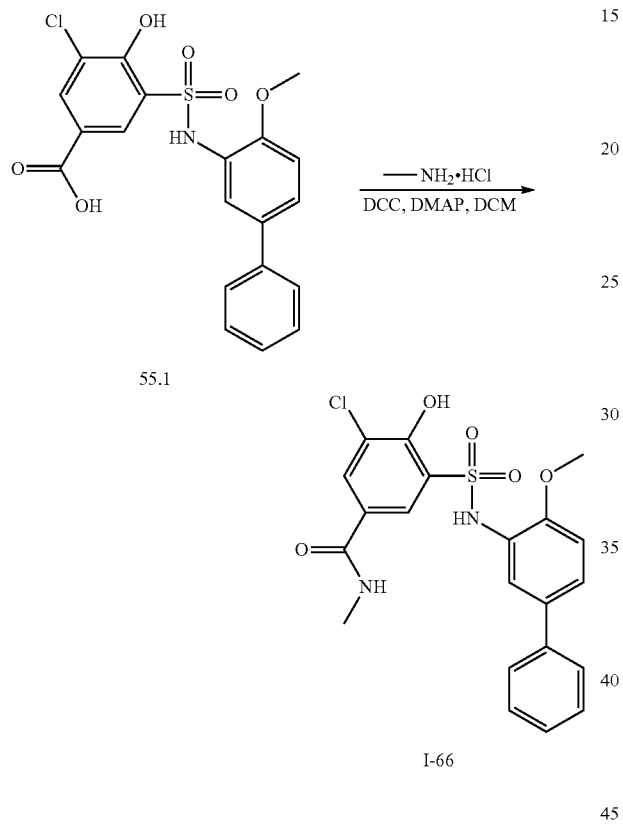

Synthesis of I-66

Into a 10-mL sealed tube purged and maintained with an inert atmosphere of nitrogen, was placed 55.1 (121.3 mg, 0.28 mmol, 1 equiv), $CH_3NH_2 \cdot HCl$ (188.8 mg, 2.80 mmol, 10 equiv), DCC (115.4 mg, 0.56 mmol, 2 equiv), DMAP (102.5 mg, 0.84 mmol, 3 equiv), DCM (3 mL). The resulting solution was stirred for 12 h at 25° C. Then, added 20 mL of $H_2O$ to the solution and extracted with 3×20 mL of ethyl acetate. The layers were separated, and the organic phase was washed with 50 mL of brine, then, concentrated under vacuum. The solids were filtered out. The crude product was purified by Flash-Prep-HPLC with the following conditions (IntelFlash-1): Column, C18; mobile phase, MeCN: $H_2O$=10% increasing to MeCN:$H_2O$=60% within 16 min. This resulted in 28.7 mg (22.97%) of I-66 as a white solid. (ES, m/z): [M−H]− 445.0, 1H-NMR (300 MHz, DMSO-$d_6$, ppm): δ2.67-2.68 (d, 3H), δ3.77 (s, 3H), δ6.99-7.02 (d, J=8.4 Hz, 1H), δ7.20-7.23 (m, 1H), δ7.27-7.31 (m, 1H), δ7.36-7.46 (m, 3H), δ7.62-7.63 (d, J=2.1 Hz, 1H), δ7.75-7.76 (d, J=2.1 Hz, 1H), δ7.94-7.99 (m, 2H).

Example 65. Synthesis of 2-[3-chloro-4-hydroxy-5-[(2-methoxy-5-phenylphenyl) sulfamoyl]phenyl] acetic Acid, I-68

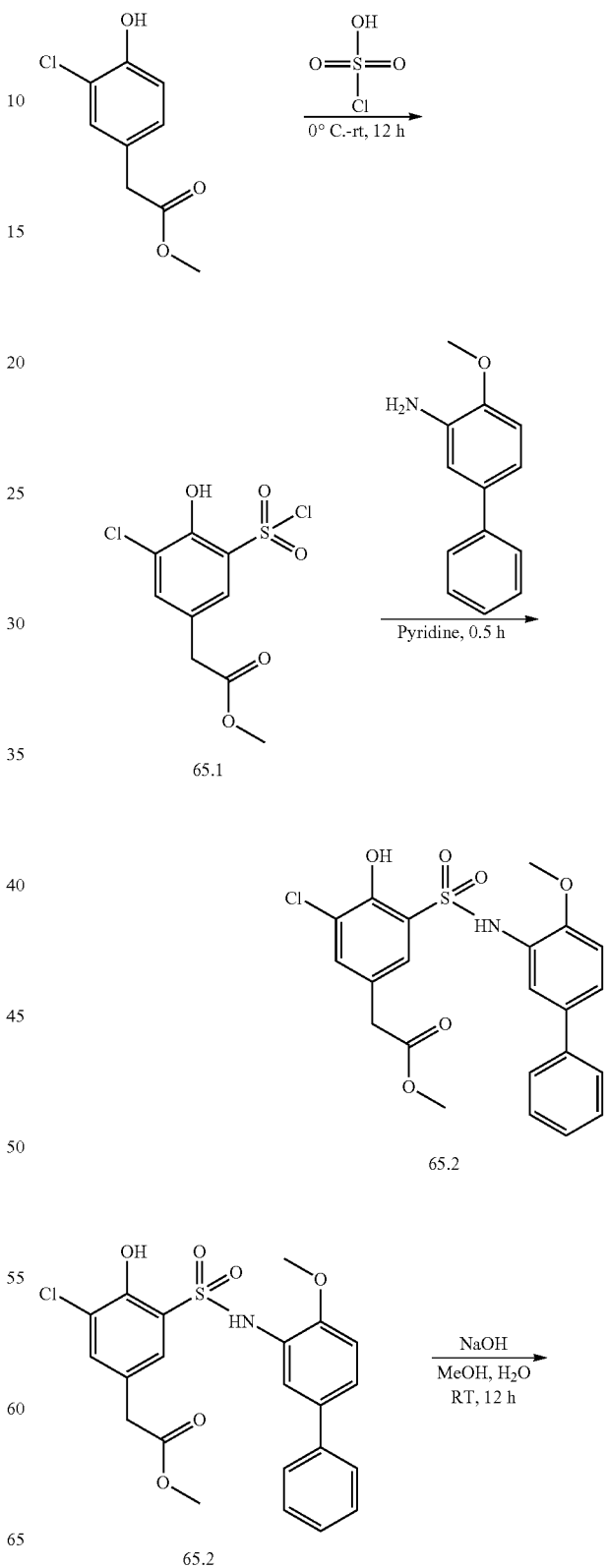

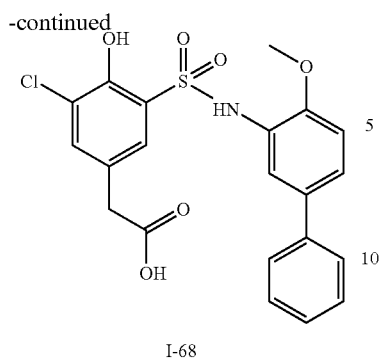

I-68

Synthesis of Compound 65.1

Into a 100-mL round-bottom flask purged and maintained with an inert atmosphere of nitrogen, was placed methyl 2-(3-chloro-4-hydroxyphenyl)acetate (2 g, 9.97 mmol, 1 equiv), O-(chlorosulfonyl)oxidanol (6.9 g, 59.82 mmol, 6.000 equiv). The resulting solution was stirred for 2 h at room temperature. The reaction was then quenched by the addition of 20 mL of water/ice. The resulting solution was extracted with 3×20 mL of ethyl acetate. The organic layers was washed with 20 mL of brine, dried and concentrated. This resulted in 1.5 g (50.30%) of 65.1 as colorless oil. (ES, m/z): [M−H]⁻ 296.9.

Synthesis of Compound 65.2

Into a 100-mL round-bottom flask purged and maintained with an inert atmosphere of nitrogen, was placed 65.1 (300 mg, 1.00 mmol, 1 equiv), 2-methoxy-5-phenylaniline (239.8 mg, 1.20 mmol, 1.2 equiv), pyridine (10 mL). The resulting solution was stirred for 0.5 h at room temperature. The resulting mixture was concentrated. The residue was applied onto a silica gel column with ethyl acetate/petroleum ether (1:2). This resulted in 90 mg (19.43%) of 65.2 as a white solid. (ES, m/z): [M−H]⁻ 460.0.

Synthesis of I-68

Into a 100-mL round-bottom flask purged and maintained with an inert atmosphere of nitrogen, was placed 65.2 (80 mg, 0.17 mmol, 1 equiv), sodiumol (13.9 mg, 0.35 mmol, 2 equiv), MeOH (4 mL), H₂O (1 mL). The resulting solution was stirred for 2 h at room temperature. The pH value of the solution was adjusted to 7 with 1 M HCl. The resulting solution was extracted with 3×10 mL of ethyl acetate. The combined organic extracts was washed with 10 mL of brine, dried and concentrated under vacuum. The residue was applied onto a silica gel column with ethyl acetate/petroleum ether (1:2). This resulted in 27.9 mg (35.97%) of I-68 as a white solid. (ES, m/z): [M−H]⁻ 446.0, ¹H-NMR (400 MHz, DMSO-d₆, ppm): δ3.55 (s, 2H), δ3.67 (s, 3H), δ7.02-7.04 (d, J=8.8 Hz, 1H), δ7.30-7.33 (m, 1H), δ7.36-7.38 (m, 1H), δ7.41-7.44 (m, 2H), δ7.47-7.49 (m, 3H), δ7.54 (s, 2H).

Example 66. Synthesis of 3,5-dichloro-N-(2,5-difluorophenyl)-2-hydroxybenzene-1-sulfonamide, I-69

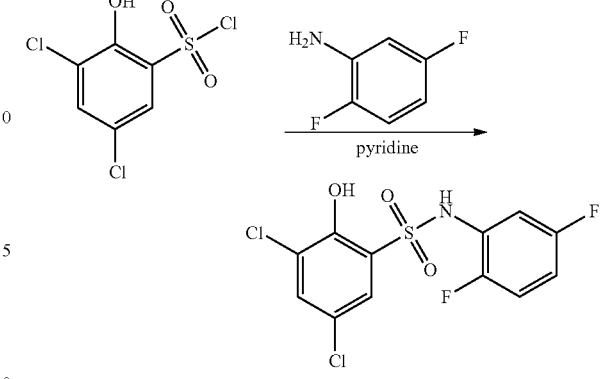

I-69

Synthesis of I-69

Into a 100-mL round-bottom flask purged and maintained with an inert atmosphere of nitrogen, was placed 3,5-dichloro-2-hydroxybenzene-1-sulfonyl chloride (500 mg, 1.91 mmol, 1 equiv), 2,5-difluoroaniline (296.2 mg, 2.29 mmol, 1.2 equiv), pyridine (5 mL). The resulting solution was stirred for 0.5 h at room temperature. After being quenched with 10 mL of water, the reaction solution was extracted with 3×10 mL of ethyl acetate. The combined organic phase was washed with 10 mL of brine, dried over anhydrous sodium sulfate and evaporated under vacuum. The crude product was purified by a silica gel column with ethyl acetate/petroleum ether (1:0) to afford I-69 (120.4 mg, 17.78%) as a white solid. (ES, m/z): [M−H]⁻ 351.8, ¹H-NMR (400 MHz, DMSO-d₆, ppm): δ6.81 (br s, 1H), δ6.95 (s, 1H), δ7.02-7.20 (m, 3H), δ7.51-7.52 (d, J=2.8 Hz, 1H), δ7.70-7.71 (d, J=2.4 Hz, 1H).

Example 67. Synthesis of 3-chloro-5-([4-fluoro-[1,1-biphenyl]-3-yl]sulfamoyl)-4-methoxybenzoic Acid, I-70

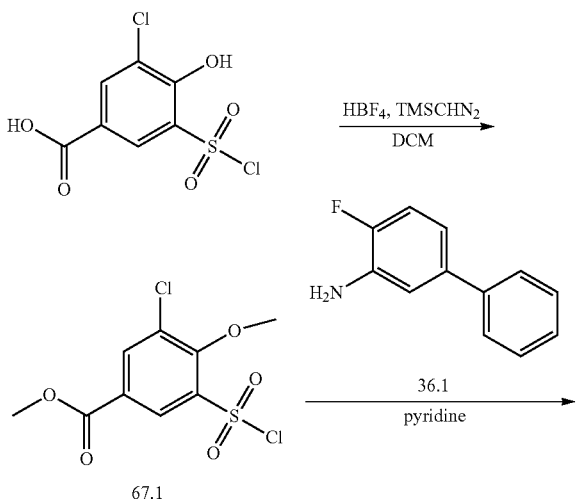

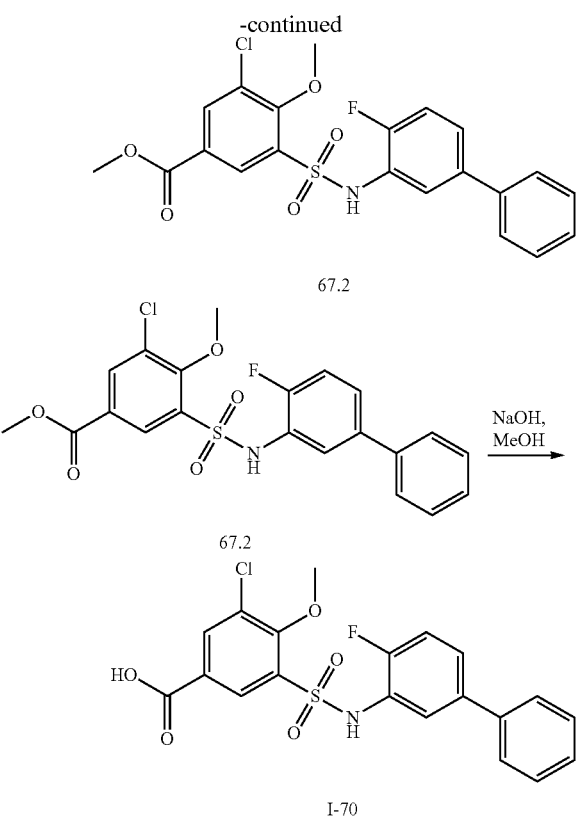

Synthesis of Compound 67.1

Into a 100-mL 3-necked round-bottom flask, was placed 3-chloro-5-(chlorosulfonyl)-4-hydroxybenzoic acid (1 g, 3.69 mmol, 1.00 equiv), DCM (10 mL), HBF$_4$ (1.6 g, 18.18 mmol, 4.93 equiv) was added at 0° C. and TMSCHN$_2$ (7.38 mL, 2M, 4 equiv) in batches at 0° C. After stirring for 2 h at 0° C., the reaction was then quenched by the addition of 50 mL of water, and extracted with 2×50 mL of dichloromethane. The organic layers was combined, and evaporated under vacuum to afford title product of 67.1 (900 mg) as brown oil. The crude was directly used in the next steps without further purification.

Synthesis of Compound 67.2

Into a 50-mL round-bottom flask, was placed 67.1 (900 mg, 3.01 mmol, 1.00 equiv), 36.1 (677.7 mg, 3.62 mmol, 1.20 equiv), pyridine (16 mL). The resulting solution was stirred overnight at 25° C. The resulting mixture was concentrated under vacuum. The crude product was purified by Flash-Prep-HPLC with the following conditions (IntelFlash-1): Column, C18; mobile phase, water:acetonitrile=90:10 increasing to water:acetonitrile=0:100 within 30 min; Detector, UV 254 nm. This resulted in 500 mg (37%) of 67.2 as a light brown solid.

Synthesis of I-70

Into a 8-mL vial, was placed 67.2 (100 mg, 0.22 mmol, 1 equiv), MeOH (1.6 mL), H$_2$O (0.4 mL), NaOH (17.8 mg, 0.44 mmol, 2 equiv). The resulting solution was stirred overnight at 25° C. The reaction was then quenched by the addition of 5 mL of water, adjusted to pH=7 with 1M HCl. The resulting solution was extracted with 2×8 mL of ethyl acetate, and the organic phase was combined and concentrated. The crude product was purified by Flash-Prep-HPLC with the following conditions (IntelFlash-1): Column, C18; mobile phase, ACN/H$_2$O=15% increasing to ACN/H$_2$O=60% within 15 min; Detector, UV 254 nm. This resulted in 74.7 mg (77.1%) of I-70 as a white solid. (ES, m/z): [M−H]$^-$ 434.2 $^1$H-NMR (400 MHz, DMSO-d$_6$, ppm): δ3.94 (s, 3H), δ7.17-7.22 (m, 1H), δ7.33-7.36 (m, 2H), δ7.41-7.48 (m, 5H), δ8.12-8.13 (d, J=1.6 Hz, 1H), δ8.25 (s, 1H).

Example 68. Synthesis of 3-chloro-2-methoxy-N-(2-methoxy-5-phenylphenyl)-5-(2H-1,2,3,4-tetrazol-5-yl)benzene-1-sulfonamide, I-71

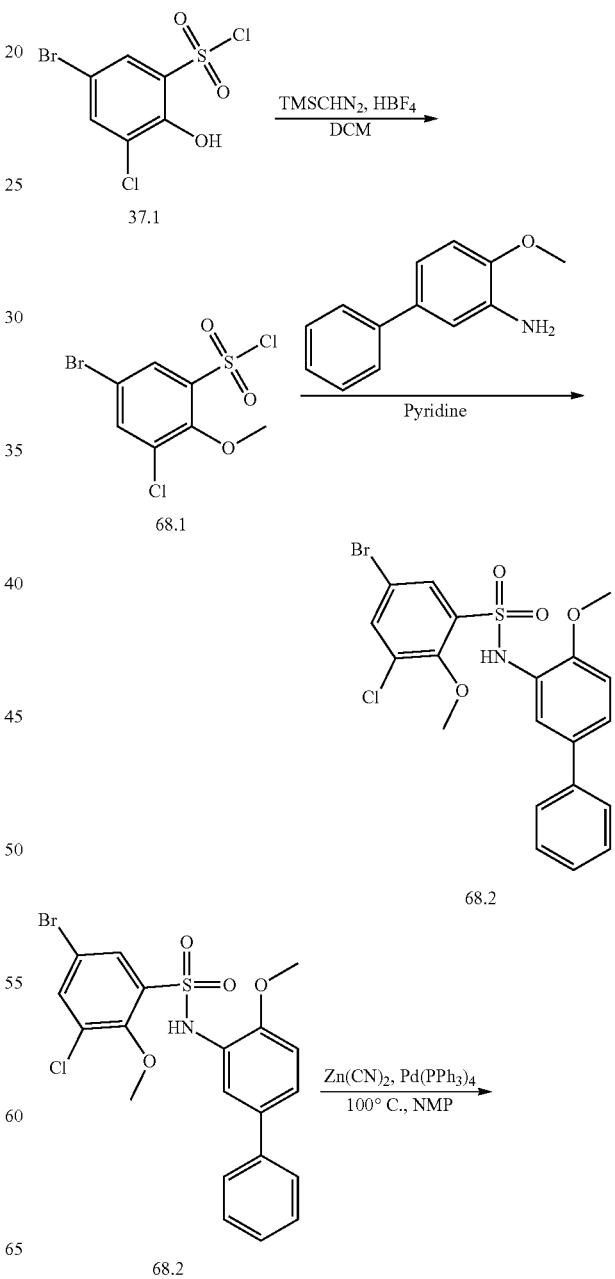

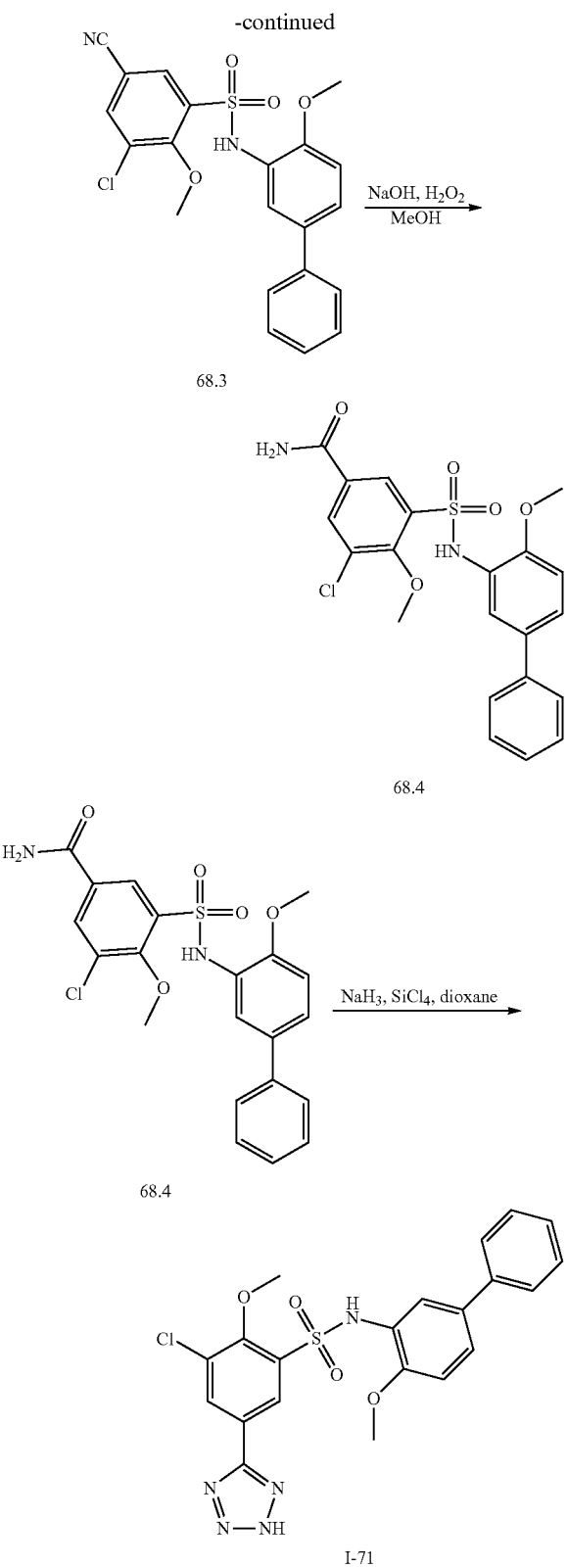

g, 13.07 mmol, 2 equiv), TMSCHN$_2$ (3.0 g, 26.15 mmol, 4 equiv) at 0° C. The resulting solution was stirred for 2 h at 0° C. The reaction was then quenched by the addition of 30 mL of water/ice. The resulting solution was extracted with 3×50 mL of ethyl acetate. The layers were separated, and the organic layers were concentrated under vacuum to dryness. This gave the title compound of 68.1 (2 g, 95%) as a yellow solid. (ES, m/z): [M−H]$^-$ 316.8.

Synthesis of Compound 68.2

Into a 100-mL round-bottom flask, was placed 68.1 (2 g, 6.25 mmol, 1 equiv), 2-methoxy-5-phenylaniline (1.5 g, 7.50 mmol, 1.2 equiv), pyridine (20 mL). The resulting solution was stirred for 2 h at 25° C. The resulting mixture was concentrated under vacuum. The residue was applied onto a silica gel column with ethyl acetate/petroleum ether (20:1). This resulted in 1.2 g (40%) of 68.2 as a solid. (ES, m/z): [M−H]$^-$ 479.9.

Synthesis of Compound 68.3

Into a 25-mL sealed tube purged and maintained with an inert atmosphere of nitrogen, was placed 68.2 (180 mg, 0.37 mmol, 1 equiv), Zn(CN)$_2$ (87.6 mg, 0.75 mmol, 2 equiv), NMP (3 mL), Pd(PPh$_3$)$_4$ (86.2 mg, 0.07 mmol, 0.2 equiv). The final reaction mixture was irradiated with microwave radiation for 1 h at 100° C. The reaction was then quenched by the addition of 20 mL of water, and extracted with 3×25 mL of ethyl acetate, followed by combined the organic phase and concentrated under vacuum. The crude product was purified by Flash-Prep-HPLC with the following conditions (IntelFlash-1): Column, C18; mobile phase, H$_2$O:ACN=15% increasing to H$_2$O:ACN=60% within 15 min; Detector, UV 254 nm. This resulted in 100 mg (62.5%) of 68.3 as a solid. (ES, m/z): [M−H]$^-$ 427.0.

Synthesis of Compound 68.4

Into a 25-mL round-bottom flask, was placed 68.3 (160 mg, 0.37 mmol, 1 equiv), MeOH (5 mL), NaOH (89.5 mg, 2.24 mmol, 6 equiv), H$_2$O$_2$ (76.1 mg, 2.24 mmol, 6 equiv). The resulting solution was stirred for 12 h at 25° C. The reaction was then quenched by the addition of 15 mL of water, extracted with 3×20 mL of ethyl acetate and the organic layers was combined to concentrated under vacuum. This gave the title compound of 68.4 (160 mg, 96.0%) as a yellow solid. (ES, m/z): [M−H]$^-$ 445.0.

Synthesis of I-71

Into a 25-mL round-bottom flask, was placed 68.4 (160 mg, 0.36 mmol, 1 equiv), dioxane (3 mL), NaN$_3$ (69.8 mg, 1.07 mmol, 3 equiv), SiCl$_4$ (182.5 mg, 1.07 mmol, 3 equiv). The resulting solution was stirred for 12 h at 100° C. The reaction was then quenched by the addition of 6 mL of sat.NaHCO$_3$. The resulting solution was extracted with 3×15 mL of ethyl acetate. And the layers were separated, and the organic phase was concentrated under vacuum. The crude product was purified by Flash-Prep-HPLC with the following conditions (IntelFlash-1): Column, C18 silica gel; mobile phase, H$_2$O:ACN=15% increasing to H$_2$O:ACN=60% within 12 min; Detector, UV 254 nm. This resulted in 28.9 mg (17.1%) of I-71 as a white solid. (ES, m/z): [M−H]$^-$ 470.1, $^1$H-NMR (300 MHz, DMSO-d$_6$, ppm):

Synthesis of Compound 68.1

Into a 100-mL 3-necked round-bottom flask, was placed 37.1 (2 g, 6.54 mmol, 1 equiv), DCM (20 mL), HBF$_4$ (1.1

δ3.56 (s, 3H), δ3.98 (s, 3H), δ6.91-7.08 (m, 2H), δ7.25-7.32 (m, 1H), δ7.32-7.42 (m, 3H), δ7.44-7.51 (m, 3H), δ8.29-8.32 (m, 2H), δ9.62 (s, 1H).

Example 69. Synthesis of 3-chloro-N-(2,4-difluoro-5-phenylphenyl)-5-(2H-1,2,3,4-tetrazol-5-yl)benzene-1-sulfonamide, I-72

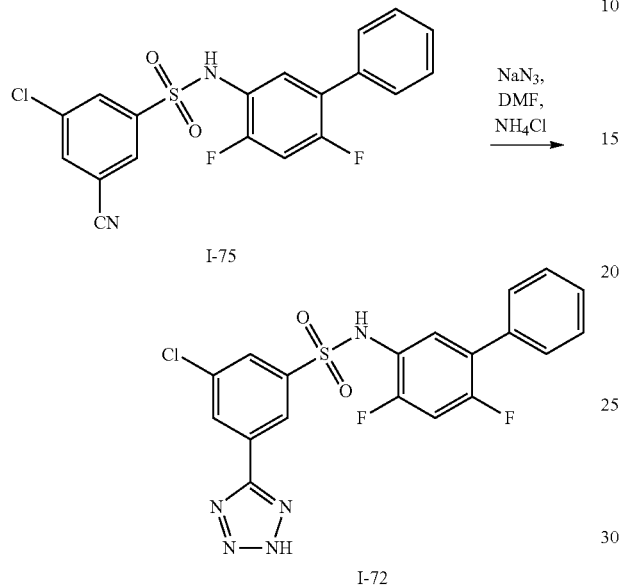

Synthesis of I-72

Into a 25-mL round-bottom flask, was placed I-75 (400 mg, 0.99 mmol, 1 equiv), DMF (5 mL), NH₄Cl (211.4 mg, 3.95 mmol, 4 equiv), NaN₃ (192.7 mg, 2.96 mmol, 3 equiv). The resulting solution was stirred for 1 h at 130° C. The solids were filtered out. The crude product was purified by Flash-Prep-HPLC with the following conditions (IntelFlash-1): Column, C18; mobile phase, MeCN:H₂O=10% increasing to MeCN:H₂O=60% within 16 min. This resulted in 373.7 mg (84.5%) of I-72 as a white solid (ES, m/z): [M−H]⁻ 446.0, ¹H-NMR (400 MHz, DMSO-d₆, ppm): δ8.31-8.32 (t, J=1.6 Hz, 1H), δ8.19-8.20 (m, 1H), δ7.58 (s, 1H), δ7.48-7.35 (m, 6H), δ7.27-7.23 (t, J=8.4 Hz, 1H), δ7.13 (br s, 2H).

Example 70. Synthesis of 3-chloro-2-hydroxy-N-(2-methoxy-5-phenylphenyl)-5-(2H-1,2,3,4-tetrazol-5-yl)benzene-1-sulfonamide, I-73

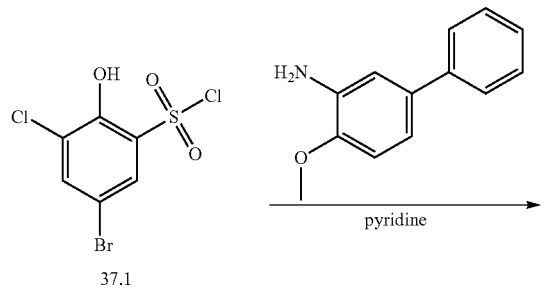

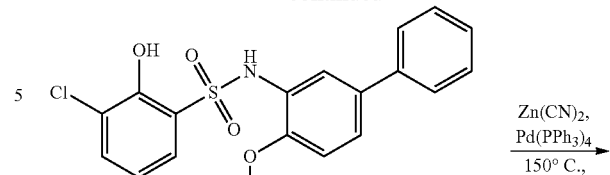

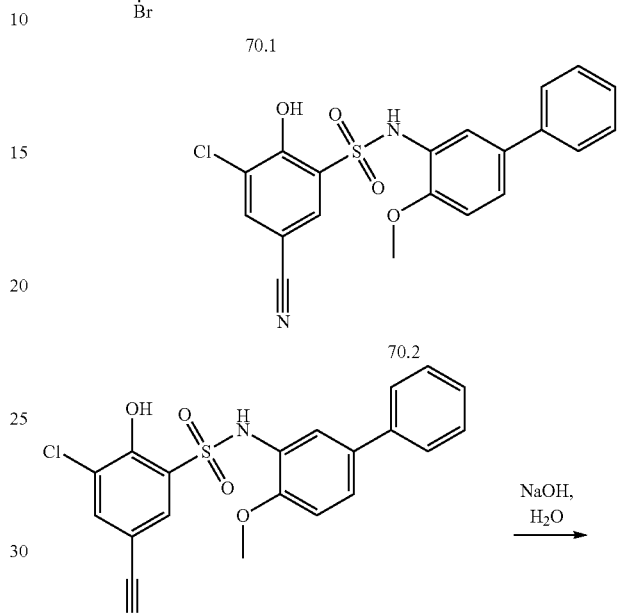

Synthesis of Compound 70.1

Into a 250-mL round-bottom flask, was placed 37.1 (5 g, 16.34 mmol, 1 equiv), 2-methoxy-5-phenylaniline (3.9 g, 19.61 mmol, 1.2 equiv), pyridine (50 mL). The resulting solution was stirred for 12 h at 25° C. The reaction was then quenched by the addition of 100 mL of diluted hydrochloric acid, and extracted with 3×150 mL of ethyl acetate. The organic layers was combined and concentrated under vacuum. The crude product was purified by Flash-Prep-HPLC with the following conditions (IntelFlash-1): Column, C18; mobile phase, H$_2$O:ACN=1 increasing to H$_2$O:ACN=60% within 18 min; Detector, UV 254 nm. This resulted in 2 g (26.11%) of 70.1 as a white solid. (ES, m/z): [M−H]$^-$ 465.9.

Synthesis of Compound 70.2

Into a 50-mL round-bottom flask purged and maintained with an inert atmosphere of nitrogen, was placed 70.1 (1 g, 2.13 mmol, 1 equiv), Zn(CN)$_2$ (0.5 g, 4.27 mmol, 2 equiv), NMP (10 mL), Pd(PPh$_3$)$_4$ (0.5 g, 0.43 mmol, 0.2 equiv). The final reaction mixture was irradiated with microwave radiation for 1 h at 150° C. The reaction was then quenched by the addition of 15 mL of water/ice, extracted with 3×30 mL of ethyl acetate. Then, the organic layers were combined and the solvent was removed under vacuum. The crude product was purified by Flash-Prep-HPLC with the following conditions (IntelFlash-1): Column, C18; mobile phase, H$_2$O:ACN=15% increasing to H$_2$O:ACN=60% within 18 min; Detector UV 254 nm. This resulted in 660 mg (74.57%) of 70.2 as a white solid. (ES, m/z): [M−H]$^-$ 413.0.

Synthesis of Compound 70.3

Into a 100-mL round-bottom flask, was placed 70.2 (1.3 g, 3.13 mmol, 1 equiv), methanol (15 mL), NaOH (0.8 g, 18.80 mmol, 6 equiv), H$_2$O$_2$ (0.6 g, 18.80 mmol, 6 equiv). The resulting solution was stirred for 12 h at 25° C. The reaction was then quenched by the addition of 15 mL of sat. Na$_2$SO$_3$ (aq.)/diluted hydrochloric acid. The resulting solution was extracted with 3×30 mL of ethyl acetate and the combined organic phase was evaporated to dryness. This resulted in 800 mg (58.98%) of 70.3 as a light yellow solid. (ES, m/z): [M−H]$^-$ 431.0.

Synthesis of I-73

Into a 50-mL round-bottom flask, was placed 70.3 (800 mg, 1.85 mmol, 1 equiv), dioxane (10 mL), NaN$_3$ (360.4 mg, 5.54 mmol, 3 equiv), SiCl$_4$ (942.0 mg, 5.54 mmol, 3 equiv). The resulting solution was stirred for 12 h at 100° C. Then, the reaction was quenched by the addition of 15 mL of sat.NaHCO$_3$. The resulting solution was extracted with 2×20 mL of ethyl acetate, followed by combined the aqueous layers and then concentrated under vacuum. The crude product was purified by Flash-Prep-HPLC with the following conditions (IntelFlash-1): Column, C18; mobile phase, H$_2$O:ACN=15% increasing to H$_2$O:ACN=60% within 15 min; Detector, UV 254 nm. This resulted in 60 mg (7.09%) of I-73 as a white solid. (ES, m/z): [M−H]$^-$ 456.3, $^1$H-NMR (300 MHz, DMSO-d$_6$, ppm): δ3.63 (s, 3H), δ7.01-7.03 (d, J=8.4 Hz, 1H), δ7.28-7.42 (m, 4H), δ7.47-7.53 (m, 3H), δ8.24-8.32 (m, 2H), δ9.38 (br s, 1H).

Example 71. Synthesis of Methyl 3-chloro-5-(N-(2,4-difluorophenyl)sulfamoyl)-4-hydroxybenzoate, I-74

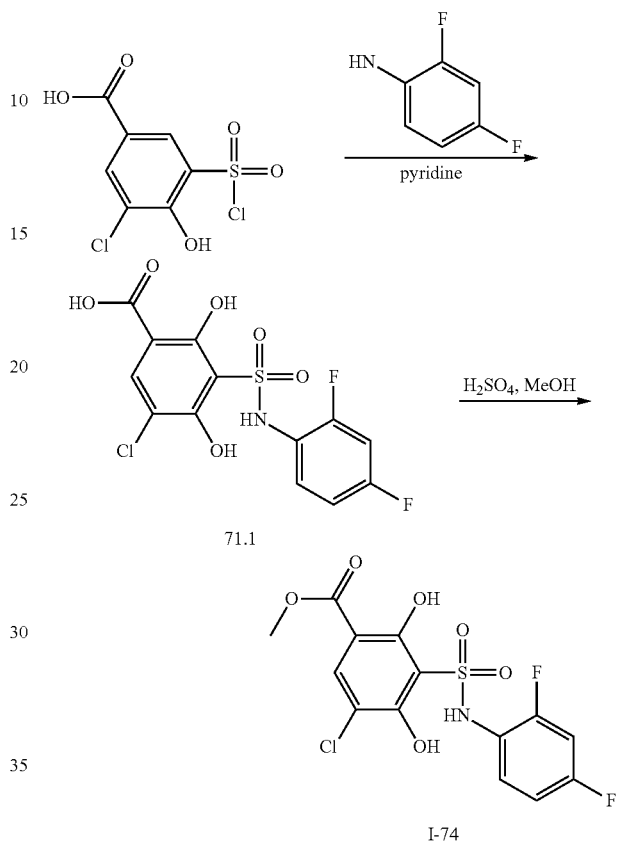

Synthesis of Compound 71.1

Into a 25-mL round-bottom flask, was placed 3-chloro-5-(chlorosulfonyl)-4-hydroxybenzoic acid (500 mg, 1.84 mmol, 1.00 equiv), 2,4-difluoroaniline (259.73 mg, 2.01 mmol, 1.09 equiv), pyridine (6 mL). The resulting solution was stirred overnight at 25° C. The resulting mixture was concentrated under vacuum. The crude product was purified by Flash-Prep-HPLC with the following conditions (IntelFlash-1): Column, C18; mobile phase, water:acetonitrile=90:10 increasing to water:acetonitrile=0:100 within 30 min; Detector, UV 250 nm. This resulted in 460 mg (69%) of 71.1 as an off-white solid. (ES, m/z): [M−H]$^-$ 361.9.

Synthesis of I-74

Into a 25-mL round-bottom flask, was placed 71.1 (200 mg, 0.55 mmol, 1 equiv), MeOH (5 mL), H$_2$SO$_4$ (161.8 mg, 1.65 mmol, 3 equiv). The resulting solution was stirred overnight at 65° C. The resulting mixture was evaporated under vacuum. The crude product was purified by Flash-Prep-HPLC with the following conditions (IntelFlash-1): Column, C18; mobile phase, ACN/H$_2$O=15% increasing to ACN/H$_2$O=60% within 15 min; Detector, UV 254 nm. This resulted in 13.9 mg (6.7%) of I-74 as a white solid. (ES, m/z): [M−H]$^-$ 376.2, $^1$H-NMR (400 MHz, CD$_3$OD, ppm):

δ3.79 (s, 3H), δ6.80-6.84 (m, 1H), δ6.87-6.92 (m, 1H), δ7.30-7.36 (m, 1H), δ7.94-7.95 (d, J=2.4 Hz, 1H), δ8.02-8.03 (d, J=2.4 Hz, 1H).

Example 72. Synthesis of 3-chloro-5-cyano-N-(2,4-difluoro-5-phenylphenyl) benzene-1-sulfonamide, I-75

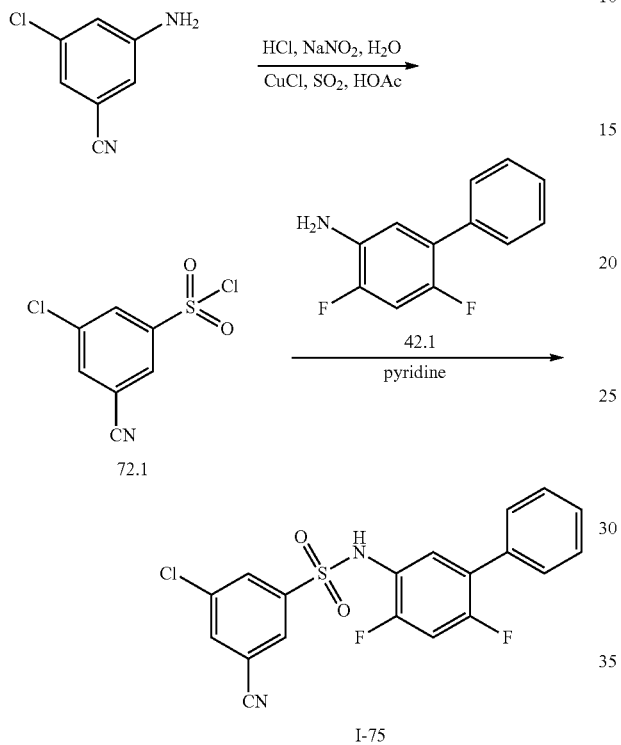

Synthesis of Compound 72.1

A solution of NaNO$_2$ (940 mg, 13.62 mmol, 1 equiv) in water (3 mL) was added to a suspension of 3-amino-5-chlorobenzonitrile (2.0 g, 13.16 mmol, 1 equiv) in conc. HCl (12.5 mL) and water (12.5 mL) at 0° C. over 5 min, and the resulting solution was stirred for a further 30 min. Then, AcOH (15.5 mL) was saturated with SO$_2$, and added CuCl (130 mg, 1.29 mmol, 0.1 equiv), meanwhile, SO$_2$ bubbled through for a further 5 min. The AcOH mixture was cooled to 5° C., and the above diazonium solution was added. The resulting mixture was stirred for a 1 h at 0° C. and additional 1 h at room temperature. The solution was diluted with water (20 mL) and extracted twice with CH$_2$Cl$_2$ (25 mL). The combined organic extracts were washed twice with water (10 mL), dried (Na$_2$SO$_4$) and the solvent was removed under reduced pressure. This gave the title compound of 72.1 (2.6 g, 84%) as a brown crude oil. (ES, m/z): [M−H]$^-$ 233.9.

Synthesis of I-75

Into a 50-mL round-bottom flask, was placed 72.1 (2.6 g, 11.01 mmol, 1 equiv), 42.1 (2.7 g, 13.22 mmol, 1.2 equiv), pyridine (10 mL). The resulting solution was stirred overnight at 25° C. The resulting mixture was concentrated under vacuum. The residue was applied onto a silica gel column with ethyl acetate/petroleum ether (1:10). This resulted in 2.7 g (60.6%) of I-75 as a yellow solid. (ES, m/z): [M−H]$^-$ 402.9, $^1$H-NMR (400 MHz, DMSO-d$_6$, ppm): δ10.62 (br s, 1H), δ8.42 (s, 1H), δ8.14 (s, 1H), δ8.07-8.06 (d, J=1.6 Hz, 1H), δ7.49-7.43 (m, 6H), δ7.31 (t, 1H).

Example 73. Synthesis of 3-chloro-5-[(2,4-difluorophenyl)sulfamoyl]-4-hydroxybenzoic Acid, I-76

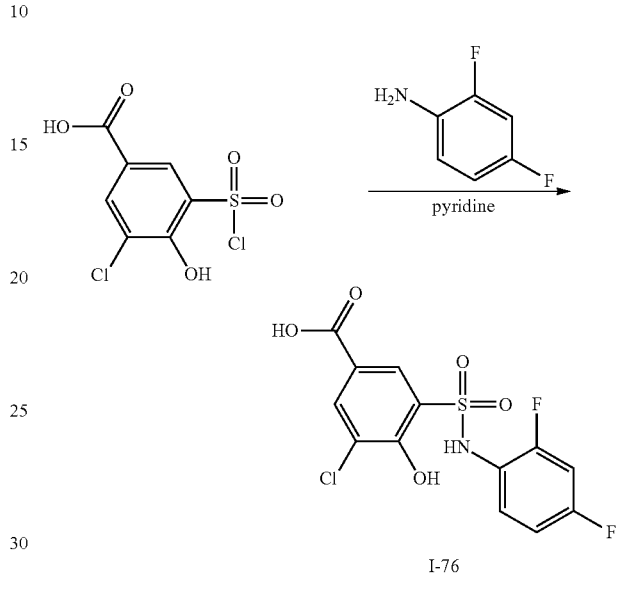

Synthesis of I-76

Into a 25-mL round-bottom flask, was placed 3-chloro-5-(chlorosulfonyl)-4-hydroxybenzoic acid (500 mg, 1.84 mmol, 1 equiv), 2,4-difluoroaniline (285.8 mg, 2.21 mmol, 1.2 equiv), pyridine (6 mL). The resulting solution was stirred overnight at 25° C. The resulting mixture was concentrated. The crude product was purified by Flash-Prep-HPLC with the following conditions (IntelFlash-1): Column, C 18; mobile phase, water:acetonitrile=90:10 increasing to water:acetonitrile=0:100 within 30 min; Detector, UV 254 nm. This resulted in 26.7 mg (4.0%) of I-76 as a yellow green solid. (ES, m/z): [M−H]$^-$ 362.1, $^1$H-NMR (400 MHz, DMSO-d$_6$, ppm): δ6.95-7.08 (m, 1H), δ7.20-7.27 (m, 2H), δ7.92-7.93 (d, J=2.4 Hz, 2H).

Example 74. Synthesis of 2-(2,4-dichloro-6-(N-(4,6-difluoro-[1,1'-biphenyl]-3-yl) sulfamoyl)phenoxy) acetic Acid, I-77

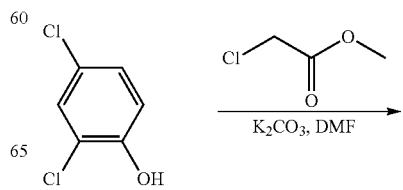

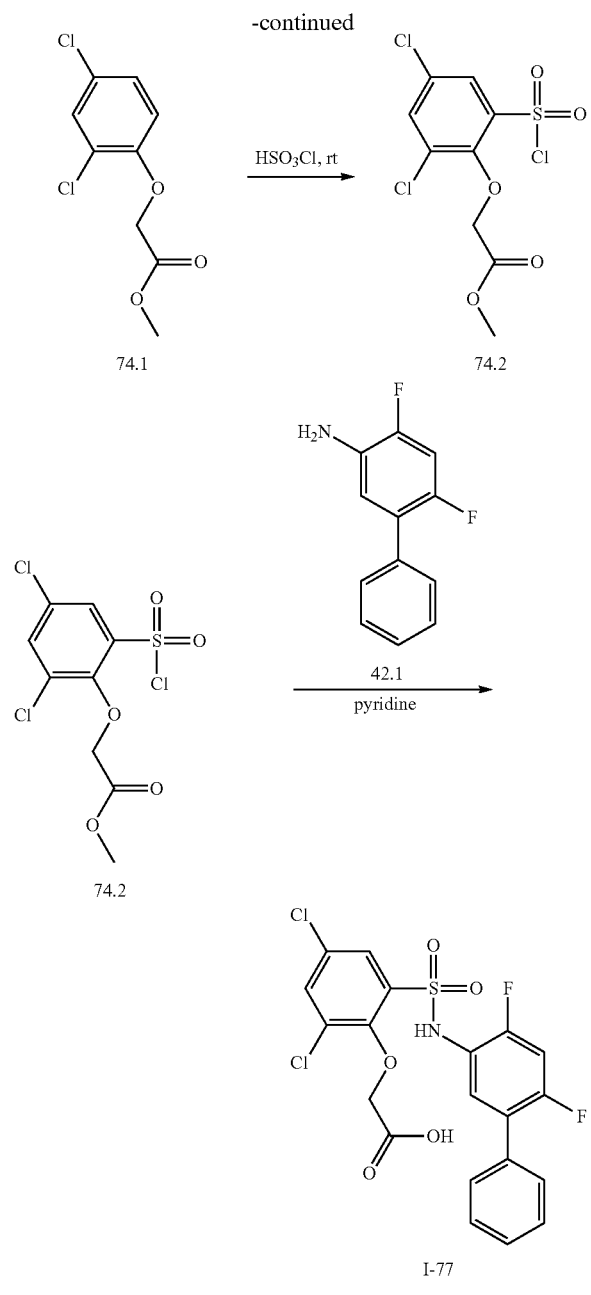

Synthesis of Compound 74.1

Into a 100-mL round-bottom flask, was placed 2,4-dichlorophenol (2 g, 12.27 mmol, 1 equiv), DMF (25 mL), methyl 2-chloroacetate (1.6 g, 14.72 mmol, 1.2 equiv), $K_2CO_3$ (3.4 g, 24.54 mmol, 2 equiv). The resulting solution was stirred for 12 h at 80° C. The reaction was quenched by the addition of 30 mL of water, and extracted with 3×35 mL of ethyl acetate. After separated the layers, the organic layers was combined and concentrated under vacuum. The crude product was applied onto a silica gel column with ethyl acetate/petroleum ether (20:1). This resulted in 2 g (69%) of 74.1 as a yellow oil. (ES, m/z): $[M+H]^+$ 234.9.

Synthesis of Compound 74.2

Into a 50-mL round-bottom flask, was placed $HSO_3Cl$ (3.35 mL), 74.1 (1 g, 4.25 mmol, 1 equiv) at 0° C. The resulting solution was stirred for 2 h at 25° C. Then, the reaction was quenched by the addition of 15 mL of water/ice, followed by extracted with 3×25 mL of ethyl acetate. The organic layers was separated and combined, then concentrated under vacuum to yield 74.2 (880 mg, 62.0%) as light yellow oil. (ES, m/z): $[M-H]^-$ 330.9.

Synthesis of I-77

Into a 50-mL 3-necked round-bottom flask, was placed 74.2 (1.1 g, 3.30 mmol, 1 equiv), 42.1 (0.8 g, 3.96 mmol, 1.2 equiv), pyridine (12 mL). The resulting solution was stirred for 12 h at 25° C. The resulting mixture was concentrated under vacuum. The crude product was purified by Flash-Prep-HPLC with the following conditions (IntelFlash-1): Column, C18; mobile phase, $H_2O:ACN=15\%$ increasing to $H_2O:ACN=60\%$ within 15 min; Detector, UV 254 nm. This resulted in 101.6 mg (6.4%) of I-77 as a white solid. (ES, m/z): $[M-H]^-$ 485.9, $^1H$-NMR (300 MHz, DMSO-$d_6$, ppm): $\delta 4.67$ (s, 2H), $\delta 7.20$-$7.27$ (m, 2H), $\delta 7.30$-$7.45$ (m, 5H), $\delta 7.48$ (s, 1H), $\delta 7.76$ (s, 1H).

Example 75. Synthesis of Methyl 2-(2-bromo-4-chloro-6-(N-(4-fluoro-[1,1'-biphenyl]-3-yl)sulfamoyl)phenoxy)acetate, I-78

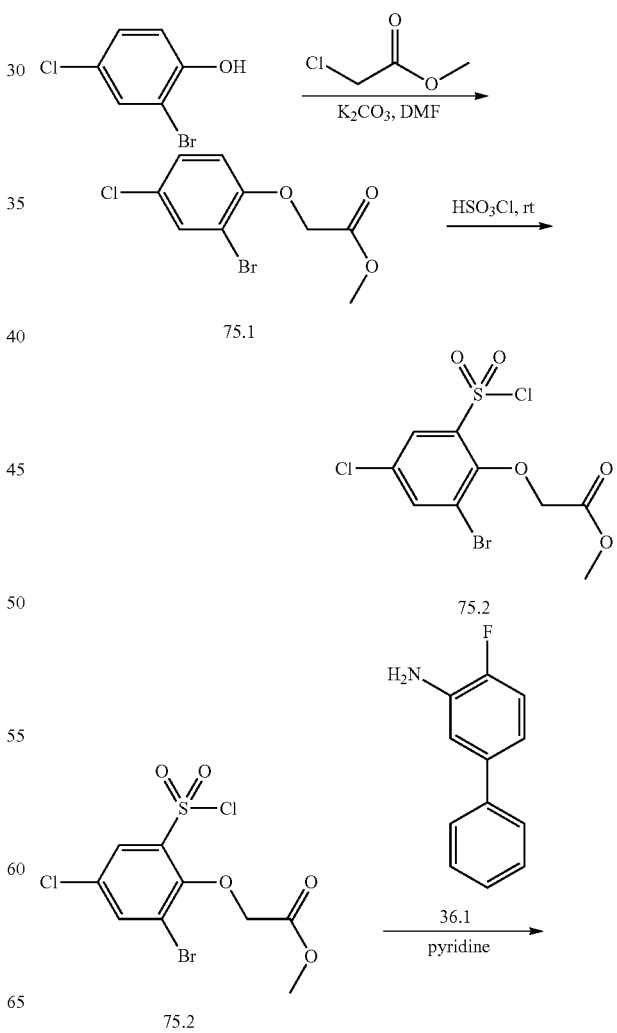

-continued

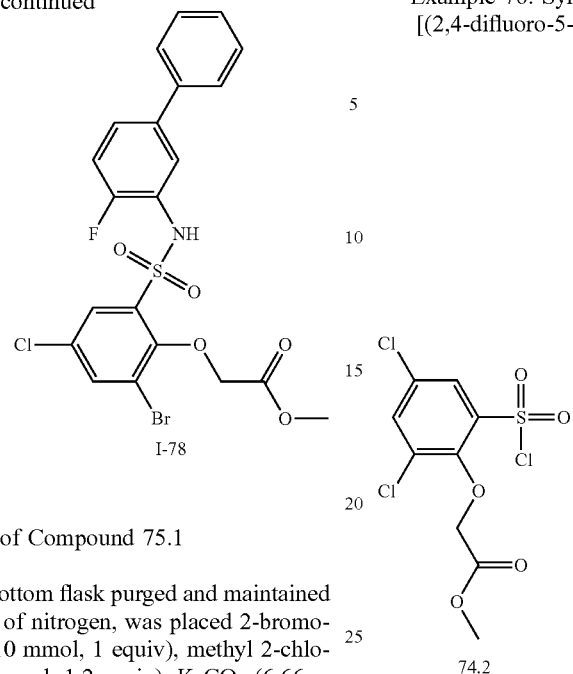

I-78

Synthesis of Compound 75.1

Into a 250-mL round-bottom flask purged and maintained with an inert atmosphere of nitrogen, was placed 2-bromo-4-chlorophenol (5 g, 24.10 mmol, 1 equiv), methyl 2-chloroacetate (3.14 g, 28.92 mmol, 1.2 equiv), K$_2$CO$_3$ (6.66 g, 48.20 mmol, 2 equiv), DMF (50 mL). The resulting solution was stirred for 12 h at 80° C. in an oil bath. The resulting solution was diluted with 40 mL of water and extracted with 3×50 mL of ethyl acetate. The combined organic layers were washed with 50 mL of brine, dried and concentrated under vacuum. The residue was applied onto a silica gel column with ethyl acetate/petroleum ether (1:3). This resulted in 5 g (74.22%) of 75.1 as a yellow solid. (ES, m/z): [M+H]$^+$ 278.9.

Synthesis of Compound 75.2

Into a 100-mL round-bottom flask purged and maintained with an inert atmosphere of nitrogen, was placed 75.1 (1 g, 3.58 mmol, 1 equiv), HSO$_3$Cl (5 g, 42.93 mmol, 12.000 equiv). The resulting solution was stirred for 12 h at room temperature. The reaction was then quenched by the addition of 50 mL of water/ice, and extracted with 3×50 mL of dichloromethane. The organic layers were combined, washed with 50 mL of brine, dried and concentrated under vacuum. This resulted in 800 mg (59.15%) of 75.2 as a white solid. (ES, m/z): [M−H]$^−$ 374.8.

Synthesis of I-78

Into a 100-mL round-bottom flask purged and maintained with an inert atmosphere of nitrogen, was placed 75.2 (118.9 mg, 0.63 mmol, 1.2 equiv), 36.1 (118.9 mg, 0.63 mmol, 1.2 equiv), pyridine (10 mL). The resulting solution was stirred for 0.5 h at room temperature. After being diluted with 10 mL of water, the reaction mixture was extracted with 3×10 mL of ethyl acetate, and the combined organic phase was washed with 10 mL of brine, dried over anhydrous sodium sulfate. The solvents were removed under vacuum, and the crude product was purified by silica gel column (ethyl acetate/petroleum ether=1:0) to afford I-78 (144.2 mg) as a white solid in 51.54% yield. (ES, m/z): [M+H]$^+$ 527.9, $^1$H-NMR (400 MHz, DMSO-d$_6$, ppm): δ3.53 (s, 3H), δ4.97 (s, 2H), δ7.27-7.31 (m, 1H), δ7.36-7.41 (m, 2H), δ7.44-7.47 (m, 3H), δ7.50-7.53 (m, 3H), δ8.05 (s, 1H), δ10.62 (s, 1H).

Example 76. Synthesis of Methyl 2-[2,4-dichloro-6-[(2,4-difluoro-5-phenylphenyl) sulfamoyl]phenoxy]acetate, I-79

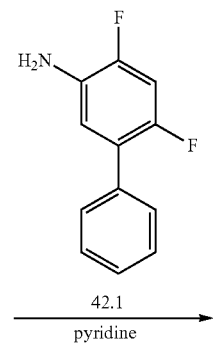

74.2

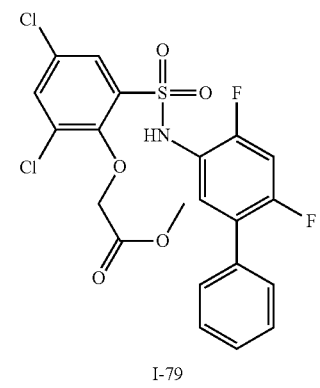

I-79

Synthesis of I-79

Into a 50-mL 3-necked round-bottom flask, was placed 74.2 (1.1 g, 3.30 mmol, 1 equiv), 42.1 (0.812 g, 3.96 mmol, 1.200 equiv), pyridine (12 mL). The resulting solution was stirred for 12 h at 25° C. The resulting mixture was concentrated under vacuum. The crude product was purified by Flash-Prep-HPLC with the following conditions (IntelFlash-1): Column, C18; mobile phase, H$_2$O:ACN=15% increasing to H$_2$O:ACN=60% within 15 min; Detector, UV 254 nm. This resulted in 38.3 mg (2.3%) of I-79 as an off-white solid. (ES, m/z): [M−H]$^−$ 500.0, $^1$H-NMR (300 MHz, DMSO-d$_6$, ppm): δ3.55 (s, 3H), δ4.99 (s, 2H), δ7.28-7.32 (m, 1H), δ7.38-7.48 (m, 7H), δ7.95 (s, 1H), δ10.61 (s, 1H).

Example 77. Synthesis of 3-chloro-N-(4,6-difluoro-[1,1'-biphenyl]-3-yl)-2-hydroxy-5-(pyrrolidine-1-carbonyl)benzenesulfonamide, I-82

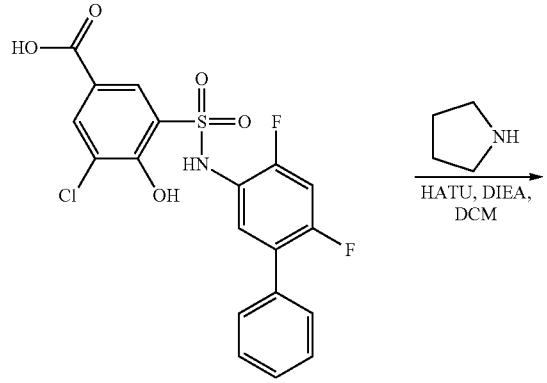

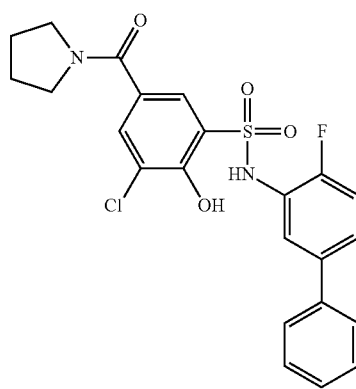

Synthesis of I-82

Into a 100-mL round-bottom flask purged and maintained with an inert atmosphere of nitrogen, was placed 78.1 (200 mg, 0.45 mmol, 1 equiv), pyrrolidine (323.4 mg, 4.55 mmol, 10 equiv), HATU (345.8 mg, 0.91 mmol, 2 equiv), DIEA (117.5 mg, 0.91 mmol, 2 equiv), DCM (5 mL) at room temperature. After stirring for 12 h, the resulting solution was diluted with 10 mL of water, and extracted with 3×10 mL of ethyl acetate. The combined organic phase was washed with 10 mL of brine, dried and concentrated under vacuum to yield a crude product which was purified by a silica gel column (ethyl acetate/petroleum ether=1:2). This resulted in 59.2 mg (26.4%) of I-82 as a white solid. (ES, m/z): [M–H]⁻ 491.0, ¹H-NMR (400 MHz, DMSO-d₆, ppm): δ1.75 (s, 4H), δ3.34 (s, 4H), δ6.91-7.23 (m, 2H), δ7.30-7.37 (m, 4H), δ7.39-7.47 (m, 3H), δ7.58-7.59 (d, J=2.4 Hz, 1H), δ7.61-7.64 (d, J=13.6 Hz, 1H).

Example 78. Synthesis of 3-chloro-5-[(2,4-difluoro-5-phenylphenyl)sulfamoyl]-4-hydroxy-N,N-dimethylbenzamide, I-83

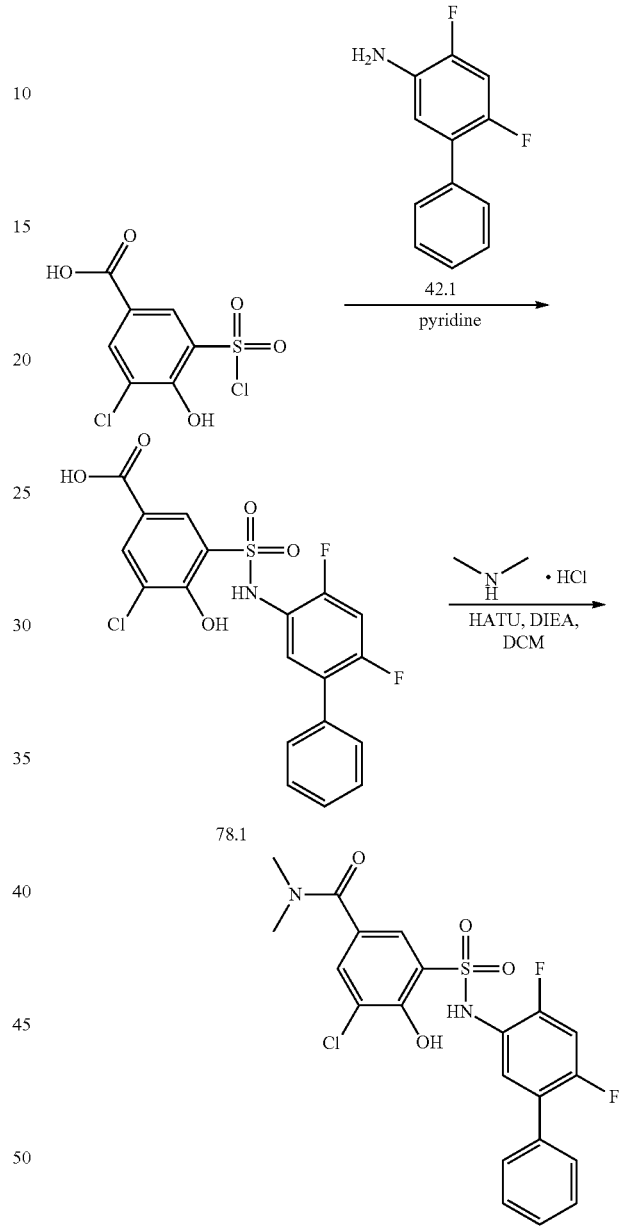

Synthesis of Compound 78.1

Into a 50-mL 3-necked round-bottom flask, was placed 3-chloro-5-(chlorosulfonyl)-4-hydroxybenzoic acid (3 g, 11.07 mmol, 1 equiv), 42.1 (2725.2 mg, 13.28 mmol, 1.2 equiv), pyridine (30 mL). The resulting solution was stirred overnight at room temperature. The resulting mixture was concentrated under vacuum, diluted with 100 mL of H₂O, and extracted with 3×200 mL of ethyl acetate. The combined organic extracts were concentrated under vacuum. The residue was applied onto a silica gel column with dichloromethane/methanol (10:1) to afford the product of 78.1 (836 mg, 17.2%) as yellow oil. (ES, m/z): [M−H]⁻ 438.0.

Synthesis of I-83

Into a 8-mL vial purged and maintained with an inert atmosphere of nitrogen, was placed 78.1 (150 mg, 0.34 mmol, 1 equiv), dimethylamine hydrochloride (55 mg, 0.68 mmol, 2 equiv), DCM (1.5 mL), DIEA (265 mg, 2.04 mmol, 6 equiv), HATU (195 mg, 0.51 mmol, 1.5 equiv). The resulting solution was stirred overnight at room temperature. The resulting solution was diluted with 10 mL of $H_2O$, and extracted with 3×20 mL of ethyl acetate and concentrated the organic extracts under vacuum. The crude product was purified by Flash-Prep-HPLC with the following conditions (IntelFlash-1): Column, C18; mobile phase, ACN/$H_2O$=15% increasing to ACN/$H_2O$=60% within 15 min; Detector, UV 254 nm. This resulted in 96.0 mg of I-83 as a white solid. (ES, m/z): [M+H]⁺ 467.2, ¹H-NMR (300 MHz, DMSO-$d_6$, ppm): δ2.87 (s, 6H), δ6.93-7.10 (m, 1H), δ7.27-7.48 (m, 9H), δ7.53-7.54 (d, J=2.1 Hz, 1H).

Example 79. Synthesis of ethyl 3-chloro-5-[(2,4-difluoro-5-phenylphenyl)sulfamoyl]-4-hydroxybenzoate, I-84

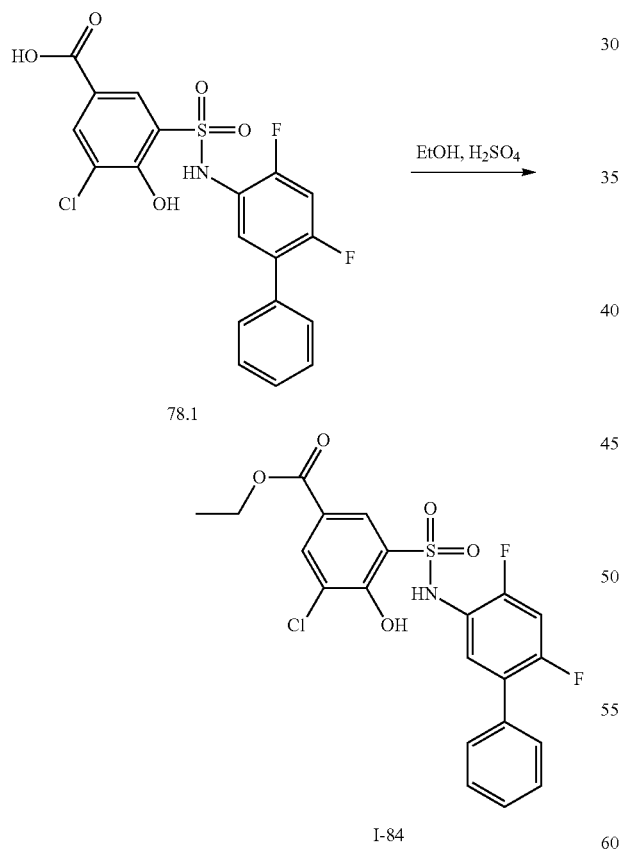

Synthesis of I-122

Into a 8-mL vial, was placed 121.1 (200 mg, 0.46 mmol, 1 equiv), EtOH (4 mL), a solution of $H_2SO_4$ (45 mg) in EtOH (1 mL). The resulting solution was stirred overnight at 80° C. in an oil bath. The reaction mixture was diluted with 20 mL of $H_2O$, extracted with 4×40 mL of ethyl acetate and the organic phase was evaporated under vacuum. The crude product was purified by Flash-Prep-HPLC with the following conditions (IntelFlash-1): Column, C18; mobile phase, ACN/$H_2O$=15% increasing to ACN/$H_2O$=60% within 15 min; Detector, UV 254 nm. This resulted in 126.9 mg of I-122 as a white solid. (ES, m/z): [M−H]⁻ 466.0, ¹H-NMR (300 MHz, DMSO-$d_6$, ppm): δ1.20-1.25 (t, J=7.2 Hz, 3H), δ4.11-4.18 (m, 2H), δ7.11 (br s, 1H), δ7.28-7.47 (m, 7H), δ7.75-7.76 (d, J=2.4 Hz, 1H), δ7.83-7.84 (d, J=2.4 Hz, 1H).

Example 80. Synthesis of 3,5-dichloro-N-(2-fluoro-5-phenylphenyl)-2-(2,2,2-trifluoroethoxy)benzene-1-sulfonamide, I-85

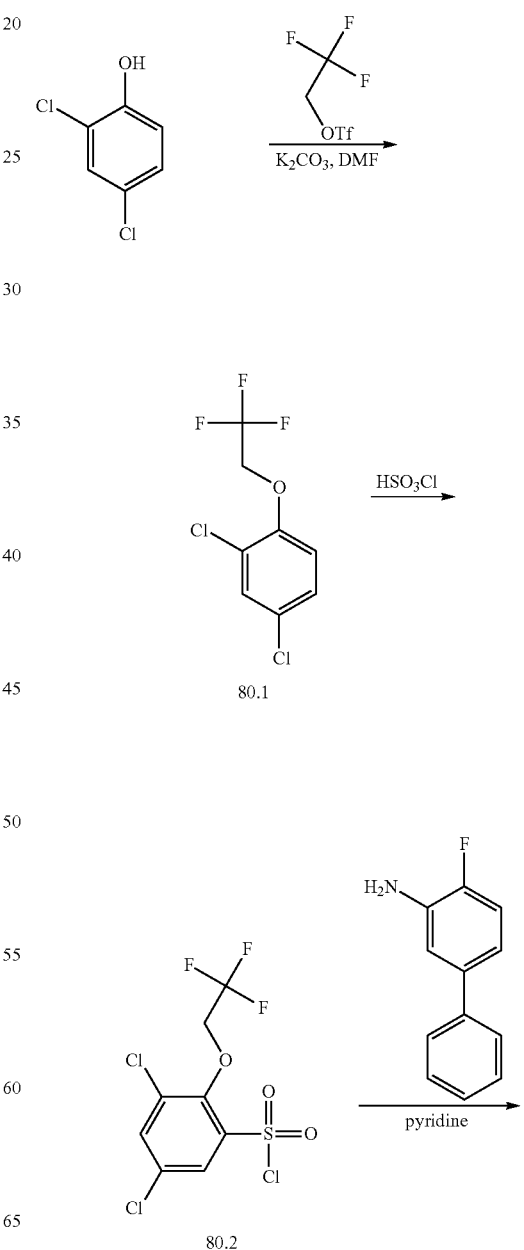

Example 81. Synthesis of propan-2-yl 3-chloro-5-[(2,4-difluoro-5-phenylphenyl) sulfamoyl]-4-hydroxybenzoate, I-86

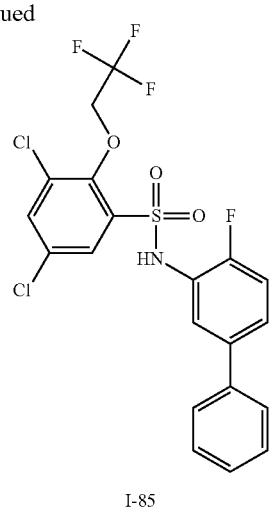

I-85

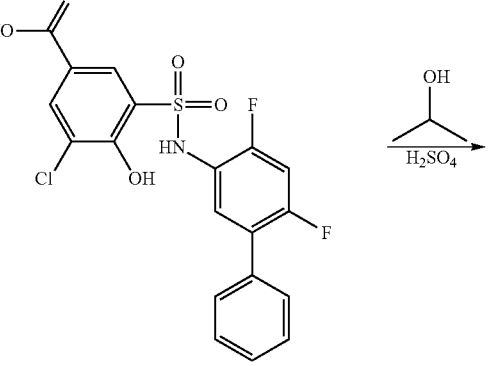

78.1

Synthesis of Compound 80.1

Into a 50-mL round-bottom flask, was placed 2,4-dichlorophenol (800 mg, 4.91 mmol, 1 equiv), DMF (10 mL), K$_2$CO$_3$ (1356.6 mg, 9.82 mmol, 2 equiv), 2,2,2-trifluoroethyl trifluoromethane sulfonate (1367.0 mg, 5.89 mmol, 1.2 equiv). The resulting solution was stirred for 12 h at 50° C. The reaction was then quenched by the addition of 15 mL of water, extracted with 3×20 mL of ethyl acetate, and the organic layers was combined, followed by evaporated to dryness under vacuum. The crude product purified by a silica gel column with ethyl acetate/petroleum ether (20:1). This resulted in 900 mg (74.8%) of 80.1 as light yellow oil. (ES, m/z): [M+H]$^+$ 244.9.

Synthesis of Compound 80.2

Into a 50-mL 3-necked round-bottom flask, was placed HSO$_3$Cl (2.28 g, 19.59 mmol, 12 equiv), 80.1 (400 mg, 1.63 mmol, 1 equiv) at 0° C. The resulting solution was stirred for 12 h at 25° C. The reaction was quenched by the addition of 15 mL of water/ice, and extracted with 3×20 mL of ethyl acetate. Then, the organic layers were combined, followed by concentrated under vacuum. This gave the title compound of 80.2 (500 mg, 89.3%) as a black solid. (ES, m/z): [M−H]$^−$ 340.8.

Synthesis of I-85

Into a 50-mL round-bottom flask, was placed 80.2 (400 mg, 1.16 mmol, 1 equiv), 2-fluoro-5-phenylaniline (261.6 mg, 1.40 mmol, 1.2 equiv), pyridine (7 mL). The reaction solution was stirred for 2 h at 25° C. The resulting mixture was concentrated under vacuum to yield the crude product which was purified by Flash-Prep-HPLC with the following conditions (IntelFlash-1): Column, C18; mobile phase, H$_2$O: ACN=15% increasing to H$_2$O:ACN=60% within 15 min; Detector, UV 254 nm. This resulted in 89.7 mg (15.6%) of I-85 as a yellow solid. $^1$H-NMR (300 MHz, DMSO-d$_6$, ppm): δ4.89-4.98 (m, 2H), δ7.24-7.30 (m, 1H), δ7.35-7.39 (m, 1H), δ7.40-7.53 (m, 6H), δ7.75 (s, 1H), δ7.99 (s, 1H), δ10.69 (s, 1H).

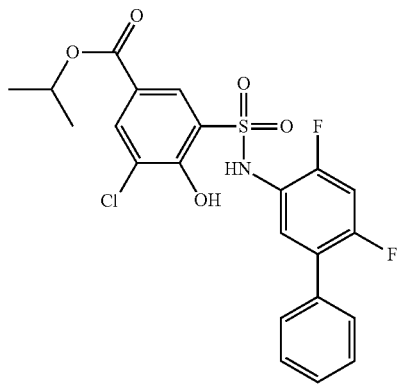

I-86

Synthesis of I-86

Into a 25-mL round-bottom flask, was placed 78.1 (200 mg, 0.45 mmol, 1 equiv), propan-2-ol (54.7 mg, 0.91 mmol, 2 equiv), sulfuric acid (5 mL, 98%). The resulting solution was stirred for 12 h at 82° C. The reaction was then quenched by the addition of 10 mL of water. The resulting solution was extracted with 3×15 mL of ethyl acetate. Then, the organic layers were combined, and concentrated under vacuum. The crude product was purified by Prep-TLC (elution solvent:dichloromethane/methanol=20:1). This gave the title compound of I-86 (131.2 mg, 59.9%) as a white solid. (ES, m/z): [M−H]$^−$ 480.2, $^1$H-NMR (300 MHz, DMSO-d$_6$, ppm): δ1.21-1.23 (d, J=6.3 Hz, 6H), δ4.94-5.02 (m, 1H), δ7.29-7.40 (m, 4H), δ7.41-7.47 (m, 3H), δ7.76-7.77 (d, J=2.4 Hz, 1H), δ7.83-7.84 (d, J=2.4 Hz, 1H).

Example 82. Synthesis of 3-chloro-5-[(2,4-difluoro-5-phenylphenyl)sulfamoyl]-4-hydroxy-N-methoxy-N-methylbenzamide, I-87

Example 83. Synthesis of 5-bromo-3-chloro-N-[4,6-difluoro-[1,1-biphenyl]-3-yl]-2-hydroxybenzene-1-sulfonamide, I-88

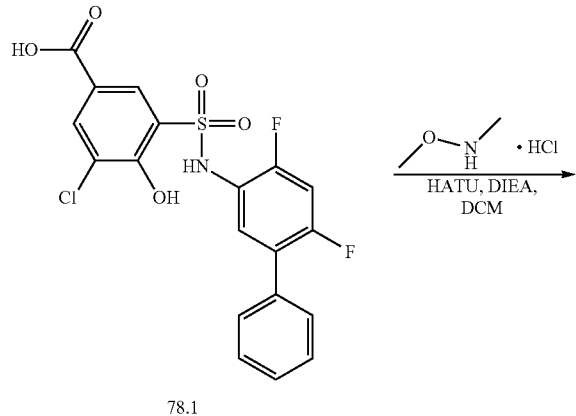

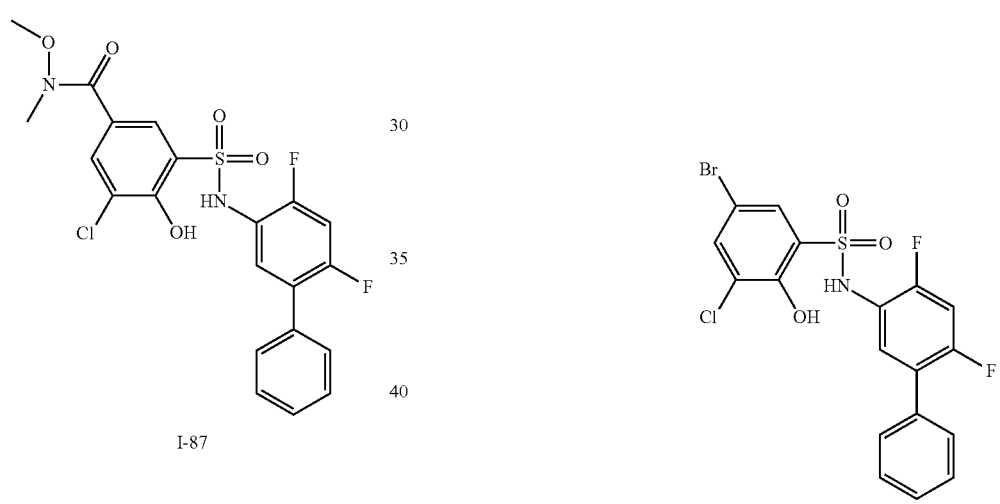

Synthesis of I-87

Into a 25-mL round-bottom flask, was placed 78.1 (100 mg, 0.23 mmol, 1 equiv), DCM (3 mL), DIEA (176.3 mg, 1.36 mmol, 6 equiv), methoxy(methyl)amine hydrochloride (44.4 mg, 0.45 mmol, 2 equiv), HATU (129.7 mg, 0.34 mmol, 1.5 equiv). The resulting solution was stirred for 12 h at 25° C. The reaction was then quenched by the addition of 5 mL of water, and extracted with 3×10 mL of dichloromethane. The organic layers was combined and concentrated under vacuum. The crude product was purified by Flash-Prep-HPLC with the following conditions (IntelFlash-1): Column, C18; mobile phase, $H_2O$:ACN=15% increasing to $H_2O$:ACN=60% within 13 min; Detector, UV 254 nm. This resulted in 13.1 mg (11.9%) of I-87 as a white solid. (ES, m/z): [M−H]⁻ 481.2, ¹H-NMR (300 MHz, DMSO-$d_6$, ppm): δ3.20 (s, 3H), δ3.38 (s, 3H), δ7.27-7.49 (m, 7H), δ7.86-7.87 (d, J=2.1 Hz, 1H), δ7.90-7.91 (d, J=2.1 Hz, 1H).

Synthesis of I-88

Into a 25-mL round-bottom flask, was placed 37.1 (300 mg, 0.98 mmol, 1 equiv), 42.1 (241.5 mg, 1.18 mmol, 1.2 equiv), pyridine (5 mL). The resulting solution was stirred overnight at 25° C. The resulting mixture was concentrated. The crude product was purified by Flash-Prep-HPLC with the following conditions (IntelFlash-1): Column, C18; mobile phase, water:acetonitrile=90:10 increasing to water:acetonitrile=0:100 within 30 min; Detector, UV 254 nm. This resulted in 104.4 mg (22.3%) of I-88 as a white solid. (ES, m/z): [M+H]⁺ 473.9, ¹H-NMR (400 MHz, CD₃OD, ppm): δ6.99-7.04 (m, 1H), δ7.32-7.36 (m, 4H), δ 7.39-7.43 (m, 3H), δ7.46-7.47 (d, J=2.8 Hz, 1H).

367

Example 84. Synthesis of 3-chloro-N-(2,4-difluoro-5-phenylphenyl)-2-hydroxy-5-(hydroxymethyl)benzene-1-sulfonamide, I-90

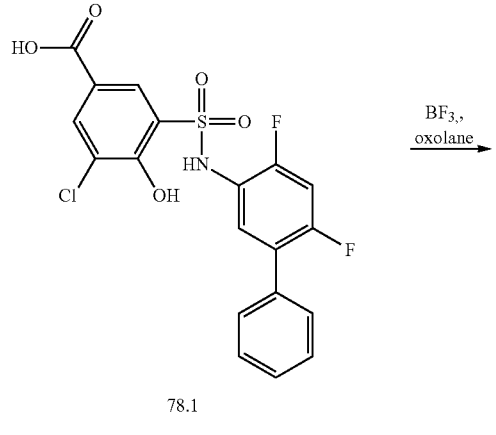

Synthesis of I-90

Into a 10-mL round-bottom flask purged and maintained with an inert atmosphere of nitrogen, was placed 78.1 (170 mg, 0.39 mmol, 1 equiv), borane (37.4 mg, 2.70 mmol, 6.994 equiv), oxolane (10 mL). The reaction mixture was stirred for 12 h at room temperature. The resulting solution was diluted with 10 mL of water, extracted with 3×10 mL of ethyl acetate, and the combined organic phase was washed with 10 mL of brine, dried and concentrated under vacuum. The residue was applied onto a silica gel column with ethyl acetate/petroleum ether (1:2) to afford 16.7 mg (10.2%) of I-90 as a white solid. (ES, m/z): [M–H]-424.0, $^1$H-NMR (400 MHz, DMSO-d$_6$, ppm): δ4.39 (s, 2H), δ5.31 (br s, 1H), δ7.28-7.32 (m, 1H), δ7.35-7.41 (m, 3H), δ7.43-7.49 (m, 2H), δ7.56 (s, 2H), δ10.30 (br s, 1H).

368

Example 85. Synthesis of 3-chloro-N-(2,4-difluoro-5-phenylphenyl)-2-hydroxy-5-(methoxymethyl)benzene-1-sulfonamide, I-91

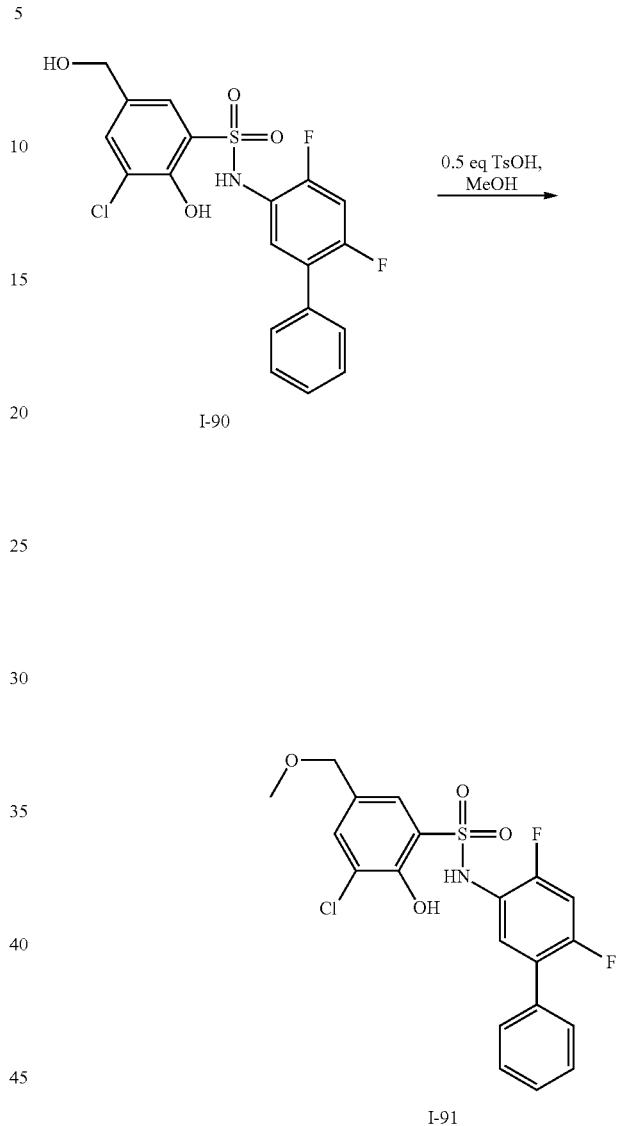

Synthesis of I-91

Into a 10-mL round-bottom flask purged and maintained with an inert atmosphere of nitrogen, was placed I-90 (100 mg, 0.23 mmol, 1 equiv), TsOH (8.1 mg, 0.05 mmol, 0.2 equiv), MeOH (2 mL). The resulting solution was stirred for 12 h at 65° C. in an oil bath. The resulting mixture was concentrated under vacuum to yield a crude product that was purified by a silica gel column with ethyl acetate/petroleum ether (1:1). This resulted in 57.6 mg (55.8%) of I-91 as a white solid. (ES, m/z): [M–H]$^-$ 438.0, $^1$H-NMR (400 MHz, DMSO-d$_6$, ppm): δ3.18 (s, 3H), δ4.29 (s, 2H), δ7.28-7.52 (m, 9H).

369

Example 86. Synthesis of 3-chloro-5-[(2,4-difluoro-5-phenylphenyl)sulfamoyl]-4-hydroxy-N-methyl-benzamide, I-92

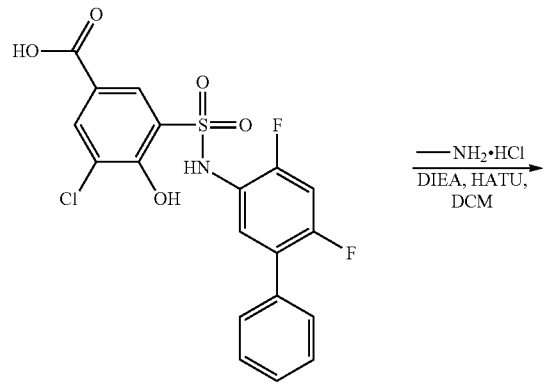

78.1

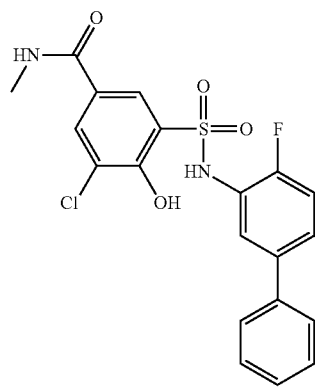

I-92

Synthesis of I-92

Into a 25-mL round-bottom flask, was placed 78.1 (200 mg, 0.45 mmol, 1 equiv), DCM (5 mL), DIEA (352.6 mg, 2.73 mmol, 6 equiv), methanamine hydrochloride (61.4 mg, 0.91 mmol, 2 equiv), HATU (259.4 mg, 0.68 mmol, 1.5 equiv). The resulting solution was stirred for 12 h at 25° C. The reaction was then quenched by the addition of 15 mL of water, and extracted with 3×20 mL of dichloromethane. After separated the layers, the combined organic phase was concentrated under vacuum. The crude product was purified by Flash-Prep-HPLC with the following conditions (Intel-Flash-1): Column, C18; mobile phase, $H_2O$:ACN=15% increasing to $H_2O$:ACN=60% within 15 min; Detector, UV 254 nm. This resulted in 85.9 mg (41.71%) of I-92 as a white solid. (ES, m/z): [M−H]⁻ 451.0, ¹H-NMR (300 MHz, CD$_3$OD, ppm): δ2.84 (s, 3H), δ6.98-7.05 (m, 1H), δ7.35-7.46 (m, 6H), δ8.01-8.02 (d, J=2.4 Hz, 1H), δ8.07-8.08 (d, J=2.4 Hz, 1H).

370

Example 87. Synthesis of N-[4-fluoro-[1,1-biphenyl]-3-yl]-2-methoxybenzene-1-sulfonamide I-93.

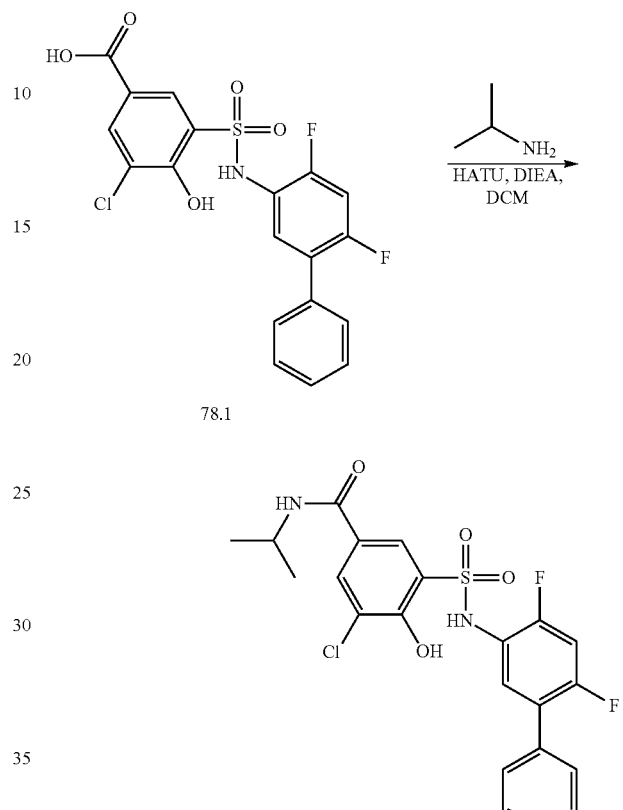

Synthesis of I-93

Into a 100-mL round-bottom flask purged and maintained with an inert atmosphere of nitrogen, was placed 78.1 (200 mg, 0.45 mmol, 1 equiv), propan-2-amine (268.8 mg, 4.55 mmol, 10 equiv), HATU (345.8 mg, 0.91 mmol, 2 equiv), DIEA (117.5 mg, 0.91 mmol, 2 equiv), DCM (5 mL). The resulting solution was stirred for 12 h at room temperature. The reaction mixture was diluted with water (10 mL) and extracted with 3×10 mL of ethyl acetate. The organic phase was washed with 10 mL of brine, dried over anhydrous sodium sulfate and evaporated under vacuum to yield crude product which was directly purified by a silica gel column (ethyl acetate/petroleum ether=1:2). This resulted in 16 mg (7.5%) of I-93 as a white solid. (ES, m/z): [M−H]⁻ 479.0, ¹H-NMR (400 MHz, DMSO-d$_6$, ppm): δ1.09-1.17 (m, 6H), δ4.01-4.07 (m, 1H), δ6.96-7.33 (m, 1H), δ7.35-7.48 (m, 7H), δ8.06-8.22 (m, 2H).

Example 88. Synthesis of Methyl 2-[3-chloro-4-hydroxy-5-[(2-methoxy-5-phenylphenyl) sulfamoyl]phenyl]acetate, I-94

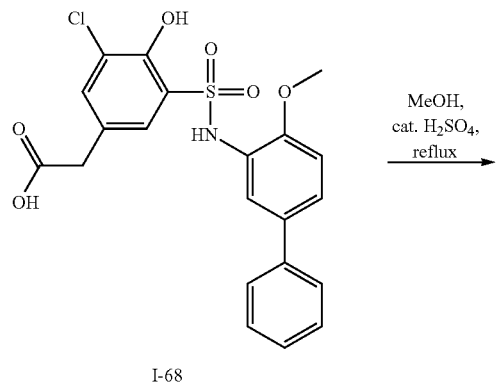

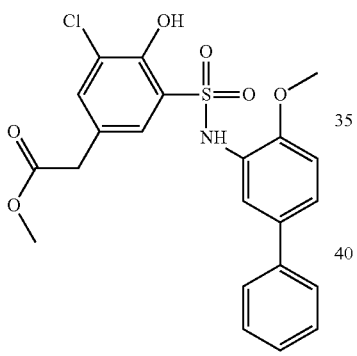

Synthesis of I-94

Into a 8-mL sealed tube, was placed I-68 (24.1 mg, 0.05 mmol, 1 equiv), methanol (0.5 mL), sulfuric acid (10.6 mg, 0.11 mmol, 2 equiv, 98%). The resulting solution was stirred for 12 h at 65° C. The reaction was then quenched by the addition of 2 mL of water, followed by extracted with 3×5 mL of ethyl acetate. Then, the organic layers was combined and concentrated under vacuum. The residue was applied onto Prep-TLC with dichloromethane/methanol (20:1). This resulted in 13.8 mg (55.5%) of I-94 as a white solid. (ES, m/z): [M−H]⁻ 460.2, ¹H-NMR (300 MHz, DMSO-d$_6$, ppm): δ3.54 (s, 3H), δ3.61 (s, 2H), δ3.69 (s, 3H), δ7.00-7.03 (d, J=8.4 Hz, 1H), δ7.29-7.33 (m, 2H), δ7.40-7.52 (m, 7H).

Example 89. Synthesis of N-(2,4-difluoro-5-phenylphenyl)-3-(2H-1,2,3,4-tetrazol-5-yl)benzene-1-sulfonamide, I-96

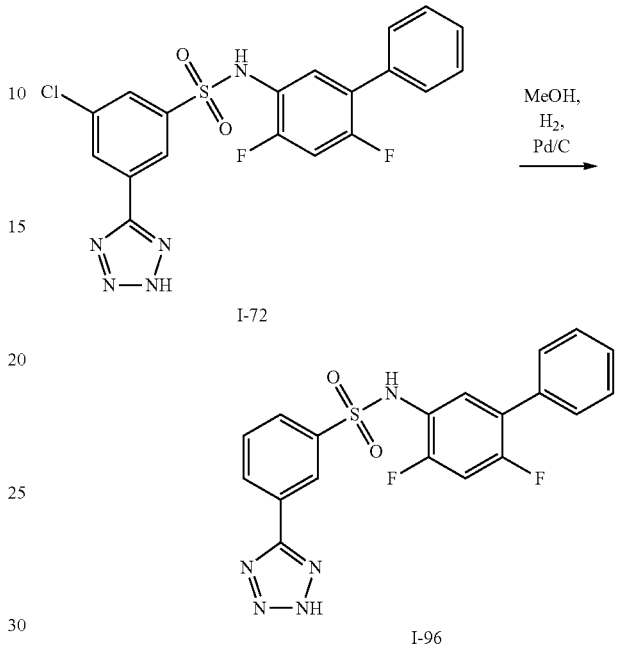

Synthesis of I-96

Into a 25-mL round-bottom flask, was placed I-72 (150 mg, 0.34 mmol, 1 equiv), MeOH (10 mL), Pd/C (30 mg). The flask was evacuated and flushed three times with nitrogen, followed by flushing with hydrogen. The mixture was stirred 2 days at room temperature. The solids were filtered out. The resulting mixture was concentrated under vacuum. The crude product was purified by Flash-Prep-HPLC with the following conditions (IntelFlash-1): Column, C18; mobile phase, ACN/H$_2$O=15% increasing to ACN/H$_2$O=60% within 15 min; Detector, UV 254. This resulted in 88.1 mg (63.6%) of I-96 as a white solid. (ES, m/z): [M−H]⁻ 412.0, ¹H-NMR (300 MHz, DMSO-d$_6$, ppm): δ7.06-7.25 (m, 3H), δ7.34-7.46 (m, 6H), δ7.57-7.62 (m, 2H), δ8.21-8.25 (m, 1H), δ8.42 (s, 1H).

Example 90. Synthesis of 3,5-dichloro-N-(2-fluoro-5-phenylphenyl)-2-(1,3-thiazol-2-yloxy)benzene-1-sulfonamide, I-97

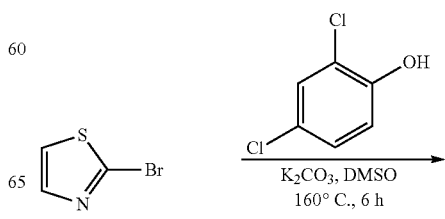

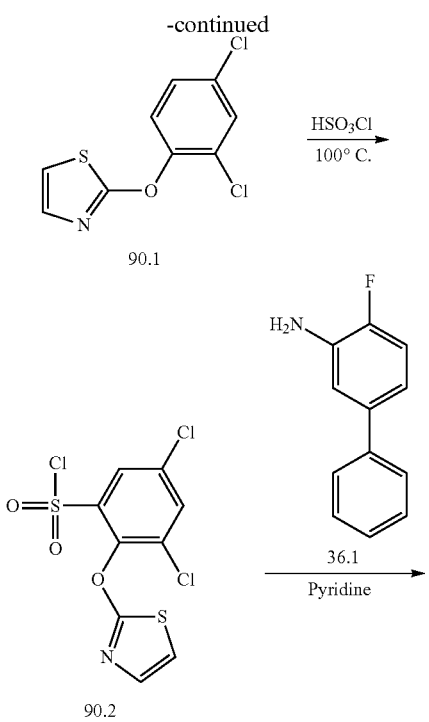

bath. The reaction was then quenched by the addition of 100 mL of water/ice, and extracted with 2×100 mL of EtOAc. The combined organic phase was evaporated under vacuum to afford the product of 90.2 (1.4 g, 98%) as a black solid. (ES, m/z): [M−H]⁻ 341.8.

Synthesis of I-97

Into a 25-mL round-bottom flask, was placed 90.2 (500 mg, 1.45 mmol, 1.00 equiv), 36.1 (327.21 mg, 1.75 mmol, 1.20 equiv), pyridine (10 mL). The reaction solution was stirred overnight at 25° C. The resulting mixture was concentrated under vacuum. The crude product was purified by Flash-Prep-HPLC with the following conditions (IntelFlash-1): Column, C18; mobile phase, water:acetonitrile=90:10 increasing to water:acetonitrile=0:100 within 30 min; Detector, UV 254 nm. This resulted in 15.6 mg (2%) of I-97 as a white solid. (ES, m/z): [M+H]⁺ 495.1, ¹H-NMR (400 MHz, DMSO-d₆, ppm): δ7.14-7.15 (d, J=4.0 Hz, 1H), δ7.25-7.26 (d, J=3.6 Hz, 1H), δ7.28-7.33 (m, 1H), δ7.37-7.39 (m, 1H), δ7.42-7.46 (m, 3H), δ7.51-7.52 (m, 3H), δ8.03 (s, 1H), δ8.19 (s, 1H), δ10.82 (s, 1H).

Example 91. Synthesis of 3-chloro-N-(2,4-difluoro-5-phenylphenyl)-2-hydroxy-5-propanoylbenzene-1-sulfonamide, I-101

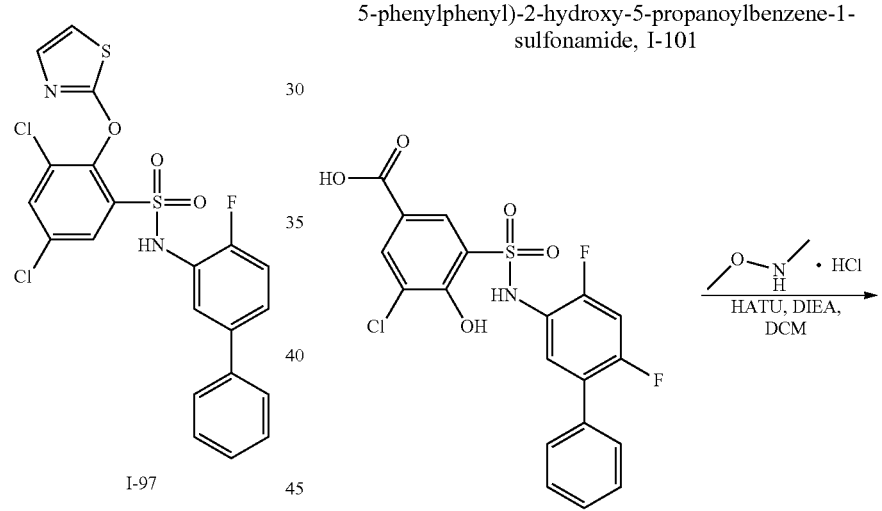

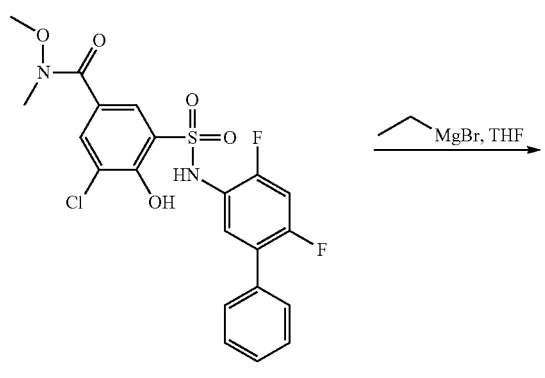

Synthesis of Compound 90.1

Into a 250-mL round-bottom flask purged and maintained with an inert atmosphere of nitrogen, was placed 2-bromo-1,3-thiazole (2.55 g, 15.55 mmol, 1.00 equiv), 2,4-dichlorophenol (2.30 g, 14.11 mmol, 0.91 equiv), DMSO (50 mL), potassium carbonate (2.19 g, 15.85 mmol, 1.02 equiv). The resulting solution was stirred for 7 h at 160° C. in an oil bath. The reaction was then quenched by the addition of 200 mL of water, and extracted with 2×250 mL of ethyl acetate. The organic layers were combined, and concentrated under vacuum. The residue was applied onto a silica gel column with ethyl acetate/petroleum ether (1:3). This resulted in 2.6 g (68%) of 90.1 as a white solid. (ES, m/z): [M+H]⁺ 245.9.

Synthesis of Compound 90.2

Into a 25-mL round-bottom flask, was placed 90.1 (1 g, 4.06 mmol, 1.00 equiv), chloranesulfonic acid (10 mL). The resulting solution was stirred overnight at 100° C. in an oil

375
-continued

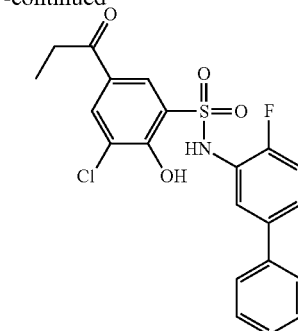

I-101

376

Example 92. Synthesis of 3-chloro-N-(2,4-difluoro-5-phenylphenyl)-2-hydroxy-5-[(piperidin-1-yl)carbonyl]benzene-1-sulfonamide, I-102

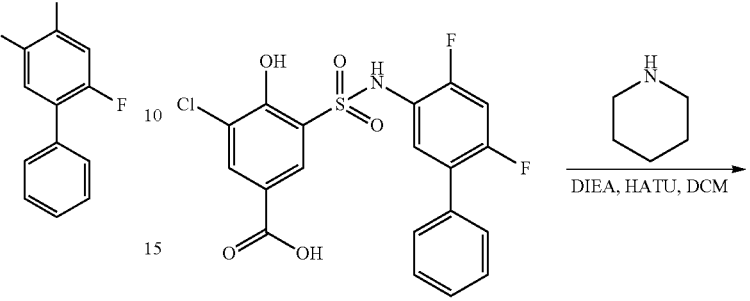

Synthesis of Compound 91.1

Into a 25-mL round-bottom flask, was placed 78.1 (300 mg, 0.68 mmol, 1 equiv), DCM (7 mL), DIEA (528.9 mg, 4.09 mmol, 6 equiv), methoxy(methyl)amine hydrochloride (133.1 mg, 1.36 mmol, 2 equiv), HATU (389.0 mg, 1.02 mmol, 1.5 equiv). The resulting solution was stirred for 12 h at 25° C. The reaction was then quenched by the addition of 15 mL of water, extracted with 3×20 mL of dichloromethane. The organic layers was combined and concentrated under vacuum. The crude product was purified by Flash-Prep-HPLC with the following conditions (IntelFlash-1): Column, C18; mobile phase, $H_2O$:ACN=15% increasing to $H_2O$:ACN=60% within 13 min; Detector, UV 254 nm. This resulted in 210 mg (63.8%) of 91.1 as a white solid. (ES, m/z): $[M-H]^-$ 481.0.

Synthesis of I-101

Into a 8-mL sealed tube, was placed 91.1 (100 mg, 0.21 mmol, 1 equiv), oxolane (1.5 mL), bromo(ethyl)magnesium (110.4 mg, 0.83 mmol, 4 equiv) at 0° C. The resulting solution was stirred for 0.5 h at 40° C. The reaction was then quenched by the addition of 3 mL of sat.$NH_4Cl$. The resulting solution was extracted with 3×5 mL of ethyl acetate, and the organic layers was combined, then, concentrated under vacuum. The crude product was purified by Prep-HPLC with the following conditions (2 #SHIMADZU (HPLC-01)): Column, XBridge Prep OBD C18 Column, 19*250 mm, 5 um; mobile phase, water (10 mmol/L $NH_4HCO_3$+0.1% $NH_3.H_2O$) and ACN (35% Phase B up to 65% in 7 min); Detector, MS, UV 254/220 nm. This resulted in 6.9 mg (7.4%) of I-101 as a white solid. (ES, m/z): $[M-H]^-$ 450.0, $^1$H-NMR (400 MHz, DMSO-$d_6$, ppm): δ0.99-1.03 (t, J=7.2 Hz, 3H), δ2.90-2.95 (m, 2H), δ7.29-7.40 (m, 4H), δ7.41-7.49 (m, 3H), δ8.07-8.08 (d, J=2.4 Hz, 1H), δ8.16-8.17 (d, J=2.4 Hz, 1H).

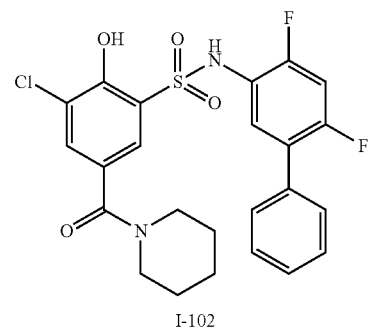

I-102

Synthesis of I-102

To a stirred mixture of 78.1 (70 mg, 0.16 mmol, 1 equiv) and piperidine (13.6 mg, 0.16 mmol, 1 equiv) in DCM (1 mL) were added DIEA (41.1 mg, 0.32 mmol, 2 equiv) and HATU (90.8 mg, 0.24 mmol, 1.5 equiv) at room temperature under nitrogen atmosphere. After 12 h, the reaction was quenched by the addition of water (50 mL) at room temperature. The resulting solution was extracted with EtOAc (2×50 mL), and the combined organic layers were concentrated under vacuum. The crude product was purified by Flash-Prep-HPLC with the following conditions (IntelFlash-1): Column, C 18; mobile phase, $CH_3CN$:$H_2O$=0:100 to $CH_3CN$:$H_2O$=50:50 in 30 min; Detector, UV 254/220 nm. This resulted in 1-102 (15.4 mg, 19.1%) as a white solid. (ES, m/z): $[M+H]^+$ 507.2, $^1$H-NMR (400 MHz, DMSO-$d_6$, ppm): δ7.52-7.28 (m, 9H), δ3.36-3.35 (d, J=4.4 Hz, 4H), δ2.08 (s, 1H), δ1.55-1.54 (d, J=4.0 Hz, 2H), δ1.40 (s, 4H).

Example 93. Synthesis of 3-chloro-N-(2,4-difluoro-5-phenylphenyl)-2-hydroxy-5-[[(3S)-3-methoxypyrrolidin-1-yl]carbonyl]benzene-1-sulfonamide, I-103

Example 94. Synthesis of 3-chloro-N-(2,4-difluoro-5-phenylphenyl)-2-hydroxy-5-[[(3R)-3-methoxypyrrolidin-1-yl]carbonyl]benzene-1-sulfonamide, I-104

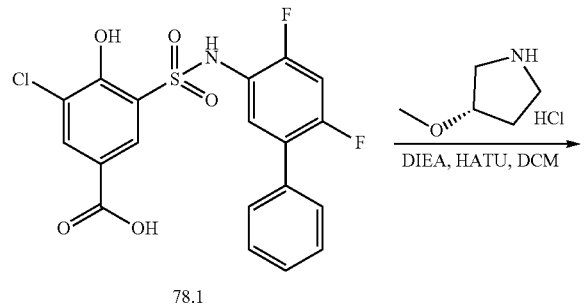

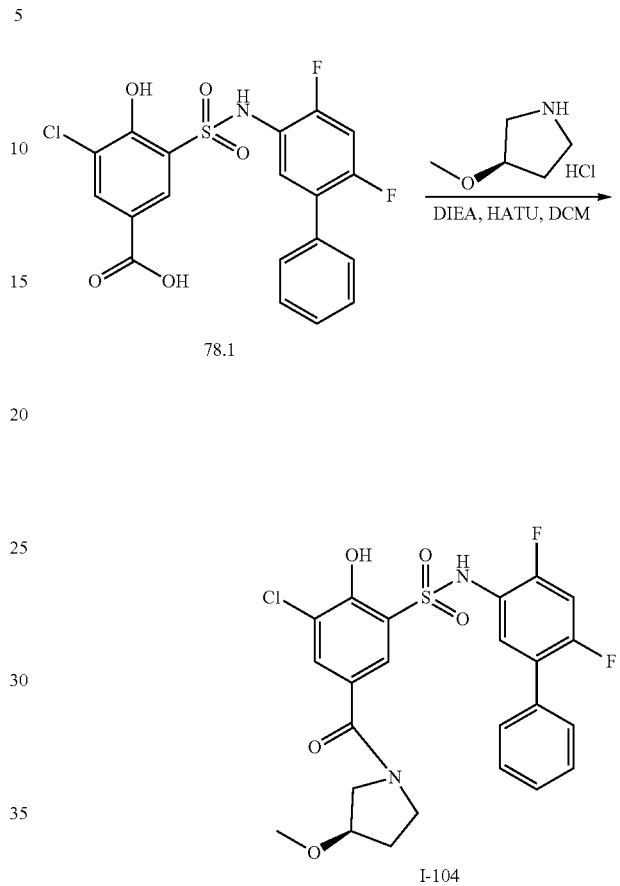

Synthesis of I-103

To a stirred mixture of 78.1 (400 mg, 0.91 mmol, 1 equiv) and (3 S)-3-methoxypyrrolidine (128.8 mg, 1.27 mmol, 1.400 equiv) in DCM (4 mL) were added DIEA (470.2 mg, 3.64 mmol, 4 equiv) and HATU (518.7 mg, 1.36 mmol, 1.500 equiv) at room temperature under nitrogen atmosphere. After 12 h, the reaction was quenched with water (100 mL). The resulting mixture was extracted with EtOAc (2×100 mL), and the combined organic layers were concentrated under vacuum. The residue was purified by Flash-Prep-HPLC with the following conditions (IntelFlash-1): Column, C 18; mobile phase, $CH_3CN:H_2O=0:100$ to $CH_3CN:H_2O=40:60$ in 30 min; Detector, UV 254/220 nm. This resulted in I-103 (100 mg, 21.0%) as a white solid. (ES, m/z): $[M-H]^-$ 521.0, $^1$H-NMR (300 MHz, DMSO-$d_6$, ppm): δ7.55-7.54 (d, J=2.4 Hz, 1H), δ7.51-7.50 (d, J=2.4 Hz, 1H), δ7.48-7.29 (m, 7H), δ7.10 (br s, 2H), δ3.88 (s, 1H), δ3.56-3.33 (m, 4H), δ3.15-3.10 (d, J=15.3 Hz, 3H), δ1.88-1.87 (d, J=4.0 Hz, 2H).

Synthesis of I-104

To a stirred mixture of 78.1 (400 mg, 0.91 mmol, 1 equiv) and (3R)-3-methoxypyrrolidine (128.8 mg, 1.27 mmol, 1.4 equiv) in DCM (4 mL) were added DIEA (470.2 mg, 3.64 mmol, 4 equiv) and HATU (518.7 mg, 1.36 mmol, 1.5 equiv) at room temperature under nitrogen atmosphere. After 12 h, the reaction was quenched with water (100 mL) at room temperature. The resulting mixture was extracted with EtOAc (2×100 mL) and the combined organic layers were concentrated under vacuum. The residue was purified by Flash-Prep-HPLC with the following conditions (IntelFlash-1): Column, C 18; mobile phase, $CH_3CN:H_2O=0:100$ to $CH_3CN:H_2O=40:60$ in 30 min; Detector, UV 254/220 nm. This resulted in 1-104 (100 mg, 21.0%) as a white solid. (ES, m/z): $[M-H]^-$ 521.0, $^1$H-NMR (300 MHz, DMSO-$d_6$, ppm): δ7.55-7.54 (d, J=2.4 Hz, 1H), δ7.51-7.50 (d, J=2.4 Hz, 1H), δ7.47-7.29 (m, 7H), δ7.08 (br s, 2H), δ3.88 (s, 1H), δ3.45-3.34 (m, 4H), δ3.17-3.15 (d, J=5.1 Hz, 3H), δ1.88 (br s, 2H).

Example 95. Synthesis of (S)-3-chloro-N-(4,6-difluoro-[1,1'-biphenyl]-3-yl)-2-hydroxy-5-(3-hydroxy-pyrrolidine-1-carbonyl)benzenesulfonamide, I-105

Example 96. Synthesis of (R)-3-chloro-N-(4,6-difluoro-[1,1'-biphenyl]-3-yl)-2-hydroxy-5-(3-hydroxy-pyrrolidine-1-carbonyl)benzenesulfonamide, I-106

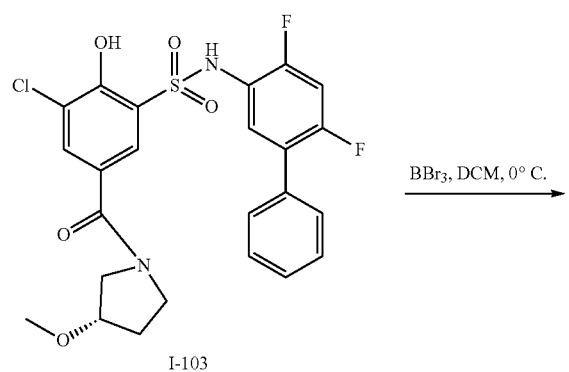

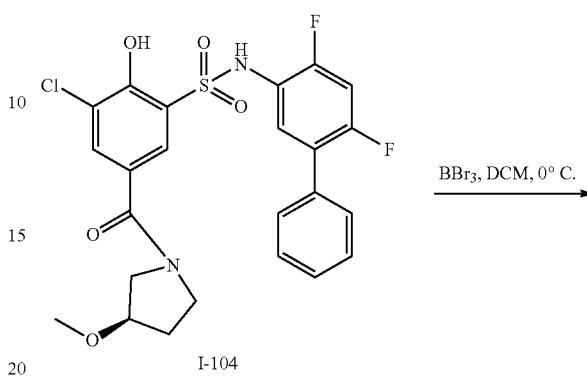

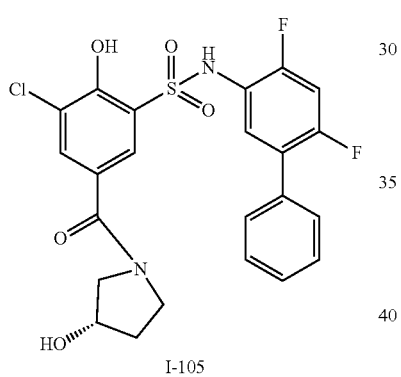

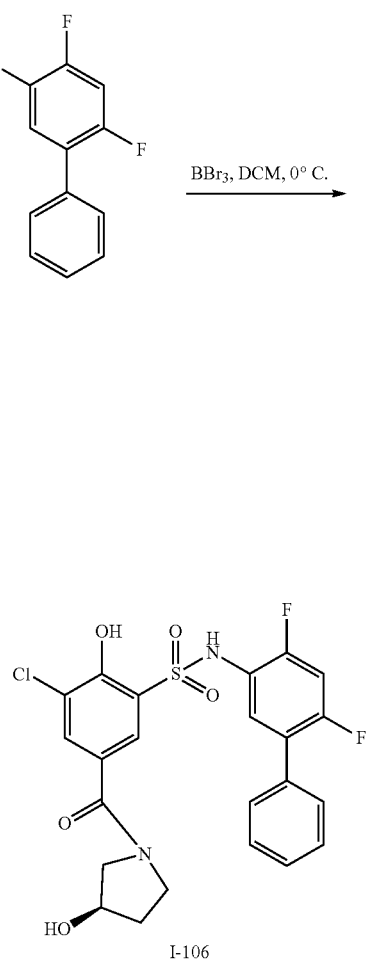

Synthesis of I-105

Synthesis of I-106

Into a 5 mL sealed tube, a stirred solution of I-103 (70 mg, 0.13 mmol, 1 equiv) in DCM (1 mL) were added BBr$_3$ (100.6 mg, 0.40 mmol, 3 equiv) at 0° C. under nitrogen atmosphere. After 5 h, the reaction was quenched with sat.NaHCO$_3$ at 0° C. The resulting solution was extracted with EtOAc (2×50 mL), and the combined organic layers were concentrated under vacuum. The residue was purified by Prep-TLC (CH$_2$Cl$_2$/MeOH=20:1) to afford I-105 (57.3 mg, 84.1%) as a white solid. (ES, m/z): [M+H]$^+$ 508.9, $^1$H-NMR (400 MHz, DMSO-d$_6$, ppm): δ7.81 (s, 1H), δ7.44-7.32 (m, 3H), δ7.31-7.26 (m, 3H), δ7.23-7.19 (m, 1H), δ6.96-6.91 (t, J=11.2 Hz, 1H), δ4.88 (br s, 1H), δ4.14 (br s, 1H), δ3.66-3.50 (m, 3H), δ3.25-3.28 (d, J=11.6 Hz, 1H), δ1.74 (br s, 1H), δ1.63 (br s, 1H).

Into a 5 mL sealed tube, were added I-104 (60 mg, 0.11 mmol, 1 equiv) and BBr$_3$ (86.2 mg, 0.34 mmol, 3 equiv) in DCM (1 mL) at 0° C. under nitrogen atmosphere. The resulting mixture was stirred for 3 h, followed by quenched with sat. Na$_2$CO$_3$ at 0° C. The resulting solution was extracted with EtOAc (2×50 mL), and the combined organic layers were concentrated. The residue was purified by Prep-TLC (CH$_2$Cl$_2$/MeOH=20:1) to afford I-106 (44.6 mg, 76.4%) as a white solid. (ES, m/z): [M+H]$^+$ 508.9, $^1$H-NMR (400 MHz, DMSO-d$_6$, ppm): δ7.81 (s, 1H), δ7.44-7.36 (m, 3H), δ7.32-7.26 (m, 3H), δ7.23-7.19 (m, 1H), δ6.96-6.93 (t, J=8.8 Hz, 1H), δ4.86 (br s, 1H), δ4.14 (br s, 1H), δ3.67-3.50 (m, 3H), δ3.28-3.25 (d, J=11.6 Hz, 1H), δ1.76 (br s, 1H), δ1.63 (br s, 1H).

381

Example 97. Synthesis of 3-chloro-5-[(2-fluoro-5-phenylphenyl)sulfamoyl]-4-hydroxybenzoic Acid, I-107

382

Example 98. Synthesis of Methyl 3-(N-allyl-N-(4-fluoro-[1,1'-biphenyl]-3-yl) sulfamoyl)-5-chloro-4-hydroxybenzoate, I-108

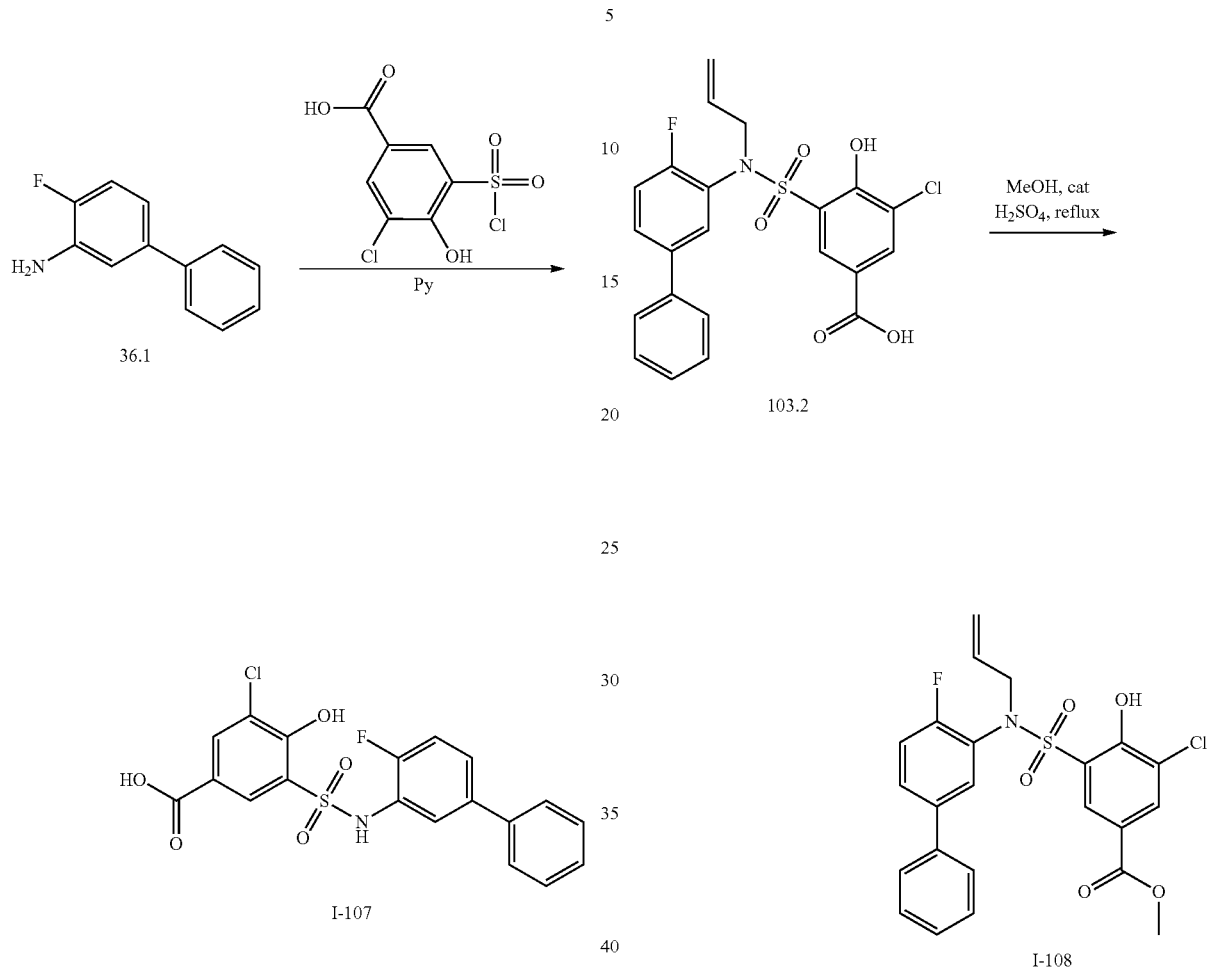

Synthesis of I-107

Into a 8-mL vial, was placed 36.1 (160 mg, 0.856 mmol, 1.2 equiv), 3-chloro-5-(chlorosulfonyl)-4-hydroxybenzoic acid (200 mg, 0.741 mmol, 1 equiv), pyridine (2 mL). After stirred overnight at room temperature, the reaction solution was concentrated under vacuum. The resulting mixture was diluted with additional of 30 mL of H$_2$O, and extracted with 3×40 mL of ethyl acetate. The organic layers was concentrated to afford the crude product that was purified by Flash-Prep-HPLC with the following conditions (IntelFlash-1): Column, C18; mobile phase, ACN/H$_2$O=15% increasing to ACN/H$_2$O=60% within 15 min; Detector, UV 254 nm. This resulted in 72.4 mg (23.2%) of I-107 as a white solid. (ES, m/z): [M−H]$^−$ 420.2, $^1$H-NMR (300 MHz, DMSO-d$_6$, ppm): δ7.24-7.28 (m, 1H), δ7.31-7.54 (m, 7H), δ8.06-8.07 (d, J=2.1 Hz, 1H), δ8.15-8.16 (d, J=2.1 Hz, 1H), δ13.25 (br s, 1H).

Synthesis of I-108

Into a 8-mL vial purged and maintained with an inert atmosphere of nitrogen, was placed 103.2 (100 mg, 0.22 mmol, 1 equiv), MeOH (2 mL), H$_2$SO$_4$ (21.2 mg, 0.22 mmol, 1 equiv). The reaction solution was stirred overnight at 80° C. in an oil bath. Meanwhile, the reaction mixture was heated to reflux. The resulting solution was diluted with 10 mL of H$_2$O, followed by extracted with 3×20 mL of ethyl acetate. The organic phase was concentrated under vacuum to yield the crude product that was applied onto a prep TLC with ethyl acetate/petroleum ether (1:1). This resulted in 30.5 mg (29.6%) of I-108 as a white solid. (ES, m/z): [M−H]$^−$ 474.0, $^1$H-NMR (300 MHz, CDCl$_3$, ppm): δ3.89 (s, 3H), δ4.25-4.27 (d, J=6.6 Hz, 2H), δ5.09-5.17 (m, 2H), δ5.71-5.84 (m, 1H), δ7.10-7.16 (m, 1H), δ7.35-7.48 (m, 6H), δ7.52-7.56 (m, 1H), δ8.23-8.25 (d, J=6.0 Hz, 2H).

Example 99. Synthesis of Methyl 3-chloro-5-[(2,4-difluoro-3-phenylphenyl) sulfamoyl]-4-hydroxybenzoate, I-110

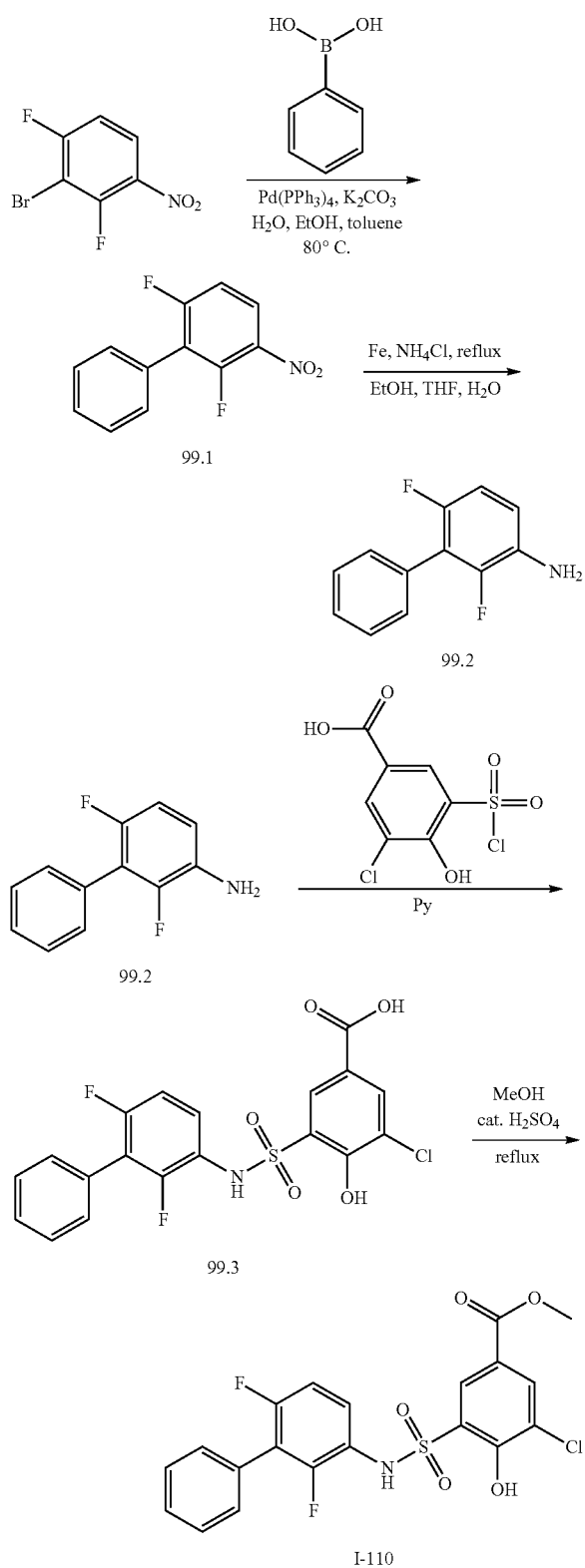

Synthesis of Compound 99.1

Into a 250-mL 3-necked round-bottom flask purged and maintained with an inert atmosphere of nitrogen, was placed 2-bromo-1,3-difluoro-4-nitrobenzene (5 g, 21.01 mmol, 1 equiv), water (18 mL), ethanol (18 mL), toluene (18 mL), phenylboronic acid (3.1 g, 25.21 mmol, 1.2 equiv), $K_2CO_3$ (14.6 g, 105.05 mmol, 5 equiv), $Pd(PPh_3)_4$ (4.9 g, 4.20 mmol, 0.2 equiv). The resulting solution was stirred for 12 h at 80° C. Then, the resulting mixture was concentrated under vacuum. The residue was applied onto a silica gel column with ethyl acetate/petroleum ether (50:1). This resulted in 4 g (81.0%) of 99.1 as a light yellow solid.

Synthesis of Compound 99.2

Into a 250-mL 3-necked round-bottom flask, was placed 99.1 (4 g, 17.01 mmol, 1 equiv), $H_2O$ (7.5 mL), THF (15 mL), EtOH (30 mL), $NH_4Cl$ (20 mL), Fe (4.0 g, 71.43 mmol, 4.2 equiv). The solution was heated to reflux, then, the resulting solution was stirred for 2 h at 95° C. The solids were filtered out. The resulting mixture was concentrated under vacuum to yield crude product which was purified by a silica gel column with ethyl acetate/petroleum ether (100:1). This resulted in 2 g (57.3%) of 99.2 as an off-white solid.

Synthesis of Compound 99.3

Into a 50-mL round-bottom flask, was placed 99.2 (454 mg, 2.21 mmol, 1.2 equiv), 3-chloro-5-(chlorosulfonyl)-4-hydroxybenzoic acid (500 mg, 1.67 mmol, 1 equiv), pyridine (7 mL). The resulting solution was stirred for 12 h at 25° C. The reaction was then quenched by the addition of 20 mL of 1M hydrochloric acid, and extracted with 3×25 mL of ethyl acetate. After separated the layers, the organic phase was combined and concentrated under vacuum. The crude product was purified by Flash-Prep-HPLC with the following conditions (IntelFlash-1): Column, C18; mobile phase, $H_2O:ACN=15\%$ increasing to $H_2O:ACN=60\%$ within 10 min; Detector, UV 254 nm. This resulted in 250 mg (23.9%) of 99.3 as a white solid.

Synthesis of I-110

Into a 8-mL sealed tube, was placed 99.3 (100 mg, 0.23 mmol, 1 equiv), MeOH (1 mL), $H_2SO_4$ (44.6 mg, 0.45 mmol, 2 equiv, 98%). The resulting solution was heated to reflux, meanwhile, stirred for 12 h at 65° C. Then, the reaction was quenched by the addition of 1.5 mL of water, extracted with 3×2 mL of ethyl acetate. After separated the layers, the organic extracts was combined and concentrated under vacuum. The residue was applied onto Prep-TLC with dichloromethane/methanol (20:1). This resulted in 56.7 mg (55.0%) of I-110 as a white solid. (ES, m/z): [M−H]⁻ 452.2, ¹H-NMR (300 MHz, DMSO-d₆, ppm): δ3.69 (s, 3H), δ7.07-7.17 (m, 1H), δ7.19-7.25 (m, 1H), δ7.38-7.52 (m, 5H), δ7.73-7.74 (d, J=2.4 Hz, 1H), δ7.85-7.86 (d, J=2.7 Hz, 1H).

385

Example 100. Synthesis of Methyl 3-chloro-5-[(2,3-difluoro-5-phenylphenyl) sulfamoyl]-4-hydroxybenzoate, I-111

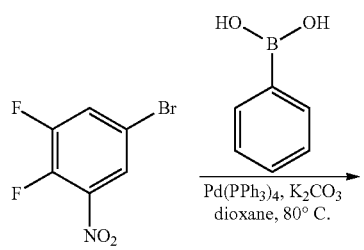

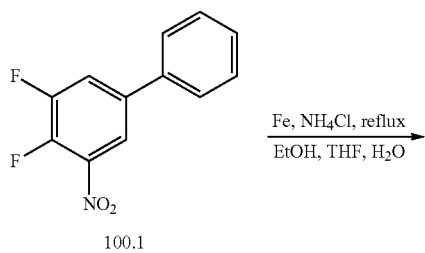

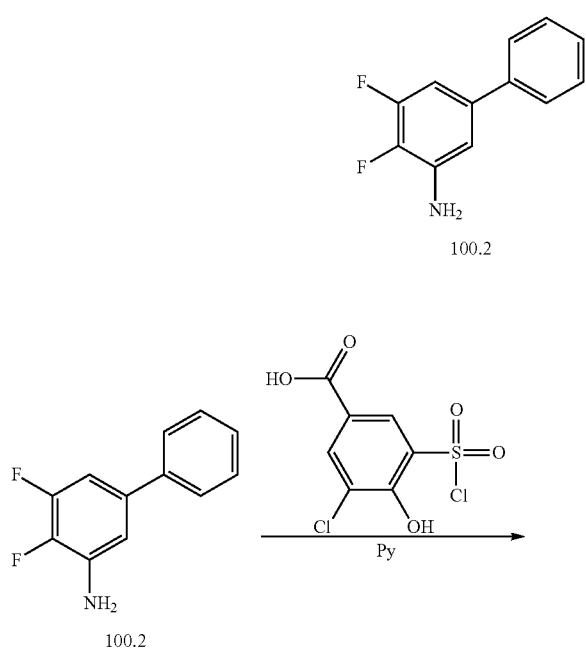

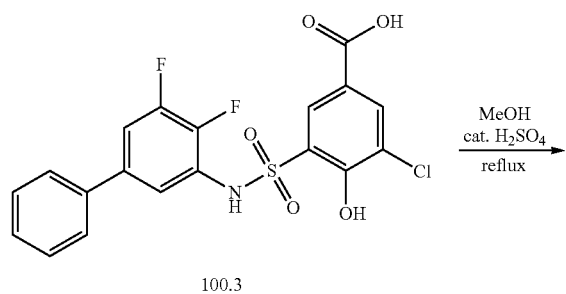

386

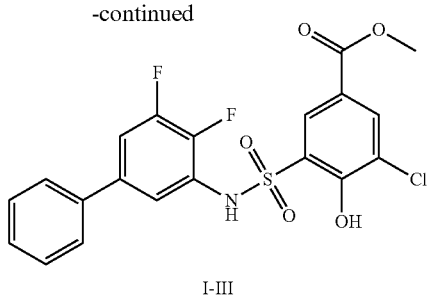

I-III

Synthesis of Compound 100.1

Into a 250-mL 3-necked round-bottom flask purged and maintained with an atmosphere of nitrogen, was placed 5-bromo-1,2-difluoro-3-nitrobenzene (5 g, 21.01 mmol, 1 equiv), toluene (20 mL), ethanol (20 mL), water (20 mL), phenylboronic acid (3.1 g, 25.21 mmol, 1.2 equiv), $K_2CO_3$ (14.6 g, 105.05 mmol, 5 equiv), $Pd(pph_3)_4$ (4.9 g, 4.20 mmol, 0.2 equiv). The resulting solution was stirred for 12 h at 80° C. The resulting mixture was concentrated under vacuum. The residue was applied onto a silica gel column with ethyl acetate/petroleum ether (100:1). This resulted in 3.6 g (72.9%) of 100.1 as yellow oil.

Synthesis of Compound 100.2

Into a 250-mL 3-necked round-bottom flask, was placed 100.1 (3.6 g, 15.31 mmol, 1 equiv), $H_2O$ (5 mL), THF (10 mL), EtOH (20 mL), $NH_4Cl$ (18 mL), Fe (3.6 g, 64.29 mmol, 4.2 equiv). The resulting solution was stirred for 2 h at 95° C. meanwhile, the mixture was heated to reflux. The solids were filtered out. The resulting mixture was concentrated under vacuum. The residue was applied onto a silica gel column with ethyl acetate/petroleum ether (50:1). This resulted in 1.6 g (50.9%) of 100.2 as red oil.

Synthesis of Compound 100.3

Into a 50-mL round-bottom flask, was placed 3-chloro-5-(chlorosulfonyl)-4-hydroxybenzoic acid (400 mg, 1.48 mmol, 1 equiv), 100.2 (363.4 mg, 1.77 mmol, 1.2 equiv), pyridine (5 mL). The resulting solution was stirred for 2 h at 25° C. The resulting mixture was concentrated under vacuum. The crude product was purified by Flash-Prep-HPLC with the following conditions (IntelFlash-1): Column, C18; mobile phase, $H_2O$:ACN=15% increasing to $H_2O$:ACN=60% within 15 min; Detector, 254/220 nm. This resulted in 150 mg (23.6%) of 100.3 as a white solid.

Synthesis of I-111

Into a 8-mL sealed tube, was placed 100.3 (88 mg, 0.20 mmol, 1 equiv), MeOH (1 mL), $H_2SO_4$ (39.2 mg, 0.40 mmol, 2 equiv, 98%). The resulting solution was stirred for 12 h at 65° C. The reaction was then quenched by the addition of 1.5 mL of water, and extracted with 3×2 mL of ethyl acetate. The organic layers was combined and concentrated under vacuum. The residue was purified by Prep-TLC with dichloromethane/methanol (20:1). This resulted in 43.1 mg (47.5%) of I-111 as a white solid. (ES, m/z): [M−H]⁻ 452.2, ¹H-NMR (300 MHz, DMSO-$d_6$, ppm): δ3.70 (s, 3H), δ7.33-7.49 (m, 7H), δ7.75-7.76 (d, J=2.4 Hz, 1H), δ7.94-7.95 (d, J=2.4 Hz, 1H).

Example 101. Synthesis of 2-acetamidoethyl 3-chloro-5-(N-(4,6-difluoro-[1,1'-biphenyl]-3-yl)sulfamoyl)-4-hydroxybenzoate, I-112

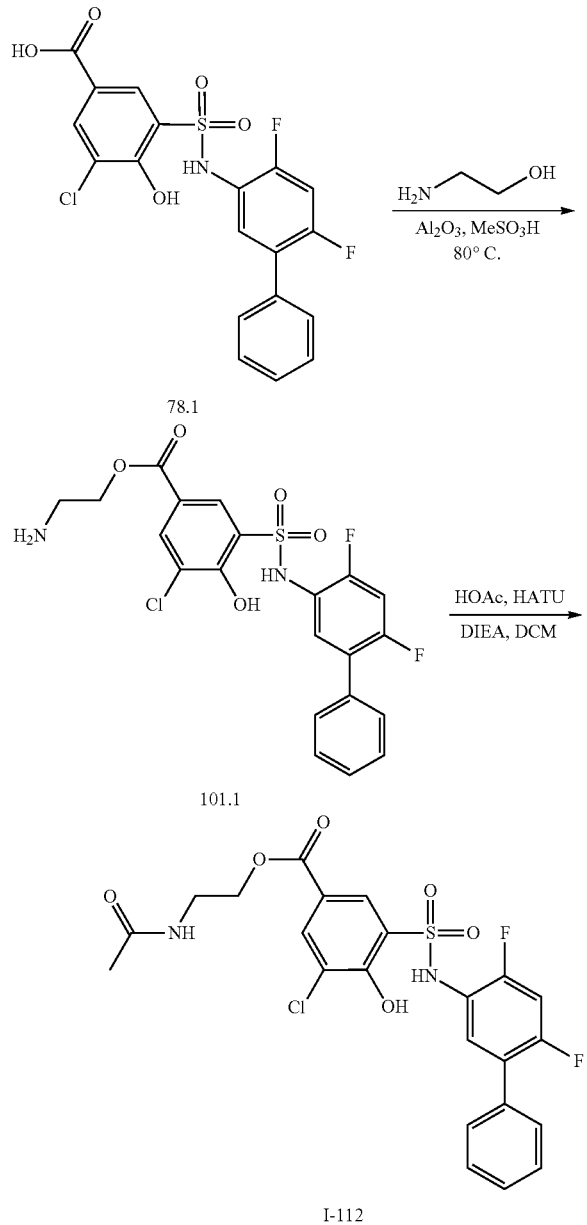

Synthesis of Compound 101.1

Into a 10-mL round-bottom flask purged and maintained with an inert atmosphere of nitrogen, was placed 78.1 (500 mg, 1.136 mmol, 1 equiv), 2-aminoethan-1-ol (69.2 mg, 1.15 mmol, 1 equiv), methanesulfonic acid (1638 mg, 17.05 mmol, 15 equiv), Al$_2$O$_3$ (348.8 mg, mmol, 3 equiv). The reaction mixture was stirred for 12 h at 80° C. in an oil bath. The resulting solution was diluted with 20 mL of water, and extracted with 3×20 mL of ethyl acetate. The organic extracts were washed with 20 mL of brine, dried over anhydrous sodium sulfate and evaporated under vacuum. The crude product was applied onto a silica gel column with ethyl acetate/petroleum ether (1:1). This resulted in 40 mg (18.2%) of 101.1 as a white solid. (ES, m/z): [M−H]⁻ 481.0.

Synthesis of I-112

Into a 50-mL round-bottom flask purged and maintained with an inert atmosphere of nitrogen, was placed 101.1 (100 mg, 0.21 mmol, 1 equiv), HOAc (12.4 mg, 0.21 mmol, 1 equiv), HATU (118.1 mg, 0.31 mmol, 1.5 equiv), DIEA (40.1 mg, 0.31 mmol, 1.5 equiv), DMF (1 mL) at room temperature. After stirring for 1 h, the resulting solution was added water (10 mL) and extracted with 3×10 mL of ethyl acetate. The organic phase was combined, washed with 10 mL of brine, dried and concentrated. The crude product was purified by Prep-HPLC with the following conditions (2 #SHIMADZU (HPLC-01)): Column: XBridge Prep OBD C18 Column, 30×150 mm 5 um; Mobile Phase A: water (10 mmol/L NH$_4$HCO$_3$), Mobile Phase B: ACN; Flow rate: 60 mL/min; Gradient: hold 32% B in 6 min, Detector, UV 254/220 nm; Rt: 4.50 min. This resulted in 36.1 mg (33.2%) of I-112 as a white solid. (ES, m/z): [M−H]⁻ 523.3, $^1$H-NMR (400 MHz, DMSO-d$_6$, ppm): δ1.78 (s, 3H), δ3.30-3.34 (m, 2H), δ4.08-4.11 (t, J=5.6 Hz, 2H), δ6.96 (s, 1H), δ7.10 (s, 1H), δ7.22 (s, 1H), δ7.30-7.38 (m, 3H), δ7.39-7.47 (m, 3H), δ7.85-7.89 (m, 2H), δ8.05-8.08 (m, 1H).

Example 102. Synthesis of N5-bromo-N-(2-fluoro-5-phenylphenyl)-2-hydroxybenzene-1-sulfonamide, I-113

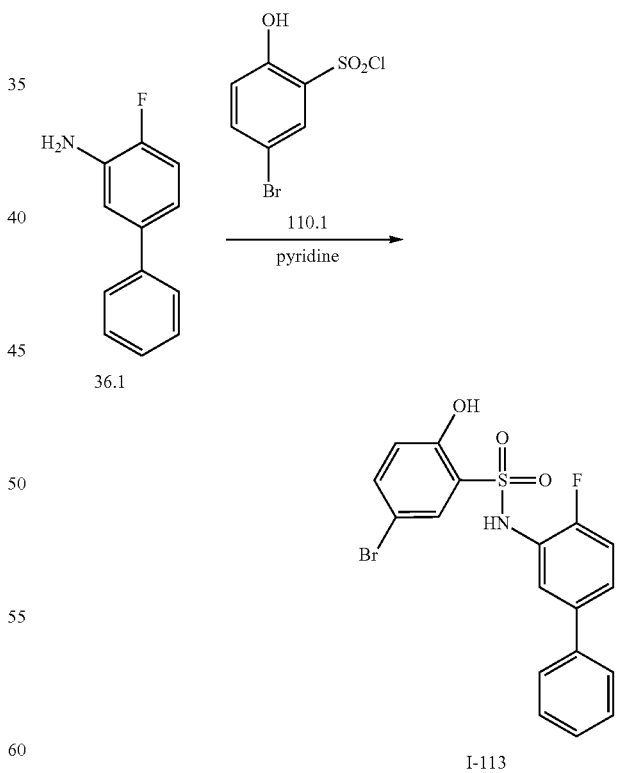

Synthesis of I-113

Into a 50-mL round-bottom flask purged and maintained with an inert atmosphere of nitrogen, was placed 110.1 (100 mg, 0.37 mmol, 1 equiv), 36.1 (82.7 mg, 0.44 mmol, 1.2 equiv), pyridine (1 mL). The resulting solution was stirred for 0.5 h at room temperature. The resulting mixture was concentrated under vacuum to remove the solvent. The residue was purified on a silica gel column with ethyl acetate/petroleum ether (1:1). This resulted in 28.2 mg (18.1%) of I-113 as a white solid. (ES, m/z): [M+H]$^+$ 421.9, $^1$H-NMR (400 MHz, DMSO-d$_6$, ppm): δ2.54 (s, 1H), δ6.90-6.92 (d, J=8.8 Hz, 1H), δ 7.16-7.24 (m, 2H), δ7.30-7.37 (m, 1H), δ7.42-7.55 (m, 6H), δ7.66-7.67 (d, J=2.8 Hz, 1H).

Example 103. Synthesis of 2-[2-chloro-6-([4-fluoro-[1,1-biphenyl]-3-yl]sulfamoyl)-4-(methoxycarbonyl)phenoxy]acetic Acid, I-114

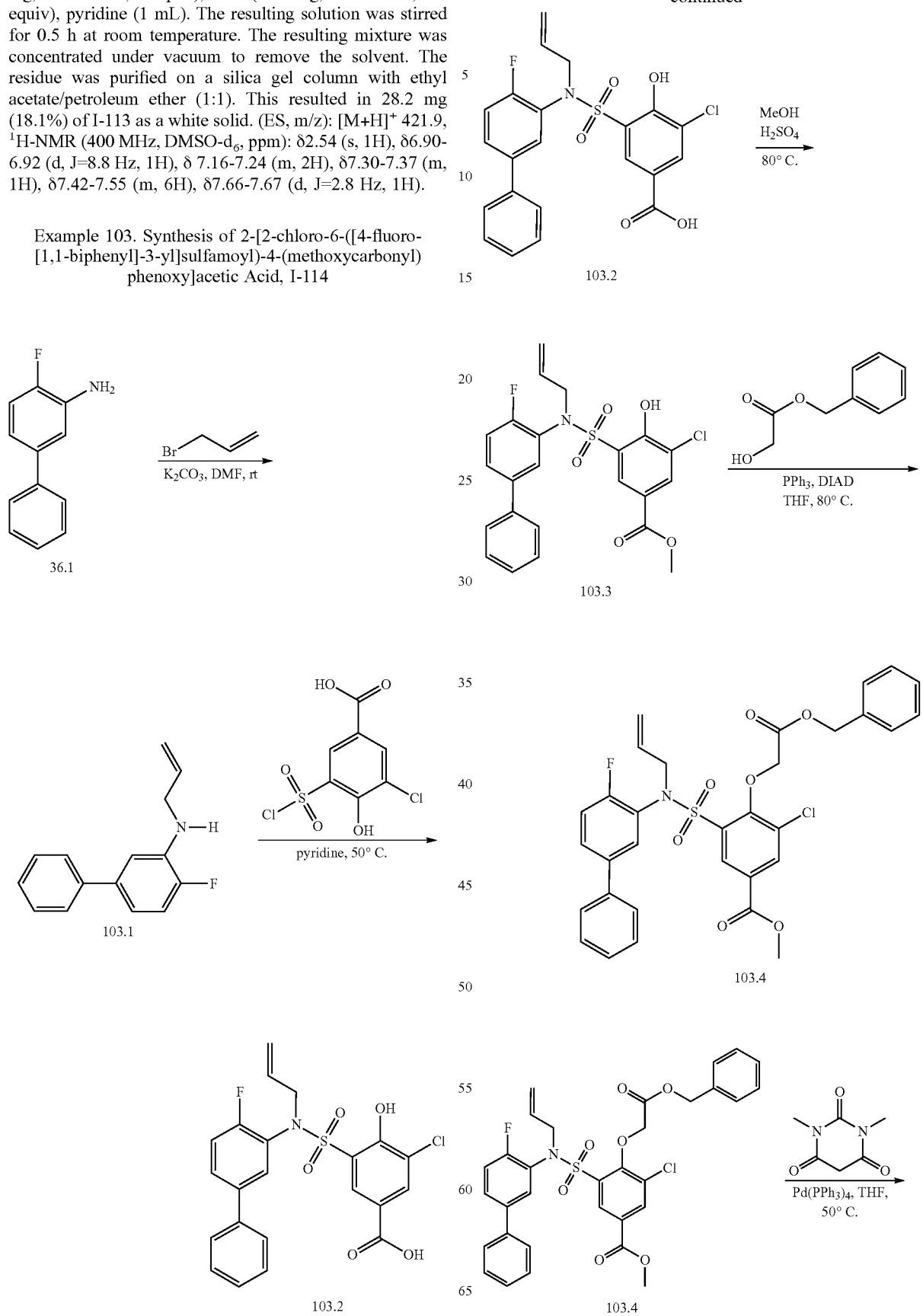

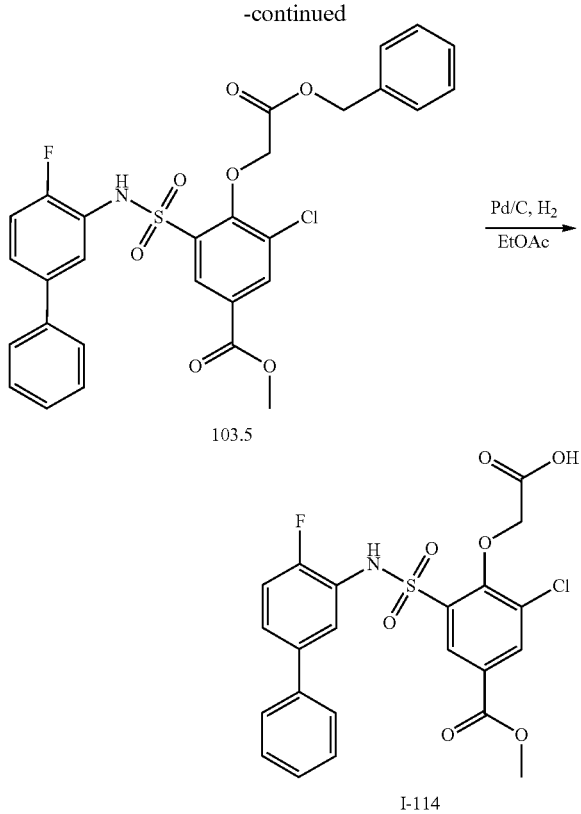

Synthesis of Compound 103.1

Into a 50-mL 3-necked round-bottom flask, was placed 36.1 (3 g, 1 equiv), DMF (30 mL), K$_2$CO$_3$ (4.43 g, 2 equiv), 3-bromoprop-1-ene (2.31 g, 1.2 equiv). The resulting solution was stirred for 1 overnight at room temperature. The resulting solution was diluted with 90 mL of H$_2$O. The resulting solution was extracted with 3×100 ml of ethyl acetate concentrated under vacuum. The residue was applied onto a silica gel column with ethyl acetate/petroleum ether (1:50). This resulted in 2.2 g of 103.1 as yellow oil. (ES, m/z): [M+H]$^+$ 228.1.

Synthesis of Compound 103.2

Into a 50-mL 3-necked round-bottom flask, was placed 103.1 (6.19 g, 1 equiv), 3-chloro-5-(chlorosulfonyl)-4-hydroxybenzoic acid (11.76 mg, 1.6 equiv), pyridine. The resulting solution was stirred overnight at 50° C. in an oil bath. The resulting mixture was concentrated under vacuum. The resulting solution was diluted with 100 mL of H$_2$O. The resulting solution was extracted with 3×200 ml of ethyl acetate and concentrated under vacuum. The residue was applied onto a silica gel column with dichloromethane/methanol (1:20). This resulted in 1.7 g of 103.2 as a yellow oil. (ES, m/z): [M−H]$^−$ 460.0.

Synthesis of Compound 103.3

Into a 50-mL 3-necked round-bottom flask, was placed 103.2 (960 mg, 1 equiv), MeOH, H$_2$SO$_4$ (205 mg, 1 equiv). The resulting solution was stirred overnight at 80° C. in an oil bath. The resulting solution was diluted with 100 mL of H$_2$O. The resulting solution was extracted with 3×200 ml of ethyl acetate concentrated under vacuum. The residue was applied onto a silica gel column with dichloromethane/methanol (1:50). This resulted in 670 mg of 103.3 as a white solid. (ES, m/z): [M−H]$^−$ 474.0.

Synthesis of Compound 103.4

Into a 8-mL vial purged and maintained with an inert atmosphere of nitrogen, was placed 103.3 (420 mg, 0.88 mmol, 1 equiv), THF (4 mL), benzyl 2-hydroxyacetate (293.3 mg, 1.77 mmol, 2 equiv), DIAD (214.1 mg, 1.06 mmol, 1.2 equiv), PPh$_3$ (462.9 mg, 1.77 mmol, 2 equiv). The resulting solution was stirred for 1 overnight at 80° C. in an oil bath. The resulting solution was diluted with 10 mL of H$_2$O. The resulting solution was extracted with 3×20 ml of ethyl acetate concentrated under vacuum. The residue was applied onto a Prep TLC with ethyl acetate/petroleum ether (1:10). This resulted in 245 mg (44.5%) of 103.4 as a white solid. (ES, m/z): [M−H]$^−$ 622.1.

Synthesis of Compound 103.5

Into a 8-mL vial purged and maintained with an inert atmosphere of nitrogen, was placed 103.4 (280 mg, 0.45 mmol, 1 equiv), THF (2 mL), 1,3-dimethyl-1,3-diazinane-2,4,6-trione (210.2 mg, 1.35 mmol, 3 equiv), Pd(PPh$_3$)$_4$ (58.8 mg, 0.22 mmol, 0.5 equiv). The resulting solution was stirred overnight at 50° C. in an oil bath. The resulting solution was diluted with 10 mL of H$_2$O. The resulting solution was extracted with 3×20 ml of ethyl acetate concentrated under vacuum. The residue was applied onto a prep TLC with ethyl acetate/petroleum ether (1:2). This resulted in 245 mg (93.5%) of 103.5 as yellow oil. (ES, m/z): [M−H]$^−$ 582.0.

Synthesis of I-114

Into a 25-mL round-bottom flask purged and maintained with an inert atmosphere of nitrogen, was placed 103.5 (100 mg, 0.17 mmol, 1 equiv), EA (5 mL), Pd(OH)$_2$/C (10 mg, 0.07 mmol, 0.42 equiv). The flask was evacuated and flushed three times with nitrogen, followed by flushing with hydrogen. The mixture was stirred 1 h at room temperature under an atmosphere of hydrogen (balloon). The solids were filtered out. The resulting mixture was concentrated under vacuum. The crude product was purified by Flash-Prep-HPLC with the following conditions (IntelFlash-1): Column, C18 silica gel; mobile phase, ACN/H$_2$O=15% increasing to ACN/H$_2$O=60% within 15 min; Detector, UV: 254. This resulted in 31.5 mg (37.3%) of I-114 as a white solid. (ES, m/z): [M+H]$^+$ 494.1, $^1$H-NMR (DMSO-d$_6$, 300 MHz, ppm): δ 8.13-8.18 (m, 2H), 7.54-7.44 (m, 4H), 7.38-7.22 (m, 3H), 7.20-7.16 (m, 3H), 4.70 (s, 2H), 3.82 (s, 3H).

393

Example 104. Synthesis of 3-chloro-5-[(2,3-difluoro-5-phenylphenyl)sulfamoyl]-4-hydroxybenzoic Acid, I-115

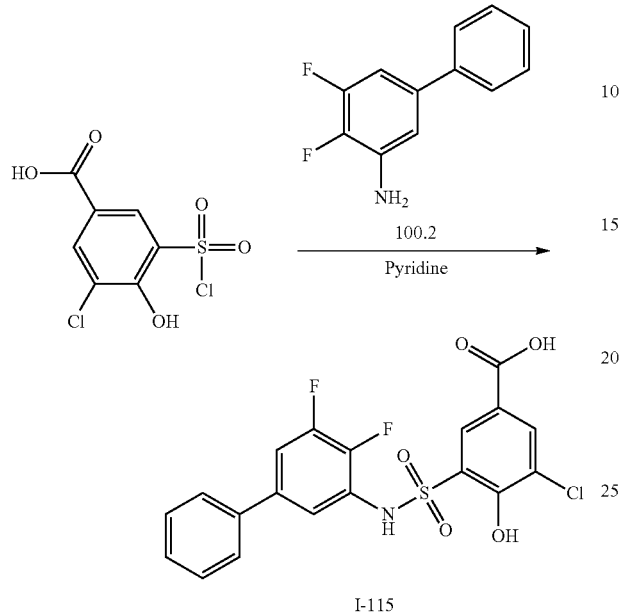

Synthesis of I-115

Into a 25-mL round-bottom flask, was placed 3-chloro-5-(chlorosulfonyl)-4-hydroxybenzoic acid (100 mg, 0.37 mmol, 1 equiv), 100.2 (90.8 mg, 0.44 mmol, 1.2 equiv), and pyridine (3 mL). The resulting solution was stirred for 2 hr at 25° C. The resulting mixture was concentrated under vacuum. The crude product was purified by Flash-Prep-HPLC with the following conditions (IntelFlash-1): Column, C18 silica gel; mobile phase, $H_2O:ACN=10\%$ increasing to $H_2O:ACN=60\%$ within 12 min; Detector, UV: 254. This resulted in 13.0 mg (8.0%) of I-115 as a white solid. (ES, m/z): [M−H]⁻ 438.2, ¹H-NMR (300 MHz, DMSO-d₆) δ 7.97-7.96 (d, J=2.1 Hz, 1H), 7.78-7.77 (d, J=2.4 Hz, 1H), 7.55-7.32 (m, 7H), 7.26-6.92 (m, 3H).

Example 105. Synthesis of 3-chloro-N-[4,6-difluoro-[1,1-biphenyl]-3-yl]-2-hydroxy-5-(1,3-oxazol-2-yl)benzene-1-sulfonamide, I-116

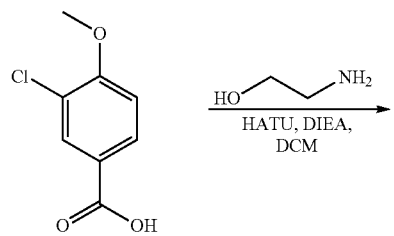

394

-continued

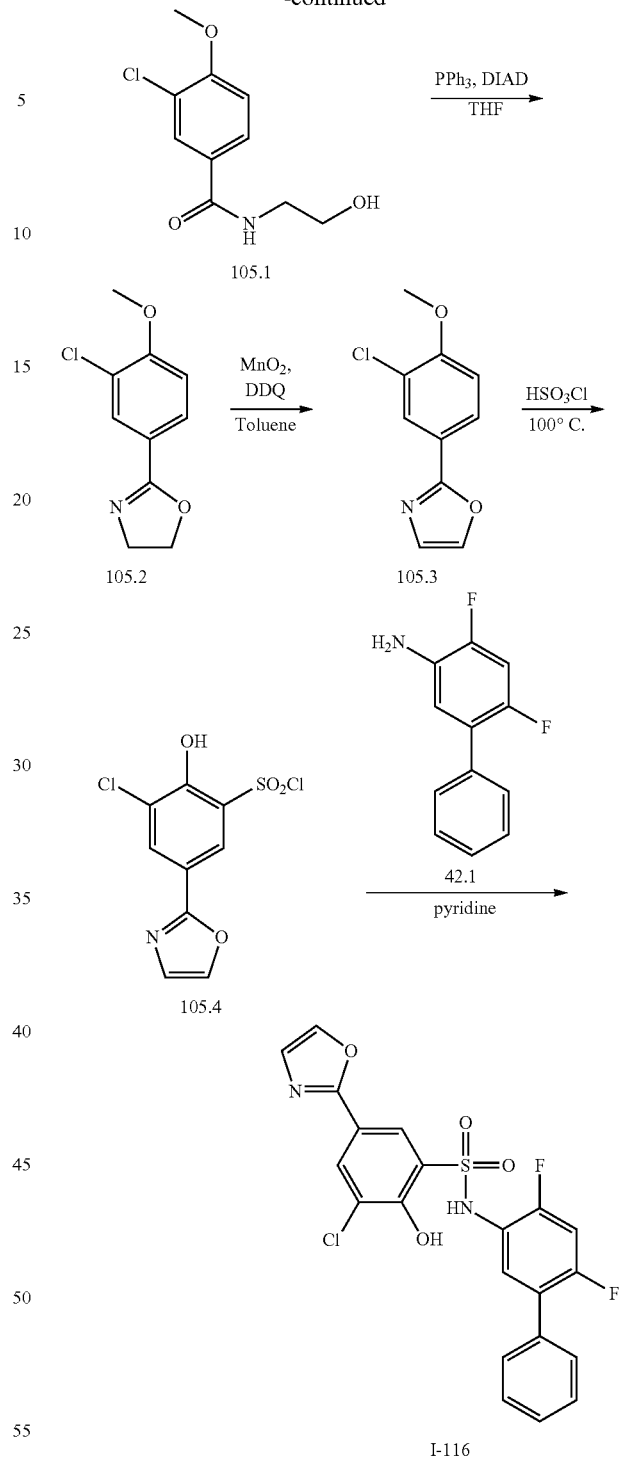

Synthesis of Compound 105.1

Into a 250-mL round-bottom flask, was placed 3-chloro-4-methoxybenzoic acid (5 g, 26.80 mmol, 1 equiv), 2-aminoethan-1-ol (1.8 g, 0.03 mmol, 1 equiv), DCM (50 mL), HATU (12.2 g, 0.03 mmol, 1.2 equiv), DIEA (10.4 g, 0.08 mmol, 3 equiv). The resulting solution was stirred overnight at 25° C. The resulting mixture was concentrated under vacuum. Then, added 300 mL of H₂O to the residue, and extracted with 2×300 mL of EtOAc. The combined organic phase was concentrated under vacuum. The residue was purified with a silica gel column with EtOAc/PE (1:10) to afford 105.1 (5.7 g, 92.6%) as a white solid.

Synthesis of Compound 105.2

Into a 250-mL 3-necked round-bottom flask purged and maintained with an inert atmosphere of nitrogen, was placed 105.1 (5.7 g, 24.82 mmol, 1 equiv), THF (60 mL), PPh₃ (9.8 g, 0.04 mmol, 1.5 equiv). The resulting solution was stirred at 0° C., and DIAD (7.5 g, 0.04 mmol, 1.5 equiv) was added. Then, the reaction solution was stirred overnight at 25° C. The resulting mixture was concentrated under reduced pressure, and applied onto a silica gel column with EtOAc/PE (1:10) to give the title compound of 105.2 (4 g, 76.1%) as a white solid.

Synthesis of Compound 105.3

Into a 100-mL round-bottom flask, was placed 105.2 (1000 mg, 4.72 mmol, 1 equiv), toluene (20 mL), DDQ (214.5 mg, 0.94 mmol, 0.2 equiv), MnO₂ (2464.5 mg, 28.35 mmol, 6 equiv). The reaction solution was stirred for 2 days at 80° C. The resulting mixture was concentrated under vacuum. The residue was applied onto a silica gel column with ethyl acetate/petroleum ether (1:10). This resulted in 200 mg (20.2%) of 105.3 as a brown liquid.

Synthesis of Compound 105.4

Into a 8-mL vial, was placed 105.3 (200 mg, 0.95 mmol, 1 equiv), sulfonoperoxoyl chloride (2 mL). The resulting solution was stirred overnight at 100° C. The reaction was then quenched by the addition of 20 mL of water/ice, followed by extracted with 2×20 mL of ethyl acetate, and the solvent was removed under vacuum. This resulted in 300 mg (crude) of 105.4 as a dark brown liquid.

Synthesis of I-116

Into a 25-mL round-bottom flask, was placed 105.4 (300 mg, 1.02 mmol, 1 equiv), 42.1 (251.2 mg, 1.22 mmol, 1.2 equiv), pyridine (5 mL). The resulting solution was stirred overnight at 25° C. The resulting mixture was concentrated under vacuum. The crude product was purified by Flash-Prep-HPLC with the following conditions (IntelFlash-1): Column, C18; mobile phase, water:acetonitrile=90:10 increasing to water:acetonitrile=0:100 within 30 min; Detector, UV 254 nm. This resulted in 34.2 mg (7.2%) of I-116 as a light brown solid. (ES, m/z): [M−H]⁻ 461.0, ¹H-NMR (400 MHz, CD₃OD, ppm): δ6.99-7.04 (m, 1H), δ7.14-7.15 (d, J=0.4 Hz, 1H), δ7.31-7.38 (m, 5H), δ7.41-7.45 (m, 1H), δ7.82-7.83 (d, J=0.8 Hz, 1H), δ8.01-8.02 (d, J=2.4 Hz, 1H), δ8.07-8.08 (d, J=2.4 Hz, 1H).

Example 106. Synthesis of 3-chloro-N-(4,6-difluoro-[1,1'-biphenyl]-3-yl)-2-hydroxy-5-(trifluoromethyl)benzenesulfonamide, I-117

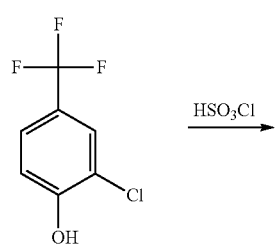

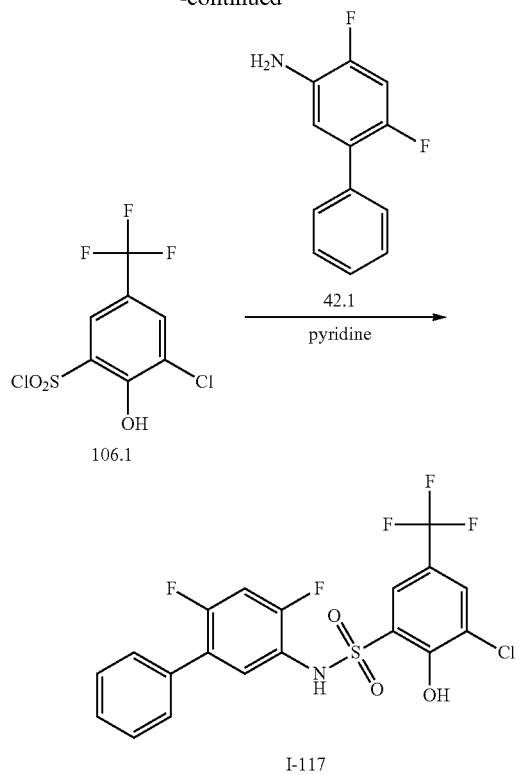

Synthesis of Compound 106.1

Into a 250 mL 3-necked round-bottom flask were added 2-chloro-4-(trifluoromethyl)phenol (2 g, 10.18 mmol, 1 equiv) and sulfurochloridic acid (14.2 g, 122.11 mmol, 12 equiv) at 0° C. The temperature was up to room temperature. The resulting solution was stirred for 2 h at room temperature. The reaction was quenched by the addition of water/ice (20 mL) at room temperature, and then the resulting mixture was extracted with EtOAc (2×20 mL). The combined organic layers were concentrated under reduced pressure. This resulted in 106.1 (2.4 g, 79.9%) as a brown solid. (ES, m/z): [M−H]⁻ 292.9.

Synthesis of I-117

To a stirred solution of 42.1 (417.3 mg, 2.03 mmol, 1.20 equiv) in pyridine (10 mL) was added 106.1 (500 mg, 1.69 mmol, 1 equiv) at room temperature under nitrogen atmosphere. The resulting solution was stirred for 0.5 h at room temperature. The resulting mixture was concentrated under reduced pressure. The crude product was purified by Flash-Prep-HPLC with the following conditions (IntelFlash-1): Column, C18; mobile phase, ACN/H₂O=10% increasing to ACN/H₂O=60% within 25 min; Detector, UV 254 nm. This resulted in product I-117 (235.9 mg, 30.0%) as a white solid. (ES, m/z): [M−H]⁻ 462.0, ¹H-NMR (300 MHz, CD₃OD, ppm): δ7.00-7.07 (m, 1H), δ7.34-7.49 (m, 6H), δ7.70 (s, 2H).

Example 107. Synthesis of N-(2-methoxy-5-phenylphenyl)-3-(2-methyl-2H-1,2,3,4-tetrazol-5-yl)benzene-1-sulfonamide, I-436

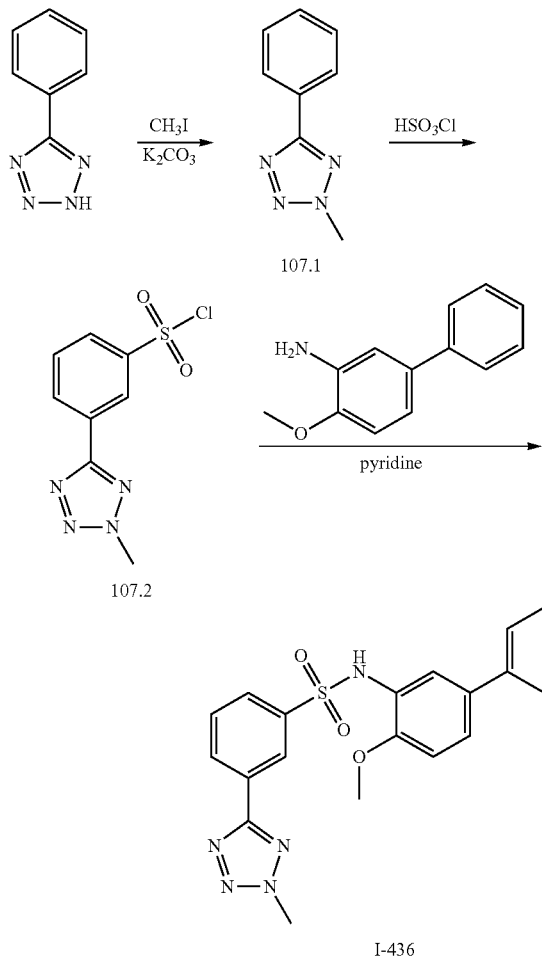

Synthesis of Compound 107.1

Into a 8-mL vial purged and maintained with an inert atmosphere of nitrogen, was placed 5-phenyl-2H-1,2,3,4-tetrazole (450 mg, 3.08 mmol, 1 equiv), DMF (5 mL), $K_2CO_3$ (851.1 mg, 6.16 mmol, 2 equiv), $CH_3I$ (437.0 mg, 3.08 mmol, 1 equiv), followed by stirring at room temperature for 12 h. The reaction mixture was then quenched by the addition of 10 mL of water and extracted with ethyl acetate (3×10 mL). The combined organic layers were concentrated under vacuum. The residue was applied onto a silica gel column with dichloromethane/methanol (80:1). This resulted in 380 mg (77.0%) of 107.1 as a white solid.

Synthesis of Compound 107.2

Into a 8-mL vial purged and maintained with an inert atmosphere of nitrogen, was placed 107.1 (50 mg, 0.31 mmol, 1 equiv), sulfonoperoxoyl chloride (3 mL). The resulting solution was stirred for 12 h at room temperature. The reaction was then quenched by the addition of 10 mL of water/ice. The resulting solution was extracted with ethyl acetate (3×10 mL) and the combined organic layers were concentrated under vacuum. This resulted in 54 mg (66.9%) of 107.2 as a white solid.

Synthesis of I-436

Into a 8-mL vial purged and maintained with an inert atmosphere of nitrogen, was placed 107.2 (54 mg, 0.21 mmol, 1 equiv), pyridine (2 mL), 2-methoxy-5-phenylaniline (49.9 mg, 0.25 mmol, 1.2 equiv). The resulting solution was stirred for 2 h at room temperature and concentrated under vacuum. The residue was applied onto a silica gel column with dichloromethane/methanol (60:1). This resulted in 22.6 mg (25.7%) of I-436 as a white solid. (ES, m/z): [M+H]$^+$ 422.2, $^1$H-NMR (400 MHz, DMSO-d$_6$, ppm): δ3.47 (s, 3H), δ4.45 (s, 3H), δ6.97-7.00 (m, 1H), δ7.30-7.34 (m, 1H), δ7.40-7.47 (m, 3H), δ7.49-7.53 (m, 3H), δ7.72-7.76 (m, 1H), δ7.84-7.91 (m, 1H), δ8.20-8.28 (m, 1H), δ8.47 (s, 1H), δ9.89 (s, 1H).

Example 108. Synthesis of N-(2-methoxy-5-phenylphenyl)-3-(1-methyl-1H-1,2,3,4-tetrazol-5-yl)benzene-1-sulfonamide, I-437

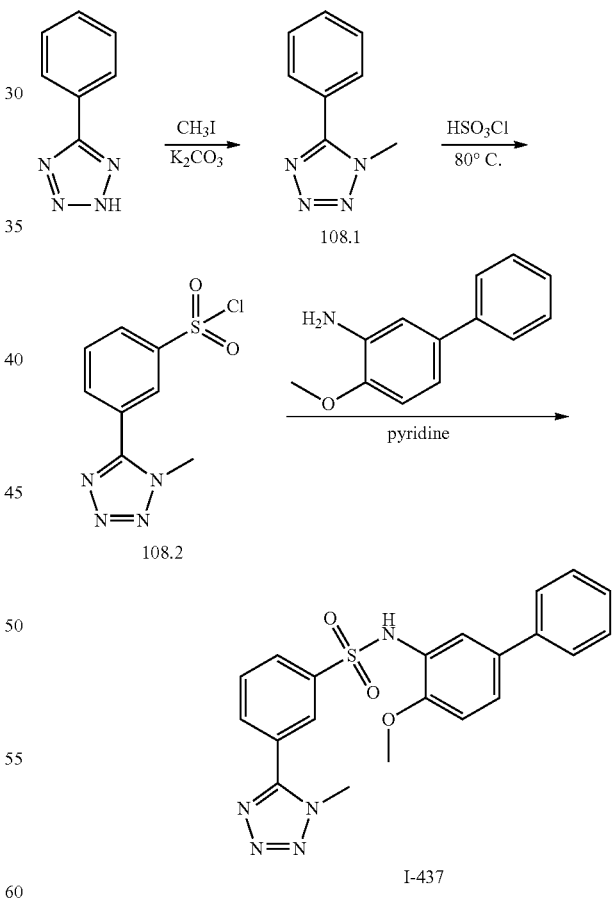

Synthesis of Compound 108.1

Into a 8-mL vial purged and maintained with an inert atmosphere of nitrogen, was placed 5-phenyl-2H-1,2,3,4-tetrazole (450 mg, 3.08 mmol, 1 equiv), DMF (5 mL), $CH_3I$ (437.0 mg, 3.08 mmol, 1 equiv), K₂CO₃ (851.1 mg, 6.16 mmol, 2 equiv). The resulting solution was stirred for 12 h at room temperature. The reaction mixture was then quenched by the addition of 10 mL of water and extracted with ethyl acetate (3×10 mL). The combined organic layers were concentrated under vacuum. The residue was applied onto a silica gel column (dichloromethane/methanol=80:1) to afford 108.1 (40 mg, 8.1%) as a white solid.

Synthesis of Compound 108.2

Into a 8-mL vial purged and maintained with an inert atmosphere of nitrogen, was placed 108.1 (40 mg, 0.25 mmol, 1 equiv), sulfonoperoxoyl chloride (2 mL). The reaction solution was stirred for 12 h at room temperature, and quenched by the addition of 10 mL of water/ice. The resulting solution was extracted with ethyl acetate (3×10 mL) and the combined organic layers were concentrated under vacuum. This resulted in 43 mg (67%) of 108.2 as a white solid.

Synthesis of I-437

Into a 8-mL vial purged and maintained with an inert atmosphere of nitrogen, was placed 108.2 (43 mg, 0.17 mmol, 1 equiv), pyridine (2 mL), 2-methoxy-5-phenylaniline (39.7 mg, 0.20 mmol, 1.2 equiv). The resulting solution was stirred for 12 h at room temperature, followed by concentrated under vacuum. The residue was applied onto a silica gel column with dichloromethane/methanol (60:1). This resulted in 9.7 mg (13.85%) of I-437 as a white solid. (ES, m/z): [M−H]⁻ 420.1. ¹H-NMR (300 MHz, DMSO-d₆, ppm): δ3.50 (s, 3H), δ4.08 (s, 3H), δ6.99-7.01 (d, J=8.4 Hz, 1H), δ7.31-7.37 (m, 1H), δ7.41-7.46 (m, 3H), δ7.53-7.55 (m, 3H), δ7.78-7.88 (m, 1H), δ7.95-8.04 (m, 1H), δ8.09-8.12 (d, J=7.5 Hz, 1H), δ8.22 (s, 1H), δ9.92 (s, 1H).

Example 109. Synthesis of Methyl 3-chloro-5-([4-fluoro-[1,1-biphenyl]-3-yl]sulfamoyl)-4-(propanoyloxy)benzoate, I-120

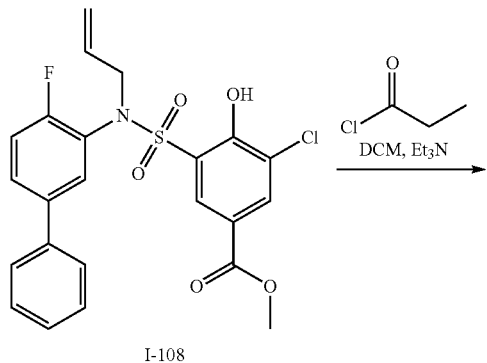

I-108

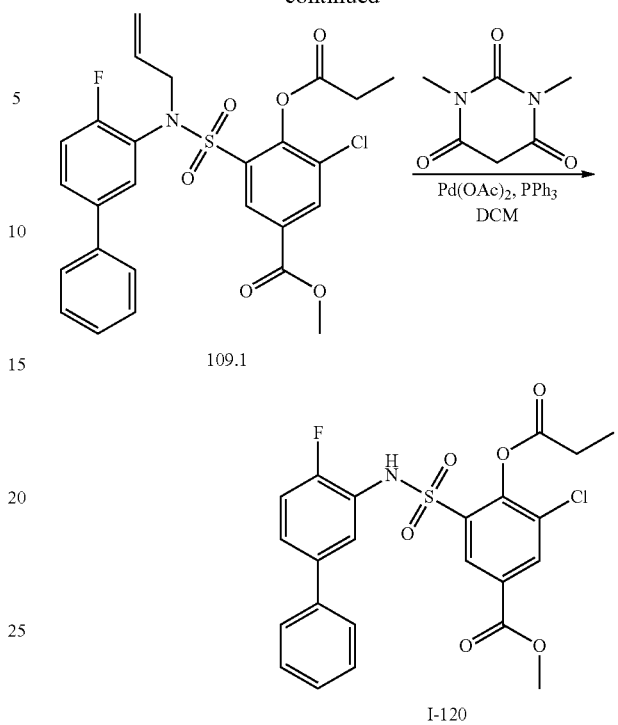

109.1

I-120

Synthesis of Compound 109.1

Into a 8-mL vial purged and maintained with an inert atmosphere of nitrogen, was placed I-108 (300 mg, 0.63 mmol, 1 equiv), DCM (5 mL), Et₃N (127.6 mg, 1.26 mmol, 2 equiv), propanoyl chloride (116.6 mg, 1.26 mmol, 2 equiv). The resulting solution was stirred overnight at room temperature. The reaction mixture was diluted with 20 mL of H₂O, and extracted with 3×30 mL of ethyl acetate. The combined organic layers were concentrated under vacuum to yield the crude product which was purified by a prep-TLC with ethyl acetate/petroleum ether (1:1). This resulted in 245 mg (73.1%) of 109.1 as yellow oil. (ES, m/z): [M−H]⁻ 530.0.

Synthesis of I-120

Into a 8-mL vial purged and maintained with an inert atmosphere of nitrogen, was placed 109.1 (100 mg, 0.19 mmol, 1 equiv), DCM (2 mL), 1,3-dimethyl-1,3-diazinane-2,4,6-trione (88.1 mg, 0.56 mmol, 3 equiv), PPh₃ (24.7 mg, 0.09 mmol, 0.5 equiv), Pd(OAc)₂ (8.4 mg, 0.04 mmol, 0.2 equiv). The resulting solution was stirred for 2 h at 35° C. in an oil bath. The resulting solution was diluted with 10 mL of H₂O. The resulting solution was extracted with 3×20 mL of ethyl acetate and the organic phase was evaporated under vacuum. The residue was applied onto a prep TLC with ethyl acetate/petroleum ether (1:1) to afford the product of I-120 (10.9 mg, 11.79%) as a white solid. (ES, m/z): [M−H]⁻ 490.2, ¹H-NMR (300 MHz, DMSO-d₆, ppm): δ0.98-1.09 (m, 3H), δ2.67-2.74 (m, 2H), δ3.70-3.90 (m, 3H), δ7.28-7.50 (m, 7H), δ7.63 (s, 1H), δ7.80-7.84 (m, 1H), δ7.88 (s, 1H), δ7.99-8.03 (d, J=7.5 Hz, 1H).

Example 110. Synthesis of 2-[(2-fluoro-5-phenylphenyl)sulfamoyl]phenyl Propanoate, I-121

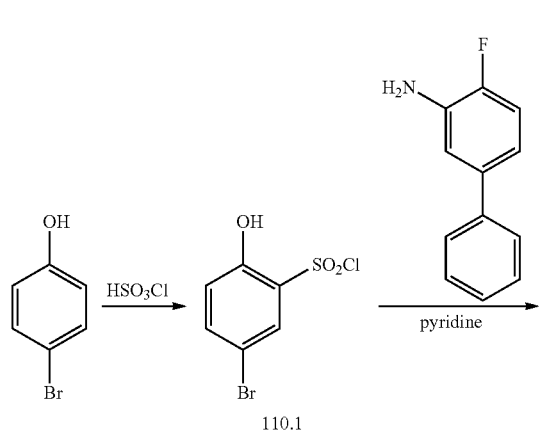

110.1

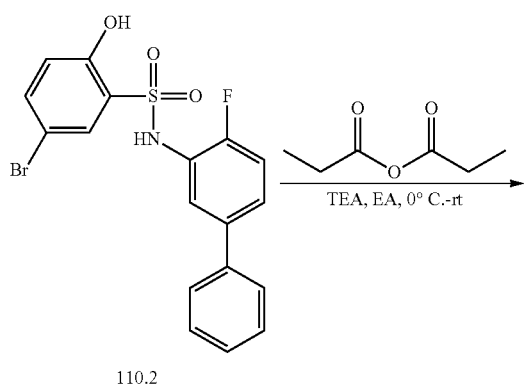

110.2

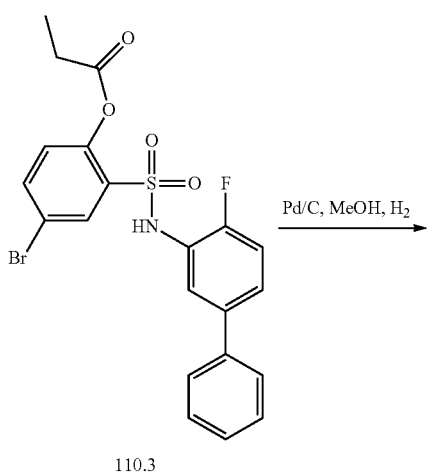

110.3

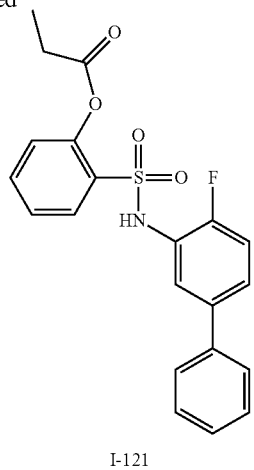

I-121

Synthesis of Compound 110.1

Into a 50-mL round-bottom flask purged and maintained with an inert atmosphere of nitrogen, was placed 4-bromophenol (2 g, 11.56 mmol, 1 equiv), HSO$_3$Cl (16.2 g, 138.72 mmol, 12.00 equiv). The resulting solution was stirred for 1 h at 0° C. in an ice/salt bath. The reaction was then quenched by the addition of 50 mL of water/ice, and extracted with 3×50 mL of ethyl acetate. The combined organic layers was washed with 50 mL of brine, dried over anhydrous sodium sulfate and concentrated under vacuum. This resulted in 2 g (63.7%) of 110.1 as a yellow solid. (ES, m/z): [M–H]$^-$ 268.8.

Synthesis of Compound 110.2

Into a 100-mL round-bottom flask purged and maintained with an inert atmosphere of nitrogen, was placed 110.1 (1 g, 3.68 mmol, 1 equiv), 4-fluoro-[1,1-biphenyl]-3-amine (689.5 mg, 3.68 mmol, 1 equiv), pyridine (20 mL). The resulting solution was stirred for 0.5 h at room temperature. The resulting mixture was concentrated. The residue was applied onto a silica gel column with ethyl acetate/petroleum ether (1:1). This resulted in 400 mg (25.7%) of 110.2 as a yellow solid. (ES, m/z): [M–H]$^-$ 419.9.

Synthesis of Compound 110.3

Into a 50-mL round-bottom flask purged and maintained with an inert atmosphere of nitrogen, was placed 110.2 (200 mg, 0.47 mmol, 1 equiv), propanoyl propanoate (61.6 mg, 0.47 mmol, 1 equiv), EA (5 mL). Then, TEA (52.7 mg, 0.52 mmol, 1.1 equiv) was added to the solution at 0° C. The reaction mixture was stirred for 1 h at room temperature. The resulting solution was diluted with H$_2$O (20 mL) and extracted with 3×20 mL of ethyl acetate. The organic phase was combined, washed with 20 mL of brine, dried over anhydrous sodium sulfate and concentrated under vacuum. The residue was applied onto a silica gel column with ethyl acetate/petroleum ether (1:3). This resulted in 140 mg (61.8%) of 110.3 as a white solid. (ES, m/z): [M–H]$^-$ 476.0.

Synthesis of Compound I-121

Into a 100-mL round-bottom flask purged and maintained with an inert atmosphere of nitrogen, was placed 110.3 (130 mg, 0.27 mmol, 1 equiv), Pd/C (30 mg), MeOH (10 mL). The resulting solution was stirred for 12 h at room temperature. The solids were filtered out, followed by removed the solvent under vacuum. The residue was applied onto a silica gel column with ethyl acetate/petroleum ether (3:1). This resulted in 40 mg (36.8%) of I-121 as a white solid. (ES, m/z): [M−H]⁻ 398.0, ¹H-NMR (400 MHz, DMSO-$d_6$, ppm): δ 0.98-1.02 (t, J=7.6 Hz, 3H), δ2.40-2.45 (m, 2H), δ7.26-7.53 (m, 10H), δ7.66-7.72 (m, 1H), δ7.85-7.87 (m, 1H), δ10.2 (s, 1H).

Example 111. Synthesis of 3,5-dichloro-N-(4-fluoro-[1,1'-biphenyl]-3-yl)-2-(oxetan-3-yloxy)benzenesulfonamide, I-122

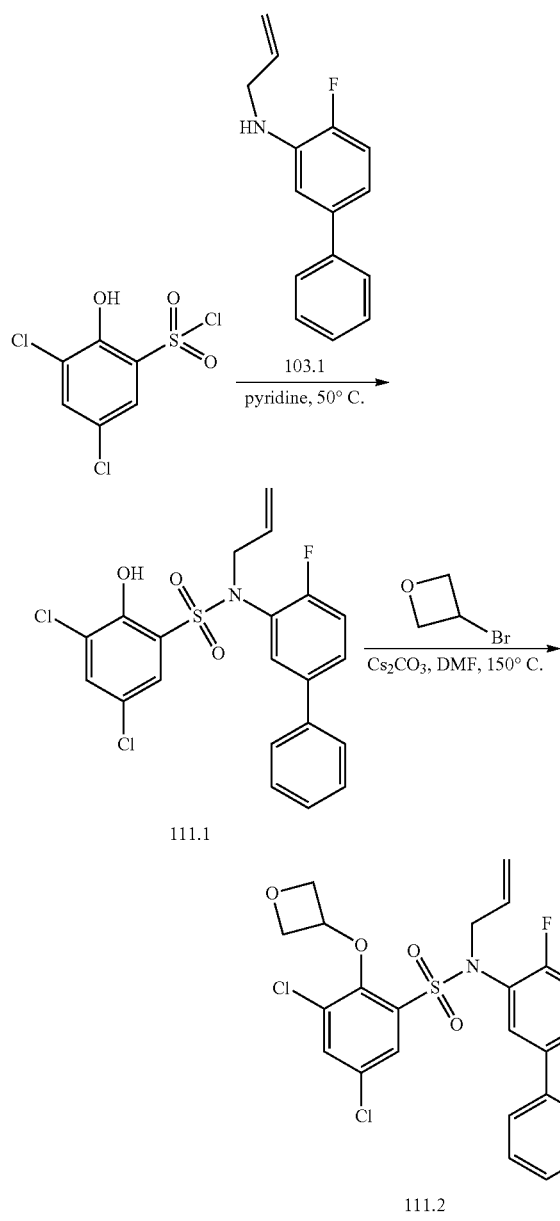

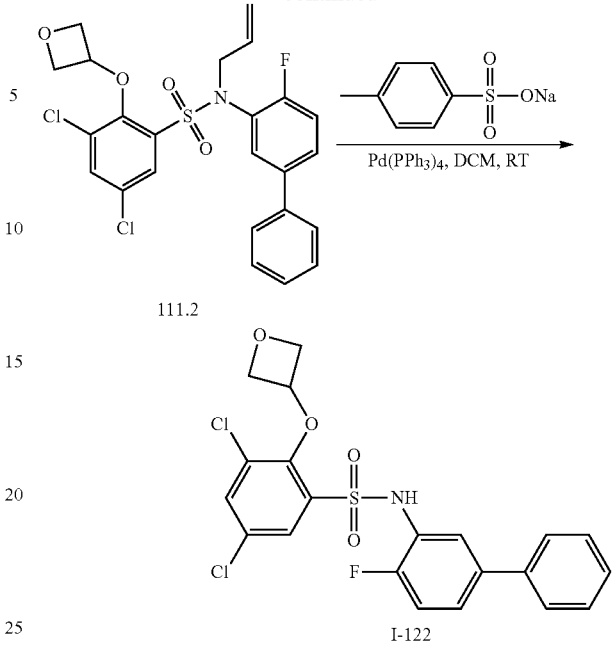

Synthesis of Compound 111.1

A mixture of 3,5-dichloro-2-hydroxybenzene-1-sulfonyl chloride (600 mg, 2.29 mmol, 1 equiv) and 103.1 (521.5 mg, 2.29 mmol, 1 equiv) in pyridine (6 mL) was stirred for 12 h at 50° C. under nitrogen atmosphere. The reaction was quenched with 1M HCl at room temperature. The resulting mixture was washed with 2×100 mL of EtOAc. The crude product was purified by reverse phase flash with the following conditions (IntelFlash-1): Column, C 18; mobile phase, CH₃CN:H₂O=0:100 to CH₃CN:H₂O=40:60 in 30 min; Detector, UV 254/220 nm. This resulted in 111.1 (530 mg, 51.1%) as a brown solid. (ES, m/z): [M−H]⁻ 450.0.

Synthesis of Compound 111.2

To a stirred solution of 111.1 (500 mg, 1.11 mmol, 1 equiv) and 3-bromooxetane (2.3 g, 16.58 mmol, 15 equiv) in DMF (5 mL) was added Cs₂CO₃ (1.8 g, 5.53 mmol, 5 equiv) in portions at room temperature under nitrogen atmosphere. The resulting mixture was stirred for 12 h at 140° C. under nitrogen atmosphere. The resulting mixture was filtered, the filter cake was washed with EtOAc (2×100 mL). The filtrate was concentrated under reduced pressure. The residue was purified by Prep-TLC (PE/EtOAc=10:1) to afford 111.2 (150 mg, 26.7%) as a yellow solid. (ES, m/z): [M−H]⁻ 506.0.

Synthesis of I-122

To a stirred mixture of 111.2 (110 mg, 0.22 mmol, 1 equiv) and sodium 4-methylbenzene-1-sulfonate (126.0 mg, 0.65 mmol, 3 equiv) in DCM (2 mL) was added Pd(PPh₃)₄ (125.0 mg, 0.11 mmol, 0.5 equiv) in portions at room temperature under nitrogen atmosphere. After 12 h, the resulting mixture was washed with 2×100 mL of water. The resulting mixture was filtered, the filter cake was washed with EtOAc (2×100 mL). The filtrate was concentrated under reduced pressure. The residue was purified by Prep-TLC (CH₂Cl₂/MeOH=20:1) to afford I-122 (18.9 mg, 18.6%) as a white solid. (ES, m/z): [M−H]⁻ 466.0, ¹H-NMR (400 MHz, DMSO-d₆, ppm): δ4.67-4.70 (m, 2H), δ4.73-4.76 (m, 2H), δ4.99-5.04 (m, 1H), δ7.34-7.40 (m, 2H), δ7.45-7.49 (m, 3H), δ7.55-7.57 (m, 3H), δ7.67-7.68 (d, J=2.8 Hz, 1H), δ8.06-8.07 (d, J=2.4 Hz, 1H), δ10.32 (s, 1H).

Example 112. Synthesis of 3-chloro-N-(4,6-difluoro-[1,1'-biphenyl]-3-yl)-2-hydroxy-5-(thiazol-5-yl)benzenesulfonamide, I-123

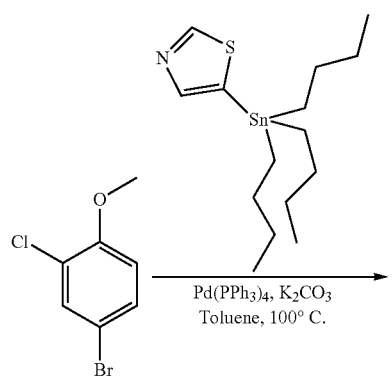

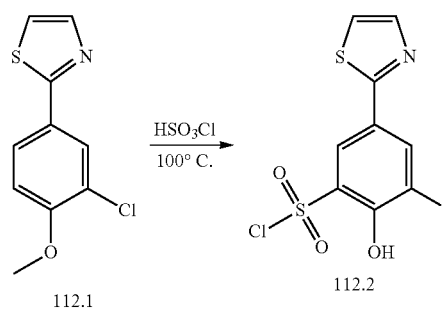

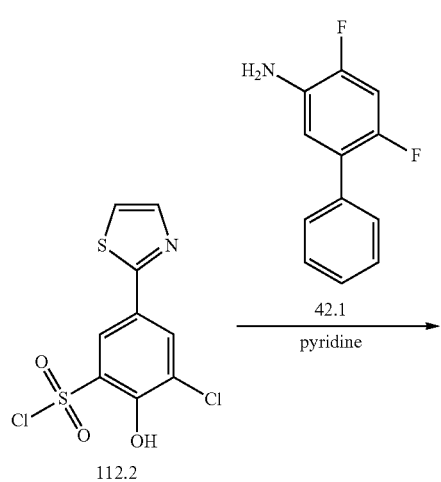

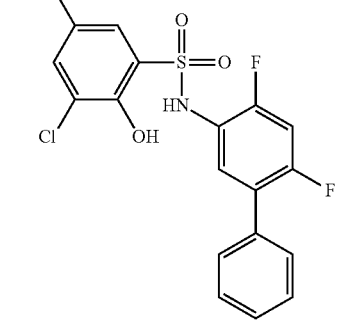

I-123

Synthesis of 112.1

To a stirred mixture of 2,4-dibromo-1-methoxybenzene (1000 mg, 3.76 mmol, 1 equiv) and 5-(tributylstannyl)-1,3-thiazole (1407.0 mg, 3.76 mmol, 1 equiv) in toluene (10 mL) was added Pd(PPh₃)₄ (434.5 mg, 0.38 mmol, 0.1 equiv) in portions at room temperature under nitrogen atmosphere. The reaction solution was stirred for 12 h at 100° C. under nitrogen atmosphere. The resulting mixture was concentrated under reduced pressure. The residue was purified by silica gel column chromatography, eluted with PE/EtOAc (10:1) to afford 112.1 (610 mg, 71.9%) as a brown solid.

Synthesis of 112.2

Into a 25 mL round-bottom flask were added 112.1 (600 mg, 2.66 mmol, 1 equiv) and HSO₃Cl (6 mL). The resulting mixture was stirred for 1 h at 100° C. The reaction was quenched with 10 mL of water/ice, and extracted with EtOAc (2×30 mL). The combined organic layers were concentrated under reduced pressure. This resulted in 112.2 (300 mg, 36.4%) as a yellow solid.

Synthesis of Compound I-123

Into a 25 mL round-bottom flask, were added 159.2 (480 mg, 1.55 mmol, 1 equiv) and 42.1 (317.6 mg, 1.55 mmol, 1.00 equiv) in pyridine (4 mL). The resulting mixture was stirred for 12 h at 50° C. under nitrogen atmosphere. The reaction was quenched by the addition of 1 M HCl. The resulting mixture was extracted with EtOAc (2×30 mL), and the combined organic layers were concentrated under reduced pressure. The crude product was purified by reverse phase flash with the following conditions (IntelFlash-1): Column, C 18; mobile phase, CH₃CN:H₂O=0:100 to CH₃CN:H₂O=40:60 in 30 min; Detector, UV 254/220 nm. This resulted in I-123 (81.2 mg, 11.0%) as a yellow solid. (ES, m/z): [M−H]⁻ 476.9, ¹H-NMR (400 MHz, DMSO-d₆, ppm): δ6.97-7.22 (m, 1H), δ7.30-7.45 (m, 7H), δ7.66-7.67 (d, J=2.4 Hz, 1H), δ7.99-8.00 (d, J=3.2 Hz, 1H), δ8.23 (s, 1H), δ9.02 (s, 1H).

Example 113. Synthesis of 3-chloro-N-[4,6-difluoro-[1,1-biphenyl]-3-yl]-2-hydroxy-5-methanesulfonylbenzene-1-sulfonamide, I-124

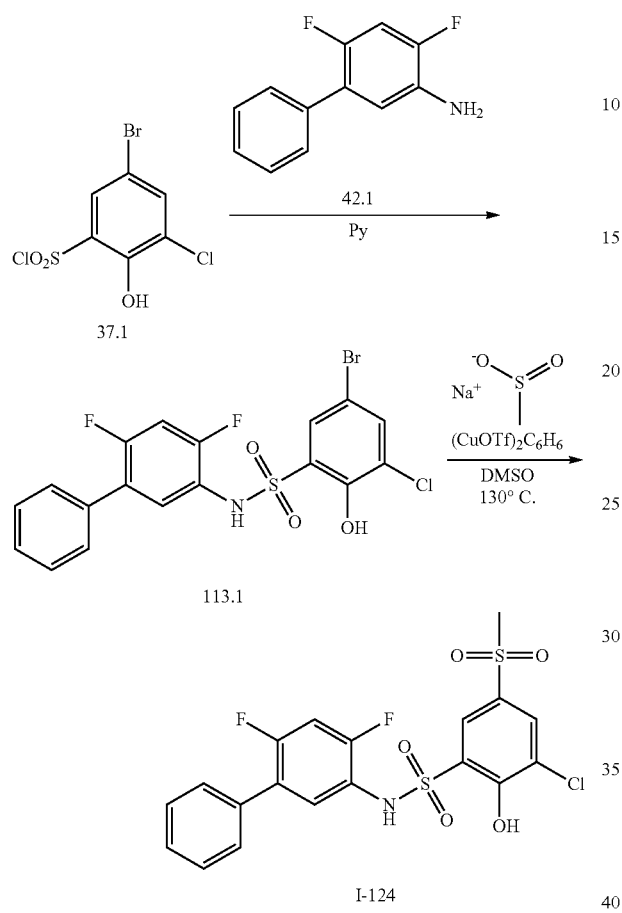

Synthesis of 113.1

To a stirred solution of 37.1 (1 g, 3.27 mmol, 1 equiv) and 42.1 (0.7 g, 3.27 mmol, 1 equiv) in pyridine (10 mL) was stirred for overnight at room temperature under nitrogen atmosphere. The resulting mixture was concentrated under reduced pressure. The resulting mixture was extracted with EtOAc (2×20 mL). The residue was purified by Prep-TLC (ChromatSolvents Ratio) to afford 113.1 (800 mg, 51.6%) as a white solid.

Synthesis of I-124

To a stirred solution of 113.1 (300 mg, 0.63 mmol, 1 equiv) and [(methylsulfanyl)oxy]sodium (163.2 mg, 1.90 mmol, 3 equiv) in DMSO (5 mL) was added $Cu(OTf)_2C_6H_6$ (22.9 mg, 0.06 mmol, 0.1 equiv) in portions at room temperature under nitrogen atmosphere. The resulting mixture was stirred for overnight at 130° C. under nitrogen atmosphere. The resulting mixture was extracted with EtOAc (2×20 mL). The residue was purified by Prep-TLC ($CH_2Cl_2$/MeOH 20:1) to I-124 (162.4 mg, 54.2%) as a white solid. (ES, m/z): [M–H]⁻ 472.0, ¹H-NMR (400 MHz, DMSO-$d_6$, ppm): 7.67 (s, 2H), 7.46-7.41 (m, 2H), 7.39-7.37 (m, 1H), 7.35-7.32 (m, 3H), 7.15 (s, 1H), 7.09 (s, 1H), 6.96 (s, 1H), 3.00 (s, 3H).

Example 114. Synthesis of Methyl 5-chloro-3-([4,6-difluoro-[1,1-biphenyl]-3-yl] sulfamoyl)-4-hydroxy-2-methylbenzoate, I-126

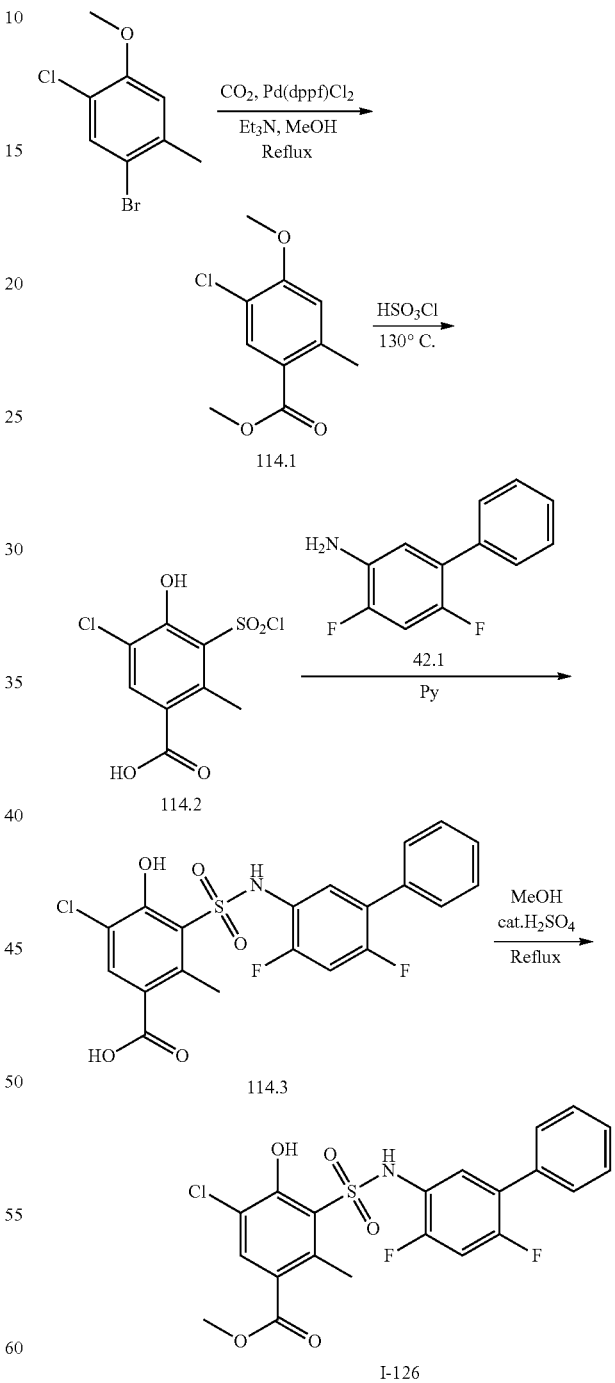

Synthesis of 114.1

Into a 1000-mL round-bottom flask, was placed 1-bromo-5-chloro-4-methoxy-2-methylbenzene (2 g, 8.49 mmol, 1 equiv), MeOH (400 mL), Et₃N (1718.7 mg, 16.98 mmol, 2 equiv), Pd(dppf)Cl2 (621.4 mg, 0.85 mmol, 0.1 equiv). The flask was evacuated and flushed three times with nitrogen, followed by flushing with CO. The reaction mixture was stirred for 2 days at 80° C. in an oil bath. Meanwhile, the reaction mixture was heated to reflux. The resulting mixture was concentrated under vacuum, diluted with 300 mL of H₂O and extracted with 3×200 mL of ethyl acetate. The combined organic phase was concentrated under vacuum to afford the crude product that purified by a silica gel column with ethyl acetate/petroleum ether (1:50). This resulted in 340 mg (18.6%) of 114.1 as a yellow solid. (ES, m/z): [M−H]⁻ 213.0.

Synthesis of 114.2

Into a 8-mL vial, was placed 114.1 (320 mg, 1.49 mmol, 1 equiv), HSO₃Cl (4 mL). The resulting solution was stirred for 1 day at 130° C. in an oil bath. The reaction was then quenched by the addition of 20 mL of water/ice. The resulting solution was extracted with 3×30 mL of ethyl acetate and the organic extracts were concentrated under vacuum. This resulted in 245 mg (57.6%) of 114.2 as a yellow solid. (ES, m/z): [M−H]⁻ 282.9.

Synthesis of 114.3

Into a 20-mL vial, was placed 42.1 (529.1 mg, 2.58 mmol, 3 equiv), pyridine (5 mL), 114.2 (245 mg, 0.86 mmol, 1 equiv) at room temperature. After stirred overnight, the resulting mixture was concentrated under vacuum. The resulting solution was diluted with 10 mL of H₂O and extracted with 3×20 mL of ethyl acetate. Then, the organic phase was evaporated under vacuum. The crude product was purified by Flash-Prep-HPLC with the following conditions (IntelFlash-1): Column, C18; mobile phase, ACN/H₂O=15% increasing to ACN/H₂O=60% within 15 min; Detector, UV 254 nm. This resulted in 210 mg (53.8%) of 114.3 as a yellow solid. (ES, m/z): [M−H]⁻ 452.0.

Synthesis of Compound I-126 into a 8-mL vial, was placed 114.3 (70 mg, 0.15 mmol, 1 equiv), MeOH (1.2 mL), H₂SO₄ (15.1 mg, 0.15 mmol, 1 equiv). The resulting solution was stirred overnight at 80° C. in an oil bath and heated to reflux. The resulting solution was diluted with 20 mL of H₂O, extracted with 3×20 mL of ethyl acetate and the organic layers were concentrated under vacuum. The crude product was purified by Flash-Prep-HPLC with the following conditions (IntelFlash-1): Column, C18; mobile phase, ACN/H₂O=15% increasing to ACN/H₂O=60% within 15 min; Detector, UV 254 nm. This resulted in 22.6 mg (31.3%) of I-126 as a yellow solid. (ES, m/z): [M−H]⁻ 466.0, ¹H-NMR (300 MHz, DMSO-d₆, ppm): δ2.67 (s, 3H), δ3.74 (s, 3H), δ7.30-7.49 (m, 7H), δ7.81 (s, 1H).

Example 115. Synthesis of Methyl 3-chloro-5-[(5-cyclopropyl-2,4-difluorophenyl) sulfamoyl]-4-hydroxybenzoate, I-127

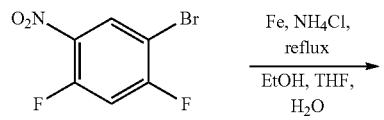

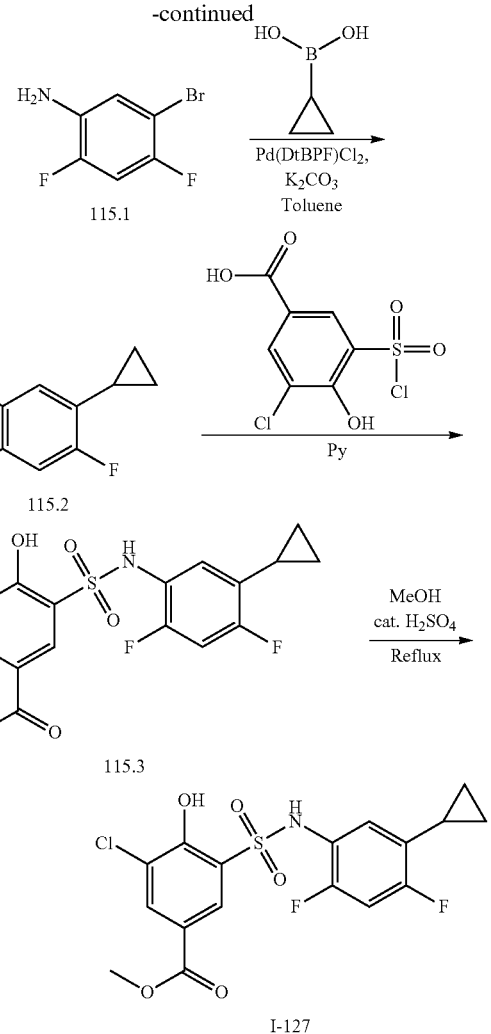

Synthesis of 115.1

Into a 500-mL 3-necked round-bottom flask, was placed 1-bromo-2,4-difluoro-5-nitrobenzene (10 g, 42.02 mmol, 1 equiv), H₂O (15 mL), THF (30 mL), EtOH (60 mL), NH₄Cl (48 mL), Fe (9.9 g, 176.48 mmol, 4.2 equiv). The resulting solution was stirred for 2 h at 95° C. The solids were filtered out. The resulting mixture was concentrated under vacuum. The residue was applied onto a silica gel column with ethyl acetate/petroleum ether (50:1). This resulted in 3 g (34.3%) of 115.1 as yellow oil. (ES, m/z): [M+H]⁺ 207.9.

Synthesis of 115.2

Into a 100-mL 3-necked round-bottom flask purged and maintained with an inert atmosphere of nitrogen, was placed 115.1 (1 g, 4.81 mmol, 1 equiv), toluene (10 mL), cyclopropylboronic acid (0.8 g, 9.62 mmol, 2 equiv), K₂CO₃ (2.0 g, 14.42 mmol, 3 equiv), Pd(DtBPF)Cl₂ (0.3 g, 0.48 mmol, 0.1 equiv). The resulting solution was stirred for 2 h at 60° C. The resulting mixture was concentrated under vacuum. The residue was applied onto a silica gel column with ethyl acetate/petroleum ether (50:1). This resulted in 420 mg (51.6%) of 115.2 as dark grey oil. (ES, m/z): [M+H]⁺ 170.0.

411

Synthesis of 115.3

Into a 100-mL round-bottom flask, was placed 3-chloro-5-(chlorosulfonyl)-4-hydroxybenzoic acid (500 mg, 1.84 mmol, 1 equiv), 115.2 (374.4 mg, 2.21 mmol, 1.2 equiv), pyridine (6 mL). The resulting solution was stirred for 2 h at 25° C. The reaction was then quenched by the addition of 15 mL of diluted hydrochloric acid. The resulting solution was extracted with 3×20 mL of ethyl acetate. The organic layers were combined, concentrated under vacuum. The crude product was purified by Flash-Prep-HPLC with the following conditions (IntelFlash-1): Column, C18; mobile phase, $H_2O:ACN=10\%$ increasing to $H_2O:ACN=50\%$ within 10 min; Detector, UV 254 nm. This resulted in 220 mg (24.7%) of 115.3 as a white solid. (ES, m/z): [M–H]⁻ 402.0.

Synthesis of I-127

Into a 8-mL sealed tube, was placed 115.3 (100 mg, 0.25 mmol, 1 equiv), MeOH (3 mL), $H_2SO_4$ (48.6 mg, 0.50 mmol, 2 equiv, 98%). The resulting solution was stirred for 12 h at 65° C. The reaction was then quenched by the addition of 3 mL of water and extracted with 3×5 mL of ethyl acetate. Then, the organic layers was combined and concentrated under vacuum. The residue was applied onto Prep-TLC with dichloromethane/methanol (20:1). This resulted in 57.2 mg (55.3%) of I-127 as a white solid. (ES, m/z): [M–H]⁻ 416.0, ¹H-NMR (300 MHz, DMSO-$d_6$, ppm): δ0.33-0.35 (m, 2H), δ0.84-0.90 (m, 2H), δ1.82-1.91 (m, 1H), δ3.68 (s, 3H), δ6.63-6.69 (t, J=8.4 Hz, 1H), δ7.10-7.17 (t, J=10.2 Hz, 1H), δ7.74-7.77 (m, 2H).

Example 116. Synthesis of Methyl 3-[[5-(1-benzothiophen-2-yl)-2,4-difluorophenyl]sulfamoyl]-5-chloro-4-hydroxybenzoate, I-128

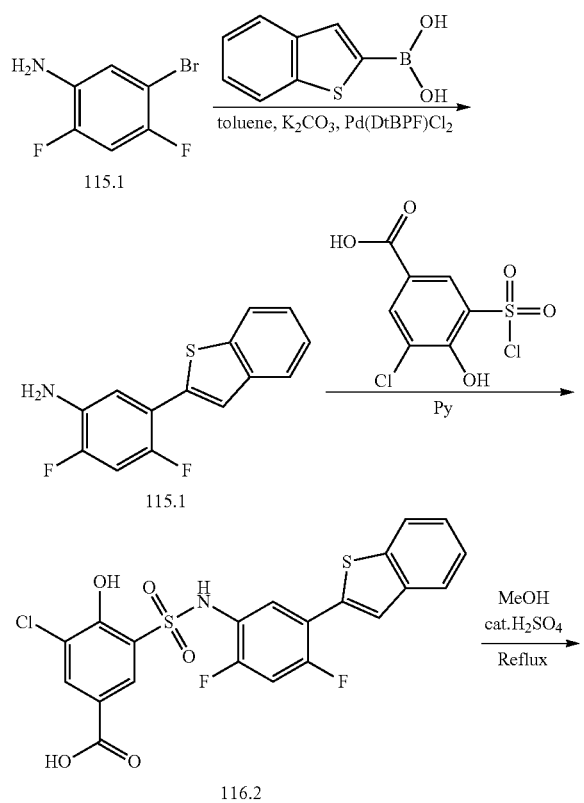

412

-continued

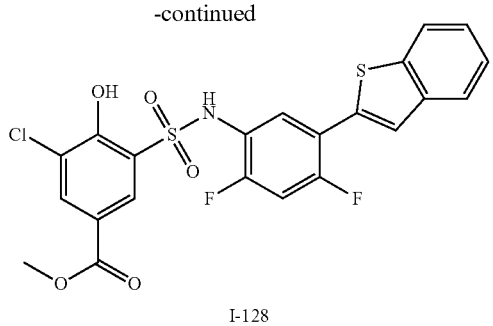

I-128

Synthesis of Compound 116.1

Into a 100-mL 3-necked round-bottom flask, was placed 115.1 (1 g, 4.81 mmol, 1 equiv), toluene (10 mL), (1-benzothiophen-2-yl)boronic acid (1.7 g, 9.62 mmol, 2 equiv), $K_2CO_3$ (2.0 g, 14.42 mmol, 3 equiv), Pd(DtBPF)Cl₂ (0.3 g, 0.48 mmol, 0.1 equiv). The resulting solution was stirred for 2 h at 80° C. The resulting mixture was concentrated under vacuum. The residue was applied onto a silica gel column with ethyl acetate/petroleum ether (1:30). This resulted in 1.1 g (87.6%) of 116.1 as a light yellow solid.

Synthesis of Compound 116.2

Into a 25-mL round-bottom flask, was placed 3-chloro-5-(chlorosulfonyl)-4-hydroxybenzoic acid (500 mg, 1.84 mmol, 1 equiv), 116.1 (578.3 mg, 2.21 mmol, 1.2 equiv), pyridine (6 mL). The resulting solution was stirred for 2 h at 25° C. The reaction was then quenched by the addition of 15 mL of 1M hydrochloric acid. The resulting solution was extracted with 3×20 mL of ethyl acetate and the combined organic layers were concentrated under vacuum. The crude product was purified by Flash-Prep-HPLC with the following conditions (IntelFlash-1): Column, C18; mobile phase, $H_2O:ACN=15\%$ increasing to $H_2O:ACN=60\%$ within 10 min; Detector, UV 254/220 nm. This resulted in 210 mg (22.9%) of 116.2 as a white solid.

Synthesis of Compound I-128

Into a 8-mL sealed tube, was placed 116.2 (100 mg, 0.20 mmol, 1 equiv), MeOH (2 mL), $H_2SO_4$ (39.6 mg, 0.40 mmol, 2 equiv). The resulting solution was stirred for 12 h at 65° C. The reaction was then quenched by the addition of 3 mL of water, and extracted with 3×5 mL of ethyl acetate. The combined organic layers were concentrated under vacuum. The residue was applied onto Prep-TLC with dichloromethane/methanol (20:1). This resulted in 61.3 mg (59.61%) of I-128 as a white solid. (ES, m/z): [M–H]⁻ 508.0, ¹H-NMR (300 MHz, DMSO-$d_6$, ppm): δ3.67 (s, 3H), δ7.36-7.49 (m, 3H), δ7.61-7.67 (m, 2H), δ7.76-7.77 (d, J=2.4 Hz, 1H), δ7.87-7.91 (m, 2H), δ9.96-8.00 (m, 1H).

Example 117. Synthesis of 3-chloro-4-methoxy-5-(N-(4-methoxy-[1,1'-biphenyl]-3-yl)sulfamoyl)-N,N-dimethylbenzamide, I-434

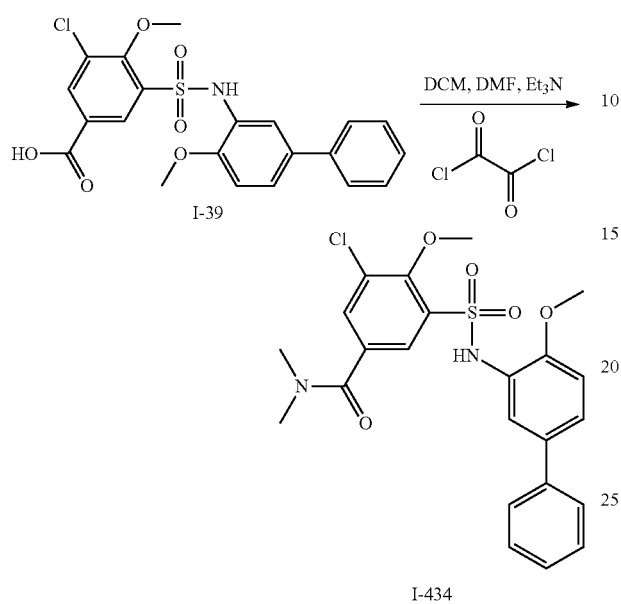

Synthesis of I-434

Into a 25-mL round-bottom flask, was placed I-39 (60 mg, 0.13 mmol, 1 equiv), DCM (3 mL), oxalic dichloride (18.7 mg, 0.15 mmol, 1.1 equiv), DMF (1 mL) at 0° C. The resulting solution was stirred for 30 min at room temperature. Then Et₃N (40.7 mg, 0.40 mmol, 3 equiv) was added. The resulting solution was stirred for 2 h at room temperature. The resulting mixture was concentrated under vacuum. The residue was applied onto Prep-TLC with dichloromethane/methanol (20:1). This resulted in 31.9 mg (50.1%) of I-434 as a white solid. (ES, m/z): [M+H]⁺ 475.2, ¹H-NMR (300 MHz, DMSO-d₆, ppm): δ9.63 (s, 1H), δ7.85-7.84 (d, J=2.1 Hz, 1H), δ7.59-7.58 (d, J=1.8 Hz, 1H), δ7.53-7.50 (m, 2H), δ7.45-7.40 (m, 4H), δ7.34-7.32 (d, J=7.2 Hz, 1H), δ7.02-6.99 (d, J=9.3 Hz, 1H), δ3.97 (s, 3H), δ3.56 (s, 3H), δ2.91 (s, 3H), δ2.70 (s, 3H).

Example 118. Synthesis of Methyl 5-chloro-2-methoxy-3-(N-(4-methoxy-[1,1'-biphenyl]-3-yl)sulfamoyl)benzoate, I-435

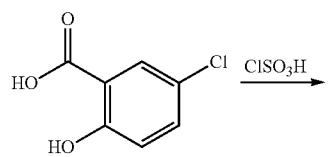

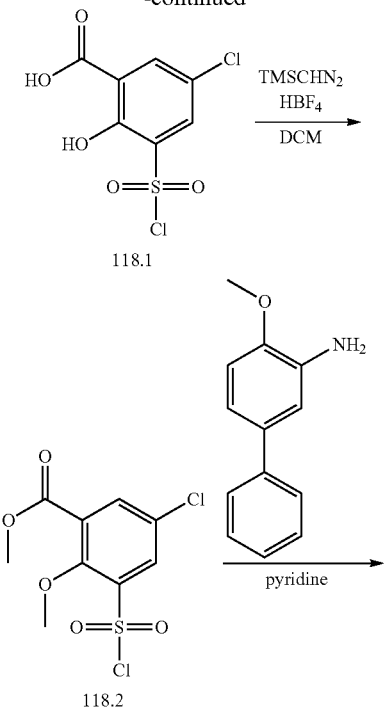

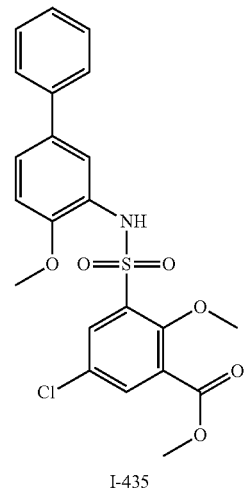

Synthesis of Compound 118.1

Into a 50-mL round-bottom flask, was placed 5-chloro-2-hydroxybenzoic acid (2 g, 11.59 mmol, 1 equiv), chloranesulfonic acid (10 mL). The resulting solution was stirred for 4 h at 80° C. The reaction was then quenched by the addition of 20 mL of water/ice. The resulting solution was extracted with ethyl acetate (2×20 mL). The organic layers were combined and concentrated under vacuum. This resulted in 2.3 g (73.2%) of 118.1 as a light yellow solid. (ES, m/z): [M−H]⁻ 268.9.

Synthesis of Compound 118.2

Into a 50-mL round-bottom flask, was placed 118.1 (1 g, 3.69 mmol, 1 equiv), DCM (10 mL), HBF₄ (1.22 g, 5.56 mmol, 1.5 equiv), TMSCHN₂ (7.4 mL, 2 M, 4 equiv). The resulting solution was stirred for 2 h at 0° C. The reaction was then quenched by the addition of water (10 mL). The resulting solution was extracted with ethyl acetate (2×10 mL). The organic layers were combined and concentrated under vacuum. This resulted in 1.08 g (97.8%) of 118.2 as a light yellow solid. (ES, m/z): [M−H]⁻ 296.9.

Synthesis of I-435

Into a 50-mL round-bottom flask was placed 349.2 (1.08 g, 3.61 mmol, 1 equiv), 2-methoxy-5-phenylaniline (863.3 mg, 4.33 mmol, 1.2 equiv), pyridine (10 mL). The resulting solution was stirred for 6 h at room temperature. The resulting mixture was washed with 1 M HCl. The resulting solution was extracted with ethyl acetate (2×10 mL). The organic layers were combined and concentrated under vacuum. The residue was applied onto Prep-TLC with dichloromethane/methanol (20:1). This resulted in 470 mg (28.2%) of methyl 5-chloro-2-methoxy-3-[(2-methoxy-5-phenylphenyl)sulfamoyl]benzoate as a yellow solid. The 60 mg crude product was purified by Flash-Prep-HPLC with the following conditions (IntelFlash-1): Column, C 18; mobile phase, ACN/H₂O (0.1% NH₄HCO₃)=0 increasing to ACN/H₂O (0.1% NH₄HCO₃)=6/4 within 30 min; Detector, UV 254 nm. This resulted in 34.4 mg I-435 as a white solid. (ES, m/z): [M−H]⁻ 460.0, ¹H-NMR (400 MHz, DMSO-d₆, ppm): δ9.66 (s, 1H), δ8.00-7.99 (d, J=2.8 Hz, 1H), δ7.84-7.83 (d, J=2.8 Hz, 1H), δ7.55-7.42 (m, 6H), δ7.35-7.32 (t, J=7.2 Hz, 1H), δ7.05-7.03 (d, J=8.4 Hz, 1H), δ3.92 (s, 3H), δ3.88 (s, 3H), δ3.56 (s, 3H).

Example 119. Synthesis of 3-chloro-2-hydroxy-N-[4-methoxy-[1,1-biphenyl]-3-yl]-5-(1-methyl-1H-imidazol-2-yl)benzene-1-sulfonamide, I-131

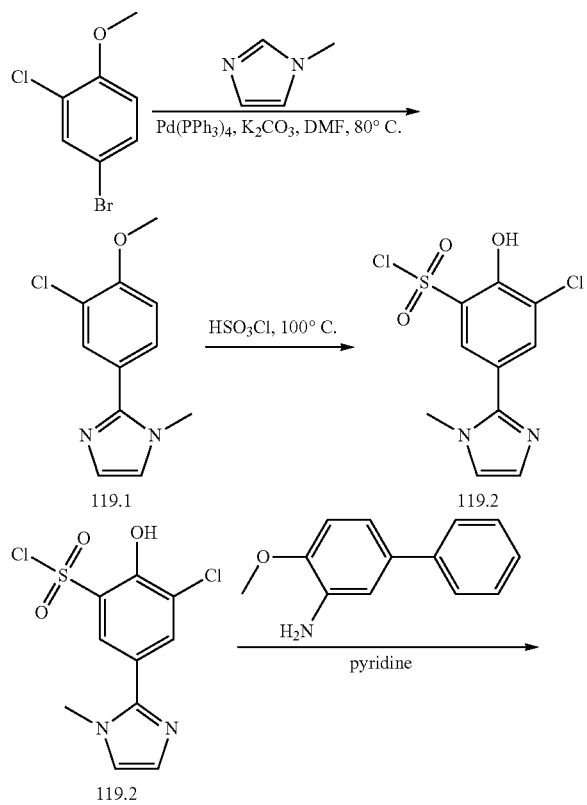

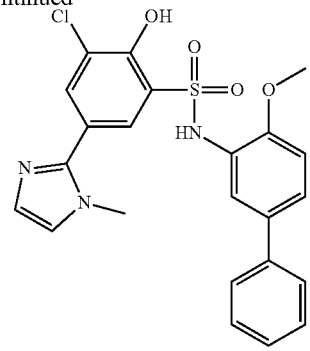

I-131

Synthesis of Compound 119.1

Into a 100-mL round-bottom flask purged and maintained with an inert atmosphere of nitrogen, was placed (3-chloro-4-methoxyphenyl)boronic acid (1000 mg, 5.36 mmol, 1 equiv), 2-bromo-1-methyl-1H-imidazole (950.1 mg, 5.90 mmol, 1.1 equiv), DMF (20 mL), K₂CO₃ (8 mL, 2 M, 3 equiv), Pd(PPh₃)₄ (619.9 mg, 0.54 mmol, 0.1 equiv). The resulting solution was stirred for 12 h at 100° C. The resulting mixture was concentrated under vacuum. The residue was applied onto a silica gel column with ethyl acetate/petroleum ether (20:1). This resulted in 1 g (83.7%) of 119.1 as a dark brown liquid.

Synthesis of Compound 119.2

Into a 8-mL vial, was placed 119.1 (190 mg, 0.85 mmol, 1 equiv), HSO₃Cl (298.3 mg, 2.56 mmol, 3.00 equiv). The resulting solution was stirred overnight at 100° C. This resulted in 488 mg (crude) of 119.2 as a liquid. The crude product was directly used in the next step without further purification.

Synthesis of I-131

Into a 8-mL vial, was placed 119.2 (488 mg, 1.52 mmol, 1 equiv), 4-methoxy-[1,1-biphenyl]-3-amine (484.4 mg, 2.43 mmol, 1.6 equiv), and pyridine (4 mL). The resulting solution was stirred overnight at 25° C. The resulting mixture was concentrated. The crude product was purified by Flash-Prep-HPLC with the following conditions (IntelFlash-1): Column, C18; mobile phase, H₂O/ACN=90:10 increasing to H₂O/ACN=0:100 within 30 min; Detector, UV 254 nm. This resulted in 19.4 mg (2.7%) of I-131 as a light brown solid. (ES, m/z): [M+H]⁺ 470.2, ¹H-NMR (300 MHz, DMSO-d₆, ppm): δ3.64 (s, 3H), δ3.78 (s, 3H), δ7.03-7.06 (d, J=8.4 Hz, 1H), δ7.26-7.32 (m, 2H), δ7.36-7.52 (m, 6H), δ7.63-7.67 (m, 2H), δ7.74-7.75 (d, J=2.7 Hz, 1H).

Example 120. Synthesis of 5-chloro-3-([4,6-difluoro-[1,1-biphenyl]-3-yl] sulfamoyl)-4-hydroxy-2-methylbenzoic Acid, I-132

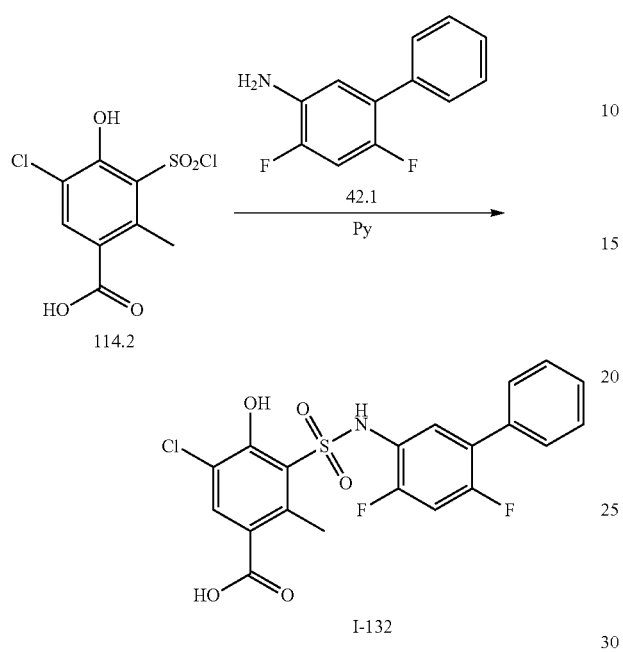

Synthesis of Compound I-132

Into a 8-mL vial, was placed 42.1 (108.0 mg, 0.53 mmol, 3 equiv), pyridine (1 mL), 114.2 (50 mg, 0.18 mmol, 1 equiv). The resulting solution was stirred overnight at room temperature. The resulting mixture was concentrated under vacuum. The residue was diluted with 10 mL of $H_2O$, extracted with 3×10 mL of ethyl acetate. Then, the organic phase was concentrated under vacuum, followed by applied onto Flash-Prep-HPLC with the following conditions (IntelFlash-1): Column, C18; mobile phase, $ACN/H_2O=15\%$ increasing to $ACN/H_2O=60\%$ within 15 min; Detector, UV 254. This resulted in 6.6 mg (8.3%) of I-132 as a yellow solid. (ES, m/z): [M−H]⁻ 451.9, $^1$H-NMR (400 MHz, DMSO-$d_6$, ppm): δ2.72 (s, 3H), δ6.92-7.21 (m, 2H), δ7.31-7.37 (m, 1H), δ7.39-7.58 (m, 7H), δ7.88 (s, 1H).

Example 121. Synthesis of 3-chloro-2-hydroxy-N-(4-hydroxy-[1,1'-biphenyl]-3-yl)-5-(1-methyl-1H-imidazol-2-yl)benzenesulfonamide, I-133

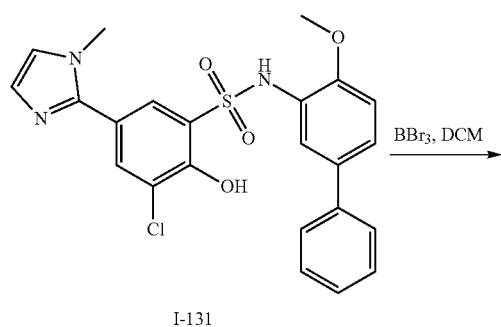

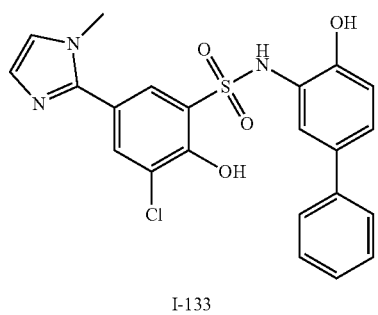

Synthesis of I-133

Into a 25-mL round-bottom flask, was placed I-131 (100 mg, 0.21 mmol, 1 equiv), DCM (3 mL), $BBr_3$ (159.9 mg, 0.64 mmol, 3 equiv). The resulting solution was stirred for 2 h at 25° C. The reaction was then quenched by the addition of 10 mL of water/ice. The resulting solution was extracted with 2×10 mL of dichloromethane and concentrated under vacuum. The crude product was purified by Flash-Prep-HPLC with the following conditions (IntelFlash-1): Column, C18; mobile phase, $H_2O:ACN=90:10$ increasing to $H_2O:ACN=0:100$ within 30 min; Detector, UV 254 nm. This resulted in 10.9 mg (11.2%) of I-133 as a brown solid. (ES, m/z): [M+H]⁺ 455.9, $^1$H-NMR (400 MHz, DMSO-$d_6$, ppm): δ3.70 (s, 3H), δ6.80-6.82 (d, J=8.4 Hz, 1H), δ7.23-7.29 (m, 2H), δ7.37-7.41 (m, 2H), δ7.47-7.50 (m, 4H), δ7.55 (s, 1H), δ7.70-7.75 (m, 2H), δ8.87 (br s, 1H), δ10.68 (br s, 1H).

Example 122. Synthesis of 3-chloro-N-[4,6-difluoro-[1,1-biphenyl]-3-yl]-5-fluoro-2-hydroxybenzene-1-sulfonamide, I-135

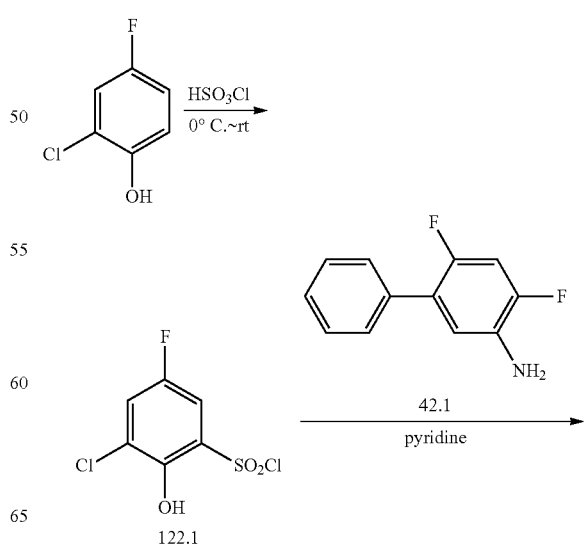

-continued

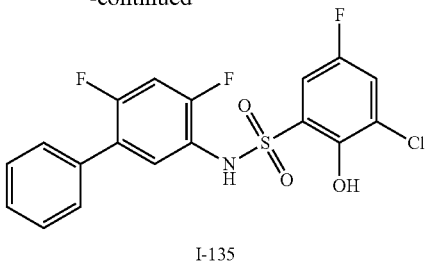

I-135

Synthesis of Compound 122.1

Into a 250 mL 3-necked round-bottom flask were added 2-chloro-4-fluorophenol (1 g, 6.82 mmol, 1 equiv) and sulfonoperoxoyl chloride (954.1 mg, 8.19 mmol, 1.2 equiv) at 0° C. The resulting mixture was stirred for 2 h at room temperature. The reaction was quenched by the addition of water/ice (10 mL). The resulting mixture was extracted with EtOAc (2×15 mL). The combined organic layers were concentrated under reduced pressure. This resulted in 1.02 g (61%) of 122.1 as a brown solid. (ES, m/z): [M–H]⁻ 242.9.

Synthesis of I-135

To a stirred solution of 42.1 (301.5 mg, 1.47 mmol, 1.20 equiv) in pyridine (10 mL) were added 122.1 (300 mg, 1.22 mmol, 1 equiv) at room temperature under nitrogen atmosphere. The resulting mixture was stirred for 0.5 h at room temperature. The resulting mixture was concentrated under reduced pressure. The crude product was purified by Flash-Prep-HPLC with the following conditions (IntelFlash-1): Column, C18; mobile phase, ACN/H$_2$O=10% increasing to ACN/H$_2$O=60% within 25 min; Detector, UV 254 nm. This resulted in 141.1 mg (27.8%) of I-135 as a white solid. (ES, m/z): [M–H]⁻ 411.9, ¹H-NMR (300 MHz, DMSO-d$_6$, ppm): δ6.93-7.09 (m, 1H), δ7.27-7.51 (m, 8H), δ7.71-7.74 (m, 1H).

Example 123. Synthesis of 5-(azetidine-1-carbonyl)-3-chloro-N-(3-fluoro-[1,1'-biphenyl]-4-yl)-2-hydroxybenzenesulfonamide, I-136

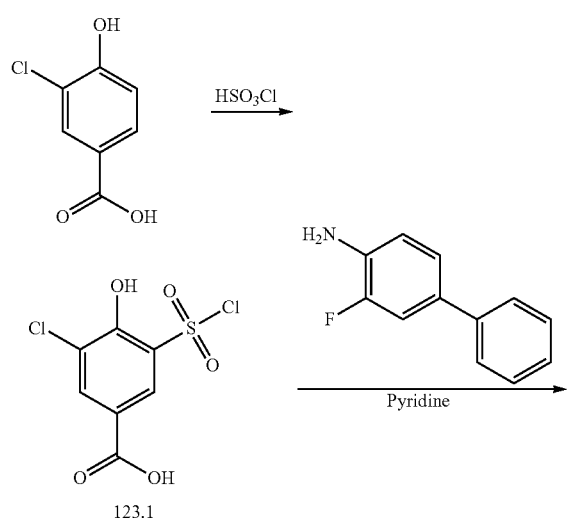

-continued

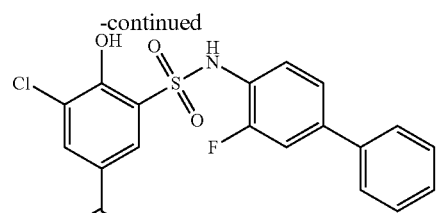

123.2

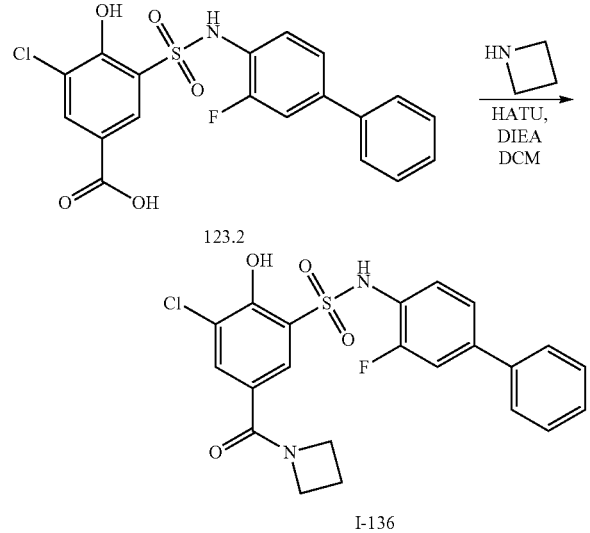

I-136

Synthesis of Compound 123.1

Into a 50-mL round-bottom flask, was placed 3-chloro-4-hydroxybenzoic acid (500.00 mg, 2.898 mmol, 1.00 equiv), sulfonoperoxoyl chloride (2025.73 mg, 17.385 mmol, 6.00 equiv). The resulting solution was stirred for 1 overnight at 80° C. The reaction was then quenched by the addition of 50 mL of water. The resulting solution was extracted with 2×50 mL of ethyl acetate. This resulted in 500 mg (63.6%) of 123.1 as a brown solid. (ES, m/z): [M–H]⁻ 268.9.

Synthesis of Compound 123.2

Into a 50-mL round-bottom flask, was placed 170.1 (500.00 mg, 1.845 mmol, 1.00 equiv), 3-fluoro-[1,1-biphenyl]-4-amine (414.41 mg, 2.214 mmol, 1.20 equiv), Pyridine (10.00 mL, 124.235 mmol, 67.35 equiv). The resulting solution was stirred for 1 overnight at 25° C. The resulting mixture was concentrated. The residue was applied onto a silica gel column with ethyl acetate/petroleum ether (1:1). This resulted in 700 mg (89.9%) of 123.2 as a white solid. (ES, m/z): [M–H]⁻ 420.0.

Synthesis of I-136

Into a 8-mL vial, was placed 123.2 (100 mg, 0.24 mmol, 1 equiv), DCM (2 mL), azetidine (27.1 mg, 0.47 mmol, 2 equiv), HATU (135.2 mg, 0.36 mmol, 1.5 equiv), DIEA (122.6 mg, 0.95 mmol, 4 equiv). The resulting solution was stirred overnight at 25° C. The reaction was quenched by 5 mL of water, and extracts with 2×5 mL of DCM, followed by combined the organic layers and concentrated under vacuum. The residue was applied onto a prep TLC with ethyl acetate/petroleum ether (1:1). The crude product was purified by Flash-Prep-HPLC with the following conditions (IntelFlash-1): Column, C18; mobile phase, water:acetonitrile=90:10 increasing to water:acetonitrile=0:100 within 30 min; Detector, UV 254 nm. This resulted in 13.6 mg (12.5%) of I-136 as a white solid. (ES, m/z): [M+H]$^+$ 461.2, $^1$H-NMR (400 MHz, DMSO-d$_6$, ppm): δ2.14-2.17 (m, 2H), δ3.91-4.04 (m, 4H), δ7.21-7.25 (m, 2H), δ7.34-7.36 (m, 1H), δ7.41-7.49 (m, 4H), δ7.54-7.58 (m, 2H), δ7.64 (s, 1H).

Example 124. Synthesis of 5-(azetidine-1-carbonyl)-3-chloro-N-(5-cyclopropyl-2,4-difluorophenyl)-2-hydroxybenzene-1-sulfonamide, I-137

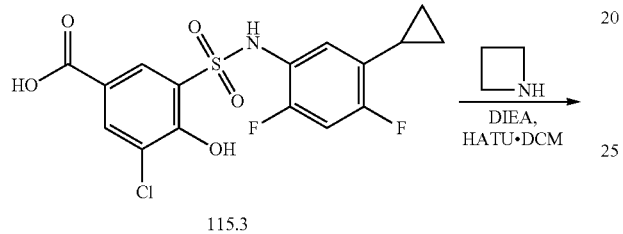

115.3

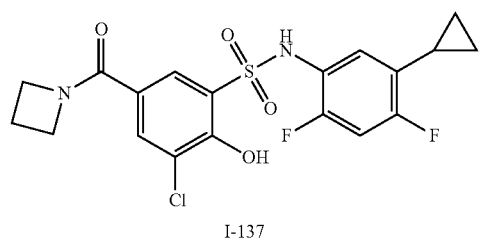

I-137

Synthesis of I-137

Into a 8-mL sealed tube, was placed 115.3 (100 mg, 0.25 mmol, 1 equiv), DCM (1.5 mL), DIEA (96.0 mg, 0.74 mmol, 3 equiv), azetidine (28.3 mg, 0.50 mmol, 2 equiv), HATU (131.8 mg, 0.35 mmol, 1.4 equiv). The resulting solution was stirred for 2 h at 25° C. The reaction was then quenched by the addition of 5 mL of water, and extracted with 3×10 mL of ethyl acetate. The organic layers was combined and concentrated under vacuum. The residue was applied onto Prep-TLC with dichloromethane/methanol (20:1). The crude product was purified by Flash-Prep-HPLC with the following conditions (IntelFlash-1): Column, C18; mobile phase, ACN:H$_2$O=15% increasing to ACN:H$_2$O=60% within 15 min; Detector UV 254 nm. This resulted in 9.8 mg (8.94%) of I-137 as a white solid. 1H-NMR (400 MHz, CD$_3$OD, ppm): δ 0.47-0.51 (s, 2H), δ0.87-0.95 (m, 2H), δ1.87-1.95 (m, 1H), δ2.30-2.38 (m, 2H), δ4.13-4.31 (m, 4H), δ6.76-6.86 (m, 2H), δ7.66-7.67 (d, J=2.4 Hz, 1H), δ7.75-7.76 (d, J=2.4 Hz, 1H).

Example 125. Synthesis of 5-(azetidine-1-carbonyl)-N-[5-(1-benzothiophen-2-yl)-2,4-difluorophenyl]-3-chloro-2-hydroxybenzene-1-sulfonamide, I-138

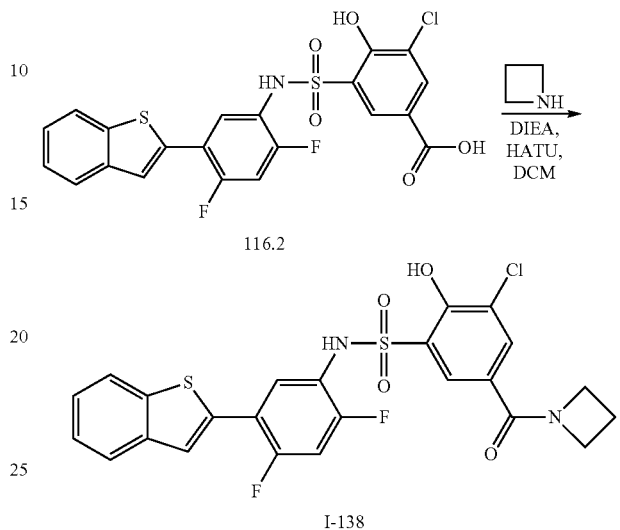

Synthesis of I-138

Into a 8-mL sealed tube, was placed 116.2 (100 mg, 0.20 mmol, 1 equiv), DCM (1.5 mL), DIEA (78.2 mg, 0.60 mmol, 3 equiv), azetidine (23.0 mg, 0.40 mmol, 2 equiv), HATU (107.3 mg, 0.28 mmol, 1.4 equiv). The resulting solution was stirred for 3 h at 25° C. The reaction was then quenched by the addition of 5 mL of water. The resulting solution was extracted with 3×15 mL of ethyl acetate. The organic layers was combined and concentrated under vacuum. The residue was applied onto Prep-TLC with dichloromethane/methanol (20:1). The crude product was purified by Flash-Prep-HPLC with the following conditions (IntelFlash-1): Column, C18; mobile phase, ACN:H$_2$O=15% increasing to ACN:H$_2$O=60% within 15 min; Detector, UV 254 nm. This resulted in 7.3 mg (6.8%) of I-138 as a white solid. (ES, m/z): [M−H]$^-$ 533.1, $^1$H-NMR (300 MHz, DMSO-d$_6$, ppm): δ2.09-2.14 (m, 2H), δ4.06 (br s, 4H), δ7.38-7.47 (m, 3H), δ7.55-7.56 (d, J=2.4 Hz, 1H), δ7.64-7.70 (m, 3H), δ7.89-7.92 (m, 1H), δ7.98-8.01 (m, 1H).

Example 126. Synthesis of 3-chloro-4-methoxy-5-(N-(4-methoxy-[1,1'-biphenyl]-3-yl)sulfamoyl)-N-methylbenzamide, I-433

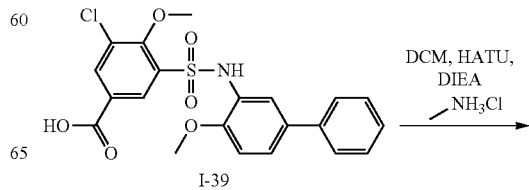

I-39

423
-continued

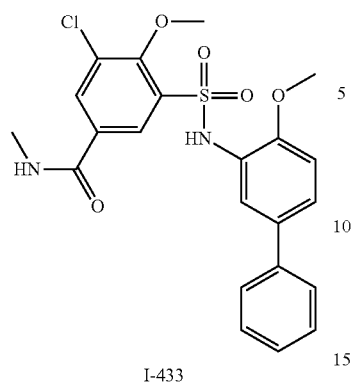

I-433

Synthesis of I-433

Into a 25-mL round-bottom flask, was placed I-39 (60 mg, 0.13 mmol, 1 equiv), DCM (3 mL), chloro(methyl)amine (87.7 mg, 1.35 mmol, 10 equiv), HATU (101.9 mg, 0.27 mmol, 2 equiv), DIEA (51.9 mg, 0.40 mmol, 3 equiv). The resulting solution was stirred for 12 h at room temperature. The resulting mixture was concentrated under vacuum. The crude product was purified by Flash-Prep-HPLC with the following conditions (IntelFlash-1): Column, C 18; mobile phase, ACN/H$_2$O (0.1% NH$_4$HCO$_3$)=0 increasing to ACN/H$_2$O (0.10% NH$_4$HCO$_3$)=1/1 within 25 min; Detector, UV 254 nm. This resulted in 10.1 mg (16.4%) of I-433 as a white solid. (ES, m/z): [M−H]$^-$ 459.2, $^1$H-NMR (300 MHz, DMSO-d$_6$, ppm): δ9.60 (s, 1H), δ8.71-8.70 (d, J=2.4 Hz, 1H), δ8.23-8.22 (m, 2H), δ7.53-7.50 (m, 2H), δ7.47-7.40 (m, 4H), δ7.35-7.30 (m, 1H), δ7.02-6.99 (m, 1H), δ3.98 (s, 3H), δ3.53 (s, 3H), δ2.76-2.75 (d, J=4.5 Hz, 3H).

Example 127. Synthesis of 3-chloro-N-[4-fluoro-[1,1-biphenyl]-3-yl]-2-hydroxy-5-[(3R)-3-methoxypyrrolidine-1-carbonyl]benzene-1-sulfonamide, I-141

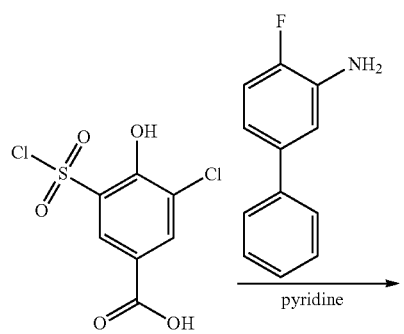

424
-continued

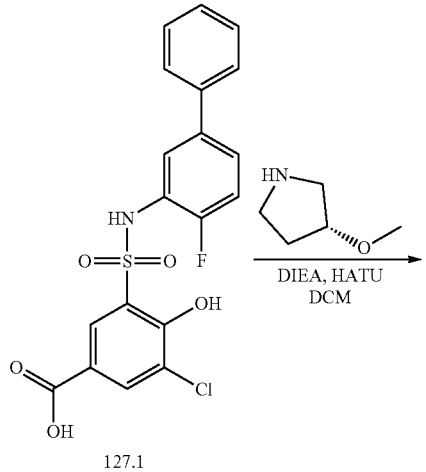

127.1

Synthesis of 127.1

Into a 100-mL round-bottom flask, was placed 3-chloro-5-(chlorosulfonyl)-4-hydroxybenzoic acid (3 g, 11.07 mmol, 1 equiv), 4-fluoro-[1,1-biphenyl]-3-amine (2.5 g, 13.28 mmol, 1.2 equiv), pyridine (30 mL). The resulting solution was stirred for 12 h at 25° C. The reaction was then quenched by the addition of 50 mL of 1M HCl. The resulting solution was extracted with 3×70 mL of EtOAc. And the organic layers were combined, followed by concentrated under vacuum. The crude product was purified by Flash-Prep-HPLC with the following conditions (IntelFlash-1): Column, C18; mobile phase, ACN:H$_2$O=15% increasing to ACN:H$_2$O=70% within 15 min; Detector, UV 254 nm. This resulted in 820 mg (17.6%) of 127.1 as a white solid. (ES, m/z): [M−H]$^-$ 420.0.

Synthesis of I-141

To a stirred mixture of 127.1 (100 mg, 240 mmol, 1 equiv) and (3R)-3-methoxypyrrolidine (33.6 mg, 330 mmol, 1.4 equiv) in DCM (1 mL) were added DIEA (122.6 mg, 0.95 mmol, 4 equiv) and HATU (135.2 mg, 0.36 mmol, 1.5 equiv in portions at room temperature under nitrogen atmosphere. After 2 h, the resulting mixture was diluted with 5 mL of water, and extracted with EtOAc (3×10 mL). The combined organic layers were washed with EtOAc (2×10 mL), dried over anhydrous Na$_2$SO$_4$. After filtration, the filtrate was concentrated under reduced pressure. The crude product was purified by reverse phase flash with the following conditions (from CH$_3$CN/H$_2$O=0:100 to CH$_3$CN/H$_2$O=40:60 in 30 min; Detector UV 254/220 nm) to afford I-141 (31.6 mg, 26.4%) as a white solid. (ES, m/z): [M+H]$^+$ 505.2, $^1$H-NMR (400 MHz, DMSO-d$_6$, ppm): δ1.85 (br s, 2H), δ3.14-3.36 (m, 5H), δ3.48-3.52 (m, 1H), δ3.84 (br s, 2H), δ6.96-7.08 (m, 2H), δ7.22-7.27 (m, 1H), δ7.34-7.37 (m, 2H), δ7.42-7.49 (m, 4H), δ7.52-7.54 (m, 1H), δ7.62-7.63 (m, 2H).

Example 128. Synthesis of 3-chloro-N-[4-fluoro-[1,1-biphenyl]-3-yl]-2-hydroxy-5-[(3S)-3-methoxypyrrolidine-1-carbonyl]benzene-1-sulfonamide, I-142

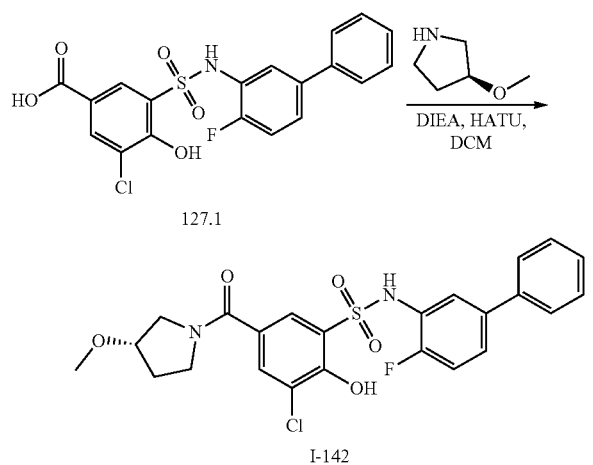

Synthesis of I-142

To a stirred mixture of 127.1 (100 mg, 0.24 mmol, 1 equiv) and (3S)-3-methoxypyrrolidine (33.6 mg, 0.33 mmol, 1.4 equiv) in DCM (1 mL) were added DIEA (122.6 mg, 0.95 mmol, 4 equiv) and HATU (135.2 mg, 0.36 mmol, 1.5 equiv) in portions at room temperature under nitrogen atmosphere. After 3 h, the resulting mixture was diluted with 5 mL of water, and extracted with EtOAc (3×5 mL). The combined organic layers were washed with EtOAc (2×10 mL), dried over anhydrous Na$_2$SO$_4$. After filtration, the filtrate was concentrated under reduced pressure. The crude product was purified by reverse phase flash with the following conditions (from CH$_3$CN/H$_2$O=0:100 to CH$_3$CN/H$_2$O=40:60 in 30 min; Detector, UV 254/220 nm) to yield product of I-142 (14.9 mg, 12.5%) as a white solid. (ES, m/z): [M+H]$^+$ 505.2, $^1$H-NMR (400 MHz, DMSO-d$_6$, ppm): δ1.84 (br s, 2H), δ3.16-3.31 (m, 5H), δ3.47-3.51 (m, 2H), δ3.82 (br s, 1H), δ6.95-7.21 (m, 2H), δ7.22-7.27 (m, 1H), δ7.34-7.38 (m, 2H), δ7.42-7.53 (m, 5H), δ7.63-7.70 (m, 2H).

Example 129. Synthesis of 2-(2,4-dichloro-6-[[([4-fluoro-[1,1-biphenyl]-3-yl]amino)oxy]sulfonyl]phenoxy)acetic Acid, I-143

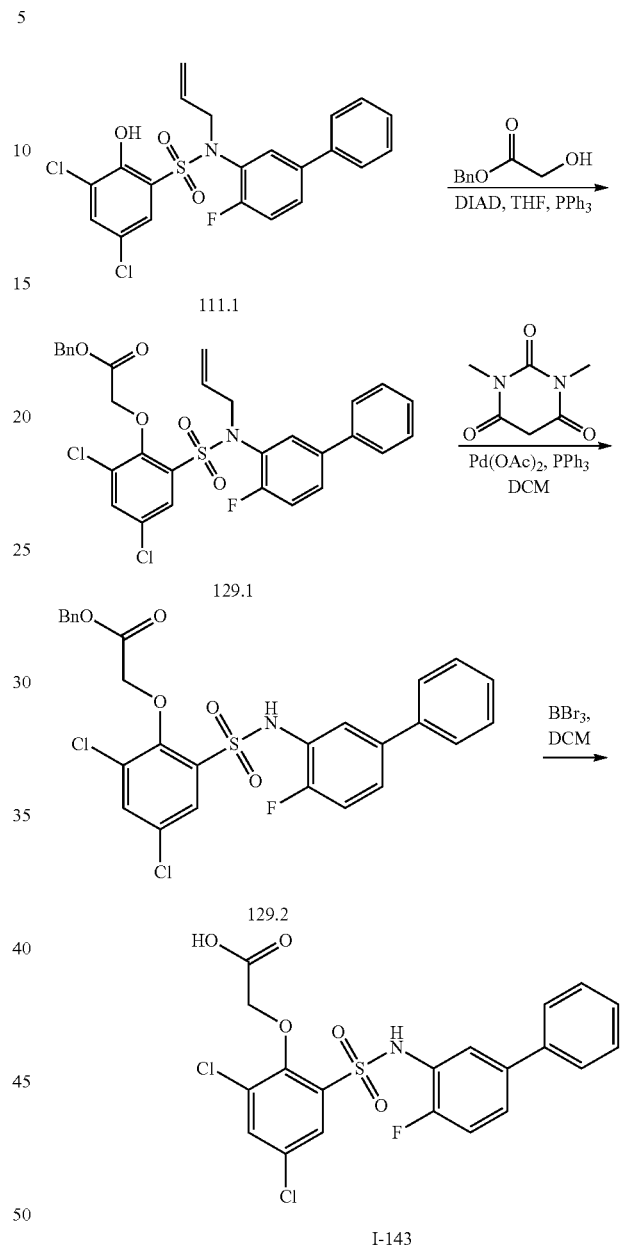

Synthesis of 129.1

To a stirred mixture of 111.1 (500 mg, 1.11 mmol, 1 equiv) and benzyl 2-hydroxyacetate (183.7 mg, 1.11 mmol, 1 equiv) in THF (10 mL, 61.71 mmol, 55.83 equiv) were added DIAD (447.0 mg, 2.21 mmol, 2 equiv) and PPh$_3$ (434.9 mg, 1.66 mmol, 1.5 equiv) in portions at 0° C. under nitrogen atmosphere. The resulting solution was stirred for overnight room temperature under nitrogen atmosphere. The resulting mixture was filtered and the filter cake was washed with EtOAc (2×100 mL). The filtrate was concentrated under reduced pressure. The residue was purified by silica gel column chromatography, eluted with PE/EtOAc (10:1) to afford 129.1 (300 mg, 45.2%) as a white solid. (ES, m/z): [M−H]⁻ 598.0.

Synthesis of 129.2

To a stirred mixture of 129.1 (1 g, 1.67 mmol, 1 equiv) and 1,3-dimethyl-1,3-diazinane-2,4,6-trione (780.1 mg, 5.00 mmol, 3.00 equiv) in THF (10 mL, 123.43 mmol, 74.12 equiv) was added Pd(PPh$_3$)$_4$ (577.3 mg, 0.50 mmol, 0.30 equiv) in portions at room temperature under nitrogen atmosphere. The resulting solution was stirred for overnight at 50° C. under nitrogen atmosphere. The reaction was quenched by the addition of water (100 mL) at room temperature. The aqueous layer was extracted with EtOAc (2×100 mL). The residue was purified by Prep-TLC (PE/EtOAc 10:1) to afford 129.2 (920 mg, 98.6%) as a white solid. (ES, m/z): [M−H]⁻ 558.0.

Synthesis of I-143

To a mixture of 129.2 (878 mg, 1.52 mmol, 1 equiv) and Pd(OH)$_2$/C (175.6 mg, 1.25 mmol, 0.82 equiv) in EtOAc (10.0 mL, 113.49 mmol, 67.06 equiv) was stirred for overnight at room temperature under hydrogen atmosphere. The resulting mixture was filtered the filter cake was washed with EtOAc (2×100 mL). The crude product was purified by reverse phase flash with the following conditions (from CH$_3$CN/H$_2$O=0:100 to CH$_3$CN/H$_2$O=40:60 in 30 mins; Detector UV: 254/220) to afford I-143 (500 mg, 67.5%) as a white solid. (ES, m/z): [M−H]⁻ 468.0, ¹H-NMR (300 MHz, DMSO-d$_6$, ppm): δ4.54 (s, 2H), δ7.17-7.22 (m, 3H), δ7.33-7.48 (m, 7H), δ7.62-7.63 (s, 1H), δ7.90-7.91 (s, 1H).

Example 130. Synthesis of 5-(azetidine-1-carbonyl)-3-chloro-2-hydroxy-N-[2-methoxy-5-(pyridin-3-yl)phenyl]benzene-1-sulfonamide, I-144

Synthesis of I-144

To a stirred solution of 48.1 (25 mg, 0.06 mmol, 1 equiv) and azetidine (6.6 mg, 0.11 mmol, 2 equiv) in DCM (0.5 mL) were added DIEA (14.9 mg, 0.11 mmol, 2 equiv) and HATU (32.8 mg, 0.09 mmol, 1.5 equiv in portions. The resulting mixture was stirred for overnight at room temperature under nitrogen atmosphere. The residue was purified by Prep-TLC (CH$_2$Cl$_2$/MeOH 20:1) to afford I-144 (6.2 mg, 22.8%) as a white solid. (ES, m/z): [M−H]⁻ 472.1, ¹H-NMR (300 MHz, DMSO-d$_6$, ppm): 8.68 (s, 1H), 8.51-8.50 (d, J=3.6 Hz, 1H), 7.85-7.82 (d, J=8.4 Hz, 1H), 7.66-7.63 (d, J=6.0 Hz, 2H), 7.48-7.43 (m, 2H), 7.31-7.28 (m, 1H), 7.20-7.05 (m, 3H), 4.00 (s, 4H), 3.92 (s, 3H), 2.16-2.06 (m, 2H).

Example 131. Synthesis of 5-(azetidine-1-carbonyl)-3-chloro-2-hydroxy-N-[4-methoxy-[1,1-biphenyl]-3-yl]benzene-1-sulfonamide, I-145

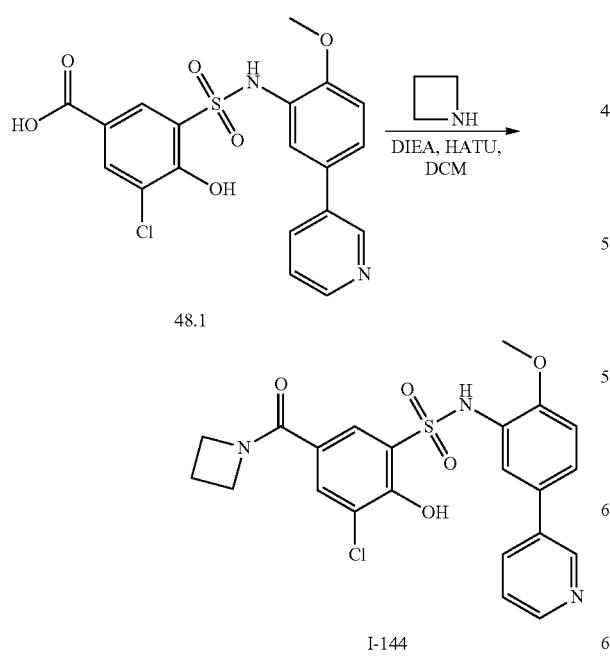

I-144

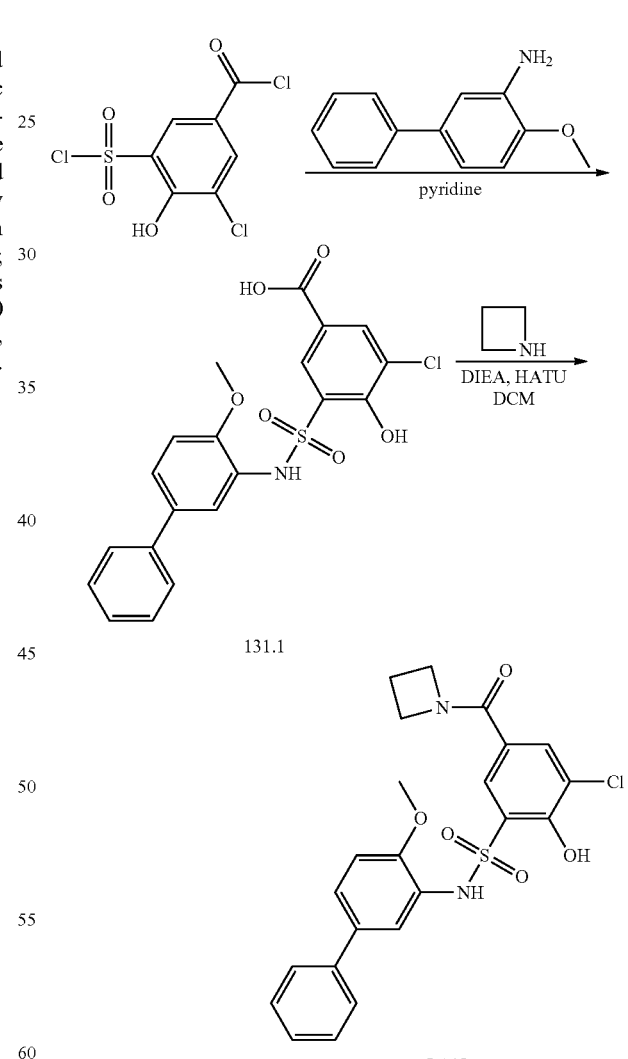

131.1

I-145

Synthesis of Compound 131.1

To a stirred solution of 4-methoxy-[1,1-biphenyl]-3-amine (441.1 mg, 2.21 mmol, 1.2 equiv) in pyridine (10 mL)

were added 3-chloro-5-(chlorosulfonyl)-4-hydroxybenzoic acid (500 mg, 1.84 mmol, 1 equiv) at room temperature under nitrogen atmosphere. The resulting mixture was stirred for 0.5 h. the resulting mixture was concentrated under reduced pressure. The residue was purified by Prep-TLC (CH$_2$Cl$_2$/MeOH=10:1) to afford 131.1 (313 mg, 39.1%) as a white solid.

Synthesis of I-145

To a stirred solution of 131.1 (313 mg, 0.72 mmol, 1 equiv) in DCM (10 mL) were added azetidine (49.4 mg, 0.87 mmol, 1.2 equiv), DIEA (186.5 mg, 1.44 mmol, 2 equiv) and HATU (411.5 mg, 1.08 mmol, 1.5 equiv) at room temperature under nitrogen atmosphere. The resulting mixture was stirred for 12 h. The resulting mixture was diluted was water (10 mL). The resulting mixture was extracted with EtOAc (3×10 mL) and the combined organic layers were concentrated under reduced pressure. The crude product was purified by Prep-HPLC with the following conditions (Intel-Flash-1): Column, C18; mobile phase, ACN/H$_2$O=10% increasing to ACN/H$_2$O=60% within 25 min; Detector, UV 254 nm. This resulted in 37.5 mg (11.0%) of I-145 as a white solid. (ES, m/z): [M+H]$^+$ 473.2, $^1$H-NMR (300 MHz, DMSO-d$_6$, ppm): δ2.07-2.17 (m, 2H), δ3.77 (s, 3H), δ4.01 (br s, 4H), δ6.96-7.33 (m, 5H), δ7.38-7.48 (m, 4H), δ7.54-7.55 (d, J=2.1 Hz, 1H), δ7.60-7.61 (d, J=2.1 Hz, 1H), δ7.69-7.70 (d, J=2.4 Hz, 1H).

Example 132. Synthesis of 3-chloro-5-(N-(4,6-difluoro-[1,1'-biphenyl]-3-yl)sulfamoyl)benzoic Acid, I-147

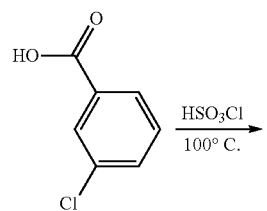

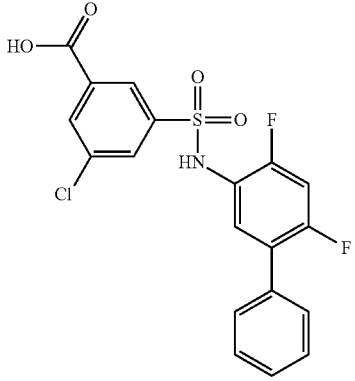

I-147

Synthesis of Compound 132.1

Into a 50-mL round-bottom flask purged and maintained with an inert atmosphere of nitrogen, was placed 3-chlorobenzoic acid (3 g, 19.16 mmol, 1 equiv), HSO$_3$Cl (5 mL). The resulting solution was stirred for 12 hr at 130° C. in an oil bath. The reaction was then quenched by the addition of 20 mL of water/ice. The resulting solution was extracted with 3×20 ml of ethyl acetate. The resulting mixture was washed with 1×20 ml of brine. The mixture was dried over anhydrous sodium sulfate and concentrated. The resulting mixture was concentrated. This resulted in 2 g (yield=41%) of 132.1 as a yellow solid. (ES, m/z): [M–H]$^-$ 252.9.

Synthesis of I-147

Into a 25-mL round-bottom flask purged and maintained with an inert atmosphere of nitrogen, was placed 132.1 (200 mg, 0.78 mmol, 1 equiv), 42.1 (160.9 mg, 0.78 mmol, 1.00 equiv), and pyridine (2 mL). The resulting solution was stirred for 0.5 hr at room temperature. The resulting mixture was concentrated. The residue was applied onto a silica gel column with ethyl acetate/petroleum ether (1:1). This resulted in 38.5 mg (yield=12%) of I-147 as a white solid. (ES, m/z): [M–H]$^-$ 422.0, $^1$H-NMR (DMSO-d$_6$, 400 MHz, ppm): δ13.90 (s, 1H), δ10.60 (s, 1H), δ8.17-8.16 (m, 2H), δ7.95 (s, 1H), δ7.52-7.38 (m, 6H), δ7.38-7.21 (m, 1H).

Example 133. Synthesis of 3-chloro-4-hydroxy-5-(N-(2-methoxy-5-(pyridin-3-yl)phenyl)sulfamoyl) benzoic Acid, I-427

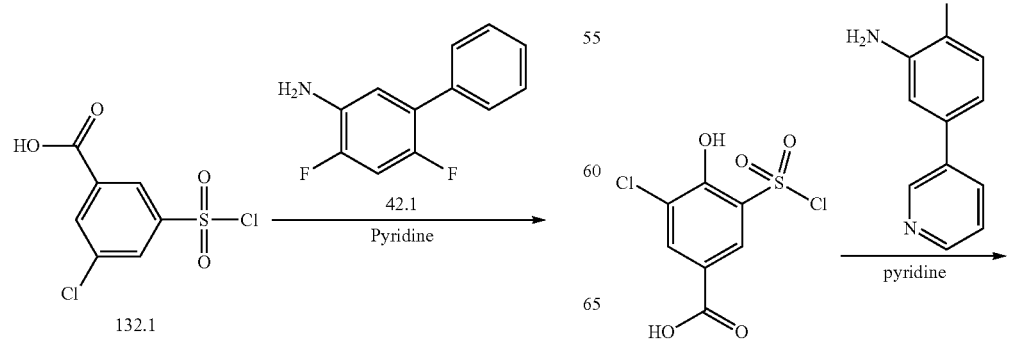

431

-continued

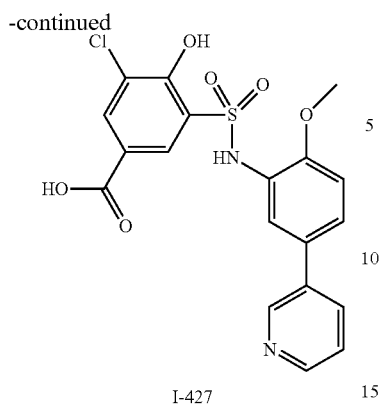

I-427

Synthesis of I-427

Into a 8-mL vial purged and maintained with an inert atmosphere of nitrogen, was placed 3-chloro-5-(chlorosulfonyl)-4-hydroxybenzoic acid (200 mg, 0.74 mmol, 1 equiv), 2-methoxy-5-(pyridin-3-yl)aniline (177.3 mg, 0.89 mmol, 1.2 equiv), pyridine (5 mL). The reaction solution was stirred for 5 h at room temperature. The resulting mixture was concentrated under vacuum. The crude product was purified by Prep-HPLC with the following conditions (2 #-AnalyseHPLC-SHIMADZU(HPLC-10)): Column: XBridge Prep OBD C18 Column 30×150 mm 5 um; Mobile Phase A: water (0.05% NH3.H$_2$O), Mobile Phase B: ACN; Flow rate: 60 mL/min; Gradient: 5% B to 5% B in 7 min; Detector UV 254/220 nm; Rt: 8.88 min. This resulted in 82 mg (25.6%) of I-427 as a white solid. (ES, m/z): [M+H]$^+$ 434.9, $^1$H-NMR (400 MHz, DMSO-d$_6$, ppm): δ3.78 (s, 3H), δ6.98-7.23 (m, 2H), δ7.33-7.35 (m, 1H), δ7.42-7.45 (m, 1H), δ7.62-7.63 (d, J=2.0 Hz, 1H), δ7.71 (s, 1H), δ7.84-7.87 (m, 1H), δ7.98-7.99 (d, J=2.4 Hz, 1H), δ8.51-8.53 (m, 1H), δ8.70 (s, 1H), δ11.95 (br s, 1H).

Example 134. Synthesis of Methyl 3-chloro-4-methoxy-5-(N-(4-methoxy-[1,1'-biphenyl]-3-yl)sulfamoyl)benzoate, I-428

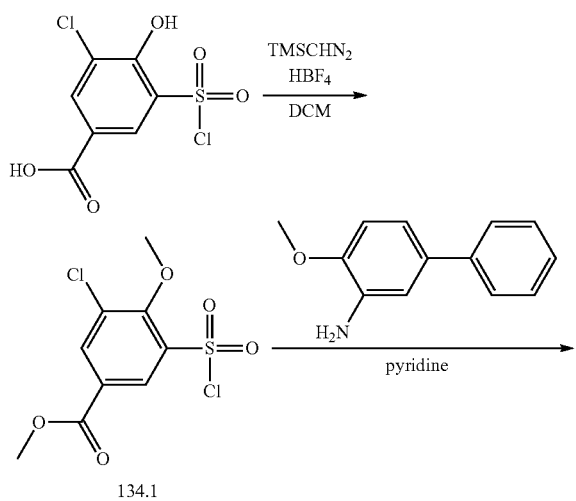

432

-continued

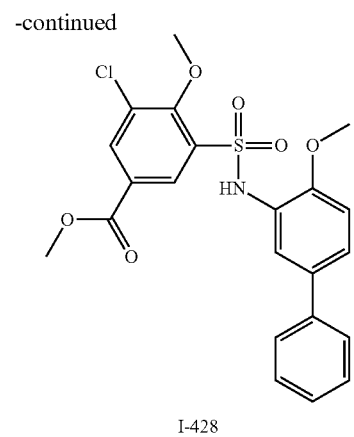

I-428

Synthesis of Compound 134.1

Into a 50-mL 3-necked round-bottom flask was placed 3-chloro-5-(chlorosulfonyl)-4-hydroxybenzoic acid (200 mg, 0.74 mmol, 1 equiv), DCM (5 mL), HBF4 (244 mg, 1.11 mmol, 1.5 equiv), TMSCHN$_2$ (1.48 mL, 2 M, 4 equiv). The resulting solution was stirred for 2 h at 0° C. The reaction was then quenched by the addition of water (5 mL). The resulting solution was extracted with dichloromethane (3×5 mL) and the combined organic layers were concentrated under vacuum. This resulted in 170 mg (77.0%) of 134.1 as a light yellow solid.

Synthesis of I-428

Into a 25-mL round-bottom flask, was placed methyl 134.1 (170 mg, 0.57 mmol, 1 equiv), 2-methoxy-5-phenylaniline (135.9 mg, 0.68 mmol, 1.2 equiv), pyridine (3 mL). The resulting solution was stirred for 4 h at room temperature. The resulting mixture was washed with 1 M HCl (aq.). The resulting solution was extracted with ethyl acetate (3×5 mL) and the combined organic layers were concentrated under vacuum. The crude product was purified by Flash-Prep-HPLC with the following conditions (Intel-Flash-1): Column, C 18; mobile phase, ACN/H$_2$O (0.10% NH$_4$HCO$_3$)=0 increasing to ACN/H$_2$O (0.10% NH$_4$HCO$_3$)= 1/1 within 25 min; Detector, UV 254 nm. This resulted in 13.4 mg (5.1%) of I-428 as a white solid. (ES, m/z): [M−H]$^−$ 460.0, $^1$H-NMR (400 MHz, DMSO-d$_6$, ppm): δ9.77 (s, 1H), δ8.24-8.23 (d, J=2.4 Hz, 1H), δ8.16-8.15 (d, J=2.4 Hz, 1H), δ7.55-7.52 (m, 2H), δ7.49-7.42 (m, 4H), δ7.35-7.31 (m, 1H), δ7.03-7.00 (m, 1H), δ4.01 (s, 3H), δ3.85 (s, 3H), δ3.53 (s, 3H).

Example 135. Synthesis of 5-chloro-2-methoxy-3-(N-(4-methoxy-[1,1'-biphenyl]-3-yl)sulfamoyl)benzoic Acid, I-430

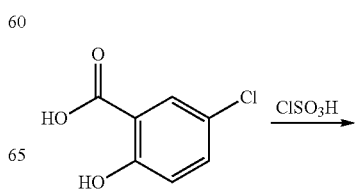

433

-continued

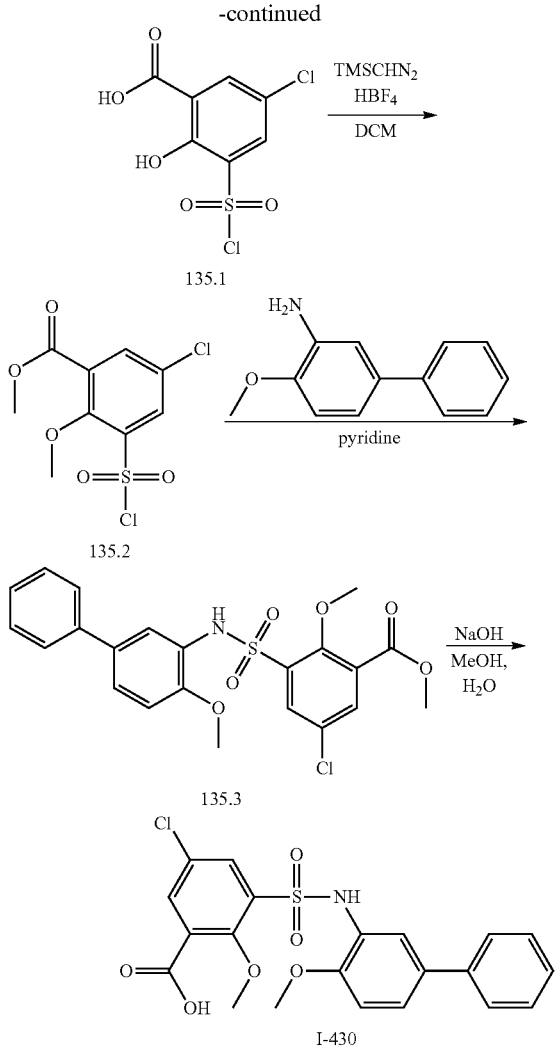

Synthesis of Compound 135.1

Into a 50-mL round-bottom flask, was placed 5-chloro-2-hydroxybenzoic acid (2 g, 11.59 mmol, 1 equiv), chloranesulfonic acid (16.2 g, 139.08 mmol, 12 equiv). The resulting solution was stirred for 4 h at 80° C. The reaction was then quenched by the addition of water/ice (20 mL). The resulting solution was extracted with ethyl acetate (2×10 mL). The organic layers were combined and concentrated under vacuum. This resulted in 2.3 g (73.2%) of 135.1 as a light yellow solid. (ES, m/z): [M–H]⁻ 268.9.

Synthesis of Compound 135.2

Into a 50-mL round-bottom flask, was placed 135.1 (1 g, 3.69 mmol, 1 equiv), DCM (10 mL), HBF₄ (1.22 g, 5.56 mmol, 4 equiv), TMSCHN₂ (7.4 mL, 14.8 mmol, 1.5 equiv). The resulting solution was stirred for 2 h at 0° C. The reaction was then quenched by the addition of water (10 mL). The resulting solution was extracted with ethyl acetate (3×10 mL). The organic layers were combined and concentrated under vacuum. This resulted in 1.08 g (97.9%) of 135.2 as a light yellow solid. (ES, m/z): [M–H]⁻ 296.9.

434

Synthesis of Compound 135.3

Into a 50-mL round-bottom flask was placed methyl 135.2 (1.08 g, 3.61 mmol, 1 equiv), 2-methoxy-5-phenylaniline (863.3 mg, 4.33 mmol, 1.2 equiv), pyridine (10 mL). The resulting solution was stirred for 6 h at 0° C. The resulting mixture was washed with 1 M HCl (aq.). The resulting solution was extracted with of ethyl acetate (3×10 mL) and the combined organic layers were concentrated under vacuum. The residue was applied onto TLC with dichloromethane/methanol (20:1). This resulted in 470 mg (28.2%) of 135.3 as a yellow solid.

Synthesis of I-430

Into a 50-mL round-bottom flask was placed 135.3 (100 mg, 0.22 mmol, 1 equiv), MeOH (2 mL), H₂O (0.2 mL), NaOH (34.6 mg, 0.87 mmol, 4 equiv). The resulting solution was stirred for 4 h at room temperature. The pH value of the solution was adjusted to 7 with CH₃COOH. The resulting mixture was concentrated under vacuum. The crude product was purified by Flash-Prep-HPLC with the following conditions (IntelFlash-1): Column, C 18; mobile phase, ACN/H₂O (0.1% NH₄HCO₃)=0 increasing to ACN/H₂O (0.10% NH₄HCO₃)=1/1 within 25 min; Detector, UV 254 nm. This resulted in 68.6 mg (70.8%) of I-430 as a white solid. (ES, m/z): [M–H]⁻ 446.2, ¹H-NMR (300 MHz, DMSO-d₆, ppm): δ9.29 (br s, 1H), δ7.74-7.73 (s, 1H), δ7.68 (s, 1H), δ7.53-7.50 (m, 2H), δ7.47-7.41 (m, 4H), δ7.34-7.30 (m, 1H), δ7.04-7.01 (d, J=8.4 Hz, 1H), δ3.92 (s, 3H), δ3.62 (s, 3H).

Example 136. Synthesis of Methyl 5-chloro-2-hydroxy-3-(N-(4-methoxy-[1,1'-biphenyl]-3-yl)sulfamoyl)benzoate, I-431

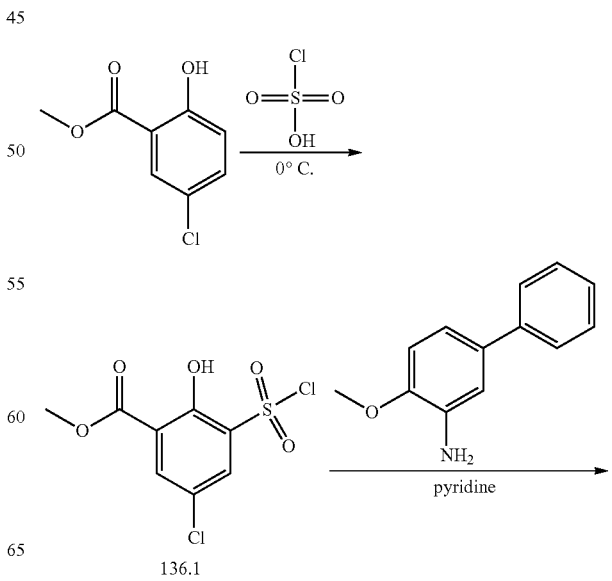

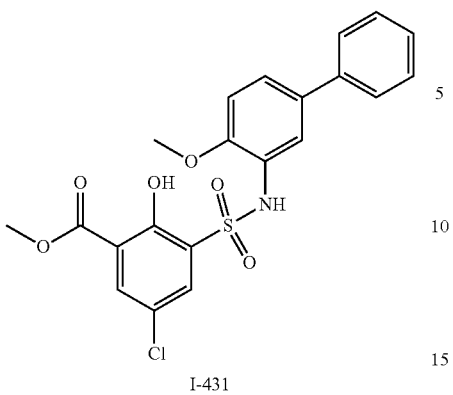

I-431

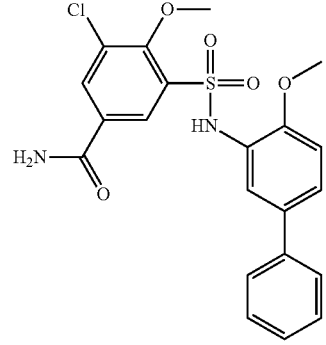

I-432

Synthesis of Compound 136.1

Into a 25-mL round-bottom flask purged and maintained with an inert atmosphere of nitrogen, was placed methyl 5-chloro-2-hydroxybenzoate (1 g, 5.36 mmol, 1 equiv), chloranesulfonic acid (3.75 mg, 32.16 mmol, 6 equiv). The resulting solution was stirred for 12 h at room temperature. The reaction was then quenched by the addition of 20 mL of water/ice. The resulting solution was extracted with 3×20 mL of dichloromethane. The combined organic layers were with 20 mL of brine, dried and concentrated under vacuum. This resulted in 550 mg (36%) of 136.1 as a yellow solid.

Synthesis of I-431

Into a 100-mL round-bottom flask purged and maintained with an inert atmosphere of nitrogen, was placed 136.1 (500 mg, 1.75 mmol, 1 equiv), 2-methoxy-5-phenylaniline (419.3 mg, 2.10 mmol, 1.2 equiv), pyridine (10 mL). The resulting solution was stirred for 0.5 h at room temperature. The resulting mixture was concentrated. The residue was applied onto a silica gel column with ethyl acetate/petroleum ether (1:2). This resulted in 24.8 mg (3%) of I-431 as a white solid (ES, m/z): [M+H]⁺ 448.2, ¹H-NMR (400 MHz, DMSO-d₆, ppm): δ7.97-7.96 (d, J=2.8 Hz, 1H), δ7.83-7.82 (d, J=2.8 Hz, 1H), δ7.53-7.42 (m, 6H), δ7.35-7.31 (m, 1H), δ7.05-7.03 (d, J=8.4 Hz, 1H), δ3.93 (s, 3H), δ3.61 (s, 3H).

Example 137. Synthesis of 3-chloro-4-methoxy-5-(N-(4-methoxy-[1,1'-biphenyl]-3-yl)sulfamoyl)benzamide, I-432

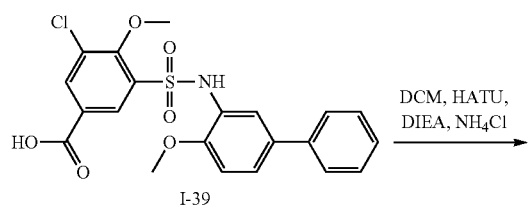

I-39

Synthesis of I-432

Into a 25-mL round-bottom flask was placed I-39 (60 mg, 0.13 mmol, 1 equiv), DCM (3 mL), HATU (101.9 mg, 0.27 mmol, 2 equiv), NH₄Cl (71.7 mg, 1.34 mmol, 10 equiv), DIEA (51.9 mg, 0.40 mmol, 3 equiv). The resulting solution was stirred for 12 h at room temperature. The resulting mixture was concentrated under vacuum. The crude product was purified by Flash-Prep-HPLC with the following conditions (IntelFlash-1): Column, C 18; mobile phase, ACN/H₂O (0.1% NH₄HCO₃)=0 increasing to ACN/H₂O (0.1% NH₄HCO₃)=1/1 within 25 min; Detector, UV 254 nm. This resulted in 11.0 mg (18.4%) of I-432 as a white solid (ES, m/z): [M−H]⁻ 445.2, ¹H-NMR (300 MHz, DMSO-d₆, ppm): δ9.60 (s, 1H), δ8.28-8.27 (d, J=2.1 Hz, 1H), δ8.21-8.19 (m, 2H), δ7.62 (s, 1H), δ7.52-7.50 (d, J=7.2 Hz, 2H), δ7.45-7.40 (m, 4H), δ7.35-7.30 (m, 1H), δ7.03-7.00 (d, J=9.0 Hz, 1H), δ3.98 (s, 3H), δ3.54 (s, 3H).

Example 138. Synthesis of 5-(azetidine-1-carbonyl)-3-bromo-N-(4-fluoro-[1,1'-biphenyl]-3-yl)-2-methoxybenzenesulfonamide, I-154

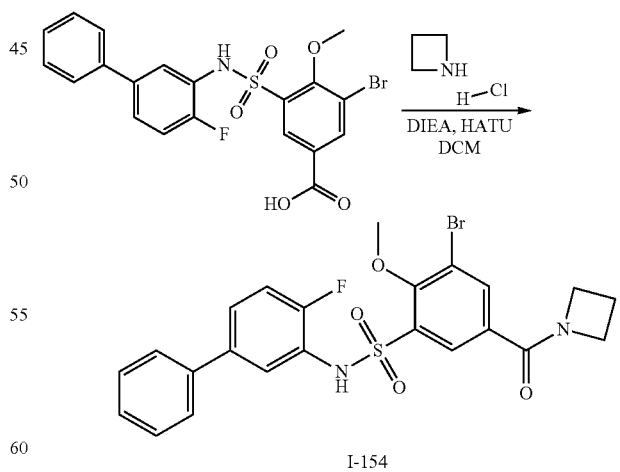

I-154

Synthesis of I-154

To a stirred solution of 3-bromo-5-([4-fluoro-[1,1-biphenyl]-3-yl]sulfamoyl)-4-methoxybenzoic acid (130 mg, 0.27 mmol, 1 equiv) in DCM (10 mL) were added azetidine hydrochloride (50.6 mg, 0.54 mmol, 2 equiv) and DIEA (139.9 mg, 1.08 mmol, 4 equiv) and HATU (154.4 mg, 0.41 mmol, 1.5 equiv) at room temperature under nitrogen atmosphere. The resulting mixture was stirred for 12 h at room temperature. The resulting mixture was diluted with water (10 mL). The resulting mixture was extracted with EtOAc (3×10 mL). The combined organic layers were concentrated under reduced pressure. The residue was purified by Prep-TLC (hexane/EtOAc=1:1) to afford I-154 (24.7 mg, 17.6%) as a white solid. (ES, m/z): [M+H]⁺ 519.1, ¹H-NMR (300 MHz, DMSO-d₆, ppm): δ2.11-2.22 (m, 2H), δ3.97-4.12 (m, 7H), δ7.25-7.31 (m, 1H), δ7.35-7.52 (m, 7H), δ7.87 (s, 1H), δ8.09 (s, 1H), δ10.44 (s, 1H).

Example 139. Synthesis of 3-chloro-4-methoxy-5-(N-(2-methoxy-5-(pyridin-3-yl)phenyl)sulfamoyl) benzoic Acid, I-425

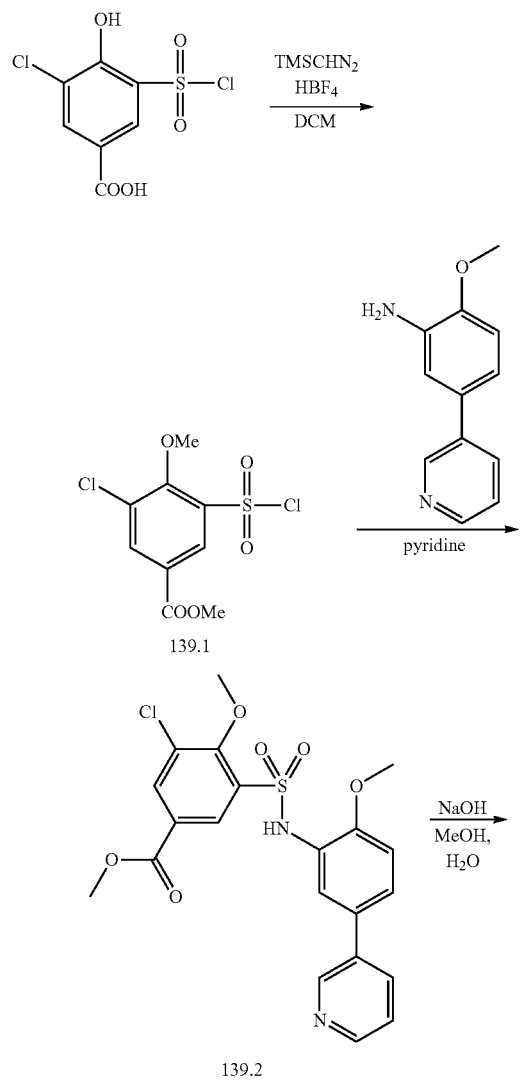

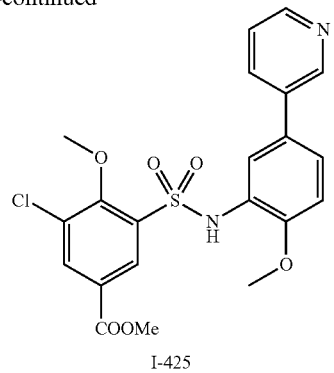

I-425

Synthesis of Compound 139.1

Into a 50-mL 3-necked round-bottom flask purged and maintained with an inert atmosphere of nitrogen, was placed 3-chloro-5-(chlorosulfonyl)-4-hydroxybenzoic acid (800 mg, 2.95 mmol, 1 equiv), DCM (3 mL), HBF4 (1036.6 mg, 11.80 mmol, 4 equiv), TMSCHN₂ (505.6 mg, 4.43 mmol, 1.5 equiv). The resulting solution was stirred for 2 h at 0° C. The reaction was then quenched by the addition of water (10 mL). The resulting solution was extracted with dichloromethane (3×10 mL) and the combined organic layers were concentrated under vacuum. This resulted in 660 mg (74.8%) of 139.1 as a white solid. (ES, m/z): [M−H]⁻ 296.9.

Synthesis of Compound 341.2

Into a 50-mL round-bottom flask was placed methyl 139.1 (660 mg, 2.21 mmol, 1 equiv), 2-methoxy-5-(pyridin-3-yl) aniline (530.2 mg, 2.65 mmol, 1.200 equiv), pyridine (10 mL). The resulting solution was stirred for 4 h at room temperature. The resulting mixture was concentrated. The resulting mixture was washed with 1M HCl (aq). The resulting solution was extracted with ethyl acetate (3×10 mL) and the combined organic layers were concentrated under vacuum. The residue was applied onto TLC with dichloromethane/methanol (10:1). This resulted in 470 mg (46.0%) of 341.2 as a yellow solid (ES, m/z): [M−H]⁻ 461.0.

Synthesis of I-425

Into a 50-mL round-bottom flask, was placed 341.2 (100 mg, 0.22 mmol, 1 equiv), MeOH (2 mL), H₂O (0.2 mL), NaOH (34.6 mg, 0.86 mmol, 4 equiv). The resulting solution was stirred for 6 h at room temperature. The pH value of the solution was adjusted to 7 with CH₃COOH. The resulting mixture was concentrated. The crude product was purified by Flash-Prep-HPLC with the following conditions (IntelFlash-1): Column, C 18; mobile phase, ACN/H₂O (0.1% NH₄HCO₃)=0 increasing to ACN/H₂O (0.1% NH₄HCO₃)= 4/6 within 25 mins; Detector, UV 254 nm. This resulted in 35.2 mg (36.3%) of I-425 as a white solid. (ES, m/z): [M+H]⁺ 449.2, ¹H-NMR (400 MHz, DMSO-d₆, ppm): δ13.60 (s, 1H), δ9.70 (s, 1H), δ8.77-8.76 (d, J=2.0 Hz, 1H), δ8.54-8.53 (m, 1H), δ8.20-8.19 (d, J=2.0 Hz, 1H), δ8.15-8.14 (d, J=2.0 Hz, 1H), δ7.97-7.94 (m, 1H), δ7.57-7.53 (m, 2H), δ7.47-7.44 (m, 1H), δ7.07-7.05 (d, J=8.4 Hz, 1H), δ3.99 (s, 3H), δ3.53 (s, 3H).

Example 140. Synthesis of 3-chloro-N-(4,6-difluoro-[1,1'-biphenyl]-3-yl)-2-hydroxy-5-methylbenzenesulfonamide, I-157

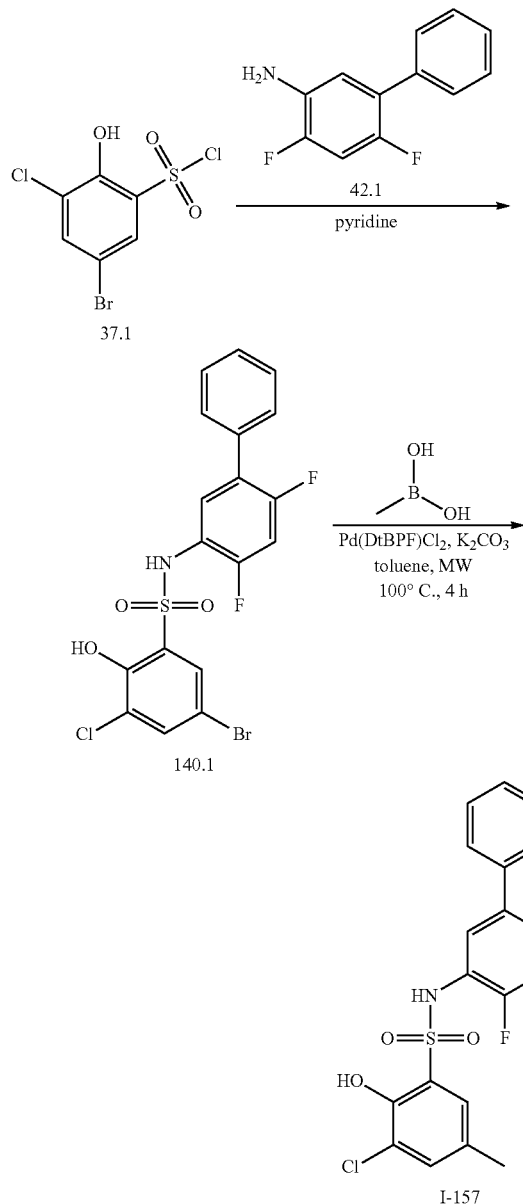

Synthesis of 140.1

Into a 50-mL round-bottom flask, was placed 37.1 (300 mg, 0.98 mmol, 1 equiv), 42.1 (241.5 mg, 1.18 mmol, 1.2 equiv), pyridine (5 mL). The resulting solution was stirred for 12 hr at 25° C. The reaction was then quenched by the addition of 15 mL of diluted hydrochloric acid. The resulting solution was extracted with 3×20 ml of ethyl acetate and the organic layers combined and concentrated under vacuum. The residue was applied onto Prep-TLC with dichloromethane/methanol (20:1). This resulted in 200 mg (42.9%) of 140.1 as a brown solid. (ES, m/z): [M−H]⁻ 471.9.

Synthesis of I-157

Into a 10-mL sealed tube, was placed 140.1 (173 mg, 0.36 mmol, 1 equiv), toluene (2 mL), methylboronic acid (130.9 mg, 2.19 mmol, 6 equiv), $K_2CO_3$ (151.1 mg, 1.09 mmol, 3 equiv), Pd(DtBPF)Cl₂ (23.8 mg, 0.04 mmol, 0.1 equiv). The final reaction mixture was irradiated with microwave radiation for 4 h at 100° C. The reaction was then quenched by the addition of 5 mL of water. The resulting solution was extracted with 3×15 mL of ethyl acetate and the organic layers combined and concentrated under vacuum. The residue was applied onto Prep-TLC with dichloromethane/methanol (20:1). This resulted in 9.8 mg (6.6%) of I-157 as a grey solid. (ES, m/z): [M−H]⁻ 408.0, ¹H-NMR (300 MHz, DMSO-d₆, ppm): δ2.21 (s, 3H), δ7.27-7.50 (m, 9H).

Example 141. Synthesis of 2-fluoro-N-(2-fluoro-5-phenylphenyl)-5-(2H-1,2,3,4-tetrazol-5-yl)benzene-1-sulfonamide, I-424

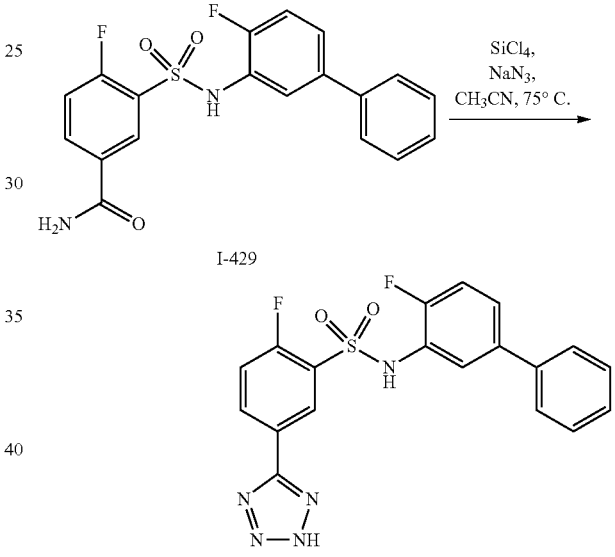

Synthesis of I-424

Into a 8-mL vial purged and maintained with an inert atmosphere of nitrogen, was placed SiCl₄ (175.0 mg, 1.03 mmol, 2 equiv), NaN₃ (67.0 mg, 1.03 mmol, 2 equiv), CH₃CN (3 mL)

The above mixture was stirred for 1 hour at 75° C. Then, I-429 (200 mg, 0.51 mmol, 1 equiv) was added, followed by stirring at 75° C. for 12 h. The reaction was quenched by the addition of 5 mL of water. The solids were filtered out. The crude product was purified by Prep-HPLC with the following conditions (2 #-AnalyseHPLC-SHIMADZU (HPLC-10)): Column, XBridge Prep OBD C18 Column, 30*150 mm 5 um; mobile phase, water (0.05% NH3H₂O) and ACN (3% PhaseB up to 27% in 7 min); Detector, UV 254/220 nm. This resulted in 101.2 mg (47.5%) of I-424 as a white solid. (ES, m/z): [M−H]⁻ 412.0, ¹H-NMR (400 MHz, CD₃OD, ppm): δ7.10-7.15 (m, 1H), δ7.33-7.41 (m, 4H), δ7.47-7.52 (m, 3H), δ7.66-7.68 (m, 1H), δ8.33-8.35 (m, 1H), δ8.55-8.58 (m, 1H).

Example 142. Synthesis of 3-chloro-N-[4,5-difluoro-[1,1-biphenyl]-3-yl]-2-hydroxy-5-(pyrrolidine-1-carbonyl)benzene-1-sulfonamide, I-159

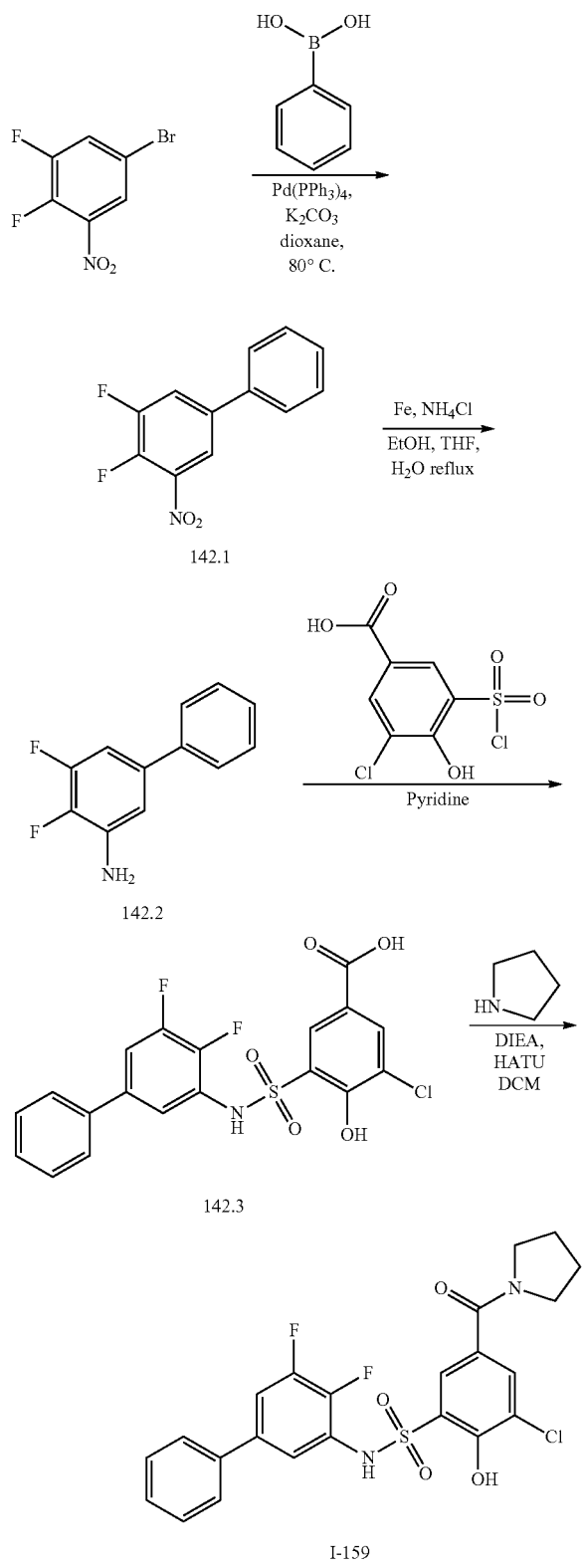

Synthesis of Compound 142.1

Into a 250-mL 3-necked round-bottom flask purged and maintained with an inert atmosphere of nitrogen, was placed 5-bromo-1,2-difluoro-3-nitrobenzene (10 g, 42.02 mmol, 1 equiv), dioxane (100 mL, 1.14 mmol, 0.03 equiv), phenylboronic acid (6148.0 mg, 50.42 mmol, 1.20 equiv), $K_2CO_3$ (29036.2 mg, 210.09 mmol, 5.00 equiv), $Pd(PPh_3)_4$ (4855.5 mg, 4.20 mmol, 0.10 equiv). The resulting solution was stirred for 1 overnight at 800° C. in an oil bath. The resulting mixture was concentrated under vacuum. The resulting solution was diluted with 100 mL of $H_2O$. The resulting solution was extracted with 2×100 ml of ethyl acetate. The resulting mixture was concentrated under vacuum. The residue was applied onto a silica gel column with ethyl acetate/petroleum ether (1:1). This resulted in 7.47 g (75.6%) of 142.1 as a yellow solid. (ES, m/z): [M−H]⁻ 234.0.

Synthesis of Compound 142.2

Into a 500-mL 3-necked round-bottom flask purged and maintained with an inert atmosphere of nitrogen, was placed 142.1 (7.4 g, 31.46 mmol, 1 equiv), $NH_4Cl$ (16830.4 mg, 314.64 mmol, 10 equiv), EtOH (140 mL, 2409.89 mmol, 76.59 equiv), THF (70 mL, 0.97 mmol, 0.03 equiv), $H_2O$ (35 mL, 1.94 mmol, 0.06 equiv), and Fe (7028.4 mg, 125.86 mmol, 4 equiv). The resulting solution was stirred overnight at 90° C. in an oil bath. The resulting mixture was concentrated under vacuum. The resulting solution was diluted with 200 mL of $H_2O$. The resulting solution was extracted with 3×100 ml of ethyl acetate. The resulting mixture was concentrated under vacuum. The residue was applied onto a silica gel column with ethyl acetate/petroleum ether (1:1). This resulted in 6.2 g (96.0%) of 142.2 as a yellow solid. (ES, m/z): [M−H]⁻ 204.0.

Synthesis of Compound 142.3

Into a 100-mL 3-necked round-bottom flask, was placed 142.2 (2.7 g, 1.2 equiv), 3-chloro-5-(chlorosulfonyl)-4-hydroxybenzoic acid (3 g, 1 equiv), pyridine (30 mL). The resulting solution was stirred for 1 overnight at room temperature. The resulting mixture was concentrated under vacuum. The residue was applied onto a silica gel column with dichloromethane/methanol (20:1). This resulted in 1.8 g (36.9%) of 142.3 as a yellow solid. (ES, m/z): [M−H]⁻ 438.0.

Synthesis of I-159

Into a 8-mL vial purged and maintained with an inert atmosphere of nitrogen, was placed 142.3 (100 mg, 0.23 mmol, 1 equiv), DCM (1 mL, 0.01 mmol, 0.05 equiv), DIEA (88.2 mg, 0.68 mmol, 3 equiv), pyrrolidine (48.5 mg, 0.68 mmol, 3 equiv), and HATU (172.9 mg, 0.45 mmol, 2 equiv). The resulting solution was stirred overnight at room temperature. The resulting solution was diluted with 10 mL of $H_2O$. The resulting solution was extracted with 3×20 ml of ethyl acetate concentrated under vacuum. The crude product was purified by Flash-Prep-HPLC with the following conditions (IntelFlash-1): Column, C18 silica gel; mobile phase, ACN/$H_2O$=15% increasing to ACN/$H_2O$=60% within 15 min; Detector, UV: 254. This resulted in 56.4 mg (50.3%) of I-159 as a white solid. (ES, m/z): [M−H]⁻ 491.0, ¹H-NMR (400 MHz, DMSO-$d_6$, ppm): 1.76 (s, 4H), δ3.39 (s, 4H), δ6.91-7.13 (m, 2H), δ7.19-7.28 (m, 1H), δ7.33-7.39 (m, 2H), δ7.40-7.46 (m, 2H), δ7.46-7.51 (m, 2H), δ7.61-7.62 (d, J=2.4 Hz, 1H), δ7.67-7.68 (d, J=2.4 Hz, 1H).

Example 143. Synthesis of 5-(azetidine-1-carbonyl)-3-chloro-N-[4,5-difluoro-[1,1-biphenyl]-3-yl]-2-hydroxybenzene-1-sulfonamide, I-160

Example 144. Synthesis of benzyl 2-(2-(N-benzyl-N-(4-fluoro-[1,1'-biphenyl]-3-yl) sulfamoyl)-6-bromo-4-chlorophenoxy)acetate, I-420

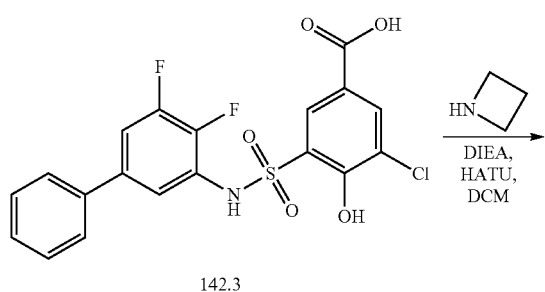

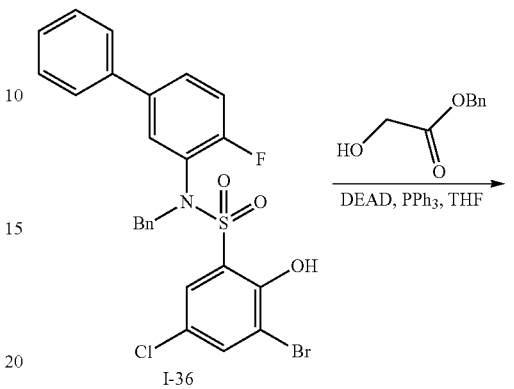

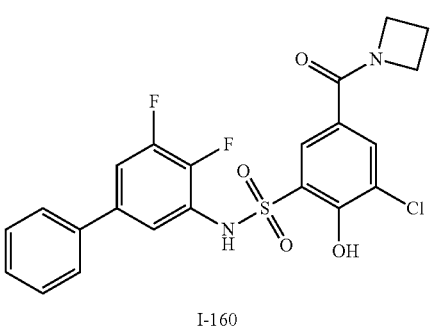

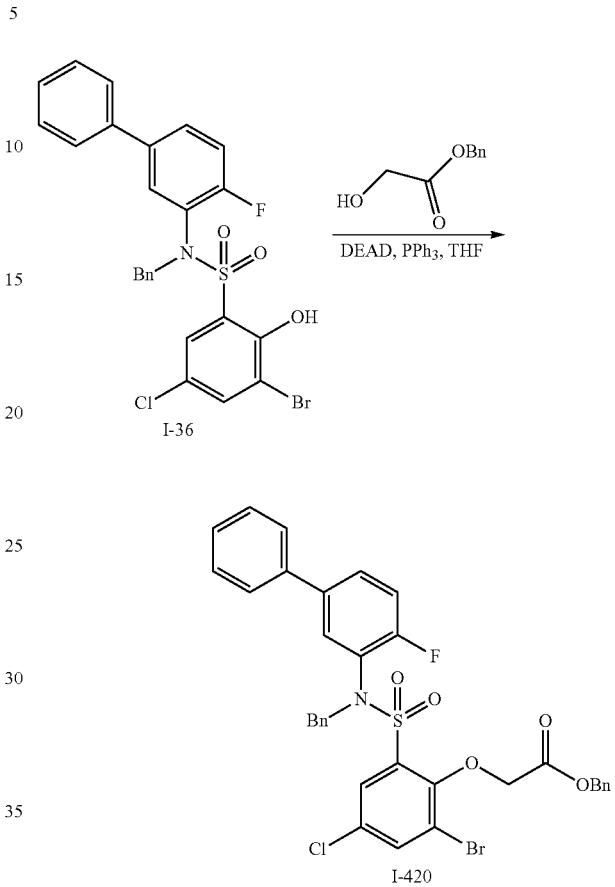

Synthesis of I-160

Synthesis of I-420

Into a 8-mL vial purged and maintained with an inert atmosphere of nitrogen, was placed 142.3 (100 mg, 0.23 mmol, 1 equiv), DCM (1 mL, 0.01 mmol, 0.05 equiv), DIEA (88.2 mg, 0.68 mmol, 3 equiv), azetidine (38.9 mg, 0.68 mmol, 3 equiv), and HATU (172.9 mg, 0.45 mmol, 2 equiv). The resulting solution was stirred overnight at room temperature. The resulting solution was diluted with 10 mL of H$_2$O. The resulting solution was extracted with 3×20 ml of ethyl acetate concentrated under vacuum. The crude product was purified by Flash-Prep-HPLC with the following conditions (IntelFlash-1): Column, C18 silica gel; mobile phase, ACN/H$_2$O=15% increasing to ACN/H$_2$O=60% within 15 min; Detector, UV: 254. This resulted in 30.6 mg (28.1%) of I-160 as a white solid. (ES, m/z): [M–H]$^-$ 477.0, $^1$H-NMR (400 MHz, DMSO-d$_6$, ppm): δ2.05-2.25 (m, 2H), δ3.89-4.25 (s, 4H), δ6.95-7.26 (m, 1H), δ7.26-7.59 (m, 7H), δ7.56-7.70 (m, 2H).

Into a 100-mL round-bottom flask purged and maintained with an inert atmosphere of nitrogen, was placed I-36 (400 mg, 0.73 mmol, 1.00 equiv), DEAD (260 mg, 1.49 mmol, 2.00 equiv), PPh$_3$ (380 mg, 1.45 mmol, 2.00 equiv), tetrahydrofuran (10 mL), and benzyl 2-hydroxyacetate (180 mg, 1.08 mmol, 1.50 equiv). The resulting mixture was diluted with 10 mL of water. The resulting solution was stirred for 12 h at room temperature. The resulting solution was extracted with 3×10 mL of ethyl acetate. The organic layers were combined, washed with 10 mL of brine, dried and concentrated under vacuum. The residue was applied onto a silica gel column with ethyl acetate/petroleum ether (1:5). This resulted in 230 mg (44%) of I-420 as a white solid. (ES, m/z): [M+H+H$_2$O]$^+$713.2, $^1$H-NMR (400 MHz, DMSO-d$_6$, ppm): δ8.31 (s, 1H), δ7.60-7.57 (m, 1H), δ7.51 (s, 1H), δ7.45-7.31 (m, 10H), δ7.30-7.21 (m, 7H), δ5.19 (s, 2H), δ5.04 (s, 2H), δ4.86 (s, 2H).

Example 145. Synthesis of 3-chloro-5-cyano-N-(2-methoxy-5-phenylphenyl)benzene-1-sulfonamide, I-422

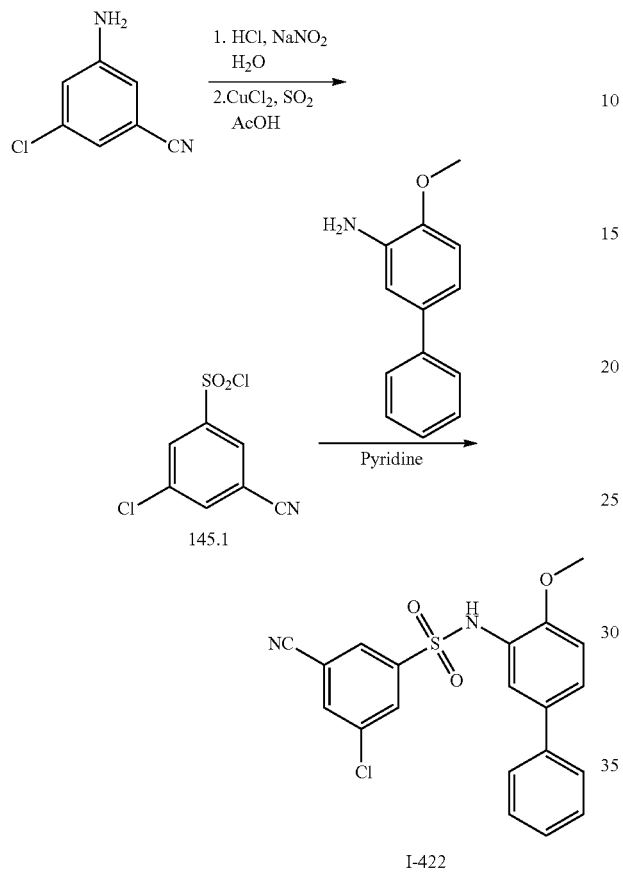

Synthesis of Compound 145.1

A solution of NaNO$_2$ (940 mg, 13.65 mmol, 1 equiv) in water (3 mL) was added to a suspension of 3-amino-5-chlorobenzonitrile (2.0 g, 13.16 mmol, 1 equiv) in 6 M HCl (12.5 mL) and water (12.5 mL) at 0° C. over 5 mins. After the completion of addition, the resulting solution was stirred for a further 30 mins. Meanwhile, AcOH (15.5 mL) was saturated with SO$_2$, then CuCl$_2$ (130 mg, 1.10 mmol, 0.08 equiv) was added and SO$_2$ bubbled through for a further 5 mins. The AcOH mixture was cooled to 5° C., then the above diazonium solution was added over 5 mins. The resulting mixture was stirred for a further 1 h at 0° C. then 1 h at room temperature. The solution was diluted with water (20 mL) and extracted with CH$_2$Cl$_2$ (3×20 mL). The combined organic extracts were washed twice with water, dried (Na$_2$SO$_4$) and concentrated under vacuum. This gave the title compound of 145.1 (3.0 g, 97%) as a white solid. (ES, m/z): [M–H]$^-$ 233.9.

Synthesis of I-422

Into a 50-mL 3-necked round-bottom flask, was placed 2-methoxy-5-phenylaniline (2.18 g, 10.94 mmol, 1 equiv), pyridine (10 mL), 145.1 (3.1 g, 13.13 mmol, 1.2 equiv). The resulting solution was stirred overnight at 25° C. The pH value of the solution was adjusted to 7-8 with 1M HCl (aq.). The resulting solution was extracted with ethyl acetate (3×20 mL). The combined organic layers were washed with H$_2$O and concentrated under vacuum. The residue was applied onto a silica gel column with ethyl acetate/petroleum ether (1:10) and purified by crystallization with ethyl acetate/petroleum ether (1:30). This resulted in 3.1 g (71.0%) of I-422 as a grey solid. (ES, m/z): [M–H]$^-$ 396.9, $^1$H-NMR (400 MHz, DMSO-d$_6$, ppm): δ10.17 (s, 1H), δ8.38-8.37 (d, J=1.6 Hz, 1H), δ8.11-8.10 (d, J=1.6 Hz, 1H), δ8.06-8.05 (d, J=1.6 Hz, 1H), δ7.59-7.43 (m, 6H), δ7.36-7.32 (m, 1H), δ7.06-7.04 (d, J=8.4 Hz, 1H), δ3.53 (s, 3H).

Example 146. Synthesis of 3-[(3,5-dichloro-2-hydroxybenzene)sulfonamido]-4-fluoro-N-methanesulfonylbenzamide, I-423

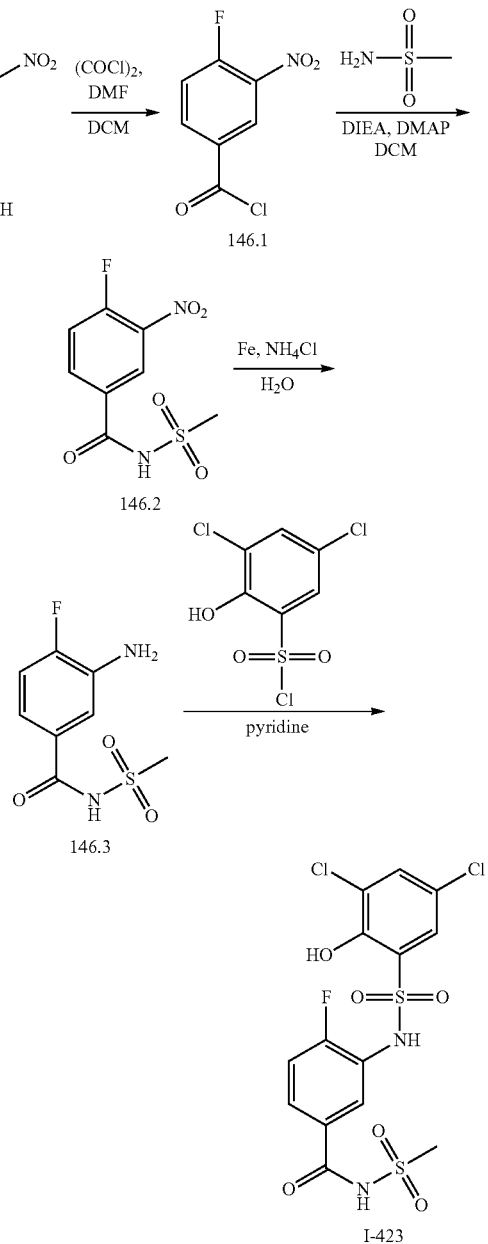

Synthesis of Compound 146.1

To a stirred solution of 4-fluoro-3-nitrobenzoic acid (5 g, 27.01 mmol, 1 equiv) in DCM (50 mL) were added (COCl)$_2$ (4.1 g, 32.41 mmol, 1.2 equiv) and DMF (20 mL) at room temperature under nitrogen atmosphere. The resulting mixture was stirred for 1 h at room temperature under nitrogen atmosphere. The resulting mixture was concentrated under reduced pressure. This resulted in 146.1 (6 g, crude) as a yellow oil. (ES, m/z): [M+H]$^+$203.9.

Synthesis of Compound 146.2

To a stirred solution of methanesulfonamide (1.3 g, 13.67 mmol, 1 equiv) and 146.1 (3.1 g, 15.03 mmol, 1.1 equiv) in DCM (30 mL) was added DIEA (7.1 g, 54.67 mmol, 4 equiv) and DMAP (0.2 g, 1.64 mmol, 0.120 equiv) at room temperature under nitrogen atmosphere. The resulting mixture was stirred for 2 h at room temperature. The resulting mixture was concentrated under reduced pressure. The residue was purified by silica gel column chromatography eluted with CH$_2$Cl$_2$/MeOH (100:1) to afford 146.2 (3.4 g, 94.9%) as a yellow solid. (ES, m/z): [M–H]$^-$ 261.0.

Synthesis of Compound 146.3

To a stirred solution of 146.2 (1.5 g, 5.72 mmol, 1 equiv) in H$_2$O (15 mL) was added Fe (1.0 g, 17.16 mmol, 3 equiv) and NH$_4$Cl (1.5 g, 28.60 mmol, 5 equiv). The resulting mixture was stirred for 1 h at 100° C. The reaction was quenched by the addition of water (10 mL) at room temperature. The resulting mixture was filtered, and the filter cake was washed with DCM (2×30 mL). The aqueous layer was extracted with DCM (2×50 mL). The resulting mixture was concentrated under reduced pressure. The residue was purified by silica gel column chromatography, eluted with CH$_2$Cl$_2$/MeOH (50:1) to afford 146.3 (800 mg, 60.2%) as a yellow oil. (ES, m/z): [M–H]$^-$ 231.0.

Synthesis of I-423

Into a 8-mL sealed tube, was placed 3,5-dichloro-2-hydroxybenzene-1-sulfonyl chloride (200 mg, 0.76 mmol, 1 equiv), 146.3 (213.1 mg, 0.92 mmol, 1.200 equiv), pyridine (4 mL). The resulting solution was stirred for 1 h at room temperature. The reaction was then quenched by the addition of 20 mL of water. The resulting solution was extracted with 2×20 mL of ethyl acetate and the combined organic layers were concentrated under vacuum. The crude product (200 mg) was purified by Prep-HPLC with the following conditions (2 #-AnalyseHPLC-SHIMADZU (HPLC-10)): Column, XBridge Prep OBD C18 Column, 30×150 mm×5 um; mobile phase, water (0.05% NH$_3$/H$_2$O) and ACN (5% Phase B up to 25% in 7 min); Detector, UV 254/220 nm. This resulted in 28.6 mg (8.2%) of I-423 as a white solid. (ES, m/z): [M+H]$^+$ 456.8, $^1$H-NMR (400 MHz, DMSO-d$_6$, ppm): δ3.11 (s, 3H), δ6.97-7.10 (br s, 1H), δ7.11-7.16 (m, 3H), δ7.38-7.39 (d, J=2.8 Hz, 1H), δ7.48-7.53 (m, 2H), δ7.88-7.90 (m, 1H).

Example 147. Synthesis of 4-fluoro-3-(N-(4-fluoro-[1,1'-biphenyl]-3-yl)sulfamoyl)benzamide, I-429

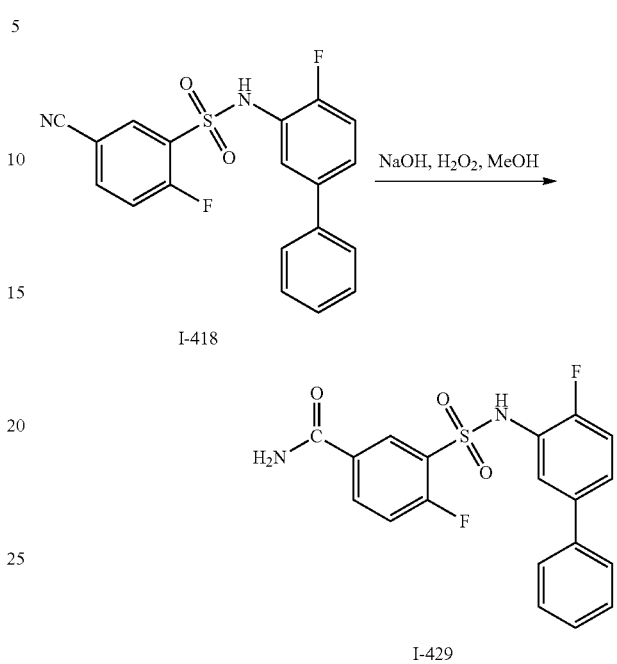

Synthesis of I-429

Into a 50-mL round-bottom flask, was placed I-418 (1.0 g, 2.70 mmol, 1 equiv), MeOH (15 mL), NaOH (647.9 mg, 16.20 mmol, 6 equiv), H$_2$O$_2$ (551.0 mg, 16.20 mmol, 6 equiv). The resulting solution was stirred overnight at 25° C. The resulting mixture was concentrated under vacuum. The crude product was purified by Flash-Prep-HPLC with the following conditions (IntelFlash-1): Column, C 18; mobile phase, MeCN/H$_2$O=10% increasing to MeCN/H$_2$O=70% within 16 min; Detector, UV 254 nm. This resulted in 400 mg (38.1%) of I-429 as an off-white solid. (ES, m/z): [M–H]$^-$ 387.0, $^1$H-NMR (300 MHz, DMSO-d$_6$, ppm): δ10.66 (s, 1H), δ8.32-8.29 (m, 1H), δ8.23-8.18 (m, 2H), δ7.61-7.38 (m, 9H), δ7.30-7.23 (m, 1H).

Example 148. Synthesis of 2-(4-(azetidine-1-carbonyl)-2-bromo-6-(N-(4-fluoro-[1,1'-biphenyl]-3-yl)sulfamoyl)phenoxy)acetic Acid, I-192

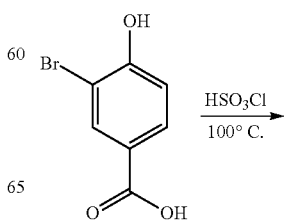

449
-continued

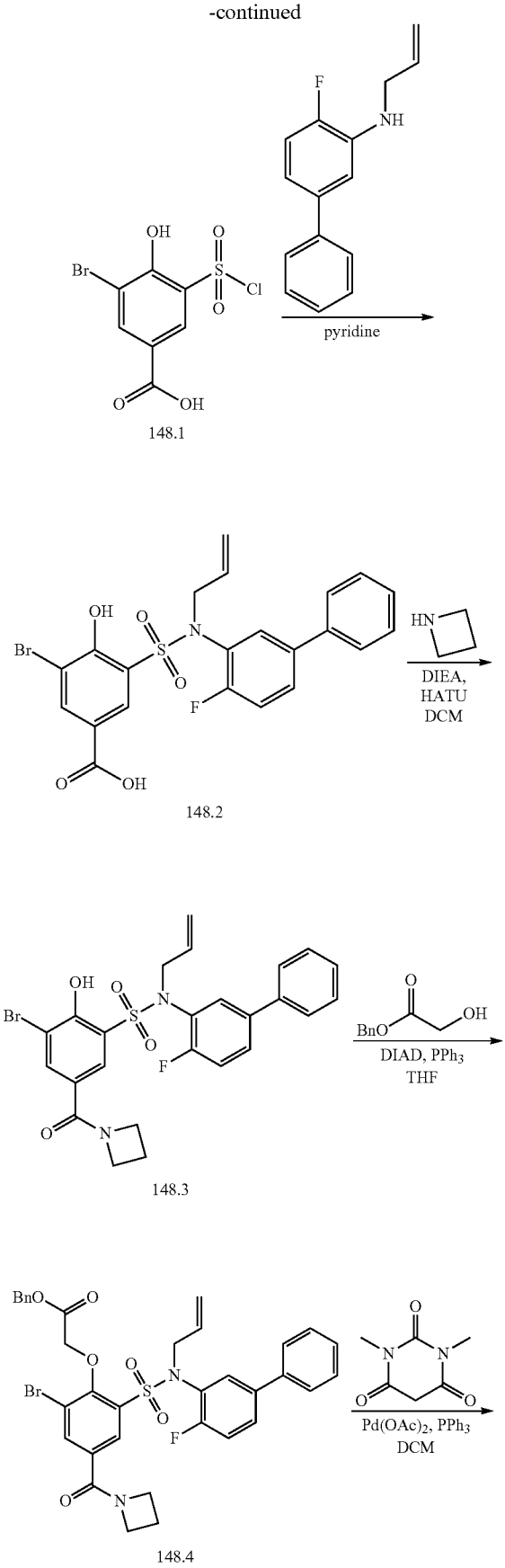

450
-continued

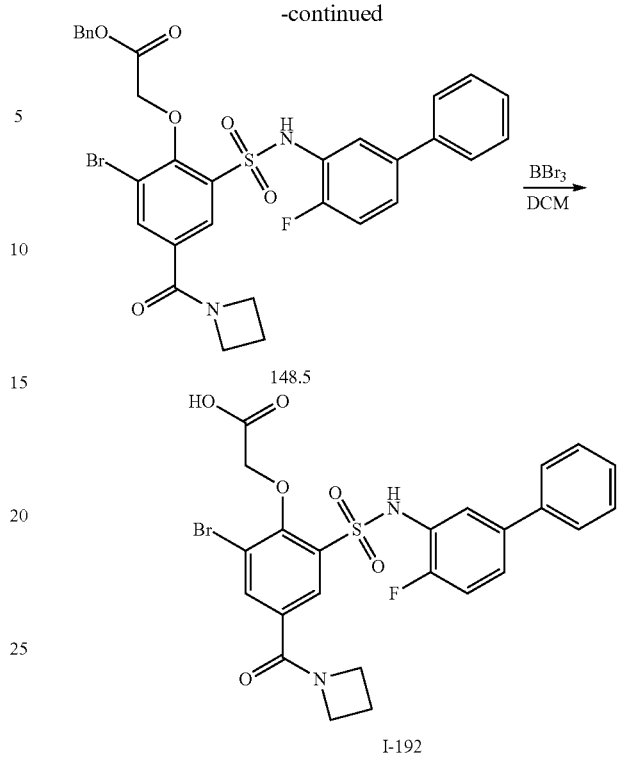

Synthesis of Compound 148.1

Into a 50-mL round-bottom flask purged and maintained with an inert atmosphere of nitrogen, was placed 3-bromo-4-hydroxybenzoic acid (10 g, 46.08 mmol, 1 equiv), HSO$_3$Cl (10 mL). The resulting solution was stirred for 12 hr at 100° C. in an oil bath. The reaction was then quenched by the addition of 20 g of water/ice. The resulting solution was extracted with 3×20 ml of ethyl acetate. The resulting mixture was washed with 20 mL of brine. The mixture was dried over anhydrous sodium sulfate and concentrated. The resulting mixture was concentrated. This resulted in 13 g (yield=89%) of 148.1 as a yellow solid. (ES, m/z): [M−H]⁻ 312.8.

Synthesis of Compound 148.2

Into a 100-mL round-bottom flask purged and maintained with an inert atmosphere of nitrogen, was placed 148.1 (3 g, 9.51 mmol, 1 equiv), 4-fluoro-N-(prop-2-en-1-yl)-[1,1-biphenyl]-3-amine (2.2 g, 0.01 mmol, 1 equiv), pyridine (20 mL). The resulting solution was stirred for 0.5 hr at room temperature. The resulting mixture was concentrated. The residue was applied onto a silica gel column with ethyl acetate/petroleum ether (1:1). This resulted in 400 mg (yield=8%) of 148.2 as a white solid. (ES, m/z): [M−H]⁻ 504.0.

Synthesis of Compound 148.3

Into a 50-mL round-bottom flask purged and maintained with an inert atmosphere of nitrogen, was placed 148.2 (500 mg, 0.99 mmol, 1 equiv), azetidine hydrochloride (184.8 mg, 1.97 mmol, 2 equiv), DIEA (382.9 mg, 2.96 mmol, 3 equiv), HATU (750.9 mg, 1.97 mmol, 2 equiv), DCM (10 mL). The resulting solution was stirred for 12 hr at room temperature. The reaction was then quenched by the addition of 20 mL of water. The resulting solution was extracted with 3×20 ml of ethyl acetate. The resulting mixture was washed with 20 mL of brine. The mixture was dried over anhydrous sodium sulfate and concentrated. The resulting mixture was concentrated. The residue was applied onto a silica gel column with ethyl acetate/petroleum ether (1:1). This resulted in 360 mg (yield=67%) of 148.3 as a white solid. (ES, m/z): [M−H]⁻ 543.1.

Synthesis of Compound 148.4

Into a 50-mL round-bottom flask purged and maintained with an inert atmosphere of nitrogen, was placed 148.3 (340 mg, 0.62 mmol, 1 equiv), tert-butyl 2-hydroxyacetate (98.9 mg, 0.75 mmol, 1.2 equiv), DIAD (252.1 mg, 1.25 mmol, 2 equiv), PPh₃ (327.0 mg, 1.25 mmol, 2 equiv), THF (5 mL). The resulting solution was stirred for 12 hr at room temperature. The reaction was then quenched by the addition of 10 mL of water. The resulting solution was extracted with 3×10 mL of ethyl acetate. The resulting mixture was washed with 10 mL of brine. The mixture was dried over anhydrous sodium sulfate and concentrated. The resulting mixture was concentrated. The residue was applied onto a silica gel column with ethyl acetate/petroleum ether (1:1). This resulted in 260 mg (yield=63%) of 148.4 as a white solid. (ES, m/z): [M−H]⁻ 691.1.

Synthesis of Compound 148.5

Into a 50-mL round-bottom flask purged and maintained with an inert atmosphere of nitrogen, was placed 148.4 (240 mg, 0.36 mmol, 1 equiv), 1,3-dimethyl-1,3-diazinane-2,4,6-trione (170.4 mg, 1.09 mmol, 3 equiv), Pd(PPh₃)₄ (126.1 mg, 0.11 mmol, 0.3 equiv), THF (5 mL). The resulting solution was stirred for 12 hr at 50° C. in an oil bath. The reaction was then quenched by the addition of 20 mL of water. The resulting solution was extracted with 3×20 ml of ethyl acetate. The resulting mixture was washed with 20 mL of brine. The mixture was dried over anhydrous sodium sulfate and concentrated. The resulting mixture was concentrated. The residue was applied onto a silica gel column with ethyl acetate/petroleum ether (1:1). This resulted in 200 mg (yield=89%) of 148.5 as a white solid. (ES, m/z): [M−H]⁻ 651.0.

Synthesis of I-192

Into a 25-mL round-bottom flask purged and maintained with an inert atmosphere of nitrogen, was placed 148.5 (100 mg, 0.16 mmol, 1 equiv), CF₃COOH (55.2 mg, 0.48 mmol, 3.00 equiv), DCM (5 mL). The resulting solution was stirred for 12 hr at room temperature. The reaction was then quenched by the addition of 10 mL of water. The resulting solution was extracted with 3×10 ml of dichloromethane. The resulting mixture was washed with 10 mL of brine. The mixture was dried over anhydrous sodium sulfate. The resulting mixture was concentrated. The residue was applied onto a silica gel column with dichloromethane/methanol (10:1). This resulted in 37.9 mg (yield=41%) of I-192 acid as a white solid. (ES, m/z): [M+H+]⁻ 563.0, 1H-NMR (400 MHz, DMSO-d₆, ppm): δ7.98-7.88 (m, 2H), δ7.43-7.16 (m, 8H), δ4.56 (s, 2H), δ4.18-4.15 (t, J=7.2 Hz, 2H), δ4.02-3.99 (t, J=6.8 Hz, 2H), δ2.23-2.15 (m, 2H).

Example 149. Synthesis of 3-chloro-N-(5-cyclopropyl-2,4-difluorophenyl)-2-hydroxy-5-(pyrrolidine-1-carbonyl)benzene-1-sulfonamide, I-193

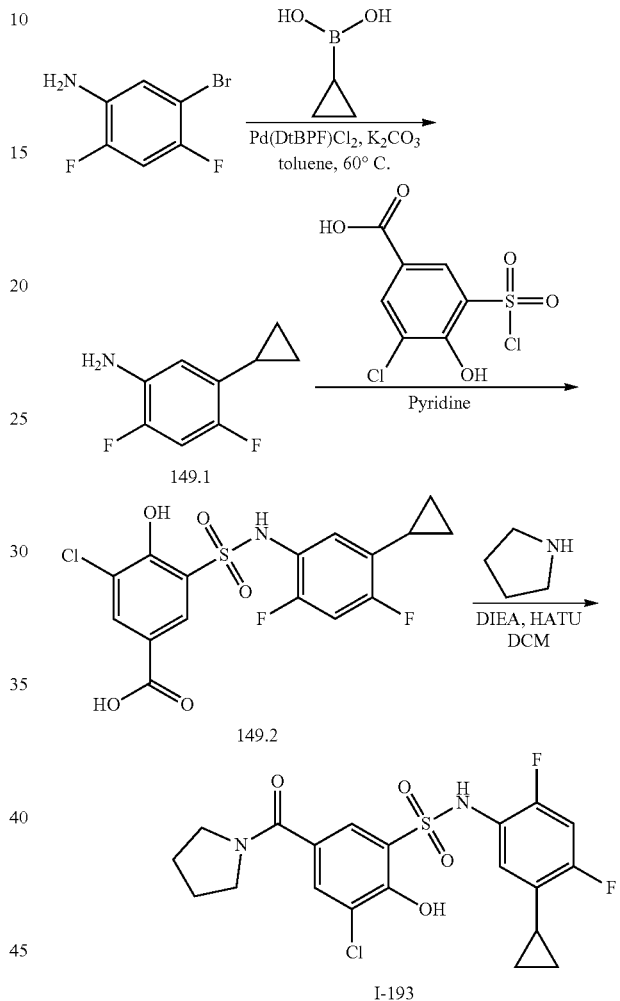

Synthesis of Compound 149.1

Into a 100-mL round-bottom flask, was placed 5-bromo-2,4-difluoroaniline (1 g, 4.81 mmol, 1 equiv), toluene (10 mL, 93.99 mmol, 19.55 equiv), cyclopropylboronic acid (0.8 g, 9.62 mmol, 2 equiv), K₂CO₃ (2.0 g, 14.42 mmol, 3 equiv), Pd(DtBPF)Cl₂ (0.3 g, 0.48 mmol, 0.1 equiv). The resulting solution was stirred for 2 hr at 60° C. The resulting mixture was concentrated under vacuum. The residue was applied onto a silica gel column with ethyl acetate/petroleum ether (10:1). This resulted in 1 g (122.9%) of 149.1 as a light yellow solid. (ES, m/z): [M−H]⁻ 168.0.

Synthesis of Compound 149.2

Into a 50-mL round-bottom flask, was placed 3-chloro-5-(chlorosulfonyl)-4-hydroxybenzoic acid (500 mg, 1.84 mmol, 1 equiv), 149.1 (374.5 mg, 2.21 mmol, 1.2 equiv), Pyridine (7 mL). The resulting solution was stirred for 12 hr at 25° C. The resulting mixture was concentrated under vacuum. The crude product was purified by Flash-Prep-HPLC with the following conditions (IntelFlash-1): Column, C18 silica gel; mobile phase, ACN:H$_2$O=10% increasing to ACN:H$_2$O=40% within 10 min. This resulted in 300 mg (40.3%) of 149.2 as a white solid. (ES, m/z): [M−H]$^-$ 402.0.

Synthesis of I-193

Into a 8-mL sealed tube, was placed 149.2 (100 mg, 0.25 mmol, 1 equiv), DCM (1.5 mL), DIEA (96.0 mg, 0.74 mmol, 3 equiv), pyrrolidine (35.2 mg, 0.50 mmol, 2 equiv), HATU (131.8 mg, 0.35 mmol, 1.4 equiv). The resulting solution was stirred for 12 hr at 25° C. The reaction was then quenched by the addition of 5 mL of water. The resulting solution was extracted with 3×10 mL of dichloromethane and the organic layers combined and concentrated under vacuum. The residue was applied onto Prep-TLC with dichloromethane/methanol (10:1). The crude product was purified by Flash-Prep-HPLC with the following conditions (IntelFlash-1): Column, C18 silica gel; mobile phase, ACN:H$_2$O=10% increasing to ACN:H$_2$O=50% within 10 min. This resulted in 4.3 mg (3.8%) of I-193 as a white solid. (ES, m/z): [M+H]$^+$ 457.2, $^1$H-NMR (300 MHz, DMSO-d$_6$, ppm): δ0.46-0.48 (m, 2H), δ0.90-0.95 (m, 2H), δ1.80-1.89 (s, 4H), δ1.90-1.95 (m, 1H), δ3.25-3.44 (m, 4H), δ6.67-6.72 (t, J=2.4 Hz, 1H), δ7.14-7.21 (t, J=10.2 Hz, 1H), δ7.54-7.55 (d, J=2.1 Hz, 1H), δ7.78-7.79 (d, J=2.1 Hz, 1H).

Example 150. Synthesis of 3-chloro-N-(5-cyclopropyl-2,4-difluorophenyl)-5-(3-fluoroazetidine-1-carbonyl)-2-hydroxybenzene-1-sulfonamide, I-194

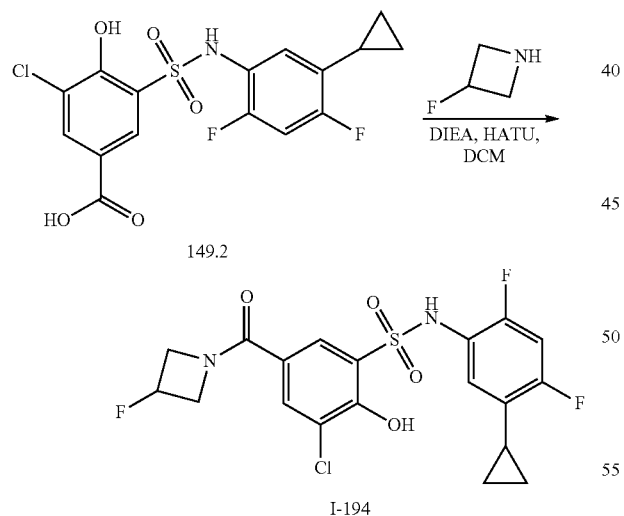

Synthesis of I-194

Into a 8-mL sealed tube, was placed 149.2 (100 mg, 0.25 mmol, 1 equiv), DCM (1.5 mL), DIEA (96.0 mg, 0.74 mmol, 3 equiv), 3-fluoroazetidine (37.2 mg, 0.50 mmol, 2 equiv), and HATU (131.8 mg, 0.35 mmol, 1.4 equiv). The resulting solution was stirred for 12 hr at 25° C. The reaction was then quenched by the addition of 5 mL of water. The resulting solution was extracted with 3×10 mL of dichloromethane and the organic layers combined and concentrated under vacuum. The residue was applied onto Prep-TLC with dichloromethane/methanol (10:1). The crude product was purified by Flash-Prep-HPLC with the following conditions (IntelFlash-1): Column, C18 silica gel; mobile phase, ACN:H$_2$O=10% increasing to ACN:H$_2$O=50% within 10 min. This resulted in 22.5 mg (19.7%) of I-194 as a white solid. (ES, m/z): [M+H]$^+$ 461.1, $^1$H-NMR (300 MHz, DMSO-d$_6$, ppm): δ0.41-0.42 (d, J=3.9 Hz, 2H), δ0.88-0.90 (d, J=4.8 Hz, 2H), δ1.89 (s, 1H), δ4.12-4.20 (m, 2H), δ4.36-4.43 (m, 2H), δ5.23-5.48 (m, 1H), δ6.67-6.73 (t, J=7.8 Hz, 1H), δ6.96-7.30 (m, 3H), δ7.42-7.47 (s, 1H), δ7.60-7.70 (s, 1H).

Example 151. Synthesis of 3-cyano-N-(2-fluoro-5-phenylphenyl)benzene-1-sulfonamide, I-419

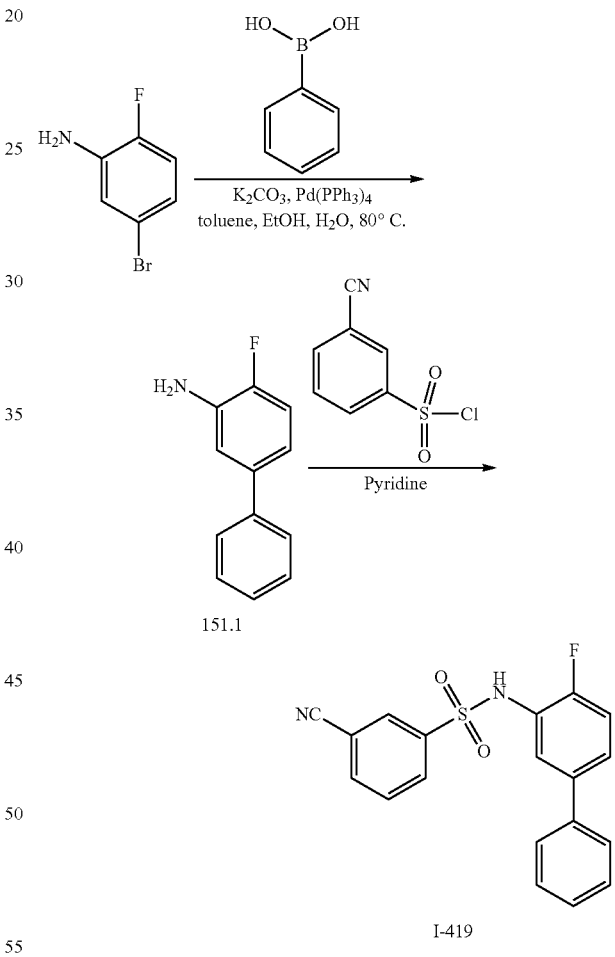

Synthesis of Compound 151.1

Into a 500-mL 3-necked round-bottom flask purged and maintained with an inert atmosphere of nitrogen, was placed 5-bromo-2-fluoroaniline (15 g, 78.94 mmol, 1 equiv), phenylboronic acid (11.6 g, 94.73 mmol, 1.2 equiv), K$_2$CO$_3$ (54.6 g, 394.71 mmol, 5 equiv), toluene (60 mL), EtOH (60 mL), H$_2$O (60 mL), Pd(PPh$_3$)$_4$ (9.1 g, 7.89 mmol, 0.1 equiv). The resulting solution was stirred overnight at 80° C. in an oil bath. The resulting mixture was concentrated under vacuum. The residue was applied onto a silica gel column with ethyl acetate/petroleum ether (1/20). This resulted in 14.2 g (93.2%) of 151.1 as an off-white solid.

Synthesis of I-419

Into a 50-mL round-bottom flask, was placed 151.1 (557 mg, 1.2 equiv), 3-cyanobenzene-1-sulfonyl chloride (500 mg, 1 equiv), pyridine (10 mL). The resulting solution was stirred overnight at 25° C. The pH value of the solution was adjusted to 7-8 with 1 M HCl (aq.). The resulting solution was washed with H₂O (20 mL). The resulting solution was extracted with 3×15 mL of ethyl acetate, and the combined organic layers were concentrated under vacuum. The residue was applied onto a silica gel column with ethyl acetate/petroleum ether (1/10). This resulted in 630 mg (70.6%) of I-419 as a light yellow solid. (ES, m/z): [M–H]⁻ 351.0, ¹H-NMR (300 MHz, DMSO-d₆, ppm): δ10.56 (s, 1H), δ8.19-8.15 (m, 2H), δ8.07-8.04 (m, 1H), δ7.84-7.79 (m, 1H), δ7.56-7.25 (m, 8H).

Example 152. Synthesis of 4-chloro-3-cyano-N-(4,6-difluoro-[1,1'-biphenyl]-3-yl) benzenesulfonamide, I-196

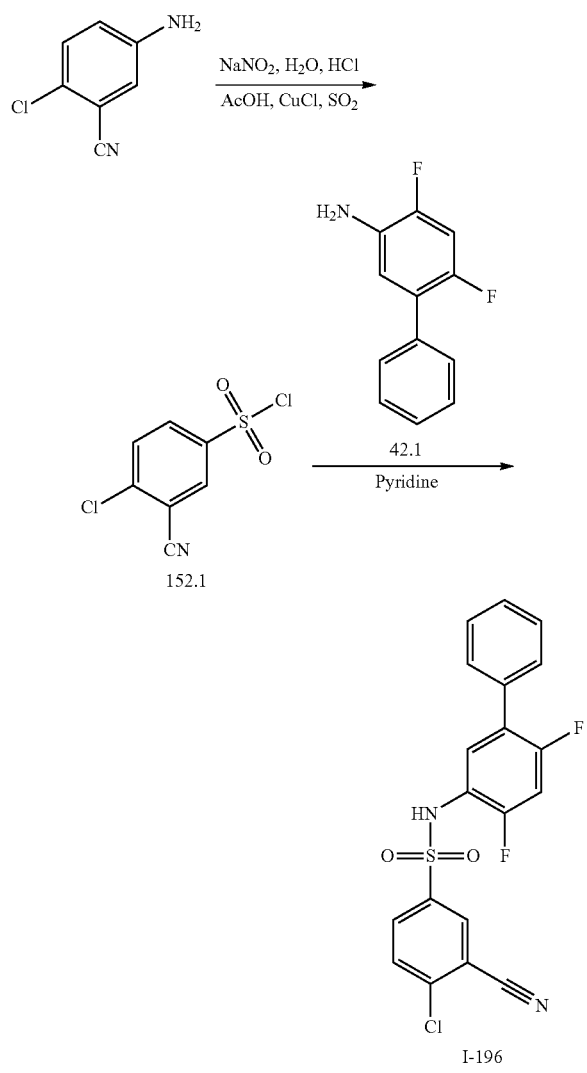

Synthesis of Compound 152.1

Into a 50-mL round-bottom flask purged and maintained with an inert atmosphere of nitrogen, was placed 5-amino-2-chlorobenzonitrile (500 mg, 3.28 mmol, 1 equiv) and HCl (5 mL), then to the solution was added a solution of NaNO₂ (339.1 mg, 4.92 mmol, 1.5 equiv) in H₂O (2 mL) at 0° C., the solution of A was stirred at 0° C. for 1 h; then to another 50-mL round-bottom flask was placed AcOH (5 mL) and CuCl (97.3 mg, 0.98 mmol, 0.3 equiv), to the solution was through SO₂ over 0.5 h. The solution A was added to solution B dropwised over 10 mins. The resulting solution was stirred for 1 hr at room temperature. The reaction was then quenched by the addition of 10 mL of water. The resulting solution was extracted with 3×10 ml of ethyl acetate. The resulting mixture was washed with 1×10 ml of brine. The mixture was dried over anhydrous sodium sulfate and concentrated. The resulting mixture was concentrated. This resulted in 600 mg (yield=65%) of 152.1 as a white solid.

Synthesis of I-196

Into a 25-mL round-bottom flask purged and maintained with an inert atmosphere of nitrogen, was placed 152.1 (200 mg, 0.85 mmol, 1 equiv), 42.1 (208.6 mg, 1.02 mmol, 1.20 equiv), and pyridine (5 mL). The resulting solution was stirred for 0.5 hr at room temperature. The resulting mixture was concentrated. The residue was applied onto a silica gel column with ethyl acetate/petroleum ether (1:1). This resulted in 209.2 mg (yield=61%) of I-196 as a brown yellow solid. (ES, m/z): [M–H]⁻ 402.9, ¹H-NMR (DMSO-d₆, 400 MHz, ppm): δ10.56 (s, 1H), δ8.27 (s, 1H), δ8.02-7.96 (m, 2H), δ7.51-7.34 (m, 6H), δ7.33-7.28 (m, 1H).

Example 153. Synthesis of 5-(azetidine-1-carbonyl)-3-chloro-N-[2,4-difluoro-5-(pyridin-3-yl)phenyl]-2-hydroxybenzene-1-sulfonamide, I-197

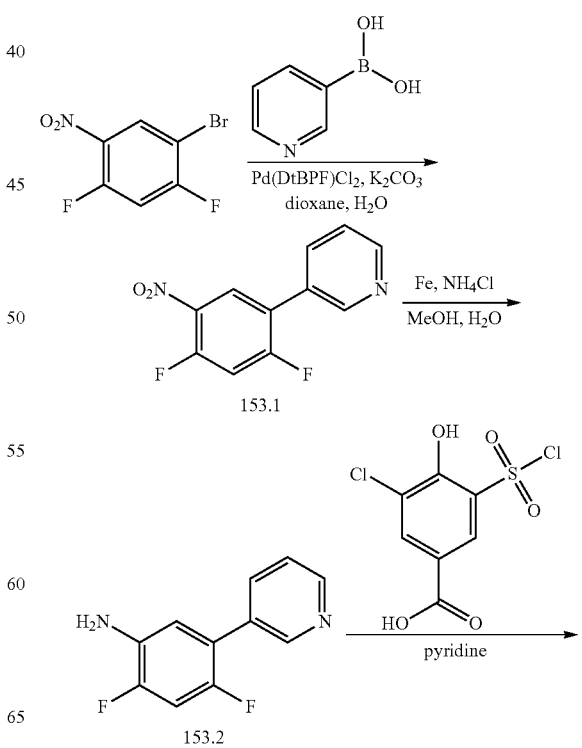

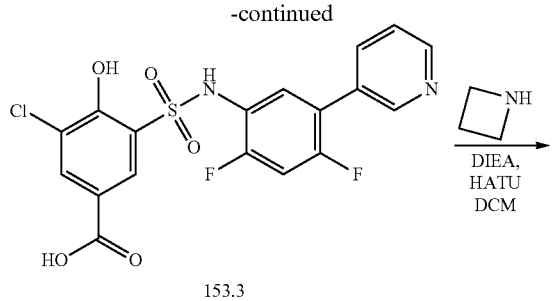

153.3

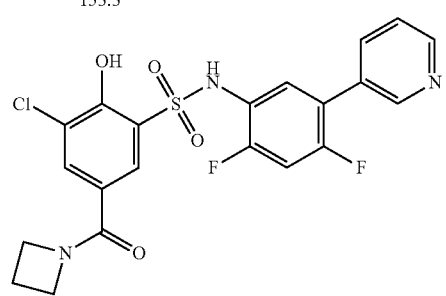

I-197

Synthesis of Compound 153.1

Into a 250-mL 3-necked round-bottom flask, was placed 1-bromo-2,4-difluoro-5-nitrobenzene (10 g, 42.02 mmol, 1 equiv), dioxane (100 mL), H$_2$O (25 mL), (pyridin-3-yl)boronic acid (7.7 g, 63.03 mmol, 1.5 equiv), K$_2$CO$_3$ (11.6 g, 84.04 mmol, 2 equiv), Pd(dppf)Cl$_2$ (3.1 g, 4.20 mmol, 0.1 equiv). The resulting solution was stirred for 12 hr at 100° C. The reaction was then quenched by the addition of 100 mL of water. The resulting solution was extracted with 3×150 mL of ethyl acetate and the organic layers combined and concentrated under vacuum. The residue was applied onto a silica gel column with ethyl acetate/petroleum ether (10:1). This resulted in 1.1 g (11%) of 153.1 as a solid.

Synthesis of Compound 153.2

Into a 100-mL round-bottom flask, was placed 153.1 (1.1 g, 4.66 mmol, 1 equiv), EtOH (5 mL), THF (15 mL), H$_2$O (2.5 mL), NH$_4$Cl (5.28 mL), Fe (1.1 g, 19.56 mmol, 4.2 equiv). The resulting solution was stirred for 2 hr at 95° C. The resulting mixture was concentrated under vacuum. The residue was applied onto a silica gel column with ethyl acetate/petroleum ether (20:1). This resulted in 0.9 g (90%) of 153.2 as a grey solid.

Synthesis of Compound 153.3

Into a 100-mL round-bottom flask, was placed 3-chloro-5-(chlorosulfonyl)-4-hydroxybenzoic acid (500 mg, 1.84 mmol, 1 equiv), 153.2 (456.4 mg, 2.21 mmol, 1.2 equiv), pyridine (7 mL). The resulting solution was stirred for 12 hr at 25° C. The resulting mixture was concentrated under vacuum. The crude product was purified by Flash-Prep-HPLC with the following conditions (IntelFlash-1): Column, C18 silica gel; mobile phase, ACN:H$_2$O=10% increasing to ACN:H$_2$O=30% within 10 min. This resulted in 150 mg (18.4%) of 153.3 as a white solid.

Synthesis of I-197

Into a 8-mL sealed tube, was placed 153.3 (100 mg, 0.23 mmol, 1 equiv), DCM (1.5 mL), DIEA (88.0 mg, 0.68 mmol, 3 equiv), azetidine (25.9 mg, 0.45 mmol, 2 equiv), HATU (129.4 mg, 0.34 mmol, 1.5 equiv). The resulting solution was stirred for 12 hr at 25° C. The reaction was then quenched by the addition of 5 mL of water. The resulting solution was extracted with 3×10 mL of dichloromethane and the organic layers combined and concentrated under vacuum. The crude product was purified by Prep-HPLC with the following conditions (2 #SHIMADZU (HPLC-01)): Column, XBridge Prep OBD C18 Column, 30-150 mm 5 um; mobile phase, Water (0.05% NH$_3$H$_2$O) and ACN (20% PhaseB up to 23% in 7 min); Detector, UV. This resulted in 16.9 mg (15.5%) of I-197 as a white solid. (ES, m/z): [M+H]$^+$ 480.1, $^1$H-NMR (300 MHz, DMSO-d$_6$, ppm): δ2.16 (s, 2H), δ3.77-4.04 (m, 4H), δ7.29-7.79 (m, 7H), δ8.54-8.59 (m, 2H).

Example 154. Synthesis of Methyl 3-chloro-5-(N-(2,4-difluoro-5-isopropylphenyl)sulfamoyl)-4-hydroxybenzoate, I-198

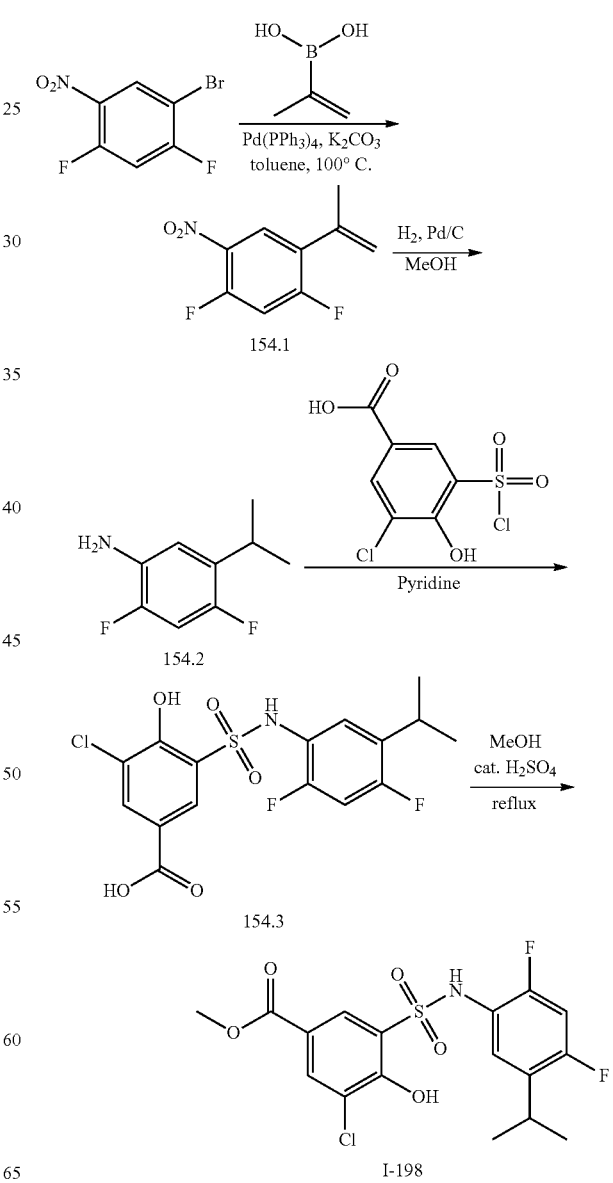

I-198

Synthesis of Compound 154.1

Into a 250-mL 3-necked round-bottom flask purged and maintained with an inert atmosphere of nitrogen, was placed 1-bromo-2,4-difluoro-5-nitrobenzene (5 g, 21.01 mmol, 1 equiv), (prop-1-en-2-yl)boronic acid (2707.1 mg, 31.51 mmol, 1.5 equiv), toluene (50 mL), $K_2CO_3$ (5807.2 mg, 42.02 mmol, 2 equiv), $Pd(PPh_3)_4$ (2427.8 mg, 2.10 mmol, 0.1 equiv). The resulting solution was stirred for 1 overnight at 100° C. The resulting mixture was concentrated. The residue was dissolved in 100 mL of $CH_2Cl_2$. The resulting mixture was washed with 2×100 ml of $H_2O$. The residue was applied onto a silica gel column with ethyl acetate/petroleum ether (1:1). This resulted in 3.84 g (91.7%) of 154.1 as a yellow oil.

Synthesis of Compound 154.2

Into a 50-mL round-bottom flask purged and maintained with an inert atmosphere of nitrogen, was placed 154.1 (1 g, 5.02 mmol, 1 equiv), MeOH (10 mL), Pd/C (200 mg, 1.88 mmol, 0.37 equiv), H2 (100 mL, 49.61 mmol, 9.88 equiv). The resulting solution was stirred for 2 hr at 25° C. The solids were filtered out. The residue was applied onto a silica gel column with ethyl acetate/petroleum ether (1:5). This resulted in 600 mg (69.0%) of 154.2 as brown oil.

Synthesis of Compound 154.3

Into a 8-mL vial, was placed 154.2 (100 mg, 0.58 mmol, 1 equiv), 3-chloro-5-(chlorosulfonyl)-4-hydroxybenzoic acid (180.2 mg, 0.70 mmol, 1.2 equiv), and pyridine (3 mL). The resulting solution was stirred overnight at 25° C. The resulting mixture was concentrated. The residue was applied onto a Prep TLC with ethyl acetate/petroleum ether (1:1). This resulted in 175 mg crude of 154.3 as a brown solid.

Synthesis of I-198

Into a 8-mL vial, was placed 154.3 (175 mg, 0.43 mmol, 1 equiv), MeOH (2 mL), $H_2SO_4$ (84.6 mg, 0.86 mmol, 2.00 equiv). The resulting solution was stirred for 1 overnight at 70° C. The reaction was then quenched by the addition of 20 mL of water. The resulting solution was extracted with 2×20 mL of ethyl acetate. The crude product was purified by Flash-Prep-HPLC with the following conditions (IntelFlash-1): Column, C18 silica gel; mobile phase, water/acetonitrile=90:10 increasing to water/acetonitrile=0:100 within 40 min; Detector, 254 UV. This resulted in 61.9 mg of I-198 as a white solid. (ES, m/z): $[M+H]^+$ 420.0, $^1$H-NMR (DMSO-$d_6$, 400 MHz, ppm): δ1.02-1.07 (s, 6H), δ2.97-3.01 (m, 1H), δ3.74-3.76 (s, 3H), δ6.95-7.21 (m, 4H), δ7.92-7.94 (m, 2H).

Example 155. Synthesis of 2-[4-(azetidine-1-carbonyl)-2-chloro-6-([4,6-difluoro-[1,1-biphenyl]-3-yl]sulfamoyl)phenoxy]acetic Acid, I-199

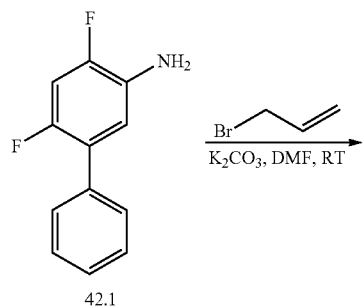

42.1

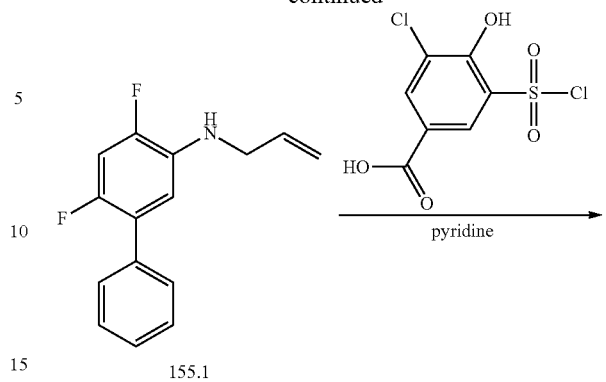

155.1

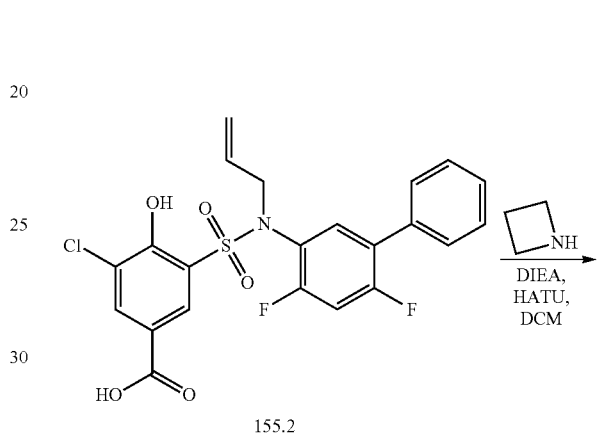

155.2

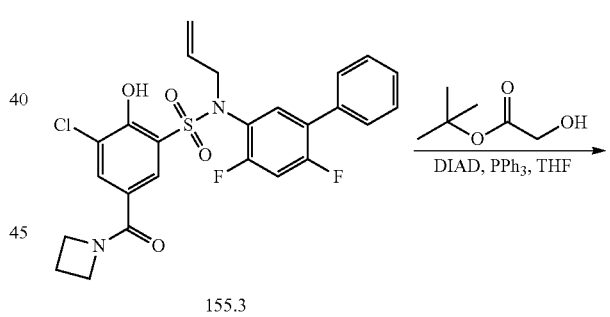

155.3

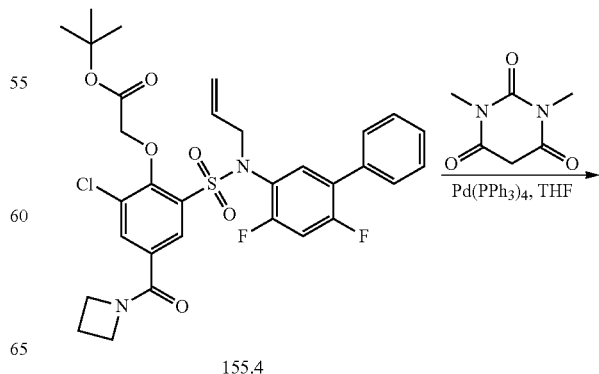

155.4

-continued

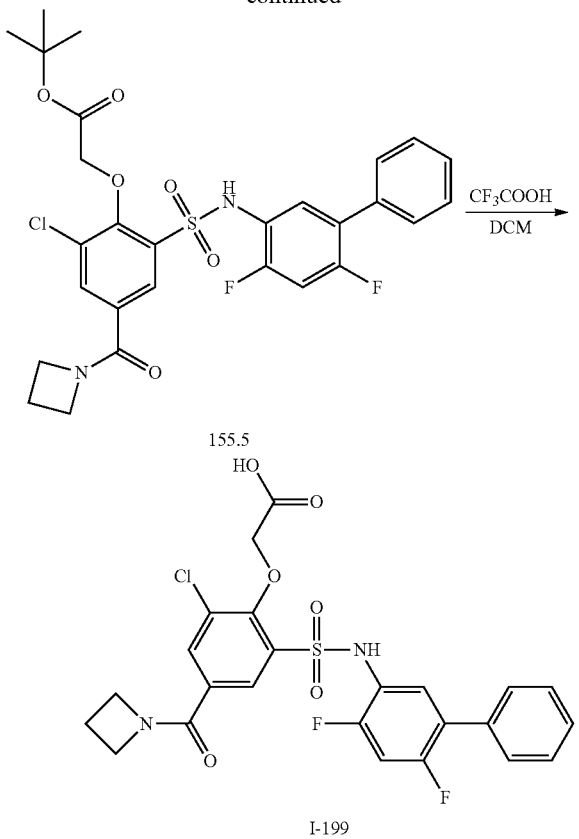

Synthesis of Compound 155.1

To a stirred mixture of 42.1 (5 g, 24.37 mmol, 1 equiv) and K$_2$CO$_3$ (6.7 g, 48.73 mmol, 2 equiv) in DMF (50 mL) was added 3-bromoprop-1-ene (3.5 g, 29.24 mmol, 1.2 equiv) in portions at room temperature under nitrogen atmosphere with stirring for overnight. The resulting mixture was filtered and the filter cake was washed with EtOAc (2×100 mL). The filtrate was concentrated under reduced pressure. The residue was purified by silica gel column chromatography, eluted with PE/EtOAc (80:1) to afford 155.1 (4.4 g, 73.6%) as a brown oil. (ES, m/z): [M−H]$^-$ 244.1.

Synthesis of Compound 155.2

A mixture of 155.1 (2.948 g, 12.02 mmol, 1 equiv) and 3-chloro-5-(chlorosulfonyl)-4-hydroxybenzoic acid (3.3 g, 12.02 mmol, 1 equiv) in Pyridine (30 mL, 372.71 mmol, 31.01 equiv) was stirred for 12 h at 50° C. under nitrogen atmosphere. The crude product was purified by reverse phase flash with the following conditions (from CH$_3$CN/H$_2$O=0:100 to CH$_3$CN/H$_2$O=40:60 in 30 mins UV: 254/220) to afford 155.2 (1.52 g, 26.3%) as a yellow green solid. (ES, m/z): [M−H]$^-$ 478.0.

Synthesis of Compound 155.3

To a stirred mixture of 155.2 (1.516 g, 3.16 mmol, 1 equiv) and azetidine (252.5 mg, 4.42 mmol, 1.4 equiv) in DCM (15 mL, 235.95 mmol, 74.69 equiv) were added DIEA (1.6 g, 12.64 mmol, 4 equiv) and HATU (1.8 g, 4.74 mmol, 1.5 equiv) in portions at room temperature under nitrogen atmosphere. The resulting mixture was stirred for overnight under nitrogen atmosphere. The reaction was quenched by the addition of water (200 mL) at room temperature. The aqueous layer was extracted with EtOAc (2×100 mL). The crude product was purified by reverse phase flash with the following conditions (from CH$_3$CN/H$_2$O=0:100 to CH$_3$CN/H$_2$O=40:60 in 30 mins UV: 254/220) to afford 155.3 (500 mg, 30.5%) as a green solid. (ES, m/z): [M−H]$^-$ 517.0.

Synthesis of Compound 155.4

To a stirred mixture of 155.3 (450 mg, 0.87 mmol, 1 equiv) and tert-butyl 2-hydroxyacetate (114.6 mg, 0.87 mmol, 1 equiv) in THF (5 mL, 61.71 mmol, 71.17 equiv) were added DIAD (350.7 mg, 1.73 mmol, 2 equiv) and PPh3 (341.1 mg, 1.30 mmol, 1.5 equiv) dropwise at 0° C. under nitrogen atmosphere. The resulting mixture was stirred for overnight under nitrogen atmosphere. The filtrate was concentrated under reduced pressure. The residue was purified by Prep-TLC (CH$_2$Cl$_2$/MeOH 20:1) to afford 155.4 (140 mg, 25.5%) as a yellow solid. (ES, m/z): [M−H]$^-$ 631.1.

Synthesis of Compound 155.5

To a stirred mixture of 155.4 (350 mg, 0.55 mmol, 1 equiv) and 1,3-dimethyl-1,3-diazinane-2,4,6-trione (259.0 mg, 1.66 mmol, 3 equiv) in THF (4 mL, 49.37 mmol, 89.31 equiv) was added Pd(PPh$_3$)$_4$ (191.7 mg, 0.17 mmol, 0.3 equiv) in portions at room temperature under nitrogen atmosphere. The resulting mixture was stirred for overnight under nitrogen atmosphere. The resulting mixture was extracted with water (2×100 ml). The combined organic layers were washed with EtOAc (2×100 mL), dried over anhydrous Na$_2$SO$_4$. After filtration, the filtrate was concentrated under reduced pressure. The crude product was purified by reverse phase flash with the following conditions (from CH$_3$CN/H$_2$O=0:100 to CH$_3$CN/H$_2$O=40:60 in 30 mins UV: 254/220) to afford 155.5 (300 mg, 91.5%) as a white solid. (ES, m/z): [M−H]$^-$ 591.1.

Synthesis of I-199

A mixture of 155.5 (160 mg, 0.27 mmol, 1 equiv) and CF$_3$COOH (1.67 mL, 22.48 mmol, 83.33 equiv) in DCM (8.3 mL, 130.56 mmol, 483.92 equiv) was stirred for 2 h at room temperature under nitrogen atmosphere. The reaction was quenched with NaHCO$_3$ (1 M) at room temperature. The aqueous layer was extracted with EtOAc (2×100 mL). The crude product was purified by reverse phase flash with the following conditions (from CH$_3$CN/H$_2$O=0:100 to CH$_3$CN/H$_2$O=40:60 in 30 mins UV: 254/220) to afford I-199 (33.3 mg, 22.9%) as a white solid. (ES, m/z): [M−H]$^-$ 535.0, $^1$H-NMR (400 MHz, DMSO-d$_6$, ppm): δ2.15-2.23 (m, 2H), δ3.99-4.03 (m, 2H), δ4.13-4.17 (m, 2H), δ4.69 (s, 2H), δ6.99-7.22 (t, J=2.8 Hz, 2H), δ7.22-7.27 (m, 1H), δ7.29-7.48 (m, 6H), δ7.82 (s, 1H), δ7.92 (s, 1H).

Example 156. Synthesis of 5-(3-aminoazetidine-1-carbonyl)-3-chloro-N-[4,6-difluoro-[1,1-biphenyl]-3-yl]-2-hydroxybenzene-1-sulfonamide, I-200

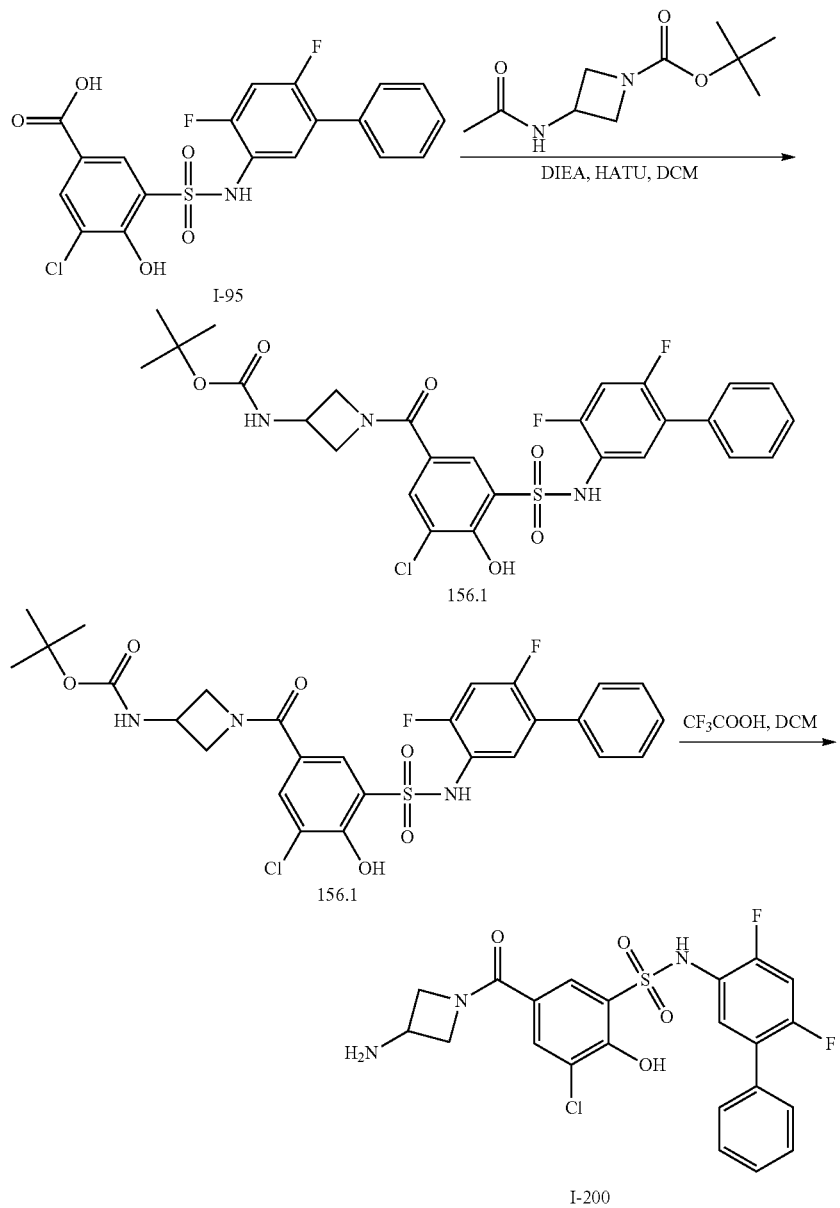

Synthesis of Compound 156.1

To a stirred mixture of I-95 (200 mg, 0.45 mmol, 1 equiv) and tert-butyl 3-acetamidoazetidine-1-carboxylate (136.4 mg, 0.64 mmol, 1.4 equiv) in DCM (2 mL, 31.46 mmol, 69.18 equiv) were added DIEA (235.1 mg, 1.82 mmol, 4 equiv) and HATU (345.8 mg, 0.91 mmol, 2 equiv) in portions at room temperature under nitrogen atmosphere. The resulting solution was stirred for overnight at room temperature under nitrogen atmosphere. The resulting mixture was extracted with Water (100 ml). The combined organic layers were washed with EtOAc (2×100 mL), dried over anhydrous $Na_2SO_4$. After filtration, the filtrate was concentrated under reduced pressure. The crude product was purified by reverse phase flash with the following conditions (from $CH_3CN/H_2O$=0:100 to $CH_3CN/H_2O$=40:60 in 30 mins UV: 254/220) to afford 156.1 (114 mg, 42.2%) as a white solid. (ES, m/z): [M−H]⁻ 592.1.

Synthesis of I-200

A mixture of 156.1 (78 mg, 0.13 mmol, 1 equiv) and $CF_3COOH$ (0.2 mL, 2.69 mmol, 20.51 equiv) in DCM (1 mL, 15.73 mmol, 119.80 equiv) was stirred for 12 h at room temperature under nitrogen atmosphere. The reaction was quenched with $NaHCO_3$ (1 M) at room temperature. The aqueous layer was extracted with EtOAc (2×100 mL). The crude product was purified by reverse phase flash with the following conditions (from $CH_3CN/H_2O$=0:100 to $CH_3CN/H_2O$=40:60 in 30 mins UV: 254/220) to afford I-200 (3.5 mg, 5.4%) as a white solid. (ES, m/z): [M−H]⁻ 492.0, ¹H-NMR (400 MHz, DMSO-d₆, ppm): δ3.87-3.94 (s, 2H), δ4.00-4.02 (m, 1H), δ4.22-4.37 (s, 2H), δ7.25-7.39 (m, 4H), δ7.41-7.46 (m, 3H), δ7.52-7.57 (s, 2H).

Example 157. Synthesis of 5-cyano-2-fluoro-N-(2-fluoro-5-phenylphenyl) benzene-1-sulfonamide, I-418

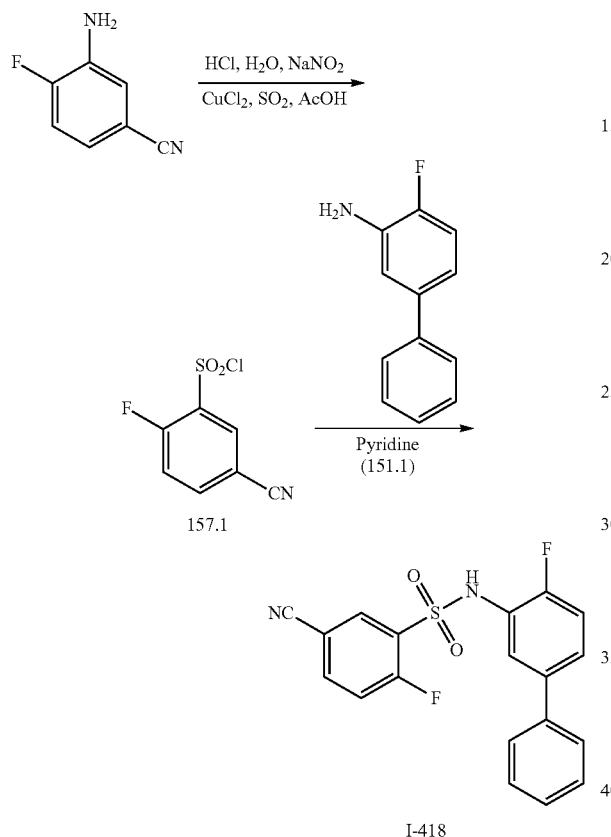

Synthesis of Compound 157.1

A solution of NaNO₂ (760 mg, 11.02 mmol, 0.67 equiv) in water (4 mL) was added to a suspension of 3-amino-4-fluorobenzonitrile (1.0 g, 7.35 mmol, 1 equiv) in concentrated HCl (10 mL) and water (10 mL) at 0° C. over 5 mins. The resulting solution was stirred for a further 30 mins. Meanwhile, AcOH (12.5 mL) was saturated with SO₂, then CuCl₂ (296 mg, 2.2 mmol, 0.30 equiv) was added and SO₂ bubbled through for a further 5 mins. The AcOH mixture was cooled to 5° C., then the above diazonium solution was added over 5 mins. The resulting mixture was stirred for a further 1 h at 0° C. then 1 h at room temperature. The solution was diluted with water (10 mL) and extracted with CH₂Cl₂ (3×10 mL). The combined organic extracts were washed twice with water, dried (Na₂SO₄) and the solvent removed in vacuo. This gave the title compound (1.6 g, 98%) of 157.1 as a brown crude oil.

Synthesis of I-418

Into a 50-mL 3-necked round-bottom flask, was placed 151.1 (1.14 g, 6.10 mmol, 1 equiv), pyridine (10 mL), 157.1 (1.6 g, 7.27 mmol, 1.2 equiv). The resulting solution was stirred overnight at 25° C. The pH value of the solution was adjusted to 7-8 with 1M HCl (aq.). The resulting solution was extracted with ethyl acetate (3×10 mL). The combined organic layers were washed with H₂O, dried and concentrated under reduced pressure. The residue was applied onto a silica gel column with ethyl acetate/petroleum (1/10). This resulted in 1.45 g (64.2%) of I-418 as a grey solid. (ES, m/z): [M–H]⁻ 369.0, ¹H-NMR (300 MHz, DMSO-d₆, ppm): δ10.90 (s, 1H), δ8.31-8.21 (m, 2H), δ7.95-7.68 (m, 1H), δ7.60-7.27 (m, 8H).

Example 158. Synthesis of 5-(azetidine-1-carbonyl)-3-chloro-N-[2-fluoro-5-(pyridin-4-yl)phenyl]-2-hydroxybenzene-1-sulfonamide, I-202

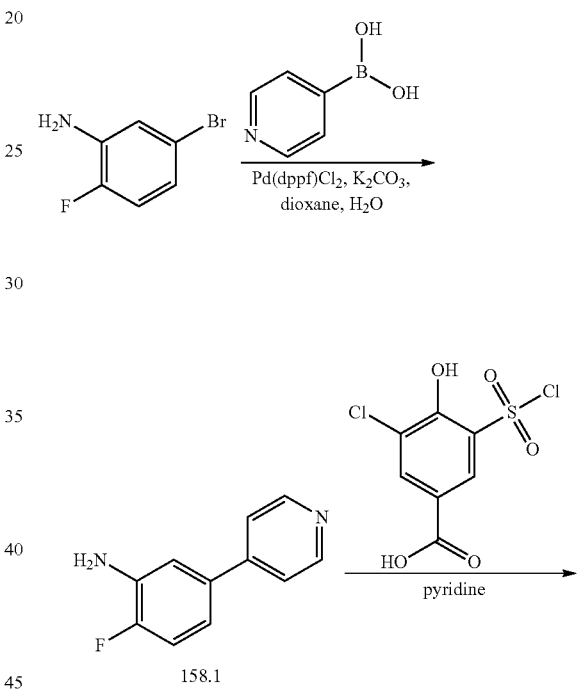

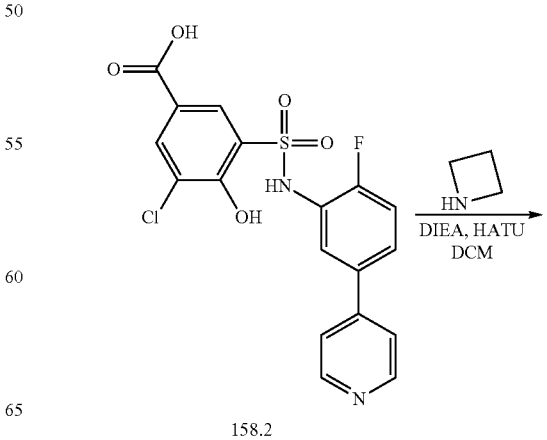

467

-continued

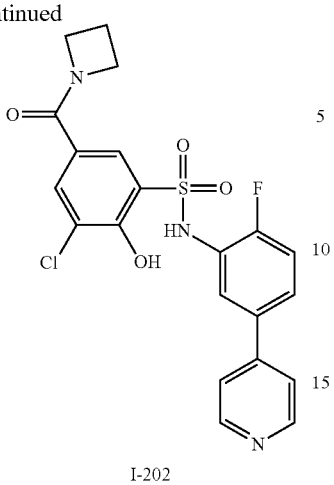

I-202

Synthesis of Compound 158.1

Into a 50-mL round-bottom flask, was placed 5-bromo-2-fluoroaniline (1 g, 5.26 mmol, 1 equiv), $H_2O$ (3 mL), dioxane (12 mL), (pyridin-4-yl)boronic acid (1.0 g, 7.89 mmol, 1.5 equiv), $K_2CO_3$ (1.5 g, 10.53 mmol, 2 equiv), Pd(dppf)Cl2 (0.4 g, 0.53 mmol, 0.1 equiv). The resulting solution was stirred for 12 hr at 100° C. The resulting mixture was concentrated under vacuum. The residue was applied onto a silica gel column with ethyl acetate/petroleum ether (20:1). This resulted in 700 mg (70.6%) of 158.1 as a light yellow solid.

Synthesis of Compound 158.2

Into a 50-mL round-bottom flask, was placed 3-chloro-5-(chlorosulfonyl)-4-hydroxybenzoic acid (500 mg, 1.84 mmol, 1 equiv), 158.1 (416.6 mg, 2.21 mmol, 1.2 equiv), pyridine (7 mL). The resulting solution was stirred for 12 hr at 25° C. The resulting mixture was concentrated under vacuum. The crude product was purified by Flash-Prep-HPLC with the following conditions (IntelFlash-1): Column, C18 silica gel; mobile phase, $ACN:H_2O=10\%$ increasing to $ACN:H_2O=40\%$ within 7 min. This resulted in 300 mg (38.4%) of 158.2 as a white solid.

Synthesis of I-202

Into a 8-mL sealed tube, was placed 158.2 (100 mg, 0.24 mmol, 1 equiv), DCM (2 mL), DIEA (91.7 mg, 0.71 mmol, 3 equiv), azetidine (27.0 mg, 0.47 mmol, 2 equiv), HATU (125.9 mg, 0.33 mmol, 1.4 equiv). The resulting solution was stirred for 12 hr at 25° C. The reaction was then quenched by the addition of 10 mL of water. The resulting solution was extracted with 3×15 mL of dichloromethane and the organic layers combined and concentrated under vacuum. The residue was applied onto Prep-TLC with dichloromethane/methanol (10:1). The crude product was purified by Flash-Prep-HPLC with the following conditions (IntelFlash-1): Column, C18 silica gel; mobile phase, ACN:$H_2O=10\%$ increasing to ACN:$H_2O=50\%$ within 10 min. This resulted in 14.7 mg (13.4%) of I-202 as a white solid. (ES, m/z): [M−H]− 460.0, $^1$H-NMR (300 MHz, DMSO-$d_6$, ppm): δ2.11-2.21 (m, 2H), δ4.05 (s, 4H), δ6.92-7.09 (m, 1H), δ7.26-7.30 (m, 1H), δ7.56 (s, 3H), δ7.66-7.68 (d, J=7.2 Hz, 1H), δ7.75-7.77 (d, J=6.3 Hz, 2H), δ8.63 (s, 2H).

468

Example 159. Synthesis of N-(5-(benzo[b]thiophen-2-yl)-2,4-difluorophenyl)-3-chloro-5-cyanobenzenesulfonamide, I-203

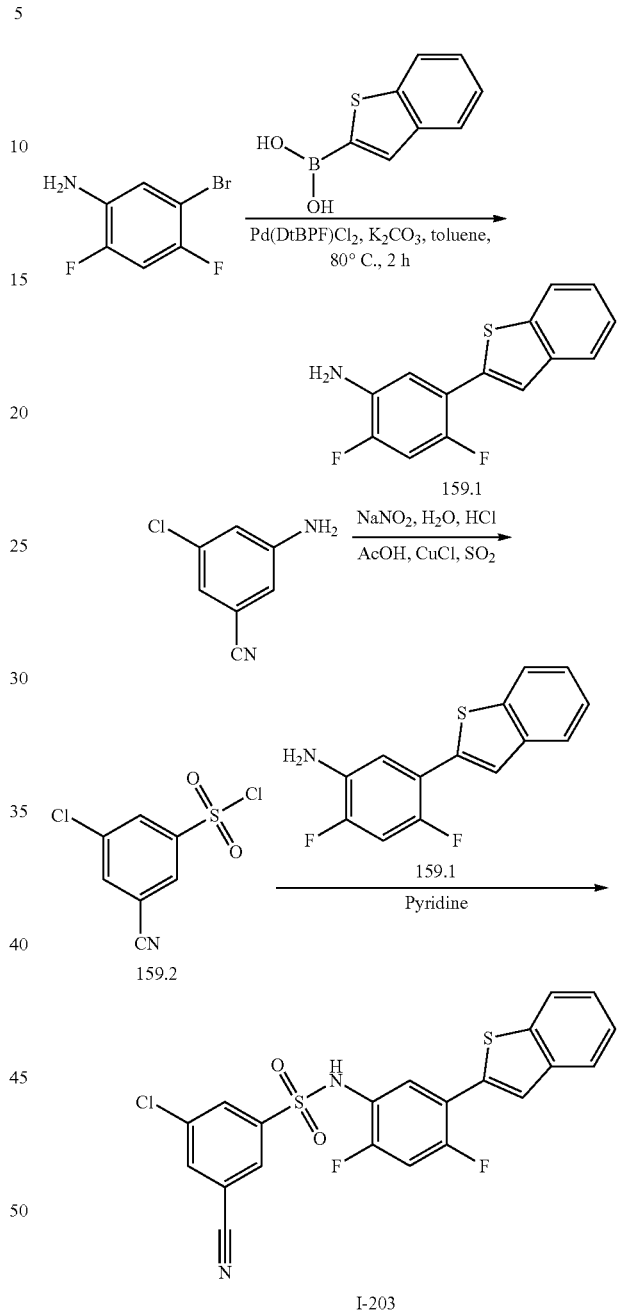

Synthesis of Compound 159.1

Into a 100-mL round-bottom flask purged and maintained with an inert atmosphere of nitrogen, was placed 5-bromo-2,4-difluoroaniline (1 g, 4.81 mmol, 1 equiv), (1-benzothiophen-2-yl)boronic acid (1.7 g, 0.01 mmol, 2 equiv), Pd(DTBPF)Cl2 (0.3 g, 0.1 equiv), $K_2CO_3$ (2.0 g, 0.01 mmol, 3 equiv), toluene (10 mL). The resulting solution was stirred for 2 hr at 80° C. in an oil bath. The reaction was then quenched by the addition of 20 mL of water. The resulting solution was extracted with 3×20 mL of ethyl acetate. The

469 resulting mixture was washed with 1×20 mL of brine. The mixture was dried over anhydrous sodium sulfate and concentrated. The resulting mixture was concentrated. The residue was applied onto a silica gel column with ethyl acetate/petroleum ether (1:3). This resulted in 1.2 g (yield=96%) of 159.1 as a brown solid.

Synthesis of Compound 159.2

Into a 50-mL round-bottom flask purged and maintained with an inert atmosphere of nitrogen, was placed 3-amino-5-chlorobenzonitrile (500 mg, 3.28 mmol, 1 equiv) and HCl (5 mL), then to the solution was added a solution of NaNO₂ (339.1 mg, 4.92 mmol, 1.5 equiv) in H₂O (2 mL) at 0° C., the solution of A was stirred at 0° C. for 1 h; then to another 50-mL round-bottom flask was placed AcOH (5 mL) and CuCl (97.3 mg, 0.98 mmol, 0.3 equiv), to the solution was through SO₂ over 0.5 h. The solution A was added to solution B dropwised over 10 mins. The resulting solution was stirred for 1 hr at room temperature. The reaction was then quenched by the addition of 10 mL of water. The resulting solution was extracted with 3×10 mL of ethyl acetate. The resulting mixture was washed with 1×10 mL of brine. The mixture was dried over anhydrous sodium sulfate and concentrated. The resulting mixture was concentrated. This resulted in 600 mg (yield=41%) of 159.2 as a white solid.

Synthesis of I-203

Into a 25-mL round-bottom flask purged and maintained with an inert atmosphere of nitrogen, was placed 159.2 (200 mg, 0.85 mmol, 1.00 equiv), 159.1 (221.4 mg, 0.85 mmol, 1.00 equiv), Pyridine (5 mL). The resulting solution was stirred for 0.5 hr at room temperature. The resulting mixture was concentrated. The residue was applied onto a silica gel column with ethyl acetate/petroleum ether (1:1). This resulted in 110 mg (yield=28%) of I-203 as a white solid. (ES, m/z): [M−H]⁻ 458.9, ¹H-NMR (DMSO-d₆, 400 MHz, ppm): δ10.71 (s, 1H), δ8.40-8.39 (m, 1H), δ8.16-8.15 (m, 1H), δ8.09-8.08 (m, 1H), δ8.03-7.97 (m, 1H), δ7.95-7.91 (m, 1H), δ7.81 (s, 1H), δ7.61-7.57 (t, J=8.4 Hz, 1H), δ7.53-7.50 (t, J=10.4 Hz, 1H), δ7.48-7.39 (m, 2H).

Example 160. Synthesis of N-benzyl-N-(2-methoxy-5-phenylphenyl)-1H-pyrazole-4-sulfonamide, I-417

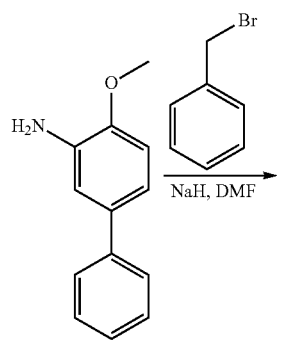

470

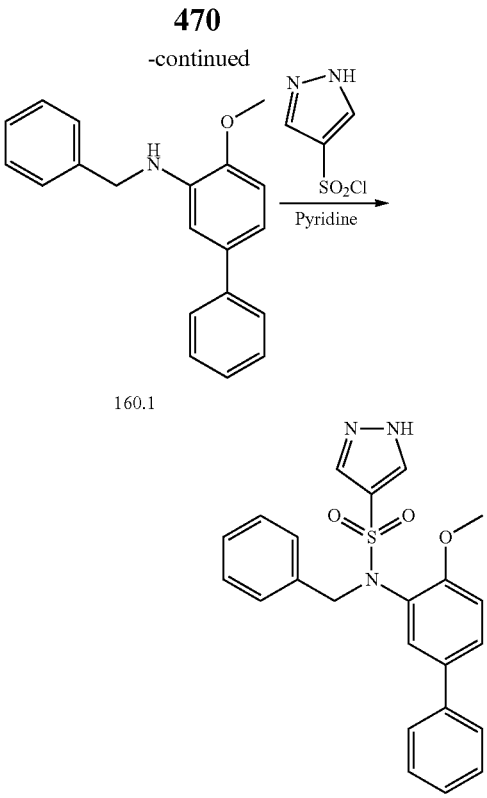

Synthesis of Compound 160.1

Into a 100-mL 3-necked round-bottom flask, was placed 2-methoxy-5-phenylaniline (5 g, 25.09 mmol, 1 equiv), DMF (20 mL), NaH (1.1 g, 27.60 mmol, 1.1 equiv). The resulting solution was stirred for 1 h at 0° C. Then added (bromomethyl)benzene (4.7 g, 27.60 mmol, 1.1 equiv). The resulting solution was stirred overnight at 25° C. The resulting solution was diluted with of H₂O (50 mL), then extracted with ethyl acetate (3×30 mL). The combined organic layers were dried and concentrated under vacuum. The residue was applied onto a silica gel column with ethyl acetate/petroleum ether (1/10). This resulted in 1.7 g (23.4%) of 160.1 as a white solid.

Synthesis of I-417

Into a 50-mL 3-necked round-bottom flask, was placed 160.1 (1.0 g, 3.46 mmol, 1 equiv), pyridine (10 mL), 1H-pyrazole-4-sulfonyl chloride (690.8 mg, 4.15 mmol, 1.2 equiv). The resulting solution was stirred overnight at 25° C. The pH value of the solution was adjusted to 7-8 with 1 M HCl. The resulting solution was extracted with ethyl acetate (3×30 mL). The combined organic layers were washed with H₂O (40 mL), and concentrated under vacuum. The crude product was purified by Flash-Prep-HPLC with the following conditions (IntelFlash-1): Column, C18; mobile phase, MeCN/H₂O=10% increasing to MeCN/H₂O=70% within 17 mins; Detector UV 254 nm. This resulted in 490 mg (33.8%) of I-417 as a solid. (ES, m/z): [M−H]⁻ 418.1, ¹H-NMR (300 MHz, CD₃OD, ppm): δ7.95 (s, 2H), δ7.52-7.48 (m, 1H), δ7.40-7.17 (m, 11H), δ7.02-6.99 (d, J=8.7 Hz, 1H), δ4.82 (s, 2H), δ3.61-3.63 (d, J=6.9 Hz, 3H).

Example 161. Synthesis of 5-(azetidine-1-carbonyl)-3-chloro-N-[2-fluoro-5-(pyridin-2-yl)phenyl]-2-hydroxybenzene-1-sulfonamide, I-206

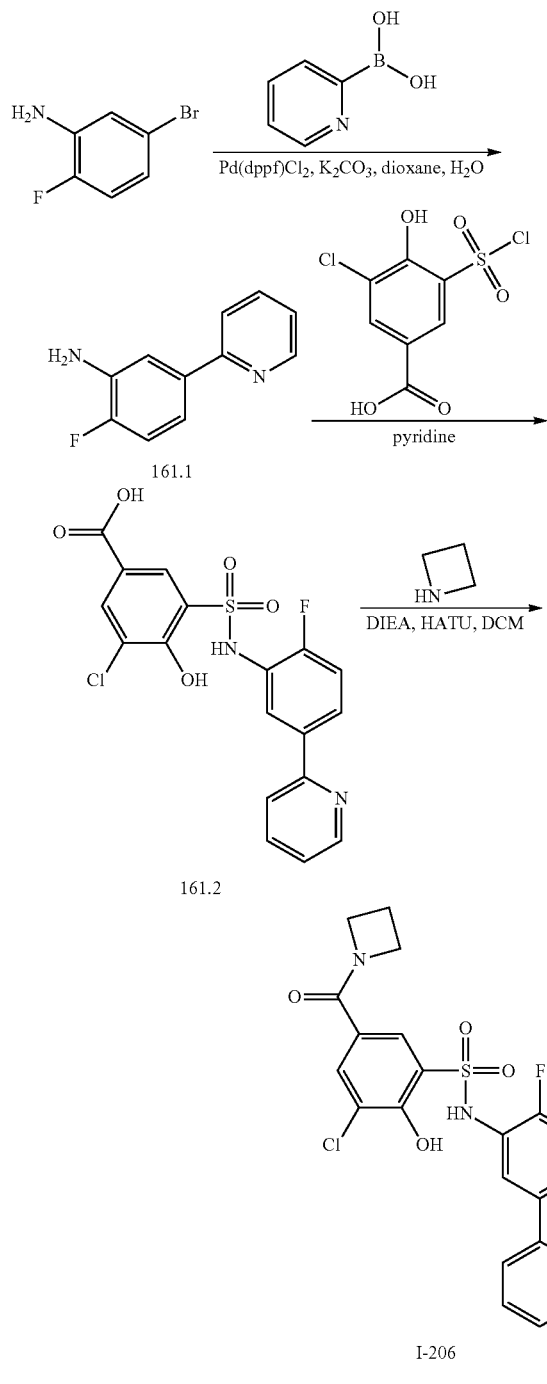

Synthesis of Compound 161.1

Into a 100-mL round-bottom flask, was placed 5-bromo-2-fluoroaniline (1 g, 5.26 mmol, 1 equiv), H₂O (3 mL), dioxane (12 mL), (pyridin-2-yl)boronic acid (0.8 g, 6.32 mmol, 1.2 equiv), K₂CO₃ (1.5 g, 10.53 mmol, 2 equiv), Pd(dppf)Cl₂ (0.4 g, 0.53 mmol, 0.1 equiv). The resulting solution was stirred for 12 hr at 100° C. The resulting mixture was concentrated under vacuum. The residue was applied onto a silica gel column with ethyl acetate/petroleum ether (10:1). This resulted in 300 mg (30.29%) of 161.1 as a light yellow solid. (ES, m/z): [M+H]⁺ 189.0.

Synthesis of Compound 161.2

Into a 50-mL round-bottom flask, was placed 3-chloro-5-(chlorosulfonyl)-4-hydroxybenzoic acid (280 mg, 1.03 mmol, 1 equiv), 161.1 (233.3 mg, 1.24 mmol, 1.2 equiv), pyridine (5 mL). The resulting solution was stirred for 12 hr at 25° C. The resulting mixture was concentrated under vacuum. The crude product was purified by Flash-Prep-HPLC with the following conditions (IntelFlash-1): Column, C18 silica gel; mobile phase, ACN:H₂O=10% increasing to ACN:H₂O=50% within 10 min. This resulted in 200 mg (45.9%) of 161.2 as an off-white solid. (ES, m/z): [M−H]⁻ 421.0.

Synthesis of I-206

Into a 50-mL round-bottom flask, was placed 161.2 (100 mg, 0.24 mmol, 1 equiv), DCM (5 mL), DIEA (91.7 mg, 0.71 mmol, 3 equiv), azetidine (27.0 mg, 0.47 mmol, 2 equiv), HATU (134.9 mg, 0.35 mmol, 1.5 equiv). The resulting solution was stirred for 12 hr at 25° C. The reaction was then quenched by the addition of 15 mL of water. The resulting solution was extracted with 3×25 ml of dichloromethane and the organic layers combined and concentrated under vacuum. The crude product was purified by Prep-HPLC with the following conditions (2 #SHIMADZU (HPLC-01)): Column, XBridge Prep OBD C18 Column, 30??150 mm 5 um; mobile phase, Water (0.05% NH₃H₂O) and ACN (15% PhaseB up to 25% in 7 min); Detector, UV. This resulted in 6.7 mg (6.1%) of I-206 as a white solid. (ES, m/z): [M−H]⁻ 460.0, ¹H-NMR (400 MHz, DMSO-d₆, ppm): δ2.10-2.18 (m, 2H), δ4.04-4.19 (s, 4H), δ6.96-7.29 (m, 1H), δ7.32-7.34 (m, 1H), δ7.67 (s, 1H), δ7.72-7.79 (m, 3H), δ7.81-7.88 (m, 1H), δ8.08-8.10 (m, 1H), δ8.62 (s, 1H).

Example 162. Synthesis of 3,5-dichloro-2-fluoro-N-[4-fluoro-[1,1-biphenyl]-3-yl]benzene-1-sulfonamide, I-207

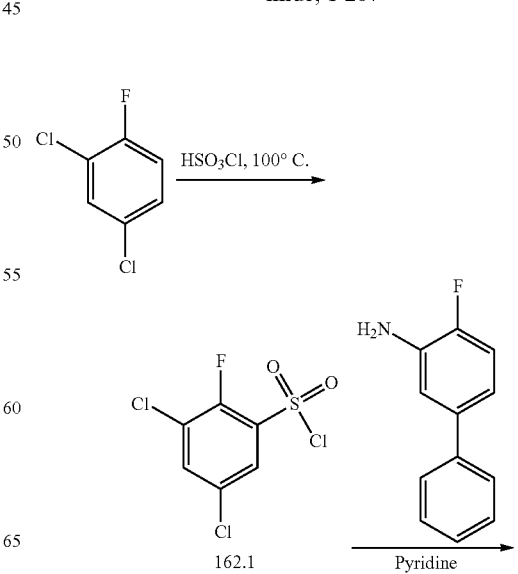

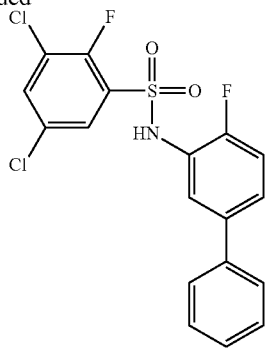

I-207

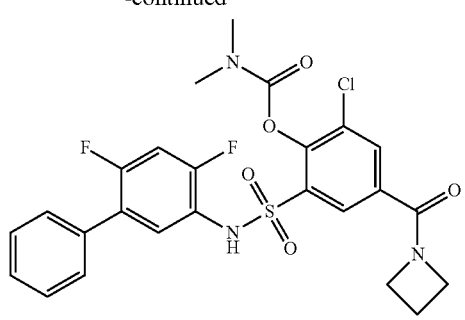

I-209

Synthesis of Compound 162.1

Into a 100-mL 3-necked round-bottom flask, was placed sulfurochloridic acid (20 mL), 2,4-dichloro-1-fluorobenzene (2 g, 12.12 mmol, 1 equiv). The resulting solution was stirred for 12 hr at 100° C. The reaction was then quenched by the addition of 80 mL of water/ice. The resulting solution was extracted with 3×120 ml of ethyl acetate and the organic layers combined and concentrated under vacuum. This resulted in 2 g (62.6%) of 162.1 as black oil. (ES, m/z): [M−H]⁻ 260.8.

Synthesis of I-207

Into a 50-mL round-bottom flask, was placed 162.1 (300 mg, 1.14 mmol, 1 equiv), 4-fluoro-[1,1-biphenyl]-3-amine (255.8 mg, 1.37 mmol, 1.20 equiv), pyridine (10 mL). The resulting solution was stirred for 12 hr at 25° C. The reaction was then quenched by the addition of 20 mL of diluted hydrochloric acid. The resulting solution was extracted with 3×30 ml of ethyl acetate and the organic layers combined and concentrated under vacuum. The crude product was purified by Prep-HPLC with the following conditions (2 #SHIMADZU (HPLC-01)): Column, XBridge Prep OBD C18 Column, 30-150 mm 5 um; mobile phase, Water (0.05% NH₃H₂O) and ACN (29% PhaseB up to 44% in 7 min); Detector, UV. This resulted in 50.9 mg (10.7%) of I-207 as a white solid. (ES, m/z): [M−H]⁻ 411.9, ¹H-NMR (400 MHz, DMSO-d₆, ppm): δ6.99-7.09 (m, 1H), δ7.10-7.15 (s, 1H), δ7.23-7.31 (m, 1H), δ7.36-7.46 (m, 5H), δ7.63-7.69 (m, 1H), δ7.89-8.05 (m, 1H).

Example 163. Synthesis of 4-(azetidine-1-carbonyl)-2-chloro-6-([4,6-difluoro-[1,1-biphenyl]-3-yl]sulfamoyl)phenyl N,N-dimethylcarbamate, I-209

Synthesis of I-209

Into a 8-mL vial, was placed 176.2 (100 mg, 0.21 mmol, 1 equiv), pyridine (2 mL), N,N-dimethylcarbamoyl chloride (134.7 mg, 1.25 mmol, 6.00 equiv). The resulting solution was stirred for 1 overnight at room temperature. The resulting mixture was concentrated under vacuum. The resulting solution was diluted with 50 mL of H₂O. The resulting solution was extracted with 3×50 ml of ethyl acetate. The resulting mixture was concentrated under vacuum. The crude product was purified by Flash-Prep-HPLC with the following conditions (IntelFlash-1): Column, C18 silica gel; mobile phase, ACN/H₂O=15% increasing to ACN/H₂O=60% within 15 min; Detector, UV 254 nm. This resulted in 16.5 mg (14.3%) of I-209 as a white solid. (ES, m/z): [M−H]⁻ 548.0, ¹H-NMR (DMSO-d₆, 300 MHz, ppm): 2.15-2.29 (m, 2H), δ2.79-2.95 (s, 6H), δ3.99-4.09 (m, 2H), δ4.11-4.28 (m, 2H), δ7.21-7.35 (t, J=8.4 Hz, 1H), δ7.36-7.53 (m, 6H), δ7.95 (s, 1H), δ8.05 (s, 1H), δ10.49 (s, 1H).

Example 164. Synthesis of 4-(azetidine-1-carbonyl)-2-chloro-6-(N-(4,6-difluoro-[1,1'-biphenyl]-3-yl)sulfamoyl)phenyl Pivalate, I-210

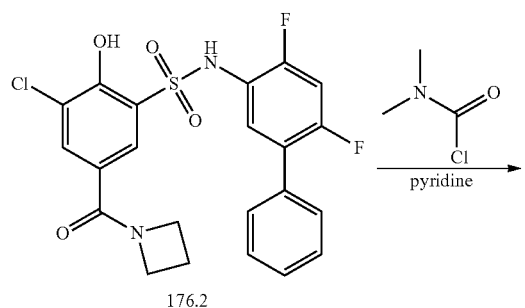

176.2

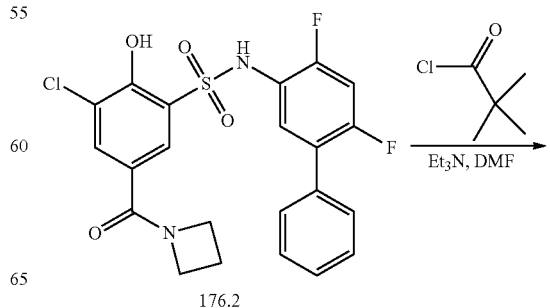

176.2

475
-continued

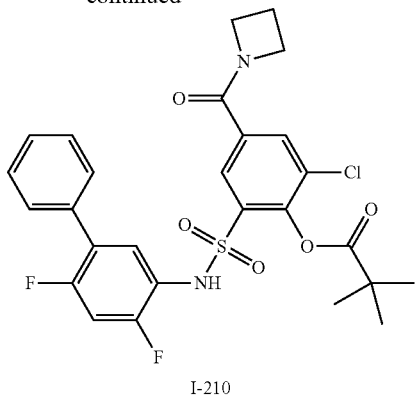

I-210

Synthesis of I-210

Into a 8-mL vial, was placed 176.2 (50 mg, 0.10 mmol, 1 equiv), DMF (1 mL, 0.01 mmol, 0.11 equiv), Et₃N (21.1 mg, 0.21 mmol, 2 equiv), 2,2-dimethylpropanoyl chloride (25.2 mg, 0.21 mmol, 2 equiv). The resulting solution was stirred for 1 overnight at room temperature. The resulting solution was diluted with 50 mL of H₂O. The resulting solution was extracted with 3×50 ml of ethyl acetate concentrated under vacuum. The crude product was purified by Flash-Prep-HPLC with the following conditions (IntelFlash-1): Column, C18 silica gel; mobile phase, ACN/H₂O=15% increasing to ACN/H₂O=60% within 15 min; Detector, UV 254 nm, to provide I-210. (ES, m/z): [M−H]⁻ 561.1, ¹H-NMR (DMSO-d₆, 300 MHz, ppm): 1.15 (s, 9H), δ2.15-2.35 (m, 2H), δ3.95-4.15 (m, 2H), δ4.15-4.33 (m, 2H), δ7.20-7.31 (t, 1H), δ7.35-7.59 (t, J=10.8 Hz, 6H), δ7.91-8.23 (d, J=7.2 Hz, 2H), δ10.41 (s, 1H).

Example 165. Synthesis of 2-[[3-(3,5-dichloro-2-hydroxybenzenesulfonamido)-[1,1-biphenyl]-4-yl]oxy]acetic Acid, I-212

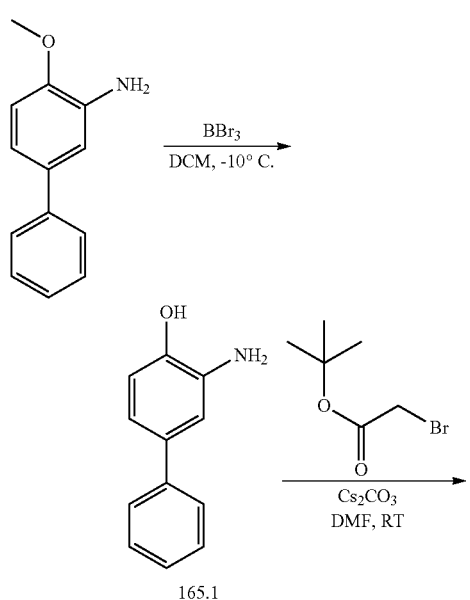

476
-continued

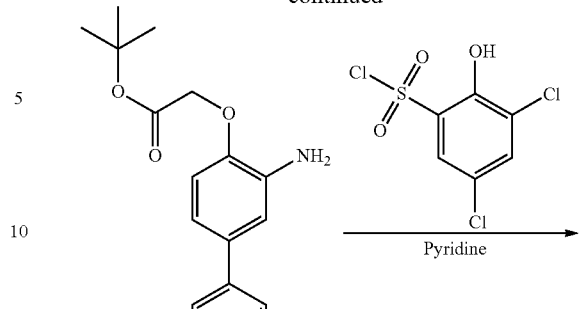
165.2

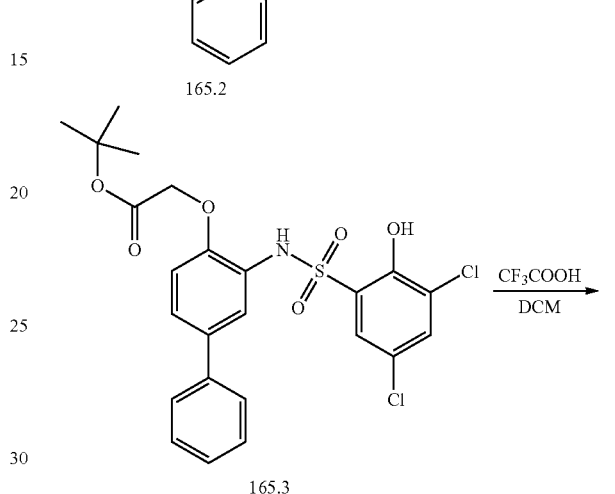
165.3

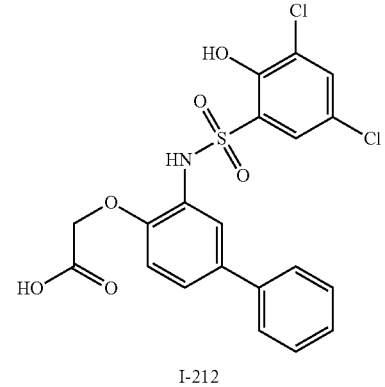 [SMILES: O=C(O)COc1ccc(-c2ccccc2)cc1NS(=O)(=O)c1cc(Cl)cc(Cl)c1O]
I-212

Synthesis of Compound 165.1

Into a 100-mL 3-necked round-bottom flask, was placed 4-methoxy-[1,1-biphenyl]-3-amine (1.5 g, 7.53 mmol, 1 equiv), DCM (20 mL), BBr₃ (5.6 g, 0.02 mmol, 2.98 equiv). The resulting solution was stirred for 12 hr at 25° C. The reaction was then quenched by the addition of 25 mL of water/ice. The resulting solution was extracted with 2×50 ml of ethyl acetate and the aqueous layers combined and concentrated under vacuum. This resulted in 1 g (71.7%) of 165.1 as a light yellow solid. (ES, m/z): [M+H]⁺ 186.0.

Synthesis of Compound 165.2

Into a 100-mL round-bottom flask, was placed 165.1 (700 mg, 3.78 mmol, 1 equiv), DMF (10 mL), tert-butyl 2-bromoacetate (1105.7 mg, 5.67 mmol, 1.5 equiv), Cs₂CO₃ (2462.7 mg, 7.56 mmol, 2 equiv). The resulting solution was stirred for 5 hr at 25° C. The reaction was then quenched by the addition of 25 mL of water. The resulting solution was extracted with 3×35 mL of ethyl acetate and the organic layers combined and concentrated under vacuum. The residue was applied onto Prep-TLC with ethyl acetate/petroleum ether (2:1). This resulted in 600 mg (53.0%) of 165.2 as a solid. (ES, m/z): [M+H]$^+$ 299.9.

Synthesis of Compound 165.3

Into a 100-mL sealed tube, was placed 3,5-dichloro-2-hydroxybenzene-1-sulfonyl chloride (500 mg, 1.91 mmol, 1 equiv), 165.2 (686.9 mg, 2.29 mmol, 1.2 equiv), Pyridine (10 mL). The resulting solution was stirred for 12 hr at 25° C. The resulting mixture was concentrated under vacuum. The residue was applied onto Prep-TLC with dichloromethane/methanol (20:1). This resulted in 250 mg (24.9%) of 165.3 as a solid. (ES, m/z): [M−H]$^-$ 522.0.

Synthesis of I-212

Into a 25-mL round-bottom flask, was placed 165.3 (150 mg, 0.29 mmol, 1 equiv), DCM (2 mL), CF$_3$COOH (0.5 mg). The resulting solution was stirred for 12 hr at 25° C. The resulting mixture was concentrated under vacuum. The crude product was purified by Flash-Prep-HPLC with the following conditions (IntelFlash-1): Column, C18 silica gel; mobile phase, ACN:H$_2$O=10% increasing to ACN:H$_2$O=50% within 10 min. This resulted in 89.9 mg of I-212 as a white solid. (ES, m/z): [M−H]$^-$ 466.0, $^1$H-NMR (400 MHz, DMSO-d$_6$, ppm): δ4.54 (s, 2H), δ6.90-7.09 (m, 2H), δ7.11-7.17 (s, 1H), δ7.31-7.35 (m, 3H), δ7.42-7.54 (m, 5H), δ7.63 (s, 1H).

Example 166. Synthesis of 2-chloro-6-(N-(4,6-difluoro-[1,1'-biphenyl]-3-yl) sulfamoyl)-4-(thiazol-5-yl)phenyl Isobutyrate, I-213

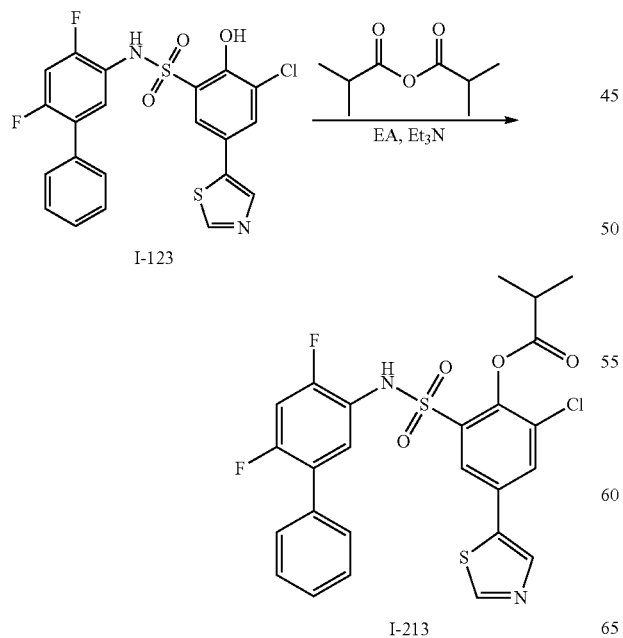

Synthesis of I-213

I Into a 25-mL round-bottom flask purged and maintained with an inert atmosphere of nitrogen, was placed I-123 (65 mg, 0.14 mmol, 1 equiv), 2-methylpropanoyl 2-methylpropanoate (23.6 mg, 0.15 mmol, 1.10 equiv), Et$_3$N (15.1 mg, 0.15 mmol, 1.10 equiv), EA (5 mL). The resulting solution was stirred for 1 hr at room temperature. The reaction was then quenched by the addition of 10 mL of water. The resulting solution was extracted with 3×10 mL of ethyl acetate. The resulting mixture was washed with 1×10 mL of brine. The mixture was dried over anhydrous sodium sulfate and concentrated. The resulting mixture was concentrated. The residue was applied onto a silica gel column with ethyl acetate/petroleum ether (1:1). This resulted in 9.3 mg (yield=12%) of I-213 as a white solid. (ES, m/z): [M+H]$^+$ 549.0, $^1$H-NMR (DMSO-d$_6$, 400 MHz, ppm): δ10.55 (s, 1H), δ9.21 (s, 1H), δ8.49 (s, 1H), δ8.36 (s, 1H), δ7.79 (s, 1H), δ7.51-7.41 (m, 6H), δ7.35-7.31 (t, J=8.4 Hz, 1H), δ2.60-2.51 (m, 1H), δ1.17-1.16 (d, J=5.6 Hz, 3H), δ1.05-1.04 (d, J=5.6 Hz, 3H).

Example 167. Synthesis of tert-butyl 2-[[3-(3,5-dichloro-2-hydroxybenzenesulfonamido)-[1,1-biphenyl]-4-yl]oxy]acetate, I-214

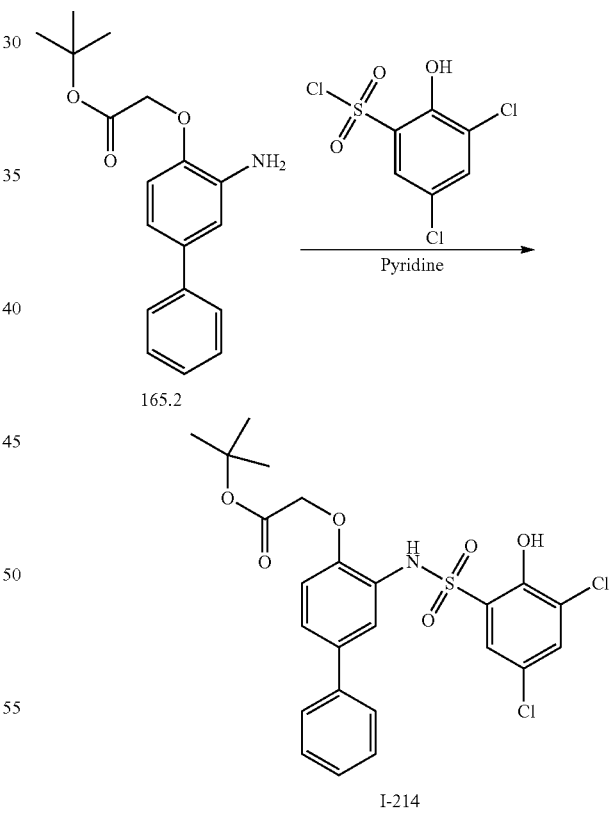

Synthesis of I-214

Into a 8-mL sealed tube, was placed 165.2 (100 mg, 0.33 mmol, 1 equiv), 3,5-dichloro-2-hydroxybenzene-1-sulfonyl chloride (87.4 mg, 0.33 mmol, 1.00 equiv), Pyridine (1 mL). The resulting solution was stirred for 12 hr at 25° C. The resulting mixture was concentrated under vacuum. The residue was applied onto Prep-TLC with dichloromethane/methanol (10:1). The crude product was purified by Flash-Prep-HPLC with the following conditions (IntelFlash-1): Column, C18 silica gel; mobile phase, ACN:H$_2$O=10% increasing to ACN:H$_2$O=65% within 10 min. This resulted in 27.8 mg of I-214 as an off-white solid. (ES, m/z): [M–H]$^-$ 522.0, $^1$H-NMR (400 MHz, DMSO-d$_6$, ppm): δ1.45 (s, 9H), δ4.64 (s, 2H), δ6.90-6.92 (d, J=8.4 Hz, 1H), δ7.19-7.33 (m, 6H), δ7.41-7.48 (m, 4H), δ7.61 (s, 1H).

Example 168. Synthesis of N-[5-(azetidine-1-carbonyl)-3-chloro-2-hydroxyphenyl]-4-fluoro-[1,1-biphenyl]-3-sulfonamide, I-215

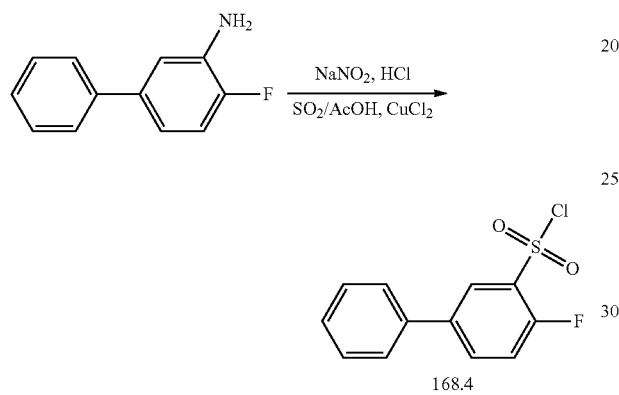

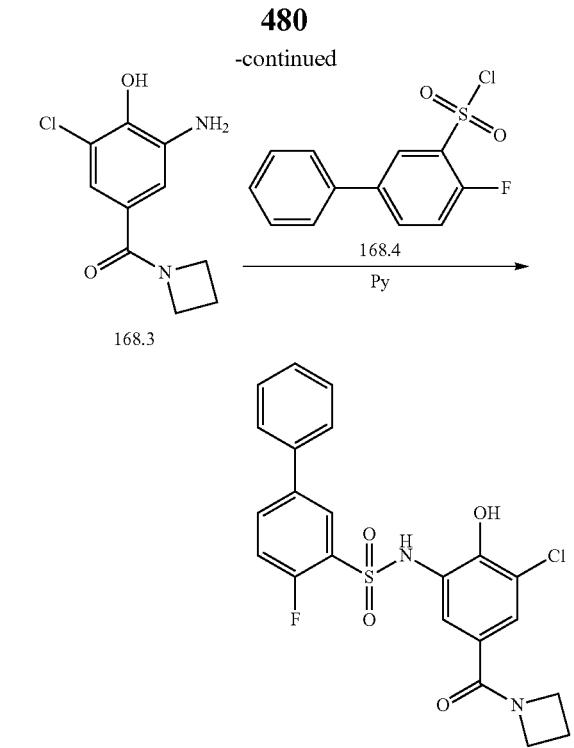

Synthesis of Compound 168.1

Into a 25-mL 2-necked round-bottom flask, was placed 3-chloro-4-hydroxybenzoic acid (1 g, 5.80 mmol, 1 equiv). This was followed by the addition of H$_2$SO$_4$ (1.5 mL, 28.14 mmol, 4.86 equiv) at 0° C. in an ice/salt bath. To this was added HNO$_3$ (0.6 mL, 0.01 mmol) in 1 hr. The resulting solution was stirred for 0.5 hr at 0° C. in an ice/salt bath. The resulting solution was diluted with 100 mL of H$_2$O. The resulting solution was extracted with 3×100 ml of dichloromethane. The crude product was re-crystallized from EA/PE in the ratio of 1:2. This resulted in 580 mg (46.0%) of 168.1 as a yellow solid. (ES, m/z): [M–H]$^-$ 215.9.

Synthesis of Compound 168.2

Into a 8-mL vial, was placed 168.1 (570 mg, 2.62 mmol, 1 equiv), DCM (2 mL, 0.02 mmol, 0.01 equiv), azetidine (448.8 mg, 7.86 mmol, 3 equiv), DIEA (1015.8 mg, 7.86 mmol, 3 equiv), and HATU (1992.4 mg, 5.24 mmol, 2 equiv). The resulting solution was stirred for 1 overnight at room temperature. The resulting solution was diluted with 50 mL of H$_2$O. The resulting solution was extracted with 3×50 ml of ethyl acetate concentrated under vacuum. The residue was applied onto a Prep TLC with ethyl acetate/petroleum ether (1:10). This resulted in 371 mg (55.1%) of 168.2 as a yellow solid. (ES, m/z): [M–H]$^-$ 255.0.

Synthesis of Compound 168.3

Into a 8-mL vial, was placed 168.2 (361 mg, 1.41 mmol, 1 equiv), AcOH (2 mL, 0.03 mmol, 0.02 equiv), Zn (552.0 mg, 8.44 mmol, 6 equiv). The resulting solution was stirred for 1 hr at room temperature. The solids were filtered out. The resulting solution was diluted with 50 mL of H$_2$O. The resulting solution was extracted with 3×50 ml of ethyl acetate concentrated under vacuum. The residue was applied onto a silica gel column with ethyl acetate/petroleum ether (1:10). This resulted in 190 mg (59.5%) of 168.3 as a white solid. (ES, m/z): [M−H]⁻ 225.0.

Synthesis of Compound 168.4

Into a 20-mL vial, was placed 4-fluoro-[1,1-biphenyl]-3-amine (500 mg, 2.67 mmol, 1 equiv). This was followed by the addition of HCl (2.5 mL, 82.28 mmol, 30.81 equiv). To this was added a solution of NaNO₂ (276.4 mg, 4.01 mmol, 1.5 equiv) in H₂O (2.5 mL). The resulting solution A was stirred for 0.5 hr at 0° C. in a water/ice bath. To a 20-mL vial was placed CuCl₂ (107.7 mg, 0.80 mmol, 0.3 equiv), a solution of SO₂ in AcOH (10 mL). Then added the solution A. The resulting solution was stirred for 0.5 hr at 0° C. in a water/ice bath. The resulting solution was diluted with 30 mL of H₂O. The resulting solution was extracted with 3×20 ml of ethyl acetate, which was concentrated under vacuum. (ES, m/z): [M−H]⁻ 268.9.

Synthesis of I-215

Into a 8-mL vial, was placed 168.3 (70 mg, 0.31 mmol, 1.00 equiv), 168.4 (100 mg, 0.37 mmol, 1.20 equiv), pyridine (1 mL). The resulting solution was stirred for 1 overnight at room temperature. The resulting mixture was concentrated under vacuum. The resulting solution was diluted with 50 mL of H₂O. The resulting solution was extracted with 3×50 mL of ethyl acetate and the organic layers combined. The resulting mixture was concentrated under vacuum. The crude product was purified by Flash-Prep-HPLC with the following conditions (IntelFlash-1): Column, C18 silica gel; mobile phase, ACN/H₂O=15% increasing to ACN/H₂O=60% within 15 min; Detector, UV 254 nm. This resulted in 10 mg (7%) of I-215 as a white solid. (ES, m/z): [M+H]⁺ 461.0, ¹H-NMR (300 MHz, DMSO-d₆, ppm): δ 10.22 (s, 1H), 8.03-7.93 (m, 1H), 7.89 (m, 1H), 7.65-7.34 (m, 7H), 7.30-7.31 (d, J=2.1 Hz, 1H), 3.99-4.07 (m, 4H), 2.17-2.02 (m, 2H).

Example 169. Synthesis of 4-(azetidine-1-carbonyl)-2-chloro-6-[(1-cyclopropyl-N-[4,6-difluoro-[1,1-biphenyl]-3-yl]formamido)sulfonyl]phenylcyclopropanecarboxylate, I-217

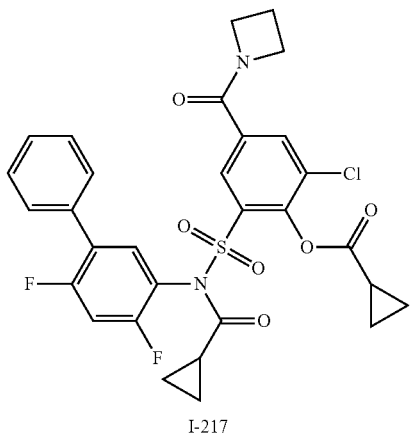

I-217

Synthesis of I-217

Into a 50-mL round-bottom flask, was placed 176.2 (100 mg, 0.21 mmol, 1 equiv), cyclopropanecarbonyl chloride (43.7 mg, 0.42 mmol, 2 equiv), pyridine (5 mL). The resulting solution was stirred for 12 hr at 25° C. The resulting mixture was concentrated under vacuum. The residue was applied onto Prep-TLC with ethyl acetate/petroleum ether (2:1). The crude product was purified by Flash-Prep-HPLC with the following conditions (IntelFlash-1): Column, C18 silica gel; mobile phase, ACN:H₂O=10% increasing to ACN:H₂O=65% within 15 min. This resulted in 30 mg (23.3%) of I-217 as a white solid. (ES, m/z): [M+H]⁺ 615.0, ¹H-NMR (400 MHz, DMSO-d₆, ppm): δ0.38-0.86 (m, 8H), δ1.24-1.54 (m, 2H), δ2.25-2.33 (m, 2H), δ4.08-4.11 (m, 2H), δ4.37-4.52 (s, 2H), δ7.25-7.62 (m, 5H), δ7.71-7.79 (m, 1H), δ7.82-8.16 (m, 1H), δ8.28-8.37 (s, 2H).

Example 170. Synthesis of 3-chloro-5-cyano-N-[4-hydroxy-[1,1-biphenyl]-3-yl]benzene-1-sulfonamide, I-218

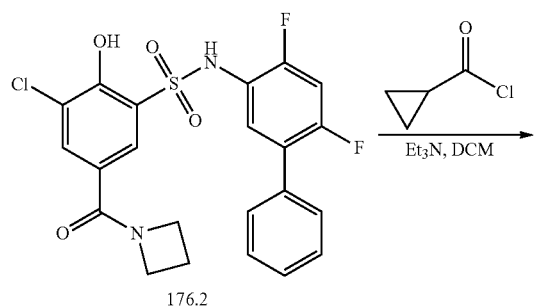

176.2

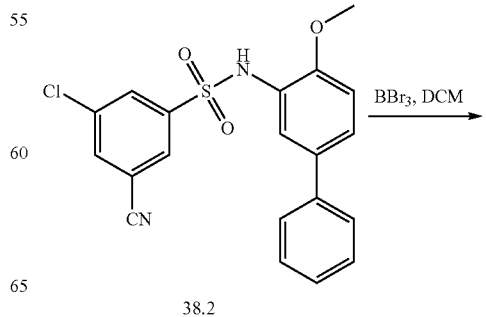

38.2

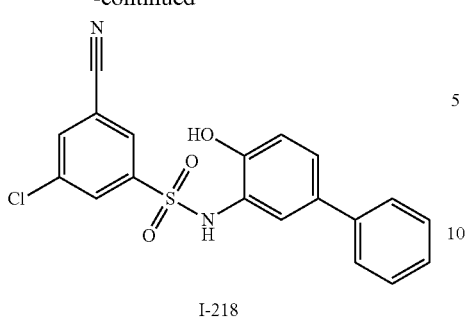

I-218

Synthesis of I-218

Into a 50-mL round-bottom flask, was placed 38.2 (100 mg, 0.25 mmol, 1 equiv), DCM (5 mL), and BBr$_3$ (69.1 mg, 0.28 mmol, 1.10 equiv). The resulting solution was stirred for 2 hr at 25° C. The reaction was then quenched by the addition of 10 mL of water. The resulting solution was extracted with 3×15 ml of ethyl acetate and the organic layers combined. The crude product was purified by Flash-Prep-HPLC with the following conditions (IntelFlash-1): Column, C18 silica gel; mobile phase, ACN:H$_2$O=15% increasing to ACN:H$_2$O=60% within 10 min. This resulted in 81.1 mg of I-218 as an off-white solid. (ES, m/z): [M−H]$^−$ 382.9, $^1$H-NMR (400 MHz, DMSO-d$_6$, ppm): δ6.82-6.84 (d, J=8.4 Hz, 1H), δ7.28-7.35 (m, 2H), δ7.40-7.42 (m, 3H), δ7.44-7.52 (t, J=7.2 Hz, 2H), δ8.05-8.11 (m, 2H), δ8.34-8.35 (s, 1H), δ9.87 (s, 2H).

Example 171. Synthesis of 3-chloro-4-hydroxy-N-(2-methoxy-5-phenylphenyl)benzene-1-sulfonamide, I-416

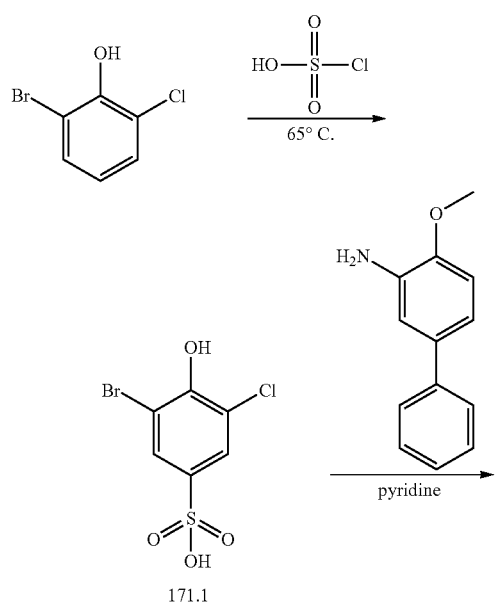

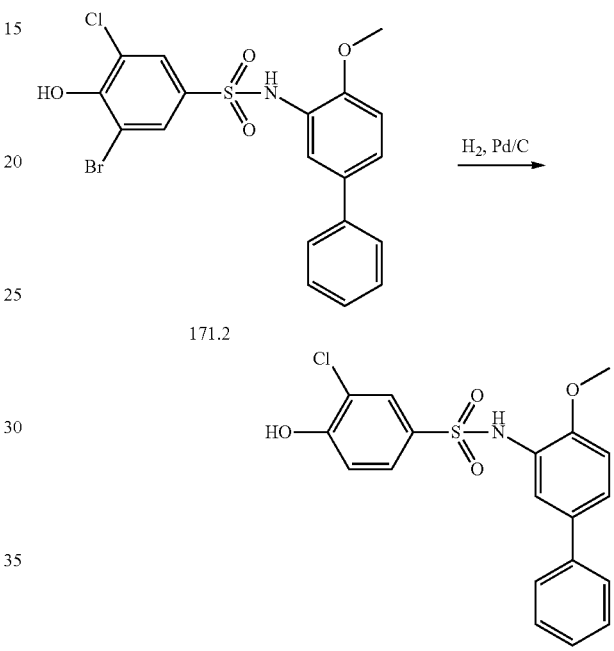

Synthesis of Compound 171.1

Into a 8-mL sealed tube, was placed O-(chlorosulfonyl) oxidanol (1 mL), 2-bromo-6-chlorophenol (500 mg, 2.41 mmol, 1 equiv). The resulting solution was stirred for 2 h at 65° C. The reaction was then quenched by the addition of 5 mL of water/ice. The resulting solution was extracted with 3×15 mL of ethyl acetate and the organic layers combined and concentrated under vacuum. This resulted in 600 mg (81%) of 171.1 as a yellow solid. (ES, m/z): [M−H]$^−$ 284.8.

Synthesis of Compound 171.2

Into a 100-mL round-bottom flask, was placed 332.1 (555 mg, 1.81 mmol, 1 equiv), 2-methoxy-5-phenylaniline (433.7 mg, 2.18 mmol, 1.2 equiv), pyridine (7 mL). The resulting solution was stirred for 2 h at 25° C. The reaction was then quenched by the addition of 15 mL of diluted hydrochloric acid (aq.). The resulting solution was extracted with 3×30 mL of ethyl acetate and the organic layers combined and concentrated under vacuum. The residue was applied onto Prep-TLC with dichloromethane/methanol (20:1). This resulted in 350 mg (41.1%) of 171.2 as a yellow solid. (ES, m/z): [M−H]$^−$ 465.9.

485

Synthesis of Compound I-416

Into a 100-mL round-bottom flask, was placed MeOH (8 mL), 171.2 (200 mg, 0.43 mmol, 1 equiv), Pd/C (40 mg). The flask was evacuated and flushed three times with nitrogen, followed by flushing with hydrogen. The mixture was stirred 1 h at room temperature. The solids were filtered out. The filtrate was concentrated under vacuum. The residue was applied Prep-TLC with dichloromethane/methanol (20:1). This resulted in 70.3 mg (42.2%) of I-416 as a white solid. (ES, m/z): [M–H]⁻ 388.0, ¹H-NMR (300 MHz, DMSO-d₆, ppm): δ3.60 (s, 3H), δ7.00-7.03 (d, J=5.4 Hz, 2H), δ7.30-7.35 (m, 1H), δ7.41-7.54 (m, 7H), δ7.70-7.71 (d, J=2.4 Hz, 1H), δ9.55 (s, 1H), δ11.28 (s, 1H).

Example 172. Synthesis of 5-(azetidine-1-carbonyl)-3-chloro-N-(6-fluoro-1-benzothiophen-5-yl)-2-hydroxybenzene-1-sulfonamide, I-221

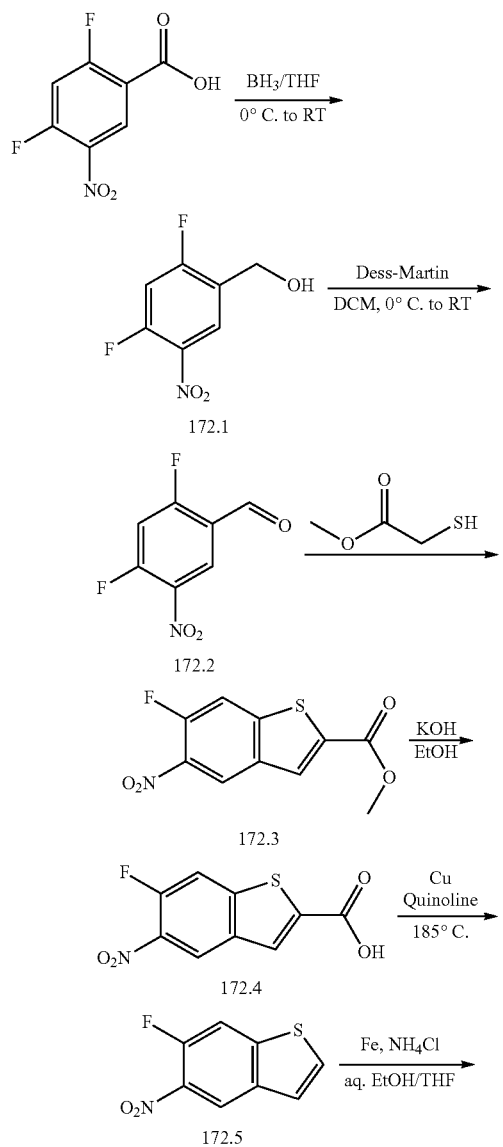

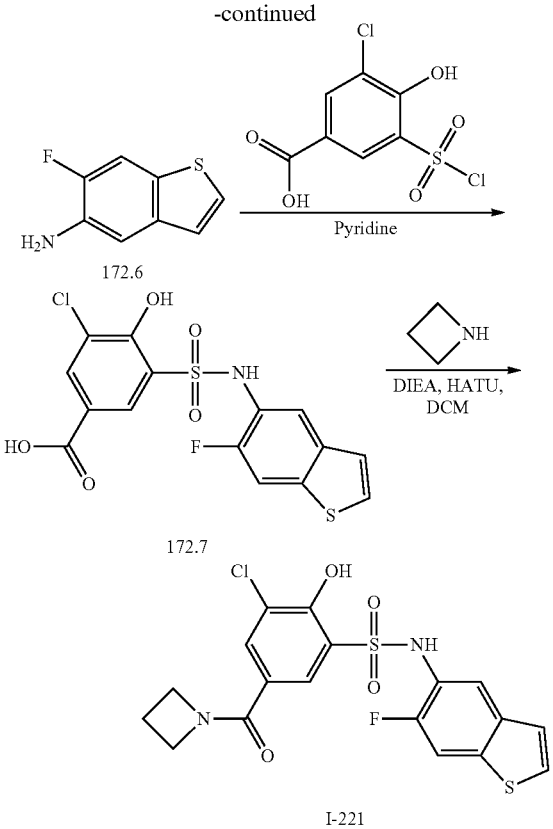

Synthesis of Compound 172.1

Into a 250 mL 3-necked round-bottom flask were added 2,4-difluoro-5-nitrobenzoic acid (20 g, 1 equiv) and BH₃-THF (120 mL) at 0° C. with stirring for 3 h. The reaction was quenched with NaHCO₃ (1 M) at room temperature. The resulting mixture was extracted with EtOAc (2×100 mL). The combined organic layers were washed with EtOAc (2×100 mL), dried over anhydrous Na₂SO₄. After filtration, the filtrate was concentrated under reduced pressure. The residue was purified by silica gel column chromatography, eluted with PE/EtOAc (10:1) to afford 172.1 (20 g, 107.39%) as a brown oil.

Synthesis of Compound 172.2

A mixture of 172.1 (20 g, 105.75 mmol, 1 equiv) and Dess-Martin (53.8 g, 126.90 mmol, 1.2 equiv) in DCM (400 mL, 6292.02 mmol, 59.50 equiv) was stirred for 2 h at 0° C. under nitrogen atmosphere. The resulting mixture was filtered, the filter cake was washed with EtOAc (2×100 mL). The filtrate was concentrated under reduced pressure. The reaction was quenched with NaHCO₃ (1 M) at room temperature the filtrate was concentrated under reduced pressure. The residue was purified by silica gel column chromatography, eluted with PE/EtOAc (10:1) to afford 172.2 (18.7 g, 94.5%) as a brown oil.

Synthesis of Compound 172.3

A mixture of 172.2 (5 g, 26.72 mmol, 1 equiv) and K₂CO₃ (7.4 g, 53.45 mmol, 2 equiv) in DMF (50 mL, 646.09 mmol, 24.18 equiv) was stirred for 1 h at 60° C. under nitrogen atmosphere. To the above mixture was added methyl 2-sulfanylacetate (2.8 g, 26.72 mmol, 1 equiv) dropwise over 0.1 h at 60° C. The resulting mixture was stirred for additional 12 h at 60° C. The resulting mixture was extracted with EtOAc (2×100 mL). The combined organic layers were washed with EtOAc (2×100 mL), dried over anhydrous Na$_2$SO$_4$. After filtration, the filtrate was concentrated under reduced pressure. The crude product mixture was used in the next step directly without further purification.

Synthesis of Compound 172.4

A mixture of 172.3 (5 g, 19.59 mmol, 1 equiv) and KOH (5.5 g, 97.95 mmol, 5 equiv) in EtOH, H$_2$O (100 mL, 1721.35 mmol, 87.86 equiv) was stirred for 2 h at 60° C. under nitrogen atmosphere. The reaction was quenched with HCl (1 M) at room temperature. The aqueous layer was extracted with EtOAc (2×100 mL). The residue was purified by Prep-TLC (CH$_2$Cl$_2$/MeOH 20:1) to afford 172.4 (1.2 g, 25%) as a yellow solid.

Synthesis of Compound 172.5

A mixture of 172.4 (1.05 g, 4.35 mmol, 1 equiv) and Cu (0.8 g, 13.06 mmol, 3 equiv) in Quinoline (5 mL, NaN mmol, NaN equiv) was stirred for 4 h at 185° C. under nitrogen atmosphere. The reaction was quenched with HCl (1 M) at room temperature. The aqueous layer was extracted with EtOAc (2×100 mL). After filtration, the filtrate was concentrated under reduced pressure. The residue was purified by Prep-TLC (PE/EtOAc 2:1) to afford 172.5 (320 mg, 37%) as a yellow solid.

Synthesis of Compound 172.6

To a stirred mixture of 172.5 (310 mg, 1.57 mmol, 1 equiv) and Fe (351.2 mg, 6.29 mmol, 4 equiv) in EtOH (6 mL, 103.28 mmol, 65.69 equiv), H$_2$O (1.5 mL, 83.26 mmol, 52.96 equiv) and THF (3 mL, 37.03 mmol, 23.55 equiv) was added NH$_4$Cl (841.0 mg, 15.72 mmol, 10 equiv) in portions at 100° C. under nitrogen atmosphere. The resulting mixture was extracted with EtOAc (2×100 mEL). The combined organic layers were washed with EtOAc (2×100 mL), dried over anhydrous Na$_2$SO$_4$. After filtration, the filtrate was concentrated under reduced pressure. The residue was purified by Prep-TLC (PE/EtOAc 2:1) to afford 172.6 (230 mg, 87%) as a white solid.

Synthesis of Compound 172.7

A mixture of 6-fluoro-1-benzothiophen-5-amine 172.6 (180 mg, 1.08 mmol, 1 equiv) and 3-chloro-5-(chlorosulfonyl)-4-hydroxybenzoic acid (583.6 mg, 2.15 mmol, 2 equiv) in pyridine (6 mL) was stirred for 2 h at 50° C. under nitrogen atmosphere. The filtrate was concentrated under reduced pressure. The crude product was purified by reverse phase flash with the following conditions (from CH$_3$CN/H$_2$O=0:100 to CH$_3$CN/H$_2$O=40:60 in 30 mins UV: 254/220) to afford 172.7 (130 mg, 30%) as a yellow solid.

Synthesis of I-221

To a stirred mixture of 172.7 (130 mg, 0.32 mmol, 1 equiv) and azetidine (55.4 mg, 0.97 mmol, 3 equiv) in DMF (1.3 mL, 16.80 mmol, 51.92 equiv) were added DIEA (167.3 mg, 1.29 mmol, 4 equiv) and HATU (246.0 mg, 0.65 mmol, 2 equiv) in portions at room temperature under nitrogen atmosphere. The resulting solution was stirred for overnight at room temperature under nitrogen atmosphere. The resulting mixture was extracted with EtOAc (2×100 mL). The combined organic layers were washed with EtOAc (2×100 mL), dried over anhydrous Na$_2$SO$_4$. After filtration, the filtrate was concentrated under reduced pressure. The residue was purified by Prep-TLC (CH$_2$Cl$_2$/MeOH 10:1) to afford I-221 (23.8 mg, 16.7%) as a white solid. (ES, m/z): [M–H]$^-$ 439.0. $^1$H-NMR (400 MHz, DMSO-d$_6$, ppm): δ2.16-2.23 (m, 2H), δ3.90-4.29 (s, 4H), δ7.34-7.35 (d, J=5.6 Hz, 1H), δ7.52-7.53 (d, J=2.4 Hz, 1H), δ7.63-7.67 (m, 2H), δ7.73-7.75 (d, J=7.6 Hz, 1H), δ7.86-7.87 (d, J=2.4 Hz, 1H).

Example 173. Synthesis of 5-(azetidine-1-carbonyl)-3-chloro-N-(5-fluoro-2-phenylpyridin-4-yl)-2-hydroxybenzene-1-sulfonamide, I-222

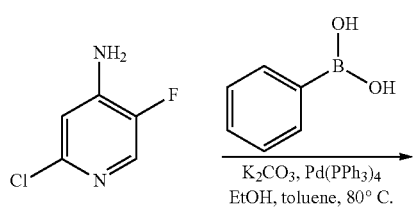

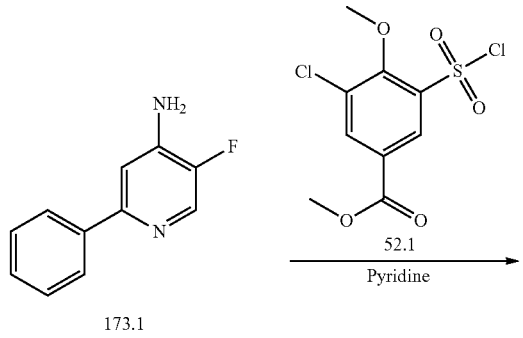

173.1

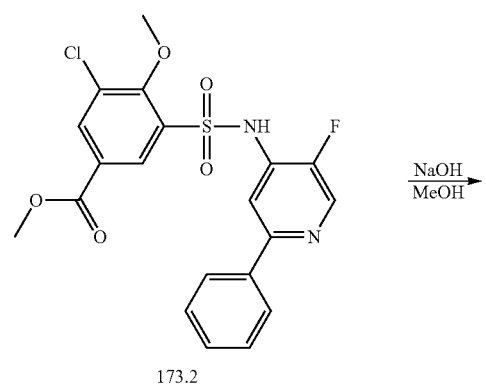

173.2

-continued

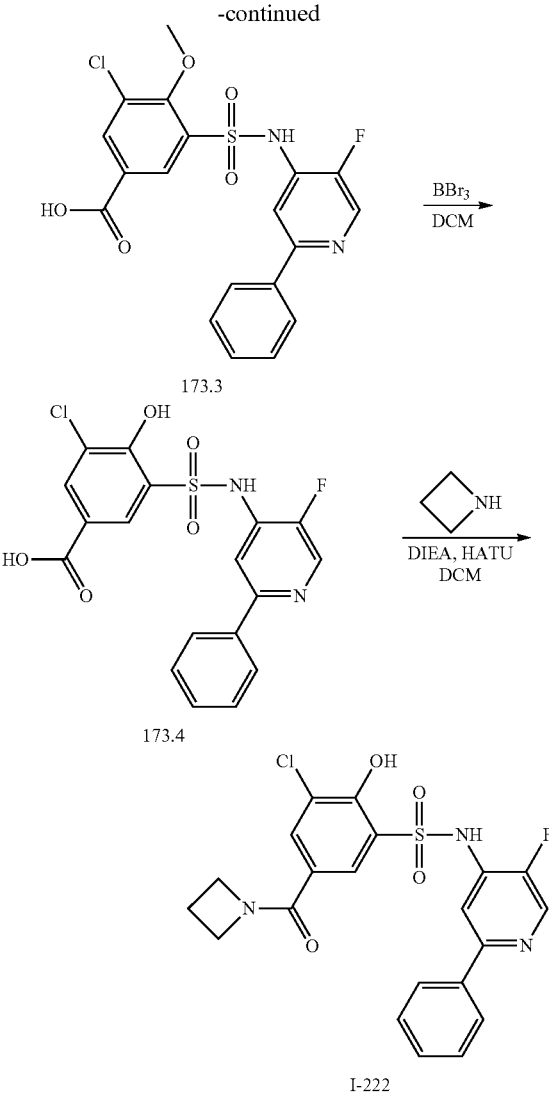

Synthesis of 173.1

Into a 50-mL 3-necked round-bottom flask purged and maintained with an inert atmosphere of nitrogen, was placed 2-chloro-5-fluoropyridin-4-amine (1 g, 6.82 mmol, 1 equiv), phenylboronic acid (998.4 mg, 8.19 mmol, 1.2 equiv), $K_2CO_3$ (4715.3 mg, 34.12 mmol, 5 equiv), EtOH (10 mL, 172.14 mmol, 25.23 equiv), toluene (10 mL, 93.99 mmol, 13.77 equiv), $Pd(PPh_3)_4$ (2365.5 mg, 2.05 mmol, 0.3 equiv). The resulting solution was stirred overnight at 80° C. in an oil bath. The resulting solution was diluted with 200 mL of $H_2O$. The resulting solution was extracted with 3×100 mL of ethyl acetate concentrated under vacuum. The crude product was purified by Flash-Prep-HPLC with the following conditions (IntelFlash-1): Column, C18 silica gel; mobile phase, $ACN/H_2O=15\%$ increasing to $ACN/H_2O=60\%$ within 15 min; Detector, UV 254 nm. This resulted in 998 mg (77.7%) of 173.1 as a white solid. (ES, m/z): $[M-H]^-$ 187.0.

Synthesis of 173.2

Into a 8-mL vial, was placed 173.1 (500 mg, 2.66 mmol, 1 equiv), 52.1 (953.6 mg, 3.19 mmol, 1.2 equiv), pyridine (3 mL, 37.27 mmol, 14.03 equiv). The resulting solution was stirred for 1 overnight at room temperature. The resulting mixture was concentrated under vacuum. The crude product was purified by Flash-Prep-HPLC with the following conditions (IntelFlash-1): Column, C18 silica gel; mobile phase, $ACN/H_2O=15\%$ increasing to $ACN/H_2O=60\%$ within 15 min; Detector, UV 254 nm. This resulted in 200 mg (16.7%) of 238.2 as a yellow solid. (ES, m/z): $[M-H]^-$ 449.0.

Synthesis of 173.3

Into a 50-mL 3-necked round-bottom flask, was placed 173.2 (180 mg, 0.40 mmol, 1 equiv), MeOH (5 mL, 123.49 mmol, 309.33 equiv), NaOH (79.8 mg, 2.00 mmol, 5 equiv), $H_2O$ (5 mL, 0.28 mmol, 0.70 equiv). The resulting solution was stirred for 1 overnight at room temperature. The resulting solution was diluted with 200 mL of $H_2O$. The pH value of the solution was adjusted to 7 with AcOH. The resulting solution was extracted with 3×100 mL of ethyl acetate. The residue was applied onto a prep TLC with dichloromethane/methanol (8:1). This resulted in 70 mg (40%) of 173.3 as a yellow solid. (ES, m/z): $[M-H]^-$ 435.0.

Synthesis of 173.4

Into a 8-mL vial, was placed 173.3 (60 mg, 0.14 mmol, 1 equiv), DCM (1 mL, 0.01 mmol, 0.09 equiv), $BBr_3$ (412.9 mg, 1.65 mmol, 12 equiv). The resulting solution was stirred for 0.5 hr at 0° C. in a water/ice bath. The resulting solution was stirred overnight at room temperature. The resulting solution was diluted with 100 mL of $H_2O$. The resulting solution was extracted with 3×100 mL of ethyl acetate concentrated under vacuum. The residue was applied onto a silica gel column with dichloromethane/methanol (8:1). This resulted in 45 mg (77%) of 173.4 as a yellow solid. (ES, m/z): $[M-H]^-$ 399.0.

Synthesis of I-222

Into a 8-mL vial, was placed 173.4 (45 mg, 0.11 mmol, 1 equiv), azetidine (30.4 mg, 0.53 mmol, 5 equiv), DIEA (41.3 mg, 0.32 mmol, 3 equiv), DCM (1 mL, 0.01 mmol, 0.11 equiv), HATU (60.7 mg, 0.16 mmol, 1.5 equiv). The resulting solution was stirred for 1 overnight at room temperature. The resulting mixture was concentrated under vacuum. The crude product was purified by Flash-Prep-HPLC with the following conditions (IntelFlash-1): Column, C18 silica gel; mobile phase, $ACN/H_2O=15\%$ increasing to $ACN/H_2O=60\%$ within 15 min; Detector, UV 254 nm. This resulted in 2 mg (4%) of I-222 as a white solid. (ES, m/z): $[M-H]^-$ 460.1, $^1H$-NMR (300 MHz, DMSO-$d_6$, ppm): 2.22-2.27 (m, 2H), δ4.09-4.32 (m, 4H), δ7.41-7.55 (t, J=1.5 Hz, 3H), δ7.69-7.79 (m, 2H), δ7.79-7.81 (s, 1H), δ7.81-7.91 (s, 1H), δ7.99-8.11 (s, 1H), δ8.21-8.35 (s, 1H).

Example 174. Synthesis of 5-chloro-N-[4-fluoro-[1,1-biphenyl]-3-yl]-1-benzofuran-7-sulfonamide, I-223

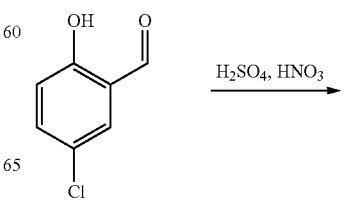

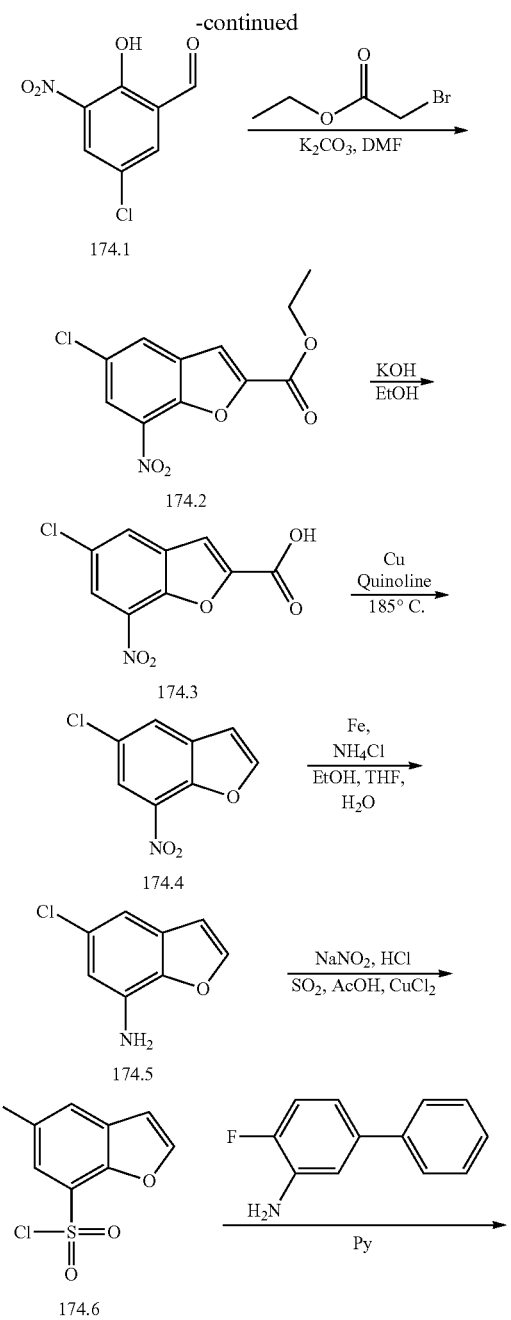

Synthesis of 174.1

I Into a 100-mL 3-necked round-bottom flask, was placed 5-chloro-2-hydroxybenzaldehyde (10 g, 63.87 mmol, 1 equiv). This was followed by the addition of $H_2SO_4$ (15 mL, 281.41 mmol, 4.41 equiv) at 0° C. To this was added $HNO_3$ (6 mL, 133.78 mmol, 2.09 equiv) dropwise with stirring at 0° C. in 1 hr. The resulting solution was stirred for 10 min at 0° C. in an ice/salt bath. The reaction was then quenched by the addition of 200 mL of water/ice. The resulting solution was extracted with 3×100 mL of dichloromethane concentrated under vacuum. The crude product was re-crystallized from EA/PE in the ratio of 1:3. This resulted in 7.946 g (61.7%) of 174.1 as a yellow solid.

Synthesis of 174.2

Into a 100-mL 3-necked round-bottom flask purged and maintained with an inert atmosphere of nitrogen, was placed 174.1 (4 g, 19.85 mmol, 1 equiv), DMF (40 mL, 516.87 mmol, 26.05 equiv), $K_2CO_3$ (8228.2 mg, 59.54 mmol, 3 equiv), ethyl 2-bromoacetate (3645.6 mg, 21.83 mmol, 1.1 equiv). The resulting solution was stirred for 2 hr at room temperature. The resulting solution was allowed to react, with stirring, for an additional 1 hr while the temperature was maintained at 800° C. in an oil bath. The resulting solution was diluted with 100 mL of $H_2O$. The resulting solution was extracted with 3×100 mL of ethyl acetate concentrated under vacuum. The residue was applied onto a silica gel column with ethyl acetate/petroleum ether (1:10). This resulted in 1.2 g (22%) of 174.2 as a yellow solid.

Synthesis of 174.3

Into a 50-mL 3-necked round-bottom flask, was placed 174.2 (1.1 g, 4.08 mmol, 1 equiv), EtOH (10 mg, 0.22 mmol, 0.05 equiv), KOH (457.8 mg, 8.16 mmol, 2 equiv). The resulting solution was stirred for 1 overnight at room temperature. The resulting solution was diluted with 100 mL of $H_2O$. The pH value of the solution was adjusted to 6 with AcOH. The resulting solution was extracted with 2×100 mL of ethyl acetate concentrated under vacuum. The crude product was purified by Flash-Prep-HPLC with the following conditions (IntelFlash-1): Column, C18 silica gel; mobile phase, $ACN/H_2O=15\%$ increasing to $ACN/H_2O=60\%$ within 15 min; Detector: UV 254 nm. This resulted in 600 mg (61%) of 174.3 as a yellow solid.

Synthesis of 174.4

Into a 100-mL 3-necked round-bottom flask purged and maintained with an inert atmosphere of nitrogen, was placed 174.3 (580 mg, 2.40 mmol, 1 equiv), quinoline (30 ml), CuO (192 mg, 2.4 mmol, 1 equiv). The resulting solution was stirred for 4 hr at 185° C. The resulting solution was diluted with 200 mL of $H_2O$. The resulting solution was extracted with 3×100 mL of ethyl acetate. The resulting mixture was washed with 2×50 ml of HCl (aq). The resulting mixture was concentrated under vacuum. The crude product was purified by Flash-Prep-HPLC with the following conditions (Intel-Flash-1): Column, C18 silica gel; mobile phase, $ACN/H_2O=15\%$ increasing to $ACN/H_2O=60\%$ within 15 min; Detector: UV 254 nm. This resulted in 320 mg (67%) of 174.4 as a yellow solid.

Synthesis of 174.5

Into a 50-mL 3-necked round-bottom flask purged and maintained with an inert atmosphere of nitrogen, was placed 174.4 (490 mg, 2.48 mmol, 1 equiv), Fe (554.0 mg, 9.92 mmol, 4 equiv), $NH_4Cl$ (1326.6 mg, 24.80 mmol, 10 equiv), EtOH (10 mL, 172.14 mmol, 69.41 equiv), $H_2O$ (5 mL, 277.54 mmol, 111.91 equiv), THF (5 mL, 61.71 mmol, 24.88 equiv). The resulting solution was stirred for 1 overnight at 90° C. in an oil bath. The resulting solution was diluted with 100 mL of $H_2O$. The resulting solution was extracted with 3×100 mL of ethyl acetate concentrated under vacuum. The residue was applied onto a Prep TLC with ethyl acetate/petroleum ether (1:5). This resulted in 264 mg (63.5%) of 174.5 as a yellow solid.

Synthesis of 174.6

Into a 8-mL vial, the mixture A was placed 174.5 (120 mg, 0.72 mmol, 1 equiv). This was followed by the addition of HCl (1.2 mL, 0.03 mmol, 0.05 equiv) at 0° C. To this was added a solution of $NaNO_2$ (74.1 mg, 1.07 mmol, 1.5 equiv) in $H_2O$ (0.6 mL) dropwise with stirring at 0° C. The mixture B was added a solution of $SO_2$ in AcOH (3 mL) at 0° C. To the mixture B was added $CuCl_2$ (57.8 mg, 0.43 mmol, 0.6 equiv) at 0° C. The resulting solution B was stirred for 0.5 hr at 0° C. in a water/ice bath. The resulting solution A was allowed to react, with stirring, for an additional 0.5 hr while the temperature was maintained at 0° C. in a water/ice bath. The resulting solution was diluted with 100 mL of $H_2O$. The resulting solution was extracted with 3×100 mL of ethyl acetate concentrated under vacuum. This resulted in 140 mg (78%) of 174.6 as a yellow solid.

Synthesis of I-223

Into a 8-mL vial, was placed 174.6 (130 mg, 0.52 mmol, 1 equiv), 4-fluoro-[1,1-biphenyl]-3-amine (116.3 mg, 0.62 mmol, 1.2 equiv), pyridine (1 mL, 0.01 mmol, 0.02 equiv). The resulting solution was stirred for 0.5 hr at room temperature. The resulting mixture was concentrated under vacuum. The crude product was purified by Flash-Prep-HPLC with the following conditions (IntelFlash-1): Column, C18 silica gel; mobile phase, $ACN/H_2O$=15% increasing to $ACN/H_2O$=60% within 15 min; Detector: UV 254 nm. This resulted in 149.7 mg (71.9%) of I-223 as a white solid. (ES, m/z): $[M+H]^+$ 402.0, $^1$H-NMR (300 MHz, DMSO-$d_6$, ppm): 7.09 (s, 1H), δ7.12-7.23 (m, 1H), δ7.32-7.52 (m, 7H), δ7.60 (s, 1H), δ8.05 (s, 1H), δ8.23 (s, 1H), δ10.67-10.81 (s, 1H).

Example 175. Synthesis of 3,5-dichloro-N-(4-hydroxy-[1,1'-biphenyl]-3-yl)benzenesulfonamide, I-224

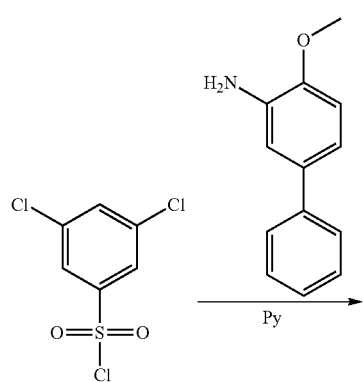

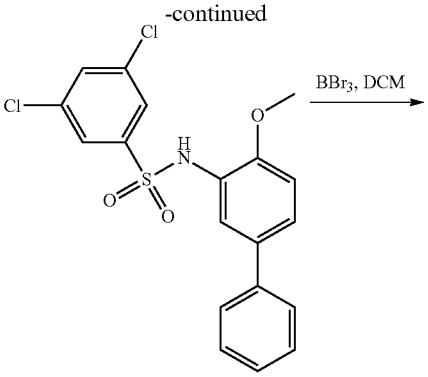

175.1

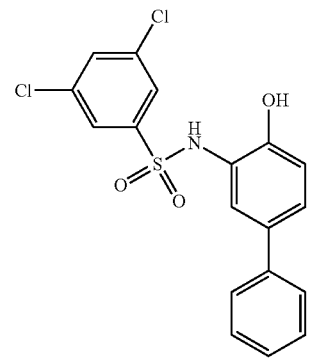

I-224

Synthesis of Compound 175.1

Into a 25-mL round-bottom flask purged and maintained with an inert atmosphere of nitrogen, was placed 3,5-dichlorobenzene-1-sulfonyl chloride (200 mg, 0.81 mmol, 1 equiv), pyridine (5 mL), 4-methoxy-[1,1-biphenyl]-3-amine (162.3 mg, 0.81 mmol, 1 equiv). The resulting solution was stirred for 0.5 hr at room temperature. The resulting mixture was concentrated. The residue was applied onto a silica gel column with ethyl acetate/petroleum ether (1:1). This resulted in 200 mg (yield=60%) of 175.1 as a white solid.

Synthesis of I-224

Into a 20-mL round-bottom flask purged and maintained with an inert atmosphere of nitrogen, was placed 175.1 (180 mg, 0.44 mmol, 1 equiv), $BBr_3$ (0.9 mL, 1M in DCM, 0.9 mmol, 2.00 equiv), DCM (5 mL). The resulting solution was stirred for 12 hr at room temperature. The resulting solution was extracted with 3×10 mL of ethyl acetate. The resulting mixture was washed with 1×10 mL of brine. The mixture was dried over anhydrous sodium sulfate and concentrated. The resulting mixture was concentrated. The residue was applied onto a silica gel column with ethyl acetate/petroleum ether (1:1). This resulted in 88.9 mg (yield=51%) of I-224 as a white solid. (ES, m/z): $[M-H]^-$ 391.9, $^1$H-NMR (DMSO-$d_6$, 400 MHz, ppm): δ9.89 (s, 2H), δ7.95 (s, 1H), δ7.72 (s, 2H), δ7.52-7.44 (m, 2H), δ7.42-7.41 (m, 3H), δ7.36-7.29 (m, 2H), δ6.86-6.84 (d, J=8.4 Hz, 1H).

495

Example 176. Synthesis of N-((5-(azetidine-1-carbonyl)-3-chloro-2-hydroxyphenyl) sulfonyl)-N-(4,6-difluoro-[1,1'-biphenyl]-3-yl)cyclopropanecarboxamide, I-229

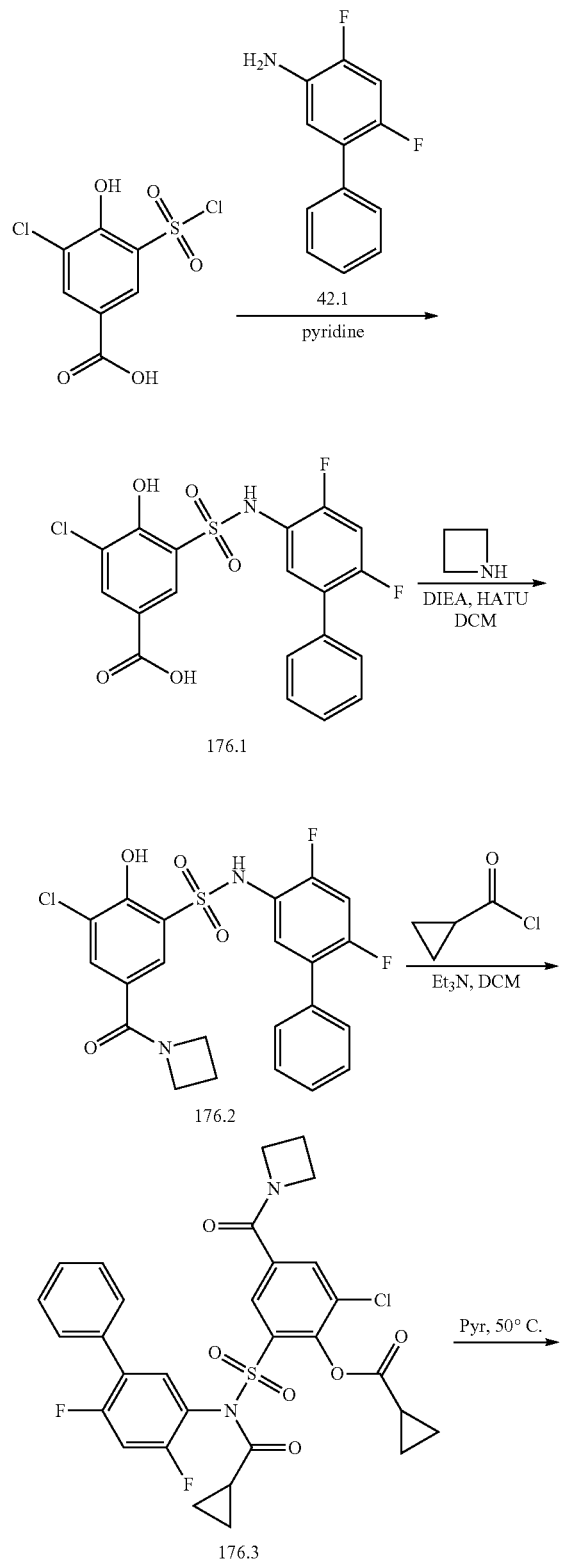

496

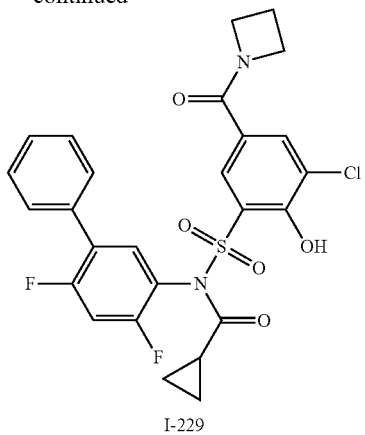

I-229

Synthesis of Compound 176.1

Into a 100-mL 3-necked round-bottom flask, was placed 3-chloro-5-(chlorosulfonyl)-4-hydroxybenzoic acid (3 g, 11.07 mmol, 1 equiv), 42.1 (2725.4 mg, 13.28 mmol, 1.2 equiv), pyridine (30 mL). The resulting solution was stirred for 1 overnight at room temperature. The resulting mixture was concentrated under vacuum. The resulting solution was diluted with 100 mL of $H_2O$. The resulting solution was extracted with 3×100 ml of ethyl acetate. The resulting mixture was concentrated under vacuum. The residue was applied onto a silica gel column with dichloromethane/methanol (10:1). This resulted in 2.7 g (55%) of 176.1 as a yellow solid. (ES, m/z): $[M-H]^-$ 438.0.

Synthesis of Compound 176.2

Into a 25-mL round-bottom flask, was placed 241.1 (300 mg, 0.68 mmol, 1 equiv), DCM (5 mL), DIEA (264.5 mg, 2.05 mmol, 3 equiv), azetidine (77.9 mg, 1.36 mmol, 2 equiv), HATU (389.0 mg, 1.02 mmol, 1.5 equiv). The resulting solution was stirred for 12 hr at 25° C. The reaction was then quenched by the addition of 15 mL of water. The resulting solution was extracted with 3×20 ml of ethyl acetate and the organic layers combined. The residue was applied onto Prep-TLC with dichloromethane/methanol (10:1). This resulted in 220 mg (67%) of 176.2 as a light yellow solid. (ES, m/z): $[M-H]^-$ 477.0.

Synthesis of Compound 176.3

Into a 50-mL round-bottom flask, was placed 241.2 (100 mg, 0.21 mmol, 1 equiv), cyclopropanecarbonyl chloride (43.7 mg, 0.42 mmol, 2 equiv), pyridine (5 mL). The resulting solution was stirred for 12 hr at 25° C. The resulting mixture was concentrated under vacuum. The residue was applied onto Prep-TLC with ethyl acetate/petroleum ether (2:1). The crude product was purified by Flash-Prep-HPLC with the following conditions (IntelFlash-1): Column, C18 silica gel; mobile phase, $ACN:H_2O=10\%$ increasing to $ACN:H_2O=65\%$ within 15 min; Detector, UV 254 nm. This resulted in 30 mg (23%) of 176.3 as a white solid. (ES, m/z): $[M-H]^-$ 613.1.

Synthesis of I-229

Into a 25-mL round-bottom flask, was placed 176.3 (20 mg, 0.03 mmol, 1 equiv), pyridine (5 mL). The resulting solution was stirred for 12 hr at 50° C. The resulting mixture was concentrated under vacuum. The crude product was purified by Flash-Prep-HPLC with the following conditions (IntelFlash-1): Column, C18 silica gel; mobile phase, ACN:$H_2O$=15% increasing to ACN:$H_2O$=60% within 10 min; Detector, UV 254 nm. This resulted in 1-229 (6.1 mg, 34%) as a white solid. (ES, m/z): [M−H]⁻ 545.0, ¹H-NMR (400 MHz, DMSO-$d_6$, ppm): δ0.61-0.76 (s, 2H), δ0.86-0.93 (s, 2H), δ1.69-1.78 (m, 1H), δ2.21-2.33 (m, 2H), δ3.97-4.19 (m, 4H), δ6.95-7.30 (m, 1H), δ7.31-7.35 (m, 1H), δ7.43-7.52 (m, 3H), δ7.54-7.68 (m, 3H), δ7.85-8.31 (t, J=3.6 Hz, 1H).

Example 177. Synthesis of N-[4,6-difluoro-[1,1-biphenyl]-3-yl]-2-hydroxybenzene-1-sulfonamide, I-230

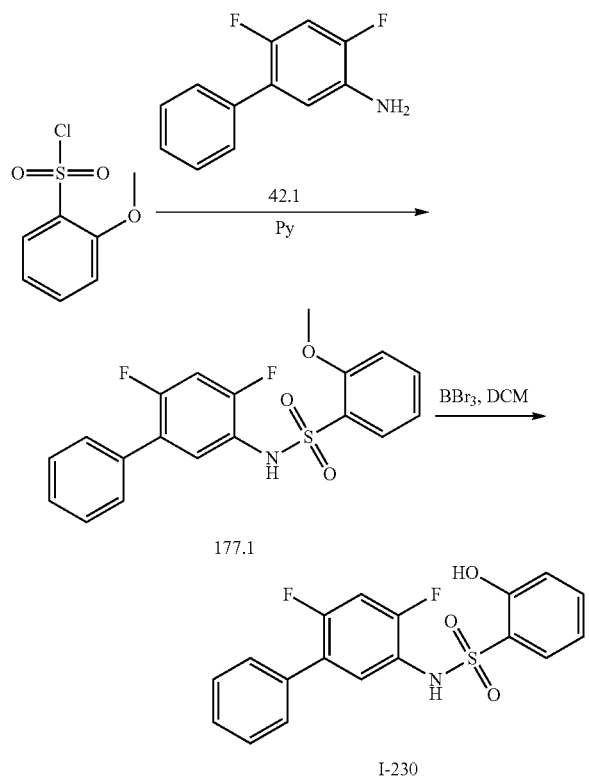

Synthesis of Compound 177.1

Into a 8-mL vial, was placed 2-methoxybenzene-1-sulfonyl chloride (200 mg, 0.97 mmol, 1 equiv), pyridine (2 mL), 42.1 (198.6 mg, 0.97 mmol, 1 equiv). The resulting solution was stirred overnight at room temperature. The resulting mixture was concentrated under vacuum. The crude product was purified by Flash-Prep-HPLC with the following conditions (IntelFlash-1): Column, C18; mobile phase, ACN/$H_2O$=15% increasing to ACN/$H_2O$=65% within 15 mins; Detector, UV 254 nm. This resulted in 164 mg (45.1%) of 177.1 as a white solid.

Synthesis of I-230

Into a 8 mL vial, was placed 177.1 (200 mg, 0.53 mmol, 1 equiv), DCM (2 mL). BBr₃ (400.4 mg, 1.60 mmol, 3 equiv) was added at 0° C. The resulting solution was stirred overnight in a water/ice bath. The reaction was then quenched by the addition of 50 mL of water. The resulting solution was extracted with 3×50 ml of ethyl acetate and concentrated under vacuum. The residue was purified by Prep-TLC (PE/EtOAc=2:1) to afford I-230 (55.2 mg, 28.6%) as a white solid. (ES, m/z): [M−H]⁻ 359.9, ¹H-NMR (400 MHz, DMSO-$d_6$, ppm): 6.84-6.88 (t, J=7.2 Hz, 1H), 6.99-7.01 (d, J=8.0 Hz, 1H), 7.09-7.36 (m, 4H), 7.38-7.48 (m, 4H), 7.55-7.57 (m, 1H).

Example 178. Synthesis of 3-chloro-5-(N-(5-cyclopropyl-2,4-difluorophenyl) sulfamoyl)-4-hydroxy-N,N-dimethylbenzamide, I-231

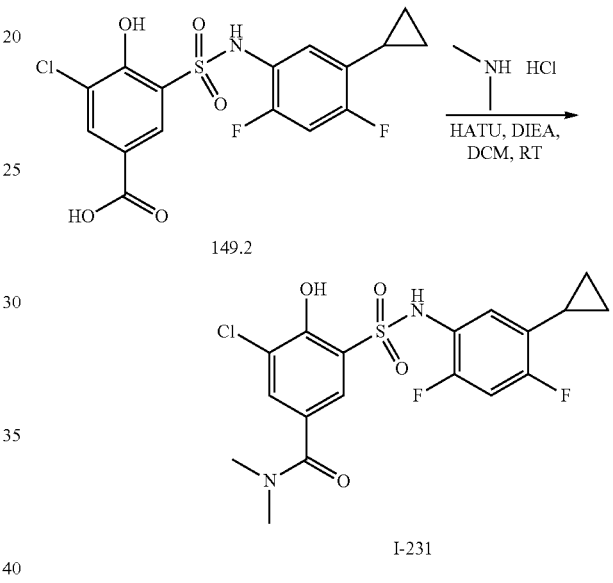

Synthesis of I-231

To a stirred solution of 149.2 (100 mg, 0.25 mmol, 1 equiv) and dimethylamine hydrochloride (40.4 mg, 0.50 mmol, 2.00 equiv) in DCM (2 mL) were added DIEA (64.0 mg, 0.50 mmol, 2.00 equiv) and HATU (141.3 mg, 0.37 mmol, 1.50 equiv). The resulting mixture was stirred for overnight at room temperature under nitrogen atmosphere. The resulting mixture was diluted with water (10 mL). The aqueous layer was extracted with $CH_2Cl_2$ (3×10 mL). The resulting mixture was concentrated under reduced pressure. The residue was purified by reverse flash chromatography with the following conditions: column, C 18 silica gel; mobile phase, ACN in water ($NH_4HCO_3$), 0% to 75% gradient in 35 min; detector, UV 254 nm. This resulted in 1-231 (30.6 mg, 28.6%) as a white solid. (ES, m/z): [M+H]⁺ 431.1, ¹H-NMR (300 MHz, DMSO-$d_6$, ppm): δ0.40-0.44 (m, 2H), δ0.85-0.91 (m, 2H), δ1.85-1.90 (m, 1H), δ2.89 (s, 6H), δ6.68-6.74 (t, J=8.4 Hz, 1H), δ6.87-7.32 (m, 3H), δ7.36-7.37 (d, J=2.4 Hz, 1H), δ7.52-7.53 (d, J=1.8 Hz, 1H).

Example 179. Synthesis of 3,5-dichloro-N-(2-fluoro-4-(pyridin-2-yl)phenyl)-2-hydroxybenzenesulfonamide, I-235

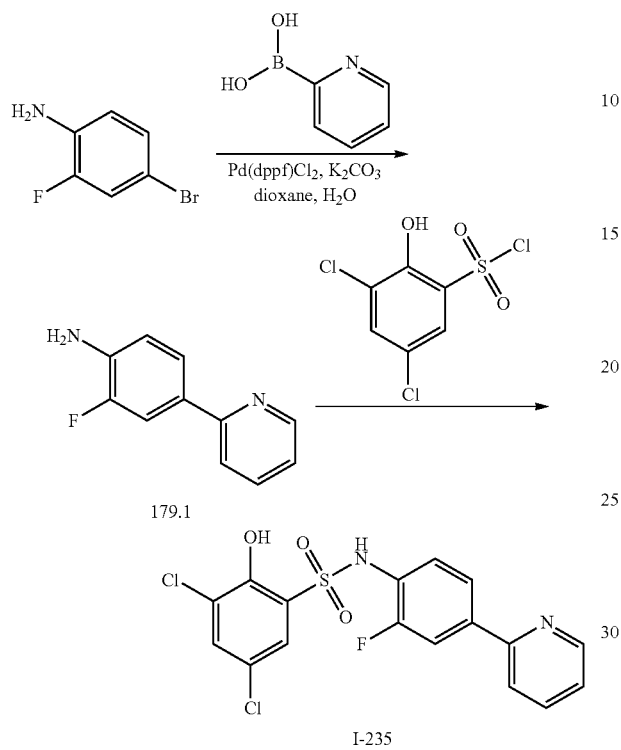

Synthesis of Compound 179.1

Into a 50-mL round-bottom flask purged and maintained with an inert atmosphere of nitrogen, was placed 4-bromo-2-fluoroaniline (1 g, 5.26 mmol, 1 equiv), (pyridin-2-yl)boronic acid (970.3 mg, 7.89 mmol, 1.5 equiv), dioxane (10 mL), $H_2O$ (2 mL), $K_2CO_3$ (1454.7 mg, 10.53 mmol, 2 equiv), Pd(dppf)$Cl_2$ (385.1 mg, 0.53 mmol, 0.1 equiv). The resulting solution was stirred overnight at 90° C. The resulting mixture was concentrated. The residue was dissolved in 100 mL of $H_2O$. The resulting solution was extracted with 2×100 mL of ethyl acetate. The residue was applied onto a silica gel column with ethyl acetate/petroleum ether (1:1). This resulted in 100 mg (10.1%) of 179.1 as a brown solid.

Synthesis of I-235

Into a 8-mL vial, was placed 179.1 (70 mg, 0.37 mmol, 1 equiv), 3,5-dichloro-2-hydroxybenzene-1-sulfonyl chloride (116.7 mg, 0.45 mmol, 1.2 equiv), Pyridine (2 mL). The resulting solution was stirred overnight at 25° C. The resulting mixture was concentrated. The residue was applied onto a Prep TLC with ethyl acetate/petroleum ether (1:1). The crude product was purified by Flash-Prep-HPLC with the following conditions (IntelFlash-1): Column, silica gel; mobile phase, water/acetonitrile=90:10 increasing to water/acetonitrile=0:100 within 30 min; Detector, UV 254 nm. This resulted in 6 mg (4%) of I-235 as a white solid. (ES, m/z): [M+H]$^+$ 413.1, $^1$H-NMR (400 MHz, DMSO-$d_6$, ppm): δ6.95-7.26 (m, 3H), δ7.28-7.33 (m, 1H), δ7.35-7.43 (s, 1H), δ7.44-7.61 (s, 1H), δ7.61-7.79 (s, 1H), δ7.81-7.95 (m, 2H), δ8.05-8.06 (d, J=2.0 Hz, 1H), δ8.64-8.65 (m, 1H).

Example 180. Synthesis of 4-(azetidine-1-carbonyl)-2-chloro-6-(N-(4,6-difluoro-[1,1'-biphenyl]-3-yl)sulfamoyl)phenyl cyclopropanecarboxylate, I-236

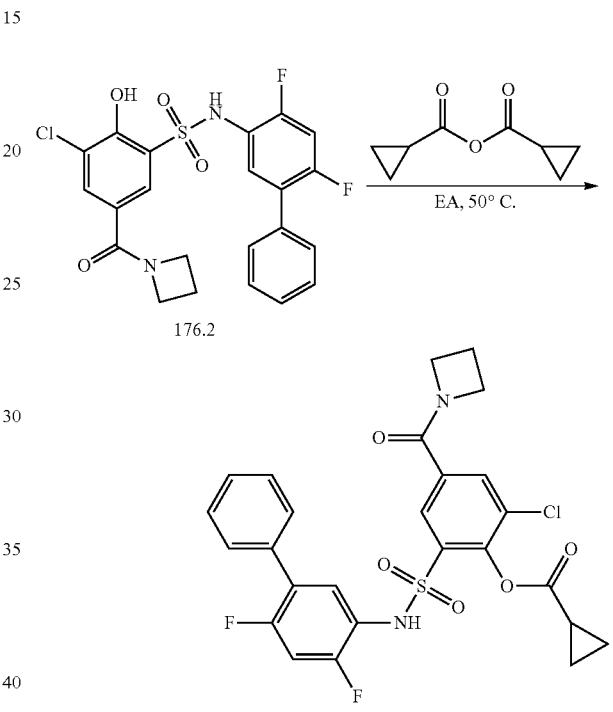

Synthesis of I-236

Into a 50-mL round-bottom flask, was placed 176.2 (100 mg, 0.21 mmol, 1 equiv), EA (5 mL), Et$_3$N (23.2 mg, 0.23 mmol, 1.10 equiv), cyclopropanecarbonyl cyclopropanecarboxylate (161.0 mg, 1.04 mmol, 5.00 equiv). The resulting solution was stirred for 12 hr at 65° C. The reaction was then quenched by the addition of 10 mL of water. The resulting solution was extracted with 3×15 mL of ethyl acetate and the organic layers combined. The crude product was purified by Flash-Prep-HPLC with the following conditions (IntelFlash-1): Column, C18 silica gel; mobile phase, ACN:$H_2O$=15% increasing to ACN:$H_2O$=60% within 15 min; Detector, UV 254 nm. This resulted in 18.0 mg of I-236 as a white solid. (ES, m/z): [M−H]$^-$ 545.0, $^1$H-NMR (400 MHz, DMSO-$d_6$, ppm): δ0.61-0.74 (d, J=7.6 Hz, 3H), δ0.93-1.01 (s, 1H), δ1.69-1.72 (m, 1H), δ2.16-2.27 (m, 2H), δ4.02-4.18 (m, 4H), δ7.29-7.61 (m, 7H), δ7.81-8.05 (m, 1H), δ8.34 (s, 1H).

Example 181. Synthesis of 2-((3-((3-chloro-5-fluorophenyl)sulfonamido)-[1,1'-biphenyl]-4-yl)oxy)acetic Acid, I-238

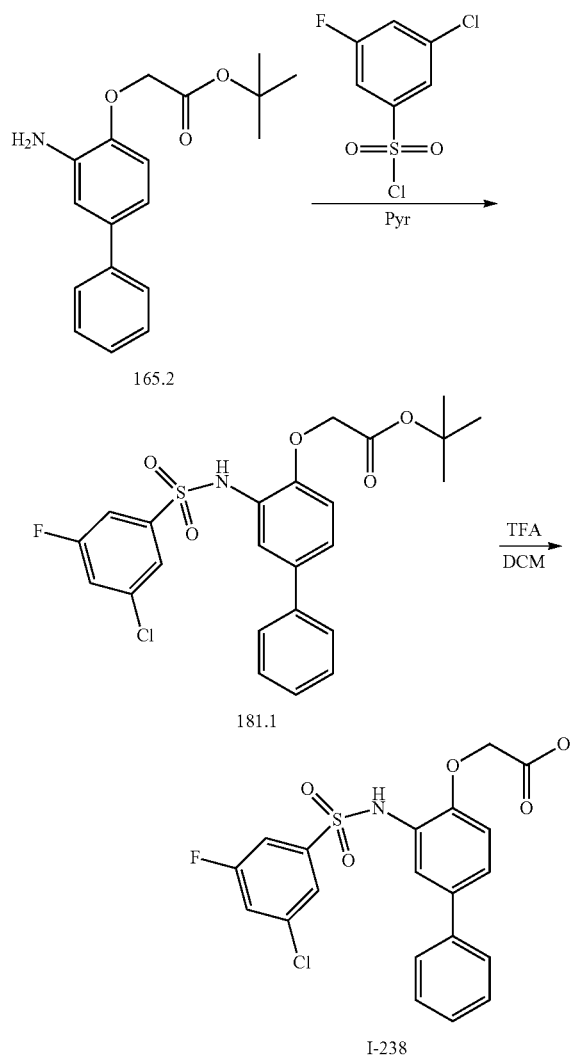

Synthesis of Compound 181.1

A solution of 165.2 (280 mg, 0.94 mmol, 1 equiv) and 3-chloro-5-fluorobenzenesulfonyl chloride (214.2 mg, 0.94 mmol, 1.00 equiv) in Pyridine (2.8 mL) was stirred overnight at room temperature under nitrogen atmosphere. The resulting mixture was concentrated under reduced vacuum. The residue was purified by Prep-TLC (PE/EtOAc=5/1) to afford 181.1 (250 mg, 54.3%) as a yellow solid. (ES, m/z): [M−H]⁻ 490.1.

Synthesis of I-238

A solution of 181.1 (150 mg, 0.30 mmol, 1 equiv) in DCM (2.5 mL) and TFA (0.5 mL) was stirred overnight at room temperature. The resulting mixture was concentrated under reduced pressure. The residue was purified by reverse flash chromatography with the following conditions: column, C18 silica gel; mobile phase, ACN in water (NH₄HCO₃), 0% to 45% gradient in 18 min; detector, UV 254 nm. This resulted in 1-238 (78.1 mg, 58.7%) as a white solid. (ES, m/z): [M−H]⁻ 434.0, ¹H-NMR (300 MHz, DMSO-d₆, ppm): δ4.33 (s, 2H), δ6.98-7.03 (m, 1H), δ7.31-7.37 (m, 2H), δ7.42-7.53 (m, 5H), δ7.58-7.62 (m, 1H), δ7.68-7.74 (m, 2H).

Example 182. Synthesis of 2-((3-((3,5-dichloro-2-hydroxyphenyl)sulfonamido)-[1,1'-biphenyl]-4-yl)oxy)-2-methylpropanoic Acid, I-239

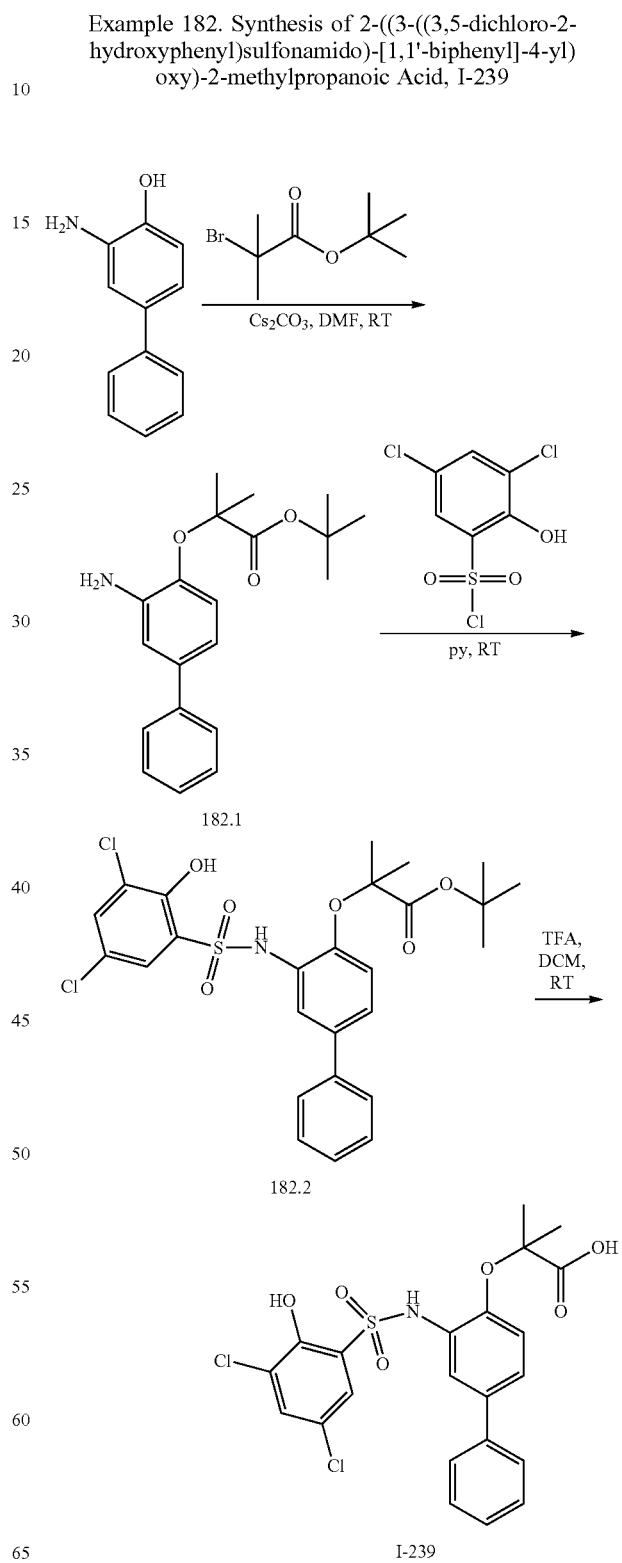

Synthesis of Compound 182.1

To a stirred solution of 3-amino-[1,1'-biphenyl]-4-ol (500 mg, 2.70 mmol, 1 equiv) and tert-butyl 2-bromo-2-methyl-propanoate (903.4 mg, 4.05 mmol, 1.5 equiv) in DMF (12.5 mL) was added $Cs_2CO_3$ (1.8 g, 5.40 mmol, 2 equiv). The resulting mixture was stirred for overnight at room temperature under nitrogen atmosphere. The resulting mixture was diluted with water (20 mL). The aqueous layer was extracted with EtOAc (2×20 mL). The combined organic layers were washed with sat.NaCl (aq.) (3×20 mL). The resulting mixture was concentrated under reduced pressure. The residue was purified by Prep-TLC (PE/EtOAc=5/1) to afford 182.1 (650 mg, 65.4%) as a yellow oil. (ES, m/z): [M−H]⁻ 326.1.

Synthesis of Compound 182.2

A solution of 182.1 (650 mg, 1.99 mmol, 1 equiv) and 3,5-dichloro-2-hydroxybenzene-1-sulfonyl chloride (519.1 mg, 1.99 mmol, 1 equiv) in Pyridine (6.5 mL) was stirred for overnight at room temperature under nitrogen atmosphere. The resulting mixture was concentrated under vacuum. The residue was purified by Prep-TLC ($CH_2Cl_2$/MeOH=50/1) to afford 182.2 (815 mg, 74.31%) as a yellow solid. (ES, m/z): [M−H]⁻ 550.0.

Synthesis of I-239

A solution of 247.2 (100 mg, 1 equiv) in TFA (0.5 mL) and DCM (2.5 mL) was stirred for 2 h at room temperature. The resulting mixture was concentrated under reduced pressure. The residue was purified by reverse-phase flash chromatography with the following conditions: column, C18 silica gel; mobile phase, ACN in water ($NH_4HCO_3$), 0% to 48% gradient in 30 min; detector, UV 254 nm. This resulted in 1-239 (80.8 mg, 89.9%) as a white solid. (ES, m/z): [M−H]⁻ 494.0, ¹H-NMR (300 MHz, $CD_3OD$, ppm): δ1.51 (s, 6H), δ6.94-6.97 (d, J=8.7 Hz, 1H), δ7.17-7.21 (m, 1H), δ7.27-7.32 (t, J=6.9 Hz, 1H), δ7.38-7.43 (t, J=7.8 Hz, 2H), δ7.48-7.50 (d, J=6.6 Hz, 3H), δ7.61-7.64 (m, 2H).

Example 183. Synthesis of 3,5-dichloro-N-(3-chloro-5-(thiazol-2-yl)phenyl)-2-hydroxybenzenesulfonamide, I-240

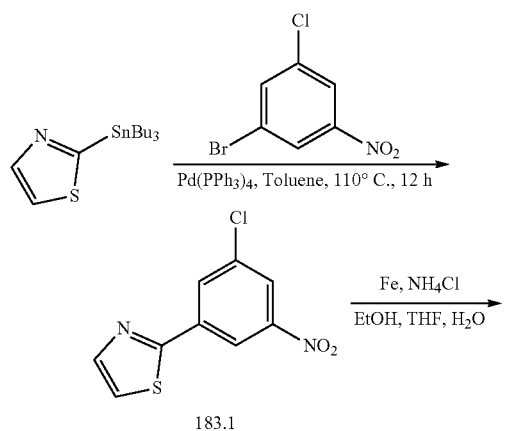

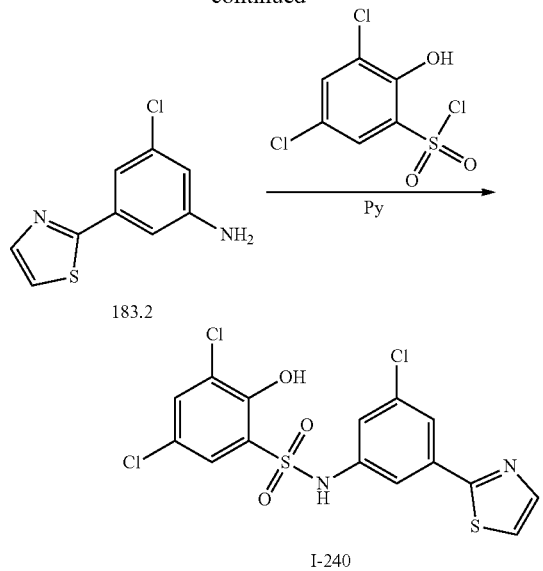

Synthesis of Compound 183.1

Into a 50-mL round-bottom flask purged and maintained with an inert atmosphere of nitrogen, was placed 2-(tributylstannyl)-1,3-thiazole (500 mg, 1.34 mmol, 1 equiv), 1-bromo-3-chloro-5-nitrobenzene (379.2 mg, 1.60 mmol, 1.2 equiv), $Pd(PPh_3)_4$ (154.4 mg, 0.13 mmol, 0.1 equiv), Toluene (10 mL). The resulting solution was stirred for 12 hr at 110° C. in an oil bath. The reaction was then quenched by the addition of 20 mL of water. The resulting solution was extracted with 3×20 mL of ethyl acetate. The resulting mixture was washed with 1×20 mL of brine. The mixture was dried over anhydrous sodium sulfate and concentrated. The resulting mixture was concentrated. The residue was applied onto a silica gel column with ethyl acetate/petroleum ether (1:5). This resulted in 300 mg (yield=93%) of 183.1 as a yellow solid.

Synthesis of Compound 183.2

Into a 50-mL round-bottom flask purged and maintained with an inert atmosphere of nitrogen, was placed 183.1 (300 mg, 1.25 mmol, 1 equiv), Fe (278.5 mg, 4.99 mmol, 4.00 equiv), $NH_4Cl$ (666.8 mg, 12.47 mmol, 10.00 equiv), EtOH (5 mL), THF (10 mL), $H_2O$ (5 mL). The resulting solution was stirred for 3 hr at 80° C. in an oil bath. The reaction was then quenched by the addition of 50 mL of water. The resulting solution was extracted with 3×50 mL of ethyl acetate. The resulting mixture was washed with 1×50 mL of brine. The mixture was dried over anhydrous sodium sulfate and concentrated. The resulting mixture was concentrated. The residue was applied onto a silica gel column with ethyl acetate/petroleum ether (1:5). This resulted in 200 mg (yield=76%) of 183.2 as a white solid.

Synthesis of I-240

Into a 25-mL round-bottom flask purged and maintained with an inert atmosphere of nitrogen, was placed 183.2 (100 mg, 0.38 mmol, 1 equiv), 3-chloro-5-(1,3-thiazol-2-yl)aniline (80.6 mg, 0.38 mmol, 1.00 equiv), Pyridine (5 mL). The resulting solution was stirred for 0.5 hr at room temperature.

The pH value of the solution was adjusted to 3 with HCl (1 mol/L). The resulting solution was extracted with 3×20 mL of ethyl acetate. The resulting mixture was washed with 1×20 mL of brine. The mixture was dried over anhydrous sodium sulfate and concentrated. The resulting mixture was concentrated. The residue was applied onto a silica gel column with ethyl acetate/petroleum ether (1:1). This resulted in 41.2 mg (yield=25%) of I-240 as a white solid. (ES, m/z): [M+H]$^+$ 434.8, $^1$H-NMR (400 MHz, DMSO-d$_6$, ppm): δ7.94 (s, 1H), δ7.74 (s, 1H), δ7.55-7.49 (m, 4H), δ7.11 (s, 1H).

Example 184. Synthesis of 5-(azetidine-1-carbonyl)-3-chloro-N-(2-fluoro-5-(2H-1,2,3-triazol-2-yl)phenyl)-2-hydroxybenzenesulfonamide, I-241

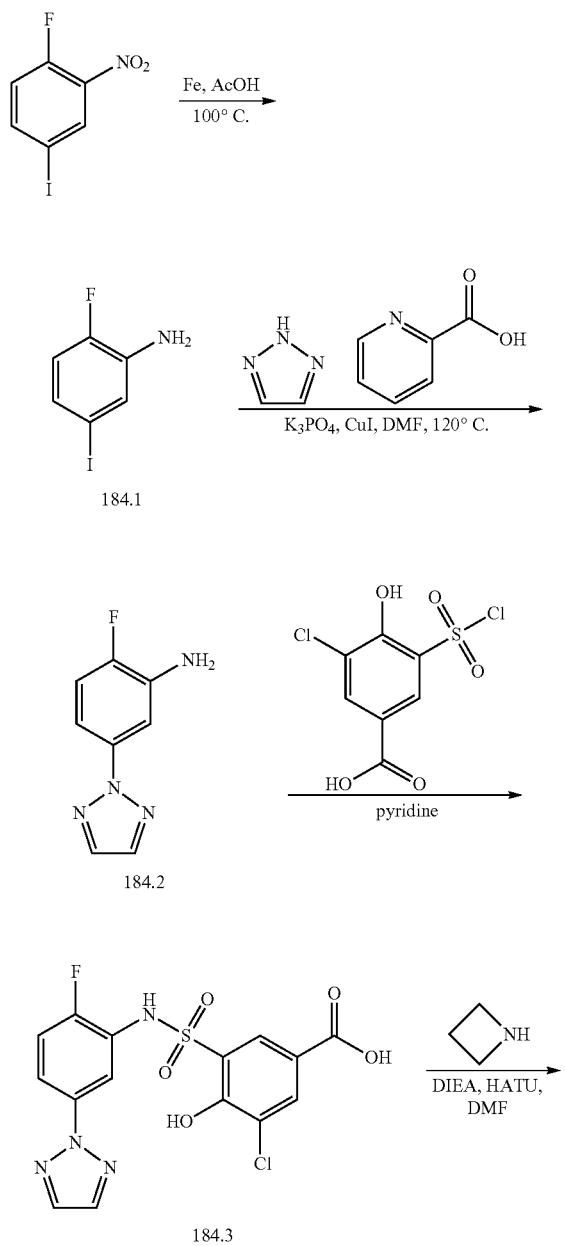

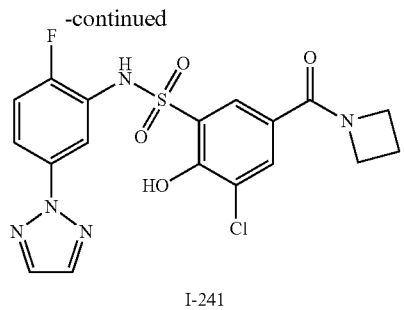

Synthesis of Compound 184.1

Into a 250-mL round-bottom flask purged and maintained with an inert atmosphere of nitrogen, was placed 1-fluoro-4-iodo-2-nitrobenzene (5 g, 18.73 mmol, 1 equiv), Fe (4183.2 mg, 74.91 mmol, 4 equiv), AcOH (50 mL). The resulting solution was stirred for 1 hr at 100° C. in an oil bath. The resulting solution was diluted with 300 mL of H$_2$O. The resulting solution was extracted with 3×100 mL of ethyl acetate concentrated under vacuum. The residue was applied onto a silica gel column with ethyl acetate/petroleum ether (1:20). This resulted in 3.55 g (79.9%) of 184.1 as yellow oil.

Synthesis of Compound 184.2

Into a 100-mL 3-necked round-bottom flask purged and maintained with an inert atmosphere of nitrogen, was placed 184.1 (1.5 g, 6.33 mmol, 1 equiv), 2H-1,2,3-triazole (480.8 mg, 6.96 mmol, 1.1 equiv), pyridine-2-carboxylic acid (311.7 mg, 2.53 mmol, 0.4 equiv), K$_3$PO$_4$ (3358.4 mg, 15.82 mmol, 2.5 equiv), DMF (35 mL), CuI (241.1 mg, 1.27 mmol, 0.2 equiv). The resulting solution was stirred for 1 overnight at 120° C. in an oil bath. The resulting solution was diluted with 200 mL of H$_2$O. The resulting solution was extracted with 3×100 mL of ethyl acetate concentrated under vacuum. The residue was applied onto a silica gel column with ethyl acetate/petroleum ether (1:2). This resulted in 477 mg (42.3%) of 184.2 as a yellow solid.

Synthesis of Compound 184.3

Into a 20-mL vial, was placed 184.2 (250 mg, 1.40 mmol, 1 equiv), 3-chloro-5-(chlorosulfonyl)-4-hydroxybenzoic acid (380.3 mg, 1.40 mmol, 1 equiv), pyridine (8 mL). The resulting solution was stirred for 1 overnight at room temperature. The resulting mixture was concentrated under vacuum. The residue was applied onto a prep TLC with dichloromethane/methanol (10:1). This resulted in 300 mg (51.8%) of 184.3 as a yellow solid.

Synthesis of I-241

Into a 8-mL vial purged and maintained with an inert atmosphere of nitrogen, was placed 184.3 (100 mg, 0.24 mmol, 1 equiv), azetidine (41.5 mg, 0.73 mmol, 3.00 equiv), DIEA (93.9 mg, 0.73 mmol, 3.00 equiv), DMF (2 mL), HATU (184.2 mg, 0.48 mmol, 2.00 equiv). The resulting solution was stirred for 1 overnight at room temperature. The resulting solution was diluted with 100 mL of H$_2$O. The resulting solution was extracted with 3×100 mL of ethyl acetate concentrated under vacuum. The residue was applied onto a prep TLC with dichloromethane/methanol (10:1). The crude product was purified by Flash-Prep-HPLC with the following conditions (IntelFlash-1): Column, C18 silica gel; mobile phase, ACN/H$_2$O=15% increasing to ACN/H$_2$O=60% within 15 min; Detector, UV 254 nm. This resulted in 15.3 mg (13.9%) of I-241 as a white solid. (ES, m/z): [M−H]⁻ 450.0, $^1$H-NMR (300 MHz, DMSO-d$_6$, ppm): δ 8.25-8.00 (m, 3H), 7.72-7.81 (d, J=2.1 Hz, 1H), 7.55-7.68 (m, 2H), 7.31-7.38 (t, J=9.3 Hz, 1H), 4.11 (s, 4H), 2.12-2.32 (m, 2H).

Example 185. Synthesis of 2-[[3-(3,5-dichlorobenzenesulfonamido)-[1,1-biphenyl]-4-yl]oxy]acetic Acid, I-244

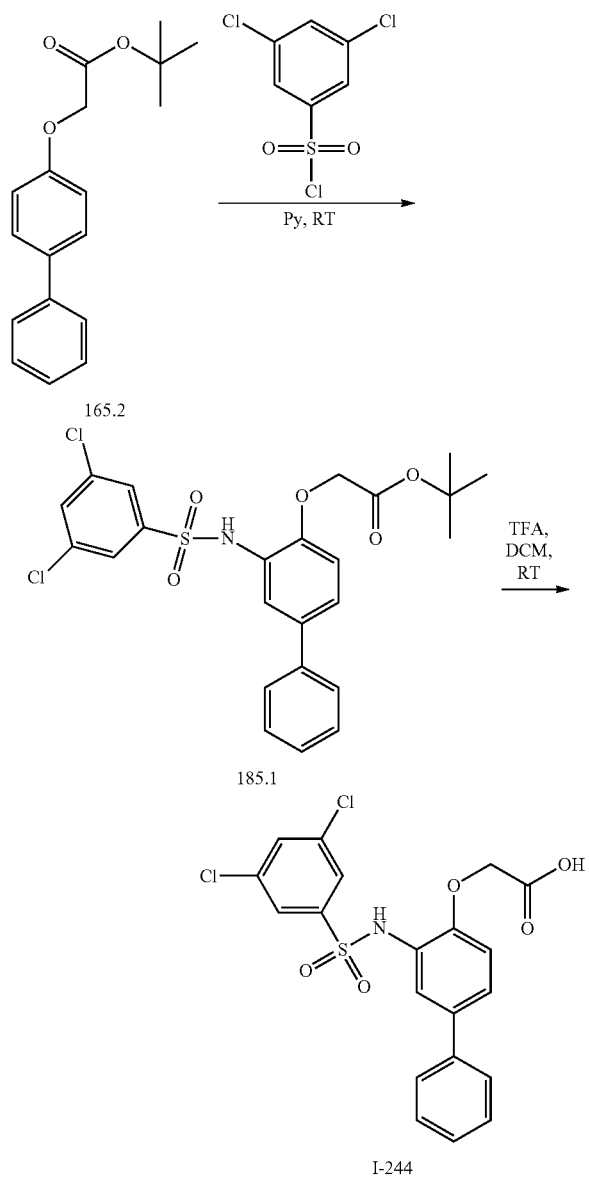

Synthesis of Compound 185.1

A mixture of 165.2 (108 mg, 0.36 mmol, 1 equiv) and 3,5-dichlorobenzene-1-sulfonyl chloride (88.6 mg, 0.36 mmol, 1 equiv) in pyridine (2 mL, 24.85 mmol, 68.87 equiv) was stirred for 2 h at 50° C. under nitrogen atmosphere. The reaction was quenched with HCl (1 M) at room temperature. The aqueous layer was extracted with EtOAc (2×100 mL). The residue was purified by Prep-TLC (CH$_2$Cl$_2$/MeOH 20:1) to afford 185.1 (65 mg, 35%) as a white solid.

Synthesis of I-244

A mixture of 185.1 (65 mg, 0.13 mmol, 1 equiv) and CF$_3$COOH (0.12 mL, 1.62 mmol, 12.64 equiv) in DCM (0.6 mL, 9.44 mmol, 73.82 equiv) was stirred for 2 h at room temperature under nitrogen atmosphere. The resulting mixture was extracted with water ice. The combined organic layers were washed with EtOAc (2×100 mL), dried over anhydrous Na$_2$SO$_4$. After filtration, the filtrate was concentrated under reduced pressure. The crude product was purified by reverse-phase flash with the following conditions (from CH$_3$CN:H$_2$O=1:20 to CH$_3$CN:H$_2$O=50:50 in 30 mins; UV: 254/220) to afford I-244 (13.2 mg, 22.8%) as a white solid. (ES, m/z): [M−H]⁻ 450.0, $^1$H-NMR (400 MHz, DMSO-d$_6$, ppm): δ4.50 (s, 2H), δ6.97-6.99 (d, J=8.8 Hz, 1H), δ7.33-7.34 (t, J=7.2 Hz, 1H), δ7.43-7.62 (m, 6H), δ7.66-7.76 (s, 2H), δ7.80-7.91 (s, 1H).

Example 186. Synthesis of 3-bromo-5-chloro-N-(4,6-difluoro-[1,1′-biphenyl]-3-yl)benzenesulfonamide, I-246

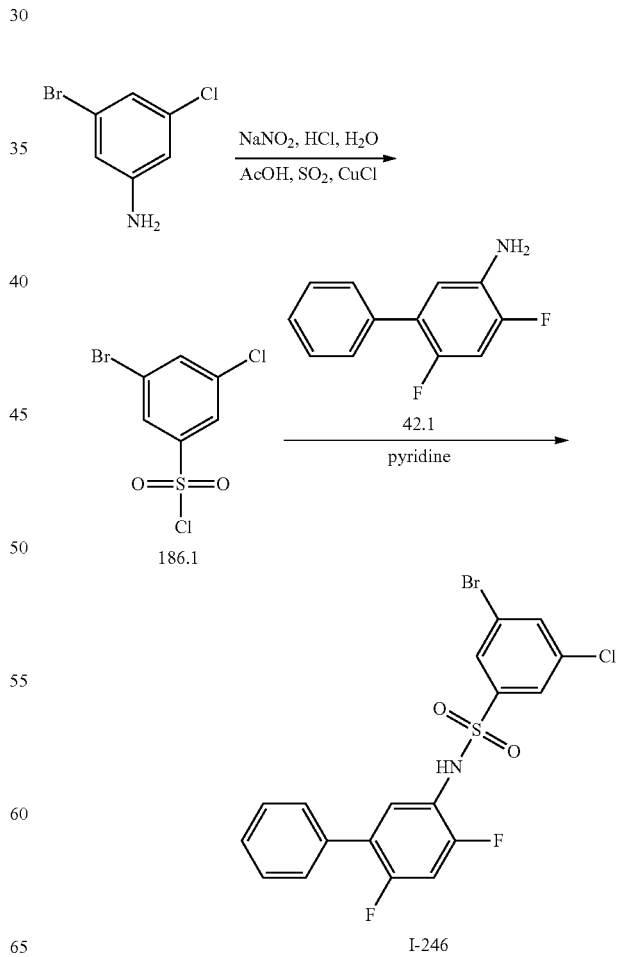

Synthesis of Compound 186.1

A solution of NaNO$_2$ (1.0 g, 14.53 mmol, 1.5 equiv) in H$_2$O (7.6 mL) was added to a suspension of 3-bromo-5-chloroaniline (2 g, 9.69 mmol, 1 equiv) in HCl (20 mL) at 0° C. over 10 min, and the solution stirred for a further 30 min. Meanwhile, AcOH (20 mL) was saturated with SO$_2$ over 1 h, then CuCl (0.3 g, 2.91 mmol, 0.3 equiv) was added and SO$_2$ bubbled through for a further 5 min. The AcOH mixture was cooled to 5° C., then the diazonium solution was added over 10 min. The resulting mixture was stirred for a further 20 min at 0° C. then 1.5 h at RT. The solution was diluted with water and extracted twice with DCM. The combined organic extracts were washed twice with water, dried over Na$_2$SO$_4$ and the solvent removed in vacuum. The crude product was used in the next step directly without further purification.

Synthesis of I-246

A mixture of 186.1 (500 mg, 1.72 mmol, 1 equiv) and 42.1 (353.9 mg, 1.72 mmol, 1.0 equiv) in pyridine (5 mL) was stirred overnight at room temperature under nitrogen atmosphere. The resulting mixture was concentrated under reduced pressure. The residue was purified by Prep-TLC (PE/EtOAc=3/1) to afford I-246 (480 mg, 60.6%) as a white solid. (ES, m/z): [M+H]$^+$ 457.9, $^1$H-NMR (300 MHz, DMSO-d$_6$, ppm): δ7.25-7.31 (t, J=8.4 Hz, 1H), δ7.41-7.53 (m, 6H), δ7.74-7.75 (t, J=1.8 Hz, 1H), δ7.82-7.83 (t, J=1.5 Hz, 1H), δ8.14-8.15 (t, J=1.8 Hz, 1H), δ10.55 (s, 1H).

Example 187. Synthesis of 3-chloro-5-[[2,4-difluoro-5-(thiophen-2-yl)phenyl] sulfamoyl]-4-hydroxybenzoic Acid, I-248

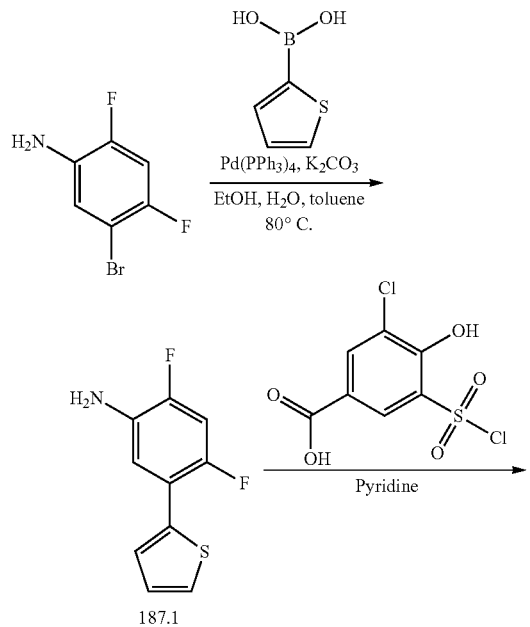

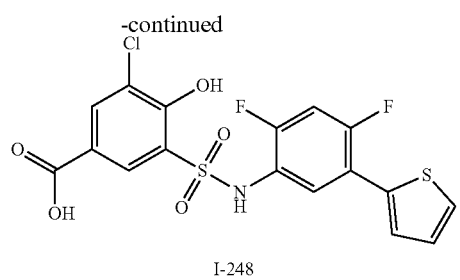

I-248

Synthesis of Compound 187.1

Into a 50-mL round-bottom flask, was placed 5-bromo-2,4-difluoroaniline (1000 mg, 4.81 mmol, 1 equiv), toluene (4 mL), H$_2$O (4 mL), EtOH (4 mL), (thiophen-2-yl)boronic acid (738.2 mg, 5.77 mmol, 1.2 equiv), K$_2$CO$_3$ (1993.3 mg, 14.42 mmol, 3 equiv), Pd(PPh$_3$)$_4$ (555.5 mg, 0.48 mmol, 0.1 equiv). The resulting solution was stirred for 12 hr at 80° C. The resulting mixture was concentrated under vacuum. The residue was applied onto a silica gel column with ethyl acetate/petroleum ether (20:1). This resulted in 350 mg (34.4%) of 187.1 as a light yellow solid.

Synthesis of I-248

Into a 25-mL round-bottom flask, was placed 3-chloro-5-(chlorosulfonyl)-4-hydroxybenzoic acid (100 mg, 0.37 mmol, 1 equiv), 187.1 (93.5 mg, 0.44 mmol, 1.20 equiv), pyridine (2 mL). The resulting solution was stirred for 12 hr at 25° C. The resulting mixture was concentrated under vacuum. The crude product was purified by Flash-Prep-HPLC with the following conditions (IntelFlash-1): Column, C18 silica gel; mobile phase, ACN:H$_2$O=15% increasing to ACN:H$_2$O=60% within 15 min. This resulted in 60.4 mg (36.7%) of I-248 as a white solid. (ES, m/z): [M–H]$^-$ 444.0, $^1$H-NMR (400 MHz, DMSO-d$_6$) δ 7.88-7.87 (d, J=2.4 Hz, 1H), δ7.78-7.77 (d, J=2.4 Hz, 1H), δ7.65-7.64 (d, J=4.0 Hz, 1H), δ7.54-7.40 (m, 1H), δ7.38-7.35 (d, J=10.8 Hz, 1H), δ7.31-7.30 (d, J=3.6 Hz, 1H), δ7.22-6.98 (m, 4H).

Example 188. Synthesis of 3-amino-N-(3-fluoro-[1,1'-biphenyl]-4-yl)-2-hydroxybenzenesulfonamide, I-261

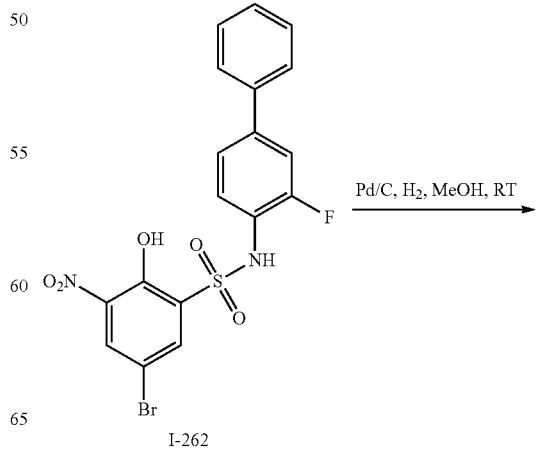

I-262

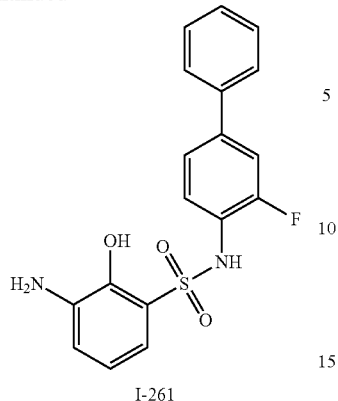

I-261

Synthesis of I-261

To a stirred solution of I-262 (715 mg, 1.53 mmol, 1 equiv) in MeOH (15 mL) was added Pd/C (143 mg) under nitrogen atmosphere. The flask was evacuated and flushed three times with nitrogen, followed by flushing with hydrogen. The mixture was stirred overnight at room temperature under an atmosphere of hydrogen. After filtration, the filter cake was washed with MeOH (5×10 mL). The filtrate was concentrated under reduced pressure. The residue was purified by Prep-TLC (CH$_2$Cl$_2$/MeOH=50/1) to afford a crude product of I-255 (530 mg, 96.65%) as a grey solid. I-261 (100 mg) was purified by reverse flash chromatography with the following conditions: column, C18 silica gel; mobile phase, ACN in water, 0% to 75% gradient in 30 min; detector, UV 254 nm. This resulted in I-261 (48.2 mg) as a grey solid. (ES, m/z): [M+H]$^+$ 359.0, $^1$H-NMR (300 MHz, DMSO-d$_6$, ppm): δ6.62-6.68 (m, 1H), δ6.77-6.80 (m, 1H), δ6.84-6.87 (m, 1H), δ7.16-7.22 (m, 2H), δ7.33-7.37 (m, 1H), δ7.41-7.53 (m, 5H).

Example 189. Synthesis of 5-bromo-N-(3-fluoro-[1,1'-biphenyl]-4-yl)-2-hydroxy-3-nitrobenzenesulfonamide, I-262

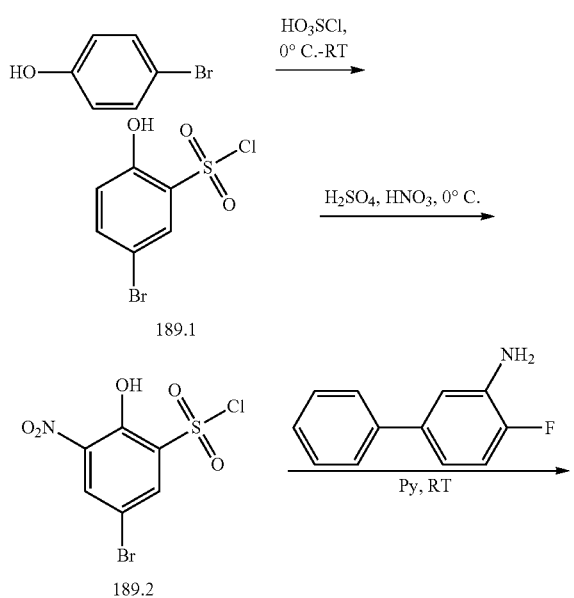

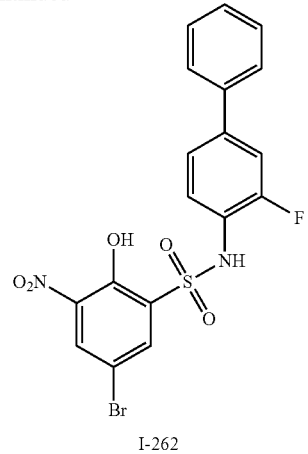

I-262

Synthesis of Compound 189.1

A mixture of 4-bromophenol (1 g, 5.78 mmol, 1 equiv) in ClHO$_3$S (10 mL) was stirred 3 h at 0° C. under nitrogen atmosphere. The resulting mixture was diluted with water (50 mL). The resulting mixture was extracted with EtOAc (3×50 mL). The combined organic layers were dried over anhydrous Na$_2$SO$_4$. After filtration, the filtrate was concentrated under reduced pressure. This resulted in 189.1 (1.5 g, 71%) as a white solid. (ES, m/z): [M−H]$^-$ 268.8.

Synthesis of Compound 189.2

To a stirred solution of 189.1 (1.5 g, 5.52 mmol, 1 equiv) in H$_2$SO$_4$ (4.5 mL) was added HNO$_3$ (3 mL) dropwise at 0° C. under nitrogen atmosphere. The resulting mixture was stirred for 0.5 h at 0° C. under nitrogen atmosphere. The resulting mixture was diluted with water (10 mL). The resulting mixture was extracted with CH$_2$Cl$_2$ (3×10 mL). The combined organic layers were concentrated under reduced pressure. The crude product was used in the next step directly without further purification. (ES, m/z): [M−H]$^-$ 313.8.

Synthesis of I-262

A mixture of 189.2 (2 g, 6.32 mmol, 1 equiv) and 4-fluoro-[1,1'-biphenyl]-3-amine (1.2 g, 6.32 mmol, 1 equiv) in pyridine (10 mL) was stirred overnight at room temperature under nitrogen atmosphere. The resulting mixture was concentrated under reduced pressure. The residue was purified by silica gel column chromatography, eluted with CH$_2$Cl$_2$/MeOH=50/1 to afford a crude product of I-262 (815 mg, 27.6%) as an orange solid. I-256 (100 mg) was purified by reverse flash chromatography with the following conditions: column, C18 silica gel; mobile phase, ACN in water, 0% to 65% gradient in 30 min; detector, UV 254 nm. This resulted in I-262 (65.7 mg) as an orange solid. (ES, m/z): [M+H]$^+$ 466.9, $^1$H-NMR (300 MHz, DMSO-d$_6$, ppm): δ7.24-7.27 (m, 1H), δ7.34-7.54 (m, 9H), δ7.93-7.94 (d, J=3.0 Hz, 1H).

Example 190. Synthesis of 3,5-dichloro-2-methane-sulfonamido-N-[4-methoxy-[1,1-biphenyl]-3-yl]benzene-1-sulfonamide, I-263

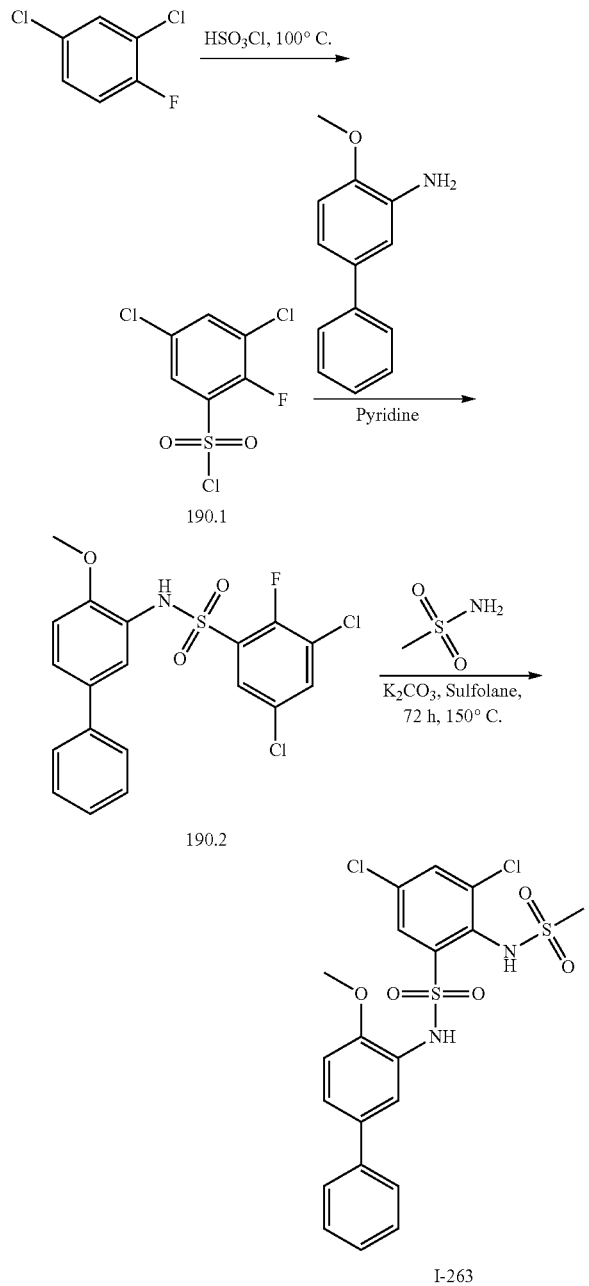

Synthesis of Compound 190.1

Into a 100-mL round-bottom flask, was placed HSO₃C₁ (20 mL), 2,4-dichloro-1-fluorobenzene (2 g, 12.12 mmol, 1 equiv). The resulting solution was stirred for 12 hr at 100° C. The reaction was then quenched by the addition of 100 mL of water/ice. The resulting solution was extracted with 3×150 mL of ethyl acetate and the organic layers combined and concentrated under vacuum. This resulted in 1.5 g (46%) of 190.1 as a black solid. (ES, m/z): [M−H]⁻ 260.8.

Synthesis of 190.2

Into a 50-mL round-bottom flask, was placed 190.1 (200 mg, 0.76 mmol, 1 equiv), 4-methoxy-[1,1-biphenyl]-3-amine (181.5 mg, 0.91 mmol, 1.20 equiv), Pyridine (5 mL). The resulting solution was stirred for 12 hr at 25° C. The resulting mixture was concentrated under vacuum. The residue was applied onto Prep-TLC with dichloromethane/methanol (20:1). This resulted in 45.9 mg (14.1%) of 190.2 as a white solid (ES, m/z): [M+H]⁺ 425.9, ¹H-NMR (400 MHz, DMSO-d₆) δ 10.08 (s, 1H), δ8.12-8.11 (d, J=6.4 Hz, 1H), δ7.84-7.82 (d, J=8.8 Hz, 1H), δ7.57-7.48 (m, 3H), δ7.48-7.40 (m, 3H), δ7.35-7.31 (t, J=7.2 Hz, 1H), δ7.03-7.05 (d, J=8.8 Hz, 1H), δ3.56 (s, 3H).

Synthesis of I-263

Into a 50-mL round-bottom flask, was placed 190.2 (200 mg, 0.47 mmol, 1 equiv), sulfolane (5 mL), methanesulfonamide (133.9 mg, 1.41 mmol, 3.00 equiv), K₂CO₃ (259.4 mg, 1.88 mmol, 4.00 equiv). The resulting solution was stirred for 24 hr at 140° C. The reaction was then quenched by the addition of 15 mL of water. The resulting solution was extracted with 3×20 mL of ethyl acetate and the organic layers combined and concentrated under vacuum. The crude product was purified by Flash-Prep-HPLC with the following conditions (IntelFlash-1): Column, C18 silica gel; mobile phase, ACN:H₂O=10% increasing to ACN:H₂O=65% within 15 min. This resulted in 90.0 mg (38.2%) of I-263 as an off-white solid. (ES, m/z): [M−H]⁻ 498.9, ¹H-NMR (400 MHz, DMSO-d₆, ppm) δ 9.93 (s, 1H), δ9.79 (s, 1H), δ7.98 (s, 1H), δ7.91 (s, 1H), δ7.55-7.39 (m, 6H), δ7.37-7.28 (m, 1H), δ7.02-7.04 (d, J=6 Hz, 1H), δ3.56 (s, 3H), δ2.93 (s, 3H).

Example 191. Synthesis of 2-([3-[3-chloro-2-hydroxy-5-(trifluoromethyl) benzenesulfonamido]-[1,1-biphenyl]-4-yl]oxy)acetic Acid, I-264

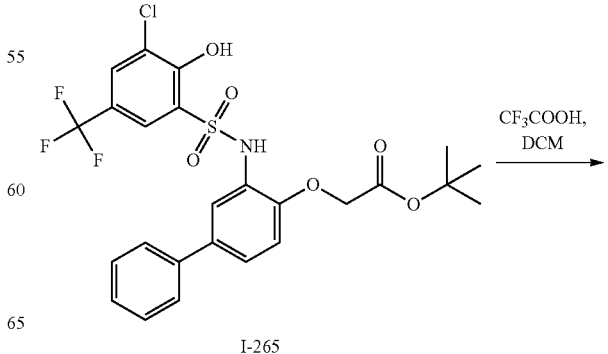

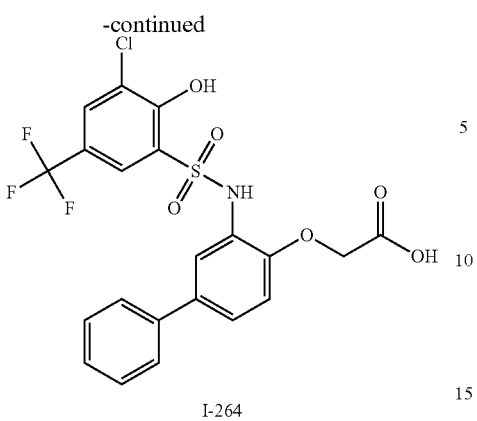

I-264

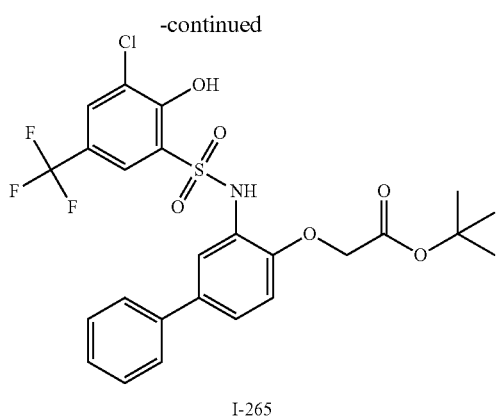

I-265

Synthesis of I-264

A mixture of tert-butyl I-265 100 mg, 0.18 mmol, 1 equiv) and CF$_3$CH$_2$OH (0.2 mL, 2.78 mmol, 15.51 equiv) in DCM (1 mL, 15.73 mmol, 87.77 equiv) was stirred for 2 h at room temperature under nitrogen atmosphere. The reaction was quenched with NaHCO$_3$ (1 M) at room temperature. The aqueous layer was extracted with CH$_2$Cl$_2$ (2×100 mL). The crude product was purified by reverse phase flash with the following conditions (from CH$_3$CN:H$_2$O=1:20 to CH$_3$CN:H$_2$O=50:50 in 30 mins, UV: 254/220) to afford I-264 (24.5 mg, 27.2%) as an off-white solid. (ES, m/z): [M−H]$^-$ 500.0, $^1$H-NMR (400 Hz, DMSO-d$_6$, ppm): δ4.60 (s, 2H), δ6.95-7.07 (m 1H), δ7.31-7.51 (m, 7H), δ7.83 (s, 1H), δ8.02 (s, 1H).

Example 192. Synthesis of tert-butyl 2-([3-[3-chloro-2-hydroxy-5-(trifluoromethyl)benzenesulfonamido]-[1,1-biphenyl]-4-yl]oxy)acetate, I-265

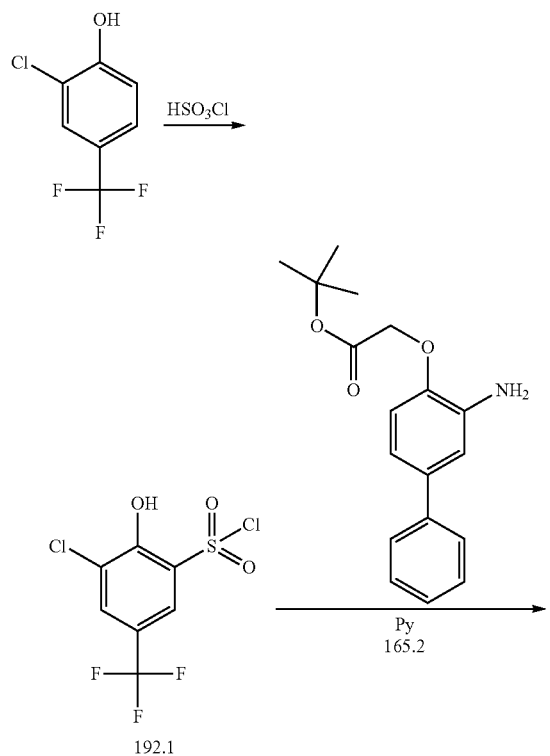

Synthesis of Compound 192.1

Into a 50 mL 3-necked round-bottom flask were added 2-chloro-4-(trifluoromethyl) phenol (1 g, 5.09 mmol, 1 equiv) and sulfonoperoxoyl chloride (12 mL) at room temperature. The resulting solution was stirred for overnight at room temperature under nitrogen atmosphere. The reaction was quenched with Water at room temperature. The aqueous layer was extracted with EtOAc (2×100 mL). The crude product was purified by reverse phase flash with the following conditions (from CH$_3$CN:H$_2$O=1:20 to CH$_3$CN:H$_2$O=50:50 in 30 mins, UV: 254/220) to afford 192.1 (1.2 g, 79%) as a yellow solid.

Synthesis of I-265

A mixture of 165.2 (560 mg, 1.87 mmol, 1 equiv) and 192.1 (551.9 mg, 1.87 mmol, 1 equiv) in Pyridine (6 mL, 74.54 mmol, 39.85 equiv) was stirred for 2 h at 50° C. under nitrogen atmosphere. The reaction was quenched with Water/Ice at room temperature. The aqueous layer was extracted with EtOAc (2×100 mL). The crude product was purified by reverse phase flash with the following conditions (from CH$_3$CN:H$_2$O=1:20 to CH$_3$CN:H$_2$O=50:50 in 30 mins, UV: 254/220) to afford I-265 (500 mg, 47.9%) as an off-white solid. (ES, m/z): [M−H]$^-$ 556.0, $^1$H-NMR (400 Hz, DMSO-d$_6$, ppm): δ1.45 (s, 9H), δ4.66 (s, 2H), δ6.92-6.95 (m, H), δ7.08-7.15 (m, 1H), δ7.19-7.22 (m 2H), δ7.29-7.33 (m, 1H), δ7.40-7.44 (m, 5H), δ7.57-7.60 (t, J=2.0 Hz, 2H).

517

Example 193. Synthesis of tert-butyl 2-((3-((5-(azetidine-1-carbonyl)-3-chloro-2-hydroxyphenyl)sulfonamido)-[1,1'-biphenyl]-4-yl)oxy)acetate, I-266

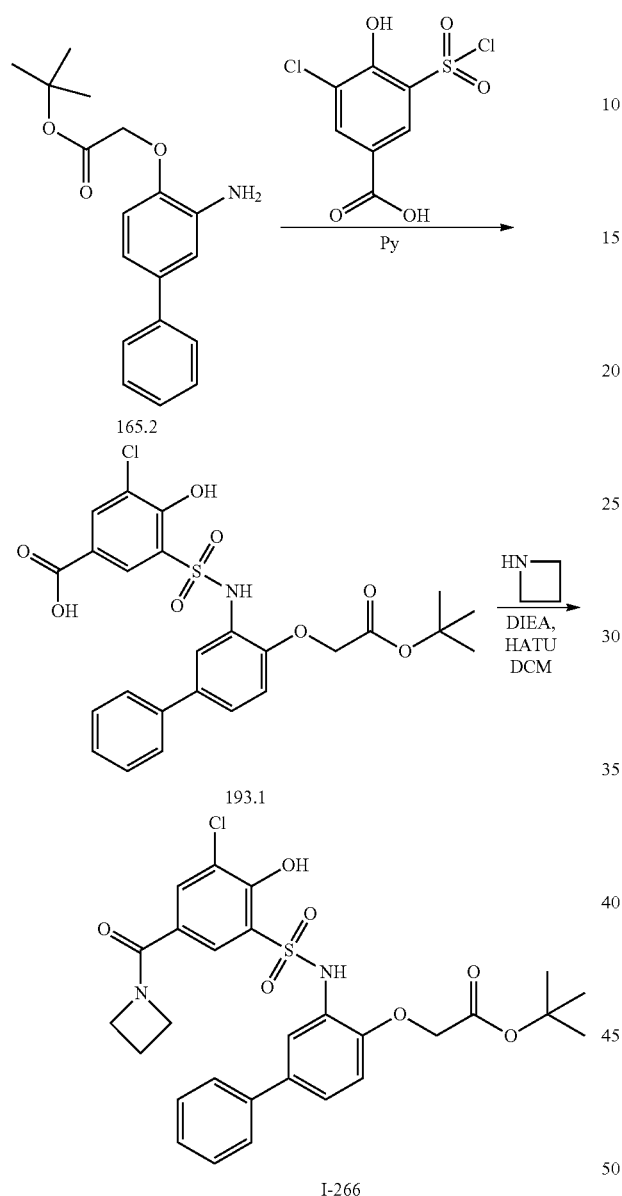

Synthesis of Compound 193.1

A mixture of 165.2 (400 mg, 1.34 mmol, 1 equiv) and 3-chloro-5-(chlorosulfonyl)-4-hydroxybenzoic acid (362.2 mg, 1.34 mmol, 1 equiv) in Pyridine (4 mL, 49.69 mmol, 37.19 equiv) was stirred for 2 h at 50° C. under nitrogen atmosphere. The reaction was quenched with Water/Ice at room temperature. The aqueous layer was extracted with EtOAc (2×100 mL). The crude product was purified by reverse phase flash with the following conditions (from $CH_3CN:H_2O=1:20$ to $CH_3CN:H_2O=50:50$ in 30 mins, UV: 254/220) to afford 193.1 (170 mg, 23.8%) as an off-white solid. (ES, m/z): [M–H]⁻ 532.0.

518

Synthesis of I-266

To a stirred mixture of 193.1 (170 mg, 0.32 mmol, 1 equiv) and azetidine (36.4 mg, 0.64 mmol, 2 equiv) in DCM (2 mL, 31.46 mmol, 98.82 equiv) were added DIEA (164.6 mg, 1.27 mmol, 4 equiv) and HATU (242.1 mg, 0.64 mmol, 2 equiv) in portions at room temperature under nitrogen atmosphere. The resulting solution was stirred for overnight at room temperature under nitrogen atmosphere. The reaction was quenched with $NH_4Cl$ (1 M) at room temperature. The aqueous layer was extracted with EtOAc (2×100 mL). The crude product was purified by reverse phase flash with the following conditions (from $CH_3CN:H_2O=1:20$ to $CH_3CN:H_2O=50:50$ in 30 mins, UV: 254/220) to afford I-266 (200 mg, 109%) as an off-white solid. (ES, m/z): [M–H]⁻ 571.0, ¹H-NMR (400 MHz, DMSO-d₆, ppm): δ1.43 (s, 9H), δ2.10-2.16 (m, 2H), δ4.01 (s, 4H), δ4.62 (s, 2H), δ6.93-6.95 (d, J=8.8 Hz, 1H), δ7.08 (s, 1H), δ7.30-7.35 (m, 2H), δ7.40-7.42 (m, 2H), δ7.44-7.48 (m, 2H), δ7.55-7.56 (s, 1H), δ7.71 (s, 1H), δ7.77 (s, 1H).

Example 194. Synthesis of 5-(azetidine-1-carbonyl)-3-chloro-N-(2-fluorophenyl)-2-hydroxybenzene-1-sulfonamide, I-268

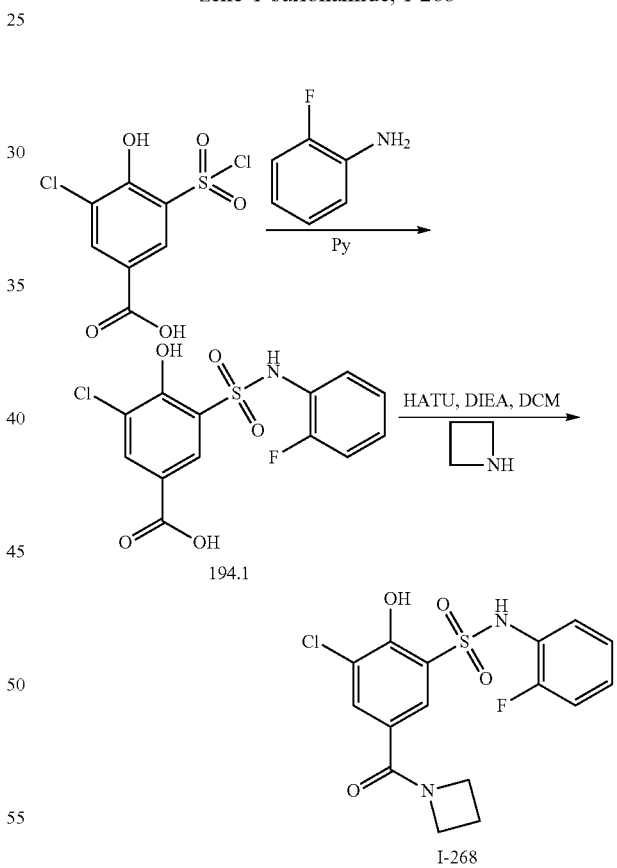

Synthesis of Compound 194.1

Into a 8-mL vial, was placed 2-fluoroaniline (147.58 mg, 1.328 mmol, 1.2 equiv), pyridine (3 mL), 3-chloro-5-(chlorosulfonyl)-4-hydroxybenzoic acid (300 mg, 1.107 mmol, 1 equiv). The resulting solution was stirred for 1 hr at room temperature. The resulting mixture was concentrated under vacuum. The residue was applied onto a silica gel column with ethyl acetate/petroleum ether (1:5). This resulted in 300 mg (78.4%) of 194.1 as a yellow solid. (ES, m/z): [M−H]⁻ 343.9.

Synthesis of I-268

Into a 8-mL vial purged and maintained with an inert atmosphere of nitrogen, was placed 194.1 (150 mg, 0.434 mmol, 1 equiv), DCM (3 mL), DIEA (168.22 mg, 1.302 mmol, 3.00 equiv), azetidine (74.32 mg, 1.302 mmol, 3.00 equiv), HATU (247.45 mg, 0.651 mmol, 1.50 equiv). The resulting solution was stirred for 1 overnight at 40° C. in an oil bath. The resulting solution was diluted with 20 mL of H₂O. The resulting solution was extracted with 3×10 mL of ethyl acetate concentrated under vacuum. The crude product was purified by Flash-Prep-HPLC with the following conditions (IntelFlash-1): Column, C18 silica gel; mobile phase, ACN/H₂O=15% increasing to ACN/H₂O=60% within 15 min; Detector, UV: 254. This resulted in 20.8 mg (12.4%) of I-268 as a white solid. (ES, m/z): [M−H]⁻ 383.0, ¹H-NMR (300 MHz, DMSO-d₆, ppm): δ7.70-7.62 (m, 2H), 7.30-7.03 (m, 5H), 6.92 (s, 1H), 4.10 (s, 4H), 2.34-2.13 (m, 2H).

Example 195. Synthesis of 3-chloro-N-[4,6-difluoro-[1,1-biphenyl]-3-yl]-2-hydroxy-5-(1H-1,2,3,4-tetrazol-5-yl)benzene-1-sulfonamide, I-269

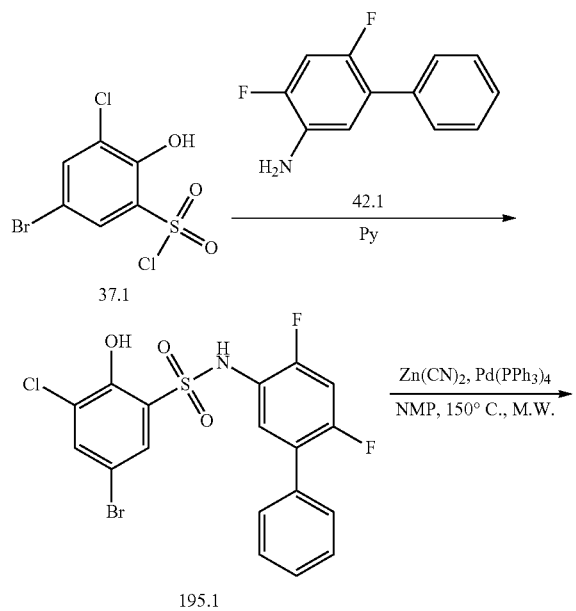

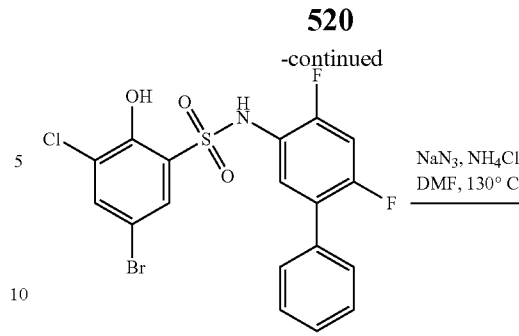

Synthesis of Compound 195.1

Into a 50-mL round-bottom flask, was placed 42.1 (804.87 mg, 3.922 mmol, 1.2 equiv), pyridine (10 mL), and 37.1 (1 g, 3.269 mmol, 1 equiv). The resulting solution was stirred for 1 hr at room temperature. The resulting mixture was concentrated under vacuum. The residue was applied onto a silica gel column with ethyl acetate/petroleum ether (1:1). This resulted in 650 mg (41.8%) of 195.1 as a yellow solid. (ES, m/z): [M−H]⁻ 471.9.

Synthesis of Compound 195.2

Into a 20-mL round-bottom flask purged and maintained with an inert atmosphere of nitrogen, was placed 195.1 (300 mg, 0.632 mmol, 1 equiv), Zn(CN)₂ (148.44 mg, 1.264 mmol, 2 equiv), NMP (10 mL), Pd(PPh₃)₄ (73.03 mg, 0.063 mmol, 0.1 equiv). The resulting solution was stirred for 4 hr in M.W. at 150° C. The crude product was purified by Flash-Prep-HPLC with the following conditions (IntelFlash-1): Column, C18 silica gel; mobile phase, ACN/H₂O=15% increasing to ACN/H₂O=60% within 15 min; Detector, UV: 254. This resulted in 267 mg (97.7%) of 195.2 as a white solid. (ES, m/z): [M−H]⁻ 419.0.

Synthesis of I-269

Into a 8-mL vial purged and maintained with an inert atmosphere of nitrogen, was placed 195.2 (80 mg, 0.190 mmol, 1 equiv), DMF (4 mL), NH₄Cl (40.68 mg, 0.760 mmol, 4 equiv), NaN₃ (37.08 mg, 0.570 mmol, 3 equiv). The resulting solution was stirred for 1 overnight at 130° C. in an oil bath. The solids were filtered out. The resulting mixture was concentrated under vacuum. The crude product was purified by Flash-Prep-HPLC with the following conditions (IntelFlash-1): Column, C18 silica gel; mobile phase, ACN/H₂O=15% increasing to ACN/H₂O=60% within 15 min; Detector, UV: 254. This resulted in 3.2 mg (3.6%) of I-269 as a white solid. (ES, m/z): [M−H]⁻ 462.0, ¹H-NMR (400 MHz, DMSO-d₆, ppm): δ 8.16 (m, 2H), 7.49-7.28 (m, 7H), 7.23-6.89 (m, 1H).

521

Example 196. Synthesis of 2-([3-[5-(azetidine-1-carbonyl)-3-chloro-2-hydroxybenzenesulfonamido]-[1,1-biphenyl]-4-yl]oxy)acetic Acid, I-270

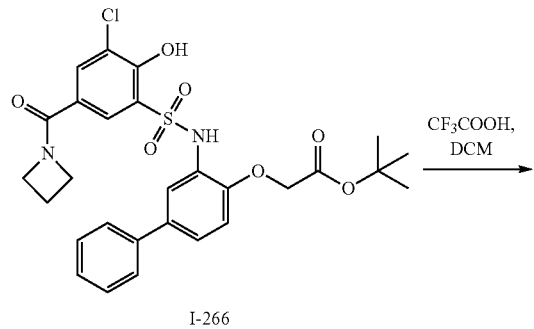

I-266

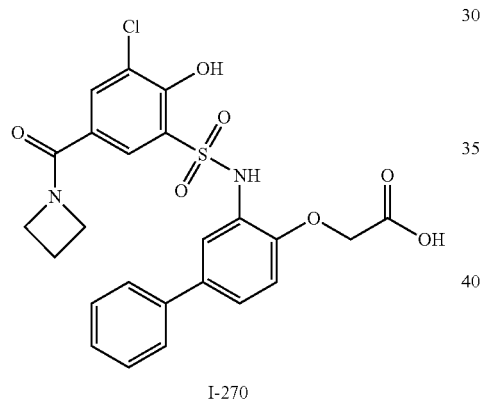

I-270

Synthesis of I-270

A mixture of I-266 (100 mg, 0.17 mmol, 1 equiv) and CF$_3$COOH (0.2 mL, 2.69 mmol, 15.43 equiv) in DCM (1 mL, 15.73 mmol, 90.14 equiv) was stirred for 2 h at room temperature under nitrogen atmosphere. The reaction was quenched with NaHCO$_3$ (1 M) at room temperature. The aqueous layer was extracted with CH$_2$Cl$_2$ (2×100 mL). The crude product was purified by reverse phase flash with the following conditions (from CH$_3$CN:H$_2$O=1:20 to CH$_3$CN:H$_2$O=50:50 in 30 mins, UV: 254/220) to afford I-270 (35.5 mg, 39.3%) as a pink solid. (ES, m/z): [M−H]$^−$ 515.1, $^1$H-NMR (400 MHz, DMSO-d$_6$, ppm): δ2.07-2.15 (m, 2H), δ4.00 (s, 4H), δ4.59 (s, 2H), δ6.95-6.97 (m, 2H), δ7.08 (s, 1H), δ7.21 (s, 1H), δ7.25-7.34 (m, 2H), δ7.40-7.44 (m, 2H), δ7.48-7.50 (m, 2H), δ7.56-7.57 (s, 1H), δ7.63 (s, 2H).

522

Example 197. Synthesis of 5-(azetidin-1-ylmethyl)-3-chloro-N-(4,6-difluoro-[1,1'-biphenyl]-3-yl)-2-hydroxybenzenesulfonamide, I-272

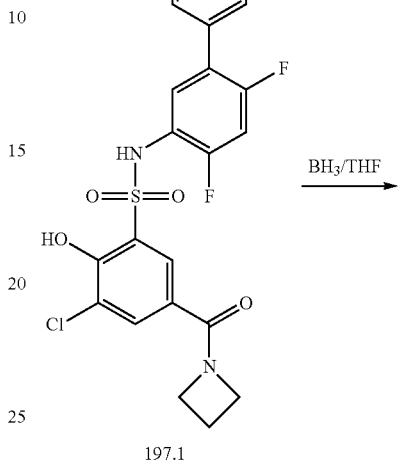

197.1

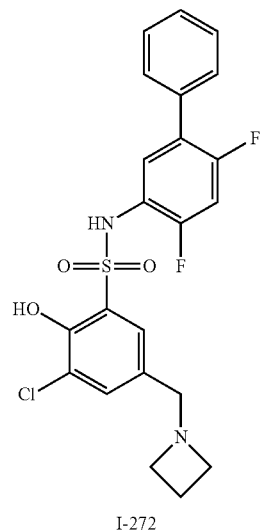

I-272

Synthesis of I-272

Into a 8-mL round-bottom flask purged and maintained with an inert atmosphere of nitrogen, was placed 197.1 (100 mg, 0.21 mmol, 1 equiv), borane (14.4 mg, 1.04 mmol, 5.00 equiv), and oxolane (5 mL). The resulting solution was stirred for 12 hr at 50° C. in an oil bath. The resulting mixture was concentrated. The crude product was purified by Flash-Prep-HPLC with the following conditions (IntelFlash-1): Column, C18 silica gel; mobile phase, CH$_3$CN/H$_2$O=1:2 increasing to CH$_3$CN/H$_2$O=1:1 within 20 mins. This resulted in 8 mg (yield=8%) of I-272 as a white solid. (ES, m/z): [M+H]$^+$ 465.1, $^1$H-NMR (400 MHz, CD$_3$OD, ppm): δ7.69-7.64 (m, 2H), δ7.48-7.36 (m, 6H), δ7.06-7.00 (m, 1H), δ3.80 (s, 2H), δ3.73-3.66 (m, 2H), δ3.33-3.24 (m, 2H), δ2.46-2.39 (m, 1H), δ1.89-1.81 (m, 1H).

Example 198. Synthesis of 5-(3-aminoazetidine-1-carbonyl)-3-chloro-2-hydroxy-N-[4-methoxy-[1,1-biphenyl]-3-yl]benzene-1-sulfonamide, I-276

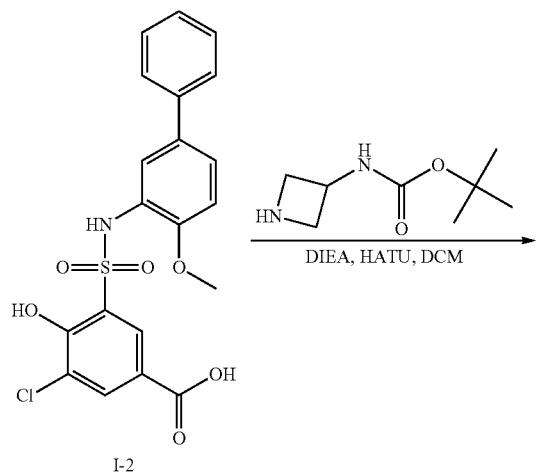

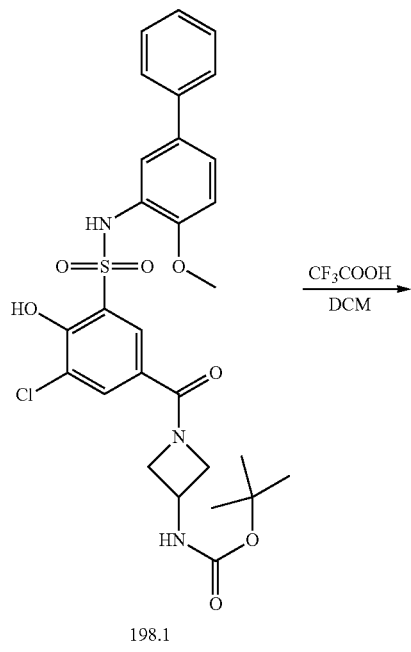

Synthesis of Compound 198.1

To a stirred mixture of I-2 (200 mg, 0.46 mmol, 1 equiv) and tert-butyl N-(azetidin-3-yl)carbamate (158.8 mg, 0.92 mmol, 2 equiv) in DCM (2 mL, 31.46 mmol, 68.25 equiv) were added DIEA (238.3 mg, 1.84 mmol, 4 equiv) and HATU (350.6 mg, 0.92 mmol, 2 equiv) in portions at room temperature under nitrogen atmosphere. The resulting solution was stirred for overnight at room temperature under nitrogen atmosphere. The reaction was quenched with Water/Ice at room temperature. The aqueous layer was extracted with EtOAc (2×100 mL). The crude product was purified by reverse phase flash with the following conditions (from $CH_3CN:H_2O=1:20$ to $CH_3CN:H_2O=50:50$ in 30 mins, UV: 254/220) to afford 198.1 (110 mg, 40.5%) as an off-white solid. (ES, m/z): $[M+H]^+$ 588.1.

Synthesis of I-276

A mixture of 198.1 (100 mg, 0.17 mmol, 1 equiv) and $CF_3COOH$ (0.2 mL, 2.69 mmol, 15.83 equiv) in DCM (1 mL, 15.73 mmol, 92.50 equiv) was stirred for 30 min at room temperature under nitrogen atmosphere. The reaction was quenched with $NaHCO_3$ (1 M) at room temperature. The aqueous layer was extracted with EtOAc (2×100 mL). The crude product was purified by reverse phase flash with the following conditions (from $CH_3CN:H_2O=1:20$ to $CH_3CN:H_2O=50:50$ in 30 mins, UV: 254/220) to afford I-276 (30.2 mg, 36.4%) as an off-white solid. (ES, m/z): $[M+H]^+$ 488.1, $^1$H-NMR (400 MHz, DMSO-$d_6$, ppm): δ3.80 (s, 3H), δ3.95-4.02 (m, 3H), δ4.32 (s, 2H), δ7.02-7.04 (d, J=8.8 Hz, 1H), δ7.23-7.25 (m, 1H), δ7.29-7.31 (m, 1H), δ7.40-7.39 (m, 5H), δ7.63 (s, 1H), δ7.69-7.76 (s, 1H).

Example 199. Synthesis of 3-chloro-2-hydroxy-N-[4-methoxy-[1,1-biphenyl]-3-yl]-5-(piperazine-1-carbonyl)benzene-1-sulfonamide, I-277

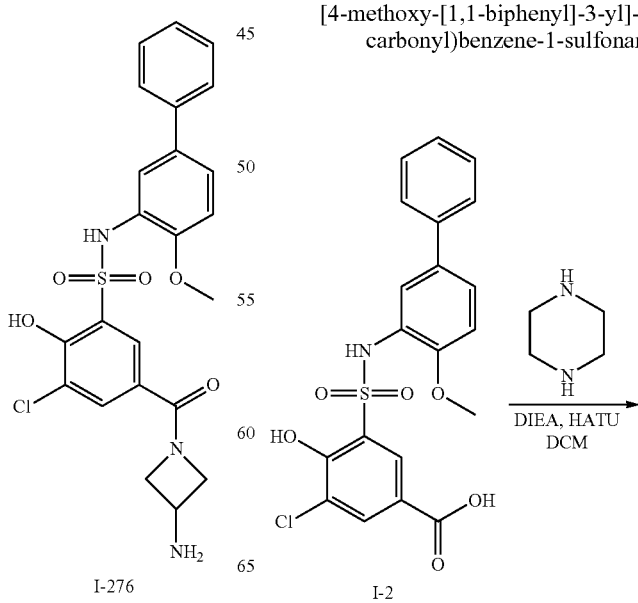

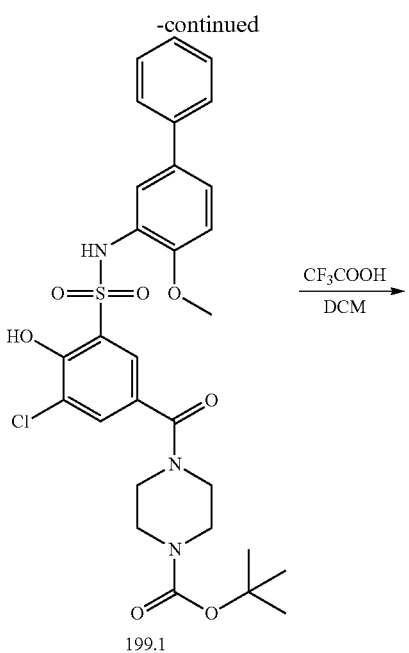

199.1

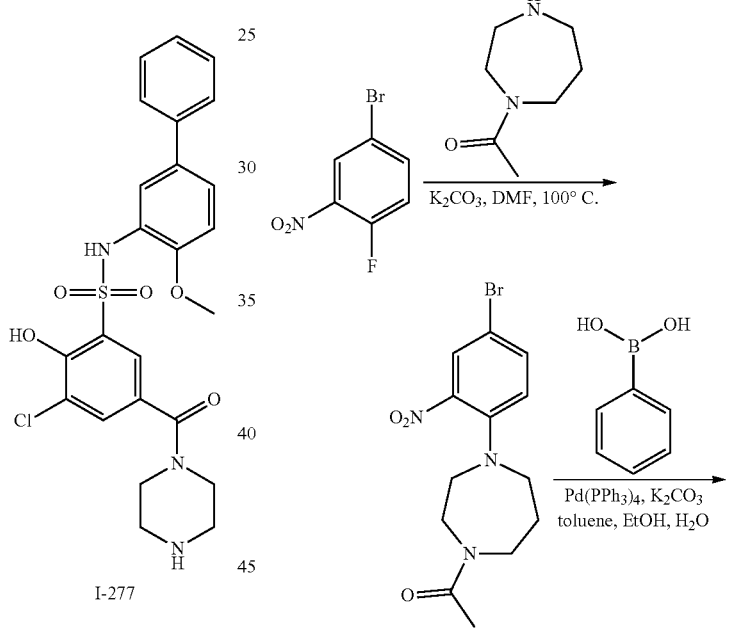

mL, 15.73 mmol, 118.39 equiv) was stirred for 30 min at room temperature under nitrogen atmosphere. The reaction was quenched with NaHCO$_3$ (1 M) at room temperature. The aqueous layer was extracted with EtOAc (2×100 mL). The crude product was purified by reverse phase flash with the following conditions (from CH$_3$CN:H$_2$O=1:20 to CH$_3$CN:H$_2$O=50:50 in 30 mins, UV: 254/220) to afford I-277 (25.6 mg, 38.3%) as an off-white solid. (ES, m/z): [M+H]$^+$ 502.2, $^1$H-NMR (400 MHz, DMSO-d$_6$, ppm): δ3.01-3.04 (m, 4H), δ3.60-3.63 (m, 4H), δ3.79 (s, 3H), δ7.02-7.04 (d, J=8.8 Hz, 1H), δ7.21-7.24 (t, J=6.0 Hz, 1H), δ7.29-7.33 (m, 1H), δ7.37-7.47 (m, 5H), δ7.53 (s, 1H), δ7.62 (s, 1H), δ8.48-9.00 (s, 2H).

Example 200. Synthesis of N-[4-(4-acetyl-1,4-diazepan-1-yl)-[1,1-biphenyl]-3-yl]-3,5-dichloro-2-hydroxybenzene-1-sulfonamide, I-279

Synthesis of Compound 199.1

To a stirred mixture of I-2 (200 mg, 0.46 mmol, 1 equiv) and tert-butyl piperazine-1-carboxylate (171.7 mg, 0.92 mmol, 2 equiv) in DCM (2 mL, 31.46 mmol, 68.25 equiv) were added DIEA (238.3 mg, 1.84 mmol, 4 equiv) and HATU (350.6 mg, 0.92 mmol, 2 equiv) in portions at room temperature under nitrogen atmosphere. The reaction was quenched with Water/Ice at room temperature. The aqueous layer was extracted with EtOAc (2×100 mL). The crude product was purified by reverse phase flash with the following conditions (from CH$_3$CN:H$_2$O=1:20 to CH$_3$CN:H$_2$O=50:50 in 30 mins, UV: 254/220) to afford 199.1 (90 mg, 32%) as an off-white solid. (ES, m/z): [M−H]$^-$ 600.1.

Synthesis of I-277

A mixture of 199.1 (80 mg, 0.13 mmol, 1 equiv) and CF$_3$COOH (0.2 mL, 2.69 mmol, 20.27 equiv) in DCM (1

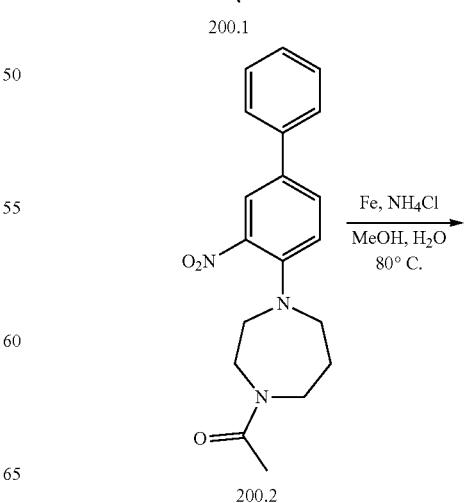

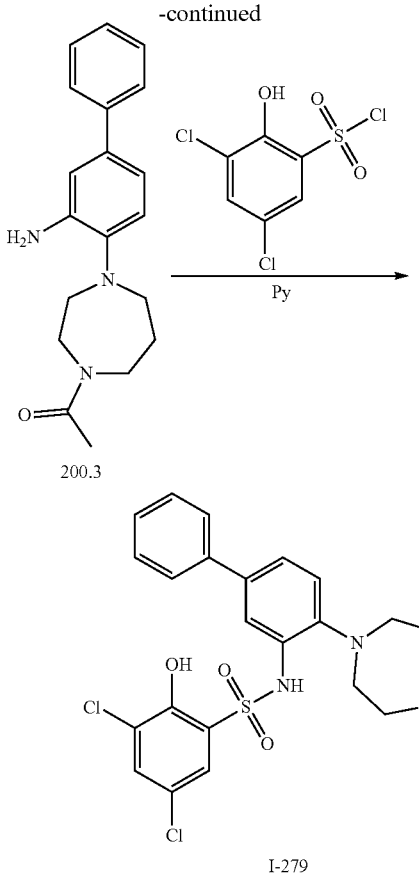

200.3

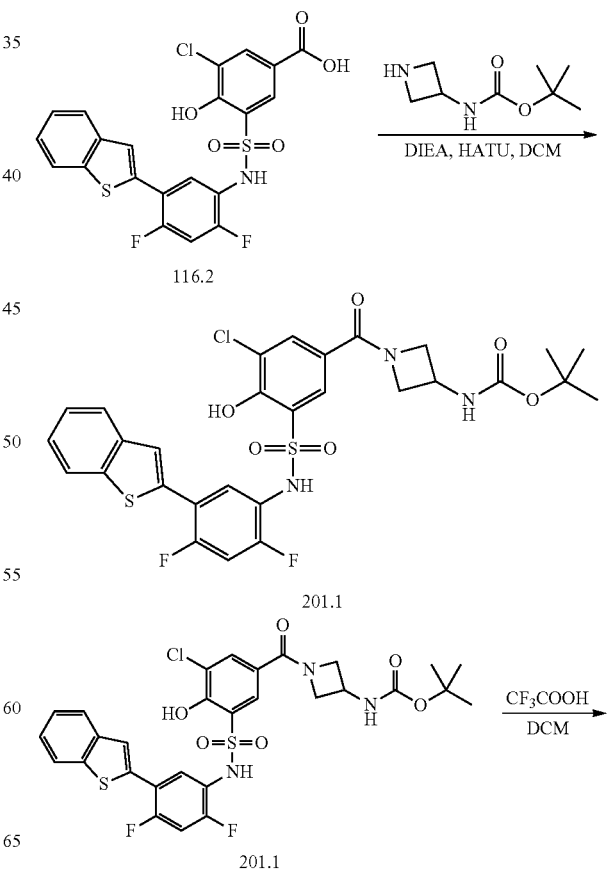

I-279

Synthesis of Compound 200.1

To a stirred mixture of 4-bromo-1-fluoro-2-nitrobenzene (1 g, 4.55 mmol, 1 equiv) and 1-(1,4-diazepan-1-yl)ethan-1-one (775.7 mg, 5.45 mmol, 1.2 equiv) in DMF (20 mL, 258.44 mmol, 56.85 equiv) was added $K_2CO_3$ (1.9 g, 13.64 mmol, 3 equiv) in portions at 100° C. under nitrogen atmosphere. The resulting solution was stirred for overnight at 100° C. under nitrogen atmosphere. The resulting mixture was filtered the filter cake was washed with EtOAc (2×100 mL). The filtrate was concentrated under reduced pressure. The residue was purified by silica gel column chromatography, eluted with PE/EtOAc (10:1) to afford 200.1 (1.3 g, 83%) as an off-white solid. (ES, m/z): [M+H]⁺ 342.0.

Synthesis of Compound 200.2

To a stirred mixture of 200.1 (1.3 g, 3.80 mmol, 1 equiv) and phenylboronic acid (555.9 mg, 4.56 mmol, 1.2 equiv) in Toluene, EtOH, $H_2O$ (20 mL, 187.98 mmol, 49.48 equiv) were added $Pd(PPh_3)_4$ (219.5 mg, 0.19 mmol, 0.05 equiv) and $K_2CO_3$ (2.6 g, 19.00 mmol, 5 equiv) in portions at 90° C. with stirring for overnight under nitrogen atmosphere. The resulting mixture was filtered the filter cake was washed with EtOAc (2×100 mL). The filtrate was concentrated under reduced pressure. The residue was purified by silica gel column chromatography, eluted with PE/EtOAc (10:1) to afford 200.2 (1 g, 77%) as an off-white solid. (ES, m/z): [M+H]⁺ 340.1.

Synthesis of Compound 200.3

To a stirred mixture of 200.2 (500 mg, 1.47 mmol, 1 equiv) and Fe (246.8 mg, 4.42 mmol, 3 equiv) in MeOH, $H_2O$ (5 mL, 123.49 mmol, 83.83 equiv) was added $NH_4Cl$ (472.8 mg, 8.84 mmol, 6 equiv) in portions at 80° C. with stirring for 3 h under nitrogen atmosphere. The resulting mixture was filtered the filter cake was washed with EtOAc (2×100 mL). The filtrate was concentrated under reduced pressure. The residue was purified by Prep-TLC (PE/EtOAc 10:1) to afford 200.3 (140 mg, 30.7%) as a brown oil. (ES, m/z): [M+H]⁺ 310.1.

Synthesis of I-279

A mixture of 200.3 (140 mg, 0.45 mmol, 1 equiv) and 3,5-dichloro-2-hydroxybenzene-1-sulfonyl chloride (118.3 mg, 0.45 mmol, 1 equiv) in Pyridine (2 mL, 24.85 mmol, 54.91 equiv) was stirred for 2 h at 50° C. under nitrogen atmosphere. The reaction was quenched with HCl (1 M) at room temperature. The aqueous layer was extracted with EtOAc (2×100 mL). The crude product was purified by reverse phase flash with the following conditions (from $CH_3CN:H_2O=1:20$ to $CH_3CN:H_2O=50:50$ in 30 mins, UV: 254/220) to afford I-279 (30.1 mg, 12.4%) as an off-white solid. (ES, m/z): [M+H]⁺ 534.2, ¹H-NMR (400 MHz, DMSO-$d_6$, ppm): δ1.87-1.91 (m, 1H), δ1.97-2.03 (m, 1H), δ2.06 (s, 3H), δ2.91-3.20 (m, 4H), δ3.61-3.67 (m, 4H), δ6.97-7.60 (m, 11H), δ10.19 (s, 1H).

Example 201. Synthesis of 5-(3-aminoazetidine-1-carbonyl)-N-(5-(benzo[b] thiophen-2-yl)-2,4-difluorophenyl)-3-chloro-2-hydroxybenzenesulfonamide, I-282

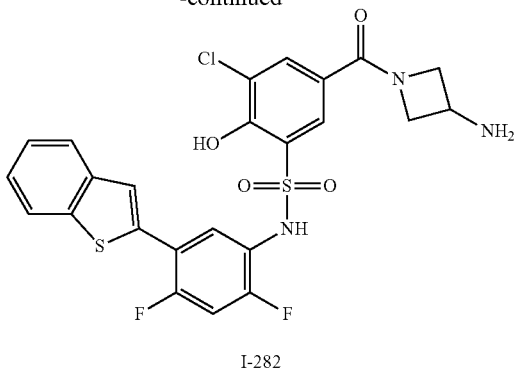

I-282

Synthesis of Compound 201.1

Into a 25-mL round-bottom flask purged and maintained with an inert atmosphere of nitrogen, was placed 116.2 (170 mg, 0.34 mmol, 1 equiv), tert-butyl N-(azetidin-3-yl)carbamate (118.1 mg, 0.69 mmol, 2 equiv), DIEA (88.6 mg, 0.69 mmol, 2 equiv), HATU (391.0 mg, 1.03 mmol, 3 equiv), DCM (5 mL). The resulting solution was stirred for 12 hr at room temperature. The reaction was then quenched by the addition of 10 mL of water. The resulting solution was extracted with 3×10 mL of dichloromethane. The resulting mixture was washed with 1×10 mL of brine. The mixture was dried over anhydrous sodium sulfate and concentrated. The residue was applied onto a silica gel column with ethyl acetate/petroleum ether (1:1). This resulted in 100 mg (yield=45%) of 201.1 as a white solid. (ES, m/z): [M–H]⁻ 648.0.

Synthesis of I-282

Into a 8-mL round-bottom flask purged and maintained with an inert atmosphere of nitrogen, was placed 201.1 (80 mg, 0.12 mmol, 1 equiv), TFA (14.0 mg, 0.12 mmol, 1.00 equiv), DCM (5 mL). The resulting solution was stirred for 12 hr at room temperature. The reaction was then quenched by the addition of 2 mL of H$_2$O. The resulting solution was extracted with 3×5 mL of ethyl acetate. The resulting mixture was washed with 1×5 mL of brine. The mixture was dried over anhydrous sodium sulfate and concentrated. The residue was applied onto a silica gel column with ethyl acetate/petroleum ether (1:1). This resulted in 3.5 mg (yield=5%) of I-282 as a white solid. (ES, m/z): [M+H]⁺ 550.0, ¹H-NMR (400 MHz, DMSO-d$_6$, ppm): δ7.98-7.96 (d, J=8.4 Hz, 1H), δ7.91-7.89 (d, J=6.8 Hz, 1H), δ7.68-7.57 (m, 4H), δ7.47-7.32 (m, 3H), δ4.32 (s, 2H), δ4.01-3.95 (m, 3H).

Example 202. Synthesis of 2-amino-3,5-dichloro-N-(2-methoxy-5-phenylphenyl) benzene-1-sulfonamide, I-414

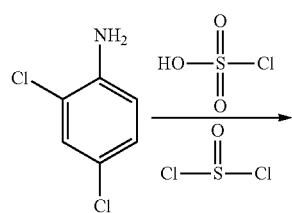

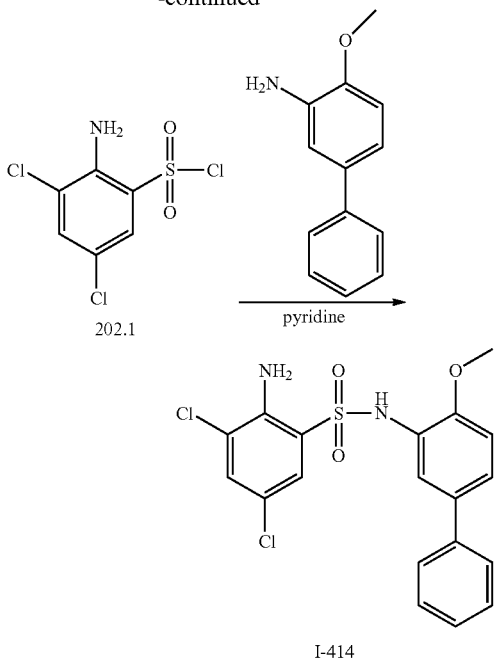

I-414

Synthesis of Compound 202.1

Into a 100-mL 3-necked round-bottom flask, 2,4-dichloroaniline (2 g, 12.3 mmol, 1 equiv) was added to chlorosulfonic acid (7 mL) in an ice/water bath. The suspension was then refluxed and added thionyl chloride (2 mL) after 1 h. The reflux was maintained for another 30 min. The reaction was then quenched by the addition of 15 mL of water/ice. The resulting solution was extracted with ethyl acetate (3×15 mL) and the combined organic layers were concentrated under vacuum. This resulted in 2 g (62%) of 202.1 as a grey solid.

Synthesis of I-414

Into a 50-mL round-bottom flask, was placed 202.1 (500 mg, 1.92 mmol, 1 equiv), 2-methoxy-5-phenylaniline (764.8 mg, 3.84 mmol, 2 equiv), pyridine (5 mL). The resulting solution was stirred for 2 h at 25° C. The resulting mixture was concentrated under vacuum. The residue was applied onto Prep-TLC with dichloromethane/methanol (20:1). The crude product was purified by Flash-Prep-HPLC with the following conditions (IntelFlash-1): Column, C18; mobile phase, H$_2$O:ACN=15% increasing to H$_2$O:ACN=60% within 15 min; Detector, 254 nm. This resulted in 40.1 mg (4.9%) of I-414 as a brown solid. (ES, m/z): [M–H]⁻ 421.0, ¹H-NMR (300 MHz, DMSO-d$_6$, ppm): δ3.66 (s, 3H), δ6.33 (s, 2H), δ7.03-7.06 (d, J=8.4 Hz, 1H), δ7.30-7.35 (m, 1H), δ7.40-7.46 (m, 5H), δ7.50-7.52 (m, 2H), δ7.66-7.67 (d, J=2.4 Hz, 1H), δ10.06 (s, 1H).

531

Example 203. Synthesis of 5-chloro-N-(2-fluoro-5-phenylphenyl)-1-methyl-2-oxo-1,2-dihydropyridine-3-sulfonamide, I-415

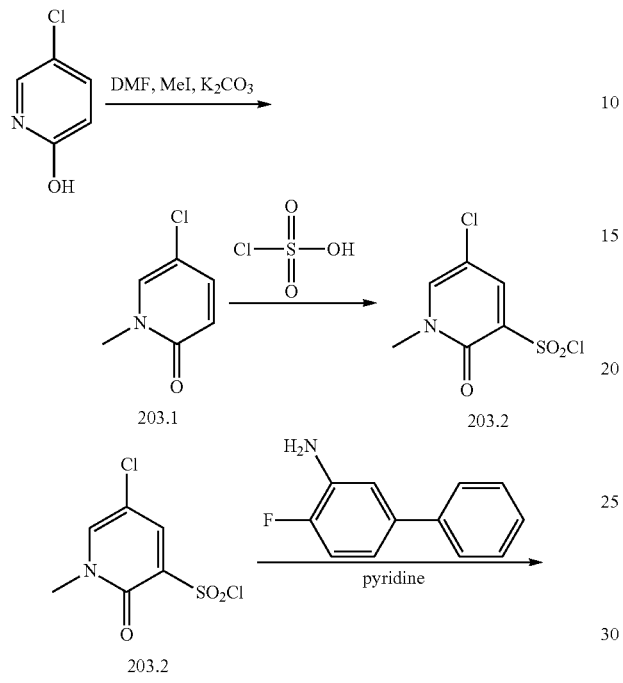

Synthesis of Compound 203.1

Into a 250-mL 3-necked round-bottom flask, was placed 5-chloropyridin-2-ol (5 g, 38.60 mmol, 1.00 equiv), N,N-dimethylformamide (100 mL), K2CO3 (15.9 g, 114.21 mmol, 3.00 equiv), iodomethane (10.9 g, 76.79 mmol, 2.00 equiv). The resulting solution was stirred for 4 h at 80° C. The solids were filtered out. The resulting mixture was concentrated under vacuum. The residue was applied onto a silica gel column with dichloromethane/methanol (20:1). This resulted in 4.2 g (76%) of 203.1 as light yellow oil. (ES, m/z): [M–H]⁻ 142.0.

Synthesis of Compound 203.2

Into a 100-mL 3-necked round-bottom flask, was placed 203.1 (2.5 g, 17.41 mmol, 1 equiv), chloranesulfonic acid (30 mL). The resulting solution was stirred for 6 h at 160° C. The reaction was then quenched by the addition of water/ice (20 mL). The resulting solution was extracted with 2×20 mL of ethyl acetate. The combined organic layers were concentrated under vacuum. This resulted in 1.5 g (35%) of 203.2 as a brown solid. (ES, m/z): [M–H]⁻ 239.9.

532

Synthesis of I-415

Into a 50-mL round-bottom flask, was placed 203.2 (300 mg, 1.24 mmol, 1 equiv), 2-fluoro-5-phenylaniline (278.4 mg, 1.49 mmol, 1.200 equiv), pyridine (5 mL). The resulting solution was stirred for 4 h at room temperature. The resulting mixture was concentrated under vacuo. The residue was applied onto Prep-TLC with dichloromethane/methanol (10:1). This resulted in 26.4 mg (5.4%) of I-415 as a white solid. (ES, m/z): [M+H]⁺ 393.1, ¹H-NMR (300 MHz, DMSO-d₆, ppm): δ10.05 (s, 1H), δ8.43-8.42 (d, J=3.0 Hz, 1H), δ7.98-7.97 (d, J=3.0 Hz, 1H), δ7.56-7.48 (m, 6H), δ7.46-7.37 (m, 1H), δ7.31-7.24 (m, 1H), δ3.53 (s, 3H).

Example 204. Synthesis of 3,5-dichloro-N-(2-fluoro-5-phenylphenyl)-2-(2,2,2-trifluoroethoxy)benzene-1-sulfonamide, I-286

533

-continued

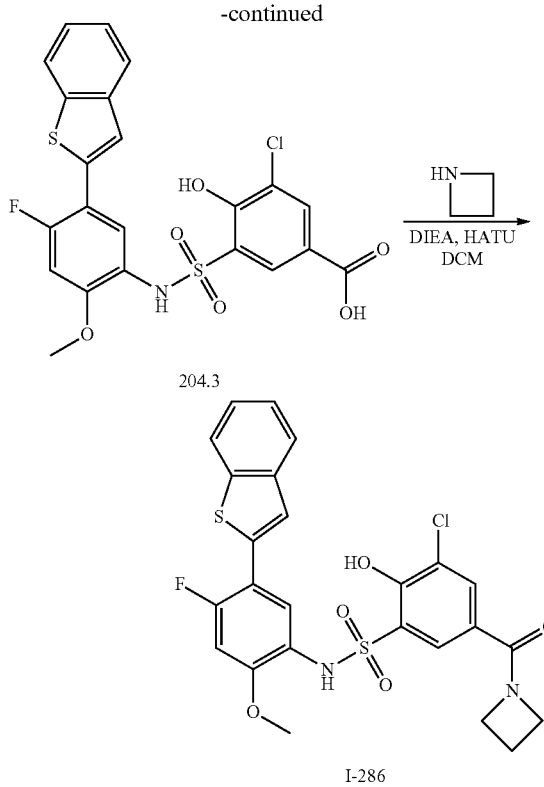

204.3

I-286

Synthesis of Compound 204.1

Into a 100-mL round-bottom flask purged and maintained with an inert atmosphere of nitrogen, was placed 1-bromo-2-fluoro-4-methoxy-5-nitrobenzene (500 mg, 2.000 mmol, 1 equiv), (1-benzothiophen-2-yl)boronic acid (533.98 mg, 3.000 mmol, 1.5 equiv), Pd(DtBPF)Cl$_2$ (130.34 mg, 0.200 mmol, 0.1 equiv), K$_2$CO$_3$ (829.16 mg, 5.999 mmol, 3 equiv), toluene (10 mL). The resulting solution was stirred for 2 hr at 800° C. in an oil bath. The reaction was then quenched by the addition of 20 mL of water. The resulting solution was extracted with 3×20 mL of ethyl acetate. The resulting mixture was washed with 1×20 mL of brine. The mixture was dried over anhydrous sodium sulfate and concentrated. The residue was applied onto a silica gel column with ethyl acetate/petroleum ether (1:5). This resulted in 500 mg (yield=82%) of 204.1 as a white solid. (ES, m/z): [M+H]$^+$ 304.0.

Synthesis of Compound 204.2

Into a 100-mL round-bottom flask purged and maintained with an inert atmosphere of nitrogen, was placed 204.1 (500 mg, 1.648 mmol, 1 equiv), Fe (368.24 mg, 6.594 mmol, 4 equiv), NH$_4$Cl (440.89 mg, 8.242 mmol, 5 equiv), EtOH (10 mL), THF (5 mL), H$_2$O (5 mL). The resulting solution was stirred for 12 hr at 80° C. in an oil bath. The resulting solution was extracted with 3×20 mL of ethyl acetate. The resulting mixture was washed with 1×20 mL of brine. The mixture was dried over anhydrous sodium sulfate and concentrated. This resulted in 240 mg (yield=53%) of 204.2 as a white solid. (ES, m/z): [M−H]$^−$ 272.0.

Synthesis of Compound 204.3

Into a 25-mL round-bottom flask purged and maintained with an inert atmosphere of nitrogen, was placed 204.2 (220

534 mg, 0.805 mmol, 1 equiv), 3-chloro-5-(chlorosulfonyl)-4-hydroxybenzoic acid (218.17 mg, 0.805 mmol, 1 equiv), pyridine (5 mL). The resulting solution was stirred for 0.5 hr at room temperature. The resulting mixture was concentrated. The residue was applied onto a silica gel column with dichloromethane/methanol (5:1). This resulted in 200 mg (yield=49%) of 204.3 as a white solid. (ES, m/z): [M−H]$^−$ 506.0.

Synthesis of I-286

Into a 50-mL round-bottom flask purged and maintained with an inert atmosphere of nitrogen, was placed 204.3 (200 mg, 0.39 mmol, 1 equiv), azetidine (112.4 mg, 1.97 mmol, 5 equiv), HATU (449.2 mg, 1.18 mmol, 3 equiv), DIEA (203.6 mg, 1.58 mmol, 4 equiv), DCM (5 mL). The resulting solution was stirred for 12 hr at room temperature. The reaction was then quenched by the addition of 10 mL of water. The resulting solution was extracted with 3×10 mL of dichloromethane. The resulting mixture was washed with 1×10 mL of brine. The mixture was dried over anhydrous sodium sulfate and concentrated. The residue was applied onto a silica gel column with ethyl acetate/petroleum ether (1:1). This resulted in 38.1 mg (yield=18%) of I-286 as a white solid. (ES, m/z): [M+H]$^+$ 547.2, $^1$H-NMR (400 MHz, DMSO-d$_6$, ppm): δ7.98-7.96 (t, J=1.2 Hz, 1H), δ7.89-7.87 (m, 1H), δ7.68-7.60 (m, 4H), δ7.42-7.34 (m, 2H), δ7.63-6.99 (m, 3H), δ4.14 (s, 4H), δ3.76 (s, 3H), δ2.10-2.02 (m, 2H).

Example 205. Synthesis of 3,5-dichloro-N-[2,4-difluoro-5-(2H-1,2,3-triazol-2-yl)phenyl]-2-hydroxy-benzene-1-sulfonamide, I-290

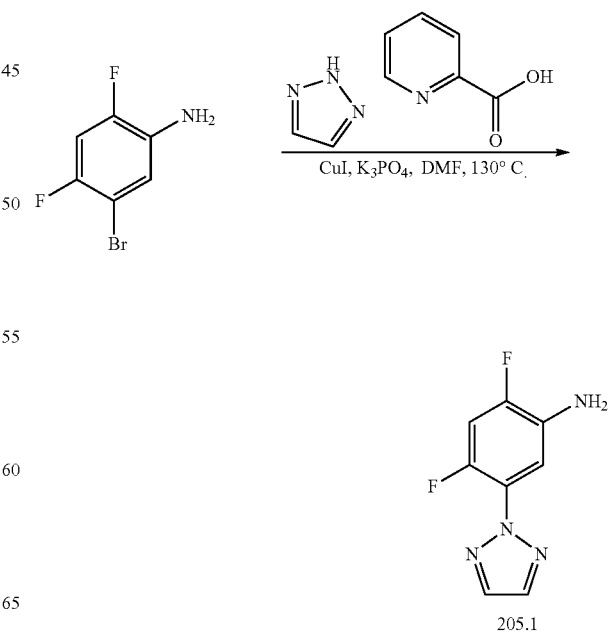

205.1

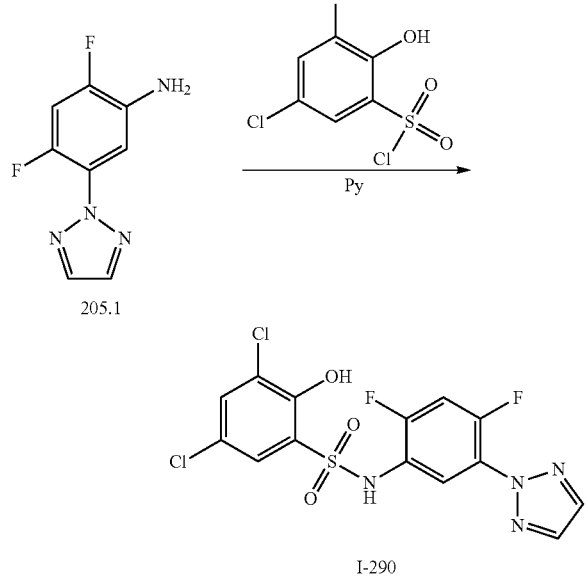

Synthesis of Compound 205.1

Into a 20-mL vial purged and maintained with an inert atmosphere of nitrogen, was placed 5-bromo-2,4-difluoroaniline (400 mg, 1.923 mmol, 1 equiv), 2H-1,2,3-triazole (146.10 mg, 2.115 mmol, 1.1 equiv), pyridine-2-carboxylic acid (94.70 mg, 0.769 mmol, 0.4 equiv), $K_3PO_4$ (1020.48 mg, 4.808 mmol, 2.5 equiv), DMF (8 mL), CuI (73.25 mg, 0.385 mmol, 0.2 equiv). The resulting solution was stirred for 1 overnight at 130° C. in an oil bath. The resulting solution was diluted with 20 mL of $H_2O$. The resulting solution was extracted with 3×20 mL of ethyl acetate concentrated under vacuum. The residue was applied onto a prep TLC with ethyl acetate/petroleum ether (1:1). This resulted in 100 mg (26%) of 205.1 as a white solid.

Synthesis of I-290

Into a 8-mL vial, was placed 205.1 (100 mg, 0.510 mmol, 1 equiv), pyridine (1 mL), 3,5-dichloro-2-hydroxybenzene-1-sulfonyl chloride (119.98 mg, 0.459 mmol, 0.90 equiv). The resulting solution was stirred for 3 hr at room temperature. The resulting mixture was concentrated under vacuum. The crude product was purified by Prep-HPLC with the following conditions (2 #SHIMADZU (HPLC-01)): Column, Column: SunFire C18 OBD Prep Column, 100 Å, 5 μm, 19 mm×250 mm; Mobile Phase A: Water (1% HAC), Mobile Phase B: ACN; Flow rate: 25 mL/min; Gradient: 75% B to 90% B in 7.5 min; 254/220 nm; Rt: 5.97 min. This resulted in 18.1 mg (8.4%) of I-290 as a white solid. (ES, m/z): [M−H]⁻ 419.0, $^1$H-NMR (300 MHz, DMSO-$d_6$, ppm): δ 8.18 (s, 2H), 7.87-7.86 (d, J=2.7 Hz, 1H), 7.80-7.74 (m, 1H), 7.74-7.61 (m, 1H), 7.55-7.54 (d, J=2.4 Hz, 1H).

Example 206. Synthesis of 4-[[3-(3,5-dichlorobenzenesulfonamido)-[1,1-biphenyl]-4-yl]oxy]butanoic Acid, I-291

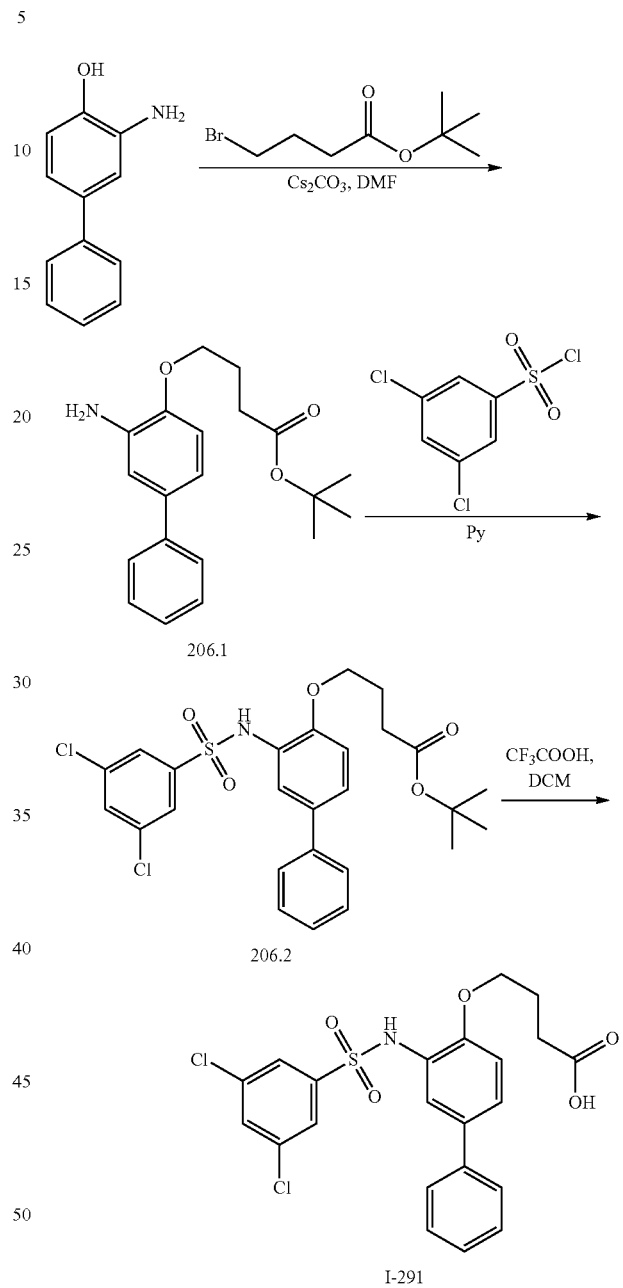

Synthesis of Compound 206.1

Into a 50-mL round-bottom flask purged and maintained with an inert atmosphere of nitrogen, was placed 3-amino-[1,1-biphenyl]-4-ol (500 mg, 2.699 mmol, 1 equiv), DMF (25 mL), $Cs_2CO_3$ (1759.04 mg, 5.399 mmol, 2.00 equiv), tert-butyl 4-bromobutanoate (903.40 mg, 4.049 mmol, 1.50 equiv). The resulting solution was stirred for 1 overnight at 70° C. in an oil bath. The resulting solution was diluted with 100 mL of $H_2O$. The resulting solution was extracted with 3×50 mL of ethyl acetate concentrated under vacuum. The residue was applied onto a prep TLC with ethyl acetate/petroleum ether (1:20). This resulted in 360 mg (40.7%) of 206.1 as a red oil.

Synthesis of Compound 206.2

Into a 8-mL vial, was placed 206.1 (239 mg, 0.730 mmol, 1 equiv), pyridine (3 mL), 3,5-dichlorobenzene-1-sulfonyl chloride (179.20 mg, 0.730 mmol, 1 equiv). The resulting solution was stirred for 1 hr at room temperature. The resulting mixture was concentrated under vacuum. The residue was applied onto a prep TLC with ethyl acetate/petroleum ether (1:3). This resulted in 338 mg (86.3%) of 206.2 as a yellow oil.

Synthesis of I-291

Into a 8-mL vial, was placed 206.2 (328 mg, 0.61 mmol, 1 equiv), DCM (2 mL), $CF_3COOH$ (0.1 mL, 1.35 mmol, 2.20 equiv). The resulting solution was stirred for 1 overnight at room temperature. The resulting mixture was concentrated under vacuum. The crude product was purified by Flash-Prep-HPLC with the following conditions (IntelFlash-1): Column, C18 silica gel; mobile phase, $ACN/H_2O=15\%$ increasing to $ACN/H_2O=60\%$ within 15 min; Detector: UV 254 nm. This resulted in 141.2 mg (48.1%) of I-291 as a yellow solid. (ES, m/z): $[M–H]^-$ 478.0, $^1H$-NMR (300 MHz, DMSO-$d_6$, ppm): δ 12.09 (s, 1H), 10.01 (s, 1H), 7.94-7.92 (t, J=1.8 Hz, 1H), 7.65-7.64 (d, J=2.1 Hz, 2H), 7.60-7.40 (m, 6H), 7.38-7.29 (m, 1H), 7.04-7.01 (d, J=8.4 Hz, 1H), 3.82-3.78 (t, J=6.3 Hz, 2H), 2.39-2.35 (t, J=7.2 Hz, 2H), 1.83-1.69 (m, 2H).

Example 207. Synthesis of 5-chloro-N-[4,6-difluoro-[1,1-biphenyl]-3-yl]-2-oxo-1,2-dihydropyridine-3-sulfonamide, I-298

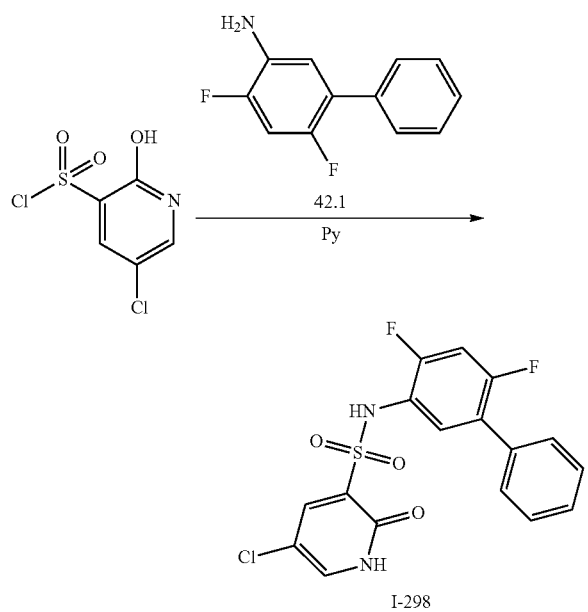

Synthesis of I-298

Into a 8-mL vial, was placed 5-chloro-2-hydroxypyridine-3-sulfonyl chloride (44 mg, 0.193 mmol, 1 equiv), 42.1 (47.51 mg, 0.232 mmol, 1.2 equiv), pyridine (2 mL). The resulting solution was stirred for 2 hr at room temperature. The resulting mixture was concentrated under vacuum. The crude product was purified by Flash-Prep-HPLC with the following conditions (IntelFlash-1): Column, C18 silica gel; mobile phase, $ACN/H_2O=15\%$ increasing to $ACN/H_2O=60\%$ within 15 min; Detector, UV: 254. This resulted in 9.1 mg (11%) of I-298 as an off-white solid. (ES, m/z): $[M–H]^-$ 395.0, $^1H$-NMR (400 MHz, DMSO-$d_6$, ppm): δ 8.05-8.04 (d, J=2.4 Hz, 1H), 7.92-7.91 (d, J=2.8 Hz, 1H), 7.50-7.48 (t, J=8.4 Hz, 2H), 7.46-7.35 (m, 5H).

Example 208. Synthesis of 3-[(3,5-dichloro-2-methoxybenzene)sulfonamido]-4-fluorobenzoic Acid, I-413

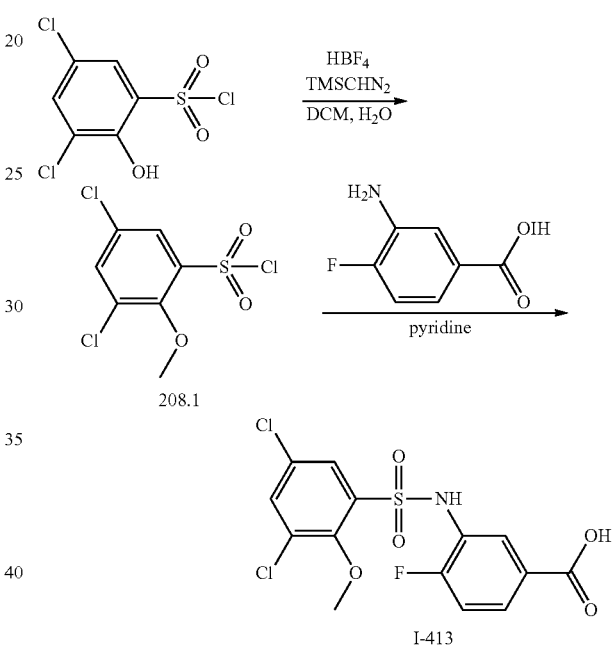

Synthesis of 208.1

Into a 25-mL 3-necked round-bottom flask purged and maintained with an inert atmosphere of nitrogen, was placed 3,5-dichloro-2-hydroxybenzene-1-sulfonyl chloride (200 mg, 0.76 mmol, 1 equiv), DCM (5 mL), $TMSCHN_2$ (174.7 mg, 1.53 mmol, 2 equiv), $HBF_4$ (335 mg, 3.81 mmol, 4.988 equiv, 40%). The resulting solution was stirred for 1 h at 0° C. And then the reaction was quenched by the addition of 5 mL of $H_2O$, followed by extraction with 3×10 mL of ethyl acetate and the combined organic layers were concentrated under vacuum. This resulted in 180 mg (crude) of 208.1 as a white solid.

Synthesis of I-413

Into a 8-mL vial purged and maintained with an inert atmosphere of nitrogen, was placed 208.1 (180 mg, 0.65 mmol, 1 equiv), pyridine (2 mL), 3-amino-4-fluorobenzoic acid (121.6 mg, 0.78 mmol, 1.2 equiv). The resulting solution was stirred for 2 h at room temperature. Then, the reaction was quenched by the addition of 2 mL of 1M HCl and extracted with ethyl acetate (3×5 mL). The combined organic layers were concentrated under vacuum. The residue was applied onto a silica gel column with dichloromethane/methanol (20:1). The crude product was purified by Prep-HPLC with the following conditions (2 #-AnalyseHPLC-SHIMADZU (HPLC-10)): Column: XBridge Prep OBD C18 Column 30×150 mm 5 um; Mobile Phase A: water (0.05% NH₃.H₂O), Mobile Phase B: ACN; Flow rate: 60 mL/min; Gradient: 10% B to 20% B in 7 min; Detector, UV 254/220 nm; Rt: 4.55 min. This resulted in 47.4 mg (18.4%) of I-413 as a white solid (ES, m/z): [M−H]⁻ 392.1, ¹H-NMR (300 MHz, CDCl₃, ppm): δ4.10 (s, 3H), δ7.01 (br s, 1H), δ7.54 (s, 1H), δ7.67 (s, 1H), δ7.83 (br s, 1H), δ8.21 (br s, 1H).

Example 209. Synthesis of N-[4-fluoro-[1,1-biphenyl]-3-yl]-2-oxo-5-(trifluoromethyl)-1,2-dihydropyridine-3-sulfonamide, I-355

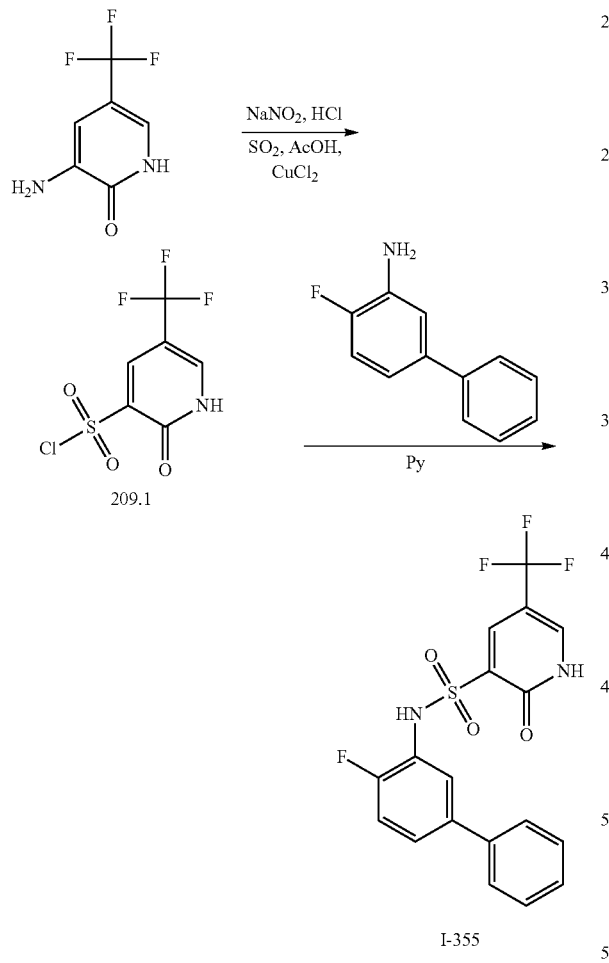

I-355

Synthesis of Compound 209.1

The mixture A: Into a 8-mL vial, was placed 3-amino-5-(trifluoromethyl)-1,2-dihydropyridin-2-one (200 mg, 1.123 mmol, 1 equiv), HCl (2 mL), the mixture was cooled to 0° C., then was added NaNO₂ (116.21 mg, 1.684 mmol, 1.5 equiv) in 1 ml of H₂O. The resulting solution was stirred for 0.5 hr at 0° C. in an ice/salt bath. The mixture B: Into a 20-ml vial, was placed AcOH(SO₂) (8 mL) and CuCl₂ under an atmosphere of SO₂. The resulting solution was stirred for 5 min at 0° C. in an ice/salt bath. Then added the solution A to B. The resulting solution was allowed to react, with stirring, for an additional 2 hr while the temperature was maintained at 0° C. in an ice/salt bath. The resulting solution was diluted with 30 mL of H₂O. The resulting solution was extracted with 3×30 mL of ethyl acetate concentrated under vacuum. This resulted in 258 mg (87.8%) of 209.1 as yellow oil. (ES, m/z): [M−H]⁻ 259.9.

Synthesis of I-355

Into a 8-mL vial, was placed 209.1 (100 mg, 0.382 mmol, 1 equiv), 4-fluoro-[1,1-biphenyl]-3-amine (85.88 mg, 0.459 mmol, 1.2 equiv), pyridine (2 mL, 24.847 mmol, 65.00 equiv). The resulting solution was stirred for 2 hr at room temperature. The resulting mixture was concentrated under vacuum. The crude product was purified by Flash-Prep-HPLC with the following conditions (IntelFlash-1): Column, C18 silica gel; mobile phase, ACN/H₂O=15% increasing to ACN/H₂O=60% within 15 min; Detector, UV: 254. This resulted in 75.3 mg (47.7%) of I-355 as a white solid (ES, m/z): [M−H]⁻ 411.0, ¹H-NMR (400 MHz, DMSO-d₆, ppm): δ 13.26 (s, 1H), 10.17 (s, 1H), 8.38 (s, 1H), 8.08-8.07 (d, J=2.8 Hz, 1H), 7.57-7.42 (m, 6H), 7.41-7.35 (m, 1H), 7.29-7.26 (m, 1H).

Example 210. Synthesis of 3,5-dichloro-N-(2-fluoro-5-phenylphenyl)-2-hydroxybenzene-1-sulfonamide, I-22

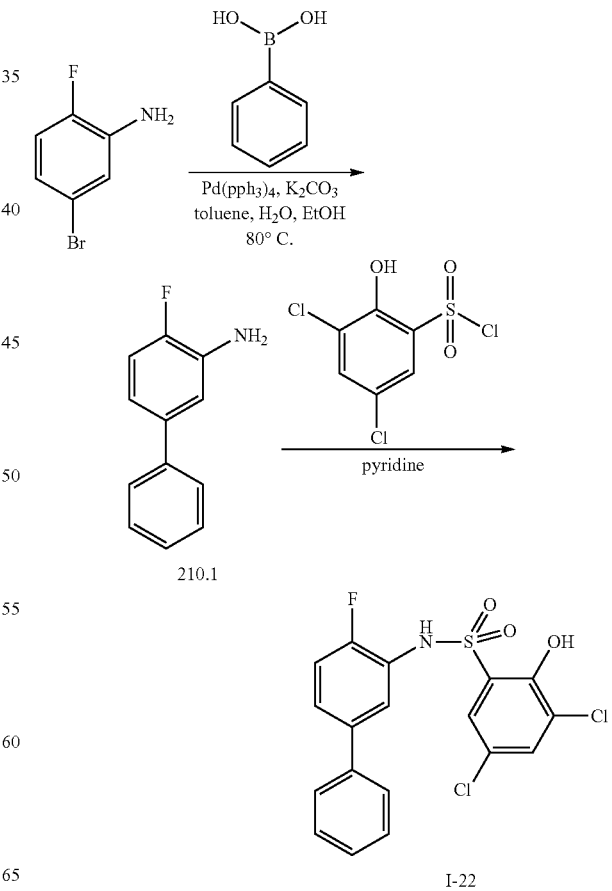

I-22

Synthesis of Compound 210.1

Into a 100-mL 3-necked round-bottom flask purged and maintained with atmosphere of nitrogen, was placed 5-bromo-2-fluoroaniline (1 g, 5.26 mmol, 1.00 equiv), toluene (5 mL), H$_2$O (5 mL), EtOH (5 mL), phenylboronic acid (770 mg, 6.32 mmol, 1.20 equiv), K$_2$CO$_3$ (3.63 g, 26.08 mmol, 5.00 equiv), Pd(PPh$_3$)$_4$ (1.22 g, 1.06 mmol, 0.20 equiv). The resulting solution was stirred for 12 h at 80° C. The resulting mixture was concentrated under vacuum. The residue was applied onto a silica gel column with dichloromethane/methanol (100:1). This resulted in 700 mg (71%) of 210.1 as a yellow solid.

Synthesis of I-22

Into a 100-mL 3-necked round-bottom flask, was placed 3,5-dichloro-2-hydroxybenzene-1-sulfonyl chloride (300 mg, 1.15 mmol, 1.00 equiv), 210.1 (259 mg, 1.38 mmol, 1.20 equiv), and pyridine (10 mL). The resulting solution was stirred for 2 h at 25° C. The reaction was then quenched by the addition of 60 mL of 1 M hydrochloric acid (aq.). The resulting solution was extracted with 3×100 mL of ethyl acetate and the organic layers combined and concentrated under vacuum. The crude product was purified by Flash-Prep-HPLC with the following conditions (IntelFlash-1): Column, C18; mobile phase, H$_2$O:ACN=15% increasing to H$_2$O:ACN=60% within 15 min; Detector, UV 254 nm. This resulted in 155.8 mg (33%) of I-22 as a light yellow solid. (ES, m/z): [M–H]$^-$ 410.1, $^1$H-NMR (300 MHz, DMSO-d$_6$, ppm): δ7.13-7.32 (m, 2H), δ7.33-7.57 (m, 7H), δ7.68-7.89 (m, 1H).

Example 211. Synthesis of 3-chloro-5-(N-(4,6-difluoro-[1,1'-biphenyl]-3-yl)sulfamoyl)-4-hydroxybenzoic Acid, I-95

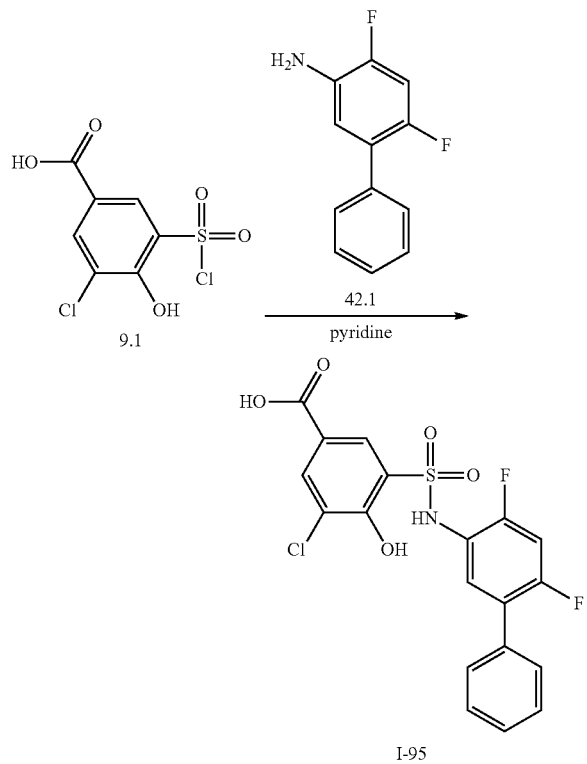

Synthesis of I-95

Into a 100-mL round-bottom flask purged and maintained with an inert atmosphere of nitrogen, was placed 9.1 (4.4 g, 16.23 mmol, 1 equiv), 42.1 (4.0 g, 19.48 mmol, 1.2 equiv), and pyridine (50 mL). The resulting solution was stirred for 0.5 h at room temperature. The resulting mixture was concentrated to afford crude product which was purified by a silica gel column (dichloromethane/methanol=10:1). This resulted in 32.1 mg (0.45%) of I-95 as a white solid. (ES, m/z): [M–H]$^-$ 438.0, $^1$H-NMR (400 MHz, DMSO-d$_6$, ppm): δ7.31-7.49 (m, 9H), δ8.02-8.08 (m, 2H).

Example 212. Synthesis of 3-chloro-N-(2,4-difluorophenyl)-5-(2H-1,2,3,4-tetrazol-5-yl)benzene-1-sulfonamide, I-373

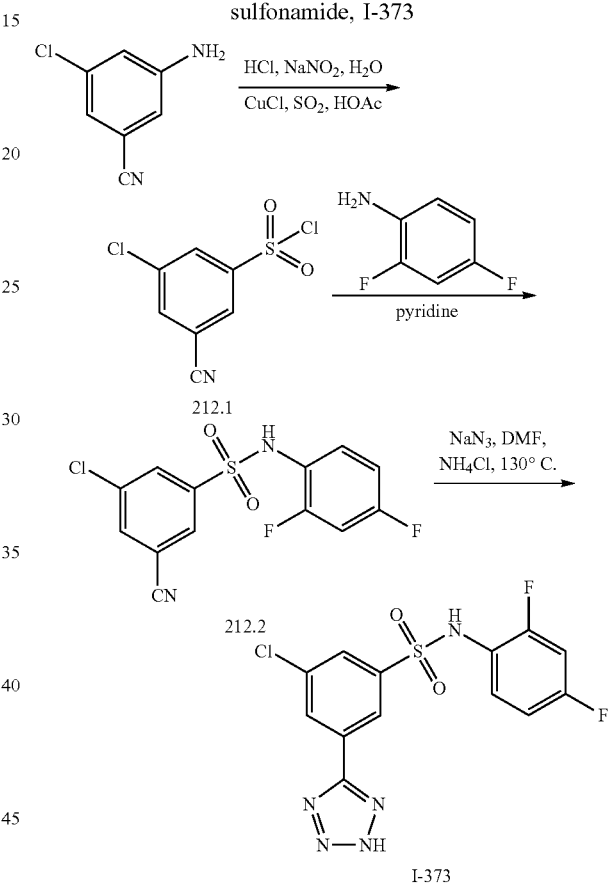

Synthesis of Compound 212.1

Into a 50-mL round-bottom flask, was placed 3-amino-5-chlorobenzonitrile (1000 mg, 6.55 mmol, 1 equiv), H$_2$O (6.25 mL), HCl (6.25 mL, 12M), NaNO$_2$ (474.8 mg, 6.88 mmol, 1.05 equiv). The resulting solution was stirred for 1 h at 0° C. Then, a solution of SO2 in AcOH (7.75 mL) and CuCl (64.9 mg, 0.66 mmol, 0.1 equiv) was added. The resulting solution was stirred for additional 2 h at 0° C. The reaction was then quenched by the addition of 100 mL of water/ice. The resulting solution was extracted with 2×100 mL of ethyl acetate and the combined organic phase was concentrated. This resulted in 1.25 g (87.6%) of 212.1 as a dark brown solid. (ES, m/z): [M–H]$^-$ 233.9.

Synthesis of Compound 212.2

Into a 100-mL round-bottom flask, was placed 212.1 (1.25 g, 5.74 mmol, 1 equiv), 2,4-difluoroaniline (889.9 mg, 6.89 mmol, 1.2 equiv), pyridine (20 mL). The resulting solution was stirred overnight at 25° C. The resulting mixture was concentrated. The residue was applied onto a silica gel column with ethyl acetate/petroleum ether (1:3). This resulted in 600 mg (31.7%) of 212.2 as a light brown solid. (ES, m/z): [M−H]⁻ 362.9.

Synthesis of I-373

Into a 25-mL round-bottom flask, was placed 212.2 (200 mg, 0.61 mmol, 1 equiv), DMF (5 mL), NaN$_3$ (118.7 mg, 1.83 mmol, 3 equiv), NH$_4$Cl (130.2 mg, 2.43 mmol, 4 equiv). The resulting solution was stirred for 2 h at 130° C. The reaction was then quenched by the addition of 20 mL of water/ice. The pH value of the solution was adjusted to 8 with sat.NaHCO$_3$. The resulting solution was extracted with 2×25 mL of ethyl acetate and concentrated under vacuum. The crude product was purified by Flash-Prep-HPLC with the following conditions (IntelFlash-1): Column, C18; mobile phase, water:acetonitrile=90:10 increasing to water:acetonitrile=0:100 within 30 min; Detector, UV 254 nm. This resulted in 87.6 mg (38.7%) of I-373 as a white solid. (ES, m/z): [M+H]⁺ 372.0, $^1$H-NMR (300 MHz, CD$_3$OD, ppm): δ6.89-7.01 (m, 2H), δ7.43-7.51 (m, 1H), δ7.66-7.67 (m, 1H), δ8.27-8.28 (d, J=1.5 Hz, 1H), δ8.37-8.38 (d, J=1.5 Hz, 1H).

Example 213. Synthesis of 3-chloro-4-methoxy-5-[(2-methoxy-5-phenylphenyl)sulfamoyl]benzoic Acid, I-26

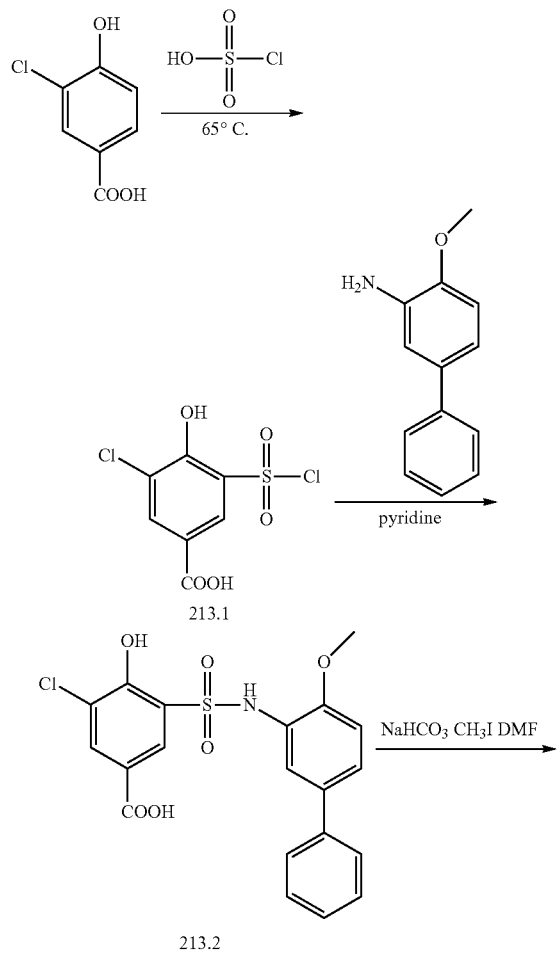

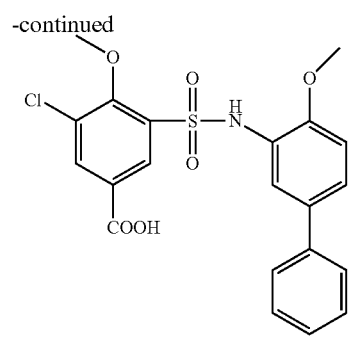

I-26

Synthesis of Compound 213.1

Into a 100-mL 3-necked round-bottom flask, was placed O-(chlorosulfonyl)oxidanol (8.1 g, 69.51 mmol, 6.00 equiv), 3-chloro-4-hydroxybenzoic acid (2 g, 11.59 mmol, 1.00 equiv). The resulting solution was stirred for 2 h at 65° C. The resulting mixture was concentrated under vacuum. This resulted in 2 g (64%) of 213.1 as a yellow solid. (ES, m/z): [M−H]⁻ 268.9.

Synthesis of Compound 213.2

Into a 100-mL 3-necked round-bottom flask, was placed 213.1 (600 mg, 2.21 mmol, 1.00 equiv), 2-methoxy-5-phenylaniline (528 mg, 2.65 mmol, 1.20 equiv), pyridine (10 mL). The resulting solution was stirred for 2 h at 25° C. The reaction was then quenched by the addition of 100 mL of 1M hydrochloric acid (aq.). The resulting solution was extracted with 3×150 mL of ethyl acetate and the organic layers combined and concentrated under vacuum. The residue was applied onto Prep-TLC with dichloromethane/methanol (20:1). This resulted in 122 mg (13%) of 213.2 as a light yellow solid. (ES, m/z): [M−H]⁻ 432.0.

Synthesis of I-26

Into a 50-mL 3-necked round-bottom flask, was placed 213.2 (139 mg, 0.32 mmol, 1 equiv), NaHCO$_3$ (32 mg, 0.38 mmol, 1.189 equiv), DMF (3 mL), CH$_3$I (54.7 mg, 0.39 mmol, 1.203 equiv). The resulting solution was stirred for 5 h at 25° C. The reaction was then quenched by the addition of 5 mL of water. The resulting solution was extracted with 3×15 mL of ethyl acetate and the organic layers combined and concentrated under vacuum. The crude product was purified by Prep-HPLC with the following conditions (2 #-AnalyseHPLC-SHIMADZU(HPLC-10)): Column: Xselect CSH OBD Column 30*150 mm 5 um; Mobile Phase A: water (0.05% TFA), Mobile Phase B: ACN; Flow rate: 60 mL/min; Gradient: 58% B to 68% B in 7 min; 254/220 nm; Rt: 6.77 min. This resulted in 6.1 mg (4.2%) of I-26 as a light yellow solid. (ES, m/z): [M−H]⁻ 446.1, $^1$H-NMR (300 MHz, CDCl$_3$, ppm): δ3.63-3.71 (s, 3H), δ3.88-3.93 (s, 3H), δ6.83-6.93 (m, 1H), δ7.31-7.38 (m, 2H), δ7.43-7.48 (m, 2H), δ7.52-7.63 (m, 2H), δ7.70-7.73 (m, 1H), δ8.17-8.18 (d, J=1.8 Hz, 1H), δ8.24-8.25 (d, J=2.1 Hz, 1H).

Example 214. Synthesis of (S)-3-chloro-N-(4,6-difluoro-[1,1'-biphenyl]-3-yl)-5-(3-fluoropyrrolidin-1-carbonyl)-2-hydroxybenzenesulfonamide, I-118

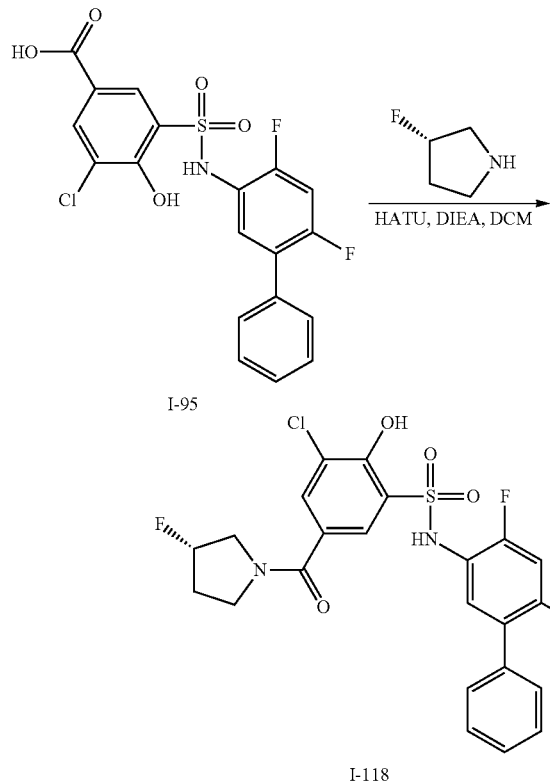

Synthesis of I-118

To a stirred mixture of I-95 (100 mg, 0.23 mmol, 1 equiv) and (3S)-3-fluoropyrrolidine (28.4 mg, 0.32 mmol, 1.40 equiv) in DCM (2 mL) was added HATU (129.7 mg, 0.34 mmol, 1.50 equiv) and DIEA (117.5 mg, 0.91 mmol, 4.00 equiv) at room temperature under nitrogen atmosphere. After 12 h, the reaction was quenched with water (20 mL). The resulting mixture was extracted with EtOAc (2×30 mL), and the combined organic layers were concentrated under reduced pressure. The crude product was purified by reverse phase flash with the following conditions (IntelFlash-1): Column, C 18; mobile phase, $CH_3CN:H_2O=0:100$ to $CH_3CN:H_2O=40:60$ in 30 min; Detector, UV 254/220 nm. This obtained I-118 (12.1 mg, 10.42%) as a white solid. (ES, m/z): $[M+H]^+$ 511.2, $^1$H-NMR (400 MHz, DMSO-$d_6$, ppm): δ1.97-2.04 (m, 2H), δ3.46 (br s, 4H), δ5.23 (br s, 1H), δ7.25-7.47 (m, 7H), δ7.62 (s, 1H), δ7.78 (s, 1H).

Example 215. Synthesis of Additional Amides of I-95

Using similar methodology as used in Example 214, additional exemplary compounds were prepared. The characterization data is provided in Table 3 below.

TABLE 3

Characterization data for exemplary compounds.

| Compound No. | Name | MS (ES, m/z) | 1H-NMR |
|---|---|---|---|
| I-98 | 5-(azetidine-1-carbonyl)-3-chloro-N-(4,6-difluoro-[1,1'-biphenyl]-3-yl)-2-hydroxybenzenesulfonamide | $[M - H]^-$ 477.0 | (300 MHz, DMSO-$d_6$, ppm): δ7.62 (s, 2H), δ7.39-7.52 (m, 3H), δ7.30-7.35 (m, 4H), δ6.95-7.12 (m, 2H), δ4.05 (br s, 4H), δ2.12-2.22 (m, 2H). |
| I-99 | 3-chloro-N-(4,6-difluoro-[1,1'-biphenyl]-3-yl)-2-hydroxy-5-(morpholine-4-carbonyl)benzenesulfonamide | $[M - H]^-$ 507.1 | (300 MHz, DMSO-$d_6$, ppm): δ7.49-7.37 (m, 4H), δ7.33-7.23 (m, 5H), δ3.47 (s, 4H), δ3.38-3.37 (m, 4H). |
| I-100 | 3-chloro-N-(4,6-difluoro-[1,1'-biphenyl]-3-yl)-2-hydroxy-5-(isoindoline-2-carbonyl)benzenesulfonamide | $[M - H]^-$ 539.1 | (300 MHz, DMSO-$d_6$, ppm): δ7.73-7.70 (d, J = 9.0 Hz, 1H), δ7.63-7.62 (d, J = 2.4 Hz, 1H), δ7.51-7.19 (m, 11H), δ4.81 (s, 4H). |
| I-119 | (R)-3-chloro-N-(4,6-difluoro-[1,1'-biphenyl]-3-yl)-5-(3-fluoropyrrolidine-1-carbonyl)-2-hydroxybenzenesulfonamide | $[M + H]^+$ 511.2 | (300 MHz, DMSO-$d_6$, ppm): δ1.91-2.08 (m, 2H), δ3.51 (br s, 4H), δ5.17-5.34 (br s, 1H), δ7.30-7.35 (m, 4H), δ7.37-7.47 (m, 3H), δ7.52-7.56 (m, 2H). |
| I-129 | 3-chloro-N-(4,6-difluoro-[1,1'-biphenyl]-3-yl)-2-hydroxy-5-(3-hydroxyazetidine-1-carbonyl)benzenesulfonamide | $[M - H]^-$ 493.0 | (300 MHz, DMSO-$d_6$, ppm): δ3.77-3.80 (m, 2H), δ4.24-4.26 (m, 2H), δ4.40-4.42 (m, 1H), δ6.92 (s, 1H), δ7.09 (s, 1H), δ7.26-7.38 (m, 4H), δ7.40-7.49 (m, 3H), δ7.65-7.68 (m, 2H). |

TABLE 3-continued

Characterization data for exemplary compounds.

| Compound No. | Name | MS (ES, m/z) | 1H-NMR |
|---|---|---|---|
| I-130 | 3-chloro-N-(4,6-difluoro-[1,1'-biphenyl]-3-yl)-5-(3-fluoroazetidine-1-carbonyl)-2-hydroxybenzenesulfonamide | [M − H]⁻ 495 | (400 MHz, DMSO-d₆, ppm): δ 4.04-4.13 (m, 2H), δ4.33-4.41 (m, 2H), δ5.24-5.43 (m, 1H), δ7.22-7.34 (m, 4H), δ7.37-7.47 (m, 4H), δ7.56-7.58 (m, 2H). |
| I-140 | 3,5-dichloro-2-methoxy-N-(4-methoxy-[1,1'-biphenyl]-3-yl)benzenesulfonamide | | (400 MHz, DMSO-d₆, ppm): δ10.59 (s, 1H), δ8.17 (s, 1H), δ8.08-8.07 (d, J = 2.0 Hz, 1H), δ7.95-7.94 (d, J = 2.0 Hz, 1H), δ7.57-7.42 (m, 6H), δ7.33-7.29 (m, 1H), δ4.18 (s, 2H), δ4.06-4.02 (m, 2H), δ2.33-2.18 (m, 2H), δ2.18 (s, 1H), δ1.07-1.03 (t, J = 6.0 Hz, 3H), δ0.92-0.84 (m, 1H). |
| I-148 | (R)-3-chloro-N-(4,6-difluoro-[1,1'-biphenyl]-3-yl)-2-hydroxy-5-(3-hydroxy-3-methylpyrrolidine-1-carbonyl)benzenesulfonamide | [M − H]⁻ 521.0 | (300 MHz, DMSO-d₆, ppm): δ1.16-1.21 (s, 3H), δ1.73 (s, 2H), δ3.16-3.37 (m, 3H), δ3.47-3.60 (m, 2H), δ7.29-7.34 (m, 4H), δ7.36-7.46 (m, 3H), δ7.52-7.56 (t, J = 2.0 Hz, 2H). |
| I-149 | (S)-3-chloro-N-(4,6-difluoro-[1,1'-biphenyl]-3-yl)-2-hydroxy-5-(3-hydroxy-3-methylpyrrolidine-1-carbonyl)benzenesulfonamide | [M − H]⁻ 521.0 | (300 MHz, DMSO-d₆, ppm): δ1.16-1.21 (s, 3H), δ1.73 (s, 2H), δ3.16-3.37 (m, 3H), δ3.47-3.60 (m, 1H), δ7.29-7.34 (m, 2H), δ7.36-7.46 (m, 7H), δ7.58-7.63 (m, 2H). |
| I-158 | 4-(azetidine-1-carbonyl)-2-chloro-6-([4,6-difluoro-[1,1-biphenyl]-3-yl]sulfamoyl)phenyl 2-methylpropanoate | [M − H]⁻ 547.2 | (400 MHz, DMSO-d₆, ppm): δ0.97-1.10 (m, 4H), δ1.11-1.17 (m, 2H), δ2.19-2.33 (m, 2H), δ2.54-2.63 (m, 1H), δ4.03-4.20 (m, 4H), δ7.29-7.33 (t, J = 8.4 Hz, 1H), δ7.42-7.61 (m, 6H), δ7.98-7.99 (d, J = 1.6 Hz, 2H), δ10.55 (s, 1H). |
| I-161 | N-(2-[[3-chloro-5-([4,6-difluoro-[1,1-biphenyl]-3-yl]sulfamoyl)-4-hydroxyphenyl]formamido]ethyl)acetamide | [M + H]⁺ 524.2 | (400 MHz, DMSO-d₆, ppm): δ1.76-1.77 (s, 3H), δ3.10-3.15 (m, 2H), δ3.18-3.24 (m, 2H), δ6.95 (s, 1H), δ7.08 (s, 1H), δ7.15-7.20 (s, 1H), δ7.30-7.32 (d, J = 7.6 Hz, 1H), δ7.32-7.40 (m, 3H), δ7.40-7.46 (m, 2H), δ7.90 (m, 3H), δ8.18 (s, 1H). |
| I-162 | N-[1-[3-chloro-5-([4,6-difluoro-[1,1-biphenyl]-3-yl]sulfamoyl)-4-hydroxybenzoyl]azetidin-3-yl]acetamide | | (400 MHz, DMSO-d₆, ppm): δ1.81 (s, 3H), δ3.86 (s, 2H), δ4.28-4.42 (m, 3H), δ6.95 (s, 1H), δ7.08 (s, 1H), δ7.16 (s, 1H), δ7.21-7.46 (m, 6H), δ7.60 (s, 2H), δ8.46 (s, 1H). |
| I-201 | tert-butyl N-[1-[3-chloro-5-([4,6-difluoro-[1,1-biphenyl]-3-yl]sulfamoyl)-4-hydroxybenzoyl]azetidin-3-yl]carbamate | [M − H]⁻ 592.1 | (400 MHz, DMSO-d₆, ppm): δ1.24-1.38 (s, 9H), δ3.77-3.90 (s, 2H), δ4.07 (s, 1H), δ4.25 (s, 2H), δ6.95-7.30 (m, 2H), δ7.32-7.51 (m, 8H), δ7.64-7.67 (m, 2H). |

549

Example 216. Synthesis of 5-(azetidine-1-carbonyl)-3-chloro-2-methoxy-N-[4-methoxy-[1,1-biphenyl]-3-yl]benzene-1-sulfonamide, I-374

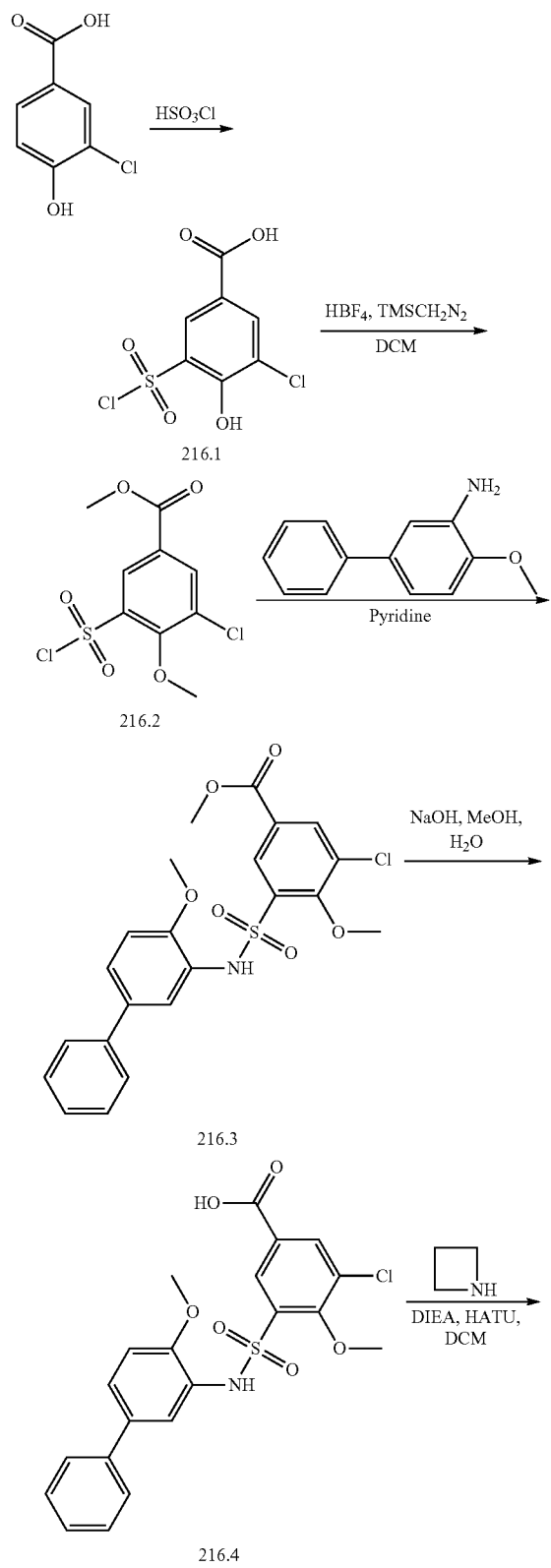

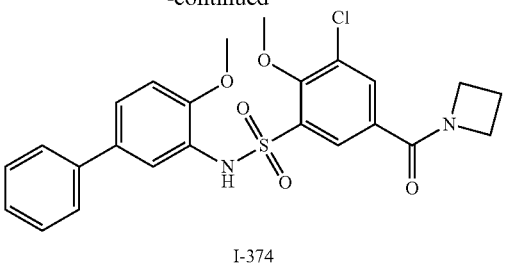

I-374

Synthesis of Compound 216.1

Into a 250 mL 3-necked round-bottom flask were added 3-chloro-4-hydroxybenzoic acid (5 g, 28.98 mmol, 1 equiv) and sulfonoperoxoyl chloride (40.5 g, 347.71 mmol, 12 equiv) at 0° C. The temperature was up to 65° C. The resulting mixture was stirred for 0.5 h. The reaction was quenched by the addition of water/ice (50 mL). The resulting mixture was extracted with EtOAc (3×30 mL). The combined organic layers were washed with water (20 mL), dried over anhydrous Na2SO4. After filtration, the filtrate was concentrated under reduced pressure. This resulted in 6.03 g (76.7%) of 216.1 as a brown solid. (ES, m/z): [M−H]⁻ 268.9.

Synthesis of Compound 216.2

To a stirred solution of 216.1 (2 g, 7.38 mmol, 1 equiv) in DCM (20 mL) were added $HBF_4$ (3.2 g, 14.68 mmol, 2 equiv, 40%) and $TMSCH_2N_2$ (14.76 mL) dropwise at 0° C. under nitrogen atmosphere. The resulting mixture was stirred for 5 h. The resulting mixture was diluted with water (30 mL). The resulting mixture was extracted with EtOAc (3×30 mL) and the combined organic layers were concentrated under reduced pressure. The residue was purified by Prep-TLC (hexane/EtOAc=5:1) to afford 216.2 (540 mg, 24.4%) as a yellow oil. (ES, m/z): [M−H]⁻ 296.9.

Synthesis of Compound 216.3

To a stirred solution of 4-methoxy-[1,1-biphenyl]-3-amine (431.7 mg, 2.17 mmol, 1.2 equiv) in pyridine (10 mL) were added 216.2 (540 mg, 1.81 mmol, 1 equiv) at room temperature under nitrogen atmosphere. The resulting mixture was stirred for 0.5 h. The resulting mixture was concentrated under reduced pressure. The residue was purified by Prep-TLC (hexane/EtOAc=5:1) to afford 216.3 (720 mg, 86.3%) as a white solid. (ES, m/z): [M−H]⁻ 460.0.

Synthesis of Compound 216.4

To a stirred solution of methyl 216.3 (666 mg, 1.44 mmol, 1 equiv) in MeOH (50 mL) and water (12.5 mL) were added NaOH (115.3 mg, 2.88 mmol, 2 equiv) at room temperature under nitrogen atmosphere. The resulting mixture was stirred for 12 h. The resulting mixture was extracted with EtOAc (2×30 mL). The combined organic layers were concentrated under reduced pressure. The residue was purified by Prep-TLC (hexane/EtOAc=1:1) to afford 216.4 (613 mg, 94.9%) as a white solid. (ES, m/z): [M−H]⁻ 446.0.

Synthesis of Compound I-374

To a stirred solution of 216.4 (300 mg, 0.67 mmol, 1 equiv) in DCM (10 mL) were added azetidine (45.9 mg, 0.80 mmol, 1.2 equiv), DIEA (173.1 mg, 1.34 mmol, 2 equiv) and HATU (382.0 mg, 1.00 mmol, 1.5 equiv) at room temperature under nitrogen atmosphere. The resulting mixture was stirred for 12 h. The resulting mixture was diluted with 10 mL of water. The resulting mixture was extracted with EtOAc (3×10 mL) and the combined organic layers were concentrated under reduced pressure. The residue was purified by Prep-TLC (hexane/EtOAc=1:1) to afford I-374 (116.7 mg, 35.8%) as a white solid. (ES, m/z): [M+H]+ 487.2, $^1$H-NMR (300 MHz, DMSO-$d_6$, ppm): δ2.11-2.21 (m, 2H), δ3.55 (s, 3H), δ3.97-4.08 (m, 7H), δ7.00-7.03 (m, 1H), δ7.30-7.36 (m, 1H), δ7.41-7.53 (m, 6H), δ7.77-7.78 (d, J=2.1 Hz, 1H), δ7.93-7.94 (d, J=2.1 Hz, 1H), δ9.67 (s, 1H).

Example 217. Synthesis of 2-(2,4-dichloro-6-(N-(4-fluoro-[1,1'-biphenyl]-3-yl) sulfamoyl)phenoxy) acetamide, I-151

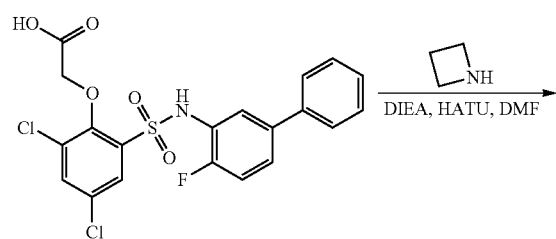

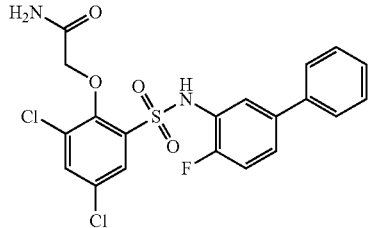

Synthesis of Compound I-151

To a stirred mixture of I-143 (100 mg, 0.21 mmol, 1 equiv) and NH$_4$Cl (33.0 mg, 0.62 mmol, 3 equiv) in DCM (1 mL, 15.73 mmol, 76.49 equiv) were added DIEA (159.5 mg, 1.23 mmol, 6 equiv) and HATU (117.3 mg, 0.31 mmol, 1.5 equiv) in portions at room temperature under nitrogen atmosphere. The resulting solution was stirred for overnight at room temperature under nitrogen atmosphere. The resulting mixture was extracted with water (2×100 ml). The combined organic layers were washed with EtOAc (2×100 mL), dried over anhydrous Na$_2$SO$_4$. After filtration, the filtrate was concentrated under reduced pressure. The crude product was purified by reverse phase flash with the following conditions (from CH$_3$CN/H$_2$O=0:100 to CH$_3$CN/H$_2$O=40:60 in 30 mins, UV: 254/220) to afford I-151 (33.4 mg, 33.4%) as a white solid. (ES, m/z): [M–H]– 467.0, $^1$H-NMR (400 MHz, DMSO-$d_6$, ppm): δ4.62 (s, 2H), δ7.29-7.30 (m, 2H), δ7.44-7.53 (m, 6H), δ7.65-7.71 (m, 3H), δ8.08-8.09 (s, 1H), δ10.82 (s, 1H).

Additional Compounds Prepared According to Example 217

Additional compounds were prepared by coupling I-143 using the amide formation conditions of Example 217.

2-(2,4-dichloro-6-(N-(4-fluoro-[1,1'-biphenyl]-3-yl) sulfamoyl)phenoxy)-N-methylacetamide, I-152

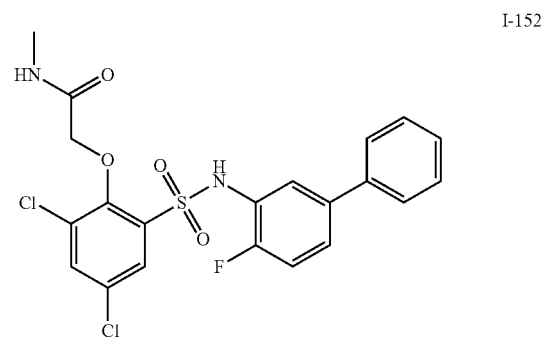 [SMILES: CNC(=O)COc1c(Cl)cc(Cl)cc1S(=O)(=O)Nc1cc(-c2ccccc2)ccc1F]

I-152 (50.6 mg, 49.2%) was isolated as a white solid. (ES, m/z): [M–H]– 481.0, $^1$H-NMR (400 MHz, DMSO-$d_6$, ppm): δ2.70-2.73 (s, 3H), δ4.62 (s, 2H), δ7.21-7.53 (m, 8H), δ7.72 (s, 1H), δ8.09 (s, 2H), δ10.79 (s, 1H).

2-(2-(azetidin-1-yl)-2-oxoethoxy)-3,5-dichloro-N-(4-fluoro-[1,1'-biphenyl]-3-yl)benzenesulfonamide, I-153

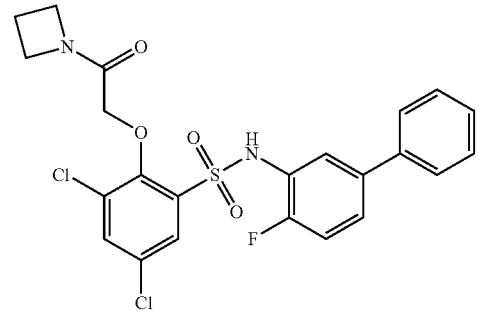

I-153 (15.5 mg, 14.3%) was isolated as a white solid. (ES, m/z): [M–H]– 507.0, $^1$H-NMR (400 MHz, DMSO-$d_6$, ppm): δ2.21-2.33 (m, 2H), δ3.95-3.98 (t, J=7.6 Hz, 2H), δ4.19-4.26 (t, J=8.0 Hz, 2H), δ4.78 (s, 2H), δ7.30-7.40 (m, 2H), δ7.44-7.54 (m, 6H), δ7.74 (s, 1H), δ8.07 (s, 1H), δ11.01 (s, 1H).

Example 217b. Synthesis of 2-(2-(N-(4-fluoro-[1,1'-biphenyl]-3-yl)sulfamoyl) phenoxy)acetic Acid, I-379

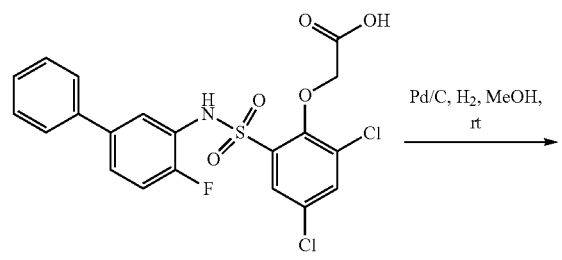

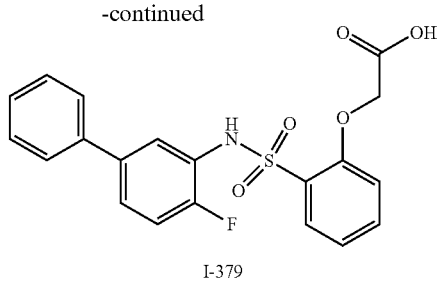

I-379

Synthesis of Compound I-379

Into a 10-mL round-bottom flask purged and maintained with an inert atmosphere of nitrogen, was placed I-27 (7 mg, 0.01 mmol, 1 equiv), methanol (5 mL), Pd/C (2 mg, 0.02 mmol, 1.26 equiv). The resulting solution was stirred for 12 hr at room temperature. The solids were filtered out. The resulting mixture was concentrated. The residue was purified TLC with dichloromethane/methanol (3:1). This resulted in 1.6 mg (yield=27%) of I-379 as a white solid. (ES, m/z): [M−H]⁻ 400.2, 1H-NMR (DMSO, 400 MHz, ppm): δ7.68-7.66 (m, 1H), δ7.60-7.56 (m, 1H), δ7.51-7.30 (m, 7H), δ7.19-7.17 (m, 1H), δ7.07-6.99 (m, 2H), δ4.66 (s, 2H), δ1.30 (s, 2H). I-379 was isolated as a white solid (1.6 mg; yield=27%). (ES, m/z): [M−H]⁻ 400.2, $^1$H-NMR (400 MHz, DMSO-d$_6$, ppm): δ7.68-7.66 (m, 1H), δ7.60-7.56 (m, 1H), δ7.51-7.30 (m, 7H), δ7.19-7.17 (m, 1H), δ7.07-6.99 (m, 2H), δ4.66 (s, 2H), δ1.30 (s, 2H).

Example 218. Synthesis of benzyl 2-(4-(azetidine-1-carbonyl)-2-chloro-6-(N-(4,6-difluoro-[1,1'-biphenyl]-3-yl)sulfamoyl)phenoxy)acetate, I-375

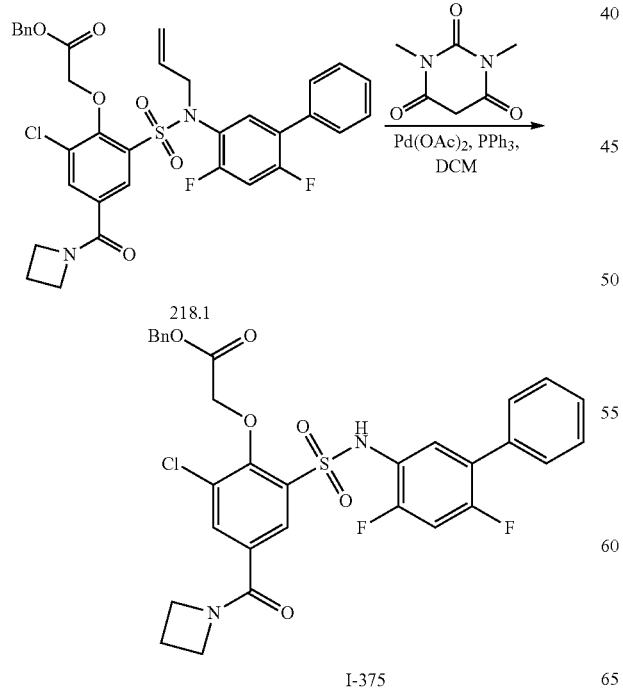

Synthesis of I-375

Into a 25-mL round-bottom flask purged and maintained with an inert atmosphere of nitrogen, was placed benzyl 2-[4-(azetidine-1-carbonyl)-2-chloro-6-([4,6-difluoro-[1,1-biphenyl]-3-yl](prop-2-en-1-yl)sulfamoyl)phenoxy]acetate 218.1 (60 mg, 0.09 mmol, 1 equiv), 1,3-dimethyl-1,3-diazinane-2,4,6-trione (42.1 mg, 0.27 mmol, 3 equiv), tetrakis(triphenylphosphane) palladium (31.2 mg, 0.03 mmol, 0.3 equiv), DCM (0.5 mg). The resulting solution was stirred for 12 hr at 50° C. in an oil bath. The reaction was then quenched by the addition of 10 mL of water. The resulting solution was extracted with 3×10 ml of ethyl acetate. The resulting mixture was washed with 1×10 ml of brine. The mixture was dried over anhydrous sodium sulfate and concentrated. The resulting mixture was concentrated. The residue was applied onto a silica gel column with ethyl acetate/petroleum ether (1:0). This resulted in 16.3 mg (yield=29%) of I-375 as a white solid. (ES, m/z): [M−H]⁻ 625.1, $^1$H-NMR (400 MHz, DMSO-d$_6$, ppm): δ10.26 (s, 1H), δ7.97-7.96 (d, J=2.0 Hz, 1H), δ7.86-7.85 (d, J=2.0 Hz, 1H), δ7.48-7.31 (s, 12H), δ5.21 (s, 2H), δ4.89 (s, 2H), δ4.15-4.11 (t, J=8.0 Hz, 2H), δ4.03-3.99 (t, J=8.0 Hz, 2H), δ2.22-2.15 (m, 2H).

Example 219. Synthesis of 5-chloro-N-(4,6-difluoro-[1,1'-biphenyl]-3-yl)-2-fluorobenzenesulfonamide, I-156

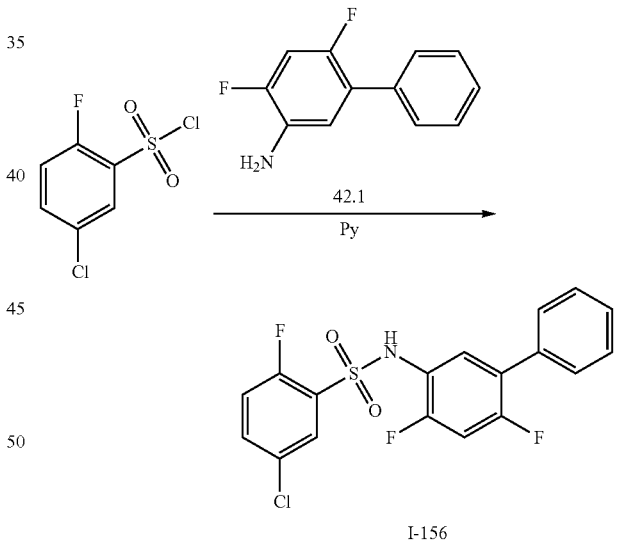

I-156

Synthesis of I-156

Into a 50-mL round-bottom flask purged and maintained with an inert atmosphere of nitrogen, was placed 5-chloro-2-fluorobenzene-1-sulfonyl chloride (200 mg, 0.87 mmol, 1 equiv), 42.1 (215.0 mg, 1.05 mmol, 1.2 equiv), and pyridine (1 mL). The resulting solution was stirred for 0.5 hr at room temperature. The resulting mixture was concentrated. The residue was applied onto a silica gel column with ethyl acetate/petroleum ether (1:2). This resulted in 205.1 mg (yield=59%) of I-156 as a white solid. (ES, m/z): [M–H]⁻ 395.9, ¹H-NMR (400 MHz, DMSO-d₆, ppm): δ10.14 (s, 1H), δ7.85-7.81 (m, 1H), δ7.72-7.70 (m, 1H), δ7.59-7.55 (t, J=9.6 Hz, 1H), δ7.51-7.41 (m, 6H), δ7.37-7.33 (t, J=8.4 Hz, 1H).

Example 220. Additional Examples Prepared According to Example 219

Table 4 below provides characterization data for compounds prepared according to the method of Example 219.

TABLE 4

Characterization data for additional exemplary compounds.

| Compound No. | Name | MS | 1H-NMR |
|---|---|---|---|
| I-190 | 2,3-dichloro-N-[4,6-difluoro-[1,1-biphenyl]-3-yl]benzene-1-sulfonamide | [M − H]⁻ 411.9 | (400 MHz, DMSO-d₆, ppm): δ10.68 (s, 1H), δ7.91-7.98 (m, 1H), δ7.89-7.91 (m, 1H), δ7.50-7.55 (m, 3H), δ7.39-7.40 (m, 4H), δ7.31-7.40 (m, 1H). |
| I-191 | methyl 3-([4,6-difluoro-[1,1-biphenyl]-3-yl]sulfamoyl)benzoate | [M − H]⁻ 402.0.0 | (400 MHz, DMSO-d₆, ppm): 10.43 (s, 1H), δ8.29 (s, 1H), δ8.22-8.24 (m, 1H), δ8.96-8.98 (m, 1H), δ7.74-7.78 (m, 1H), δ7.38-7.51 (m, 6H), δ7.24-7.28 (m, 1H), δ3.89 (s, 3H). |
| I-195 | 3-chloro-N-(4,6-difluoro-[1,1'-biphenyl]-3-yl)-2-fluorobenzenesulfonamide | [M − H]⁻ 395.9 | (400 MHz, DMSO-d₆, ppm): δ10.74 (s, 1H), δ7.95-7.91 (m, 1H), δ7.71-7.67 (m, 1H), δ7.50-7.33 (m, 8H). |
| I-204 | 3-chloro-N-[4,6-difluoro-[1,1-biphenyl]-3-yl]-5-(trifluoromethyl)benzene-1-sulfonamide | [M − H]⁻ 445.9 | (300 MHz, DMSO-d₆, ppm): δ7.22-7.33 (m, 1H), δ7.41-7.48 (m, 6H), δ7.96 (s, 1H), δ8.05 (s, 1H), δ8.30 (s, 1H), δ10.65 (s, 1H). |
| I-219 | 3,5-dichloro-N-(2,4-difluorophenyl)-2-hydroxybenzene-1-sulfonamide | [M − H]⁻ 351.9 | (300 MHz, DMSO-d₆, ppm): 6.95-7.09 (m, 1H), δ7.19-7.32 (m, 2H), δ7.43-7.44 (d, J = 2.7 Hz, 1H), δ7.75-7.76 (d, J = 2.4 Hz, 1H). |
| I-283 | 3-chloro-5-[(2-fluorophenyl)sulfamoyl]-4-hydroxybenzoic acid | [M − H]⁻ 344.0 | (400 MHz, DMSO-d₆, ppm): δ 8.09-8.03 (m, 2H), 7.28-7.06 (m, 4H). |
| I-285 | 3,5-dichloro-2-hydroxy-N-(2-phenoxyphenyl)benzene-1-sulfonamide | [M − H]⁻ 408.0 | (300 MHz, DMSO-d₆, ppm) δ 7.63-7.62 (d, J = 2.7 Hz, 1H), δ7.45-7.34 (m, 2H), δ7.34-7.22 (m, 2H), δ7.18-7.01 (m, 3H), δ6.78-6.65 (m, 3H). |
| I-354 | 5-chloro-N-[4-methoxy-[1,1-biphenyl]-3-yl]-2-oxo-1,2-dihydropyridine-3-sulfonamide | [M − H]⁻ 389.0 | (300 MHz, DMSO-d₆, ppm): δ 8.01-8.00 (d, J = 2.7 Hz, 1H), 7.88-7.87 (d, J = 3.0 Hz, 1H), 7.51-7.31 (m, 7H), 7.08-7.05 (d, J = 8.7 Hz, 1H), 3.69 (s, 3H). |
| I-376 | N-(4,6-difluoro-[1,1 biphenyl]-3-yl)naphthalene-1-sulfonamide | [M − H]⁻ 394.0 | (400 MHz, DMSO-d₆, ppm): δ10.51 (s, 1H), δ8.70-8.68 (d, J = 8.0 Hz, 1H), δ8.27-8.25 (d, J = 8.4 Hz, 1H), δ8.08-8.12 (m, 2H), δ7.74-7.59 (m, 3H), δ7.24-7.46 (m, 6H), δ7.16-7.12 (t, J = 8.4 Hz, 1H). |
| I-380 | 5-bromo-N-[4,6-difluoro-[1,1-biphenyl]-3-yl]-2-methoxybenzene-1-sulfonamide | [M + H]⁺ 453.9 | (300 MHz, DMSO-d₆, ppm): 3.84 (s, 3H), δ7.20-7.38 (m, 2H), δ7.38-7.58 (m, 6H), δ7.68-7.75 (d, J = 2.4 Hz, 1H), δ7.75-7.89 (m, 1H), δ10.11 (s, 1H). |
| I-381 | 3-cyano-N-(4,6-difluoro-[1,1'-biphenyl]-3-yl)-4-fluorobenzenesulfonamide | [M − H]⁻ 387.0 | (400 MHz, DMSO-d₆, ppm): δ10.51 (s, 1H), δ8.31-8.29 (m, 1H), δ8.12-8.08 (m, 1H), δ7.78-7.74 (m, 1H), δ7.51-6.90 (m, 7H) |

TABLE 4-continued

Characterization data for additional exemplary compounds.

| Compound No. | Name | MS | 1H-NMR |
|---|---|---|---|
| I-383 | N-[4,6-difluoro-[1,1-biphenyl]-3-yl]-2,3-dihydro-1,4-benzodioxine-5-sulfonamide | [M − H]⁻ 402.0 | (300 MHz, DMSO-$d_6$, ppm): 4.29 (s, 4H), δ6.85-6.94 (t, J = 7.8 Hz, 1H), δ7.11-7.17 (m, 1H), δ7.17-7.23 (m, 1H), δ7.25-7.55 (m, 7H), δ9.95(s, 1H). |
| I-385 | N-[4,6-difluoro-[1,1-biphenyl]-3-yl]-2-methanesulfonylbenzene-1-sulfonamide | [M − H]⁻ 422.0 | (300 MHz, DMSO-$d_6$, ppm): 3.50 (s, 3H), δ7.29-7.59 (m, 7H), δ7.80-8.02 (m, 3H), δ8.19-8.33 (t, J = 1.2 Hz, 1H), δ9.20 (s, 1H). |
| I-390 | N-(4,6-difluoro-[1,1 biphenyl]-3-yl)benzo[c][1,2,5]thiadiazole-4-sulfonamide | [M − H]⁻ 401.9 | (400 MHz, DMSO-$d_6$, ppm): δ10.49 (s, 1H), δ8.43-8.42 (d, J = 0.8 Hz, 1H), δ8.41-8.40 (d, J = 0.8 Hz, 1H), δ7.86-7.82 (m, 1H), δ7.49-7.24 (m, 7H). |
| I-396 | 3-cyano-N-(2-methoxy-5-phenylphenyl) benzene-1-sulfonamide | [M − H]⁻ 363.0 | (300 MHz, DMSO-$d_6$, ppm): δ3.49 (s, 3H), δ7.00-7.03 (t, J = 2.4 Hz, 1H), δ7.31-7.36 (m, 1H), δ7.42-7.57 (m, 6H), δ7.74-7.77 (t, J = 7.8 Hz, 1H), δ7.99-8.09 (m, 1H), δ8.10-8.13 (m, 2H), δ10.00 (s, 1H). |

Example 221. Synthesis of N-[4-fluoro-[1,1-biphenyl]-3-yl]-1H-indole-7-sulfonamide, I-377

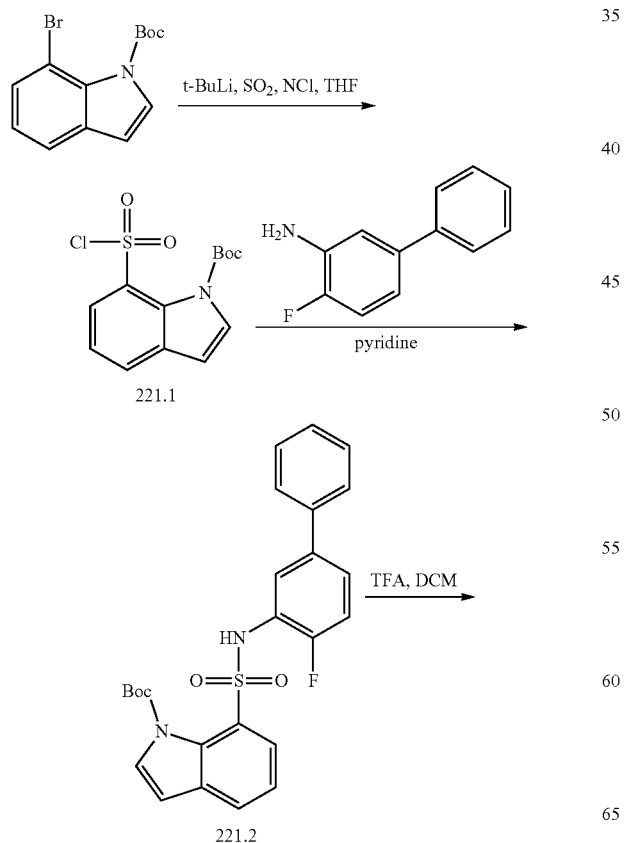

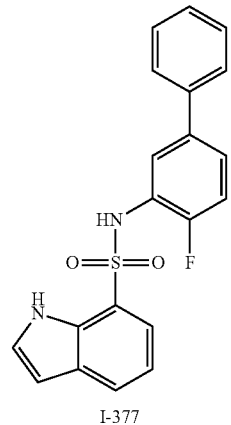

I-377

Synthesis of Compound 221.1

Into a 100-mL 3-necked round-bottom flask, was placed tert-butyl 7-bromo-1H-indole-1-carboxylate (500 mg, 1.69 mmol, 1 equiv), SO₂.THF (10 mL), t-BuLi (119.0 mg, 1.86 mmol, 1.1 equiv), NCS (225.4 mg, 1.69 mmol, 1 equiv). The resulting solution was stirred for 2 hr at −78° C. The reaction was then quenched by the addition of 15 mL of ammonium chloride solution. The resulting solution was extracted with 3×20 ml of ethyl acetate and the organic layers combined and concentrated under vacuum. This resulted in 500 mg (93.7%) of 221.1 as a white solid. (ES, m/z): [M−H]⁻ 314.0.

Synthesis of Compound 221.2

Into a 25-mL round-bottom flask, was placed 221.1 (300 mg, 0.95 mmol, 1 equiv), 4-fluoro-[1,1-biphenyl]-3-amine (213.4 mg, 1.14 mmol, 1.2 equiv), pyridine (5 mL, 62.12 mmol, 65.38 equiv). The resulting solution was stirred for 12 hr at 25° C. The resulting mixture was concentrated under vacuum. The residue was applied onto Prep-TLC with ethyl acetate/petroleum ether (2:1). This resulted in 100 mg (22.5%) of 221.1 as a white solid. (ES, m/z): [M−H]⁻ 465.1.

Synthesis of I-377

Into a 8-mL sealed tube, was placed 221.1 (90 mg, 0.19 mmol, 1 equiv), DCM (1 mL), TFA (0.2 mL). The resulting solution was stirred for 2 hr at 25° C. The reaction was then quenched by the addition of 5 mL of sodium bicarbonatesolution. The resulting solution was extracted with 3×10 mL of dichloromethane and the organic layers combined and concentrated under vacuum. The residue was applied onto Prep-TLC with ethyl acetate/petroleum ether (2:1). This resulted in 11.9 mg (16.8%) of I-377 as a grey solid. (ES, m/z): [M−H]⁻ 365.0, $^1$H-NMR (300 MHz, DMSO-d$_6$, ppm): δ6.63 (s, 1H), δ7.13-7.23 (m, 2H), δ7.35-7.52 (m, 7H), δ7.55-7.77 (m, 2H), δ7.80-7.89 (d, 1H), δ10.27 (s, 1H), δ11.05-11.22 (s, 1H).

Example 222. Synthesis of 5-(azetidine-1-carbonyl)-3-chloro-N-[4,6-difluoro-[1,1-biphenyl]-3-yl]-2-methoxybenzene-1-sulfonamide, I-378

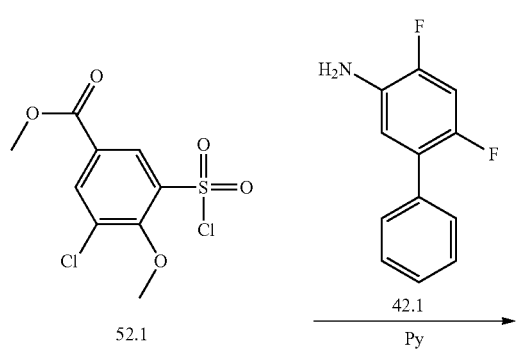

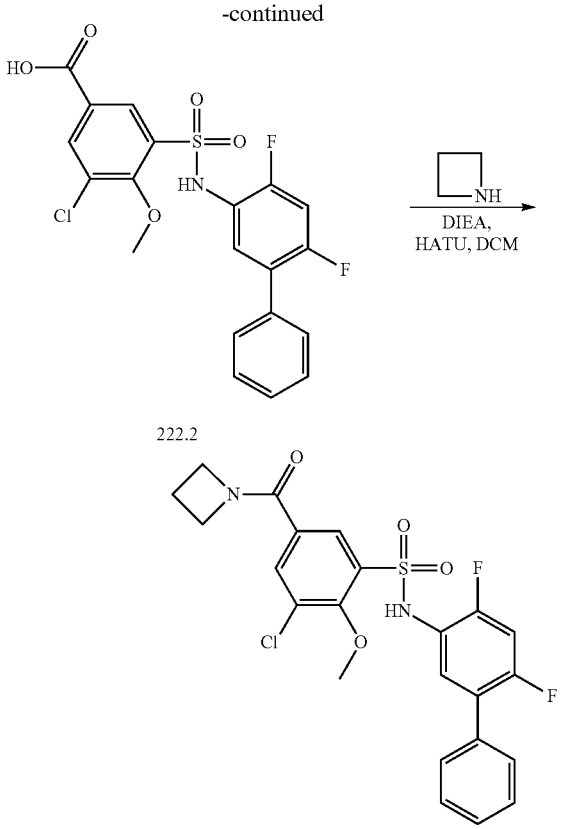

Synthesis of Compound 222.1

Into a 20-mL vial, was placed 52.1 (740 mg, 2.47 mmol, 1 equiv), 42.1 (609.2 mg, 2.97 mmol, 1.2 equiv), and pyridine (10 mL). The resulting solution was stirred for 1 overnight at room temperature. The resulting mixture was concentrated under vacuum. The resulting solution was diluted with 100 mL of H$_2$O. The resulting solution was extracted with 2×100 ml of ethyl acetate. The resulting mixture was concentrated under vacuum. The residue was applied onto a silica gel column with dichloromethane/methanol (10:1). This resulted in 300 mg (25.9%) of 222.1 as a yellow solid. (ES, m/z): [M−H]⁻ 466.0.

Synthesis of Compound 222.2

Into a 20-mL vial, was placed 222.1 (280 mg, 0.60 mmol, 1 equiv), MeOH (6 mL, 148.19 mmol, 247.63 equiv), NaOH (47.9 mg, 1.20 mmol, 2 equiv). The resulting solution was stirred for 1 overnight at room temperature. The resulting mixture was concentrated under vacuum. The resulting solution was diluted with 50 mL of H$_2$O. The pH value of the solution was adjusted to 7 with AcOH. The resulting solution was extracted with 2×50 ml of ethyl acetate. The resulting mixture was concentrated under vacuum. The residue was applied onto a Prep TLC with ethyl acetate/petroleum ether (1:1). This resulted in 254 mg (93.5%) of 222.2 as a yellow solid. (ES, m/z): [M−H]⁻ 452.0.

Synthesis of I-378

Into a 8-mL vial purged and maintained with an inert atmosphere of nitrogen, was placed 222.2 (230 mg, 0.51 mmol, 1 equiv), DCM (3 mL, 47.19 mmol, 93.12 equiv), azetidine (86.8 mg, 1.52 mmol, 3 equiv), DIEA (196.5 mg, 1.52 mmol, 3 equiv), HATU (385.4 mg, 1.01 mmol, 2 equiv). The resulting solution was stirred for 1 overnight at room temperature. The resulting solution was diluted with 20 mL of H₂O. The resulting solution was extracted with 3×10 ml of ethyl acetate concentrated under vacuum. The crude product was purified by Flash-Prep-HPLC with the following conditions (IntelFlash-1): Column, C18 silica gel; mobile phase, ACN/H₂O=15% increasing to ACN/H₂O=60% within 15 min; Detector, UV 254 nm. This resulted in 155.1 mg (62.0%) of I-378 as a white solid. (ES, m/z): [M+H]⁺ 493.2, ¹H-NMR (300 MHz, DMSO-d₆, ppm): 2.13-2.25 (m, 2H), δ3.89-3.99 (s, 3H), δ3.99-4.09 (t, J=7.8 Hz, 2H), δ4.09-4.22 (t, J=7.2 Hz, 2H), δ7.22-7.55 (m, 7H), δ7.79-7.85 (d, J=2.1 Hz, 1H), δ7.92-8.01 (d, J=1.8 Hz, 1H), δ10.29-10.45 (s, 1H).

Example 223. Synthesis of tert-butyl 7-(N-(4-fluoro-[1,1'-biphenyl]-3-yl) sulfamoyl)-1H-indole-1-carboxylate, I-382

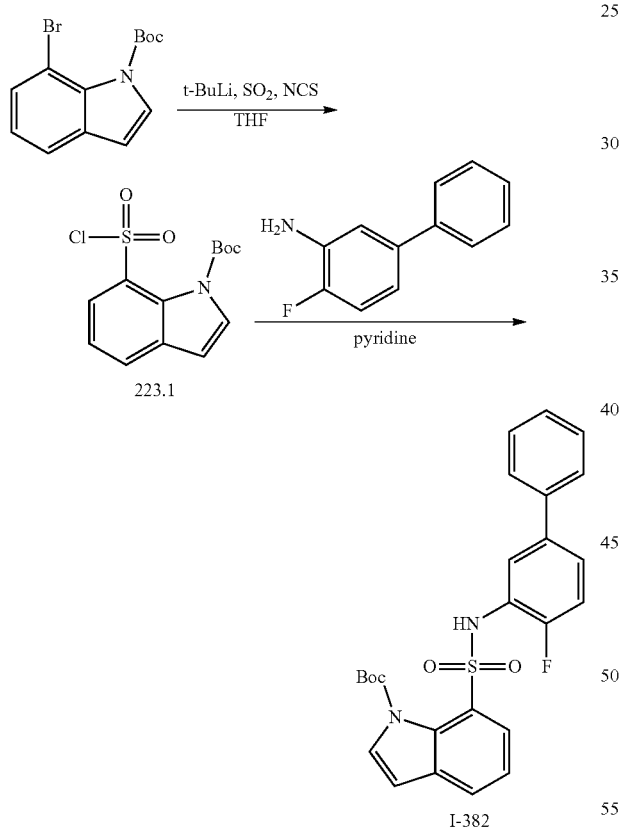

Synthesis of Compound 223.1

To a solution of tert-butyl 7-bromo-1H-indole-1-carboxylate (500 mg, 1.69 mmol, 1 equiv) in SO₂.THF (10 mL) was added t-BuLi (119.0 mg, 1.86 mmol, 1.1 equiv), NCS (225.4 mg, 1.69 mmol, 1 equiv). The resulting solution was stirred for 2 hr at −78° C. The reaction was then quenched by the addition of 15 mL of NH₄Cl (aq). The resulting solution was extracted with 3×20 ml of ethyl acetate and the organic layers combined and concentrated under vacuum. This resulted in 500 mg (94%) of 223.1 as a white solid.

Synthesis of I-382

To a solution of 223.1 (200 mg, 0.63 mmol, 1 equiv) in pyridine (6 mL) was added 4-fluoro-[1,1-biphenyl]-3-amine (142.3 mg, 0.76 mmol, 1.20 equiv). The resulting solution was stirred for 12 hr at 25° C. The resulting mixture was concentrated under vacuum. The residue was applied onto Prep-TLC with ethyl acetate/petroleum ether (5:1). The crude product was purified by Prep-HPLC with the following conditions (2 #SHIMADZU (HPLC-01)): Column, XBridge Prep OBD C18 Column, 19*250 mm, 5 um; mobile phase, Water (10 mmol/L NH₄HCO₃+0.1% NH₃.H₂O) and ACN (hold 73% PhaseB in 15 min); Detector 254 nm. This resulted in 5.4 mg (2%) of I-382 as a light yellow solid. (ES, m/z): [M−H]⁻ 465.1, ¹H-NMR (300 MHz, DMSO-d₆, ppm): δ9.90 (s, 1H), 8.05-8.02 (d, J=8.7 Hz, 1H), 7.75-7.73 (d, J=7.8 Hz, 1H), 7.61-7.60 (d, J=2.4 Hz, 1H), 7.59-7.26 (m, 10H), 1.71 (s, 9H).

Example 224. Synthesis of 5-(azetidine-1-carbonyl)-N-[4,6-difluoro-[1,1-biphenyl]-3-yl]-2-methoxybenzene-1-sulfonamide, I-384

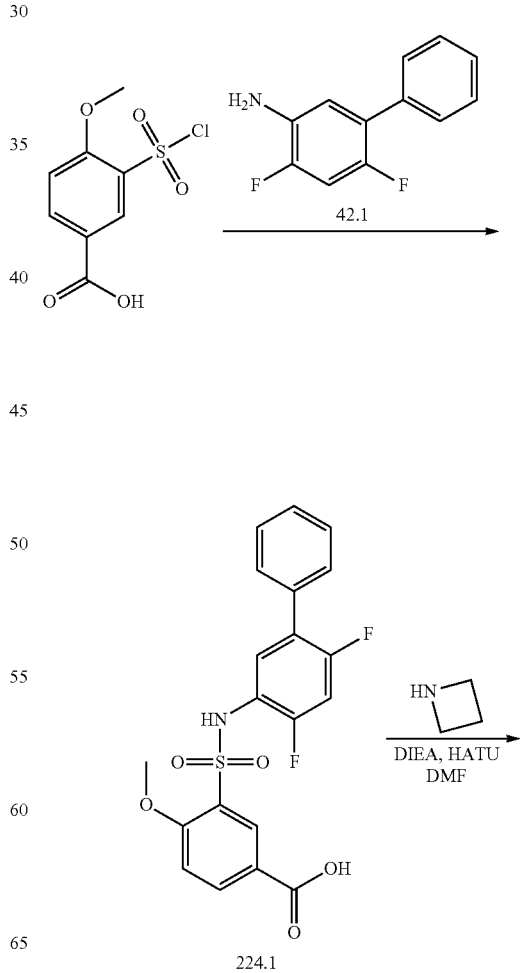

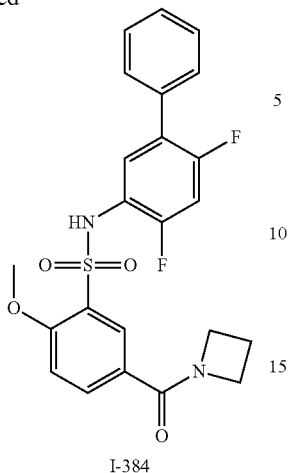

I-384

Synthesis of Compound 224.1

Into a 8-mL vial, was placed 3-(chlorosulfonyl)-4-methoxybenzoic acid (400 mg, 1.60 mmol, 1 equiv), 42.1 (491.2 mg, 2.39 mmol, 1.5 equiv), pyridine (4 mL). The resulting solution was stirred for 1 overnight at room temperature. The resulting mixture was concentrated under vacuum. The resulting solution was diluted with 100 mL of H₂O. The resulting solution was extracted with 3×100 ml of ethyl acetate. The resulting mixture was concentrated under vacuum. The residue was applied onto a silica gel column with dichloromethane/methanol (20:1). This resulted in 459 mg (68.5%) of 224.1 as a yellow solid.

Synthesis of I-384

Into a 8-mL vial purged and maintained with an inert atmosphere of nitrogen, was placed 224.1 (200 mg, 0.48 mmol, 1 equiv), DMF (2 mL), azetidine (81.7 mg, 1.43 mmol, 3 equiv), DIEA (184.9 mg, 1.43 mmol, 3 equiv), HATU (362.6 mg, 0.95 mmol, 2 equiv). The resulting solution was stirred for 1 overnight at room temperature. The resulting solution was diluted with 50 mL of H₂O. The resulting solution was extracted with 3×50 ml of ethyl acetate concentrated under vacuum. The crude product was purified by Flash-Prep-HPLC with the following conditions (IntelFlash-1): Column, C18 silica gel; mobile phase, ACN/H₂O=15% increasing to ACN/H₂O=60% within 15 min; Detector, UV 254 nm. This resulted in 85.3 mg (39.0%) of I-384 as a white solid. (ES, m/z): [M+H]⁺ 459.2, ¹H-NMR (300 MHz, DMSO-d₆, ppm): 2.11-2.25 (m, 2H), δ3.90 (s, 3H), δ3.93-4.08 (m, 2H), δ4.08-4.23 (m, 2H), δ7.25-7.35 (m, 2H), δ7.35-7.54 (m, 6H), δ7.79-7.85 (m, 2H), δ10.08 (s, 1H).

Example 225. Synthesis of 3-(azetidine-1-carbonyl)-5-chloro-N-(4,6-difluoro-[1,1'-biphenyl]-3-yl)benzenesulfonamide, I-386

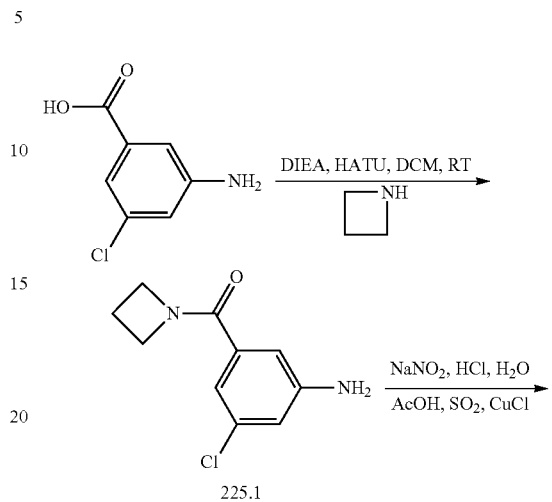

I-386

Synthesis of Compound 225.1

Into a 250-mL round-bottom flask purged and maintained with an inert atmosphere of nitrogen, was placed 3-amino-5-chlorobenzoic acid (2000 mg, 11.66 mmol, 1 equiv), azetidine (1331.1 mg, 23.31 mmol, 2 equiv), DIEA (4519.5 mg, 34.97 mmol, 3 equiv), HATU (8864.2 mg, 23.31 mmol, 2 equiv), DCM (100 mL, 1573.00 mmol, 134.95 equiv). The resulting solution was stirred for 12 hr at room temperature. The reaction was then quenched by the addition of 100 mL of water. The resulting solution was extracted with 3×100 ml of ethyl acetate. The resulting mixture was washed with 1×100 ml of brine. The mixture was dried over anhydrous sodium sulfate and concentrated. The resulting mixture was concentrated. The residue was applied onto a silica gel column with ethyl acetate/petroleum ether (1:1). This resulted in 800 mg (yield=32%) of 225.1 as a white solid. (ES, m/z): [M–H]⁻ 209.0.

Synthesis of Compound 225.2

Into a 50-mL round-bottom flask purged and maintained with an inert atmosphere of nitrogen, was placed 225.1 (400 mg, 1.90 mmol, 1 equiv) and HCl (4 mL), then to the solution was added a solution of $NaNO_2$ (196.5 mg, 2.85 mmol, 1.5 equiv) in $H_2O$ (1.6 mL) at 0° C., the solution of A was stirred at 0° C. for 1 h; then to another 50-mL round-bottom flask was placed AcOH (4 mL) and CuCl (56.4 mg, 0.57 mmol, 0.3 equiv), to the solution was through $SO_2$ over 0.5 h. The solution A was added to solution B dropwise over 10 mins. The resulting solution was stirred for 1 hr at room temperature. The reaction was then quenched by the addition of 10 mL of water. The resulting solution was extracted with 3×10 ml of ethyl acetate. The resulting mixture was washed with 1×10 ml of brine. The mixture was dried over anhydrous sodium sulfate and concentrated. The resulting mixture was concentrated. This resulted in 400 mg (yield=26%) of 225.2 as a white solid. (ES, m/z): [M–H]⁻ 291.9.

Synthesis of I-386

Into a 25-mL round-bottom flask purged and maintained with an inert atmosphere of nitrogen, was placed 225.2 (200 mg, 0.68 mmol, 1 equiv), 42.1 (167.4 mg, 0.82 mmol, 1.20 equiv), and pyridine (2 mL). The resulting solution was stirred for 0.5 hr at room temperature. The resulting mixture was concentrated. The residue was applied onto a silica gel column with ethyl acetate/petroleum ether (1:1). This resulted in 156.2 mg (yield=50%) of I-386 as a white solid. (ES, m/z): [M–H]⁻ 463.2, ¹H-NMR (400 MHz, DMSO-d₆, ppm): δ10.51 (s, 1H), δ7.85-7.77 (m, 3H), δ7.59-7.31 (m, 6H), δ7.28-7.23 (t, J=8.8 Hz, 1H), δ4.16-4.12 (m, 2H), δ4.05-4.01 (m, 2H), δ2.33-2.17 (m, 2H).

Example 226. Synthesis of tert-butyl 2-[4-(azetidine-1-carbonyl)-2-chloro-6-([4,6-difluoro-[1,1-biphenyl]-3-yl]sulfamoyl)phenoxy]acetate, I-387

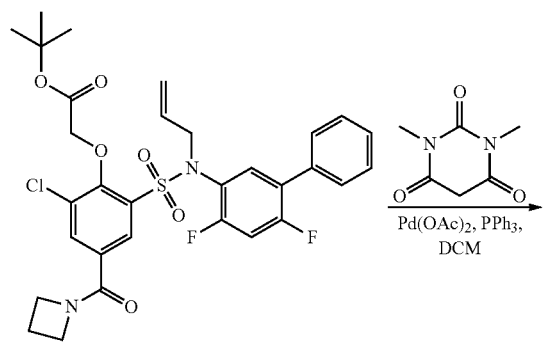

155.4

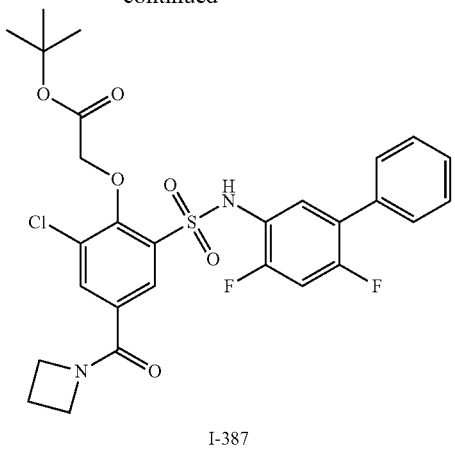

I-387

Synthesis of I-387

To a stirred mixture of 155.4 (350 mg, 0.55 mmol, 1 equiv) and 1,3-dimethyl-1,3-diazinane-2,4,6-trione (259.0 mg, 1.66 mmol, 3 equiv) in THF (4 mL, 49.37 mmol, 89.31 equiv) was added $Pd(PPh_3)_4$ (191.7 mg, 0.17 mmol, 0.3 equiv) in portions at room temperature under nitrogen atmosphere. The resulting solution was stirred for overnight at room temperature under nitrogen atmosphere. The resulting mixture was extracted with water. The combined organic layers were washed with EtOAc (2×100 mL), dried over anhydrous $Na_2SO_4$. After filtration, the filtrate was concentrated under reduced pressure. The crude product was purified by reverse phase flash with the following conditions (from $CH_3CN/H_2O$=0:100 to $CH_3CN/H_2O$=40:60 in 30 mins, UV: 254/220) to afford I-387 (300 mg, 91.5%) as a white solid. (ES, m/z): [M–H]⁻ 591.1, ¹H-NMR (400 MHz, DMSO-d₆, ppm): δ1.42 (s, 9H), δ2.16-2.23 (m, 2H), δ3.99-4.03 (t, J=7.6 Hz, 2H), δ4.12-4.16 (t, J=7.6 Hz, 2H), δ4.73 (s, 2H), δ7.34-7.49 (m, 7H), δ7.85-7.86 (d, J=2.0 Hz, 1H), δ7.96-7.97 (d, J=2.0 Hz, 1H), δ10.13 (s, 1H).

Example 227. Synthesis of (R)-3-chloro-N-(4,6-difluoro-[1,1'-biphenyl]-3-yl)-5-(3-methoxypyrrolidine-1-carbonyl)benzenesulfonamide, I-388

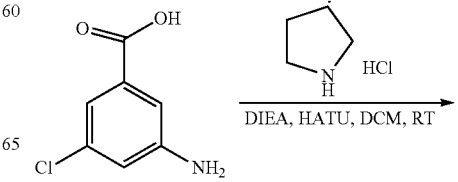

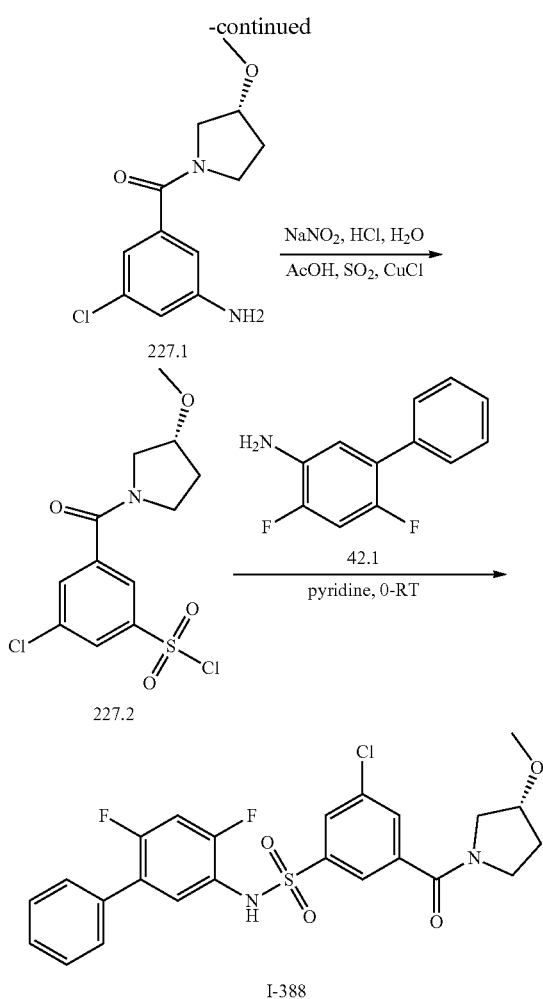

Synthesis of Compound 227.1

Into a 50-mL round-bottom flask purged and maintained with an inert atmosphere of nitrogen, was placed 3-amino-5-chlorobenzoic acid (400 mg, 2.33 mmol, 1 equiv), (3S)-3-methoxypyrrolidine hydrochloride (641.6 mg, 4.66 mmol, 2 equiv), DIEA (903.9 mg, 6.99 mmol, 3 equiv), HATU (1772.8 mg, 4.66 mmol, 2 equiv), DCM (10 mL). The resulting solution was stirred for 12 hr at room temperature. The reaction was then quenched by the addition of 10 mL of water. The resulting solution was extracted with 3×10 ml of ethyl acetate. The resulting mixture was washed with 1×10 mL of brine. The mixture was dried over anhydrous sodium sulfate and concentrated. The resulting mixture was concentrated. The residue was applied onto a silica gel column with ethyl acetate/petroleum ether (1:1). This resulted in 500 mg (yield=80%) of 227.1 as a white solid.

Synthesis of Compound 227.2

Into a 25-mL round-bottom flask purged and maintained with an inert atmosphere of nitrogen, was placed 227.1 (300 mg, 1.18 mmol, 1 equiv) and HCl (3 mL), then to the solution was added a solution of NaNO$_2$ (121.9 mg, 1.77 mmol, 1.5 equiv) in H$_2$O (1.2 mL) at 0° C., the solution of A was stirred at 0° C. for 1 h; then to another 25-mL round-bottom flask was placed AcOH (3 mL) and CuCl (35.0 mg, 0.35 mmol, 0.30 equiv), to the solution was through SO$_2$ over 0.5 h. The solution A was added to solution B dropwised over 10 mins. The resulting solution was stirred for 1 hr at room temperature. The reaction was then quenched by the addition of 10 mL of water. The resulting solution was extracted with 3×10 ml of ethyl acetate. The resulting mixture was washed with 1×10 mL of brine. The mixture was dried over anhydrous sodium sulfate and concentrated. The resulting mixture was concentrated. This resulted in 200 mg (yield=26%) of 227.2 as a white solid.

Synthesis of I-388

Into a 50-mL round-bottom flask purged and maintained with an inert atmosphere of nitrogen, was placed 227.2 (180 mg, 0.53 mmol, 1 equiv), 42.1 (131.1 mg, 0.64 mmol, 1.2 equiv), pyridine (5 mL). The resulting solution was stirred for 0.5 hr at room temperature. The resulting mixture was concentrated. The residue was applied onto a silica gel column with ethyl acetate/petroleum ether (1:1). This resulted in 101.4 mg (yield=38%) of I-388 as a white solid. (ES, m/z): [M+H]$^+$ 507.2, $^1$H-NMR (400 MHz, DMSO-d$_6$, ppm): δ10.51 (s, 1H), δ7.90-7.88 (m, 1H), δ7.82-7.81 (m, 1H), δ7.73-7.71 (m, 1H), δ7.51-7.38 (m, 8H), δ7.30-7.25 (m, 1H), δ4.00-3.86 (m, 1H), δ3.54-3.44 (m, 2H), δ3.31-3.12 (m, 4H), δ1.99-1.88 (m, 2H).

Example 228. Synthesis of (S)-3-chloro-N-(4,6-difluoro-[1,1'-biphenyl]-3-yl)-5-(3-methoxypyrrolidine-1-carbonyl)benzenesulfonamide, I-389

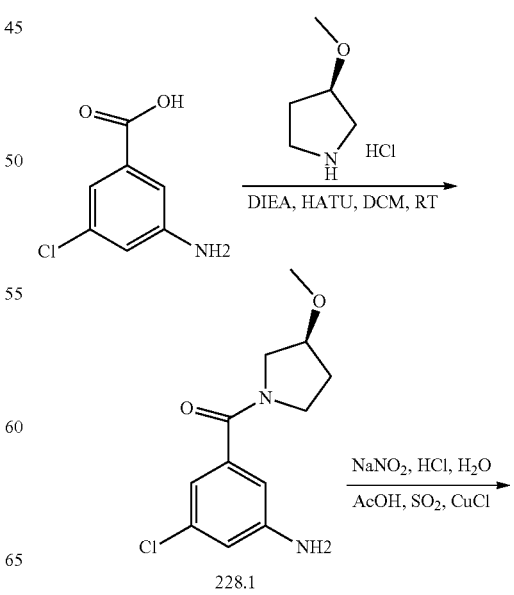

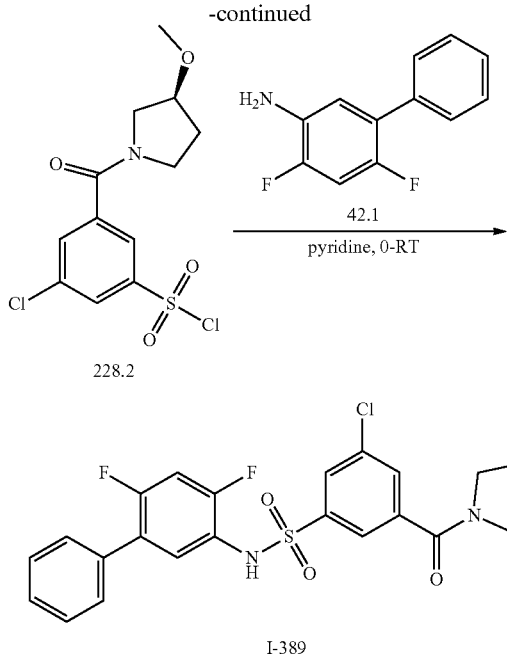

Synthesis of Compound 228.1

Into a 50-mL round-bottom flask purged and maintained with an inert atmosphere of nitrogen, was placed 3-amino-5-chlorobenzoic acid (400 mg, 2.33 mmol, 1 equiv), (3R)-3-methoxypyrrolidine hydrochloride (641.6 mg, 4.66 mmol, 2 equiv), DIEA (903.9 mg, 6.99 mmol, 3 equiv), HATU (1772.8 mg, 4.66 mmol, 2 equiv), DCM (10 mL). The resulting solution was stirred for 12 hr at room temperature. The reaction was then quenched by the addition of 10 mL of water. The resulting solution was extracted with 3×10 ml of ethyl acetate. The resulting mixture was washed with 1×10 mL of brine. The mixture was dried over anhydrous sodium sulfate and concentrated. The resulting mixture was concentrated. The residue was applied onto a silica gel column with ethyl acetate/petroleum ether (1:1). This resulted in 530 mg (yield=86%) of 228.1 as a white solid.

Synthesis of Compound 228.2

Into a 25-mL round-bottom flask purged and maintained with an inert atmosphere of nitrogen, was placed 228.1 (300 mg, 1.18 mmol, 1 equiv) and HCl (3 mL), then to the solution was added a solution of NaNO₂ (121.9 mg, 1.77 mmol, 1.5 equiv) in H₂O (1.2 mL) at 0° C., the solution of A was stirred at 0° C. for 1 h; then to another 25-mL round-bottom flask was placed AcOH (3 mL) and CuCl (35.0 mg, 0.35 mmol, 0.30 equiv), to the solution was through SO₂ over 0.5 h. The solution A was added to solution B dropwised over 10 mins. The resulting solution was stirred for 1 hr at room temperature. The reaction was then quenched by the addition of 10 mL of water. The resulting solution was extracted with 3×10 mL of ethyl acetate. The resulting mixture was washed with 1×10 mL of brine. The mixture was dried over anhydrous sodium sulfate and concentrated. The resulting mixture was concentrated. This resulted in 220 mg (yield=33%) of 228.2 as a white solid.

Synthesis of I-389

Into a 50-mL round-bottom flask purged and maintained with an inert atmosphere of nitrogen, was placed 228.2 (200 mg, 0.59 mmol, 1 equiv), 42.1 (121.4 mg, 0.59 mmol, 1 equiv), pyridine (5 mL). The resulting solution was stirred for 0.5 hr at room temperature. The resulting mixture was concentrated. The residue was applied onto a silica gel column with ethyl acetate/petroleum ether (1:1). This resulted in 28.4 mg (yield=9%) of I-389 as a white solid. (ES, m/z): (ES, m/z): [M–H]⁻ 505.0 ¹H-NMR (400 MHz, DMSO-d₆, ppm): δ7.82-7.75 (m, 3H), δ7.75-7.65 (m, 1H), δ7.52-7.40 (m, 5H), δ6.90-6.85 (m, 2H), δ4.02-3.89 (m, 1H), δ3.79-3.64 (m, 2H), δ3.46-3.34 (m, 2H), δ3.28-3.24 (m, 2H), δ2.04-1.88 (m, 2H).

Example 229. Synthesis of N-(3,5-dichloro-2-hydroxybenzyl)-N-(4-methoxy-[1,1′-biphenyl]-3-yl)methanesulfonamide, I-391

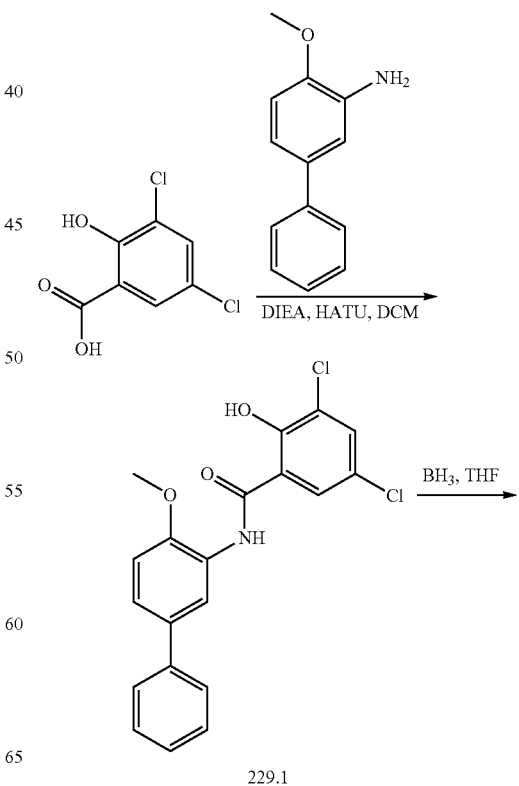

229.1

-continued

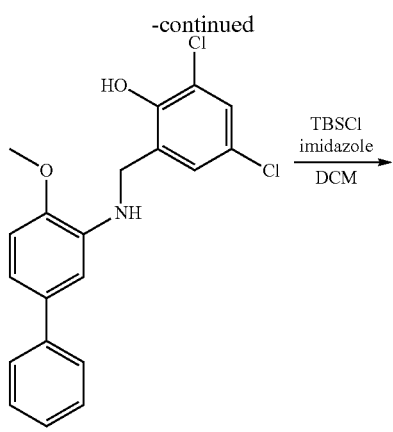

229.2

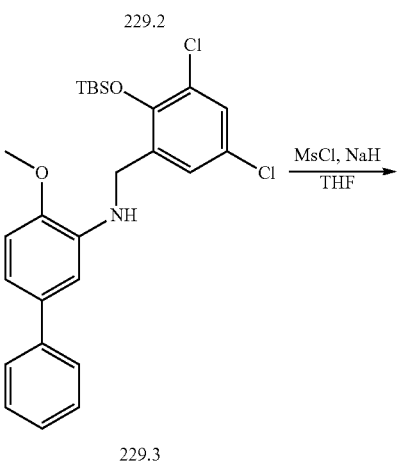

229.3

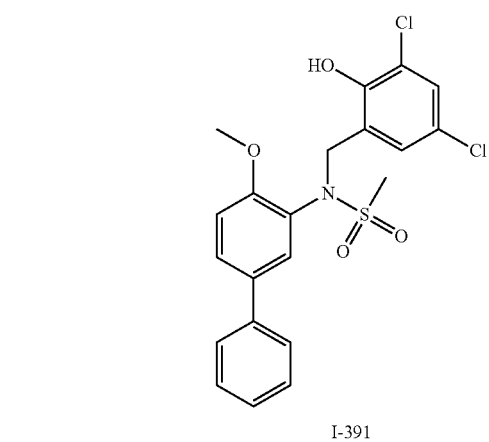 [SMILES: COc1ccc(-c2ccccc2)cc1N(Cc1cc(Cl)cc(Cl)c1O)S(C)(=O)=O]

I-391

Synthesis of Compound 229.1

Into a 100-mL round-bottom flask purged and maintained with an inert atmosphere of argon, was placed 3,5-dichloro-2-hydroxybenzoic acid (2 g, 9.66 mmol, 1 equiv), 4-methoxy-[1,1-biphenyl]-3-amine (2.3 g, 11.59 mmol, 1.20 equiv), DIEA (2.5 g, 19.32 mmol, 2 equiv), HATU (7.3 g, 19.32 mmol, 2 equiv), DCM (20 mL). The resulting solution was stirred for 12 hr at room temperature. The reaction was then quenched by the addition of 20 mL of water. The resulting solution was extracted with 3×20 ml of dichloromethane. The resulting mixture was washed with 1×20 ml of brine. The mixture was dried over anhydrous sodium sulfate and concentrated. The resulting mixture was concen- trated. The residue was applied onto a silica gel column with ethyl acetate/petroleum ether (1:2). This resulted in 1 g (27%) of 229.1 as a white solid. (ES, m/z): [M−H]⁻ 386.0.

Synthesis of Compound 229.2

Into a 100-mL round-bottom flask purged and maintained with an inert atmosphere of nitrogen, was placed 229.1 (500 mg, 1.29 mmol, 1 equiv), borane (89.1 mg, 6.44 mmol, 5 equiv), THF (5 mL). The resulting solution was stirred for 12 hr at 50° C. in an oil bath. The resulting solution was extracted with 3×10 ml of ethyl acetate. The resulting mixture was washed with 1×10 ml of brine. The mixture was dried over anhydrous sodium sulfate and concentrated. The resulting mixture was concentrated. The residue was applied onto a silica gel column with ethyl acetate/petroleum ether (1:1). This resulted in 160 mg (33%) of 229.2 as a white solid. (ES, m/z): [M−H]⁻ 372.0.

Synthesis of Compound 229.3

Into a 25-mL round-bottom flask purged and maintained with an inert atmosphere of nitrogen, was placed 229.2 (160 mg, 0.43 mmol, 1 equiv), TBSCl (77.3 mg, 0.51 mmol, 1.2 equiv), imidazole (58.2 mg, 0.86 mmol, 2 equiv), DCM (5 mL). The resulting solution was stirred for 12 hr at room temperature. The reaction was then quenched by the addition of 10 mL of water. The resulting solution was extracted with 3×10 ml of dichloromethane. The resulting mixture was washed with 1×10 ml of brine. The mixture was dried over anhydrous sodium sulfate and concentrated. The resulting mixture was concentrated. The residue was applied onto a silica gel column with ethyl acetate/petroleum ether (1:3). This resulted in 160 mg (77%) of 229.3 as a white solid. (ES, m/z): [M−H]⁻ 486.1.

Synthesis of I-391

Into a 25-mL round-bottom flask purged and maintained with an inert atmosphere of nitrogen, was placed 229.3 (140 mg, 0.29 mmol, 1 equiv), THF (5 mL), then to the solution was added NaH (17.2 mg, 0.43 mmol, 1.50 equiv, 60%) at 0° C., the mixture was stirred at 0° C. for 0.5 h, then to the mixture was added MSCl (49.2 mg, 0.43 mmol, 1.50 equiv), The resulting solution was stirred for 1 hr at 0° C. in a water/ice bath. The reaction was then quenched by the addition of 5 mL of NH₄Cl (aq.). The resulting solution was extracted with 3×10 ml of ethyl acetate. The resulting mixture was washed with 1×10 ml of brine. The resulting mixture was concentrated. The residue was applied onto a silica gel column with ethyl acetate/petroleum ether (1:1). This resulted in 24.5 mg (19%) of I-391 as a white solid. (ES, m/z): [M+H]⁺ 452.1, ¹H-NMR (400 MHz, DMSO-d₆, ppm): δ7.71 (s, 1H), 7.44-7.33 (m, 5H), 7.26-7.22 (m, 1H), 6.94-6.86 (m, 2H), 6.54 (s, 1H), 6.00-5.97 (t, J=6.4 Hz, 1H), 4.56-4.54 (d, J=6.4 Hz, 2H), 3.87 (s, 3H), 3.69 (s, 3H).

Example 230. Synthesis of 3-chloro-N-(4,6-difluoro-[1,1'-biphenyl]-3-yl)-5-(methylsulfonyl)benzenesulfonamide, I-392

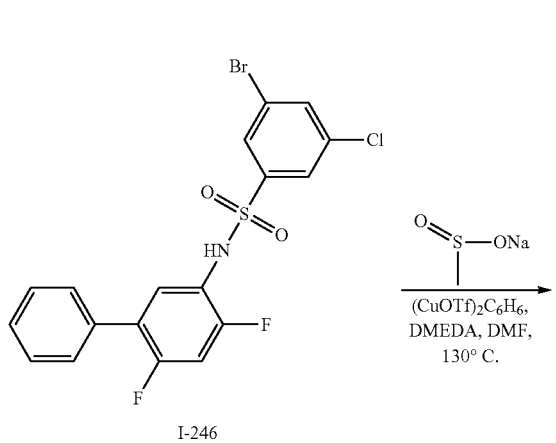

Example 231. Synthesis of N-(3-fluoro-[1,1'-biphenyl]-4-yl)benzo[d]oxazole-7-sulfonamide, I-393

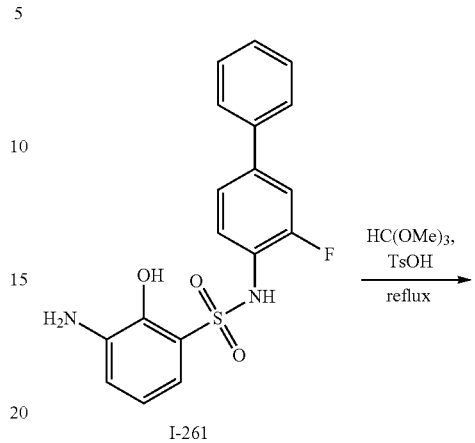

Synthesis of I-392

To a stirred mixture of I-246 (200 mg, 0.44 mmol, 1 equiv) and sodium methanesulfinate (178.0 mg, 1.74 mmol, 4.00 equiv) in DMF (2 mL) were added DMEDA (7.7 mg, 0.09 mmol, 0.20 equiv) and (CuOTf)$_2$C$_6$H$_6$ (21.9 mg, 0.04 mmol, 0.1 equiv). The resulting mixture was stirred for 2 days at 130° C. under nitrogen atmosphere. The resulting mixture was diluted with water (10 mL). The resulting mixture was extracted with EtOAc (3×10 mL). The combined organic layers were concentrated under reduced pressure. The residue was purified by reverse flash chromatography with the following conditions: column, C 18 silica gel; mobile phase, ACN in water, 0% to 80% gradient in 35 min; detector, UV 254 nm. This resulted in I-392 (15.6 mg, 7.8%) as a white solid. (ES, m/z): [M+H+H$_2$O]$^+$475.2, $^1$H-NMR (300 MHz, DMSO-d$_6$, ppm): δ3.33-3.36 (d, J=9.3 Hz, 3H), δ7.28-7.34 (t, J=8.7 Hz, 1H), δ7.42-7.52 (m, 6H), δ8.08 (s, 1H), δ8.14 (s, 1H), δ8.37 (s, 1H), δ10.66 (s, 1H).

Synthesis of I-393

To a stirred mixture of I-261 (430 mg, 1.20 mmol, 1 equiv) in HC(OMe)$_3$ (5 mL) was added TsOH (20.7 mg, 0.12 mmol, 0.10 equiv). The resulting mixture was stirred overnight at 130° C. under nitrogen atmosphere. The resulting mixture was concentrated under reduced pressure. The residue was purified by Prep-TLC (CH$_2$Cl$_2$/MeOH=100/1) to afford I-393 (201.9 mg, 45.6%) as a light pink solid. (ES, m/z): [M+H]$^+$ 369.0, $^1$H-NMR (400 MHz, DMSO-d$_6$, ppm): δ7.18-7.22 (m, 1H), δ7.35-7.51 (m, 7H), δ7.54-7.58 (t, J=8.0 Hz, 1H), δ7.74-7.76 (d, J=6.8 Hz, 1H), δ8.12-8.14 (d, J=7.2 Hz, 1H), δ8.92 (s, 1H), δ10.67 (s, 1H).

Example 232. Synthesis of 3,5-dichloro-2-fluoro-N-[4-methoxy-[1,1-biphenyl]-3-yl]benzene-1-sulfonamide, I-394

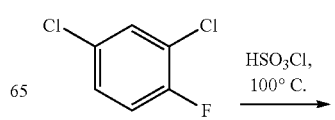

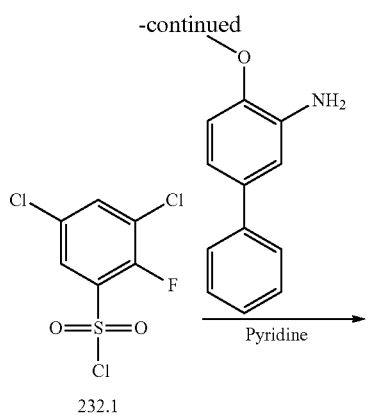

Synthesis of Compound 232.1

Into a 100-mL round-bottom flask, was placed HSO₃Cl (20 mL), 2,4-dichloro-1-fluorobenzene (2 g, 12.12 mmol, 1 equiv). The resulting solution was stirred for 12 hr at 100° C. The reaction was then quenched by the addition of 100 mL of water/ice. The resulting solution was extracted with 3×150 mL of ethyl acetate and the organic layers combined and concentrated under vacuum. This resulted in 1.5 g (46%) of 232.1 as a black solid. (ES, m/z): [M−H]⁻ 260.8.

Synthesis of I-394

Into a 50-mL round-bottom flask, was placed 232.1 (200 mg, 0.76 mmol, 1 equiv), 4-methoxy-[1,1-biphenyl]-3-amine (181.5 mg, 0.91 mmol, 1.20 equiv), and pyridine (5 mL). The resulting solution was stirred for 12 hr at 25° C. The resulting mixture was concentrated under vacuum. The residue was applied onto Prep-TLC with dichloromethane/methanol (20:1). This resulted in 45.9 mg (14.2%) of I-394 as a white solid (ES, m/z): [M+H]⁺ 425.9, ¹H-NMR (400 MHz, DMSO-d₆, ppm) δ 10.08 (s, 1H), δ8.12-8.11 (d, J=6.4 Hz, 1H), δ7.84-7.82 (d, J=8.8 Hz, 1H), δ7.57-7.48 (m, 3H), δ7.48-7.40 (m, 3H), δ7.35-7.31 (t, J=7.2 Hz, 1H), δ7.03-7.05 (d, J=8.8 Hz, 1H), δ3.56 (s, 3H).

Example 233. Synthesis of 3,5-dichloro-N-(2,4-difluoro-5-(piperazin-1-yl) phenyl)-2-hydroxybenzenesulfonamide, I-395

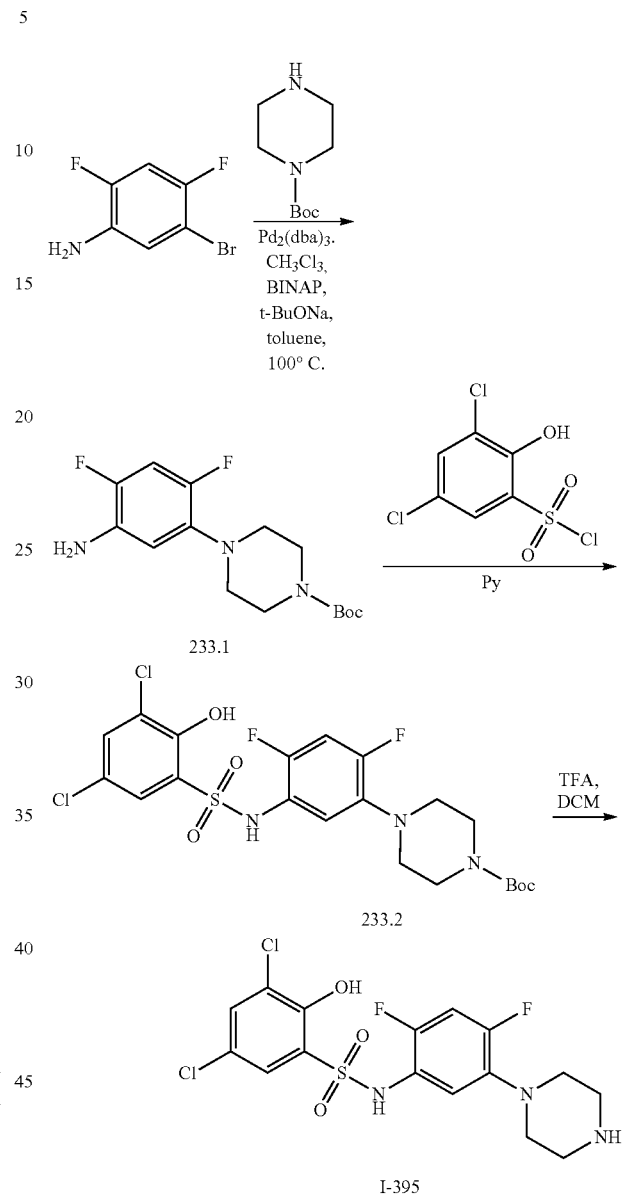

Synthesis of Compound 233.1

Into a 100-mL round-bottom flask purged and maintained with an inert atmosphere of nitrogen, was placed 5-bromo-2,4-difluoroaniline (2 g, 9.615 mmol, 1 equiv), tert-butyl piperazine-1-carboxylate (5.37 g, 28.845 mmol, 3.00 equiv), BINAP (1.20 g, 1.923 mmol, 0.2 equiv), t-BuONa (2.77 g, 28.845 mmol, 3 equiv), toluene (50 mL), Pd₂(dba)₃·CHCl₃ (0.99 g, 0.962 mmol, 0.1 equiv). The resulting solution was stirred for 12 hr at 100° C. in an oil bath. The reaction was then quenched by the addition of 50 mL of water. The resulting solution was extracted with 3×50 mL of ethyl acetate. The resulting mixture was washed with 1×50 mL of brine. The solid was dried in an oven under reduced pressure. The residue was applied onto a silica gel column with ethyl acetate/petroleum ether (1:3). This resulted in 180 mg (yield=6%) of 233.1 as a white solid.

Synthesis of Compound 233.2

Into a 25-mL round-bottom flask purged and maintained with an inert atmosphere of nitrogen, was placed 233.1 (180 mg, 0.574 mmol, 1 equiv), 3,5-dichloro-2-hydroxybenzene-1-sulfonyl chloride (150.22 mg, 0.574 mmol, 1 equiv), pyridine (5 mL). The resulting solution was stirred for 0.5 hr at room temperature. The resulting mixture was concentrated. The residue was applied onto a silica gel column with ethyl acetate/petroleum ether (1:3). This resulted in 80 mg (yield=26%) of 233.2 as a white solid.

Synthesis of I-395

Into a 25-mL round-bottom flask purged and maintained with an inert atmosphere of nitrogen, was placed 233.2 (80 mg, 0.15 mmol, 1 equiv), TFA (1 mL), DCM (4 mL). The resulting solution was stirred for 12 hr at room temperature. The pH value of the solution was adjusted to 7 with NaHCO₃ (1 mol/L). The resulting solution was extracted with 3×20 mL of dichloromethane. The resulting mixture was washed with 1×20 mL of brine. The mixture was dried over anhydrous sodium sulfate and concentrated. The residue was applied onto a silica gel column with ethyl acetate/petroleum ether (1:1). This resulted in 18.7 mg (yield=29%) of I-395 as a white solid. (ES, m/z): [M−H]⁻ 436.0, ¹H-NMR (400 MHz, DMSO-d₆, ppm): δ8.81 (s, 1H), δ7.43 (s, 1H), δ7.25 (s, 1H), δ7.19-7.13 (m, 1H), δ7.00-6.96 (t, J=8.8 Hz, 1H), δ3.24-3.21 (m, 4H), δ3.05-3.03 (m, 4H).

Example 234. Synthesis of N-benzyl-2-(benzyloxy)-3,5-dichloro-N-(4-methoxy-[1,1'-biphenyl]-3-yl)-6-methylbenzenesulfonamide, I-397

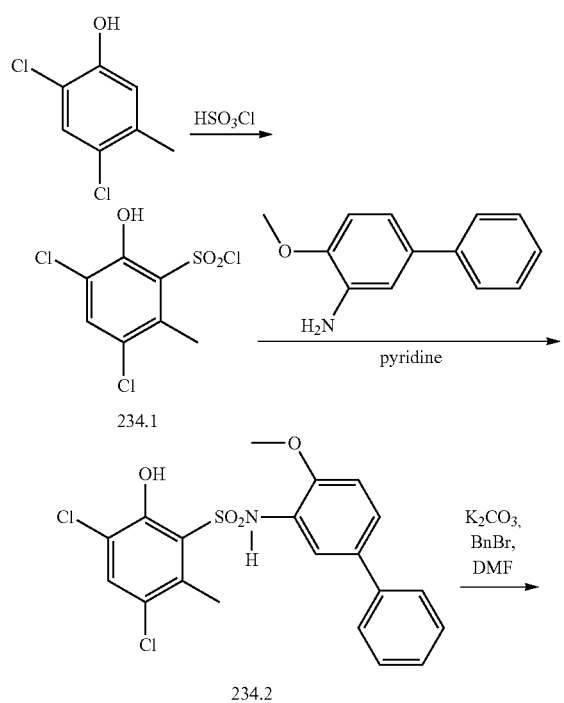

-continued

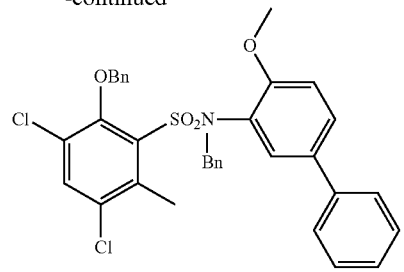

I-397

Synthesis of Compound 234.1

Into a 25-mL 3-necked round-bottom flask purged and maintained with an inert atmosphere of nitrogen, was placed 2,4-dichloro-5-methylphenol (1.3 g, 7.34 mmol, 1.00 equiv), chlorosulfonic acid (13 mL). The resulting solution was stirred overnight at 65° C. The reaction was then quenched by the addition of 50 mL of water/ice. The resulting solution was extracted with 3×20 mL of ethyl acetate and the organic layers combined and concentrated under vacuum. This resulted in 1.13 g (crude) of 234.1 as a white solid. (ES, m/z): [M−H]⁻ 272.9.

Synthesis of Compound 234.2

Into a 50-mL 3-necked round-bottom flask purged and maintained with an inert atmosphere of nitrogen, was placed 234.1 (995 mg, 3.61 mmol, 1.00 equiv), 2-methoxy-5-phenylaniline (870 mg, 4.37 mmol, 1.20 equiv), pyridine (15 mL). The resulting solution was stirred for 2 h at room temperature. The reaction solution was then quenched by the addition of 50 mL of 1M hydrogen chloride and extracted with 3×20 mL of ethyl acetate. The organic layers were combined and concentrated under vacuum. The residue was applied onto a silica gel column with dichloromethane/methanol (20:1). This resulted in 600 mg (38%) of 234.2 as a white solid. (ES, m/z): [M−H]⁻ 436.0.

Synthesis of I-397

Into a 10-mL round-bottom flask purged and maintained with an inert atmosphere of nitrogen, was placed 234.2 (50 mg, 0.11 mmol, 1.00 equiv), N,N-dimethylformamide (2 mL), potassium carbonate (47.3 mg, 0.34 mmol, 3.00 equiv), BnBr (42.69 mg, 0.25 mmol, 2.20 equiv). The resulting mixture was stirred overnight at room temperature. The reaction was then quenched by the addition of 4 mL of water. The resulting solution was extracted with 3×5 mL of ethyl acetate and the organic layers combined and concentrated under vacuum. The residue was applied onto a silica gel column with ethyl acetate/petroleum ether (1:3). This resulted in 35.2 mg (50%) of I-397 as a white solid. (ES, m/z): [M+Na]+ 640.2, ¹H-NMR (300 MHz, DMSO-d₆, ppm): δ2.19 (s, 3H), δ3.39 (s, 3H), δ4.83 (br s, 2H), δ5.12 (s, 2H), δ6.95-6.98 (d, J=8.7 Hz, 1H), δ7.15-7.42 (m, 14H), δ7.52-7.56 (m, 3H), δ8.11 (s, 1H).

Example 235. Synthesis of 2,4-dichloro-6-(N-(4-methoxy-[1,1'-biphenyl]-3-yl)sulfamoyl) Benzoic Acid, I-398

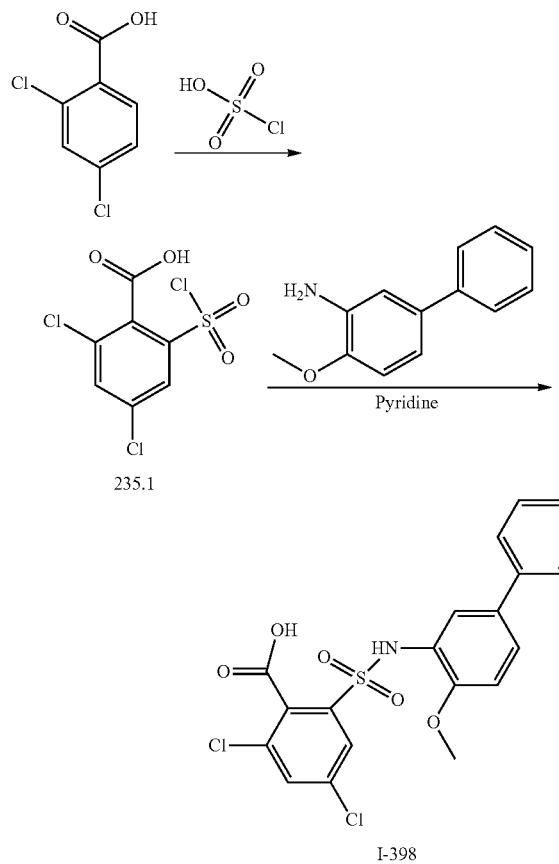

Synthesis of Compound 235.1

Into a 100-mL 3-necked round-bottom flask purged and maintained with an inert atmosphere of nitrogen, was placed chloranesulfonic acid (5 g, 42.91 mmol, 1.00 equiv), 2,4-dichlorobenzoic acid (9.15 g, 47.90 mmol, 3.00 equiv). The resulting solution was stirred for 18 h at 1150° C. in an oil bath. The reaction was then quenched by the addition of 20 mL of water/ice. The solids were collected by filtration and concentrated under vacuum. This resulted in 4.7 g (38%) of 235.1 as a white solid.

Synthesis of I-398

Into a 25-mL round-bottom flask purged and maintained with an inert atmosphere of nitrogen, was placed 235.1 (200 mg, 0.69 mmol, 1.00 equiv), pyridine (2 mL), 2-methoxy-5-phenylaniline (160 mg, 0.80 mmol, 1.20 equiv). The resulting solution was stirred for 12 h at room temperature. The reaction was then quenched by the addition of 5 mL of 1M HCl (aq.). The resulting solution was extracted with 3×5 mL of ethyl acetate and the combined organic layers were concentrated under vacuum. The residue was applied onto a silica gel column with $CH_2Cl_2$:MeOH (10:1). This resulted in 100.7 mg (32%) of I-398 as an off-white solid. (ES, m/z): [M+H]$^+$ 452.1, $^1$H-NMR (400 MHz, $CD_3OD$, ppm): δ3.93 (s, 3H), δ7.13-7.15 (d, J=8.4 Hz, 1H), δ7.28-7.31 (m, 1H), δ7.40-7.47 (m, 3H), δ7.60-7.62 (m, 2H), δ7.69 (s, 1H), δ8.27 (s, 1H), δ8.33-8.34 (d, J=2 Hz, 1H).

Example 236. Synthesis of 3-(3-chloro-5-(N-(3,5-difluorophenyl)sulfamoyl)-4-hydroxyphenyl) Propanoic Acid, I-399

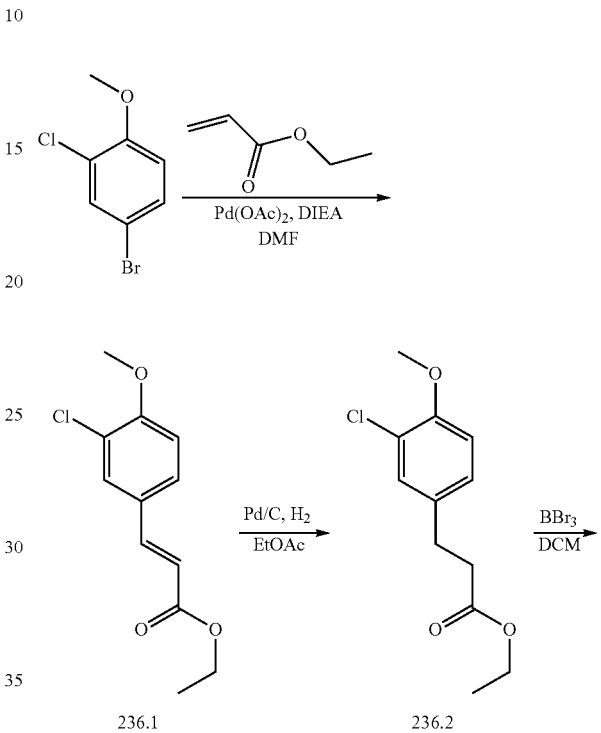

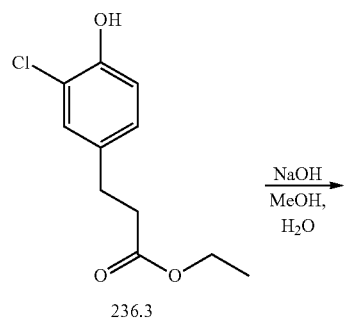

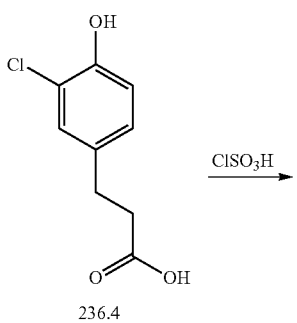

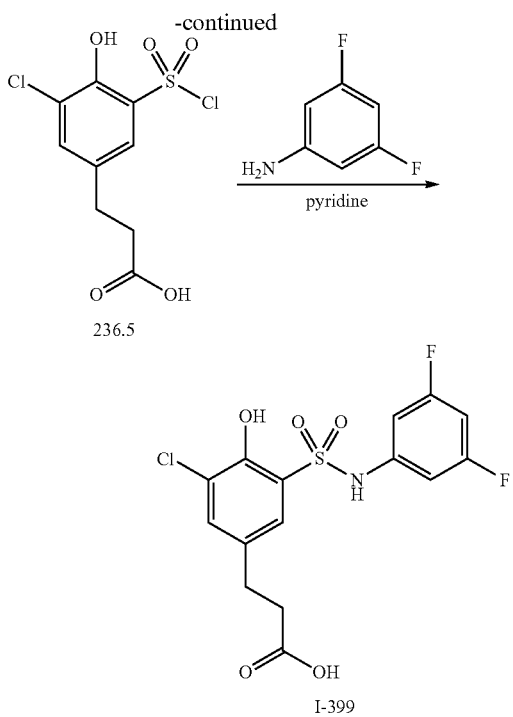

Synthesis of Compound 236.1

Into a 250-mL 3-necked round-bottom flask purged and maintained with an inert atmosphere of nitrogen, was placed 4-bromo-2-chloro-1-methoxybenzene (5 g, 22.58 mmol, 1.00 equiv), DMF (50 mL), DIEA (5.8 g, 44.88 mmol, 2.00 equiv), ethyl prop-2-enoate (3.4 g, 33.96 mmol, 1.50 equiv), tris(2-methylphenyl)phosphane (2.06 g, 6.77 mmol, 0.30 equiv), Pd(OAc)$_2$ (500 mg, 2.23 mmol, 0.10 equiv). The resulting solution was stirred overnight at 100° C. The reaction was then quenched by the addition of 200 mL of water. The resulting solution was extracted with ethyl acetate (2×100 mL) and the organic layers combined and concentrated under vacuum. The residue was applied onto a silica gel column with ethyl acetate/petroleum ether (1:20). This resulted in 4.1 g (75%) of 236.1 as a white solid.

Synthesis of Compound 236.2

Into a 25-mL round-bottom flask, was placed 321.1 (1 g, 4.15 mmol, 1.00 equiv), ethyl acetate (10 mL). This was followed by the addition of Pd/C (200 mg). The flask was evacuated and flushed three times with hydrogen, followed by flushing with hydrogen. The resulting solution was stirred for 2 h at room temperature. The solids were filtered out. The filtrate was concentrated under vacuum. This resulted in 940 mg (93%) of 236.2 as a white solid.

Synthesis of Compound 236.3

Into a 20-mL sealed tube purged and maintained with an inert atmosphere of nitrogen, was placed 236.2 (900 mg, 3.71 mmol, 1.00 equiv), dichloromethane (10 mL), BBr$_3$ (1.82 g, 7.26 mmol, 2.00 equiv). The resulting solution was stirred overnight at room temperature. The reaction was then quenched by the addition of 20 mL of sat.NH$_4$Cl (aq.). The resulting solution was extracted with of ethyl acetate (2×10 mL) and the organic layers combined and concentrated under vacuum. The residue was applied onto a silica gel column with CH$_2$Cl$_2$/MeOH (1:80). This resulted in 580 mg (68%) of 236.3 as a white solid.

Synthesis of Compound 236.4

Into a 25-mL 3-necked round-bottom flask purged and maintained with an inert atmosphere of nitrogen, was placed 236.3 (580 mg, 2.54 mmol, 1.00 equiv), methanol (5 mL), water (1 mL), sodium hydroxide (202 mg, 5.05 mmol, 2.00 equiv). The resulting solution was stirred overnight at room temperature. The reaction was then quenched by the addition of 10 mL of water. The pH value of the solution was adjusted to 6 with acetic acid. The resulting solution was extracted with of ethyl acetate (2×10 mL) and the organic layers combined and concentrated under vacuum. The residue was applied onto a silica gel column with dichloromethane/methanol (20:1). This resulted in 470 mg (92%) of 236.4 as a white solid.

Synthesis of Compound 236.5

Into a 25-mL 3-necked round-bottom flask purged and maintained with an inert atmosphere of nitrogen, was placed 236.4 (320 mg, 1.60 mmol, 1.00 equiv), O-(chlorosulfonyl)oxidanol (5 mL). The resulting solution was stirred overnight at room temperature. The reaction was then quenched by the addition of 20 mL of water/ice. The resulting solution was extracted with of ethyl acetate (2×10 mL) and the organic layers combined and concentrated under vacuum. This resulted in 270 mg (57%) of 236.5 as a white solid.

Synthesis of I-399

Into a 25-mL 3-necked round-bottom flask purged and maintained with an inert atmosphere of nitrogen, was placed 236.5 (320 mg, 1.07 mmol, 1.00 equiv), 3,5-difluoroaniline (157.77 mg, 1.22 mmol, 1.20 equiv), pyridine (5 mL). The resulting solution was stirred overnight at room temperature. The resulting mixture was concentrated under vacuum. The residue was applied onto a silica gel column with dichloromethane/methanol (30:1). The crude product was purified by Prep-HPLC with the following conditions (2 #-AnalyseHPLC-SHIMADZU(HPLC-10)): Column: SunFire C18 OBD Prep Column, 100 Å, 5 μm, 19 mm×250 mm; Mobile Phase A:water (0.1% FA), Mobile Phase B: ACN; Flow rate: 25 mL/min; Gradient: 36% B to 70% B in 7 min; 254/220 nm; Rt: 5.82 min. This resulted in 73.3 mg (17%) of I-399 as a white solid. (ES, m/z): [M−H]$^-$ 390.1, $^1$H-NMR (400 MHz, DMSO-d$_6$, ppm): δ2.49-2.52 (m, 2H), δ2.76-2.80 (m, 2H), δ6.71-6.75 (m, 2H), δ6.81-6.84 (m, 1H), δ7.55-7.56 (d, J=2.4 Hz, 1H), δ7.65-7.66 (d, J=2 Hz, 1H), δ10.55-10.85 (br s, 1H), δ11.96-12.15 (br s, 1H).

Example 237. Synthesis of 5-chloro-N-(4-methoxy-[1,1'-biphenyl]-3-yl)-1,3-dimethyl-1H-pyrazole-4-sulfonamide, I-400

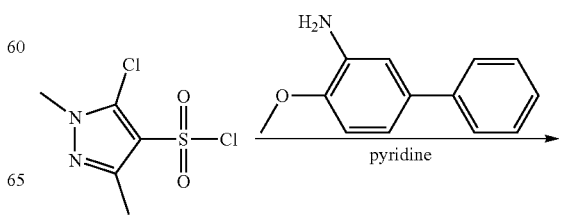

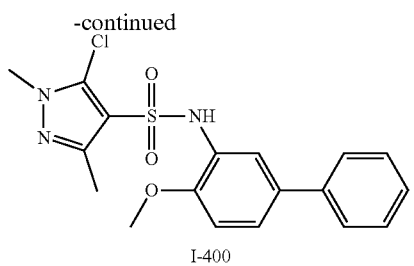

I-400

Synthesis of I-400

A solution of 5-chloro-1,3-dimethyl-1H-pyrazole-4-sulfonyl chloride (1.15 g, 1.2 equiv), 2-methoxy-5-phenylaniline (1 g, 1 equiv) in pyridine (10 mL) was stirred at room temperature under nitrogen atmosphere for 2 hours. The resulting mixture was concentrated under vacuum. The crude product (800 mg) was purified by Flash-Prep-HPLC with the following conditions (IntelFlash-1: Column, C18 silica gel). This resulted in 1-400 (221.3 mg, 12.94%). (ES, m/z): [M+H]$^+$ 392.2, $^1$H-NMR (400 MHz, CD$_3$OD, ppm): δ2.17 (s, 3H), δ3.69-3.71 (d, J=8 Hz, 6H), δ6.95-6.97 (m, 1H), δ7.29-7.31 (m, 1H), δ7.38-7.42 (m, 3H), δ7.52-54 (m, 2H), δ7.66-7.67 (d, J=2 Hz, 1H).

Example 238. Synthesis of additional exemplary compounds

Additional exemplary compounds were prepared using a one step method similar to example 237. Characterization data for these compounds is provided in Table 5, below.

TABLE 5

Characterization data for additional exemplary compounds.

| Compound No. | Name | MS (ES, m/z) | 1H-NMR |
|---|---|---|---|
| I-16 | N-benzhydryl-3,5-dichloro-2-hydroxybenzenesulfonamide | [M − H]$^-$ 406.1 | (300 MHz, CDCl$_3$, ppm): δ5.30-5.46 (m, 1H), δ5.60-5.62 (m, 1H), δ7.02-7.14 (m, 4H), δ7.17-7.26 (m, 5H), δ7.32-7.34 (d, J = 4.8 Hz, 3H), δ7.97 (br s, 1H). |
| I-326 | 5-chloro-N-(4,6-difluoro-[1,1'-biphenyl]-3-yl)-2-oxo-1,2-dihydropyridine-3-sulfonamide | [M − H]$^-$ 395.0 | (DMSO-d$_6$, 400 MHz, ppm): δ 8.05-8.04 (d, J = 2.4 Hz, 1H), 7.92-7.91 (d, J = 2.8 Hz, 1H), 7.50-7.48 (t, J = 8.4 Hz, 2H), 7.46-7.35 (m, 5H). |
| I-404 | 3-((3,5-dichloro-2-hydroxyphenyl)sulfonamido)-4-methoxybenzoic acid, | [M − H]$^-$ 389.9 | (300 MHz, CD$_3$OD, ppm): δ3.75 (s, 3H), δ6.97-7.00 (d, J = 8.7 Hz, 1H), δ7.53-7.54 (d, J = 2.7 Hz, 1H), δ7.60-7.61 (d, J = 2.4 Hz, 1H), δ7.83-7.86 (m, 1H), δ8.07-8.08 (d, J = 2.1 Hz, 1H). |
| I-405 | 3,5-dichloro-N-(4-methoxy-[1,1'-biphenyl]-3-yl)benzenesulfonamide | [M − H]$^-$ 406.0 | (300 MHz, CDCl$_3$, ppm): δ3.72 (s, 3H), δ6.83-6.86 (d, J = 8.7 Hz, 1H), δ7.03 (s, 1H), δ7.30-7.36 (m, 2H), δ7.40-7.48 (m, 3H), δ7.52-7.55 (m, 2H), δ7.65-7.66 (d, J = 1.8 Hz, 2H), δ7.75-7.76 (d, J = 2.1 Hz, 1H). |
| I-406 | 3-(N-(4-methoxy-[1,1'-biphenyl]-3-yl)sulfamoyl)benzoic acid | [M − H]$^-$ 382.0 | (300 MHz, DMSO-d$_6$, ppm): δ9.84 (s, 1H), δ8.33-8.30 (d, J = 6 Hz, 1H), δ8.15-8.12 (d, 7.8 Hz, 1H), δ7.92-7.89 (d, J = 7.8 Hz, 1H), δ7.68-7.63 (m, 1H), δ7.54-7.41 (m, 6H), δ7.35-7.30 (m, 1H), δ7.00-6.97 (d, J = 8.4 Hz, 1H), δ3.59 (s, 3H). |
| I-408 | 5-(N-(4-methoxy-[1,1'-biphenyl]-3-yl)sulfamoyl) thiophene-3-carboxylic acid | [M − H]$^-$ 388.0 | (400 MHz, DMSO-d$_6$, ppm): δ3.64 (s, 3H), δ7.00-7.02 (d, J = 8.8 Hz, 1H), δ7.30-7.37 (m, 2H), δ7.41-7.45 (m, 2H), δ7.51-7.59 (m, 3H), δ7.59 (s, 1H), δ7.77-7.94 (s, 2H), δ8.02 (s, 1H). |
| I-409 | 4-fluoro-3-[(2-methoxy-5-phenylbenzene)sulfonamido]benzoic acid | [M + H]$^+$ 402.2 | (300 MHz, DMSO-d$_6$, ppm): δ3.86 (s, 3H), δ7.24-7.38 (m, 3H), δ7.43-7.48 (m, 2H), δ7.57-7.59 (m, 2H), δ7.66-7.72 (m, 1H), δ7.88-7.96 (m, 3H). |
| I-410 | 4-cyano-N-(2-methoxy-5-phenylphenyl)benzene-1-sulfonamide | [M − H]$^-$ 363.1 | (300 MHz, DMSO-d$_6$, ppm): δ3.46 (s, 3H), δ6.98-7.01 (m, 1H), δ7.30-7.56 (m, 7H), δ7.85-7.87 (d, 8.4 Hz, 2H), δ8.03-8.05 (d, J = 8.7 Hz, 2H), δ10.01 (s, 1H). |

TABLE 5-continued

Characterization data for additional exemplary compounds.

| Compound No. | Name | MS (ES, m/z) | 1H-NMR |
|---|---|---|---|
| I-412 | 2-chloro-4-[(3,5-dichloro-2-hydroxybenzene)sulfonamido]benzoic acid | [M + H]+ 396.0 | (400 MHz, DMSO-$d_6$, ppm): δ7.07-7.14 (m, 1H), δ7.19-7.20 (d, J = 2.0 Hz, 1H), δ7.72-7.75 (m, 2H), δ7.82-7.83 (d, J = 1.6 Hz, 1H), δ11.00-11.35 (brs, 1H), δ13.00-13.06 (brs, 1H). |
| I-421 | methyl 3-(N-(4-methoxy-[1,1'-biphenyl]-3-yl)sulfamoyl)benzoate | [M + H]+ 398.0 | (400 MHz, DMSO-$d_6$, ppm): δ9.92 (s, 1H), δ8.34-8.33 (d, J = 1.6 Hz, 1H), δ8.19-8.16 (m, 1H), δ7.97-7.95 (m, 1H), δ7.73-7.69 (m, 1H), δ7.55-7.54 (d, J = 1.2 Hz, 2H), δ7.52-7.42 (m, 4H), δ7.35-7.31 (m, 1H), δ7.00-6.98 (d, J = 8.4 Hz, 1H), δ3.89 (s, 3H), δ3.48 (s, 3H). |
| I-426 | 3-chloro-4-hydroxy-5-[(2-methoxy-5-phenylphenyl)(methyl)sulfamoyl]benzoic acid | [M − H]− 446.2 | (400 MHz, CDCl$_3$, ppm): δ3.31 (s, 3H), δ3.59 (s, 3H), δ6.94-6.97 (d, J = 8.4 Hz, 1H), δ7.31-7.47 (m, 3H), δ7.55-7.61 (m, 4H), δ8.31-8.39 (m, 2H). |
| I-438 | 4-chloro-3-[(2-methoxy-5-phenylphenyl)sulfamoyl]benzoic acid | [M − H]− 416.0 | (300 MHz, DMSO-$d_6$, ppm): δ8.41-8.39 (m, 1H), δ8.09-8.05 (m, 1H), δ7.74-7.72 (d, J = 8.1 Hz, 1H), δ7.51-7.49 (m, 2H), δ7.46-7.40 (m, 4H), δ7.34-7.29 (m, 1H), δ7.03-7.00 (m, 1H), Δ3.55 (s, 3H). |
| I-441 | N-[4-fluoro-[1,1'-biphenyl]-3-yl]-2-methoxybenzene-1-sulfonamide | [M + H]+ 358.2 | (400 MHz, DMSO-$d_6$, ppm): δ3.85 (s, 3H), δ7.00-7.03 (t, J = 7.2 Hz, 1H), δ7.20-7.25 (m, 2H), δ7.36-7.43 (m, 2H), δ7.45-7.48 (m, 5H), δ7.58-7.60 (m, 1H), δ7.68-7.71 (m, 1H), δ 9.86 (s, 1H). |
| I-444 | 3-chloro-5-[(2,4-difluoro-3-phenylphenyl)sulfamoyl]-4-hydroxybenzoic acid | [M − H]− 438.2 | (300 MHz, DMSO-$d_6$) δ 7.86-7.81 (m, 1H), 7.74-772 (m, 1H), 7.56-7.36 (m, 5H), 7.24-7.20 (m, 1H), 7.10-7.06 (m, 1H). |

Example 239. Synthesis of 3,5-dichloro-2-methoxy-N-(4-methoxy-[1,1'-biphenyl]-3-yl)benzenesulfonamide, I-402

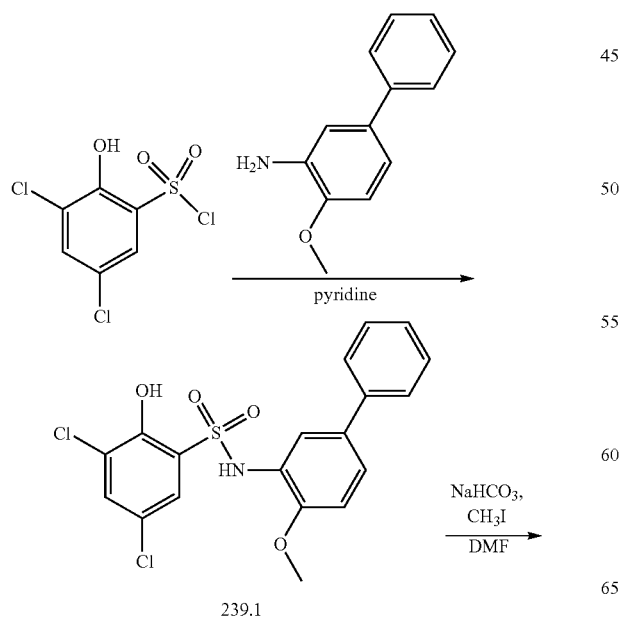

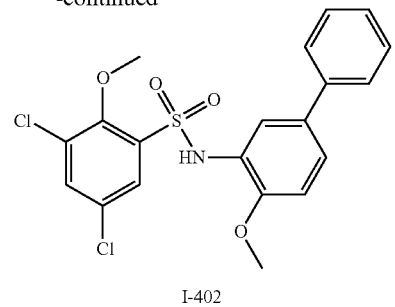

I-402

Synthesis of Compound 239.1

Into a 50-mL 3-necked round-bottom flask purged and maintained with an inert atmosphere of nitrogen, was placed 3,5-dichloro-2-hydroxybenzene-1-sulfonyl chloride (2 g, 7.65 mmol, 1 equiv), 2-methoxy-5-phenylaniline (1.8 g, 9.18 mmol, 1.2 equiv), pyridine (20 mL). The reaction solution was stirred for 2 h at room temperature. The resulting mixture was concentrated under vacuum. The residue was applied onto a silica gel column with dichloromethane/methanol (40:1). This resulted in 3.2 g (98%) of 239.1 as a yellow solid.

Synthesis of I-402

Into a 25-mL 3-necked round-bottom flask purged and maintained with an inert atmosphere of nitrogen, was placed 239.1 (300 mg, 0.71 mmol, 1.00 equiv), N,N-dimethylformamide (5 mL), sodium bicarbonate (60 mg, 0.71 mmol, 1.00 equiv), $CH_3I$ (100 mg, 0.7 mmol, 1.00 equiv). The solution was stirred overnight at room temperature. The reaction was then quenched by the addition of 5 mL of water, and extracted with 3×10 mL of ethyl acetate. Then, the organic layers combined and concentrated under vacuum. The residue was applied onto a silica gel column with dichloromethane/methanol (50:1). The crude product was purified by Prep-HPLC with the following conditions (Column: XBridge Prep OBD C18 Column 30×150 mm 5 um; Mobile Phase A: water (10 mmol/L $NH_4HCO_3$+0.1% $NH_3.H_2O$), Mobile Phase B: ACN; Flow rate: 60 mL/min; Gradient: 68% B to 90% B in 7 min; 254/220 nm; Rt: 5.20, 6.07 min. This resulted in 47 mg (15%) of I-402 as a white solid. (ES, m/z): [M−H]⁻ 436.0, ¹H-NMR (300 MHz, $CDCl_3$, ppm): δ3.72 (s, 3H), δ4.10 (s, 3H), δ6.80-6.83 (d, J=8.7 Hz, 1H), δ7.26-7.32 (m, 2H), δ7.34-7.44 (m, 2H), δ7.49-7.57 (m, 4H), δ7.70-7.73 (m, 2H).

Example 240. Synthesis of 3,5-dichloro-2-methoxy-N-(4-methoxy-[1,1'-biphenyl]-3-yl)-N-methylbenzenesulfonamide, I-401

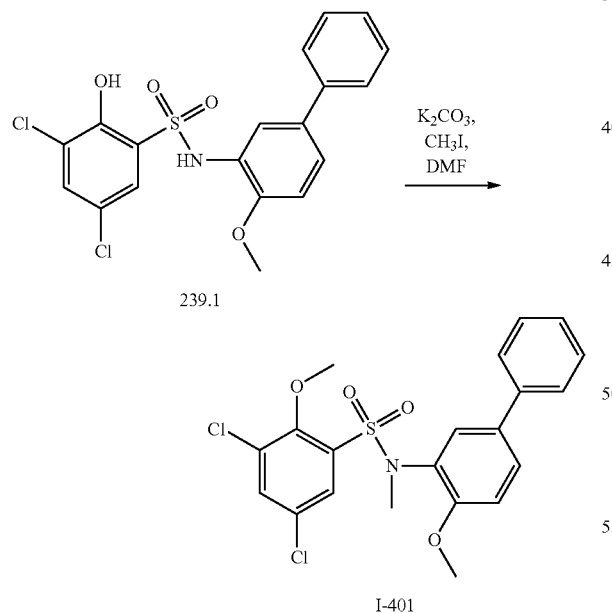

mmol, 2.4 equiv). The resulting solution was stirred for 12 h at room temperature. The reaction was then quenched by the addition of 10 mL of water, followed by extracted with 3×10 mL of ethyl acetate and the organic layers combined and concentrated under vacuum. The residue was applied onto a silica gel column with dichloromethane/methanol (30:1). The crude product was purified by Flash-Prep-HPLC with the following conditions (IntelFlash-1): Column, C 18; mobile phase, $CH_3CN/H_2O$ ($NH_4HCO_3$)=1:9 increasing to $CH_3CN/H_2O$ ($NH_4HCO_3$)=17:3 within 40 min; Detector, UV 254 nm. This gave the title compound of I-401 (285.7 mg, 53.6%) as a white solid. (ES, m/z): [M+H]⁺ 452.2, 1H-NMR (400 MHz, $CDCl_3$, ppm): δ3.40 (s, 3H), δ3.54 (s, 3H), δ3.97 (s, 3H), δ6.85-6.87 (d, J=8.4 Hz, 1H), δ7.29-7.33 (m, 1H), δ7.39-7.43 (m, 2H), δ7.49-7.55 (m, 5H), δ7.64-7.65 (d, J=2.4 Hz, 1H).

Example 241. Synthesis of 3,5-dichloro-N-(3-methoxy-[1,1'-biphenyl]-4-yl)-2-methylbenzenesulfonamide, I-403

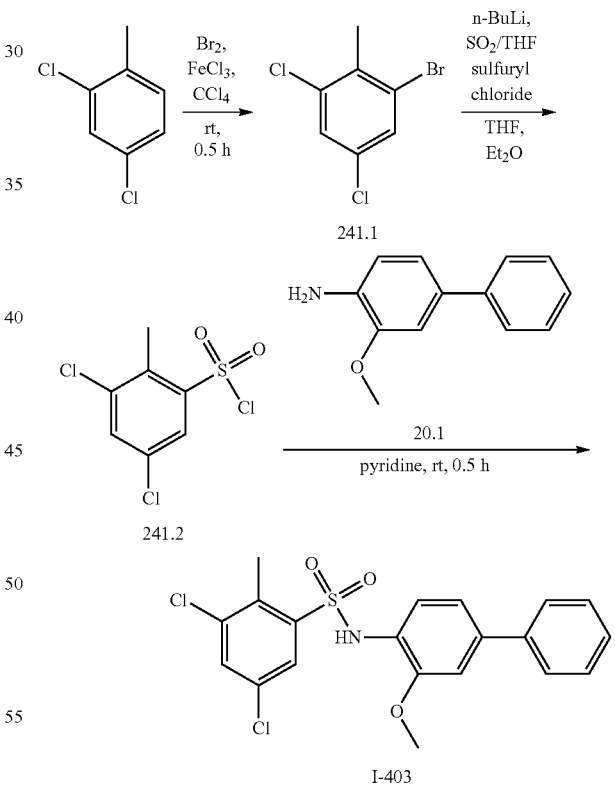

Synthesis of I-401

Into a 25-mL 3-necked round-bottom flask purged and maintained with an inert atmosphere of nitrogen, was placed 324.1 (500 mg, 1.18 mmol, 1 equiv), DMF (5 mL), $K_2CO_3$ (651.5 mg, 4.71 mmol, 4 equiv), $CH_3I$ (401.4 mg, 2.83

Synthesis of 241.1

Into a 250-mL round-bottom flask purged and maintained with an inert atmosphere of nitrogen, was placed 2,4-dichloro-1-methylbenzene (5 g, 31.05 mmol, 1.00 equiv), $FeCl_3$ (50 mg, 0.308 mmol, 0.01 equiv), $CCl_4$ (50 mL), $Br_2$ (6 g, 37.54 mmol, 1.20 equiv). The resulting solution was stirred for 0.5 h at room temperature. The reaction was then quenched by the addition of 50 mL of sat.NaSO₃ (aq.). The resulting solution was extracted with 3×50 mL of dichloromethane. The organic layers combined, washed with 1×50 mL of brine, dried and concentrated under vacuum. The residue was applied onto a silica gel column with ethyl acetate/petroleum ether (1:10). This resulted in 5 g (67%) of 241.1 as a white solid.

Synthesis of 241.2

Into a 100-mL round-bottom flask purged and maintained with an inert atmosphere of nitrogen, was placed 241.1 (2.0 g, 8.34 mmol, 1.00 equiv), THF (20 mL), ether (20 mL), to the solution was added n-BuLi (3.33 mL, 2.5 M, 1.00 equiv) at −78° C., the solution was stirred at −78° C. for 0.5 h. To the solution was added SO₂/THF (8 mL), the solution was stirred at room temperature for another 1.5 h, the solvent was concentrated under vacuum. The residue was dissolved in hexane, then the mixture was added sulfuryl chloride (2.3 g, 17.04 mmol, 2.00 equiv) at 0° C. The resulting solution was stirred for 10 h at room temperature. The solids were collected by filtration. The resulting mixture was concentrated under vacuum. This resulted in 1.8 g (83%) of 241.2 as a white solid.

Synthesis of I-403

Into a 50-mL round-bottom flask purged and maintained with an inert atmosphere of nitrogen, was placed 241.2 (400 mg, 1.54 mmol, 1.00 equiv), 20.1 (368 mg, 1.85 mmol, 1.20 equiv), pyridine (5 mL). The resulting solution was stirred for 0.5 h at room temperature. The reaction was then quenched by the addition of 5 mL of 1 M HCl (aq.). The resulting solution was extracted with 3×5 mL of ethyl acetate and the organic layers combined. The solids were collected by filtration. The resulting mixture was concentrated under vacuum. The residue was applied onto a silica gel column with ethyl acetate/petroleum ether (1:3). This resulted in 63.5 mg (10%) of I-403 as a white solid. (ES, m/z): [M−H]⁻ 419.9, ¹H-NMR (400 MHz, DMSO-d₆, ppm): δ2.32 (s, 3H), δ3.58 (s, 3H), δ7.02-7.04 (m, 1H), δ7.31-7.34 (m, 1H), δ7.41-7.51 (m, 6H), δ7.84-7.88 (m, 2H), δ9.79 (s, 1H).

Example 242. Synthesis of N-(2-methoxy-5-phenylphenyl)-4-(2H-1,2,3,4-tetrazol-5-yl)benzene-1-sulfonamide, I-407

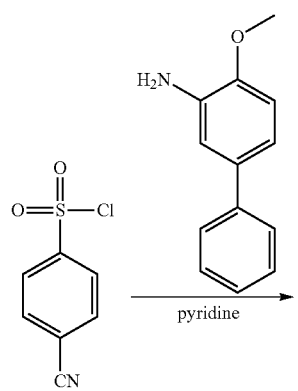

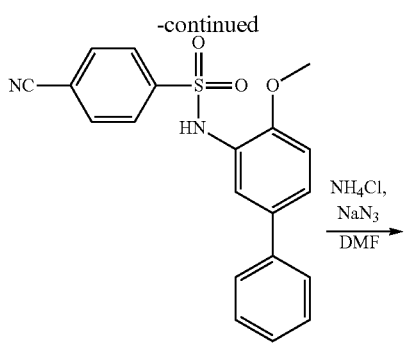

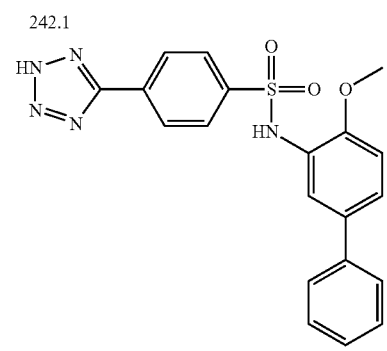

Synthesis of Compound 242.1

Into a 100-mL 3-necked round-bottom flask purged and maintained with an inert atmosphere of nitrogen, was placed 4-cyanobenzene-1-sulfonyl chloride (500 mg, 2.48 mmol, 1.00 equiv), 2-methoxy-5-phenylaniline (594 mg, 2.98 mmol, 1.20 equiv), pyridine (13 mL). The resulting solution was stirred for 2 h at 25° C. The reaction was then quenched by the addition of 60 mL of 1M hydrochloric acid (aq.). The resulting solution was extracted with 3×100 mL of ethyl acetate and the organic layers combined and concentrated under vacuum. The residue was applied onto a silica gel column with dichloromethane/methanol (100:1). This resulted in 810 mg (90%) of 242.1 as a red solid. (ES, m/z): [M−H]⁻ 363.1.

Synthesis of I-407

Into a 100-mL 3-necked round-bottom flask, was placed 242.1 (300 mg, 0.82 mmol, 1.00 equiv), NH₄Cl (176 mg, 3.29 mmol, 4.00 equiv), DMF (15 mL), NaN₃ (162 mg, 2.49 mmol, 3.00 equiv). The resulting solution was stirred for 12 h at 130° C. The solids were filtered out. The crude product was purified by Prep-HPLC with the following conditions (2 #-AnalyseHPLC-SHIMADZU(HPLC-10)): Column: XBridge Prep OBD C18 Column 30×150 mm 5 um; Mobile Phase A: water (10 mmol/L NH₄HCO₃+0.1% NH₃.H₂O), Mobile Phase B: ACN; Flow rate: 60 mL/min; Gradient: 20% B to 43% B in 8 min; 254/220 nm; Rt: 7.45 min. This resulted in 37.1 mg (11%) of I-407 as a white solid. (ES, m/z): [M−H]⁻ 406.1, ¹H-NMR (300 MHz, DMSO-d₆, ppm): δ3.53 (s, 3H), δ6.89-7.01 (m, 1H), δ7.32-7.37 (m, 1H), δ7.40-7.50 (m, 3H), δ7.51-7.54 (d, J=7.5 Hz, 3H), δ7.72-7.75 (d, J=8.4 Hz, 2H), δ8.08-8.11 (d, J=8.7 Hz, 2H).

Example 243. Synthesis of cyclopropyl 3-((3,5-dichloro-2-hydroxyphenyl) sulfonamido)-4-methoxybenzoate, I-411

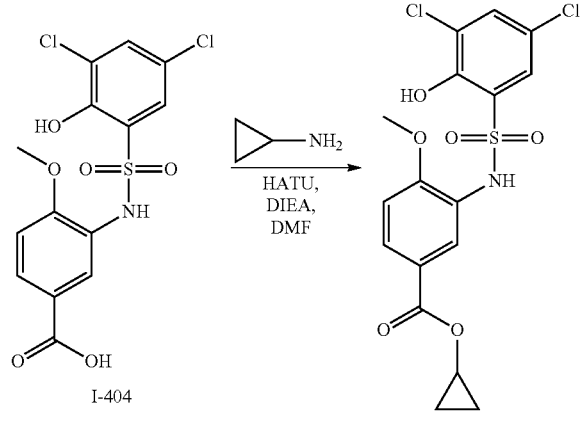

Synthesis of I-411

Into a 25-mL round-bottom flask purged and maintained with an inert atmosphere of nitrogen, was placed I-404 (28 mg, 0.07 mmol, 1.00 equiv), DIEA (18 mg, 0.14 mmol, 2.00 equiv), N,N-dimethylformamide (5 mL), cyclopropanamine (20 mg, 0.35 mmol, 5.00 equiv), HATU (54 mg, 0.14 mmol, 2.00 equiv). The resulting solution was stirred for 12 h at room temperature. The resulting solution was extracted with of ethyl acetate and the organic layers combined. The resulting mixture was washed with 1×5 mL of brine. The mixture was dried over anhydrous sodium sulfate and concentrated under vacuum. The residue was applied onto a silica gel column with ethyl acetate/petroleum ether (1:0). This resulted in 9.8 mg (32%) of I-411 as a white solid. (ES, m/z): [M−H]⁻ 428.9, $^1$H-NMR (DMSO-$d_6$, 400 MHz, ppm): δ8.30 (s, 1H), 7.77 (s, 1H), 7.67 (s, 1H), 7.62-7.60 (d, J=8.8 Hz, 1H), 7.39 (s, 1H), 6.98-6.96 (d, J=8.4 Hz, 1H), 3.62 (s, 3H), 2.83-2.77 (m, 1H), 0.69-0.62 (m, 2H), 0.56-0.53 (m, 2H).

Example 244. 4-bromo-2-(3,5-dichlorobenzamido) benzoic Acid, I-519, and 4-(benzo[b]thiophen-2-yl)-2-(3,5-dichlorobenzamido)benzoic Acid, I-515

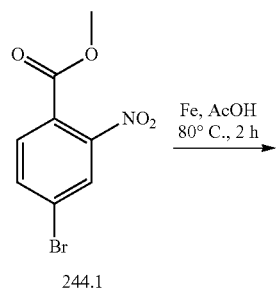

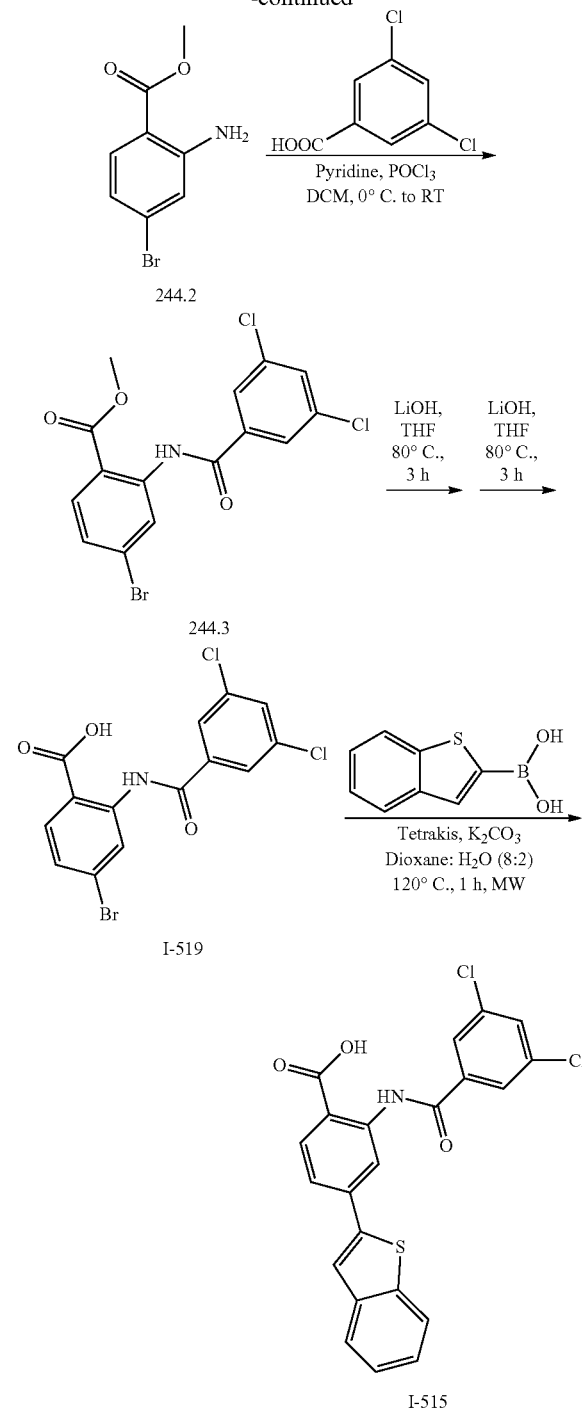

Synthesis of Compound 244.2

Iron powder (3.0 g, 100% w/w) was added to 244.1 (3 g, 11.6 mmol, 1 eq) in ethanol:acetic acid (1:1) (30 mL) at room temperature. The reaction mixture was heated at 80° C. for 2 h. After completion of reaction, the reaction mixture was allowed to cool to room temperature then concentrated under vacuum. Residue was neutralized with saturated sodium bicarbonate solution and extracted with ethyl acetate (3×50 mL). Combined organic layer was washed with brine, dried over sodium sulphate and concentrated under reduced pressure to obtain crude material. The crude reaction mixture was purified by column chromatography and compound was eluted in 10-15% ethyl acetate in hexane to obtain pure 244.2. (2.2 g, 82%). MS(ES): m/z 230.13 [M–H]+.

Synthesis of Compound 244.3

Pyridine (13 mL, 153 mmol, 10 eq) was added to solution of 244.2 (1 g, 15.3 mmol, 1 eq) and 3,5-dichlorobenzoic acid (3 g, 18.4 mmol, 1.2 eq) in dry DCM (30 mL) at room temperature. POCl$_3$ (15 mL, 169 mmol, 11 eq) was added to reaction mixture at 0° C. and the mixture was allowed to stir at room temperature. After completion of reaction, the reaction mixture was quenched by saturated sodium bicarbonate solution and extracted with DCM (3×40 mL). Combined organic layer was washed with brine, dried over sodium sulphate and concentrated under reduced pressure to obtain crude material. The crude reaction mixture was purified by column chromatography and compound was eluted in 18% ethyl acetate in hexane to obtain pure 244.3 (1.1 g, 62%). MS(ES): m/z 402.2 [M–H]−.

Synthesis of I-519

Compound was synthesized as per experimental protocol 244.3 to obtain I-519 (0.6 g, 62%). MS(ES): m/z 388.2 [M+H]+, LCMS purity: 100%, $^1$H NMR (400 MHz, DMSO-d6) δ 7.47 (dd, J=8.4, 2.1 Hz, 1H), 7.89-8.01 (m, 4H), 8.80 (d, J=2.1 Hz, 1H), 12.34 (br s, 1H), 14.19 (br s, 1H).

Synthesis of I-515

K$_2$CO$_3$ (0.266 g, 1.43 mmol, 3 eq) was added to a suspension of I-519 (0.25 g, 0.64 mmol, 1 eq) and benzo-thiophene boronic acid (0.137 g, 0.77 mmol, 1.2 eq) in dioxane:water (9:1, 10 mL, 40V) in a 30 mL sealed tube. The reaction mixture was purged with argon for 30 minutes and tetrakis(triphenylphosphine)palladium(0) (0.074 g, 0.064 mmol, 0.1 eq) was added to reaction mixture. Reaction mixture was heated at 140° C. under microwave irradiation for 1 h. After completion of reaction, water (50 mL) was added to reaction mixture and was extracted using ethyl acetate (3×20 mL). Combined organic layer was washed with brine, dried over sodium sulphate and concentrated under reduced pressure to obtain crude material. This was further purified by column chromatography and compound was eluted in 2% methanol in DCM to afford pure I-515 (0.05 g, 12%). MS(ES): m/z 440.4 [M–H]−, LCMS purity: 96.85%, $^1$H NMR (400 MHz, DMSO-d6) δ 7.40-7.49 (m, 2H), 7.71 (d, J=8.3 Hz, 1H), 7.95 (d, J=10.1 Hz, 4H), 8.04 (d, J=10.1 Hz, 2H), 8.12 (d, J=8.3 Hz, 1H), 9.05 (s, 1H), 12.39 (br s, 1H), 14.04 (br s, 1H).

Example 245. 1-((3,5-difluoro-2-hydroxyphenyl)sulfonyl)-2-(1-methyl-1H-pyrazol-4-yl)-1H-indole-5-carbonitrile, I-512

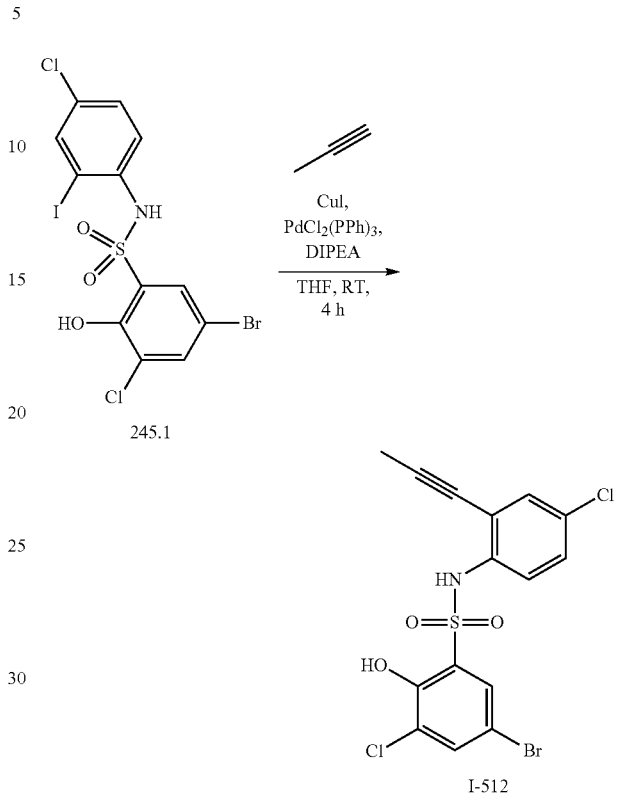

Synthesis of I-512

PdCl$_2$(PPh$_3$)$_2$ (0.0671 g, 0.095 mmol, 0.2 eq) and CuI (0.0182 g, 0.095 mmol, 0.2 eq) were added to a suspension of 245.1 (0.25 g, 0.478 mmol, 1 eq), in anhydrous THF (2.5 mL) in a 30 mL seal tube. Reaction mixture was purged with argon for 10 min and prop-1-yne (0.057 g, 1.43 mmol, 3 eq) and diisopropylamine (1 mL) were added. The purging with argon was continued for another 15 min, and the reaction tube was sealed with Teflon cap. The reaction mixture was stirred at room temperature for 4 h. Water (10 mL) was added to reaction mixture and acidified using 10% HCl solution. The reaction mixture was extracted using EtOAc (10 mL×2) and combined organic layer was washed with brine, dried over sodium sulphate and concentrated under reduced pressure to obtain crude material. This was further purified by column chromatography and compound was eluted in 9% ethyl acetate in hexane. The resulting material was further purified by reverse phase preparative HPLC carried out using SUNFIRE C 18 (150*19) mm, 5 m column and 0.1% formic acid in water and 100% ACN as mobile phase. The pure fractions were collected and lyophilized to afford pure I-512 (0.01 g, 5%). MS(ES): m/z 434.2 [M–H]+. LCMS purity: 100%, $^1$H NMR (400 MHz, DMSO-d6) δ 2.00 (s, 3H), 7.26-7.33 (m, 1H), 7.33-7.40 (m, 2H), 7.58 (d, J=2.5 Hz, 1H), 7.95 (d, J=2.5 Hz, 1H), 9.62 (br s, 1H), 11.07 (br s, 1H).

Example 246. 5-bromo-3-chloro-N-(4-chloro-2-(prop-1-yn-1-yl)phenyl)-2-hydroxy-N-methylbenzenesulfonamide, I-516

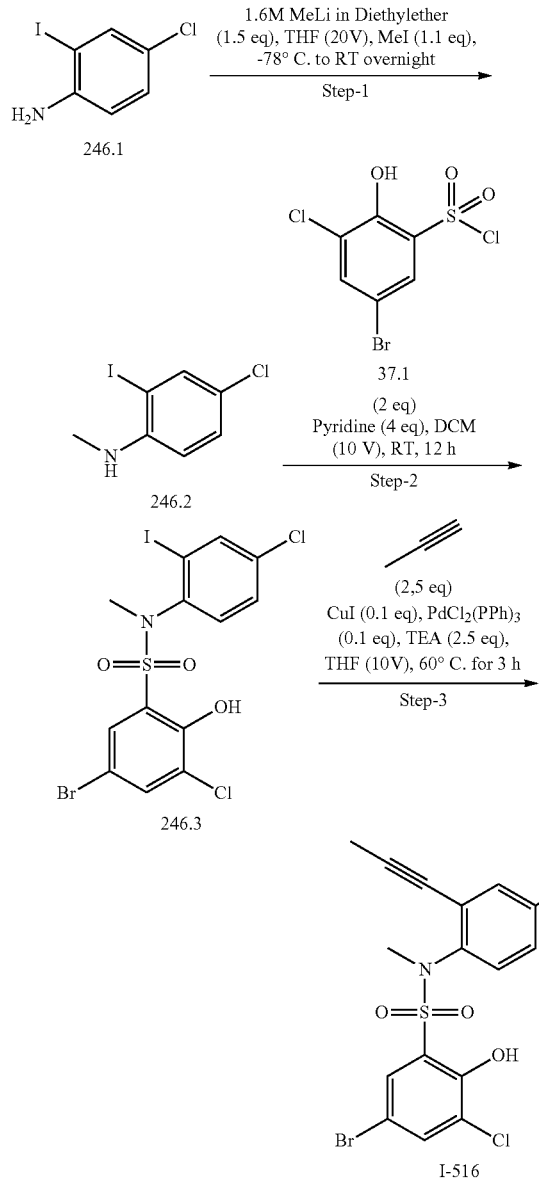

Synthesis of Compound 246.2

Methyl lithium (1.6M, 25.9 mL, 41.5 mmol, 1.5 eq) was added to solution of 4-chloro-2-iodoaniline (7 g, 27.6 mmol, 1 eq) in anhydrous THF at −78° C. under nitrogen atmosphere. The reaction mixture was stirred for 45 min at same temperature. Methyl iodide (1.91 mL, 30.4 mmol, 1.1 eq) was added to reaction mixture at −78° C. and reaction was allowed to stir at room temperature for 15 h. After completion of reaction, water (200 mL) was added to reaction mixture and was extracted using ethyl acetate (50 mL×3). Combined organic layer was washed with brine, dried over sodium sulphate and concentrated under reduced pressure to obtain crude material. The residue was purified by column chromatography using 8% ethyl acetate in hexane to afford pure 246.2 (4.5 g, 60%). MS(ES): m/z 267.99 [M−H]$^+$.

Synthesis of Compound 246.3

Compound 246.3 was synthesized as per experimental protocol of 242.1 to obtain 246.3 (0.45 g, 7.47%). MS (ES): m/z 536.1 [M−H]$^-$.

Synthesis of I-516

Compound was synthesized as per experimental protocol of I-36: PdCl$_2$(PPh$_3$)$_2$ (0.2 eq) and CuI (0.2 eq) were added to a suspension of 246.3 (1 eq), in anhydrous THF (10V) in a 30 mL seal tube. Reaction mixture was purged with argon for 10 min and prop-1-yne (3 eq) and TEA (5V) were added. The purging with argon was continued for another 15 min and reaction tube was sealed with Teflon cap. The reaction mixture was stirred for 16 h at room temperature and then after heated at 70° C. for 3 h. Water was added to reaction mixture and acidified using 10% HCl solution. The reaction mixture was extracted using EtOAc (10 mL×2) and combined organic layer was washed with brine, dried over sodium sulphate and concentrated under reduced pressure to obtain crude material. This was further purified by column chromatography and compound was eluted in ethyl acetate in hexane to afford I-516 (0.04 g, 17.93%). MS (ES): m/z 448.1 [M−H]$^-$. LCMS purity: 99.09%, $^1$H NMR (400 MHz, DMSO-d$_6$, ppm) δ 1.93 (s, 3H), 3.37 (s, 3H), 7.26 (d, J=8.4 Hz, 1H), 7.41-7.51 (m, 3H), 7.94 (s, 1H), 11.08 (br s, 1H).

Example 247. Synthesis of 2-((3,5-dichlorophenyl)sulfonamido)-4-methylbenzoic Acid, I-321

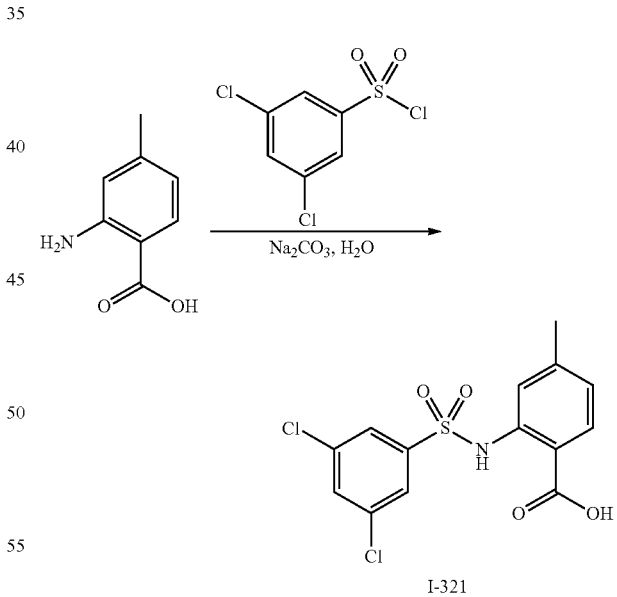

Synthesis of I-321

To a solution of 2-amino-4-methylbenzoic acid (200 mg, 1.323 mmol, 1 equiv) in H$_2$O (3 mL) was added Na$_2$CO$_3$ (280.4 mg, 2.646 mmol, 2 equiv) and 3,5-dichlorobenzene-1-sulfonyl chloride (324.8 mg, 1.323 mmol, 1 equiv). The resulting solution was stirred for 2 hr at 100° C. in an oil bath. The resulting solution was diluted with 100 mL of H₂O. The resulting solution was extracted with 3×50 mL of ethyl acetate, then concentrated under vacuum. The crude product was purified by Flash-Prep-HPLC with the following conditions (IntelFlash-1): Column, C18 silica gel; mobile phase, ACN/H₂O=15% increasing to ACN/H₂O=60% within 15 min; Detector, UV: 254 nm. This resulted in 95.5 mg (20%) of I-321 as a purple solid. (ES, m/z): [M−H]⁻ 358.6, ¹H-NMR (300 MHz, DMSO-d₆, ppm): δ7.76-7.73 (t, J=2.1 Hz, 1H), 7.72-7.70 (d, J=7.8 Hz, 1H), 7.64-7.63 (d, J=1.8 Hz, 2H), 7.13 (s, 1H), 6.71-6.54 (m, 1H), 2.17 (s, 3H).

Example 248. Synthesis of 2-((3,5-dichlorophenyl)sulfonamido)-4-morpholinobenzoic Acid, I-323

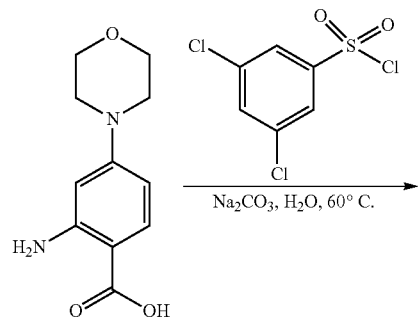

Synthesis of Compound I-323

To a mixture of 2-amino-4-(morpholin-4-yl)benzoic acid (100 mg, 0.45 mmol, 1 equiv) in MeOH (1 mL) was added Na₂CO₃ (120 mg, 1.13 mmol, 2.5 equiv), H₂O (0.2 ml) and 3,5-dichlorobenzene-1-sulfonyl chloride (111 mg, 0.45 mmol, 1 equiv). The resulting mixture was stirred overnight at 60° C. The resulting mixture was diluted with water (10 mL). The pH value of the solution was adjusted to 4 with 0.1M HCl. The combined mixture was filtered under reduced pressure. After filtration, the solids were collected. This resulted in I-323 (70.2 mg, 36%) as a white solid. (ES, m/z): [M+H]⁺ 429.0, ¹H-NMR (400 MHz, DMSO-d₆, ppm): δ 7.74 (m, 1H), 7.67-7.60 (m, 3H), 6.71 (s, 1H), 6.38 (m, 1H), 3.70-3.67 (t, J=4.4 Hz, 4H), 3.07-3.04 (t, J=6.8 Hz, 4H).

Example 248b. Synthesis of 2-((3,5-dichlorophenyl)sulfonamido)-4-(trifluoromethyl)benzoic Acid, I-324

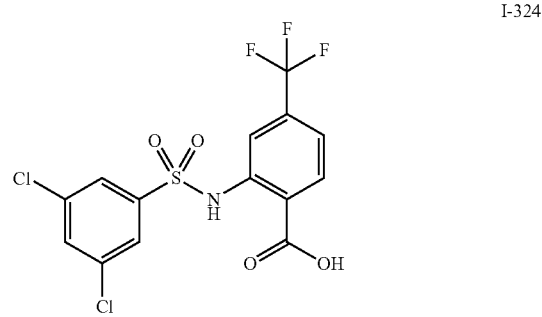 [SMILES: O=C(O)c1ccc(C(F)(F)F)cc1NS(=O)(=O)c1cc(Cl)cc(Cl)c1]

I-324 (37 mg, 9%) was isolated as a white solid according to the procedure described for 1-323, using 2-amino-4-(trifluoromethyl)benzoic acid instead of 2-amino-4-(morpholin-4-yl)benzoic acid. (ES, m/z): [M−H]⁻ 412.0, ¹H-NMR (400 MHz, DMSO-d₆, ppm): δ 8.03-8.00 (d, J=12 Hz, 1H), 7.80 (s, 1H), 7.65-7.60 (m, 3H), 7.10-7.08 (d, J=9.6 Hz, 1H).

Example 249. Synthesis of 3-((3,5-dichlorophenyl)sulfonamido)-[1,1'-biphenyl]-4-carboxylic Acid, I-208

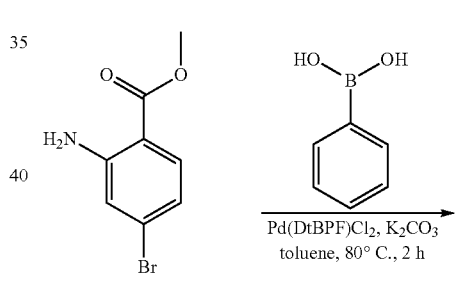

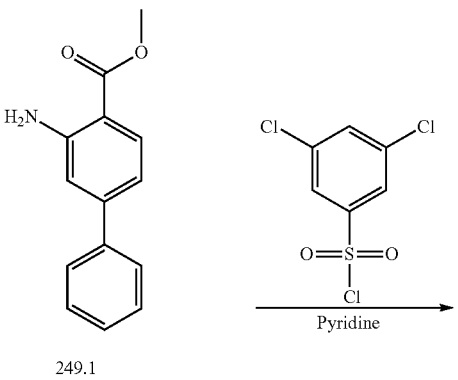

249.1

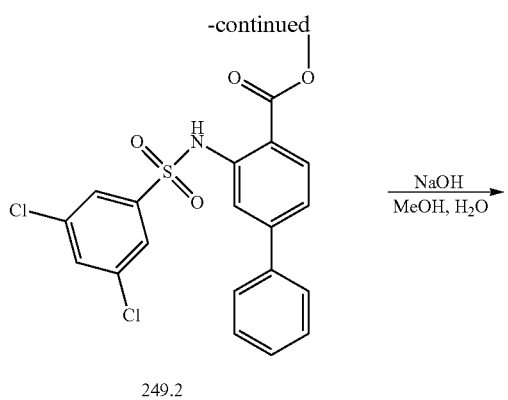

249.2

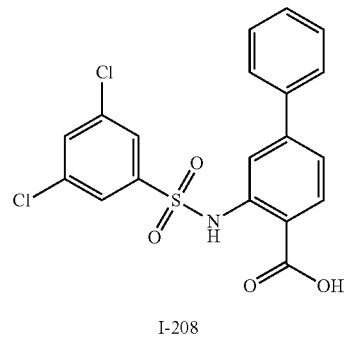

I-208

Synthesis of Compound 249.1

To a solution of methyl 2-amino-4-bromobenzoate (1000 mg, 4.35 mmol, 1 equiv) in toluene (10 mL) was added phenylboronic acid (1060.0 mg, 8.69 mmol, 2 equiv), Pd(DtBPF)Cl$_2$ (283.3 mg, 0.43 mmol, 0.1 equiv), and K$_2$CO$_3$ (1802.2 mg, 13.04 mmol, 3 equiv) under N$_2$ (g). The resulting solution was stirred for 12 hr at 90° C. in an oil bath. The reaction was then quenched by the addition of 20 mL of water. The resulting solution was extracted with 3×20 mL of ethyl acetate. The resulting mixture was washed with 10 mL of brine. The mixture was dried over anhydrous sodium sulfate and concentrated. The residue was applied onto a silica gel column with ethyl acetate/petroleum ether (1:5). This resulted in 800 mg (yield=78%) of 249.1 as a white solid.

Synthesis of Compound 249.2

To a solution of 249.2 (300 mg, 1.32 mmol, 1 equiv) in pyridine (10 mL) was added 3,5-dichlorobenzenesulfonyl chloride (324.1 mg, 1.32 mmol, 1 equiv). The resulting solution was stirred for 0.5 hr at room temperature. The resulting mixture was concentrated. The residue was applied onto a silica gel column with ethyl acetate/petroleum ether (1:1). This resulted in 280 mg (yield=34%) of 249.2 as a white solid.

Synthesis of I-208

To a solution of 249.2 (260 mg, 0.60 mmol, 1 equiv) in MeOH (4 mL) and H$_2$O (1 mL) was added NaOH (47.7 mg, 1.19 mmol, 2.00 equiv). The resulting solution was stirred for 12 hr at room temperature. The pH value of the solution was adjusted to 7 with HCl (1M). The resulting solution was extracted with 3×10 mL of ethyl acetate. The resulting mixture was washed with 10 mL of brine. The mixture was dried over anhydrous sodium sulfate and concentrated. The residue was applied onto a silica gel column with dichloromethane/methanol (5:1). This resulted in 46.1 mg (yield=18%) of I-208 as a white solid. (ES, m/z): [M−H]$^-$ =420.0, $^1$H-NMR (400 MHz, DMSO-d$_6$, ppm): δ 7.91-7.89 (d, 1H), 7.79-7.77 (s, 1H), 7.71 (s, 2H), 7.52-7.45 (m, 5H), 7.41-7.37 (m, 1H), 7.10-7.07 (m, 1H).

Example 250. Additional examples prepared according to Example 249

Table 6 and Table 7 below provide characterization data for compounds prepared according to the method of Example 249, varying the sulfonyl chloride, boronic acid, and/or bromide starting material(s). The final saponification step was conducted using LiOH, KOH, or NaOH in water with a co-solvent of methanol, THF, or a mixture of the two.

TABLE 6

Characterization data.

| Compound Number | Structure | Max peak | Ret time | MW | Mass spec + ion mode | Mass spec − ion mode |
|---|---|---|---|---|---|---|
| I-274 | ![structure] | 90.23 | 1.571 | 359.44 | 383 (+Na) | 358 |

TABLE 6-continued
Characterization data.
| Compound Number | Structure | Max peak | Ret time | MW | Mass spec + ion mode | Mass spec − ion mode |
|---|---|---|---|---|---|---|
| I-327 | 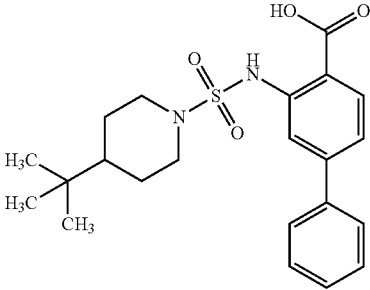 [SMILES: CC(C)(C)C1CCN(S(=O)(=O)Nc2cc(-c3ccccc3)ccc2C(=O)O)CC1] | 100 | 1.716 | 416.53 | 417.2 | 415.2 |
| I-328 | 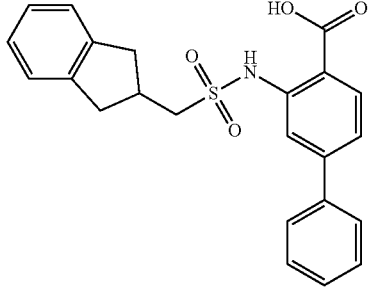 [SMILES: O=C(O)c1ccc(-c2ccccc2)cc1NS(=O)(=O)CC1Cc2ccccc2C1] | 96.63 | 1.604 | 407.48 | 430.2 (+Na) | 406.2 |
| I-329 | 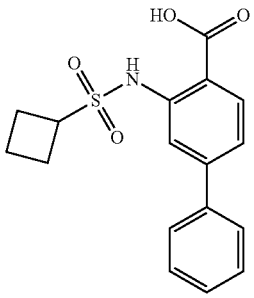 [SMILES: O=C(O)c1ccc(-c2ccccc2)cc1NS(=O)(=O)C1CCC1] | 100 | 1.448 | 331.39 | 332 | 330.2 |
| I-330 | 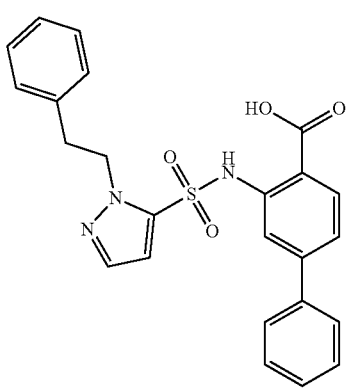 [SMILES: O=C(O)c1ccc(-c2ccccc2)cc1NS(=O)(=O)c1ccnn1CCc1ccccc1] | 100 | 1.602 | 447.51 | 448 | 446.2 |

TABLE 6-continued

Characterization data.

| Compound Number | Structure | Max peak | Ret time | MW | Mass spec + ion mode | Mass spec − ion mode |
|---|---|---|---|---|---|---|
| I-331 | 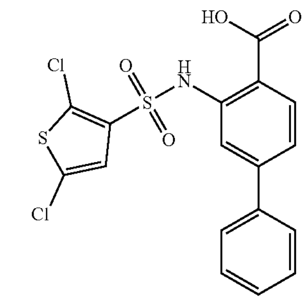 [SMILES: O=C(O)c1ccc(-c2ccccc2)cc1NS(=O)(=O)c1cc(Cl)sc1Cl] | 95.14 | 1.536 | 428.31 | 442 (+Na) | 426 |
| I-332 | 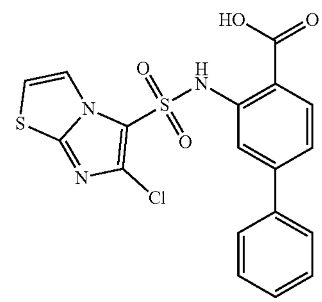 [SMILES: O=C(O)c1ccc(-c2ccccc2)cc1NS(=O)(=O)c1c(Cl)nc2sccn12] | 100 | 1.421 | 433.89 | 434 | 432 |
| I-333 | 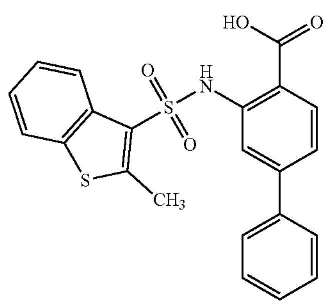 [SMILES: Cc1sc2ccccc2c1S(=O)(=O)Nc1cc(-c2ccccc2)ccc1C(=O)O] | 100 | 1.625 | 423.5 | 424 | 422 |
| I-334 | 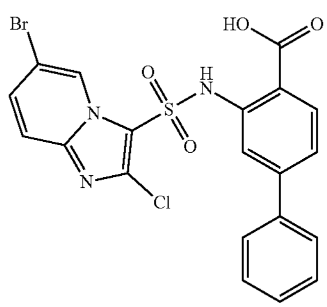 [SMILES: O=C(O)c1ccc(-c2ccccc2)cc1NS(=O)(=O)c1c(Cl)nc2ccc(Br)cn12] | 100 | 1.556 | 506.76 | 508 | 504 |
| I-335 | 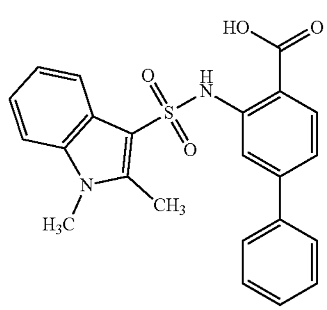 [SMILES: Cc1c(S(=O)(=O)Nc2cc(-c3ccccc3)ccc2C(=O)O)c2ccccc2n1C] | 97.16 | 1.517 | 420.48 | 444 (+Na) | 419.2 |

TABLE 6-continued

Characterization data.

| Compound Number | Structure | Max peak | Ret time | MW | Mass spec + ion mode | Mass spec − ion mode |
|---|---|---|---|---|---|---|
| I-336 | 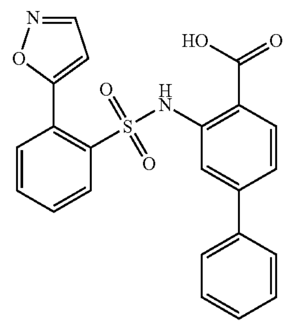 [SMILES: O=C(O)c1ccc(-c2ccccc2)cc1NS(=O)(=O)c1ccccc1-c1ccno1] | 92.09 | 1.414 | 420.44 | | 419 |
| I-337 | 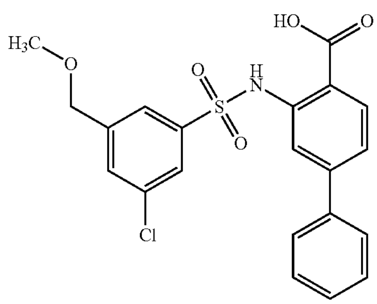 [SMILES: COCc1cc(Cl)cc(S(=O)(=O)Nc2cc(-c3ccccc3)ccc2C(=O)O)c1] | 100 | 1.588 | 431.89 | 432 | 430 |
| I-338 | 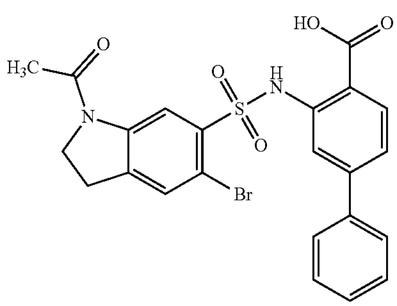 [SMILES: CC(=O)N1CCc2cc(Br)c(S(=O)(=O)Nc3cc(-c4ccccc4)ccc3C(=O)O)cc21] | 90.18 | 1.405 | 515.38 | | 514 |
| I-339 | 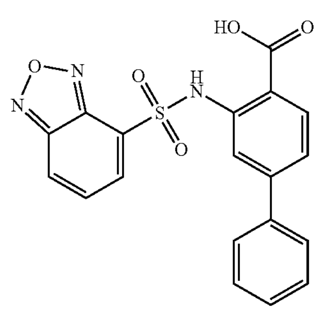 [SMILES: O=C(O)c1ccc(-c2ccccc2)cc1NS(=O)(=O)c1cccc2nonc12] | 100 | 1.469 | 395.39 | 418 (+Na) | 394 |

TABLE 6-continued

Characterization data.

| Compound Number | Structure | Max peak | Ret time | MW | Mass spec + ion mode | Mass spec − ion mode |
|---|---|---|---|---|---|---|
| I-340 | 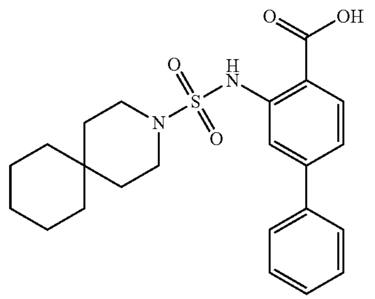 [SMILES: O=C(O)c1ccc(-c2ccccc2)cc1NS(=O)(=O)N1CCC2(CCCCC2)CC1] | 100 | 1.743 | 428.54 | 429.2 | 427 |
| I-356 | 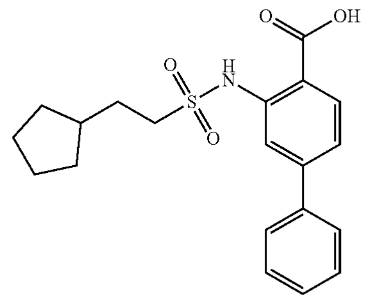 [SMILES: O=C(O)c1ccc(-c2ccccc2)cc1NS(=O)(=O)CCC1CCCC1] | 95.74 | 1.61 | 373.47 | | 372 |
| I-357 | 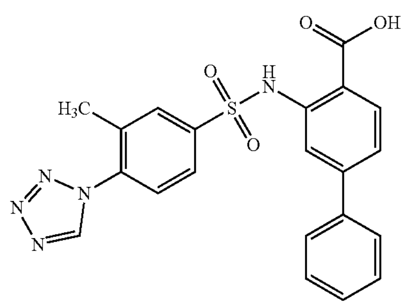 [SMILES: Cc1cc(S(=O)(=O)Nc2cc(-c3ccccc3)ccc2C(=O)O)ccc1-n1cnnn1] | 93.16 | 1.395 | 435.46 | 436 | 435 |
| I-358 | 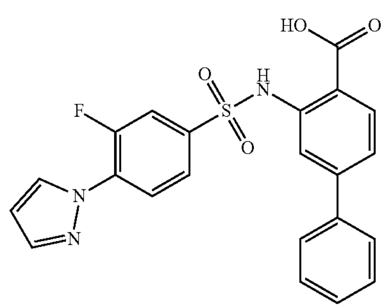 [SMILES: O=C(O)c1ccc(-c2ccccc2)cc1NS(=O)(=O)c1ccc(-n2cccn2)c(F)c1] | 99.2 | 1.581 | 437.44 | 438.2 | 436.0 |
| I-359 | 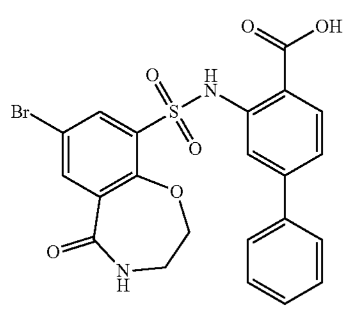 [SMILES: O=C(O)c1ccc(-c2ccccc2)cc1NS(=O)(=O)c1cc(Br)cc2c1OCCNC2=O] | 100 | 1.43 | 517.35 | | 512.0 |

TABLE 6-continued

Characterization data.

| Compound Number | Structure | Max peak | Ret time | MW | Mass spec + ion mode | Mass spec − ion mode |
|---|---|---|---|---|---|---|
| I-360 | 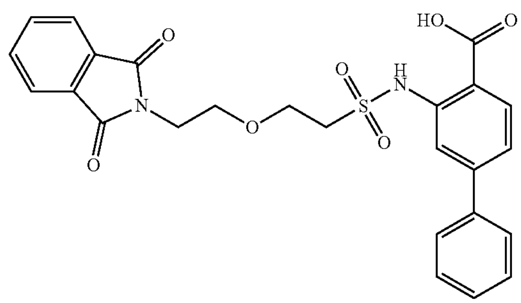 [SMILES: O=C(O)c1ccc(-c2ccccc2)cc1NS(=O)(=O)CCOCCN1C(=O)c2ccccc2C1=O] | 100 | 1.396 | 494.52 | 495.2 | 493.2 |
| I-372 | 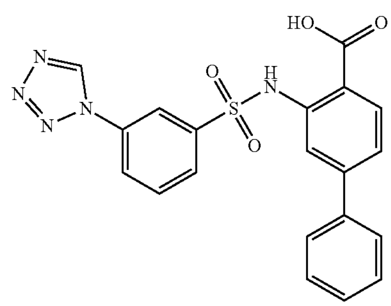 [SMILES: O=C(O)c1ccc(-c2ccccc2)cc1NS(=O)(=O)c1cccc(-n2cnnn2)c1] | 95.91 | 1.369 | 421.43 | 422 | 420 |
| I-445 | 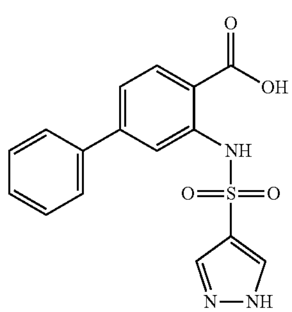 [SMILES: O=C(O)c1ccc(-c2ccccc2)cc1NS(=O)(=O)c1cn[nH]c1] | 100 | 1.261 | 343.36 | 344 | 342 |
| I-446 | 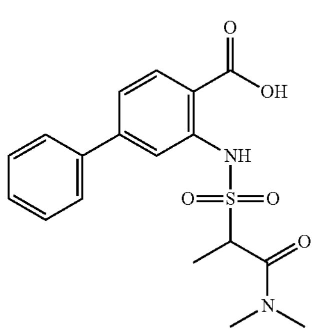 [SMILES: CC(C(=O)N(C)C)S(=O)(=O)Nc1cc(-c2ccccc2)ccc1C(=O)O] | 90.49 | 1.261 | 376.43 | 377.2 | 375.2 |

TABLE 6-continued

Characterization data.

| Compound Number | Structure | Max peak | Ret time | MW | Mass spec + ion mode | Mass spec − ion mode |
|---|---|---|---|---|---|---|
| I-447 | 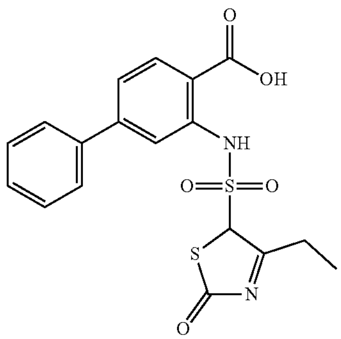 [SMILES: CCC1=NC(=O)SC1S(=O)(=O)Nc1cc(-c2ccccc2)ccc1C(=O)O] | 100 | 1.384 | 404.46 | 405 | 403 |
| I-448 | 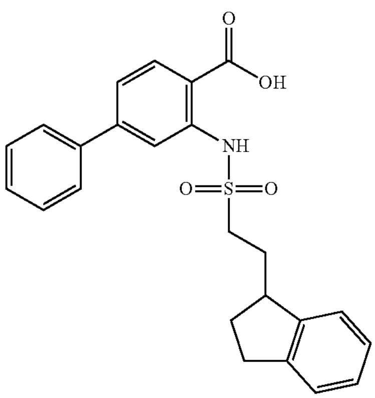 | 100 | 1.567 | 421.51 | 444.2 (+Na) | 420 |
| I-449 | 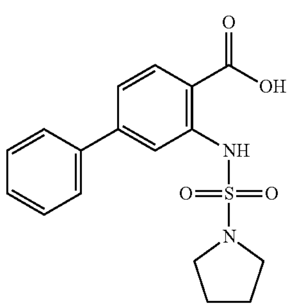 [SMILES: O=C(O)c1ccc(-c2ccccc2)cc1NS(=O)(=O)N1CCCC1] | 100 | 1.358 | 346.4 | 347.1 | 345.1 |
| I-450 | 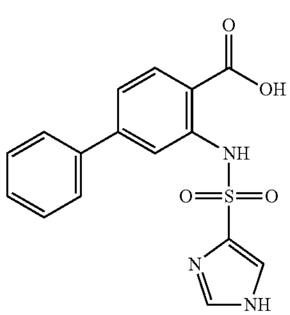 [SMILES: O=C(O)c1ccc(-c2ccccc2)cc1NS(=O)(=O)c1c[nH]cn1] | 100 | 1.221 | 343.36 | 344 | 342.2 |

TABLE 6-continued

Characterization data.

| Compound Number | Structure | Max peak | Ret time | MW | Mass spec + ion mode | Mass spec − ion mode |
|---|---|---|---|---|---|---|
| I-451 | 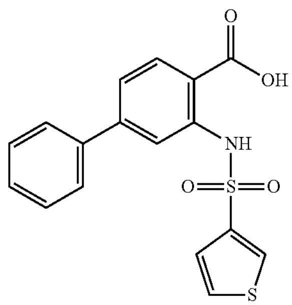 [SMILES: O=C(O)c1ccc(-c2ccccc2)cc1NS(=O)(=O)c1ccsc1] | 100 | 1.451 | 359.42 | 360 | 358 |
| I-452 | 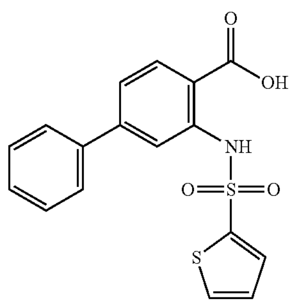 [SMILES: O=C(O)c1ccc(-c2ccccc2)cc1NS(=O)(=O)c1cccs1] | 100 | 1.462 | 359.42 | 382 (+Na) | 358 |
| I-453 | 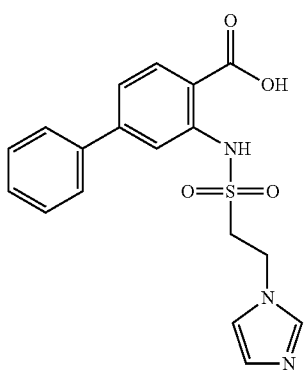 [SMILES: O=C(O)c1ccc(-c2ccccc2)cc1NS(=O)(=O)CCn1ccnc1] | 93.74 | 1.031 | 371.41 | 372.1 | 370 |
| I-454 | 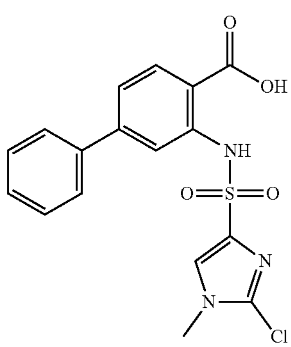 [SMILES: Cn1cc(S(=O)(=O)Nc2cc(-c3ccccc3)ccc2C(=O)O)nc1Cl] | 100 | 1.248 | 391.83 | 392 | 390 |

TABLE 6-continued

Characterization data.

| Compound Number | Structure | Max peak | Ret time | MW | Mass spec + ion mode | Mass spec − ion mode |
|---|---|---|---|---|---|---|
| I-455 | 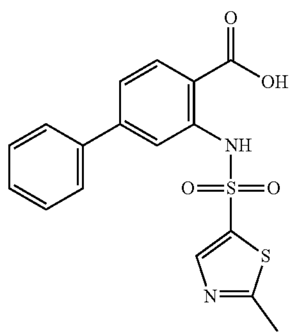 [SMILES: Cc1ncc(S(=O)(=O)Nc2cc(-c3ccccc3)ccc2C(=O)O)s1] | 100 | 1.361 | 374.43 | 375 | 373 |
| I-456 | 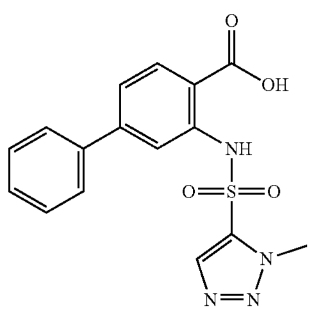 [SMILES: Cn1nncc1S(=O)(=O)Nc1cc(-c2ccccc2)ccc1C(=O)O] | 100 | 1.355 | 358.37 | 359 | 357 |
| I-457 | 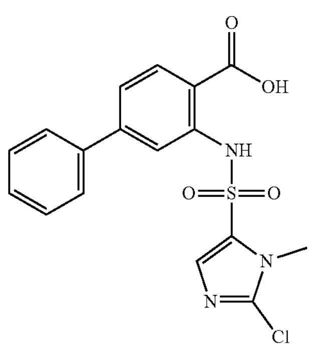 [SMILES: Cn1c(S(=O)(=O)Nc2cc(-c3ccccc3)ccc2C(=O)O)cnc1Cl] | 100 | 1.352 | 391.83 | 392 | 390 |
| I-458 | 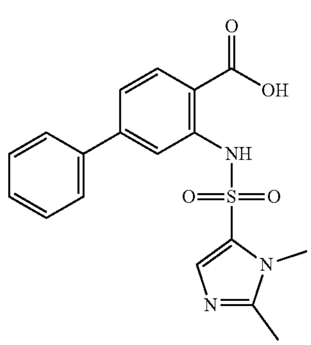 [SMILES: Cc1ncc(S(=O)(=O)Nc2cc(-c3ccccc3)ccc2C(=O)O)n1C] | 100 | 1.213 | 371.41 | 372 | 370 |

TABLE 6-continued

Characterization data.

| Compound Number | Structure | Max peak | Ret time | MW | Mass spec + ion mode | Mass spec − ion mode |
|---|---|---|---|---|---|---|
| I-459 | 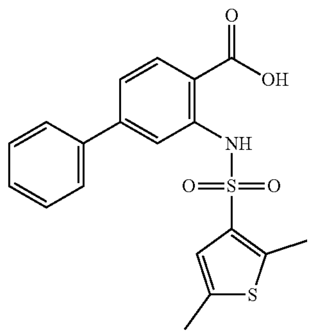 [SMILES: Cc1cc(S(=O)(=O)Nc2cc(-c3ccccc3)ccc2C(=O)O)c(C)s1] | 100 | 1.459 | 387.47 | 388 | 386.1 |
| I-460 | 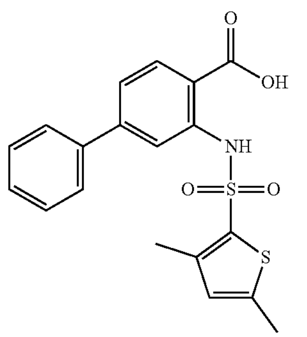 [SMILES: Cc1cc(C)c(S(=O)(=O)Nc2cc(-c3ccccc3)ccc2C(=O)O)s1] | 100 | 1.448 | 387.47 | 388 | 386.1 |
| I-461 | 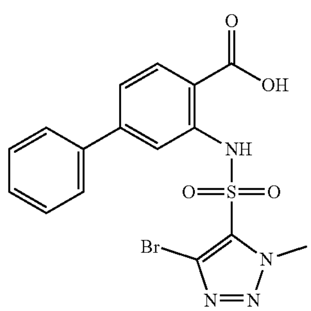 [SMILES: Cn1nnc(Br)c1S(=O)(=O)Nc1cc(-c2ccccc2)ccc1C(=O)O] | 100 | 1.415 | 437.27 | 437 | 434.8 |
| I-462 | 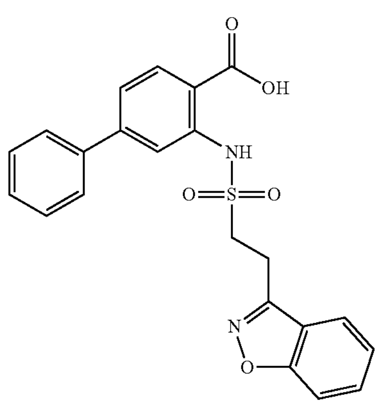 [SMILES: O=C(O)c1ccc(-c2ccccc2)cc1NS(=O)(=O)CCc1noc2ccccc12] | 100 | 1.477 | 422.45 | 445 (+Na) | 421 |

TABLE 6-continued
Characterization data.
| Compound Number | Structure | Max peak | Ret time | MW | Mass spec + ion mode | Mass spec − ion mode |
|---|---|---|---|---|---|---|
| I-463 | 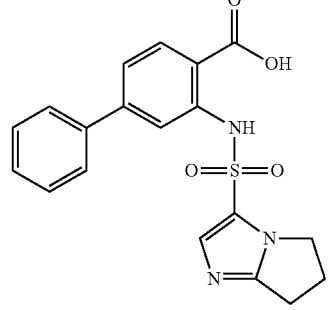 | 96.56 | 1.313 | 383.42 | 384 | 382 |
| I-464 | 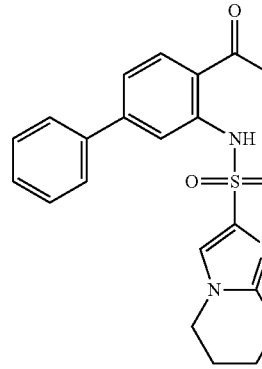 | 95.17 | 1.352 | 397.45 | 398 | 396.2 |
| I-465 | 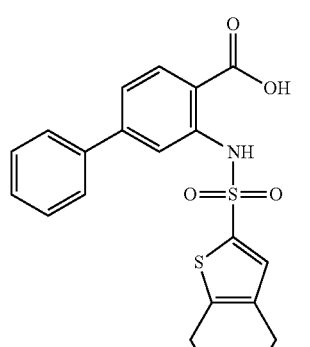 | 100 | 1.311 | 456.54 | 457 | 455.1 |
| I-466 | 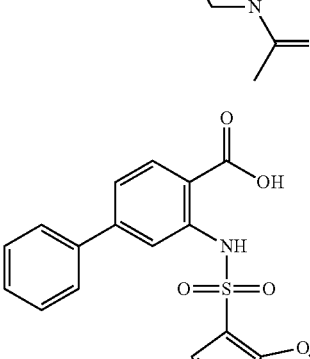 | 96.88 | 1.313 | 399.42 | 400 | 398 |

TABLE 6-continued

Characterization data.

| Compound Number | Structure | Max peak | Ret time | MW | Mass spec + ion mode | Mass spec − ion mode |
|---|---|---|---|---|---|---|
| I-467 | 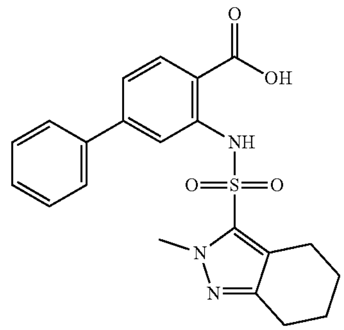 [SMILES: Cn1nc2c(c1S(=O)(=O)Nc1cc(-c3ccccc3)ccc1C(=O)O)CCCC2] | 100 | 1.504 | 411.47 | 412.2 | 410 |
| I-468 | 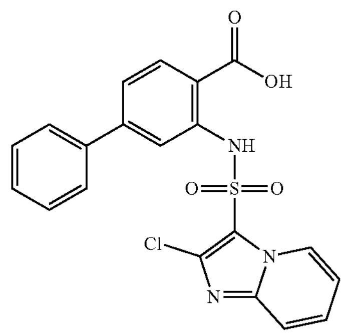 [SMILES: O=C(O)c1ccc(-c2ccccc2)cc1NS(=O)(=O)c1c(Cl)nc2ccccn12] | 96.81 | 1.458 | 427.86 | 428 | 426 |
| I-469 | 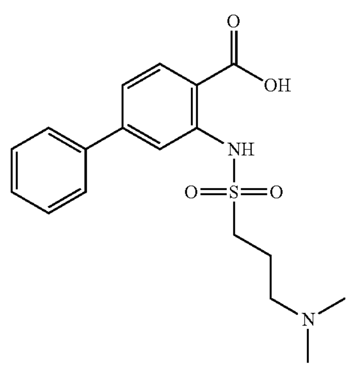 [SMILES: CN(C)CCCS(=O)(=O)Nc1cc(-c2ccccc2)ccc1C(=O)O] | 100 | 0.988 | 362.44 | 363.2 | 361.2 |
| I-470 | 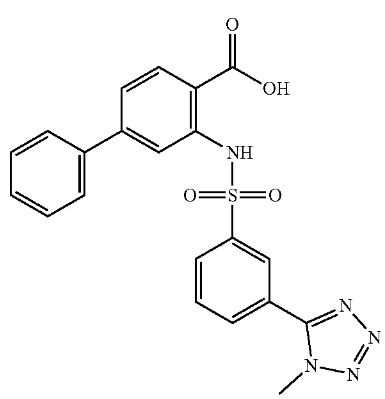 [SMILES: Cn1nnnc1-c1cccc(S(=O)(=O)Nc2cc(-c3ccccc3)ccc2C(=O)O)c1] | 96.95 | 1.384 | 435.46 | 436 | 434 |

TABLE 6-continued
Characterization data.
| Compound Number | Structure | Max peak | Ret time | MW | Mass spec + ion mode | Mass spec − ion mode |
|---|---|---|---|---|---|---|
| I-471 | 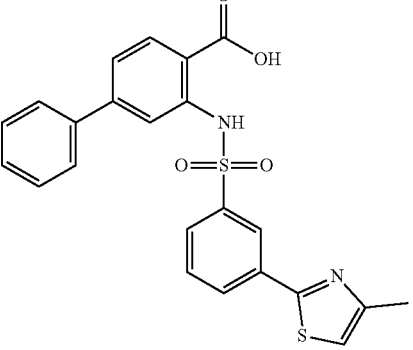 | 100 | 1.518 | 450.53 | 451 | 449 |
| I-472 | 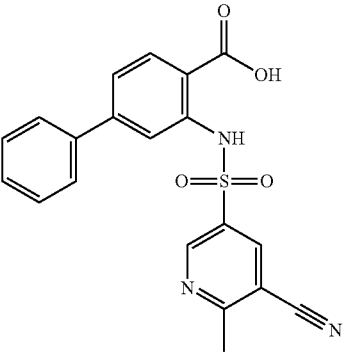 [SMILES: Cc1ncc(S(=O)(=O)Nc2cc(-c3ccccc3)ccc2C(=O)O)cc1C#N] | 100 | 1.446 | 393.42 | 394.2 | 392.2 |
| I-473 | 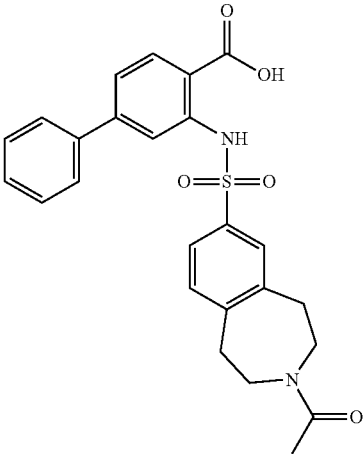 [SMILES: CC(=O)N1CCc2ccc(S(=O)(=O)Nc3cc(-c4ccccc4)ccc3C(=O)O)cc2CC1] | 98.73 | 1.394 | 464.53 | 465.2 | 463.2 |

TABLE 6-continued

Characterization data.

| Compound Number | Structure | Max peak | Ret time | MW | Mass spec + ion mode | Mass spec − ion mode |
|---|---|---|---|---|---|---|
| I-474 | 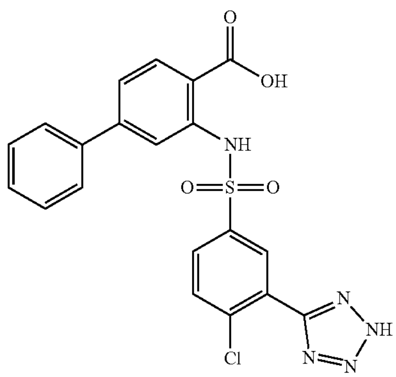 [SMILES: O=C(O)c1ccc(-c2ccccc2)cc1NS(=O)(=O)c1ccc(Cl)c(-c2nn[nH]n2)c1] | 100 | 1.386 | 455.87 | 456.2 | 454 |
| I-475 | 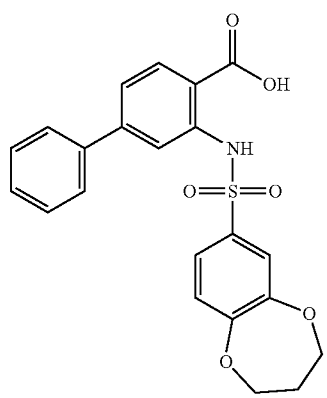 [SMILES: O=C(O)c1ccc(-c2ccccc2)cc1NS(=O)(=O)c1ccc2c(c1)OCCCO2] | 100 | 1.5 | 425.45 | 426 | 424 |
| I-476 | 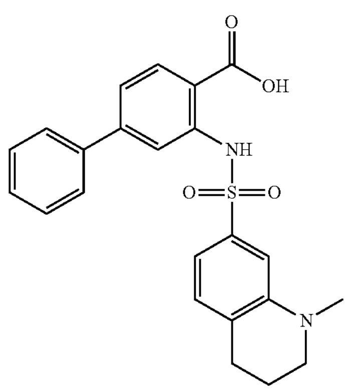 [SMILES: CN1CCCc2ccc(S(=O)(=O)Nc3cc(-c4ccccc4)ccc3C(=O)O)cc21] | 100 | 1.485 | 422.5 | 423.1 | 421.2 |
| I-477 | 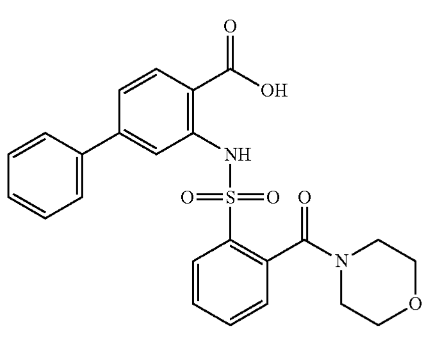 [SMILES: O=C(O)c1ccc(-c2ccccc2)cc1NS(=O)(=O)c1ccccc1C(=O)N1CCOCC1] | 100 | 1.365 | 466.51 | 467 | 465 |

TABLE 6-continued
Characterization data.
| Compound Number | Structure | Max peak | Ret time | MW | Mass spec + ion mode | Mass spec − ion mode |
|---|---|---|---|---|---|---|
| I-478 | 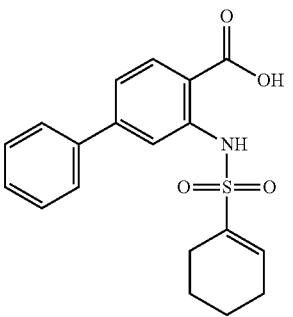 [SMILES: O=C(O)c1ccc(-c2ccccc2)cc1NS(=O)(=O)C1=CCCCC1] | 100 | 1.386 | 357.42 | 358 | 356 |
| I-479 | 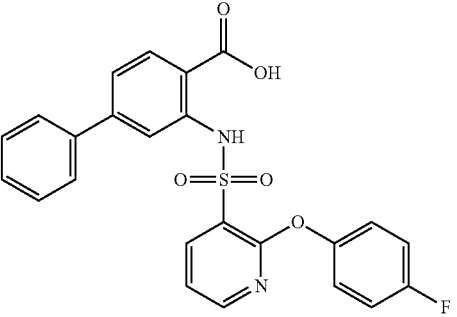 [SMILES: O=C(O)c1ccc(-c2ccccc2)cc1NS(=O)(=O)c1cccnc1Oc1ccc(F)cc1] | 95.94 | 1.545 | 464.47 | 465 | 463 |
| I-480 | 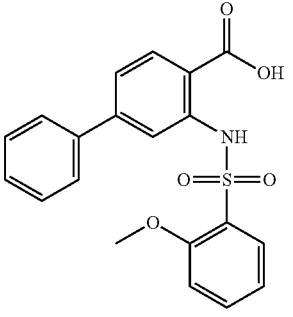 [SMILES: COc1ccccc1S(=O)(=O)Nc1cc(-c2ccccc2)ccc1C(=O)O] | 100 | 1.384 | 383.42 | 384 | 382 |
| I-481 | 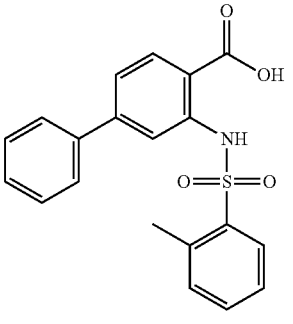 [SMILES: Cc1ccccc1S(=O)(=O)Nc1cc(-c2ccccc2)ccc1C(=O)O] | 100 | 1.424 | 367.42 | 390 (+Na) | 366 |

TABLE 6-continued

Characterization data.

| Compound Number | Structure | Max peak | Ret time | MW | Mass spec + ion mode | Mass spec − ion mode |
|---|---|---|---|---|---|---|
| I-482 | 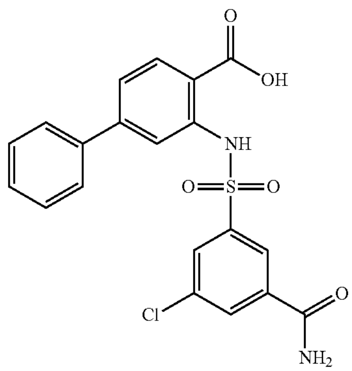 [SMILES: NC(=O)c1cc(Cl)cc(S(=O)(=O)Nc2cc(-c3ccccc3)ccc2C(=O)O)c1] | 100 | 1.449 | 430.86 | 449 (M + H + H₂O) | 430 |
| I-483 | 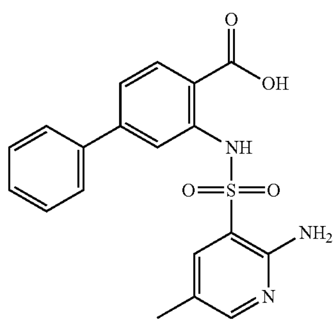 [SMILES: Cc1cnc(N)c(S(=O)(=O)Nc2cc(-c3ccccc3)ccc2C(=O)O)c1] | 96.69 | 1.34 | 383.42 | 384 | 382 |
| I-484 | 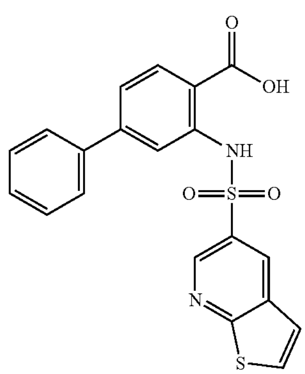 [SMILES: O=C(O)c1ccc(-c2ccccc2)cc1NS(=O)(=O)c1cnc2sccc2c1] | 96.17 | 1.458 | 410.47 | 411 | 409 |
| I-485 | 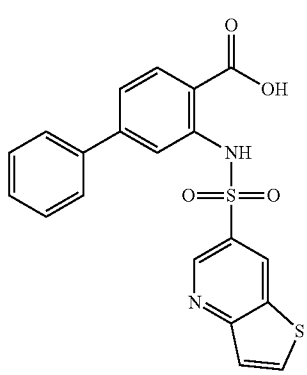 [SMILES: O=C(O)c1ccc(-c2ccccc2)cc1NS(=O)(=O)c1cnc2ccsc2c1] | 96.64 | 1.46 | 410.47 | 411 | 409 |

TABLE 6-continued

Characterization data.

| Compound Number | Structure | Max peak | Ret time | MW | Mass spec + ion mode | Mass spec − ion mode |
|---|---|---|---|---|---|---|
| I-486 | 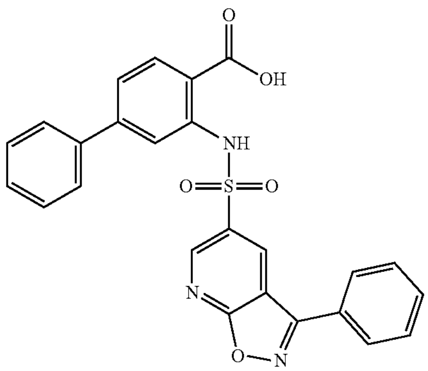 [SMILES: O=C(O)c1ccc(-c2ccccc2)cc1NS(=O)(=O)c1cnc2onc(-c3ccccc3)c2c1] | 100 | 1.614 | 471.48 | 472 | 470 |
| I-487 | 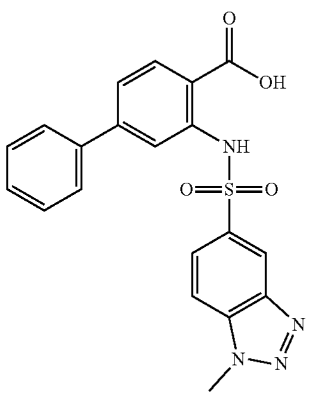 [SMILES: Cn1nnc2cc(S(=O)(=O)Nc3cc(-c4ccccc4)ccc3C(=O)O)ccc21] | 100 | 1.316 | 408.43 | 409 | 407.2 |
| I-488 | 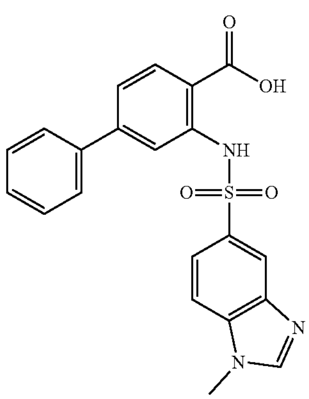 [SMILES: Cn1cnc2cc(S(=O)(=O)Nc3cc(-c4ccccc4)ccc3C(=O)O)ccc21] | 100 | 1.301 | 407.44 | 408.2 | 406 |
| I-489 | 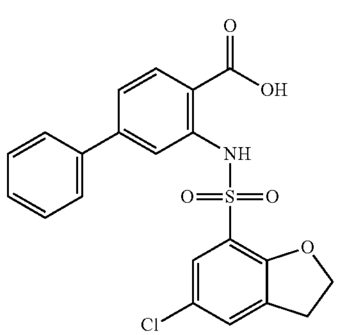 [SMILES: O=C(O)c1ccc(-c2ccccc2)cc1NS(=O)(=O)c1cc(Cl)cc2c1OCC2] | 100 | 1.575 | 429.87 | 430 | 428 |

TABLE 6-continued

Characterization data.

| Compound Number | Structure | Max peak | Ret time | MW | Mass spec + ion mode | Mass spec − ion mode |
|---|---|---|---|---|---|---|
| I-490 | 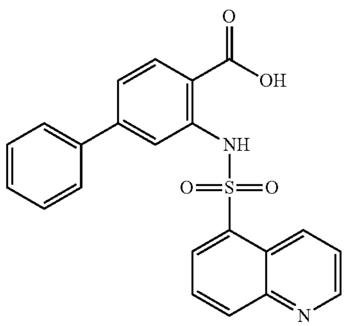 [SMILES: O=C(O)c1ccc(-c2ccccc2)cc1NS(=O)(=O)c1cccc2ncccc12] | 100 | 1.447 | 404.44 | 405 | 403 |
| I-491 | 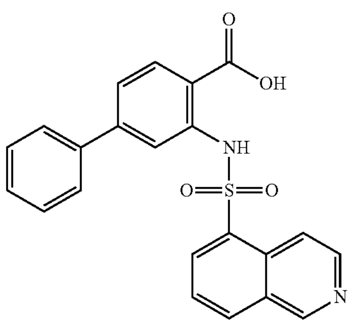 [SMILES: O=C(O)c1ccc(-c2ccccc2)cc1NS(=O)(=O)c1cccc2cnccc12] | 94.17 | 1.376 | 404.44 | 405 | 403 |
| I-492 | 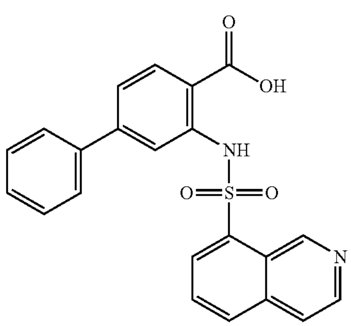 [SMILES: O=C(O)c1ccc(-c2ccccc2)cc1NS(=O)(=O)c1cccc2ccncc12] | 100 | 1.386 | 404.44 | 405 | 403 |
| I-493 | 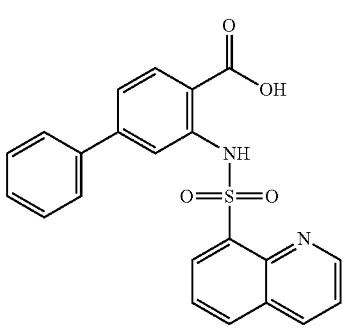 [SMILES: O=C(O)c1ccc(-c2ccccc2)cc1NS(=O)(=O)c1cccc2cccnc12] | 97.09 | 1.457 | 404.44 | 405 | 403 |

TABLE 6-continued

Characterization data.

| Compound Number | Structure | Max peak | Ret time | MW | Mass spec + ion mode | Mass spec − ion mode |
|---|---|---|---|---|---|---|
| I-494 | 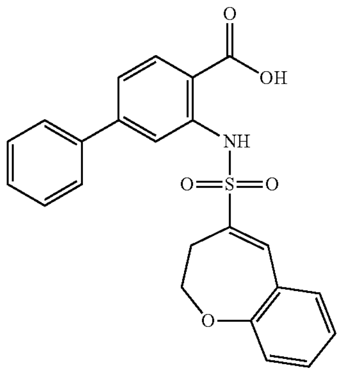 [SMILES: O=C(O)c1ccc(-c2ccccc2)cc1NS(=O)(=O)C1=Cc2ccccc2OCC1] | 91.64 | 1.455 | 421.47 | 422 | 420 |
| I-495 | 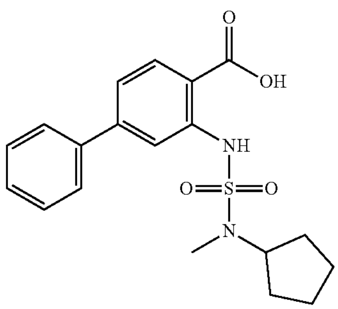 [SMILES: CN(C1CCCC1)S(=O)(=O)Nc1cc(-c2ccccc2)ccc1C(=O)O] | 98.24 | 1.566 | 374.45 | 375.2 | 373 |
| I-496 | 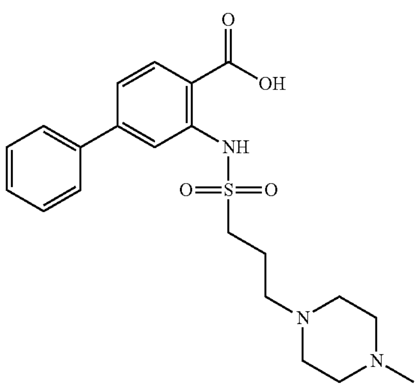 [SMILES: CN1CCN(CCCS(=O)(=O)Nc2cc(-c3ccccc3)ccc2C(=O)O)CC1] | 100 | 1.029 | 417.52 | 418.2 | 416.1 |
| I-497 | 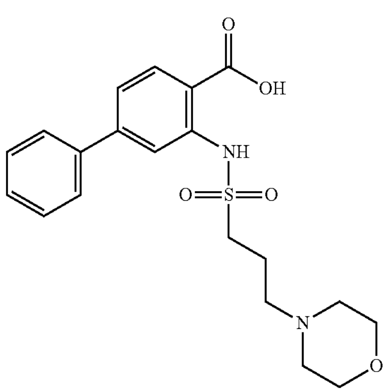 [SMILES: O=C(O)c1ccc(-c2ccccc2)cc1NS(=O)(=O)CCCN1CCOCC1] | 100 | 1.026 | 404.48 | 405.2 | 403 |

TABLE 6-continued

Characterization data.

| Compound Number | Structure | Max peak | Ret time | MW | Mass spec + ion mode | Mass spec − ion mode |
|---|---|---|---|---|---|---|
| I-498 | 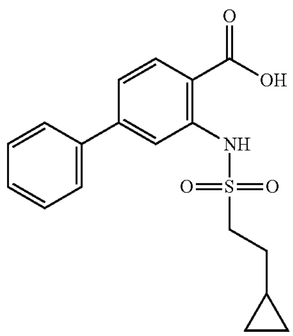 [SMILES: O=C(O)c1ccc(-c2ccccc2)cc1NS(=O)(=O)CCC1CC1] | 100 | 1.499 | 345.41 | 368 (+Na) | 344 |
| I-499 | 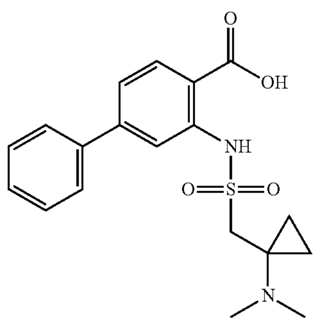 [SMILES: CN(C)C1(CS(=O)(=O)Nc2cc(-c3ccccc3)ccc2C(=O)O)CC1] | 100 | 1.125 | 374.45 | 375 | 373.2 |
| I-500 | 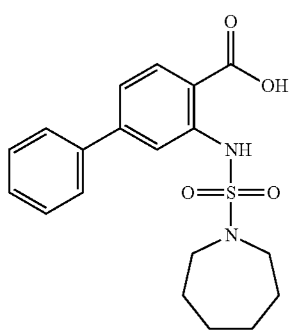 [SMILES: O=C(O)c1ccc(-c2ccccc2)cc1NS(=O)(=O)N1CCCCCC1] | 100 | 1.554 | 374.45 | 375 | 373 |
| I-501 | 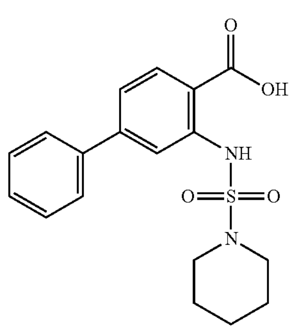 [SMILES: O=C(O)c1ccc(-c2ccccc2)cc1NS(=O)(=O)N1CCCCC1] | 97.19 | 1.528 | 360.43 | 383 (+Na) | 359.2 |

TABLE 6-continued

Characterization data.

| Compound Number | Structure | Max peak | Ret time | MW | Mass spec + ion mode | Mass spec − ion mode |
|---|---|---|---|---|---|---|
| I-502 | 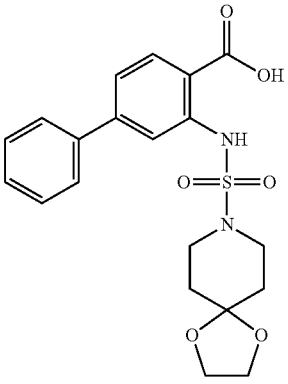 [SMILES: O=C(O)c1ccc(-c2ccccc2)cc1NS(=O)(=O)N1CCC2(CC1)OCCO2] | 91.82 | 1.391 | 418.46 | 419 | 417 |

TABLE 7

Characterization data for additional exemplary compounds.

| Compound No. | Name | MS (ES, m/z) | 1H-NMR |
|---|---|---|---|
| I-220 | 3-((3-chloro-5-(trifluoromethyl)phenyl)sulfonamido)-[1,1'-biphenyl]-4-carboxylic acid | [M − H]⁻ 453.9 | (400 MHz, DMSO-$d_6$, ppm): δ8.09-8.06 (d, J = 14 Hz, 2H), δ8.06-7.98 (s, 1H), δ7.92-7.90 (m, 1H), δ7.51-7.39 (m, 6H), δ7.38-6.95 (m, 2H). |
| I-226 | 3-((3-chloro-5-cyanophenyl)sulfonamido)-[1,1'-biphenyl]-4-carboxylic acid | [M − H]⁻ 411.0 | (300 MHz, DMSO-$d_6$, ppm): δ8.18 (s, 1H), 8.12 (s, 1H), 8.04 (s, 1H), 7.92-7.90 (d, J = 6 Hz, 1H), 7.50-7.45 (m, 5H), 7.41-7.38 (m, 1H), 7.11-7.09 (d, J = 6 Hz, 1H). |
| I-232 | 3-((3,5-dimethylphenyl)sulfonamido)-[1,1'-biphenyl]-4-carboxylic acid | [M − H]⁻ 380.1 | (400 MHz, DMSO-$d_6$, ppm): δ 7.94-7.92 (d, J = 8 Hz, 1H), 7.76 (s, 1H), 7.69-7.41 (m, 7H), 7.29-6.93 (m, 3H), 2.29 (s, 6H). |
| I-233 | 3-((3-chloro-5-fluorophenyl)sulfonamido)-[1,1'-biphenyl]-4-carboxylic acid | [M − H]⁻ 403.9 | (400 MHz, DMSO-$d_6$, ppm): δ 7.97-7.95 (d, J = 8 Hz, 1H), 7.78-7.76 (d, J = 8.8 Hz, 1H), 7.70 (s, 1H), 7.67-7.65 (d, J = 7.6 Hz, 1H), 7.62 (s, 1H), 7.60-7.58 (d, J = 7.2 Hz, 2H), 7.53-7.49 (t, J = 14.8 Hz, 2H), 7.46-7.42 (t, J = 14 Hz, 1H), 7.39-7.37 (d, J = 7.6 Hz, 1H), 7.21-6.96 (t, 1H). |
| I-249 | 3-((3,5-dichloro-2-hydroxyphenyl)sulfonamido)-[1,1'-biphenyl]-4-carboxylic acid | [M − H]⁻ 436.0 | (400 MHz, DMSO-$d_6$, ppm): δ7.94-7.92 (d, J = 8 Hz, 1H), 7.62-7.60 (m, 2H), 7.53-7.37 (m, 6H), 7.30-6.90 (m, 4H). |
| I-273 | 3-((3-chlorophenyl)sulfonamido)-[1,1'-biphenyl]-4-carboxylic acid | [M − H]⁻ 386.0 | (400 MHz, DMSO-$d_6$, ppm): δ13.97 (s, 1H), 7.95-7.93 (d, J = 8 Hz, 1H), 7.83 (s, 1H), 7.78-7.76 (d, J = 7.6 Hz, 1H), 7.69-7.41 (m, 7H), 7.32-7.30 (d, J = 8 Hz, 1H), 7.21-6.96 (m, 2H). |

TABLE 7-continued

Characterization data for additional exemplary compounds.

| Compound No. | Name | MS (ES, m/z) | 1H-NMR |
|---|---|---|---|
| I-275 | 2-((3,5-dichlorophenyl)sulfonamido)-4-(thiophen-2-yl)benzoic acid | [M + H]⁺ 428.0 | (300 MHz, DMSO-d₆, ppm): δ 11.31 (s, 1H), 7.99 (s, 1H), 7.94-7.92 (d, J = 6.3 Hz, 1H), 7.87 (s, 2H), 7.71 (s, 1H), 7.62-7.59 (m, 2H), 7.53-7.51 (d, J = 6.3 Hz, 1H), 7.21 (s, 1H). |
| I-278 | 4-((3,5-dichlorophenyl)sulfonamido)-[1,1'-biphenyl]-3-carboxylic acid | [M − H]⁻ 419.9 | (300 MHz, DMSO-d₆, ppm) δ 8.14 (s, 1H), 7.90-7.89 (t, J = 1.8 Hz, 1H), 7.78-7.74 (m, 3H), 7.62-7.61 (d, J = 1.2 Hz, 2H), 7.48-7.41 (m, 3H), 7.35-7.31 (m, 1H), 7.25-6.91 (m, 2H). |
| I-284 | 3-((3,4-dichlorophenyl)sulfonamido)-[1,1'-biphenyl]-4-carboxylic acid | [M − H]⁻ 419.9 | (300 MHz, DMSO-d₆, ppm): δ8.02 (s, 1H), 7.96-7.94 (d, J = 8.1 Hz, 1H), 7.84-δ7.74 (m, 2H), 7.64 (s, 1H), 7.59-7.36 (m, 5H), 7.25 (s, 1H), 7.25-7.19 (m, 1H). |
| I-288 | 3-((2,5-dichlorophenyl)sulfonamido)-[1,1'-biphenyl]-4-carboxylic acid | [M − H]⁻ 420.0 | (300 MHz, CD₃OD, ppm): δ8.31 (s, 1H), 8.11-8.08 (d, 8.1 Hz, 1H), 7.73 (s, 1H), 7.64-7.61 (d, J = 8.7 Hz, 1H), 7.57 (s, 1H), 7.54-7.31 (m, 5H), 7.34-7.31 (m, 1H). |
| I-292 | 3-((3-(trifluoromethyl)phenyl)sulfonamido)-[1,1'-biphenyl]-4-carboxylic acid | [M − H]⁻ 420.0 | (400 MHz, DMSO-d₆, ppm): δ8.13-8.11 (d, J = 8 Hz, 1H), 8.08 (s, 1H), 8.01-7.99 (d, J = 8 Hz, 1H), 7.99-7.92 (d, 1H), 7.80-7.78 (t, J = 8 Hz, 1H), 7.64 (s, 1H), 7.56-7.51 (m, 2H), 7.51-7.46 (m, 2H), 7.46-7.40 (m, 1H), 7.34-7.32 (d, 7.2 Hz, 1H), 7.25-6.93 (m, 1H). |
| I-293 | 4-(benzo[b]thiophen-2-yl)-2-((3,5-dichlorophenyl)sulfonamido)benzoic acid | [M − H]⁻ 476.0 | (400 MHz, DMSO-d₆, ppm): δ 8.06-8.04 (d, J = 8 Hz, 1H), 7.98 (s, 1H), 7.92-7.83 (m, 2H), 7.80-7.79 (m, 3H), 7.71 (s, 1H), 7.60-7.58 (d, J = 8.4 Hz, 1H), 7.39-7.37 (m, 2H). |
| I-299 | 3-(((4-(trifluoromethyl)phenyl)methyl)sulfonamido)-[1,1'-biphenyl]-4-carboxylic acid | [M − H]⁻ 434.0 | (400 MHz, DMSO-d₆, ppm): δ 13.90 (s, 1H), 10.92 (s, 1H), 8.06-8.04 (d, J = 3.6 Hz, 1H), 7.68-7.59 (m, 5H), 7.53-7.42 (m, 6H), 4.95 (s, 2H). |
| I-305 | 3-(((3,5-dichlorophenyl)methyl)sulfonamido)-[1,1'-biphenyl]-4-carboxylic acid | [M − H]⁻ 434.0 | (400 MHz, DMSO-d₆, ppm): δ 11.66 (s, 1H), 8.07-8.05 (d, J = 8 Hz, 1H), 7.66-7.61 (m, 3H), 7.54-7.40 (m, 5H), 7.29-7.28 (d, J = 2 Hz, 2H), 4.84 (s, 2H). |
| I-306 | 3-((3-bromo-5-(trifluoromethyl)phenyl)sulfonamido)-[1,1'-biphenyl]-4-carboxylic acid | [M + H]⁺ 500.0 | (400 MHz, DMSO-d₆, ppm): δ 8.37-8.24 (m, 2H), 8.05 (s, 1H), 7.96-7.94 (d, J = 8.4 Hz, 1H), 7.61-7.37 (m, 7H). |
| I-310 | 3-((m-tolylmethyl)sulfonamido)-[1,1'-biphenyl]-4-carboxylic acid | [M − H]⁻ 380.1 | (400 MHz, DMSO-d₆, ppm), δ8.04-8.02 (d, J = 8 Hz, 1H), 7.65 (s, 1H), 7.61-7.59 (m, 2H), 7.53-7.49 (m, 2H), 7.45-7.42 (m, 1H), 7.35-7.33 (d, J = 8 Hz, 1H), 7.17-7.13 (t, J = 7.6 Hz, 1H), 7.08-7.04 (t, J = 8.4 Hz, 2H), 6.98 (s, 1H), 4.59 (s, 2H), 2.19 (s, 3H). |

TABLE 7-continued

Characterization data for additional exemplary compounds.

| Compound No. | Name | MS (ES, m/z) | 1H-NMR |
|---|---|---|---|
| I-311 | 3-((4,5-dichlorothiophene)-2-sulfonamido)-[1,1'-biphenyl]-4-carboxylic acid | [M − H]⁻ 425.9 | (300 MHz, CD₃OD, ppm): δ8.12-8.10 (d, J = 8.4 Hz, 1H), 7.92 (s, 1H), 7.68-7.65 (m, 2H), 7.51-7.41 (m, 5H). |
| I-319 | 3-((4-bromothiophene)-2-sulfonamido)-[1,1'-biphenyl]-4-carboxylic acid | [M + H]⁺ 437.9 | (300 MHz, DMSO-d₆, ppm): δ7.92-7.90 (d, J = 8.1 Hz, 1H), 7.78-7.77 (d, J = 1.5 Hz, 1H), 7.64-7.63 (d, J = 1.5 Hz, 1H), 7.54-7.47 (m, 4H), 7.44-7.36 (m, 2H), 7.11-7.09 (d, J = 6.3 Hz, 1H). |
| I-344 | 2-((3-chloro-5-(trifluoromethyl)phenyl)sulfonamido)-4-cyclopropylbenzoic acid | [M − H]⁻ 418.0 | (400 MHz, DMSO-d₆, ppm): δ 11.16 (s, 1H), 8.26 (s, 1H), 8.14 (s, 1H), 7.96 (s, 1H), 7.76-7.74 (d, J = 8.4 Hz, 1H), 7.08 (s, 1H), 6.91-6.89 (d, J 6.8 Hz, 1H), 2.00-1.95 (m, 1H), 1.07-1.96 (m, 2H), 0.69-0.62 (m, 2H). |
| I-350 | 3-((5-chloro-2-oxo-1,2-dihydropyridine-3-sulfonamido)-[1,1'-biphenyl]-4-carboxylic acid | [M − H]⁻ 403.0 | (300 MHz, DMSO-d₆, ppm): δ12.56 (s, 1H), δ8.17 (s, 1H), δ7.97-7.82 (m, 2H), δ7.59 (m, 1H), δ7.57-7.35 (m, 6H), δ7.30-7.10 (m, 1H), δ7.11-6.83 (m, 1H). |
| I-353 | 3-((4-(trifluoromethyl)phenyl)sulfonamido)-[1,1'-biphenyl]-4-carboxylic acid | [M − H]⁻ 420.1 | (400 MHz, DMSO-d₆, ppm): δ 11.35 (s, 1H), 8.07-8.03 (m, 2H), 7.99-7.97 (m, 3H), 7.72 (s, 1H), 7.61-7.60 (m, 2H), 7.54-7.44 (m, 4H). |
| I-520 | 3-[[5-(1-benzothiophen-2-yl)-4-fluoro-2-methoxyphenyl]sulfamoyl]-4-hydroxybenzoic acid | [M + H]⁺ 474 | ¹H NMR(400 MHz, DMSO-d₆): δ 8.15 (d, J = 2.4 Hz, 1H), 8.01-7.94 (m, 1H), 7.93-7.86 (m, 1H), 7.74-7.64 (m, 2H), 7.60 (s, 1H), 7.38 (pd, J = 7.2, 1.4 Hz, 2H), 7.03 (d. J = 13.0 Hz, 1H), 6.59 (d, J = 8.8 Hz, 1H), 3.79 (s, 3H). |
| I-522 | 2-((3,5-dichlorophenyl)sulfonamido)benzoic acid | [M + H]⁺ 345.9 | 1H-NMR: (400 MHz, DMSO-d₆, ppm): δ7.85-7.82(m, 1H), 7.76-7.75 (m, 1H), 7.63 (m, 2H), 7.29-7.22 (m, 2H), 6.84-6.76 (m, 1H). |
| I-523 | 4-(ethylsulfonamido)-N-(4-fluoro-[1,1'-biphenyl]-3-yl)-2-methoxybenzenesulfonamide | [M + H]⁺ 465.0 | |
| I-525 | methyl 2-((3,5-dichloro-2-hydroxyphenyl)sulfonamido)isonicotinate | [M + H]⁺ 377.0 | 1H-NMR: (300 MHz, DMSO, ppm): δ8.25-8.23 (d, J = 5.7 Hz, 1H), δ7.82-7.81 (d, J = 2.7 Hz, 1H), δ7.74-7.73 (d, J = 2.4 Hz, 1H), δ7.64 (s, 1H), δ7.34-7.32 (d, J = 5.1 Hz, 1H), δ3.89 (s, 3H). |
| I-527 | 2-((3,5-dichlorophenyl)sulfonamido)-6-methylnicotinic acid | [M − H]⁻ 358.9 | 1H-NMR: (400 MHz, DMSO-d₆, ppm): δ7.96-7.93 (m, 3H), 7.73 (s, 1H), δ6.67-6.65 (d, J = 7.6 Hz, 1H), δ2.28 (s, 3H). |
| I-528 | 2-hydroxy-N-(4-methoxy-[1,1'-biphenyl]-3-yl)benzenesulfonamide | [M − H]⁻ 354 | 1H-NMR: (400 MHz, DMSO, ppm): δ3.73 (s, 3H), δ6.85-6.89 (m, 1H), δ6.98-7.04 (m, 2H), δ7.29-7.33 (m, 2H), δ7.39-7.46 (m, 5H), δ7.50-7.51 (m, 1H), δ7.63-7.66 (m, 1H), δ8.35-8.58 (brs, 1H), δ10.85-11.05 (brs, 1H) |

TABLE 7-continued

Characterization data for additional exemplary compounds.

| Compound No. | Name | MS (ES, m/z) | 1H-NMR |
|---|---|---|---|
| I-529 | 3-(N-(4,6-difluoro-[1,1'-biphenyl]-3-yl)sulfamoyl)-4-methoxybenzoic acid | [M − H]⁻ 418.0 | 1H-NMR: (300 MHz, DMSO, ppm): δ3.92 (s, 3H), δ 7.29-7.50 (m, 8H), δ8.14-8.17 (m, 1H), δ8.20-8.21 (d, J = 2.1 Hz, 1H), δ10.10 (brs, 1H), δ13.05 (brs, 1H) |
| I-530 | methyl 2-(3-((3,5-dichlorophenyl)sulfonamido)-[1,1'-biphenyl]-4-yl)acetate | [M + H]⁻ 447.9 | 1H-NMR: (DMSO, 400 MHz, ppm): δ10.04 (s, 1H), δ8.03 (s, 1H), δ7.65 (s, 2H), δ7.54-7.51 (m, 1H), δ7.48-7.38 (m, 6H), δ6.99 (s, 1H), δ3.75 (s, 2H), δ3.60 (s, 3H). |
| I-531 | 2-chloro-5-(quinoline-5-carboxamido)benzoic acid | [M + H]⁺ 327.2 | 1H-NMR: (300 MHz, DMSO, ppm): δ7.61-7.71 (m, 2H), δ7.92-8.02 (m, 3H), δ8.25-8.28 (d, J = 8.4 Hz, 1H), δ8.40 (s, 1H), δ8.71-8.74 (d, J = 8.7 Hz, 1H), δ9.05-9.06 (d, J = 2.7 Hz, 1H), δ10.96 (s, 1H), δ13.48 (brs, 1H) |
| I-533 | 2-((3,5-dichlorophenyl)sulfonamido)-3-methylbenzoic acid | [M − H]⁻ 358.0 | 1-NMR: (400 MHz, DMSO-d₆, ppm): δ7.91 (s, 1H), δ7.60-7.58 (d, J = 7.2 Hz, 1H), δ7.42-7.40 (m, 3H), δ7.22-7.16 (t, J = 8 Hz, 2H), δ2.19 (s, 3H). |
| I-535 | 2-chloro-5-(5-fluoro-1H-benzo[d]imidazole-7-carboxamido)benzoic acid | [M + H]⁺ 334.2 | 1H-NMR: (400 MHz, DMSO, ppm): δ7.53-7.56 (d, J = 8.8 Hz, 1H), δ7.72-7.75 (d, J = 8 4 Hz, 2H), δ7.92-7.95 (m, 1H), δ8.16 (brs, 1H), δ8.64 (brs, 1H), δ10.63 (brs, 1H) |

Example 251. Additional Examples Prepared According to Example 249

Table 8 below provides characterization data for compounds prepared from commercially available aminoheteroaryls and sulfonyl chlorides according to the second and third steps of Example 249. The saponification step was conducted using LiOH, KOH, or NaOH in water with a co-solvent of methanol, THF, or a mixture of the two.

TABLE 8

Characterization data for additional exemplary compounds.

| Compound No. | Name | MS (ES, m/z) | 1H-NMR |
|---|---|---|---|
| I-316 | 3-((3,5-dichlorophenyl)sulfonamido)furan-2-carboxylic acid | [M − H]⁻ 333.9 | (400 MHz, DMSO-d₆, ppm) δ 8.16-7.94 (m, 3H), 7.78-7.71(m, 1H), 6.72 (s, 1H). |
| I-322 | 5-(4-chlorophenyl)-3-((3,5-dichlorophenyl)sulfonamido)thiophene-2-carboxylic acid | [M + H]⁺ 461.9 | (400 MHz, DMSO-d₆, ppm): δ10.60 (m, 1H), δ7.98 (s, 3H), 7.81-7.73 (m, 2H), 7.58-7.49 (m, 3H), 7.27-6.92 (m, 1H). |
| I-341 | 2-((3,5-dichlorophenyl)sulfonamido)-5,6-dihydro-4H-cyclopenta[b]thiophene-3-carboxylic acid | [M − H]⁻ 389.9 | (400 MHz, DMSO-d₆, ppm) δ7.86 (s, 1H), 7.68 (s, 2H), 2.73-2.67 (m, 4H), 2.64-2.17 (m, 2H). |
| I-361 | 2-((3,5-dichlorophenyl)sulfonamido)benzo[b]thiophene-3-carboxylic acid | [M − H]⁻ 399.7 | (300 MHz, DMSO-d₆, ppm): δ8.28-8.26 (d, J = 6 Hz, 1H), δ7.85 (s, 1H), δ7.75 (s, 2H), δ7.72-7.69 (d, J = 7.8 Hz, 1H), 7.28-7.25 (t, J = 7.2 Hz, 1H), 7.18-7.13 (t, J = 7.8 Hz, 1H). |

TABLE 8-continued

Characterization data for additional exemplary compounds.

| Compound No. | Name | MS (ES, m/z) | 1H-NMR |
|---|---|---|---|
| I-532 | N-(2-(1H-pyrazol-1-yl)phenyl)-3,5-dichloro-2-hydroxybenzenesulfonamide | [M − H]⁻ 400.98 | |
| I-524 | 3-fluoro-N-(4-fluoro-[1,1'-biphenyl]-3-yl)-4-((1-methylethyl)sulfonamido)benzenesulfonamide | [M − H]⁻ 466.1 | |
| I-526 | 2-(3-(N-(4-fluoro-[1,1'-biphenyl]-3-yl)sulfamoyl)-2,6-dimethylphenoxy)acetic acid | [M − H]⁻ 428 | |

Example 252. Synthesis of N-(5-(benzo[b]thiophen-2-yl)-2-fluorophenyl)-5-chloro-2-oxo-1,2-dihydropyridine-3-sulfonamide, I-367

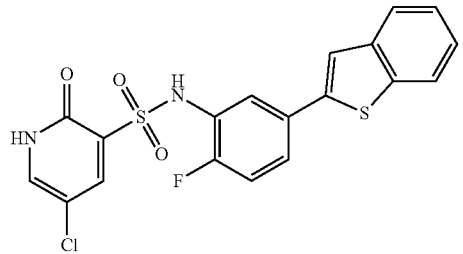

I-367

I-367 was prepared from 5-bromo-2-fluoroaniline, (1-benzothiophen-2-yl)boronic acid, and 5-chloro-2-oxo-1,2-dihydropyridine-3-sulfonyl chloride according to the procedures of the first and second steps of Example 249. I-367 was purified by prep-TLC (DCM:MeOH=20:1) to afford a pink solid (24 mg, 11% over two steps). (ES, m/z): [M−H]⁻ 432.8, ¹H-NMR (400 MHz, DMSO-d₆, ppm): δ 8.06 (s, 1H), 8.00-7.93 (m, 2H), 7.90-7.82 (m, 1H), 7.76 (s, 1H), 7.65-7.64 (d, J=1.6 Hz, 1H), 7.59-7.58 (t, J=3.6 Hz, 1H), 7.44-7.27 (m, 3H).

Example 253. Synthesis of 5-((3-chloro-5-(trifluoromethyl)phenyl)sulfonamido)-2-methyl-[1,1'-biphenyl]-4-carboxylic Acid, I-364

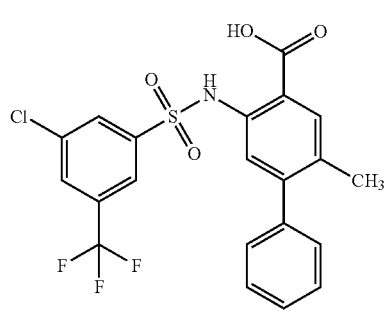

I-364

I-364 was prepared from 2-amino-4-bromo-5-methylbenzoic acid, phenylboronic acid, and 3-chloro-5-(trifluoromethyl)benzene-1-sulfonyl chloride according to the procedures of the first and second steps of Example 249. Compound I-364 was purified by Flash-Prep-HPLC with the following conditions (IntelFlash-1): Column, silica gel; mobile phase, CH₃CN/H₂O=1:1 increasing to CH₃CN/H₂O=1:2 within 30 min. This resulted in 40.5 mg (7% over two steps) of I-364 as a solid. (ES, m/z): [M−H]⁻ 468.2, ¹H-NMR (400 MHz, DMSO-d₆, ppm): δ 8.20 (s, 1H), 8.06 (s, 1H), 7.90 (s, 1H), 7.81 (s, 1H), 7.48-7.40 (m, 3H), 7.24-7.21 (m, 3H), 7.09-6.96 (m, 1H), 2.47 (s, 3H).

Example 254. Synthesis of 3-((3,5-dichlorophenyl)sulfonamido)-5-phenylpicolinic Acid, I-243

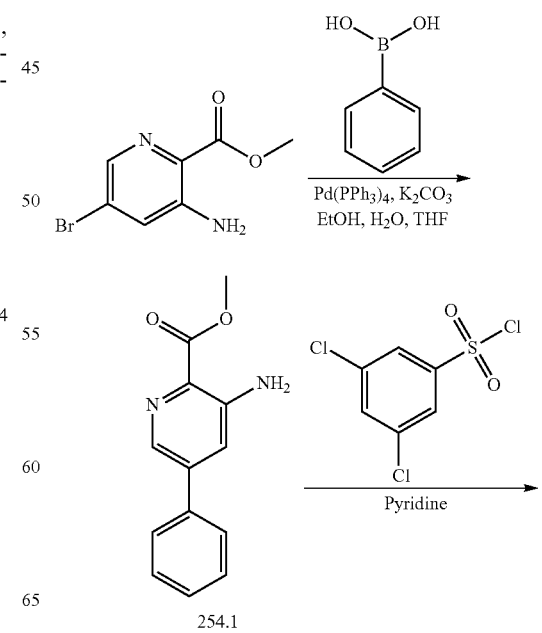

254.1

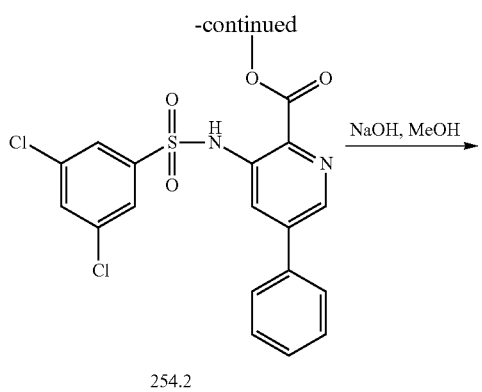

254.2

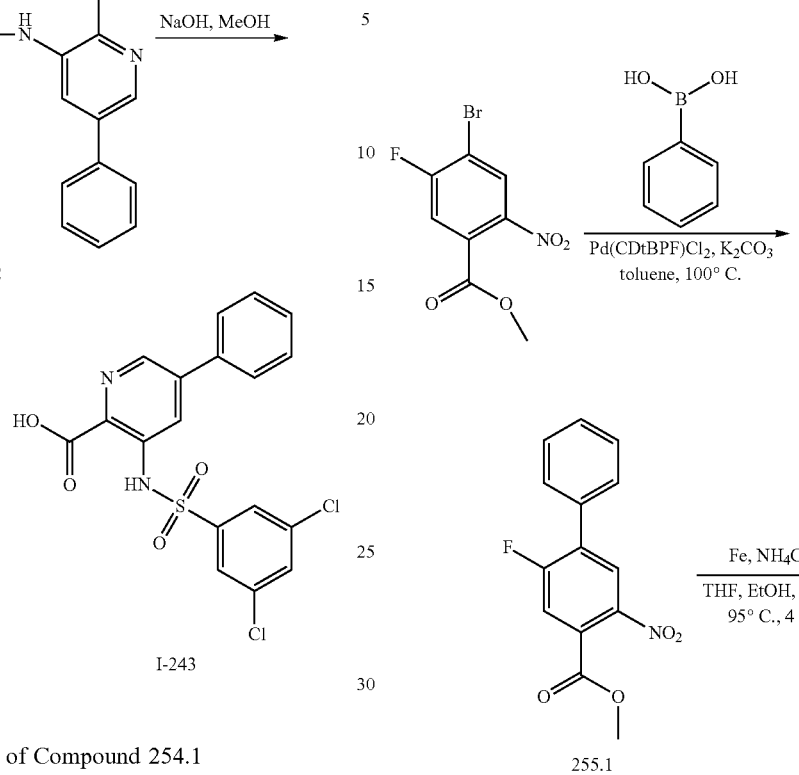

I-243

Synthesis of Compound 254.1

To a solution of methyl 3-amino-5-bromopicolinate (1.34 g, 5.80 mmol, 1 equiv) in EtOH (12 mL), H$_2$O (3 mL), and THF (3 mL) was added K$_2$CO$_3$ (1.6 g, 11.60 mmol, 2 equiv), phenylboronic acid (1.1 g, 8.70 mmol, 1.5 equiv), and Pd(PPh$_3$)$_4$ (0.4 g, 0.58 mmol, 0.1 equiv). The resulting solution was stirred for 12 hr at 80° C. The reaction was then quenched by the addition of 50 mL of water. The resulting solution was extracted with 3×80 ml of ethyl acetate and the organic layers combined and concentrated under vacuum. The residue was applied onto a silica gel column with ethyl acetate/petroleum ether (20:1). This resulted in 680 mg (51%) of 254.1 as a light yellow solid.

Synthesis of I-254

I-254 was prepared from 254.1 according to the procedures for the second and third steps of Example 249. Compound I-254 was purified by Flash-Prep-HPLC with the following conditions (IntelFlash-1): Column, C18 silica gel; mobile phase, ACN:H$_2$O=15% increasing to ACN:H$_2$O=60% within 10 min; Detector, 254 nm. This resulted in 41.9 mg (5% yield over two steps) of I-243 as a white solid. (ES, m/z): [M–H]$^-$ 420.9, $^1$H-NMR (400 MHz, DMSO-d$_6$, ppm): δ 11.81-11.54 (br s, 1H), 8.73 (s, 1H), 8.04-7.96 (m, 2H), 7.88 (s, 2H), 7.74-7.67 (m, 2H), 7.61-7.52 (m, 3H).

Example 255. Synthesis of 5-((3,5-dichlorophenyl)sulfonamido)-2-fluoro-[1,1'-biphenyl]-4-carboxylic Acid, I-287

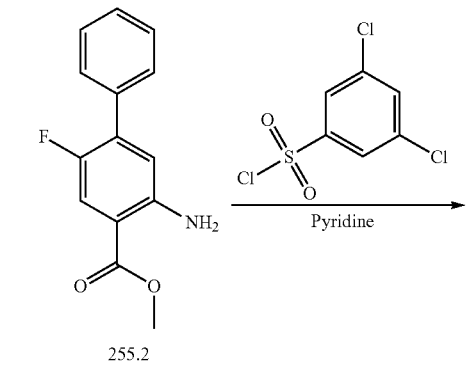

255.1

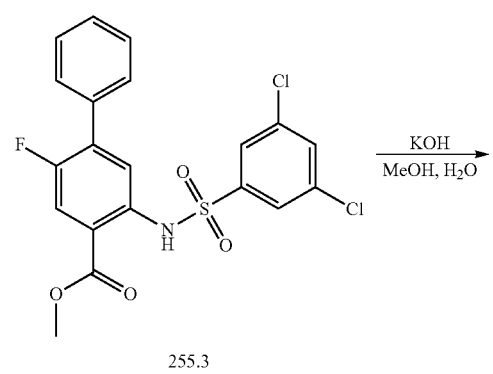

255.2

255.3

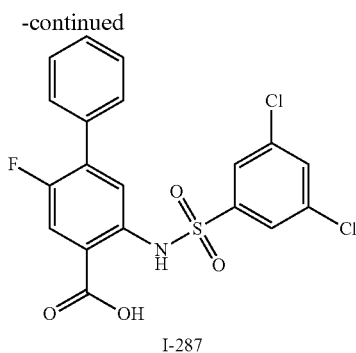

I-287

Synthesis of Compound 255.1

Into a 50-mL 3-necked round-bottom flask, was placed methyl 4-bromo-5-fluoro-2-nitrobenzoate (2 g, 7.193 mmol, 1 equiv), toluene (20 mL), phenylboronic acid (2.63 g, 21.570 mmol, 3.00 equiv), and $K_2CO_3$ (2.98 g, 21.562 mmol, 3.00 equiv). The resulting solution was stirred for overnight at 100° C. The resulting mixture was concentrated. The crude product was purified by Flash-Prep-HPLC with the following conditions (IntelFlash-1): Column, C18 silica gel; mobile phase, $ACN/H_2O=15\%$ increasing to $ACN/H_2O=60\%$ within 15 min. This resulted in 1.4 g (70%) of 255.1 as a yellow solid.

Synthesis of Compound 255.2

Into a 10-mL, 3-necked round-bottom flask, was placed 255.1 (1.4 g, 5.087 mmol, 1 equiv), $NH_4Cl$ (2.72 g, 50.850 mmol, 10.00 equiv), THF (15 mL, 185.145 mmol, 36.40 equiv), EtOH (30 mL, 516.406 mmol, 101.52 equiv), $H_2O$ (7.5 mL, 416.313 mmol, 81.85 equiv), and Fe (1.42 g, 25.433 mmol, 5.00 equiv). The resulting solution was stirred for 4 h at 95° C. The mixture was filtered, and the filtrate was concentrated. The crude product was purified by Flash-Prep-HPLC with the following conditions (IntelFlash-1): Column, C18 silica gel; mobile phase, $ACN/H_2O=15\%$ increasing to $ACN/H_2O=60\%$ within 15 min. This resulted in 600 mg (48%) of 255.2 as a yellow solid.

Synthesis of Compound 255.3

Into a 50-mL, 3-necked round-bottom flask, was placed 255.2 (400 mg, 1.631 mmol, 1 equiv), 3,5-dichlorobenzene-1-sulfonyl chloride (400.40 mg, 1.631 mmol, 1.00 equiv), and pyridine (10 mL). The resulting solution was stirred overnight at room temperature, then concentrated. The crude product was purified by Flash-Prep-HPLC with the following conditions (IntelFlash-1): Column, C18 silica gel; mobile phase, $ACN/H_2O=15\%$ increasing to $ACN/H_2O=60\%$ within 15 min. This resulted in 380 mg (51%) of 255.3 as a solid.

Synthesis of I-255

Into a 50-mL, 3-necked round-bottom flask, was placed 255.3 (200 mg, 0.44 mmol, 1 equiv), MeOH (10 mL), $H_2O$ (10 mL), and KOH (98.8 mg, 1.76 mmol, 4 equiv). The resulting solution was stirred overnight at 40° C., then concentrated. The crude product was purified by Flash-Prep-HPLC with the following conditions (IntelFlash-1): Column, C18 silica gel; mobile phase, $ACN/H_2O=15\%$ increasing to $ACN/H_2O=60\%$ within 15 min. This resulted in 61.2 mg (32%) of I-287 as a white solid. (ES, m/z): $[M-H]^-$ 438.0, $^1H$-NMR (300 MHz, $CD_3OD$, ppm): δ7.77-7.70 (m, 5H), δ7.57-7.43 (m, 5H).

Example 256. Synthesis of 5-((3,5-dichloro-2-hydroxyphenyl)sulfonamido)-2-fluoro-[1,1'-biphenyl]-4-carboxylic Acid, I-289

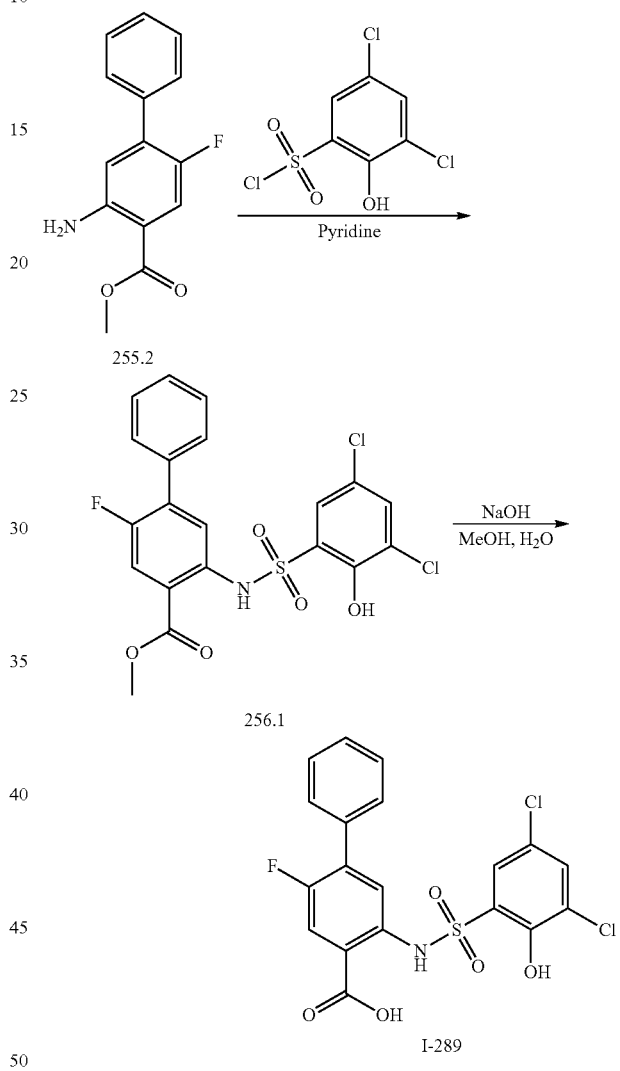

Synthesis of Compound 256.1

Into a 50-mL round-bottom flask purged and maintained with an inert atmosphere of nitrogen, was placed 255.2 (200 mg, 0.815 mmol, 1 equiv), 3,5-dichloro-2-hydroxybenzene-1-sulfonyl chloride (213.25 mg, 0.815 mmol, 1 equiv), and pyridine (5 mL). The resulting solution was stirred for 0.5 hr at room temperature, then concentrated. The residue was applied onto a silica gel column with ethyl acetate/petroleum ether (1:1). This resulted in 150 mg (yield=39%) of 256.1 as a white solid.

Synthesis of I-289

Into a 25-mL round-bottom flask purged and maintained with an inert atmosphere of nitrogen, was placed 256.1 (150 mg, 0.32 mmol, 1 equiv), NaOH (51.0 mg, 1.28 mmol, 4.00 equiv), MeOH (8 mL), and H₂O (2 mL). The resulting solution was stirred for 12 hr at 40° C. in an oil bath. The pH value of the solution was adjusted to 5 with HCl (1 M). The solids were collected by filtration. This resulted in 11.7 mg (yield=8%) of I-289 as a white solid. (ES, m/z): [M−H]⁻ 454.0, ¹H-NMR (400 MHz, DMSO-d₆, ppm): δ7.79 (s, 1H), 7.76-7.73 (d, J=11.2 Hz, 1H), 7.64 (s, 1H), 7.61-7.60 (d, J=2.4 Hz, 1H), 7.48-7.41 (m, 5H).

Example 257. Synthesis of 3,5-dichloro-2-hydroxy-N-(3-methoxy-[1,1'-biphenyl]-2-yl)benzenesulfonamide, I-14

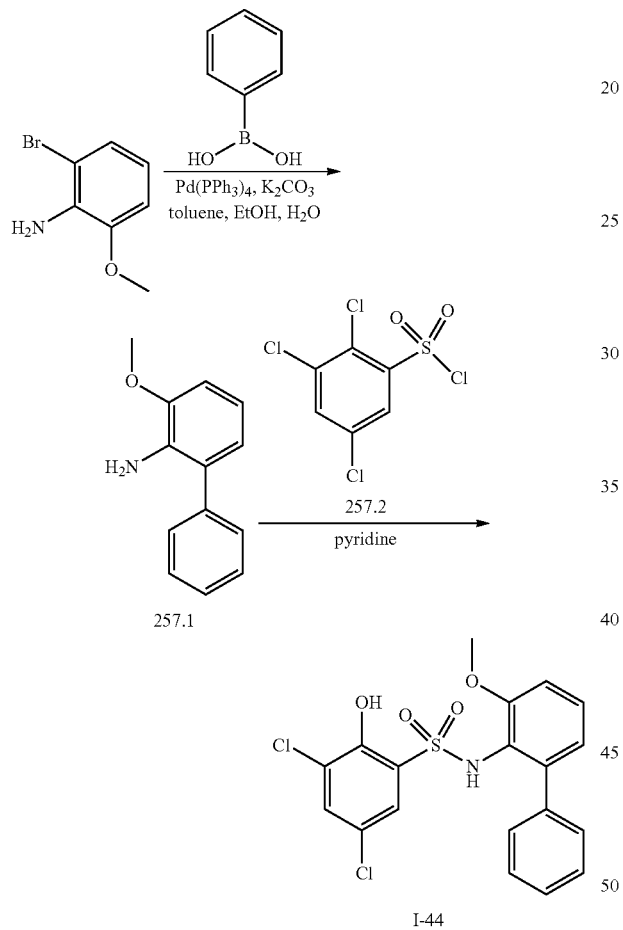

Synthesis of Compound 257.1

Into a 50-mL, 3-necked round-bottom flask purged and maintained with an inert atmosphere of nitrogen, was placed 2-bromo-6-methoxyaniline (1 g, 4.95 mmol, 1.00 equiv), phenylboronic acid (725 mg, 5.95 mmol, 1.20 equiv), potassium carbonate (3.42 g, 24.74 mmol, 5.00 equiv), toluene (4 mL), ethanol (4 mL), water (4 mL), and Pd(PPh₃)₄ (860 mg, 0.74 mmol, 0.15 equiv). The resulting solution was stirred for 12 h at 80° C. The resulting solution was extracted with 3×10 mL of ethyl acetate. The organic layers were combined, washed with 10 mL of saturated brine, dried, and concentrated under vacuum. The residue was applied onto a silica gel column with ethyl acetate/petroleum ether (1:5). This resulted in 0.5 g (51%) of 257.1 as a white solid.

Synthesis of I-14

Into a 50-mL, 3-necked round-bottom flask purged and maintained with an inert atmosphere of nitrogen, was placed 257.1 (500 mg, 1.91 mmol, 1.00 equiv), 257.2 (787 mg, 3.95 mmol, 1.20 equiv), and pyridine (5 mL). The resulting solution was stirred for 30 mins at room temperature. The reaction was then quenched by the addition of 5 mL of 1 M HCl (aq.). The resulting solution was extracted with 3×5 mL of ethyl acetate. The organic layers were combined, washed with 1×5 mL of brine, dried, and concentrated under vacuum. The residue was applied onto a silica gel column with ethyl acetate/petroleum ether (1:2). This resulted in 297.5 mg (37%) of I-14 as a white solid. (ES, m/z): [M−H]⁻ 421.9, ¹H-NMR (400 MHz, DMSO-d₆, ppm): δ3.48 (s, 3H), δ6.85-6.87 (m, 1H), δ6.95-6.98 (m, 1H), δ7.08-7.09 (d, J=2.4 Hz, 1H), δ7.18-7.22 (m, 1H), δ7.25-7.30 (m, 3H), δ7.32-7.38 (m, 2H), δ7.57-7.58 (d, J=2.4 Hz, 1H).

Example 258. Synthesis of 2-((3,5-dichlorophenyl)sulfonamido)-5-phenylthiophene-3-carboxylic Acid, I-242

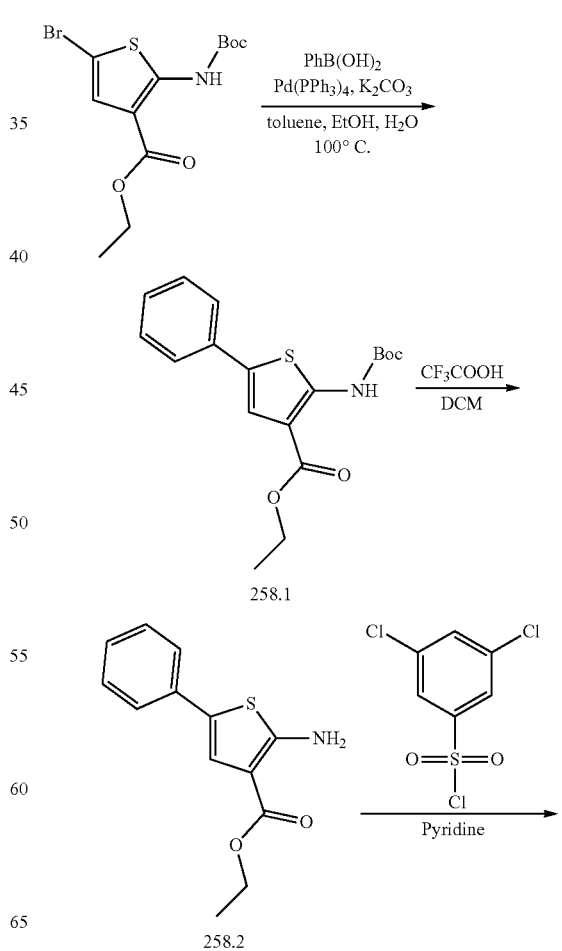

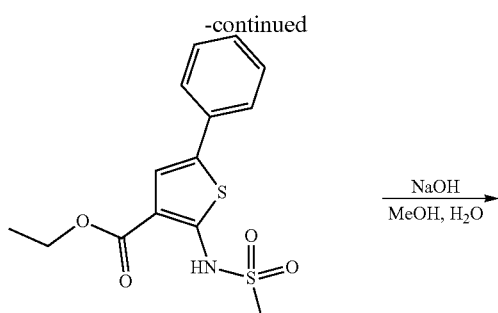

258.3

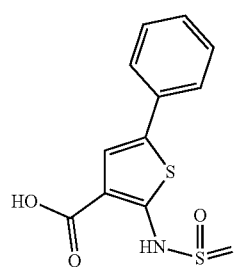

I-242

Synthesis of Compound 258.1

To a stirred mixture of ethyl 5-bromo-2-[[(tert-butoxy)carbonyl]amino]thiophene-3-carboxylate (1 g, 2.86 mmol, 1 equiv) and phenylboronic acid (417.8 mg, 3.43 mmol, 1.2 equiv) in toluene (7 mL), EtOH (7 mL) and H$_2$O (7 mL) were added Pd(PPh$_3$)$_4$ (329.9 mg, 0.29 mmol, 0.1 equiv) and K$_2$CO$_3$ (2.0 g, 14.28 mmol, 5 equiv) in portions at 80° C. with stirring for overnight under nitrogen atmosphere. The resulting mixture was extracted with EtOAc (2×100 mL). The combined organic layers were washed with EtOAc (2×100 mL) and dried over anhydrous Na$_2$SO$_4$. After filtration, the filtrate was concentrated under reduced pressure. The residue was purified by silica gel column chromatography, eluted with PE/EtOAc (10:1) to afford 258.1 (880 mg, 88.7%) as a yellow solid.

Synthesis of Compound 258.2

A mixture of 258.1 (850 mg, 2.45 mmol, 1 equiv) and CF$_3$COOH (2 mL, 26.93 mmol, 11.01 equiv) in DCM (8 mL) was stirred for 30 min at 60° C. under nitrogen atmosphere. The reaction was quenched with NaHCO$_3$ (1 M) at room temperature. The aqueous layer was extracted with EtOAc (2×100 mL). The residue was purified by Prep-TLC (PE/EtOAc 5:1) to afford 258.2 (413 mg, 68.2%) as a white solid.

Synthesis of Compound 258.3

A mixture of 258.2 (468 mg, 2.01 mmol, 1 equiv) and 3,5-dichlorobenzene-1-sulfonyl chloride (492.5 mg, 2.01 mmol, 1 equiv) in pyridine (5 mL) was stirred for 12 h at 50° C. under nitrogen atmosphere. The reaction was quenched with HCl (1 M) at room temperature. The aqueous layer was extracted with EtOAc (2×100 mL). The residue was purified by Prep-TLC (CH$_2$Cl$_2$/MeOH 10:1) to afford 258.3 (220 mg, 24.0%) as a white solid.

Synthesis of I-242

A mixture of 258.3 (130 mg, 0.28 mmol, 1 equiv) and NaOH (170.9 mg, 4.27 mmol, 15 equiv) in MeOH (2.6 mL) and H$_2$O (1.3 mL) was stirred for 2 h at room temperature under nitrogen atmosphere. The reaction was quenched with HCl (1 M) at room temperature. The aqueous layer was extracted with EtOAc (2×100 mL). The crude product was purified by reverse phase flash with the following conditions (from CH$_3$CN:H$_2$O=1:20 to CH$_3$CN:H$_2$O=50:50 in 30 mins, UV: 254/220) to afford I-242 (12.2 mg, 10.0%) as a white solid. (ES, m/z): [M−H]$^-$ 425.8, $^1$H-NMR (400 MHz, DMSO-d$_6$, ppm): δ7.94-7.93 (d, J=1.6 Hz, 1H), 7.78-7.77 (s, J=1.6 Hz, 2H), 7.59-7.57 (d, J=7.2 Hz, 2H), 7.44 (s, 1H), 7.40-7.37 (t, J=12 Hz, 2H), 7.30-7.27 (t, J=12 Hz, 1H).

Example 259. Synthesis of 3,5-dichloro-2-hydroxy-N-(1-methyl-4-phenyl-1H-pyrazol-5-yl)benzenesulfonamide, I-109

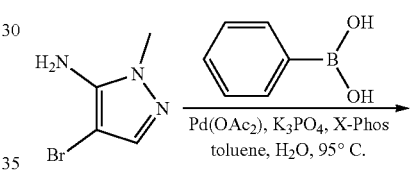

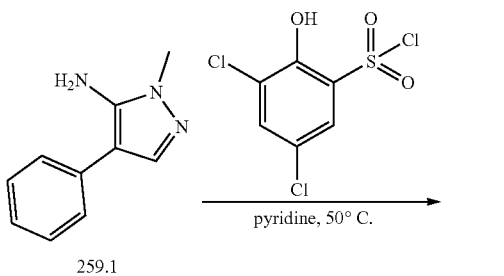

259.1

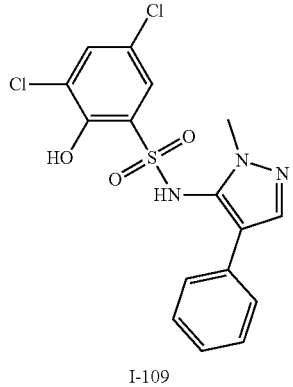

I-109

Synthesis of Compound 259.1

To a stirred mixture of 4-bromo-1-methyl-1H-pyrazol-5-amine (1.5 g, 8.52 mmol, 1 equiv) and phenylboronic acid (1.5 g, 11.93 mmol, 1.4 equiv) in toluene (24 mL) and H$_2$O (8 mL) were added X-Phos (406.3 mg, 0.85 mmol, 0.1 equiv), K$_3$PO$_4$ (3.6 g, 17.04 mmol, 2 equiv), and Pd(OAc)$_2$ (95.7 mg, 0.43 mmol, 0.05 equiv). The resulting mixture was stirred for 12 h at 95° C. under nitrogen atmosphere. The precipitated solids were removed by filtration and washed with EtOAc (2×50 mL). The filtrate was concentrated under vacuum and purified by silica gel column chromatography (elution solvent:PE/EtOAc=10:1) to afford 259.1 (700 mg, 47.4%) as a red solid.

Synthesis of I-109

To a stirred solution of 259.1 (200 mg, 1.15 mmol, 1 equiv) in pyridine (3 mL) was added 3,5-dichloro-2-hydroxybenzene-1-sulfonyl chloride (300 mg, 1.15 mmol, 0.99 equiv) in portions under nitrogen atmosphere. The resulting mixture was stirred for 12 h at 50° C. The reaction was quenched with 1M HCl at room temperature, and the resulting mixture was extracted with EtOAc (2×30 mL). The combined organic layers were concentrated under reduced pressure. The crude product was purified by reverse phase flash with the following conditions (IntelFlash-1): Column, C 18; mobile phase, CH$_3$CN/H$_2$O=0:100 to CH$_3$CN/H$_2$O=40:60 in 30 min; Detector, UV 254/220 nm. This resulted in 1-109 (67.7 mg, 14.7%) as a white solid. (ES, m/z): [M−H]$^-$ 395.9, $^1$H-NMR (400 MHz, DMSO-d$_6$, ppm): δ3.61 (s, 3H), δ6.97-7.01 (m, 1H), δ7.08-7.12 (m, 2H), δ7.15-7.16 (d, J=2.4 Hz, 1H), δ7.33-7.34 (d, J=2.8 Hz, 1H), δ7.48-7.49 (d, J=3.2 Hz, 2H), δ7.54 (s, 1H).

Example 260. Synthesis of 3-((3-chloro-5-(thiazol-2-yl)phenyl)sulfonamido)-[1,1'-biphenyl]-4-carboxylic Acid, I-234

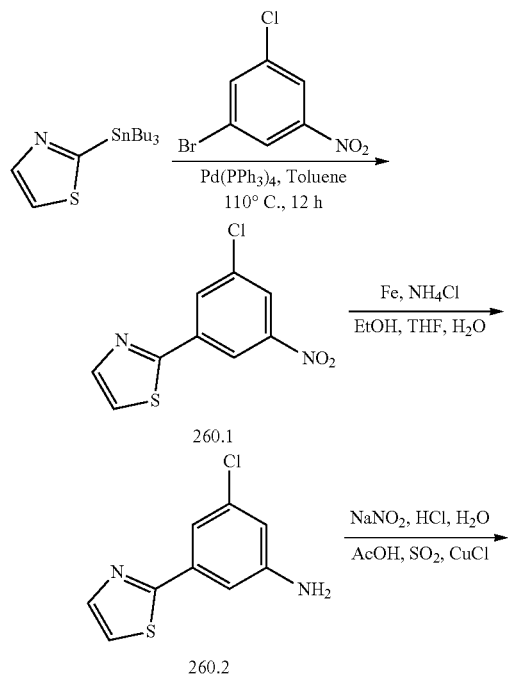

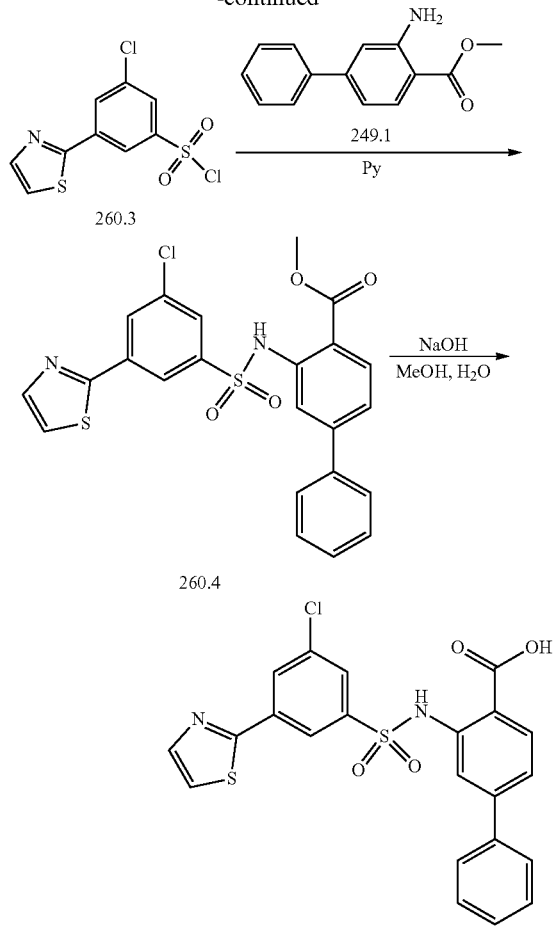

Synthesis of Compound 260.1

Into a 100-mL round-bottom flask purged and maintained with an inert atmosphere of nitrogen, was placed 2-(tributylstannyl)-1,3-thiazole (2 g, 5.35 mmol, 1 equiv), 1-bromo-3-chloro-5-nitrobenzene (1.5 g, 6.41 mmol, 1.2 equiv), Pd(PPh$_3$)$_4$ (0.6 g, 0.53 mmol, 0.1 equiv), and toluene (20 mL). The resulting solution was stirred for 12 hr at 110° C. in an oil bath. The reaction was then quenched by the addition of 20 mL of water. The resulting solution was extracted with 3×20 mL of ethyl acetate. The resulting mixture was washed with 20 mL of brine. The mixture was dried over anhydrous sodium sulfate and concentrated. The residue was applied onto a silica gel column with ethyl acetate/petroleum ether (1:5). This resulted in 1.1 g (yield=86%) of 260.1 as a white solid.

Synthesis of Compound 260.2

Into a 100-mL round-bottom flask purged and maintained with an inert atmosphere of nitrogen, was placed 260.1 (1.1 g, 4.57 mmol, 1 equiv), Fe (1.0 g, 18.28 mmol, 4 equiv), NH$_4$Cl (2.4 g, 45.71 mmol, 10 equiv), EtOH (10 mL), THF (5 mL), and H$_2$O (5 mL). The resulting solution was stirred for 3 hr at 110° C. in an oil bath. The solids were filtered out. The reaction was then quenched by the addition of 20 mL of water. The resulting solution was extracted with 3×20 mL of ethyl acetate. The resulting mixture was washed with 20 mL of brine. The mixture was dried over anhydrous sodium sulfate and concentrated. The residue was applied onto a silica gel column with ethyl acetate/petroleum ether (1:1). This resulted in 0.9 g (yield=93%) of 260.2 as a white solid.

Synthesis of Compound 260.3

Into a 50-mL round-bottom flask purged and maintained with an inert atmosphere of nitrogen, was placed 260.2 (800 mg, 3.80 mmol, 1 equiv) and HCl (8 mL). To this solution (Solution A) was added a solution of NaNO$_2$ (393.0 mg, 5.70 mmol, 1.50 equiv) in H$_2$O (3.2 mL) at 0° C., and the solution A was stirred at 0° C. for 1 h. In another 50-mL round-bottom flask was placed AcOH (8 mL) and CuCl (112.8 mg, 1.14 mmol, 0.3 equiv), and the solution was purged with SO$_2$ over 0.5 h to generate Solution B. The Solution A was added to Solution B dropwise over 10 mins. The resulting solution was stirred for 1 hr at room temperature. The reaction was then quenched by the addition of 10 mL of water. The resulting solution was extracted with 3×10 mL of ethyl acetate. The resulting mixture was washed with 10 mL of brine. The mixture was dried over anhydrous sodium sulfate and concentrated. This resulted in 800 mg (yield=72%) of 260.3 as a white solid.

Synthesis of Compound 260.4

Into a 50-mL round-bottom flask purged and maintained with an inert atmosphere of nitrogen, was placed 260.3 (400 mg, 1.36 mmol, 1 equiv), 249.1 (309.0 mg, 1.36 mmol, 1 equiv), and pyridine (5 mL). The resulting solution was stirred for 0.5 hr at room temperature, then concentrated. The residue was applied onto a silica gel column with ethyl acetate/petroleum ether (1:2). This resulted in 220 mg (yield=33%) of 260.4 as a white solid.

Synthesis of I-323

Into a 25-mL round-bottom flask purged and maintained with an inert atmosphere of nitrogen, was placed 260.4 (100 mg, 0.21 mmol, 1 equiv), NaOH (16.5 mg, 0.41 mmol, 2 equiv), MeOH (4 mL), and H$_2$O (1 mL). The resulting solution was stirred for 12 hr at room temperature. The pH value of the solution was adjusted to 3 with HCl (1 M). The solids were collected by filtration and dried under reduce pressure. This resulted in 43.3 mg (yield=45%) of I-323 as a white solid. (ES, m/z): [M+H]$^+$ 471.0, $^1$H-NMR (400 MHz, DMSO-d$_6$, ppm): δ 11.42 (s, 1H), 8.33 (s, 1H), 8.23 (s, 1H), 8.03 (s, 1H), 7.97-7.92 (m, 3H), 7.72 (s, 1H), 7.65-7.59 (m, 2H), 7.50-7.42 (m, 4H).

Example 261. Synthesis of 3-(N-(5-(benzo[b]thiophen-2-yl)-4-fluoro-2-methoxyphenyl) sulfamoyl)-5-fluoro-4-hydroxybenzoic Acid, I-517

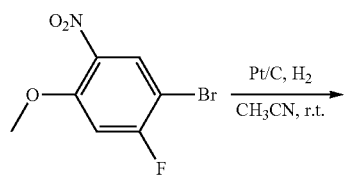

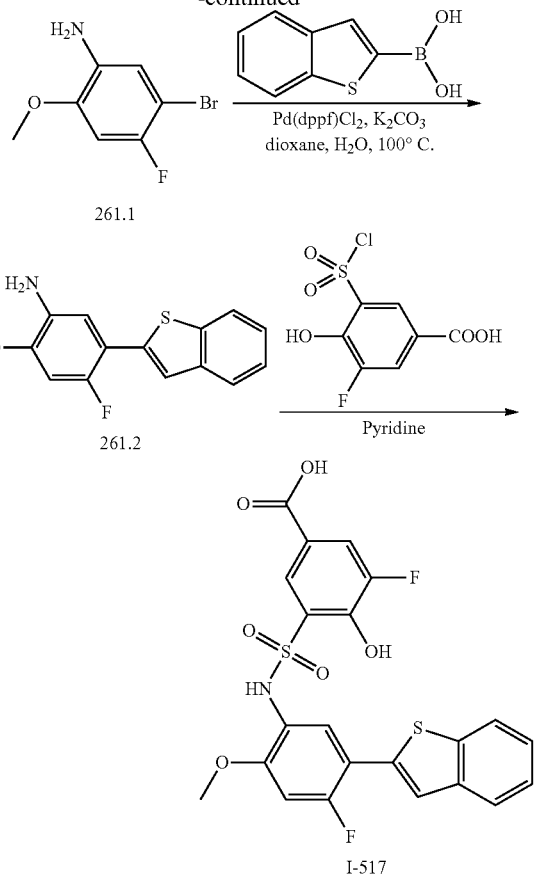

Synthesis of Compound 261.1

To a stirred mixture of 1-bromo-2-fluoro-4-methoxy-5-nitrobenzene (3.80 g, 15.2 mmol, 1.00 equiv) in acetonitrile (100 mL) under hydrogen atmosphere was added Pt/C (0.39 g, 2.0 mmol, 0.13 equiv). The resulting mixture was stirred overnight at room temperature under hydrogen atmosphere. The mixture was filtered, and the filtrate was concentrated. The residue was purified by silica gel column chromatography, eluted with PE/EtOAc (3:1) to afford 261.1 (3.3 g, 99%) as a yellow solid. (ES, m/z): 221 [M+H]$^+$.

Synthesis of Compound 261.2

To a stirred mixture of 261.1 (1.80 g, 8.180 mmol, 1.00 equiv) and 1-benzothiophen-2-ylboronic acid (1.75 g, 9.83 mmol, 1.20 equiv) in dioxane (30 mL) and water (3 mL) under nitrogen atmosphere were added K$_2$CO$_3$ (2.26 g, 16.4 mmol, 2 equiv) and Pd(dppf)Cl2 (1.20 g, 1.63 mmol, 0.2 equiv). The resulting mixture was stirred overnight at 100° C. under nitrogen atmosphere, then concentrated. The residue was purified by silica gel column chromatography, eluted with PE/EtOAc (5:1) to afford 261.2 (1.3 g, 58%) as a yellow solid. (ES, m/z): 274 [M+H]$^+$.

Synthesis of I-517

Into a 25-mL round-bottom flask, was placed 261.2 (273.0 mg, 0.999 mmol, 1.00 equiv), pyridine (5.0 mL), 3-(chlorosulfonyl)-5-fluoro-4-hydroxybenzoic acid (610.3 mg, 2.397 mmol, 2.40 equiv). The resulting solution was stirred overnight at room temperature, then concentrated under vacuum. The crude product was purified by Prep-HPLC with the following conditions: Column, XBridge Prep OBD C18 Column 30*150 mm 5 um; Mobile Phase A: water (10 mmol/L NH$_4$HCO$_3$+0.1% NH$_3$.H$_2$O), Mobile Phase B: ACN; Flow rate: 60 mL/min; Gradient: 15% B to 30% B in 7 min; Detector UV 254/210 nm, Rt: 5.94 min. This resulted in I-517 (18.8 mg, 3.8%) as a white solid. (ES, m/z): [M+H]$^+$ 492.0, $^1$H-NMR (400 MHz, DMSO-d$_6$, ppm): δ 8.01-7.92 (m, 2H), 7.89 (dd, J=7.3, 1.9 Hz, 1H), 7.69 (d, J=8.1 Hz, 1H), 7.61 (s, 1H), 7.38 (pd, J=7.1, 1.5 Hz, 2H), 7.22 (s, 1H), 7.09 (s, 1H), 7.09 (d, J=12.9 Hz, 1H), 6.97 (s, 1H), 3.80 (s, 3H), 2.55 (m, 3H).

Example 262. Synthesis of 3-(N-(5-(benzo[b]thiophen-2-yl)-2,4-difluorophenyl)sulfamoyl)-5-chloro-4-hydroxybenzoic Acid, I-507; and ethyl 3-(N-(5-(benzo[b]thiophen-2-yl)-2,4-difluorophenyl)sulfamoyl)-5-chloro-4-hydroxybenzoate, I-505

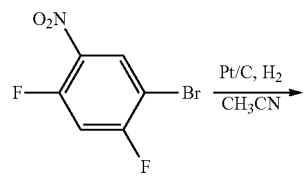

262.1

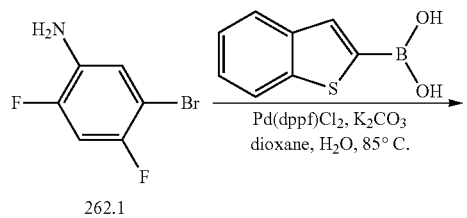

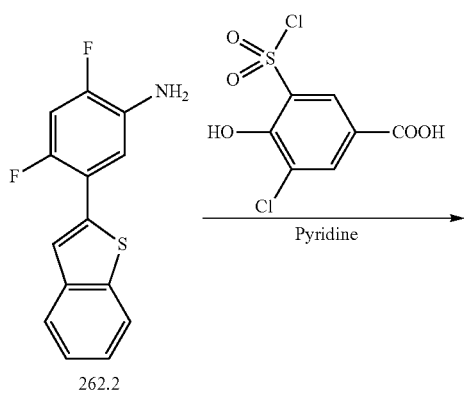

262.2

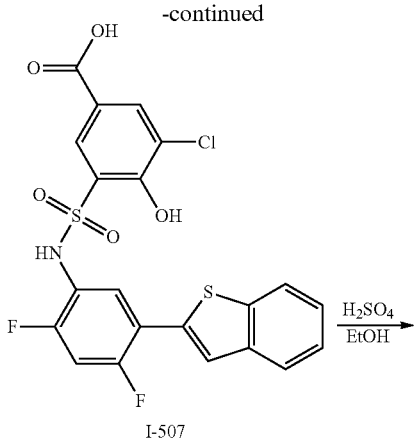

I-507

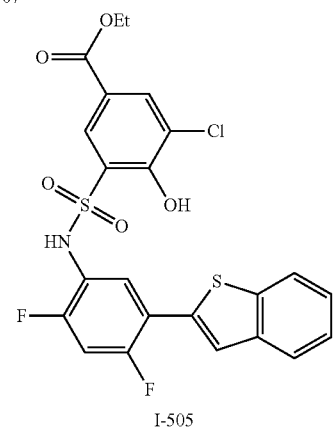

I-505

Synthesis of Compound 262.1

To a stirred solution of 1-bromo-2,4-difluoro-5-nitrobenzene (2.00 g, 8.40 mmol, 1.00 equiv) in CH$_3$CN (5.0 mL) was added Pt/C (0.80 g, 4.1 mmol, 0.49 equiv) at 25° C. under hydrogen atmosphere. The resulting mixture was stirred overnight at room temperature under hydrogen atmosphere. The resulting mixture was filtered, the filter cake was washed with acetone (3×50 mL), and the filtrate was concentrated under reduced pressure. The residue was purified by silica gel column chromatography, eluted with PE/EtOAc (20:1) to afford 262.1 (1.6 g, 92%) as a light yellow oil. (ES, m/z): 205.9 [M−H]$^−$.

Synthesis of Compound 262.2

To a stirred solution of 262.1 (800.0 mg, 3.846 mmol, 1.00 equiv), 1-benzothiophen-2-ylboronic acid (1026.95 mg, 5.769 mmol, 1.50 equiv) and K$_2$CO$_3$ (1594.6 mg, 11.538 mmol, 3.00 equiv) in dioxane (100 mL)/H$_2$O (10 mL) at 25° C. under nitrogen atmosphere was added Pd(dppf)Cl$_2$ (1125.6 mg, 1.538 mmol, 0.40 equiv). The resulting mixture was stirred overnight at 85° C. under nitrogen atmosphere, then concentrated under reduced pressure. The residue was purified by silica gel column chromatography, eluted with CH$_2$Cl$_2$/MeOH (20:1) to afford 262.2 (650 mg, 64.6%) as a light yellow solid. (ES, m/z): 260.0 [M−H]$^−$.

Synthesis of I-507

To a stirred mixture of 262.2 (100.0 mg, 0.383 mmol, 1.00 equiv) in pyridine (10 mL) were added 3-chloro-5-(chlorosulfonyl)-4-hydroxybenzoic acid (207.4 mg, 0.765 mmol, 2.00 equiv) in portions at 25° C. under air atmosphere. The resulting mixture was stirred overnight at room temperature, then diluted with HCl (1N, 5 mL). The resulting mixture was extracted with EtOAc (5×20 mL). The combined organic layers were washed with brine (10 mL), dried over anhydrous $Na_2SO_4$, filtered, and concentrated under reduced pressure. The residue was purified by Prep-TLC ($CH_2Cl_2$/ MeOH=5:1) to afford I-507 (110 mg). This material (100 mg) was further purified by Prep-HPLC with the following conditions: Column, XBridge Prep OBD C18 Column 19*150 mm 5 um; Mobile Phase A: water (10 mmol/L $NH_4HCO_3$+0.1% $NH_3.H_2O$), Mobile Phase B: ACN; Flow rate: 25 mL/min; Gradient: 30% B to 60% B in 7 min; Detector UV 254/210 nm, Rt: 5.88 min. This resulted in I-507 (50 mg, 26%) as a white solid. (ES, m/z): [M–H]⁻ 494.0, ¹H-NMR (400 MHz, DMSO-$d_6$, ppm): δ 8.03-7.96 (m, 1H), 7.90 (dd, J=6.0, 2.5 Hz, 2H), 7.76 (d, J=2.4 Hz, 1H), 7.71-7.62 (m, 2H), 7.50-7.35 (m, 3H), 7.10 (m, 3H).

Synthesis of I-505

Into a 25-mL vial was placed I-507 (110.0 mg, 0.222 mmol, 1.00 equiv), EtOH (3.0 mL), and a solution of $H_2SO_4$ (20.0 mg, 0.204 mmol, 0.92 equiv) in EtOH (0.5 mL). The resulting solution was stirred overnight at 80° C. in an oil bath. The reaction mixture was diluted with 10 mL of $H_2O$ and extracted with 3×20 mL of ethyl acetate. The combined organic layers were evaporated under vacuum. The crude product (100 mg) was purified by Prep-HPLC with the following conditions (Column: XBridge Prep C18 OBD Column, 19 Å—150 mm 5 um; Mobile Phase A:Water (10 mM $NH_4HCO_3$+0.1% $NH_3.H_2O$), Mobile Phase B: ACN; Flow rate: 25 mL/min; Gradient: 30% to 60% B in 7 min; Detector 210/254 nm; Ret. Time: 5.88. This afforded I-505 (50 mg, 43%) as a white solid. (ES, m/z): [M–H]⁻ 521.9, ¹H-NMR (400 MHz, DMSO-$d_6$, ppm): δ 7.82-7.74 (m, 1H), 7.70 (q, J=3.4, 3.0 Hz, 2H), 7.45 (s, 1H), 7.45 (d, J=16.7 Hz, 2H), 7.30-7.15 (m, 3H), 6.62 (s, 2H), 3.94 (q, J=7.1 Hz, 2H), 1.02 (t, J=7.1 Hz, 3H).

Example 263. Synthesis of 3,5-dichloro-N-((4-fluoro-[1,1'-biphenyl]-3-yl)methyl)-2-hydroxybenzenesulfonamide, I-125

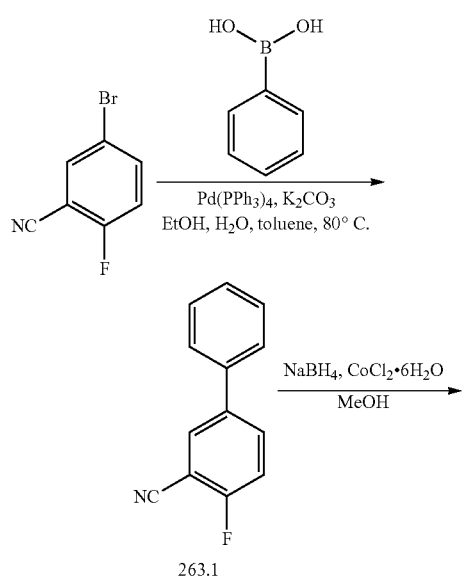

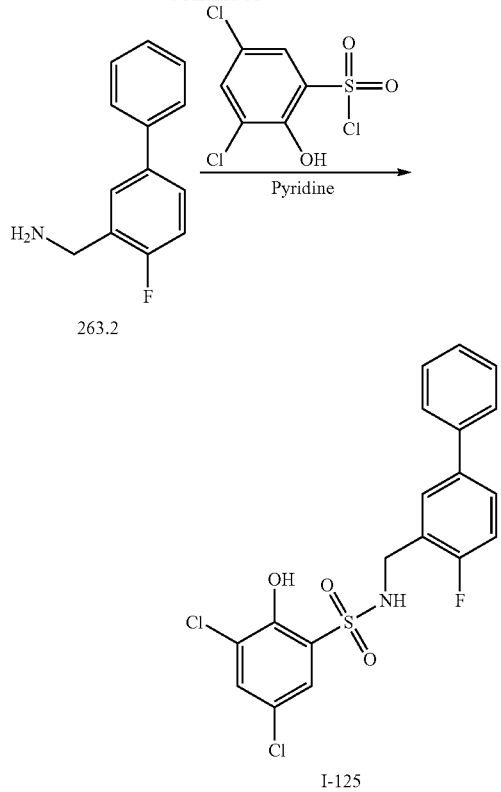

Synthesis of Compound 263.1

Into a 500-mL, 3-necked round-bottom flask purged and maintained with an atmosphere of nitrogen, was placed 5-bromo-2-fluorobenzonitrile (10 g, 50.0 mmol, 1 equiv), toluene (50 mL), EtOH (50 mL), $H_2O$ (50 mL), $K_2CO_3$ (34.5 g, 249.9 mmol, 5 equiv), and Pd(PPh₃)₄ (11.6 g, 10.00 mmol, 0.2 equiv). The resulting solution was stirred for 12 h at 80° C. The resulting mixture was concentrated under vacuum. The residue was applied onto a silica gel column with ethyl acetate/petroleum ether (20:1). This resulted in 5.4 g (54%) of 263.1 as a light yellow solid.

Synthesis of Compound 263.2

Into a 100-mL round-bottom flask, was placed 263.1 (1.0 g, 5.1 mmol, 1 equiv), methanol (10 g), CoCl₂.6H₂O (2.4 g, 10.1 mmol, 2 equiv), NaBH₄ (1.9 g, 50.7 mmol, 10 equiv). The resulting solution was stirred for 0.5 h at 25° C. The reaction was then quenched by the addition of 10 mL of water. The resulting solution was extracted with 3×15 mL of ethyl acetate and the combined organic layers were concentrated under vacuum. This resulted in 1 g (98%) of 263.2 as a black solid.

Synthesis of I-125

Into a 50-mL round-bottom flask, was placed 3,5-dichloro-2-hydroxybenzene-1-sulfonyl chloride (300 mg, 1.15 mmol, 1 equiv), 263.2 (277.0 mg, 1.38 mmol, 1.2 equiv), and pyridine (5 mL). The resulting solution was stirred for 12 h at 25° C. The reaction was then quenched by the addition of 15 mL of 1 M hydrochloric acid. The resulting solution was extracted with 3×20 mL of ethyl acetate. The crude product was purified by Flash-Prep-HPLC with the following conditions (IntelFlash-1): Column, C18; mobile phase, ACN:H$_2$O=15% increasing to ACN:H$_2$O=60% within 15 min; Detector, UV 254 nm. This resulted in 51.4 mg (10.5%) of I-125 as a white solid. (ES, m/z): [M−H]⁻ 423.9, ¹H-NMR (400 MHz, DMSO-d$_6$, ppm): δ4.02 (s, 2H), δ7.16-7.26 (m, 5H), δ7.30-7.40 (m, 1H), δ7.44-7.48 (m, 2H), δ7.52-7.61 (m, 4H).

Example 264. Synthesis of 2-(3-((3,5-dichlorophenyl)sulfonamido)-[1,1'-biphenyl]-4-yl)acetic Acid, I-228

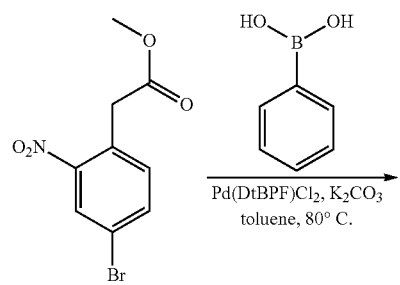

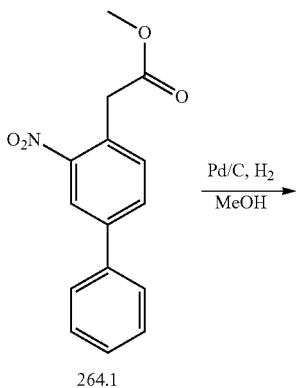

264.1

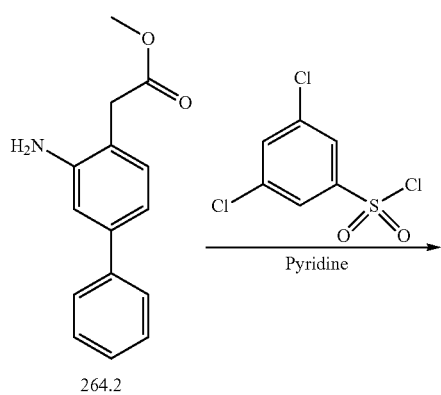

264.2

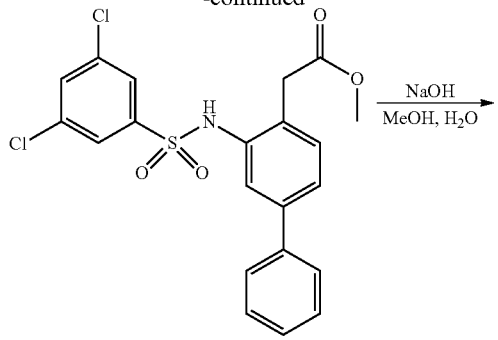

264.3

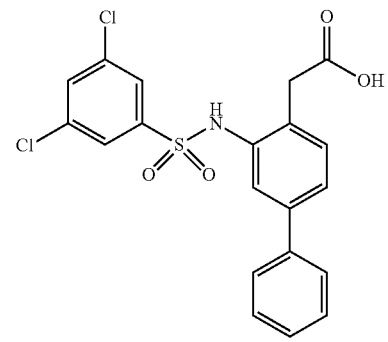

I-228

Synthesis of Compound 264.1

Into a 100-mL round-bottom flask purged and maintained with an inert atmosphere of nitrogen, was placed methyl 2-(4-bromo-2-nitrophenyl)acetate (2 g, 7.30 mmol, 1 equiv), phenylboronic acid (1.8 g, 14.5 mmol, 2 equiv), Pd(DtBPF)Cl$_2$ (0.5 g, 0.73 mmol, 0.1 equiv), K$_2$CO$_3$ (3.0 g, 21.89 mmol, 3 equiv), and toluene. The resulting solution was stirred for 2 hr at 80° C. in an oil bath. The reaction was then quenched by the addition of 20 mL of water. The resulting solution was extracted with 3×20 mL of ethyl acetate. The combined organics were washed with 20 mL of brine, dried over anhydrous sodium sulfate, and concentrated. The residue was applied onto a silica gel column with ethyl acetate/petroleum ether (1:5). This resulted in 1.9 g (yield=96%) of 264.1 as a white solid.

Synthesis of Compound 264.2

Into a 100-mL round-bottom flask purged and maintained with an inert atmosphere of nitrogen, was placed 264.1 (1.8 g, 6.6 mmol, 1 equiv), Pd/C (0.2 g, 1.9 mmol, 0.28 equiv), and MeOH (20 mL). The resulting solution was stirred for 12 hr at room temperature. The solids were filtered out, and the filtrate was concentrated. This resulted in 1.5 g (yield=94%) of 264.2 as a white solid.

Synthesis of Compound 264.3

Into a 25-mL round-bottom flask purged and maintained with an inert atmosphere of nitrogen, was placed 264.2 (300 mg, 1.24 mmol, 1 equiv), 3,5-dichlorobenzene-1-sulfonyl chloride (305.2 mg, 1.24 mmol, 1 equiv), and pyridine (5 mL). The resulting solution was stirred for 0.5 hr at room temperature, then concentrated. The residue was applied onto a silica gel column with ethyl acetate/petroleum ether (1:1). This resulted in 300 mg (yield=54%) of 264.3 as a white solid.

Synthesis of I-228

Into a 25-mL round-bottom flask purged and maintained with an inert atmosphere of nitrogen, was placed 264.3 (200 mg, 0.44 mmol, 1 equiv), NaOH (35.5 mg, 0.89 mmol, 2.00 equiv), MeOH (4 mL), and H₂O (1 mL). The resulting solution was stirred for 12 hr at 40° C. in an oil bath. The pH value of the solution was adjusted to 7 with HCl (1 M). The resulting solution was extracted with 3×10 mL of ethyl acetate. The combined organics were washed with 10 mL of brine, dried over anhydrous sodium sulfate, and concentrated. The residue was applied onto a silica gel column with dichloromethane/methanol (10:1). This resulted in 147.1 mg (yield=76%) of I-228 as a white solid. (ES, m/z): [M+H]⁺ 436.0, ¹H-NMR (300 MHz, DMSO-d₆, ppm): δ10.12 (br s, 1H), δ8.02 (s, 1H), δ7.68 (s, 2H), δ7.54-7.34 (m, 7H), δ6.94 (s, 1H), δ3.69 (s, 1H).

Example 265. Synthesis of 3-(((3,5-dichlorophenyl)sulfonamido)methyl)-[1,1'-biphenyl]-4-carboxylic Acid, I-304

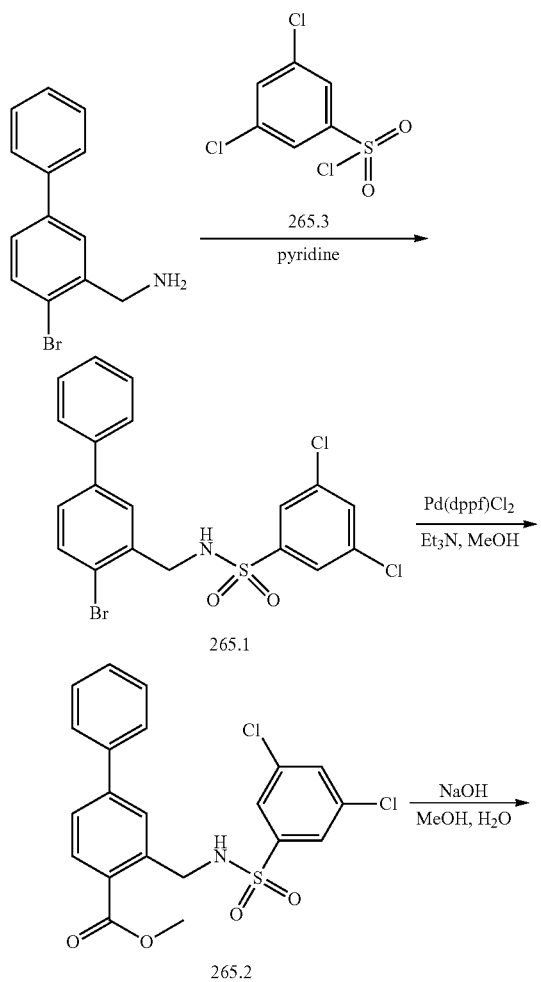

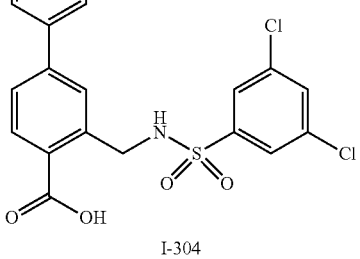

Synthesis of Compound 265.1

Into a 100-mL round-bottom flask, was placed 3,5-dichlorobenzene-1-sulfonyl chloride (500 mg, 2.03 mmol, 1 equiv), 265.3 (640.69 mg, 2.444 mmol, 1.2 equiv), and pyridine (10 mL). The resulting solution was stirred for 12 hr at 25° C. The reaction was then quenched by the addition of 20 mL of diluted hydrochloric acid. The resulting solution was extracted with 3×25 mL of ethyl acetate, and the combined organic layers were concentrated. The residue was applied onto a silica gel column with ethyl acetate/petroleum ether (2:1). This resulted in 500 mg (52.1%) of 265.1 as a light yellow solid.

Synthesis of Compound 265.2

Into a 250-mL pressure tank reactor, was placed 265.1 (300 mg, 0.637 mmol, 1 equiv), MeOH (150 mL), Et₃N (322.1 mg, 3.183 mmol, 5 equiv), and Pd(dppf)Cl₂ (69.8 mg, 0.096 mmol, 0.15 equiv) under an atmosphere of CO. The resulting solution was stirred for 12 hr at 120° C., then concentrated under vacuum. The residue was applied onto Prep-TLC with ethyl acetate/petroleum ether (5:1). This resulted in 120 mg (41.8%) of 265.2 as an off-white solid.

Synthesis of I-304

Into a 50-mL round-bottom flask, was placed 265.2 (100 mg, 0.222 mmol, 1 equiv), H₂O (3 mL), MeOH (3 mL), NaOH (63.8 mg, 2.66 mmol, 12 equiv). The resulting solution was stirred for 12 hr at 25° C. The reaction was then quenched by the addition of 10 mL of diluted hydrochloric acid. The resulting solution was extracted with 3×15 mL of ethyl acetate, and the organic layers were combined and concentrated under vacuum. The crude product was purified by Flash-Prep-HPLC with the following conditions (Intel-Flash-1): Column, C18 silica gel; mobile phase, ACN:H₂O=10% increasing to ACN:H₂O=65% within 15 min. This resulted in 42.2 mg (43.6%) of I-304 as an off-white solid. (ES, m/z): [M–H]⁻ 434.0, ¹H-NMR (400 MHz, DMSO-d₆, ppm): δ 13.08 (s, 1H), 8.45 (s, 1H), 7.89-7.87 (d, J=8.0 Hz, 1H), 7.74 (s, 1H), 7.60-7.52 (m, 6H), 7.51-7.43 (m, 3H), 4.62 (s, 2H).

Example 266. Synthesis of 5-bromo-3-chloro-N-(4,6-difluoro-[1,1'-biphenyl]-3-yl)-2-hydroxybenzamide, I-139; methyl 3-chloro-5-((4,6-difluoro-[1,1'-biphenyl]-3-yl)carbamoyl)-4-hydroxybenzoate, I-146; 3-chloro-5-((4,6-difluoro-[1,1'-biphenyl]-3-yl)carbamoyl)-4-hydroxybenzoic Acid, I-155; and 3-chloro-N-(4,6-difluoro-[1,1'-biphenyl]-3-yl)-2-hydroxy-5-(pyrrolidine-1-carbonyl)benzamide, I-150

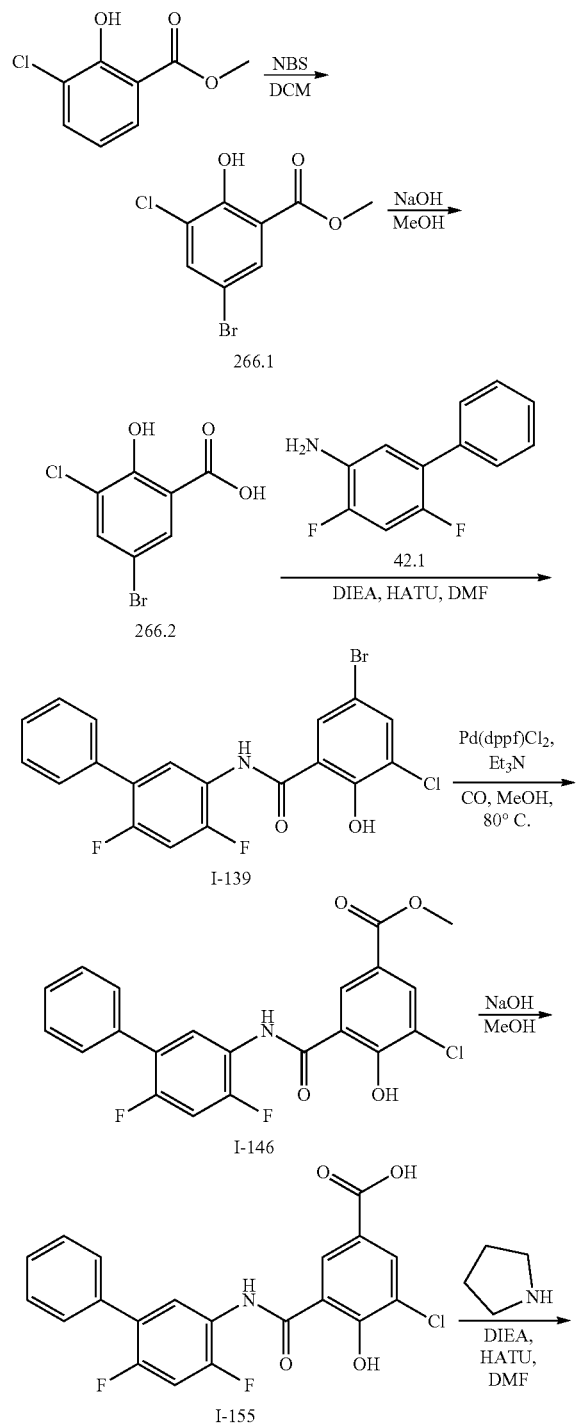

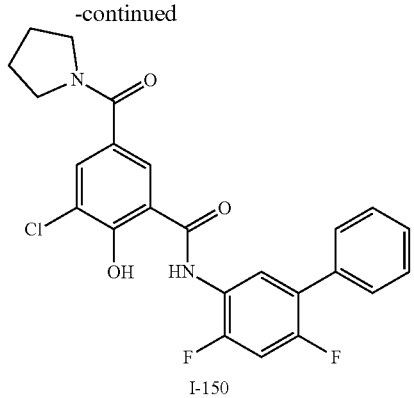

Synthesis of Compound 266.1

To a stirred solution of methyl 3-chloro-2-hydroxybenzoate (4.83 g, 25.9 mmol, 1 equiv) in DCM (50 mL) was added NBS (4.6 g, 25.9 mmol, 1 equiv) in portions at room temperature under nitrogen atmosphere. The resulting mixture was stirred for 2 h at room temperature under nitrogen atmosphere. The resulting mixture was extracted with EA. The combined organic layers were washed with water (2×50 mL), dried over anhydrous $Na_2SO_4$, filtered, and concentrated under reduced pressure to afford 266.1 (6.46 g, 94.0%) as a white solid.

Synthesis of Compound 266.2

To a stirred solution of 266.1 (6.46 g, 24.3 mmol, 1 equiv) in MeOH (50 mL) were added NaOH (1.9 g, 48.6 mmol, 2 equiv) and $H_2O$ (5 mL) at room temperature. The resulting mixture was stirred for 3 h at room temperature, then acidified to pH 6 with conc. HCl. The resulting mixture was extracted with EtOAc (2×50 mL). The combined organic layers were washed with brine (2×20 mL), dried over anhydrous $Na_2SO_4$, filtered, and concentrated under reduced pressure to afford 266.2 (6.0 g, 98%) as a white solid.

Synthesis of I-139

To a stirred solution of 266.2 (3.0 g, 11.9 mmol, 1 equiv) and 42.1 (2.4 g, 11.9 mmol, 1 equiv) in DMF (30 mL) were slowly added DIEA (3.1 g, 23.8 mmol, 2 equiv) and HATU (6.8 g, 17.90 mmol, 1.5 equiv) at room temperature under nitrogen atmosphere. The resulting mixture was stirred overnight at room temperature under nitrogen atmosphere. The resulting mixture was extracted with EtOAc (2×20 mL). The combined organic layers were dried over anhydrous $Na_2SO_4$, filtered, and concentrated under reduced pressure. The residue was purified by silica gel column chromatography, eluted with PE/EtOAc (2:1) to afford I-139 (4.2 g, 80%) as a white solid. (ES, m/z): [M+H]+ 437.9, $^1$H-NMR (400 MHz, DMSO-$d_6$, ppm): δ 12.78 (br s, 1H), 10.88 (s, 1H), 8.23 (s, 1H), 7.95 (s, 1H), 7.86-7.82 (m, 1H), 7.59-7.42 (m, 6H).

Synthesis of I-146

To a stirred solution of I-139 (1.52 g, 3.47 mmol, 1 equiv) and Pd(dppf)$Cl_2$ (253.5 mg, 0.35 mmol, 0.1 equiv) in $CH_3OH$ (20 mL) was added $Et_3N$ (0.7 g, 6.9 mmol, 2 equiv) at room temperature. The resulting mixture was stirred overnight at 80° C. under 10 atm CO atmosphere. The mixture was allowed to cool to room temperature, then filtered, and the filter cake was washed with EtOAc (2×10 mL). The filtrate was concentrated under reduced pressure. The residue was purified by Prep-TLC (PE/EtOAc 2:1) to afford I-146 (810 mg, 55.9%) as a white solid. (ES, m/z): [M−H]⁻ 416.0, ¹H-NMR (400 MHz, DMSO-$d_6$, ppm): δ 11.46 (s, 1H), 8.68 (s, 1H), 8.11 (s, 1H), 7.39-7.11 (m, 1H), 7.58-7.49 (m, 5H), 7.46-7.42 (m, 1H), 3.87 (s, 3H).

Synthesis of I-155

To a stirred solution of I-146 (530 mg, 1.27 mmol, 1 equiv) in MeOH (2 mL) and $H_2O$ (1 mL) was added NaOH (371 mg, 9.28 mmol, 7.31 equiv) in portions at room temperature. The resulting mixture was stirred for 2 h at room temperature. The residue was acidified to pH 6 with HCl (aq.). The resulting mixture was extracted with EA. The organics were dried over anhydrous $Na_2SO_4$, filtered, and concentrated under reduced pressure. The residue was purified by Prep-TLC ($CH_2Cl_2$/MeOH 10:1) to afford I-155 (470 mg, 91.7%) as a white solid. (ES, m/z): [M−H]⁻ 402.0, ¹H-NMR (400 MHz, DMSO-$d_6$, ppm): δ 11.51 (s, 1H), 8.67 (s, 1H), 8.08 (s, 1H), 7.93-7.89 (m, 1H), 7.57-7.42 (m, 6H).

Synthesis of I-150

To a stirred solution of I-155 (105 mg, 0.26 mmol, 1 equiv) and pyrrolidine (27.7 mg, 0.39 mmol, 1.5 equiv) in DMF (2 mL) was added DIEA (67.2 mg, 0.52 mmol, 2 equiv) and HATU (148.3 mg, 0.39 mmol, 1.5 equiv) in portions at room temperature under nitrogen atmosphere. The resulting mixture was stirred overnight at room temperature under nitrogen atmosphere. The resulting mixture was extracted with EtOAc (2×20 mL). The combined organic layers were washed with water (2×10 mL), dried over anhydrous $Na_2SO_4$, filtered, and concentrated under reduced pressure. The residue was purified by Prep-TLC ($CH_2Cl_2$/MeOH 20:1) to afford I-150 (74.7 mg, 62.8%) as a white solid. (ES, m/z): [M−H]⁻ 455.0, ¹H-NMR (400 MHz, DMSO-$d_6$, ppm): δ 13.09 (br s, 1H), 8.38 (s, 1H), 8.22 (s, 1H), 7.72 (s, 1H), 7.67-7.41 (m, 6H), 7.23-7.68 (m, 1H), 3.74 (s, 4H), 1.84 (s, 4H).

Example 267. Synthesis of 5-bromo-3-chloro-N-(6-fluoro-[1,1'-biphenyl]-3-yl)-2-hydroxybenzamide, I-80; and 3-chloro-5-cyano-N-(6-fluoro-[1,1'-biphenyl]-3-yl)-2-hydroxybenzamide, I-81

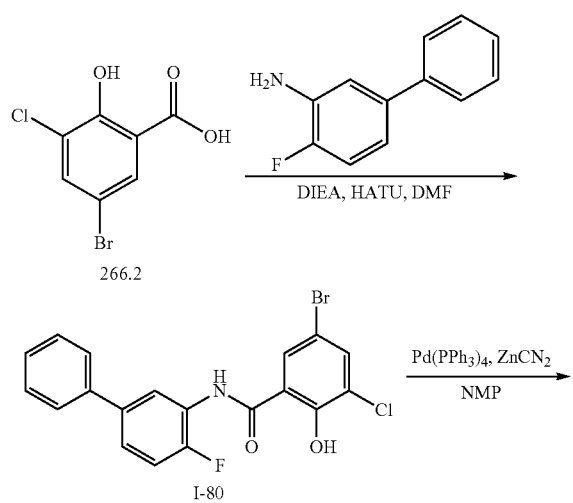

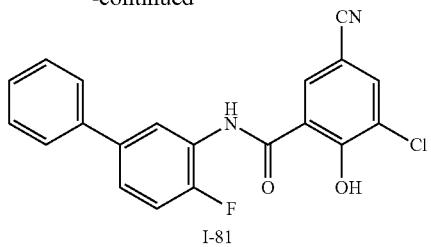

Synthesis of I-80

Into a 100-mL, 3-necked round-bottom flask, was placed 266.2 (1.36 g, 5.41 mmol, 1 equiv), 2-fluoro-5-phenylaniline (1.52 g, 8.11 mmol, 1.5 equiv), DIEA (1.40 g, 10.82 mmol, 2 equiv), HATU (4.11 g, 10.8 mmol, 2 equiv), and DMF (10 mL). The resulting solution was stirred for 5 h at room temperature, then diluted with 10 mL of water. The resulting mixture was extracted with 3×30 mL of ethyl acetate. The combined organic layers were washed with 2×20 mL of $H_2O$, then concentrated under vacuum. The crude product was re-crystallized from PE:EA in the ratio of 10:1. This resulted in 11.5 mg (0.51%) of I-80 as a grey solid. (ES, m/z): [M−H]⁻ 417.9, ¹H-NMR (400 MHz, DMSO-$d_6$, ppm): δ15.19 (s, 1H), δ8.92-8.90 (m, 1H), δ7.75-7.74 (d, J=2.4 Hz, 1H), δ7.63-7.61 (m, 2H), δ7.50-7.46 (m, 2H), δ7.39-7.35 (m, 1H), δ7.33-7.28 (m, 3H).

Synthesis of I-81

Into a 30-mL sealed tube, was placed I-80 (200 mg, 0.48 mmol, 1 equiv), NMP (3 mL), $Zn(CN)_2$ (111.7 mg, 0.95 mmol, 2 equiv), and $Pd(PPh_3)_4$ (109.9 mg, 0.10 mmol, 0.200 equiv). The final reaction mixture was irradiated with microwave radiation for 1 h at 120° C. The resulting mixture was diluted with 5 mL of water, then extracted with 3×20 mL of dichloromethane. The combined organic layers were concentrated under vacuum. The crude product was purified by Flash-Prep-HPLC with the following conditions (IntelFlash-1): Column, C18; mobile phase, water:acetonitrile=90:10 increasing to water:acetonitrile=0:100 within 40 min, Detector, 254 nm. This resulted in 12.4 mg (7.1%) of I-81 as a grey solid. (ES, m/z): [M−H]⁻ 365.2, ¹H-NMR (300 MHz, DMSO-$d_6$, ppm): δ8.91-8.89 (m, 1H), δ8.01-8.00 (d, J=2.4 Hz, 1H), δ7.63-7.61 (m, 2H), δ7.57-7.56 (d, J=2.4 Hz, 1H), δ7.51-7.46 (m, 2H), δ7.39-7.27 (m, 3H).

Example 268. Synthesis of 5-(3,5-dichlorobenzamido)-2-fluoro-[1,1'-biphenyl]-4-carboxylic Acid, I-318

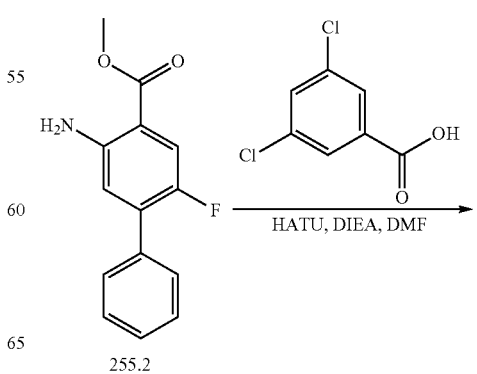

673

-continued

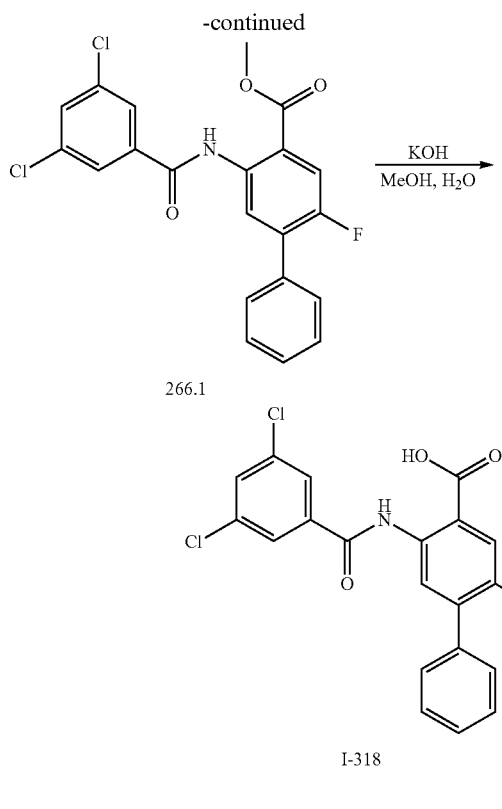

266.1

I-318

Synthesis of Compound 268.1

To a solution of 255.2 (150 mg, 0.612 mmol, 1 equiv) in DMF (2 mL) was added 3,5-dichlorobenzoic acid (140.1 mg, 0.734 mmol, 1.2 equiv), DIEA (158.0 mg, 1.223 mmol, 2 equiv), and HATU (348.8 mg, 0.917 mmol, 1.5 equiv). The resulting solution was stirred overnight at 40° C. in an oil bath, then diluted with 50 mL of H₂O and extracted with 3×20 mL of ethyl acetate. The combined organics were concentrated under vacuum. The residue was applied onto a prep TLC with ethyl acetate/petroleum ether (1:1). This resulted in 130 mg (51%) of 268.1 as a yellow solid.

Synthesis of I-318

To a solution of 268.1 (120 mg, 0.287 mmol, 1 equiv) in MeOH (10 mL)/H₂O (10 mL) was added KOH (160.9 mg, 2.869 mmol, 10 equiv). The resulting solution was stirred overnight at 40° C. in an oil bath. The solution was concentrated under vacuum, then the resulting solution was diluted with 100 mL of H₂O. The pH value of the solution was adjusted to 6 with AcOH. The resulting solution was extracted with 3×50 mL of ethyl acetate. The combined organics were concentrated. The crude product was purified by Flash-Prep-HPLC with the following conditions (Intel-Flash-1): Column, C18 silica gel; mobile phase, ACN/H₂O=15% increasing to ACN/H₂O=60% within 15 min; Detector, UV: 254 nm. This resulted in 15.5 mg (13%) of I-318 as a white solid. (ES, m/z): [M−H]⁻ 402.0, ¹H-NMR (400 MHz, DMSO-d₆, ppm): δ12.35 (s, 1H), 8.66-8.64 (d, J=7.6 Hz, 1H), 7.94-7.91 (d, J=12 Hz, 3H), 7.90-7.84 (t, J=8.4 Hz, 1H), 7.65-7.59 (m, 2H), 7.59-7.53 (m, 2H), 7.53-7.46 (m, 1H).

674

Example 269. Synthesis of 3-(2-(3,5-dichlorophenyl)acetamido)-[1,1'-biphenyl]-4-carboxylic Acid, I-280

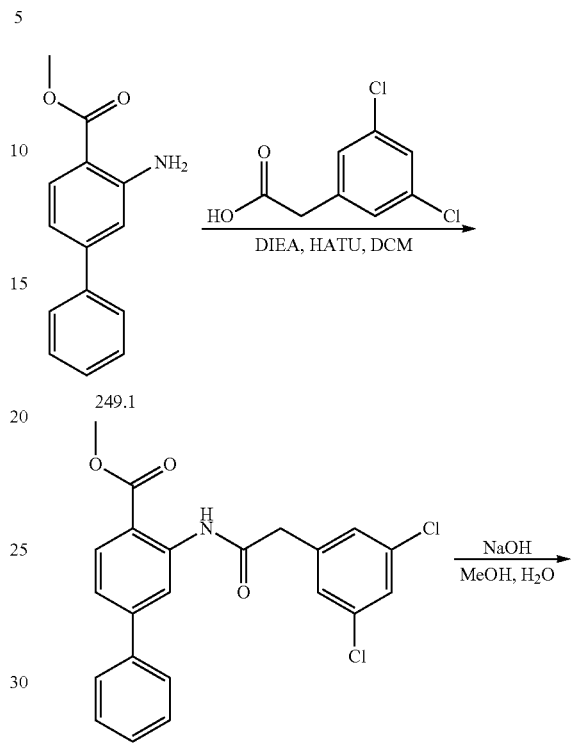

249.1

269.1

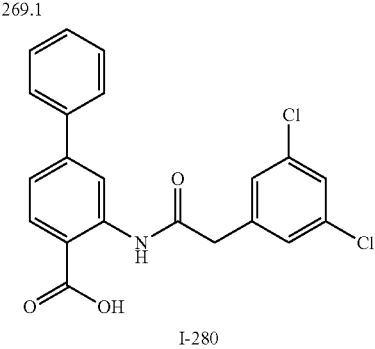

I-280

Synthesis of Compound 269.1

To a stirred mixture of 2-(3,5-dichlorophenyl)acetic acid (400 mg, 1.95 mmol, 1 equiv) and 249.1 (886.8 mg, 3.90 mmol, 2 equiv) in DCM (4 mL) were added DIEA (1008.6 mg, 7.80 mmol, 4 equiv) and HATU (1483.6 mg, 3.90 mmol, 2 equiv) in portions at room temperature under nitrogen atmosphere. The resulting solution was stirred overnight at room temperature under nitrogen atmosphere, then quenched with water. The aqueous layer was extracted with EtOAc (2×100 mL). The crude product was purified by reverse phase flash with the following conditions (from CH₃CN:H₂O=1:20 to CH₃CN:H₂O=50:50 in 30 mins, UV: 254/220) to afford 269.1 (500 mg, 61.8%) as an off-white solid.

Synthesis of I-280

A mixture of 269.1 (200 mg, 0.48 mmol, 1 equiv) and NaOH (96.5 mg, 2.41 mmol, 5 equiv) in MeOH/H₂O (3 mL)

was stirred for 2 h at room temperature under nitrogen atmosphere. The reaction was quenched with HCl (1 M). The aqueous layer was extracted with EtOAc (2×100 mL). The residue was purified by Prep-TLC (CH$_2$Cl2/MeOH 10:1) to afford I-280 (134.7 mg, 69.7%) as an off-white solid. (ES, m/z): [M+H]$^+$ 400.1, $^1$H-NMR (400 MHz, DMSO-d$_6$, ppm): δ 13.65 (s, 1H), 11.21 (s, 1H), 8.84 (s, 1H), 8.06-7.98 (m, 1H), 7.72-7.42 (m, 9H), 3.90 (s, 2H).

Example 270. Synthesis of 3,5-dichloro-N-(4-fluoro-[1,1'-biphenyl]-3-yl)-2-hydroxybenzamide, I-27

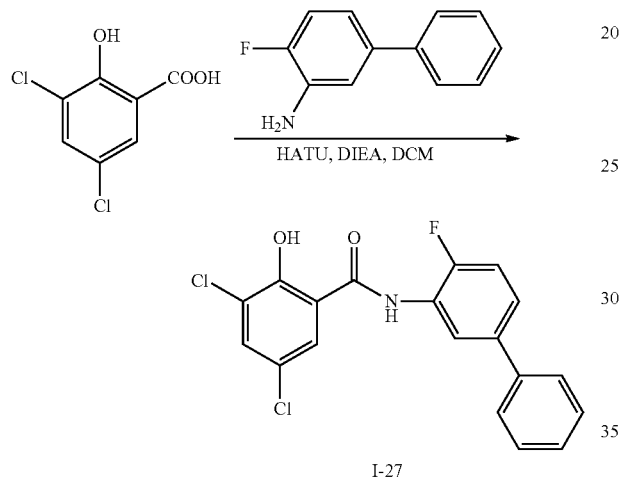

I-27

Synthesis of I-27

Into a 50-mL, 3-necked round-bottom flask, was placed DCM (5 mL), 3,5-dichloro-2-hydroxybenzoic acid (55 mg, 0.27 mmol, 1 equiv), DIEA (103.0 mg, 0.80 mmol, 3 equiv), 2-fluoro-5-phenylaniline (99.5 mg, 0.53 mmol, 2 equiv), and HATU (141.4 mg, 0.37 mmol, 1.4 equiv). The resulting solution was stirred for 12 h at 25° C. The reaction was then quenched by the addition of 10 mL of water. The resulting mixture was extracted with 3×20 mL of ethyl acetate, and the organic layers were combined and concentrated under vacuum. The residue was applied onto Prep-TLC with dichloromethane/methanol (20:1). The resulting material was further purified by Flash-Prep-HPLC with the following conditions (IntelFlash-1): Column, C18; mobile phase, H$_2$O:ACN=15% increasing to H$_2$O:ACN=60% within 10 min; Detector, 220/254 nm. This resulted in 27.1 mg (27.1%) of I-27 as a white solid. (ES, m/z): [M–H]$^-$ 373.9, $^1$H-NMR (300 MHz, CD$_3$OD, ppm): δ7.28-7.47 (m, 2H), δ7.48-7.53 (m, 3H), δ7.63-7.66 (m, 3H), δ8.03-8.28 (m, 1H), δ8.31-8.32 (d, J=2.4 Hz, 1H).

Example 271. Synthesis of 3,5-dichloro-2-hydroxy-N-(4-methoxy-[1,1'-biphenyl]-3-yl)benzamide, I-18

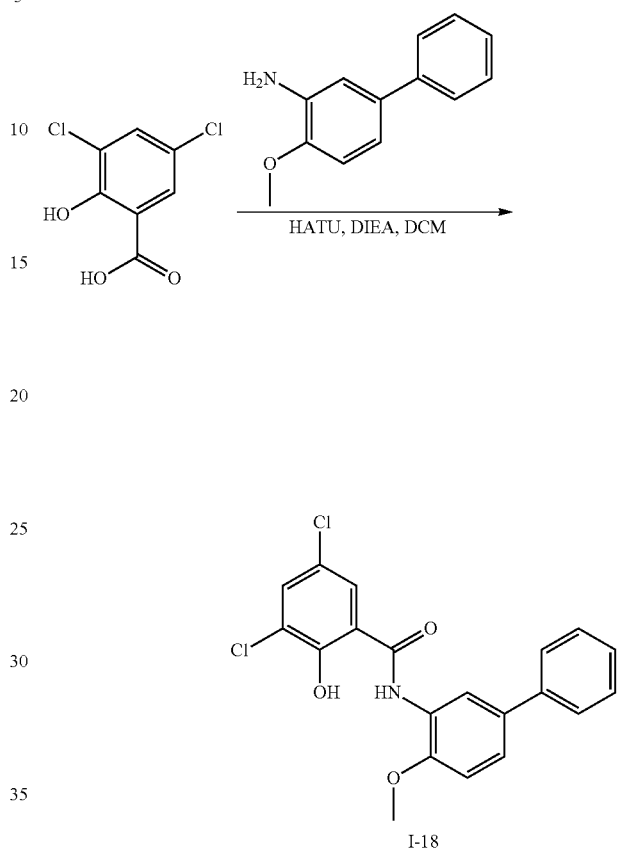

I-18

Synthesis of I-18

Into a 100-mL, 3-necked round-bottom flask purged and maintained with an inert atmosphere of nitrogen, was placed 3,5-dichloro-2-hydroxybenzoic acid (2 g, 9.66 mmol, 1.00 equiv), 2-methoxy-5-phenylaniline (2.3 g, 11.5 mmol, 1.20 equiv), DIEA (2.5 g, 19.3 mmol, 2.00 equiv), DCM (20 mL), and HATU (7.3 g, 19.20 mmol, 2.00 equiv). The resulting solution was stirred for 12 h at room temperature, then diluted with 20 mL of water. The resulting mixture was extracted with 3×20 mL of dichloromethane. The organic layers were combined, washed with 20 mL of saturated brine, dried, and concentrated under vacuum. The residue was applied onto a silica gel column with ethyl acetate/petroleum ether (1:1). This resulted in 61.2 mg (2%) of I-18 as a white solid. (ES, m/z): [M+H]$^+$ 388.1, $^1$H-NMR (400 MHz, DMSO-d$_6$, ppm): δ3.92 (s, 3H), δ7.21-7.23 (m, 1H), δ7.32-7.36 (m, 1H), δ7.44-7.48 (m, 2H), δ7.52-7.54 (m, 1H), δ7.62-7.63 (m, 2H), δ7.83 (s, 1H), δ8.12 (s, 1H), δ8.24 (s, 1H), δ10.78 (s, 1H), δ12.68 (br s, 1H).

Example 272. Synthesis of 3-(3,5-dichlorobenzamido)-[1,1'-biphenyl]-4-carboxylic Acid, I-260

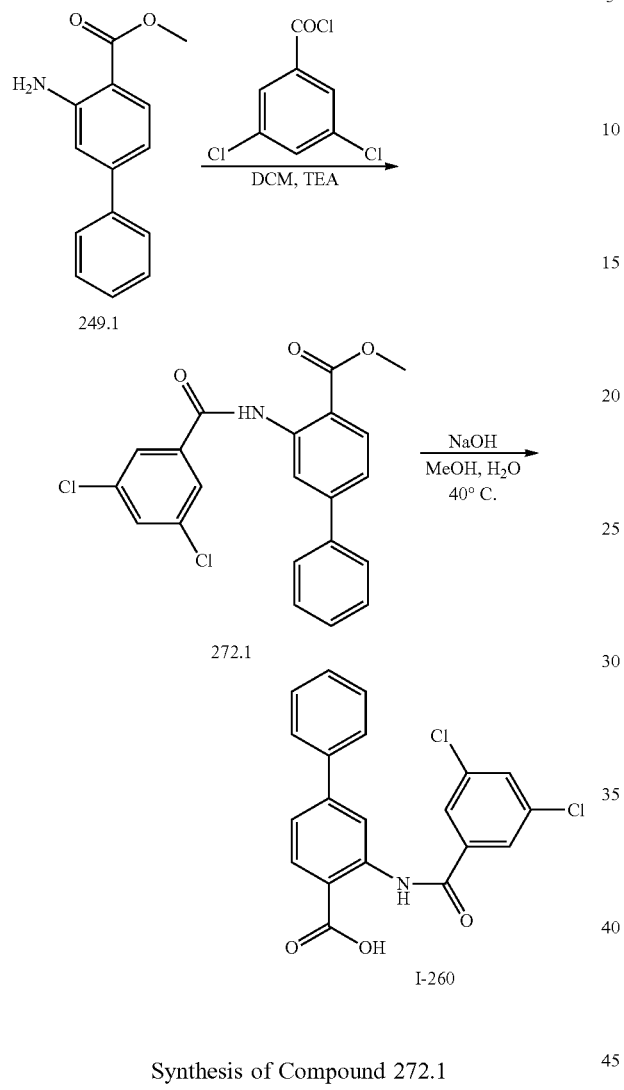

Synthesis of Compound 272.1

Into a 10-mL round-bottom flask, was placed 249.1 (200 mg, 0.88 mmol, 1 equiv), DCM (3 mL), TEA (267.1 mg, 2.64 mmol, 3.00 equiv), 3,5-dichlorobenzoyl chloride (202.7 mg, 0.96 mmol, 1.10 equiv). The resulting solution was stirred overnight at room temperature, then concentrated. The crude product was purified by Flash-Prep-HPLC with the following conditions (IntelFlash-1): Column, C18 silica gel; mobile phase, ACN/H$_2$O=15% increasing to ACN/H$_2$O=60% within 15 min. This resulted in 352 mg (99%) of 272.1 as a yellow solid.

Synthesis of I-260

Into a 50-mL, 3-necked round-bottom flask, was placed 272.1 (50 mg, 0.12 mmol, 1 equiv), MeOH (16 mL), H$_2$O (2 mL), and NaOH (15.0 mg, 0.38 mmol, 3.00 equiv). The resulting solution was stirred overnight at 40° C., then concentrated. The residue was applied onto a silica gel column with dichloromethane/methanol (10:1). This resulted in 7.8 mg (16%) of I-260 as a white solid. (ES, m/z): [M+H]$^+$ 386.1, $^1$H-NMR (400 MHz, DMSO-d$_6$, ppm): δ 14.24 (s, 1H), 8.97 (s, 1H), 8.20-8.18 (d, J=8 Hz, 1H), 7.85 (s, 2H), 7.76 (s, 1H), 7.70-7.68 (d, J=7.6 Hz, 2H), 7.54-7.51 (t, J=7.2 Hz, 2H), 7.44-7.42 (m, 2H).

Example 273. Synthesis of 3-bromo-5-chloro-N-(4-fluoro-[1,1'-biphenyl]-3-yl)-2-hydroxy-N-methyl-benzenesulfonamide, I-370

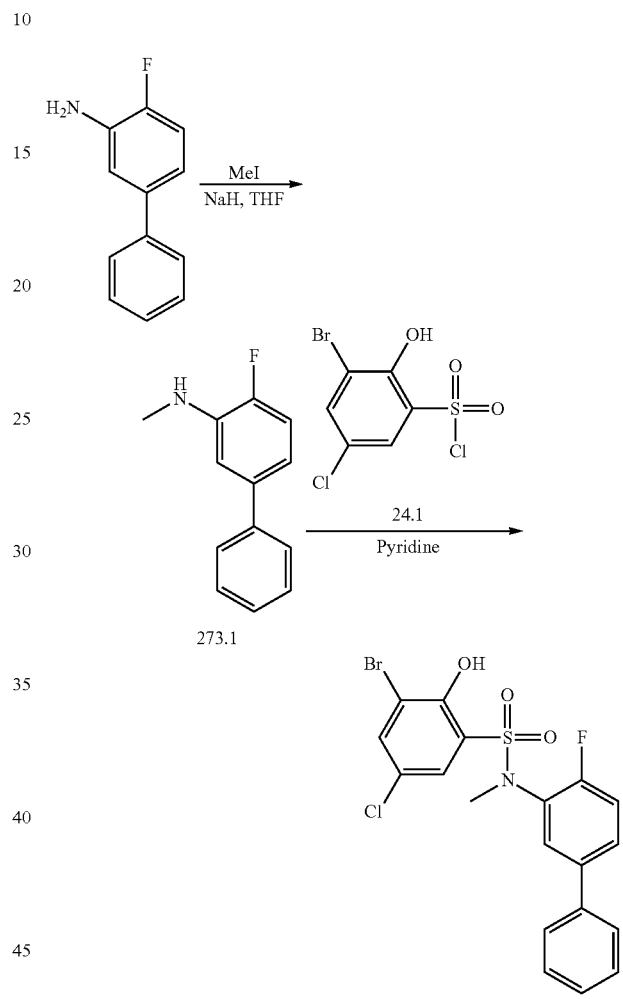

Synthesis of Compound 273.1

Into a 8-mL vial, was placed 4-fluoro-[1,1-biphenyl]-3-amine (200 mg, 1.06 mmol, 1 equiv), THF (4 mL), NaH (51.2 mg, 2.13 mmol, 2 equiv), and iodomethane (333.2 mg, 2.13 mmol, 2 equiv). The resulting solution was stirred for 2 hr at 0° C. in an ice/salt bath. The crude product was purified by Flash-Prep-HPLC with the following conditions (IntelFlash-1): Column, C18 silica gel; mobile phase, ACN/H$_2$O=15% increasing to ACN/H$_2$O=60% within 9 min; Detector, UV: 254 nm. This resulted in 142 mg (66.05%) of 273.1 as a yellow solid.

Synthesis of I-370

Into a 8-mL vial, was placed 273.1 (113 mg, 0.562 mmol, 1 equiv), pyridine (5 mL), and 24.1 (206.1 mg, 0.674 mmol, 1.2 equiv). The resulting solution was stirred for 2 h at room temperature. The crude product was purified by Flash-Prep-HPLC with the following conditions (IntelFlash-1): Column, C18 silica gel; mobile phase, ACN/H$_2$O=16% increasing to ACN/H$_2$O=60% within 20 min; Detector, UV: 254 nm. This resulted in 38.4 mg (14.5%) of I-370 as a white solid. (ES, m/z): [M+H]$^+$ 469.8, $^1$H-NMR (400 MHz, DMSO-d$_6$, ppm): δ11.25 (s, 1H), δ7.99 (s, 1H), δ7.68-7.62 (m, 1H), δ7.62-7.31 (m, 8H), δ3.30 (s, 3H).

Example 274. Synthesis of N-([1,1'-biphenyl]-3-ylmethyl)-N-benzyl-3,5-dichloro-2-hydroxybenzenesulfonamide, I-67

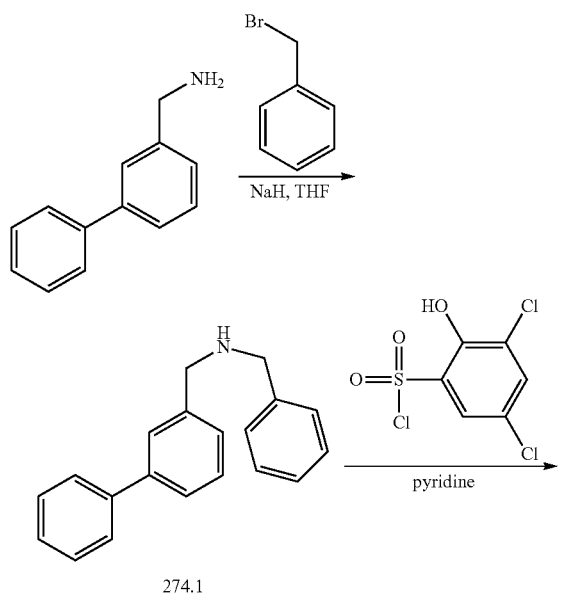

Synthesis of Compound 274.1

Into a 250-mL, 3-necked round-bottom flask purged and maintained with an inert atmosphere of nitrogen, was placed (3-phenylphenyl)methanamine (1 g, 5.5 mmol, 1 equiv), NaH (0.2 g, 5 mmol, 1.5 equiv), THF (24 mL), and (bromomethyl)benzene (1.4 g, 8.2 mmol, 1.5 equiv). The resulting solution was stirred for 12 h at 0° C. The reaction was then quenched by the addition of 50 mL of water. The resulting solution was extracted with 3×50 mL of ethyl acetate, and the combined organic layers were concentrated under vacuum. The residue was applied onto a silica gel column with dichloromethane/methanol (10:1). This resulted in 199.1 mg (13.3%) of 274.1 as a white solid.

Synthesis of I-67

Into a 100-mL round-bottom flask purged and maintained with an inert atmosphere of nitrogen, was placed 274.1 (199 mg, 0.73 mmol, 1 equiv), 3,5-dichloro-2-hydroxybenzene-1-sulfonyl chloride (228.4 mg, 0.87 mmol, 1.2 equiv), and pyridine (5 mL). The resulting solution was stirred for 0.5 h at room temperature. The resulting solution was diluted with 10 mL of water, then extracted with 3×10 mL of ethyl acetate. The organic layers were washed with 10 mL of brine, dried, and concentrated under reduced pressure. The residue was applied onto a silica gel column with ethyl acetate/petroleum ether (1:1). This resulted in 52.8 mg (14.5%) of I-67 as a yellow semi-solid. (ES, m/z): [M–H]$^-$ 496.0, $^1$H-NMR (400 MHz, DMSO-d$_6$, ppm): δ4.49-4.52 (d, J=14.4 Hz, 4H), δ7.09-7.11 (d, J=7.6 Hz, 1H), δ7.20-7.40 (m, 8H), δ7.43-7.49 (m, 5H), δ7.56-7.57 (d, J=2.4 Hz, 1H), δ7.68-7.69 (d, J=2.8 Hz, 1H).

Example 275. Synthesis of 5-((3,5-dichlorobenzyl)amino)-2-fluoro-[1,1'-biphenyl]-4-carboxylic Acid, I-317

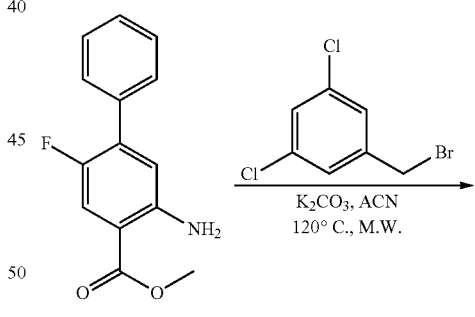

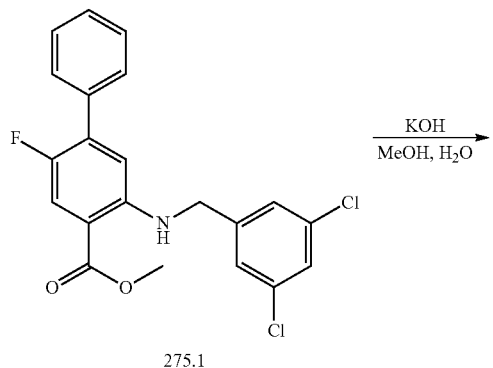

-continued

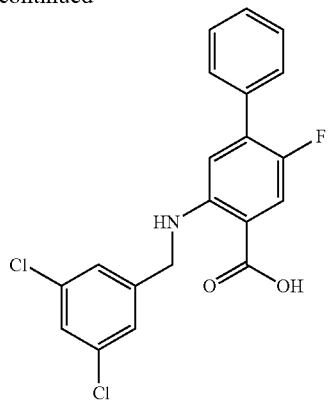

I-317

Synthesis of Compound 275.1

Into a 20-mL round-bottom flask, was placed 255.2 (180 mg, 0.734 mmol, 1 equiv), 1-(bromomethyl)-3,5-dichlorobenzene (176.0 mg, 0.734 mmol, 1 equiv), $K_2CO_3$ (202.8 mg, 1.468 mmol, 2 equiv), and ACN (10 mL). The resulting solution was stirred for 2 h at 120° C. with microwave irradiation. The solids were filtered out, and the filtrate was concentrated under vacuum. The residue was applied onto a prep TLC with ethyl acetate/petroleum ether (1:1). This resulted in 129 mg (43%) of 275.1 as a yellow oil.

Synthesis of I-317

Into a 50-mL round-bottom flask, was placed 275.1 (119 mg, 0.294 mmol, 1 equiv), MeOH (10 mL), KOH (165.1 mg, 2.944 mmol, 10 equiv), and $H_2O$ (10 mL). The resulting solution was stirred overnight at 60° C. in an oil bath, then concentrated under vacuum. The resulting solution was diluted with 100 mL of $H_2O$, and the pH value was adjusted to 6 with AcOH. The resulting solution was extracted with 3×50 mL of ethyl acetate. The combined organics were concentrated under vacuum. The crude product was purified by Flash-Prep-HPLC with the following conditions (IntelFlash-1): Column, C18 silica gel; mobile phase, ACN/$H_2O$=15% increasing to ACN/$H_2O$=60%; Detector, UV: 254. This resulted in 19.7 mg (17%) of I-317 as a yellow solid. (ES, m/z): [M–H]⁻ 388.0, ¹H-NMR (400 MHz, DMSO-$d_6$, ppm): δ 7.64-7.61 (d, J=11.6 Hz, 1H), 7.53-7.39 (m, 8H), 6.69-6.67 (d, J=6.4 Hz, 1H), 4.59 (s, 2H).

Example 276. Synthesis of 5-((3,5-dichloro-N-methylphenyl)sulfonamido)-2-fluoro-[1,1'-biphenyl]-4-carboxylic Acid, I-325

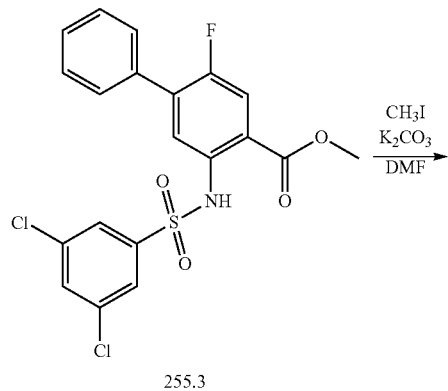

255.3

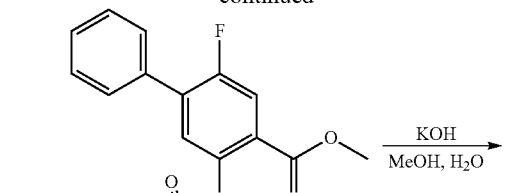

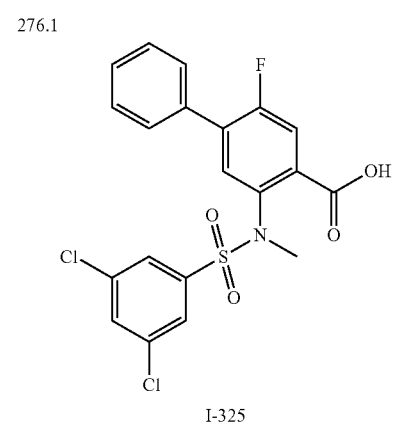

276.1

I-325

Synthesis of Compound 276.1

Into a 20-mL vial purged and maintained with an inert atmosphere of nitrogen, was placed 255.3 (180 mg, 0.396 mmol, 1 equiv), DMF (8 mL), $K_2CO_3$ (109.5 mg, 0.792 mmol, 2 equiv), and $CH_3I$ (112.4 mg, 0.792 mmol, 2 equiv). The resulting solution was stirred overnight at 50° C. in an oil bath. The mixture was diluted with 50 mL of $H_2O$, then extracted with 3×30 mL of ethyl acetate. The combined organics were concentrated under vacuum. The residue was applied onto a prep TLC with ethyl acetate/petroleum ether (1:2). This resulted in 182 mg (98%) of 276.1 as a yellow oil.

Synthesis of I-325

Into a 50-mL round-bottom flask, was placed 276.1 (182 mg, 0.389 mmol, 1 equiv), MeOH (10 mL), KOH (218.0 mg, 3.886 mmol, 10 equiv), and $H_2O$ (10 mL). The resulting solution was stirred overnight at 60° C. in an oil bath. The pH value of the solution was adjusted to 6 with AcOH. The resulting mixture was concentrated under vacuum. The resulting solution was diluted with 100 mL of $H_2O$, then extracted with 3×50 mL of ethyl acetate. The combined organics were concentrated under vacuum. The crude product was purified by Flash-Prep-HPLC with the following conditions (IntelFlash-1): Column, C18 silica gel; mobile phase, ACN/$H_2O$=15% increasing to ACN/$H_2O$=60% within 15 min; Detector, UV: 254. This resulted in 12.1 mg (7%) of I-325 as a white solid. (ES, m/z): [M–H]⁻ 452.0, ¹H-NMR (300 MHz, DMSO-$d_6$, ppm): δ 8.02 (s, 1H), 7.69 (s, 2H), 7.56-7.41 (m, 6H), 7.15-7.13 (d, J=7.2 Hz, 1H), 3.25 (s, 3H).

Example 277. Synthesis of 3-((3,5-dichloro-2-ethoxyphenyl)sulfonamido)-[1,1'-biphenyl]-4-carboxylic Acid, I-348

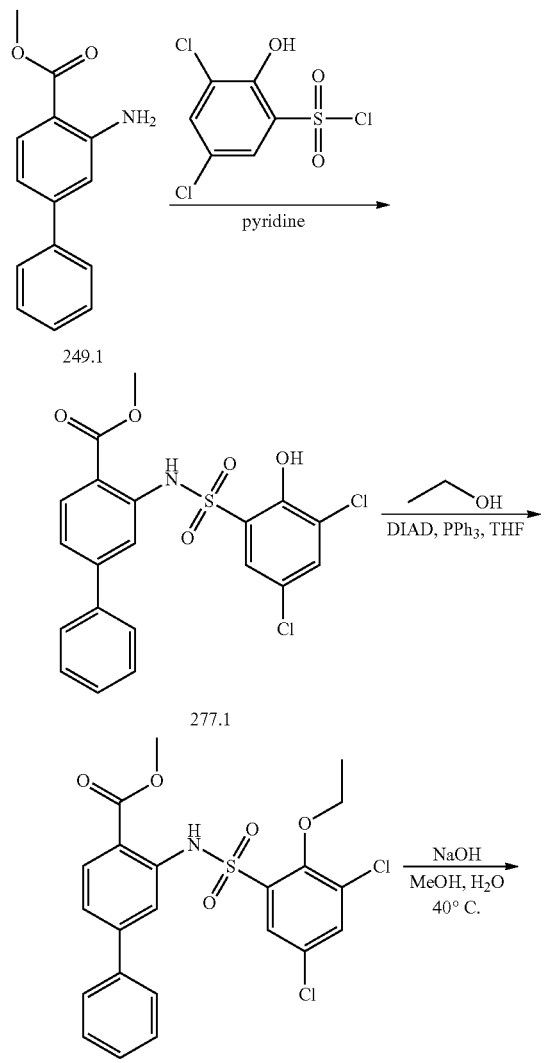

Synthesis of Compound 277.1

Into a 25-mL round-bottom flask, was placed 249.1 (200 mg, 0.880 mmol, 1 equiv), pyridine (4 mL), and 3,5-dichloro-2-hydroxybenzene-1-sulfonyl chloride (230.13 mg, 0.880 mmol, 1 equiv). The resulting solution was stirred for 10 min at room temperature, then concentrated. The pH value of the solution was adjusted to 5-6 with HCl (1 mol/L). The resulting solution was extracted with 3×20 mL of ethyl acetate, and the combined organic layers were concentrated. The residue was applied onto a silica gel column with dichloromethane/methanol (10:1). This resulted in 170 mg (43%) of 277.1 as a solid.

Synthesis of Compound 277.2

Into a 25-mL round-bottom flask, was placed 277.1 (150 mg, 0.332 mmol, 1 equiv), THF (4 mL), DIAD (134.1 mg, 0.663 mmol, 2 equiv), ethanol (15.2 mg, 0.332 mmol, 1 equiv), and PPh$_3$ (173.9 mg, 0.663 mmol, 2 equiv). The resulting solution was stirred for 12 h at room temperature. The resulting solution was extracted with 3×20 mL of ethyl acetate. The combined organics were concentrated. The residue was applied onto a silica gel column with ethyl acetate/petroleum ether (1:10). This resulted in 165 mg (92%) of 277.2 as a solid.

Synthesis of I-348

Into a 25-mL round-bottom flask, was placed 277.2 (100 mg, 0.208 mmol, 1 equiv), MeOH (4 mL), H$_2$O (1 mL), and NaOH (166.5 mg, 4.164 mmol, 20 equiv). The resulting solution was stirred for 12 h at 40° C. in an oil bath. The pH value of the solution was adjusted to 5-6 with HCl (1 mol/L). The solids were collected by filtration. The crude product was purified by Flash-Prep-HPLC with the following conditions (IntelFlash-1): Column, C18 silica gel; mobile phase, CH$_3$CN/H$_2$O=1:1 to CH$_3$CN/H$_2$O=1:2 within 25 min; This resulted in 25.8 mg (27%) of I-348 as a white solid. (ES, m/z): [M−H]$^-$ 464.0, $^1$H-NMR (400 MHz, DMSO-d$_6$, ppm): δ 8.02-7.96 (m, 3H), 7.62-7.20 (m, 7H), 4.20-4.17 (m, 2H), 1.43-1.39 (t, J=6.4 Hz, 3H).

Example 278. Synthesis of 3-((3,5-dichloro-2-fluorophenyl)sulfonamido)-[1,1'-biphenyl]-4-carboxylic Acid, I-342

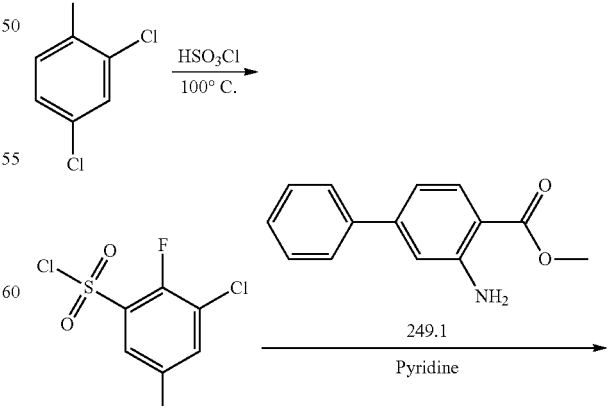

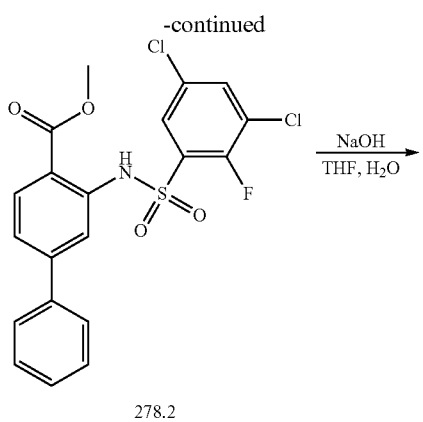

278.2

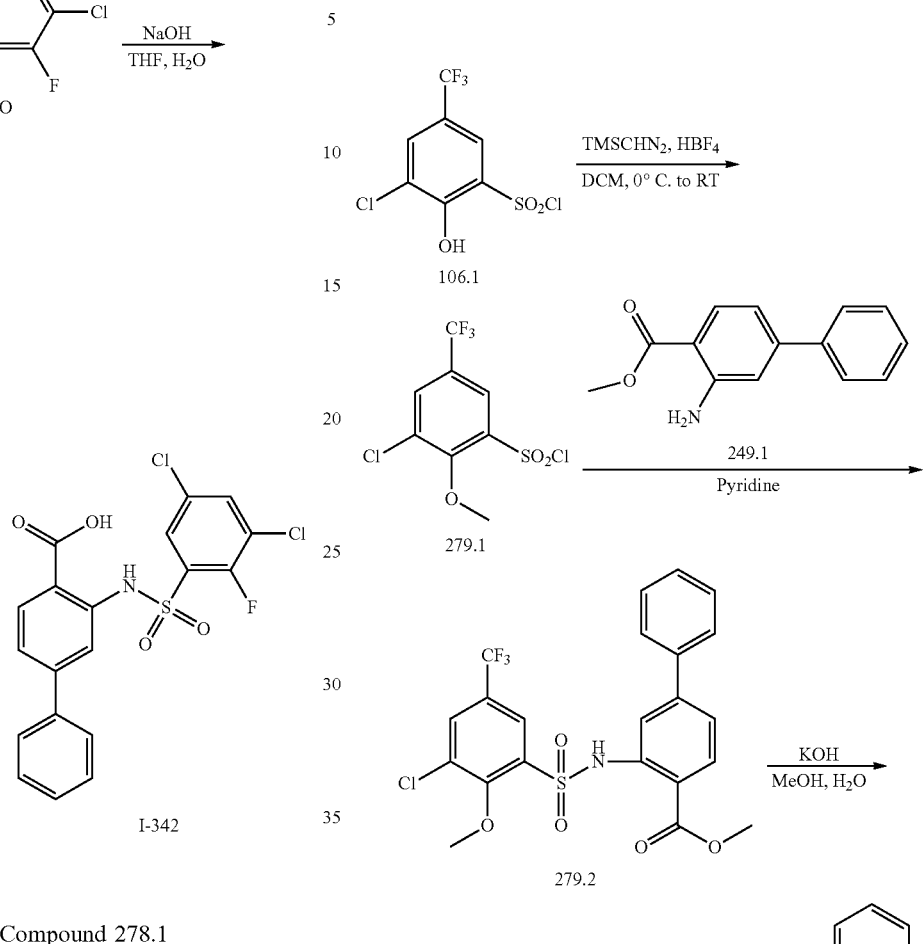

Synthesis of Compound 278.1

Into a 100-mL round-bottom flask, was placed sulfonoperoxoyl chloride (10 mL) and 2,4-dichloro-1-fluorobenzene (1 g, 6.0 mmol, 1 equiv). The resulting solution was stirred for 12 hr at 100° C. The reaction was then quenched by the addition of 100 mL of water/ice. The resulting solution was extracted with 3×150 mL of ethyl acetate. The organic layers were combined and concentrated. This resulted in 1 g (63%) of 278.1 as a black solid.

Synthesis of I-342

I-342 was prepared from 278.1 and 249.1 according to the procedures of the second and third steps of Example 249. I-342 was purified by Flash-Prep-HPLC with the following conditions (IntelFlash-1): Column, C18 silica gel; mobile phase, ACN:H$_2$O=10% increasing to ACN:H$_2$O=60% within 15 min; Detector, 254 nm. This resulted in 5.1 mg (1%, over two steps) of I-342 as an off-white solid. (ES, m/z): [M−H]⁻ 438.0, ¹H-NMR (400 MHz, DMSO-d$_6$, ppm): δ8.24-8.15 (m, 1H), δ7.99-7.89 (m, 2H), δ7.58-7.38 (m, 6H), δ7.27-7.21 (m, 1H), δ7.19-6.98 (m, 2H).

Example 279. Synthesis of 3-((3-chloro-2-methoxy-5-(trifluoromethyl)phenyl)sulfonamido)-[1,1'-biphenyl]-4-carboxylic Acid, I-296

Synthesis of Compound 279.1

Into a 50-mL, 3-necked round-bottom flask, was placed 106.1 (367 mg, 1.244 mmol, 1 equiv), DCM (20 mL), and HBF$_4$ (218.4 mg, 2.488 mmol, 2.00 equiv), then TMSCHN$_2$ (568.3 mg, 4.975 mmol, 4.00 equiv) was added dropwise at 0° C. The resulting solution was stirred for 1 h at room temperature, then concentrated. The crude product was purified by Flash-Prep-HPLC with the following conditions (IntelFlash-1): Column, C18 silica gel; mobile phase, ACN/H$_2$O=15% increasing to ACN/H$_2$O=60% within 15 min; Detector, 254 nm. This resulted in 284 mg (74%) of 279.1 as a yellow solid.

687

Synthesis of I-296

I-296 was prepared from 279.1 and 249.1 according to the procedures of the second and third steps of Example 249. I-296 was purified by Flash-Prep-HPLC with the following conditions (IntelFlash-1): Column, C18 silica gel; mobile phase, ACN/H$_2$O=15% increasing to ACN/H$_2$O=60% within 15 min. This resulted in 68.5 mg (16% over two steps) of I-296 as a white solid. (ES, m/z): [M−H]$^-$ 484.0, $^1$H-NMR (300 MHz, CD$_3$OD, ppm) δ 8.27-8.26 (d, J=1.8 Hz, 1H), 8.12-8.01 (m, 2H), 7.71-7.70 (d, J=1.8 Hz, 1H), 7.53-7.36 (m, 5H), 7.32-7.28 (m, 1H), 4.12 (s, 3H).

Example 279b. Synthesis of 3-((3,5-dichloro-2-methoxyphenyl)sulfonamido)-[1,1'-biphenyl]-4-carboxylic Acid, I-281

I-281

Synthesis of I-281

I-281 was prepared from 3,5-dichloro-2-hydroxybenzene-1-sulfonyl chloride and 249.1 according to the procedure described for I-296. I-281 was purified by Flash-Prep-HPLC with the following conditions (IntelFlash-1): Column, C18 silica gel; mobile phase, ACN/H$_2$O=15% increasing to ACN/H$_2$O=60% within 15 min. This resulted in 17.5 mg (3% over three steps) of I-281 as a white solid. (ES, m/z): [M−H]$^-$ 450.0, $^1$H-NMR (400 MHz, DMSO-d$_6$, ppm) δ 7.96-7.89 (m, 3H), 7.49-7.46 (m, 5H), 7.40-7.36 (m, 1H), 7.24-7.21 (d, J=12 Hz, 1H), 3.87 (s, 3H).

Example 280. Synthesis of 4-(benzo[b]thiophen-2-yl)-2-((3,5-dichloro-2-methoxyphenyl) sulfonamido) benzoic Acid, I-297

688

-continued

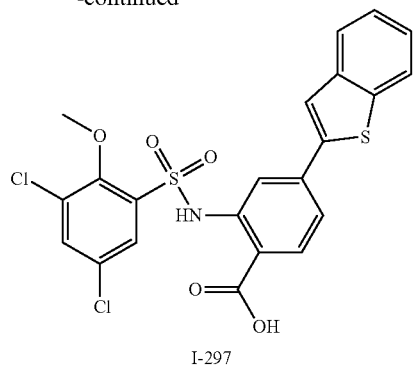

I-297

Synthesis of Compound 280.1

Compound 280.1 was prepared according to the procedure described for 279.2, replacing 3-chloro-2-hydroxy-5-(trifluoromethyl)benzene-1-sulfonyl chloride with 3,5-dichloro-2-hydroxybenzene-1-sulfonyl chloride and replacing 249.1 with 295.1.

Synthesis of I-297

Into a 25-mL round-bottom flask purged and maintained with an inert atmosphere of nitrogen, was placed 280.1 (100 mg, 0.19 mmol, 1 equiv), NaOH (38.3 mg, 0.96 mmol, 5.00 equiv), MeOH (8 mL), and H$_2$O (4 mL). The resulting solution was stirred for 12 h at 40° C. in an oil bath. The pH value of the solution was adjusted to 5 with HCl (1 M). The solids were collected by filtration. The resulting mixture was concentrated. This resulted in 33.6 mg (35%) of I-297 as a white solid. (ES, m/z): [M−H]$^-$ 505.9, $^1$H-NMR (400 MHz, DMSO-d$_6$, ppm) δ 8.01-7.94 (m, 4H), 7.91-7.86 (m, 2H), 7.66 (s, 1H), 7.44-7.37 (m, 3H), 7.23-6.95 (m, 2H), 3.89 (s, 3H).

Example 281. Synthesis of 5-(azetidine-1-carbonyl)-N-(4-fluoro-[1,1'-biphenyl]-3-yl)-2-oxo-1,2-dihydropyridine-3-sulfonamide, I-369

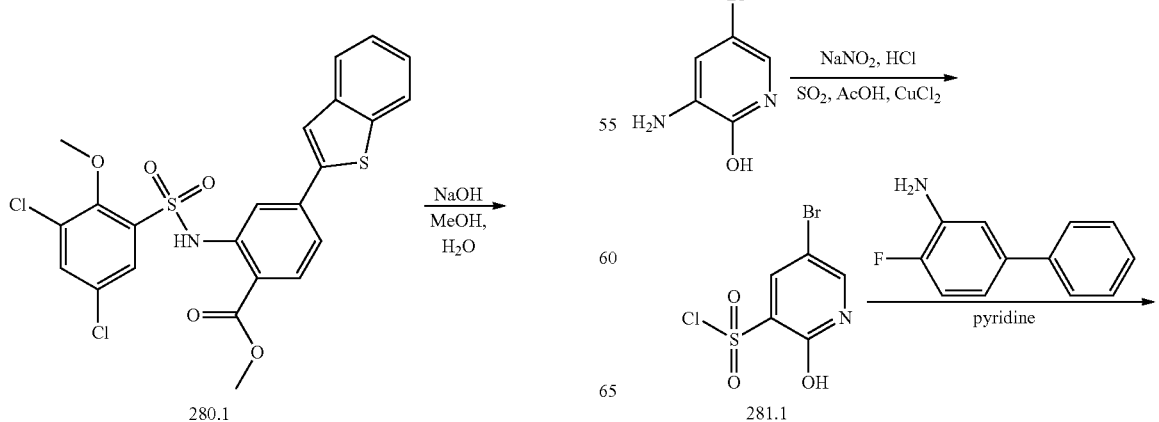

280.1

281.1

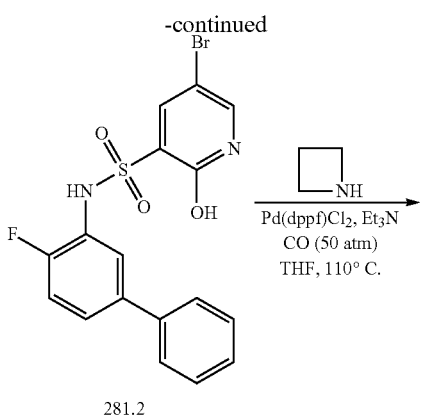

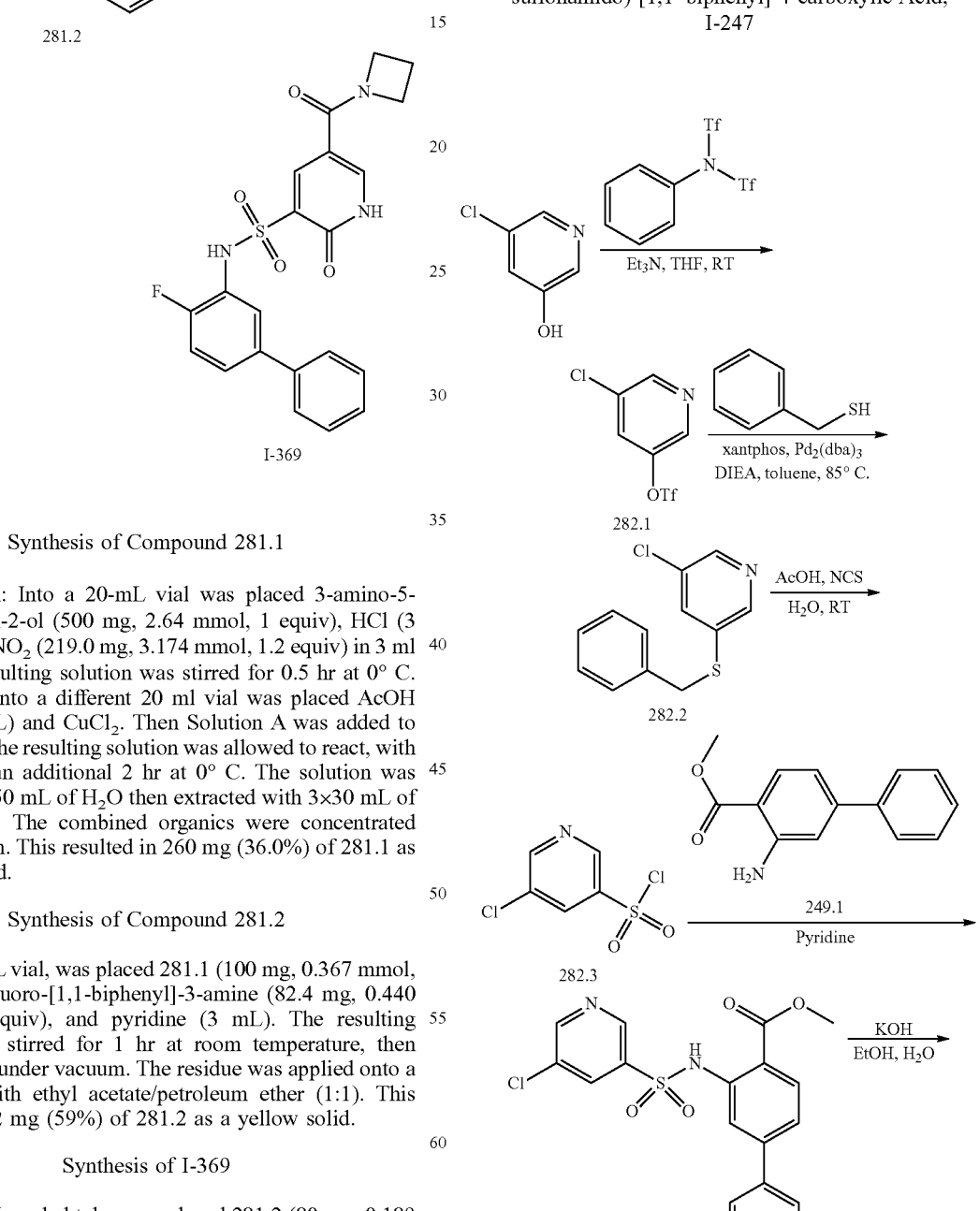

atmospheres of carbon monoxide. The residue was purified by reverse phase flash chromatography with the following conditions: column, C18 silica gel; mobile phase, MeOH in water, 10% to 50% gradient in 10 min; Detector, UV 254 nm. This resulted in 10.2 mg of I-369 as a white solid. (ES, m/z): [M+H]+ 428.3, $^1$H-NMR (300 MHz, CD$_3$OD, ppm) δ 8.30 (s, 1H), 8.14 (s, 1H), 7.68-7.67 (d, J=2.1 Hz, 1H), 7.57-7.49 (m, 2H), 7.48-7.41 (m, 2H), 7.40-7.30 (m, 1H), 7.14-7.11 (t, J=8.7 Hz, 1H), 4.13 (s, 4H), 2.23-2.20 (t, J=7.8 Hz, 2H).

Example 282. Synthesis of 3-((5-chloropyridine)-3-sulfonamido)-[1,1'-biphenyl]-4-carboxylic Acid, I-247

Synthesis of Compound 281.1

Solution A: Into a 20-mL vial was placed 3-amino-5-bromopyridin-2-ol (500 mg, 2.64 mmol, 1 equiv), HCl (3 mL), and NaNO$_2$ (219.0 mg, 3.174 mmol, 1.2 equiv) in 3 ml H$_2$O. The resulting solution was stirred for 0.5 hr at 0° C. Solution B: Into a different 20 ml vial was placed AcOH (SO$_2$) (10 mL) and CuCl$_2$. Then Solution A was added to Solution B. The resulting solution was allowed to react, with stirring, for an additional 2 hr at 0° C. The solution was diluted with 50 mL of H$_2$O then extracted with 3×30 mL of ethyl acetate. The combined organics were concentrated under vacuum. This resulted in 260 mg (36.0%) of 281.1 as a yellow solid.

Synthesis of Compound 281.2

Into a 8-mL vial, was placed 281.1 (100 mg, 0.367 mmol, 1 equiv), 4-fluoro-[1,1'-biphenyl]-3-amine (82.4 mg, 0.440 mmol, 1.2 equiv), and pyridine (3 mL). The resulting solution was stirred for 1 hr at room temperature, then concentrated under vacuum. The residue was applied onto a prep TLC with ethyl acetate/petroleum ether (1:1). This resulted in 92 mg (59%) of 281.2 as a yellow solid.

Synthesis of I-369

Into a 8-mL sealed tube, was placed 281.2 (80 mg, 0.189 mmol, 1 equiv), THF (10 mL), Et$_3$N (38.2 mg, 0.378 mmol, 2.00 equiv), azetidine (12.9 mg, 0.227 mmol, 1.20 equiv), and Pd(dppf)Cl2 (27.6 mg, 0.038 mmol, 0.20 equiv). The resulting solution was stirred for 2 hr at 110° C. under 50

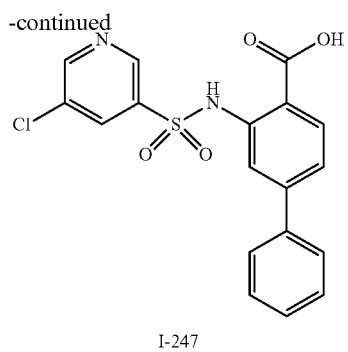

I-247

Synthesis of Compound 282.1

To a solution of 5-chloropyridin-3-ol (2 g, 15.4 mmol, 1 equiv) in THF (80 mL) was added Et$_3$N (1874.8 mg, 18.53 mmol, 1.2 equiv) and 1,1,1-trifluoro-N-phenyl-N-trifluoromethanesulfonylmethanesulfonamide (6067.1 mg, 16.98 mmol, 1.1 equiv). The resulting solution was stirred for 2 hr at room temperature, then concentrated under vacuum. The residue was applied onto a silica gel column with ethyl acetate/petroleum ether (1:3). This resulted in 3.57 g (88%) of 282.1 as a yellow oil.

Synthesis of Compound 282.2

To a solution of 282.1 (2 g, 7.65 mmol, 1 equiv) in toluene (40 mL) was added phenylmethanethiol (1044.5 mg, 8.41 mmol, 1.1 equiv), DIEA (1976.2 mg, 15.29 mmol, 2 equiv), xantphos (442.4 mg, 0.76 mmol, 0.1 equiv), and Pd$_2$(dba)$_3$ (350.0 mg, 0.38 mmol, 0.05 equiv). The resulting solution was stirred overnight at 85° C. in an oil bath. The solution was diluted with 200 mL of H$_2$O, then extracted with 3×100 mL of ethyl acetate. The combined organics were concentrated under vacuum. The residue was applied onto a silica gel column with ethyl acetate/petroleum ether (1:10). This resulted in 1.8 g (99%) of 282.2 as a yellow oil.

Synthesis of Compound 282.3

To a solution of 282.2 (1 g, 4.24 mmol, 1 equiv) in AcOH (15 mL)/H$_2$O (5 mL) was added NCS (1699.4 mg, 12.73 mmol, 3 equiv). The resulting solution was stirred for 2 hr at room temperature. The resulting mixture was concentrated under vacuum. This resulted in 600 mg (67%) of 282.3 as a yellow solid.

Synthesis of I-247

I-247 was prepared from 282.3 and 249.1 according to the procedures of the second and third steps of Example 249. I-247 was purified by Flash-Prep-HPLC with the following conditions (IntelFlash-1): Column, C18 silica gel; mobile phase, ACN/H$_2$O=15% increasing to ACN/H$_2$O=60% within 15 min, Detector, UV 254 nm. This resulted in 31.9 mg (12% over two steps) of I-247 as a white solid. (ES, m/z): [M−H]$^-$ 386.9, $^1$H-NMR (300 MHz, DMSO-d$_6$, ppm) δ 8.91-8.90 (d, J=2.1 Hz, 2H), 8.39 (s, 1H), 8.02-7.92 (m, 1H), 7.72-7.60 (m, 3H), 7.58-7.40 (m, 4H).

Example 283. Synthesis of 3,5-dichloro-N-(furan-3-yl)benzenesulfonamide, I-368

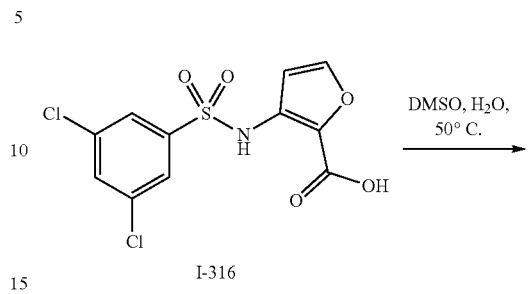

Synthesis of I-368

Into an 8-mL round-bottom flask, was placed I-316 (100 mg, 0.297 mmol, 1 equiv), DMSO (2 mL), and H$_2$O (0.4 mL). The resulting solution was stirred for 12 h at 50° C., then concentrated. The crude product was purified by Prep-HPLC with the following conditions: Column, 19*250 mm, 10 um; Mobile Phase A: Water (1% HAC), Mobile Phase B: ACN; Flow rate: 25 mL/min; Gradient: 52% B to 72% B in 7 min; Detector, 254/220 nm. This resulted in 38.4 mg (44.2%) of I-368 as a white solid. (ES, m/z): [M−H]$^-$ 290.1, $^1$H-NMR (300 MHz, DMSO-d$_6$, ppm) δ 10.23 (s, 1H), 7.99 (s, 1H), 7.72-7.71 (d, J=2.1 Hz, 2H) 7.54-7.51 (m, 2H), 6.28 (s, 1H).

Example 284. Synthesis of 3,5-dichloro-N-(3-(4-fluorophenyl)-1-isopropyl-1H-indol-2-yl)-2-hydroxybenzenesulfonamide, I-134

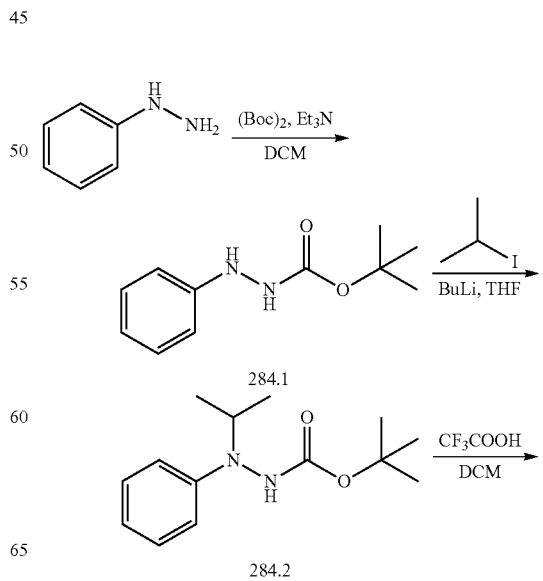

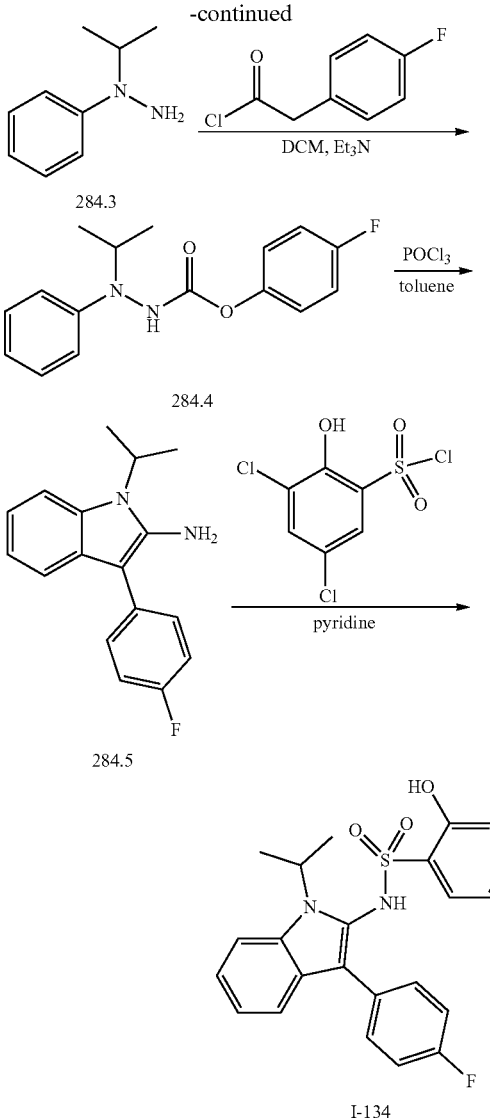

Synthesis of Compound 284.1

To a stirred solution of phenylhydrazine (5 g, 46.2 mmol, 1 equiv) and Et₃N (4.7 g, 46.2 mmol, 1 equiv) in DCM (50 mL) in an ice-water bath under nitrogen atmosphere was added di-tert-butyl dicarbonate (10.1 g, 46.2 mmol, 1 equiv) in portions. The resulting mixture was stirred overnight at room temperature under nitrogen atmosphere. The reaction was quenched by the addition of 20 mL of sat. NH₄Cl (aq.), then extracted with EtOAc (2×50 mL). The combined organics were dried over anhydrous Na₂SO₄, filtered, then concentrated under reduced pressure to afford 284.1 (8 g, 81%) as a white solid.

Synthesis of Compound 284.2

To a stirred solution of 284.1 in THF (80 mL) at −78° C. under nitrogen atmosphere was added n-BuLi (30 mL, 2.5 M, 2 equiv) dropwise over 30 min. The resulting mixture was stirred for 30 min at −78° C. under nitrogen atmosphere. To the above mixture was added 2-iodopropane (6.0 g, 35.5 mmol, 1 equiv) dropwise over 10 min at −78° C. The resulting mixture was stirred for an additional 2 h at room temperature. The reaction was quenched by the addition of 10 mL of sat.NH₄Cl (aq.), then extracted with EtOAc (2×50 mL). The combined organics were concentrated. The residue was purified by silica gel column chromatography, eluted with PE/EtOAc (5:1) to afford 284.2 (6.4 g, 72%) as a white solid.

Synthesis of Compound 284.3

To a stirred solution of 284.2 (3.0 g, 11.9 mmol, 1 equiv) in DCM was added CF₃COOH (3 mL, 40.3 mmol, 3.37 equiv) dropwise at room temperature under nitrogen atmosphere. The resulting mixture was stirred for 1 h, then neutralized to pH 7 with saturated NaHCO₃ (aq.). The aqueous layer was extracted with EtOAc (2×50 mL). The combined organics were concentrated under reduced pressure to afford 284.3 (1.8 g, 99%) as a white solid.

Synthesis of Compound 284.4

To a stirred solution of 284.3 (1.8 g, 11.9 mmol, 1 equiv) and 2-(4-fluorophenyl)acetyl chloride (1.8 g, 11.9 mmol, 1 equiv) in DCM (20 mL) was added Et₃N (3.1 g, 23.96 mmol, 2 equiv) in portions at room temperature under nitrogen atmosphere. The resulting mixture was stirred overnight at room temperature, then quenched by the addition of 10 mL of sat.NH₄Cl (aq.). The aqueous layer was extracted with EtOAc (2×30 mL). The combined organics were concentrated. The residue was purified by silica gel column chromatography, eluted with hexane/EtOAc (2:1) to afford 284.4 (3.0 g, 87%) as a white solid.

Synthesis of Compound 284.5

To a stirred solution of 284.4 (1.0 g, 3.49 mmol, 1 equiv) in toluene (10 ml) at room temperature under nitrogen atmosphere was added POCl₃ (1.1 g, 6.98 mmol, 2 equiv) in portions. The resulting mixture was stirred for 2 h at 100° C. under air atmosphere. The mixture was allowed to cool down to room temperature. The reaction was quenched by the addition of ice-water (20 mL), then basified to pH 7 with saturated NaHCO₃ (aq.). The aqueous layer was extracted with EtOAc (2×30 mL). The combined organics were concentrated. The residue was purified by Prep-TLC (PE/EtOAc 1:1) to afford 284.4 (530 mg, 56%) as a white solid.

Synthesis of I-134

To a stirred solution of 284.4 (200 mg, 0.75 mmol, 1 equiv) in pyridine (2 mL) was added 3,5-dichloro-2-hydroxybenzene-1-sulfonyl chloride (194.9 mg, 0.75 mmol, 1 equiv) at room temperature under nitrogen atmosphere. The resulting mixture was stirred overnight, then concentrated under reduced pressure. The residue was purified by Prep-TLC (CH₂Cl₂/MeOH=20:1) to afford I-134 (34.3 mg, 9%) as a white solid. (ES, m/z): [M−H]⁻ 491.0, ¹H-NMR (300 MHz, DMSO-d₆, ppm) δ 10.83 (s, 1H), δ7.73-7.71 (d, J=8.1 Hz, 1H), 7.49 (s, 1H), 7.42-7.40 (d, J=8.1 Hz, 1H), 7.28-7.20 (m, 3H), 7.17-7.01 (m, 2H), 6.98-6.92 (m, 2H), 6.07-4.98 (m, 1H), 1.63-1.61 (d, J=6.9 Hz, 6H).

Example 285. Synthesis of 3-((3-bromo-5-(methoxycarbonyl)phenyl)sulfonamido)-[1,1'-biphenyl]-4-carboxylic Acid, I-295; and 3-((3-bromo-5-carboxyphenyl)sulfonamido)-[1,1'-biphenyl]-4-carboxylic Acid, I-303

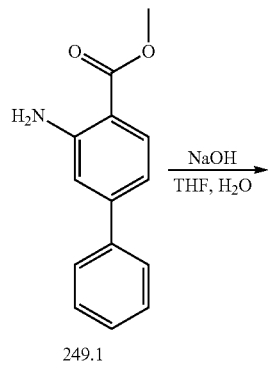

249.1

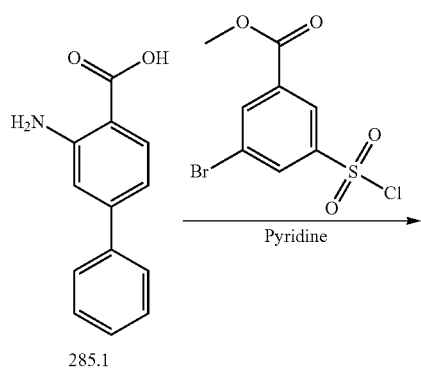

285.1

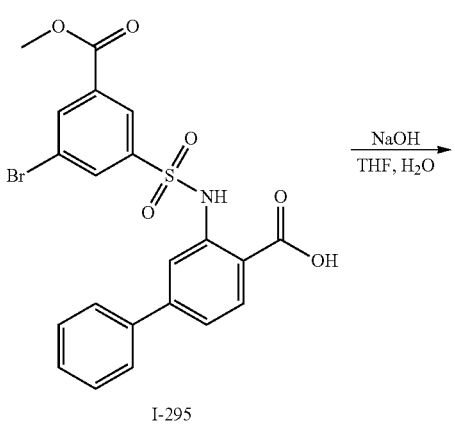

I-295

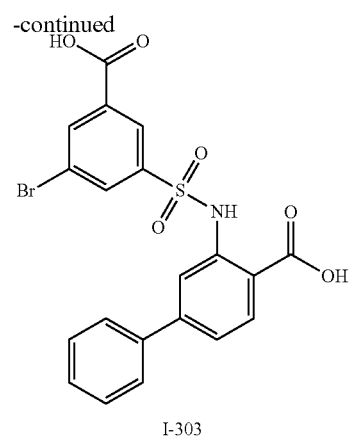

I-303

Synthesis of Compound 285.1

Into a 100-mL round-bottom flask, was placed 249.1 (200 mg, 0.880 mmol, 1 equiv), H$_2$O (5 mL), THF (5 mL), and NaOH (351.9 mg, 8.800 mmol, 10 equiv). The resulting solution was stirred for 12 h at 25° C. The reaction was then quenched by the addition of 20 mL of dilute hydrochloric acid. The resulting solution was extracted with 3×30 mL of ethyl acetate, and the combined organic layers were concentrated under vacuum. This resulted in 180 mg (95.9%) of 285.1 as a yellow solid.

Synthesis of I-295

Into a 50-mL round-bottom flask, was placed methyl 3-bromo-5-(chlorosulfonyl)benzoate (200 mg, 0.64 mmol, 1 equiv), 285.1 (163.2 mg, 0.77 mmol, 1.2 equiv), and pyridine (5 mL). The resulting solution was stirred for 12 h at 25° C. The reaction was then quenched by the addition of 20 mL of dilute hydrochloric acid. The resulting solution was extracted with 3×30 mL of ethyl acetate. The combined organic layers were concentrated under vacuum. The crude product was purified by Flash-Prep-HPLC with the following conditions (IntelFlash-1): Column, C18 silica gel; mobile phase, ACN:H$_2$O=15% increasing to ACN:H$_2$O=50%; Detector, 254 nm. This resulted in 30.4 mg (10%) of I-295 as a white solid. (ES, m/z): [M+H]$^+$490.0, $^1$H-NMR (400 MHz, DMSO-d$_6$, ppm) δ 8.28 (s, 1H), 8.22 (s, 2H), 7.94-7.92 (d, J=7.6 Hz, 1H), 7.62-7.44 (m, 6H), 7.33 (s, 1H), 7.22-6.95 (m, 1H), 3.87 (s, 3H).

Synthesis of I-303

Into a 50-mL round-bottom flask, was placed I-295 (30 mg, 0.06 mmol, 1 equiv), H$_2$O (3 mL), MeOH (3 mL), and NaOH (24.5 mg, 0.61 mmol, 10 equiv). The resulting solution was stirred for 12 h at 25° C. The reaction was then quenched by the addition of 10 mL of dilute hydrochloric acid. The resulting solution was extracted with 3×15 mL of ethyl acetate, and the combined organic layers were concentrated under vacuum. The crude product was purified by Flash-Prep-HPLC with the following conditions (IntelFlash-1): Column, C18 silica gel; mobile phase, ACN:H$_2$O=15% increasing to ACN:H$_2$O=60%; Detector, 254 nm. This resulted in 13.8 mg (17%) of I-303 as a white solid. (ES, m/z): [M+H]$^+$ 475.9, $^1$H-NMR (300 MHz, DMSO-d$_6$, ppm)

δ8.30 (s, 1H), δ8.12 (s, 2H), δ7.90-7.88 (d, J=8.1 Hz, 1H), δ7.55-7.37 (m, 6H), δ7.35 (s, 1H), δ7.25-7.14 (m, 2H), δ7.06-6.89 (m, 1H).

Example 286. Synthesis of 2-(3-((3,5-dichlorophenyl)sulfonamido)-[1,1'-biphenyl]-4-yl)acetamide, I-245

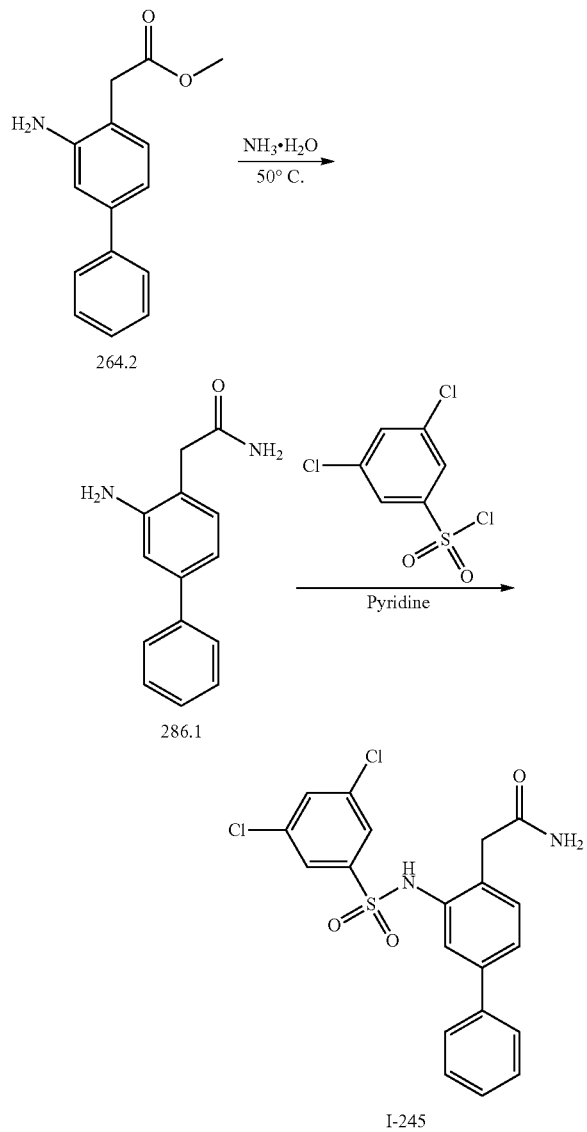

Synthesis of Compound 286.1

Into a 25-mL round-bottom flask purged and maintained with an inert atmosphere of nitrogen, was placed 264.2 (300 mg, 1.24 mmol, 1 equiv) and amine hydrate. The resulting solution was stirred for 12 hr at 50° C. in an oil bath, then concentrated. The residue was applied onto a silica gel column with dichloromethane/methanol (10:1). This resulted in 30 mg (11%) of 286.1 as a white solid.

Synthesis of I-245

Into an 8-mL round-bottom flask purged and maintained with an inert atmosphere of nitrogen, was placed 286.1 (30 mg, 0.13 mmol, 1 equiv), 3,5-dichlorobenzene-1-sulfonyl chloride (32.5 mg, 0.13 mmol, 1.00 equiv), and pyridine (0.5 mL). The resulting solution was stirred for 30 min at room temperature, then concentrated. The residue was applied onto a silica gel column with ethyl acetate/petroleum ether (1:1). This resulted in 50.5 mg (88%) of I-245 as a white solid. (ES, m/z): [M–H]⁻ 432.9, ¹H-NMR (400 MHz, DMSO-d₆, ppm) δ10.54 (s, 1H), δ8.02 (s, 1H), δ7.49-7.31 (m, 8H), δ7.19-7.18 (m, 2H), δ7.14-7.13 (m, 2H), δ3.51 (s, 2H).

Example 287. Synthesis of 5-(azetidine-1-carbonyl)-N-(5-(benzo[b]thiophen-2-yl)-2-methoxyphenyl)-3-chloro-2-hydroxybenzenesulfonamide, I-503

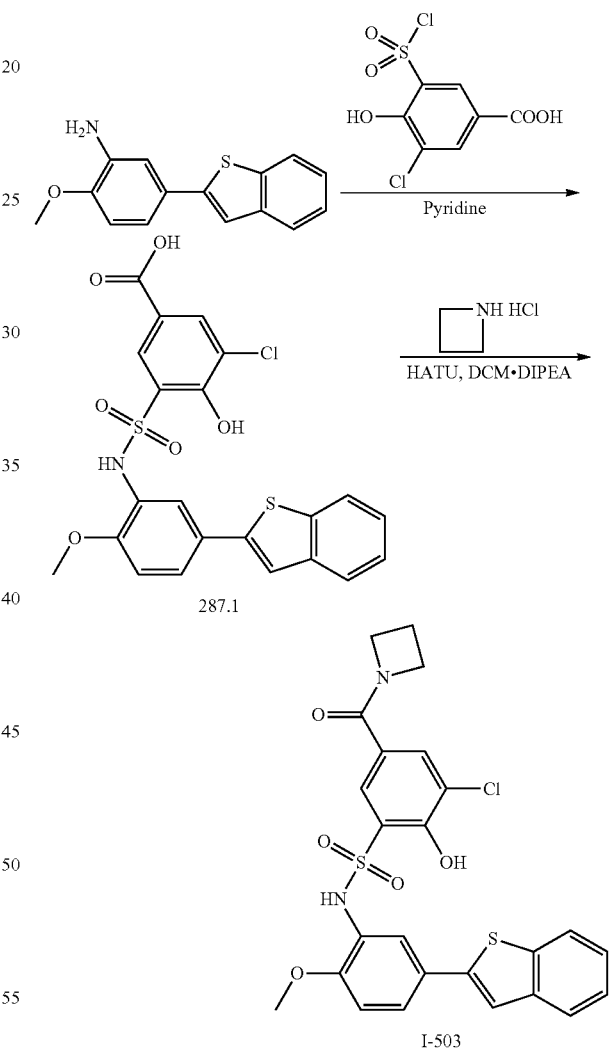

Synthesis of Compound 287.1

Into a 25-mL round-bottom flask, was placed 5-(1-benzothiophen-2-yl)-2-methoxyaniline (200.0 mg, 0.783 mmol, 1.00 equiv), pyridine (5.0 mL), and 3-chloro-5-(chlorosulfonyl)-4-hydroxybenzoic acid (254.7 mg, 0.940 mmol, 1.20 equiv). The resulting solution was stirred overnight at room temperature, then concentrated under vacuum. This resulted in 360 mg (97.0%) of 287.1 as a white crude solid. (ES, m/z): [M+H]$^+$ 490.

Synthesis of I-503

Into a 25-mL round-bottom flask, was placed 287.1 (360.00 mg, 0.735 mmol, 1.00 equiv), DCM (8.0 mL), HATU (419.0 mg, 1.102 mmol, 1.50 equiv), DIPEA (284.9 mg, 2.204 mmol, 3.00 equiv), and azetidine (62.9 mg, 1.10 mmol, 1.50 equiv). The resulting solution was stirred overnight at room temperature, then concentrated under vacuum. The residue was applied onto a silica gel column with ethyl acetate/petroleum ether (1:3). The resulting material was further purified by Prep-HPLC with the following conditions: Column: XBridge Prep C18 OBD Column, 19 Å—150 mm 5 um; Mobile Phase A: Water (10 mM NH$_4$HCO$_3$+0.1% NH$_3$.H$_2$O), Mobile Phase B: ACN; Flow rate: 25 mL/min; Gradient: 0% to 40% B in 7 min; 210/254 nm; Ret. Time: 5.43. This resulted in 23.6 mg (5.9%) of I-503 as a white solid. (ES, m/z): [M+H]$^+$ 529.0, $^1$H-NMR (400 MHz, DMSO-d$_6$, ppm) δ 7.94 (d, J=7.8 Hz, 2H), 7.86-7.79 (m, 2H), 7.76 (d, J=2.4 Hz, 2H), 7.71 (d, J=2.3 Hz, 2H), 7.46-7.29 (m, 3H), 7.11 (s, 1H), 7.05 (d, J=8.5 Hz, 2H), 4.03 (s, 4H), 3.75 (s, 3H), 2.12-1.99 (m, 2H), 1.30-1.22 (m, 1H).

Example 288. Synthesis of ethyl 3-(N-(5-(benzo[b]thiophen-2-yl)-4-fluoro-2-methoxyphenyl)sulfamoyl)-5-chloro-4-hydroxybenzoate, I-506

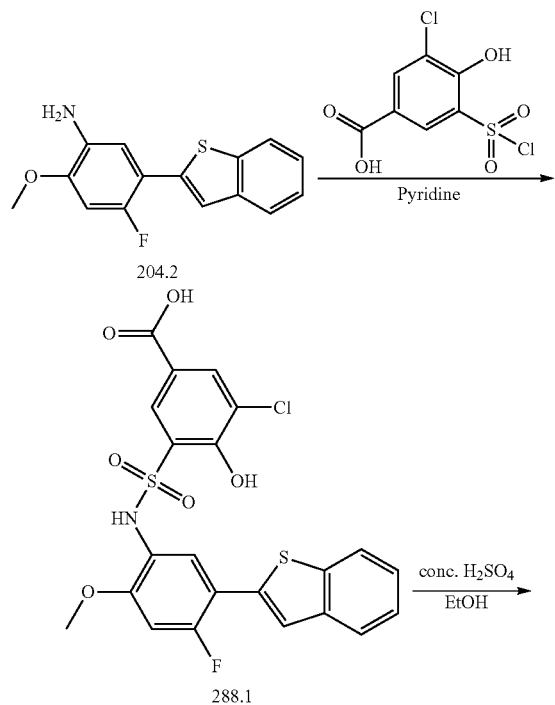

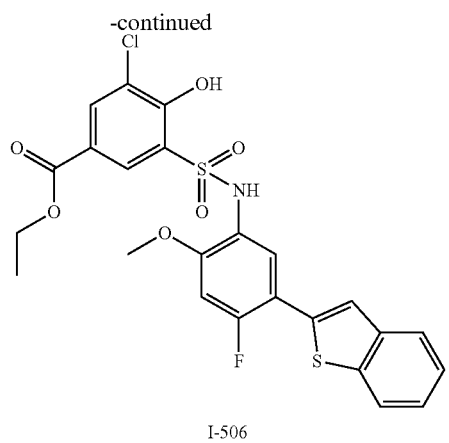

Synthesis of Compound 288.1

Into a 25-mL round-bottom flask, was placed 204.2 (150.0 mg, 0.549 mmol, 1.00 equiv), pyridine (5.0 mL), and 3-chloro-5-(chlorosulfonyl)-4-hydroxybenzoic acid (446.2 mg, 1.646 mmol, 3.00 equiv). The resulting solution was stirred for 12 hr at room temperature, then concentrated under vacuum. This resulted in 100 mg (35.8%) of 288.1 as a crude solid. (ES, m/z): [M+H]$^+$ 508.

Synthesis of I-506

Into a 25-mL round-bottom flask, was placed 288.1 (50.0 mg, 0.098 mmol, 1.00 equiv), ethyl alcohol (10.0 mL), and sulfuric acid (0.05 mL). The resulting solution was stirred overnight at 80° C. in an oil bath, then cooled to room temperature and concentrated under vacuum. The crude product was purified by Prep-HPLC with the following conditions: Column: XSelect CSH Prep C18 OBD Column, 5 um19*150 mm; Mobile Phase A: Water (10 mM NH$_4$HCO$_3$), Mobile Phase B: ACN; Flow rate: 25 mL/min; Gradient: 36% to 54% B in 7 min; Detector 210/254 nm; Ret. Time: 6.20. This resulted in 23.7 mg (44.9%) of I-506 as a white solid. (ES, m/z): [M+H]$^+$ 536.0, $^1$H-NMR (400 MHz, DMSO-d$_6$, ppm) δ 8.04-7.93 (m, 2H), 7.88 (d, J=7.3 Hz, 1H), 7.78 (s, 1H), 7.68 (d, J=8.2 Hz, 1H), 7.63 (s, 1H), 7.45-7.33 (m, 2H), 7.22 (s, 1H), 7.13-7.05 (m, 2H), 6.96 (s, 1H), 4.17 (q, J=7.1 Hz, 2H), 3.78 (s, 3H), 1.23 (t, J=7.1 Hz, 3H).

Example 289. Synthesis of 3,5-dichloro-2-hydroxy-N-(4-(trifluoromethoxy)-[1,1'-biphenyl]-3-yl)benzenesulfonamide, I-509

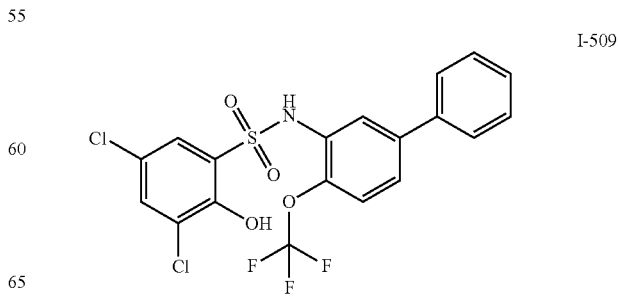

I-509 was prepared from 5-bromo-2-(trifluoromethoxy) aniline, phenylboronic acid, and 3,5-dichloro-2-hydroxy-benzenesulfonyl chloride by analogy to the procedures of the first and second steps of Example 249. I-367 was purified by column chromatography and compound was eluted in 20% ethyl acetate in hexane to afford the title compound (45 mg, 10% over two steps). (ES, m/z): [M−H]⁻ 476.1, ¹H-NMR (400 MHz, DMSO-$d_6$, ppm): δ 7.41 (d, J=5.1 Hz, 1H), 7.41-7.52 (m, 2H), 7.56 (dt, J=19.4, 9.4 Hz, 6H), 7.89 (d, J=2.6 Hz, 1H), 10.29 (br s, 1H), 11.18 (br s, 1H).

Example 290. Synthesis of 3-(3,5-dichloro-N-methylbenzamido)-[1,1'-biphenyl]-4-carboxylic Acid, I-347

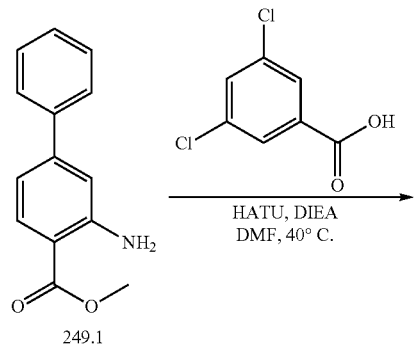

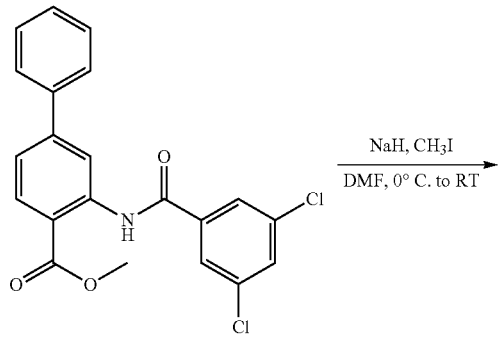

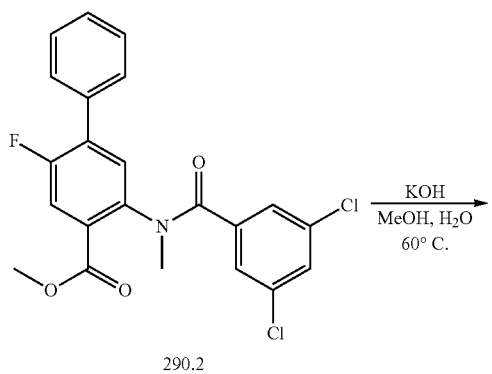

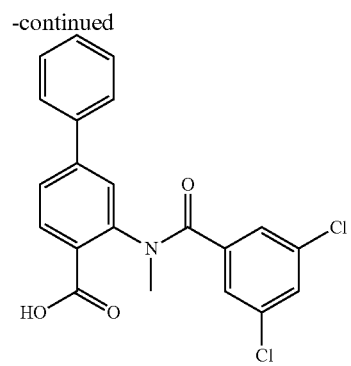

I-347

Synthesis of Compound 290.1

Into a 20-mL vial purged and maintained with an inert atmosphere of nitrogen was placed 249.1 (500 mg, 2.20 mmol, 1 equiv), 3,5-dichlorobenzoic acid (504.2 mg, 2.640 mmol, 1.2 equiv), DMF (10 mL), DIEA (568.6 mg, 4.400 mmol, 2 equiv), and HATU (1254.8 mg, 3.300 mmol, 1.5 equiv). The resulting solution was stirred overnight at 40° C. in an oil bath. The solution was diluted with 30 mL of H₂O, then extracted with 3×20 mL of ethyl acetate. The combined organics were concentrated under vacuum. The crude product was purified by re-crystallization from MeOH. This resulted in 597 mg (68%) of 290.1 as a white solid.

Synthesis of Compound 290.2

Into a 20-mL vial was placed 290.1 (300 mg, 0.750 mmol, 1 equiv), DMF, and NaH (35.9 mg, 1.49 mmol, 2 equiv). The resulting solution was stirred for 0.5 h at 0° C., then CH₃I (531.9 mg, 3.748 mmol, 5 equiv) was added dropwise. The resulting solution was stirred overnight at room temperature. The reaction was then quenched by the addition of NH₄Cl (aq), diluted with 30 mL of H₂O, and extracted with 3×20 mL of ethyl acetate. The combined organics were concentrated under vacuum. The residue was applied onto a silica gel column with ethyl acetate/petroleum ether (1:1). This resulted in 294 mg (91%) of 290.2 as a yellow oil.

Synthesis of I-347

Into a 50-mL round-bottom flask was placed 290.2 (294 mg, 0.680 mmol, 1 equiv), MeOH (10 mL), H₂O (10 mL), and KOH (381.5 mg, 6.801 mmol, 10 equiv). The resulting solution was stirred overnight at 60° C. in an oil bath. The solution was acidified with AcOH to a pH value of 6, diluted with 100 mL of H₂O, then extracted with 3×50 mL of ethyl acetate. The combined organics were concentrated under vacuum. The crude product was purified by Flash-Prep-HPLC with the following conditions (IntelFlash-1): Column, C18 silica gel; mobile phase, ACN/H₂O=15% increasing to ACN/H₂O=60% within 15 min; Detector, UV: 254 nm. This resulted in 106.1 mg (39%) of I-347 as a white solid. (ES, m/z): [M+H]⁺ 400.1, ¹H-NMR (400 MHz, CD₃OD, ppm) δ 7.98-7.92 (d, 1H), 7.79-7.73 (m, 1H), 7.68-7.61 (m, 3H), 7.56-7.38 (m, 3H), 7.35-7.30 (t, 1H), 7.30-7.27 (m, 2H), 3.46 (s, 3H).

Example 291. Synthesis of 3,5-dichloro-2-hydroxy-N-(3-phenylthiophen-2-yl) benzenesulfonamide, I-89

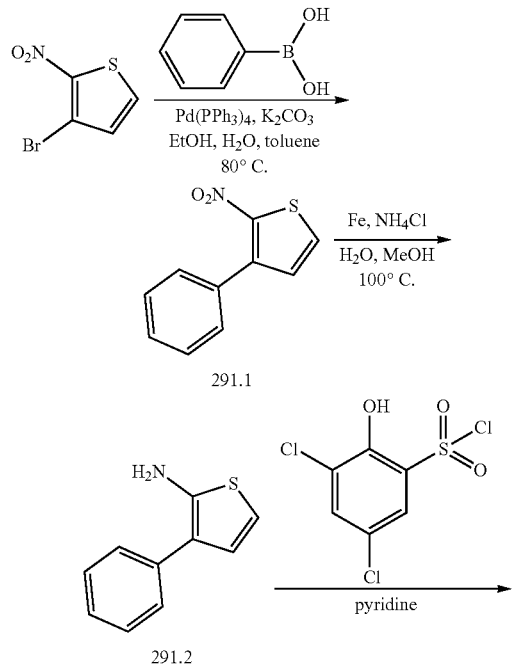

Synthesis of Compound 291.1

To a stirred mixture of 3-bromo-2-nitrothiophene (3 g, 14.4 mmol, 1 equiv) and phenylboronic acid (2.1 g, 17.3 mmol, 1.2 equiv) in toluene (10 mL), H₂O (10 mL), and EtOH (10 mL) were added Pd(PPh₃)₄ (3.3 g, 2.88 mmol, 0.2 equiv) and K₂CO₃ (10.0 g, 72.1 mmol, 5 equiv) at 25° C. under nitrogen atmosphere. The resulting mixture was stirred for 12 h at 80° C. The precipitated solids were removed by filtration and washed with EtOAc (2×100 mL). The filtrate was concentrated under vacuum. The residue was purified by silica gel column chromatography, eluted with PE/EtOAc (80:1). This resulted in 291.1 (1.05 g, 35.4%) as a yellow solid.

Synthesis of Compound 291.2

Into a 25 mL round-bottom flask were added 291.1 (1 g, 4.87 mmol, 1 equiv), Fe (816.3 mg, 14.62 mmol, 3 equiv), and NH₄Cl (1.6 g, 29.2 mmol, 6 equiv) in H₂O (6 mL) and MeOH (3 mL) at 25° C. The resulting mixture was stirred for 30 min at 100° C. under nitrogen atmosphere. The precipitated solids were removed by filtration and washed with EtOAc (2×100 mL). The filtrate was diluted with water (100 mL), then extracted with EtOAc (2×100 mL). The combined organics were concentrated under vacuum. The residue was purified by silica gel column chromatography, eluted with PE/EtOAc (80:1) to afford 291.2 (700 mg, 81.9%) as a white solid.

Synthesis of I-89

Into a 25 mL round-bottom flask were added 3,5-dichloro-2-hydroxybenzene-1-sulfonyl chloride (200 mg, 0.76 mmol, 1 equiv), 291.2 (134.0 mg, 0.76 mmol, 1 equiv), and pyridine (2 mL). The resulting mixture was stirred for 12 h at 50° C. under nitrogen atmosphere. The reaction was quenched with 1M HCl at room temperature. The resulting solution was extracted with EtOAc (2×100 mL), and the combined organic layers were concentrated. The residue was purified by Flash-Prep-HPLC with the following conditions (IntelFlash-1): Column, C 18; mobile phase, CH₃CN/H₂O=0:100 to CH₃CN/H₂O=50:50 in 30 min; Detector, UV 254/220 nm. This resulted in I-89 (33.1 mg, 10.8%) as a brown solid. (ES, m/z): [M−H]⁻ 397.9, $^1$H-NMR (300 MHz, CDCl₃, ppm) δ7.36-7.26 (m, 5H), δ7.22-7.20 (d, J=5.7 Hz, 1H), δ7.12-7.09 (d, J=2.7 Hz, 2H), δ6.95-6.93 (d, J=5.1 Hz, 1H).

Example 292. Synthesis of 5-bromo-3-chloro-N-(4-chlorophenyl)-N-ethyl-2-hydroxybenzene Sulfonamide, I-513

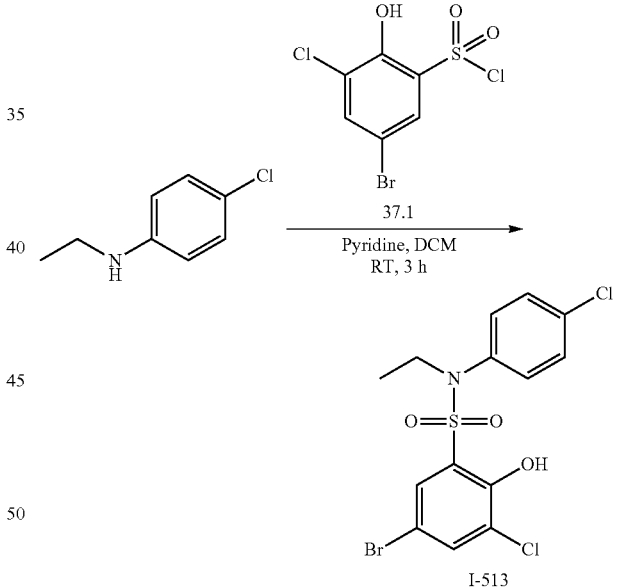

Synthesis of I-513

Pyridine (0.38 mL, 4.8 mmol, 3 eq) was added to a solution of 4 chloro-N-ethylaniline (0.25 g, 1.6 mmol, 1 eq) and 37.1 (0.983 g, 3.2 mmol, 2 eq) in anhydrous DCM (2.5 mL) at 0° C. The reaction mixture was stirred at room temperature for 3 h. Water (20 mL) was added, and the mixture was extracted using DCM (2×10 mL). The combined organic layers were washed with brine, dried over anhydrous sodium sulphate, and concentrated under reduced pressure. The residue was purified by silica gel column chromatography, and compound was eluted using 10%

EtOAc in hexanes to afford pure 1-513 (0.44 g, 65%). (ES, m/z): [M+H]+424.1, LCMS purity: 100%, ¹H-NMR (400 MHz, DMSO-d₆, ppm) δ 1.01 (t, J=7.1 Hz, 3H), 3.82 (q, J=7.1 Hz, 2H), 7.16-7.24 (m, 2H), 7.41-7.51 (m, 2H), 7.65 (s, 1H), 7.97 (d, J=2.5 Hz, 1H), 11.20 (br s, 1H).

Example 293. Synthesis of N-((5-bromo-3-chloro-2-hydroxyphenyl)sulfonyl)-N-(4-chlorophenyl)thiazole-5-carboxamide, I-511

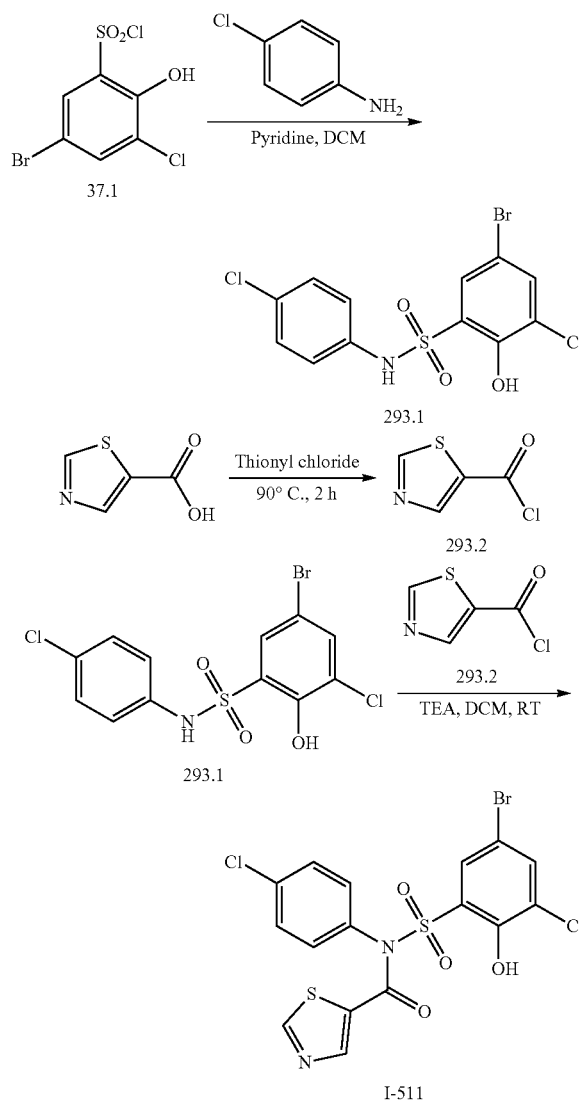

Synthesis of Compound 293.1

Compound 293.1 was prepared in 27% yield from 37.1 and 4-chloroaniline according to the procedure of Example 292. (ES, m/z): [M+H]+ 398.

Synthesis of Compound 293.2

Thiazole-5-carboxylic acid (0.3 g) was taken in thionyl chloride (10 volumes) and heated at 90° C. for 2 h. The reaction mixture was concentrated under reduced pressure to afford thiazole-5-carbonyl chloride which was used in next step without further purification and without prolonged storage. Yield: 81%.

Synthesis of I-511

Triethylamine (0.58 mL, 4 mmol, 4 eq) was added to a solution of 293.1 (0.4 g, 1 mmol, 1 eq) and 293.2 (0.298 g, 2 mmol, 2 eq) in anhydrous DCM (8 mL) at 0° C. The reaction mixture was stirred at room temperature for 16 h. Water (20 mL) was added, and the mixture was extracted with DCM (3×10 mL). The combined organic layers were washed with brine, dried over anhydrous sodium sulphate, and concentrated under reduced pressure. The residue was purified by silica gel column chromatography, and compound was eluted using 45% EtOAc in hexanes. The resulting materials was further purified by reverse phase preparative HPLC carried out using SUNFIRE C18 (150*19) mm, 5 column and 0.1% formic acid in water and 100% ACN as mobile phase. The pure fractions were collected and lyophilized to afford pure 1-511 (0.025 g, 5%). (ES, m/z): [M+H]+ 507.1, LCMS purity: 100%, ¹H-NMR (400 MHz, DMSO-d₆, ppm) δ 7.07-7.15 (m, 2H), 7.35-7.42 (m, 2H), 7.99 (d, J=2.3 Hz, 1H), 8.36 (d, J=2.3 Hz, 1H), 8.77 (s, 1H), 9.58 (s, 1H), 10.87 (s, 1H).

Example 294. Synthesis of 5-bromo-3-chloro-N-(4-chlorophenyl)-2-hydroxy-N-(thiazol-5-ylmethyl) benzenesulfonamide, I-514

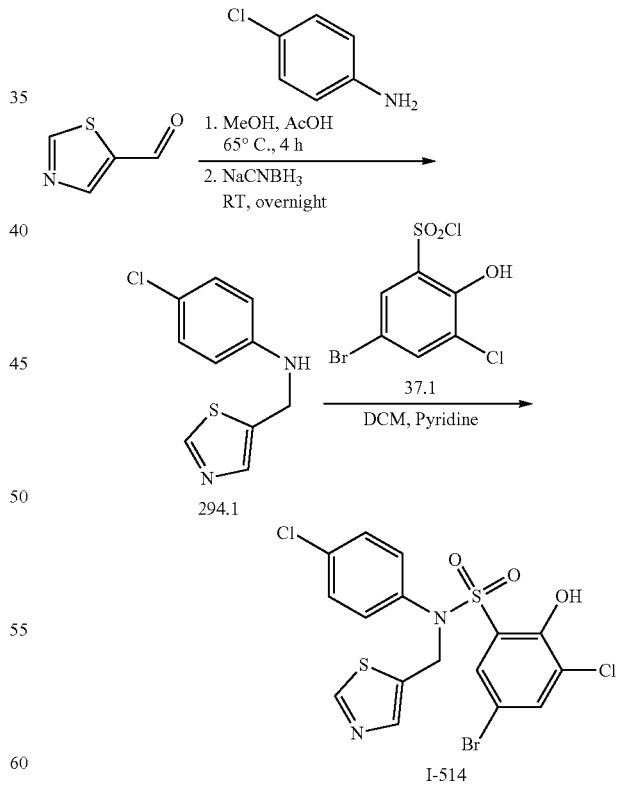

Synthesis of Compound 294.1

A solution of thiazole-5-carbaldehyde (0.1 g, 0.88 mmol, 1 eq) and 4-chloroaniline (0.112 g, 0.88 mmol, 1 eq) in MeOH (10 volumes) containing a few drops of acetic acid was refluxed for 4 h, then cooled to room temperature. Sodium cyanoborohydride (0.11 g, 1.77 mmol, 2 eq) was added, and the mixture was stirred at room temperature overnight. The volatiles were removed under reduced pressure, then water (10 mL) was added, and the mixture was extracted using EtOAc (2×20 mL). The combined organic layers were dried over anhydrous sodium sulphate, then concentrated under reduced pressure. The residue was purified by column chromatography. The compound was eluted in 5% MeOH in DCM to obtain 294.1 (0.17 g, 80%). MS (ES): m/z 223.6 [M–H]⁻.

Synthesis of I-514

A solution of 37.1 (0.408 g, 1.33 mmol, 2 eq) in DCM (2 mL) was added dropwise to a solution of 294.1 (0.7 g, 0.66 mmol, 1 eq) and pyridine (0.11 mL, 2.00 mmol, 3 eq) in DCM (2 mL) at room temperature, and the resulting mixture was stirred overnight at room temperature. Water (20 mL) was added to the reaction mixture, then it was acidified using 10% HCl solution. The mixture was extracted using DCM (2×20 mL). The combined organic layers were washed with brine, dried over sodium sulphate, and concentrated under reduced pressure to obtain crude material. This was purified by column chromatography, and compound was eluted in 2% MeOH in DCM. The resulting material was further purified by reverse phase preparative HPLC carried out using SUNFIRE C18 (150*19) mm, 5 column and 0.1% formic acid in water and 100% ACN as mobile phase. The pure fractions were collected and lyophilized to afford pure I-514 (0.06 g, 18%). (ES, m/z): [M+H]⁺ 495.2, LCMS purity: 100%, ¹H-NMR (400 MHz, DMSO-d₆, ppm) δ 5.26 (s, 2H), 7.14 (d, J=8.4 Hz, 2H), 7.39 (d, J=8.4 Hz, 2H), 7.52 (d, J=2.2 Hz, 1H), 7.64 (s, 1H), 8.04 (s, 1H), 9.03 (s, 1H), 11.53 (br s, 1H).

Example 295. Synthesis of 4-(benzo[b]thiophen-2-yl)-2-((3-chloro-5-(trifluoromethyl) phenyl)sulfonamido)benzoic Acid, I-294

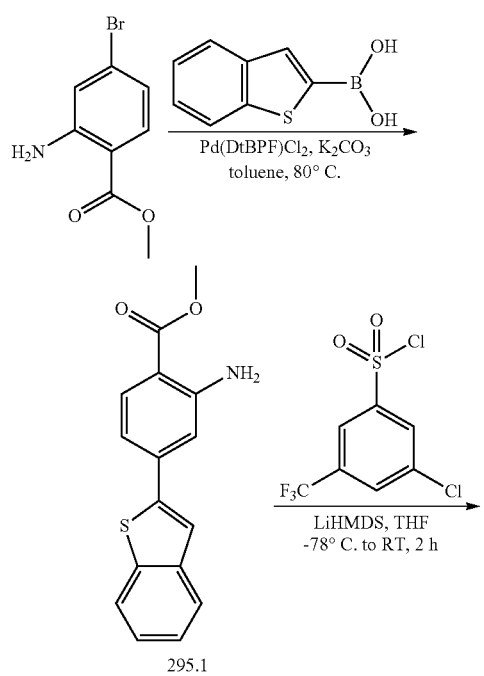

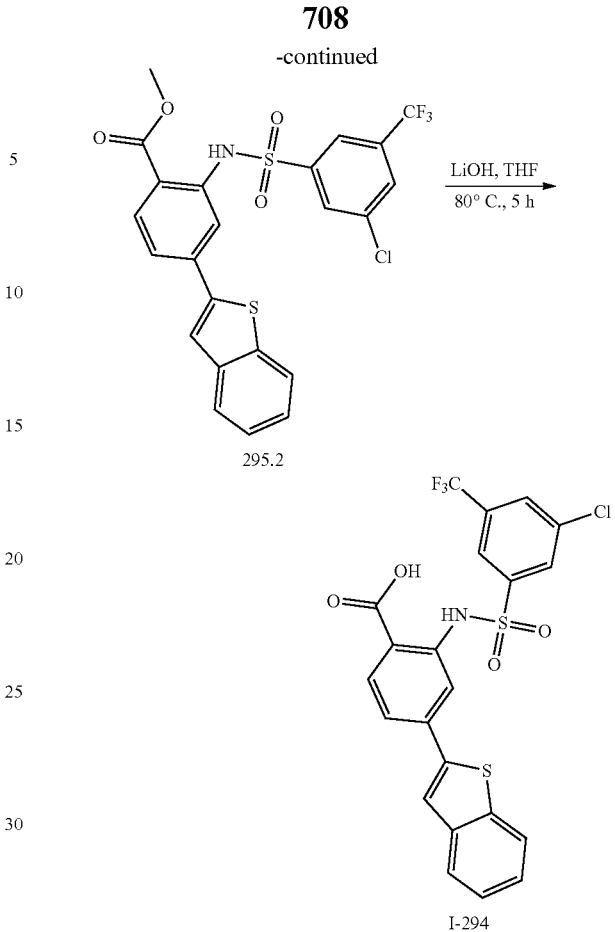

Synthesis of Compound 295.1

Into a 100-mL round-bottom flask purged and maintained with an inert atmosphere of nitrogen, was placed methyl 2-amino-4-bromobenzoate (1 g, 4.34 mmol, 1 equiv), (1-benzothiophen-2-yl)boronic acid (0.77 g, 4.34 mmol, 1 equiv), Pd(DtBPF)Cl₂ (0.28 g, 0.435 mmol, 0.1 equiv), K₂CO₃ (1.80 g, 13.04 mmol, 3 equiv), toluene (50 mL). The resulting solution was stirred for 2 h at 80° C. in an oil bath. The resulting mixture was concentrated. The residue was applied onto a silica gel column with ethyl acetate/petroleum ether (1:3). This resulted in 950 mg (77%) of 295.1 as a white solid.

Synthesis of Compound 295.2

To a solution of aniline analog 295.1 (1 eq), in anhydrous tetrahydrofuran (12.5 mL, 10V) was added 1M solution of LiHMDS in THF (7.7 mL, 7.7 mmol, 3 eq) at −78° C. and stirred for 1.5 h. The temperature was increased to 0° C. A solution of 3-chloro-5-(trifluoromethyl)benzenesulfonyl chloride (1.5 eq) in anhydrous THF (12.5 mL, 10V) was added drop wise to above reaction mixture at −78° C. The reaction mixture was allowed to warm to room temperature and stirred for 2 h. After completion of reaction, water (150 mL) was added and extracted using EtOAc (50 mL×2). Organic layer was combined, washed with brine solution, dried over sodium sulphate and concentrated under reduced pressure to obtain crude material. The crude reaction mixture was purified by column chromatography and compound was eluted in 20-25% ethyl acetate in hexane to obtain 295.2 (0.2 g, 21%). MS (ES): m/z 524.2 [M–H]⁻, LCMS purity: 100.0%, ¹H NMR (400 MHz, CDCl₃, ppm) δ 3.93 (s, 3H), 7.38-7.42 (m, 2H), 7.43-7.46 (m, 1H), 7.68 (s, 1H), 7.77 (s, 1H), 7.83-7.88 (m, 2H), 7.78-8.01 (m, 2H), 8.01 (s, 2H), 10.9 (br s, 1H).

Synthesis of I-294

LiOH monohydrate (0.078 g, 0.19 mmol, 5 eq) was added to solution of 295.1 (0.2 g, 0.38 mmol, 1 eq) in THF (2 mL) at room temperature and stirred at 80° C. for 5 h. Water (20 mL) was added, then the mixture was acidified by addition of 10% HCl solution. The mixture was extracted using EtOAc (2×20 mL). The combined organic layers were washed with brine, dried over sodium sulphate, and concentrated under reduced pressure to obtain crude material. This was further purified by column chromatography, and compound was eluted in 5% MeOH in DCM to obtain I-294 (0.08 g, 41%). (ES, m/z): [M–H]⁻ 510.3, LCMS purity: 100%, ¹H-NMR (400 MHz, DMSO-d₆, ppm) δ 7.43-7.46 (m, 2H), 7.66 (d, J=8 Hz, 1H), 7.71 (s, 1H), 7.91-7.93 (m, 1H), 7.98-8.04 (m, 3H), 8.13 (s, 1H), 8.29 (s, 2H), 11.45 (br s, 1H).

Example 296. Synthesis of 3-(N-(5-(benzo[b]thiophen-2-yl)-4-fluoro-2-(trifluoromethoxy) phenyl) sulfamoyl)-5-chloro-4-hydroxybenzoic Acid, I-508; and 5-(azetidine-1-carbonyl)-N-(5-(benzo[b]thiophen-2-yl)-4-fluoro-2-(trifluoromethoxy)phenyl)-3-chloro-2-hydroxy benzenesulfonamide, I-504

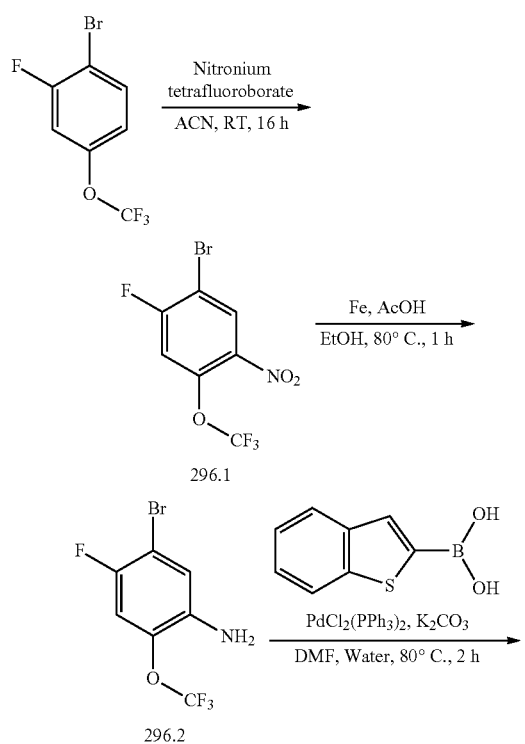

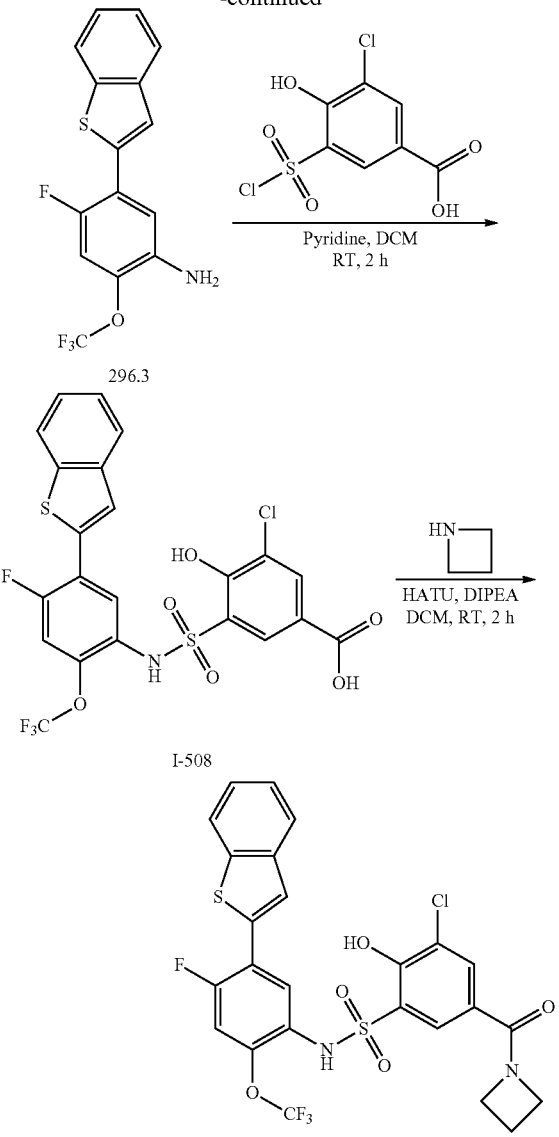

Synthesis of Compound 296.1

Nitronium tetrafluoroborate (2.15 g, 15 mmol, 1 eq) was added to a solution of 1-bromo-2-fluoro-4-(trifluoromethoxy)benzene (4 g, 15 mmol, 1 eq) in acetonitrile (60 mL) at 0° C. The reaction mixture was warmed to room temperature and stirred for 16 h. Water (100 mL) was added, and the mixture was extracted using EtOAc (3×75 mL). The combined organic layers were washed with brine (100 mL), dried over anhydrous sodium sulphate, and concentrated under reduced pressure. The crude material was purified by silica gel column chromatography, and compound was eluted using 10% EtOAc in hexanes to afford pure 296.1 (3 g, 64%). MS (ES): m/z 303.3 [M–H]⁻.

Synthesis of Compound 296.2

Iron powder (0.9 g, 16.4 mmol, 5 eq) was added to a solution of 296.1 (1 g, 3.2 mmol, 1 eq) in AcOH:EtOH (1:1)

and heated at 80° C. for an hour. The reaction mixture was filtered through a celite bed, and washed with EtOAc (20 mL). The filtrate was concentrated under reduced pressure. The crude material was purified by silica gel column chromatography, and compound was eluted using 10% EtOAc in hexanes to afford 296.2 (0.8 g, 88%). MS (ES): m/z 273.3 [M−H]⁻.

Synthesis of Compound 296.3

A 10 mL reaction vial was charged with 296.2 (1 eq), boronic acid analog, (1.2 eq), PdCl$_2$(PPh$_3$)$_2$ (0.1 eq) and K$_2$CO$_3$ (4 eq) in DMF/Water (0.9 mL, 30V, 13:3) and purged with Argon gas for 10 min. The vial was sealed with Teflon cap and stirred for overnight at 70° C. After completion of reaction, water (3 mL) was added to reaction mixture and acidified using 10% HCl solution. The reaction mixture was extracted using EtOAc (10 mL×3), and combined organic layer was washed with brine, dried over sodium sulphate and concentrated under reduced pressure to obtain crude material which was purified by column chromatography and compound was eluted in 30% ethyl acetate in hexane to obtain white solid 296.3 (0.3 g, 80%).

Synthesis of I-508

Pyridine (1.85 g, 10 mmol, 3 eq) was added to a solution of 296.3 (1.2 g, 3.6 mmol, 1 eq) and 3-chloro-5-(chlorosulfonyl)-4-hydroxybenzoic acid (1.9 g, 7.3 mmol, 2 eq) in anhydrous DCM (12 mL) at 0° C. The reaction mixture was stirred at room temperature for 3 h. Water (20 mL) was added, and the mixture was extracted using DCM (2×10 mL). The combined organic layers were washed with brine, dried over anhydrous sodium sulphate, and concentrated under reduced pressure. The crude material was purified by silica gel column chromatography, and compound was eluted using 20% EtOAc in hexanes to afford pure I-508 (0.18 g, 9%). (ES, m/z): [M−H]⁻ 560.3, LCMS purity: 100%, ¹H-NMR (400 MHz, DMSO-d$_6$, ppm) δ 7.46 (q, J=5.0, 4.4 Hz, 2H), 7.56 (d, J=11.0 Hz, 1H), 7.77 (d, J=7.9 Hz, 1H), 7.85 (s, 1H), 7.97 (q, J=4.9, 4.5 Hz, 1H), 8.00-8.13 (m, 2H), 8.18 (d, J=2.2 Hz, 1H), 13.12 (br s, 1H).

Synthesis of I-504

Into a 50-mL round-bottom flask purged and maintained with an inert atmosphere of nitrogen, was placed I-508 (0.15 g, 0.26 mmol, 1 eq), azetidine HCl (0.05 g, 0.53 mmol, 2 eq), HATU (0.121 g, 0.32 mmol, 1.2 eq), DIPEA (0.18 mL, 1.06 mmol, 4 eq), and DCM (1.5 mL). The resulting solution was stirred for 2 h at room temperature. The reaction was then quenched by the addition of 10 mL of water. The resulting mixture was extracted with DCM (3×10 mL). The combined organic layers were washed with brine, dried over anhydrous sodium sulphate, and concentrated under reduced pressure. The crude material was purified by silica gel column chromatography, and compound was eluted using 3% MeOH in DCM. The resulting material was further purified by reverse phase preparative HPLC carried out using SUNFIRE C18 (150*19) mm, 5 column and 0.1% formic acid in water and 100% ACN as mobile phase. The pure fractions were collected and lyophilized to afford pure I-504 (0.005 g, 4%). (ES, m/z): [M−H]⁻ 599.9, LCMS purity: 100%, ¹H-NMR (400 MHz, DMSO-d$_6$, ppm) δ 2.13 (q, J=7.5 Hz, 2H), 3.99 (s, 2H), 4.18 (s, 2H), 7.45 (d, J=5.8 Hz, 2H), 7.55 (d, J=11.0 Hz, 1H), 7.76 (d, J=7.4 Hz, 1H), 7.83 (s, 3H), 7.92-8.00 (m, 1H), 8.00-8.07 (m, 1H), 11.22 (br s, 1H).

Example 297. Synthesis of 3-(3-chloro-5-(trifluoromethyl)benzamido)-[1,1'-biphenyl]-4-carboxylic Acid, I-349

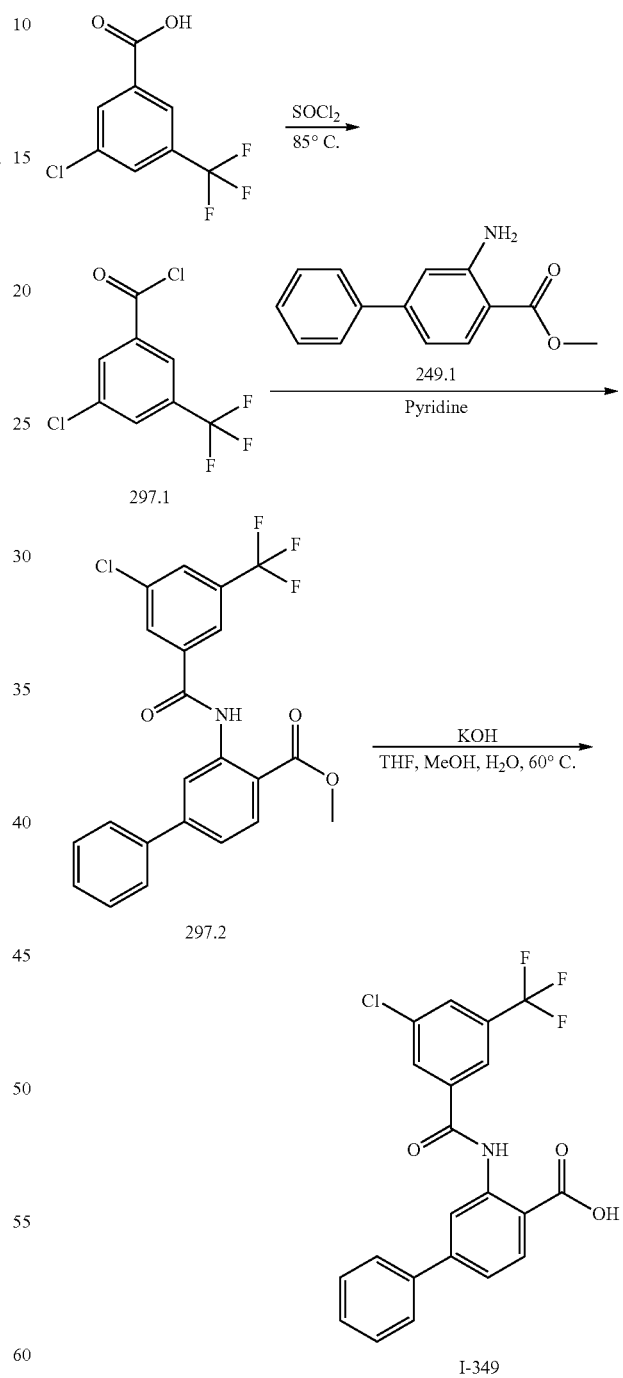

Synthesis of Compound 297.1

Into a 50 mL round-bottom flask were added 3-chloro-5-(trifluoromethyl)benzoic acid (300 mg, 1.336 mmol, 1 equiv) and thionyl chloride (3 mL) at 0° C. The resulting mixture was stirred for 2 h at 85° C., then concentrated under vacuum to afford 105 mg (31%) of 297.1 as a colorless oil.

Synthesis of Compound 297.2

To a stirred solution of 249.1 (98.2 mg, 0.432 mmol, 1.00 equiv) in pyridine (5 mL) at 0° C. was added in portions 297.1 (105 mg, 0.432 mmol, 1 equiv). The resulting mixture was stirred overnight at room temperature, then concentrated under vacuum. The residue was purified by Prep-TLC (PE/EtOAc 10:1) to afford 91.2 mg (48%) of 297.2 as an off-white solid.

Synthesis of I-349

To a stirred solution of 297.2 (91.2 mg, 0.210 mmol, 1 equiv) in THF and MeOH at 0° C. was added dropwise potassium hydroxide (58.9 mg, 1.05 mmol, 5.00 equiv) in H$_2$O (1 mL). The resulting mixture was stirred for 3 h at room temperature, then concentrated under reduced pressure. The residue was dissolved in H$_2$O (15 mL). The mixture was acidified to pH 4 with conc. HCl. The resulting mixture was filtered, and the filter cake was washed with H$_2$O (2×2 mL). The collected solid was dried under reduced pressure to afford 38.9 mg (44%) of I-349 as a white solid. (ES, m/z): [M−H]$^−$ 418.0, $^1$H-NMR (400 MHz, DMSO-d$_6$, ppm) δ8.91 (s, 1H), δ8.29 (s, 1H), δ8.24-8.21 (d, J=11.6 Hz, 2H), δ8.14-8.12 (d, J=8 Hz, 1H), δ7.74-7.72 (d, J=8.8 Hz, 2H), δ7.58-7.53 (m, 3H), δ7.48-7.45 (m, 1H).

Example 300. Synthesis of 3-chloro-4-methoxy-5-(N-(4-phenylpyridin-2-yl)sulfamoyl)benzoic Acid, I-536

Synthesis of 300.1

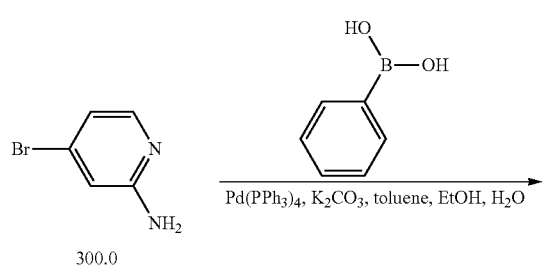

300.0

To a stirred mixture of 4-bromopyridin-2-amine (2 g, 11.56 mmol, 1 equiv) and phenylboronic acid (1.7 g, 13.87 mmol, 1.2 equiv) in toluene, H$_2$O, EtOH (20 mL, 10 mL, 16 mL) were added Pd(PPh$_3$)$_4$ (1.3 g, 1.16 mmol, 0.1 equiv) and K$_2$CO$_3$ (8.0 g, 57.80 mmol, 5 equiv) in portions at room temperature under nitrogen atmosphere. After stirring for 12 h at 90° C. under nitrogen atmosphere, the resulting mixture was filtered, and the filter cake was washed with EtOAc (2×100 mL). The combined filtrate was concentrated under reduced pressure. The residue was purified by silica gel column chromatography eluting with PE/EtOAc (1:1) to afford 300.1 (1.8 g, 91.48%) as a yellow solid.

Synthesis of 300.2

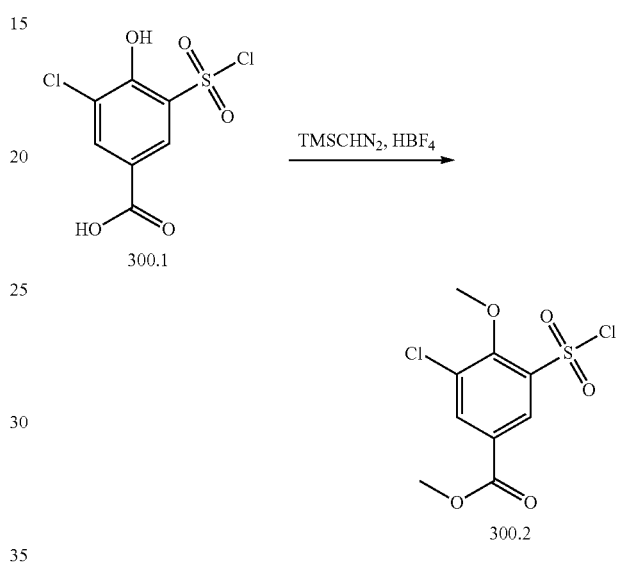

To a stirred mixture of 300.1 (8 g, 29.51 mmol, 1 equiv) and HBF$_4$ (13.03 g, 148.38 mmol, 5.03 equiv) in DCM (80 mL, 1258.40 mmol, 42.64 equiv) was added TMSCHN$_2$ (59 mL, 4 equiv) dropwise at 0° C. After stirring for 2 h under nitrogen atmosphere, the reaction was quenched with water at room temperature and extracted with DCM (2×100 mL). The combined organic solution was dried over anhydrous Na$_2$SO$_4$, filtered and concentrated under reduced pressure. The residue was purified by silica gel column chromatography, eluting with PE/EtOAc (10:1) to afford 300.2 (2.4 g, 27.19%) as a white solid.

Synthesis of 300.3

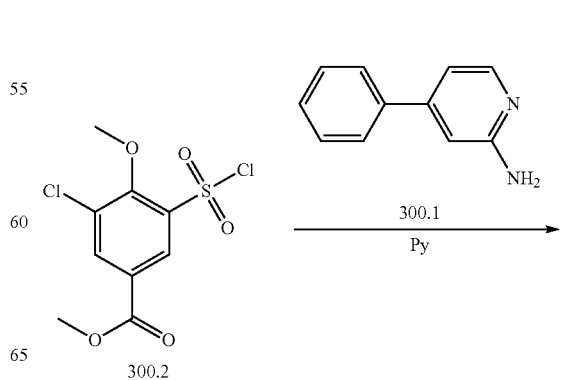

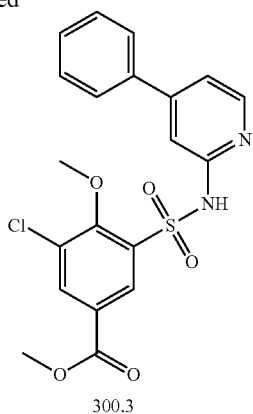

300.3

To a mixture of 300.1 (853.6 mg, 5.01 mmol, 1 equiv) in pyridine (15 mL, 186.35 mmol, 37.16 equiv) was added 300.2 (1.5 g, 5.01 mmol, 1 equiv). After stirring for 12 h at 50° C. under nitrogen atmosphere, the reaction mixture was concentrated under reduced pressure. The residue was purified by Prep-TLC (PE/EtOAc 5:1) to afford 300.3 (350 mg, 16.12%) as a white solid.

Synthesis of 300.4

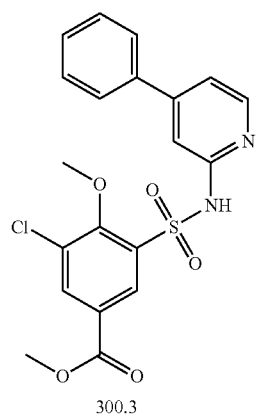

300.3

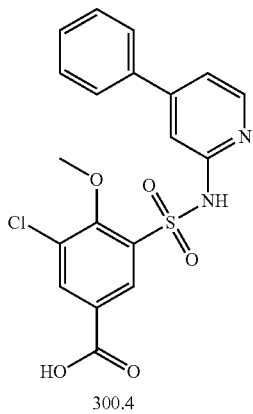

300.4

To a stirred mixture of 300.3 (325 mg, 0.75 mmol, 1 equiv) in MeOH (2 mL, 49.40 mmol, 65.79 equiv) were added H$_2$O (1 mL, 55.51 mmol, 73.93 equiv) and NaOH (300 mg) in portions at room temperature under nitrogen atmosphere. After stirring for 2 h, the reaction mixture was quenched with HCl (1 M) and extracted with EtOAc (2×100 mL). The combined organic layers were washed with brine, dried over anhydrous Na$_2$SO$_4$, filtered and concentrated under reduced pressure. The residue was purified by Prep-TLC (CH$_2$Cl$_2$/MeOH 20:1) to afford 300.4 (140 mg, 44.52%) as a white solid.

Synthesis of I-536

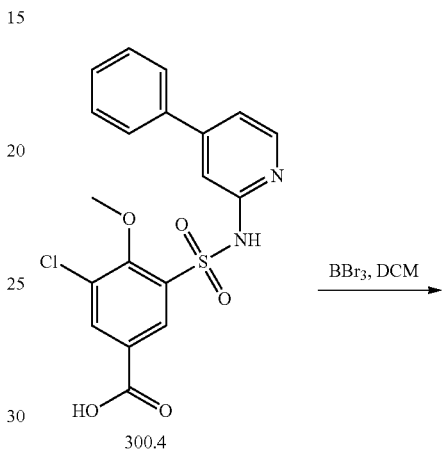

300.4

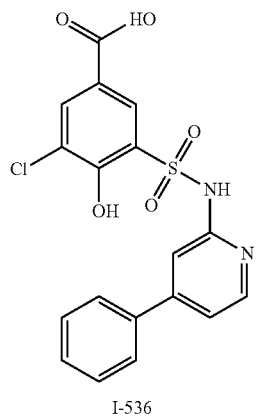

I-536

To a mixture of 300.4 (80 mg, 0.19 mmol, 1 equiv) in DCM (0.8 mL, 12.58 mmol, 65.89 equiv) was added BBr$_3$ (287.1 mg, 1.15 mmol, 6 equiv). After stirring for 30 min at 0° C. under nitrogen atmosphere, the reaction was quenched by the addition of NH$_4$Cl (1 M) (100 mL) at 0° C. and extracted with EtOAc (2×100 mL). The combined organic layers were washed with brine, dried over anhydrous Na$_2$SO$_4$, filtered and concentrated under reduced pressure. The crude product was purified by reverse phase flash (CH$_3$CN/H$_2$O=0:100 to CH$_3$CN/H$_2$O=40:60 in 30 mins UV: 254/220) to afford I-536 (1.1 mg, 1.42%) as a white solid. (ES, m/z): [M+H]$^+$ 404.9 1H-NMR (400 MHz, DMSO, ppm): δ 7.29-7.31 (d, J=6.0 Hz, 1H), δ 7.50-756 (m, 4H), δ 7.70-7.72 (m, 2H), δ 8.03-8.04 (d, J=1.2 Hz, 1H), δ 8.12-8.14 (d, J=6.0 Hz, 1H), δ 8.31 (s, 1H).

Example 301: Synthesis of (3-chloro-5-(((4,6-difluoro-[1,1'-biphenyl]-3-yl)methyl)thio)-4-hydroxyphenyl)(pyrrolidin-1-yl)methanone (I-205)

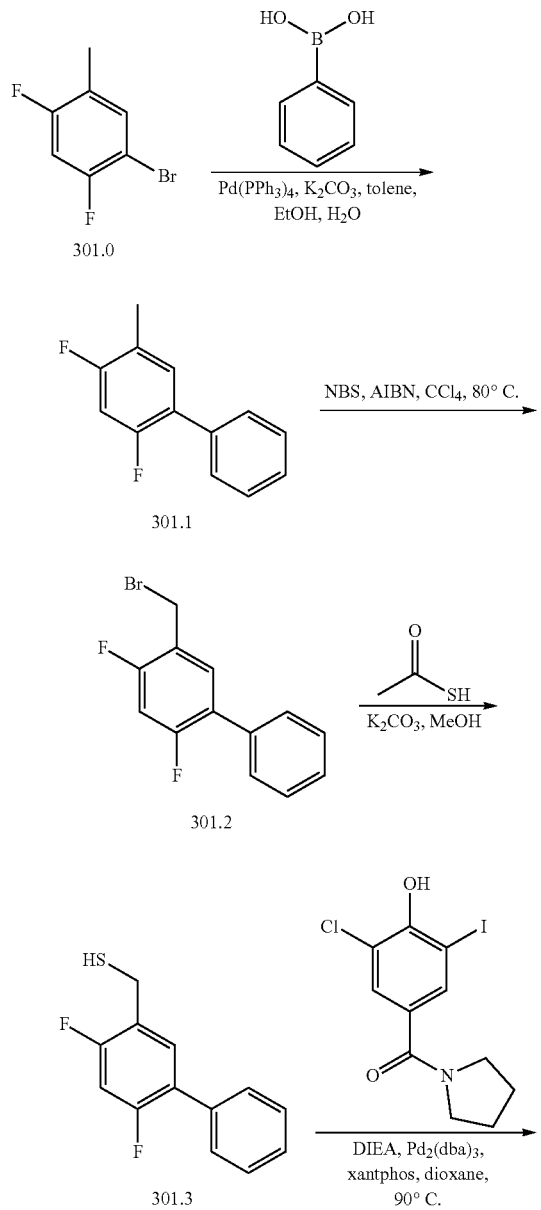

Synthesis of 301.2

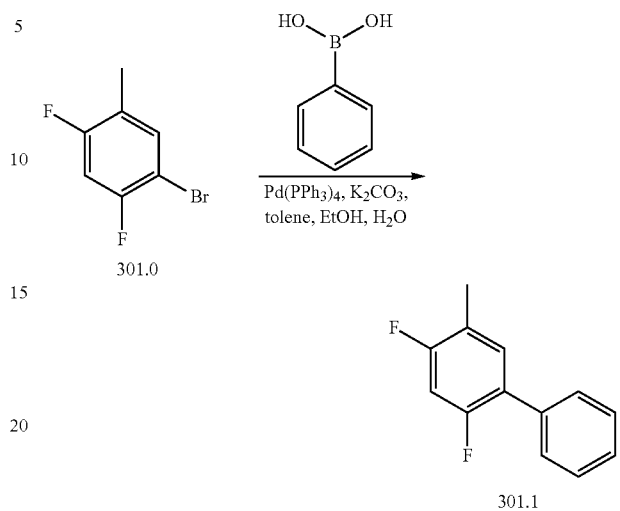

To a stirred solution of 1-bromo-2,4-difluoro-5-methylbenzene (2 g, 9.66 mmol, 1 equiv) and phenylboronic acid (1178.0 mg, 9.66 mmol, 1 equiv) in EtOH (7 mL), H2O (7 mL) and toluene (7 mL) were added Pd(PPh3)4 (1116.4 mg, 0.97 mmol, 0.1 equiv) and $K_2CO_3$ (2670.4 mg, 19.32 mmol, 2 equiv) at room temperature under nitrogen atmosphere. After stirring for overnight at 100° C. under nitrogen atmosphere, the resulting mixture was concentrated under reduced pressure. The residue was purified by silica gel column chromatography, eluting with PE/EtOAc (10:1) to afford 301.1 (1.6 g, 81%) as white oil.

Synthesis of 301.2

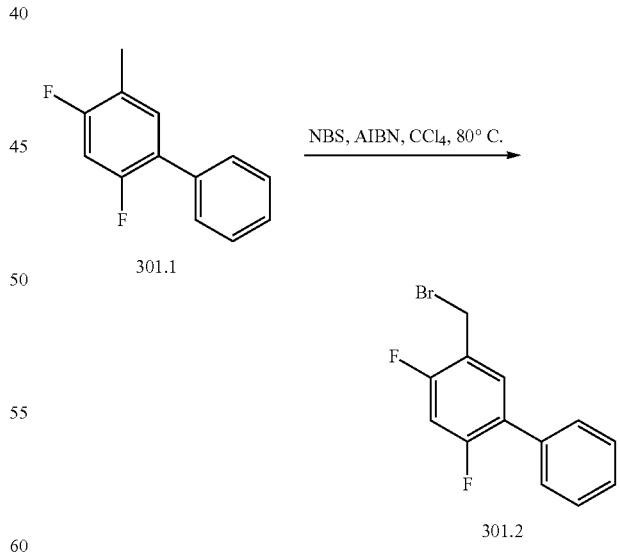

To a stirred solution of 301.1 (6.46 g, 24.33 mmol, 1 equiv) in MeOH (50 mL) were added NaOH (1.9 g, 48.66 mmol, 2 equiv) and $H_2O$ (5 mL) at room temperature. After stirring for 3 h at room temperature, the mixture was acidified to pH 6 with conc. HCl and extracted with EtOAc (2×50 mL). The combined organic layers were washed with brine (2×20 mL), dried over anhydrous Na₂SO₄, filtered and concentrated under reduced pressure to afford 301.2 (6 g, 98%) as a white solid.

Synthesis of 301.3

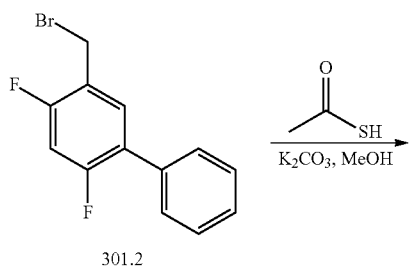

To a stirred solution of 301.2 (6.46 g, 24.33 mmol, 1 equiv) in MeOH (50 mL) were added NaOH (1.9 g, 48.66 mmol, 2 equiv) and H₂O (5 mL) at room temperature. After stirring for 3 h at room temperature, the mixture was acidified to pH 6 with conc. HCl and extracted with EtOAc (2×50 mL). The combined organic layers were washed with brine (2×20 mL), dried over anhydrous Na₂SO₄, filtered and concentrated under reduced pressure to afford 301.3 (6 g, 98%) as a white solid.

Synthesis of I-205

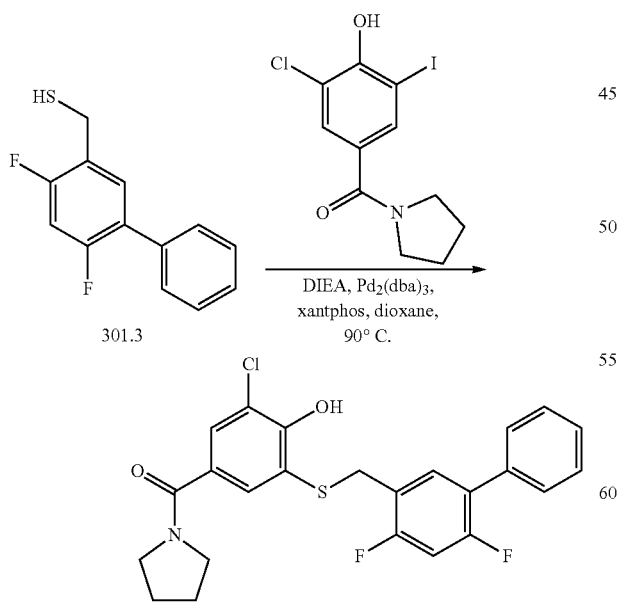

To a stirred solution of 301.3 (590 mg, 2.50 mmol, 1 equiv) and 2-chloro-6-iodo-4-(pyrrolidinecarbonyl)phenol (877.9 mg, 2.50 mmol, 1.00 equiv) in dioxane (5 mL) were added DIEA (645.5 mg, 4.99 mmol, 2.00 equiv), Pd₂(dba)₃ (228.7 mg, 0.25 mmol, 0.10 equiv) and xantphos (144.5 mg, 0.25 mmol, 0.10 equiv) at rt under nitrogen atmosphere. After stirring for overnight at room temperature under nitrogen atmosphere, the resulting mixture was extracted with EtOAc (2×20 mL). The combined organic layers were washed with brine (2×20 mL), dried over anhydrous Na₂SO₄, filtered and concentrated under reduced pressure. The residue was purified by PrepTLC (CH₂Cl₂/MeOH 20:1) to afford I-205 (130 mg, 11%) as a white solid (ES, m/z): [M+H]⁺ 460.2 1H NMR: (DMSO, 400 MHz, ppm): δ10.22 (s, 1H), δ7.49-7.29 (m, 9H), δ4.20 (s, 2H), δ3.37-3.31 (m, 2H), δ3.17 (s, 2H), δ1.78-1.63 (m, 4H).

Example 302. Synthesis of N-(5-(azetidine-1-carbonyl)-3-chloro-2-hydroxyphenyl)-4-fluoro-[1,1'-biphenyl]-3-carboxamide (I-216)

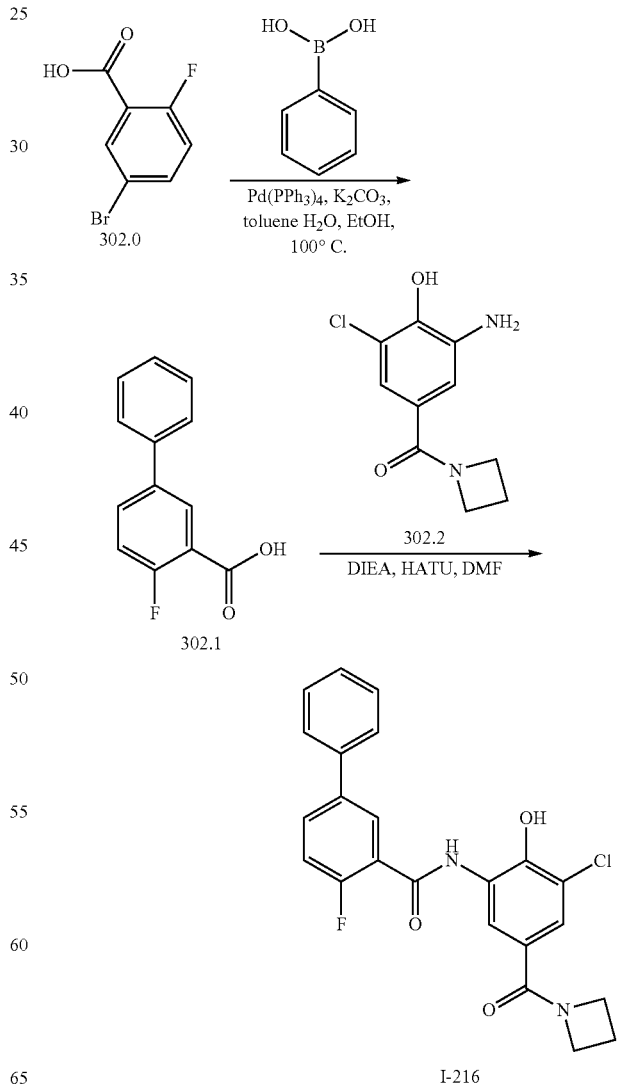

Synthesis of 302.1

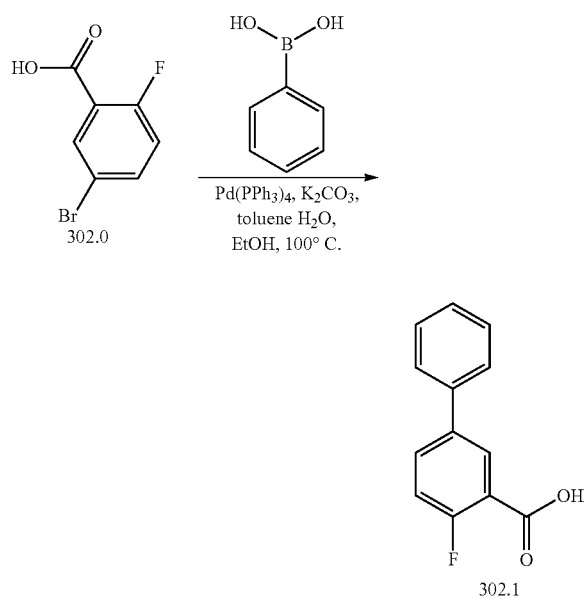

Into a 20-mL vial purged and maintained with an inert atmosphere of nitrogen, were placed 5-bromo-2-fluorobenzoic acid (500 mg, 2.28 mmol, 1 equiv), phenylboronic acid (334.0 mg, 2.74 mmol, 1.2 equiv), Pd(PPh$_3$)$_4$ (263.8 mg, 0.23 mmol, 0.1 equiv), K$_2$CO$_3$ (946.6 mg, 6.85 mmol, 3 equiv), toluene (3 mL, 0.03 mmol, 0.01 equiv), H$_2$O (3 mL, 0.17 mmol, 0.07 equiv), and EtOH (3 mL, 0.07 mmol, 0.03 equiv). After stirring for overnight at 100° C. in an oil bath, the resulting solution was diluted with H$_2$O (20 mL) and extracted with 3×20 mL of ethyl acetate. The combined organic solution was concentrated under vacuum. The residue was purified by Prep TLC with ethyl acetate/petroleum ether (1:5) to afford 400 mg (81.04%) of 302.1 as a yellow solid.

Synthesis of I-216

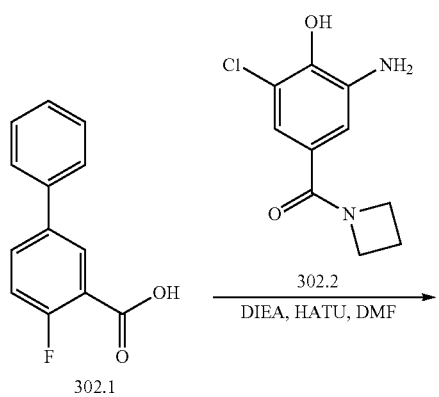

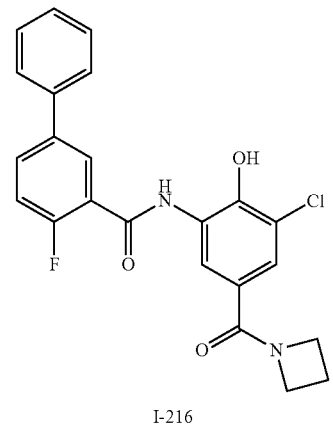

I-216

Into a 8-mL vial purged and maintained with an inert atmosphere of nitrogen were placed 302.1 (70 mg, 0.32 mmol, 1 equiv), 302.2 (88.1 mg, 0.39 mmol, 1.20 equiv), DIEA (125.5 mg, 0.97 mmol, 3.00 equiv), DMF (0.5 mL, 0.01 mmol, 0.02 equiv), and HATU (184.7 mg, 0.49 mmol, 1.50 equiv). After stirring overnight at room temperature, the resulting solution was diluted with H$_2$O (10 mL) and extracted with 3×20 ml of ethyl acetate. The combined organic solution was concentrated under vacuum. The residue was purified by Flash-Prep-HPLC with the following conditions: IntelFlash-1, Column, C18 silica gel; mobile phase, ACN/H$_2$O=15% increasing to ACN/H$_2$O=60% within 15; Detector, UV 254 nm. The crude product was re-crystallized from PE/EA in the ratio of 4:1 to afford 2.5 mg (1.82%) of I-216 as a white solid.

[M+H]$^+$ 425.0; 1H-NMR: (DMSO, 300 MHz, ppm): 2.22-2.33 (m, 2H), δ3.92-4.49 (m, 4H), δ7.39-7.55 (m, 5H), δ7.73-7.76 (d, J=7.5 Hz, 2H), δ7.86-8.01 (s, 1H), δ8.05-8.29 (m, 2H), δ9.95 (s, 1H), δ10.52 (s, 1H).

Example 303: Synthesis of 3-(phenylsulfonamido)-[1,1'-biphenyl]-4-carboxylic Acid (I-225)

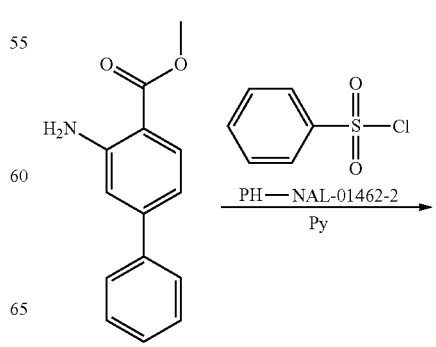

723

-continued

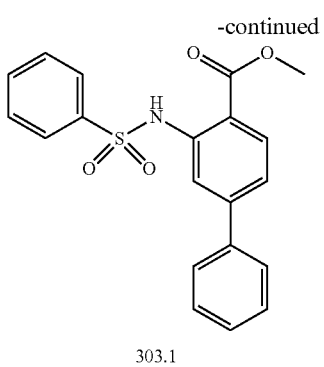

303.1

NaOH, MeOH, H₂O →

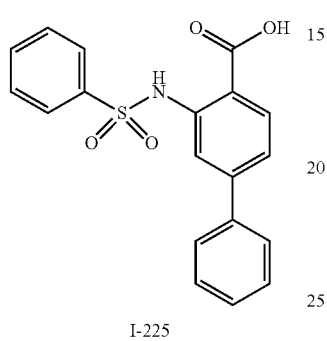

I-225

Synthesis of 303.1

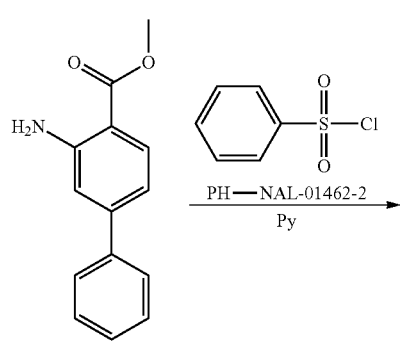

PH—NAL-01462-2
Py →

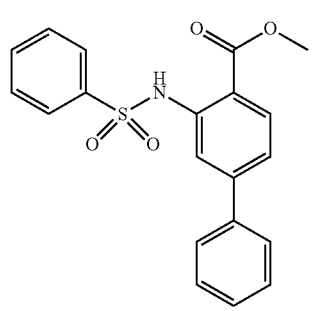

303.1

To a solution of methyl 3-amino-[1,1'-biphenyl]-4-carboxylate (257.4 mg, 1.13 mmol, 1 equiv) in pyridine (5 mL) was added benzenesulfonyl chloride (200 mg, 1.13 mmol, 1 equiv). After stirring for 0.5 hr at room temperature, the resulting mixture was concentrated. The residue was purified by silica gel column with ethyl acetate/petroleum ether (1:1) to afford 303.1 (100 mg, 24% yield) as a white solid.

724

Synthesis of I-225

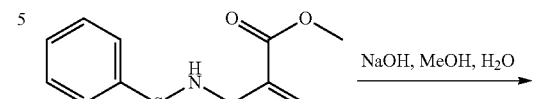

303.1

NaOH, MeOH, H₂O →

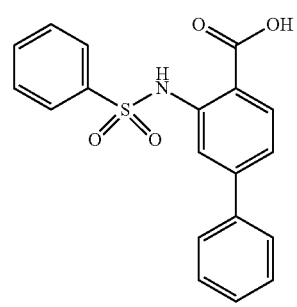

I-225

To a solution of 303.1 (150 mg, 0.41 mmol, 1 equiv) in MeOH (8 mL)/H₂O (2 mL) was added NaOH (32.7 mg, 0.82 mmol, 2.00 equiv). After stirring for 12 hr at 40° C., the reaction mixture pH was adjusted to 7 with HCl (1M) and then extracted with 20 mL of ethyl acetate. The organic solution was washed with brine (20 mL), dried over anhydrous sodium sulfate and concentrated. The residue was purified by silica gel column with dichloromethane/methanol (10:1) to afford I-225 (34.1 mg, 24% yield) as a white solid. (ES, m/z): [M–H]⁻ 352.0; 1H-NMR: (400 MHz, DMSO-d6, ppm): δ7.93-7.91 (m, 1H), δ7.82-7.80 (m, 2H), δ7.64 (s, 1H), δ7.58-7.38 (m, 8H), δ7.24-7.21 (m, 1H).

Example 304: Synthesis of 3-((3-(azetidine-1-carbonyl)-5-chlorophenyl)sulfonamido)-[1,1'-biphenyl]-4-carboxylic Acid (I-227)

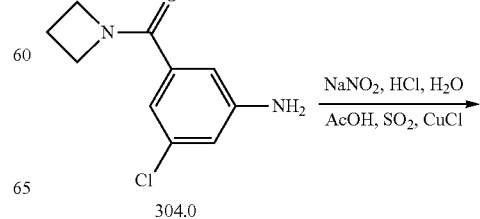

304.0

NaNO₂, HCl, H₂O / AcOH, SO₂, CuCl →

725
-continued

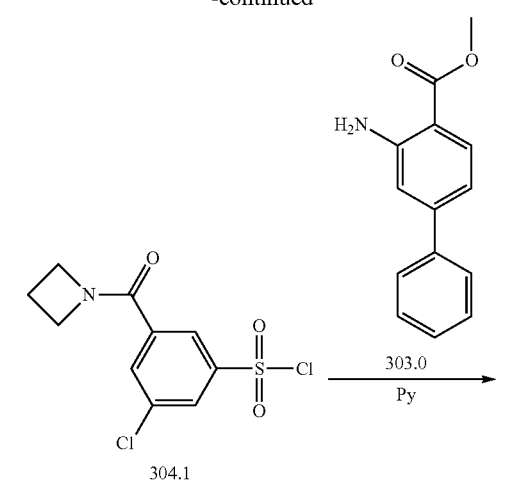

303.0
Py

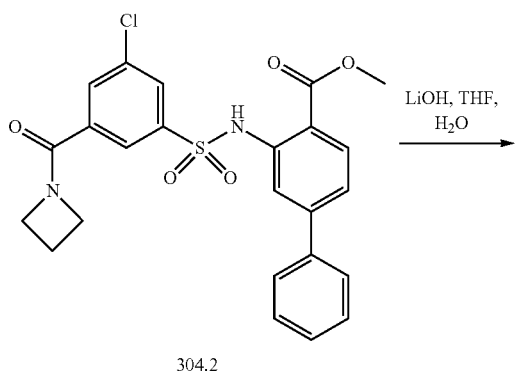

LiOH, THF,
H₂O 304.2

I-227

Synthesis of 304.1

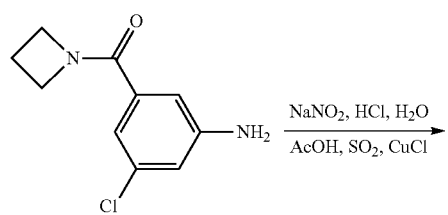

NaNO₂, HCl, H₂O
―――――――――
AcOH, SO₂, CuCl

726
-continued

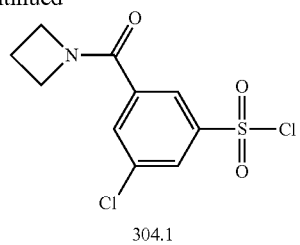

304.1

Into a 100-mL round-bottom flask purged and maintained with an inert atmosphere of nitrogen, were added 3-(azetidine-1-carbonyl)-5-chloroaniline (300 mg, 1.42 mmol, 1 equiv) and HCl (3 mL), and then a solution of NaNO₂ (147.4 mg, 2.14 mmol, 1.5 equiv) in H₂O (1.2 mL) at 0° C. After stirring at 0° C. for 1 h; a solution of AcOH (3 mL) and CuCl (42.3 mg, 0.43 mmol, 0.3 equiv) with SO₂ (bubbled into over 0.5 h prior to addition to diazonium solution) was added dropwised over 10 mins. After stirring for 1 h at room temperature, the reaction was then quenched by the addition of water (10 mL) and extracted with 3×10 mL of ethyl acetate. The organic solution was washed with brine (10 mL), dried over anhydrous sodium sulfate and concentrated to afford 304.1 (400 mg, 42% yield) as a white solid.

Synthesis of 304.2

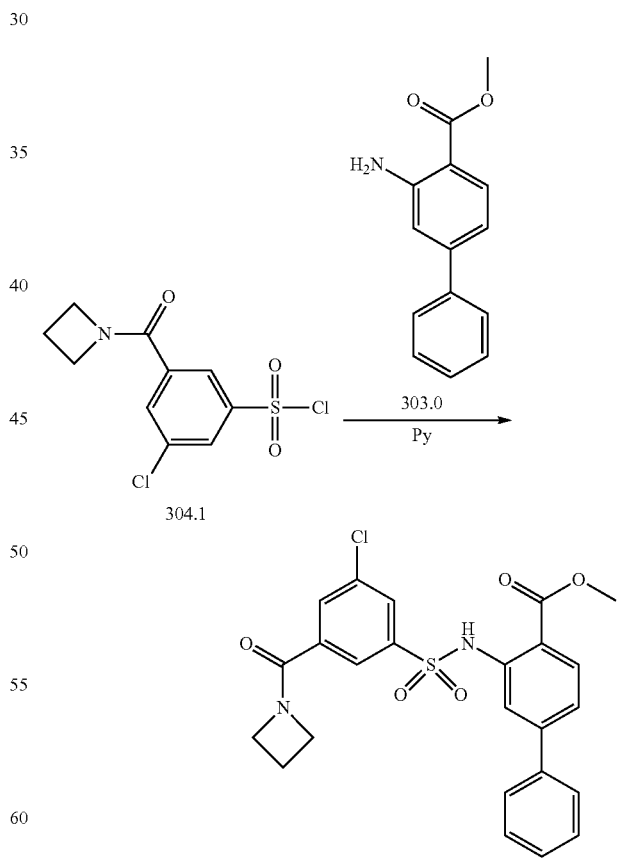

Into a 25-mL round-bottom flask purged and maintained with an inert atmosphere of nitrogen, were placed 304.1 (200 mg, 0.68 mmol, 1 equiv), 303.0 (154.5 mg, 0.68 mmol, Synthesis of I-227

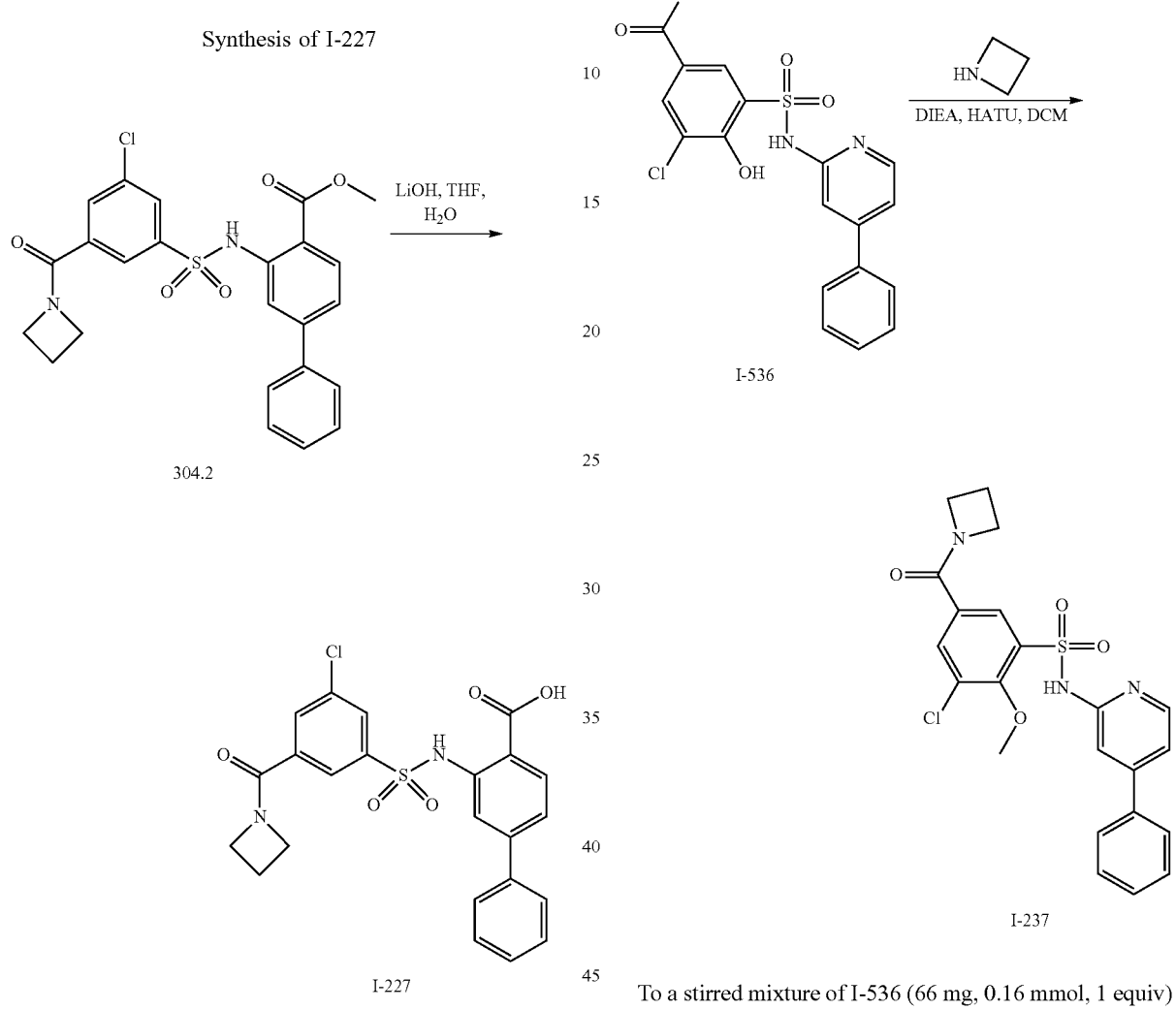

Example 305: Synthesis of 5-(azetidine-1-carbonyl)-3-chloro-2-methoxy-N-(4-phenylpyridin-2-yl)benzenesulfonamide (1-237)

Into a 50-mL round-bottom flask purged and maintained with an inert atmosphere of nitrogen, were placed 304.2 (90 mg, 0.19 mmol, 1 equiv), LiOH (8.9 mg, 0.37 mmol, 2.00 equiv), THF (4 mL), and H₂O (1 mL). After stirring for 12 hr at room temperature, the pH value of the solution was adjusted to 7 with HCl (1 mol/L) and extracted with ethyl acetate (3×10 mL). The organic layer was washed with 1×10 mL of brine, dried over anhydrous sodium sulfate and concentrated. The residue was purified by silica gel column with dichloromethane/methanol (10:1) to afford I-227 (22.3 mg, 26% yield) of a white solid. (ES, m/z): [M–H]⁻ 469; 1H-NMR: (400 MHz, DMSO-d6, ppm): δ8.02-8.01 (d, J=4 Hz, 1H), 7.96-7.95 (t, J=1.6 Hz, 1H), 7.90-7.87 (m, 2H), 7.81-7.80 (t, J=1.6 Hz, 1H), 7.64-7.62 (m, 2H), 7.52-7.48 (m, 2H), 7.44-7.40 (m, 1H), 7.36-7.34 (m, 1H), 4.12-4.01 (m, 4H), 2.24-2.16 (m, 2H).

To a stirred mixture of I-536 (66 mg, 0.16 mmol, 1 equiv) and azetidine (27.9 mg, 0.49 mmol, 3 equiv) in DMF (1 mL, 12.92 mmol, 79.26 equiv) were added DIEA (84.3 mg, 0.65 mmol, 4 equiv) and HATU (124.0 mg, 0.33 mmol, 2 equiv) in portions at room temperature under nitrogen atmosphere. The resulting solution was stirred overnight at room temperature under nitrogen atmosphere. The reaction was quenched with water at room temperature. The aqueous layer was extracted with EtOAc (2×100 mL). The combined organic solution was concentrated and the residue was purified by reverse phase flash with the following conditions (from CH₃CN:H₂O=1:20 to CH₃CN:H₂O=50:50 in 30 mins UV: 254/220) to afford I-237 (2.3 mg, 3.18%) as a brown solid. LC-MS: (ES, m/z): [M–H]⁻ 442.1. 1H-NMR: (400 MHz, DMSO, ppm): δ 2.11-2.22 (m, 2H), δ3.95-4.27 (s, 4H), δ7.15-7.20 (s, 1H), δ 7.27-7.31 (s, 1H), δ 7.49 (m, 3H), δ 7.53 (s, 1H), δ 7.60-7.67 (m, 2H), δ 7.81 (s, 1H), δ 8.09 (s, 1H).

Example 306: Synthesis of 3-((3,5-dichlorobenzyl)amino)-[1,1'-biphenyl]-4-carboxylic Acid

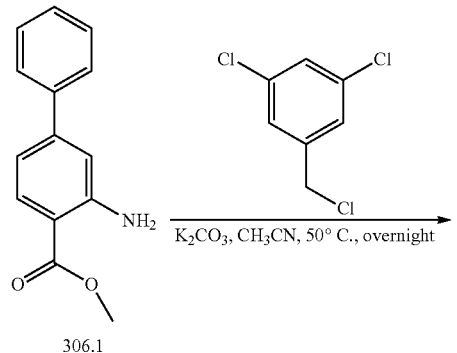

306.1

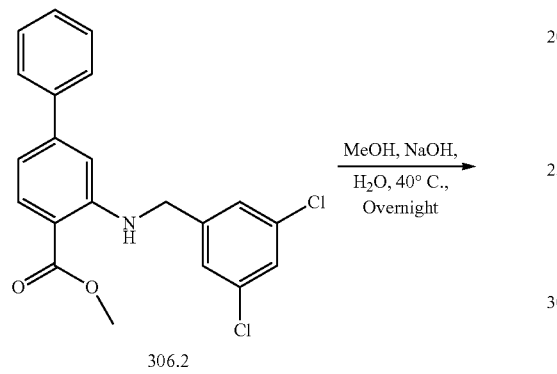

306.2

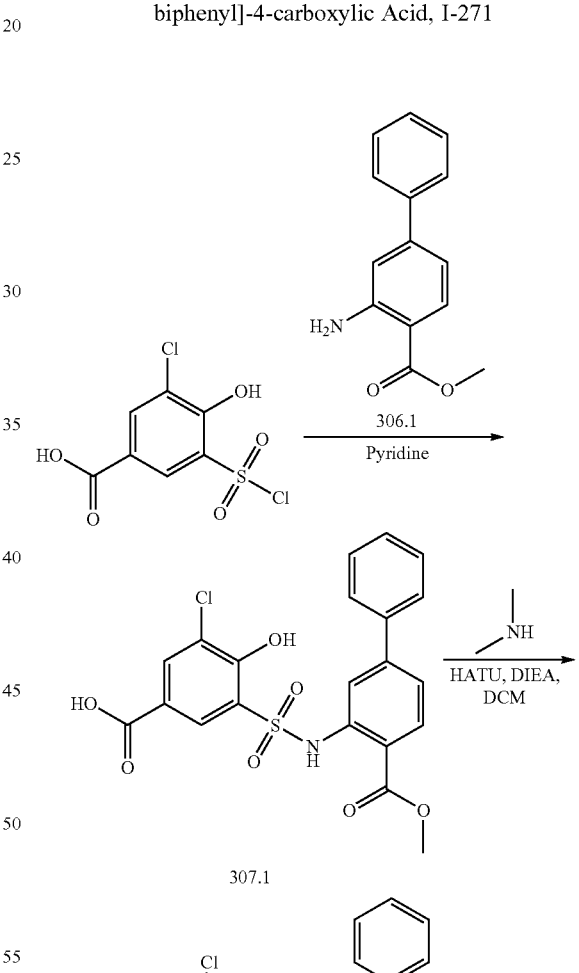

I-267

Synthesis of 306.2

Into a 50-mL 3-necked round-bottom flask were placed methyl 3-amino-[1,1'-biphenyl]-4-carboxylate (200 mg, 0.880 mmol, 1 equiv), CH₃CN (10 mg), K₂CO₃ (121.63 mg, 0.880 mmol, 1.00 equiv), and 1,3-dichloro-5-(chloromethyl)benzene (172.02 mg, 0.880 mmol, 1.00 equiv). The resulting solution was stirred for overnight at 50° C. The mixture was filtered and the filtrate was concentrated. The crude product was purified by Flash-Prep-HPLC with the following conditions (IntelFlash-1): Column, C18 silica gel; mobile phase, ACN/H2O=15% increasing to ACN/H2O=60% within 15 min to give 65 mg (19%) of 306.2.

Synthesis of I-267

Into a 50-mL 3-necked round-bottom flask were placed 306.1 (50 mg, 0.13 mmol, 1 equiv), MeOH (5 mL, 123.49 mmol, 954.04 equiv), H₂O (5 mL, 277.54 mmol, 2144.12 equiv), and NaOH (4 mg, 0.10 mmol, 0.77 equiv). The resulting solution was stirred for overnight at 40° C. The pH of the solution was adjust to 5 by adding 1N HCl, then extracted with EA (10 mL). The combined organic solution was washed with brine (10 mL) and concentrated in vacuum. The crude product was purified by Flash-Prep-HPLC with the following conditions (Intel Flash-1): Column, C18 silica gel; mobile phase, ACN/H2O=15% increasing to ACN/H2O=60% within 15 min. to give 3 mg (6%) of I-267 as a solid. LC-MS: (ES, m/z): [M+H]⁺ 372.0. 1H-NMR: (400 MHz, DMSO-d6, ppm): δ12.70 (s, 1H), 8.46 (s, 1H), 7.90-7.88 (d, J=7.6 Hz, 1H), 7.63-7.61 (m, 2H), 7.58-7.38 (m, 6H), 6.89-6.80 (m, 2H), 4.63 (s, 2H).

Example 307: Synthesis of 3-((3-chloro-5-(dimethylcarbamoyl)-2-hydroxyphenyl)sulfonamido)-[1,1'-biphenyl]-4-carboxylic Acid, I-271

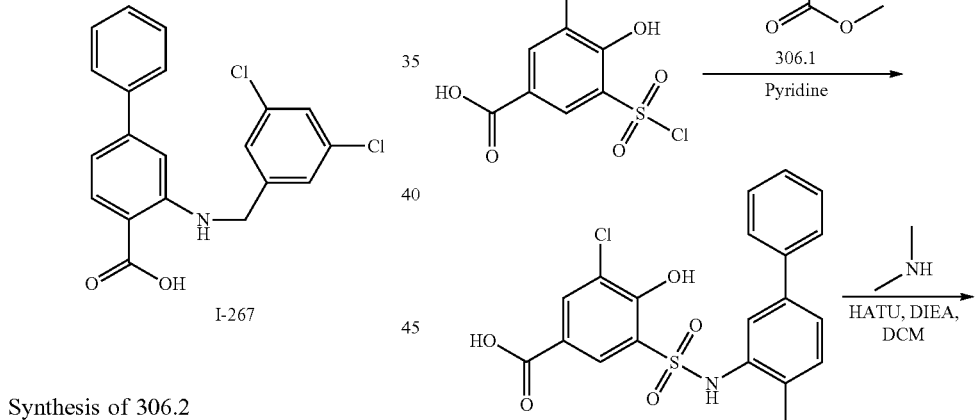

307.1

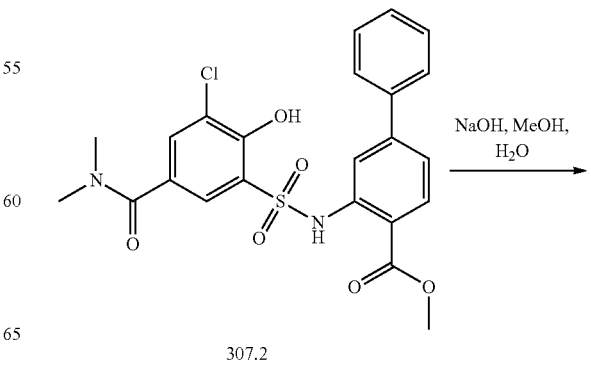

307.2

731

-continued

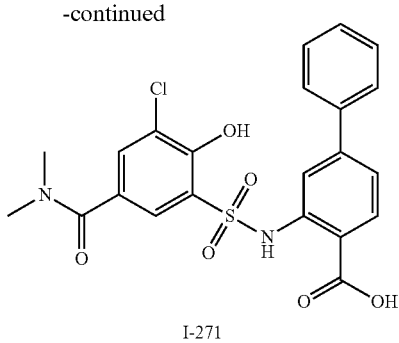

I-271

Synthesis of 307.1

Into a 50-mL 2-necked round-bottom flask were placed 3-chloro-5-(chlorosulfonyl)-4-hydroxybenzoic acid (500 mg, 1.84 mmol, 1 equiv), 306.1 (503.1 mg, 2.21 mmol, 1.2 equiv), and pyridine (7 mL). The resulting solution was stirred for 12 h at 25° C. The resulting mixture was concentrated under vacuum. The crude product was purified by Flash-Prep-HPLC with the following conditions (IntelFlash-1): Column, C18 silica gel; mobile phase, ACN:H₂O=10% increasing to ACN:H2O=60% within 15 min to give 190 mg (22%) of 307.1 as a light yellow solid.

Synthesis of 307.2

Into a 100-mL round-bottom flask were placed 307.1 (150 mg, 0.325 mmol, 1 equiv), dimethylamine (29.28 mg, 0.650 mmol, 2 equiv), DCM (6 mL), DIEA (209.87 mg, 1.624 mmol, 5 equiv), and HATU (185.23 mg, 0.487 mmol, 1.5 equiv). The resulting solution was stirred for 12 h at 25° C. The reaction was then quenched by the addition of 15 mL of water. The resulting solution was extracted with ethyl acetate (3×25 mL). The combined organic layers were concentrated under vacuum. The residue was applied onto Prep-TLC eluting with dichloromethane/methanol (20:1) to give 100 mg (63%) of 307.2 as an off-white solid.

Synthesis of I-271

Into a 100-mL round-bottom flask were placed 307.2 (100 mg, 0.205 mmol, 1 equiv), H₂O (3 mL), MeOH (3 mL), and NaOH (81.80 mg, 2.045 mmol, 10.00 equiv). The resulting solution was stirred for 12 h at 25° C. The reaction was then quenched by the addition of 15 mL of diluted hydrochloric acid. The resulting solution was extracted with 3×25 mL of ethyl acetate. The combined organic layers were concentrated under vacuum. The crude product was purified by Flash-Prep-HPLC with the following conditions (IntelFlash-1): Column, C18 silica gel; mobile phase, ACN:H2O=15% increasing to ACN:H2O=60% within 15 min to give 34.8 mg (36%) of I-271 as a white solid. LC-MS: (ES, m/z): [M+H]⁺ 475.0. H-NMR: (400 MHz, DMSO-d6, ppm) δ 7.92-7.90 (d, J=8 Hz, 1H), 7.66 (d, J=2.4 Hz, 1H), 7.56 (d, J=1.2 Hz, 1H), 7.49-7.36 (m, 6H), 7.15-7.12 (m, 1H), 2.82 (s, 6H).

732

Example 308: Synthesis of 3-(1H-indazole-5-sulfonamido)-[1,1'-biphenyl]-4-carboxylic Acid, I-301

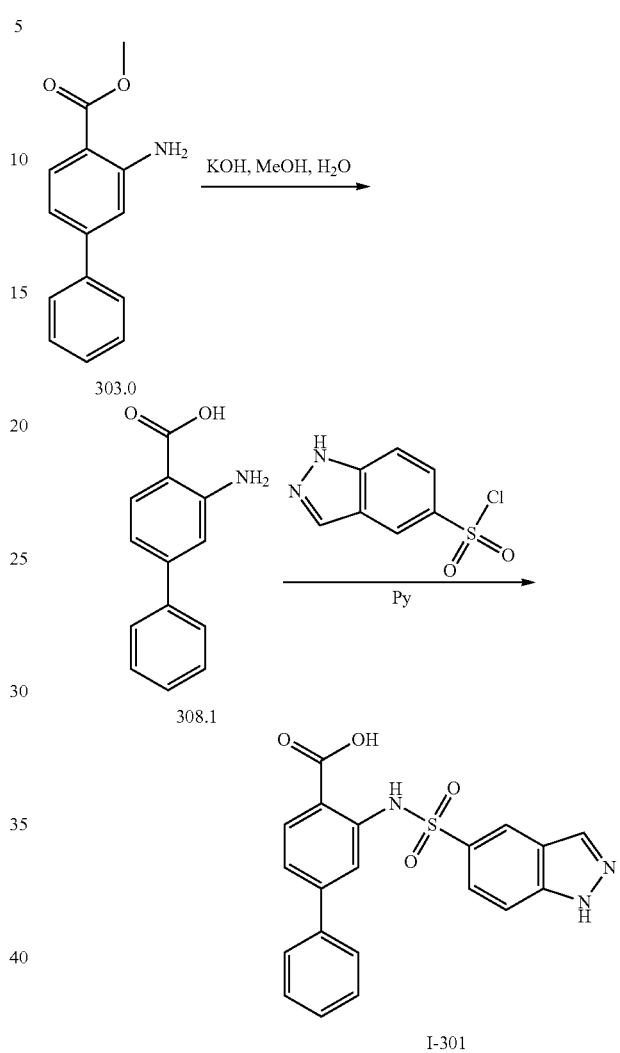

Synthesis of 308.1

Into a 50-mL round-bottom flask were placed 303.0 (300 mg, 1.320 mmol, 1 equiv), MeOH (10 mL), H₂O (10 mL), and KOH (740.63 mg, 13.201 mmol, 10 equiv). The resulting solution was stirred for overnight at 40° C. in an oil bath. The resulting mixture was concentrated under vacuum. The resulting solution was diluted with 20 mL of H₂O. The pH value of the solution was adjusted to 6 with AcOH. The resulting solution was extracted with 3×20 mL of ethyl acetate. The resulting mixture was concentrated under vacuum. The residue was applied onto a prep TLC with ethyl acetate/petroleum ether (1:1) to give 220 mg (78%) of 308.1 as a white solid.

Synthesis of I-301

Into a 8-mL vial were placed 308.1 (182.87 mg, 0.844 mmol, 1 equiv) and pyridine (2 mL). The resulting solution was stirred for overnight at 50° C. in an oil bath. The resulting mixture was concentrated under vacuum. The crude product was purified by Prep-HPLC with the following conditions: Column, Column: XBridge Prep OBD C18 Column 19*250 mm, 5 um; Mobile Phase A: Water (0.05% $NH_3H_2O$), Mobile Phase B: ACN; Flow rate: 20 mL/min; Gradient: 32% B to 37% B in 8 min; 254/220 nm; Rt: 5.92 min; mobile phase to provide 8.7 mg (3%) of I-301 as a white solid. LC-MS: (ES, m/z): [M−H]⁻ 392.1. H-NMR: (300 MHz, DMSO-d6, ppm): δ13.49 (s, 1H), 8.42 (s, 1H), 8.28 (s, 1H), 7.91-7.89 (d, J=8.4 Hz, 1H), 7.73-7.64 (s, 3H), 7.52-7.39 (m, 5H), 7.25-7.23 (d, J=8.4 Hz, 1H).

Example 309: Synthesis of 3-((2-chloropyridine)-3-sulfonamido)-[1,1'-biphenyl]-4-carboxylic Acid, I-302

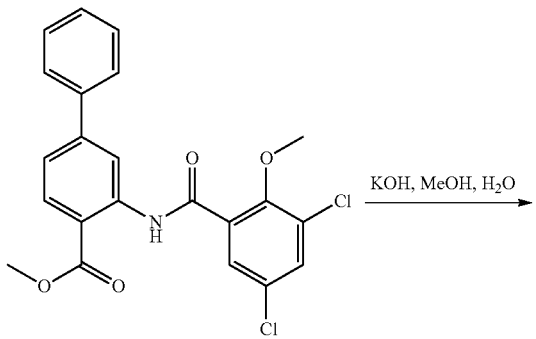

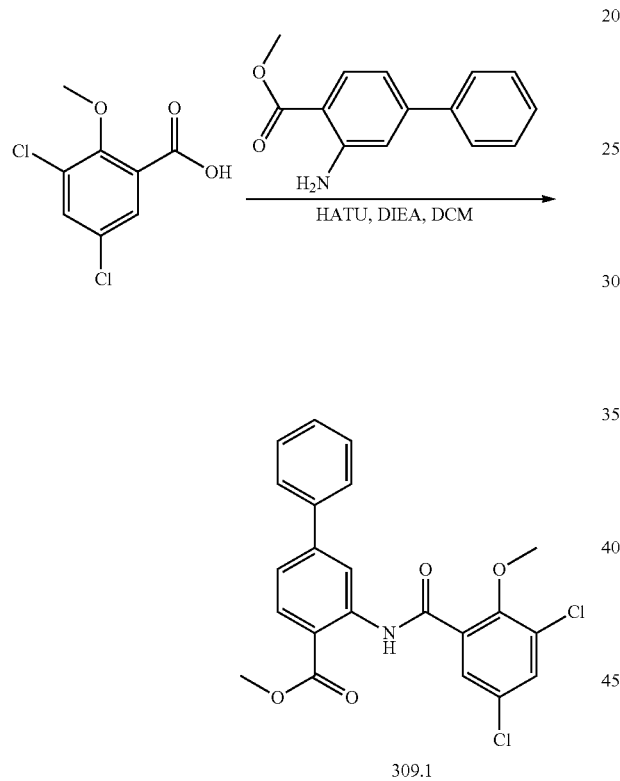

Synthesis of 309.1

Into a 50-mL round-bottom flask, was placed 3,5-dichloro-2-methoxybenzoic acid (1 g, 4.524 mmol, 1 equiv), methyl 3-amino-[1,1-biphenyl]-4-carboxylate (1233.84 mg, 5.429 mmol, 1.2 equiv), DIEA (1169.46 mg, 9.049 mmol, 2 equiv), DCM (20 mL), HATU (2580.40 mg, 6.786 mmol, 1.5 equiv). The resulting solution was stirred for overnight at 40° C. in an oil bath. The resulting solution was diluted with 60 mL of $H_2O$. The resulting solution was extracted with 3×50 mL of ethyl acetate. The resulting mixture was concentrated under vacuum. This resulted in 1.3 g (67%) of 309.1 as a solid.

Synthesis of I-302

To a solution of 309.1 (100 mg, 0.23 mmol, 1 equiv) in MeOH (10 mL)/$H_2O$ (10 mL) was added KOH (78.2 mg, 1.39 mmol, 6 equiv). The resulting solution was stirred for 1 overnight at 60° C. in an oil bath. The resulting mixture was concentrated under vacuum. The resulting solution was diluted with 30 mL of $H_2O$. The resulting solution was extracted with 3×20 mL of ethyl acetate. The resulting mixture was concentrated under vacuum. The crude product was purified by Flash-Prep-HPLC with the following conditions (IntelFlash-1): Column, silica gel; mobile phase, ACN/$H_2O$=15% increasing to ACN/$H_2O$=60% within 15 min; Detector, UV: 254 nm. This resulted in 21.2 mg (22%) of I-302 as a white solid. LC-MS-I-302: (ES, m/z): [M+H]⁺ 416. H-NMR: (300 MHz, DMSO-d6, ppm): δ13.68 (s, 1H), 12.17 (s, 1H), 8.97 (s, 1H), 8.12-8.09 (d, J=8.1 Hz, 1H), 7.93-7.92 (d, J=2.7 Hz, 1H), 7.85-7.84 (d, J=2.4 Hz, 1H), 7.77-7.70 (m, 2H), 7.55-7.49 (m, 3H), 7.41-7.39 (m, 1H), 3.90 (s, 3H).

Example 310: Synthesis of 3-((cyclobutylmethyl)sulfonamido)-[1,1'-biphenyl]-4-carboxylic Acid, I-307

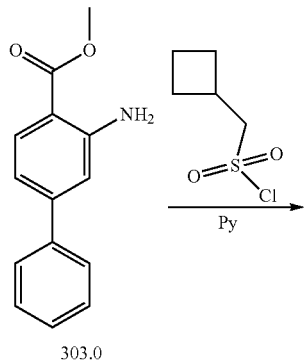

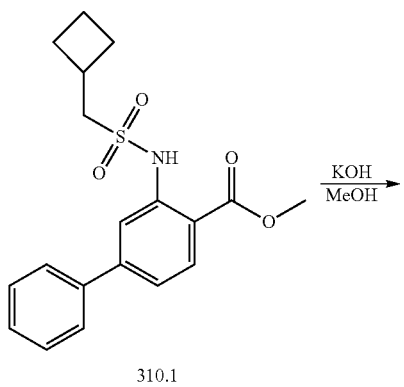

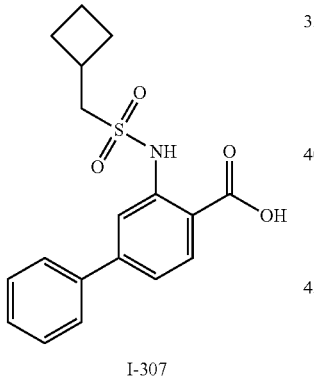

Synthesis of 310.1

To a solution of 303.0 (227 mg, 0.999 mmol, 1 equiv) in pyridine (5 mL, 0.063 mmol, 0.06 equiv) was added cyclobutylmethanesulfonyl chloride (202.13 mg, 1.199 mmol, 1.2 equiv). The resulting solution was stirred overnight at room temperature. The resulting mixture was concentrated. The crude product (3 mL) was purified by Flash-Prep-HPLC with the following conditions (IntelFlash-1): Column, C18 silica gel; mobile phase, $H_2O$/ACN=100/0 increasing to $H_2O$/ACN=0/100 within 40 min; Detector, 254 nm to give 110 mg (18%) of 310.1 as a white solid.

Synthesis of I-307

To a solution of 310.1 (130 mg, 0.362 mmol, 1 equiv) in THF (3 mL)/MeOH (1 mL)/$H_2O$ (1 mL) was added KOH (202.92 mg, 3.617 mmol, 10 equiv). The resulting solution was stirred overnight at 40° C. in an oil bath. The resulting mixture was concentrated. The crude product (3 mL) was purified by Flash-Prep-HPLC with the following conditions (IntelFlash-1): Column, C18 silica gel; mobile phase, $H_2O$/ACN=100/0 increasing to $H_2O$/ACN=0/100 within 40 min; Detector, 254 nm to give 22.9 mg (37%) of I-307 as a white solid. LC-MS: (ES, m/z): [M−H]⁻ 344.1. H-NMR: (400 MHz, DMSO-d6, ppm): δ8.05-8.03 (d, J=8 Hz, 1H), 7.71-7.69 (m, 1H), 7.65-7.63 (d, J=7.2 Hz, 2H), 7.51-7.45 (m, 2H), 7.45-7.39 (m, 1H), 7.31-7.28 (m, 1H), 3.30-3.28 (d, J=7.2 Hz, 2H), 2.73-2.64 (m, 1H), 2.02-1.98 (m, 2H), 1.85-1.70 (m, 4H).

Example 311: Synthesis of 3-(2-(carboxymethoxy)-3,5-dichlorobenzamido)-[1,1'-biphenyl]-4-carboxylic Acid, I-308

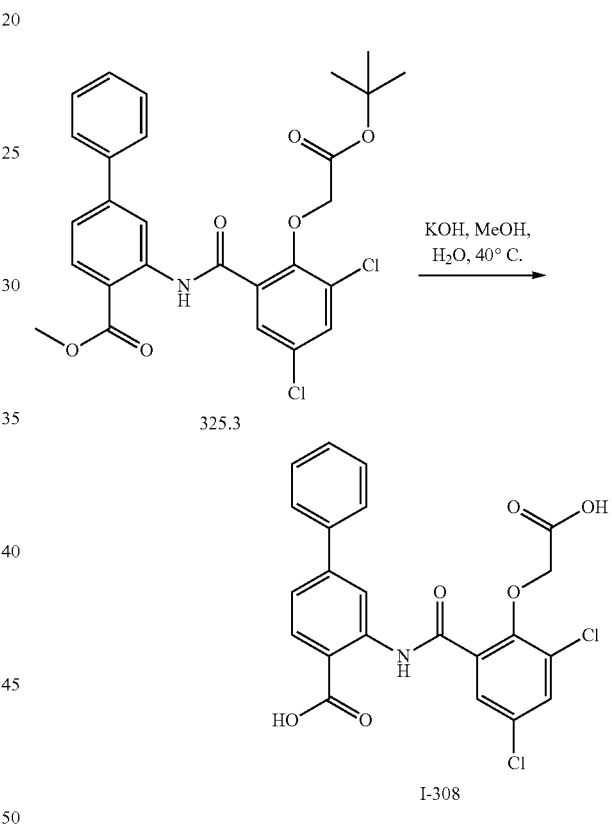

To a solution of 325.3 (85 mg, 0.160 mmol, 1 equiv) in MeOH (10 mL)/$H_2O$ (10 mL) was added KOH (89.91 mg, 1.603 mmol, 10 equiv). The resulting solution was stirred for 1 overnight at 40° C. in an oil bath. The resulting mixture was concentrated under vacuum. The resulting solution was diluted with 20 mL of $H_2O$. The pH value of the solution was adjusted to 6 with AcOH. The resulting solution was extracted with 3×20 mL of ethyl acetate. The resulting mixture was concentrated under vacuum. The crude product was purified by Flash-Prep-HPLC with the following conditions (IntelFlash-1): Column, silica gel; mobile phase, ACN/$H_2O$=15% increasing to ACN/$H_2O$=60% within 15 min; Detector, UV: 254 nm to give 29.3 mg (40%) of I-308 as a white solid. LC-MS: (ES, m/z): [M+H]⁺ 460. H-NMR: (300 MHz, DMSO-d6, ppm): δ8.89 (s, 1H), 8.05-8.03 (d, J=7.8 Hz, 1H), 7.88-7.85 (t, J=4.8 Hz, 1H), 7.75-7.74 (d, J=2.7 Hz, 1H), 7.73-7.62 (m, 2H), 7.59-7.46 (m, 2H), 7.45-7.34 (m, 2H), 7.25-7.15 (m, 2H), 4.57 (s, 2H).

Example 312: Synthesis of 3-((3,5-dichlorobenzamido)methyl)-[1,1'-biphenyl]-4-carboxylic Acid, I-309

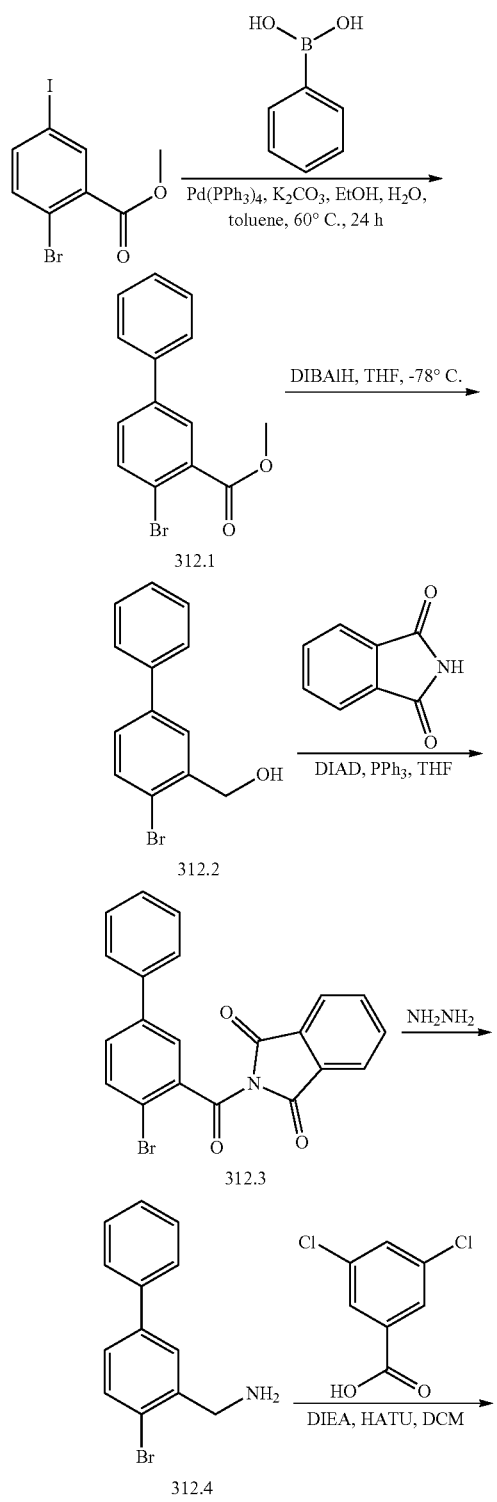

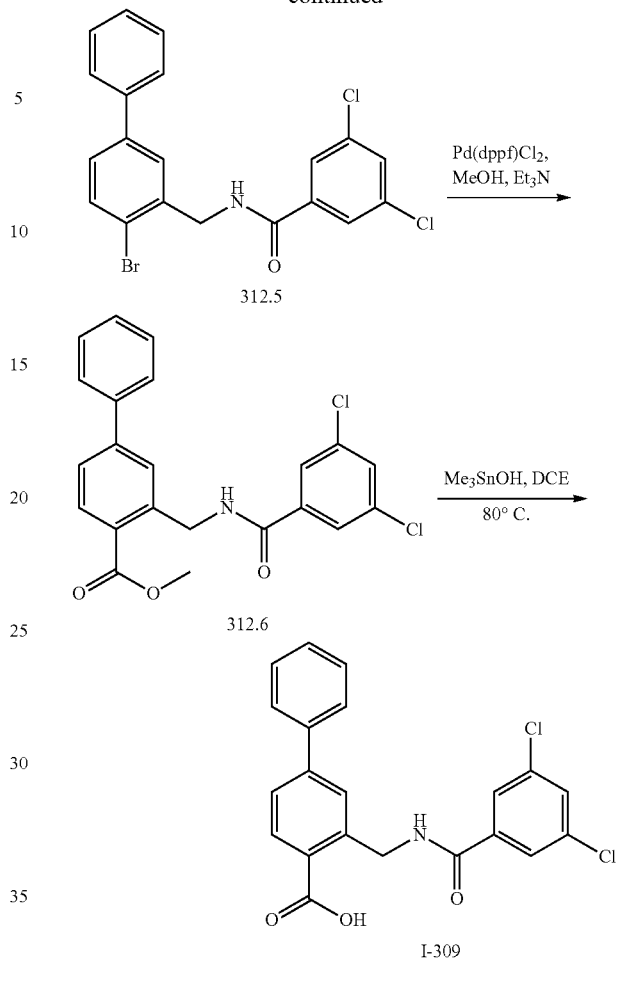

Synthesis of 312.1

Into a 250-mL 3-necked round-bottom flask were placed methyl 2-bromo-5-iodobenzoate (5 g, 14.665 mmol, 1 equiv), toluene (20 mL), H2O (20 mL), EtOH (20 mL), phenylboronic acid (2.32 g, 19.065 mmol, 1.3 equiv), Pd(PPh3)4 (1.69 g, 1.467 mmol, 0.1 equiv), and K2CO3 (6.08 g, 43.996 mmol, 3 equiv). The resulting solution was stirred for 24 hr at 60° C. The reaction was then quenched by the addition of 100 mL of water. The resulting solution was extracted with 3×150 mL of ethyl acetate. The combined organic layers were concentrated under vacuum. The residue was applied onto a silica gel column eluting with ethyl acetate/petroleum ether (20:1 to give 2.9 g (67.92%) of 312.1 as a light yellow solid.

Synthesis of 312.2

Into a 250-mL 3-necked round-bottom flask were placed 312.1 (2.9 g, 9.961 mmol, 1 equiv), THF (0.5 mL), and DIBALH (50 mL, 298.134 mmol, 29.93 equiv). The resulting solution was stirred for 24 hr at 25° C. The reaction was then quenched by the addition of 50 mL of water. The resulting solution was extracted with 3×100 mL of ethyl acetate. The combined organic layers were concentrated under vacuum. The residue was applied onto a silica gel column eluting with ethyl acetate/petroleum ether (20:1) to give 1.8 g (68.68%) of 312.2 as a yellow solid.

Synthesis of 312.3

Into a 100-mL 3-necked round-bottom flask purged and maintained with an inert atmosphere of nitrogen were placed 312.2 (1.8 g, 6.841 mmol, 1 equiv), THF (30 mL), 2,3-dihydro-1H-isoindole-1,3-dione (1.21 g, 8.209 mmol, 1.2 equiv), DIAD (2.77 g, 13.681 mmol, 2 equiv), and PPh3 (2.69 g, 10.261 mmol, 1.5 equiv). The resulting solution was stirred for 12 hr at 25° C. The resulting mixture was concentrated under vacuum. The residue was applied onto a silica gel column eluting with ethyl acetate/petroleum ether (20:1) to give 2.5 g (93.17%) of 312.3 as a light yellow solid.

Synthesis of 312.4

Into a 100-mL round-bottom flask were placed 312.3 (2.5 g, 6.373 mmol, 1 equiv), $NH_2NH_2.H_2O$ (0.64 g, 12.747 mmol, 2 equiv), EtOH (35 mL). The resulting solution was stirred for 2 hr at 60° C. The reaction was then quenched by the addition of 70 mL of water. The resulting solution was extracted with 3×100 mL of ethyl acetate. The combined organic layers were concentrated under vacuum. The residue was applied onto a silica gel column eluting with ethyl acetate/petroleum ether (2:1) to give 1.5 g (89.78%) of 312.4 as a yellow solid.

Synthesis of 312.5

Into a 100-mL round-bottom flask were placed 3,5-dichlorobenzoic acid (500 mg, 2.618 mmol, 1 equiv), DCM (20 mL, 314.601 mmol, 120.18 equiv), 312.4 (1372.44 mg, 5.235 mmol, 2 equiv), DIEA (1014.95 mg, 7.853 mmol, 3 equiv), and HATU (1492.97 mg, 3.926 mmol, 1.5 equiv). The resulting solution was stirred for 12 hr at 25° C. The reaction was then quenched by the addition of water. The resulting solution was extracted with 3×35 mL of ethyl acetate. The combined organic layers were concentrated under vacuum. The residue was applied onto Prep-TLC eluting with ethyl acetate/petroleum ether (5:1) to give 320 mg (28.09%) of 312.5 as a light yellow solid.

Synthesis of 312.6

Into a 250-mL pressure tank reactor was placed 312.5 (260 mg, 0.598 mmol, 1 equiv), MeOH (150 mL), $Et_3N$ (302.31 mg, 2.988 mmol, 5 equiv), Pd(dppf)Cl2 (65.58 mg, 0.090 mmol, 0.15 equiv), and $CO_{(g)}$. The resulting solution was stirred for 12 hr at 120° C. The resulting mixture was concentrated under vacuum. The residue was applied onto a silica gel column eluting with ethyl acetate/petroleum ether (5:1) to give 90 mg (36.36%) of 312.6 as a off-white solid.

Synthesis of I-309

Into a 50-mL round-bottom flask were placed 312.6 (50 mg, 0.121 mmol, 1 equiv), DCE (7 mL), and trimethylstannanol (261.88 mg, 1.448 mmol, 12 equiv). The resulting solution was stirred for 24 hr at 85° C. The reaction was then quenched by the addition of 10 mL of diluted hydrochloric acid. The resulting solution was extracted with 3×15 mL of ethyl acetate and the organic layers combined and concentrated under vacuum. The crude product was purified by Flash-Prep-HPLC with the following conditions (IntelFlash-1): Column, C18 silica gel; mobile phase, ACN:H2O=15% increasing to ACN:H2O=60% within 15 min to give 4.0 mg (8.28%) of I-309 as a white solid. LC-MS: (ES, m/z): $[M+H]^+$ 400. H-NMR: (400 MHz, DMSO-d6) δ 9.36 (s, 1H), 7.96-7.94 (d, J=8.4 Hz, 1H), 7.91-7.90 (d, J=1.2 Hz, 2H), 7.82 (s, 1H), 7.72 (s, 4H), 7.66-7.48 (m, 3H), 4.88-4.87 (d, J=5.2 Hz, 2H).

Example 313: Synthesis of 3-((6-(trifluoromethyl)pyridine)-2-sulfonamido)-[1,1'-biphenyl]-4-carboxylic Acid, I-312

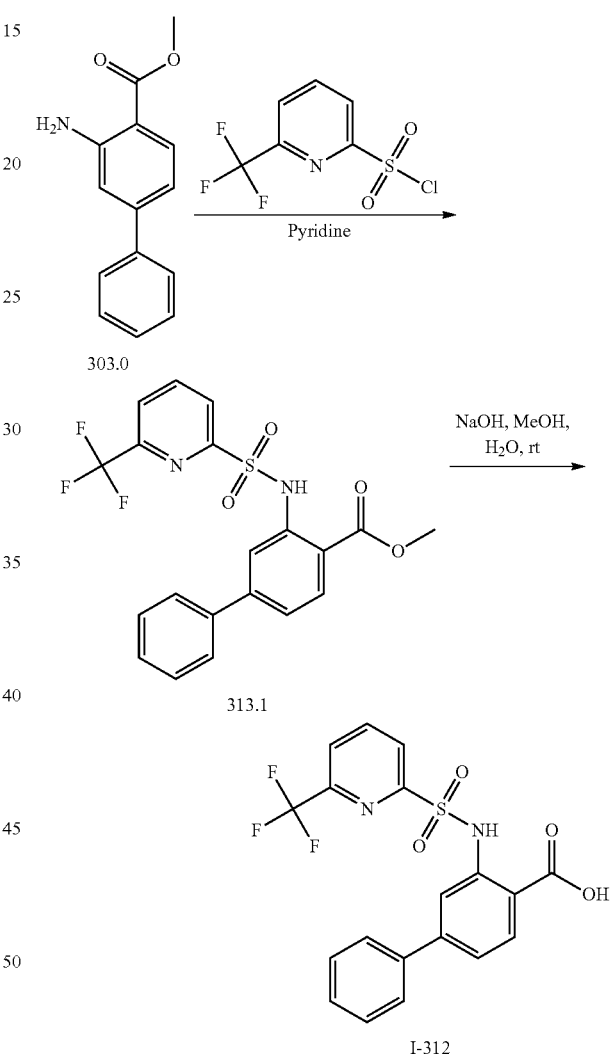

Synthesis of 313.1

To a solution of 303.0 (200 mg, 0.880 mmol, 1 equiv) in pyridine (6 mL) was added 6-(trifluoromethyl)pyridine-2-sulfonyl chloride (216.14 mg, 0.880 mmol, 1 equiv). The resulting solution was stirred for 12 hr at 25° C. The resulting mixture was concentrated under vacuum. The residue was applied onto a silica gel column eluting with ethyl acetate/petroleum ether (2:1) to give 110 mg (29%) of 313.1 as a white solid.

Synthesis of I-312

To a solution of 313.1 (100 mg, 0.229 mmol, 1 equiv) in H$_2$O (3 mL)/MeOH (3 mL) was added NaOH (91.65 mg, 2.291 mmol, 10 equiv). The resulting solution was stirred for 12 hr at 25° C. The reaction was then quenched by the addition of 15 mL of diluted hydrochloric acid. The resulting solution was extracted with 3×20 mL of ethyl acetate. The combined organic layers were concentrated under vacuum. The crude product was purified by Flash-Prep-HPLC with the following conditions (IntelFlash-1): Column, C18 silica gel; mobile phase, ACN:H$_2$O=10% increasing to ACN:H$_2$O=50% within 10 min; Detector, 254 nm to give 7.8 mg (8%) of I-312 as a white solid. LC-MS: (ES, m/z): [M−H]$^-$ 421.1. H-NMR: (400 MHz, DMSO-d6, ppm): δ 8.35-8.24 (m, 2H), 8.07-8.05 (d, J=6.4 Hz, 1H), 7.95-7.85 (m, 2H), 7.61-7.54 (m, 2H), 7.51-7.36 (m, 3H), 7.19-7.08 (m, 3H).

Example 314: Synthesis of 3-((2-methoxy-5-methylphenyl)sulfonamido)-[1,1'-biphenyl]-4-carboxylic Acid, I-313

Synthesis of 314.1

To a stirred mixture of 303.0 (227 mg, 0.999 mmol, 1 equiv) in pyridine (4 mL) was added 2-methoxy-5-methylbenzene-1-sulfonyl chloride (220.41 mg, 0.999 mmol, 1 equiv) at 0° C. The resulting mixture was stirred for overnight at room temperature. The resulting mixture was concentrated under reduced pressure. The residue was purified by reverse flash chromatography with the following conditions: column, C18 silica gel; mobile phase, CH$_3$CN in water, 10% to 100% gradient in 30 min; detector, UV 254 nm to give 314.1 (360 mg, 88%) as a white solid.

Synthesis of I-313

To a stirred mixture of 314.1 (340 mg, 0.826 mmol, 1 equiv) and H$_2$O (5 mL) in MeOH (5 mL) was added NaOH (661.00 mg, 16.526 mmol, 20 equiv) at room temperature. The resulting mixture was stirred for 4 h at 45° C. The mixture was acidified to pH 3 with HCl (2M in H$_2$O). The precipitated solids were collected by filtration and washed with water (2×5 mL). The residue was purified by reverse flash chromatography with the following conditions: column, C18 silica gel; mobile phase, CH$_3$CN in water, 10% to 100% gradient in 30 min; detector, UV 254 nm to give I-313 (314.5 mg, 95.76%) as a white solid. LC-MS: (ES, m/z): [M−H]$^-$ 396. H-NMR: (400 MHz, DMSO-d6, ppm): δ 13.98 (s, 1H), 11.23 (s, 1H), 7.98-7.96 (d, J=8.4 Hz, 1H), 7.83-7.82 (d, J=1.6 Hz, 1H), 7.71-7.70 (d, J=1.6 Hz, 1H), 7.52-7.32 (m, 7H), 7.05-7.03 (d, J=8.4 Hz, 1H), 3.75 (s, 3H), 2.29 (s, 3H).

Example 315: Synthesis of 3-((3-acetylphenyl)sulfonamido)-[1,1'-biphenyl]-4-carboxylic Acid, I-314

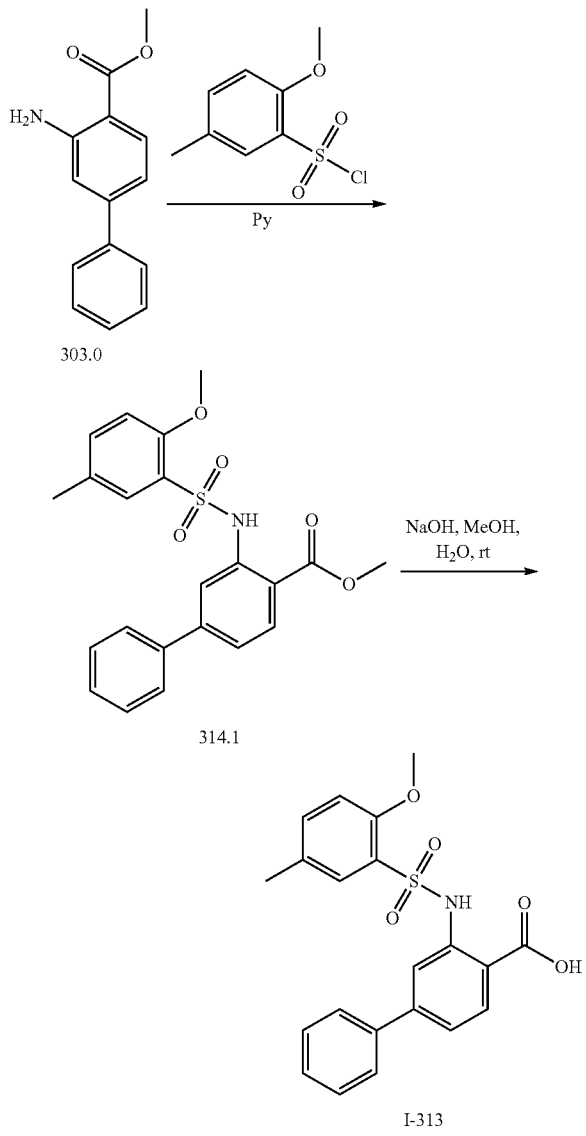

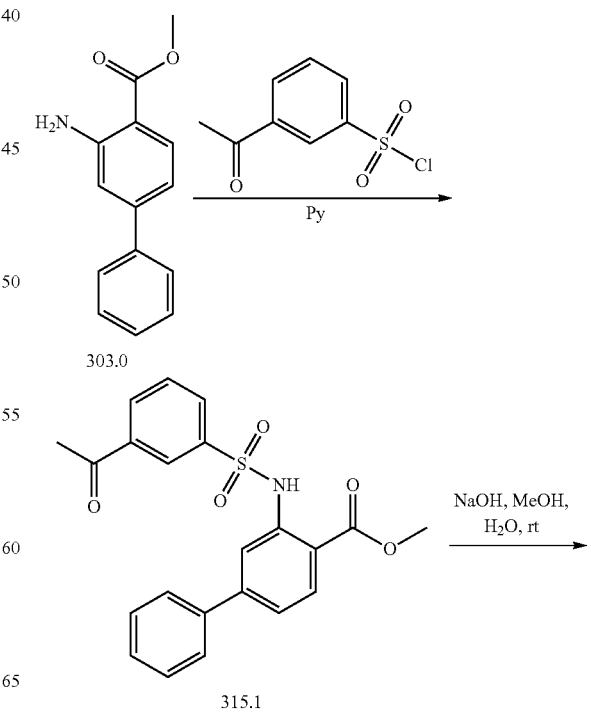

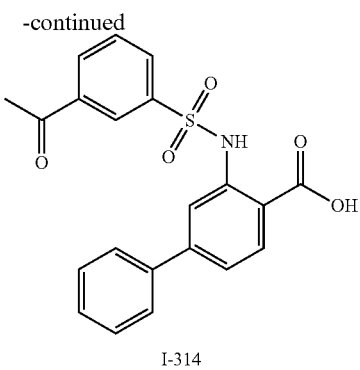

I-314

Synthesis of 315.1

To a stirred mixture of 303.0 (227 mg, 0.999 mmol, 1 equiv) in pyridine (4 mL) was added 3-acetylbenzene-1-sulfonyl chloride (218.40 mg, 0.999 mmol, 1 equiv) at 0° C. The resulting mixture was stirred overnight at room temperature. The resulting mixture was concentrated under reduced pressure. The residue was purified by reverse flash chromatography with the following conditions: column, C18 silica gel; mobile phase, $CH_3CN$ in water, 10% to 100% gradient in 30 min; detector, UV 254 nm to give 315.1 (380 mg, 93%) as a white solid.

Synthesis of I-314

To a stirred mixture of 315.1 (310 mg, 0.757 mmol, 1 equiv) and $H_2O$ (5 mL) in MeOH (5 mL) were added NaOH (605.63 mg, 15.142 mmol, 20 equiv) at room temperature. The resulting mixture was stirred for 4 h at 45° C. The mixture was acidified to pH 3 with HCl (2M in $H_2O$). The precipitated solids were collected by filtration and washed with water (2×5 mL). The residue was purified by reverse flash chromatography with the following conditions: column, C18 silica gel; mobile phase, $CH_3CN$ in water, 10% to 100% gradient in 30 min; detector, UV 254 nm to give I-314 (226.6 mg, 76%) as a white solid. LC-MS: (ES, m/z): [M−H]⁻ 394. H-NMR: (400 MHz, DMSO-d6, ppm): δ11.23 (s, 1H), 8.32 (s, 1H), 8.23-8.21 (d, J=7.6 Hz, 1H), 8.10-8.08 (m, 1H), 7.96-7.94 (d, J=8.4 Hz, 1H), 7.94-7.73 (m, 2H), 7.61-7.44 (m, 6H), 2.57 (s, 3H).

Example 316: Synthesis of 3-((5-fluoro-2-methoxyphenyl)sulfonamido)-[1,1'-biphenyl]-4-carboxylic Acid, I-315

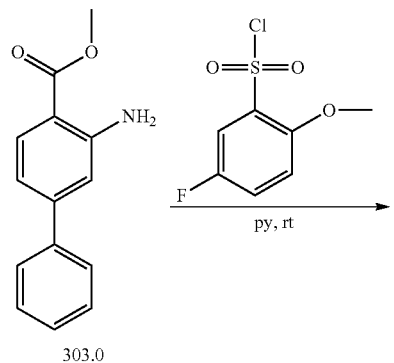

303.0

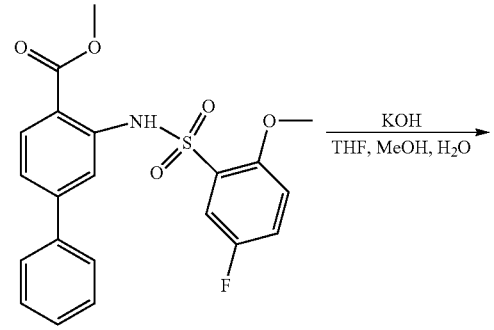

316.1

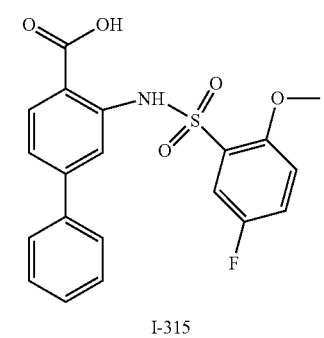

I-315

Synthesis of 316.1

To a solution of 303.0 (227 mg, 0.999 mmol, 1 equiv) in pyridine (2.5 mL) was added 5-fluoro-2-methoxybenzene-1-سulfonyl chloride (269.24 mg, 1.199 mmol, 1.2 equiv). The resulting solution was stirred for 12 hr at 25° C. The resulting mixture was concentrated under vacuum. The crude product was purified by Flash-Prep-HPLC with the following conditions (IntelFlash-1): Column, C18 silica gel; mobile phase, $ACN/H_2O$=10% increasing to $ACN/H_2O$=60% within 10 minutes; Detector 254/220 nm to give 40 mg (10%) of 316.1 as a white solid.

Synthesis of I-315

To a solution of 316.1 (40 mg, 0.096 mmol, 1 equiv) in THF (1.5 ml)/MeOH (0.5 ml)/$H_2O$ (0.3 ml) was added potassium hydroxide (27.01 mg, 0.481 mmol, 5 equiv). The resulting solution was stirred for 12 hr at 50° C. The reaction was then quenched by the addition of 10 mL water. The pH value of the solution was adjusted to 4 with HCl (1 mol/L). The resulting solution was extracted with 3×10 mL of ethyl acetate and the organic layers combined. The crude product was purified by Flash-Prep-HPLC with the following conditions (IntelFlash-1): Column, C18 silica gel; mobile phase, $ACN/H_2O$=10% increasing to $ACN/H_2O$=60% within 10 minutes; Detector 254/220 nm to give 2.0 mg (5%) of I-315 as a white solid. LC-MS: (ES, m/z): [M−H]⁻ 400.0. H-NMR: (400 MHz, DMSO-d6, ppm): δ7.98-7.96 (d, J=8.4 Hz, 1H), 7.80-7.75 (m, 1H), 7.73 (s, 1H), 7.58-7.41 (m, 6H), 7.32-7.29 (d, J=8 Hz, 1H), 7.25-6.98 (m, 1H), 3.79 (s, 3H).

Example 317: Synthesis of 5-chloro-2-((3,5-dichlorophenyl)sulfonamido)benzoic Acid, I-343

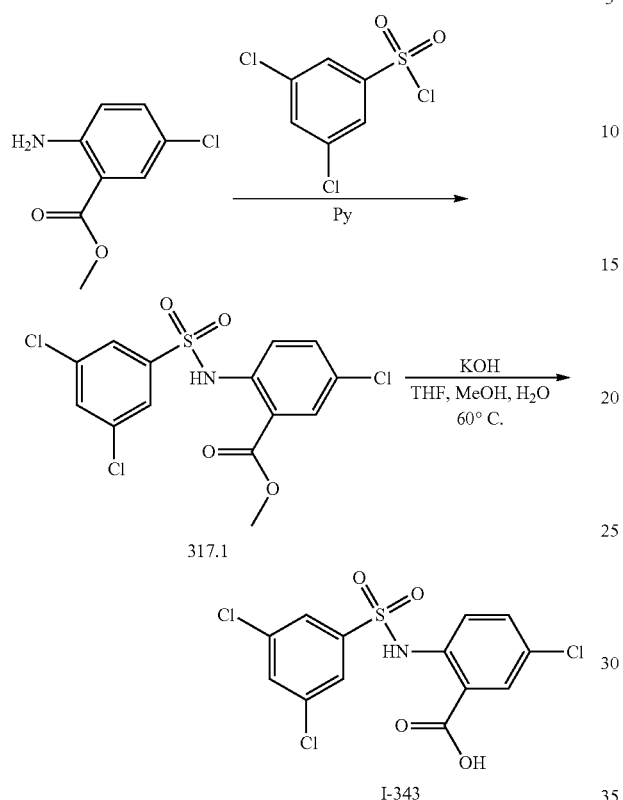

Synthesis of 317.1

To a solution of methyl 2-amino-5-chlorobenzoate (200 mg, 1.078 mmol, 1 equiv) in pyridine (5 mL) was added 3,5-dichlorobenzenesulfonyl chloride (317.44 mg, 1.293 mmol, 1.2 equiv). The resulting solution was stirred for 2 h at room temperature. The resulting mixture was concentrated. The crude product (3 mL) was purified by Flash-Prep-HPLC with the following conditions (IntelFlash-1): Column, C18 silica gel; mobile phase, $H_2O$/ACN=100/0 increasing to $H_2O$/ACN=0/100 within 40 min; Detector, 254 nm to give 200 mg (45%) of 317.1 as a white solid.

Synthesis of I-343

To a solution of 317.1 (200 mg, 0.507 mmol, 1 equiv) in THF (6 mL)/MeOH (6 mL)/$H_2O$ (2 mL) was added potassium hydroxide (142.16 mg, 2.534 mmol, 5 equiv). The resulting solution was stirred overnight at room temperature. The resulting mixture was concentrated. The resulting solution was diluted with $H_2O$. The pH value of the solution was adjusted to 5 with HCl (1 mol/L). The solids were collected by filtration. The crude product was purified by Prep-HPLC with the following conditions Column: XBridge Prep OBD C18 Column 19*250 mm, 5 um; Mobile Phase A: Water (0.05% $NH_3H_2O$), Mobile Phase B: ACN; Flow rate: 20 mL/min; Gradient: 30% B to 50% B in 8 min; 254/220 nm; Rt: 6.12 min to give 135 mg (68%) of I-343 as a white solid. LC-MS: (ES, m/z): [M–H]⁻ 377.9. H-NMR: (400 MHz, CD3OD, ppm): δ7.92 (s, 1H), 7.69 (s, 2H), 7.63 (s, 1H), 7.60-7.57 (d, J=8.8 Hz, 1H), 7.37-7.35 (d, J=8.8 Hz, 1H).

Example 318: Synthesis of 3-((5-chloro-1,3-dimethyl-1H-pyrazole)-4-sulfonamido)-[1,1'-biphenyl]-4-carboxylic Acid, I-345

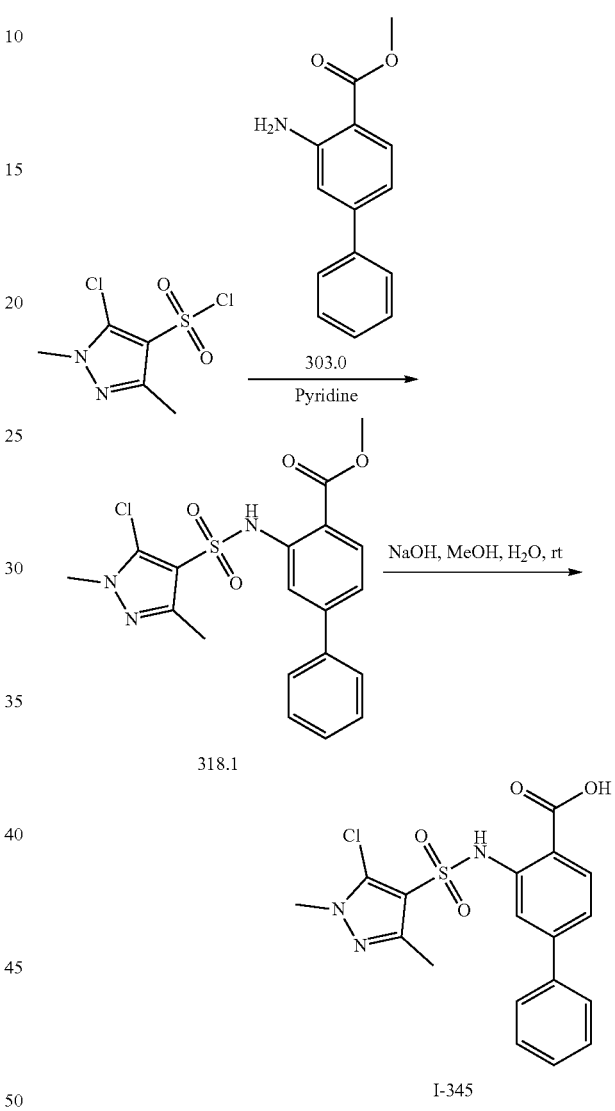

Synthesis of 318.1

Into a 100-mL round-bottom flask were placed 5-chloro-1,3-dimethyl-1H-pyrazole-4-sulfonyl chloride (200 mg, 0.873 mmol, 1 equiv), 303.0 (198.41 mg, 0.873 mmol, 1 equiv), and pyridine (6 mL). The resulting solution was stirred for 12 h at 25° C. The resulting mixture was concentrated under vacuum. The residue was purified by silica gel column with ethyl acetate/petroleum ether (2:1) to give 110 mg (30%) of 318.1 as a white solid.

Synthesis of I-345

Into a 100-mL round-bottom flask were placed 318.1 (100 mg, 0.238 mmol, 1 equiv), $H_2O$ (3 mL), MeOH (3 mL), and NaOH (95.26 mg, 2.382 mmol, 10 equiv). The resulting solution was stirred for 12 h at 25° C. The reaction was then quenched by the addition of 15 mL of diluted hydrochloric acid. The resulting solution was extracted with 3×20 mL of ethyl acetate and the organic layers combined and concentrated under vacuum. The crude product was purified by Flash with the following conditions (IntelFlash-1): Column, C18 silica gel; mobile phase, ACN:H₂O=15% increasing to ACN:H₂O=60% within 10 min to give 46.5 mg (48%) of I-345 as an off-white solid. LC-MS: (ES, m/z): [M−H]⁻ 404.0. H-NMR: (400 MHz, DMSO-d6) δ11.47 (s, 1H), δ8.03-8.01 (d, J=8.4 Hz, 1H), δ7.71 (s, 1H), 7.62-7.61 (d, J=7.2 Hz, 2H), 7.55-7.53 (t, J=7.8 Hz, 2H), 7.48-7.46 (d, J=7.2 Hz, 2H), 3.71 (s, 3H), 2.27 (s, 3H).

Example 319: Synthesis of methyl 3-((5-chloro-2-hydroxypyridine)-3-sulfonamido)-[1,1'-biphenyl]-4-carboxylate, I-346

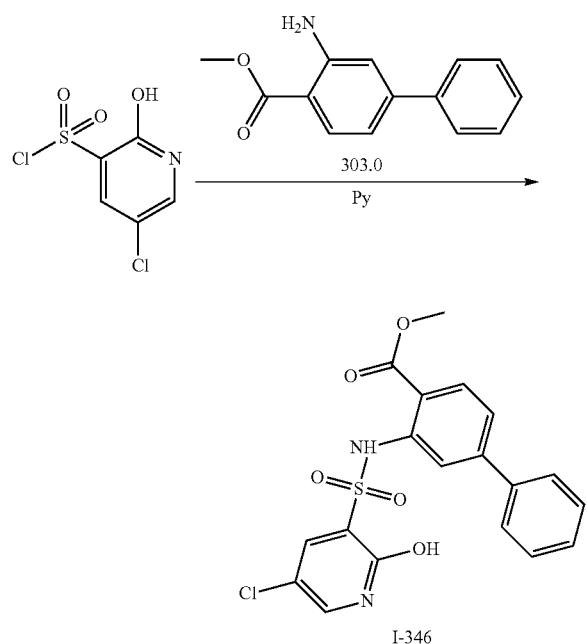

I-346

Into a 8-mL vial were placed 5-chloro-2-hydroxypyridine-3-sulfonyl chloride (50 mg, 0.219 mmol, 1 equiv), 303.0 (59.80 mg, 0.263 mmol, 1.2 equiv), and pyridine (2 mL). The resulting solution was stirred for 2 h at room temperature. The resulting mixture was concentrated under vacuum. The crude product was purified by Flash-Prep-HPLC with the following conditions (IntelFlash-1): Column, C18 silica gel; mobile phase, ACN/H₂O=15% increasing to ACN/H₂O=60% within 15 min; Detector, UV: 254 nm to give 6.1 mg (7%) of I-346 as a white solid. LC-MS: (ES, m/z): [M−H]⁻ 417. H-NMR: (300 MHz, DMSO-d6, ppm): δ8.26 (s, 1H), 8.07-7.94 (m, 2H), 7.74 (s, 1H), 7.63-7.56 (m, 2H), 7.56-7.37 (m, 4H), 3.91 (s, 3H).

Example 320: Synthesis of 2-((3,5-dichlorophenyl)sulfonamido)thiophene-3-carboxylic Acid, I-352

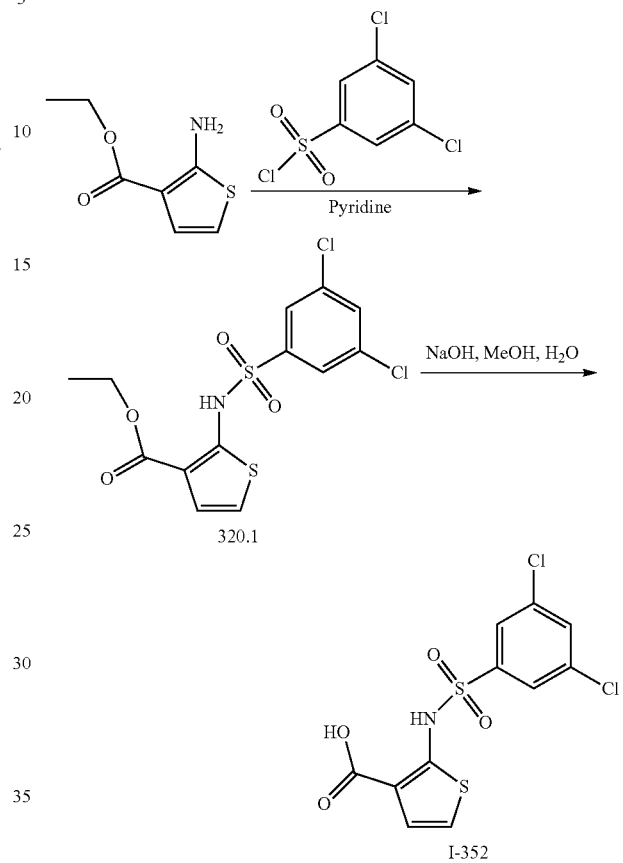

I-352

Synthesis of 320.1

Into a 100-mL round-bottom flask, was placed ethyl 2-aminothiophene-3-carboxylate (200 mg, 1.168 mmol, 1 equiv), 3,5-dichlorobenzenesulfonyl chloride (286.78 mg, 1.168 mmol, 1 equiv), and pyridine (6 mL). The resulting solution was stirred for 12 h at 25° C. The resulting mixture was concentrated under vacuum. The residue was applied onto Prep-TLC eluting with ethyl acetate/petroleum ether (2:1) to give 80 mg (18%) of 320.1 as a white solid.

Synthesis of I-352

Into a 100-mL round-bottom flask were placed 320.1 (80 mg, 0.210 mmol, 1 equiv), H₂O (3 mL), MeOH (3 mL), and NaOH (84.15 mg, 2.104 mmol, 10 equiv). The resulting solution was stirred for 12 h at 25° C. The reaction was then quenched by the addition of 20 mL of diluted hydrochloric acid. The resulting solution was extracted with 3×30 mL of ethyl acetate and the organic layers combined and concentrated. The crude product was purified by Flash-Prep-HPLC with the following conditions (IntelFlash-1): Column, C18 silica gel; mobile phase, ACN:H₂O=15% increasing to ACN:H₂O=60% within 15 min; Detector, 254 nm to give 20.5 mg (28%) of I-352 as a white solid. LC-MS: (ES, m/z): [M+H]⁺ 352. H-NMR: (400 MHz, MeOH, ppm): δ7.77-7.74 (m, 3H), 7.18-7.15 (t, J=9.6 Hz, 1H), 6.96-6.95 (d, J=5.6 Hz, 1H).

Example 321: Synthesis of 3-((3-chloro-5-(trifluoromethyl)phenyl)sulfonamido)-2-methyl-[1,1'-biphenyl]-4-carboxylic Acid, I-365

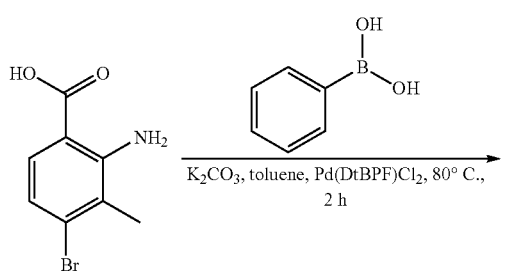

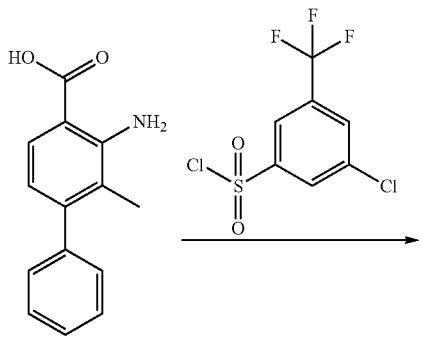

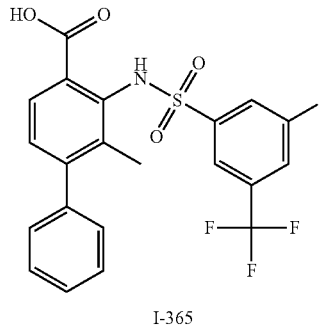

I-365

Synthesis of 321.1

Into a 50-mL round-bottom flask purged and maintained with an inert atmosphere of argon were placed 2-amino-4-bromo-3-methylbenzoic acid (500 mg, 2.173 mmol, 1 equiv), phenylboronic acid (397.49 mg, 3.260 mmol, 1.50 equiv), $K_2CO_3$ (900 mg, 6.512 mmol, 3.00 equiv), toluene (10 mL), and $Pd(DtBPF)Cl_2$ (141 mg, 0.216 mmol, 0.10 equiv). The resulting solution was stirred for 2 h at 80° C. in an oil bath. The pH value of the solution was adjusted to 5-6 with HCl (1 mol/L). The resulting solution was extracted with 3×25 mL of ethyl acetate and the organic layers combined and dried over anhydrous sodium sulfate to give 400 mg (81%) of 321.1 as a brown solid.

Synthesis of I-365

Into a 25-mL round-bottom flask were placed 321.1 (150 mg, 0.660 mmol, 1 equiv), $Na_2CO_3$ (209.87 mg, 1.980 mmol, 3 equiv), $H_2O$ (1.5 mL, 83.263 mmol, 126.15 equiv), and 3-chloro-5-(trifluoromethyl) benzene-1-sulfonyl chloride (221.02 mg, 0.792 mmol, 1.2 equiv). The resulting solution was stirred for 12 h at 60° C. The resulting solution was extracted with 3×20 mL of ethyl acetate concentrated. The crude product was purified by Flash-Prep-HPLC with the following conditions (IntelFlash-1): Column, silica gel; mobile phase, $CH_3CN/H_2O$=1:1 increasing to $CH_3CN/H_2O$=1:2 within 30 min to give 13.5 mg (4%) of I-365 as a solid. LC-MS: (ES, m/z): $[M-H]^-$ 468.3. H-NMR: (400 MHz, DMSO-d6, ppm): δ8.09 (s, 1H), 7.74 (s, 1H), 7.65-7.63 (d, J=8 Hz, 1H), 7.57 (s, 1H), 7.48-7.44 (m, 2H), 7.40-7.36 (m, 1H), 7.30-7.28 (m, 2H), 7.04-7.02 (m, 1H), 2.11 (s, 3H).

Example 322: Synthesis of 3-((3,5-dichlorobenzyl)amino)-[1,1'-biphenyl]-4-carboxylic Acid, I-371

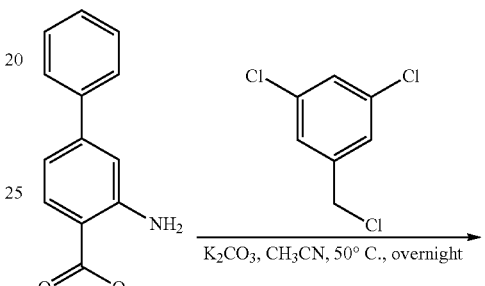

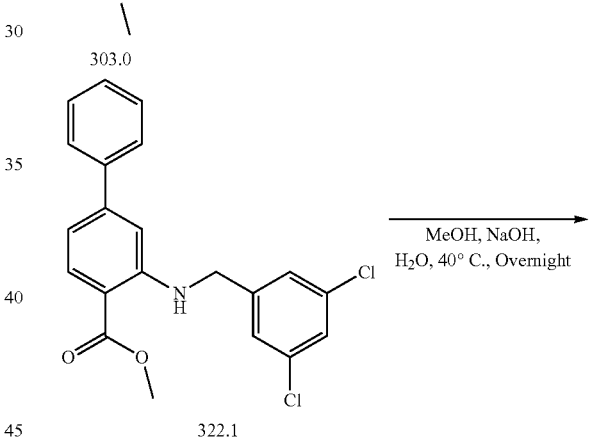

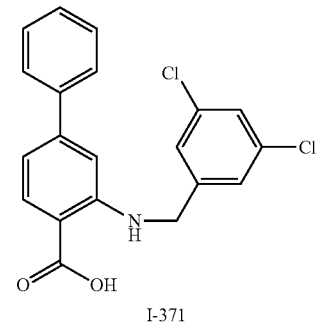

I-371

Synthesis of 322.1

Into a 50-mL 3-necked round-bottom flask were placed 303.0 (200 mg, 0.880 mmol, 1 equiv), $CH_3CN$ (10 mg), $K_2CO_3$ (121.63 mg, 0.880 mmol, 1.00 equiv), and 1,3-dichloro-5-(chloromethyl)benzene (172.02 mg, 0.880 mmol, 1.00 equiv). The resulting solution was stirred overnight at 50° C. The mixture was filtered, and the filtrate was concentrated. The crude product was purified by Flash-Prep-HPLC with the following conditions (IntelFlash-1): Column, C18 silica gel; mobile phase, ACN/H₂O=15% increasing to ACN/H₂O=60% within 15 min to give 65 mg (19%) of 322.1 as a yellow solid.

Synthesis of I-371

Into a 50-mL 3-necked round-bottom flask were placed 322.1 (50 mg, 0.13 mmol, 1 equiv), MeOH (5 mL, 123.49 mmol, 954.04 equiv), H₂O (5 mL, 277.54 mmol, 2144.12 equiv), and NaOH (4 mg, 0.10 mmol, 0.77 equiv). The resulting solution was stirred overnight at 40° C. The pH of the solution was adjusted to 5 by adding 1N HCl, and then extracted with EA (10 mL). The combined organic layer washed with brine (10 mL) and then concentrated in vacuum. The crude product was purified by Flash-Prep-HPLC with the following conditions (Intel Flash-1): Column, C18 silica gel; mobile phase, ACN/H₂O=15% increasing to ACN/H₂O=60% within 15 min to give 3 mg (6%) of I-371 as a solid. LC-MS: (ES, m/z): [M+H]⁺ 372.0; H-NMR: (400 MHz, DMSO-d6, ppm): δ12.70 (s, 1H), 8.46 (s, 1H), 7.90-7.88 (d, J=7.6 Hz, 1H), 7.63-7.61 (m, 2H), 7.58-7.38 (m, 6H), 6.89-6.80 (m, 2H), 4.63 (s, 2H).

Example 323: Synthesis of 3-((3-chloro-5-(dimethylcarbamoyl)-2-hydroxyphenyl)sulfonamido)-[1,1'-biphenyl]-4-carboxylic Acid, I-518

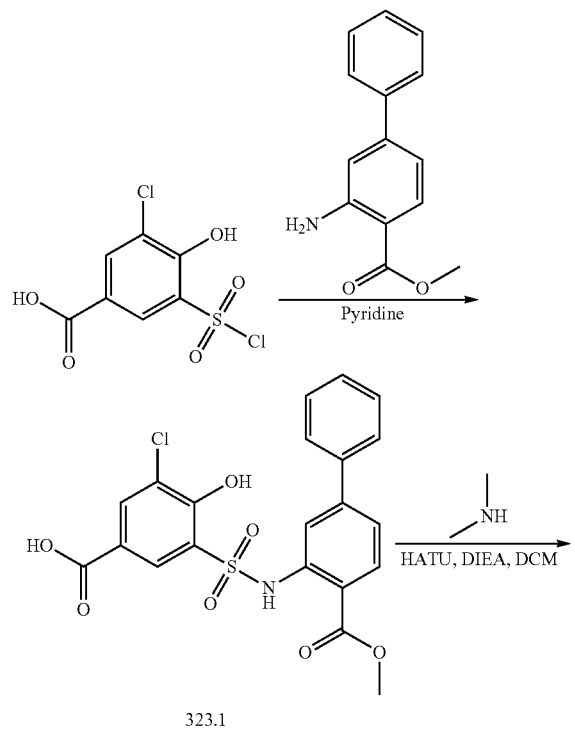

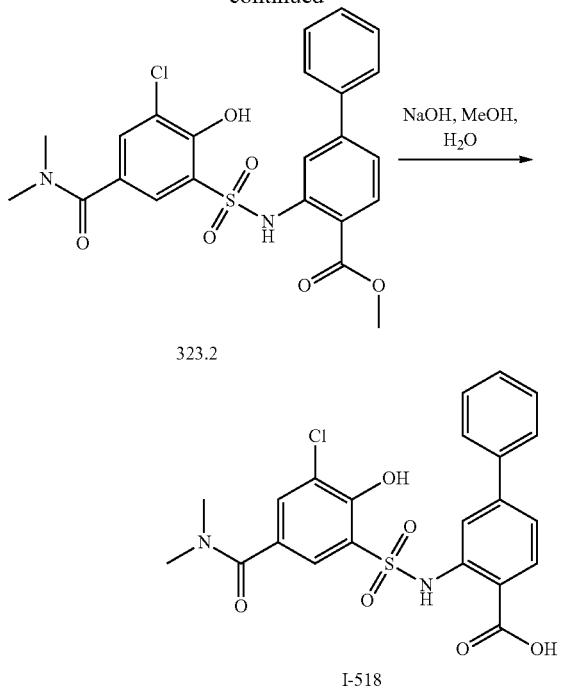

Synthesis of 323.1

Into a 50-mL 2-necked round-bottom flask were placed 3-chloro-5-(chlorosulfonyl)-4-hydroxybenzoic acid (500 mg, 1.84 mmol, 1 equiv), 303.0 (503.1 mg, 2.21 mmol, 1.2 equiv) and pyridine (7 mL). The resulting solution was stirred for 12 h at 25° C. The resulting mixture was concentrated under vacuum. The crude product was purified by Flash-Prep-HPLC with the following conditions (IntelFlash-1): Column, C18 silica gel; mobile phase, ACN:H₂O=10% increasing to ACN:H2O=60% within 15 min to give 190 mg (22%) of 323.1 as a light yellow solid.

Synthesis of 323.2

Into a 100-mL round-bottom flask were placed 323.1 (150 mg, 0.325 mmol, 1 equiv), dimethylamine (29.28 mg, 0.650 mmol, 2 equiv), DCM (6 mL), DIEA (209.87 mg, 1.624 mmol, 5 equiv), and HATU (185.23 mg, 0.487 mmol, 1.5 equiv). The resulting solution was stirred for 12 h at 25° C. The reaction was then quenched by the addition of 15 mL of water. The resulting solution was extracted with 3×25 mL of ethyl acetate and the organic layers combined and concentrated under vacuum. The residue was applied onto Prep-TLC with dichloromethane/methanol (20:1) to give 100 mg (63%) of 323.2 as an off-white solid.

Synthesis of I-518

Into a 100-mL round-bottom flask were placed 323.2 (100 mg, 0.205 mmol, 1 equiv), H₂O (3 mL), MeOH (3 mL), and NaOH (81.80 mg, 2.045 mmol, 10.00 equiv). The resulting solution was stirred for 12 h at 25° C. The reaction was then quenched by the addition of 15 mL of diluted hydrochloric acid. The resulting solution was extracted with 3×25 mL of ethyl acetate and the organic layers were combined and concentrated under vacuum. The crude product was purified by Flash-Prep-HPLC with the following conditions (Intel-Flash-1): Column, C18 silica gel; mobile phase, ACN:H2O=15% increasing to ACN:H2O=60% within 15 min to give 34.8 mg (36%) of I-518 as a white solid. LC-MS: (ES, m/z): [M+H]$^+$ 475.0. H-NMR: (400 MHz, DMSO-d6, ppm) δ 7.92-7.90 (d, J=8 Hz, 1H), 7.66 (d, J=2.4 Hz, 1H), 7.56 (d, J=1.2 Hz, 1H), 7.49-7.36 (m, 6H), 7.15-7.12 (m, 1H), 2.82 (s, 6H).

Example 324: Synthesis of (3-chloro-5-(((4,6-difluoro-[1,1'-biphenyl]-3-yl)methyl)sulfonyl)-4-hydroxyphenyl)(pyrrolidin-1-yl)methanone, I-211

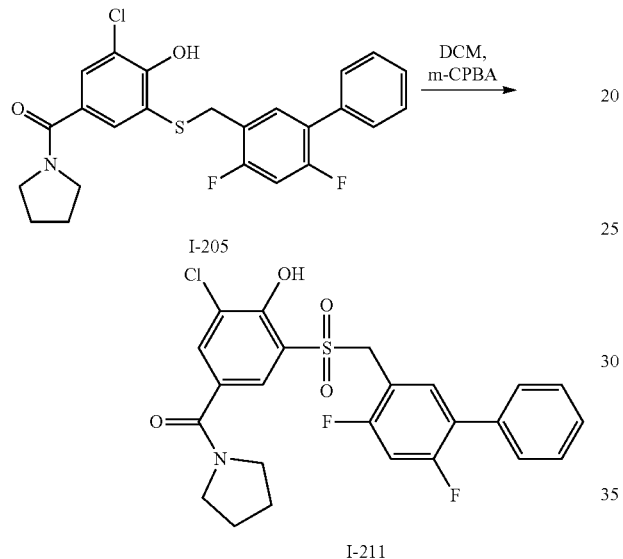

To a stirred solution of I-205 (100 mg, 0.22 mmol, 1 equiv) in DCM (2 mL) was added m-CPBA (75.0 mg, 0.43 mmol, 2 equiv) in portions at room temperature under nitrogen atmosphere. The residue was purified by Prep-TLC (CH$_2$Cl$_2$/MeOH 20:1) to afford I-211 (19.5 mg, 18.23%) as a white solid. LC-MS: (ES, m/z): [M+H]$^+$ 492.2. H-NMR: (300 MHz, DMSO-d6, ppm): 7.70 (s, 1H), 7.64-7.30 (m, 5H), 7.27-7.20 (m, 3H), 4.82 (s, 2H), 3.29-3.32 (m, 4H), 1.55-1.81 (m, 4H).

Example 325: Synthesis of 3-(2-(2-amino-2-oxoethoxy)-3,5-dichlorobenzamido)-[1,1'-biphenyl]-4-carboxylic Acid, I-320

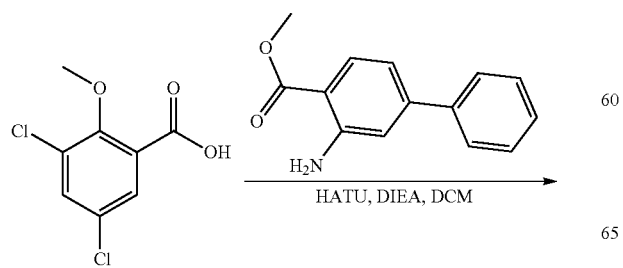

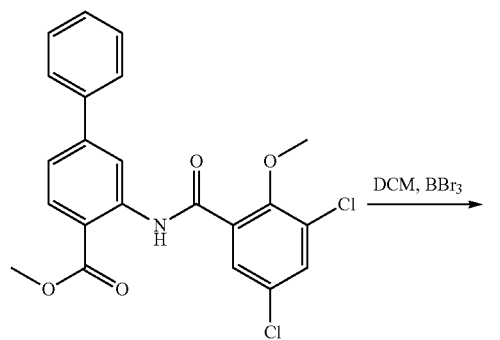

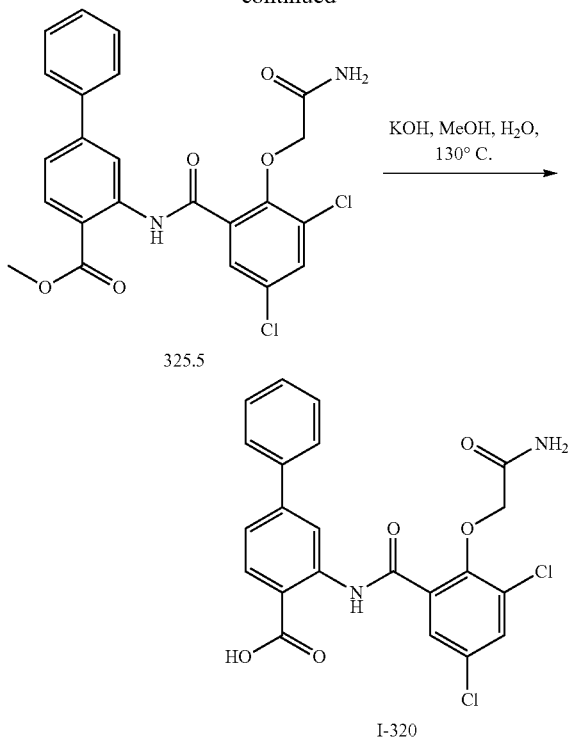

Synthesis of 325.1

Into a 50-mL round-bottom flask were placed 3,5-dichloro-2-methoxybenzoic acid (1 g, 4.524 mmol, 1 equiv), methyl 3-amino-[1,1-biphenyl]-4-carboxylate (1233.84 mg, 5.429 mmol, 1.2 equiv), DIEA (1169.46 mg, 9.049 mmol, 2 equiv), DCM (20 mL), and HATU (2580.40 mg, 6.786 mmol, 1.5 equiv). The resulting solution was stirred for overnight at 40° C. in an oil bath. The resulting solution was diluted with 60 mL of $H_2O$ and extracted with 3×50 mL of ethyl acetate. The combined organic layer was concentrated under vacuum to give 1.3 g (67%) of 325.1 as a solid.

Synthesis of 325.2

Into a 20-mL vial were placed 325.1 (1.18 g, 2.742 mmol, 1 equiv), DCM (10 mL), and $BBr_3$ (4122.21 mg, 16.454 mmol, 6 equiv). The resulting solution was stirred for overnight at room temperature. The resulting solution was diluted with 100 mL of $H_2O$. The resulting solution was extracted with 3×50 mL of dichloromethane concentrated under vacuum. The residue was applied onto a prep TLC eluting with ethyl acetate/petroleum ether (1:1) to give 721 mg (63%) of 325.2 as a solid.

Synthesis of 325.3

Into a 100-mL 3-necked round-bottom flask were placed 325.2 (530 mg, 1.273 mmol, 1 equiv), tert-butyl 2-hydroxyacetate (201.93 mg, 1.528 mmol, 1.2 equiv), DIAD (386.20 mg, 1.910 mmol, 1.5 equiv), THF (25 mL), and $PPh_3$ (834.90 mg, 3.183 mmol, 2.5 equiv). The resulting solution was stirred for 1 h at 0° C. in a water/ice bath. The resulting solution was diluted with 100 mL of $H_2O$ and extracted with 3×30 mL of ethyl acetate. The combined organic layers were concentrated under vacuum. The residue was applied onto a silica gel column eluting with ethyl acetate/petroleum ether (1:20) to give 395 mg (58%) of 325.3 as yellow oil.

Synthesis of 325.4

Into a 20-mL vial were placed 325.3 (300 mg, 0.566 mmol, 1 equiv), DCM (10 mL), and TFA (2 mL, 26.926 mmol, 47.61 equiv). The resulting solution was stirred for overnight at room temperature. The resulting mixture was concentrated under vacuum. The crude product was purified by Flash-Prep-HPLC with the following conditions (Intel-Flash-1): Column, C18 silica gel; mobile phase, ACN/$H_2O$=15% increasing to ACN/$H_2O$=60% within 15 min; Detector, UV: 254 to give 210 mg (78%) of 325.4 as a yellow solid.

Synthesis of 325.5

Into a 20-mL vial were placed 325.4 (190 mg, 0.401 mmol, 1 equiv), $NH_4Cl$ (32.14 mg, 0.601 mmol, 1.50 equiv), DIEA (103.55 mg, 0.801 mmol, 2.00 equiv), DCM (5 mL), and HATU (228.48 mg, 0.601 mmol, 1.50 equiv). The resulting solution was stirred for overnight at room temperature. The resulting solution was diluted with 100 mL of $H_2O$ and extracted with 3×50 mL of ethyl acetate. The combined organic layer was concentrated under vacuum. The residue was applied onto a prep TLC eluting with ethyl acetate/petroleum ether (1:1) to give 160 mg (84%) of 325.5 as a white solid.

Synthesis of I-320

Into a 8-mL vial were placed 325.5 (50 mg, 0.106 mmol, 1 equiv), MeOH (10 mL), $H_2O$ (10 mL), and NaOH (84.51 mg, 2.113 mmol, 20 equiv). The resulting solution was stirred for 2 min at 130° C. in an oil bath. The pH value of the solution was adjusted to 6 with AcOH. The resulting mixture was concentrated under vacuum. The resulting solution was diluted with 100 mL of $H_2O$ and extracted with 3×50 mL of ethyl acetate. The combined organic layers were concentrated under vacuum. The crude product was purified by Prep-HPLC eluting with the following conditions: Column: XBridge Prep OBD C18 Column 19*250 mm, 5 um; Mobile Phase A: Water (0.05% $NH_3H_2O$), Mobile Phase B: ACN; Flow rate: 20 mL/min; Gradient: 35% B to 45% B in 7 min; 254/220 nm; Rt: 6.0 min; mobile phase to give 8.6 mg (18%) of I-320 as a white solid. LC-MS: (ES, m/z): [M−H]⁻ 457.0. H-NMR: (400 MHz, DMSO-d6, ppm): δ13.66 (s, 1H), 13.31 (s, 1H), 8.83 (s, 1H), 8.10-8.07 (d, J=8.4 Hz, 1H), 7.94 (s, 1H), 7.81 (s, 1H), 7.72-7.70 (d, J=7.6 Hz, 2H), 7.56-7.52 (m, 3H), 7.47-7.43 (m, 3H), 4.48 (s, 2H).

Example 326: Synthesis of 3-((3,5-dimethylisoxazole)-4-sulfonamido)-[1,1'-biphenyl]-4-carboxylic Acid, I-351

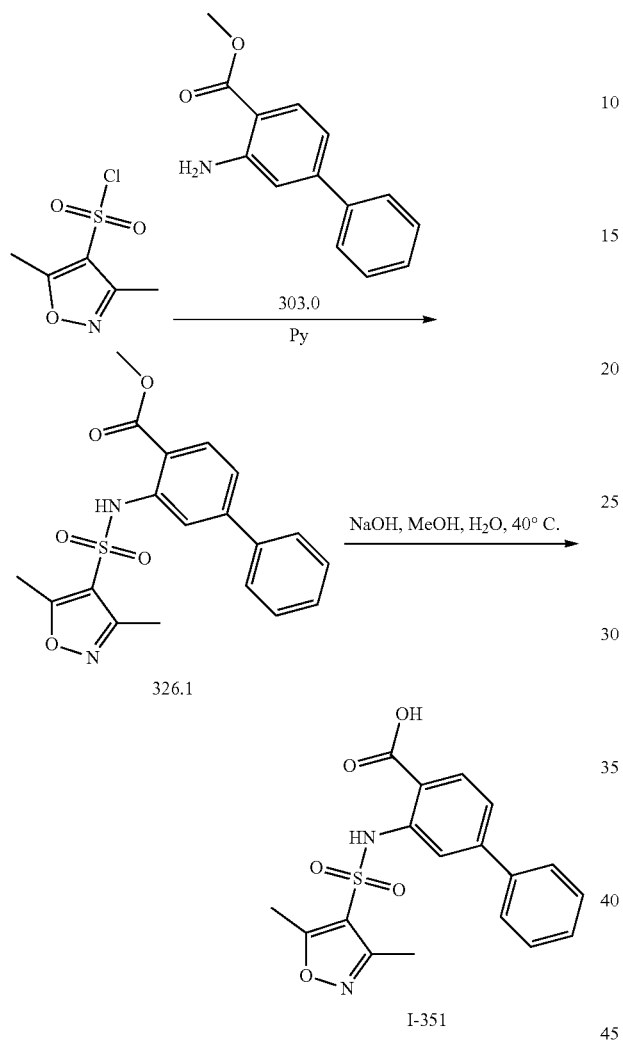

Synthesis of 326.1

Into a 25-mL round-bottom flask purged and maintained with an inert atmosphere of nitrogen were placed dimethyl-1,2-oxazole-4-sulfonyl chloride (200 mg, 1.022 mmol, 1 equiv), 303.0 (232.35 mg, 1.022 mmol, 1 equiv), and pyridine (10 mL). The resulting solution was stirred for 0.5 hr at room temperature. The resulting mixture was concentrated. The residue was applied onto a silica gel column eluting with ethyl acetate/petroleum ether (1:1) to give 200 mg (51%) of 326.1 as a white solid.

Synthesis of I-351

Into a 8-mL round-bottom flask purged and maintained with an inert atmosphere of nitrogen were placed 326.1 (100 mg, 0.259 mmol, 1 equiv), NaOH (103.51 mg, 2.588 mmol, 10.00 equiv), MeOH (8 mL), and H$_2$O (2 mL). The resulting solution was stirred for 12 h at 40° C. in an oil bath. The pH value of the solution was adjusted to 5 with HCl (1 M). The solids were collected by filtration. The resulting mixture was concentrated to give 52.3 mg (54%) of I-351 as a white solid. LC-MS: (ES, m/z): [M−H]⁻ 371.0. H-NMR: (400 MHz, DMSO-d6, ppm): δ11.11 (s, 1H), δ8.03-8.01 (d, J=8.4 Hz, 1H), δ7.72 (s, 1H), δ7.66-7.64 (d, J=8.4 Hz, 2H), δ7.60-7.45 (m, 4H), δ2.45 (s, 3H), δ2.21 (s, 3H).

Example 327: Synthesis of 3-((3,5-dichlorophenyl)sulfonamido)thiophene-2-carboxylic Acid, I-362

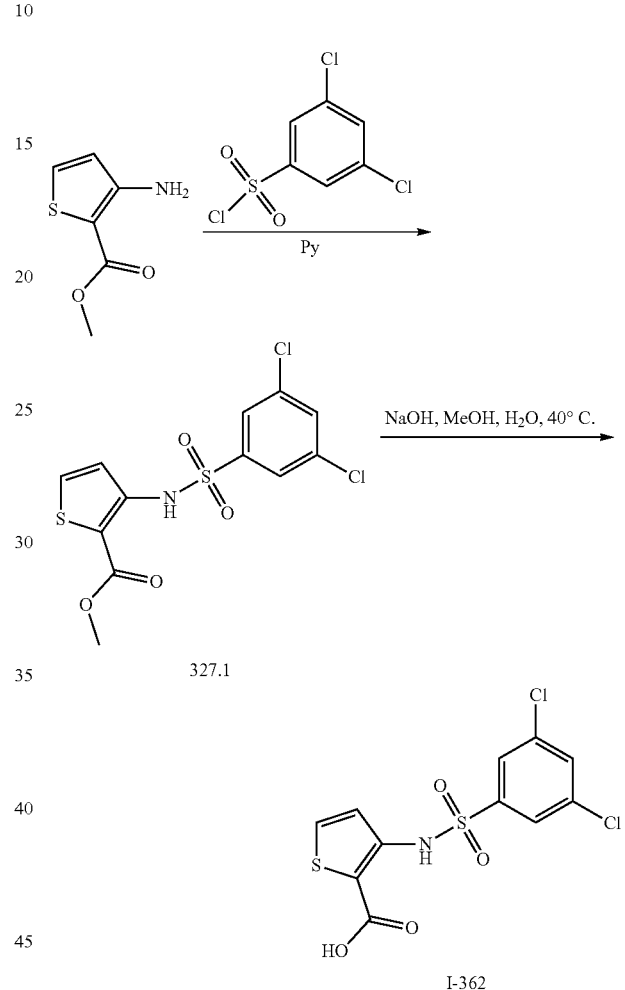

Synthesis of 327.1

Into a 50-mL round-bottom flask purged and maintained with an inert atmosphere of argon were placed methyl 3-aminothiophene-2-carboxylate (200 mg, 1.272 mmol, 1 equiv), pyridine (5 mL), and 3,5-dichlorobenzene-1-sulfonyl chloride (312.36 mg, 1.272 mmol, 1.00 equiv). The resulting solution was stirred for 12 h at room temperature. The solution was concentrated under reduced pressure. The resulting solution was extracted with 2×15 mL of ethyl acetate. The combined organic solutions were concentrated and purified by silica gel column eluting with dichloromethane/ethyl acetate (1:1) to give 245 mg (53%) of 327.1 as a solid.

Synthesis of I-362

Into a 25-mL round-bottom flask were placed 327.1 (100 mg, 0.273 mmol, 1 equiv), H$_2$O (1 mL), MeOH (4 mL), and NaOH (163.82 mg, 4.096 mmol, 15 equiv). The resulting solution was stirred for 12 h at 40° C. in an oil bath. The pH value of the solution was adjusted to 5 with HCl (1 mol/L). The solids were collected by filtration. The resulting solution was extracted with 3×20 mL of ethyl acetate. The combined organic layers were concentrated and purified by Flash-Prep-HPLC eluting with the following conditions (IntelFlash-1): Column, C18 silica gel; mobile phase, $CH_3CN/H_2O=1:1$ increasing to $CH_3CN/H_2O=1:2$ within 30 min to give 67.2 mg (69%) of I-362 as an off-white solid. LC-MS: (ES, m/z): [M−H]⁻ 349.9. H-NMR: (400 MHz, DMSO, ppm): δ10.21 (s, 1H), 7.99 (s, 1H), 7.91 (s, 2H), 7.83-7.82 (d, J=5.6 Hz, 1H), 7.20-7.18 (d, J=5.6 Hz, 1H).

Example 328: Synthesis of 2-((3,5-dichlorophenyl)sulfonamido)-4,5,6,7-tetrahydrobenzo[b]thiophene-3-carboxylic Acid, I-363

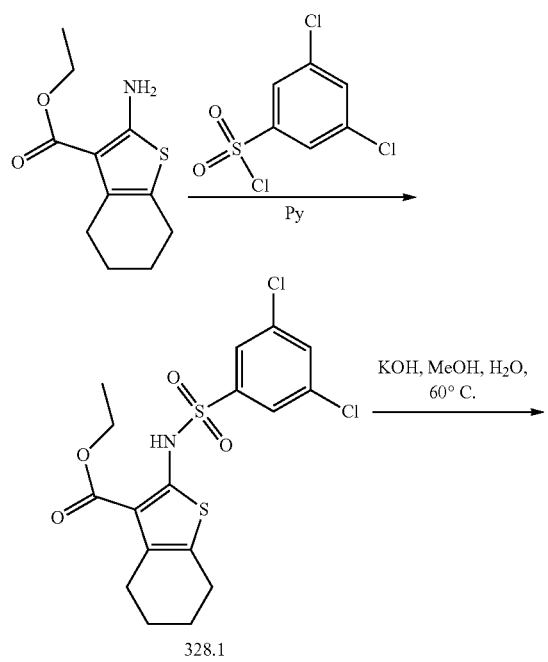

328.1

I-363

Synthesis of 328.1

Into a 8-mL vial were placed ethyl 2-amino-4,5,6,7-tetrahydro-1-benzothiophene-3-carboxylate (300 mg, 1.331 mmol, 1 equiv), 3,5-dichlorobenzene-1-sulfonyl chloride (326.88 mg, 1.331 mmol, 1 equiv), and pyridine (3 mL). The resulting solution was stirred for 1 h at room temperature. The resulting mixture was concentrated under vacuum. The residue was purified by prep TLC eluting with ethyl acetate/petroleum ether (1:2) to give 210 mg (36%) of 328.1 as a yellow solid.

Synthesis of I-363

Into a 50-mL 3-necked round-bottom flask were placed 328.1 (100 mg, 0.230 mmol, 1 equiv), MeOH (10 mL), $H_2O$ (10 mL), and KOH (184.17 mg, 4.605 mmol, 20 equiv). The resulting solution was stirred for overnight at 60° C. The resulting mixture was concentrated. The crude product was purified by Flash-Prep-HPLC eluting with the following conditions (IntelFlash-1): Column, C18 silica gel; mobile phase, $ACM/H_2O=15\%$ increasing to $ACM/H_2O=60\%$ within 15 min; Detector, 254 nm to give 43.8 mg (47%) of I-363 as an off-white solid. LC-MS: (ES, m/z): [M−H]⁻ 404; H-NMR: (300 MHz, MeOD, ppm): δ7.70 (s, 2H), 7.65 (s, 1H), 2.79-2.49 (m, 4H), 1.85-1.62 (m, 4H).

Example 329: Synthesis of Additional Compounds

Compound I-32 was synthesized in a manner similar to the one used to synthesize I-20. Compounds I-163 to I-189, I-250, I-251, I-252, I-253, I-254, I-255, I-256, I-257, I-258, I-259, and I-300, were synthesized in a manner similar to the one used to synthesize I-22. Compound I-510 was synthesized in a manner similar to the one used to synthesize I-506 and I-347.

TABLE 9

Characterization data for additional exemplary compounds

| Compound | MS [M + H]+ | MS [M + Na]+ |
|---|---|---|
| I-163 | 393.9 | |
| I-164 | 443.9 | |
| I-165 | 492.9 | |
| I-166 | 375.9 | |
| I-167 | | 412 |
| I-168 | 418 | |
| I-169 | 402 | |
| I-170 | 384 | |
| I-171 | 423.8 | |
| I-172 | 429 | |
| I-173 | 381 | |
| I-174 | 416.8 | |
| I-175 | 475.8 | |
| I-176 | 458 | |
| I-177 | 385 | |
| 1-178 | 403 | |
| I-179 | 403 | |
| I-180 | 375 | |
| I-181 | 399 | |
| I-182 | 421 | |
| I-183 | 387 | |
| I-184 | 417.8 | |
| I-185 | 388 | |
| I-186 | 386 | |
| I-187 | 404 | |
| I-188 | 376 | |
| I-189 | 400.8 | |

Example 330. ADP-Glo Assay

TABLE 10

Materials and Instruments Used in the ADP-Glo Assay

| | Vendor | Cat No. |
|---|---|---|
| Materials | | |
| ACL | Sino Biological | 11769-H07B |
| CoANa2 | Sigma | C3144 |
| Potassium Citrate | Sigma | 89306 |
| ATP | Promega | V915B |
| ADP-GloTM Kinase Assay kit | Promega | V9102 |
| HEPES | Life Technologies | 15630080 |
| MgCl2 | Sigma | M1028 |
| Brij 35 detergent | Merck | 203728 |
| DTT | Sigma | 646563 |
| DMSO | MP | 196055 |
| Optiplate-384, White 384-well | Perkin Elmer | 6007290 |
| 384 dilution plate | Corning | 3657 |
| Topseal A | Perkin Elmer | E5341 |
| 96-well plate | Nunc | 249944 |
| Instrument | | |
| Plate reader | Perkin Elmer | Envision 2104 |
| Centrifuge | Eppendorf | 5810R |

Compounds of the present invention were evaluated in an ADP-GLO assay as follows:

a) Dilute cpd 1:3 in succession in DMSO by hand for each cpds for 12 pts b) Add 0.1 µL diluted cpd solution to assay plate, each dose with 2 replicates c) Centrifuge 1000 RPM for 1 min d) Add 5 µL ACL working solution to 384-well assay plate, centrifuge 1000 RPM for 1 min e) Incubate at 25° C. for 15 min f) Add 5 µL substrate working solution to initiate reaction g) Final ACL reaction concentrations: 3 nM ACL, 15 µM ATP, 3 µM CoA, 300 µM Citrate, 0.01% Brij35, 4 mM DTT, 1% DMSO;

h) Reference final conc: 30 uM starting Conc, 3× dilution, 11+0 points. Test cpd conc: 30/100 uM starting Conc, 3× dilution, 11+0 points.

i) Incubate at 25° C. for 60 min j) Add 10 µL ADP Glo reagent, centrifuge 1000 RPM for 1 min k) Incubate at 25° C. for 40 min l) Add 20 µL kinase detection reagent, centrifuge 1000 RPM for 1 min m) Incubate at 25° C. for 40 min n) Read on Envision for US LUM as RLU Results of the ADP-Glo Assay are provided in Table 11 below. Compounds which had an $IC_{50}$ result of <0.050 µM in the assay are labeled "A", compounds which had an $IC_{50}$ result of ≥0.050 µM and <0.50 µM in the assay are labeled "B", compounds which had an $IC_{50}$ result of ≥0.50 µM and <20.0 µM in the assay are labeled "C", and compounds which had an $IC_{50}$ result of ≥20 µM in the assay are labeled "D".

TABLE 11

ADP-Glo Assay results.

| Compound Number | ACL-ADP-Glo (IC50) [µM] |
|---|---|
| I-1 | B |
| I-2 | C |
| I-3 | C |
| I-4 | C |
| I-5 | C |
| I-6 | B |
| I-7 | C |
| I-8 | C |
| I-9 | B |
| I-10 | C |
| I-11 | C |
| I-12 | C |
| I-13 | C |
| I-14 | C |
| I-15 | C |
| I-16 | C |
| I-17 | C |
| I-18 | C |
| I-19 | C |
| I-20 | B |
| I-21 | B |
| I-22 | B |
| I-23 | B |
| I-24 | C |
| I-25 | C |
| I-26 | A |
| I-27 | C |
| I-28 | C |
| I-29 | C |
| I-30 | C |
| I-31 | A |
| I-32 | C |
| I-33 | B |
| I-34 | B |
| I-35 | C |
| I-36 | C |
| I-37 | C |
| I-38 | C |
| I-39 | C |
| I-40 | C |
| I-41 | A |
| I-42 | C |
| I-43 | C |
| I-44 | C |
| I-45 | C |
| I-46 | C |
| I-47 | A |
| I-48 | B |
| I-49 | C |
| I-50 | C |
| I-51 | C |
| I-52 | C |
| I-53 | C |
| I-54 | C |
| I-55 | B |
| I-56 | B |
| I-57 | C |
| I-58 | B |
| I-59 | B |
| I-60 | A |
| I-61 | C |
| I-62 | C |
| I-63 | C |
| I-64 | C |
| I-65 | A |
| I-66 | B |
| I-67 | C |
| I-68 | C |
| I-69 | C |
| I-70 | C |
| I-71 | C |
| I-72 | C |
| I-73 | C |
| I-74 | B |
| I-75 | C |

TABLE 11-continued

ADP-Glo Assay results.

| Compound Number | ACL-ADP-Glo (IC50) [μM] |
|---|---|
| I-76 | C |
| I-77 | C |
| I-78 | C |
| I-79 | C |
| I-80 | C |
| I-81 | C |
| I-82 | A |
| I-83 | A |
| I-84 | A |
| I-85 | C |
| I-86 | A |
| I-87 | A |
| I-88 | A |
| I-89 | C |
| I-90 | B |
| I-91 | B |
| I-92 | B |
| I-93 | A |
| I-94 | C |
| I-95 | B |
| I-96 | C |
| I-97 | C |
| I-98 | A |
| I-99 | C |
| I-100 | B |
| I-101 | A |
| I-102 | B |
| I-103 | A |
| I-104 | B |
| I-105 | A |
| I-106 | A |
| I-107 | C |
| I-108 | C |
| I-109 | C |
| I-110 | C |
| I-111 | A |
| I-112 | A |
| I-113 | C |
| I-114 | C |
| I-115 | C |
| I-116 | A |
| I-117 | A |
| I-118 | A |
| I-119 | A |
| I-120 | B |
| I-121 | C |
| I-122 | C |
| I-123 | A |
| I-124 | B |
| I-125 | C |
| I-126 | A |
| I-127 | A |
| I-128 | A |
| I-129 | A |
| I-130 | A |
| I-131 | B |
| I-132 | C |
| I-133 | B |
| I-134 | C |
| I-135 | B |
| I-136 | A |
| I-137 | B |
| I-138 | A |
| I-139 | C |
| I-140 | A |
| I-141 | B |
| I-142 | A |
| I-143 | C |
| I-144 | B |
| I-145 | A |
| I-146 | C |
| I-147 | C |
| I-148 | A |
| I-149 | A |
| I-150 | C |
| I-151 | C |
| I-152 | C |
| I-153 | C |
| I-154 | C |
| I-155 | C |
| I-156 | C |
| I-157 | B |
| I-158 | B |
| I-159 | A |
| I-160 | A |
| I-161 | C |
| I-162 | B |
| I-163 | C |
| I-164 | C |
| I-165 | C |
| I-166 | C |
| I-167 | C |
| I-168 | C |
| I-169 | C |
| I-170 | C |
| I-171 | C |
| I-172 | C |
| I-173 | C |
| I-174 | C |
| I-175 | C |
| I-176 | C |
| I-177 | C |
| I-178 | C |
| I-179 | C |
| I-180 | C |
| I-181 | C |
| I-182 | C |
| I-183 | C |
| I-184 | C |
| I-185 | C |
| I-186 | C |
| I-187 | C |
| I-188 | C |
| I-189 | C |
| I-190 | C |
| I-191 | C |
| I-192 | C |
| I-193 | C |
| I-194 | B |
| I-195 | C |
| I-196 | C |
| I-197 | B |
| I-198 | A |
| I-199 | C |
| I-200 | A |
| I-201 | C |
| I-202 | B |
| I-203 | C |
| I-204 | C |
| I-205 | C |
| I-206 | B |
| I-207 | C |
| I-208 | B |
| I-209 | C |
| I-210 | C |
| I-211 | C |
| I-212 | B |
| I-213 | B |
| I-214 | C |
| I-215 | C |
| I-216 | C |
| I-217 | C |
| I-218 | C |
| I-219 | C |
| I-220 | B |
| I-221 | C |
| I-222 | B |
| I-223 | C |
| I-224 | C |
| I-225 | C |

TABLE 11-continued

ADP-Glo Assay results.

| Compound Number | ACL-ADP-Glo (IC50) [μM] |
|---|---|
| I-226 | C |
| I-227 | C |
| I-228 | C |
| I-229 | A |
| I-230 | C |
| I-231 | C |
| I-232 | C |
| I-233 | C |
| I-234 | C |
| I-235 | C |
| I-236 | A |
| I-237 | C |
| I-238 | C |
| I-239 | C |
| I-240 | C |
| I-241 | B |
| I-242 | C |
| I-243 | C |
| I-244 | C |
| I-245 | C |
| I-246 | C |
| I-247 | C |
| I-248 | C |
| I-249 | C |
| I-250 | C |
| I-251 | C |
| I-252 | C |
| I-253 | C |
| I-254 | C |
| I-255 | C |
| I-256 | C |
| I-257 | C |
| I-258 | C |
| I-259 | C |
| I-260 | C |
| I-261 | C |
| I-262 | B |
| I-263 | C |
| I-264 | C |
| I-265 | C |
| I-266 | C |
| I-267 | C |
| I-268 | C |
| I-269 | C |
| I-270 | C |
| I-271 | C |
| I-272 | C |
| I-273 | C |
| I-274 | C |
| I-275 | B |
| I-276 | A |
| I-277 | C |
| I-278 | C |
| I-279 | C |
| I-280 | C |
| I-281 | B |
| I-282 | A |
| I-283 | C |
| I-284 | C |
| I-285 | C |
| I-286 | A |
| I-287 | B |
| I-288 | C |
| I-289 | C |
| I-290 | C |
| I-291 | C |
| I-292 | C |
| I-293 | C |
| I-294 | C |
| I-295 | C |
| I-296 | B |
| I-297 | C |
| I-298 | B |
| I-299 | C |
| I-300 | C |

TABLE 11-continued

ADP-Glo Assay results.

| Compound Number | ACL-ADP-Glo (IC50) [μM] |
|---|---|
| I-301 | C |
| I-302 | C |
| I-303 | C |
| I-304 | C |
| I-305 | C |
| I-306 | B |
| I-307 | C |
| I-308 | C |
| I-309 | C |
| I-310 | C |
| I-311 | C |
| I-312 | C |
| I-313 | C |
| I-314 | C |
| I-315 | C |
| I-316 | C |
| I-317 | C |
| I-318 | C |
| I-319 | C |
| I-320 | C |
| I-321 | C |
| I-322 | C |
| I-323 | C |
| I-324 | C |
| I-325 | C |
| I-326 | B |
| I-327 | C |
| I-328 | C |
| I-329 | C |
| I-330 | C |
| I-331 | C |
| I-332 | C |
| I-333 | C |
| I-334 | C |
| I-335 | C |
| I-336 | C |
| I-337 | C |
| I-338 | C |
| I-339 | C |
| I-340 | C |
| I-341 | C |
| I-342 | C |
| I-343 | C |
| I-344 | C |
| I-345 | C |
| I-346 | C |
| I-347 | C |
| I-348 | B |
| I-349 | C |
| I-350 | C |
| I-351 | C |
| I-352 | C |
| I-353 | C |
| I-354 | C |
| I-355 | B |
| I-356 | C |
| I-357 | C |
| I-358 | C |
| I-359 | C |
| I-360 | C |
| I-361 | C |
| I-362 | C |
| I-363 | C |
| I-364 | C |
| I-365 | C |
| I-366 | B |
| I-367 | C |
| I-368 | B |
| I-369 | C |
| I-370 | C |
| I-371 | C |
| I-372 | C |
| I-373 | D |
| I-374 | D |
| I-375 | D |

TABLE 11-continued

ADP-Glo Assay results.

| Compound Number | ACL-ADP-Glo (IC50) [μM] |
|---|---|
| I-376 | D |
| I-377 | D |
| I-378 | D |
| I-379 | D |
| I-380 | D |
| I-381 | D |
| I-382 | D |
| I-383 | D |
| I-384 | D |
| I-385 | D |
| I-386 | D |
| I-387 | D |
| I-388 | D |
| I-389 | D |
| I-390 | D |
| I-391 | D |
| I-392 | D |
| I-393 | D |
| I-394 | D |
| I-395 | D |
| I-396 | D |
| I-397 | D |
| I-398 | D |
| I-399 | D |
| I-400 | D |
| I-401 | D |
| I-402 | D |
| I-403 | D |
| I-404 | D |
| I-405 | D |
| I-406 | D |
| I-407 | D |
| I-408 | D |
| I-409 | D |
| I-410 | D |
| I-411 | D |
| I-412 | D |
| I-413 | D |
| I-414 | D |
| I-415 | D |
| I-416 | D |
| I-417 | D |
| I-418 | D |
| I-419 | D |
| I-420 | D |
| I-421 | D |
| I-422 | D |
| I-423 | D |
| I-424 | D |
| I-425 | D |
| I-426 | D |
| I-427 | D |
| I-428 | D |
| I-429 | D |
| I-430 | D |
| I-431 | D |
| I-432 | D |
| I-433 | D |
| I-434 | D |
| I-435 | D |
| I-436 | D |
| I-437 | D |
| I-438 | D |
| I-439 | D |
| I-440 | D |
| I-441 | D |
| I-442 | D |
| I-443 | D |
| I-444 | D |
| I-445 | D |
| I-503 | A |
| I-504 | A |
| I-505 | A |
| I-506 | A |
| I-507 | B |
| I-508 | B |
| I-509 | B |
| I-510 | C |
| I-511 | C |
| I-512 | C |
| I-513 | C |
| I-514 | C |
| I-515 | C |
| I-516 | C |
| I-517 | C |
| I-518 | C |
| I-519 | C |
| I-520 | C |
| I-522 | D |
| I-523 | D |
| I-524 | D |
| I-525 | D |
| I-526 | D |
| I-527 | D |
| I-528 | D |
| I-529 | D |
| I-530 | D |
| I-531 | D |
| I-532 | D |
| I-533 | D |
| I-535 | D |
| I-536 | D |

Example 331. ACLY-MDH Coupled Assay

TABLE 12

Materials and Instruments

| | Vendor | Cat No. |
|---|---|---|
| Materials | | |
| ACL | XTAL | |
| CoANa2 | Sigma | C3144 |
| Potassium Citrate | Sigma | 89306 |
| ATP | Promega | V915B |
| NADH | Sigma | N8129 |
| MDH from porcine heart | Sigma | M2634 |
| HEPES | Life technolgies | 15630080 |
| MgCl2 | Sigma | M1028 |
| Brij 35 detergent | Merck | 203728 |
| DTT | Sigma | 646563 |
| DMSO | MP | 196055 |
| Corning ® 96 Well Clear Flat Bottom UV-Transparent Microplate | Corning | 3635 |
| 384 dilution plate | Corning | 3657 |
| Topseal A | Perkin Elmer | E5341 |
| 96-well plate | Nunc | 249944 |
| Instrument | | |
| Plate reader | Perkin Elmer | Envision 2104 |
| Centrifuge | Eppendorf | 5810R |

Compounds of the present invention were evaluated in an ACLY Coupled Assay.

The assay protocol for the Coupled Assay (below) was followed:

a) Add 49 μL (ACL+Citrate+CoA Na) to 96 assay plate (final concentration: 8 nM ACL, 60 μM CoA Na2, 85 μM Citrate)

b) Add 1 μL cpds to 96 assay plate, Test cpd conc: 100/30/10 μM top dose, 3 folds dilution, 10+0+control (control: buffer without ACL+DMSO) points, 1000 rpm for 1 min, incubation at 25° C. for 60 min c) Add 50 µL substrate mixture to 96 assay plate (final conc: 250 µM ATP, 250 µM NADH, 0.1 units MDH), 1000 rpm for 1 min.

d) Read OD 340 nm value on Envision 2104, 1 min/point for 30 min.

Results of the Coupled Assay are provided in Table 13 below. Compounds which had an $IC_{50}$ result of <0.050 µM in the assay are labeled "A", compounds which had an $IC_{50}$ result of ≥0.050 µM and <0.50 µM in the assay are labeled "B", compounds which had an $IC_{50}$ result of ≥0.50 µM and <30.0 µM in the assay are labeled "C", and compounds which had an $IC_{50}$ result of ≥30.0 µM in the assay are labeled "D".

TABLE 13

ACLY Coupled Assay Results.

| Compound Number | ACL-MDH Coupled Assay (IC50) [µM] |
|---|---|
| I-1 | B |
| I-2 | C |
| I-6 | B |
| I-7 | C |
| I-9 | B |
| I-11 | C |
| I-12 | C |
| I-13 | C |
| I-15 | C |
| I-16 | C |
| I-19 | C |
| I-20 | A |
| I-21 | B |
| I-22 | A |
| I-23 | A |
| I-24 | C |
| I-26 | A |
| I-28 | B |
| I-29 | C |
| I-31 | B |
| I-32 | C |
| I-33 | C |
| I-34 | A |
| I-36 | C |
| I-41 | A |
| I-46 | C |
| I-47 | A |
| I-48 | C |
| I-49 | C |
| I-50 | C |
| I-53 | C |
| I-55 | C |
| I-56 | B |
| I-58 | B |
| I-59 | B |
| I-60 | A |
| I-62 | C |
| I-64 | C |
| I-65 | A |
| I-66 | C |
| I-67 | C |
| I-74 | C |
| I-82 | A |
| I-83 | A |
| I-84 | A |
| I-86 | A |
| I-87 | A |
| I-88 | A |
| I-90 | B |
| I-91 | B |
| I-92 | B |
| I-93 | B |
| I-94 | C |
| I-95 | B |
| I-98 | A |
| I-99 | C |
| I-100 | C |

TABLE 13-continued

ACLY Coupled Assay Results.

| Compound Number | ACL-MDH Coupled Assay (IC50) [µM] |
|---|---|
| I-101 | A |
| I-102 | C |
| I-103 | A |
| I-104 | C |
| I-105 | A |
| I-106 | B |
| I-107 | C |
| I-110 | C |
| I-111 | A |
| I-112 | B |
| I-113 | C |
| I-115 | C |
| I-116 | A |
| I-117 | A |
| I-118 | B |
| I-119 | B |
| I-123 | A |
| I-124 | B |
| I-126 | B |
| I-127 | A |
| I-128 | A |
| I-129 | B |
| I-130 | A |
| I-131 | B |
| I-133 | C |
| I-134 | C |
| I-135 | B |
| I-136 | A |
| I-137 | B |
| I-138 | A |
| I-139 | C |
| I-140 | B |
| I-141 | C |
| I-142 | A |
| I-143 | C |
| I-144 | C |
| I-145 | A |
| I-146 | C |
| I-148 | A |
| I-149 | B |
| I-157 | B |
| I-158 | B |
| I-159 | A |
| I-160 | A |
| I-162 | C |
| I-192 | C |
| I-193 | C |
| I-194 | C |
| I-197 | C |
| I-198 | A |
| I-200 | B |
| I-201 | C |
| I-202 | C |
| I-203 | D |
| I-206 | B |
| I-208 | B |
| I-211 | C |
| I-212 | C |
| I-213 | B |
| I-220 | B |
| I-221 | C |
| I-222 | C |
| I-226 | C |
| I-229 | B |
| I-232 | C |
| I-233 | B |
| I-235 | C |
| I-236 | B |
| I-239 | C |
| I-240 | C |
| I-241 | C |
| I-242 | C |
| I-243 | C |
| I-248 | C |
| I-249 | C |

TABLE 13-continued

ACLY Coupled Assay Results.

| Compound Number | ACL-MDH Coupled Assay (IC50) [µM] |
|---|---|
| I-260 | C |
| I-262 | B |
| I-264 | C |
| I-266 | C |
| I-269 | C |
| I-272 | C |
| I-275 | B |
| I-276 | B |
| I-281 | B |
| I-282 | A |
| I-286 | A |
| I-287 | B |
| I-289 | C |
| I-293 | C |
| I-294 | C |
| I-295 | C |
| I-296 | B |
| I-297 | C |
| I-298 | B |
| I-299 | C |
| I-302 | C |
| I-304 | C |
| I-305 | C |
| I-306 | B |
| I-311 | C |
| I-316 | C |
| I-317 | C |
| I-318 | C |
| I-322 | C |
| I-326 | B |
| I-327 | C |
| I-328 | C |
| I-329 | C |
| I-330 | C |
| I-331 | C |
| I-332 | C |
| I-333 | C |
| I-334 | C |
| I-335 | C |
| I-336 | C |
| I-338 | C |
| I-339 | C |
| I-340 | C |
| I-344 | C |
| I-347 | C |
| I-348 | B |
| I-349 | C |
| I-350 | C |
| I-355 | C |
| I-361 | C |
| I-364 | C |
| I-366 | B |
| I-367 | C |
| I-368 | D |
| I-372 | C |
| I-407 | D |
| I-503 | A |
| I-504 | A |
| I-505 | A |
| I-508 | C |
| I-509 | B |
| I-510 | C |
| I-511 | C |
| I-512 | C |
| I-513 | C |
| I-514 | C |
| I-515 | C |

Example 332. ACLY HepG2 $^{14}$C-Pyruvate Incorporation Assay (IC$_{50}$ Cholesterol and Fatty Acid Synthesis)

TABLE 14

| Materials and Instruments | | |
|---|---|---|
| | Vendor | Cat No. |
| Materials | | |
| HepG2 cell | ATCC | HB-8065 ™ |
| DMEM(without pyruvate, 25 mM Glucose) | Invitrogen | 11965-092 |
| DMEM(without pyruvate, no Glucose) | Invitrogen | 11966-025 |
| FBS(Australia) | Invitrogen | 10099141 |
| TrypLE ™ Express | Invitrogen | 12604-01 |
| Pen/Strep | GIBCO | 15140-122 |
| Pyruvic acid [2-14C] sodium salt | Pharmaron UK | |
| DPBS | Invitrogen | 14190-144 |
| NaOH | Sigma | 484024 |
| KOH | Sigma | 484016 |
| Ultima Gold ™ | PerkinElmer | 6013326 |
| DMSO | MP | D8371 |
| linoleic acid | Sigma | L1376 |
| 24-well plate | Corning | 3524 |
| Instrument | | |
| Plate reader | Perkin Elmer | Microbeta-2450 |
| Centrifuge | Cence | L550 |

Compounds of the present invention were evaluated in a HepG2 $^{14}$C-pyruvate incorporation assay. The protocol below was followed:

1. Cell Culture

HepG2 Cells (P11) were seeded in 24-well plates at a density of 2*105 cells/well, 0.5 mL with growth medium (25 mM Glucose, 10% FBS (heat inactive), 1% PS, without pyruvate). After 48 hours, change medium with fresh growth medium.

2. Adding Compounds

After 18 hours, replaced medium using 0.5 mL fresh medium (5.5 mM Glucose, without FBS, 1% PS, without Pyruvate) containing Compounds or 0.5% DMSO, incubated at 37° C., 5% CO2 for 1 hour.

3. Adding 14C-Pyruvate

Add 3 µci of [14C]-pyruvate per well to the cell samples were incubated at 37° C., 5% CO2 for 5 hours.

4. Cell Treatment

Medium was removed and placed into a 15 mL centrifuge tube. Add 0.5 mL of 0.1M NaOH to each well and then transfer the cell lysates into the corresponding 15 mL centrifuge tubes. 1.0 mL of EtOH and 0.17 mL 50% KOH were added to 15 mL tubes containing medium and cell suspensions, then shaking tube gently.

5. Saponification 15 mL tubes containing medium and cell suspensions were incubated at 90° C. for 1 hour, then cooled to room temperature.

6. Cholesterol Extraction 5 mL of petroleum ether was added per tube to extract Cholesterol, shaken vigorously, centrifuged at 1000 rpm for 5 min, and ~5 mL of the petroleum ether layer was transferred to a new glass tube (18*180 mm).

7. Acidification

The samples in 15 mL tube were acidified directly with 1 mL concentrated HCl, make sure pH was below 1.

8. Fatty Acids Extraction 5 mL of petroleum ether was added per tube, shaken vigorously, centrifuged at 1000 rpm for 5 min, 5 mL of the petroleum ether layer was transferred to the corresponding glass tube.

9. Repeat the Step 8

10. Count

The petroleum ether extracts were pooled and evaporated to dryness overnight. The residue from the petroleum ether fractions were resuspended in 500 μL of chloroform-hexane (1:1) containing 420 μg of linoleic acid as a carrier. Add 200 μL of resuspending (chloroform-hexane (1:1) containing 168 μg of linoleic acid) to 2 mL Ultima Gold™, after 30 min, count on a scintillation counter.

Results of the HepG2 Cholesterol Assay are provided in Table 15 below. Compounds which had an $IC_{50}$ result of <1.0 μM in the assay are labeled "A", compounds which had an $IC_{50}$ result of ≥1.0 μM and 5.0 μM in the assay are labeled "B", compounds which had an $IC_{50}$ result of ≥5.0 μM and <20.0 μM in the assay are labeled "C".

TABLE 15

ACLY HepG2 $^{14}$C-Pyruvate incorporation
assay with serum ($IC_{50}$ Cholesterol)

| Compound Number | ACLY HepG2 $^{14}$C-Pyruvate Assay serum free IC50 Cholesterol 96 well ($IC_{50}$) [μM] |
|---|---|
| I-22 | A |
| I-84 | A |
| I-123 | A |
| I-157 | B |
| I-220 | B |

Example 333. ACLY HepG2 $^{14}$C-Pyruvate Incorporation Assay ($IC_{50}$ Fatty Acid)

TABLE 16

Materials and Instruments

| | Vendor | Cat No. |
|---|---|---|
| Materials | | |
| HepG2 cell | ATCC | HB-8065 ™ |
| DMEM(without pyruvate, 25 mM Glucose) | Invitrogen | 11965-092 |
| DMEM(without pyruvate, no Glucose) | Invitrogen | 11966-025 |
| FBS(Australia) | Invitrogen | 10099141 |
| TrypLE ™ Express | Invitrogen | 12604-01 |
| Pen/Strep | GIBCO | 15140-122 |
| Pyruvic acid [2-14C] sodium salt | Pharmaron UK | |
| DPBS | Invitrogen | 14190-144 |
| NaOH | Sigma | 484024 |
| KOH | Sigma | 484016 |
| Ultima Gold ™ | PerkinElmer | 6013326 |
| DMSO | MP | D8371 |
| linoleic acid | Sigma | L1376 |
| 24-well plate | Corning | 3524 |
| Instrument | | |
| Plate reader | Perkin Elmer | Microbeta-2450 |
| Centrifuge | Cence | L550 |

Compounds of the invention were also assayed in a ACLY HepG2 $^{14}$C-pyruvate incorporation assay with serum ($IC_{50}$ Fatty Acid). The protocol of the assay (below) was followed:

1. Cell Culture

HepG2 Cells (P11) were seeded in 24-well plates at a density of 2*105 cells/well, 0.5 mL with growth medium (25 mM Glucose, 10% FBS (heat inactive), 1% PS, without pyruvate). After 48 hours, change medium with fresh growth medium.

2. Adding Compounds

After 18 hours, replaced medium using 0.5 mL fresh medium (5.5 mM Glucose, without FBS, 1% PS, without Pyruvate) containing Compounds or 0.5% DMSO, incubated at 37° C., 5% CO2 for 1 hour.

3. Adding 14C-Pyruvate

Add 3 μci of [14C]-pyruvate per well to the cell samples were incubated at 37° C., 5% CO2 for 5 hours.

4. Cell Treatment

Medium was removed and placed into a 15 mL centrifuge tube. Add 0.5 mL of 0.1M NaOH to each well and then transfer the cell lysates into the corresponding 15 mL centrifuge tubes. 1.0 mL of EtOH and 0.17 mL 50% KOH were added to 15 mL tubes containing medium and cell suspensions, then shaking tube gently.

5. Saponification 15 mL tubes containing medium and cell suspensions were incubated at 90° C. for 1 hour, then cooled to room temperature.

6. Cholesterol Extraction 5 mL of petroleum ether was added per tube to extract Cholesterol, shaken vigorously, centrifuged at 1000 rpm for 5 min, and ~5 mL of the petroleum ether layer was transferred to a new glass tube (18*180 mm).

7. Acidification

The samples in 15 mL tube were acidified directly with 1 mL concentrated HCl, make sure pH was below 1.

8. Fatty Acids Extraction 5 mL of petroleum ether was added per tube, shaken vigorously, centrifuged at 1000 rpm for 5 min, 5 mL of the petroleum ether layer was transferred to the corresponding glass tube.

9. Repeat the Step 8

10. Count

The petroleum ether extracts were pooled and evaporated to dryness overnight. The residue from the petroleum ether fractions were resuspended in 500 μL of chloroform-hexane (1:1) containing 420 μg of linoleic acid as a carrier. Add 200 μL of resuspending (chloroform-hexane (1:1) containing 168 μg of linoleic acid) to 2 mL Ultima Gold™, after 30 min, count on a scintillation counter.

Results of the HepG2 Fatty Acid Assay are provided in Table 17 below. Compounds which had an $IC_{50}$ result of <1.0 μM in the assay are labeled "A", compounds which had an $IC_{50}$ result of ≥1.0 μM and 5.0 μM in the assay are labeled "B", compounds which had an $IC_{50}$ result of ≥5.0 μM and <20.0 μM in the assay are labeled "C".

TABLE 17

ACLY HepG2 $^{14}$C-Pyruvate incorporation assay
with serum ($IC_{50}$ Fatty Acid) results.

| Compound Number | ACLY HepG2 $^{14}$C-Pyruvate Assay serum free IC50 FA 96 well ($IC_{50}$) [μM] |
|---|---|
| I-22 | B |
| I-84 | B |
| I-123 | B |
| I-157 | C |
| I-220 | B |

Example 334. ACLY HepG2 $^{14}$C-Pyruvate Incorporation Serum-Free Assay (IC$_{50}$ Cholesterol and Fatty Acid Synthesis)

TABLE 18

Materials and Instruments

| | Vendor | Cat No. |
|---|---|---|
| Materials | | |
| HepG2 cell | ATCC | HB-8065 ™ |
| DMEM(without pyruvate, 25 mM Glucose) | Invitrogen | 11965-092 |
| DMEM(without pyruvate, no Glucose) | Invitrogen | 11966-025 |
| FBS(Australia) | Invitrogen | 10099141 |
| TrypLE ™ Express | Invitrogen | 12604-01 |
| Pen/Strep | GIBCO | 15140-122 |
| Pyruvic acid [2-14C] sodium salt | Pharmaron UK | |
| DPBS | Invitrogen | 14190-144 |
| NaOH | Sigma | 484024 |
| KOH | Sigma | 484016 |
| Ultima Gold ™ | PerkinElmer | 6013326 |
| DMSO | MP | D8371 |
| linoleic acid | Sigma | L1376 |
| 24-well plate | Corning | 3524 |
| Instrument | | |
| Plate reader | Perkin Elmer | Microbeta-2450 |
| Centrifuge | Cence | L550 |

Compounds of the present invention were evaluated in a HepG2 $^{14}$C-pyruvate incorporation assay. The protocol below was followed:
1. Cell Culture
HepG2 Cells (P11) were seeded in 24-well plates at a density of 2*105 cells/well, 0.5 mL with growth medium (25 mM Glucose, 10% FBS (heat inactive), 1% PS, without pyruvate). After 48 hours, change medium with fresh growth medium.
2. Adding Compounds
After 18 hours, replaced medium using 0.5 mL fresh medium (5.5 mM Glucose, without FBS, 1% PS, without Pyruvate) containing Compounds or 0.5% DMSO, incubated at 37° C., 5% CO2 for 1 hour.
3. Adding 14C-Pyruvate
Add 3 µci of [14C]-pyruvate per well to the cell samples were incubated at 37° C., 5% CO2 for 5 hours.
4. Cell Treatment
Medium was removed and placed into a 15 mL centrifuge tube. Add 0.5 mL of 0.1M NaOH to each well and then transfer the cell lysates into the corresponding 15 mL centrifuge tubes. 1.0 mL of EtOH and 0.17 mL 50% KOH were added to 15 mL tubes containing medium and cell suspensions, then shaking tube gently.
5. Saponification
15 mL tubes containing medium and cell suspensions were incubated at 90° C. for 1 hour, then cooled to room temperature.
6. Cholesterol Extraction
5 mL of petroleum ether was added per tube to extract Cholesterol, shaken vigorously, centrifuged at 1000 rpm for 5 min, and ~5 mL of the petroleum ether layer was transferred to a new glass tube (18*180 mm).
7. Acidification
The samples in 15 mL tube were acidified directly with 1 mL concentrated HCl, make sure pH was below 1.
8. Fatty Acids Extraction
5 mL of petroleum ether was added per tube, shaken vigorously, centrifuged at 1000 rpm for 5 min, 5 mL of the petroleum ether layer was transferred to the corresponding glass tube.
9. Repeat the Step 8
10. Count
The petroleum ether extracts were pooled and evaporated to dryness overnight. The residue from the petroleum ether fractions were resuspended in 500 µL of chloroform-hexane (1:1) containing 420 µg of linoleic acid as a carrier. Add 200 µL of resuspending (chloroform-hexane (1:1) containing 168 µg of linoleic acid) to 2 mL Ultima Gold™, after 30 min, count on a scintillation counter.

Results of the serum-free HepG2 Cholesterol Assay are provided in Table 19 below. Compounds which had an IC$_{50}$ result of <1.0 µM in the assay are labeled "A", compounds which had an IC$_{50}$ result of ≥1.0 µM and 5.0 µM in the assay are labeled "B", compounds which had an IC$_{50}$ result of ≥5.0 µM and <20.0 µM in the assay are labeled "C".

TABLE 19

ACLY HepG2 $^{14}$C-Pyruvate incorporation serum-free assay (IC$_{50}$ Cholesterol)

| Compound Number | ACLY HepG2 $^{14}$C-Pyruvate Assay serum free IC50 Cholesterol (IC$_{50}$) [µM] |
|---|---|
| I-1 | B |
| I-6 | B |
| I-9 | B |
| I-13 | B |
| I-15 | B |
| I-16 | B |
| I-20 | B |
| I-21 | B |
| I-22 | A |
| I-23 | B |
| I-26 | B |
| I-31 | B |
| I-33 | B |
| I-34 | B |
| I-36 | B |
| I-41 | B |
| I-47 | B |
| I-48 | B |
| I-59 | B |
| I-60 | A |
| I-65 | C |
| I-82 | B |
| I-83 | B |
| I-84 | A |
| I-86 | B |
| I-87 | B |
| I-88 | B |
| I-90 | B |
| I-91 | B |
| I-98 | B |
| I-101 | A |
| I-110 | B |
| I-111 | B |
| I-113 | B |
| I-116 | B |
| I-117 | B |
| I-123 | A |
| I-126 | B |
| I-127 | B |
| I-128 | C |
| I-135 | B |
| I-136 | B |
| I-138 | B |
| I-145 | B |
| I-157 | B |
| I-198 | B |

TABLE 19-continued

ACLY HepG2 $^{14}$C-Pyruvate incorporation serum-free assay (IC$_{50}$ Cholesterol)

| Compound Number | ACLY HepG2 $^{14}$C-Pyruvate Assay serum free IC50 Cholesterol (IC$_{50}$) [μM] |
|---|---|
| I-208 | B |
| I-213 | B |
| I-220 | B |
| I-233 | C |
| I-235 | B |
| I-236 | B |
| I-260 | B |
| I-272 | B |
| I-275 | B |
| I-281 | B |
| I-286 | B |
| I-287 | B |
| I-296 | B |
| I-298 | C |
| I-318 | B |
| I-344 | B |
| I-348 | B |
| I-349 | B |
| I-361 | B |
| I-364 | B |
| I-372 | B |

Example 335. ACLY HepG2 $^{14}$C-Pyruvate Incorporation Serum-Free Assay (IC$_{50}$ Fatty Acid)

TABLE 20

Materials and Instruments

| | Vendor | Cat No. |
|---|---|---|
| Materials | | |
| HepG2 cell | ATCC | HB-8065 ™ |
| DMEM(without pyruvate, 25 mM Glucose) | Invitrogen | 11965-092 |
| DMEM(without pyruvate, no Glucose) | Invitrogen | 11966-025 |
| FBS(Australia) | Invitrogen | 10099141 |
| TrypLE ™ Express | Invitrogen | 12604-01 |
| Pen/Strep | GIBCO | 15140-122 |
| Pyruvic acid [2-14C] sodium salt | Pharmaron UK | |
| DPBS | Invitrogen | 14190-144 |
| NaOH | Sigma | 484024 |
| KOH | Sigma | 484016 |
| Ultima Gold ™ | PerkinElmer | 6013326 |
| DMSO | MP | D8371 |
| linoleic acid | Sigma | L1376 |
| 24-well plate | Corning | 3524 |
| Instrument | | |
| Plate reader | Perkin Elmer | Microbeta-2450 |
| Centrifuge | Cence | L550 |

Compounds of the invention were also assayed in a ACLY HepG2 14C-pyruvate incorporation assay with serum (IC$_{50}$ Fatty Acid). The protocol of the assay (below) was followed:

1. Cell Culture
HepG2 Cells (P11) were seeded in 24-well plates at a density of 2*105 cells/well, 0.5 mL with growth medium (25 mM Glucose, 10% FBS (heat inactive), 1% PS, without pyruvate). After 48 hours, change medium with fresh growth medium.

2. Adding Compounds
After 18 hours, replaced medium using 0.5 mL fresh medium (5.5 mM Glucose, without FBS, 1% PS, without Pyruvate) containing Compounds or 0.5% DMSO, incubated at 37° C., 5% CO2 for 1 hour.

3. Adding 14C-Pyruvate
Add 3 μci of [14C]-pyruvate per well to the cell samples were incubated at 37° C., 5% CO2 for 5 hours.

4. Cell Treatment
Medium was removed and placed into a 15 mL centrifuge tube. Add 0.5 mL of 0.1M NaOH to each well and then transfer the cell lysates into the corresponding 15 mL centrifuge tubes. 1.0 mL of EtOH and 0.17 mL 50% KOH were added to 15 mL tubes containing medium and cell suspensions, then shaking tube gently.

5. Saponification
15 mL tubes containing medium and cell suspensions were incubated at 90° C. for 1 hour, then cooled to room temperature.

6. Cholesterol Extraction
5 mL of petroleum ether was added per tube to extract Cholesterol, shaken vigorously, centrifuged at 1000 rpm for 5 min, and ~5 mL of the petroleum ether layer was transferred to a new glass tube (18*180 mm).

7. Acidification
The samples in 15 mL tube were acidified directly with 1 mL concentrated HCl, make sure pH was below 1.

8. Fatty Acids Extraction
5 mL of petroleum ether was added per tube, shaken vigorously, centrifuged at 1000 rpm for 5 min, 5 mL of the petroleum ether layer was transferred to the corresponding glass tube.

9. Repeat the Step 8

10. Count
The petroleum ether extracts were pooled and evaporated to dryness overnight. The residue from the petroleum ether fractions were resuspended in 500 μL of chloroform-hexane (1:1) containing 420 μg of linoleic acid as a carrier. Add 200 μL of resuspending (chloroform-hexane (1:1) containing 168 μg of linoleic acid) to 2 mL Ultima Gold™, after 30 min, count on a scintillation counter.

Results of the serum-free HepG2 Fatty Acid Assay are provided in Table 21 below. Compounds which had an IC$_{50}$ result of <1.0 μM in the assay are labeled "A", compounds which had an IC$_{50}$ result of ≥1.0 μM and 10.0 μM in the assay are labeled "B", and compounds which had an IC$_{50}$ result of ≥10.0 μM in the assay are labeled "C".

TABLE 21

ACLY HepG2 $^{14}$C-Pyruvate incorporation serum-free assay (IC$_{50}$ Fatty Acid) results.

| Compound Number | ACLY HepG2 $^{14}$C-Pyruvate Assay serum free IC$_{50}$ FA (IC$_{50}$) [μM] |
|---|---|
| I-1 | B |
| I-6 | C |
| I-9 | B |
| I-13 | B |
| I-15 | B |
| I-16 | B |
| I-20 | B |
| I-21 | B |
| I-22 | B |
| I-23 | B |
| I-26 | C |
| I-31 | C |
| I-33 | C |

TABLE 21-continued

ACLY HepG2 $^{14}$C-Pyruvate incorporation serum-free assay (IC$_{50}$ Fatty Acid) results.

| Compound Number | ACLY HepG2 $^{14}$C-Pyruvate Assay serum free IC$_{50}$ FA (IC$_{50}$) [μM] |
|---|---|
| I-34 | C |
| I-36 | B |
| I-41 | C |
| I-47 | B |
| I-48 | C |
| I-59 | C |
| I-60 | B |
| I-65 | C |
| I-82 | C |
| I-83 | C |
| I-84 | B |
| I-86 | C |
| I-87 | C |
| I-88 | C |
| I-90 | C |
| I-91 | B |
| I-98 | C |
| I-101 | C |
| I-110 | C |
| I-111 | C |
| I-113 | B |
| I-116 | C |
| I-117 | B |
| I-123 | B |
| I-126 | B |
| I-127 | C |
| I-128 | C |
| I-135 | B |
| I-136 | C |
| I-138 | B |
| I-145 | C |
| I-157 | B |
| I-198 | C |
| I-208 | B |
| I-213 | B |
| I-220 | B |
| I-233 | B |
| I-235 | C |
| I-236 | C |
| I-260 | B |
| I-272 | C |
| I-275 | B |
| I-281 | B |
| I-286 | B |
| I-287 | B |
| I-296 | B |
| I-298 | C |
| I-318 | B |
| I-344 | B |
| I-348 | B |
| I-349 | B |
| I-361 | C |
| I-364 | B |
| I-372 | C |

Example 336. rACLY S100 $^{14}$C-Citrate Incorporation Assay (IC$_{50}$ Fatty Acid Synthesis)

Compounds of the present invention were evaluated in a S100 $^{14}$C-citrate incorporation assay. Cell-free preparations of liver can synthesize long-chain fatty acids through a pathway which includes the formation of malonyl co-enzyme A (CoA) from acetyl CoA and $CO_2$. The ACLY enzyme, from S100 fraction of rat livers, can transfer CoA, ATP and Citrate to acetyl-CoA, which is the precursor of fatty acid synthesis. Addition of $^{14}$C-citrate to the S100 fraction enables fatty acid labeling from the ACLY reaction, and thus, the effect of ACLY inhibition can be measured in these preparations.

S100 fractions from rat livers were prepared in order to study the effect of ACLY inhibition on fatty acid synthesis using $^{14}$C-citrate as the radiolabel. Fresh livers were excised and quickly homogenized using a 15 ml dounce homogenizer (D9188-1SET from Sigma) in 1 volume of assay buffer containing 0.25 M sucrose, 1 mM potassium citrate, and protease inhibitor cocktail. Homogenates were centrifuged at 20,000×g for 20 min at 4° C. The supernatant was centrifuged at 100,000×g for 2 hours at 4° C. This fraction is S100. For compound addition, 17.5 μL of compound at the desired concentration was added to 350 μL of S100 fraction solution (derived from 0.5 g fresh liver) in 15 mL centrifuge tubes and exposed to air at 37° C. for 30 min. Radiolabeled [$^{14}$C]-citrate (60 μL, 3 μCi) was added per tube, plus 40 μL reaction buffer and 3032.5 μL substrate buffer (diluted with reaction buffer, final conc.: 1 mM ATP, 60 μM CoA, 100 μM non-radiolabeled citrate, 0.5% DMSO). Total reaction volume equaled 3.5 mL and was mixed at 37° C. for 2 hours. At the end of the reaction, each sample was saponified at 70° C. for 120 minutes in 1.5 mL of 2.5M NaOH, then cooled to room temperature. Ethanol (2.5 mL) was added to the tubes, and the solution was mixed and allowed to stand overnight. Petroleum ether (5 mL) was added per tube to extract cholesterol, the tubes were shaken vigorously, centrifuged at 1000 rpm for 5 min, and ~5 mL of the petroleum ether layer was transferred to a new glass tube (18*180 mm). Next, samples were acidified in 15 mL tubes directly with 0.6 mL concentrated HCl, to ensure pH<1. Fatty acids were extracted by adding 5 mL of petroleum ether per tube, the tubes were shaken vigorously, then centrifuged at 1000 rpm for 5 min. A 5 mL portion of the petroleum ether layer was then transferred to the corresponding glass tube. This step was repeated one additional time. The petroleum ether extracts were then pooled and evaporated to dryness at 64° C. The residue from the petroleum ether fractions was resuspended in 500 μL of chloroform-hexane (1:1) containing 420 μg of linoleic acid as a carrier. An additional 200 μL of resuspending solution (chloroform-hexane (1:1) containing 168 μg of linoleic acid) and 2 mL Ultima Gold™ were added, and after 30 min, radioactivity was counted on a scintillation counter (counts per minute (CPM)). CPM were compared between vehicle control (0.5% DMSO) and test compound to calculate % reduction in fatty acid labeling.

Results of the S100 Assay are provided in Table 22 below. Compounds which had an IC$_{50}$ result of <1.0 μM in the assay are labeled "A", compounds which had an IC$_{50}$ result of ≥1.0 μM and 5.0 μM in the assay are labeled "B", compounds which had an IC$_{50}$ result of ≥5.0 μM and <20.0 μM in the assay are labeled "C".

TABLE 22 rACLY S100 $^{14}$C-Citrate incorporation assay (IC$_{50}$ Fatty Acid) results.

| Compound Number | rACLY S100 $^{14}$C-Citrate FA IC$_{50}$ [μM] |
|---|---|
| I-22 | B |
| I-286 | B |
| I-318 | C |

While we have described a number of embodiments of this invention, it is apparent that our basic examples may be altered to provide other embodiments that utilize the compounds and methods of this invention. Therefore, it will be appreciated that the scope of this invention is to be defined

We claim:
1. A compound of formula II:

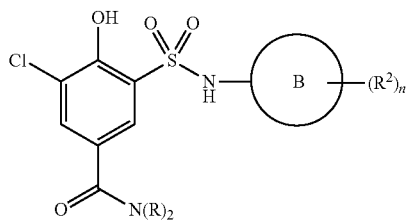

II or a pharmaceutically acceptable salt thereof, wherein:
each R is independently hydrogen, or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, a 5-6 membered heteroaryl ring having 1-4 heteroatoms independently selected from nitrogen, oxygen, and sulfur, or a bicyclic 9-11 membered saturated or partially unsaturated bicyclic heterocyclic ring having 1-4 heteroatoms independently selected from nitrogen, oxygen, and sulfur; or:
two R groups on the same nitrogen are taken together with their intervening atoms to form an optionally substituted 4-7 membered saturated, partially unsaturated, or heteroaryl ring having 0-3 heteroatoms, in addition to the nitrogen, independently selected from nitrogen, oxygen, and sulfur;
Ring B is phenyl or naphthalenyl;
each R$^2$ is independently hydrogen, halogen, —OR, —CN, —NO$_2$, —N(R)$_2$, —C(O)OR, —SR, —S(O)R, —S(O)$_2$R, —C(O)N(R)$_2$, —N(R)C(O)R, —C(O)N(R)S(O)$_2$R, —C(O)N(OR)(R), or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, an 8-10 membered bicyclic aryl or heteroaryl with 1-4 heteroatoms independently selected from nitrogen, oxygen or sulfur, and a 5-6 membered heteroaryl ring having 1-4 heteroatoms independently selected from nitrogen, oxygen, and sulfur;
wherein one instance of R$^2$ is optionally substituted phenyl;
wherein each hydrogen bound to carbon can be optionally and independently replaced by deuterium; and
n is 1, 2, 3, or 4.

2. The compound of claim 1, wherein the compound is of formula II-a:

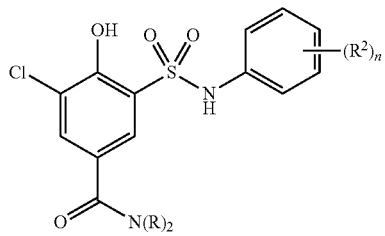

II-a or a pharmaceutically acceptable salt thereof.

3. The compound of claim 1, wherein Ring B is

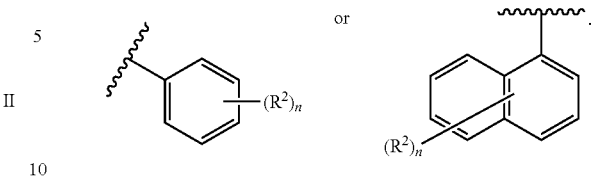

4. The compound of claim 1, wherein each instance of R$^2$ is independently selected from the group consisting of hydrogen, —F, —Cl, —Br, -Me, -i-Pr, —CF$_3$, —NH$_2$, —OH, —OMe, —OCF$_3$, —C(O)NH$_2$, —C(O)OH, —C(O)OMe,

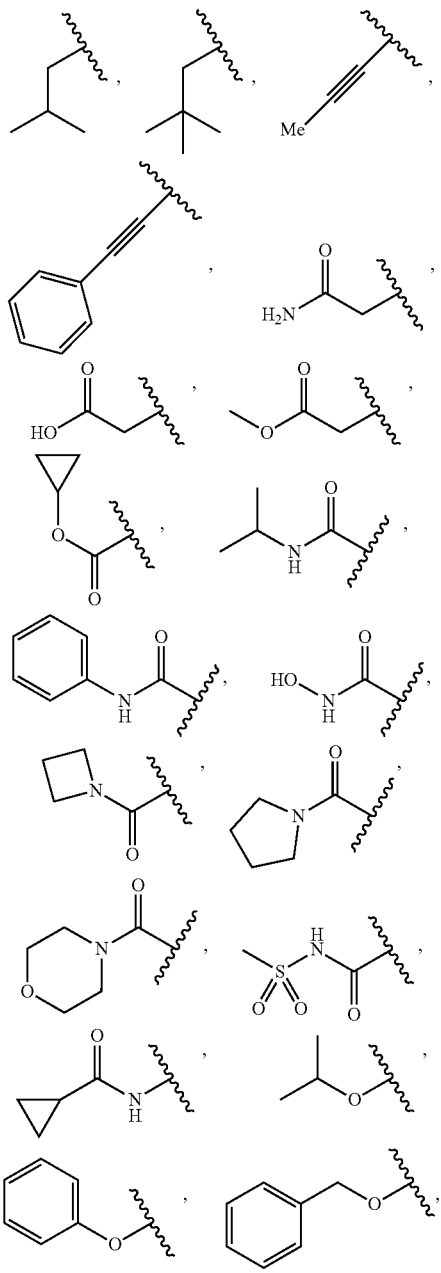

-continued
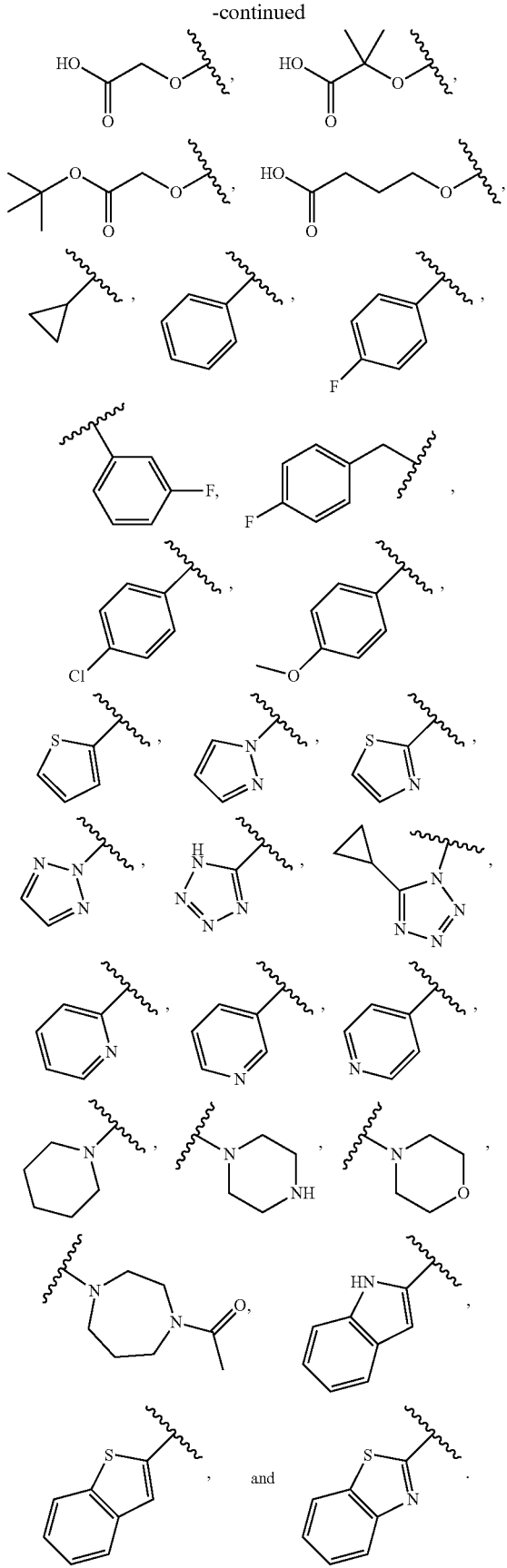
5. The compound of claim 1, wherein n is 2, 3, or 4.
6. A composition comprising a compound according to claim 1 and a pharmaceutically acceptable carrier, adjuvant, or vehicle.
7. A compound according to claim 1, wherein the compound is selected from:
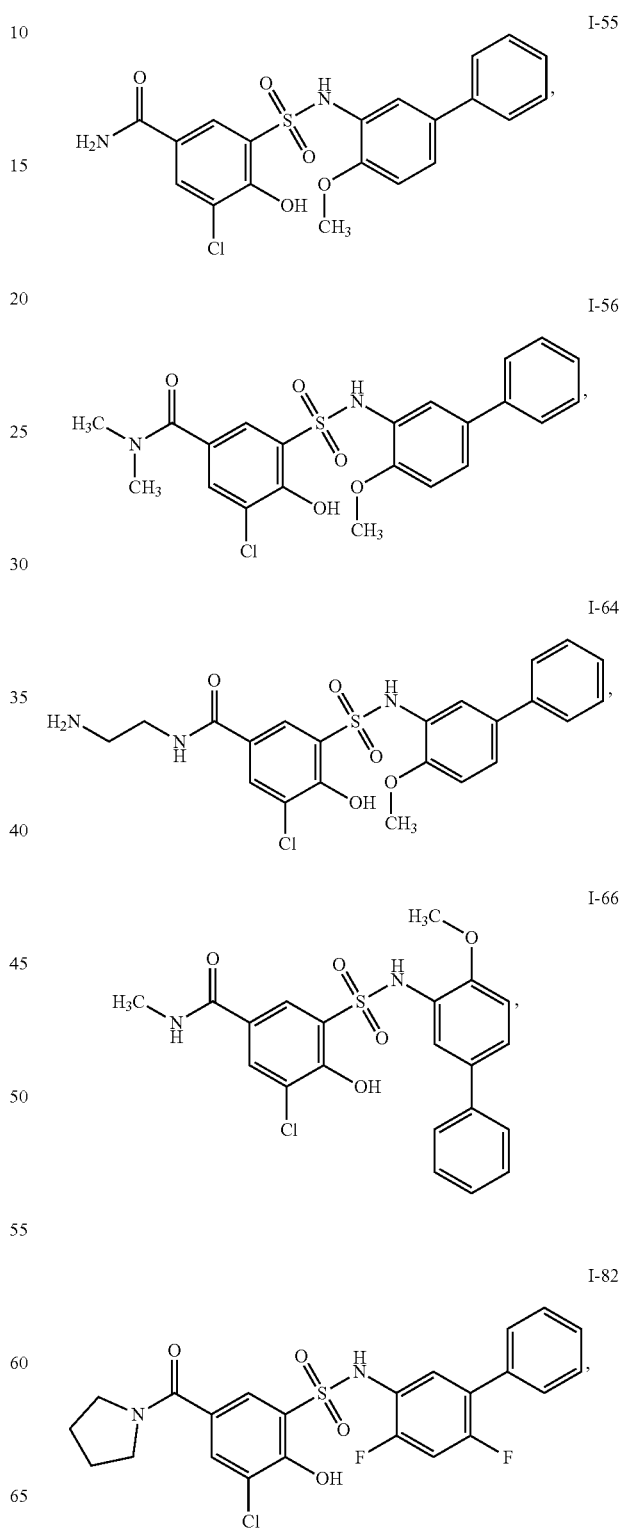

I-83
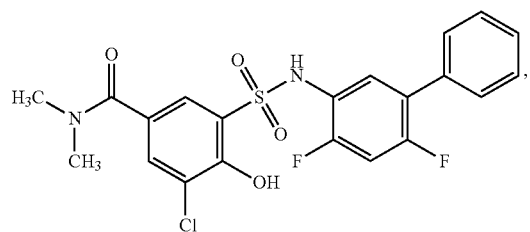
I-92
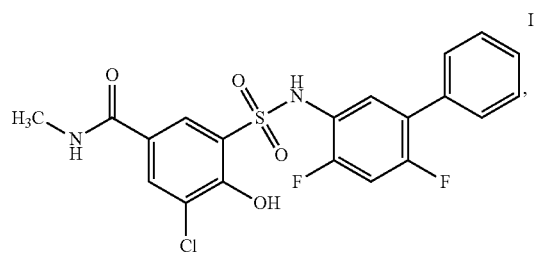
I-93
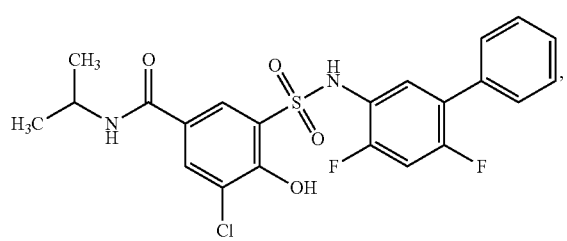
I-98
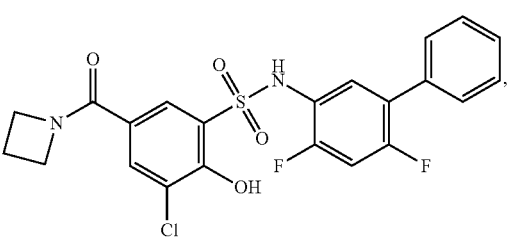
I-99
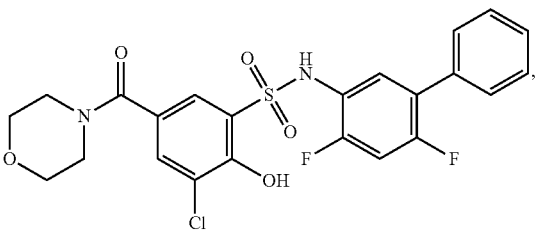
I-100
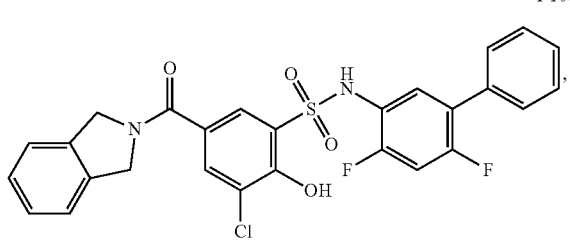
I-102
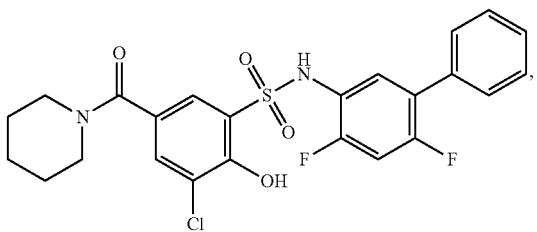
I-103
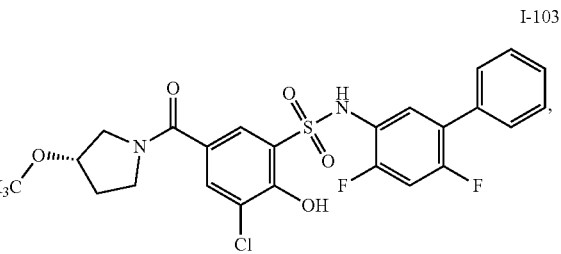
I-104
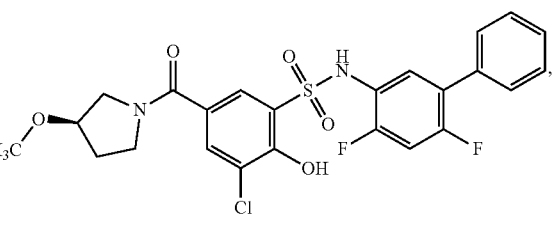
I-105
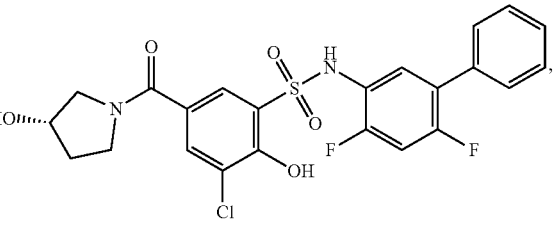
I-106
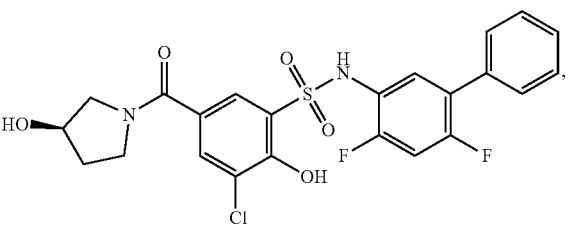
I-118
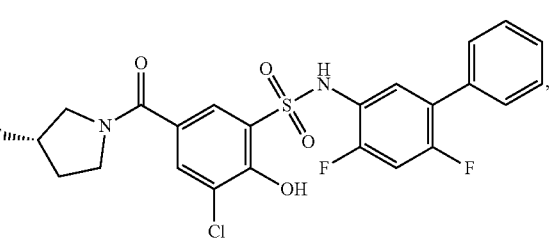

I-119
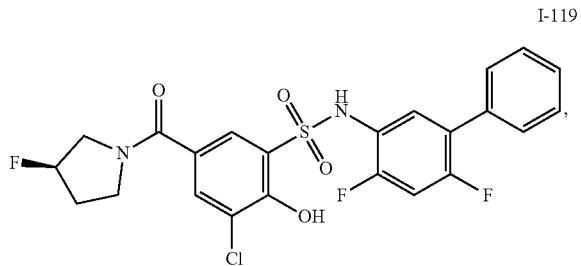
I-129
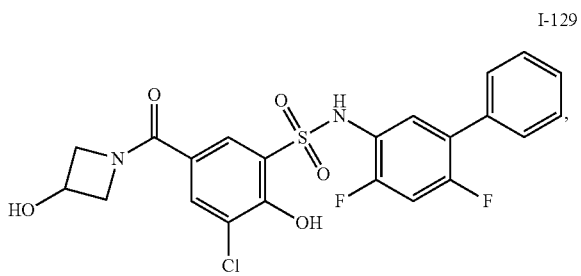
I-130
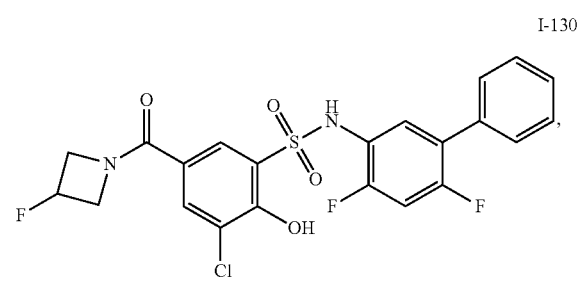
I-136
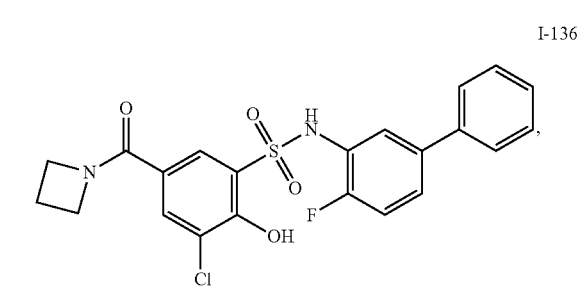
I-141
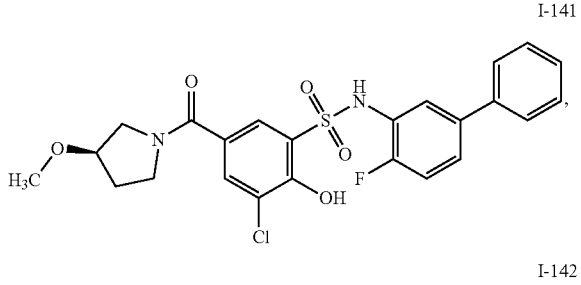
I-142
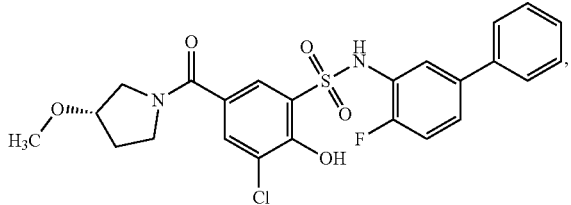
I-145
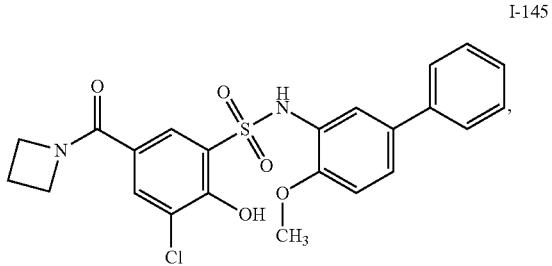
I-148
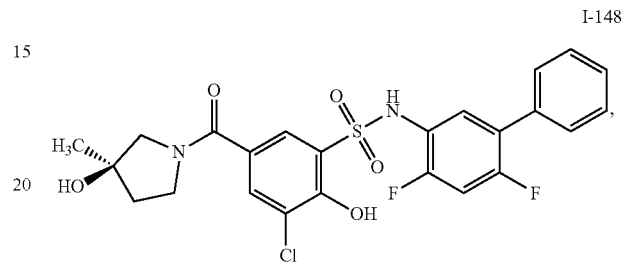
I-149
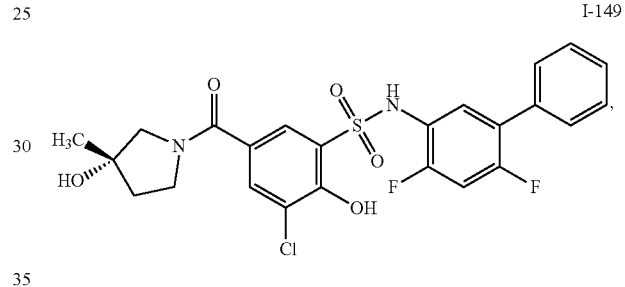
I-159
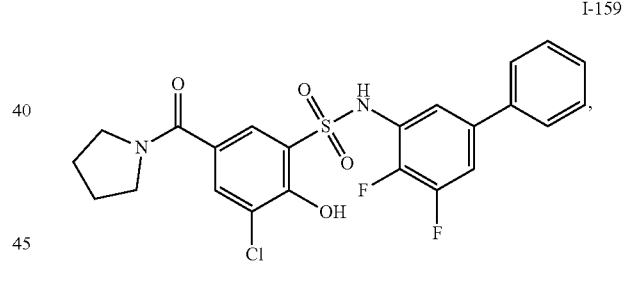
I-160
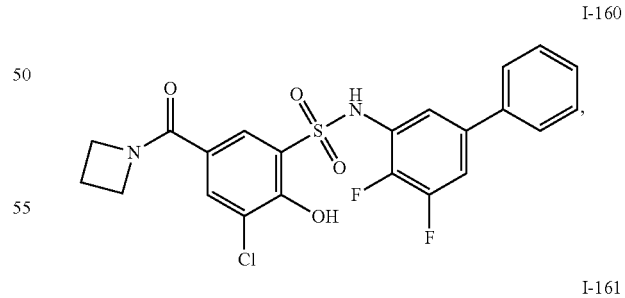
I-161
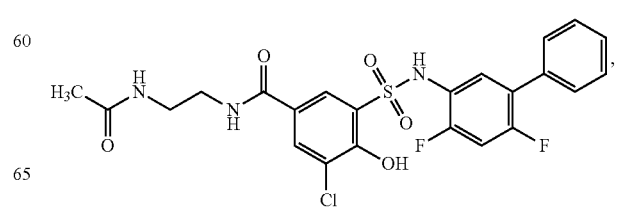

I-162
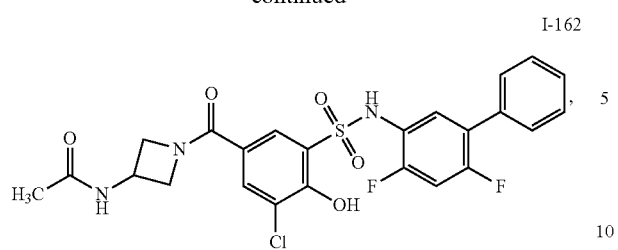
I-200
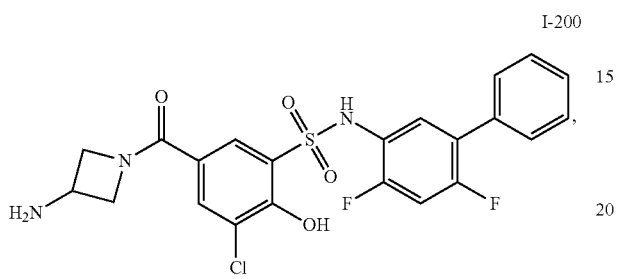
I-201
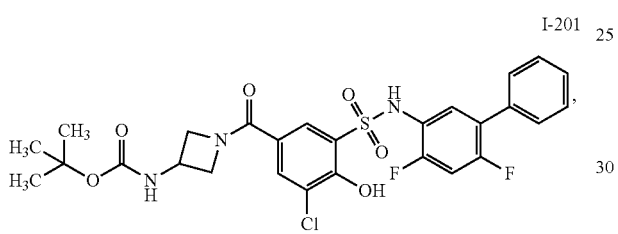
I-266
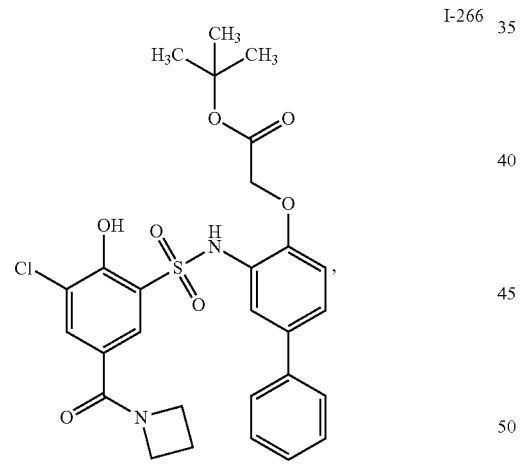
I-270
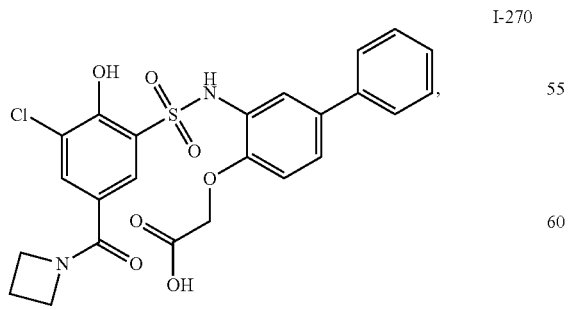
I-271
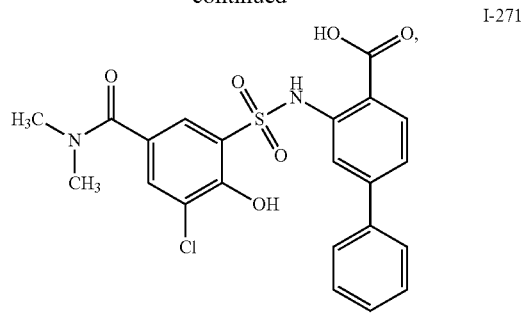
I-276
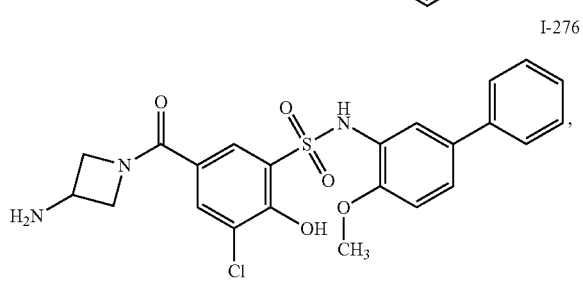
I-277
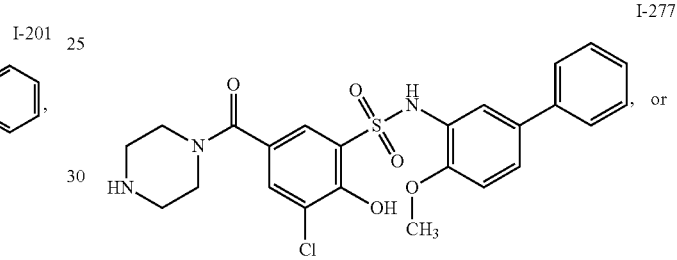
I-518
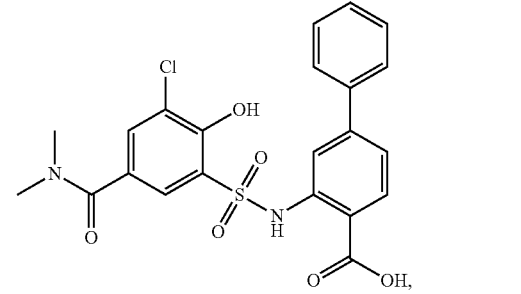
or a pharmaceutically acceptable salt thereof.
8. A compound of the following structure:
I-101
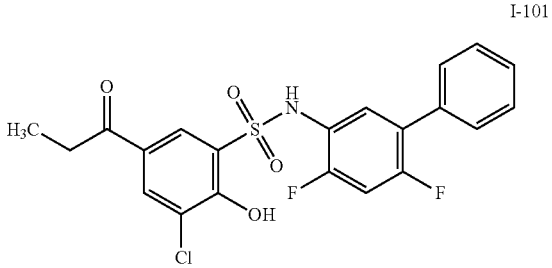 [SMILES: CCC(=O)c1cc(Cl)c(O)c(S(=O)(=O)Nc2cc(-c3ccccc3)c(F)cc2F)c1]
or a pharmaceutically acceptable salt thereof.
\* \* \* \* \*